US012799118B2

(12) United States Patent
Heinrich et al.

(10) Patent No.: US 12,799,118 B2
(45) Date of Patent: Nov. 17, 2026

(54) TRICYCLIC HETEROCYCLES

(71) Applicants: Merck Patent GmbH, Darmstadt (DE); Cancer Research Technology Ltd., London (GB)

(72) Inventors: Timo Heinrich, Darmstadt (DE); Sarah Schlesiger, Darmstadt (DE); Jakub Gunera, Darmstadt (DE); Emma Carswell, London (GB); Lisa Koetzner, Darmstadt (DE); Andreas Blum, Darmstadt (DE)

(73) Assignees: Merck Patent GmbH, Darmstadt (DE); Cancer Research Technology Ltd., London (GB)

( * ) Notice: Subject to any disclaimer, the term of this patent is extended or adjusted under 35 U.S.C. 154(b) by 794 days.

(21) Appl. No.: 17/998,030

(22) PCT Filed: May 5, 2021

(86) PCT No.: PCT/EP2021/061775

§ 371 (c)(1),
(2) Date: Nov. 5, 2022

(87) PCT Pub. No.: WO2021/224291

PCT Pub. Date: Nov. 11, 2021

(65) Prior Publication Data

US 2023/0174538 A1 Jun. 8, 2023
US 2024/0317753 A9 Sep. 26, 2024

(30) Foreign Application Priority Data

May 8, 2020 (EP) .................................... 20173755
Feb. 10, 2021 (EP) .................................... 21156317

(51) Int. Cl.

| | |
|---|---|
| ***C07D 487/04*** | (2006.01) |
| ***A61P 35/00*** | (2006.01) |
| ***C07D 471/14*** | (2006.01) |
| ***C07D 498/04*** | (2006.01) |
| ***C07D 513/04*** | (2006.01) |
| ***C07D 513/14*** | (2006.01) |
| ***C07D 519/00*** | (2006.01) |
| ***C07F 5/02*** | (2006.01) |
| ***C07H 15/26*** | (2006.01) |

(52) U.S. Cl.

CPC ............ *C07D 487/04* (2013.01); *A61P 35/00* (2018.01); *C07D 471/14* (2013.01); *C07D 498/04* (2013.01); *C07D 513/04* (2013.01); *C07D 513/14* (2013.01); *C07D 519/00* (2013.01); *C07F 5/025* (2013.01); *C07H 15/26* (2013.01)

(58) Field of Classification Search

CPC .. C07D 487/02; C07D 471/14; C07D 498/04; C07D 513/04; C07D 513/14; C07D 519/00; A61P 35/00

See application file for complete search history.

(56) References Cited

U.S. PATENT DOCUMENTS

| | | | | |
|---|---|---|---|---|
| 9,620,722 | B2 | 4/2017 | Martynova et al. | |
| 2014/0042370 | A1 | 2/2014 | Martynova et al. | |
| 2015/0225405 | A1 | 8/2015 | Cheruvallath et al. | |
| 2016/0197275 | A1 | 7/2016 | Pan et al. | |
| 2018/0148429 | A1 | 5/2018 | Fabritius et al. | |
| 2018/0277765 | A1 | 9/2018 | Yen | |
| 2024/0270748 | A1 * | 8/2024 | Heinrich | C07D 487/04 |

FOREIGN PATENT DOCUMENTS

| | | | | |
|---|---|---|---|---|
| CL | 2022002323 | A1 | 3/2023 | |
| CL | 2023001138 | A1 | 12/2023 | |
| CN | 107635986 | A | 1/2018 | |
| JP | 2011-195467 | A | 10/2011 | |
| JP | 2015-527399 | A | 9/2015 | |
| KR | 10-2014-0065769 | A | 5/2014 | |
| KR | 10-2014-0107026 | | 9/2014 | |
| KR | 20140107026 | A * | 9/2014 | H10K 85/656 |
| WO | 2012/143080 | | 10/2012 | |
| WO | 2013/177241 | | 11/2013 | |
| WO | 2014/039831 | | 3/2014 | |
| WO | 2020/097389 | | 5/2020 | |
| WO | 2021/174048 | | 9/2021 | |
| WO | 2022/090544 | | 5/2022 | |
| WO | 2022/246459 | | 11/2022 | |

OTHER PUBLICATIONS

McBride, C.; et al. "Discovery of potent, reversible MetAP2 inhibitors via fragment based drug discovery and structure based drug design—Part 2" 2016, Bioorganic and Medicinal Chemistry Letters, vol. 26, pp. 2779-2783. (Year: 2016).*
Boothroyd, S.; et al. "Why Do Some Molecules Form Hydrates or Solvates?" Cryst. Growth Des. 2018, vol. 18, pp. 1903-1908. (Year: 2018).*
Registry entry for compound with CAS RN 896594-87-9; accessed Jul. 21, 2025. (Year: 2006).*
English language translation of KR 20140107026 A; translated Jan. 30, 2026. (Year: 2026).*
Ji, J.; et al. "Three new carbazole derivatives with high thermal stability as host for efficient green phosphorescent organic-light emitting diodes", Dyes and Pigments 2019, vol. 171, 107670. (Year: 2019).*

(Continued)

*Primary Examiner* — Andrea Olson
*Assistant Examiner* — Benjamin M Brandsen
(74) *Attorney, Agent, or Firm* — Grüneberg Global IP, PLLC

(57) ABSTRACT

Tricyclic heterocycles are disclosed. These heterocyclic compounds are useful as TEAD binders and/or inhibitors of YAP-TEAD and TAZ-TEAD protein-protein interaction or binding and for the prevention and/or treatment of several medical conditions including hyperproliferative disorders and diseases, in particular cancer.

22 Claims, 1 Drawing Sheet

(56) References Cited

OTHER PUBLICATIONS

Luo, Q.-L.; et al. "Suzuki-Miyaura Coupling of Aryl Iodides, Bromides, and Chlorides Catalyzed by Bis(thiazole) Pincer Palladium Complexes", Journal of Organic Chemistry 2012, vol. 77, pp. 8332-8337. (Year: 2012).*
Heinrich et al., "Optimization of TEAD P-site Binding Fragment Hit into In Vivo Active Lead MSC-4106", Journal Medicinal Chemistry, vol. 65, 2022, pp. 9206-9229.
Crawford et al., "Hippo pathway inhibition by blocking the YAP/TAZ-TEAD interface: a patent review", Expert Opinion on Therapeutic Patents, vol. 28, No. 12, 2018, pp. 867-873.
Database Accession No. 899403-41-9, Aug. 7, 2006, 1 page.
Database Accession No. 921120-05-0, Feb. 15, 2007, 1 page.
Database Accession No. 921144-98-1, Feb. 15, 2007, 1 page.
Database Accession No. 2105452-38-6, Jul. 31, 2017, 1 page.
Database Accession No. 2114798-12-6, Aug. 16, 2017, 1 page.
Harvey et al., "The Hippo pathway and human cancer", Nature Reviews Cancer, vol. 13, Apr. 2013, pp. 246-257.
International Search Report dated Jul. 23, 2021, for PCT Application No. PCT/EP2021/061775, 5 pages.
Kim et al., "Role of the Hippo Pathway in Fibrosis and Cancer", Cells, vol. 8, 2019, pp. 1-22.
Lin et al.,"Deregulation and Therapeutic Potential of the Hippo Pathway in Cancer", Annual Review of Cancer Biology, vol. 2, 2018, pp. 59-79.
McBride et al., "Discovery of potent, reversible MetAP2 inhibitors via fragment based drug discovery and structure based drug design—Part 2", Bioorganic & Medicinal Chemistry Letters, vol. 26, 2016, pp. 2779-2783.
Pirovano et al., "Gold-Catalyzed Cascade Reactions of 4H-Furo[3,2-b]indoles with Allenamides: Synthesis of Indolin-3-one Derivatives", The Journal of Organic Chemistry, vol. 84, 2019, pp. 5150-5166.
Reggiani et al., "Multiple roles and context-specific mechanisms underlying YAP and TAZ-mediated resistance to anti-cancer therapy", BBA—Reviews on Cancer, vol. 1873, Issue 188341, 2020, pp. 1-11.
Smith et al., "Antiproliferative and Antimigratory Effects of a Novel YAP-TEAD Interaction Inhibitor Identified Using in Silico Molecular Docking", Journal of Medicinal Chemistry, vol. 62, 2019, pp. 1291-1305.
Written Opinion dated Jul. 23, 2021, for PCT Application No. PCT/EP2021/061775, 6 pages.
Xiao et al., "Hippo pathway deletion in adult resting cardiac fibroblasts initiates a cell state transition with spontaneous and self-sustaining fibrosis", Genes & Development, vol. 33, 2019, pp. 1491-1505.
Zhou et al., "Synthesis and Properties of New N-Heteroheptacenes for Solution-Based Organic Field Effect Transistors", Heteroacenes, Chemistry—A European Journal, vol. 23, 2017, pp. 12542-12549.
CAS Registry No. "2328297-66-9, 2118361-80-9, 2114798-12-6, 2114798-08-0, 2105530-03-6, 2105452-38-6, 1784000-41-4, 1578254-46-2, 1543080-96-1, 1526316-72-2, 1509356-39-1, 1368158-46-6, 1216731-23-5, 1179376-28-3, 1179363-34-8, 1052539-60-2, 1052510-72-1, 1049720-16-2, 921144-98-1, 921120-05-0, 921114-69-4, 921086-19-3, 921070-45-3, 920449-37-2, 900284-93-7, 900283-87-6, 900276-84-8, 900274-14-8,900269-55-8, 900268-62-4, 900266-93-5, 899403-41-9, 899402-06-3, 899401-28-6, 899400-03-4, 899397-05-8, 899393-61-4, 899392-20-2, 899386-40-4, 896859-90-8, 896846-83-6, 896843-73-5, 896843-23-5, 896841-52-4, 896839-58-0, 896835-34-0, 896833-32-2, 896832-69-2, 896825-43-7, 896824-65-0, 896823-89-5, 896819-83-3, 896807-77-5, 896804-30-1, 896596-72-8, 896595-64-5, 896079-89-3, 896070-09-0, 896069-36-6, 878440-63-2, 878440-62-1, 878440-60-9, 878440-59-6, 878440-58-5, 782413-36-9, 757151-24-9, 706774-21-2, 701230-95-7, 697237-33-5, 696634-94-3, 663196-68-7, 397304-16-4, 291301-05-08", Database Registry [Online], 2019, Searched on Feb. 26, 2025 , 73 pages.
Office Action received for Japanese Patent Application No. 2022-568418, mailed on Mar. 11, 2025, 14 pages with English translation.
M.S.C. Pedras et al.,"Discovery of inhibitors of brassinin oxidase based on the scaffolds of the phytoalexins brassilexin and wasalexin", Bioorganic Medical Chemistry ,18(2010), pp. 2456-2463.
Pinkin, et al.,"Synthesis of Substituted Thieno [2,3-d] Thiazoles and Indolo [3,2-d] Thiazoles", Chemistry of Hetereocyclic Compounds 1987, vol. 23, No. 3, pp. 345-352.
CAS Registry Database No. 1627587-47-6, 1627587-46-5, 1627587-48-7, 1627588-12-8, 1627588-13-9, Sep. 30, 2014, 2 pages.
CAS Registry Database No. 896594-87-9, CID 20239005, Oct. 20, 2017, 5 pages.
International Search Report received for PCT Application No. PCT/EP2021/080349, mailed on Jan. 20, 2022, 4 pages.
Oliva-Vilarnau et al., "Comparative analysis of YAP/TEAD inhibitors in 2D and 3D cultures of primary human hepatocytes reveals a novel non-canonical mechanism of CYP induction", Biochemical Pharmacology, vol. 215, No. 115755, Aug. 20, 2023, pp. 1-11.
Written Opinion received for PCT Application No. PCT/EP2021/080349, mailed on Jan. 20, 2022, 5 pages.
Office Action received for U.S. Appl. No. 18/559,048, mailed on Feb. 9, 2026, 13 pages.

* cited by examiner

TRICYCLIC HETEROCYCLES

CROSS-REFERENCE TO RELATED APPLICATIONS

This application is a National Stage entry under § 371 of International Application No. PCT/EP2021/061775, filed on May 5, 2021, and which claims the benefit of priority to European Application No. 20173755.8, filed on May 8, 2020, and European Application No. 21156317.6, filed on Feb. 10, 2021. The content of each of these applications is hereby incorporated by reference in its entirety.

BACKGROUND OF THE INVENTION

Field of the Invention

The present invention relates to tricyclic heterocycles. These heterocyclic compounds are useful as TEAD binders and/or inhibitors of YAP-TEAD protein-protein interaction or binding and for the prevention and/or treatment of several medical conditions including hyperproliferative disorders and diseases, in particular cancer.

Description of Related Art

In recent years the Hippo pathway has become a target of interest for the treatment of hyperproliferative disorders and diseases, in particular cancer (S. A. Smith et al., J. Med. Chem. 2019, 62, 1291-1305; K. C. Lin et al., Annu. Rev. Cancer Biol. 2018, 2: 59-79; C.-L. Kim et al., Cells (2019), 8, 468; K. F. Harvey et al., Nature Reviews Cancer, Vol. 13, 246-257 (2013)). The Hippo pathway regulates cell growth, proliferation, and migration. It is assumed that in mammals the Hippo pathway acts as a tumor suppressor, and dysfunction of Hippo signaling is frequently observed in human cancers.

Furthermore, as the Hippo pathway plays a role in several biological processes—like in self-renewal and differentiation of stem cells and progenitor cells, wound healing and tissue regeneration, interaction with other signaling pathways such as Wnt—its dysfunction may also play a role in human diseases other than cancer (C.-L. Kim et al., Cells (2019), 8, 468; Y. Xiao et al., Genes & Development (2019) 33: 1491-1505; K. F. Harvey et al., Nature Reviews Cancer, Vol. 13, 246-257 (2013)).

While several aspects of the pathway activity and regulation are still subject to further research, it is already established that in its "switched-on"-state the Hippo pathway involves a cascade of kinases (including Mst 1/2 and Lats 1/2) in the cytoplasm which results in the phosphorylation of two transcriptional co-activators, YAP (Yes-associated protein) and TAZ (Transcription co-activator with PDZ binding motif). Phosphorylation of YAP/TAZ leads to their sequestration in the cytoplasm and eventually to their degradation. In contrast, when the Hippo pathway is "switched-off" or dysfunctions, the non-phosphorylated, activated YAP/TAZ co-activators are translocated into the cell nucleus. Their major target transcription factors are the four proteins of the Transcriptional enhanced associate domain (TEAD) transcription factor family (TEAD1-4). Binding of YAP or TAZ to and activation of TEAD (or other transcription factors) have shown to induce the expression of several genes many of which mediate cell survival and proliferation. Thus, activated, non-phosphorylated YAP and TAZ may act as oncogenes, while the activated, switched-on Hippo pathway may act as a tumor suppressor by deactivating, i.e. phosphorylating YAP and TAZ.

Furthermore, the Hippo pathway may also play a role in resistance mechanisms of cancer cells to oncology and immune-oncology therapy (R. Reggiani et al., BBA—Reviews on Cancer 1873 (2020) 188341, 1-11).

Consequently, the dysfunction or aberrant regulation of the Hippo pathway as a tumor suppressor is believed to be an important event in the development of a wide variety of cancer types and diseases.

Therefore, inhibition of YAP, TAZ, TEAD, and YAP-TEAD or TAZ-TEAD protein-protein interaction by pharmacological intervention appears to be a reasonable and valuable strategy to prevent and/or treat cancer and other hyperproliferative disorders and diseases associated with the dysfunction of the Hippo pathway.

SUMMARY OF THE INVENTION

The present invention provides compounds that are useful in the prevention and/or treatment of medical conditions, disorders and/or diseases, in particular of hyperproliferative disorders or diseases, which compounds are TEAD binders and/or inhibitors of YAP-TEAD or TAZ-TEAD protein-protein interaction.

The invention refers in one embodiment to a compound of formula I-A

I-A

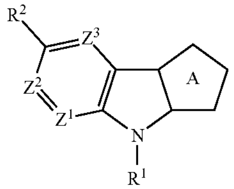

wherein

Ring A represents a five-membered heteroaromatic ring selected from the group consisting of the following ring moieties:

A-1

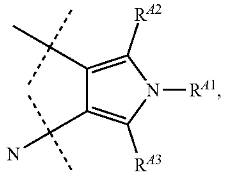

A-2

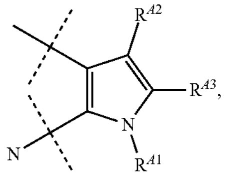

A-3

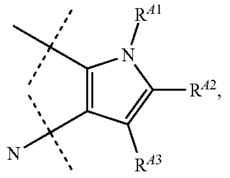

-continued
A-4
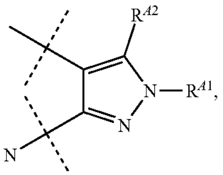
A-5
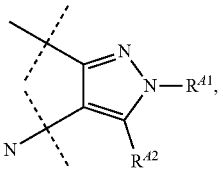
A-6
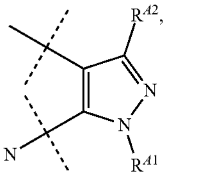
A-7
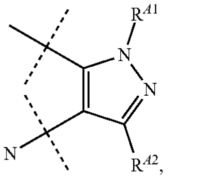
A-8
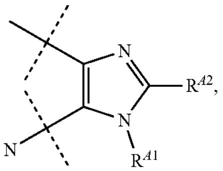
A-9
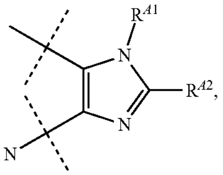
A-10
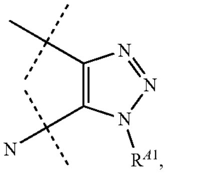
A-11
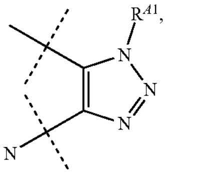
-continued
A-12
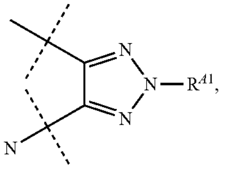
A-13
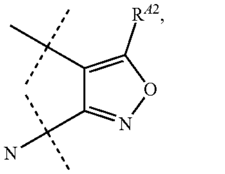
A-14
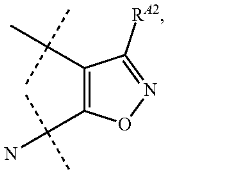
A-15
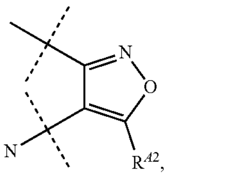
A-16
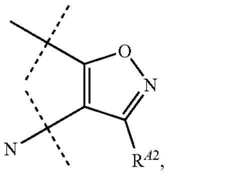
A-17
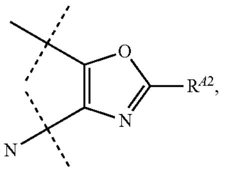
A-18
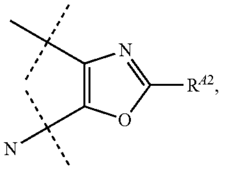
A-19
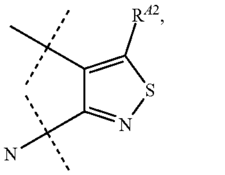

-continued

A-20

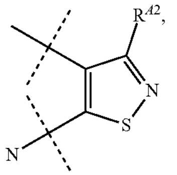

A-21

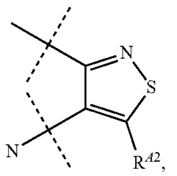

A-22

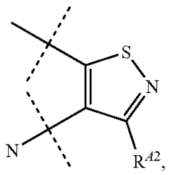

A-23

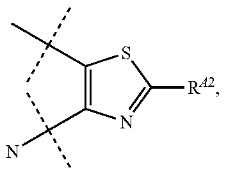

A-24

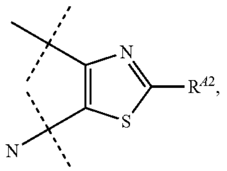

A-25

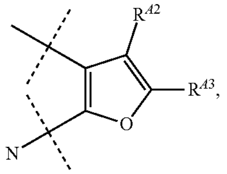

A-26

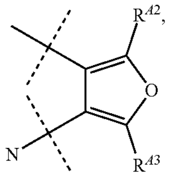

A-27

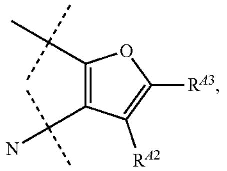

-continued

A-28

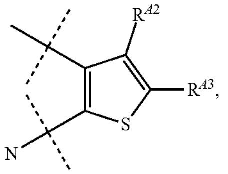

A-29

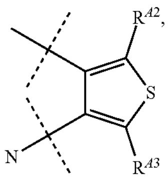

A-30

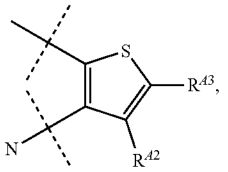

A-31

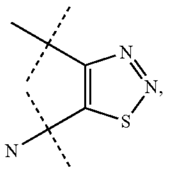

A-32

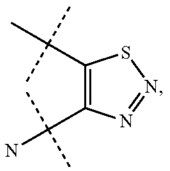

A-33

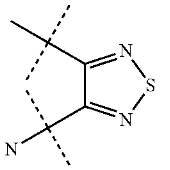

wherein $R^{A1}$ represents H, D, $C_{1-6}$-aliphatic, $—CH_2—Ar^{A1}$ or $—CH_2—CH_2—Ar^{A1}$, $R^{A2}$ represents H, D, halogen, $C_{1-6}$-aliphatic, $—CH_2—Ar^{A2}$ or $—CH_2—CH_2—Ar^{A2}$;

$R^{A3}$ represents H, D, $C_{1-6}$-aliphatic, $—CH_2—Ar^{A3}$ or $—CH_2—CH_2—Ar^{A3}$ $Z^1$ is $CR^{Z1}$ or N;

$Z^2$ is $CR^{Z2}$ or N;

$Z^3$ is $CR^{Z3}$ or N;

wherein at least two of $Z^1$, $Z^2$ and $Z^3$ are not N;

$R^1$ represents $Ar^1$, $Hetar^1$, $Cyc^1$, $Hetcyc^1$, $L^1$-$Ar^1$, $L^1$-$Hetar^1$, $L^2$-$Cyc^1$, $L^2$-$Hetcyc^1$, un-substituted or substituted, straight-chain or branched $C_{1-8}$-aliphatic;

$R^2$ represents $—C(=O)—OR^{2a}$, $—C(=O)—NR^{2b}R^{2c}$, $—(CH_2)_w—C(=O)—NR^{2b}R^{2c}$, $—(CH_2)_x—NR^{2d}—C(=O)—R^{2e}$, $—S—R^{2f}$, $—S(=O)—R^{2f}$, $—S(=O)_2—R^{2g}$, $—S(=O)_2—NR^{2h}R^{2i}$, $—S(=O)_2—OH$, $—S(=O)(=NR^{2j})—OH$, $—S(=O)(=NR^{2j})—R^{2g}$, $—S(=O)(=NR^{2k})—NR^{2l}R^{2m}$, F, Cl, Br, I, —CN, $—(CH_2)_v—CN$, $—P(=O)(OR^{2o})(OR^{2p})$, $—(CH_2)_y—$ $NR^{2g}R^{2r}$, $—(CH_2)_z—NR^{2d}—S(═O)_2—R^{2g}$, $—C(═O)—N═S(═O)—R^{2s}R^{2t}$, $—C(═O)—N═S(═N—R^{2u})—R^{2s}R^{2t}$, $—B(OH)_2$ or $Hetcyc^X$;

$Ar^{A1}$, $Ar^{A2}$, $Ar^{A3}$ represent independently from each other phenyl which may be unsubstituted or mono- or di-substituted with independently from each other $R^{A11}$ and/or $R^{A12}$;

$R^{Z1}$. represents H or halogen;

$R^{Z2}$ represents H or halogen; or forms together with $R^2$ a divalent radical $—S(═O)_2—N(H)—C(═O)—$;

$R^{Z3}$ represents H or halogen;

$R^{2a}$ represents H, un-substituted or substituted $C_{1-8}$-aliphatic, aryl, heteroaryl, saturated or partially unsaturated heterocyclyl, or carbohydrate derived radical, or Cat;

Cat represents a monovalent cation;

$R^{2b}$, $R^{2c}$, $R^{2a}$, $R^{2r}$ represent independently from each other H, un-substituted or substituted $C_{1-8}$-aliphatic including $C_{3-7}$-cycloaliphatic; or form together with the nitrogen atom to which they are attached to an unsubstituted or substituted saturated, partially unsaturated or aromatic heterocycle with 3, 4, 5, 6, 7 ring atoms wherein 1 of said ring atoms is said nitrogen atom and no or one further ring atom is a hetero atom selected from N, O or S and the remaining are carbon atoms; wherein said heterocycle may optionally be fused with $Hetar^Z$; or one of $R^{2b}$ and $R^{2c}$ represents —CN, $—NH_2$, —OH, $—O—C_{1-6}$-alkyl, $—S(═O)_2—R^{2g}$, $Ar^2$, $Hetar^2$, $Cyc^2$ or $Hetcyc^2$, while the other represents H or un-substituted or substituted $C_{1-8}$-aliphatic;

$R^{2d}$, $R^{2j}$, $R^{2k}$, $R^{2o}$, $R^{2p}$ represent independently from each other H, un-substituted or substituted $C_{1-8}$-aliphatic;

$R^{2e}$ represents H, halogen, un-substituted or substituted $C_{1-8}$-aliphatic, heteroaryl;

$R^{2f}$, $R^{2g}$ represent independently from each other un-substituted or substituted $C_{1-8}$-aliphatic;

$R^{2h}$, $R^{2l}$ represent independently from each other H, un-substituted or substituted $C_{1-8}$-aliphatic, aryl, heterocyclyl, heteroaryl; or form together with the nitrogen atom to which they are attached to an unsubstituted or substituted saturated, partially unsaturated or aromatic heterocycle with 3, 4, 5, 6, 7 ring atoms wherein 1 of said ring atoms is said nitrogen atom and no or one further ring atom is a hetero atom selected from N, O or S and the remaining are carbon atoms;

$R^{2l}$, $R^{2m}$ represent independently from each other H, un-substituted or substituted $C_{1-8}$-aliphatic; or form together with the nitrogen atom to which they are attached to an unsubstituted or substituted saturated, partially unsaturated or aromatic heterocycle with 3, 4, 5, 6, 7 ring atoms wherein 1 of said ring atoms is said nitrogen atom and no or one further ring atom is a hetero atom selected from N, O or S and the remaining are carbon atoms;

$R^{2s}$, $R^{2t}$ represent independently from each other unsubstituted or substituted $C_{1-8}$-aliphatic; or form together an unsubstituted or substituted divalent $C_{3-6}$-alkylene radical;

$R^{2u}$ represents hydrogen or unsubstituted or substituted $C_{1-6}$-aliphatic;

$Ar^1$ is a mono-, bi- or tricyclic aryl with 5, 6, 7, 8, 9, 10, 11, 12, 13, 14 ring carbon atoms, wherein that aryl may be unsubstituted or substituted with substituents $R^{B1}$, $R^{B2}$, $R^{B3}$, $R^{B4}$, $R^{B5}$, $R^{B6}$ and/or $R^{B7}$ which may be the same or different;

$Hetar^1$ is a mono-, bi- or tricyclic heteroaryl with 5, 6, 7, 8, 9, 10, 11, 12, 13, 14 ring atoms wherein 1, 2, 3, 4, 5 of said ring atoms is/are a hetero atom(s) selected from N, O and/or S and the remaining are carbon atoms, wherein that heteroaryl may be unsubstituted or substituted with substituents $R^{B1}$, $R^{B2}$, $R^{B3}$, $R^{B4}$, $R^{B5}$, $R^{B6}$ and/or $R^{B7}$ which may be the same or different;

$Cyc^1$ is a saturated or partially unsaturated, mono-, bi- or tricyclic carbocycle with 3, 4, 5, 6, 7, 8, 9, 10, 11, 12, 13, 14, 15 ring carbon atoms, wherein that carbocycle may be unsubstituted or substituted with $R^{B8}$, $R^{B9}$, $R^{B10}$, $R^{B11}$, $R^{B12}$ and/or $R^{B13}$ which may be the same or different; and wherein that carbocycle may optionally be fused to $Ar^X$ via 2 adjacent ring atoms of said $Ar^X$ and wherein that fused carbocycle may further be unsubstituted or substituted with $R^{C1}$, $R^{C2}$, $R^{C3}$, $R^{C4}$, $R^{C5}$, $R^{C6}$ which may be the same or different;

$Hetcyc^1$ is a saturated or partially unsaturated, mono-, bi- or tricyclic heterocycle with 3, 4, 5, 6, 7, 8, 9, 10, 11, 12, 13, 14, 15 ring atoms wherein 1, 2, 3, 4, 5 of said ring atoms is/are a hetero atom(s) selected from N, O and/or S and the remaining are carbon atoms, wherein that heterocycle may be unsubstituted or substituted with $R^{B8}$, $R^{B9}$, $R^{B10}$, $R^{B11}$, $R^{B12}$ and/or $R^{B13}$ which may be the same or different;

$L^1$ is a divalent radical selected from the group consisting of $—S(═O)_2—$, $—C(═O)—$, un-substituted or substituted, straight-chain or branched $C_{1-6}$-alkylene or $C_{2-6}$-alkenylene, in both of which one of the carbon units of the alkylene or alkenylene chain may be replaced by —O—;

$L^2$ is a divalent radical selected from the group consisting of un-substituted or substituted, straight-chain or branched $C_{1-6}$-alkylene or $C_{2-6}$-alkenylene, in both of which one of the carbon units of the alkylene or alkenylene chain may be replaced by —O—;

$R^{A11}$, $R^{A12}$ represent independently from each other halogen or un-substituted or substituted, straight-chain or branched $C_{1-6}$-aliphatic;

$R^{B1}$, $R^{B2}$, $R^{B3}$, $R^{B4}$, $R^{B5}$, $R^{B6}$, $R^{B7}$ represent independently from each other un-substituted or substituted, straight-chain or branched $C_{1-6}$-aliphatic, $C_{1-6}$-aliphatoxy, $—S—C_{1-6}$-aliphatic; halogen, —CN, $—S(═O)—R^{b1}$, $S(═O)_2—R^{b1}$, $—NR^{b2}NR^{b3}$, $Ar^2$, $—CH_2—Ar^2$, $Hetar^2$, $Cyc^2$, $Hetcyc^2$;

and/or two adjacent $R^{B1}$, $R^{B2}$, $R^{B3}$, $R^{B4}$, $R^{B5}$, $R^{B6}$ and/or $R^{B7}$ form together a divalent $—C_{2-4}$-alkylene radical in which one of the alkylene carbon units may be replaced by a carbonyl unit (—C(═O)—), or a divalent $—O—C_{1-3}$-alkylene radical or a divalent $—O—C_{1-3}$-alkylene-O-radical;

$R^{b1}$ represents un-substituted or substituted $C_{1-8}$-aliphatic;

$R^{b2}$, $R^{b3}$ represent independently from each other H, un-substituted or substituted $C_{1-8}$-aliphatic; or form together with the nitrogen atom to which they are attached to an unsubstituted or substituted saturated, partially unsaturated or aromatic heterocycle with 3, 4, 5, 6, 7 ring atoms wherein 1 of said ring atoms is said nitrogen atom and no or one further ring atom is a hetero atom selected from N, O or S and the remaining are carbon atoms;

$R^{B8}$, $R^{B9}$, $R^{B10}$, $R^{B11}$, $R^{B12}$, $R^{B13}$ represent independently from each other halogen, un-substituted or substituted $C_{1-6}$-aliphatic, $C_{1-6}$-aliphatoxy, $Ar^Y$; and/or two of $R^{B8}$, $R^{B9}$, $R^{B10}$, $R^{B11}$, $R^{B12}$, $R^{B13}$ which are attached to the same carbon atom of said carbocycle or said heterocycle form a divalent oxo (=O) group; and/or two of $R^{B8}$, $R^{B9}$, $R^{B10}$, $R^{B11}$, $R^{B12}$, $R^{B13}$ or four of $R^{B8}$, $R^{B9}$, $R^{B10}$, $R^{B11}$, $R^{B12}$, $R^{B13}$ which are attached to the same sulfur atom of said heterocycle form a divalent oxo (=O) group thereby forming either an —S(=O)— or an —S(=O)$_2$— moiety;

$Ar^2$ is a mono- or bicyclic aryl with 5, 6, 7, 8, 9, 10 ring carbon atoms, wherein that aryl may be unsubstituted or substituted with substituents $R^{D1}$, $R^{D2}$, $R^{D3}$, $R^{D4}$ and/or $R^{D5}$ which may be the same or different $Hetar^2$ is a mono- or bicyclic heteroaryl with 5, 6, 7, 8, 9, 10 ring atoms wherein 1, 2, 3, 4, 5 of said ring atoms is/are a hetero atom(s) selected from N, O and/or S and the remaining are carbon atoms, wherein that heteroaryl may be unsubstituted or substituted with substituents $R^{D1}$, $R^{D2}$, $R^{D3}$, $R^{D4}$ and/or $R^{D5}$ which may be the same or different;

$Cyc^2$ is a saturated or partially unsaturated monocyclic carbocycle with 3, 4, 5, 6 or 7 ring carbon atoms, wherein that carbocycle may be unsubstituted or substituted with $R^{D6}$, $R^{D7}$, $R^{D8}$, $R^{D9}$ and/or $R^{D10}$ which may be the same or different; wherein that carbocycle may optionally be fused to $Ar^Z$ or $Hetar^Z$ via 2 adjacent ring atoms of said $Ar^Z$ or $Hetar^Z$ and wherein that fused carbocycle may further be unsubstituted or substituted with $R^{C1}$, $R^{C2}$, $R^{C3}$, $R^{C4}$, $R^{C5}$, $R^{C6}$ which may be the same or different;

$Hetcyc^2$ is a saturated or partially unsaturated, monocyclic heterocycle with 3, 4, 5, 6, 7 ring atoms wherein 1 or 2 of said ring atoms is/are a hetero atom(s) selected from N, O and/or S and the remaining are carbon atoms, wherein that heterocycle may be unsubstituted or substituted with $R^{D6}$, $R^{D7}$, $R^{D8}$, $R^{D9}$ and/or $R^{D10}$ which may be the same or different; wherein that heterocycle may optionally be fused to $Ar^Z$ or $Hetar^Z$ via 2 adjacent ring atoms of said $Ar^Z$ or $Hetar^Z$ and wherein that fused heterocycle may further be unsubstituted or substituted with $R^{C1}$, $R^{C2}$, $R^{C3}$, $R^{C4}$, $R^{C5}$, $R^{C6}$ which may be the same or different;

$Ar^X$, $Ar^Z$ independently from each other an un-substituted or substituted benzo ring;

$Ar^Y$ is an un-substituted or mono- or di-substituted phenyl;

$Hetar^{Y1}$ is a 5 or 6 membered monocyclic heteroaryl wherein 1, 2, 3, 4 ring atoms are hetero atoms selected from N, O and/or S and the remaining are carbon atoms, wherein that heteroaryl may be unsubstituted or substituted with halogen, $C_{1-4}$-alkyl which may optionally be substituted with OH;

$Hetar^Z$ is an unsubstituted or substituted 5 or 6 membered heteroaryl ring selected from the group consisting of pyrrole, furan, thiophene, pyrazole, imidazole, oxaole, isoxazole, thiazole, oxadiazole, triazole, tetrazole, pyridine, pyrimidine, pyrazine, pyrane;

$Cyc^{Y1}$ is a saturated monocyclic carbocycle with 3, 4, 5, 6 or 7 ring carbon atoms, wherein that carbocycle may be unsubstituted or substituted with halogen, OH, $C_{1-4}$-alkyl;

$Hetcyc^X$ is a saturated, partially unsaturated or aromatic, monocyclic heterocycle with 3, 4, 5, 6, 7 ring atoms wherein 1, 2, 3, 4 of said ring atoms is/are a hetero atom(s) selected from N, O and/or S and the remaining are carbon atoms, wherein said heterocycle may be unsubstituted or substituted with $R^{X1}$, $R^{X2}$, $R^{X3}$, $R^{X4}$, $R^{X5}$, $R^{X6}$, $R^{X7}$ and/or $R^{X8}$ which may be the same or different, and wherein that heterocycle is optionally a carboxylic acid bioisostere;

$Hetcyc^Y$ is a saturated, partially unsaturated or aromatic, monocyclic heterocycle with 3, 4, 5, 6, 7 ring atoms wherein 1, 2, 3, 4 of said ring atoms is/are a hetero atom(s) selected from N, O and/or S and the remaining are carbon atoms;

$Hetcyc^{Y1}$ is a saturated or partially unsaturated monocyclic heterocycle with 5 or 6 ring atoms wherein 1 or 2 of said ring atoms are heteroatoms selected from N, O, and/or S and the remaining are carbon atoms;

$R^{C1}$, $R^{C2}$, $R^{C3}$, $R^{C4}$, $R^{C5}$, $R^{C6}$ represent independently from each other un-substituted or substituted $C_{1-6}$-aliphatic;

$R^{D1}$, $R^{D2}$, $R^{D3}$, $R^{D4}$, $R^{D5}$ represent independently from each other un-substituted or substituted $C_{1-6}$-aliphatic;

$R^{D6}$, $R^{D7}$, $R^{D8}$, $R^{D9}$, $R^{D10}$ represent independently from each other un-substituted or substituted $C_{1-6}$-aliphatic, unsubstituted or substituted $C_{1-6}$-aliphatoxy, halogen, hydroxy; $Hetar^{Y1}$, $CH_2$-$Hetar^{Y1}$, $Cyc^{Y1}$, $Hetcyc^{Y1}$, —$CH_2$-$Hetcyc^{Y1}$; and/or two of $R^{D6}$, $R^{D7}$, $R^{D8}$, $R^{D9}$, $R^{D10}$ which are attached to the same ring atom of said carbocycle or heterocycle may form a divalent $C_{2-6}$-alkylene radical, wherein one or two non-adjacent carbon units of said alkylene radical may optionally be replaced by independently from each other O, N—H, or N—$C_{1-4}$-alkyl, and wherein that alkylene radical may optionally be substituted with OH, $C_{1-4}$-alkyl or —O—$C_{1-4}$-alkyl; and/or two of $R^{D6}$, $R^{D7}$, $R^{D8}$, $R^{D9}$, $R^{D10}$ which are attached to different ring atoms of said carbocycle or heterocycle may form a divalent $C_{1-6}$-alkylene radical, wherein one or two non-adjacent carbon units of said alkylene radical may optionally be replaced by independently from each other O, N—H, or N—$C_{1-4}$-alkyl;

$R^{X1}$, $R^{X2}$, $R^{X3}$, $R^{X4}$, $R^{X5}$, $R^{X6}$, $R^{X7}$, $R^{X8}$ represent independently from each other un-substituted or substituted $C_{1-6}$-aliphatic, $C_{1-6}$-aliphatoxy, halogen, —OH, —$NR^{2d}$—S(=O)$_2$—$R^{2g}$, $Hetcyc^Y$, O-$Hetcyc^Y$; and/or two of $R^{X1}$, $R^{X2}$, $R^{X3}$, $R^{X4}$, $R^{X5}$, $R^{X6}$, $R^{X7}$, $R^{X8}$ which are attached to the same carbon atom of said heterocycle form a divalent oxo (=O) group; and/or two of $R^{X1}$, $R^{X2}$, $R^{X3}$, $R^{X4}$, $R^{X5}$, $R^{X6}$, $R^{X7}$, $R^{X8}$ or four of $R^{X1}$, $R^{X2}$, $R^{X3}$, $R^{X4}$, $R^{X5}$, $R^{X6}$, $R^{X7}$, $R^{X8}$ which are attached to the same sulfur atom of said heterocycle form a divalent oxo (=O) group thereby forming either an —S(=O)— or an —S(=O)$_2$— moiety;

halogen is F, Cl, Br, I;

v is 1 or 2;

w is 1 or 2;

x is 0, 1 or 2;

y is 0, 1 or 2;

z is 0, 1 or 2;

or any N-oxide, solvate, tautomer or stereoisomer thereof and/or any pharmaceutically acceptable salt of each of the foregoing, including mixtures thereof in all ratios.

The invention refers in a further embodiment to a compound of formula I

I
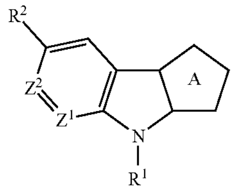
wherein
Ring A represents a five-membered heteroaromatic ring selected from the group consisting of the following ring moieties:
A-1
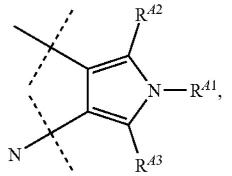
A-2
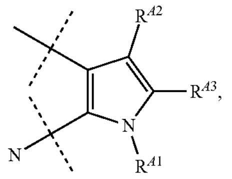
A-3
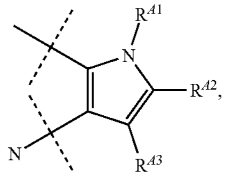
A-4
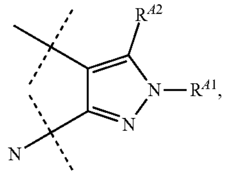
A-5
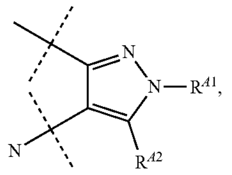
A-6
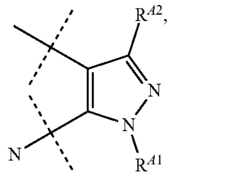
-continued
A-7
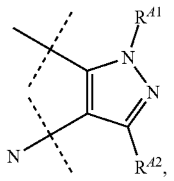
A-8
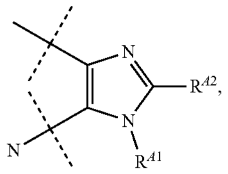
A-9
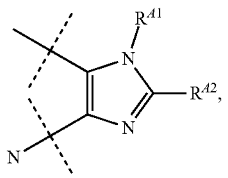
A-10
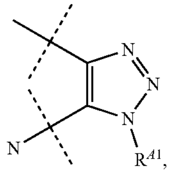
A-11
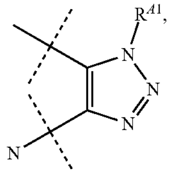
A-12
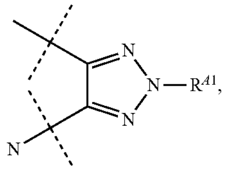
A-13
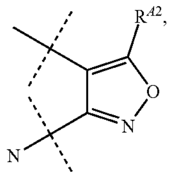
A-14
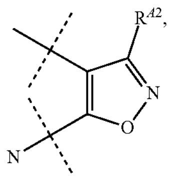

-continued
A-15
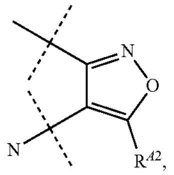
A-16
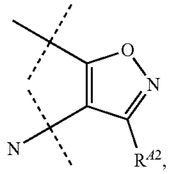
A-17
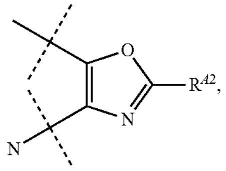
A-18
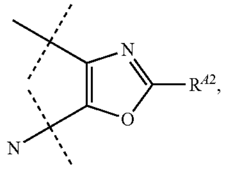
A-19
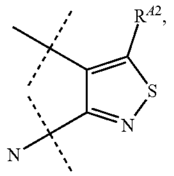
A-20
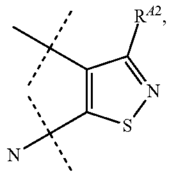
A-21
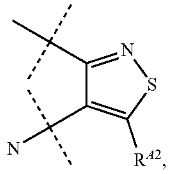
A-22
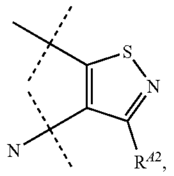
-continued
A-23
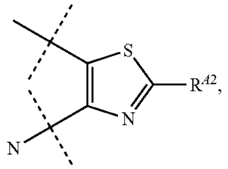
A-24
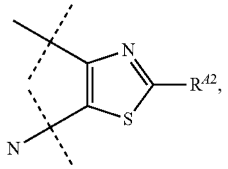
A-25
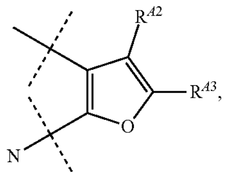
A-26
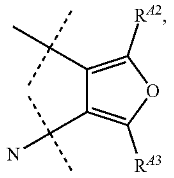
A-27
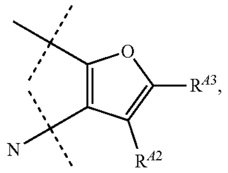
A-28
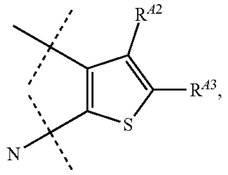
A-29
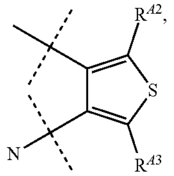
A-30
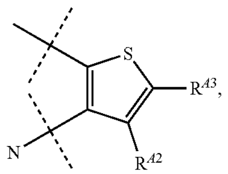

-continued

A-31

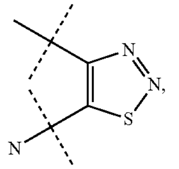

A-32

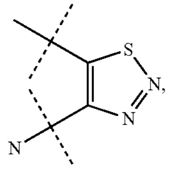

A-33

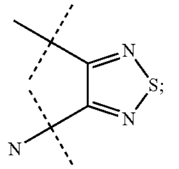

wherein $R^{A1}$ represents H, $C_{1-6}$-aliphatic, —$CH_2$—$Ar^{A1}$ or —$CH_2$—$CH_2$—$Ar^{A1}$;

$R^{A2}$ represents H, halogen, $C_{1-6}$-aliphatic, —$CH_2$—$Ar^{A2}$ or —$CH_2$—$CH_2$—$Ar^{A2}$;

$R^{A3}$ represents H, $C_{1-6}$-aliphatic, —$CH_2$—$Ar^{A3}$ or —$CH_2$—$CH_2$—$Ar^{A3}$;

$Z^1$ is $CR^{Z1}$ or N;

$Z^2$ is $CR^{Z2}$ or N;

wherein at least one of $Z^1$ and $Z^2$ is not N;

$R^1$ represents $Ar^1$, $Hetar^1$, $Cyc^1$, $Hetcyc^1$, $L^1$-$Ar^1$, $L^1$-$Hetar^1$, $L^2$-$Cyc^1$, $L^2$-$Hetcyc^1$, un-substituted or substituted, straight-chain or branched $C_{1-8}$-aliphatic;

$R^2$ represents —C(═O)—$OR^{2a}$, —C(═O)—$NR^{2b}R^{2c}$, —$(CH_2)_w$—C(═O)—$NR^{2b}R^{2c}$, —$(CH_2)_x$—$NR^{2d}$—C(═O)—$R^{2e}$, —S—$R^{2f}$, —S(═O)—$R^{2f}$, —S(═O)$_2$—$R^{2g}$, —S(═O)$_2$—$NR^{2h}R^{2i}$, —S(═O)$_2$—OH, —S(═O)(═$NR^{2j}$)—OH, —S(═O)(═$NR^{2j}$)—$R^{2g}$, —S(═O)(═$NR^{2k}$)—$NR^{2l}R^{2m}$, F, Cl, Br, I, —CN, —$(CH_2)_v$—CN, —P(═O)($OR^{2o}$)($OR^{2p}$), —$(CH_2)_y$—$NR^{2q}R^{2r}$, $(CH_2)_z$—$NR^{2d}$—S(═O)$_2$—$R^{2g}$, —C(═O)—N═S(═O)—$R^{2s}R^{2t}$, —C(═O)—N═S(═N—$R^{2u}$)—$R^{2s}R^{2t}$, —B$(OH)_2$ or $Hetcyc^X$;

$Ar^{A1}$, $Ar^{A2}$, $Ar^{A3}$ represent independently from each other phenyl which may be unsubstituted or mono- or di-substituted with independently from each other $R^{A11}$ and/or $R^{A12}$ $R^{Z1}$ represents H or halogen;

$R^{Z2}$ represents H or halogen; or forms together with $R^2$ a divalent radical —S(═O)$_2$—N(H)—C(═O)—;

$R^{2a}$ represents H, un-substituted or substituted $C_{1-8}$-aliphatic, aryl, heteroaryl, saturated or partially unsaturated heterocyclyl, or carbohydrate derived radical, or Cat;

Cat represents a monovalent cation;

$R^{2b}$, $R^{2c}$, $R^{2q}$, $R^{2r}$ represent independently from each other H, un-substituted or substituted $C_{1-8}$-aliphatic including $C_{3-7}$-cycloaliphatic; or form together with the nitrogen atom to which they are attached to an unsubstituted or substituted saturated, partially unsaturated or aromatic heterocycle with 3, 4, 5, 6, 7 ring atoms wherein 1 of said ring atoms is said nitrogen atom and no or one further ring atom is a hetero atom selected from N, O or S and the remaining are carbon atoms; wherein said heterocycle may optionally be fused with $Hetar^Z$; or one of $R^{2b}$ and $R^{2c}$ represents —CN, —$NH_2$, —OH, —O—$C_{1-6}$-alkyl, —S(═O)$_2$—$R^{2g}$, $Ar^2$, $Hetar^2$, $Cyc^2$ or $Hetcyc^2$, while the other of $R^{2b}$ and $R^{2e}$ represents H or un-substituted or substituted $C_{1-8}$-aliphatic;

$R^{2d}$, $R^{2j}$, $R^{2k}$, $R^{2o}$, $R^{2p}$ represent independently from each other H, un-substituted or substituted $C_{1-8}$-aliphatic;

$R^{2e}$ represents H, halogen, un-substituted or substituted $C_{1-8}$-aliphatic, heteroaryl;

$R^{2f}$, $R^{2g}$ represent independently from each other un-substituted or substituted $C_{1-8}$-aliphatic;

$R^{2h}$, $R^{2i}$ represent independently from each other H, un-substituted or substituted $C_{1-8}$-aliphatic, aryl, heterocyclyl, heteroaryl; or form together with the nitrogen atom to which they are attached to an unsubstituted or substituted saturated, partially unsaturated or aromatic heterocycle with 3, 4, 5, 6, 7 ring atoms wherein 1 of said ring atoms is said nitrogen atom and no or one further ring atom is a hetero atom selected from N, O or S and the remaining are carbon atoms;

$R^{2l}$, $R^{2m}$ represent independently from each other H, un-substituted or substituted $C_{1-8}$-aliphatic; or form together with the nitrogen atom to which they are attached to an unsubstituted or substituted saturated, partially unsaturated or aromatic heterocycle with 3, 4, 5, 6, 7 ring atoms wherein 1 of said ring atoms is said nitrogen atom and no or one further ring atom is a hetero atom selected from N, O or S and the remaining are carbon atoms;

$R^{2s}$, $R^{2t}$ represent independently from each other unsubstituted or substituted $C_{1-8}$-aliphatic; or form together an unsubstituted or substituted divalent $C_{3-6}$-alkylene radical;

$R^{2u}$ represents hydrogen or unsubstituted or substituted $C_{1-6}$-aliphatic;

$Ar^1$ is a mono-, bi- or tricyclic aryl with 5, 6, 7, 8, 9, 10, 11, 12, 13, 14 ring carbon atoms, wherein that aryl may be unsubstituted or substituted with substituents $R^{B1}$, $R^{B2}$, $R^{B3}$, $R^{B4}$, $R^{B5}$, $R^{B6}$ and/or $R^{B7}$ which may be the same or different;

$Hetar^1$ is a mono-, bi- or tricyclic heteroaryl with 5, 6, 7, 8, 9, 10, 11, 12, 13, 14 ring atoms wherein 1, 2, 3, 4, 5 of said ring atoms is/are a hetero atom(s) selected from N, O and/or S and the remaining are carbon atoms, wherein that heteroaryl may be unsubstituted or substituted with substituents $R^{B1}$, $R^{B2}$, $R^{B3}$, $R^{B4}$, $R^{B5}$, $R^{B6}$ and/or $R^{B7}$ which may be the same or different;

$Cyc^1$ is a saturated or partially unsaturated, mono-, bi- or tricyclic carbocycle with 3, 4, 5, 6, 7, 8, 9, 10, 11, 12, 13, 14, 15 ring carbon atoms, wherein that carbocycle may be unsubstituted or substituted with $R^{B8}$, $R^{B9}$, $R^{B10}$, $R^{B11}$, $R^{B12}$ and/or $R^{B13}$ which may be the same or different; and wherein that carbocycle may optionally be fused to $Ar^X$ via 2 adjacent ring atoms of said $Ar^X$ and wherein that fused carbocycle may further be unsubstituted or substituted with $R^{C1}$, $R^{C2}$, $R^{C3}$, $R^{C4}$, $R^{C5}$, $R^{C6}$ which may be the same or different;

$Hetcyc^1$ is a saturated or partially unsaturated, mono-, bi- or tricyclic heterocycle with 3, 4, 5, 6, 7, 8, 9, 10, 11, 12, 13, 14, 15 ring atoms wherein 1, 2, 3, 4, 5 of said ring atoms is/are a hetero atom(s) selected from N, O and/or S and the remaining are carbon atoms, wherein that heterocycle may be unsubstituted or substituted with $R^{B8}$, $R^{B9}$, $R^{B10}$, $R^{B11}$, $R^{B12}$ and/or $R^{B13}$ which may be the same or different;

$L^1$ is a divalent radical selected from the group consisting of —S(═O)$_2$—, —C(═O)—, un-substituted or substituted, straight-chain or branched $C_{1-6}$-alkylene or $C_{2-6}$-alkenylene, in both of which one of the carbon units of the alkylene or alkenylene chain may be replaced by —O—;

$L^2$ is a divalent radical selected from the group consisting of un-substituted or substituted, straight-chain or branched $C_{1-6}$-alkylene or $C_{2-6}$-alkenylene, in both of which one of the carbon units of the alkylene or alkenylene chain may be replaced by —O—;

$R^{A11}$, $R^{A12}$ represent independently from each other halogen or un-substituted or substituted, straight-chain or branched $C_{1-6}$-aliphatic;

$R^{B1}$, $R^{B2}$, $R^{B3}$, $R^{B4}$, $R^{B5}$, $R^{B6}$, $R^{B7}$ represent independently from each other un-substituted or substituted, straight-chain or branched $C_{1-6}$-aliphatic, $C_{1-6}$-aliphatoxy, —S—$C_{1-6}$-aliphatic; halogen, —CN, —S(═O)—$R^{b1}$, S(═O)$_2$—$R^{b1}$, —$NR^{b2}NR^{b3}$, $Ar^2$, —$CH_2$—$Ar^2$, $Hetar^2$, $Cyc^2$, $Hetcyc^2$; and/or two adjacent $R^{B1}$, $R^{B2}$, $R^{B3}$, $R^{B4}$, $R^{B5}$, $R^{B6}$ and/or $R^{B7}$ form together a divalent —$C_{2-4}$-alkylene radical in which one of the alkylene carbon units may be replaced by a carbonyl unit (—C(═O)—), or a divalent —O—$C_{1-3}$-alkylene radical or a divalent —O—$C_{1-3}$-alkylene-O-radical;

$R^{b1}$ represents un-substituted or substituted $C_{1-8}$-aliphatic;

$R^{b2}$, $R^{b3}$ represent independently from each other H, un-substituted or substituted $C_{1-8}$-aliphatic; or form together with the nitrogen atom to which they are attached to an unsubstituted or substituted saturated, partially unsaturated or aromatic heterocycle with 3, 4, 5, 6, 7 ring atoms wherein 1 of said ring atoms is said nitrogen atom and no or one further ring atom is a hetero atom selected from N, O or S and the remaining are carbon atoms;

$R^{B8}$, $R^{B9}$, $R^{B10}$, $R^{B11}$, $R^{B12}$, $R^{B13}$ represent independently from each other halogen, un-substituted or substituted $C_{1-6}$-aliphatic, $C_{1-6}$-aliphatoxy, $Ar^Y$; and/or two of $R^B$, $R^{B9}$, $R^{B10}$, $R^{B11}$, $R^{B12}$, $R^{B13}$ which are attached to the same carbon atom of said carbocycle or said heterocycle form a divalent oxo (═O) group; and/or two of RB $R^{B9}$, $R^{B10}$, $R^{B11}$, $R^{B12}$, $R^{B13}$ or four of $R^{B8}$, $R^{B9}$, $R^{B10}$, $R^{B11}$, $R^{B12}$, $R^{B13}$ which are attached to the same sulfur atom of said heterocycle form a divalent oxo (═O) group thereby forming either an —S(═O)— or an —S(═O)$_2$— moiety;

$Ar^2$ is a mono- or bicyclic aryl with 5, 6, 7, 8, 9, 10 ring carbon atoms, wherein that aryl may be unsubstituted or substituted with substituents $R^{D1}$, $R^{D2}$, $R^{D3}$, $R^{D4}$ and/or $R^{D5}$ which may be the same or different $Hetar^2$ is a mono- or bicyclic heteroaryl with 5, 6, 7, 8, 9, 10 ring atoms wherein 1, 2, 3, 4, 5 of said ring atoms is/are a hetero atom(s) selected from N, O and/or S and the remaining are carbon atoms, wherein that heteroaryl may be unsubstituted or substituted with substituents $R^{D1}$, $R^{D2}$, $R^{D3}$, $R^{D4}$ and/or $R^{D5}$ which may be the same or different;

$Cyc^2$ is a saturated or partially unsaturated monocyclic carbocycle with 3, 4, 5, 6 or 7 ring carbon atoms, wherein that carbocycle may be unsubstituted or substituted with $R^{D6}$, $R^{D7}$, $R^{D8}$, $R^{D9}$ and/or $R^{D10}$ which may be the same or different; wherein that carbocycle may optionally be fused to $Ar^Z$ or $Hetar^Z$ via 2 adjacent ring atoms of said $Ar^Z$ or $Hetar^Z$ and wherein that fused carbocycle may further be unsubstituted or substituted with $R^{C1}$, $R^{C2}$, $R^{C3}$, $R^{C4}$, $R^{C5}$, $R^{C6}$ which may be the same or different;

$Hetcyc^2$ is a saturated or partially unsaturated, monocyclic heterocycle with 3, 4, 5, 6, 7 ring atoms wherein 1 or 2 of said ring atoms is/are a hetero atom(s) selected from N, O and/or S and the remaining are carbon atoms, wherein that heterocycle may be unsubstituted or substituted with $R^{D6}$, $R^{D7}$, $R^{D8}$, $R^{D9}$ and/or $R^{D10}$ which may be the same or different; wherein that heterocycle may optionally be fused to $Ar^Z$ or $Hetar^Z$ via 2 adjacent ring atoms of said $Ar^Z$ or $Hetar^Z$ and wherein that fused heterocycle may further be unsubstituted or substituted with $R^{C1}$, $R^{C2}$, $R^{C3}$, $R^{C4}$, $R^{C5}$, $R^{C6}$ which may be the same or different;

$Ar^X$, $Ar^Z$ independently from each other an un-substituted or substituted benzo ring;

$Ar^Y$ is an un-substituted or mono- or di-substituted phenyl;

$Hetar^{Y1}$ is a 5 or 6 membered monocyclic heteroaryl wherein 1, 2, 3, 4 ring atoms are hetero atoms selected from N, O and/or S and the remaining are carbon atoms, wherein that heteroaryl may be unsubstituted or substituted with halogen, $C_{1-4}$-alkyl which may optionally be substituted with OH;

$Hetar^Z$ is an unsubstituted or substituted 5 or 6 membered heteroaryl ring selected from the group consisting of pyrrole, furan, thiophene, pyrazole, imidazole, oxaole, isoxazole, thiazole, oxadiazole, triazole, tetrazole, pyridine, pyrimidine, pyrazine, pyrane;

$Cyc^{Y1}$ is a saturated monocyclic carbocycle with 3, 4, 5, 6 or 7 ring carbon atoms, wherein that carbocycle may be unsubstituted or substituted with halogen, OH, $C_{1-4}$-alkyl;

$Hetcyc^X$ is a saturated, partially unsaturated or aromatic, monocyclic heterocycle with 3, 4, 5, 6, 7 ring atoms wherein 1, 2, 3, 4 of said ring atoms is/are a hetero atom(s) selected from N, O and/or S and the remaining are carbon atoms, wherein said heterocycle may be unsubstituted or substituted with $R^{X1}$, $R^{X2}$, $R^{X3}$, $R^{X4}$, $R^{X5}$, $R^{X6}$, $R^{X7}$ and/or $R^{X8}$ which may be the same or different, and wherein that heterocycle is optionally a carboxylic acid bioisostere;

$Hetcyc^Y$ is a saturated, partially unsaturated or aromatic, monocyclic heterocycle with 3, 4, 5, 6, 7 ring atoms wherein 1, 2, 3, 4 of said ring atoms is/are a hetero atom(s) selected from N, O and/or S and the remaining are carbon atoms;

$Hetcyc^{Y1}$ is a saturated or partially unsaturated monocyclic heterocycle with 5 or 6 ring atoms wherein 1 or 2 of said ring atoms are heteroatoms selected from N, O, and/or S and the remaining are carbon atoms;

$R^{C1}$, $R^{C2}$, $R^{C3}$, $R^{C4}$, $R^{C5}$, $R^{C6}$ represent independently from each other un-substituted or substituted $C_{1-6}$-aliphatic;

$R^{D1}$, $R^{D2}$, $R^{D3}$, $R^{D4}$, $R^{D5}$ represent independently from each other un-substituted or substituted $C_{1-6}$-aliphatic;

$R^{D6}$, $R^{D7}$, $R^{D8}$, $R^{D9}$, $R^{D10}$ represent independently from each other un-substituted or substituted $C_{1-6}$-aliphatic, unsubstituted or substituted $C_{1-6}$-aliphatoxy, halogen, hydroxy; $Hetar^{Y1}$, $CH_2$-$Hetar^{Y1}$, $Cyc^{Y1}$, $Hetcyc^{Y1}$, —$CH_2$-$Hetcyc^{Y1}$; and/or two of $R^{D6}$, $R^{D7}$, $R^{D8}$, $R^{D9}$, $R^{D10}$ which are attached to the same ring atom of said carbocycle or heterocycle may form a divalent $C_{2-6}$- alkylene radical, wherein one or two non-adjacent carbon units of said alkylene radical may optionally be replaced by independently from each other O, N—H, or N—$C_{1-4}$-alkyl, and wherein that alkylene radical may optionally be substituted with OH, $C_{1-4}$-alkyl or —O—$C_{1-4}$-alkyl; and/or two of $R^{D6}$, $R^{D7}$, $R^{D8}$, $R^{D9}$, $R^{D10}$ which are attached to different ring atoms of said carbocycle or heterocycle may form a divalent $C_{1-6}$-alkylene radical, wherein one or two non-adjacent carbon units of said alkylene radical may optionally be replaced by independently from each other 0, N—H, or N—$C_{1-4}$-alkyl;

$R^{X1}$, $R^{X2}$, $R^{X3}$, $R^{X4}$, $R^{X5}$, $R^{X6}$, $R^{X7}$, $R^{X8}$ represent independently from each other un-substituted or substituted $C_{1-6}$-aliphatic, $C_{1-6}$-aliphatoxy, halogen, —OH, —$NR^{2d}$—S(═O)$_2$—$R^{2g}$, $Hetcyc^Y$, O-$Hetcyc^Y$; and/or two of $R^{X1}$, $R^{X2}$, $R^{X3}$, $R^{X4}$, $R^{X5}$, $R^{X6}$, $R^{X7}$, $R^{X8}$ which are attached to the same carbon atom of said heterocycle form a divalent oxo (═O) group; and/or two of $R^{X1}$, $R^{X2}$, $R^{X3}$, $R^{X4}$, $R^{X5}$, $R^{X6}$, $R^{X7}$, RX$ or four of $R^{X1}$, $R^{X2}$, $R^{X3}$, $R^{X4}$, $R^{X5}$, $R^{X6}$, $R^{X7}$, $R^{X8}$ which are attached to the same sulfur atom of said heterocycle form a divalent oxo (═O) group thereby forming either an —S(═O)— or an —S(═O)$_2$— moiety;

halogen is F, Cl, Br, I;

v is 1 or 2;

w is 1 or 2;

x is 0, 1 or 2;

y is 0, 1 or 2;

z is 0, 1 or 2;

or any N-oxide, solvate, tautomer or stereoisomer thereof and/or any pharmaceutically acceptable salt of each of the foregoing, including mixtures thereof in all ratios.

In general, all residues, radicals, substituents, groups, moieties, variables, etc. which occur more than once may be identical or different, i.e. are independent of one another. Above and below, the residues and parameters have the meanings indicated for formulas I-A and I, unless expressly indicated otherwise. Accordingly, the invention relates, in particular, to the compounds of formulas I-A and I in which at least one of the said residues, radicals, substituents, variables, has one of the preferred meanings indicated below.

Any of those particular or even preferred embodiments of the present invention as specified below do not only refer to the specified compounds of formulas I-A and I but to N-oxides, solvates, tautomers or stereoisomers thereof as well as the pharmaceutically acceptable salts of each of the foregoing, including mixtures thereof in all ratios, too, unless indicated otherwise.

DETAILED DESCRIPTION OF THE INVENTION

Figure 1:
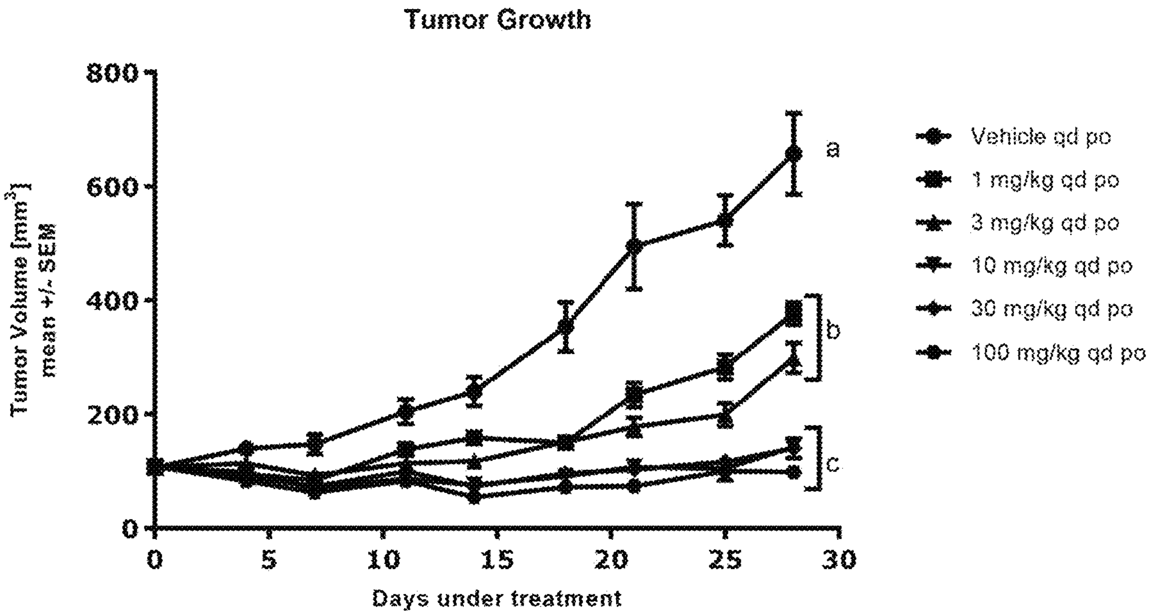
FIG. 1 shows tumor growth over time for a vehicle group and each dosage group.

In a particular embodiment, PE0, the compound of the present invention is a tricyclic heterocycle of formula I-A, or any N-oxide, solvate, tautomer or stereoisomer thereof and/or any pharmaceutically acceptable salt of each of the foregoing, including mixtures thereof in all ratios, wherein $Z^1$ is $CR^{Z1}$;

$Z^2$ is $CR^{Z2}$;

$Z^3$ is $CR^{Z3}$ or N;

$R^{Z1}$ is H or F; preferably H;

$R^{Z2}$ is H or F; or forms together with $R^2$ a divalent radical —S(═O)$_2$—N(H)—C(═O)—; is preferably H;

$R^{Z3}$ is H or F; preferably H.

In another particular embodiment, PE0a, of PE0

$Z^3$ is N.

In still another particular embodiment, PE0b, of PE0

$Z^3$ is $CR^{Z3}$;

$R^{Z3}$ is H.

It will be understood that this particular embodiment PE0b is identical to the particular embodiment PE1 as described below. In other words, a compound of formula I-A can also be described as a compound of formula I, if in formula I-A $Z^3$ denotes $CR^{Z3}$ with $R^{Z3}$ being H.

In a particular embodiment, PE1, the compound of the present invention is a tricyclic heterocycle of formula I, or any N-oxide, solvate, tautomer or stereoisomer thereof and/or any pharmaceutically acceptable salt of each of the foregoing, including mixtures thereof in all ratios, wherein $Z^1$ is $CR^{Z1}$;

$Z^2$ is $CR^{Z2}$.

$R^{Z1}$ is H or F;

$R^{Z2}$ is H or F; or forms together with $R^2$ a divalent radical —S(═O)$_2$—N(H)—C(═O)—;

and the remaining radicals and residues are as defined for formula I above or for any of the further particular embodiments described herein below.

In another particular embodiment, PE1a, of PE1 at least one of $R^{Z1}$ and $R^{Z2}$ is H. In still another particular embodiment, PE1b, of PE1a both $R^{Z1}$ and $R^{Z2}$ are H.

In a further particular embodiment, PE2, the compound of the present invention is a tricyclic heterocycle of formula I-A or I, or any N-oxide, solvate, tautomer or stereoisomer thereof and/or any pharmaceutically acceptable salt of each of the foregoing, including mixtures thereof in all ratios, wherein Ring A represents a five-membered heteroaromatic ring selected from the group consisting of the following ring moieties:

A-1

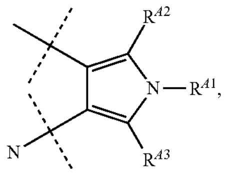

A-4

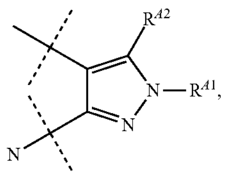

A-5

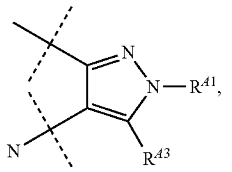

-continued

A-6

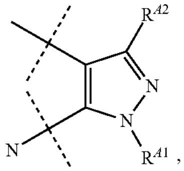

A-7

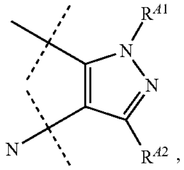

A-9

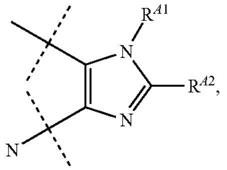

A-10

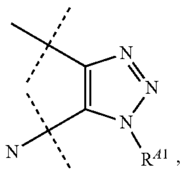

A-11

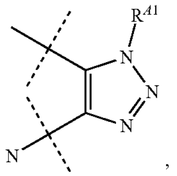

A-12

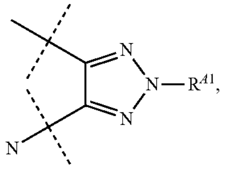

A-13

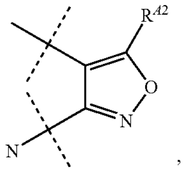

A-15

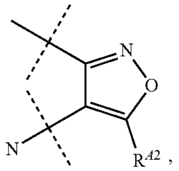

A-17

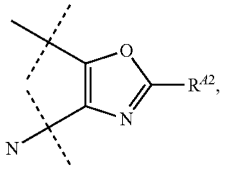

-continued

A-19

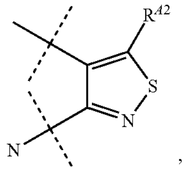

A-20

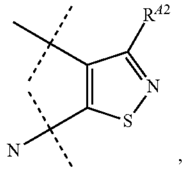

A-21

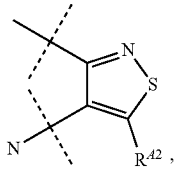

A-23

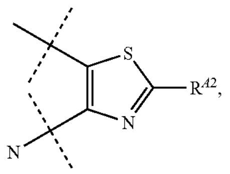

A-24

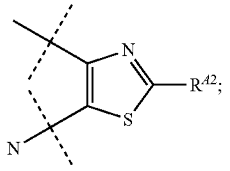

$R^{A1}$ represents $C_{1-6}$-aliphatic, —$CH_2$—$Ar^{A1}$;
$R^{A2}$ represents H, $C_{1-6}$-aliphatic;
$R^{A3}$ represents H, $C_{1-6}$-aliphatic;
$Ar^{A1}$ represents phenyl which may be unsubstituted or mono-substituted with $R^{A11}$
$R^{A11}$ represents halogen;
and the remaining radicals and residues are as defined for formula I-A or I above or for any of the further particular embodiments described herein above or below.

In another particular embodiment, PE2a, of PE2
$R^{A1}$ represents $C_{1-3}$-alkyl optionally substituted with 1, 2 or 3 F atoms or CN, $C_{2-4}$-alkynyl (in particular —$CH_2$—C≡CH), —$CH_2$—$Ar^{A1}$;
$R^{A2}$ represents H, $C_{1-6}$-aliphatic, in particular H, $C_{1-3}$-alkyl optionally substituted with 1, 2 or 3 F atoms;
$R^{A3}$ represents H;
$Ar^{A1}$ represents phenyl which may be unsubstituted or mono-substituted with $R^{A11}$
$R^{A11}$ represents F;
and the remaining radicals and residues are as defined for formula I-A or I above or for any of the further particular embodiments described herein above or below.

In still another particular embodiment, PE2b, of PE2 or PE2a, Ring A is selected from the group consisting of ring A-1, A-4, A-7, A-9, A-10, A-12, A-13, A-15, A-17, A-23 and A-24. In yet another particular embodiment of, PE2c, of PE2 or PE2a, Ring A is ring A-4 wherein preferably $R^{A1}$ is methyl, ethyl, n-propyl, or —$CH_2$—C≡CH, more preferably methyl, and $R^{A2}$ is H.

In a further particular embodiment, PE3, the compound of the present invention is a tricyclic heterocycle of formula I-A or I, or any N-oxide, solvate, tautomer or stereoisomer thereof and/or any pharmaceutically acceptable salt of each of the foregoing, including mixtures thereof in all ratios, wherein $R^1$ represents $Ar^1$, $Hetar^1$, $Cyc^1$, $Hetcyc^1$, $L^1$-$Ar^1$, $L^1$-$Hetar^1$, $L^2$-$Cyc^1$, $L^2$-$Hetcyc^1$, un-substituted or substituted, straight-chain or branched $C_{1-6}$-alkyl, $C_{2-6}$-alkenyl or $C_{2-6}$-alkynyl; wherein $Ar^1$ is a mono- or bicyclic aryl with 6 or 10 ring carbon atoms, wherein that aryl may be unsubstituted or substituted with substituents $R^{B1}$, $R^{B2}$ and/or $R^{B3}$ which may be the same or different;

$Hetar^1$ is a monocyclic heteroaryl with 5 or 6 ring atoms or a bicyclic heteroaryl with 9 or 10 ring atoms wherein 1, 2 or 3 of said ring atoms is/are a hetero atom(s) selected from N, O and/or S and the remaining are carbon atoms, wherein that heteroaryl may be unsubstituted or substituted with substituents $R^{B1}$, $R^{B2}$ and/or $R^{B3}$ which may be the same or different; preferably the heteroaryl is unsubstituted or substituted with substituents $R^{B1}$ and/or $R^{B2}$ which may be the same or different;

$Cyc^1$ is a saturated or partially unsaturated, mono- or bicyclic carbocycle with 3, 4, 5, 6, 7 or 8 ring carbon atoms, wherein that carbocycle may be unsubstituted or substituted with $R^{B8}$ and/or $R^{B9}$ which may be the same or different; and wherein that carbocycle may optionally be fused to $Ar^X$ via 2 adjacent ring atoms of said $Ar^X$ and wherein that fused carbocycle may further be unsubstituted or substituted with $R^{C1}$ and/or $R^{C2}$ which may be the same or different;

$Hetcyc^1$ is a saturated or partially unsaturated, monocyclic heterocycle with 5 or 6 ring atoms wherein 1 or 2 of said ring atoms is/are a hetero atom(s) selected from N, O and/or S and the remaining are carbon atoms, wherein that heterocycle may be unsubstituted or substituted with $R^{B8}$ and/or $R^{B9}$ which may be the same or different, wherein, if one of the heteroatoms is S, then that heterocycle may also be substituted with $R^{B8}$, $R^{B9}$, $R^{B10}$ and $R^{B11}$ $L^1$ is a divalent radical selected from the group consisting of —S(═O)$_2$—, un-substituted or substituted, straight-chain or branched $C_{1-6}$-alkylene or $C_{2-6}$-alkenylene, in both of which one of the carbon units of the alkylene or alkenylene chain may be replaced by —O—;

$L^2$ is a divalent radical selected from the group consisting of un-substituted or substituted, straight-chain or branched $C_{1-6}$-alkylene or $C_{2-6}$-alkenylene, in both of which one of the carbon units of the alkylene or alkenylene chain may be replaced by —O—;

$R^{B1}$, $R^{B2}$, $R^{B3}$ represent independently from each other straight-chain or branched $C_{1-6}$-alkyl, which $C_{1-6}$-alkyl may be unsubstituted or monosubstituted with —CN or substituted with 1, 2 or 3 halogen, straight-chain or branched $C_{1-4}$-alkoxy, which $C_{1-4}$-alkoxy may be unsubstituted or substituted with 1, 2 or 3 halogen, —O—CH—C≡CH, straight-chain or branched —S—$C_{1-4}$-alkyl, which —S—$C_{1-4}$-alkyl may be unsubstituted or substituted with 1, 2 or 3 halogen, F, Cl, Br, —CN, —S(═O)—$C_{1-3}$-alkyl, S(═O)$_2$—$C_{1-3}$-alkyl, —N($C_{1-3}$-alkyl)$_2$, $Ar^2$, —$CH_2$—$Ar^2$, $Hetar^2$, $Cyc^2$, $Hetcyc^2$; or two adjacent $R^{B1}$, $R^{B2}$ and/or $R^{B3}$ form together a divalent —$C_{3-4}$-alkylene radical in which one of the alkylene carbon units may be replaced by a carbonyl unit (—C(═O)—), or a divalent —O—$C_{2-3}$-alkylene radical;

$Ar^2$ is phenyl;

$Hetar^2$ is a monocyclic heteroaryl with 5 or 6 ring atoms wherein 1, 2, 3, 4, 5 of said ring atoms is/are a hetero atom(s) selected from N, O and/or S and the remaining are carbon atoms;

$Cyc^2$ is cyclopropyl, cyclobutyl, cyclopentyl, each of which may be unsubstituted or mono-substituted with $R^{D6}$ or di-substituted with independently from each other $R^{D6}$ and $R^{D7}$; in particular unsubstituted or mono-substituted with $R^{D6}$;

$Hetcyc^2$ is pyrrolidinyl, piperidinyl, each of which may unsubstituted or mono-substituted with $R^{D6}$ or di-substituted with independently from each other $R^{D6}$ and $R^{D7}$; in particular unsubstituted or mono-substituted with $R^{D6}$;

$R^{B8}$, $R^{B9}$ represent independently from each other F, $C_{1-2}$-alkyl, which $C_{1-2}$-alkyl may be unsubstituted or substituted with 1, 2 or 3 F, $C_{1-2}$-alkoxy, $Ar^Y$; or $R^{B8}$ and $R^{B9}$ are attached to the same carbon atom of said carbocycle $Cyc^1$ or said heterocycle $Hetcyc^1$ and form a divalent oxo (═O) group; or $R^{B8}$ and $R^{B9}$ and $R^{B10}$ and $R^{B11}$ are attached to the same sulfur atom of said heterocycle and form two divalent oxo (═O) groups thereby forming an —S(═O)$_2$— moiety;

$Ar^X$ is an unsubstituted benzo ring;

$Ar^Y$ is phenyl;

$R^{C1}$ and $R^{C2}$ represent independently from each other $C_{1-6}$-alkyl which may be independently from each other be substituted with 1, 2, or 3 F atoms;

$R^{D6}$, $R^{D7}$ represents independently from each other $C_{1-6}$-alkyl which may be substituted with 1, 2, or 3 F atoms or 1 hydroxy group; or hydroxy; halogen is F, Cl, Br;

and the remaining radicals and residues are as defined for formula I-A or I above or for any of the further particular embodiments described herein above or below.

In another particular embodiment, PE3a, of PE3

$R^1$ represents $Ar^1$, $Hetar^1$, $Cyc^1$, $Hetcyc^1$, $L^1$-$Ar^1$, $L^1$-$Hetar^1$, $L^2$-$Cyc^1$, $L^2$-$Hetcyc^1$, straight-chain or branched $C_{1-6}$-alkyl, $C_{2-6}$-alkenyl or $C_{2-6}$-alkynyl, wherein said $C_{1-6}$-alkyl, $C_{2-6}$-alkenyl or $C_{2-6}$-alkynyl is unsubstituted or substituted with 1, 2 or 3 halogen; wherein $Ar^1$ is phenyl or naphthalenyl, in particular phenyl, which may be unsubstituted or substituted with substituents $R^{B1}$ and or $R^{B2}$ which may be the same or different;

$Hetar^1$ is a monocyclic heteroaryl with 5 or 6 ring atoms or a bicyclic heteroaryl with 9 or 10 ring atoms wherein 1, 2 or 3 of said ring atoms is/are a hetero atom(s) selected from N, O and/or S and the remaining are carbon atoms, wherein that heteroaryl may be unsubstituted or substituted with substituents $R^{B1}$ and/or $R^{B2}$ which may be the same or different;

$Cyc^1$ is a saturated or partially unsaturated, mono- or bicyclic carbocycle with 3, 4, 5, 6, 7 or 8 ring carbon atoms, wherein that carbocycle may be unsubstituted or substituted with $R^{B8}$ and/or $R^{B9}$ which may be the same or different; and wherein that carbocycle may optionally be fused to $Ar^X$ via 2 adjacent ring atoms of said $Ar^X$ and wherein that fused carbocycle may further be unsubstituted or substituted with $R^{C1}$ and/or $R^{C2}$ which may be the same or different;

Hetcyc$^1$ is a saturated monocyclic heterocycle with 5 or 6 ring atoms wherein 1 of said ring atoms is a hetero atom selected from O and S and the remaining are carbon atoms, wherein that heterocycle may be unsubstituted or substituted with $R^{B8}$ and/or $R^{B9}$ which may be the same or different, wherein, if one of the heteroatoms is S, then that heterocycle may also be substituted with $R^{B8}$, $R^{B9}$, $R^{B10}$ and $R^{B11}$;

L$^1$ is a divalent radical selected from the group consisting of —S(═O)$_2$—, —CH$_2$—, —CH$_2$—CH$_2$—, —CH$_2$—CH$_2$—C(CH$_3$)H—, —CH$_2$—CH$_2$—C(CH$_3$)$_2$—, —CH$_2$—CH$_2$—O—CH$_2$——CH$_2$—CH═CH—;

L$^2$ is a divalent radical selected from the group consisting of —CH$_2$—, —CH$_2$—CH$_2$—;

$R^{B1}$, $R^{B2}$ represent independently from each other straight-chain or branched $C_{1-6}$-alkyl, which $C_{1-6}$-alkyl may be unsubstituted or monosubstituted with —CN or substituted with 1, 2 or 3 halogen, e.g. —CF$_3$, straight-chain or branched $C_{1-4}$-alkoxy, which $C_{1-4}$-alkoxy may be unsubstituted or substituted with 1, 2 or 3 halogen, e.g. —OCF$_3$, —O—CH—C≡CH, straight-chain or branched —S—$C_{1-4}$-alkyl, which —S—$C_{1-4}$-alkyl may be unsubstituted or substituted with 1, 2 or 3 halogen, F, Cl, Br, —CN, —S(═O)—$C_{1-3}$-alkyl, S(═O)$_2$—$C_{1-3}$-alkyl, —N($C_{1-3}$-alkyl)$_2$, Ar$^2$, —CH$_2$—Ar$^2$, Hetar$^2$, Cyc$^2$, Hetcyc$^2$;

or two adjacent $R^{B1}$, $R^{B2}$ form together a divalent —$C_{3-4}$-alkylene radical in which one of the alkylene carbon units may be replaced by a carbonyl unit (—C(═O)—), or a divalent —O—$C_{2-3}$-alkylene radical;

Ar$^2$ is phenyl;

Hetar$^2$ is a monocyclic heteroaryl with 5 ring atoms wherein 1 of said ring atoms is N and the remaining are carbon atoms or 1 of said ring atoms is N and 1 of said ring atoms is S and the remaining are carbon atoms;

Cyc$^2$ is cyclopropyl, 1-trifluoromethylcyclopropyl, cyclopentyl;

Hetcyc$^2$ is pyrrolidinyl;

$R^{B8}$, $R^{B9}$ represent independently from each other F, $C_{1-2}$-alkyl, which $C_{1-2}$-alkyl may be unsubstituted or substituted with 1, 2 or 3 F, $C_{1-2}$-alkoxy, Ar$^Y$; or $R^{B8}$ and $R^{B9}$ are attached to the same carbon atom of said carbocycle Cyc$^1$ or said heterocycle Hetcyc$^1$ and form a divalent oxo (═O) group; or $R^{B8}$ and $R^{B9}$ and $R^{B10}$ and $R^{B11}$ are attached to the same sulfur atom of said heterocycle and form two divalent oxo (═O) groups thereby forming an —S(═O)$_2$— moiety;

Ar$^X$ is an unsubstituted benzo ring;

Ar$^Y$ is phenyl;

$R^{C1}$ and $R^{C2}$ represent independently from each other $C_{1-2}$-alkyl which may be independently from each other be substituted with 1, 2, or 3 F atoms;

halogen is F, Cl, Br;

and the remaining radicals and residues are as defined for formula I-A or I above or for any of the further particular embodiments described herein above or below.

In still another particular embodiment, PE3b, of PE3 or PE3a

R$^1$ represents Ar$^1$, Hetar$^1$, Cyc$^1$, Hetcyc$^1$, L$^1$-Ar$^1$, L$^1$-Hetar$^1$, L$^2$-Cyc$^1$, L$^2$-Hetcyc$^1$, 2,2-dimethyl-4,4,4-trifluoropentyl, 4,4,4-trifluorobutyl, 4,4,4-trifluoro-3-methylbutyl, 3,3-dimethyl-4,4,4-trifluorobutyl or 3,3,3-trifluoroprop-1-yn-1-yl; wherein Ar$^1$ is phenyl which may be unsubstituted or substituted with substituents $R^{B1}$ and or $R^{B2}$ which may be the same or different;

Hetar$^1$ is a heteroaryl selected from the group consisting of furanyl, in particular furan-2-yl; thiophenyl, in particular thiophen-2-yl, thiophen-3-yl; thiazolyl, in particular 1,3-thiazol-2-yl or 1,3-thiazol-4-yl; pyrazolyl, in particular pyrazol-5-yl (1H-pyrazol-5-yl); imidazolyl, in particular imidazol-2-yl (1H-imidazol-2-yl), imidazol-5-yl (1H-imidazol-5-yl); oxazolyl, in particular 1,3-oxazol-2-yl; pyridinyl (pyridyl), in particular pyridin-2-yl, pyridin-3-yl, pyridin-4-yl; 5H,6H,7H-cyclopenta[b]pyridin-2-yl, 5-oxo-5H,6H,7H-cyclopenta[b]pyridin-2-yl; pyrimidinyl, in particular pyrimidin-2-yl; indolyl, in particular 1H-indol-6-yl; quinolinyl, in particular quinolin-2-yl and quinolin-4-yl; 5,6,7,8-tetrahydroquinolin-2-yl, 5-oxo-5,6,7,8-tetrahydroquinolin-2-yl; isoquinolinyl, in particular isoquinolin-3-yl; benzofuranyl, in particular 1-benzofuran-3-yl; benzothiophenyl, in particular 1-benzothiophen-3-yl; isoquinolinyl, in particular isoquinolin-3-yl; furo[3,2-b]pyridinyl, in particular quinazolin-2-yl; pyrrolo[1,2-b]pyrazolyl, in particular 4H,5H,6H-pyrrolo[1,2-b]pyrazol-3-yl; pyrazolo[1,5-a]pyridinyl, in particular pyrazolo[1,5-a]pyridin-3-yl, pyrazolo[1,5-a]pyridin-7-yl; imidazo[1,2-a]pyridinyl, in particular imidazo[1,2-a]pyridin-3-yl, imidazo[1,2-a]pyridin-5-yl; imidazo[1,5-a]pyridinyl, in particular imidazo[1,5-a]pyridin-1-yl, imidazo[1,5-a]pyridin-3-yl, imidazo[1,5-a]pyridin-5-yl; pyrazolo[1,5-c]pyrimidinyl, in particular pyrazolo[1,5-c]pyrimidin-3-yl; quinazolinyl, in particular quinazolin-2-yl; naphthyridinyl, in particular 1,5-naphthyridin-2-yl; wherein said heteroaryl may be unsubstituted or substituted with substituents $R^{B1}$ and/or $R^{B2}$ which may be the same or different;

Cyc$^1$ is selected from the group consisting of cyclobutyl, cyclopentyl, cyclohexyl, cycloheptyl, cyclopentenyl, cyclohexenyl, spiro[3.3]heptanyl, bicyclo[2.2.1]heptanyl, bicyclo[2.2.2]octanyl, bicyclo[2.2.1]heptenyl, methylbicyclo[3.1.1]heptenyl, wherein that carbocycle may be unsubstituted or substituted with $R^{B8}$ and/or $R^{B9}$ which may be the same or different; and wherein that carbocycle may optionally be fused to Ar$^X$ via 2 adjacent ring atoms of said Ar$^X$ and wherein that fused carbocycle may further be unsubstituted or substituted with $R^{C1}$ and/or $R^{C2}$ which may be the same or different:

Hetcyc$^1$ is selected from the group consisting of pyrrolidinyl, tetrahydrofuranyl and thianyl, wherein that heterocycle may be unsubstituted or substituted with $R^{B8}$ and/or $R^{B9}$ which may be the same or different, wherein, if one of the heteroatoms is S, then that heterocycle may also be substituted with $R^{B8}$, $R^{B9}$, $R^{B10}$ and $R^{B11}$;

L$^1$ is a divalent radical selected from the group consisting of —S(═O)$_2$—, —CH$_2$—, —CH$_2$—CH$_2$—, —CH$_2$—CH$_2$—CH$_2$—, —CH$_2$—CH$_2$—CH$_2$—CH$_2$—, —CH$_2$—CH$_2$—C(CH$_3$)H—, —CH$_2$—CH$_2$—C(CH$_3$)$_2$—, —CH$_2$—CH$_2$—O—CH$_2$—, —CH$_2$—CH═CH—;

L$^2$ is a divalent radical selected from the group consisting of —CH$_2$—, —CH$_2$—CH$_2$—;

$R^{B1}$, $R^{B2}$ represent independently from each other methyl, ethyl, n-propyl, 2-propyl, tert.-butyl, cyanomethyl, fluoromethyl, difluoromethyl, trifluoromethyl, 2,2,2-trifluorethyl, methoxy, ethoxy, difluoromethoxy, trifluoromethoxy, —O—CH$_2$—C≡CH, straight-chain or branched —S-methyl, —S—$CF_3$, F, Cl, Br, —CN, —S(═O)-methyl, S(═O)$_2$-methyl, —N($CH_3$)$_2$, phenyl, —$CH_2$-phenyl (benzyl), —O—$CH_2$-phenyl (benzyloxy), pyrrolyl, thiazolyl, cyclopropyl, cyclopentyl, pyrrolidinyl;

or two adjacent $R^{B1}$, $R^{B2}$ form together a divalent radical selected from the group consisting of —$CH_2$—$CH_2$—$CH_2$—, —$CH_2$—$CH_2$—$CH_2$—$CH_2$—, —O—$CH_2$—$CH_2$—, —O—$CH_2$—$CH_2$—$CH_2$—, —C(═O)—$CH_2$—$CH_2$—, —C(═O)—$CH_2$—$CH_2$—$CH_2$—, $R^{B8}$, $R^{B9}$ represent independently from each other F, methyl, ethyl, fluoromethyl, difluoromethyl, trifluoromethyl, methoxy, ethoxy, phenyl; or $R^{B8}$ and $R^{B9}$ are attached to the same carbon atom of said carbocycle $Cyc^1$ or said heterocycle $Hetcyc^1$ to form a divalent oxo (═O) group; or $R^{B8}$ and $R^{B9}$ and $R^{B10}$ and $R^{B11}$ are attached to the same sulfur atom of said heterocycle and form two divalent oxo (═O) groups thereby forming an —S(═O)$_2$— moiety;

$Ar^X$ is an unsubstituted benzo ring;

$Ar^Y$ is phenyl;

$R^{C1}$ and $R^{C2}$ represent independently from each other $CF_3$;

and the remaining radicals and residues are as defined for formula I-A or I above or for any of the further particular embodiments described herein above or below.

In a further particular embodiment, PE4, the compound of the present invention is a tricyclic heterocycle of formula I-A or I, or any N-oxide, solvate, tautomer or stereoisomer thereof and/or any pharmaceutically acceptable salt of each of the foregoing, including mixtures thereof in all ratios, wherein $R^2$ represents —C(═O)—$OR^{2a}$ or $Hetcyc^X$;

$R^{2a}$ represents H, straight-chain or branched, unsubstituted or substituted $C_{1-4}$-alkyl or Cat;

Cat represents a monovalent cation selected from the group consisting of lithium (Li), sodium (Na) and potassium (K);

$Hetcyc^X$ represents 1H-1,2,3,4-tetrazol-5-yl, 2H-1,2,3,4-tetrazol-5-yl, 2-methyl-2H-1,2,3,4-tetrazol-5-yl, 5-oxo-2,5-dihydro-1,2,4-oxadiazol-3-yl (2H-1,2,4-oxadiazol-5-on-3-yl), 5-oxo-4,5-dihydro-1,2,4-oxadiazol-3-yl (4H-1,2,4-oxadiazol-5-on-3-yl), 3-bromo-4,5-dihydro-1,2-oxazol-5-yl, 3-chloro-4,5-dihydro-1,2-oxazol-5-yl, 3-(1H-1,2,3-triazol-1-yl)-4,5-dihydro-1,2-oxazol-5-yl, 3-(2H-1,2,3-triazol-2-yl)-4,5-dihydro-1,2-oxazol-5-yl, 3-(pyrimidin-5-yloxy)-4,5-dihydro-1,2-oxazol-5-yl, 3-hydroxy-oxetan-3-yl, 5-hydroxy-4H-pyran-4-on-2-yl, 3,3-difluoropyrrolidin-2-on-4-yl, 3,3-difluoropyrrolidin-2-on-5-yl, 3,3-difluoro-2,3-dihydro-1H-pyrrol-2-on-4-yl, 3,3-difluoro-2,3-dihydro-1H-pyrrol-2-on-5-yl;

and the remaining radicals and residues are as defined for formula I-A or I above or for any of the further particular embodiments described herein above or below.

In another particular embodiment, PE4a, of PE4

$R^2$ represents —C(═O)—$OR^{2a}$;

$R^{2a}$ represents H, methyl, ethyl or Cat;

Cat represents a monovalent sodium cation;

and the remaining radicals and residues are as defined for formula I-A or I above or for any of the further particular embodiments described herein above or below.

In yet another particular embodiment, PE4b, of PE4

$R^2$ represents —C(═O)—$OR^{2a}$;

$R^{2a}$ represents $C_{1-4}$-alkyl substituted with —S(═O)—$R^{2f}$, —S(═O)$_2$—$R^{2g}$, —S(═O)$_2$—$NR^{2h}R^{2'}$, —S(═O)$_2$—OH, —S(═O)(═$NR^{2j}$)—OH, —S(═O)(═$NR^2$)—$R^{2g}$, —S(═O)(═$NR^{2k}$)—$NR^{2l}R^{2m}$ wherein $R^{2f}$, $R^{2g}$, $R^{2h}$, $R^{2i}$, $R^{2j}$, $R^{2k}$, $R^{2l}$, and $R^{2m}$ are as defined above and below in the specification for formula I-A or I;

and the remaining radicals and residues are as defined for formula I-A or I above or for any of the further particular embodiments described herein above or below.

In a further particular embodiment, PE5, the compound of the present invention is a tricyclic heterocycle of formula I-A or I, or any N-oxide, solvate, tautomer or stereoisomer thereof and/or any pharmaceutically acceptable salt of each of the foregoing, including mixtures thereof in all ratios, wherein $R^2$ represents —C(═O)—$NR^{2b}R^{2c}$;

$R^{2b}$ and $R^{2c}$ represent independently from each other H or straight-chain or branched $C_{1-8}$-aliphatic which may be unsubstituted or substituted with 1, 2, 3, 4, or 5 substituents which may be the same or different;

or form together with the nitrogen atom to which they are attached to an unsubstituted or substituted saturated, partially unsaturated or aromatic heterocycle with 3, 4, 5, 6, 7 ring atoms wherein 1 of said ring atoms is said nitrogen atom and no or one further ring atom is a hetero atom selected from N, O or S and the remaining are carbon atoms; wherein said heterocycle may optionally be fused with $Hetar^Z$ which is as defined elsewhere in the description; in particular a pyrrolidinyl ring or piperidinyl ring each of which is unsubstituted or mono-substituted with —OH or di-substituted with independently from each other $C_{1-4}$-alkyl and/or —OH;

or one of $R^{2b}$ and $R^{2c}$ represents H and the other represents Cyc- or Hetcyc; in particular it represents cyclopropyl or cyclobutyl, each of which is unsubstituted or substituted with —$CH_2$OH, or tetrahydrofuranyl, which is unsubstituted or mono-substituted with —OH;

and the remaining radicals and residues are as defined for formula I-A or I above or for any of the further particular embodiments described herein above or below.

In another particular embodiment, PE5a, of PE5

$R^{2b}$ represents hydrogen, $R^{2c}$ represents hydrogen; straight-chain or branched $C_{1-8}$-alkyl which may be unsubstituted or substituted with $R^{E1}$, $R^{E2}$, $R^{E3}$, $R^{E4}$ and/or $R^{E5}$ which may be the same or different, $Cyc^2$ or $Hetcyc^2$, wherein $R^{E1}$, $R^{E2}$, $R^{E3}$, $R^{E4}$ and/or $R^{E5}$ represent independently from each other halogen, in particular F; —$NR^{Ea}R^{Eb}$, —OH, $OR^{Ec}$, $Ar^E$, $Hetar^E$, $Cyc^E$, $Hetcyc^E$; $Ar^E$ is a mono- or bicyclic aryl with 6 or 10 ring carbon atoms, wherein that aryl may be unsubstituted or substituted with substituents $R^{F1}$, $R^{F2}$ and/or $R^{F3}$ which may be the same or different; preferably phenyl or naphthalenyl, in particular phenyl;

$Hetar^E$ is a monocyclic heteroaryl with 5 or 6 ring atoms or a bicyclic heteroaryl with 9 or 10 ring atoms wherein 1, 2, 3, or 4 of said ring atoms is/are a hetero atom(s) selected from N, O and/or S and the remaining are carbon atoms, wherein that heteroaryl may be unsubstituted or substituted with substituents $R^{F1}$, $R^{F2}$ and/or $R^{F3}$ which may be the same or different; in particular the heteroaryl is a moncyclic heteroaryl with 5 or 6 ring atoms which may be unsubstituted or substituted with substituents $R^{F1}$ and/or $R^{F2}$ which may be the same or different; preferably the heteroaryl is selected from the group consisting of imidazolyl, 1H-imidazol-1-yl, 1H-imidazol-2-yl, each of which unsubstituted or monosubstituted with $C_{1-4}$-alkyl; pyridyl, pyrid-2-yl, pyrid-3-yl, pyrid-4-yl, each of which may be unsubstituted or monosubstituted with —F; pyrimidinyl, pyrimidin-2-yl, pyrimidin-3-yl, pyrimidin-4-yl, pyrimidin-5-yl; pyrazinyl, pyrazin-2-yl; pyridazinyl, pyridazin-3-yl; furanyl, pyrrolyl, pyrazolyl, oxazolyl, isoxazolyl; oxadiazolyl, triazolyl, thiazolyl, isothiazolyl;

$Cyc^E$ is a saturated or partially unsaturated, mono- or bicyclic carbocycle with 3, 4, 5, 6, 7 or 8 ring carbon atoms, wherein that carbocycle may be unsubstituted or substituted with $R^G1$ and/or $R^{G2}$ which may be the same or different: in particular, a saturated monocyclic carbocycle with 3, 4, 5, or 6 ring carbon atoms, wherein that carbocycle may be unsubstituted or substituted with $R^{G1}$ and/or $R^{G2}$ which may be the same or different; preferably cyclopropyl, cyclobutyl, cyclohexenyl;

$Hetcyc^E$ is a saturated or partially unsaturated, monocyclic heterocycle with 4, 5 or 6 ring atoms wherein 1 or 2 of said ring atoms is/are a hetero atom(s) selected from N, O and/or S and the remaining are carbon atoms, wherein that heterocycle may be unsubstituted or substituted with $R^{G1}$ and/or $R^{G2}$ which may be the same or different; in particular a saturated monocyclic heterocycle with 5 or 6 ring atoms wherein 1 or 2 of said ring atoms is/are a hetero atom(s) selected from N and/or O and the remaining are carbon atoms, wherein that heterocycle may be unsubstituted or substituted with $R^{G1}$ and/or $R^{G2}$; preferably tetrahydrofuranyl, tetrahydrofuran-2-yl, tetrahydrofuran-3-yl each of which may be unsubstituted or monosubstituted with —OH; pyrrolindinyl, pyrrolindin-1-yl, pyrrolindin-2-yl, pyrrolindin-3-yl, each of which may be unsubstituted or monosubstituted with —OH; piperidinyl, piperidin-1-yl, piperidin-2-yl, piperidin-3-yl, piperidin-4-yl, each of which may be unsubstituted or monosubstituted with —OH; morpholinyl, morpholin-1-yl, morpholin-2-yl each of which may be unsubstituted or mono-substituted with methyl; 1,4-dioxanyl; dihydropyranyl, tetrahydropyranyl, tetrahydropyran-3-yl;

$R^{Ea}$, $R^{Eb}$ represent independently from each other H, $C_{1-4}$-alkyl, —C(═O)—$OC_{1-4}$-alkyl; in particular both represent H or one represents H and the other represents C(═O)—O-tert.-butyl;

$R^{Ec}$ represents H or $C_{1-4}$-alkyl, in particular H or methyl;

$R^{F1}$, $R^{F2}$ and/or $R^{F3}$ represent independently from each other straight-chain or branched $C_{1-6}$-alkyl, which $C_{1-6}$-alkyl may be unsubstituted or monosubstituted with —CN, OH, —O—$C_{1-4}$-alkyl or substituted with 1, 2 or 3 halogen, straight-chain or branched $C_{1-4}$-alkoxy, which $C_{1-4}$-alkoxy may be unsubstituted or substituted with 1, 2 or 3 halogen, straight-chain or branched —S—$C_{1-4}$-alkyl, which —S—$C_{1-4}$-alkyl may be unsubstituted or substituted with 1, 2 or 3 halogen; $C_{3-7}$-cyclopropyl optionally substituted with halogen, OH and/or $C_{1-4}$-alkyl; F, Cl, Br, —CN, —S(═O)—$C_{1-3}$-alkyl, $S(═O)_2$—$C_{1-3}$-alkyl, —$NH_2$, —NH($C_{1-3}$-alkyl) —N($C_{1-3}$-alkyl)$_2$, —OH; in particular methyl, hydroxymethyl, methoxymethyl, F, cyclopropyl, cyclobutyl; preferably only one of $R^{F1}$, $R^{F2}$ and $R^{F3}$ is present and represents methyl or F;

and/or two of $R^{F1}$, $R^{F2}$, $R^{F3}$ which are attached to two different ring atoms of that aryl or heteroaryl form a divalent $C_{1-6}$-alkylene radical wherein optionally one or two non-adjacent carbon units of that alkylene radical may be replaced by independently from each other O, NH, N—$C_{1-4}$-alkyl, in particular —$(CH_2)_4$—, —$CH_2$—O—$(CH_2)_2$—;

$R^{G1}$ and/or $R^{G2}$ represent independently from each other halogen, hydroxy, unsubstituted or substituted $C_{1-6}$-aliphatic, in particular $C_{1-4}$-alkyl optionally substituted with OH, $C_{1-6}$-aliphatoxy, in particular —O—$C_{1-4}$-alkyl, —C(═O)—O—$C_{1-4}$-alkyl, $Hetar^{Y2}$, —$CH_2$-$Hetar^{Y2}$, $Hetcyc^{Y2}$; preferably only one of $R^{G1}$ and $R^{G2}$ is present and represents hydroxy;

and/or $R^{G1}$ and $R^{G2}$ which are attached to the same ring atom of that carbocycle or heterocycle form a divalent $C_{2-6}$-alkylene radical wherein optionally one or two non-adjacent carbon units of that alkylene radical may be replaced by independently from each other O, NH, N—$C_{1-4}$-alkyl, and wherein that alkylene radical may optionally be substituted with OH, $C_{1-4}$-alkyl or —O—$C_{1-4}$-alkyl, in particular —$(CH_2)_2$—O—$CH_2$—, —$(CH_2)_2$—O—$(CH_2)_2$—; and/or $R^{G1}$ and $R^{G2}$ which are attached to two different ring atoms of that carbocycle or heterocycle form a divalent $C_{1-6}$-alkylene radical wherein optionally one or two non-adjacent carbon units of that alkylene radical may be replaced by independently from each other O, NH, N—$C_{1-4}$-alkyl, in particular —$CH_2$—;

$Cyc^2$ is a saturated monocyclic carbocycle with 3, 4, 5, 6 or 7 ring carbon atoms, wherein that carbocycle may be unsubstituted or substituted independently from each other with $R^{D6}$, $R^{D7}$, $R^{D8}$, $R^{D9}$ and/or $R^{D10}$ wherein that carbocycle may optionally be fused to $Ar^Z$ or $Hetar^Z$ via 2 adjacent ring atoms and wherein that fused carbocycle may optionally further be substituted with independently from each other $R^{C1}$, $R^{C2}$ and/or $R^{C3}$;

$Hetcyc^2$ is a saturated monocyclic heterocycle with 4, 5 or 6 ring atoms wherein 1 or 2 of said ring atoms is/are a hetero atom(s) selected from N, O and/or S and the remaining are carbon atoms, wherein that heterocycle may be unsubstituted or substituted independently from each other with $R^{D6}$, $R^{D7}$, $R^{D8}$, $R^{D9}$ and/or $R^{D10}$ wherein that heterocycle may optionally be fused to $Ar^Z$ or $Hetar^Z$ and wherein that fused heterocycle may optionally further be substituted with independently from each other $R^{C1}$, $R^{C2}$ and/or $R^{C3}$;

$R^{C1}$, $R^{C2}$, $R^{C3}$ represent $C_{1-4}$-alkyl;

$R^{D6}$, $R^{D7}$, $R^{D8}$, $R^{D9}$, $R^{D10}$ represent independently from each other halogen, in particular F; hydroxy; $C_{1-4}$-alkyl optionally substituted with —OH and/or halogen, in particular methyl, hydroxymethyl, 2-fluorethyl; —O—$C_{1-4}$-alkyl, in particular methoxy, ethoxy; $Hetar^{Y1}$, —$CH_2$-$Hetar^{Y1}$, $Cyc^{Y1}$, $Hetcyc^{Y1}$, —$CH_2$-$Hetcyc^{Y1}$;

and/or two of $R^{D6}$, $R^{D7}$, $R^{D8}$, $R^{D9}$, $R^{D10}$ which are attached to the same ring atom of that carbocycle or heterocycle form a divalent $C_{2-6}$-alkylene radical wherein optionally one or two non-adjacent carbon units of that alkylene radical may be replaced by independently from each other O, NH, N—$C_{1-4}$-alkyl, and wherein that alkylene radical may optionally be substituted with OH, $C_{1-4}$-alkyl or —O—$C_{1-4}$-alkyl, in particular —$(CH_2)_3$—, —$CH_2$—CH($OC_2H_5$)—$CH_2$—, —$(CH_2)_2$—O—$(CH_2)_2$—;

and/or two of $R^{D6}$, $R^{D7}$, $R^{D8}$, $R^{D9}$, $R^{D10}$ which are attached to two different ring atoms of that carbocycle or heterocycle form a divalent $C_{1-6}$-alkylene radical wherein optionally one or two non-adjacent carbon units of that alkylene radical may be replaced by independently from each other 0, NH, N—$C_{1-4}$-alkyl, in particular —$CH_2$—, —$(CH_2)_3$—, —O—$(CH_2)_2$—, —O—$(CH_2)_3$—;

$Ar^Z$ is benzo;

$Hetar^{Y1}$ is a 5 or 6 membered monocyclic heteroaryl wherein 1, 2, 3, 4 ring atoms are hetero atoms selected from N, O and/or S and the remaining are carbon atoms, wherein that heteroaryl may be unsubstituted or substituted with F, $C_{1-4}$-alkyl which may optionally be substituted with OH; in particular pyrrolyl, thiophenyl, pyrazolyl, methylpyrazolyl, imidazolyl, methylimidazolyl, triazolyl, oxadiazolyl, methyloxadiazolyl, pyrdinyl, fluoropyrdinyl, methylpyridinyl, pyrimidinyl, methylpyrimidinyl;

$Hetar^{Y2}$ is a 5 or 6 membered monocyclic heteroaryl wherein 1, 2, 3, 4 ring atoms are hetero atoms selected from N, O and/or S and the remaining are carbon atoms, wherein that heteroaryl may be unsubstituted or substituted with halogen, $C_{1-4}$-alkyl which may optionally be substituted with OH; in particular pyrrolyl, furanyl, thiophenyl, pyrazolyl, imidazolyl, triazolyl, oxazolyl, hydroxymethyloxazolyl;

$Hetar^Z$ is pyrrole, N-methyl-pyrrole, pyrazole, imidazole, triazole;

$Cyc^{Y1}$ is a saturated monocyclic carbocycle with 3, 4, 5, 6 or 7 ring carbon atoms, wherein that carbocycle may be unsubstituted or substituted with halogen, OH, $C_{1-4}$-alkyl, in particular cyclopropyl;

$Hetcyc^{Y1}$ is a saturated or partially unsaturated monocyclic heterocycle with 5 or 6 ring atoms wherein 1 or 2 of said ring atoms are heteroatoms selected from N, O, and/or S and the remaining are carbon atoms; in particular tetrahydrofuranyl;

$Hetcyc^{Y2}$ is a saturated or partially unsaturated monocyclic heterocycle with 5 or 6 ring atoms wherein 1 or 2 of said ring atoms are heteroatoms selected from N, O, and/or S and the remaining are carbon atoms; in particular tetrahydrofuranyl, morpholinyl, tetrahydropyranyl;

and the remaining radicals and residues are as defined for formula I-A or I above or for any of the further particular embodiments described herein above or below. It is understood that this particular embodiment PE5a comprises compounds of the present invention in which $R^{2b}$ represents hydrogen and $R^{2c}$ represents straight-chain or branched $C_{1-8}$-alkyl in which 1 or 2 of non-terminal and non-adjacent —$CH_2$-(methylene) groups are replaced by —O—, —S— and/or 1 or 2 non-terminal and non-adjacent —$CH_2$— or —CH— groups are replaced by —NH— or —N—.

In yet another particular embodiment, PE5aa, of PE5a $R^{2b}$ represents hydrogen, $R^{2c}$ represents hydrogen; straight-chain or branched $C_{1-8}$-alkyl which may be unsubstituted or substituted with $R^{E1}$, $R^{E2}$, $R^{E3}$, $R^{E4}$ and/or $R^{E5}$ which may be the same or different, $Cyc^2$ or $Hetcyc^2$, wherein $R^{E1}$, $R^{E2}$, $R^{E3}$, $R^{E4}$ and/or $R^{E5}$ represent independently from each other halogen, in particular F; —$NR^{Ea}R^{Eb}$, —OH, $OR^EC$, $Ar^E$, $Hetar^E$, $Cyc^E$, $Hetcyc^E$;

$Ar^E$ is a mono- or bicyclic aryl with 6 or 10 ring carbon atoms, wherein that aryl may be unsubstituted or substituted with substituents $R^{F1}$, $R^{F2}$ and/or $R^{F3}$ which may be the same or different; preferably phenyl or naphthalenyl, in particular phenyl;

$Hetar^E$ is a monocyclic heteroaryl with 5 or 6 ring atoms or a bicyclic heteroaryl with 9 or 10 ring atoms wherein 1, 2, 3, or 4 of said ring atoms is/are a hetero atom(s) selected from N, O and/or S and the remaining are carbon atoms, wherein that heteroaryl may be unsubstituted or substituted with substituents $R^{F1}$, $R^{F2}$ and/or $R^{F3}$ which may be the same or different; in particular the heteroaryl is a moncyclic heteroaryl with 5 or 6 ring atoms which may be unsubstituted or substituted with substituents $R^{F1}$ and/or $R^{F2}$ which may be the same or different; preferably the heteroaryl is selected from the group consisting of imidazolyl, 1H-imidazol-1-yl, 1H-imidazol-2-yl, each of which unsubstituted or monosubstituted with $C_{1-4}$-alkyl; pyridyl, pyrid-2-yl, pyrid-3-yl, pyrid-4-yl, each of which may be unsubstituted or monosubstituted with —F; pyrimidinyl, pyrimidin-2-yl, pyrimidin-3-yl, pyrimidin-4-yl, pyrimidin-5-yl; pyrazinyl, pyrazin-2-yl;

$Cyc^E$ is a saturated or partially unsaturated, mono- or bicyclic carbocycle with 3, 4, 5, 6, 7 or 8 ring carbon atoms, wherein that carbocycle may be unsubstituted or substituted with $R^{G1}$ and/or $R^{G2}$ which may be the same or different: in particular, a saturated monocyclic carbocycle with 3, 4, 5, or 6 ring carbon atoms, wherein that carbocycle may be unsubstituted or substituted with $R^{G1}$ and/or $R^{G2}$ which may be the same or different; preferably cyclobutyl;

$Hetcyc^E$ is a saturated or partially unsaturated, monocyclic heterocycle with 5 or 6 ring atoms wherein 1 or 2 of said ring atoms is/are a hetero atom(s) selected from N, O and/or S and the remaining are carbon atoms, wherein that heterocycle may be unsubstituted or substituted with $R^{G1}$ and/or $R^{G2}$ which may be the same or different; in particular a saturated monocyclic heterocycle with 5 or 6 ring atoms wherein 1 or 2 of said ring atoms is/are a hetero atom(s) selected from N and/or O and the remaining are carbon atoms, wherein that heterocycle may be unsubstituted or monosubstituted with $R^{G1}$; preferably tetrahydrofuranyl, tetrahydrofuran-2-yl, tetrahydrofuran-3-yl each of which may be unsubstituted or monosubstituted with —OH; pyrrolindinyl, pyrrolindin-1-yl, pyrrolindin-2-yl, pyrrolindin-3-yl, each of which may be unsubstituted or monosubstituted with —OH; piperidinyl, piperidin-1-yl, piperidin-2-yl, piperidin-3-yl, piperidin-4-yl, each of which may be unsubstituted or monosubstituted with —OH; morpholinyl, morpholin-1-yl, morpholin-2-yl;

$R^{Ea}$, $R^{Eb}$ represent independently from each other H, $C_{1-4}$-alkyl, —C(═O)—O$C_{1-4}$-alkyl; in particular both represent H or one represents H and the other represents C(═O)—O-tert.-butyl;

$R^{Ec}$ represents H or $C_{1-4}$-alkyl, in particular H or methyl;

$R^{F1}$, $R^{F2}$ and/or $R^{F3}$ represent independently from each other straight-chain or branched $C_{1-6}$-alkyl, which $C_{1-6}$-alkyl may be unsubstituted or monosubstituted with —CN OH, —O—$C_{1-4}$-alkyl or substituted with 1, 2 or 3 halogen, straight-chain or branched $C_{1-4}$-alkoxy, which $C_{1-4}$-alkoxy may be unsubstituted or substituted with 1, 2 or 3 halogen, straight-chain or branched —S—$C_{1-4}$-alkyl, which —S—$C_{1-4}$-alkyl may be unsubstituted or substituted with 1, 2 or 3 halogen, $C_{3-7}$-cyclopropyl optionally substituted with halogen, OH and/or $C_{1-4}$-alkyl, F, Cl, Br, —CN, —S(═O)—$C_{1-3}$-alkyl, S(═O)$_2$—$C_{1-3}$-alkyl, —$NH_2$, —NH($C_{1-3}$-alkyl) —N($C_{1-3}$-alkyl)$_2$, —OH; in particular methyl, F; preferably only one of $R^{F1}$, $R^{F2}$ and $R^{F3}$ is present and represents methyl or F;

$R^{G1}$ and/or $R^{G2}$ represent independently from each other halogen, hydroxy, unsubstituted or substituted $C_{1-4}$-alkyl, —O—$C_{1-4}$-alkyl, in particular hydroxy; preferably only one of $R^{G1}$ and $R^{G2}$ is present and represents hydroxy;

$Cyc^2$ is a saturated monocyclic carbocycle with 3, 4, 5, 6 or 7 ring carbon atoms, wherein that carbocycle may be unsubstituted or mono-substituted with $R^{D6}$, wherein $R^{D6}$ is $C_{1-4}$-alkyl which is unsubstituted or mono-substituted with —OH, in particular —$CH_2OH$;

in particular $Cyc^2$ is cyclopropyl, cyclobutyl or 1-hydroxymethyl-cyclobutyl;

$Hetcyc^2$ is a saturated monocyclic heterocycle with 5 or 6 ring atoms wherein 1 or 2 of said ring atoms is/are a hetero atom(s) selected from N, O and/or S and the remaining are carbon atoms, wherein that heterocycle may be unsubstituted or mono-substituted with hydroxy; in particular tetrahydrofuranyl or hydroxytetrahydrofuranyl; preferably 4-hydroxytetrahydrofuran-3-yl;

In still another particular embodiment, PE5b, of PE5

$R^{2b}$ and $R^{2c}$ form together with the nitrogen atom to which they are attached to a saturated or partially unsaturated heterocycle optionally substituted with independently from each other $R^{Y1}$, $R^{Y2}$, $R^{Y3}$, $R^{Y4}$ and/or $R^{Y5}$; wherein that heterocycle may optionally be fused with $Hetar^Z$; and wherein that heterocycle is selected from the group consisting of: azetidine, pyrrolidine, piperidine, piperazine, morpholine; wherein $R^{Y1}$, $R^{Y2}$, $R^{Y3}$, $R^{Y4}$, $R^{Y5}$ represent independently from each other halogen, in particular F; —$NH_2$, —N(H)—$C_{1-4}$-alkyl, —N(H)—C(═O)—O—$C_{1-4}$-alkyl, —N($C_{1-4}$-alkyl)$_2$; —OH; $C_{1-4}$-alkyl optionally substituted with —OH, —O—$C_{1-4}$-alkyl, —O—$C_{3-7}$-cycloalkyl, —O—$CH_2$—$C_{3-7}$-cycloalkyl, in particular methyl, —$CH_2OH$, —$(CH_2)_2OH$, —$(CH_2)_3OH$, —$CH_2OCH_3$, —$(CH_2)_{20}CH_3$, cyclopropylmethoxy; —O—$C_{1-4}$-alkyl, in particular methoxy; $Hetar^{Y2}$; —$CH_2$-$Hetar^{Y2}$; $Hetcyc^{Y2}$; and/or two of $R^{Y1}$, $R^{Y2}$, $R^{Y3}$, $R^{Y4}$, $R^{Y5}$ which are attached to the same ring atom of that heterocycle form a divalent $C_{2-6}$-alkylene radical wherein optionally one or two non-adjacent carbon units of that alkylene radical may be replaced by independently from each other O, NH, N—$C_{1-4}$-alkyl, in particular —$(CH_2)_4$—, —$(CH_2)_2$—O—$(CH_2)_2$—, —$(CH_2)_2$—O—$(CH_2)_3$—;

and/or two of $R^{Y1}$, $R^{Y2}$, $R^{Y3}$, $R^{Y4}$, $R^{Y5}$ which are attached to two different ring atoms of that heterocycle form a divalent $C_{1-6}$-alkylene radical wherein optionally one or two non-adjacent carbon units of that alkylene radical may be replaced by independently from each other O, NH, N—$C_{1-4}$-alkyl, in particular —$(CH_2)_4$—;

$Ar^Z$ is benzo;

$Hetar^{Y2}$ is a 5 or 6 membered monocyclic heteroaryl wherein 1, 2, 3, 4 ring atoms are hetero atoms selected from N, O and/or S and the remaining are carbon atoms, wherein that heteroaryl may be unsubstituted or substituted with halogen, $C_{1-4}$-alkyl which may optionally be substituted with OH; in particular pyrrolyl, thiophenyl, pyrazolyl, imidazolyl, triazolyl, oxazolyl, hydroxymethyloxazolyl, pyrimidinyl;

$Hetar^Z$ is pyrrole, N-methyl-pyrrole, pyrazole, imidazole, triazole;

$Hetcyc^{Y2}$ is a saturated or partially unsaturated monocyclic heterocycle with 5 or 6 ring atoms wherein 1 or 2 of said ring atoms are heteroatoms selected from N, O, and/or S and the remaining are carbon atoms; in particular tetrahydrofuranyl, morpholinyl, tetrahydropyranyl;

and the remaining radicals and residues are as defined for formula I-A or I above or for any of the further particular embodiments described herein above or below.

In yet another particular embodiment, PE5bb, of PE5b $R^{2b}$ and $R^{2c}$ form together with the nitrogen atom to which they are attached a 3-hydroxypyrrolidinyl, 2-methyl-3-hydroxypyrrolidinyl or 3-hydroxypiperidinyl ring.

In still another particular embodiment, PE5c, of PE5

$R^{2b}$ represents a straight-chain of branched $C_{1-4}$-alkyl optionally substituted with OH; in particular methyl, 2-hydroxyethyl;

and $R^{2c}$ represents $Cyc^2$, $Hetcyc^2$ or straight-chain or branched $C_{1-8}$-alkyl which may be unsubstituted or substituted with independently from each other $R^{E1}$, $R^{E2}$, $R^{E3}$, $R^{E4}$ and/or $R^{E5}$ which may be the same or different; wherein $Cyc^2$, $Hetcyc^2$, $R^{E1}$, $R^{E2}$, $R^{E3}$, $R^{E4}$ and $R^{E5}$ are as defined hereinabove for PE5a or PE5aa.

In a further particular embodiment, PE6, the compound of the present invention is a tricyclic heterocycle of formula I-A or I, or any N-oxide, solvate, tautomer or stereoisomer thereof and/or any pharmaceutically acceptable salt of each of the foregoing, including mixtures thereof in all ratios, wherein $R^2$ represents —$(CH_2)_x$—$NR^{2d}$—C(═O)—$R^{2e}$, —S—$R^{2f}$, —S(═O)—$R^{2f}$, —S(═O)$_2$—$R^{2g}$, —S(═O)$_2$—$NR^{2h}R^2$, —S(═O)$_2$—OH, —S(═O)(═$NR^{2j}$)—OH, —S(═O)(═$NR^{2j}$)—$R^{2g}$, —S(═O)(═$NR^{2k}$)—$NR^{2l}R^{2m}$, —$(CH_2)_z$—$NR^{2d}$—S(═O)$_2$—$R^{2g}$; in particular, —S—$CH_3$, —S(═O)—$R^{2f}$, —S(═O)$_2$—$R^{2g}$, —S(═O)$_2$—$NR^{2h}R^{21}$, —S(═O)(═$NR^{2j}$)—$R^{2g}$, —S(═O)(═$NR^{2k}$)—$NR^{2l}R^{2m}$, —$(CH_2)_z$—$NR^{2d}$—S(═O)$_2$—$R^{2g}$, —C(═O)—N═S(═O)—$R^{2s}R^{2t}$, —C(═O)—N═S(═N—$R^{2u}$)—$R^{2s}R^{2t}$; preferably, —S(═O)—$CH_3$, —S(═O)$_2$—$CH_3$, —S(═O)$_2$—$NH_2$, —S(═O)$_2$—$NHCH_3$, —S(═O)(═NH)—$CH_3$, S(═O)(═NH)—N$(CH_3)_2$, —NH—S(═O)$_2$—$CH_3$, —N($CH_3$)—S(═O)$_2$—$CH_3$, —NH—S(═O)$_2$—CH═$CH_2$, —$CH_2$—NH—S(═O)$_2$—CH═$CH_2$;

$R^{2e}$ represents H, $C_{1-6}$-alkyl optionally substituted with —OH or a monocyclic 5- or 6-membered heteroaryl; $C_{3-7}$-cycloalkyl, monocyclic 5- or 6-membered heteroaryl; in particular H, methyl, hydroxymethyl, methylpyridin-2-yl, methylpyridine-3-yl, methylpyridine-4-yl, cyclopropyl, pyridin-2-yl, pyridin-3-yl, pyridin-4-yl;

$R^{2f}$, $R^{2g}$ represent independently from each other unsubstituted or substituted $C_{1-8}$-aliphatic; in particular independently from each other $C_{1-4}$-alkyl or $C_{2-4}$-alkenyl; preferably independently from each other methyl or —CH═$CH_2$:

$R^{2h}$, $R^{2i}$ represent independently from each other H, un-substituted or substituted $C_{1-8}$-aliphatic, aryl, heterocyclyl, heteroaryl; or form together with the nitrogen atom to which they are attached to an unsubstituted or substituted saturated, partially unsaturated or aromatic heterocycle with 3, 4, 5, 6, 7 ring atoms wherein 1 of said ring atoms is said nitrogen atom and no or one further ring atom is a hetero atom selected from N, O or S and the remaining are carbon atoms; in particular independently from each other H or $C_{1-4}$-alkyl optionally substituted with —OH, pyridyl, pyrimidyl, pyrazinyl or pyridazinyl or form together with the nitrogen atom to which they are attached to a pyrrolidinyl ring which ring is optionally substituted with —OH and/or phenyl, pyridin-2-yl, pyridin-3-yl, pyridin-4-yl, pyrimidin-5-yl;

$R^{2d}$, $R^{2j}$, $R^{2k}$ represent independently from each other H, un-substituted or substituted $C_{1-8}$-aliphatic; in particular H, methyl;

$R^{2l}$, $R^{2m}$ represent independently from each other H, un-substituted or substituted $C_{1-8}$-aliphatic; or form together with the nitrogen atom to which they are attached to an unsubstituted or substituted saturated, partially unsaturated or aromatic heterocycle with 3, 4, 5, 6, 7 ring atoms wherein 1 of said ring atoms is said nitrogen atom and no or one further ring atom is a hetero atom selected from N, O or S and the remaining are carbon atoms; in particular $C_{1-4}$-alkyl; preferably methyl;

$R^{2s}$, $R^{2t}$ represent independently from each other $C_{1-6}$-alkyl which may optionally be substituted with —OH, O—$C_{1-4}$-alkyl, $NH_2$, $NHC_{1-4}$-alkyl, $N(C_{1-4}\text{-alkyl})_2$, pyrrolidinyl, piperidinyl, morpholinyl, piperazinyl; in particular methyl, ethyl, 2-hydroxyethyl, 3-hydroxy propyl, 2-aminoethyl, 3-(N,N-dimethylamino)propyl; or form together a divalent $C_{3-4}$-alkylene radical which may optionally be substituted with —$NH_2$, —CN, or a divalent $C_{2-5}$-alkylene radical wherein optionally one of the carbon units of said $C_{2-5}$-alkylene radical may be replaced by O, NH or N—$C_{1-4}$-alkyl; in particular —$(CH_2)_3$—, —$CH_2$—$C(NH_2)H$—$CH_2$—, —$CH_2$—C(CN)H—$CH_2$—, —$CH_2$—$C(CH_2$—NH—$CH_2)$—$CH_2$—, —$(CH_2)_4$—;

$R^{2u}$ represents hydrogen or $C_{1-4}$-alkyl;

x represents 0 or 1;

z is 0 or 1:

and the remaining radicals and residues are as defined for formula I-A or I above or for any of the further particular embodiments described herein above or below.

In yet a further particular embodiment, PE7, the compound of the present invention is a tricyclic heterocycle of formula I, or any N-oxide, solvate, tautomer or stereoisomer thereof and/or any pharmaceutically acceptable salt of each of the foregoing, including mixtures thereof in all ratios, wherein wherein Ring A represents a five-membered heteroaromatic ring selected from the group consisting of the following ring moieties:

A-1a

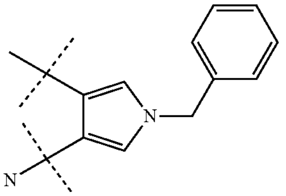

;

A-4a

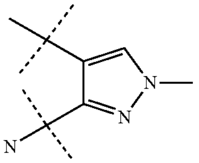

,

-continued

A-4b

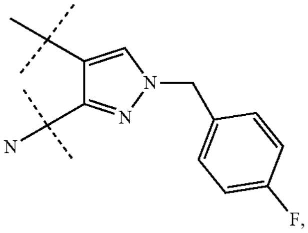

A-4c

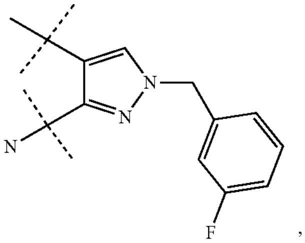

,

A-4d

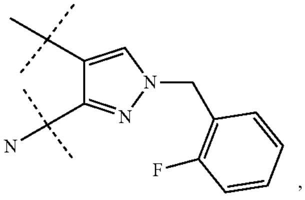

,

A-4e

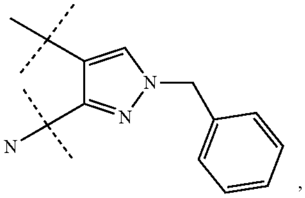

,

A-4f

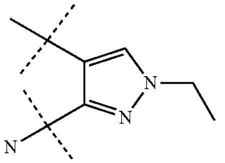

,

A-4g

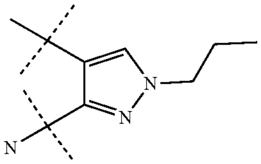

,

A-4h

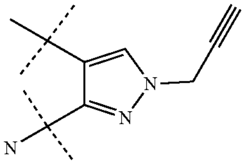

,

A-4i

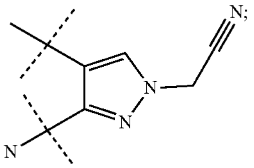

-continued
A-5a
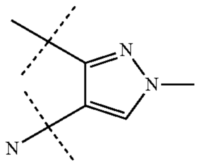
,
A-5b
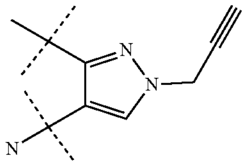
;
A-7a
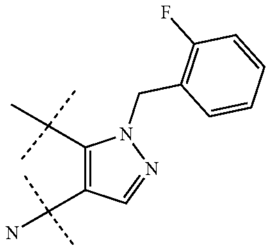
,
A-7b
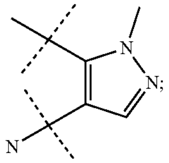
A-9a
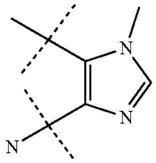
,
A-9b
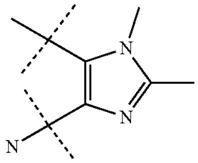
;
A-10a
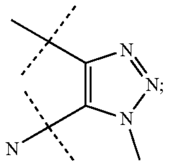
A-12a
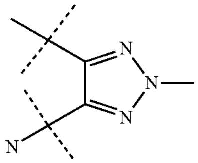
;
-continued
A-13a
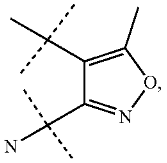
A-13b
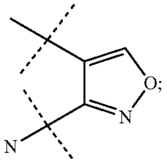
A-15a
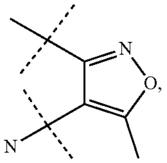
A-15b
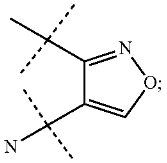
A-17a
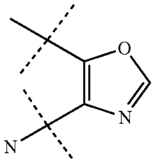
;
A-19a
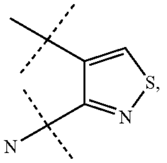
A-19b
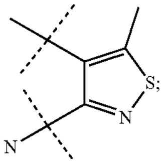
A-21a
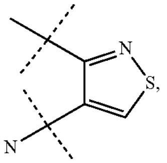
A-21b
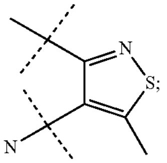

-continued

A-23a

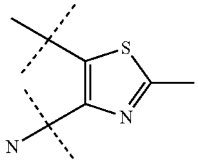

,

A-23b

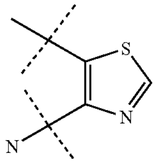

,

A-23c

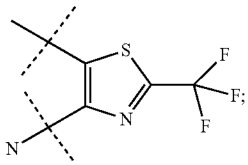

;

A-24a

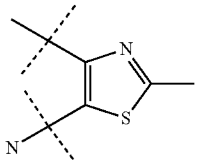

,

A-24b

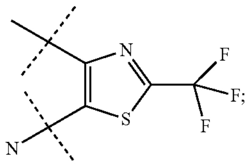

;

$Z^1$ is CH;

$Z^2$ is CH;

$R^1$ represents phenyl, 3-fluorophenyl, 4-fluorophenyl, 4-chlorophenyl, 4-methylphenyl, 4-ethylphenyl, 4-difluoromethylphenyl, 3-trifluoromethylphenyl, 4-trifluoromethylphenyl, 4-(1,1-difluorethyl)phenyl, 4-(2,2,2-trifluorethyl)phenyl, 4-(1-trifluoromethylcyclopropyl)-phen-1-yl, 4-cyclopentylphenyl, 4-ethoxyphenyl, 4-difluormethoxyphenyl, 4-trifluoromethoxyphenyl, 3-(trifluoromethyl)sulfanylphenyl, 4-(trifluoromethyl)sulfanylphenyl, 3-trifluoromethyl-4-methylphenyl, 2-fluoro-4-trifluoromethylphenyl, 2-fluoro-4-trifluoromethoxyphenyl, 3-fluoro-4-(n-propyl)phenyl, 2,3-dimethyl-4-methoxyphenyl, 6-fluoronaphth-2-yl; 5-trifluoromethylfuran-2-yl; 5-trifluoromethylthiophen-2-yl, 2-trifluoromethyl-1,3-thiazol-4-yl, 3-fluoropyridin-2-yl, 6-methylpyridin-3-yl, 6-methoxypyridin-3-yl, 3-ethylpyridin-2-yl, 6-ethylpyridin-3-yl, 4-difluoromethylpyridin-2-yl, 4-trifluoromethylpyridin-2-yl, 4-trifluoromethoxypyridin-2-yl, 4-cyanopyridin-2-yl, 5-trifluoromethylpyridin-2-yl, 6-trifluoromethylpyridin-2-yl, 6-trifluoromethylpyridin-3-yl (2-trifluoromethylpyridin-5-yl), 6-trifluoromethoxypyridin-3-yl (2-trifluoromethoxypyridin-5-yl), 5-cyanopyridin-2-yl, 5-cyanomethylpyridin-2-yl, 5-methanesulfonylpyridin-2-yl, 6-methoxypyridin-2-yl, 4-methylpyrimidin-2-yl, 4-ethylpyrimidin-2-yl, 4-methylsulfanylpyrimidin-2-yl, 5-cyclopropylpyrimidin-2-yl, 5-ethyl-pyrimidin-2-yl, 5-difluoromethylpyrimidin-2-yl, 5-trifluoromethylpyrimidin-2-yl, 5-cyanopyrimidin-2-yl, 5-cyano-3-fluoropyridin-2-yl, 5-cyano-6-methylpyridin-2-yl, 3-fluoro-5-(trifluoromethyl)pyridin-2-yl, 5-oxo-5H,6H,7H-cyclopenta[b]pyridin-2-yl, 5,6,7,8-tetrahydroquinolin-2-yl, 5-oxo-5,6,7,8-tetrahydroquinolin-2-yl, 5H,6H,7H-cyclopenta[b]pyridin-2-yl, quinolin-2-yl, isoquinolin-3-yl, 6-methylquinolin-2-yl, 8-methoxyquinolin-4-yl, furo[3,2-b]pyridin-5-yl, quinazolin-2-yl, 6-fluoroquinazolin-2-yl, 1,5-naphthyridin-2-yl; 3-methylcyclobutyl, cyclopentyl, 3-methylcyclopentyl, 3,3-dimethylcyclopentyl, 3-trifluoromethyl-bicyclo[1.1.1]petan-1-yl, cyclohexyl, 4-methylcyclohexyl, 4-(trifluoromethyl)cyclohexyl, 4,4-difluorocyclohexyl, cyclohex-1-enyl, 2-oxocycloheptyl, 6,6-difluorospiro[3.3]heptan-2-yl, 1H-inden-2-yl; benzenesulfonyl (phenylsulfonyl), 3-methylphenylsulfonyl, benzyl, 2-ethoxyphenylmethyl, 3-chlorophenylmethyl, 3-fluorophenylmethyl, 4-chlorophenylmethyl, 3-(pyrrolidine-1-yl)phenylmethyl, 3-methylphenylmethyl, 4-methylphenylmethyl, 3-ethylphenylmethyl, 3-(propan-2-yl)phenylmethyl, 3-tert-butylphenylmethyl, 3-(difluoromethoxy)phenylmethyl, 2-(difluoromethyl)phenylmethyl, 3-(difluoromethyl)phenylmethyl, 3-(trifluoromethyl)phenylmethyl, 4-(trifluoromethyl)phenyl]methyl, 2-(prop-2-yn-1-yloxy)phenylmethyl, 3-(1,3-thiazol-2-yl)phenylmethyl, 3-(trifluoromethyl)sulfanylphenylmethyl, 3-methanesulfonylphenylmethyl, 3-(dimethylamino)phenylmethyl, 3-(pyrrol-1-yl)phenylmethyl, 2-methyl-3-methoxyphenylmethyl, 3-trifluoromethyl-5-methylphenylmethyl, 2-methyl-3-(trifluoromethyl)phenylmethyl, 3-trifluoromethyl-4-fluorophenylmethyl, 2-fluoro-5-(trifluoromethoxy)phenylmethyl, 2-methoxy-3-trifluoromethoxyphenylmethyl, 2-fluoro-3-methoxyphenylmethyl, 2-fluoro-3-(trifluoromethyl)phenyl]methyl, 2-fluor-3-fluoromethoxyphenylmethyl, 2-trifluoromethoxy-5-fluorophenylmethyl, 2-fluor-5-chlor-phenylmethyl, 3-fluoro-5-methylphenyl)methyl, 3,5-difluorophenylmethyl, 5-fluoro-2-(trifluoromethyl)phenylmethyl, 3-fluoro-5-(trifluoromethyl)phenylmethyl, 2-chloro-3-(trifluoromethyl)phenylmethyl, naphthalin-1-ylmethyl, 5,6,7,8-tetrahydronaphthalen-1-ylmethyl, 2,3-dihydro-1-benzofuran-7-ylmethyl, 3,4-dihydro-2H-1-benzopyran-8-ylmethyl, 2-phenylethyl, 2-(2-methyl-phenyl)ethyl, 2-(2-methoxyphenyl)ethyl, 2-(3-methoxyphenyl)ethyl, 2-(4-methoxyphenyl)ethyl, 2-(2-fluorophenyl)-ethyl, 2-(3-fluorophenyl)-ethyl, 2-(4-fluorophenyl)-ethyl, 2-(2-chlorophenyl)-ethyl, 2-(4-chlorophenyl)-ethyl, 2-(4-bromophenyl)-ethyl, 2-[4-(trifluoromethyl)phenyl]ethyl, 2-(2,4-difluorophenyl)ethyl, 2-(difluoromethoxy)-5-fluorophenylmethyl, 2-phenylpropyl, 3-phenylpropyl, 3-methyl-3-phenylbutyl, 2-(benzyl-oxy)ethyl; 5-ethylfuran-2-ylmethyl, 5-(trifluoromethyl)furan-2-ylmethyl, 4-(propan-2-yl)-1,3-thiazol-2-ylmethyl, 2-methyl-1,3-thiazol-4-ylmethyl, 2-trifluoromethyl-1,3-thiazol-4-ylmethyl, 1-ethylpyrazol-5-ylmethyl, 1-(2-propyl)pyrazol-5-ylmethyl, 1-ethylimidazol-5-ylmethyl, 1-ethylimidazol-2-ylmethyl, 1-propylimidazol-2-ylmethyl, 1-benzylimidazol-2-yl)methyl, 1-(2-methylpropyl)-1H-imidazol-5-ylmethyl, 5-tert-butyl-1,3-oxazol-2-ylmethyl, 3-fluoropyridin-2-ylmethyl, 2-methylpyridin-4-ylmethyl, 4-trifluoromethylpyridin-2-ylmethyl, 6-(fluoromethyl)pyridin-2-ylmethyl, 6-trifluoromethylpyridin-2-ylmethyl, 2-(trifluoromethyl)pyridin-4-ylmethyl, 4-methylpyrimidin-2-ylmethyl, 2-(thiophen-3-yl)ethyl, 5-trifluoromethylthiophen-2-ylmethyl, 1-methyl-1H-indol-6-yl)methyl, 1-benzofuran-3-ylmethyl, 1-benzothiophen-3-ylmethyl, 4H,5H,6H-pyrrolo[1,2-b]pyrazol-3-ylmethyl, pyrazolo[1,5-a]pyridin-7-ylmethyl, pyrazolo[1,5-a]pyridin-3-ylmethyl, imidazo[1,2-a]pyridin-3-ylmethyl, 6-methylimidazo[1,2-a]pyridin-3-ylmethyl, imidazo[1,2-a]pyridin-5-ylmethyl, imidazo[1,5-a]pyridin-1-ylmethyl, imidazo[1,5-a]pyridin-3-ylmethyl, imidazo[1,5-a]pyridin-5-ylmethyl, pyrazolo[1,5-c]pyrimidin-3-ylmethyl, 3-(furan-2-yl)prop-2-en-1-yl; 3-trifluormethylcyclobutylmethyl, 3-fluoro-3-phenylcyclobutylmethyl, cyclohexylmethyl, 4-methylcyclo-hexylmethyl, 4-trifluoromethylcyclohexylmethyl, 4-methoxycyclohexylmethyl, 4,4-dimethylcyclohexylmethyl, 4,4-difluorocyclohexylmethyl, 3-trifluoromethyl-bicyclo[1.1.1]petan-1-ylmethyl, bicyclo[2.2.1]heptan-2-ylmethyl, bicyclo[2.2.2]octan-2-ylmethyl, bicyclo[2.2.1]hept-5-en-2-ylmethyl, 6,6-dimethylbicyclo[3.1.1]hept-2-en-2-yl]methyl; 3,3-dimethyltetrahydrofuran-2-ylmethyl, 1,1-dioxothian-4-ylmethyl, 2-(thian-4-yl)ethyl; 2,2-dimethyl-4,4,4-trifluoropentyl, 4,4,4-trifluorobutyl, 4,4,4-trifluoro-3-methylbutyl, 3,3-dimethyl-4,4,4-trifluorobutyl, 3,3,3-trifluoroprop-1-yn-1-yl; and $R^2$ represents —C(═O)—OH, —C(═O)—ONa, —C(═O)—OCH$_3$, —C(═O)—NH$_2$, —C(═O)—NHCH$_3$, —C(═O)—NHCH$_2$CH$_3$, —C(═O)—NH(CH$_2$)$_2$CH$_3$, —C(═O)—N(H)-cyclopropyl, —C(═O)—N(H)-(1-hydroxymethyl)cyclobutan-1-yl, —C(═O)—N(H)—CH$_2$CH$_2$—OH, —C(═O)—N(H)—CH$_2$CH$_2$—OCH$_3$, —C(═O)—N(H)—CH$_2$—C(H)(OH)—CH$_3$, —C(═O)—N(H)—CH$_2$C(CH$_3$)$_2$OH, —C(═O)—N(H)—C(H)(CH$_3$)—CH$_2$OH, —C(═O)—N(H)—C(H)(CH$_2$CH$_3$)—CH$_2$OH, —C(═O)—N(H)—C(H)(CH$_2$OH)—CH$_2$CH$_2$—O—CH$_3$, —C(═O)—N(H)—C(CH$_3$)$_2$CH$_2$CH$_2$OH, —C(═O)—N(H)—C(H)(CH$_2$OH)-phenyl, —C(═O)—N(H)—C(CH$_3$)(CH$_2$OH)-phenyl, —C(═O)—N(H)—C(H)(CH(OH)CH$_3$)-phenyl, —C(═O)—N(H)—CH$_2$—1 H-1-methylimidazol-2-yl, —C(═O)—N(H)—(CH$_2$)$_2$—1H-imidazol-1-yl, —C(═O)—N(H)—CH$_2$-pyridin-2-yl, —C(═O)—N(H)—CH$_2$-pyridin-3-yl, —C(═O)—N(H)—CH$_2$—pyridin-4-yl, —C(═O)—N(H)—C(H)(CH$_2$OH)-pyridin-2-yl, —C(═O)—N(H)—CH$_2$— 1,3-pyrimidin-2-yl, —C(═O)—N(H)—CH$_2$—1,3-pyrimidin-4-yl, —C(═O)—N(H)—CH$_2$-pyridazin-2-yl, —C(═O)—NH—C(CH$_2$OH)-cyclobutyl, —C(═O)—3-hydroxy-pyrrolidin-1-yl, —NH—C(═O)—CH═CH$_2$, —NH—C(═O)—CF═CH$_2$, —NH—C(═O)—CH$_2$Cl, —NH—C(═O)—C≡CH, —CH$_2$—NH—C(═O)—CH═CH$_2$, —CH$_2$—NH—C(═O)—CH$_2$Cl, —S(═O)—CH$_3$, —S(═O)$_2$—CH$_3$, —S(═O)$_2$—OH, —S(═O)$_2$—NH$_2$, —S(═O)$_2$—NHCH$_3$, —S(═O)(═NH)—N(CH$_3$)$_2$, —S(═O)(═N—CH$_3$)—N(CH$_3$)$_2$, —S(═O)(═N—CH$_3$)—OH, —S(═O)(═NH)—CH$_3$, —P(═O)(OH)$_2$, F, —CN; preferably —C(═O)—OH, —C(═O)—ONa.

In yet a further particular embodiment, PE8, the compound of the present invention is a tricyclic heterocycle of formula I-A, or any N-oxide, solvate, tautomer or stereoisomer thereof and/or any pharmaceutically acceptable salt of each of the foregoing, including mixtures thereof in all ratios, wherein wherein Ring A represents a five-membered heteroaromatic ring selected from the group consisting of the following ring moieties:

A-1a

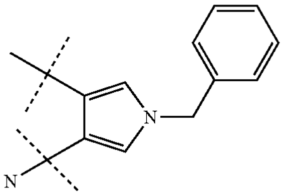

;

A-4a

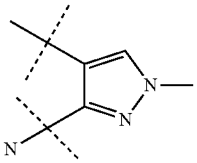

,

A-4b

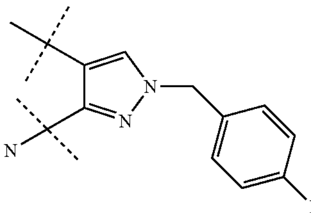

,

A-4c

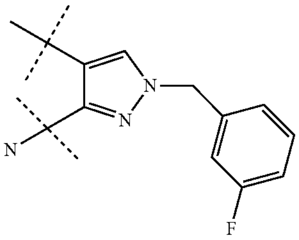

,

A-4d

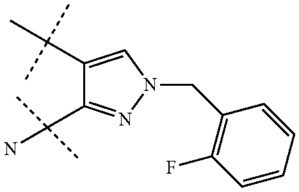

,

A-4e

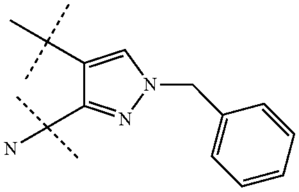

,

A-4f

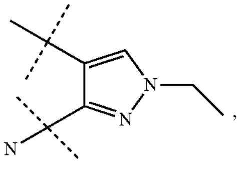

,

A-4g

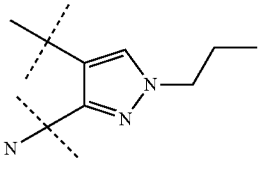

,

-continued
A-4h
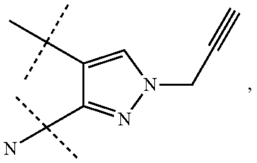
A-4i
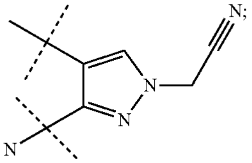
A-5a
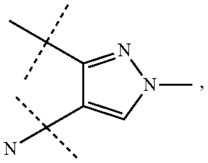
A-5b
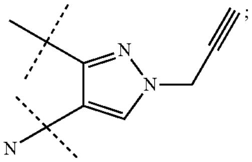
A-7a
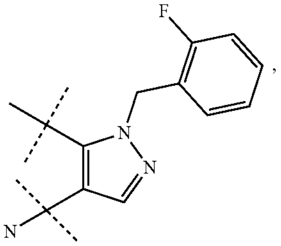
A-7b
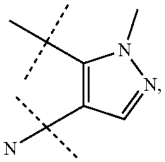
A-9a
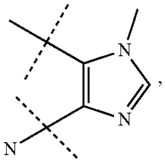
A-9b
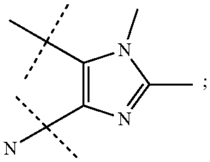
A-10a
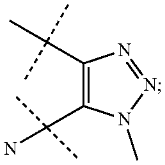
-continued
A-12a
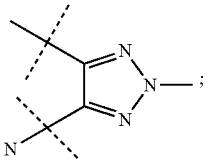
A-13a
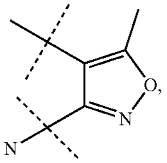
A-13b
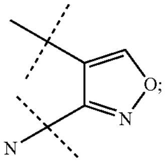
A-15a
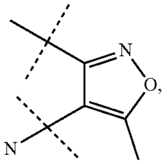
A-15b
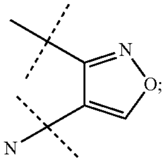
A-17a
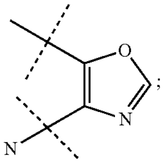
A-19a
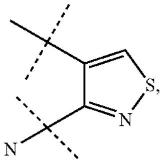
A-19b
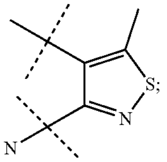
A-21a
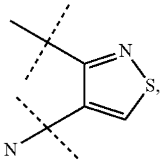

-continued

A-21b

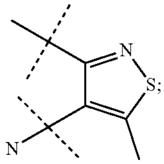

;

A-23a

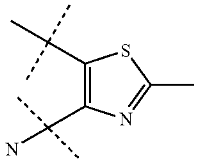

,

A-23b

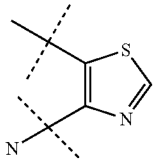

,

A-23c

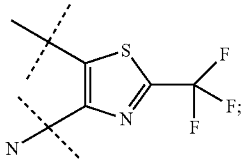

;

A-24a

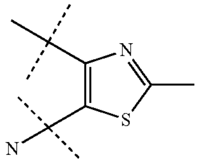

,

A-24b

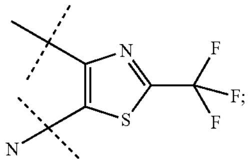

;

$Z^1$ is CH;

$Z^2$ is CH;

$Z^3$ is CH or N;

$R^1$ represents phenyl, 3-fluorophenyl, 4-fluorophenyl, 4-chlorophenyl, 4-methylphenyl, 4-ethylphenyl, 4-difluoromethylphenyl, 3-trifluoromethylphenyl, 4-trifluoromethylphenyl, 4-(1,1-difluorethyl)phenyl, 4-(2,2,2-trifluorethyl)phenyl, 4-(1-trifluoromethylcyclopropyl)-phen-1-yl, 4-cyclopentylphenyl, 4-ethoxyphenyl, 4-difluormethoxyphenyl, 4-trifluoromethoxyphenyl, 3-(trifluoromethyl)sulfanylphenyl, 4-(trifluoromethyl)sulfanylphenyl, 3-trifluoromethyl-4-methylphenyl, 2-fluoro-4-trifluoromethylphenyl, 2-fluoro-4-trifluoromethoxyphenyl, 3-fluoro-4-(n-propyl)phenyl, 2,3-dimethyl-4-methoxyphenyl, 6-fluoronaphth-2-yl; 5-trifluoromethylfuran-2-yl; 5-trifluoromethylthiophen-2-yl, 2-trifluoromethyl-1,3-thiazol-4-yl, 3-fluoropyridin-2-yl, 6-methylpyridin-3-yl, 6-methoxypyridin-3-yl, 3-ethylpyridin-2-yl, 6-ethylpyridin-3-yl, 4-difluoromethylpyridin-2-yl, 4-trifluoromethylpyridin-2-yl, 4-trifluoromethoxypyridin-2-yl, 4-cyanopyridin-2-yl, 5-trifluoromethylpyridin-2-yl, 6-trifluoromethylpyridin-2-yl, 6-trifluoromethylpyridin-3-yl (2-trifluoromethylpyridin-5-yl), 6-trifluoromethoxypyridin-3-yl (2-trifluoromethoxypyridin-5-yl), 5-cyanopyridin-2-yl, 5-cyanomethylpyridin-2-yl, 5-methanesulfonylpyridin-2-yl, 6-methoxypyridin-2-yl, 4-methylpyrimidin-2-yl, 4-ethylpyrimidin-2-yl, 4-methylsulfanylpyrimidin-2-yl, 5-cyclopropylpyrimidin-2-yl, 5-ethyl-pyrimidin-2-yl, 5-difluoromethylpyrimidin-2-yl, 5-trifluoromethylpyrimidin-2-yl, 5-cyanopyrimidin-2-yl, 5-cyano-3-fluoropyridin-2-yl, 5-cyano-6-methylpyridin-2-yl, 3-fluoro-5-(trifluoromethyl)pyridin-2-yl, 5-oxo-5H,6H,7H-cyclopenta[b]pyridin-2-yl, 5,6,7,8-tetrahydroquinolin-2-yl, 5-oxo-5,6,7,8-tetrahydroquinolin-2-yl, 5H,6H,7H-cyclopenta[b]pyridin-2-yl, quinolin-2-yl, isoquinolin-3-yl, 6-methylquinolin-2-yl, 8-methoxyquinolin-4-yl, furo[3,2-b]pyridin-5-yl, quinazolin-2-yl, 6-fluoroquinazolin-2-yl, 1,5-naphthyridin-2-yl; 3-methylcyclobutyl, cyclopentyl, 3-methylcyclopentyl, 3,3-dimethylcyclopentyl, 3-trifluoromethyl-bicyclo[1.1.1]petan-1-yl, cyclohexyl, 4-methylcyclohexyl, 4-(trifluoromethyl)cyclohexyl, 4,4-difluorocyclohexyl, cyclohex-1-enyl, 2-oxocycloheptyl, 6,6-difluorospiro[3.3]heptan-2-yl, 1H-inden-2-yl; benzenesulfonyl (phenylsulfonyl), 3-methylphenylsulfonyl, benzyl, 2-ethoxyphenylmethyl, 3-chlorophenylmethyl, 3-fluorophenylmethyl, 4-chlorophenylmethyl, 3-(pyrrolidine-1-yl)phenylmethyl, 3-methylphenylmethyl, 4-methylphenylmethyl, 3-ethylphenylmethyl, 3-(propan-2-yl)phenylmethyl, 3-tert-butylphenylmethyl, 3-(difluoromethoxy)phenylmethyl, 2-(difluoromethyl)phenylmethyl, 3-(difluoromethyl)phenylmethyl, 3-(trifluoromethyl)phenylmethyl, 4-(trifluoromethyl)phenyl]methyl, 2-(prop-2-yn-1-yloxy)phenylmethyl, 3-(1,3-thiazol-2-yl)phenylmethyl, 3-(trifluoromethyl)sulfanylphenylmethyl, 3-methanesulfonylphenylmethyl, 3-(dimethylamino)phenylmethyl, 3-(pyrrol-1-yl)phenylmethyl, 2-methyl-3-methoxyphenylmethyl, 3-trifluoromethyl-5-methylphenylmethyl, 2-methyl-3-(trifluoromethyl)phenylmethyl, 3-trifluoromethyl-4-fluorophenylmethyl, 2-fluoro-5-(trifluoromethoxy)phenylmethyl, 2-methoxy-3-trifluoromethoxyphenylmethyl, 2-fluoro-3-methoxyphenylmethyl, 2-fluoro-3-(trifluoromethyl)phenyl]methyl, 2-fluor-3-fluoromethoxyphenylmethyl, 2-trifluoromethoxy-5-fluorophenylmethyl, 2-fluor-5-chlor-phenylmethyl, 3-fluoro-5-methylphenyl)methyl, 3,5-difluorophenylmethyl, 5-fluoro-2-(trifluoromethyl)phenylmethyl, 3-fluoro-5-(trifluoromethyl)phenylmethyl, 2-chloro-3-(trifluoromethyl)phenylmethyl, naphthalin-1-ylmethyl, 5,6,7,8-tetrahydronaphthalen-1-ylmethyl, 2,3-dihydro-1-benzofuran-7-ylmethyl, 3,4-dihydro-2H-1-benzopyran-8-ylmethyl, 2-phenylethyl, 2-(2-methyl-phenyl)ethyl, 2-(2-methoxyphenyl)ethyl, 2-(3-methoxyphenyl)ethyl, 2-(4-methoxyphenyl)ethyl, 2-(2-fluorophenyl)-ethyl, 2-(3-fluorophenyl)-ethyl, 2-(4-fluorophenyl)-ethyl, 2-(2-chlorophenyl)-ethyl, 2-(4-chlorophenyl)-ethyl, 2-(4-bromophenyl)-ethyl, 2-[4-(trifluoromethyl)phenyl]ethyl, 2-(2,4-difluorophenyl)ethyl, 2-(difluoromethoxy)-5-fluorophenylmethyl, 2-phenylpropyl, 3-phenylpropyl, 3-methyl-3-phenylbutyl, 2-(benzyl-oxy)ethyl; 5-ethylfuran-2-ylmethyl, 5-(trifluoromethyl)furan-2-ylmethyl, 4-(propan-2-yl)-1,3-thiazol-2-ylmethyl, 2-methyl-1,3-thiazol-4-ylmethyl, 2-trifluoromethyl-1,3-thiazol-4-ylmethyl, 1-ethylpyrazol-5-ylmethyl, 1-(2-propyl)pyrazol-5-ylmethyl, 1-ethylimidazol-5-ylmethyl, 1-ethylimidazol-2-ylmethyl, 1-propylimidazol-2-ylmethyl, 1-benzylimidazol-2-yl)methyl, 1-(2-methylpropyl)-1H-imidazol-5-ylmethyl, 5-tert-butyl-1,3-oxazol-2-ylmethyl, 3-fluoropyridin-2-ylmethyl, 2-methylpyridin-4-ylmethyl, 4-trifluoromethylpyridin-2-ylmethyl, 6-(fluoromethyl)pyridin-2-ylmethyl, 6-trifluoromethylpyridin-2-ylmethyl, 2-(trifluoromethyl)pyridin-4-ylmethyl, 4-methylpyrimidin-2-ylmethyl, 2-(thiophen-3-yl)ethyl, 5-trifluoromethylthiophen-2-ylmethyl, 1-methyl-1H-indol-6-yl)methyl, 1-benzofuran-3-ylmethyl, 1-benzothiophen-3-ylmethyl, 4H,5H,6H-pyrrolo[1,2-b]pyrazol-3-ylmethyl, pyrazolo[1,5-a]pyridin-7-ylmethyl, pyrazolo[1,5-a]pyridin-3-ylmethyl, imidazo[1,2-a]pyridin-3-ylmethyl, 6-methylimidazo[1,2-a]pyridin-3-ylmethyl, imidazo[1,2-a]pyridin-5-ylmethyl, imidazo[1,5-a]pyridin-1-ylmethyl, imidazo[1,5-a]pyridin-3-ylmethyl, imidazo[1,5-a]pyridin-5-ylmethyl, pyrazolo[1,5-c]pyrimidin-3-ylmethyl, 3-(furan-2-yl)prop-2-en-1-yl; 3-trifluormethylcyclobutylmethyl, 3-fluoro-3-phenylcyclobutylmethyl, cyclohexylmethyl, 4-methylcyclo-hexylmethyl, 4-trifluoromethylcyclohexylmethyl, 4-methoxycyclohexylmethyl, 4,4-dimethylcyclohexylmethyl, 4,4-difluorocyclohexylmethyl, 3-trifluoromethyl-bicyclo[1.1.1]petan-1-ylmethyl, bicyclo[2.2.1]heptan-2-ylmethyl, bicyclo[2.2.2]octan-2-ylmethyl, bicyclo[2.2.1]hept-5-en-2-ylmethyl, 6,6-dimethylbicyclo[3.1.1]hept-2-en-2-yl]methyl; 3,3-dimethyltetrahydrofuran-2-ylmethyl, 1,1-dioxothian-4-ylmethyl, 2-(thian-4-yl)ethyl; 2,2-dimethyl-4,4,4-trifluoropentyl, 4,4,4-trifluorobutyl, 4,4,4-trifluoro-3-methylbutyl, 3,3-dimethyl-4,4,4-trifluorobutyl, 3,3,3-trifluoroprop-1-yn-1-yl; and $R^2$ represents —C(=O)—OH, —C(=O)—ONa, —C(=O)—$OCH_3$, —C(=O)—$NH_2$, —C(=O)—$NHCH_3$, —C(=O)—$NHCH_2CH_3$, —C(=O)—NH$(CH_2)_2CH_3$, —C(=O)—N(H)-cyclopropyl, —C(=O)—N(H)-(1-hydroxymethyl)cyclobutan-1-yl, —C(=O)—N(H)—$CH_2CH_2$—OH, —C(=O)—N(H)—$CH_2CH_2$—$OCH_3$, —C(=O)—N(H)—$CH_2$—C(H)(OH)—$CH_3$, —C(=O)—N(H)—$CH_2C(CH_3)_2OH$, —C(=O)—N(H)—C(H)($CH_3$)—$CH_2OH$, —C(=O)—N(H)—C(H)($CH_2CH_3$)—$CH_2OH$, —C(=O)—N(H)—C(H)($CH_2OH$)—$CH_2CH_2$—O—$CH_3$, —C(=O)—N(H)—$C(CH_3)_2CH_2CH_2OH$, —C(=O)—N(H)—C(H)($CH_2OH$)-phenyl, —C(=O)—N(H)—C($CH_3$)($CH_2OH$)-phenyl, —C(=O)—N(H)—C(H)(CH(OH)$CH_3$)-phenyl, —C(=O)—N(H)—$CH_2$—1 H-1-methylimidazol-2-yl, —C(=O)—N(H)—$(CH_2)_2$—1H-imidazol-1-yl, —C(=O)—N(H)—$CH_2$-pyridin-2-yl, —C(=O)—N(H)—$CH_2$-pyridin-3-yl, —C(=O)—N(H)—$CH_2$—pyridin-4-yl, —C(=O)—N(H)—C(H)($CH_2OH$)-pyridin-2-yl, —C(=O)—N(H)—$CH_2$— 1,3-pyrimidin-2-yl, —C(=O)—N(H)—$CH_2$—1,3-pyrimidin-4-yl, —C(=O)—N(H)—$CH_2$-pyridazin-2-yl, —C(=O)—NH—C($CH_2OH$)-cyclobutyl, —C(=O)—3-hydroxy-pyrrolidin-1-yl, —NH—C(=O)—CH=$CH_2$, —NH—C(=O)—CF=$CH_2$, —NH—C(=O)—$CH_2Cl$, —NH—C(=O)—C≡CH, —$CH_2$—NH—C(=O)—CH=$CH_2$, —$CH_2$—NH—C(=O)—$CH_2Cl$, —$CH_2$—NH—C(=O)—C≡CH, —S(=O)—$CH_3$, —$S(=O)_2$—$CH_3$, —$S(=O)_2$—OH, —$S(=O)_2$—$NH_2$, —$S(=O)_2$—$NHCH_3$, —S(=O)(=NH)—N$(CH_3)_2$, —S(=O)(=N—$CH_3$)—N$(CH_3)_2$, —S(=O)(=N—$CH_3$)—OH, —S(=O)(=NH)—$CH_3$, —P(=O)$(OH)_2$, F, —CN; preferably —C(=O)—OH, —C(=O)—ONa.

In still another particular embodiment of the invention, PE9, the compound of the present invention is a tricyclic heterocycle of formula I-A or I, or any N-oxide, solvate, tautomer or stereoisomer thereof and/or any pharmaceutically acceptable salt of each of the foregoing, including mixtures thereof in all ratios, wherein $R^1$ is selected from the group consisting of

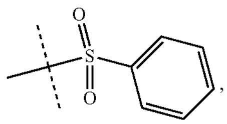,
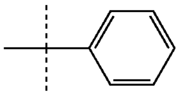,
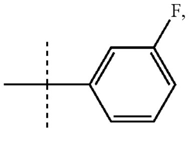
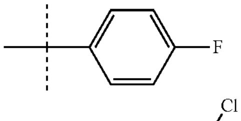
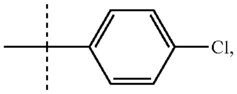
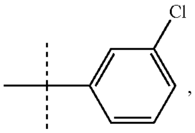,
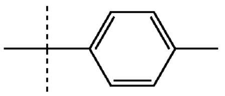,
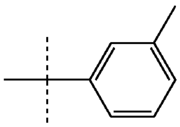,
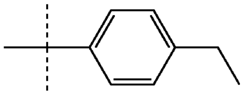,
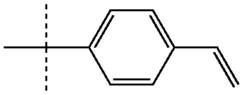,
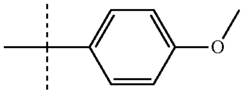,
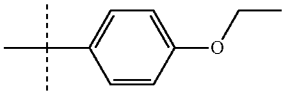,
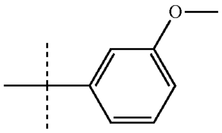,
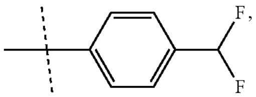
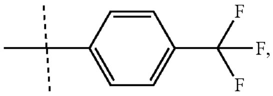
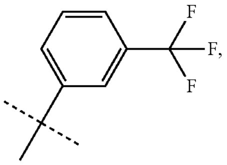
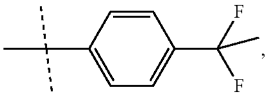,
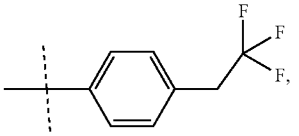
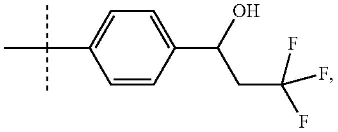

-continued
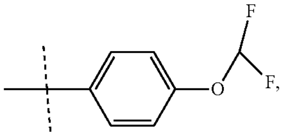
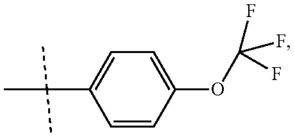
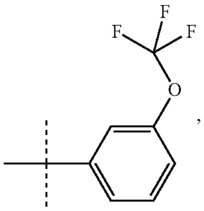
,
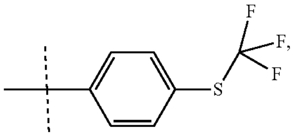
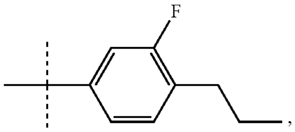
,
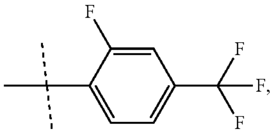
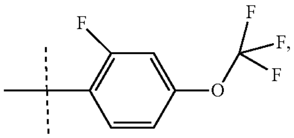
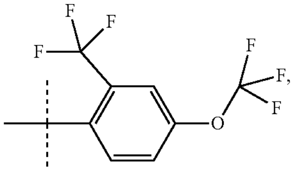
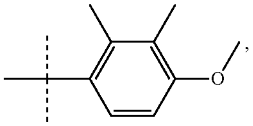
,
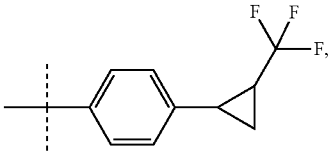
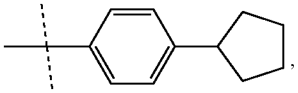
,
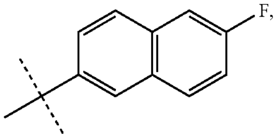
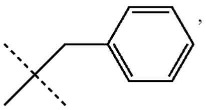
,
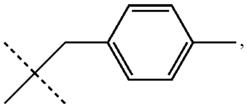
,
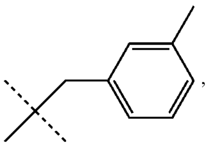
,
-continued
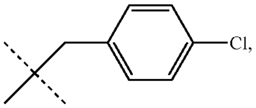
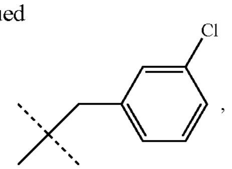
,
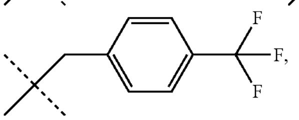
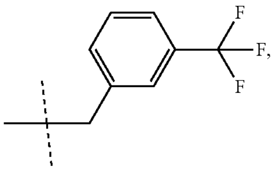
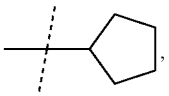
,
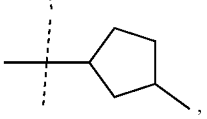
,
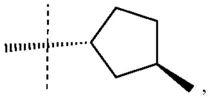
,
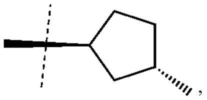
,
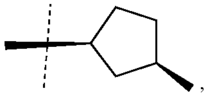
,
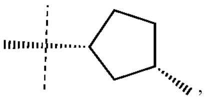
,
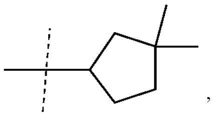
,
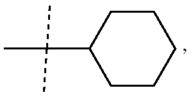
,
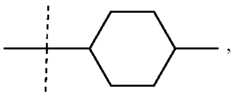
,
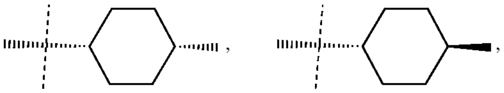
,
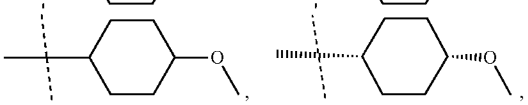
,
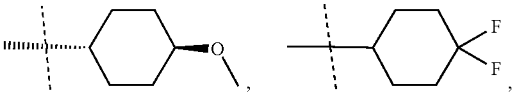
,
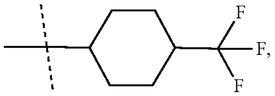
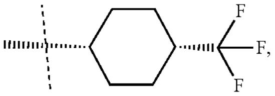
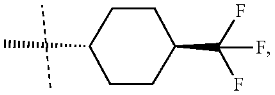
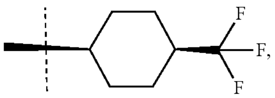
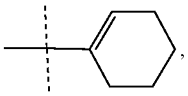
,
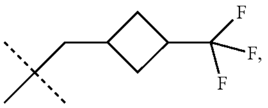
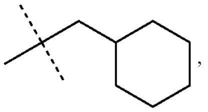
,
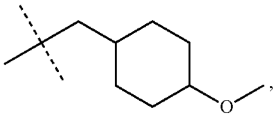
, -continued

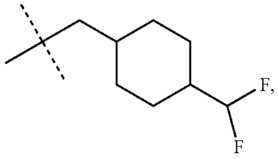

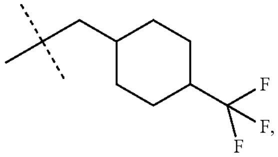

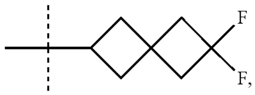

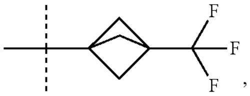,

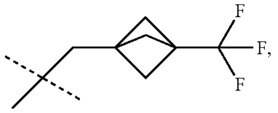

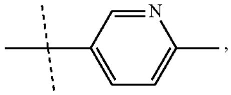

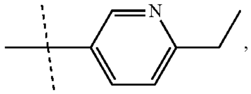

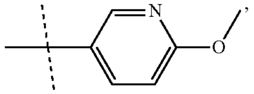

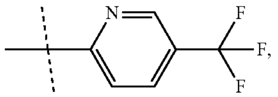

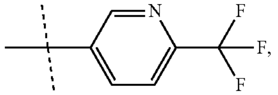

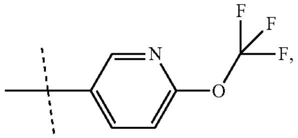

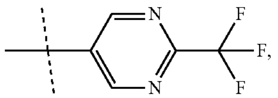

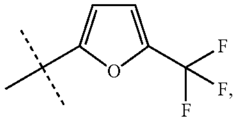

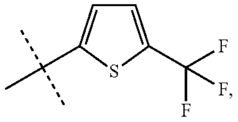

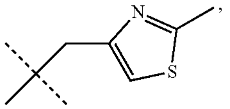

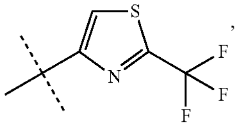

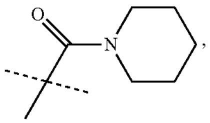

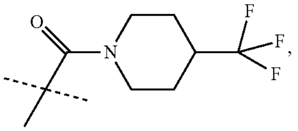

-continued $—CH_3$,

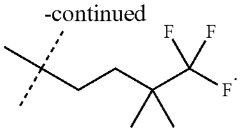

and the remaining radicals and residues are as defined for formula I-A or I above or for any of the further particular embodiments described herein above or below.

In a particular embodiment, PE9a, of PE9

$R^1$ is selected from the group consisting of

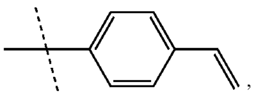

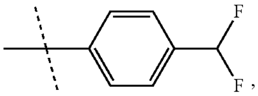

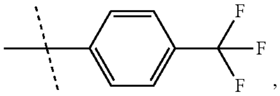

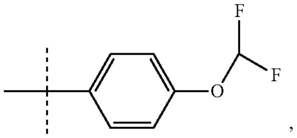

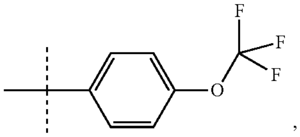

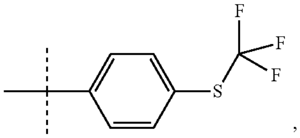

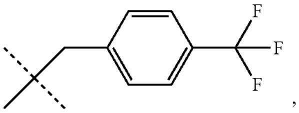

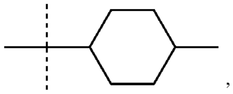

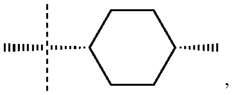

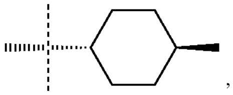

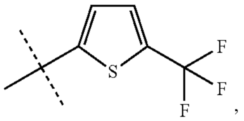

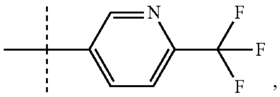

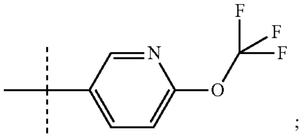

and the remaining radicals and residues are as defined for formula I-A or I above or for any of the further particular embodiments described herein above or below. Especially, $R^1$ is

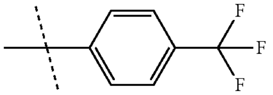

(particular embodiment PE9aa).

In yet another particular embodiment of the invention, PE10, the compound of the present invention is a tricyclic heterocycle of formula I-A or I, or any N-oxide, solvate, tautomer or stereoisomer thereof and/or any pharmaceutically acceptable salt of each of the foregoing, including mixtures thereof in all ratios, wherein $R^2$ is selected from the group consisting of

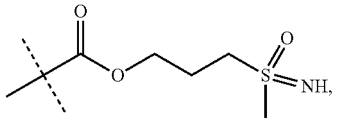

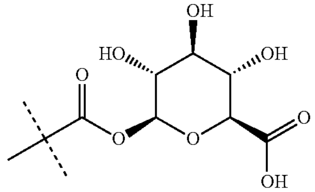

$—COOH$, $—COONa$, $—COOCH_3$, $—COOCH_3$,; $—CN$, $—F$, $—CH_2—CN$, $—B(OH)_2$;

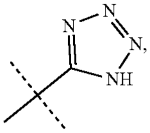 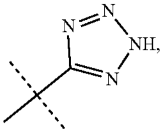 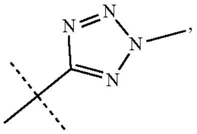

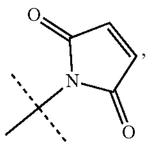 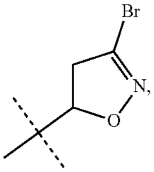 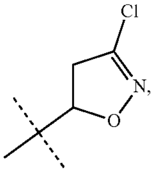

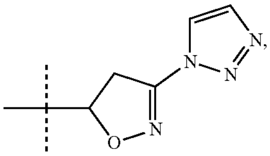 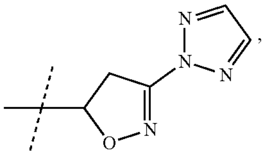

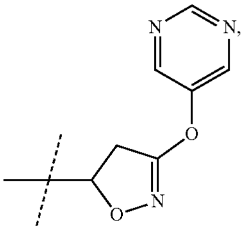 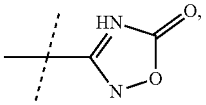

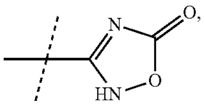 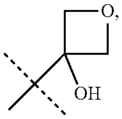 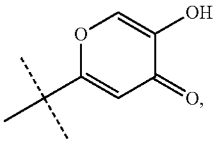

-continued

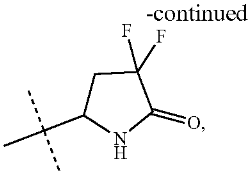 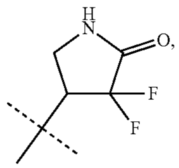

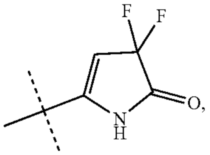 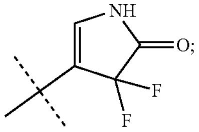

$—C(=O)—NH_2$, 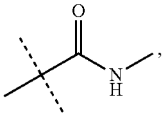

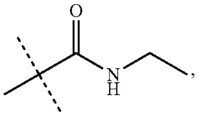 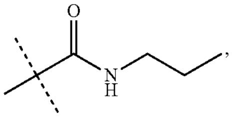

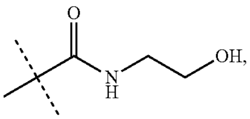 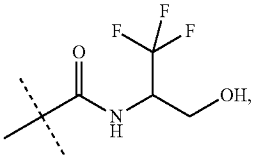

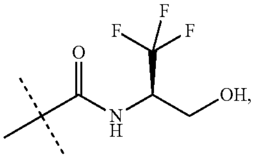 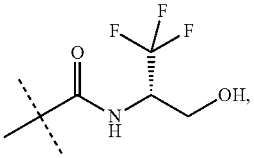

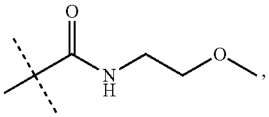

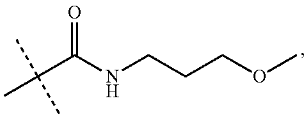

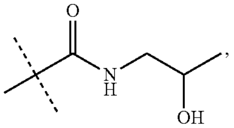 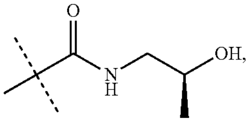

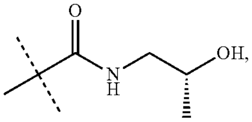 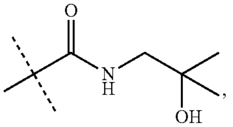

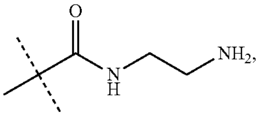 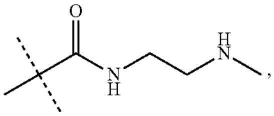

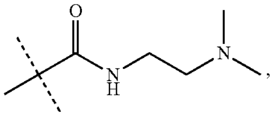

-continued
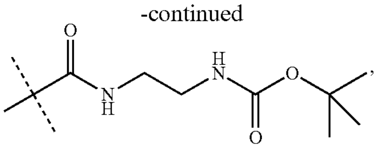
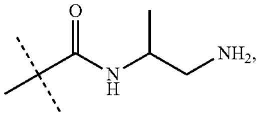
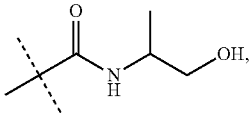
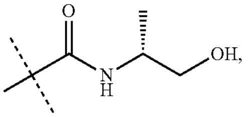
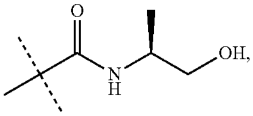
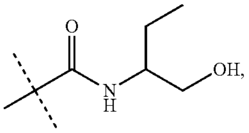
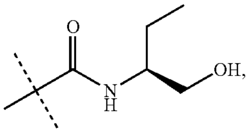
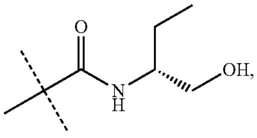
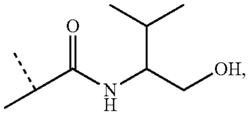
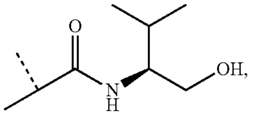
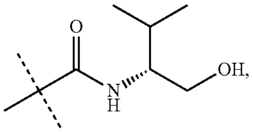
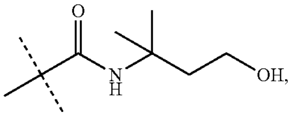
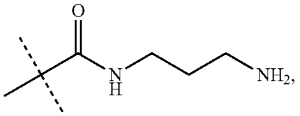
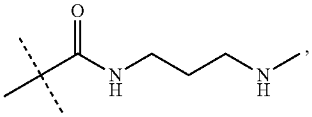
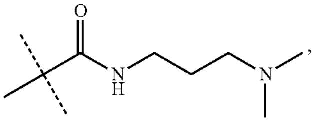
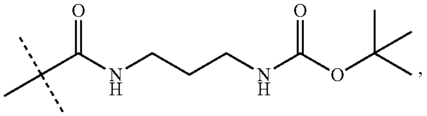
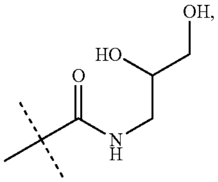
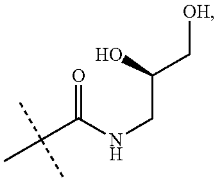
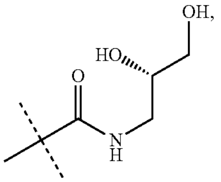
-continued
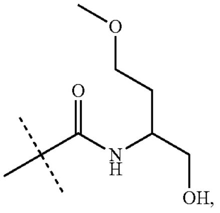
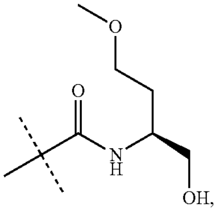
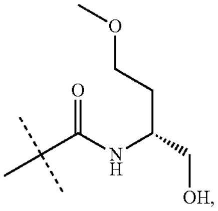
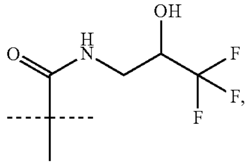
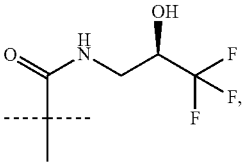
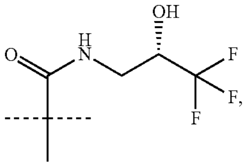
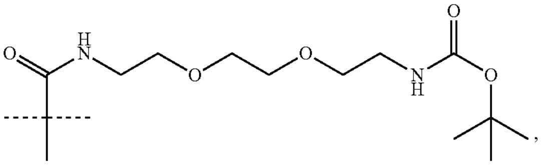
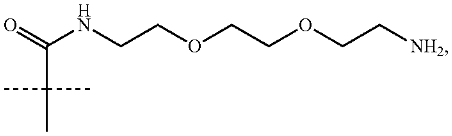
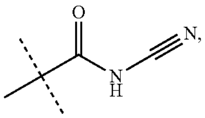
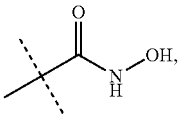
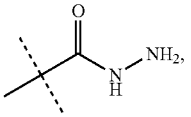
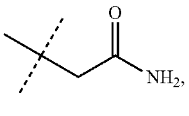
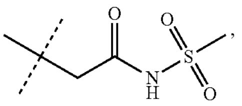
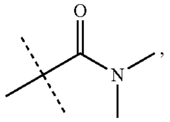
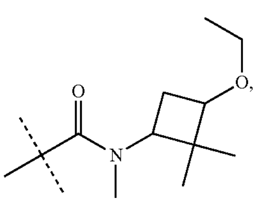
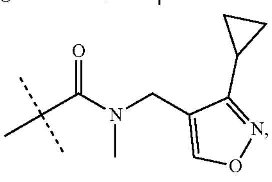
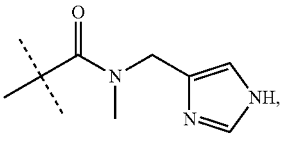
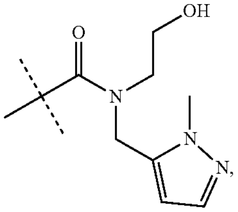

-continued
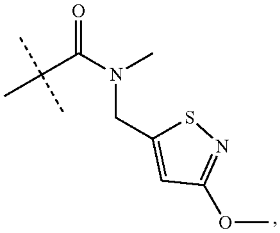
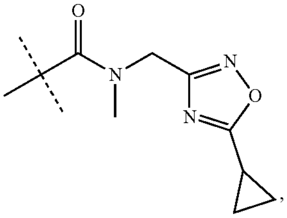
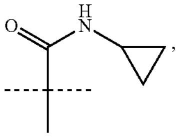
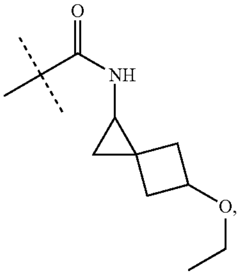
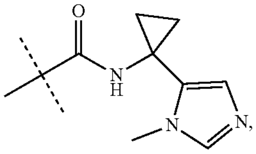
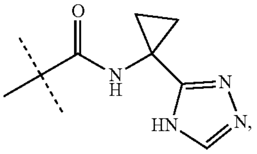
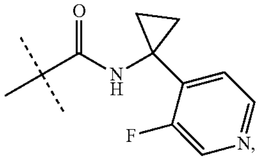
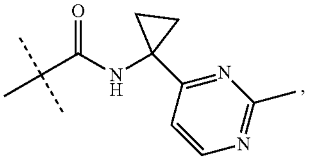
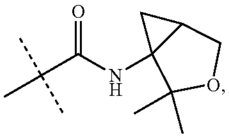
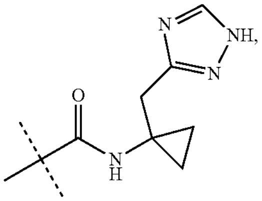
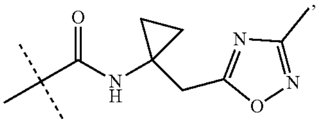
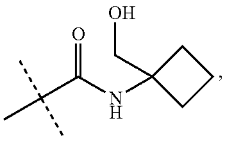
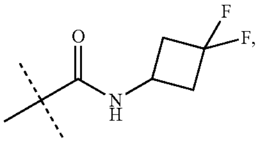
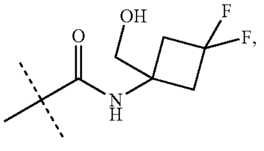
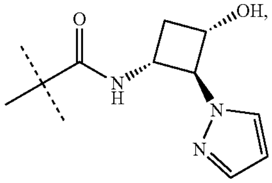
-continued
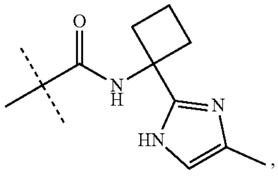
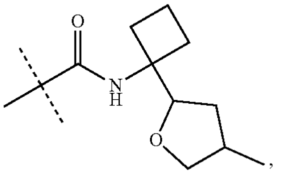
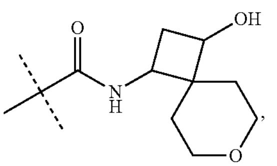
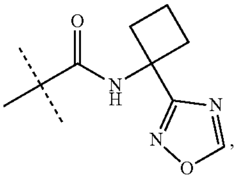
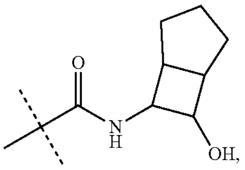
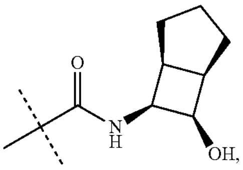
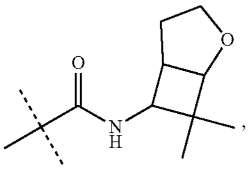
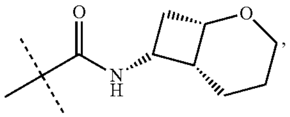
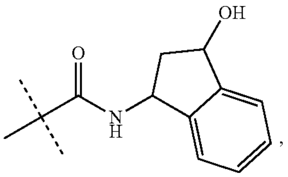
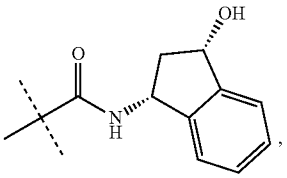
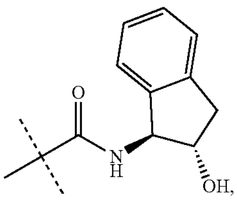
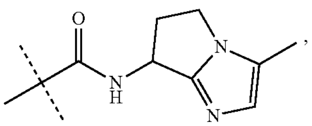
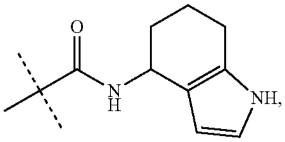
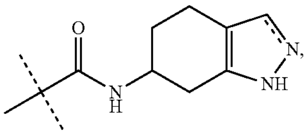
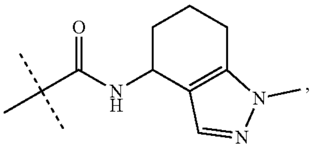

-continued
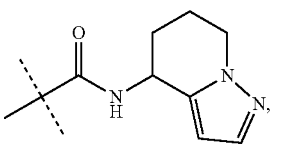
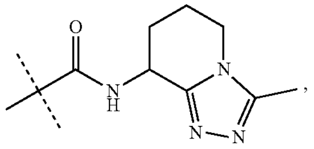
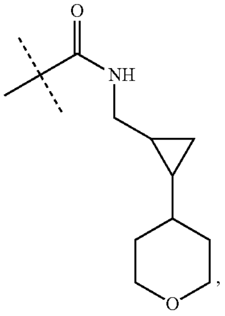
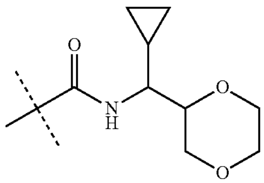
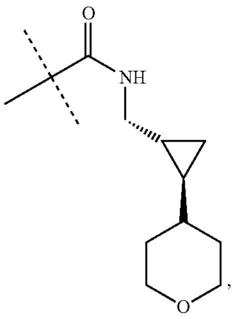
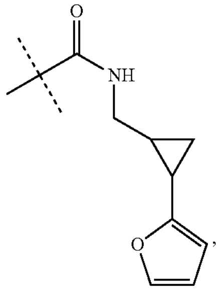
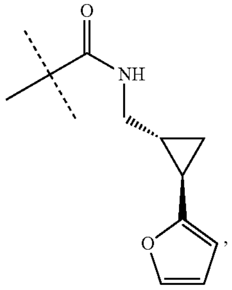
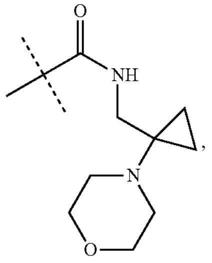
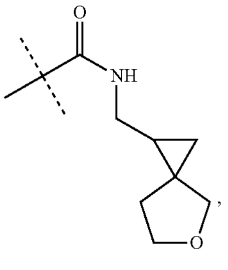
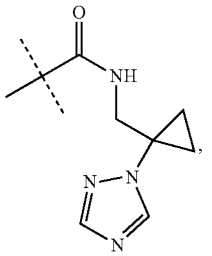
-continued
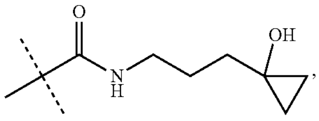
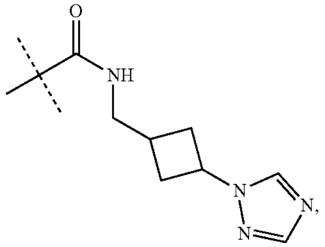
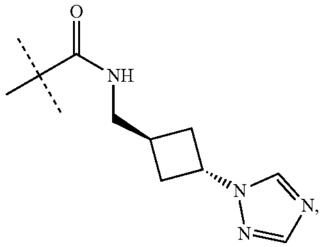
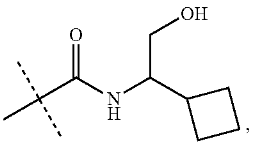
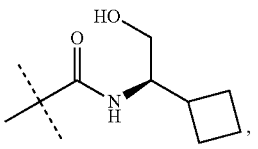
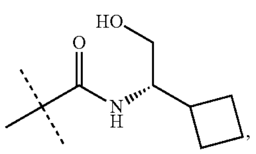
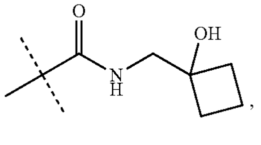
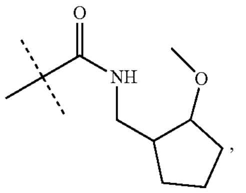
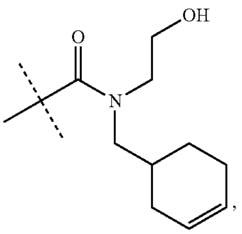
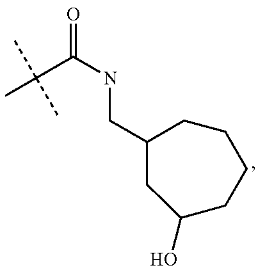
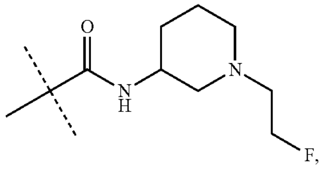
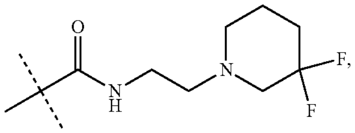

-continued
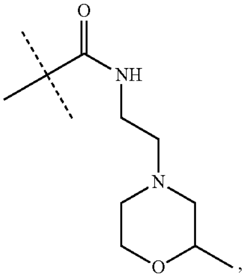
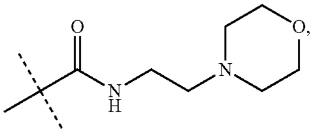
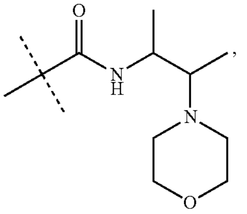
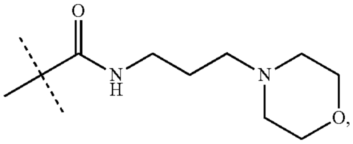
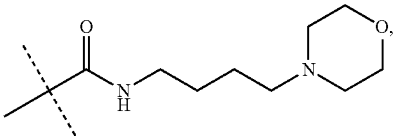
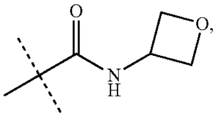
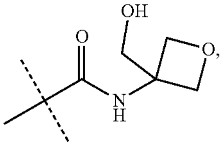
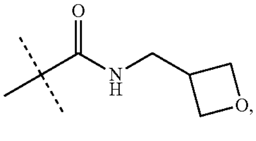
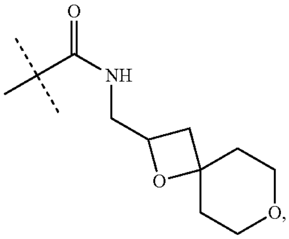
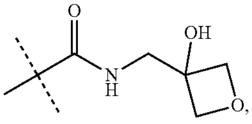
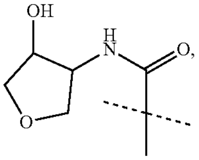
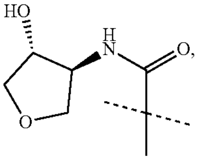
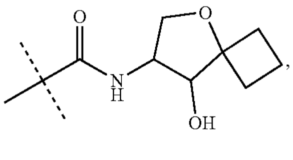
-continued
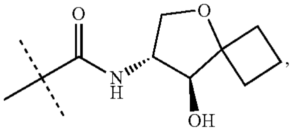
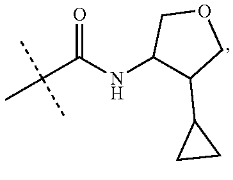
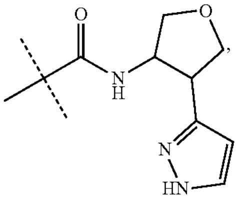
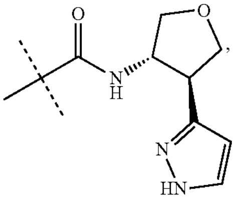
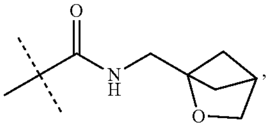
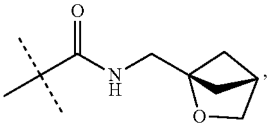
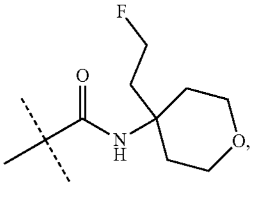
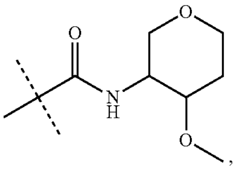
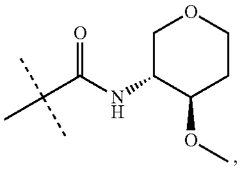
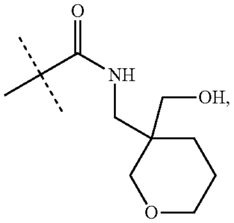
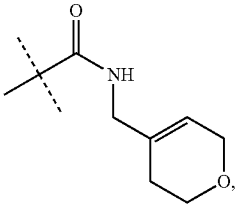
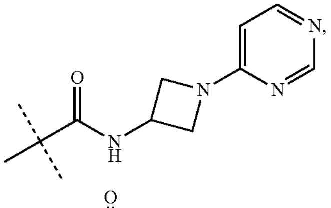
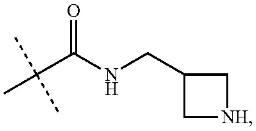
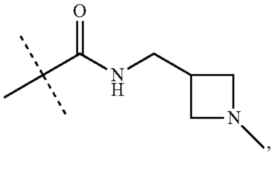

-continued
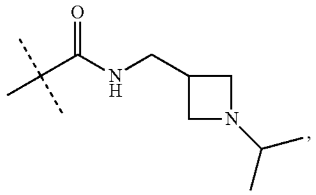
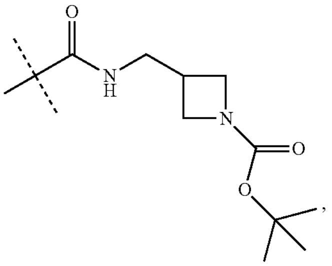
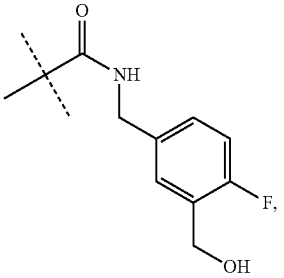
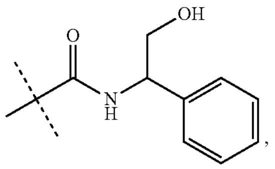
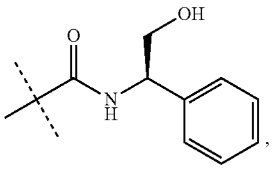
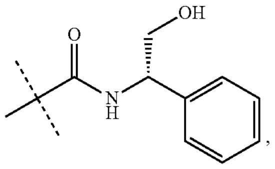
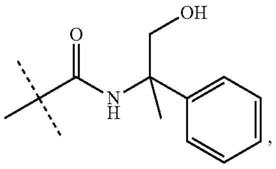
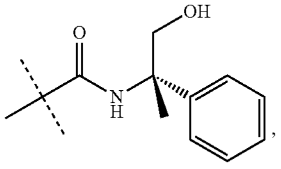
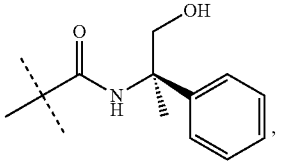
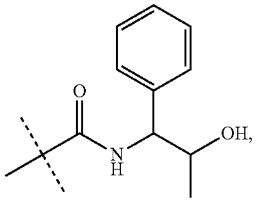
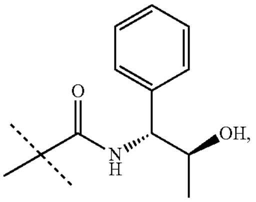
-continued
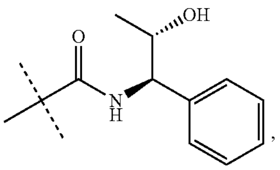
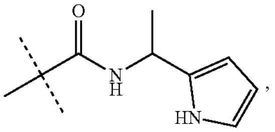
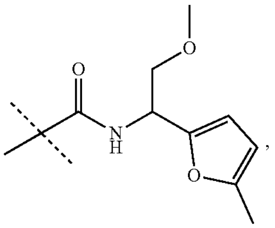
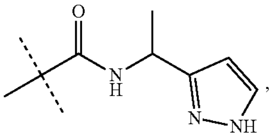
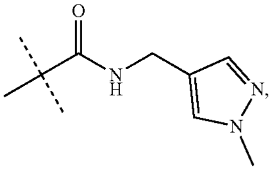
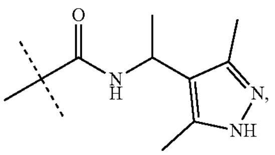
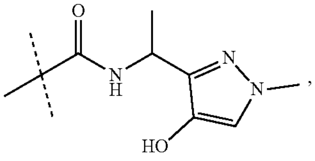
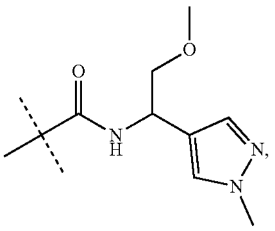
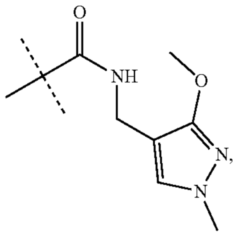
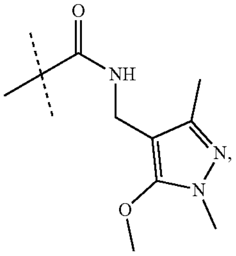
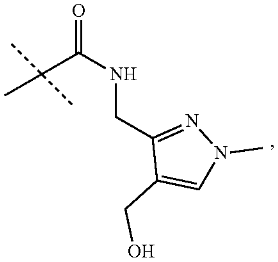

-continued
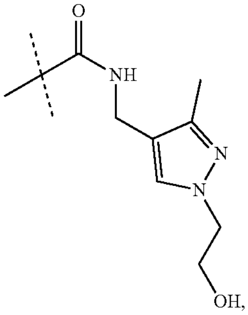
,
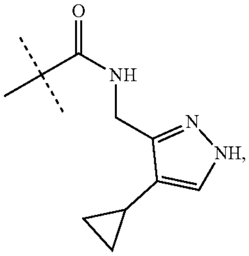
,
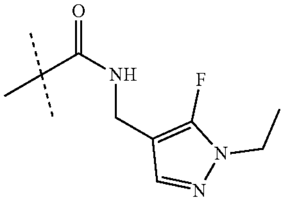
,
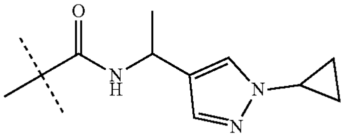
,
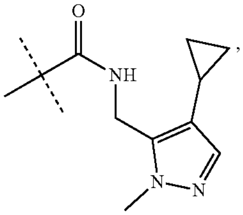
,
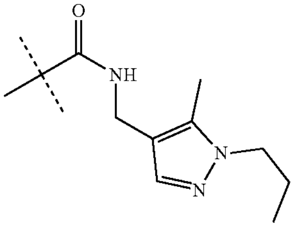
,
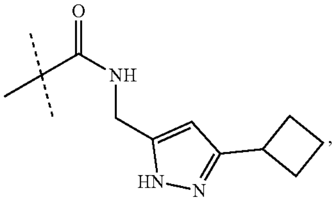
,
-continued
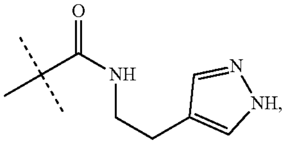
,
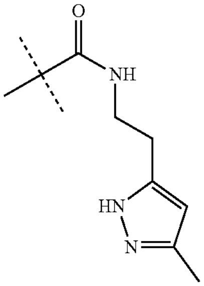
,
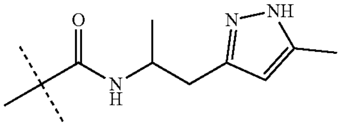
,
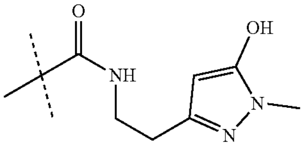
,
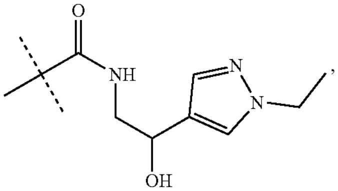
,
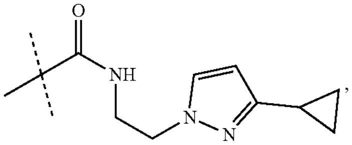
,
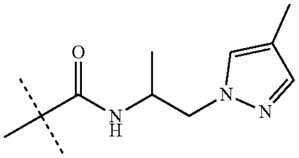
,
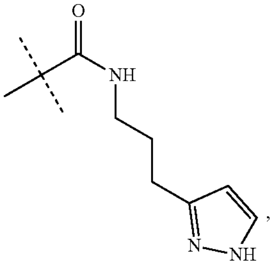
,
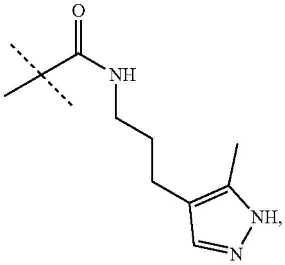
, -continued
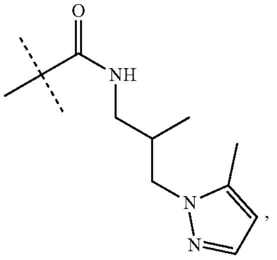
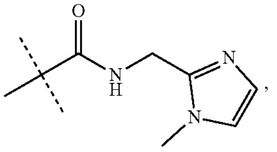
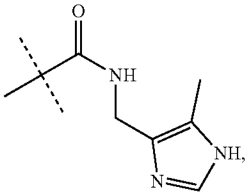
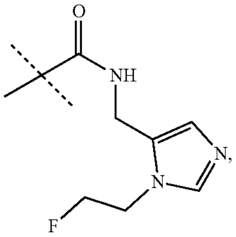
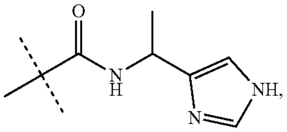
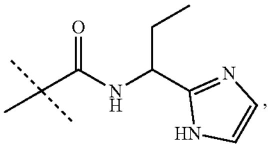
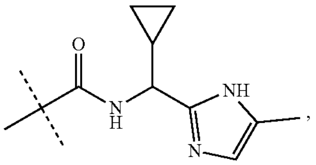
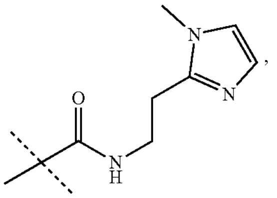
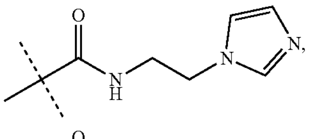
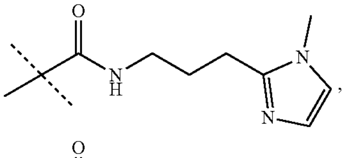
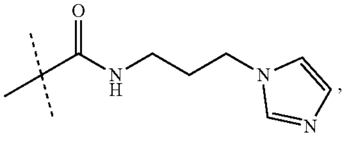
-continued
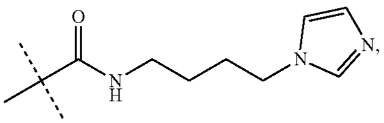
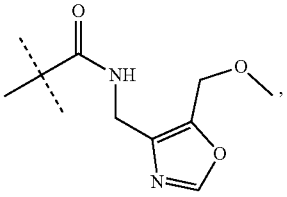
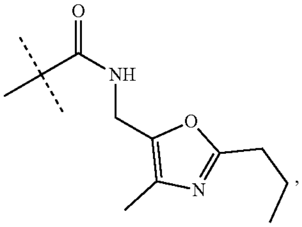
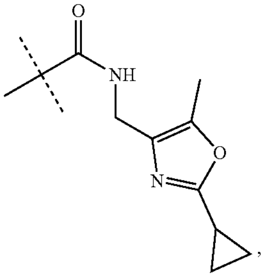
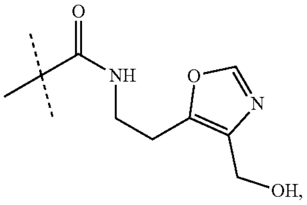
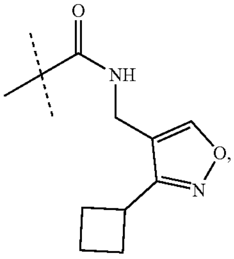
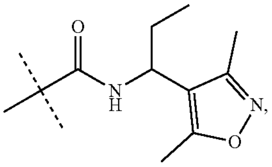
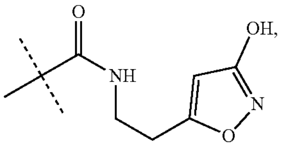
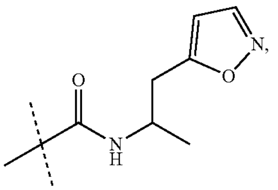

-continued
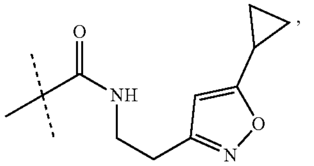
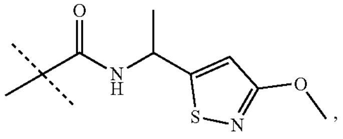
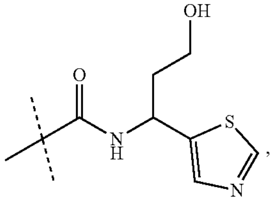
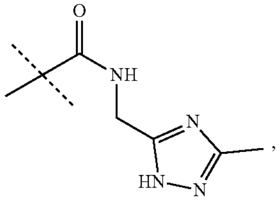
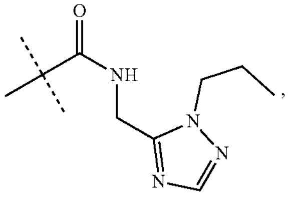
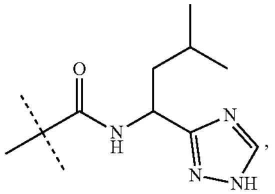
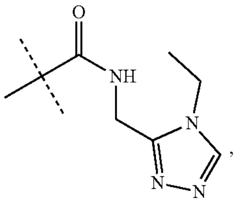
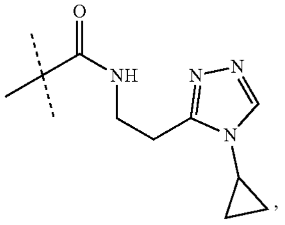
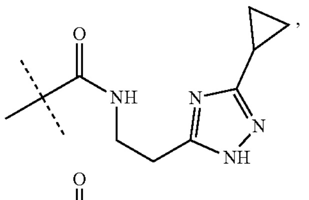
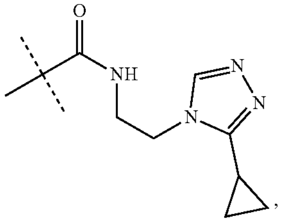
-continued
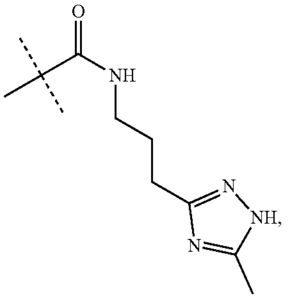
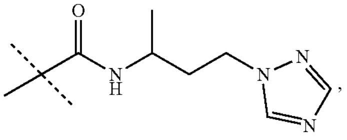
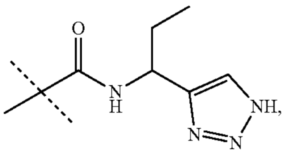
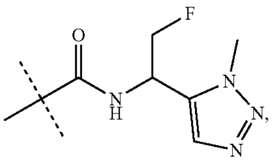
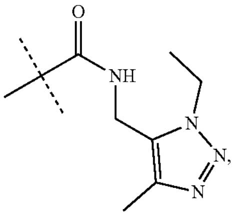
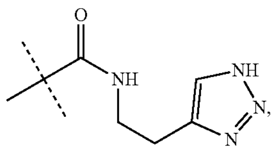
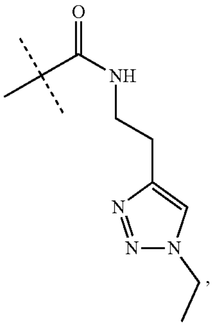
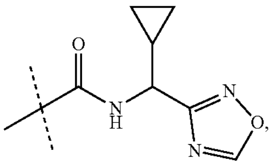
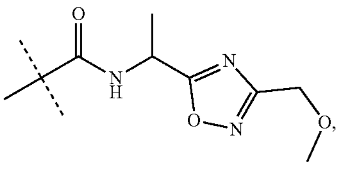

-continued
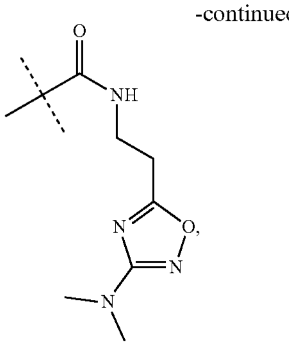,
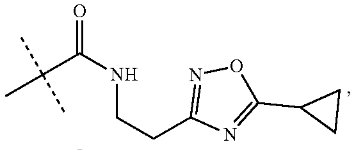,
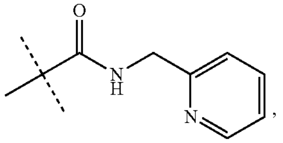,
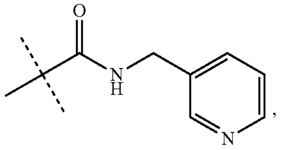,
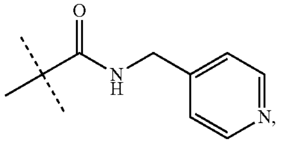,
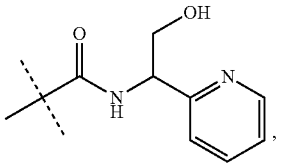,
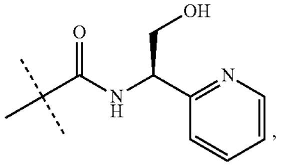,
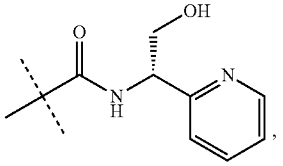,
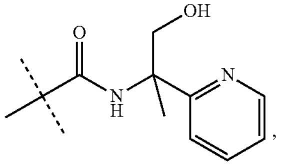,
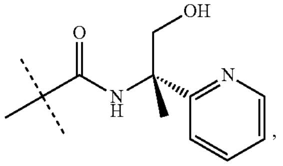,
-continued
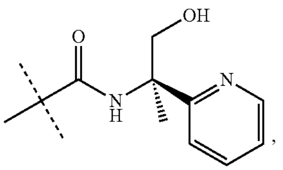,
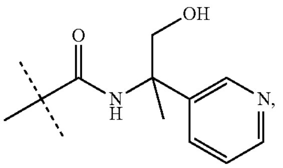,
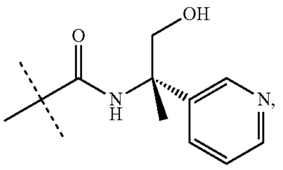,
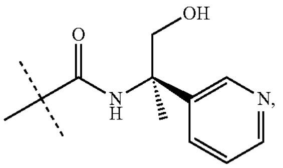,
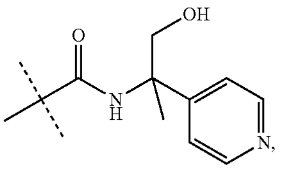,
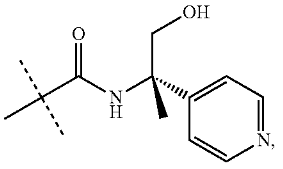,
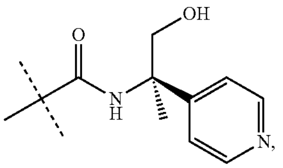,
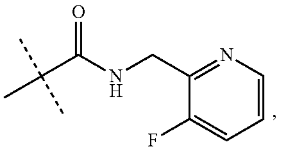,
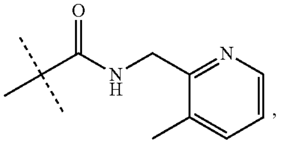,
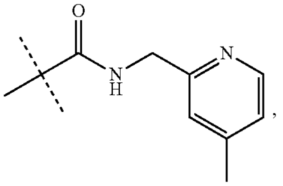, -continued
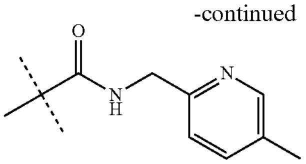,
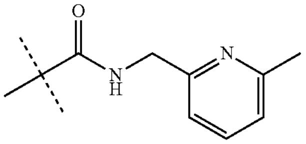,
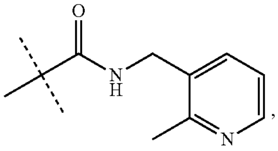,
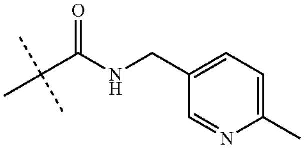,
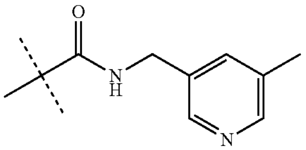,
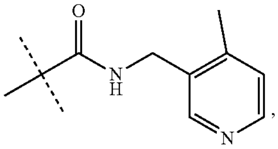,
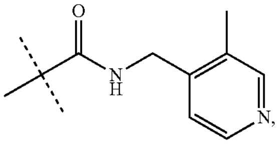,
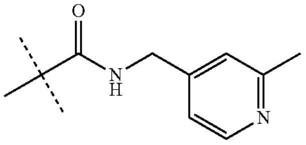,
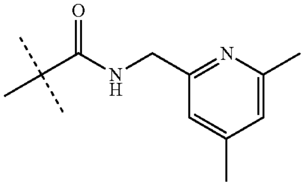,
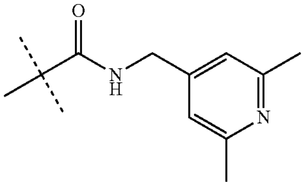,
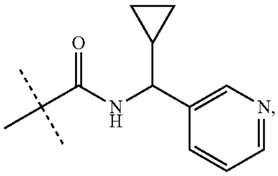,
-continued
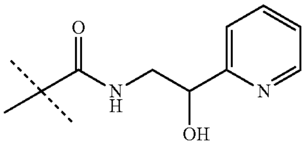,
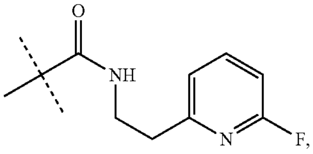,
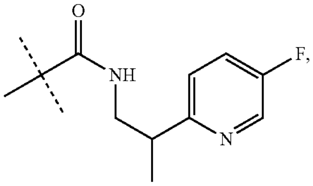,
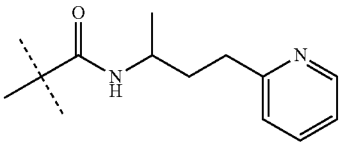,
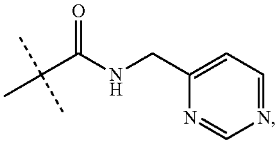,
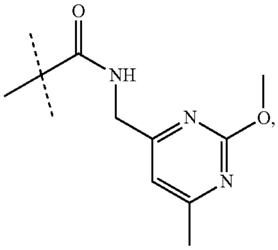,
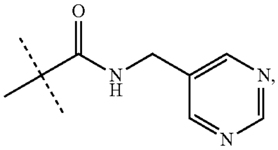,
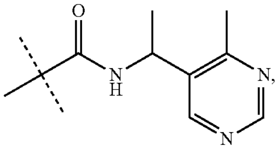,
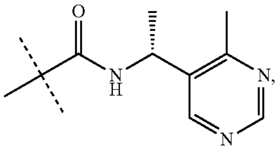,
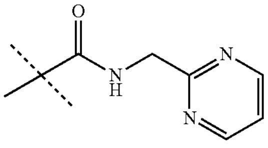, -continued
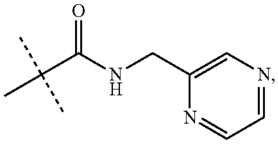
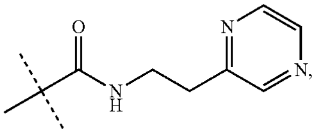
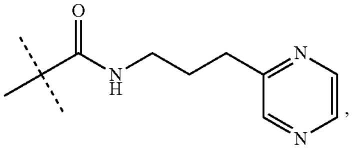
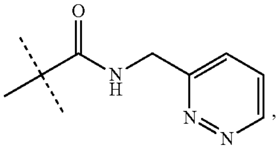
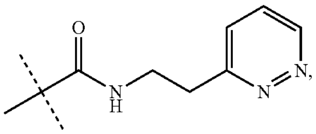
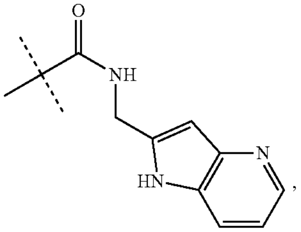
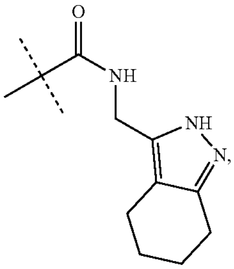
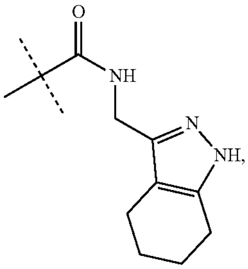
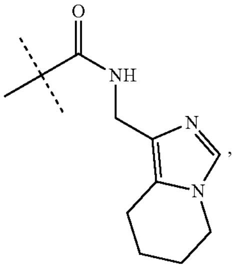
-continued
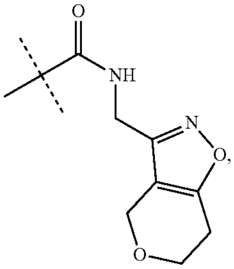
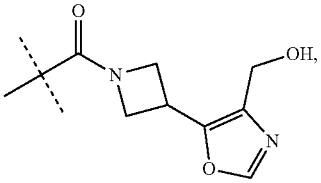
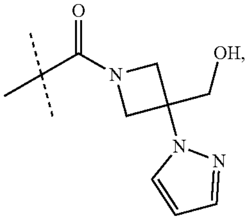
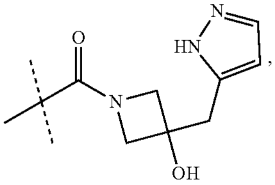
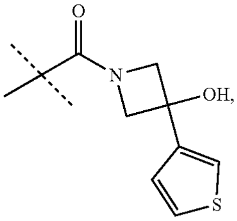
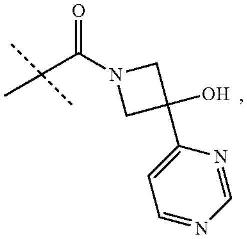
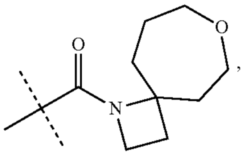
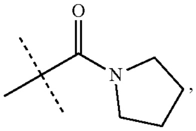
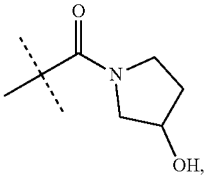
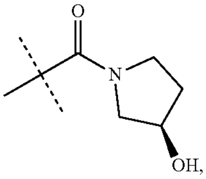
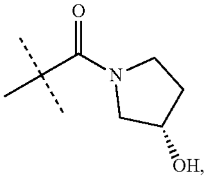
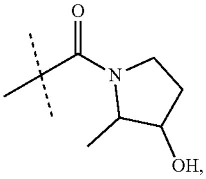

-continued
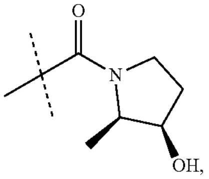
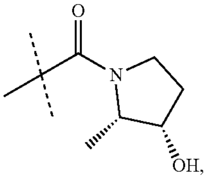
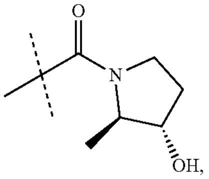
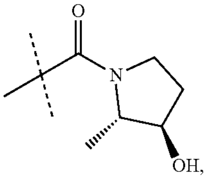
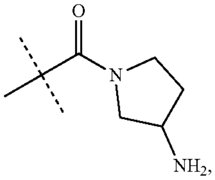
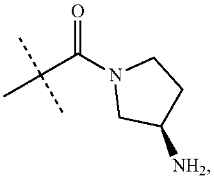
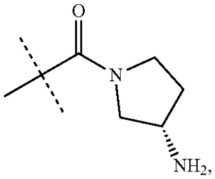
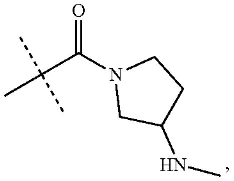
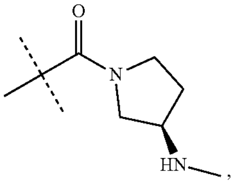
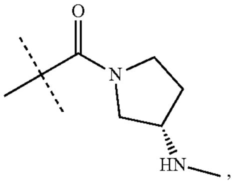
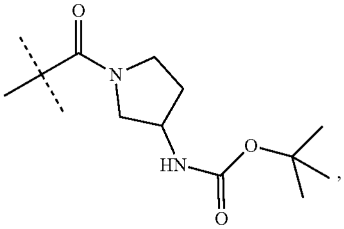
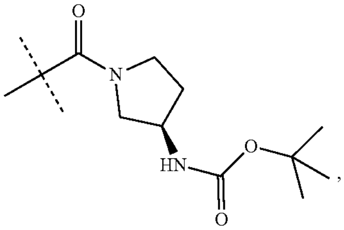
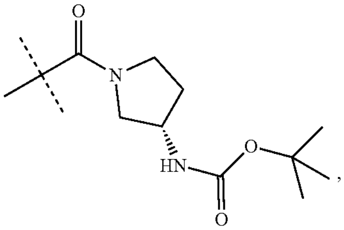
-continued
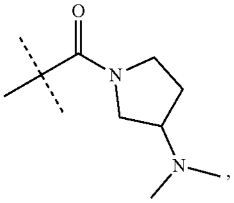
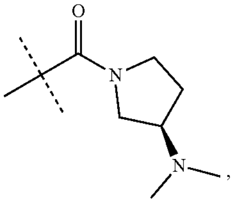
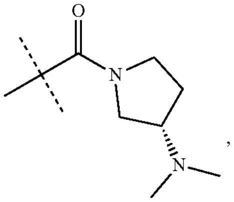
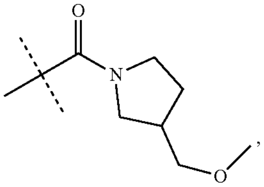
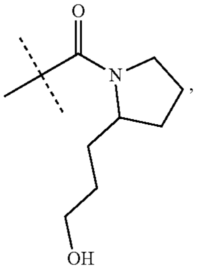
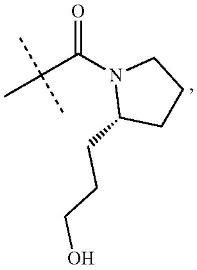
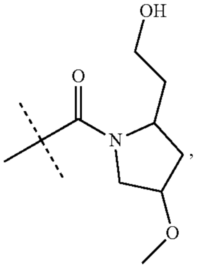
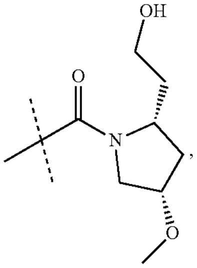
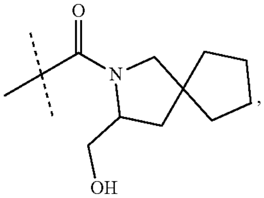
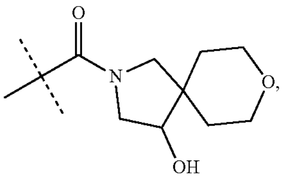
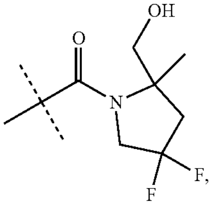
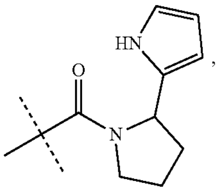
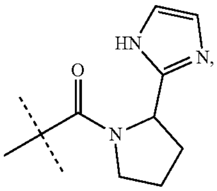

-continued
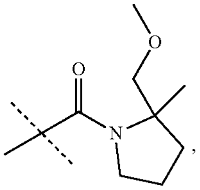
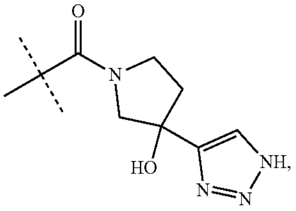
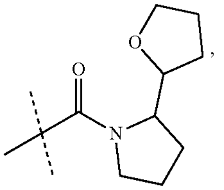
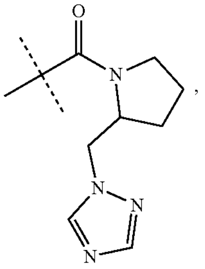
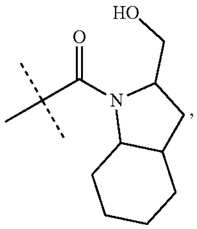
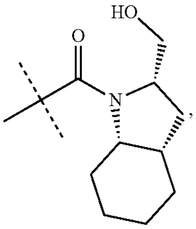
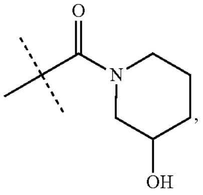
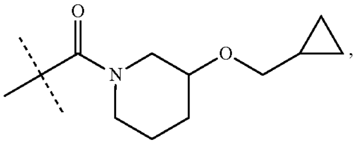
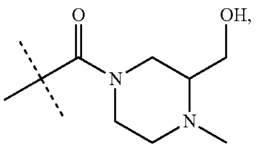
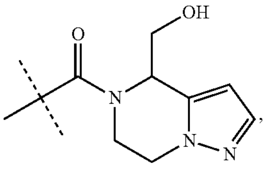
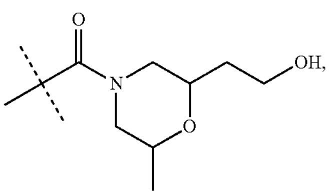
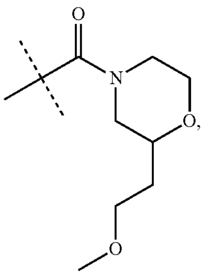
-continued
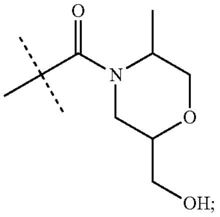
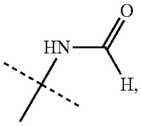
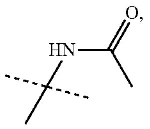
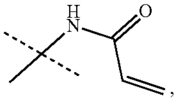
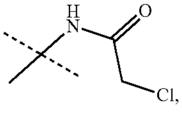
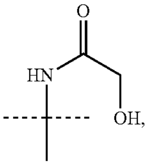
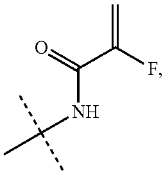
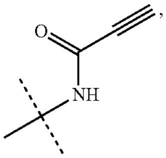
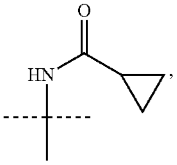
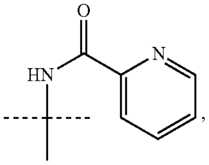
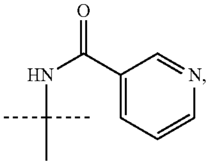
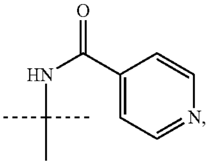
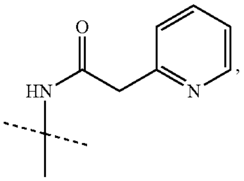
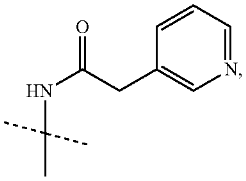
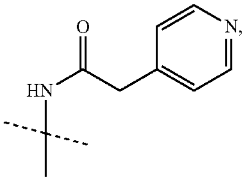
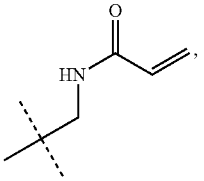

-continued
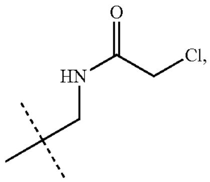
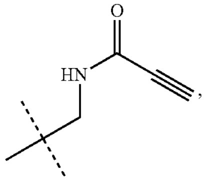
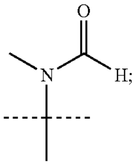
$—S—CH_3$, $—S(=O)—CH_3$,
$—S(=O)_2—CH_3$, $—S(=O)_2—NH_2$,
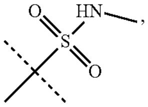
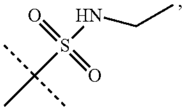
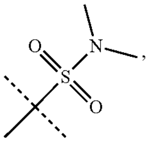
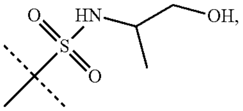
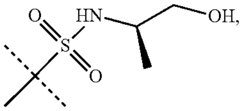
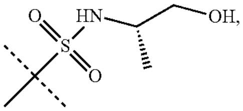
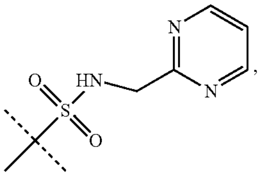
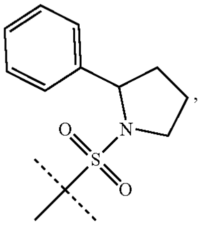
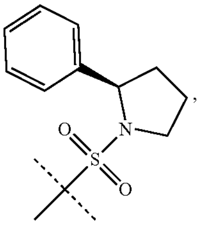
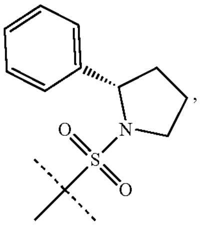
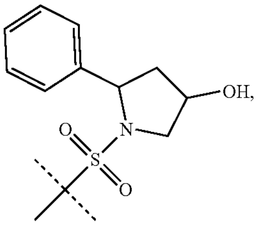
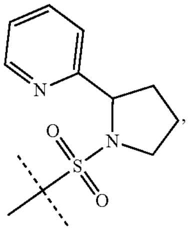
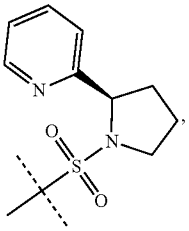
-continued
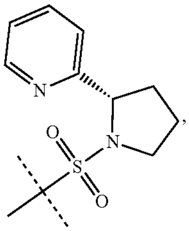
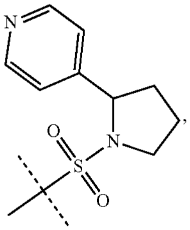
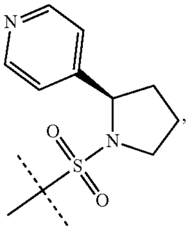
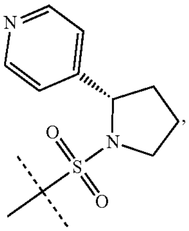
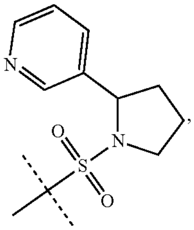
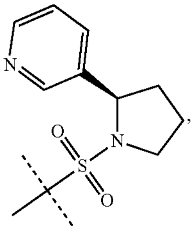
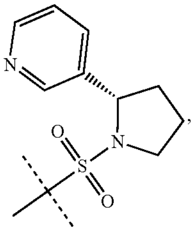
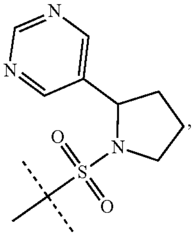
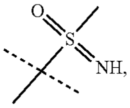
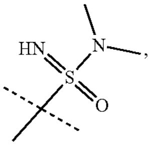
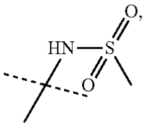
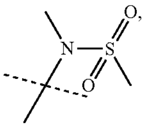
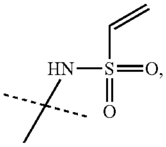
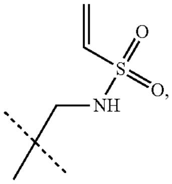
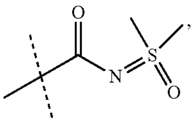
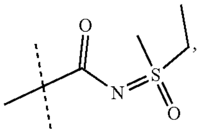
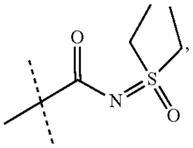
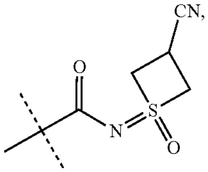

-continued

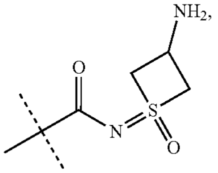,
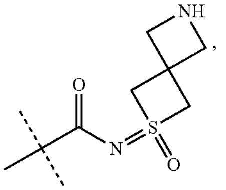,
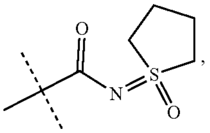,
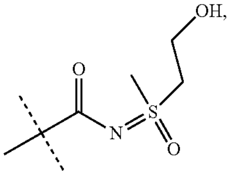,
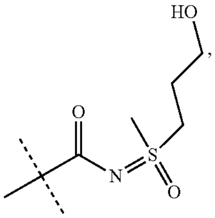,
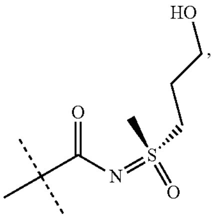,
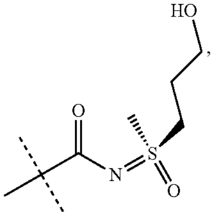,
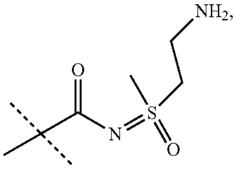,
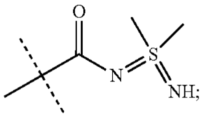
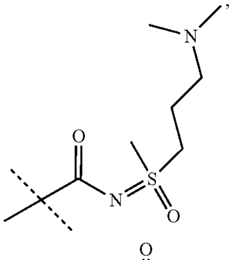,
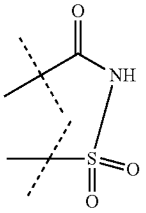
(together with $R^{Z2}$);

and the remaining radicals and residues are as defined for formula I-A or I above or for any of the further particular embodiments described herein above or below.

In a particular embodiment, PE10a, of PE10 the compound of the present invention is a tricyclic heterocycle of formula I-A or I, or any N-oxide, solvate, tautomer or stereoisomer thereof and/or any pharmaceutically acceptable salt of each of the foregoing, including mixtures thereof in all ratios, wherein $R^2$ is selected from the group consisting of —COOH, —COONa, —COOCH$_3$,

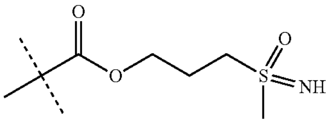,
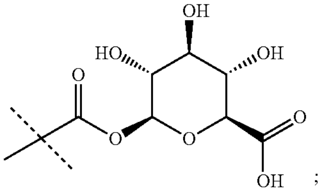;
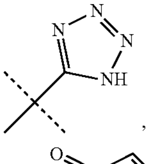,
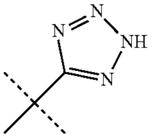,
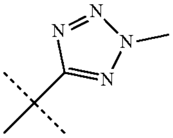,
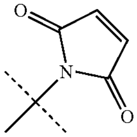,
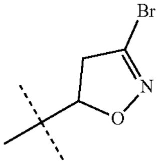,
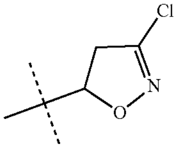,
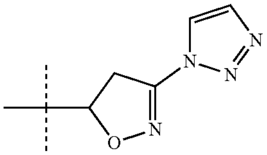,
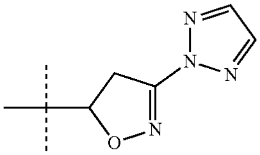,
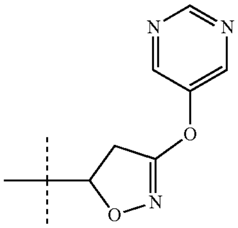,
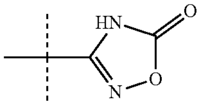,
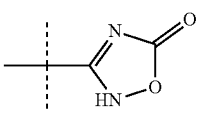,
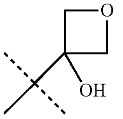,
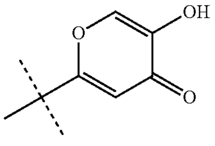,
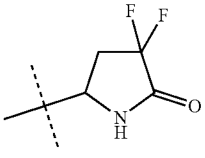,
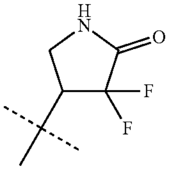,
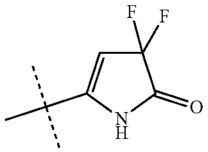,
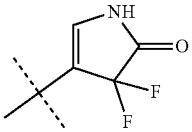;
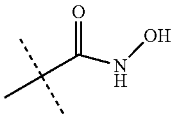;

-continued

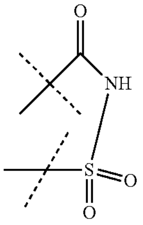

;

(together with $R^{Z2}$)

and the remaining radicals and residues are as defined for formula I-A or I above or for any of the further particular embodiments described herein above or below.

In a particular embodiment. PE10aa, of PE10a $R^2$ is selected from the group consisting of —COOH.

In a particular embodiment, PE10b, of PE10 the compound of the present invention is a tricyclic heterocycle of formula I-A or I, or any N-oxide, solvate, tautomer or stereoisomer thereof and/or any pharmaceutically acceptable salt of each of the foregoing, including mixtures thereof in all ratios, wherein $R^2$ is selected from the group consisting of

—C(=O)—$NH_2$,

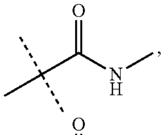 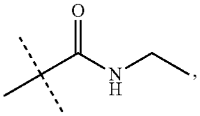

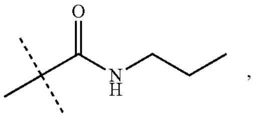

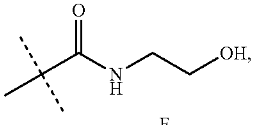 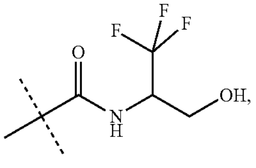

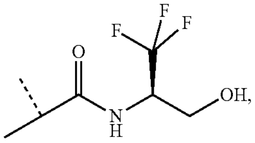

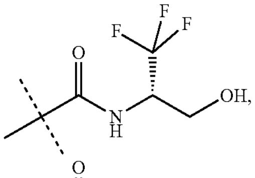 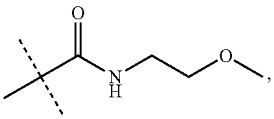

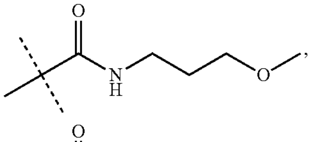

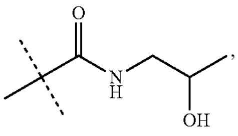 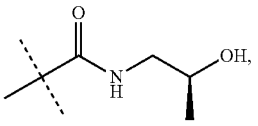

-continued

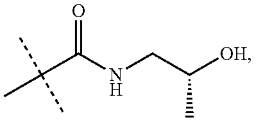 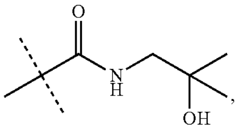

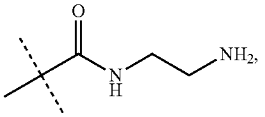

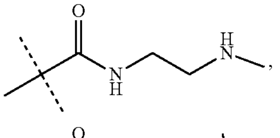

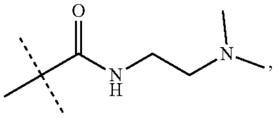

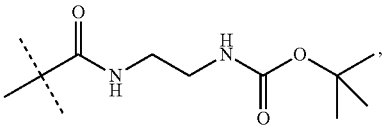

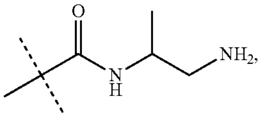 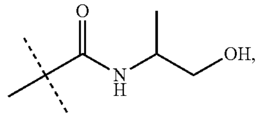

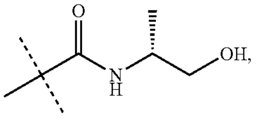 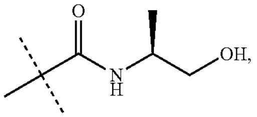

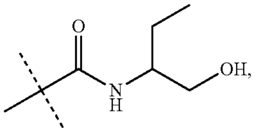 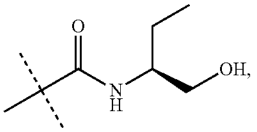

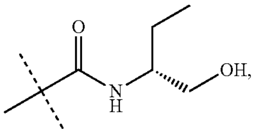 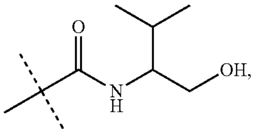

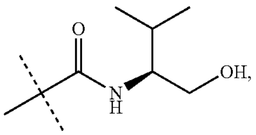 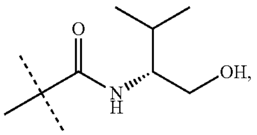

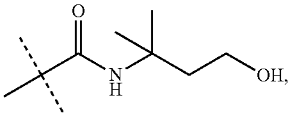

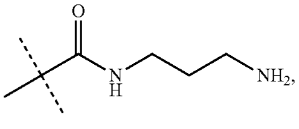

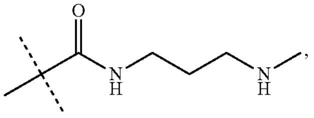

-continued
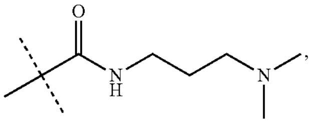
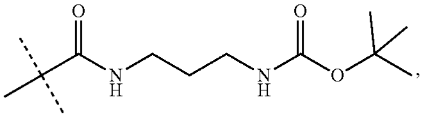
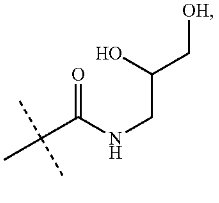
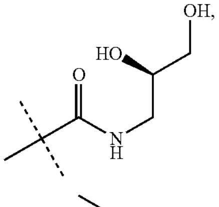
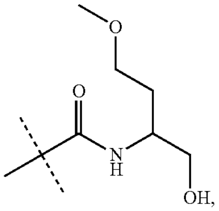
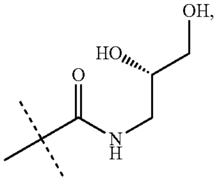
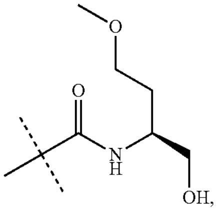
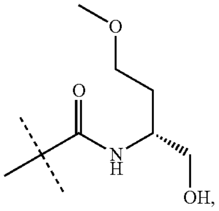
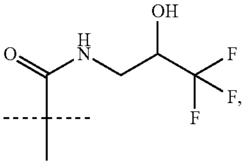
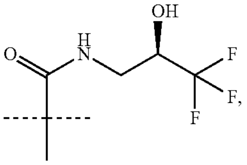
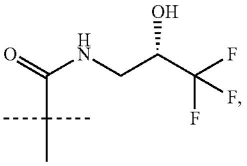
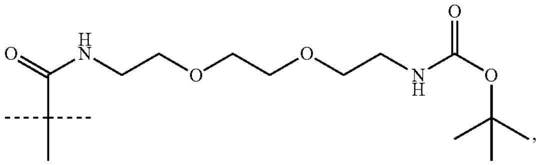
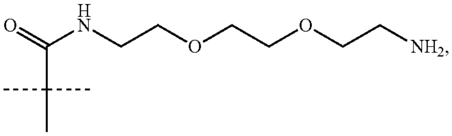
-continued
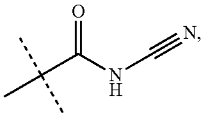
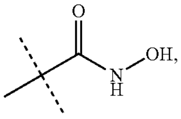
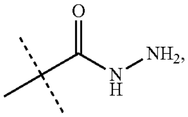
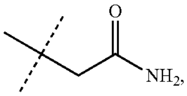
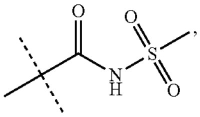
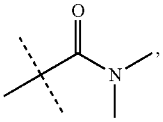
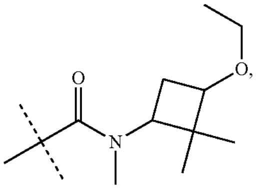
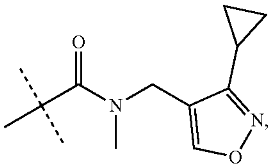
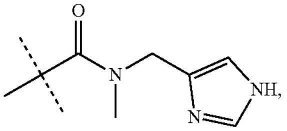
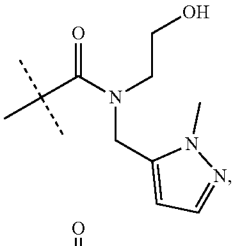
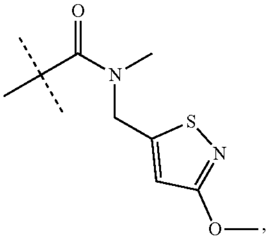
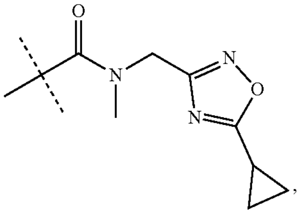
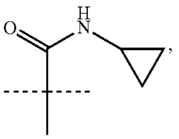
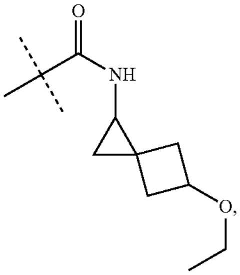
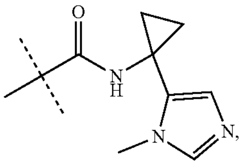

-continued
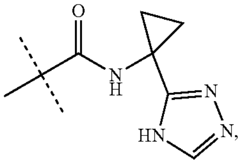
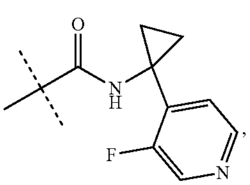
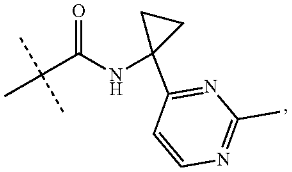
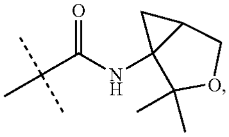
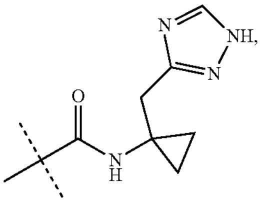
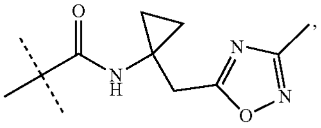
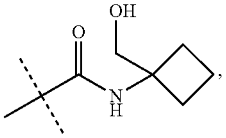
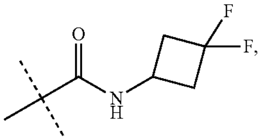
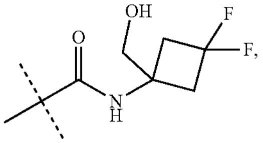
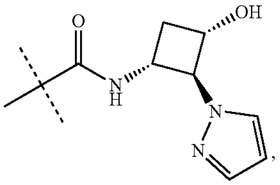
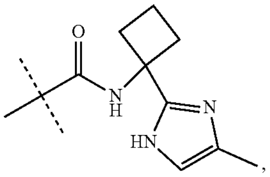
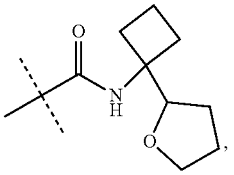
-continued
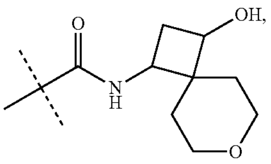
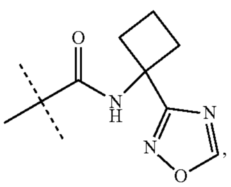
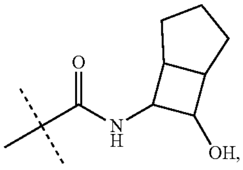
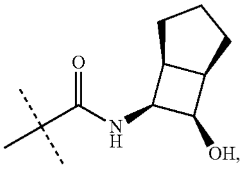
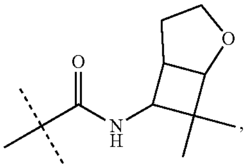
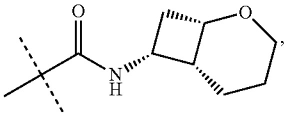
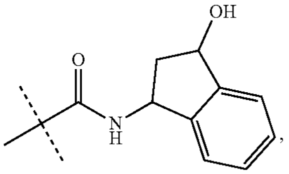
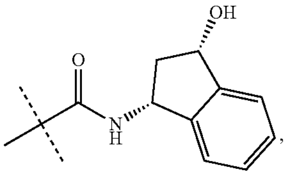
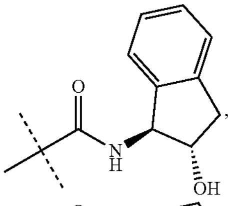
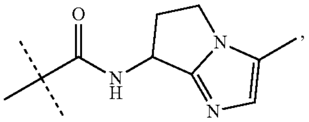
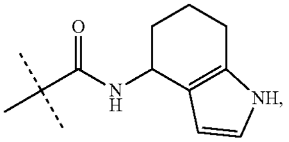
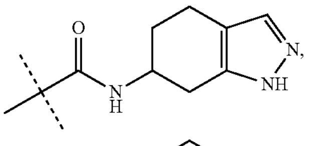
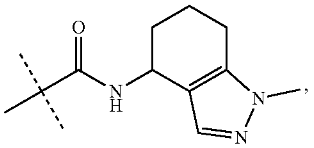
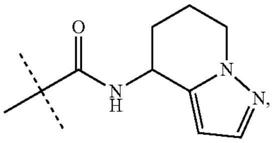

-continued
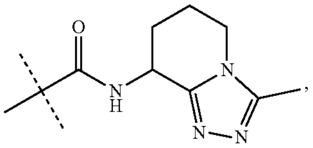
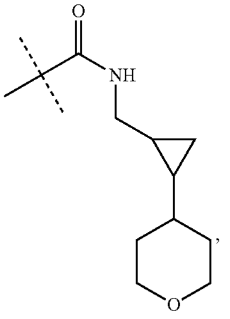
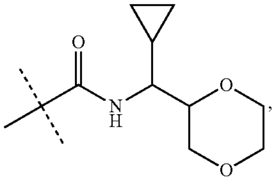
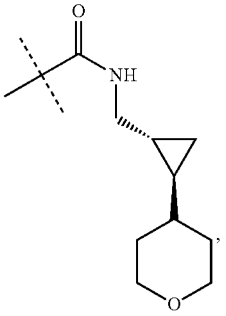
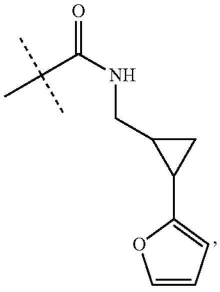
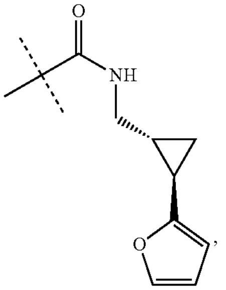
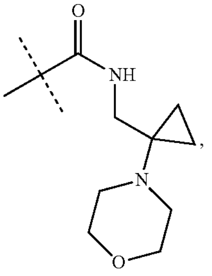
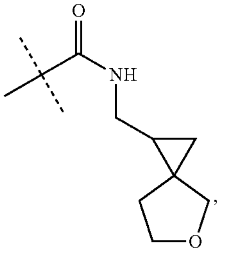
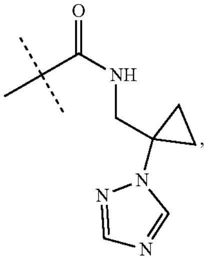
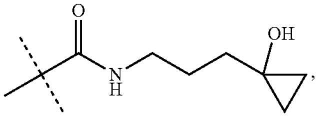
-continued
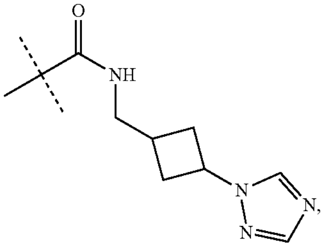
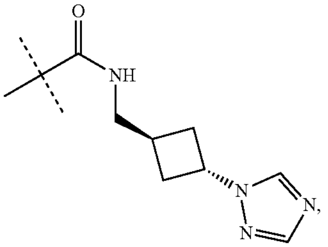
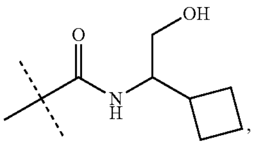
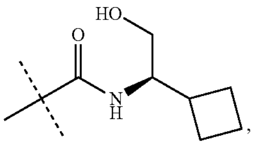
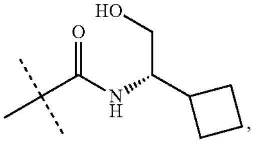
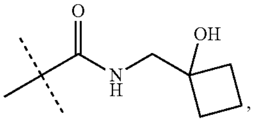
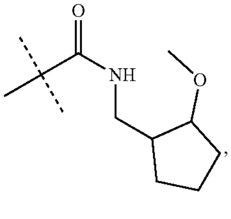
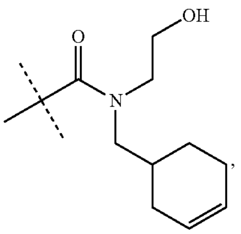
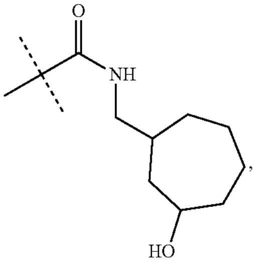
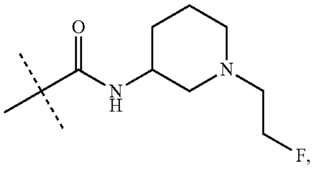
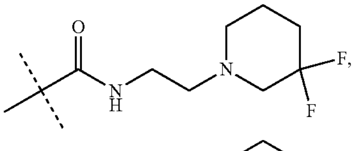
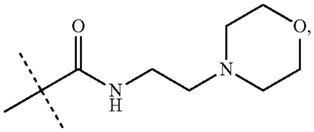

-continued
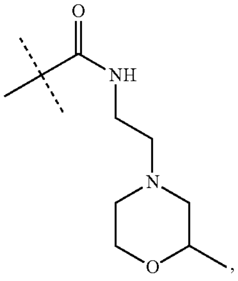
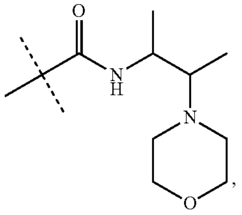
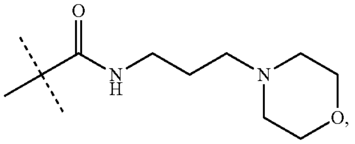
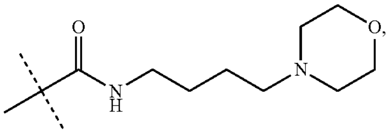
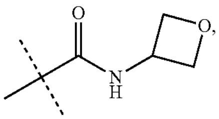
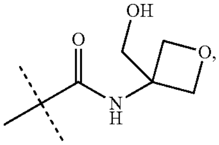
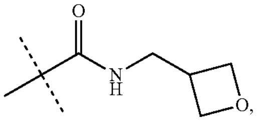
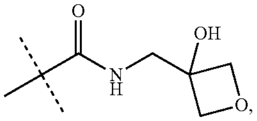
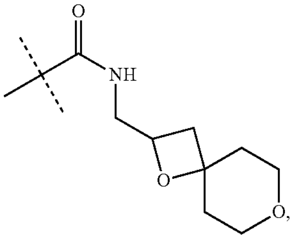
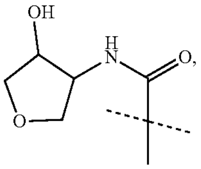
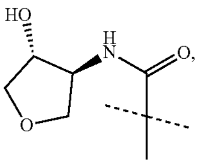
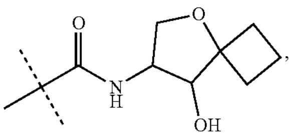
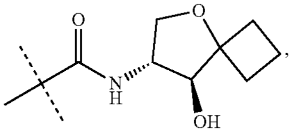
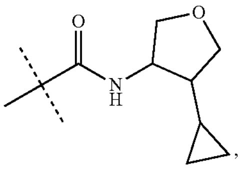
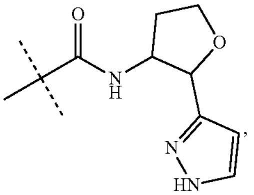
-continued
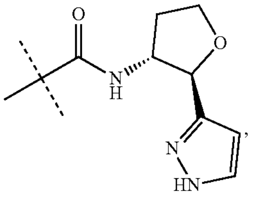
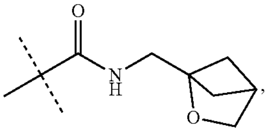
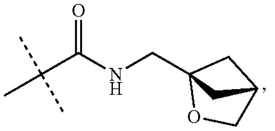
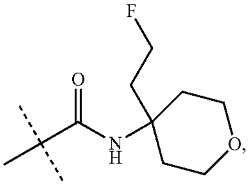
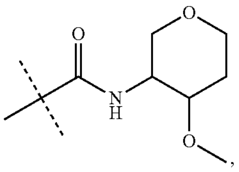
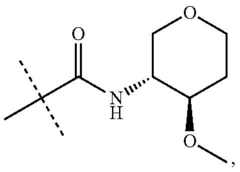
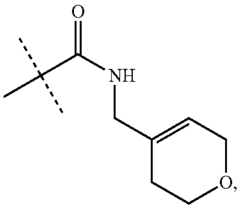
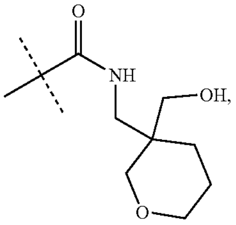
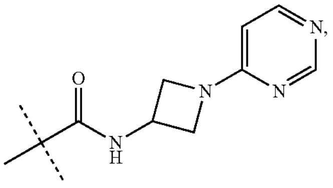
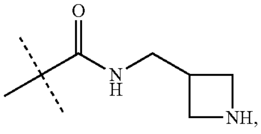
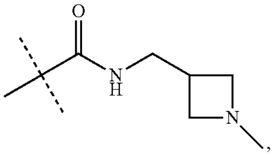
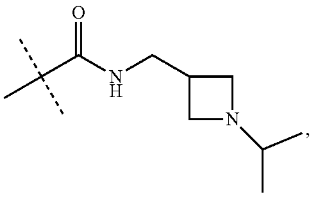

-continued
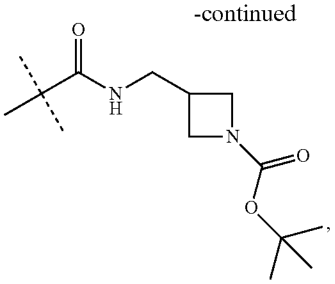
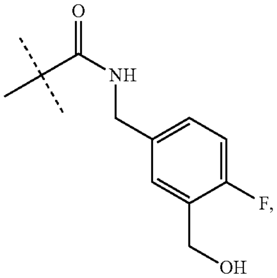
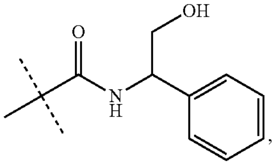
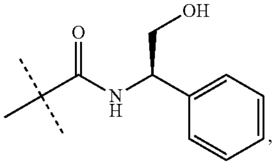
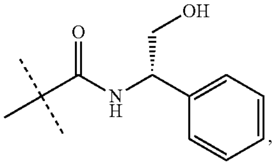
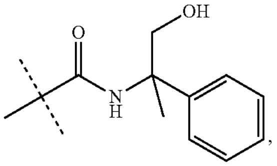
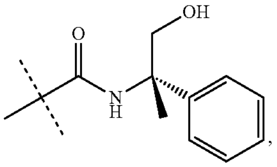
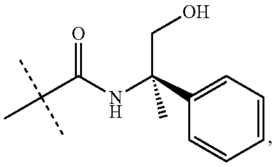
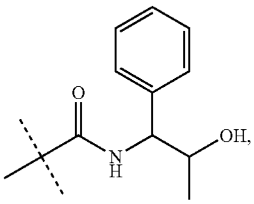
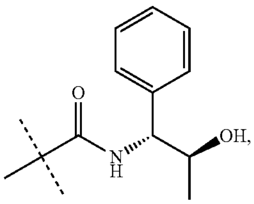
-continued
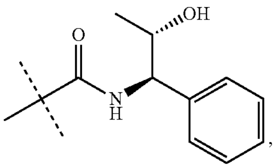
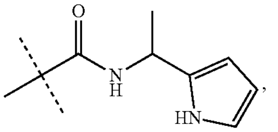
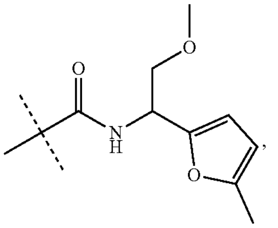
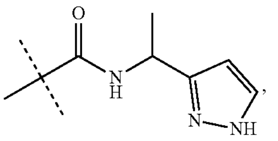
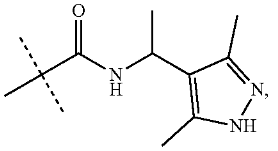
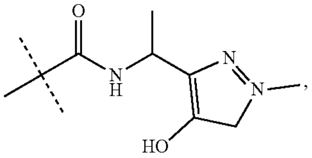
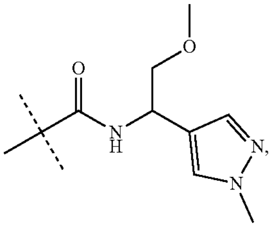
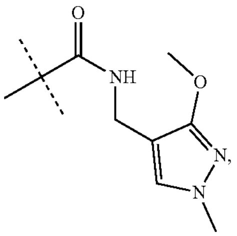
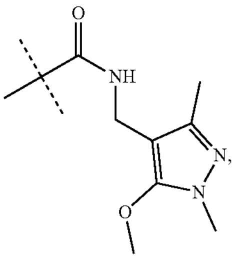
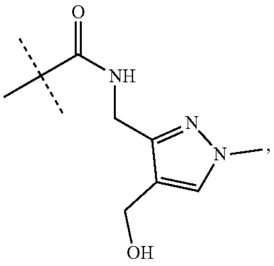

-continued
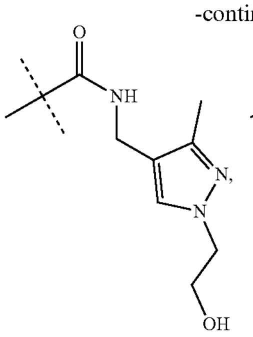
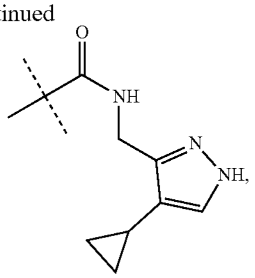
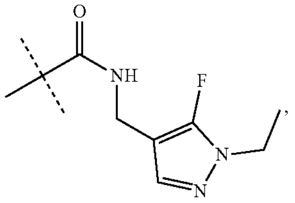
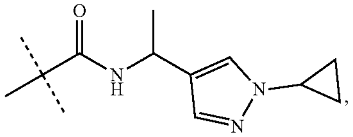
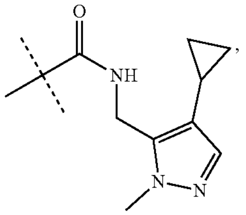
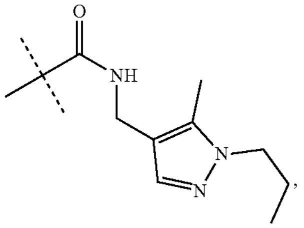
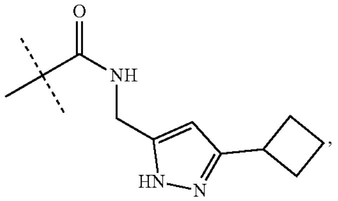
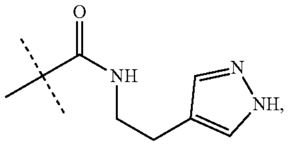
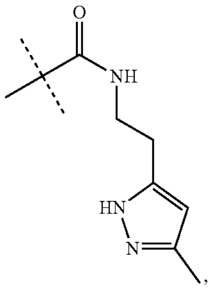
-continued
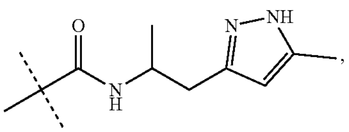
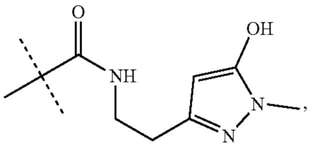
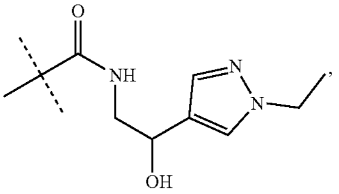
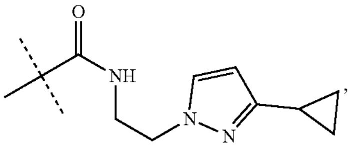
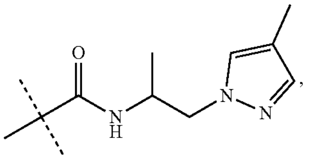
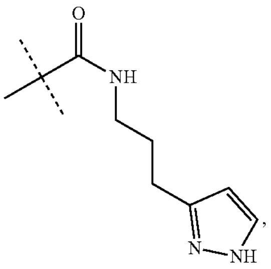
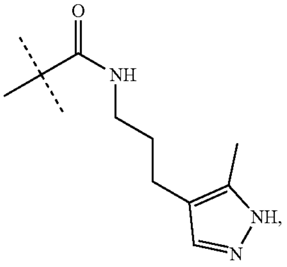
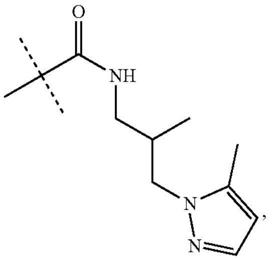

-continued
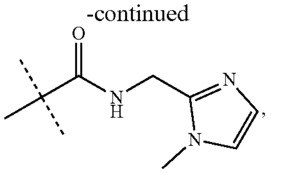
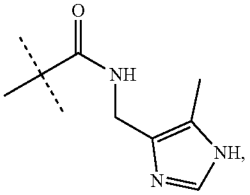
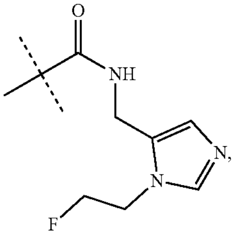
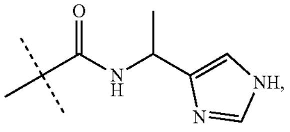
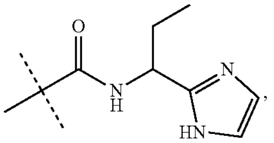
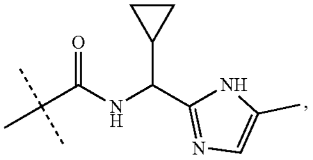
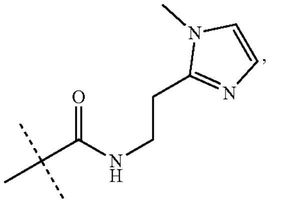
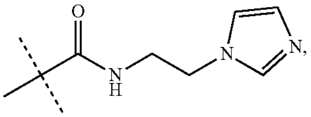
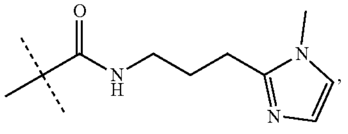
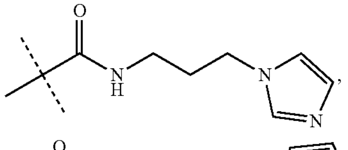
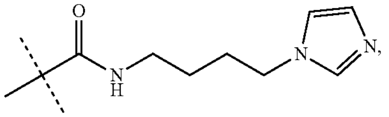
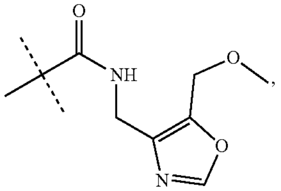
-continued
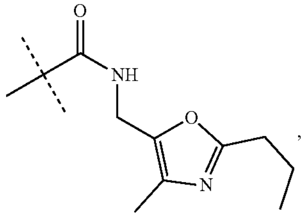
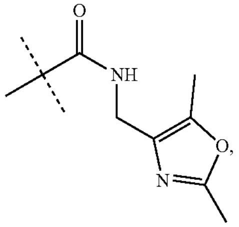
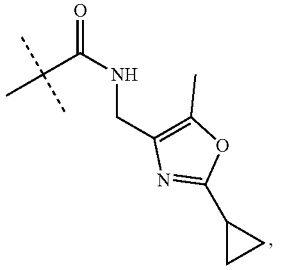
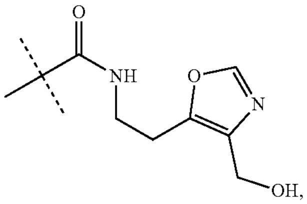
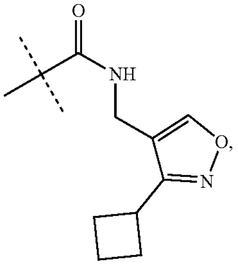
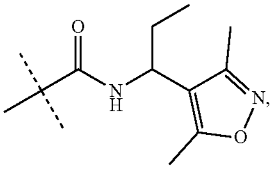
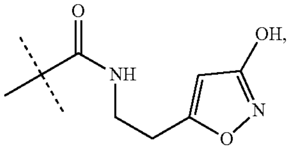
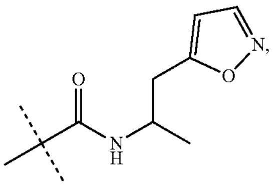
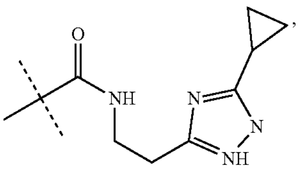
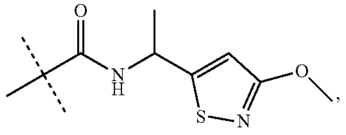
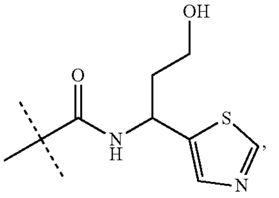

-continued
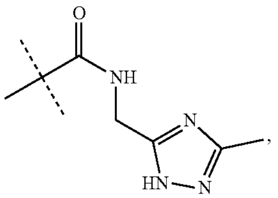
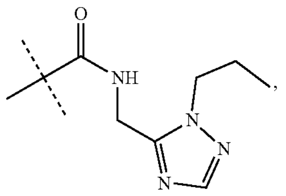
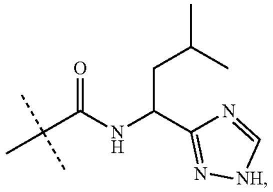
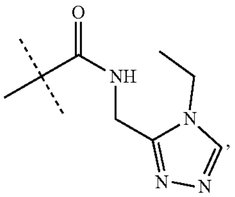
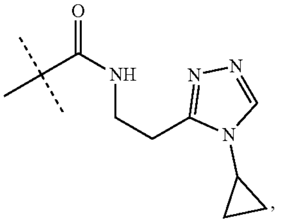
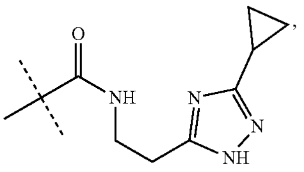
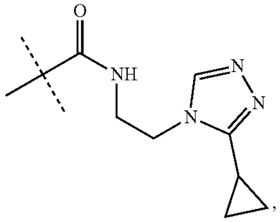
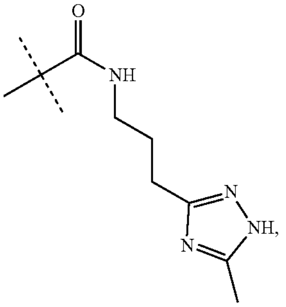
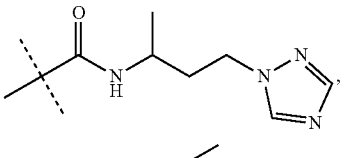
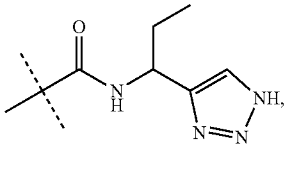
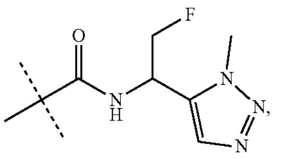
-continued
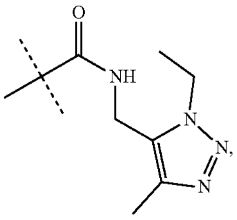
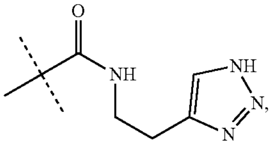
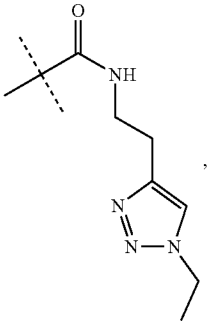
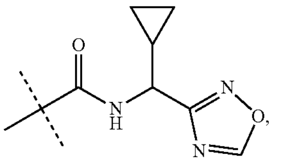
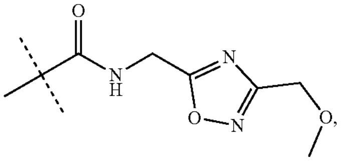
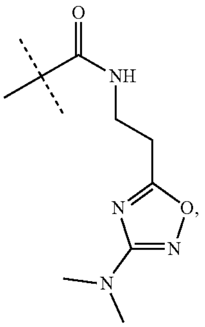
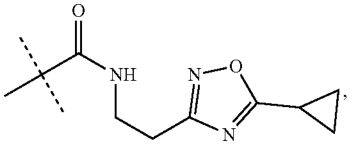
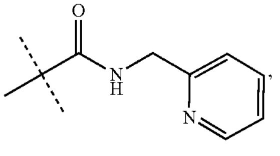
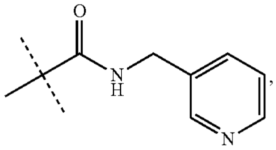
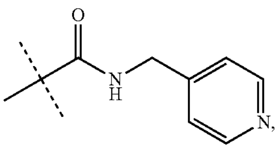
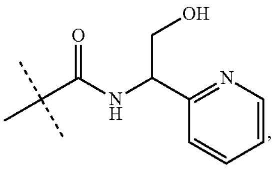
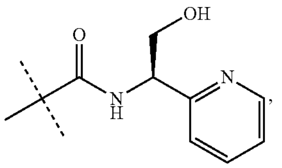
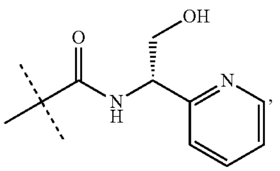
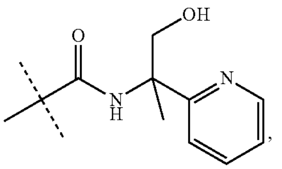
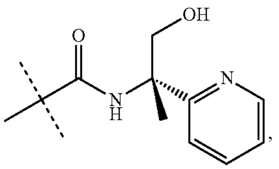

-continued
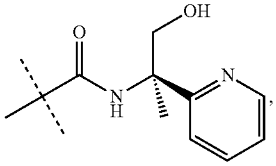
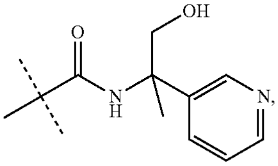
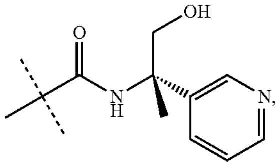
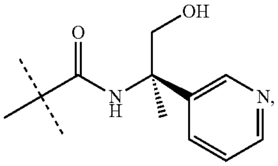
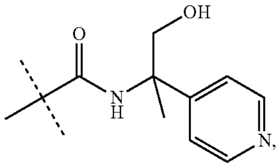
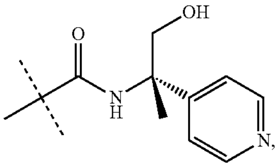
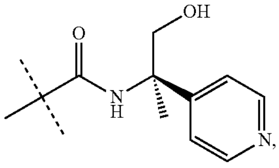
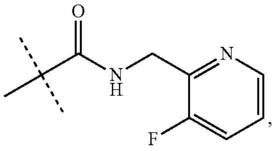
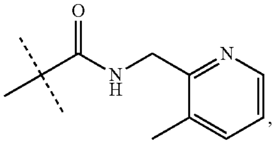
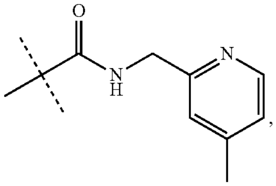
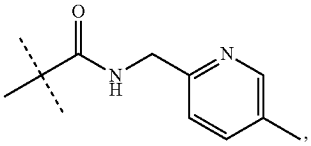
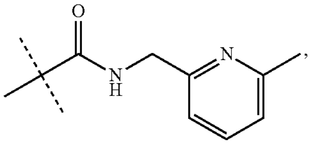
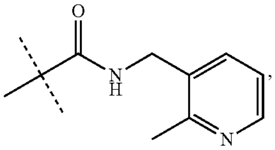
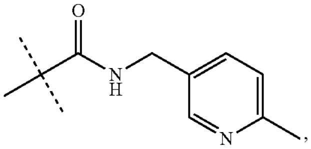
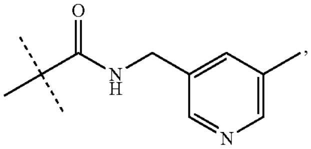
-continued
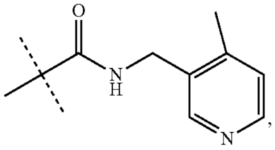
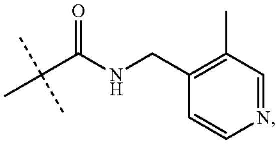
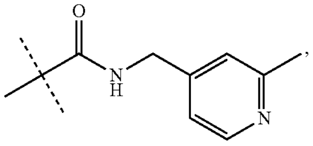
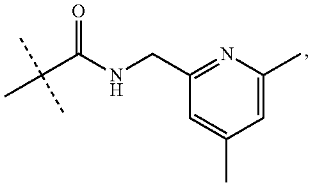
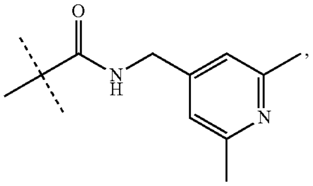
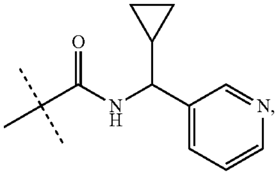
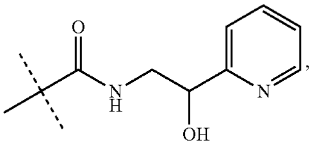
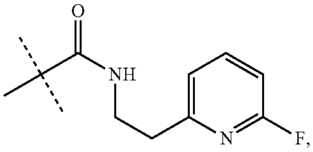
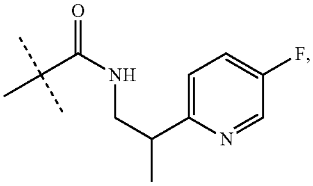
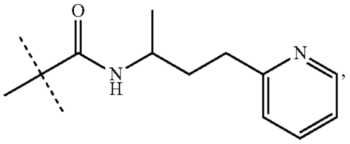
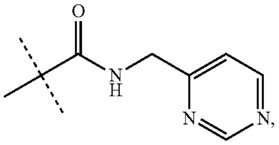

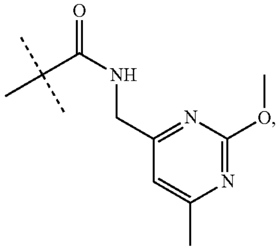
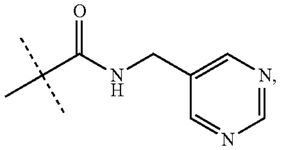
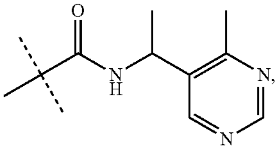
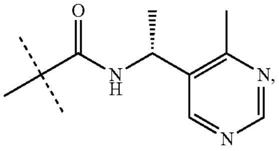
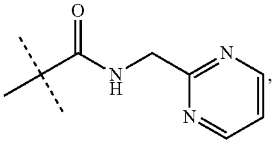
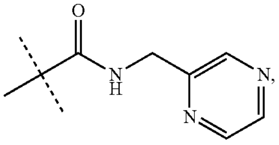
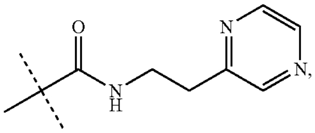
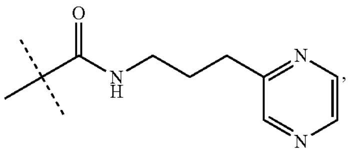
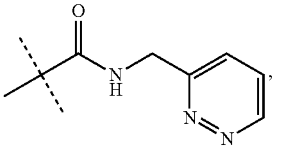
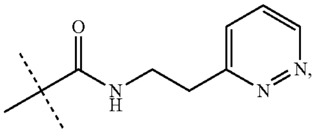
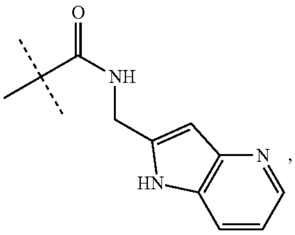
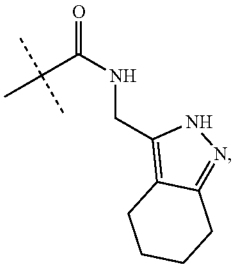
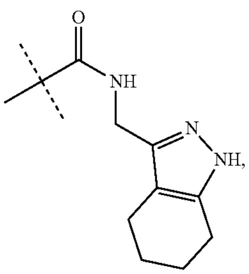
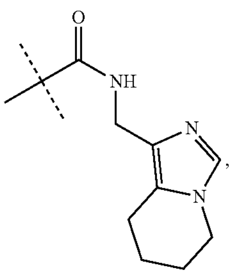
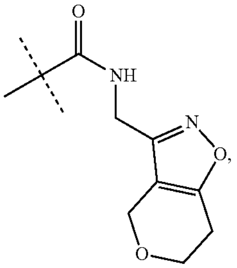
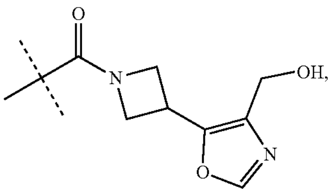
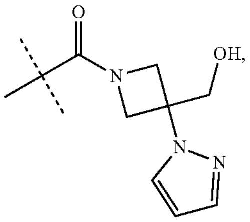
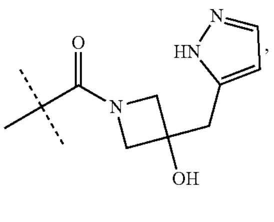
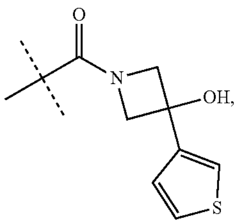
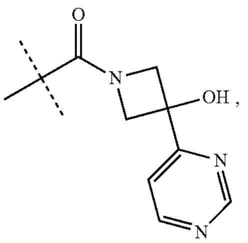
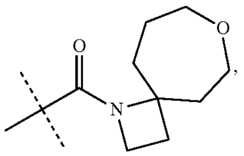
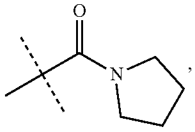
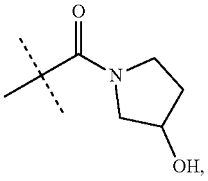
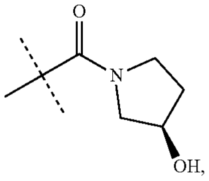
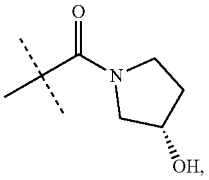
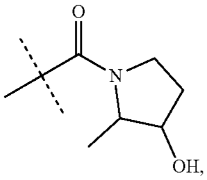
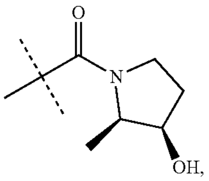
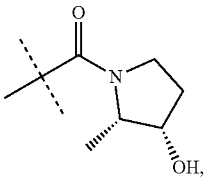
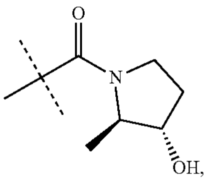
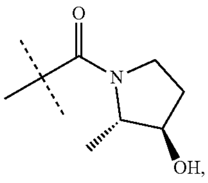

-continued
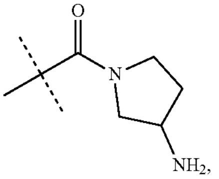
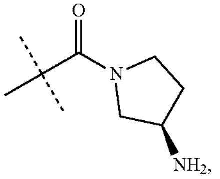
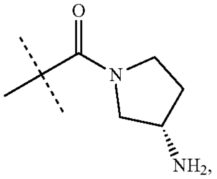
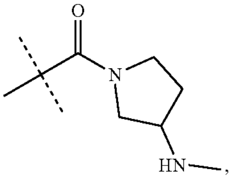
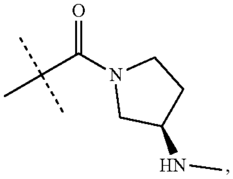
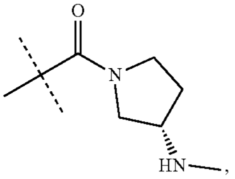
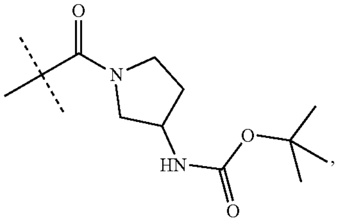
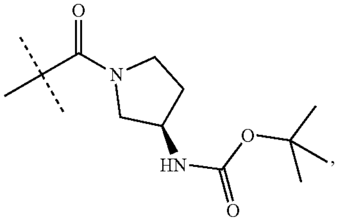
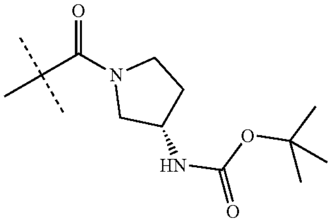
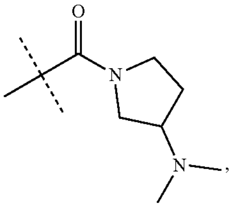
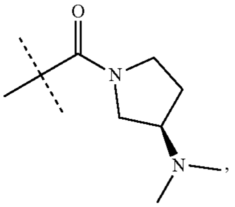
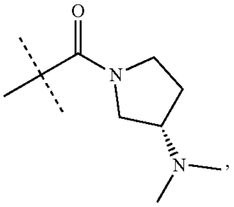
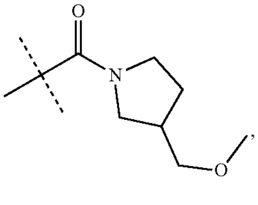
-continued
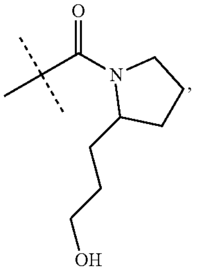
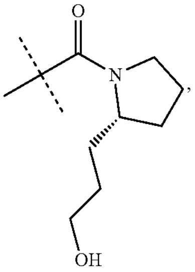
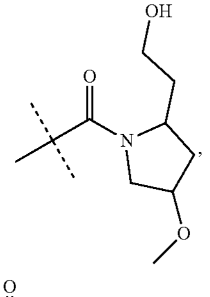
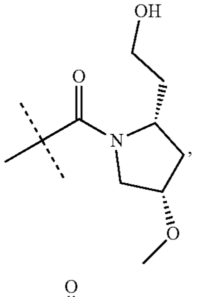
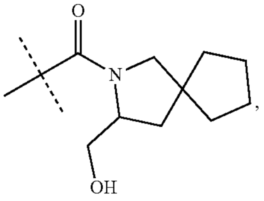
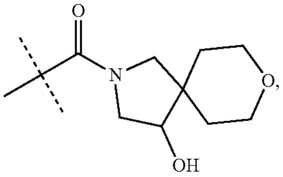
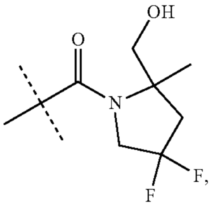
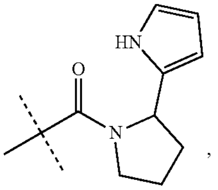
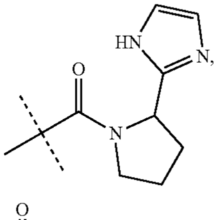
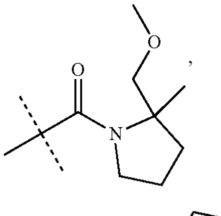
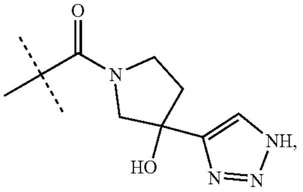
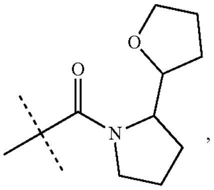
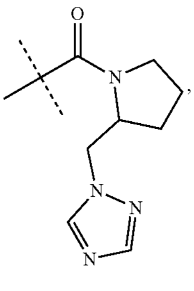
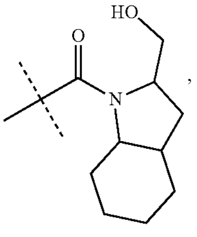

-continued
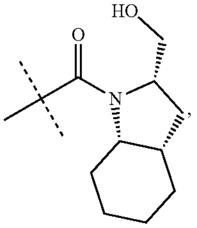
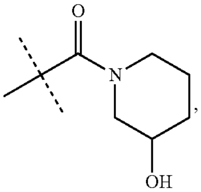
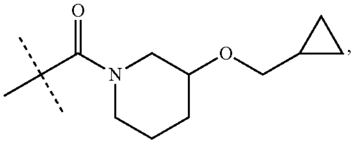
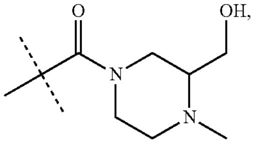
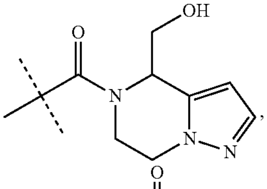
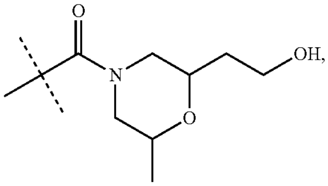
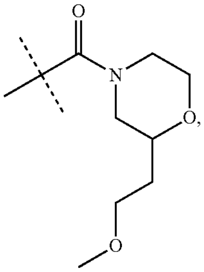
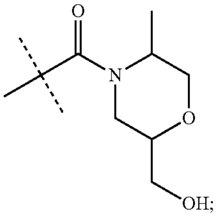
and the remaining radicals and residues are as defined for formula I-A or I above or for any of the further particular embodiments described herein above or below.
In a particular embodiment. PE10bb, of PE10b $R^2$ is selected from the group consisting of
$-C(=O)-NH_2$,
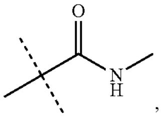
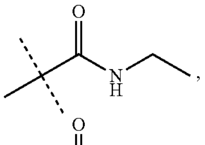
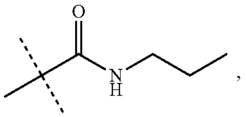
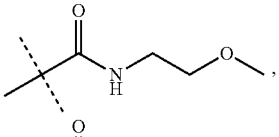
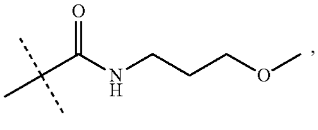
-continued
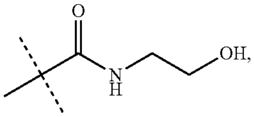
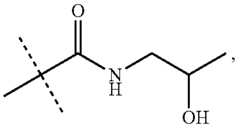
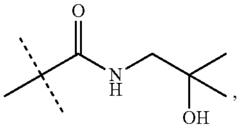
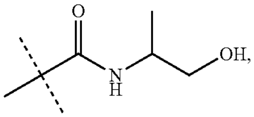
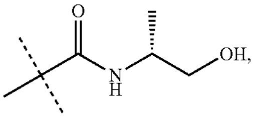
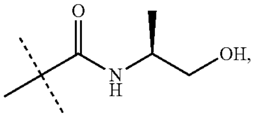
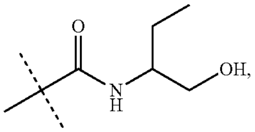
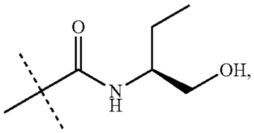
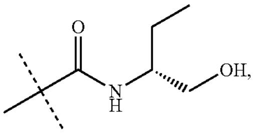
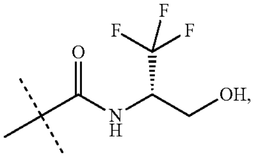
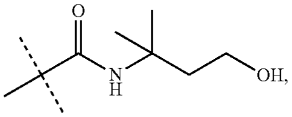
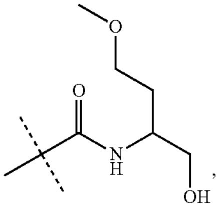
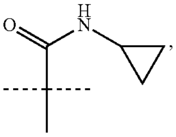
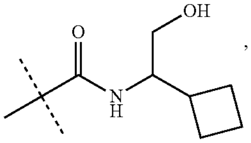
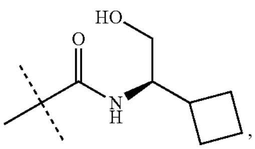
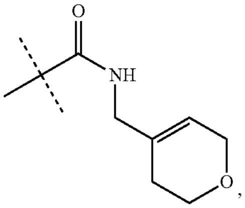
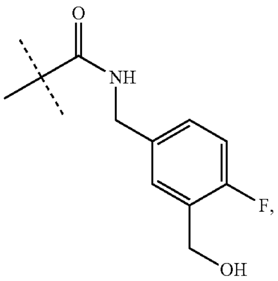

-continued
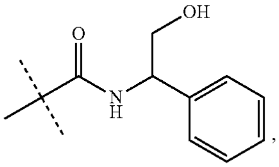
,
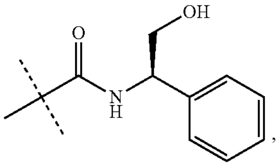
,
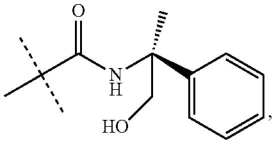
,
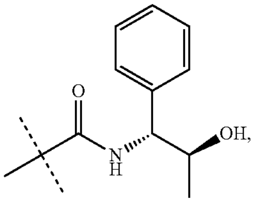
,
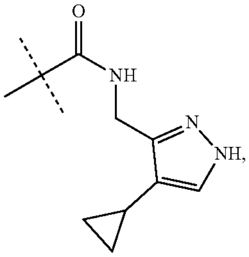
,
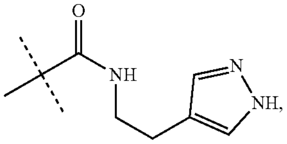
,
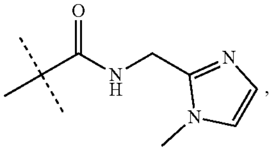
,
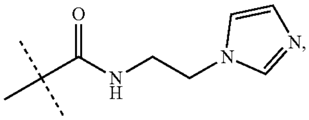
,
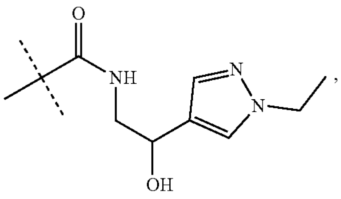
,
-continued
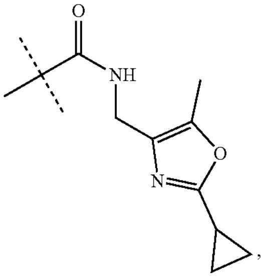
,
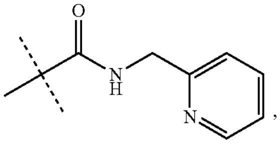
,
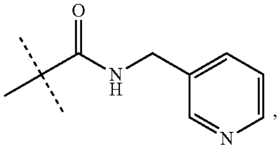
,
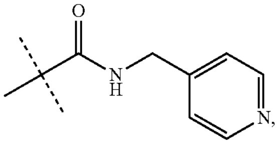
,
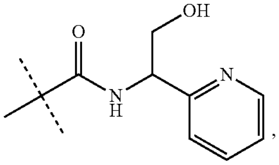
,
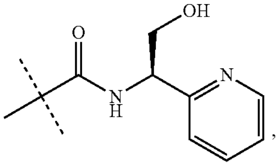
,
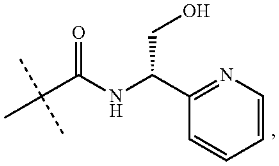
,
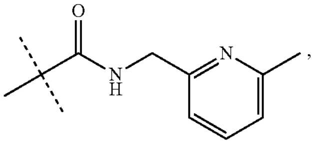
,
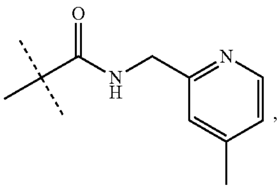
,
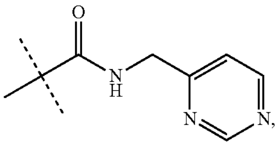
, -continued

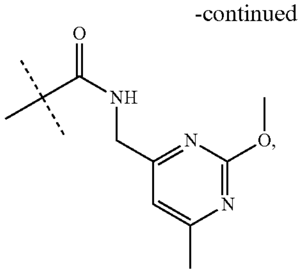

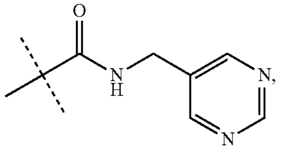

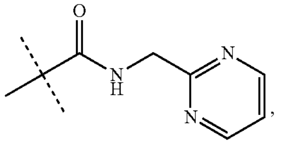

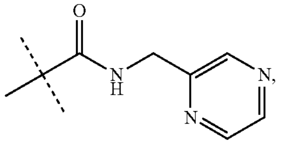

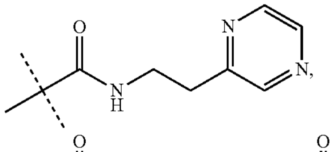

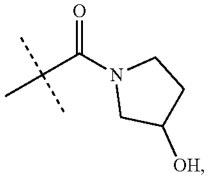 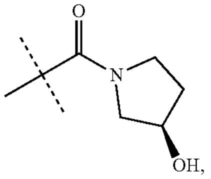

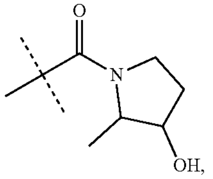

In another particular embodiment, PE10c, of PE10 the compound of the present invention is a tricyclic heterocycle of formula I-A or I, or any N-oxide, solvate, tautomer or stereoisomer thereof and/or any pharmaceutically acceptable salt of each of the foregoing, including mixtures thereof in all ratios, wherein $R^2$ is selected from the group consisting of

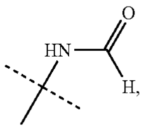 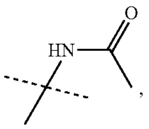 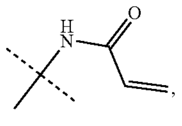

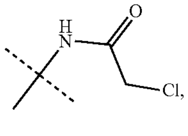 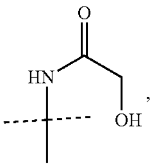

-continued

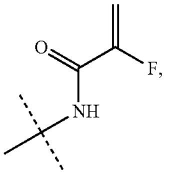 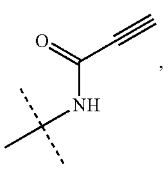

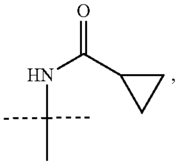 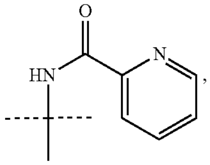

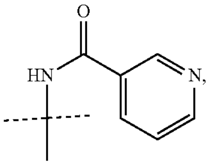 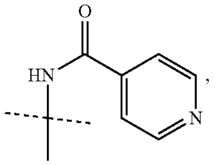

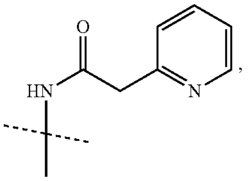 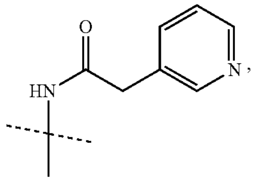

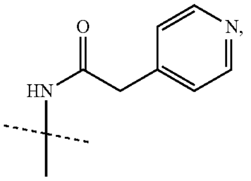 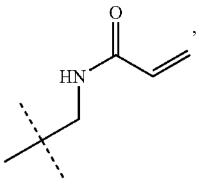

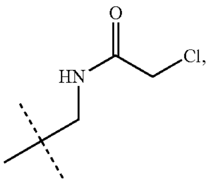 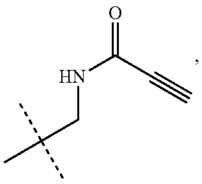

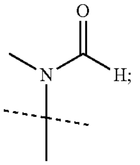 $-S-CH_3$, $-S(=O)-CH_3$, $-S(=O)_2-CH_3$, $-S(=O)_2-NH_2$,

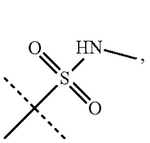 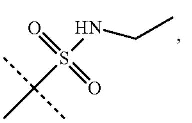 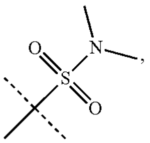

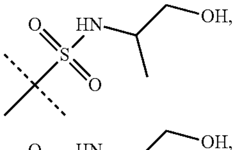 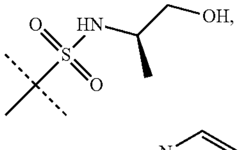

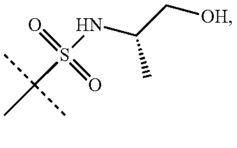 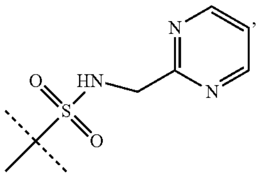

-continued
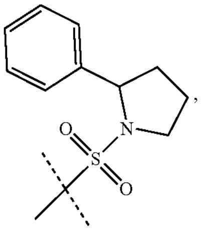
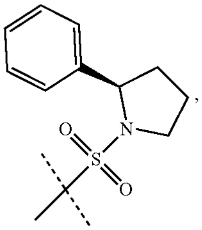
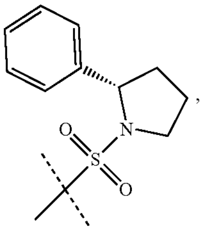
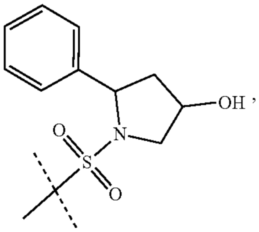
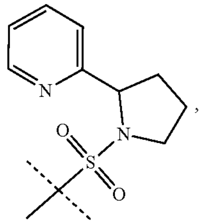
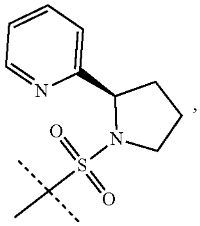
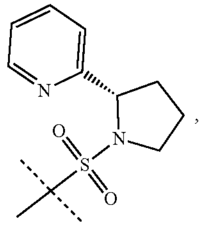
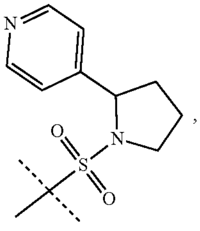
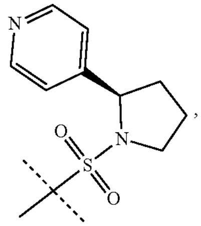
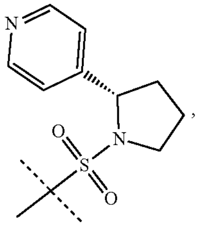
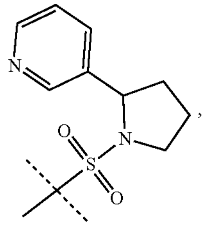
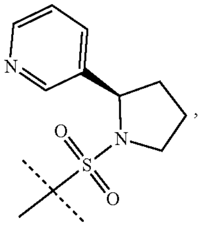
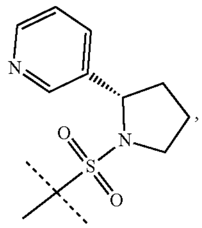
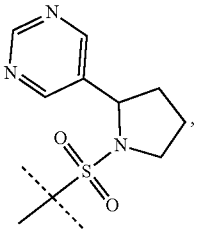
-continued
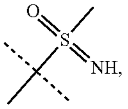
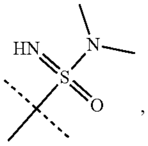
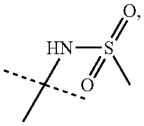
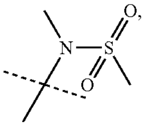
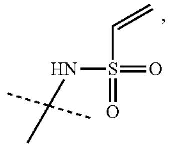
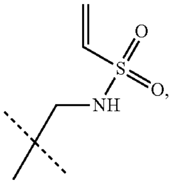
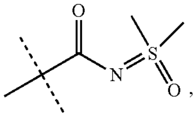
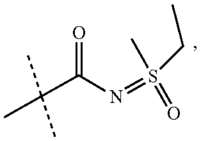
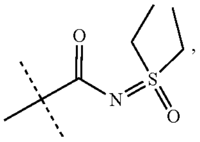
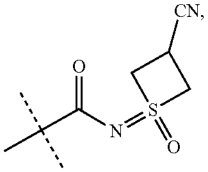
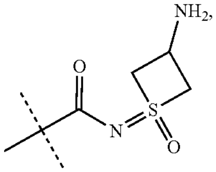
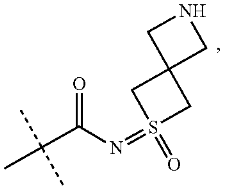
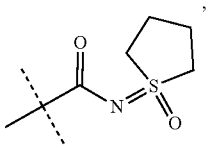
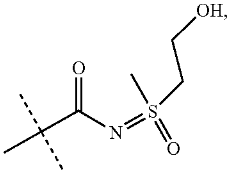
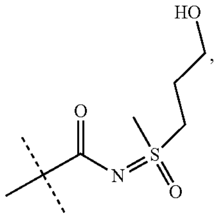
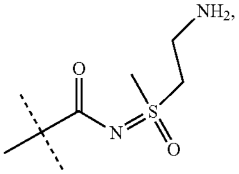
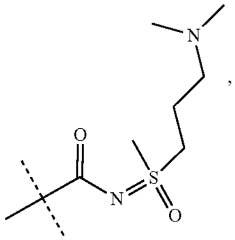
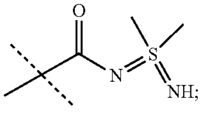

and the remaining radicals and residues are as defined for formula I-A or I above or for any of the further particular embodiments described herein above or below.

In a particular embodiment, PE10cc, of PE10c $R^2$ is selected from the group consisting of

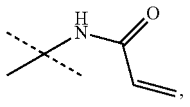

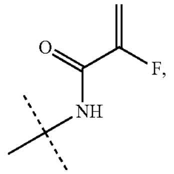

—S(=O)—$CH_3$,

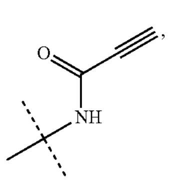

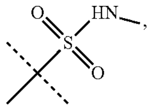

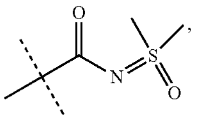

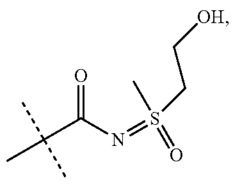

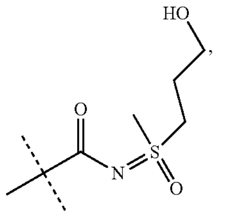

It is understood that in the embodiments PE9, PE9a, PE9aa, PE10, PE10a, PE10aa, PE10b, PE10bb, PE10c, and PE10cc shown above the dotted line ( ) is used to indicate the position where the individual radicals $R^1$ and $R^2$, respectively, are attached to the remaining of the molecule, i.e. the compound of formula I or I-A.

In still another particular embodiment of the invention, PE11, the compound of the present invention is a tricyclic heterocycle of formula I-A or I, or any N-oxide, solvate, tautomer or stereoisomer thereof and/or any pharmaceutically acceptable salt of each of the foregoing, including mixtures thereof in all ratios, wherein $R^1$ is selected from the group described for PE9 above; and $R^2$ is selected from the group described for PE10 above; and the remaining radicals and residues are as defined for formula I-A or I above or for any of the further particular embodiments described herein above or below.

It is a particular embodiment, PE11a, of PE11 wherein $R^1$ is selected from the group described for PE9a above, especially PE9aa; and $R^2$ is selected from the group described for PE10 above.

It is still another particular embodiment, PE11 b, of PE11 wherein $R^1$ is selected from the group described for PE9a above, especially PE9aa; and $R^2$ is selected from the group described for PE10a above, especially PE10aa.

It is still another particular embodiment, PE11c, of PE11 wherein $R^1$ is selected from the group described for PE9a above, especially PE9aa; and $R^2$ is selected from the group described for PE10b above, especially PE10bb.

It is still another particular embodiment, PE11d, of PE11 wherein $R^1$ is selected from the group described for PE9a above, especially PE9aa; and $R^2$ is selected from the group described for PE10c above, especially PE10cc.

It is still another particular embodiment of the invention, PE12, wherein Ring A is selected from one of the particular embodiments PE2, PE2a, PE2b, PE2c; and $R^1$ and $R^2$ are selected as described for PE11.

In a particular embodiment, PE12a, of PE12, $R^1$ and $R^2$ are selected as described for PE11a. In another particular embodiment, PE12b, of PE12, $R^1$ and $R^2$ are selected as described for PE11 b. In yet another particular embodiment, PE12c, of PE12, $R^1$ and $R^2$ are selected as described for PE11c. In still a further particular embodiment, PE12d, of PE12, $R^1$ and $R^2$ are selected as described for PE11d.

In still another particular embodiment, PE13, the compound of the present invention is a tricyclic heterocycle of formula I-A or I, or any N-oxide, solvate, tautomer or stereoisomer thereof and/or any pharmaceutically acceptable salt of each of the foregoing, including mixtures thereof in all ratios, wherein that compound is selected from the compounds shown in Table 1 and Table 1 b below, in particular in Table 1. It is understood that each single compound depicted in Table 1 and Table 1 b as well as any N-oxide, solvate, tautomer or stereoisomer thereof and/or any pharmaceutically acceptable salt of such compound represent a particular embodiment of the present invention.

As used herein, the following definitions shall apply unless otherwise indicated or defined specifically elsewhere in the description for specific substituents, radicals, residues, groups or moieties.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon or tricyclic hydrocarbon that is completely saturated or that contains one or more units of unsaturation, such as one or more C═C double bond(s) and/or C≡C triple bond(s), but which is not aromatic (also referred to herein as "carbocycle", "cycloaliphatic" or "cycloalkyl"), that has—in general and if not defined otherwise in this specification—a single point of attachment to the rest of the molecule. Unless otherwise specified, aliphatic groups contain 1-8 or 1-6 aliphatic carbon atoms ("$C_{1-8}$-aliphatic" and "$C_{1-6}$-aliphatic", respectively). In some embodiments, aliphatic groups contain 1-5 aliphatic carbon atoms ("$C_{1-5}$-aliphatic"). In other embodiments, aliphatic groups contain 1-4 aliphatic carbon atoms ("$C_{1-4}$-aliphatic"). In still other embodiments, aliphatic groups contain 1-3 aliphatic carbon atoms ("$C_{1-3}$-aliphatic"), and in yet other embodiments, aliphatic groups contain 1-2 aliphatic carbon atoms ("$C_{1-2}$-aliphatic"). In some embodiments, "cycloaliphatic" ("cycloalkyl") refers to a monocyclic $C_3$-$C_7$ hydrocarbon (i.e., a monocyclic hydrocarbon with 3, 4, 5, 6, or 7 ring carbon atoms) or to a bicyclic $C_{5-8}$ hydrocarbon (i.e. a bicyclic hydrocarbon with 5, 6, 7, or 8 ring carbon atoms) that is completely saturated or that contains one or more units of unsaturation, but which is not aromatic, that has a single point of attachment to the rest of the molecule. In another embodiment the term "cycloaliphatic" or "carbocycle"

refers to a monocyclic or bicyclic cycloaliphatic ring system which is fused to an aromatic, heteroaromatic or heterocyclic ring or ring system via 2 adjacent ring atoms of that aromatic, heteroaromatic or heterocyclic ring or ring system; in other words, such carbocycle shares two ring atoms with the ring or ring system to which it is fused thereby having two points of attachment to the rest of the molecule. In another embodiment the term "carbocycle" refers to bicyclic spiro-cycles in which two monocyclic carbocycles are fused to each other via the same single carbon atom. In general, the term "aliphatic" encompasses, to the extent chemically possible, straight-chain, i.e. unbranched, as well as branched hydrocarbon chains, if not defined differently in a particular instance. Also, in general this term encompasses, to the extent chemically possible, unsubstituted and substituted hydrocarbon moieties, if not defined differently in a particular instance. Typical substituents of an aliphatic group include, but are not limited to halogen, cyano, hydroxy, alkoxy, unsubstituted or mono- or di-substituted amino, aryl, in particular unsubstituted or substituted phenyl, heteroaryl, in particular unsubstituted or substituted pyridyl or pyrimidinyl, heterocyclyl, in particular unsubstituted or substituted pyrrolidinyl, piperidinyl, piperazinyl or morpholinyl. Suitable aliphatic groups include, but are not limited to, linear or branched, substituted or unsubstituted alkyl, alkenyl, alkynyl, cycloalkyl, cycloalkenyl groups and hybrids thereof as (cycloalkyl) alkyl, (cycloalkenyl) alkyl or (cycloalkyl) alkenyl.

The term "alkyl" usually refers to a saturated aliphatic and acyclic moiety, while the term "alkenyl" usually refers to an unsaturated aliphatic and acyclic moiety with one or more C═C double bonds and the term "alkynyl" usually refers to an aliphatic and acyclic moiety with one or more C≡C triple bonds. It is understood that the term "alkenyl" comprises all forms of isomers, i.e. E-isomers, Z-isomers as well as mixtures thereof (E/Z-isomers). Exemplary aliphatic groups are linear or branched, substituted or unsubstituted $C_{1-8}$-alkyl, $C_{1-6}$-alkyl, $C_{1-4}$-alkyl, $C_{1-3}$-alkyl, $C_{1-2}$-alkyl, $C_{2-8}$-alkenyl, $C_{2-6}$-alkenyl, $C_{2-8}$-alkynyl, $C_{2-6}$-alkynyl, $C_{2-4}$-alkynyl, groups and hybrids thereof such as (cycloalkyl)alkyl, (cycloalkenyl)alkyl or (cycloalkyl)alkenyl.

In particular, the term "$C_{1-3}$-alkyl" refers to alkyl groups, i.e. saturated acyclic aliphatic groups, having 1, 2 or 3 carbon atoms. Exemplary $C_{1-3}$-alkyl groups are methyl, ethyl, propyl and isopropyl. The term "$C_{1-4}$-alkyl" refers to alkyl groups having 1, 2, 3 or 4 carbon atoms. Exemplary $C_{1-4}$-alkyl groups are methyl, ethyl, propyl, isopropyl, butyl, isobutyl, and tert-butyl. The term "$C_{1-6}$-alkyl" refers to alkyl groups having 1, 2, 3, 4, 5 or 6 carbon atoms. Exemplary $C_{1-6}$-alkyl groups are methyl, ethyl, propyl, isopropyl, butyl, isobutyl, tert-butyl, n-pentyl, 2-pentyl, n-hexyl, and 2-hexyl. The term "$C_{1-8}$-alkyl" refers to alkyl groups having 1, 2, 3, 4, 5, 6, 7, or 8 carbon atoms. Exemplary $C_{1-8}$-alkyl groups are methyl, ethyl, propyl, isopropyl, butyl, isobutyl, tert-butyl, n-pentyl, 2-pentyl, n-hexyl, 2-hexyl n-heptyl, 2-heptyl, n-octyl, 2-octyl, and 2,2,4-trimethylpentyl. Each of these alkyl groups may be straight-chain or except for C1-alkyl and C2-alkyl-branched and may be unsubstituted or substituted with 1, 2, 3, 4 or 5 substituents that may be the same or different and may be, if not specified differently elsewhere in this specification, selected from the group comprising halogen, cyano, hydroxy, alkoxy, unsubstituted or mono- or di-substituted amino, aryl, in particular unsubstituted or substituted phenyl, heteroaryl, in particular unsubstituted or substituted pyridyl or pyrimidinyl, heterocyclyl, in particular unsubstituted or substituted pyrrolidinyl, piperidinyl, piperazinyl or morpholinyl.

In some instances the $C_{1-3}$-alkyl, $C_{1-4}$-alkyl, $C_{1-6}$-alkyl, $C_{1-8}$-alkyl groups may also comprise those residues in which 1 or 2 of non-terminal and non-adjacent —$CH_2$— (methylene) groups are replaced by —O—, —S— and/or 1 or 2 non-terminal and non-adjacent —$CH_2$— or —CH— groups are replaced by —NH— or —N—. These replacements yield, for instance, (modified) alkyl groups like —$CH_2$—$CH_2$—O—$CH_3$, —$CH_2$—$CH_2$—$CH_2$—S—$CH_3$, $CH_2$—$CH_2$—NH—$CH_2$—$CH_3$, $CH_2$—$CH_2$—O—$CH_2$—$CH_2$—O—$CH_3$, $CH_2$—$CH_2$—N($CH_3$)—$CH_2$—$CH_3$, and the like. Further and/or different replacements of —CH— and —$CH_2$-groups may be defined for specific alkyl substituents or radicals elsewhere in the description.

The term "$C_{3-7}$-cycloalkyl" refers to a cycloaliphatic hydrocarbon, as defined above, with 3, 4, 5, 6 or 7 ring carbon atoms. Likewise, the term "$C_{3-6}$-cycloalkyl" refers to a cycloaliphatic hydrocarbon with 3, 4, 5, or 6 ring carbon atoms. $C_{3-7}$-cycloalkyl groups may be unsubstituted or substituted with—unless specified differently elsewhere in this specification—1, 2 or 3 substituents that may be the same of different and are—unless specified differently elsewhere in this specification—selected from the group comprising $C_{1-6}$-alkyl, O—$C_{1-6}$-alkyl (alkoxy), halogen, hydroxy, unsubstituted or mono- or di-substituted amino, aryl, in particular unsubstituted or substituted phenyl. If substituted, $C_{3-7}$-cycloalkyl comprises all possible stereoisomers. Exemplary $C_{3-7}$-cycloalkyl groups are cyclopropyl, 2-methyl-cyclopropyl, cyclopropenyl, cyclobutyl, cyclobutenyl, cyclopentyl, cyclopentenyl, cyclohexyl, cyclohexenyl, cycloheptyl, cycloheptenyl. The term "bicyclic $C_{5-8}$-cycloalkyl" refers to a bicyclic cycloaliphatic hydrocarbon, as defined above, with 5, 6, 7, or 8 ring carbon atoms, it includes spirocyclic ring system, i.e. ring systems in which the two carbocycles of the bicyclic $C_{5-8}$-cycloalkyl are attached to each other via the same carbon atom. Bicylic $C_{5-8}$-cycloalkyl groups may be unsubstituted or substituted with—unless specified differently elsewhere in this specification—1, 2 or 3 substituents that may be the same of different and are—unless specified differently elsewhere in this specification—selected from the group comprising $C_{1-6}$-alkyl, O—$C_{1-6}$-alkyl (alkoxy), halogen, hydroxy, unsubstituted or mono- or di-substituted amino. If substituted, bicyclic $C_{5-8}$-cycloalkyl comprises all possible stereoisomers. Exemplary bicyclic $C_{5-8}$-cycloalkyl are spiro[3.3]heptanyl, bicyclo[2.2.1]heptan-2-yl, bicyclo[2.2.2]octan-2-yl, bicyclo[2.2.1]hept-5-en-2-ylmethyl, bicyclo[3.1.1]hept-2-en-2-yl.

The term "aliphatoxy" refers to saturated or unsaturated aliphatic groups or substituents as defined above that are connected to another structural moiety via an oxygen atom (—O—). The term "$C_{1-6}$-aliphatoxy" refers to an aliphatoxy radical with 1, 2, 3, 4, 5, or 6 carbon atoms within the aliphatic group. The term "alkoxy" refers to a particular subgroup of saturated aliphatoxy, i.e. to alkyl substituents and residues that are connected to another structural moiety via an oxygen atom (—O—). Sometimes, it is also referred to as "O-alkyl" and more specifically as "O—$C_{1-2}$-alkyl", "O—$C_{1-3}$-alkyl", "O—$C_{1-4}$-alkyl", "O—$C_{1-6}$-alkyl", "O—$C_{1-8}$-alkyl". Like the similar alkyl groups, it may be straight-chain or—except for —O—$C_1$-alkyl and —O—$C_2$-alkyl—branched and may be unsubstituted or substituted with 1, 2 or 3 substituents that may be the same or different and are, if not specified differently elsewhere in this specification, selected from the group comprising halogen, unsubstituted or mono- or di-substituted amino. Exemplary alkoxy groups are methoxy, difluoromethoxy, trifluoromethoxy, ethoxy, 2,2,2-trifluoroethoxy, n-propoxy, iso-propoxy, n-butoxy, sec-butoxy, tert-butoxy, n-pentoxy.

The term "alkylene" refers to a divalent (or bivalent) aliphatic group and in particular a divalent alkyl group. An "alkylene chain" is a polymethylene group, i.e., $—(CH_2)_y—$, wherein y is a positive integer, preferably 1, 2, 3, 4, 5 or 6. In the context of the present invention "$C_{1-3}$-alkylene" refers to an alkylene moiety with 1, 2 and 3, respectively, $—CH_2—$ groups; the term "alkylene", however, not only comprises linear alkylene groups, i.e. "alkylene chains", but branched alkylene groups as well. The term "$C_{1-6}$-alkylene" refers to an alkylene moiety that is either linear, i.e. an alkylene chain, or branched and has 1, 2, 3, 4, 5 or 6 carbon atoms. The term "$C_{2-6}$-alkylene" refers to an alkylene moiety with 2, 3, 4, 5, or 6 carbon atoms, while a "$C_{3-4}$-alkylene" refers to an alkylene moiety with 3 or 4 carbon atoms and "$C_{2-3}$-alkylene" refers to an alkylene moiety with 2 or 3 carbon atoms. A substituted alkylene is a group in which one or more methylene hydrogen atoms are replaced by (or with) a substituent. Suitable substituents include those described herein for a substituted alkyl group. In some instances 1 or 2 methylene groups of the alkylene chain may be replaced by, for instance, O, S and/or NH or N—$C_{1-4}$-alkyl. Exemplary alkylene groups are $—CH_2—$, $—CH_2—CH_2—$, $—CH_2—CH_2—CH_2—CH_2—$, $—O—CH_2—CH_2—$, $—O—CH_2—CH_2—CH_2—$, $—CH_2—O—CH_2—CH_2—$, $—O—CH_2—O—$, $—O—CH_2—CH_2—O—$, $—O—CH_2—CH_2—CH_2—O—$, $—CH_2—NH—CH_2—CH_2—$, $—CH_2—N(CH_3)—CH_2—CH_2—$.

The term "alkenylene" refers to a divalent alkenyl group. A substituted alkenylene chain is a polymethylene group containing at least one double bond in which one or more hydrogen atoms are replaced with a substituent. Suitable substituents include those described herein for a substituted aliphatic group. The term "alkenylene" not only refers to straight-chain divalent alkenylene radicals, i.e. an alkenylene chain, but to branched alkenylene groups as well. The term "$C_{2-6}$-alkenylene" refers to an alkenylene radical having 2, 3, 4, 5, or 6 carbon atoms.

The term "alkynylene" refers to a divalent alkynyl group. A substituted alkynylene chain is a polymethylene group containing at least one triple bond in which one or more hydrogen atoms are replaced with a substituent. Suitable substituents include those described herein for a substituted aliphatic group.

The term "halogen" means F, Cl, Br, or I.

The term "heteroatom" means one or more of oxygen (O), sulfur (S), or nitrogen (N), including, any oxidized form of nitrogen or sulfur, e.g. N-oxides, sulfoxides and sulfones; the quaternized form of any basic nitrogen or a substitutable nitrogen of a heterocyclic or heteroaromatic ring, for example N (as in 3,4-dihydro-2H-pyrrolyl), NH (as in pyrrolidinyl) or N-SUB with SUB being a suitable substituent (as in N-substituted pyrrolidinyl).

The term "aryl" used alone or as part of a larger moiety as in "aralkyl", "aralkoxy", or "aryloxyalkyl", refers to monocyclic, bicyclic and tricyclic ring systems having a total of five to fourteen ring members, that ring members being carbon atoms, wherein at least one ring in the system is aromatic, i.e., it has (4n+2) π (pi) electrons (with n being an integer selected from 0, 1, 2, 3), which electrons are delocalized over the system, and wherein each ring in the system contains three to seven ring members. Preferably, all rings in the aryl system or the entire ring system are aromatic. The term "aryl" is used interchangeably with the term "aryl ring". In certain embodiments of the present invention, "aryl" refers to an "aromatic ring system". More specifically, those aromatic ring systems may be mono-, bi- or tricyclic with 5, 6, 7, 8, 9, 10, 11, 12, 13, 14 ring carbon atoms. Even more specifically, those aromatic ring systems may be mono- or bicyclic with 6, 7, 8, 9, 10 ring carbon atoms. Exemplary aryl groups are phenyl, biphenyl, naphthyl, anthracyl and the like, which may be unsubstituted or substituted with one or more identical or different substituents. Also included within the scope of the terms "aryl" or "aromatic ring system", as they are used herein, is a group in which an aromatic ring is fused to one or more non-aromatic rings, such as indanyl, phthalimidyl, naphthimidyl, phenanthridinyl, or tetrahydronaphthyl, and the like. In the latter case the "aryl" group or substituent is attached to its pendant group via the aromatic part of the ring system.

The term "benzo" refers to a six-membered aromatic ring (with carbon ring atoms) that is fused via two adjacent carbon atoms to another ring, being it a cycloaliphatic, aromatic, heteroaromatic or heterocyclic (heteroaliphatic) ring; as a result a ring system with at least two rings is formed in which the benzo ring shares two common carbon atoms with the other ring to which it is fused. For example, if a benzo ring is fused to a phenyl ring, a napthaline ring system is formed, while fusing a benzo ring to a pyridine provides for either a quinoline or an isoquinoline; fusing a benzo ring to a cyclopentene ring provides an indene ring.

The terms "heteroaryl" and "heteroar-", used alone or as part of a larger moiety, e.g., "heteroaralkyl", or "heteroaralkoxy", refer to groups having 3, 4, 5, 6, 7, 8, 9, 10, 11, 12, 13, 14 ring atoms (which atoms are carbon and hetero atoms), preferably 5, 6, 9 or 10 ring atoms; having 6, 10, or 14 π (pi) electrons shared in a cyclic array; and having, in addition to carbon atoms, 1, 2, 3, 4 or 5 heteroatoms. The term "heteroatom" refers to nitrogen, oxygen, or sulfur, and includes any oxidized form of nitrogen or sulfur, and any quaternized form of a basic nitrogen. In other words, a "heteroaryl" ring or ring system may also be described as an aromatic heterocycle. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, furazanyl, pyridyl (pyridinyl), pyridazinyl, pyrimidinyl, pyrazinyl, indolizinyl, purinyl, naphthyridinyl, pteridinyl, and pyrrolopyridinyl, in particular pyrrolo[2,3-b]pyridinyl. The terms "heteroaryl" and "heteroar-", as used herein, also include groups in which a heteroaromatic ring is fused to one or more aryl, cycloaliphatic, or heterocyclyl rings, where the radical or point of attachment is preferably on the heteroaromatic or, if present, the aryl ring. Nonlimiting examples include indolyl, isoindolyl, benzothienyl (benzothiophenyl), benzofuranyl, dibenzofuranyl, indazolyl, benzimidazolyl, benzothiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, 9H-carbazolyl, dibenzofuranyl and pyrido[2,3-b]-1,4-oxazin-3(4H)-one. For example, an indolyl ring may be attached via one of the ring atoms of the six-membered aryl ring or via one of the ring atoms of the five-membered heteroaryl ring. A heteroaryl group is optionally mono-, bi- or tricyclic. The term "heteroaryl" is used interchangeably with the terms "heteroaryl ring", "heteroaryl group", or "heteroaromatic", any of which terms include rings that are unsubstituted or substituted with one or more identical or different substituents. The term "heteroaralkyl" refers to an alkyl group substituted by a heteroaryl, wherein the alkyl and heteroaryl portions independently are optionally substituted.

A heteroaryl ring can be attached to its pendant group at any of its hetero or carbon ring atoms which attachment results in a stable structure or molecule: any of the ring atoms may be unsubstituted or substituted.

The structures of typical examples of "heteroaryl" substituents as used in the present invention are depicted below:

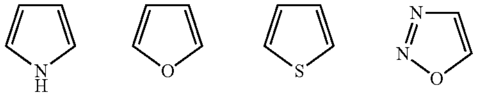

pyrrolyl, furanyl, thiophenyl, 1-oxa-2,3-diazolyl

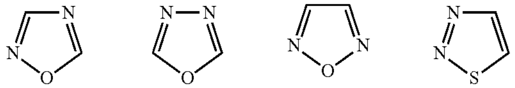

1-oxa-2,4-diazolyl, 1-oxa-3,4-diazolyl, 1-oxa-2,5-diazolyl, 1-thia-2,3-diazolyl

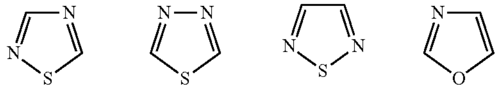

1-thia-2,4-diazolyl, 1-thia-3,4-diazolyl, 1-thia-2,5-diazolyl, oxazolyl

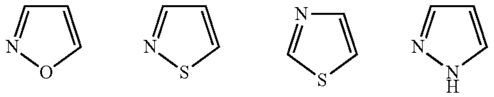

isoxazolyl, isothiazolyl, thiazolyl, pyrazolyl

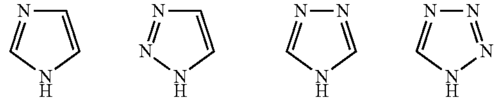

imidazolyl, 1,23-triazolyl, 1,2,4-triazolyl, tetrazolyl

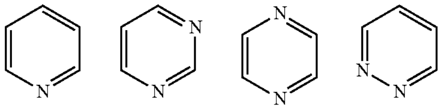

pyridinyl (pyridyl), pyrimidinyl, pyrazinyl, pyridazinyl

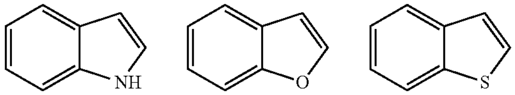

indolyl, benzofuranly, benzothiophenyl

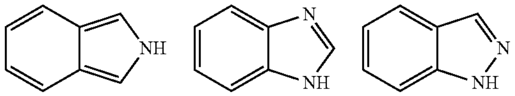

isoindolyl, benzimidazolyl, indazolyl

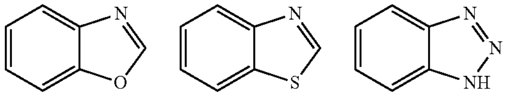

benzoxazolyl, benzothiazolyl, benzotriazolyl

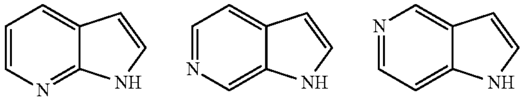

pyrrolo[2,3-b] pyridinyl, pyrrolo[2,3-c] pyridinyl, pyrrolo[3,2-c] pyridinyl

-continued

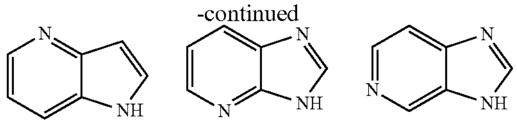

pyrrolo[3,2-b] pyridinyl, imidazo[4,5-b] pyridinyl, imidazo[4,5-c] pyridinyl

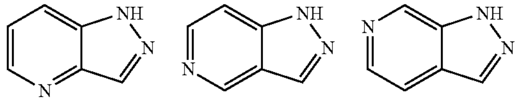

pyrazolo[4,3-d] pyridinyl, pyrazolo[4,3-c] pyridinyl, pyrazolo[3,4-c] pyridinyl

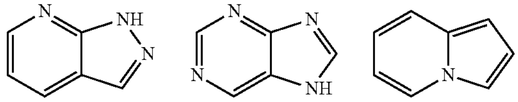

pyrazolo[3,4-b] pyridinyl, purinyl, indolizinyl

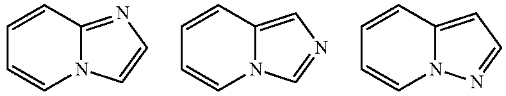

imidazo[1,2-a] pyridinyl, imidazo[1,5-a] pyridinyl, pyrazolo[1,5-a] pyridinyl

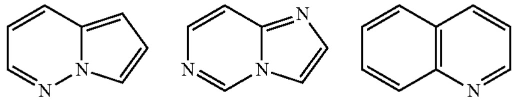

pyrrolo[1,2-b] pyridazinyl, imidazo[1,2-c] pyrimidinyl, quinolinyl

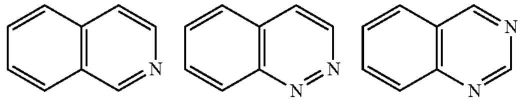

isoquinolinyl, cinnolinyl, quinazolinyl

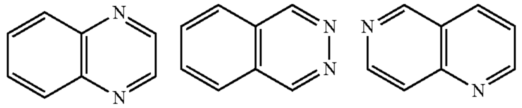

quinoxalinyl, phthalazinyl, 1,6-naphthyridinyl

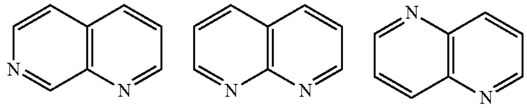

1,7-naphthyridinyl, 1,8-naphthyridinyl, 1,5-naphthyridinyl

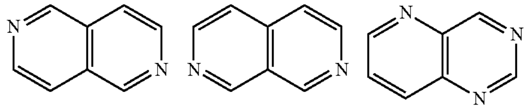

2,6-naphthyridinyl, 2,7-naphthyridinyl, pyrido[3,2-d] pyrimidinyl

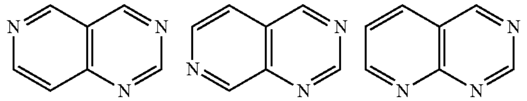

pyrido[4,3-d] pyrimidinyl, pyrido[3,4-d] pyrimidinyl, pyrido[2,3-d] pyrimidinyl

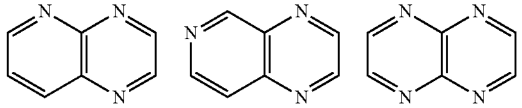

pyrido[2,3-d] pyrazinyl, pyrido[3,4-b] pyrazinyl, pyrazino[2,3-b] pyrazinyl

-continued

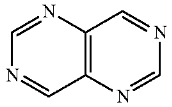

pyrimido[5,4-d] pyrimidinyl

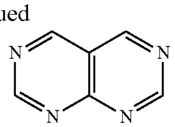

pyrimido[4,5-d] pyrimidinyl

Those heteroaryl substituents can be attached to any pendant group via any of its ring atoms suitable for such an attachment.

As used herein, the terms "heterocycle", "heterocyclyl", "heterocyclic radical", and "heterocyclic ring" are used interchangeably and refer to a stable mono-bi- or tricyclic heterocyclic moiety with 5, 6, 7, 8, 9, 10, 11, 12, 13, 14 ring atoms wherein 1, 2, 3, 4, 5 of said ring atoms are hetero atoms and wherein that heterocyclic moiety is either saturated or partially unsaturated; heterocyclic moieties that are aromatic rings or ring systems are referred to as "heteroaryl" moieties as described hereinabove. Preferably, the heterocycle is a stable saturated or partially unsaturated 3-, 4-, 5-, 6-, or 7-membered monocyclic or 7-, 8-, 9-, 10-, or 11-membered bicyclic or 11-, 12-, 13-, or 14-membered tricyclic heterocyclic moiety.

When used in reference to a ring atom of a heterocycle, the term "nitrogen" includes a substituted nitrogen. As an example, in a saturated or partially unsaturated ring having 1-3 heteroatoms selected from oxygen, sulfur or nitrogen, the nitrogen is N (as in 3,4-dihydro-2H-pyrrolyl), NH (as in pyrrolidinyl), or N-SUB with SUB being a suitable substituent (as in N-substituted pyrrolidinyl).

In the context of the term "heterocycle" the term "saturated" refers to a completely saturated heterocyclic system, like pyrrolidinyl, piperidinyl, morpholinyl, piperidinonyl, tetrahydrofuranyl, thianyl, and dioxothianyl. With regard to the term "heterocycle" the term "partially unsaturated" refers to heterocyclic systems (i) that contain one or more units of unsaturation, e.g. a C═C or a C═Heteroatom bond, but that are not aromatic, for instance, tetrahydropyridinyl; or (ii) in which a (saturated or unsaturated but non-aromatic) heterocyclic ring is fused with an aromatic or heteroaromatic ring system, wherein, however, the "partially unsaturated heterocycle" is attached to the rest of the molecule (its pendant group) via one of the ring atoms of the "heterocyclic" part of the system and not via the aromatic or heteroaromatic part. This first class (i) of "partially unsaturated" heterocycles may also be referred to as "non-aromatic partially unsaturated" heterocycles. This second class (ii) of "partially unsaturated" heterocycles may also be referred to as (bicyclic or tricyclic) "partially aromatic" heterocycles indicating that at least one of the rings of that heterocycle is a saturated or unsaturated but non-aromatic heterocycle that is fused with at least one aromatic or heteroaromatic ring system. Typical examples of these "partially aromatic" heterocycles are 1,2,3,4-tetrahydroquinolinyl and 1,2,3,4-tetrahydroisoquinolinyl.

A heterocyclic ring can be attached to its pendant group at any heteroatom or carbon atom that results in a stable structure and any of the ring atoms may be unsubstituted or substituted. Examples of such saturated or partially unsaturated heterocyclic radicals include, without limitation, tetrahydrofuranyl, tetrahydropyranyl, thianyl, dioxothianyl, tetrahydrothiophenyl, pyrrolidinyl, piperidinyl, pyrrolinyl, morpholinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group is optionally mono-, bi- or tricyclic. The term "heterocyclylalkyl" refers to an alkyl group substituted by a heterocyclyl, wherein the alkyl and heterocyclyl portions independently are unsubstituted or substituted. The term "carbohydrate derived radical" refers to monovalent organic radicals derived from any kind of carbohydrate compounds, such as aldoses and ketosis, as well as polyols, i.e. reduced carbohydrates, and carbohydrate acids, i.e. oxidized carbohydrates, derived from such aldoses and ketosis. The term comprises monovalent radicals of monosaccharides and reduced and oxidized derivatives thereof, including, but not being limited to, D/L-glycerol aldehyde, D-glycerol aldehyde, L-glycerol aldehyde, dihydroxy acetone, D/L-erythrose, D-erythrose, L-erythrose, D/L-threose, D-threose, L-threose, D/L-ribose, D-ribose, L-ribose, D/L-arabinose, D-arabinose, L-arabinose, D/L-xylose, D-xylose, L-xylose, D/L-lyxose, D-lyxose, L-lyxose, D/L-allose, D-allose, L-allose, D/L-altrose, D-altrose, L-altrose, D/L-glucose, D-glucose, L-glucose, D/L-mannose, D-mannose, L-mannose, D/L-gulose, D-gulose, D-gulose, D/L-idose, D-idose, L-idose, D/L-galactose, D-galactose, L-galactose, D/L-talose, D-talose, L-talose, D/L-fructose, D-fructose, L-fructose; D/L-sorbose, D-sorbose, L-sorbose; D/L-sorbit, D-sorbit, L-sorbit, D/L-mannit, D-mannit, L-mannit, D/L-allit, D-allit, L-allit, D/L-galacit, D-galacit, L-galacit, D/L-glucit, D-glucit, L-glucit, D/L-idit, D-idit, L-idit, D/L-altrit, D-altrit, L-altrit; D/L-glucon acid, D-glucon acid, L-glucon acid, D/L-mannon acid, D-mannon acid, L-mannon acid, D/L-allon acid, D-allon acid, L-allon acid, D/L-glucoronic acid, D-glucoronic acid, L-glucoronic acid. It further comprises monovalent radicals of di- and oligosaccharides and their respective reduced and oxidized derivatives, including sucrose, lactose, maltose, cellobiose. These carbohydrate derived radicals may be utilized in their pure D- or L-form or as a mixture of D- and L-form in each ratio possible. Likewise, each of these radicals include their open as well as their cyclic form in pure form or as a mixture in any ratio. Each of these carbohydrate derived radicals may further be substituted by suitable substituents, e.g., halogen, cyano, unsubstituted, mono- or disubstituted amino, $C_{1-6}$aliphatic, $C_{1-6}$aliphatoxy, aryl, arylalkyl, and the like. Any carbohydrate derived radical can be attached to its pendant group at any of its hetero or carbon atoms which attachment results in a stable structure or molecule. Examples of carbohydrate derived radicals are D/L-fructose, D-fructose, D/L-glucose, D-glucose, D/L-glucoronic acid, D-glucoronic acid, L-glucoronic acid.

The term "bioisostere", if used alone or in combination with other terms, e.g., "bioisostere radical", refers to a compound or a group, radical, moiety, substituent and the like, that elicits a similar biological effect as another compound, group, radical, moiety or substituent though they are structurally different to each other. In a broader sense, "bioisosteres" can be understood as compounds or groups that possess near-equal molecular shapes and volumes, approximately the same distribution of electrons, and which exhibit similar physical properties. Typical examples for bioisosteres are carboxylic acid bioisosteres which exhibit similar physico-chemical properties as a carboxylic acid group ("carboxylic acid bioisostere"). Such a carboxylic acid bioisostere group or radical may be utilized in place of a carboxylic acid group or radical thereby providing properties similar to those of the carboxylic group but potentially exhibiting some different properties when compared to the carboxylic acid group, for instance, reduced polarity, increased lipophilicity, or enhanced pharmacokinetic properties. Typical examples of carboxylic acid bioisosteres include, without being limited to, —CN, fluoro, amides, sulfonamides, sulfonimides, and several aromatic and non-aromatic heterocycles such as hydroxy-substituted isoxazoles, sulfonamido-substituted oxadiazoles and oxo-oxadiazoles, e.g., 5-oxo-2,5-dihydro-1,2,4-oxadiazol, and in particular tetrazoles, e.g. 1H-1,2,3,4-tetrazole, 2-methyl-2H-1,2,3,4-tetrazole.

The term "unsaturated", as used herein, means that a moiety or group or substituent has one or more units of unsaturation.

As used herein with reference to any rings, ring systems, ring moieties, and the like, the term "partially unsaturated" refers to a ring moiety that includes at least one double or triple bond. The term "partially unsaturated" is intended to encompass rings having multiple sites of unsaturation. In particular, it encompasses (i) non-saturated (mono-, bi- or tricyclic) ring systems without any aromatic or heteroaromatic moiety or part, and (ii) bi- or tricyclic ring systems in which one of the rings of that system is an aromatic or heteroaromatic ring which is fused with another ring that is neither an aromatic nor a heteroaromatic ring, e.g. tetrahydronaphthyl or tetrahydroquinolinyl. The first class (i) of "partially unsaturated" rings, ring systems, ring moieties may also be referred to as "non-aromatic partially unsaturated" rings, ring systems, ring moieties, while the second class (ii) may be referred to as "partially aromatic" rings, ring systems, ring moieties.

As used herein, the term "bicyclic", "bicyclic ring" or "bicyclic ring system" refers to any bicyclic ring system, i.e. carbocyclic or heterocyclic, saturated or having one or more units of unsaturation, i.e. being partially unsaturated or aromatic, having one or more atoms in common between the two rings of the ring system. Thus, the term includes any permissible ring fusion, such as ortho-fused or spirocyclic. As used herein, the term "heterobicyclic" is a subset of "bicyclic" that requires that one or more heteroatoms are present in one or both rings of the bicycle. Such heteroatoms may be present at ring junctions and are optionally substituted, and may be selected from nitrogen (including N-oxides), oxygen, sulfur (including oxidized forms such as sulfones and sulfonates), phosphorus (including oxidized forms such as phosphates), boron, etc. In some embodiments, a bicyclic group has 7-12 ring members and 0-4 heteroatoms independently selected from nitrogen, oxygen, or sulfur. Likewise, the term "tricyclic", "tricyclic ring" or "tricyclic ring system" refers to any tricyclic ring system, i.e. carbocyclic or heterocyclic, saturated or having one or more units of unsaturation, i.e. being partially unsaturated or aromatic, in which a bicyclic ring system (as defined above) is fused with another, third ring. Thus, the term includes any permissible ring fusion. As used herein, the term "heterotricyclic" is a subset of "tricyclic" that requires that one or more heteroatoms are present in one or both rings of the tricycle. Such heteroatoms may be present at ring junctions and are optionally substituted, and may be selected from nitrogen (including N-oxides), oxygen, sulfur (including oxidized forms such as sulfones and sulfonates), phosphorus (including oxidized forms such as phosphates), boron, etc. In some embodiments, a tricyclic group has 10-14 ring members and 0-5 heteroatoms independently selected from nitrogen, oxygen, or sulfur.

As described herein, certain compounds of the invention contain "substituted" or "optionally substituted" moieties. In general, the term "substituted", whether preceded by the term "optionally" or not, means that one or more hydrogens of the designated moiety are replaced with a suitable substituent. "Substituted" applies to one or more hydrogens that are either explicit or implicit from the structure. Unless otherwise indicated, a "substituted" or "optionally substituted" group has a suitable substituent at each substitutable position of the group, and when more than one position in any given structure is substituted with more than one substituent selected from a specified group, the substituent is either the same or different at every position. If a certain group, substituent, moiety or radical is "mono-substituted", it bears one (1) substituent. If it is "di-substituted", it bears two (2) substituents, being either the same or different; if it is "tri-substituted", it bears three (3) substituents, wherein all three are the same or two are the same and the third is different or all three are different from each other. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

If not specified otherwise elsewhere in the specification it is understood that each optional substituent on a substitutable carbon is a monovalent substituent independently selected from halogen; —$(CH_2)_{0-4}R^{\circ}$; —$(CH_2)_{0-4}OR^{\circ}$; —$O(CH_2)_{0-4}R^{\circ}$, —O—$(CH_2)_{0-4}C(O)OR^{\circ}$; —$(CH_2)_{0-4}CH(OR^{\circ})_2$; —$(CH_2)_{0-4}SR^{\circ}$; —$(CH_2)_{0-4}Ph$, which may be substituted with one or more $R^{\circ}$; —$(CH_2)_{0-4}O(CH_2)_{0-1}Ph$ which may be substituted with one or more $R^{\circ}$; —CH═CHPh, which may be substituted with one or more $R^{\circ}$; —$(CH_2)_{0-4}O(CH_2)_{0-1}$-pyridyl which may be substituted with one or more $R^{\circ}$; —$NO_2$; —CN; —$N_3$; —$(CH_2)_{0-4}N(R^{\circ})_2$; —$(CH_2)_{0-4}N(R^{\circ})C(O)R^{\circ}$; —$N(R^{\circ})C(S)R^{\circ}$; —$(CH_2)_{0-4}N(R^{\circ})C(O)NR^{\circ}_2$; —$N(R^{\circ})C(S)NR^{\circ}_2$; —$(CH_2)_{0-4}N(R^{\circ})C(O)OR^{\circ}$; —$N(R^{\circ})N(R^{\circ})C(O)R^{\circ}$; —$N(R^{\circ})N(R^{\circ})C(O)NR^{\circ}_2$; —$N(R^{\circ})N(R^{\circ})C(O)OR^{\circ}$; —$(CH_2)_{0-4}$ $C(O)R^{\circ}$; —$C(S)R^{\circ}$; —$(CH_2)_{0-4}C(O)OR^{\circ}$; —$(CH_2)_{0-4}C(O)SR^{\circ}$; —$(CH_2)_{0-4}$ $C(O)OSiR^{\circ}_3$; —$(CH_2)_{0-4}OC(O)R^{\circ}$; —$OC(O)(CH_2)_{0-4}SR$—, $SC(S)SR^{\circ}$; —$(CH_2)_{0-4}$ $SC(O)R^{\circ}$; —$(CH_2)_{0-4}C(O)NR^{\circ}_2$; —$C(S)NR^{\circ}_2$; —$C(S)SR^{\circ}$; —$SC(S)SR^{\circ}$, —$(CH_2)_{0-4}$—$OC(O)NR^{\circ}_2$; —$C(O)N(OR^{\circ})R^{\circ}$; —$C(O)C(O)R^{\circ}$; —$C(O)CH_2C(O)R^{\circ}$; —$C(NOR^{\circ})R^{\circ}$; —$(CH_2)_{0-4}SSR^{\circ}$; —$(CH_2)_{0-4}S(O)_2R^{\circ}$; —$(CH_2)_{0-4}S(O)_{20}R^{\circ}$; —$(CH_2)_{0-4}$—$OS(O)_2R^{\circ}$; —$S(O)_2NR^{\circ}_2$; —$S(O)(NR^{\circ})R^{\circ}$; —$S(O)_2N$═$C(NR^{\circ}_2)_2$; —$(CH_2)_{0-4}$ $S(O)R^{\circ}$; —$N(R^{\circ})S(O)_2NR^{\circ}_2$; —$N(R^{\circ})S(O)_2R^{\circ}$; —$N(OR^{\circ})R^{\circ}$; —$C(NH)NR^{\circ}_2$; —$P(O)_2R^{\circ}$; —$P(O)R^{\circ}_2$; —$OP(O)R^{\circ}_2$; —$OP(O)(OR^{\circ})_2$; $SiR^{\circ}_3$; —($C_{1-4}$ straight or branched alkylene)O—$N(R^{\circ})_2$; or —($C_{1-4}$ straight or branched alkylene)C(O)O—$N(R^{\circ})_2$. It is understood that "Ph" means phenyl; and that "—$(CH_2)_{0-4}$" means that there is either no alkylene group if the subscript is "0" (zero) or an alkylene group with 1, 2, 3 or 4 $CH_2$ units.

Each $R^{\circ}$ is independently hydrogen, halogen, $C_{1-6}$ aliphatic, —$CH_2Ph$, —$O(CH_2)_{0-1}Ph$, —$CH_2$—(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted by a divalent substituent on a saturated carbon atom of R° selected from =O and =S; or each R° is optionally substituted with a monovalent substituent independently selected from halogen, —$(CH_2)_{0-2}R^{●}$, -(halo$R^{●}$), —$(CH_2)_{0-2}OH$, —$(CH_2)_{0-2}OR^{●}$, —$(CH_2)_{0-2}CH(OR^{●})_2$; O(halo$R^{●}$), —CN, —$N_3$, —$(CH_2)_{0-2}C(O)R^{●}$, —$(CH_2)_{0-2}C(O)OH$, —$(CH_2)_{0-2}C(O)OR^{●}$, —$(CH_2)_{0-2}SR^{●}$, —$(CH_2)_{0-2}SH$, —$(CH_2)_{0-2}NH_2$, —$(CH_2)_{0-2}NHR^{●}$, —$(CH_2)_{0-2}NR°_2$, —$NO_2$, —$SiR°_3$, —$OSiR°_3$, $C(O)SR^{●}$, —($C_{1-4}$ straight or branched alkylene)$C(O)OR^{●}$, or —$SSR^{●}$. It is understood that "Ph" means phenyl; "halo" means halogen; and "—$(CH_2)_{0-2}$" means that there is either no alkylene group if the subscript is "0" (zero) or an alkylene group with 1 or 2 $CH_2$ units.

Each $R^{●}$ is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, and wherein each $R^{●}$ is unsubstituted or where preceded by halo is substituted only with one or more halogens; or wherein an optional substituent on a saturated carbon is a divalent substituent independently selected from =O, =S, =NNR*2, =NNHC(O)R*, =NNHC(O)OR*, =NNHS$(O)_2$R*, =NR*, =NOR*, —O(C(R*2))$_{2-3}$O—, or —S(C(R*$_2$))$_{2-3}$S—, or a divalent substituent bound to vicinal substitutable carbons of an "optionally substituted" group is —O(CR*2)$_{2-3}$O—, wherein each independent occurrence of R* is selected from hydrogen, $C_{1-6}$ aliphatic or an unsubstituted 5-6-membered saturated, partially unsaturated, or aryl ring having 0-4 heteroatoms independently selected from nitrogen, oxygen, or sulfur.

When R* is $C_{1-6}$ aliphatic, R* is optionally substituted with halogen, —R*, (halo$R^{●}$), OH, —$OR^{●}$, —O(halo$R^{●}$), —CN, —C(O)OH, —$C(O)OR^{●}$, —$NH_2$, —$NHR^{●}$, —$NR^{●}_2$, or —$NO_2$, wherein each $R^{●}$ is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, and wherein each $R^{●}$ is unsubstituted or where preceded by halo is substituted only with one or more halogens.

An optional substituent on a substitutable nitrogen is independently —$R^{†}$, —$NR^{†}_2$, —$C(O)R^{†}$, —$C(O)OR^{†}$, —$C(O)C(O)R^{†}$, —$C(O)CH_2C(O)R^{†}$, —$S(O)_2R^{†}$, —$S(O)_2NR^{†}_2$, —$C(S)NR^{†}_2$, —$C(NH)NR^{†}_2$, or —$N(R^{†})S(O)_2R^{†}$; wherein each $R^{†}$ is independently hydrogen, $C_{1-6}$ aliphatic, unsubstituted —OPh, or an unsubstituted 5-6-membered saturated, partially unsaturated, or aryl ring having 0-4 heteroatoms independently selected from nitrogen, oxygen, or sulfur, or, two independent occurrences of $R^{†}$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur; wherein when $R^{†}$ is $C_{1-6}$ aliphatic, $R^{†}$ is optionally substituted with halogen, —$R^{●}$, -(halo$R^{●}$), —OH, —$OR^{●}$, —O(halo$R^{●}$), —CN, —C(O)OH, —$C(O)OR^{●}$, —$NH_2$, —$NHR^{●}$, —$NR^{●}_2$, or —$NO_2$, wherein each $R^{●}$ is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, and wherein each $R^{●}$ is unsubstituted or where preceded by halo is substituted only with one or more halogens. It is understood that "Ph" means phenyl; and "halo" means halogen.

The term "solvates" means addition forms of the compounds of the present invention with solvents, preferably pharmaceutically acceptable solvents that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, e.g. a hemi-, mono- or dihydrate. If the solvent is alcohol, the solvate formed is an alcoholate, e.g., a methanolate or ethanolate.

If the solvent is an ether, the solvate formed is an etherate, e.g., diethyl etherate.

The term "N-oxides" means such compounds of the present invention that contain an amine oxide moiety, i.e. the oxide of a tertiary amine group.

The compounds of formulas I-A and I may—also depending on the nature of substituents they may bear—have one or more centers of chirality. They may accordingly occur in various enantiomeric and diastereomeric forms, as the case may be, and be in racemic or optically active form. The invention, therefore, also relates to the optically active forms, enantiomers, racemates, diastereomers, mixtures thereof in all ratios, collectively: "stereoisomers" for the purpose of the present invention, of these compounds. Since the pharmaceutical activity of the racemates or stereoisomers of the compounds according to the invention may differ, it may be desirable to use a specific stereoisomer, e.g. one specific enantiomer or diastereomer. In these cases, a compound according to the present invention obtained as a racemate or even intermediates thereof—may be separated into the stereoisomeric (enantiomeric, diastereoisomeric) compounds by chemical or physical measures known to the person skilled in the art. Another approach that may be applied to obtain one or more specific stereoisomers of a compound of the present invention in an enriched or pure form makes use of stereoselective synthetic procedures, e.g. applying starting material in a stereoisomerically enriched or pure form (for instance using the pure or enriched (R)- or (S)-enantiomer of a particular starting material bearing a chiral center) or utilizing chiral reagents or catalysts, in particular enzymes. In the context of the present invention the term "pure enantiomer" usually refers to a relative purity of one enantiomer over the other (its antipode) of equal to or greater than 95%, preferably 98%, more preferably 98.5%, still more preferably 99%.

Thus, for example, the compounds of the invention which have one or more centers of chirality and which occur as racemates or as mixtures of enantiomers or diastereoisomers can be fractionated or resolved by methods known per se into their optically pure or enriched isomers, i.e. enantiomers or diastereomers. The separation of the compounds of the invention can take place by chromatographic methods, e.g. column separation on chiral or nonchiral phases, or by recrystallization from an optionally optically active solvent or by use of an optically active acid or base or by derivatization with an optically active reagent such as, for example, an optically active alcohol, and subsequent elimination of the radical.

In the context of the present invention the term "tautomer" refers to compounds of the present invention that may exist in tautomeric forms and show tautomerism; for instance, carbonyl compounds may be present in their keto and/or their enol form and show keto-enol tautomerism. Those tautomers may occur in their individual forms, e.g., the keto or the enol form, or as mixtures thereof and are described separately and together as mixtures in any ratio. The same applies for cis/trans isomers, E/Z isomers, conformers and the like.

In one embodiment the compounds of the present invention are in the form of free base or acid—as the case may be —, i.e. in their non-salt (or salt-free) form. In another embodiment the compounds of the present invention are in the form of a pharmaceutically acceptable salt, a pharmaceutically acceptable solvate, or a pharmaceutically acceptable solvate of a pharmaceutically acceptable salt.

The term "pharmaceutically acceptable salts" refers to salts prepared from pharmaceutically acceptable bases or acids, including inorganic bases or acids and organic bases or acids. In cases where the compounds of the present invention contain one or more acidic or basic groups, the invention also comprises their corresponding pharmaceutically acceptable salts. Thus, the compounds of the present invention which contain acidic groups, such as carboxyl groups, can be present in salt form, and can be used according to the invention, for example, as alkali metal salts, alkaline earth metal salts, aluminium salts or as ammonium salts. More precise examples of such salts include lithium salts, sodium salts, potassium salts, calcium salts, magnesium salts, barium salts or salts with ammonia or organic amines such as, for example, ethylamine, ethanolamine, diethanolamine, triethanolamine, piperdine, N-methylglutamine or amino acids. These salts are readily available, for instance, by reacting the compound having an acidic group with a suitable base, e.g. lithium hydroxide, sodium hydroxide, sodium propoxide, potassium hydroxide, potassium ethoxide, magnesium hydroxide, calcium hydroxide or barium hydroxide. Other base salts of compounds of the present invention include but are not limited to copper(I), copper(II), iron(II), iron (III), manganese(II) and zinc salts. Compounds of the present invention which contain one or more basic groups, e.g. groups which can be protonated, can be present in salt form, and can be used according to the invention in the form of their addition salts with inorganic or organic acids. Examples of suitable acids include hydrogen chloride, hydrogen bromide, hydrogen iodide, phosphoric acid, sulfuric acid, nitric acid, methanesulfonic acid, p-toluenesulfonic acid, naphthalenedisulfonic acid, sulfoacetic acid, trifluoroacetic acid, oxalic acid, acetic acid, tartaric acid, lactic acid, salicylic acid, benzoic acid, carbonic acid, formic acid, propionic acid, pivalic acid, diethylacetic acid, malonic acid, succinic acid, pimelic acid, fumaric acid, malonic acid, maleic acid, malic acid, embonic acid, mandelic acid, sulfaminic acid, phenylpropionic acid, gluconic acid, ascorbic acid, isonicotinic acid, citric acid, adipic acid, taurocholic acid, glutaric acid, stearic acid, glutamic acid or aspartic acid, and other acids known to the person skilled in the art. The salts which are formed are, inter alia, hydrochlorides, chlorides, hydrobromides, bromides, iodides, sulfates, phosphates, methanesulfonates (mesylates), tosylates, carbonates, bicarbonates, formates, acetates, sulfoacetates, triflates, oxalates, malonates, maleates, succinates, tartrates, malates, embonates, mandelates, fumarates, lactates, citrates, glutarates, stearates, aspartates and glutamates. The stoichiometry of the salts formed from the compounds of the invention may moreover be an integral or non-integral multiple of one.

Compounds of the present invention which contain basic nitrogen-containing groups can be quaternized using agents such as $(C_1-C_4)$alkyl halides, for example methyl, ethyl, isopropyl and tert-butyl chloride, bromide and iodide; di$(C_1-C_4)$alkyl sulfates, for example dimethyl, diethyl and diamyl sulfate; $(C_{10}-C_{18})$alkyl halides, for example decyl, dodecyl, lauryl, myristyl and stearyl chloride, bromide and iodide; and aryl$(C_1-C_4)$alkyl halides, for example benzyl chloride and phenethyl bromide. Both water- and oil-soluble compounds according to the invention can be prepared using such salts.

If the compounds of the present invention simultaneously contain acidic and basic groups in the molecule, the invention also includes, in addition to the salt forms mentioned, inner salts or betaines (zwitterions). The respective salts can be obtained by customary methods which are known to a person skilled in the art, for example by contacting these with an organic or inorganic acid or base in a solvent or dispersant, or by anion exchange or cation exchange with other salts. The present invention also includes all salts of the compounds of the present invention which, owing to low physiological compatibility, are not directly suitable for use in pharmaceuticals but which can be used, for example, as intermediates for chemical reactions or for the preparation of pharmaceutically acceptable salts.

Therefore, the following items are also in accordance with the invention:

(a) all stereoisomers or tautomers of the compounds, including mixtures thereof in all ratios;

(b) pharmaceutically acceptable salts of the compounds and of the items mentioned under (a);

(c) pharmaceutically acceptable solvates of the compounds and of the items mentioned under (a) and (b);

(d) N-oxides of the compounds and of the items mentioned under (a), (b), and (c).

It should be understood that all references to compounds above and below are meant to include these items, in particular pharmaceutically acceptable solvates of the compounds, or pharmaceutically acceptable solvates of their pharmaceutically acceptable salts.

There is furthermore intended that a compound of the present invention includes isotope-labelled forms thereof. An isotope-labelled form of a compound of the formula I or I-A is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the present invention by well-known methods include isotopes of hydrogen, carbon, nitrogen, oxygen, phosphorus, sulfur, fluorine and chlorine, for example $^2H$ (D), $^3H$, $^{13}C$, $^{14}C$, $^{15}N$, $^{18}O$, $^{17}O$, $^{31}P$, $^{32}P$, $^{33}S$, $^{34}S$, $^{35}S$, $^{36}S$, $^{18}F$ and $^{36}Cl$, respectively. A compound of formula I or I-A or a pharmaceutically acceptable salt thereof which contains one or more of the above-mentioned isotopes and/or other isotopes of other atoms is intended to be part of the present invention. An isotope-labelled compound of formula I or I-A can be used in a number of beneficial ways. For example, an isotope-labelled compound of the present invention into which, for example, a radioisotope, such as 3H or $^{14}C$, has been incorporated is suitable for medicament and/or substrate tissue distribution assays. These radioisotopes, i.e. tritium ($^3H$) and carbon-14 ($^{14}C$), are particularly preferred owing to simple preparation and excellent detectability. Incorporation of heavier isotopes, for example deuterium ($^2H$), into a compound of formula I or I-A has therapeutic advantages owing to the higher metabolic stability of this isotope-labelled compound. Higher metabolic stability translates directly into an increased in vivo half-life or lower dosages, which under most circumstances would represent a preferred embodiment of the present invention. An isotope-labelled compound of formula I or I-A can usually be prepared by carrying out the procedures disclosed in the synthesis schemes and the related description, in the example part and in the preparation part in the present text, replacing a non-isotope-labelled reactant by a readily available isotope-labelled reactant.

Deuterium ($^2H$; D) can also be incorporated into a compound of formula I-A or I for the purpose of manipulating the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus cause a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D$=2-7 are typical. If this rate difference is successfully applied to a compound of the formula I or I-A that is susceptible to oxidation, the profile of this compound in vivo can be drastically modified and result in improved pharmacokinetic properties.

When discovering and developing therapeutic agents, the person skilled in the art attempts to optimize pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of the formula I or I-A with improved stability through resistance to such oxidative meta-bolism. Significant improvements in the pharmacokinetic profiles of compounds of the formula I or I-A are thereby obtained, and can be expressed quantitatively in terms of increases in the in vivo half-life (t1/2), concentration at maximum therapeutic effect ($C_{max}$), area under the dose response curve (AUC), and F; and in terms of reduced clearance, dose and materials costs.

The following is intended to illustrate the above: a compound of formula I or I-A which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favourable and accurate determination of the extent of the extent to which the improvement in resistance to oxidative metabolism has improved. In this way, it is deter-mined that the half-life of the parent compound can be extended by up to 100% as the result of deuterium-hydrogen exchange of this type.

Deuterium-hydrogen exchange in a compound of the present invention can also be used to achieve a favourable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1995.

Furthermore, the present invention relates to pharmaceutical compositions comprising at least one compound of formula I or I-A, or its N-oxides, solvates, tautomers or stereoisomers thereof as well as the pharmaceutically acceptable salts of each of the foregoing, including mixtures thereof in all ratios, as active ingredient, together with a pharmaceutically acceptable carrier.

For the purpose of the present invention the term “pharmaceutical composition” (or “pharmaceutical formulation”) refers to a composition or product comprising one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing at least one compound of the present invention and a pharmaceutically acceptable carrier. It may further comprise physiologically acceptable excipients, auxiliaries, adjuvants, diluents and/or additional pharmaceutically active substance other than the compounds of the invention.

The pharmaceutical compositions include compositions and pharmaceutical formulations suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

A pharmaceutical composition of the present invention may additionally comprise one or more other compounds as active ingredients (drugs), such as one or more additional compounds of the present invention. In a particular embodiment the pharmaceutical composition further comprises a second active ingredient or its derivatives, prodrugs, solvates, tautomers or stereoisomers thereof as well as the pharmaceutically acceptable salts of each of the foregoing, including mixtures thereof in all ratios, wherein that second active ingredient is other than a compound of formula I and I-A, preferably, that second active ingredient is a compound that is useful in the treatment, prevention, suppression and/or amelioration of medicinal conditions or pathologies for which the compounds of the present invention are useful as well and which are listed elsewhere hereinbefore or hereinafter. Such combination of two or more active ingredients or drugs may be safer or more effective than either drug or active ingredient alone, or the combination is safer or more effective than it would be expected based on the additive properties of the individual drugs. Such other drug(s) may be administered, by a route and in an amount commonly used contemporaneously or sequentially with a compound of the invention. When a compound of the invention is used contemporaneously with one or more other drugs or active ingredients, a combination product containing such other drug(s) and the compound of the invention—also referred to as “fixed dose combination”—is preferred.

However, combination therapy also includes therapies in which the compound of the present invention and one or more other drugs are administered on different overlapping schedules. It is contemplated that when used in combination with other active ingredients, the compound of the present invention or the other active ingredient or both may be used effectively in lower doses than when each is used alone. Accordingly, the pharmaceutical compositions of the present invention include those that contain one or more other active ingredients, in addition to a compound of the invention.

The compounds of the present invention—or N-oxides, solvates, tautomers or stereoisomers thereof and/or the pharmaceutically acceptable salts of each of the foregoing, including mixtures thereof in all ratios—can be used as medicaments. They have been found to exhibit pharmacological activity by binding to TEAD and/or disrupting and/or inhibiting YAP-TEAD and/or TAZ-TEAD protein-protein interaction. It is assumed that by this activity the compounds of the present invention may prevent or reverse dysfunction of the Hippo pathway. By preventing its dysfunction, the Hippo pathway may be capable of playing its role as a tumor suppressor. Apart from preventing or reversing dysfunction of the Hippo pathway and independent of upstream Hippo regulation, the pharmacological activity of the compounds of the present invention may also be useful in other pathophysiological scenarios where inhibition or disruption of TEAD binding and/or aberrant YAP-TEAD and/or aberrant TAZ-TEAD signaling would be beneficial.

Thus, the compounds of the present invention being TEAD binders and/or inhibitors of YAP-TEAD and/or TAZ-TEAD interaction are useful in particular in the treatment, prevention, suppression and/or amelioration of hyperproliferative disorders and cancer, in particular tumors including solid tumors, of breast cancer, lung cancer, mesothelioma, epithelioid hemangioendothelioma, uveal melanoma, liver cancer, ovarian cancer, squamous cancer, renal cancer, gastric cancer, medulloblastoma, colon cancer, pancreatic cancer, schwannoma, meningioma, glioma, basal cell carcinoma. Without wishing to commit to any specific theory or explanation it may be assumed that the compounds might be able to achieve this by direct effects on the cancer cells and/or indirectly by modulating the response of the immune system against the tumor. Furthermore, the compounds of the present invention may also be useful in the treatment, prevention, suppression and/or amelioration of non-cancerous disorders and diseases, e.g. cardiovascular diseases and fibrosis (like liver fibrosis).

In a particular embodiment the compounds of the present invention are for use in the prevention and/or treatment, especially in the treatment of any of the disorders or diseases listed above, preferably of cancer, in particular tumors including solid tumors, of the specific types of cancer disclosed in the previous paragraph; or of any of the non-cancerous disorders or diseases disclosed in the previous paragraph.

Another particular embodiment of the present invention is a method for preventing and/or treating, preferably treating a disorder or disease selected from the group consisting of hyperproliferative disorders and cancer, in particular tumors including solid tumors, of the specific types of cancer disclosed in the previous paragraphs; or of any of the non-cancerous disorders or diseases disclosed in the previous paragraphs.

Still another particular embodiment of the invention is the use of a compound of the present invention—or derivatives, N-oxides, prodrugs, solvates, tautomers or stereoisomers thereof and/or the pharmaceutically acceptable salts of each of the foregoing, including mixtures thereof in all ratios—for the manufacturing of a medicament, in particular for preventing and/or treating, preferably treating a disorder or disease selected from the group consisting of hyperproliferative disorders and cancer, in particular tumors including solid tumors, of the specific types of cancer disclosed in the previous paragraphs; or of any of the non-cancerous disorders or diseases disclosed in the previous paragraphs.

Preferably, the present invention relates to a compound of the present invention for use in the prevention and/or treatment of a disease—or, alternatively, a method for preventing and/or treating a disease by administering an effective amount of a compound of the present invention; or, in another alternative, a use of a compound of the present invention for the manufacturing of a medicament for the prevention and/or treatment of a disease—wherein that disease is a cancer, in particular tumors including solid tumors, of the specific types of cancer disclosed in the previous paragraphs; and more preferably, wherein administration of the compound is simultaneous, sequential or in alternation with administration of at least one other active drug agent.

The disclosed compounds of formula I or I-A can be administered in combination with other known therapeutic agents, including anticancer agents. As used here, the term “anticancer agent” relates to any agent which is administered to a patient with cancer for the purposes of treating the cancer.

The anti-cancer treatment defined above may be applied as a monotherapy or may involve, in addition to the herein disclosed compounds of formula I-A or I, conventional surgery or radiotherapy or medicinal therapy. Such medicinal therapy, e.g. a chemotherapy or a targeted therapy, may include one or more, but preferably one, of the following anti-tumor agents:

Alkylating Agents such as altretamine, bendamustine, busulfan, carmustine, chlorambucil, chlormethine, cyclophosphamide, dacarbazine, ifosfamide, improsulfan, tosilate, lomustine, melphalan, mitobronitol, mitolactol, nimustine, ranimustine, temozolomide, thiotepa, treosulfan, mechloretamine, carboquone; apaziquone, fotemustine, glufosfamide, palifosfamide, pipobroman, trofosfamide, uramustine, evofosfamide, VAL-083[4]; [4] no INN.

Platinum Compounds such as carboplatin, cisplatin, eptaplatin, miriplatine hydrate, oxaliplatin, lobaplatin, nedaplatin, picoplatin, satraplatin;

DNA Altering Agents such as amrubicin, bisantrene, decitabine, mitoxantrone, procarbazine, trabectedin, clofarabine;

amsacrine, brostallicin, pixantrone, laromustine[1],[3]; [1] Prop. INN (Proposed International Nonproprietary Name) [3] USAN (United States Adopted Name)

Topoisomerase Inhibitors such as etoposide, irinotecan, razoxane, sobuzoxane, teniposide, topotecan; amonafide, belotecan, elliptinium acetate, voreloxin;

Microtubule Modifiers such as cabazitaxel, docetaxel, eribulin, ixabepilone, paclitaxel, vinblastine, vincristine, vinorelbine, vindesine, vinflunine; fosbretabulin, tesetaxel;

Antimetabolites such as asparaginase[3], azacitidine, calcium levofolinate, capecitabine, cladribine, cytarabine, enocitabine, floxuridine, fludarabine, fluorouracil, gemcitabine, mercaptopurine, methotrexate, nelarabine, pemetrexed, pralatrexate, azathioprine, thioguanine, carmofur; doxifluridine, elacytarabine, raltitrexed, sapacitabine, tegafur[2],[3], trimetrexate; [2] Rec. INN (Recommended International Nonproprietary Names)

Anticancer Antibiotics such as bleomycin, dactinomycin, doxorubicin, epirubicin, idarubicin, levamisole, miltefosine, mitomycin C, romidepsin, streptozocin, valrubicin, zinostatin, zorubicin, daunurobicin, plicamycin; aclarubicin, peplomycin, pirarubicin;

Hormones/Antaqonists such as abarelix, abiraterone, bicalutamide, buserelin, calusterone, chlorotrianisene, degarelix, dexamethasone, estradiol, fluocortolone, fluoxymesterone, flutamide, fulvestrant, goserelin, histrelin, leuprorelin, megestrol, mitotane, nafarelin, nandrolone, nilutamide, octreotide, prednisolone, raloxifene, tamoxifen, thyrotropin alfa, toremifene, trilostane, triptorelin, diethylstilbestrol; acolbifene, danazol, deslorelin, epitiostanol, orteronel, enzalutamide[1],[3];

Aromatase Inhibitors such as aminoglutethimide, anastrozole, exemestane, fadrozole, letrozole, testolactone; formestane;

Small Molecule Kinase Inhibitors such as crizotinib, dasatinib, erlotinib, imatinib, lapatinib, nilotinib, pazopanib, regorafenib, ruxolitinib, sorafenib, sunitinib, vandetanib, vemurafenib, bosutinib, gefitinib, axitinib; afatinib, alisertib, dabrafenib, dacomitinib, dinaciclib, dovitinib, enzastaurin, nintedanib, lenvatinib, linifanib, linsitinib, masitinib, midostaurin, motesanib, neratinib, orantinib, perifosine, ponatinib, radotinib, rigosertib, tepotinib, tipifarnib, tivantinib, tivozanib, trametinib, pimasertib, brivanib alaninate, cediranib, apatinib[4], cabozantinib S-malatel[1],[3], ibrutinibl[1],[3], icotinib[4], buparlisib[2], cipatinib[4], cobimetinibl[1],[3], idelalisibl[1],[3], fedratinibl[1], tesevatinib;

Photosensitizers such as methoxsalen[3]; porfimer sodium, talaporfin, temoporfin;

Antibodies such as alemtuzumab, besilesomab, brentuximab vedotin, cetuximab, denosumab, ipilimumab, ofatumumab, panitumumab, rituximab, tositumomab, trastuzumab, bevacizumab, pertuzumab[2],[3]; catumaxomab, elotuzumab, epratuzumab, farletuzumab, mogamulizumab, necitumumab, nimotuzumab, obinutuzumab, ocaratuzumab, oregovomab, ramucirumab, rilotumumab, siltuximab, tocilizumab, zalutumumab, zanolimumab, matuzumab, dalotuzumab[1],[2],[3], onartuzumab[1],[3], racotumomab[1], tabalumab[1],[3], EMD-525797[4], atezolizumab, durvalumab, pembrolizumab, nivolumabl[1],[3];

Cytokines such as aldesleukin, interferon alfa2, interferon alfa2a[3], interferon alfa2b[2],[3]; celmoleukin, tasonermin, teceleukin, oprelvekin[1],[3], recombinant interferon beta-1a[4];

Drug Conjugates such as denileukin diftitox, ibritumomab tiuxetan, iobenguane I 123, prednimustine, trastuzumab emtansine, estramustine, gemtuzumab, ozogamicin, aflibercept; cintredekin besudotox, edotreotide, inotuzumab ozogamicin, naptumomab estafenatox, oportuzumab monatox, technetium (99mTc) arcitumomab[1],[3], vintafolide[1],[3];

Vaccines such as sipuleucel[3]; vitespen[3], emepepimut-S[3], oncoVAX[4], rindopepimut[3], troVax[4], MGN-1601[4], MGN-1703[4];

Miscellaneous alitretinoin, bexarotene, bortezomib, everolimus, ibandronic acid, imiquimod, lenalidomide, lentinan, metirosine, mifamurtide, pamidronic acid, pegaspargase, pentostatin, sipuleucel[3], sizofiran, tamibarotene, temsirolimus, thalidomide, tretinoin, vismodegib, zoledronic acid, vorinostat; celecoxib, cilengitide, entinostat, etanidazole, ganetespib, idronoxil, iniparib, ixazomib, Ionidamine, nimorazole, panobinostat, peretinoin, plitidepsin, pomalidomide, procodazol, ridaforolimus, tasquinimod, telotristat, thymalfasin, tirapazamine, tosedostat, trabedersen, ubenimex, valspodar, gendicine[4], picibanil[4], reolysin[4], retaspimycin hydrochloride[1],[3], trebananib[2],[3], virulizin[4], carfilzomibl[1],[3], endostatin[4], immucothel[4], belinostat[3];

PARP Inhibitors

Olaparib, Veliparib.

MCT1 Inhibitors

AZD3965[4], BAY-8002[4].

In another aspect of the invention, a set or kit is provided comprising a therapeutically effective amount of at least one compound of the invention and/or at least one pharmaceutical composition as described herein and a therapeutically effective amount of at least one further pharmacologically active substance other than the compounds of the invention. It is preferred that this set or kit comprises separate packs of a) an effective amount of a compound of formula I and I-A, or any of its N-oxides, solvates, tautomers or stereoisomers thereof as well as the pharmaceutically acceptable salts of each of the foregoing, including mixtures thereof in all ratios, and b) an effective amount of a further active ingredient that further active ingredient not being a compound of formula I and not being a compound of formula I-A.

A further embodiment of the present invention is a process for the manufacture of the pharmaceutical compositions of the present invention, characterized in that one or more compounds according to the invention and one or more compounds selected from the group consisting of solid, liquid or semiliquid excipients, auxiliaries, adjuvants, diluents, carriers and pharmaceutically active agents other than the compounds according to the invention, are converted in a suitable dosage form.

The pharmaceutical compositions (formulations) of the present invention may be administered by any means that achieve their intended purpose. For example, administration may be via oral, parenteral, topical, enteral, intravenous, intramuscular, inhalant, nasal, intraarticular, intraspinal, transtracheal, transocular, subcutaneous, intraperitoneal, transdermal, or buccal routes. Alternatively, or concurrently, administration may be via the oral route. The dosage administered will be dependent upon the age, health, and weight of the recipient, kind of concurrent treatment, if any, frequency of treatment, and the nature of the effect desired. Parenteral administration is preferred. Oral administration is especially preferred.

Suitable dosage forms include, but are not limited to capsules, tablets, pellets, dragees, semi-solids, powders, granules, suppositories, ointments, creams, lotions, inhalants, injections, cataplasms, gels, tapes, eye drops, solution, syrups, aerosols, suspension, emulsion, which can be produced according to methods known in the art, for example as described below: Tablets: mixing of active ingredient/s and auxiliaries, compression of said mixture into tablets (direct compression), optionally granulation of part of mixture before compression.

Capsules: mixing of active ingredient/s and auxiliaries to obtain a flowable powder, optionally granulating powder, filling powders/granulate into opened capsules, capping of capsules.

Semi-solids (ointments, gels, creams): dissolving/dispersing active ingredient/s in an aqueous or fatty carrier; subsequent mixing of aqueous/fatty phase with complementary fatty/aqueous phase, homogenization (creams only).

Suppositories (rectal and vaginal): dissolving/dispersing active ingredient/s in carrier material liquified by heat (rectal: carrier material normally a wax; vaginal: carrier normally a heated solution of a gelling agent), casting said mixture into suppository forms, annealing and withdrawal suppositories from the forms.

Aerosols: dispersing/dissolving active agent/s in a propellant, bottling said mixture into an atomizer.

In general, non-chemical routes for the production of pharmaceutical compositions and/or pharmaceutical preparations comprise processing steps on suitable mechanical means known in the art that transfer one or more compounds of the invention into a dosage form suitable for administration to a patient in need of such a treatment. Usually, the transfer of one or more compounds of the invention into such a dosage form comprises the addition of one or more compounds, selected from the group consisting of carriers, excipients, auxiliaries and pharmaceutical active ingredients other than the compounds of the invention. Suitable processing steps include, but are not limited to combining, milling, mixing, granulating, dissolving, dispersing, homogenizing, casting and/or compressing the respective active and nonactive ingredients. Mechanical means for performing said processing steps are known in the art, for example from Ullmann's Encyclopedia of Industrial Chemistry, 5th Edition. In this respect, active ingredients are preferably at least one compound of the invention and optionally one or more additional compounds other than the compounds of the invention, which show valuable pharmaceutical properties, preferably those pharmaceutical active agents other than the compounds of the invention, which are disclosed herein.

Particularly suitable for oral use are tablets, pills, coated tablets, capsules, powders, granules, syrups, juices or drops, suitable for rectal use are suppositories, suitable for parenteral use are solutions, preferably oil-based or aqueous solutions, furthermore suspensions, emulsions or implants, and suitable for topical use are ointments, creams or powders. The compounds of the invention may also be lyophilized and the resultant lyophilizates used, for example, for the preparation of injection preparations. The preparations indicated may be sterilized and/or comprise assistants, such as lubricants, preservatives, stabilizers and/or wetting agents, emulsifiers, salts for modifying the osmotic pressure, buffer substances, dyes, flavors and/or a plurality of further active ingredients, for example one or more vitamins.

Suitable excipients are organic or inorganic substances, which are suitable for enteral (for example oral), parenteral or topical administration and do not react with the compounds of the invention, for example water, vegetable oils, benzyl alcohols, alkylene glycols, polyethylene glycols, glycerol triacetate, gelatin, carbohydrates, such as lactose, sucrose, mannitol, sorbitol or starch (maize starch, wheat starch, rice starch, potato starch), cellulose preparations and/or calcium phosphates, for example tricalcium phosphate or calcium hydrogen phosphate, magnesium stearate, talc, gelatin, tragacanth, methyl cellulose, hydroxypropylmethylcellulose, sodium carboxymethylcellulose, polyvinyl pyrrolidone and/or vaseline.

If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries include, without limitation, flow-regulating agents and lubricants, for example, silica, talc, stearic acid or salts thereof, such as magnesium stearate or calcium stearate, and/or polyethylene glycol. Dragee cores are provided with suitable coatings, which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices or to provide a dosage form affording the advantage of prolonged action, the tablet, dragee or pill can comprise an inner dosage and an outer dosage component the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, acetyl alcohol, solutions of suitable cellulose preparations such as acetyl-cellulose phthalate, cellulose acetate or hydroxypropylmethyl-cellulose phthalate, are used. Dye stuffs or pigments may be added to the tablets or dragee coatings, for example, for identification or in order to characterize combinations of active compound doses.

Suitable carrier substances are organic or inorganic substances which are suitable for enteral (e.g. oral) or parenteral administration or topical application and do not react with the novel compounds, for example water, vegetable oils, benzyl alcohols, polyethylene glycols, gelatin, carbohydrates such as lactose or starch, magnesium stearate, talc and petroleum jelly. In particular, tablets, coated tablets, capsules, syrups, suspensions, drops or suppositories are used for enteral administration, solutions, preferably oily or aqueous solutions, furthermore suspensions, emulsions or implants, are used for parenteral administration, and ointments, creams or powders are used for topical application. The compounds of the invention can also be lyophilized and the lyophilizates obtained can be used, for example, for the production of injection preparations.

Other pharmaceutical preparations, which can be used orally include push-fit capsules made of gelatin, as well as soft, sealed capsules made of gelatin and a plasticizer such as glycerol or sorbitol. The push-fit capsules can contain the active compounds in the form of granules, which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

The liquid forms in which the novel compositions of the present invention may be incorporated for administration orally include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400).

Aqueous injection suspensions may contain substances, which increase the viscosity of the suspension, including, for example, sodium carboxymethyl cellulose, sorbitol, and/or dextran, optionally, the suspension may also contain stabilizers.

For administration as an inhalation spray, it is possible to use sprays in which the active ingredient is either dissolved or suspended in a propellant gas or propellant gas mixture (for example $CO_2$ or chlorofluorocarbons). The active ingredient is advantageously used here in micronized form, in which case one or more additional physiologically acceptable solvents may be present, for example ethanol. Inhalation solutions can be administered with the aid of conventional inhalers.

Possible pharmaceutical preparations, which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules, which consist of a combination of the active compounds with a base. Possible base materials include, for example, liquid triglycerides, polyethylene glycols, or paraffin hydrocarbons.

The pharmaceutical preparations can be employed as medicaments in human and veterinary medicine. As used herein, the term "effective amount" means that amount of a drug or pharmaceutical agent that will elicit the biological or medical response of a tissue, system, animal or human that is being sought, for instance, by a researcher or clinician. Furthermore, the term also includes within its scope a "therapeutically effective amount" which means any amount which, as compared to a corresponding subject who has not received such amount, results in improved treatment, healing, prevention, or amelioration of a disease, disorder, or side effect, or a decrease in the rate of advancement of a disease or disorder, or of symptoms associated with such disease or disorder; it may also refer to preventing or providing prophylaxis for the disease or disorder in a subject having or at risk for developing a disease disclosed herein. The term also includes within its scope amounts effective to enhance normal physiological function. Said therapeutic effective amount of one or more of the compounds of the invention is known to the skilled artisan or can be easily determined by standard methods known in the art.

"Treating" or "treatment" as used herein, means an alleviation, in whole or in part, of symptoms associated with a disorder or disease, or slowing, or halting of further progression or worsening of those symptoms, or prevention or prophylaxis of the disease or disorder in a subject at risk for developing the disease or disorder.

The compounds of the present invention and the optional additional active substances are generally administered analogously to commercial preparations. Usually, suitable doses that are therapeutically effective lie in the range between 0.0005 mg and 1000 mg, preferably between 0.005 mg and 500 mg and especially between 0.5 mg and 100 mg per dose unit. The daily dose is preferably between about 0.001 mg/kg and 10 mg/kg of body weight.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

The specific dose for the individual patient, in particular for the individual human patient, depends, however, on the multitude of factors, for example on the efficacy of the specific compounds employed, on the age, body weight, general state of health, the sex, the kind of diet, on the time and route of administration, on the excretion rate, the kind of administration and the dosage form to be administered, the pharmaceutical combination and severity of the particular disorder to which the therapy relates. The specific therapeutic effective dose for the individual patient can readily be determined by routine experimentation, for example by the doctor or physician, which advises or attends the therapeutic treatment.

The compounds of the present invention can be prepared according to the procedures of the following Schemes and Examples, using appropriate materials, and as further exemplified by the following specific examples. They may also be prepared by methods known per se, as described in the literature (for example in standard works, such as Houben-Weyl, Methoden der Organischen Chemie [Methods of Organic Chemistry], Georg Thieme Verlag, Stuttgart; Organic Reactions, John Wiley & Sons, Inc., New York), to be precise under reaction conditions which are known and suitable for the said reactions. Use can also be made of variants which are known per se, but are not mentioned here in greater detail.

Likewise, the starting materials for the preparation of compounds of the present invention can be prepared by methods as described in the examples or by methods known per se, as described in the literature of synthetic organic chemistry and known to the skilled person, or can be obtained commercially. The starting materials for the processes described and/or utilized may, if desired, also be formed in situ by not isolating them from the reaction mixture, but instead immediately converting them further into the compounds of the invention or intermediate compounds. On the other hand, in general it is possible to carry out the reaction stepwise.

Preferably, the reaction of the compounds is carried out in the presence of a suitable solvent, which is preferably inert under the respective reaction conditions. Examples of suitable solvents comprise but are not limited to hydrocarbons, such as hexane, petroleum ether, benzene, toluene or xylene; chlorinated hydrocarbons, such as trichlorethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, dimethylformamide (DMF) or N-methyl pyrrolidinone (NMP); nitriles, such as acetonitrile; sulfoxides, such as dimethyl sulfoxide (DMSO); nitro compounds, such as nitromethane or nitrobenzene; esters, such as ethyl acetate, or mixtures of the said solvents or mixtures with water.

The reaction temperature is between about −100° C. and 300° C., depending on the reaction step and the conditions used.

Reaction times are generally in the range between a fraction of a minute and several days, depending on the reactivity of the respective compounds and the respective reaction conditions. Suitable reaction times are readily determinable by methods known in the art, for example reaction monitoring. Based on the reaction temperatures given above, suitable reaction times generally lie in the range between 10 minutes and 48 hours.

Moreover, by utilizing the procedures described herein, in conjunction with ordinary skills in the art, additional compounds of the present invention described herein can be readily prepared. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds.

The present invention also refers to a process for manufacturing a compound of formula I or I-A in its most general form as well as any of the particular embodiments, PE0, PE0a, PE0b, PE1, PE1a, PE1b, PE2, PE2a, PE2b, PE3, PE3a, PE3b, PE4, PE4a, PE5, PE5a, PE5aa PE5b, PE5bb, PE5c, PE6, PE7, PE8, PE9, PE9a, PE10, PE10a, PE10aa, PE10b, PE10bb, PE10c, PE10cc, PE11, PE11a, PE11b, PE11c, PE12, PE12a, PE12b, PE12c, PE12d, PE13 described herein, or N-oxides, solvates, tautomers or stereoisomers thereof as well as the pharmaceutically acceptable salts of each of the foregoing, the process being characterized in that either (a) a compound of formula II-a or II-A-a II-a

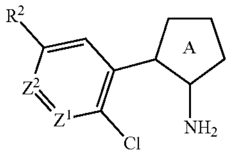

II-A-a

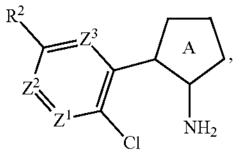, wherein $Z^1$, $Z^2$, $Z^3$, ring A and $R^2$ are as defined for the compound of formula I or I-A above wherein $R^2$ is not —C(═O)—OH or —C(═O)—OCat;

is either (a)(1) reacted with a compound of formula III $R^1$-Hal III, wherein $R^1$ is as defined for the compound of formula I or I-A above and Hal represents Cl, Br or I, in a C—N cross coupling reaction under suitable reaction conditions;

or (a)(2) is first converted into the tricyclic compound of formula IV or IV-A

IV

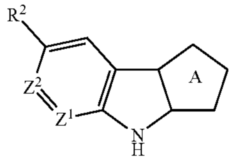

IV-A

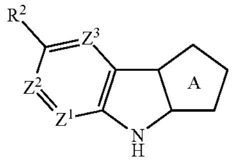

in a C—N cross coupling reaction under suitable reaction conditions; and then reacted with a compound of formula III $R^1$-Hal III, in another C—N cross coupling reaction under suitable reaction conditions;

to provide (a)(3) a compound of formula I or I-A as defined above; and optionally (a)(4) if in the compound of formula I or I-A $R^2$ is —C(═O)—$OR^{2a}$ with $R^{2a}$ being unsubstituted or substituted $C_{1-8}$-aliphatic, then this compound of formula I or I-A is subjected to a saponification reaction under suitable conditions to provide the respective compound of formula I or I-A with $R^2$ being —C(═O)—OH or —C(═O)—OCat;

or (b) a compound of formula II-b or II-A-b

II-b

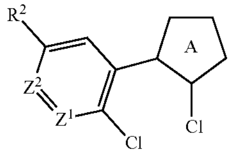

II-A-b

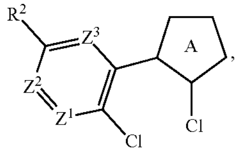, wherein $Z^1$, $Z^2$, $Z^3$, ring A and $R^2$ are as defined for the compound of formula I or I-A above wherein $R^2$ is not —C(═O)—OH or —C(═O)—OCat;

(b)(1) is reacted with a compound of formula V $R^1$—$NH_2$ V, wherein $R^1$ is as defined for the compound of formula I or I-A above, in a C—N cross coupling reaction under suitable reaction conditions to provide a compound of formula I or I-A as defined above; and optionally (b)(2) if in the compound of formula I or I-A $R^2$ is —C(═O)—$OR^{2a}$ with $R^{2a}$ being unsubstituted or substituted $C_{1-8}$-aliphatic, then this compound of formula I or I-A is subjected to a saponification reaction under suitable conditions to provide the respective compound of formula I or I-A with $R^2$ being —C(═O)—OH or —C(═O)—OCat.

As will be understood by the person skilled in the art of organic synthesis compounds of the present invention, in particular compounds of formula I and I-A, are readily accessible by various synthetic routes, some of which are exemplified in the accompanying Experimental Part. The skilled artisan will easily recognize which kind of reagents and reactions conditions are to be used and how they are to be applied and adapted in any particular instance—wherever necessary or useful—in order to obtain the compounds of the present invention. Furthermore, some of the compounds of the present invention can readily be synthesized by reacting other compounds of the present invention under suitable conditions, for instance, by converting one particular functional group being present in a compound of the present invention, or a suitable precursor molecule thereof, into another one by applying standard synthetic methods, like reduction, oxidation, addition or substitution reactions; those methods are well known to the skilled person. Likewise, the skilled artisan will apply—whenever necessary or useful—synthetic protecting (or protective) groups; suitable protecting groups as well as methods for introducing and removing them are well-known to the person skilled in the art of chemical synthesis and are described, in more detail, in, e.g., P. G. M. Wuts, T. W. Greene, "Greene's Protective Groups in Organic Synthesis", 4th edition (2006) (John Wiley & Sons).

In the following general synthetic routes that may be utilized to prepare compounds of the present invention are described in more detail in Schemes A, A-A, B and B-A below:

Scheme A

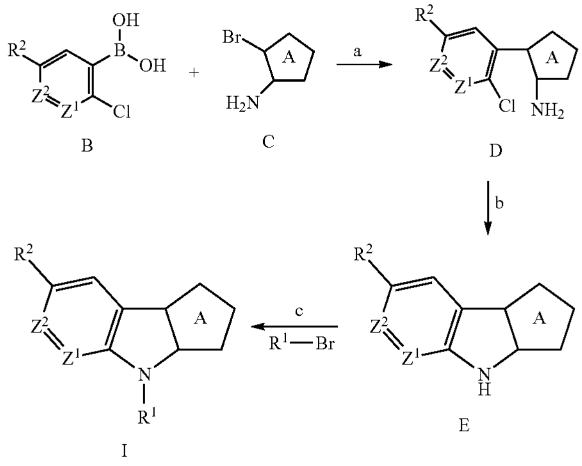

B C D E I ($Z^1$, $Z^2$, $R^1$, $R^2$ and ring A are as defined for formula I above.)

Scheme A-A

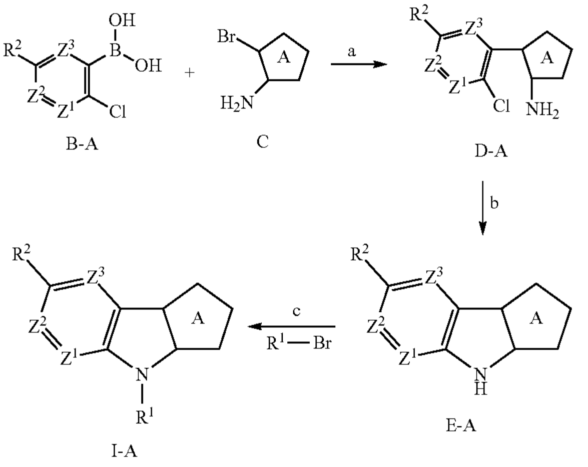

B-A C D-A E-A I-A ($Z^1$, $Z^2$, $Z^3$, $R^1$, $R^2$ and ring A are as defined for formula I-A above.)

It will be understood that the following explanation of Scheme A also applies analogously to Scheme A-A; instead of compounds B, D, E, and I Scheme A-A and its explanation refer to compounds B-A, D-A, E-A, and I-A. The synthetic procedures and method utilized are the same in Schemes A and A-A.

Scheme A above depicts a general synthesis route for preparing tricyclic heterocycles of formula I. In reaction step a the boronic acid B—which is readily available, for instance, by first reacting the respective bromo-substituted aryl or heteroaryl with a suitable organometallic base like n-butyl lithium and subsequent reaction with a suitable boron acid ester like $B(OCH_3)_3$—is reacted with the 1-amino-2-bromo-substituted heterocycle C under typical C—C cross coupling conditions, e.g., under conditions typical for Suzuki cross coupling reactions (for instance, reacting a solution of B and C in a suitable solvent like 1,4-dioxane with cesium carbonate in the presence of a Palladium catalyst like $Pd(dppf)_2Cl_2$ (1,1'-Bis(diphenylphosphino)ferrocene]palladium(II) dichloride)) to yield compound D. It is understood that ring A in that 1-amino-2-bromo-substituted heterocycle C has the same meaning as "ring A" for the compound of the present invention of formula I, i.e. is selected from the five-membered heteroaromatic rings A-1 to A-24 as defined above. For instance, if ring A is selected to be ring A-1, then the respective compound C would have the following formula C-1:

C-1

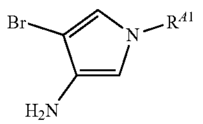

Compound D may then be subjected to an intra-molecular C—N cross-coupling reaction (step b), for instance, under conditions typical for a Hartwig-Buchwald reaction (e.g., reaction with cesium carbonate in a suitable solvent like 1,4-dioxane in the presence of a suitable palladium catalyst like di-tert-butyl[2',4',6'-tris(propan-2-yl)-[1,1'-biphenyl]-2-yl]phosphane {2'-amino-[1,1'-biphenyl]-2-yl}palladiumylium methanesulfonate) to yield the tricyclic heterocycle E. This heterocycle E may then in turn be reacted with the bromide $R^1$—Br in another C—N coupling reaction (step c) under similar conditions, for instance with cesium carbonate in the presence of a suitable palladium catalyst (e.g., Chloro(2-dicyclohexylphosphino-2',4',6'-tri-isopropyl-1,1'-biphenyl)[2-(2'-amino-1,1'-biphenyl)]palladium(II), X-Phos aminobiphenyl palladium chloride, XPhosPd G2) to provide the compound of the present invention of formula I. Depending on the nature of the various substituent $R^1$, $R^2$ and on ring A, this compound of formula I may optionally converted into further compounds of formula I. For instance, if $R^2$ is a carboxylic ester (—C(═O)—$OR^{2a}$), then this ester may be subjected to a saponification reaction using suitable acids or bases thereby providing either the respective carboxylic acid ($R^2$═—C(═O)—OH) or a salt thereof (e.g., $R^2$═—C(═O)—OCat with Cat being Li, Na, K or $NH_4$).

In some instances compound D as shown in Scheme A above (and D-A in Scheme A-A) —instead of being subjected to the subsequent reaction steps b and c, i.e. two consecutive C—N coupling reactions—may be reacted with a suitable compound $R^1$—Br under C—N coupling reactions (with as suitable base like cesium carbonate or sodium hydride in the presence of a suitable palladium catalyst) to directly provide the respective compound of formula I (or I-A in Scheme A-A).

Furthermore, it is well understood that starting from compound E compounds of formula I (or from compound E-A compounds of formula I-A) may be synthesized by utilizing suitable reaction partners other than the bromo-substituted compound $R^1$—Br under suitable reaction conditions. For instance, if $R^1$ is chosen to be $L^1$-Ar or $L^1$-$Hetar^1$ with $L^1$ being —S(═O)$_2$—, then compound E may be reacted with the respective thionyl chloride under suitable reaction conditions to yield the respective sulfonyl derivative of formula I (or I-A).

Scheme B

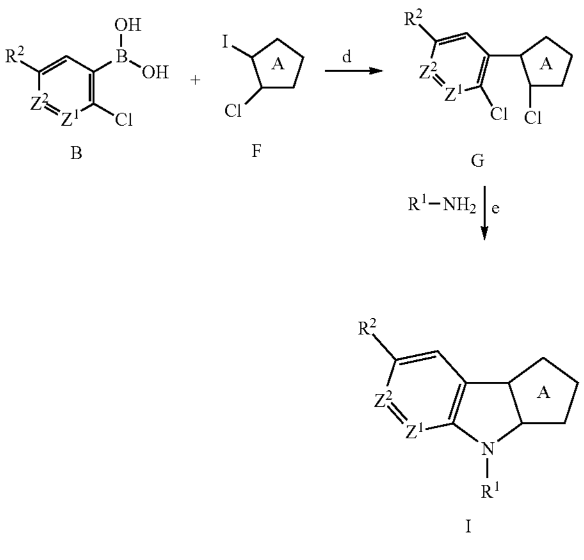

($Z^1$, $Z^2$, $R^1$, $R^2$ and ring A are as defined for formula I above.)

Scheme B-A

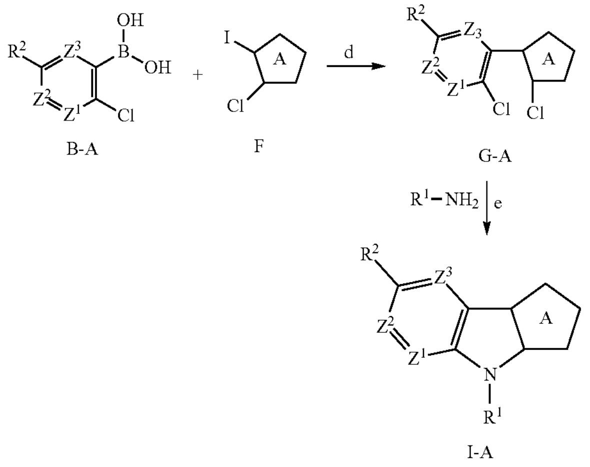

($Z^1$, $Z^2$, $Z^3$, $R^1$, $R^2$ and ring A are as defined for formula I-A above.)

It will be understood that the following explanation of Scheme B also applies analogously to Scheme B-A; instead of compounds B, G, and I Scheme B-A and its explanation refers to compounds B-A, G-A, and I-A. The synthetic procedures and method utilized are the same in Schemes B and B-A.

Scheme B above depicts another synthetic route for making compounds of the present invention. Here the boronic acid B (or a suitable boronic acid ester) is reacted in a C—C cross-coupling reaction under similar conditions described for step a in Scheme A with the 1-chloro-2-iodo-substituted heterocycle F (step d) which reaction yields the dichloro-substituted compound G. Compound G may then be converted in a C—N coupling reaction with the primary amine $R^1$—$NH_2$ (step e) in the presence of a suitable base like cesium carbonate and a suitable palladium catalyst (as described for Scheme A) into the desired compound of formula I (or I-A for Scheme B-A).

It is to be noted that—except for instances where it is specifically stated or the context provides for a different meaning—in general the number of a term, i.e. its singular and plural form, is used and can be read interchangeably. For example, the term "compound" in its singular form may also comprise or refer to a plurality of compounds, while the term "compounds" in its plural form may also comprise or refer to a singular compound.

EXAMPLES AND EXPERIMENTAL PART

The compounds of the present invention can be prepared according to the procedures of the following Schemes and Examples, using appropriate materials and are further exemplified by the following specific examples. The compounds are shown in Table 1. Analytical data of compounds made according to the following examples are shown in Table 1, too.

The invention will be illustrated, but not limited, by reference to the specific embodiments described in the following examples. Unless otherwise indicated in the schemes, the variables have the same meaning as described above.

Unless otherwise specified, all starting materials are obtained from commercial suppliers and used without further purifications. Unless otherwise specified, all temperatures are expressed in ° C. and all reactions are conducted at room temperature (RT). Compounds are purified by either silica chromatography or preparative HPLC.

$^1$H NMR:

$^1$H-NMR data is provided in Table 1 below. $^1$H NMR spectra were usually acquired on a Bruker Avance DRX 500, Bruker Avance 400. a Bruker DPX 300 or a Bruker Avance III 700 MHz (equipped with a TXI cryoprobe) NMR spectrometer under standard conditions using TMS (tetramethylsilane) as internal reference and DMSO-d6 as standard solvents, if not reported otherwise. NS (Number of Scans): 32, SF (Spectrometer Frequency) as indicated. TE (Temperature): 297 K. Chemical shifts (δ) are reported in ppm relative to the TMS signal. $^1$H NMR data are reported as follows: chemical shift (multiplicity, coupling constants and number of hydrogens). Multiplicity is abbreviated as follows: s (singlet), d (doublet), t (triplet), q (quartet), m (multiplet), dd (doublet of doublets), tt (triplet of triplets), td (triplet of doublets) br (broad) and coupling constants (J) are reported in Hz.

LC-MS:

LC-MS data provided in Table 1 are given with mass in m/z. The results can be obtained by one of the methods described below.

Syntheses

Example 1: 4-(benzenesulfonyl)-2-benzyl-2H,4H-pyrrolo[3,4-b]indole-7-carboxylic acid

Example 1-1: Synthesis of 1-(benzenesulfonyl)-5-bromo-2,3-dimethyl-1H-indole

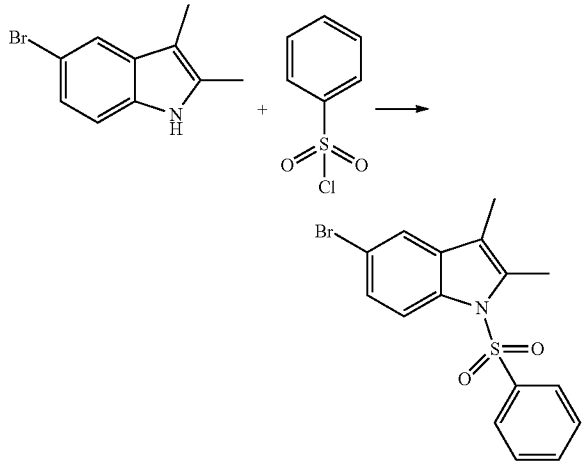

To a suspension of NaH (1.70 g; 42.50 mmol) in DMF (50 ml) was added 5-bromo-2,3-dimethyl-1H-indole (6.25 g; 27.89 mmol) in DMF (50 ml) at 0° C. slowly. The yellow brown mixture was stirred at 0° C. for 1 h, then benzenesulfonyl chloride (6 g; 34 mmol) was added at 0° C. After that, the mixture was stirred at 25° C. for 2 hours. The reaction was poured into water (500 mL) and extracted with EA (100 mL) for three times. The organic layer was washed with brine (50 mL), dried over $Na_2SO_4$, filtered and concentrated to give a residue. The residue was purified by silica gel column chromatography (petroleum ether/EA=4:1) to give the desired product. (7.20 g; 71%; pink solid).

$^1$H NMR (400 MHz, $CDCl_3$) δ 8.06 (d, J=8.4 Hz, 1H), 7.73-7.70 (m, 2H), 7.55-7.52 (m, 1H), 7.49 (d, J=2.0 Hz, 1H), 7.44-7.40 (m, 2H), 7.36 (dd, J=8.8, 2.0 Hz, 1H), 2.51 (s, 3H), 2.09 (s, 3H).

Example 1-2: Synthesis of Product 1-(benzenesulfonyl)-5-bromo-2,3-bis(bromomethyl)-1H-indole

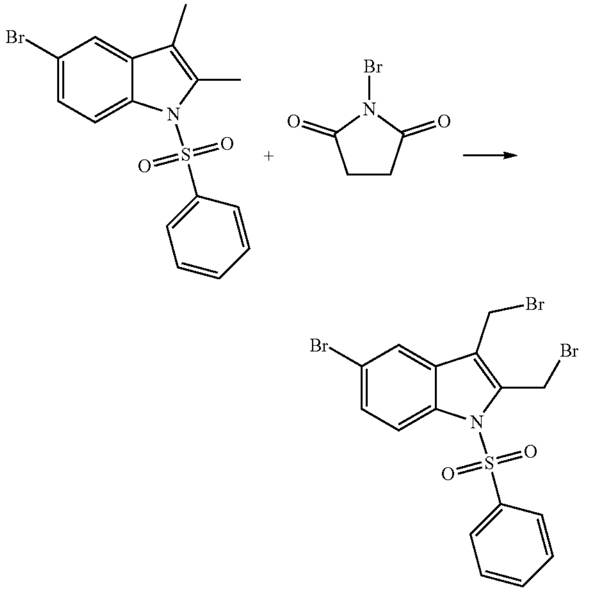

To a solution of 1-(benzenesulfonyl)-5-bromo-2,3-dimethyl-1H-indole (6.40 g; 17.57 mmol) in $CCl_4$ (120 ml) was added 1-bromopyrrolidine-2,5-dione (6.40 g; 36 mmol) and 2-[2-(1-cyano-1-methylethyl)diazen-1-yl]-2-methylpropane-nitrile (288 mg; 1.75 mmol) at 80° C. The yellow brown mixture was stirred at 80° C. under 1 bar of nitrogen balloon for 3 hours. The reaction was filtered and the filtrate was concentrated to give the crude product (8.15 g; 81%; yellow brown solid).

$^1$H NMR (400 MHz, $CDCl_3$) δ 8.00 (d, J=5.6 Hz, 1H), 7.93-7.90 (m, 2H), 7.75 (d, J=2.0 Hz, 1H), 7.61-7.58 (m, 1H), 7.50-7.45 (m, 3H), 5.08 (s, 2H), 4.59 (s, 2H).

Example 1-3: Synthesis of 4-(benzenesulfonyl)-2-benzyl-7-bromo-1H,2H,3H,4H-pyrrolo[3,4-b]indole

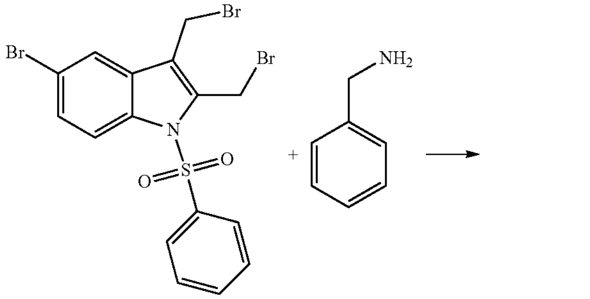

-continued

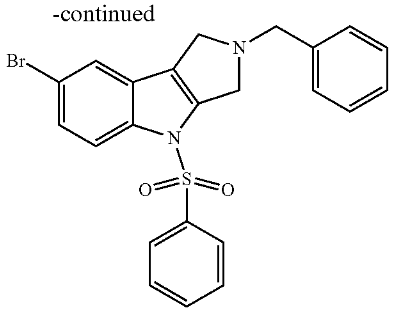

To a solution of 1-(benzenesulfonyl)-5-bromo-2,3-bis (bromomethyl)-1H-indole (8.15 g; 14.21 mmol) and $K_2CO_3$ (6.68 g; 48.34 mmol) in THF (190 mL) was added 1-phenylmethanamine (1.52 g; 14.19 mmol) in THF (280 mL) at 80° C. slowly. The yellow brown mixture was stirred at 80° C. under 1 bar of nitrogen balloon for 16 hours. The reaction was filtered and the filtrate was concentrated to give a residue. The residue was purified by silica gel column chromatography (dichloromethane/EA=5:1) to give the desired product. (3.16 g; 41%; yellow brown solid).

$^1$H NMR (400 MHz, $CDCl_3$) δ 7.85-7.79 (m, 3H), 7.57-7.53 (m, 1H), 7.46-7.24 (m, 9H), 4.28-4.26 (m, 2H), 4.01 (s, 2H), 3.91-3.89 (m, 2H).

Example 1-4: Synthesis of methyl 4-(benzenesulfonyl)-2-benzyl-1H,2H,3H,4H-pyrrolo[3,4-b]indole-7-carboxylate

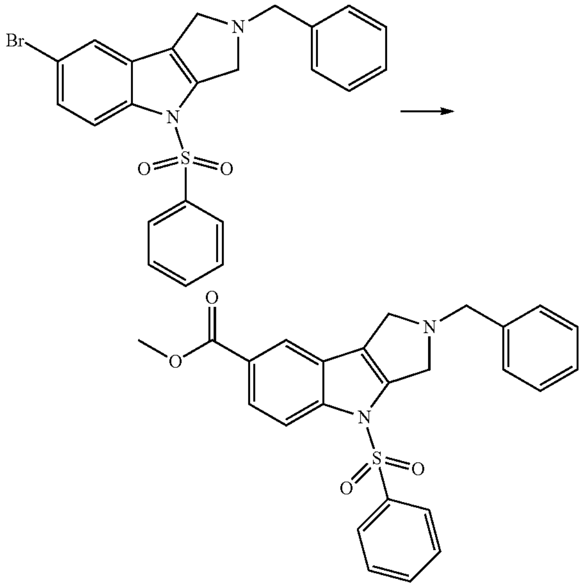

To a solution of 4-(benzenesulfonyl)-2-benzyl-7-bromo-1H,2H,3H,4H-pyrrolo[3,4-b]indole (1.50 g; 2.73 mmol), tris(dibenzylideneacetone)-dipalladium (300 mg; 0.33 mmol) and 4,5-Bis(diphenylphosphino)-9,9-dimethylxanthene (190 mg; 0.33 mmol) in DMF (10 ml) and MeOH (10 ml) was added potassium acetate (900 mg; 9.17 mmol) at 25° C. The black brown mixture was stirred at 90° C. under 1 bar of methanidylidyneoxidanium balloon for 16 hours. The reaction was poured into water (50 mL) and extracted with EA (30 mL) for three times. The organic layers were concentrated to give a residue. The residue was purified by silica gel column chromatography (petroleum ether/EA=5:1) to give the desired product. (510 mg; 39.8%; yellow brown solid).

$^1$H NMR (400 MHz, $CDCl_3$) δ 8.03-8.01 (m, 2H), 7.97-7.94 (m, 1H), 7.86-7.84 (m, 2H), 7.57-7.55 (m, 1H), 7.48-7.44 (m, 3H), 7.40-7.37 (m, 3H), 7.33-7.32 (m, 1H), 4.31 (s, 2H), 4.05 (s, 2H), 3.98 (s, 2H), 3.90 (s, 3H).

Example 1-5: Synthesis of methyl 4-(benzenesulfonyl)-2-benzyl-2H,4H-pyrrolo[3,4-b]indole-7-carboxylate

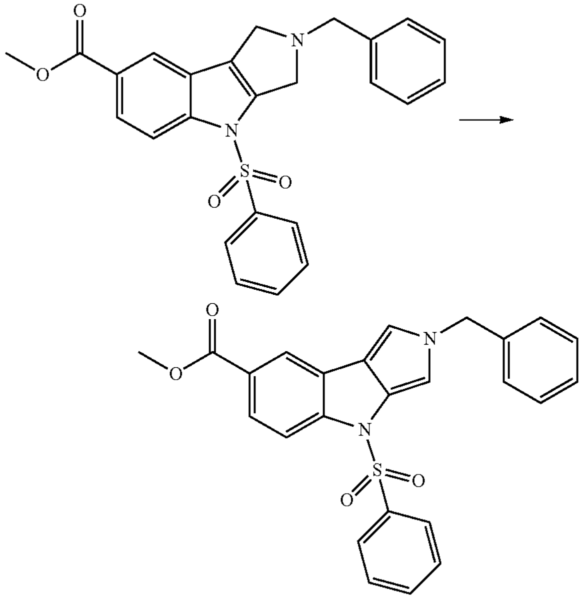

To a solution of methyl 4-(benzenesulfonyl)-2-benzyl-1H,2H,3H,4H-pyrrolo[3,4-b]indole-7-carboxylate (84 mg; 0.19 mmol) in Toluene (2 ml) was added 4,5-dichloro-3,6-dioxocyclohexa-1,4-diene-1,2-dicarbonitrile (43 mg; 0.19 mmol) at 25° C. The yellow brown mixture solution was stirred at 25° C. for 3 hours. The reaction was filtered and the filtrate was concentrated to give the crude product (60 mg; 67%; yellow brown solid).

Example 1-6: Synthesis of 4-(benzenesulfonyl)-2-benzyl-2H,4H-pyrrolo[3,4-b]indole-7-carboxylic acid (Compound 1)

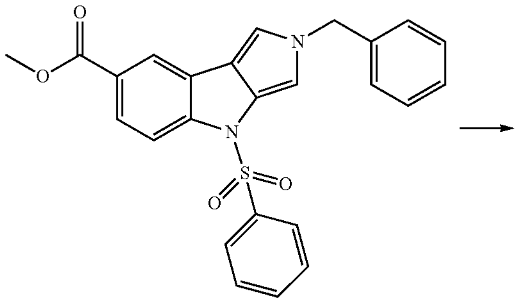

-continued

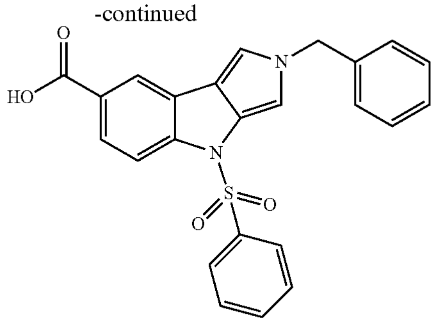

To a solution of methyl 4-(benzenesulfonyl)-2-benzyl-2H,4H-pyrrolo[3,4-b]indole-7-carboxylate (50 mg; 0.11 mmol) in iPrOH (3 ml) and Water (0.6 ml) was added NaOH (13 mg; 0.33 mmol) at 25° C. The yellow brown mixture was stirred at 70° C. for 16 hours. The reaction was diluted with water (20 mL) and extracted with ethyl acetate (20 mL) three times. The combined organic layer was concentrated to give a residue. The residue was purified by C-18 column (ACN:water=10%-95%) to give the desired product in 55% yield (25 mg; off-white solid).

$^1$H NMR (400 MHz, DMSO-d6) δ 12.86 (brs, 1H), 8.15 (d, J=1.6 Hz, 1H), 8.03-8.01 (m, 1H), 7.90-7.87 (m, 1H), 7.80-7.78 (m, 2H), 7.63-7.61 (m, 1H), 7.49-7.45 (m, 2H), 7.38-7.35 (m, 2H), 7.32-7.27 (m, 2H), 7.24-7.22 (m, 3H), 5.31 (s, 2H).

Example 2: 2-methyl-8-[4-(trifluoromethyl)phenyl]-2H,8H-pyrazolo[3,4-b]indole-5-carboxylic acid Example 2-1: Synthesis of ethyl 3-(3-amino-1-methyl-1H-pyrazol-4-yl)-4-chlorobenzoate

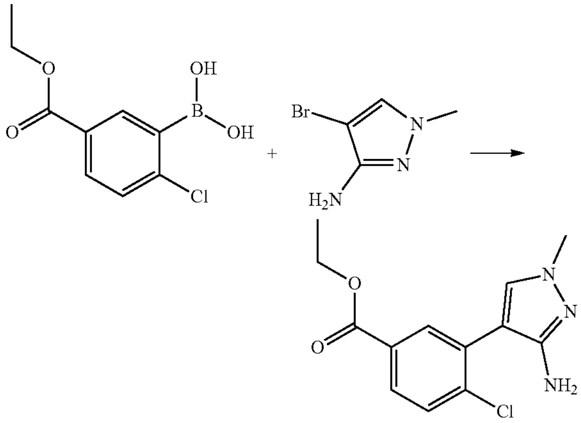

To a suspension of 2-chloro-5-(ethoxycarbonyl)phenyl] boronic acid (500 mg; 2.19 mmol) in dioxane (4 ml) and water (0.4 ml) was added 4-bromo-1-methyl-1H-pyrazol-3-amine (385 mg; 2.19 mmol), $K_2CO_3$ (605 mg; 4.38 mmol) and Pd(dppf)$Cl_2$ (160 mg). The mixture was stirred at 60° C. under $N_2$ atmosphere for 6 h. The mixture was poured into water (5 ml), and then extracted with EA (6 ml*3). The combined organic phase was collected and evaporated under vacuum. The residue was purified by C18 column chromatography (ACN/$H_2O$=5%-95%) and the purified product could be obtained (500 mg; 74%; white powder).

$^1$H NMR (400 MHz, DMSO) δ 8.07 (d, J=2.1 Hz, 1H), 7.77 (dd, J=8.4, 2.2 Hz, 1H), 7.67 (s, 1H), 7.63 (d, J=8.4 Hz, 1H), 4.58 (s, 2H), 4.32 (q, J=7.1 Hz, 2H), 3.66 (s, 3H), 1.31 (t, J=7.1 Hz, 3H).

Example 2-2: Synthesis of ethyl 2-methyl-2H,8H-pyrazolo[3,4-b]indole-5-carboxylate

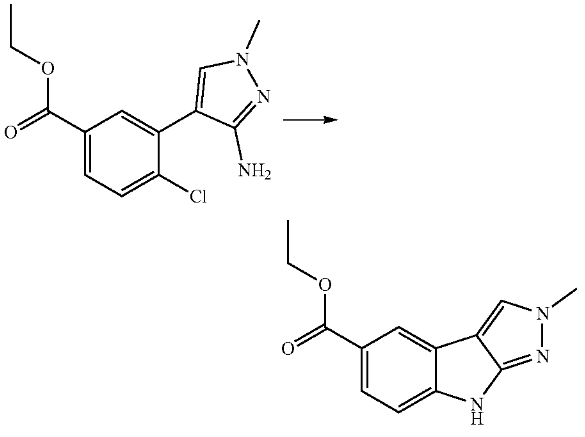

To a suspension of ethyl 3-(3-amino-1-methyl-1H-pyrazol-4-yl)-4-chlorobenzoate (300 mg; 1.1 mmol) in dioxane (15 ml) was added di-tert-butyl[2',4',6'-tris(propan-2-yl)-[1,1'-biphenyl]-2-yl]phosphane {2'-amino-[1,1'-biphenyl]-2-yl}palladiumylium methanesulfonate (85 mg; 0.11 mmol) and $Cs_2CO_3$ (699 mg; 2.14 mmol). The mixture was stirred at 120° C. under $N_2$ atmosphere for 6 h. The mixture was poured into water (5 ml), and then extracted with EA (6 ml*3). The combined organic phase was collected and evaporated under vacuum. The residue was purified by C18 column chromatography (ACN/$H_2O$=5%-95%) and the purified product could be obtained. (110 mg; 42%; white solid).

$^1$H NMR (400 MHz, DMSO) δ 8.31 (d, J=1.7 Hz, 1H), 8.03 (s, 1H), 7.83 (dd, J=8.5, 1.8 Hz, 1H), 7.32 (d, J=8.5 Hz, 1H), 4.31 (q, J=7.1 Hz, 2H), 3.97 (s, 3H), 1.34 (t, J=7.1 Hz, 3H).

Example 2-3: Synthesis of ethyl 2-methyl-8-[4-(trifluoromethyl)phenyl]-2H,8H-pyrazolo[3,4-b]indole-5-carboxylate

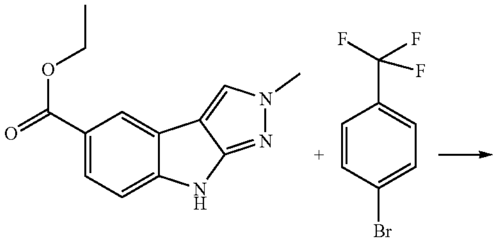

-continued

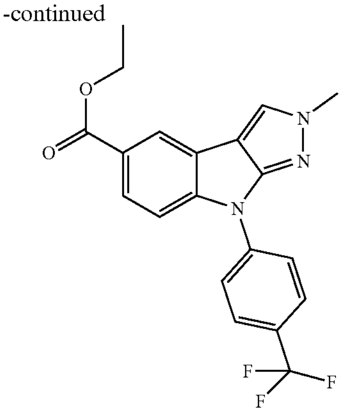

A sealed tube was charged with ethyl 2-methyl-2H,8H-pyrazolo[3,4-b]indole-5-carboxylate (85 mg; 0.35 mmol), 1-bromo-4-(trifluoromethyl)benzene (102 mg; 0.45 mmol), XPhosPd G2 (17 mg; 0.02 mmol) and $Cs_2CO_3$ (342 mg; 1.05 mmol) in dioxane (5 ml). The mixture was stirred under $N_2$ at 100° C. for 2 h. The mixture was fittered and concentrated to get crude product as a black oil. The crude product was purified by C18 ($ACN/H_2O$=5%-95%) to get the product as a white solid. (92 mg; 62%; white solid).

$^1$H NMR (400 MHz, DMSO) δ 8.45 (d, J=1.5 Hz, 1H), 8.23 (s, 1H), 8.08 (d, J=8.5 Hz, H), 7.98 (d, J=8.6 Hz, 2H), 7.93 (d, J=1.8 Hz, 1H), 7.80 (d, J=8.7 Hz, 1H), 4.35 (d, J=7.1 Hz, 2H), 4.04 (s, 3H), 1.36 (t, J=7.1 Hz, 2H).

Example 2-4: Synthesis of 2-methyl-8-[4-(trifluoromethyl)phenyl]-2H,8H-pyrazolo[3,4-b]indole-5-carboxylic acid

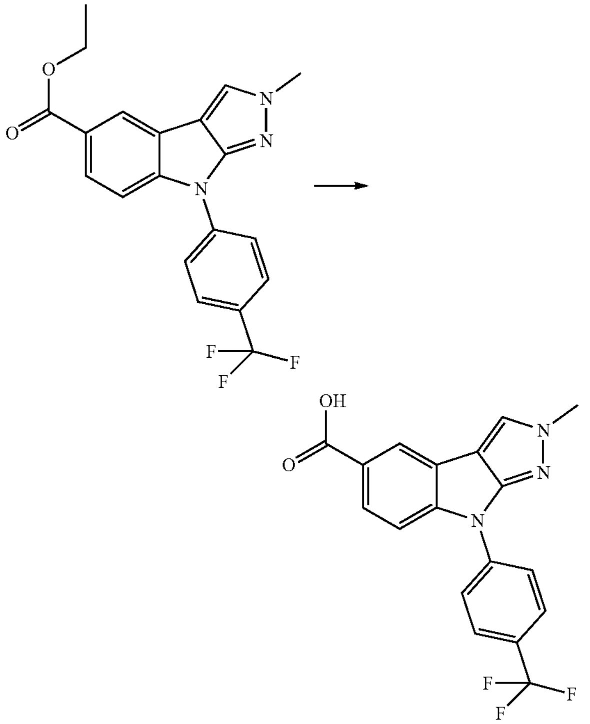

To a solution of ethyl 2-methyl-8-[4-(trifluoromethyl)phenyl]-2H,8H-pyrazolo[3,4-b]indole-5-carboxylate (90 mg; 0.21 mmol) in MeOH (40 ml) was added an aqueous solution of 1M sodium hydroxide (1 ml). The mixture was stirred under $N_2$ at 60° C. for 6 h. The mixture was concentrated and adjusted by 1N hydrochloric acid to pH=1-2. The mixture was purified by C18 (0.1% $TFA/H_2O$=20%-95%) to get the product. (59 mg; 73%; white solid).

$^1$H NMR (400 MHz, DMSO) δ 12.74 (s, 1H), 8.43 (d, J=1.7 Hz, 1H), 8.22 (s, 1H), 8.08 (d, J=8.5 Hz, 2H), 7.98 (d, J=8.6 Hz, 2H), 7.93 (dd, J=8.7, 1.8 Hz, 1H), 7.78 (d, J=8.7 Hz, 1H), 4.03 (s, 3H).

Example 3: 2-Benzyl-4-phenyl-2H,4H-pyrrolo[3,4-b]indole-7-carboxylic acid

Example 3-1: Synthesis of methyl 2-benzyl-1H,2H,3H,4H-pyrrolo[3,4-b]indole-7-carboxylate

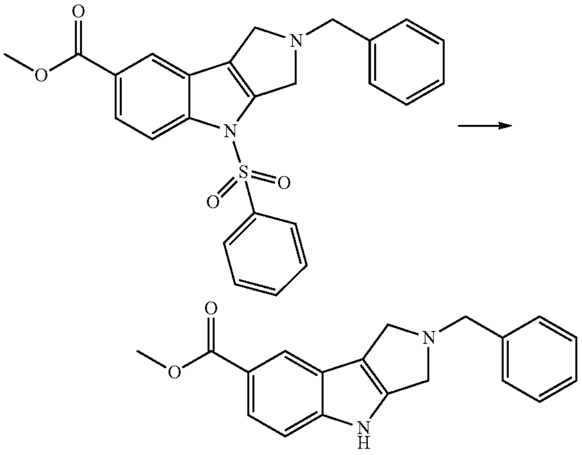

To a solution of methyl 4-(benzenesulfonyl)-2-benzyl-1H,2H,3H,4H-pyrrolo[3,4-b]indole-7-carboxylate (460 mg; 1 mmol) (see Example 1-4) in MeOH (20 ml) was added $Cs_2CO_3$ (2.68 g; 8.23 mmol) at 25° C. The yellow brown mixture was stirred at 30° C. for 16 hours. The reaction was poured into water (100 mL) and extracted with EA (30 mL) for three times. The organic layers were concentrated to give a residue. The residue was purified by C18 ($ACN/H_2O$=10%-95%) to give the desired product. (200 mg; 67%; yellow brown solid).

Example 3-2 Synthesis of methyl 2-benzyl-4-phenyl-1H,2H,3H,4H-pyrrolo[3,4-b]indole-7-carboxylate

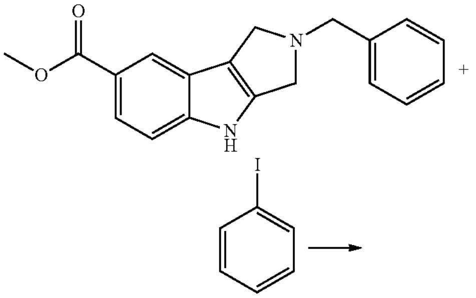

-continued

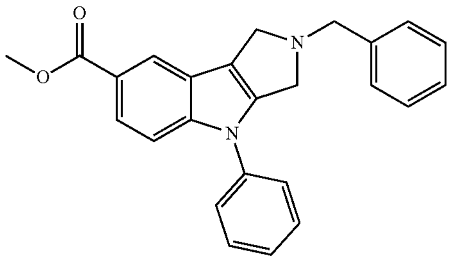

To a suspension of methyl 2-benzyl-1H,2H,3H,4H-pyrrolo[3,4-b]indole-7-carboxylate (170 mg; 0.55 mmol), iodobenzene (140 mg; 0.69 mmol) and copper iodide (17 mg; 0.1 mmol) in DMSO (5 ml) was added (2S)-pyrrolidine-2-carboxylic acid (17 mg; 0.15 mmol) and $K_2CO_3$ (150 mg; 1.1 mmol) at 25° C. The black brown mixture was stirred at 110° C. under 1 bar of nitrogen balloon for 16 hours. The reaction was poured into water (30 mL) and extracted with EA (10 mL) for three times. The combined organic layers were concentrated to give a residue. The residue was purified by silica gel chromatography (petroleum ether/EA=10:1) to give the desired product. (200 mg; 91%; yellow brown gel).

Example 3-3: Synthesis of methyl 2-benzyl-4-phenyl-2H,4H-pyrrolo[3,4-b]indole-7-carboxylate

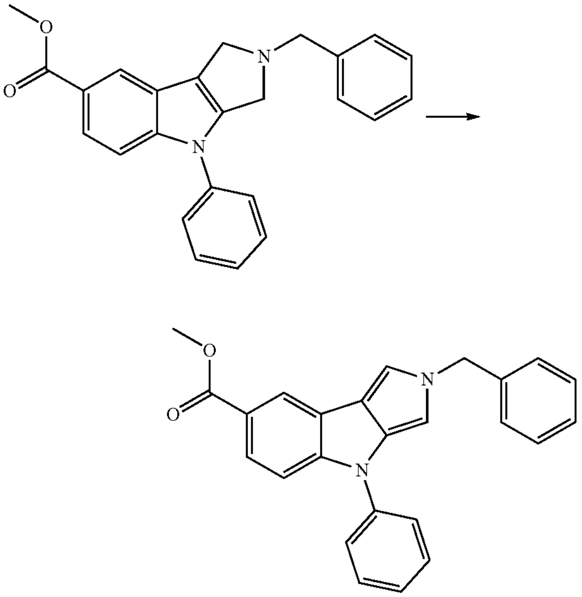

To a solution of methyl 2-benzyl-4-phenyl-1H,2H,3H,4H-pyrrolo[3,4-b]indole-7-carboxylate (170 mg; 0.43 mmol.) in toluene (5 ml) was added 4,5-dichloro-3,6-dioxocyclohexa-1,4-diene-1,2-dicarbonitrile (100 mg; 0.44 mmol) at 25° C. The yellow brown mixture was stirred at 25° C. for 3 hours. The reaction was filtered and concentrated to give a residue. The residue was purified by silica gel column chromatography (petroleum ether/EA=10:1) to give the desired product. (34 mg; 20%; yellow brown gel).

Example 3-4: Synthesis of 2-benzyl-4-phenyl-2H,4H-pyrrolo[3,4-b]indole-7-carboxylic acid

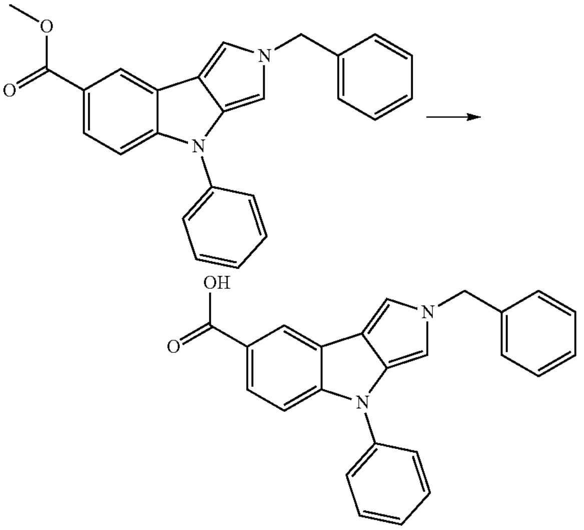

To a solution of methyl 2-benzyl-4-phenyl-2H,4H-pyrrolo[3,4-b]indole-7-carboxylate (34 mg; 0.1 mmol) in EtOH (5 ml) and $H_2O$ (1 ml) was added NaOH (35 mg; 0.9 mmol) at 25° C. The yellow brown mixture was stirred at 70° C. for 16 hours. The reaction was concentrated and water was added (5 mL). The water phase was adjusted to pH~5 and extracted with EA (10 mL) for three times. The combined organic layers were concentrated to give a residue. The residue was purified by C18 column (ACN/$H_2O$=10%-95%) to give the desired product. (17 mg; 53%; greyish green solid).

$^1H$ NMR (400 MHz, DMSO-d6) δ 12.48 (s, 1H), 8.33 (d, J=1.6 Hz, 1H), 7.84-7.82 (m, 1H), 7.68-7.66 (m, 2H), 7.60-7.55 (m, 3H), 7.39-7.27 (m, 7H), 6.98 (d, J=1.6 Hz, 1H), 5.30 (s, 2H).

Example 4: 2-methyl-4-[4-(trifluoromethyl)phenyl]-2H,4H-pyrazolo[4,3-b]indole-7-carboxylic acid Example 4-1: Synthesis of ethyl 3-(4-amino-1-methyl-1H-pyrazol-3-yl)-4-chlorobenzoate

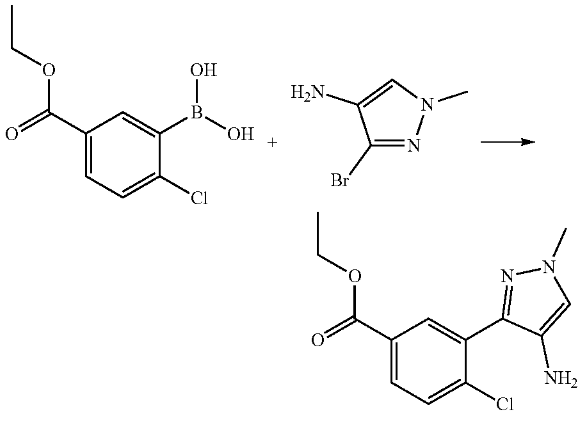

The mixture of 2-chloro-5-(ethoxycarbonyl)phenyl]boronic acid (1.20 g; 5.20 mmol), 3-bromo-1-methyl-1H-pyrazol-4-amine (915 mg; 5.20 mmol), $Cs_2CO_3$ (3.4 g; 10.40 mmol) and Pd(dppf)$Cl_2$ (380 mg; 0.52 mmol) in dioxane (20 ml) and water (2 ml) was stirred under $N_2$ atmosphere at 90° C. for 16 h. The mixture was filtered and concentrated to get crude product as a black oil. The crude was purified by C18 (ACN/$H_2O$=20%-95%) to get the product. (355 mg; 23%; light brown oil).

$^1$H NMR (400 MHz, DMSO) δ 7.97 (d, J=2.2 Hz, 1H), 7.92° C. 7.87 (m, 1H), 7.67 (d, J=8.4 Hz, 1H), 7.17 (s, 1H), 4.32 (d, J=7.1 Hz, 2H), 3.76 (s, 3H), 1.32 (t, J=7.1 Hz, 3H).

Example 4-2: Synthesis of ethyl 2-methyl-2H,4H-pyrazolo[4,3-b]indole-7-carboxylate

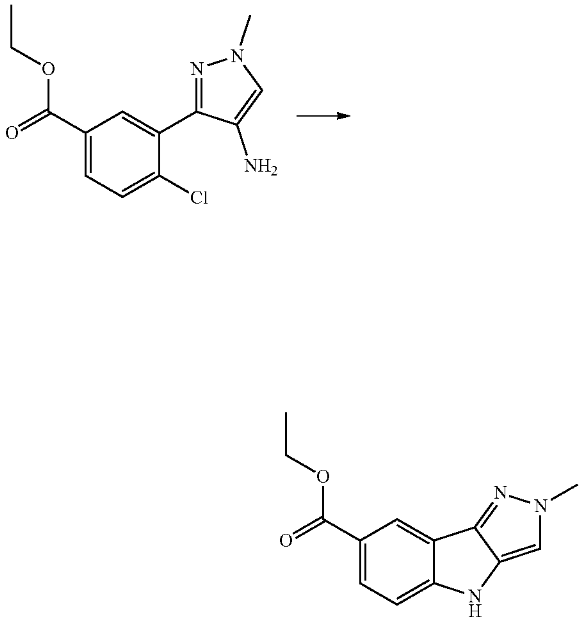

A sealed tube was charged with ethyl 3-(4-amino-1-methyl-1H-pyrazol-3-yl)-4-chlorobenzoate (350 mg; 1.24 mmol), di-tert-butyl[2',4',6'-tris(propan-2-yl)-[1,1'-biphenyl]-2-yl]phosphane {2'-amino-[1,1'-biphenyl]-2-yl}palladiumylium methanesulfonate (120 mg; 0.15 mmol) and $Cs_2CO_3$ (807 mg; 2.48 mmol) in dioxane (20 ml). The mixture was stirred under $N_2$ at 120° C. for 16 h. The LCMS showed starting materials were not gone. Di-tert-butyl[2',4',6'-tris(propan-2-yl)-[1,1'-biphenyl]-2-yl]phosphane {2'-amino-[1,1'-biphenyl]-2-yl}palladiumylium methanesulfonate (120 mg; 0.15 mmol) was added to the mixture and stirring was continued at 140° C. for 24 h. The mixture was filtered and concentrated to get crude product as a black oil. The crude product was purified by C18 (ACN/$H_2O$=5%-95%) to get the product. (50 mg; 23%; white powder).

$^1$H NMR (400 MHz, DMSO) δ 10.71 (s, 1H), 8.38 (d, J=1.6 Hz, 1H), 7.89 (dd, J=8.6, 1.7 Hz, 1H), 7.71 (s, 1H), 7.39 (d, J=8.6 Hz, 1H), 4.32 (t, J=7.1 Hz, 2H), 4.05 (s, 3H), 1.35 (dd, J=9.9, 4.3 Hz, 3H).

Example 4-3: Synthesis of ethyl 2-methyl-4-[4-(trifluoromethyl)phenyl]-2H,4H-pyrazolo[4,3-b]indole-7-carboxylate

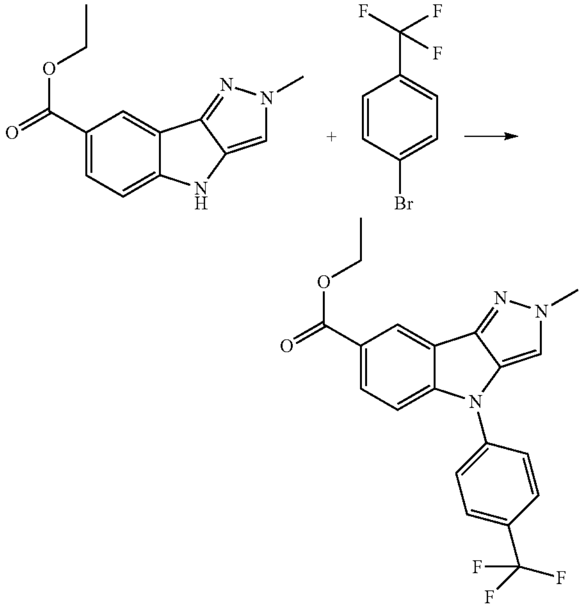

A sealed tube was charged with ethyl 2-methyl-2H,4H-pyrazolo[4,3-b]indole-7-carboxylate (65 mg; 0.25 mmol), 1-bromo-4-(trifluoromethyl)benzene (72 mg; 0.32 mmol), XPhosPd G2 (12 mg; 0.01 mmol) and $Cs_2CO_3$ (240 mg; 0.74 mmol) in dioxane (4 ml). The mixture was stirred under $N_2$ at 100° C. for 2 h. The mixture was filtered and concentrated to get crude product as a black oil. The crude product was purified by C18 (ACN/$H_2O$=5%-95%) to get product as a white powder. (80 mg; 76%; white powder).

$^1$H NMR (400 MHz, DMSO) δ 8.48 (d, J=1.6 Hz, 1H), 8.12 (s, 1H), 8.01 (dd, J=8.8, 1.7 Hz, 1H), 7.94 (s, 4H), 7.88 (d, J=8.8 Hz, 1H), 4.36 (q, J=7.1 Hz, 2H), 4.10 (s, 3H), 1.37 (t, J=7.1 Hz, 3H).

Example 4-4: Synthesis of 2-methyl-4-[4-(trifluoromethyl)phenyl]-2H,4H-pyrazolo[4,3-b]indole-7-carboxylic acid

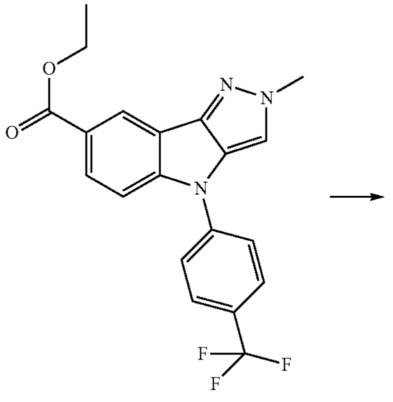

-continued

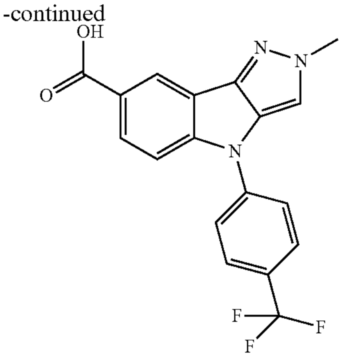

To a solution of ethyl 2-methyl-4-[4-(trifluoromethyl)phenyl]-2H,4H-pyrazolo[4,3-b]indole-7-carboxylate (80 mg; 0.19 mmol) in EtOH (4 ml) was added 1M sodium hydroxide aqueous solution (1 ml). The mixture was stirred at 60° C. for 1.5 h. The mixture was concentrated and adjusted by 1N hydrochloric acid (1 ml) to pH=1-2. The mixture was purified by HPLC to get 2-methyl-4-[4-(trifluoromethyl)phenyl]-2H,4H-pyrazolo[4,3-b]indole-7-carboxylic acid (40 mg; 59%; white solid).

$^1$H NMR (400 MHz, DMSO) δ 8.44 (d, J=1.4 Hz, 1H), 8.10 (s, 1H), 7.99 (d, J=1.7 Hz, 1H), 7.94 (s, 4H), 7.84 (d, J=8.8 Hz, 1H), 4.10 (s, 3H).

Example 5: 2-Methyl-8-{[4-(trifluoromethyl)phenyl]methyl}-2H,8H-pyrazolo[3,4-b]indole-5-carboxylic acid

Example 5-1: Synthesis of ethyl 2-methyl-8-{[4-(trifluoromethyl)phenyl]-methyl}-2H,8H-pyrazolo[3,4-b]indole-5-carboxylate

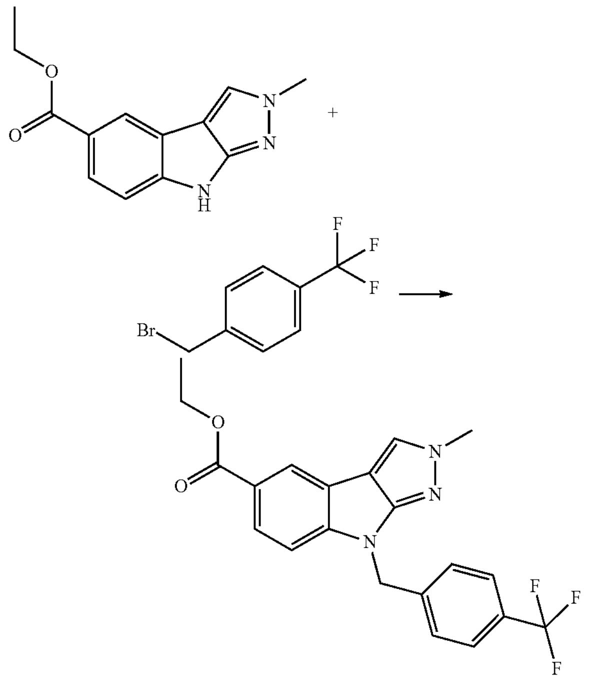

To a solution of ethyl 2-methyl-2H,8H-pyrazolo[3,4-b]indole-5-carboxylate (220 mg; 0.81 mmol) in DMF (3 ml) was added NaH (49 mg; 2.04 mmol) at 0° C. The solution was stirred at 0° C. for 30 minutes and then 1-(bromomethyl)-4-(trifluoromethyl)benzene (230 mg; 0.96 mmol) was added. The solution was stirred at 25° C. for 3 hours. The reaction mixture was filtered by filter membrane. The filtrate was purified by C-18 column (acetonitrile: water=5% to 95%) to obtain the desired purified product (260 mg; 79%; off-white solid). $^1$H NMR (400 MHz, $CDCl_3$) δ 8.44 (d, J=1.6 Hz, 1H), 7.98 (dd, J=8.4, 1.6 Hz, 1H), 7.66 (s, 1H), 7.53 (d, J=8.4 Hz, 2H), 7.34 (d, J=8.0 Hz, 2H), 7.12 (d, J=8.4 Hz, 1H), 5.44 (s, 2H), 4.39 (q, J=7.2 Hz, 2H), 4.06 (s, 3H), 1.41 (t, J=7.2 Hz, 3H).

Example 5-2: Synthesis of 2-methyl-8-{[4-(trifluoromethyl)phenyl]methyl}-2H,8H-pyrazolo[3,4-b]indole-5-carboxylic acid

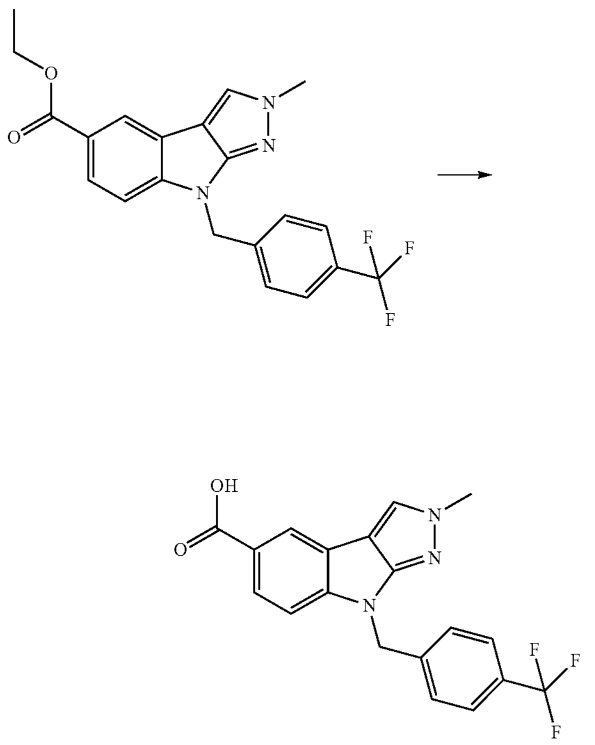

To a solution of ethyl 2-methyl-8-{[4-(trifluoromethyl)phenyl]methyl}-2H,8H-pyrazolo[3,4-b]indole-5-carboxylate (120 mg; 0.30 mmol) in EtOH (40 ml) and Water (1 ml) was added NaOH (36 mg; 0.90 mmol) at 25° C. The yellow brown solution was stirred at 70° C. for 3 hours. The solution was concentrated. To the resulting residue water (5 mL) was added. The water phase was adjusted to pH~3 by 1 N hydrochloric acid aqueous solution (5 drops) and concentrated. The resulting residue was suspended in pure water (10 mL) and filtered. The filter residue was washed three times with water (5 mL) and concentrated to obtain the desired purified product. (101 mg; 88%; off-white solid).

$^1$H NMR (400 MHz, DMSO-d6) δ 12.49 (s, 1H), 8.34 (d, J=1.6 Hz, 1H), 8.10 (s, 1H), 7.85 (dd, J=8.8, 1.6 Hz, 1H), 7.68 (d, J=8.4 Hz, 2H), 7.51-7.43 (m, 3H), 5.52 (s, 2H), 3.99 (s, 3H).

Example 6: 2-Methyl-8-[3-(trifluoromethyl)phenyl]-2H,8H-pyrazolo[3,4-b]indole-5-carboxylic acid

Example 6-1: Synthesis of ethyl 2-methyl-8-[3-(trifluoromethyl)phenyl]-2H,8H-pyrazolo[3,4-b]indole-5-carboxylate

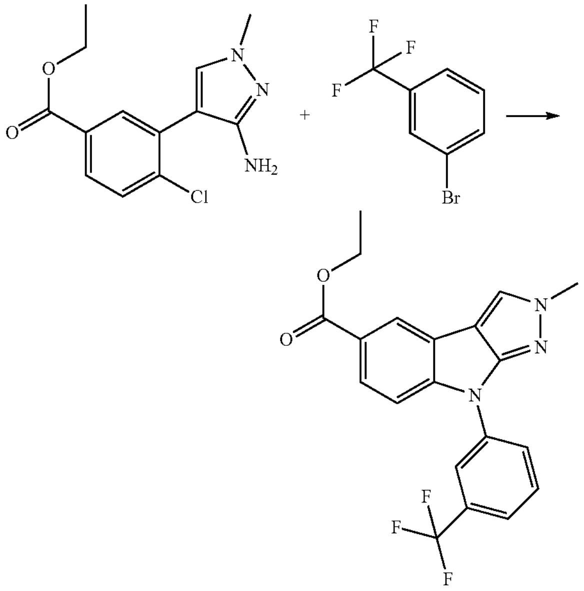 [SMILES: CCOC(=O)c1ccc(Cl)c(-c2cn(C)nc2N)c1 ; FC(F)(F)c1cccc(Br)c1 ; CCOC(=O)c1ccc2c(c1)c1cn(C)nc1n2-c1cccc(C(F)(F)F)c1]

Ethyl 3-(3-amino-1-methyl-1H-pyrazol-4-yl)-4-chlorobenzoate (200 mg; 0.64 mmol), 1-bromo-3-(trifluoromethyl)benzene (174 mg; 0.77 mmol), XPhosPd G2 (56 mg; 0.07 mmol) and $Cs_2CO_3$ (629 mg; 1.93 mmol) were suspended in Dioxane-1,4 (10 ml). The mixture was stirred under $N_2$ atmosphere at 120° C. for 16 h. The mixture was filtered. The organic phase was concentrated and purified by silica gel (PE/EA=10:1) to obtain the purified product as an off-white solid. (230 mg; 88%).

$^1$H NMR (400 MHz, DMSO) δ 8.45 (s, 1H), 8.22 (s, 1H), 8.17 C 8.08 (m, 2H), 7.94 (d, J=8.7 Hz, 1H), 7.86 (d, J=7.9 Hz, 1H), 7.76 (d, J=7.8 Hz, 1H), 7.68 (d, J=8.8 Hz, 1H), 4.35 (q, J=7.1 Hz, 2H), 4.03 (s, 3H), 1.36 (t, J=7.1 Hz, 3H).

Example 6-2: Synthesis of 2methyl-8-[3-(trifluoromethyl)phenyl]-2H,8H-pyrazolo[3,4-b]indole-5-carboxylic acid

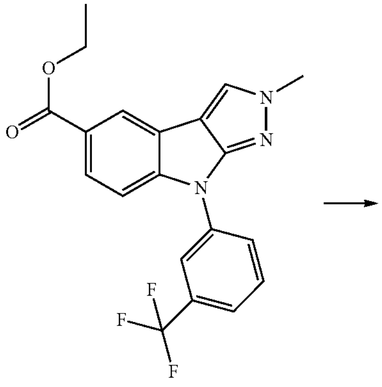

-continued

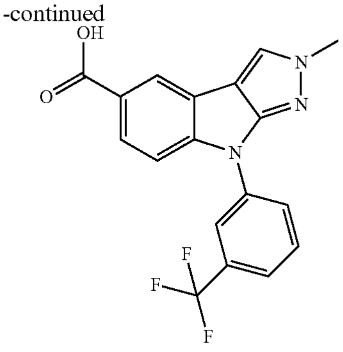

To a solution of ethyl-2-methyl-8-[3-(trifluoromethyl) phenyl]-2H,8H-pyrazolo[3,4-b]indole-5-carboxylate (230 mg; 0.56 mmol) in EtOH (6 ml) was added 1 M sodium hydroxide aqueous solution (2 ml). The reaction mixture was stirred under $N_2$ atmosphere at 60° C. for 2 h. The mixture was concentrated to dryness. Then water (10 ml) was added and the mixture was adjusted by 1N hydrochloric acid to pH=1. The solution was filtered and the residue was washed three times with $H_2O$ (10 ml). The residue was dried under vacuum to obtain the purified product. (180 mg; 89%; off-white solid).

$^1$H NMR (400 MHz, DMSO) δ 12.69 (d, J=0.6 Hz, 1H), 8.43 (d, J=1.5 Hz, 1H), 8.21 (s, 1H), 8.13 (d, J=12.1 Hz, 2H), 7.93 (dd, J=8.7, 1.7 Hz, 1H), 7.86 (t, J=7.9 Hz, H), 7.76 (d, J=7.8 Hz, 1H), 7.67 (d, J=8.7 Hz, 1H), 4.03 (s, 3H).

Example 7: 8-(3-fluorophenyl)-2-methyl-2H,8H-pyrazolo[3,4-b]indole-5-carboxylic acid

Example 7-1: Synthesis of ethyl 8-(3-fluorophenyl)-2-methyl-2H,8H-pyrazolo[3,4-b]indole-5-carboxylate

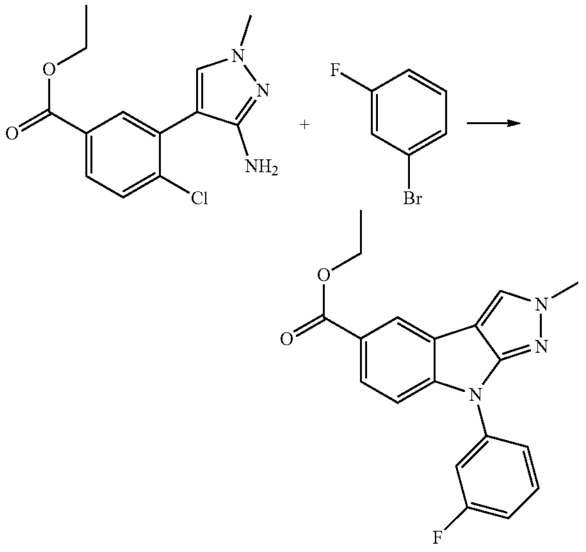

A mixture of ethyl 3-(3-amino-1-methyl-1H-pyrazol-4-yl)-4-chlorobenzoate (200 mg; 0.64 mmol), 1-bromo-3-fluorobenzene (135 mg; 0.77 mmol), XPhosPd G2 (56 mg; 0.07 mmol) and $Cs_2CO_3$ (629 mg; 1.93 mmol) were added to Dioxane-1,4 (10 ml). The mixture was stirred under $N_2$ atmosphere at 120° C. for 16 h. The reaction mixture was filtered. The organic phase was concentrated and purified by silica gel (PE/EA=5:1) to obtain the purified product (210 mg; 92%; off-white solid).

$^1$H NMR (400 MHz, DMSO) δ 8.43 (d, J=1.4 Hz, 1H), 8.21 (s, 1H), 7.91 (d, J=1.7 Hz, 1H), 7.72 (d, J=8.7 Hz, 1H), 7.67 (dd, J=6.5, 2.6 Hz, 3H), 7.28° C. 7.21 (m, H), 4.35 (d, J=7.1 Hz, 2H), 4.03 (s, 3H), 1.36 (t, J=7.1 Hz, 3H).

Example 7-2: Synthesis of 8-(3-fluorophenyl)-2-methyl-2H,8H-pyrazolo[3,4-b]indole-5-carboxylic acid

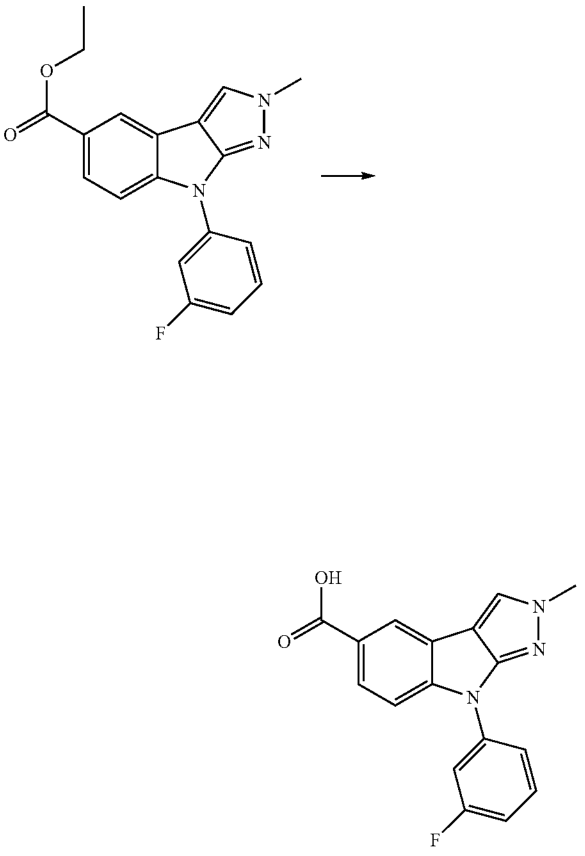

To a solution of ethyl 8-(3-fluorophenyl)-2-methyl-2H,8H-pyrazolo[3,4-b]indole-5-carboxylate (210 mg; 0.59 mmol) in EtOH (6 ml) was added 1M sodium hydroxide aqueous solution (2 ml). The mixture was stirred under $N_2$ atmosphere at 60° C. for 2 h. The mixture was concentrated to dryness. To the residue was added $H_2O$ (10 ml) and the mixture was adjusted by 1N hydrochloric acid to pH=1-2. The solution was filtered. The residue was washed with $H_2O$ (3*10 ml) and dried under vacuum to get the crude product. Ethylacetate/N-hexane=1:1 (10 ml) was added and the mixture was stirred for 30 min. Then the solution was filtered, the residue was dried under vacuum to obtain the purified product. (120 mg; 65%; off-white solid).

$^1$H NMR (400 MHz, DMSO) δ 12.68 (s, 1H), 8.41 (d, J=1.4 Hz, 1H), 8.19 (s, 1H), 7.92 (dd, J=8.7, 1.6 Hz, 1H), 7.72 C 7.63 (m, 4H), 7.27 C 7.20 (m, 1H), 4.03 (s, 3H).

Example 8: 2-Methyl-8-{[3-(trifluoromethyl)phenyl]methyl}-2H,8H-pyrazolo[3,4-b]indole-5-carboxylic acid Example 8-1: Synthesis of ethyl 2-methyl-8-{[3-(trifluoromethyl)phenyl]-methyl}-2H,8H-pyrazolo[3,4-b]indole-5-carboxylate

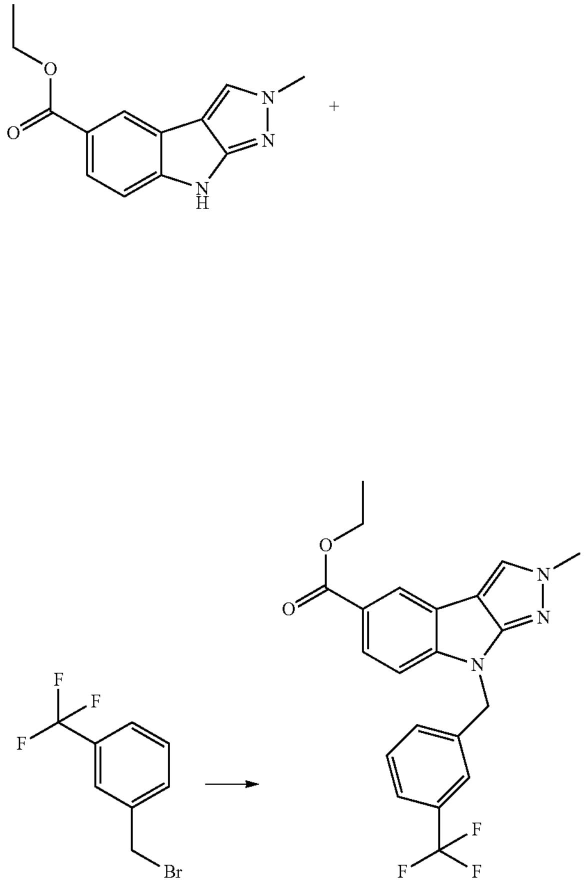

To a solution of ethyl-2-methyl-2H,8H-pyrazolo[3,4-b]indole-5-carboxylate (220 mg; 0.81 mmol) in DMF (3 ml) was added NaH (49 mg; 2.04 mmol) at 0° C. The mixture was stirred at 0° C. for 30 minutes and 1-(bromomethyl)-3-(trifluoromethyl)benzene (230 mg; 0.96 mmol) was added. The solution was stirred at 25° C. for 3 hours. The reaction was filtered, concentrated in vacuum and purified by C-18 column chromatography (ACN/$H_2O$=5%-95%) and the product could be obtained (213 mg; 64%; yellow brown solid).

$^1$H NMR (400 MHz, $CDCl_3$) δ 8.44 (d, J=2.0 Hz, 1H), 7.98 (dd, J=8.8, 1.6 Hz, 1H), 7.65 (s, 1H), 7.57 (s, 1H), 7.52-7.50 (m, 1H), 7.41-7.37 (m, 2H), 7.12 (d, J=9.2 Hz, 1H), 5.43 (s, 2H), 4.39 (q, J=7.2 Hz, 2H), 4.07 (s, 3H), 1.41 (t, J=7.2 Hz, 3H).

Example 8-2: Synthesis of 2-Methyl-8-{[3-(trifluoromethyl)phenyl]methyl}-2H,8H-pyrazolo[3,4-b]indole-5-carboxylic acid

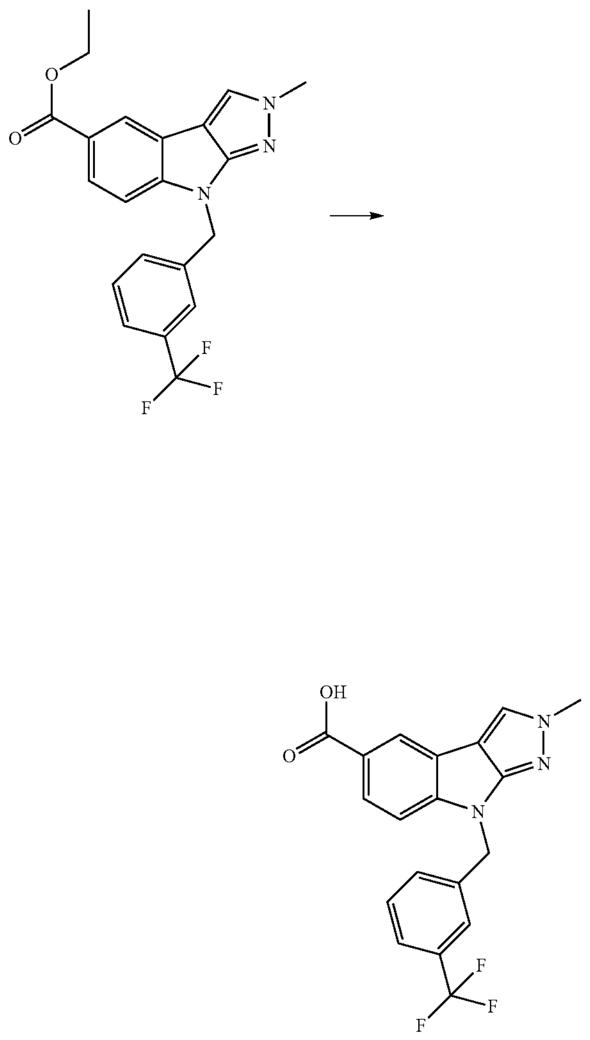

To a solution of ethyl 2-methyl-8-{[3-(trifluoromethyl)phenyl]methyl}-2H,8H-pyrazolo[3,4-b]indole-5-carboxylate (210 mg; 0.51 mmol) in EtOH (4 ml) and Water (1 ml) was added NaOH (63 mg; 1.58 mmol) at 25° C. The yellow brown mixture was stirred at 70° C. for 3 hours. The mixture was concentrated to dryness and water (5 mL) was added. The water phase was adjusted to pH~3 by 1 N hydrochloric acid aqueous solution (5 drops) and concentrated to dryness. To the residue was added water (10 mL) and the mixture was filtered. The filtered residue was washed with water (5 mL) three times and concentrated to dryness. The purified product could be obtained (150 mg; 78%; off-white solid).

$^1$H NMR (400 MHz, DMSO-d6) δ 12.51 (s, 1H), 8.34 (d, J=1.6 Hz, 1H), 8.10 (s, 1H), 7.85 (dd, J=8.8, 2.0 Hz, 1H), 7.72 (s, 1H), 7.64-7.62 (m, 1H), 7.56-7.47 (m, 3H), 5.52 (s, 2H), 3.99 (s, 3H).

Example 9: 2-Methyl-8-(4-methylphenyl)-2H,8H-pyrazolo[3,4-b]indole-5-carboxylic acid Example 9-1: Synthesis of ethyl 2-methyl-8-(4-methylphenyl)-2H,8H-pyrazolo[3,4-b]indole-5-carboxylate

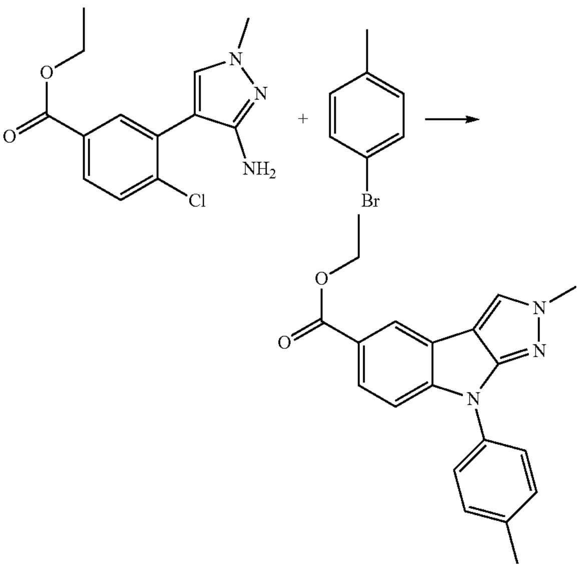

A mixture of ethyl 3-(3-amino-1-methyl-1H-pyrazol-4-yl)-4-chlorobenzoate (200 mg; 0.64 mmol), 1-bromo-4-methylbenzene (132 mg; 0.77 mmol), XPhosPd G2 (56 mg; 0.07 mmol) and $Cs_2CO_3$ (629 mg; 1.93 mmol) was added to Dioxane-1,4 (10 ml). The mixture was stirred under $N_2$ atmosphere at 120° C. for 16 h. The mixture was filtered. The organic phase was concentrated and purified by silica gel chromatography (PE/EA=10:1) and the product was obtained (207 mg; 91%; light yellow solid).

$^1$H NMR (400 MHz, $CDCl_3$) δ 8.46 (d, J=2.0 Hz, 1H), 7.99 (dd, J=8.7, 2.4 Hz, 1H), 7.67 (d, J=3.8 Hz, 1H), 7.63-7.57 (m, 2H), 7.52-7.46 (m, 1H), 7.40-7.33 (m, 2H), 4.45-4.38 (m, 2H), 4.07 (d, J=3.9 Hz, 3H), 2.43 (d, J=3.3 Hz, 3H), 1.44 (td, J=7.1, 4.1 Hz, 3H).

Example 9-2: Synthesis of 2-methyl-8-(4-methylphenyl)-2H,8H-pyrazolo[3,4-b]indole-5-carboxylic acid

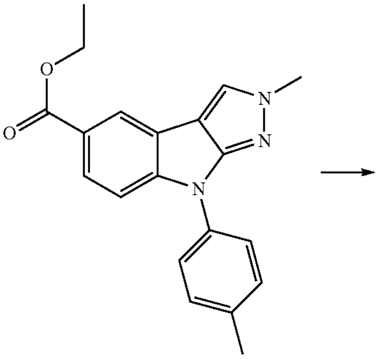

-continued

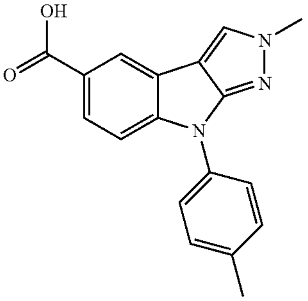

To a solution of ethyl 2-methyl-8-(4-methylphenyl)-2H,8H-pyrazolo[3,4-b]indole-5-carboxylate (200 mg; 0.57 mmol) in EtOH (6 ml) was added 1M sodium hydroxide aqueous solution (2 ml). The mixture was stirred under $N_2$ atmosphere at 60° C. for 2 h. The mixture was concentrated. To the residue $H_2O$ (10 ml) was added and the mixture was adjusted to pH=1 by 1N hydrochloric acid. The precipitate was filtered. The resulting crude product was washed three times with $H_2O$ (15 ml). The filtered residue was dried under vacuum and the purified product could be obtained (160 mg; 87%; off-white solid).

$^1H$ NMR (400 MHz, DMSO) δ 12.60 (s, 1H), 8.40 (d, J=1.5 Hz, 1H), 8.17 (s, 1H), 7.89 (dt, J=5.2, 3.3 Hz, 1H), 7.63 (d, J=8.3 Hz, 2H), 7.54 (d, J=8.7 Hz, 1H), 7.41 (d, J=8.2 Hz, 2H), 4.00 (s, 3H), 2.40 (s, 3H).

Example 10: 8-(4-fluorophenyl)-2-methyl-2H,8H-pyrazolo[3,4-b]indole-5-carboxylic acid

Example 10-1: Synthesis of ethyl 8-(4-fluorophenyl)-2-methyl-2H,8H-pyrazolo[3,4-b]indole-5-carboxylate

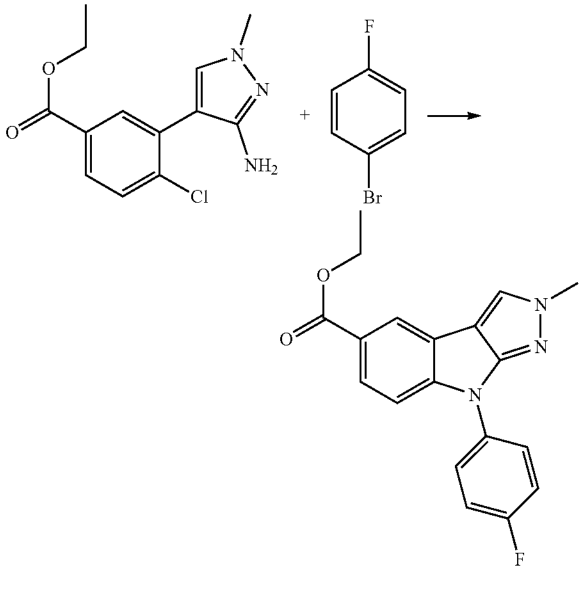

A mixture of ethyl 3-(3-amino-1-methyl-1H-pyrazol-4-yl)-4-chlorobenzoate (200 mg; 0.64 mmol), 1-bromo-4-fluorobenzene (135 mg; 0.77 mmol), XPhosPd G2 (56 mg; 0.07 mmol) and $Cs_2CO_3$ (629 mg; 1.93 mmol) was added to Dioxane-1,4 (10 ml). The mixture was stirred under $N_2$ atmosphere at 120° C. for 16 h. The mixture was filtered and the phases were separated. The organic phase was concentrated and purified by silica gel chromatography (PE/EA=10:1). The purified product could be obtained (186 mg; 81%; light yellow solid). $^1H$ NMR (400 MHz, $CDCl_3$) δ 8.47 (d, J=1.5 Hz, 1H), 8.05-7.98 (m, 1H), 7.74-7.66 (m, 3H), 7.49-7.42 (m, 1H), 7.26 (d, J=3.6 Hz, 2H), 4.42 (dd, J=7.1, 3.5 Hz, 2H), 4.07 (d, J=3.4 Hz, 3H), 1.47-1.41 (m, 3H).

Example 10-2: Synthesis of 8-(4-fluorophenyl)-2-methyl-2H,8H-pyrazolo[3,4-b]indole-5-carboxylic acid

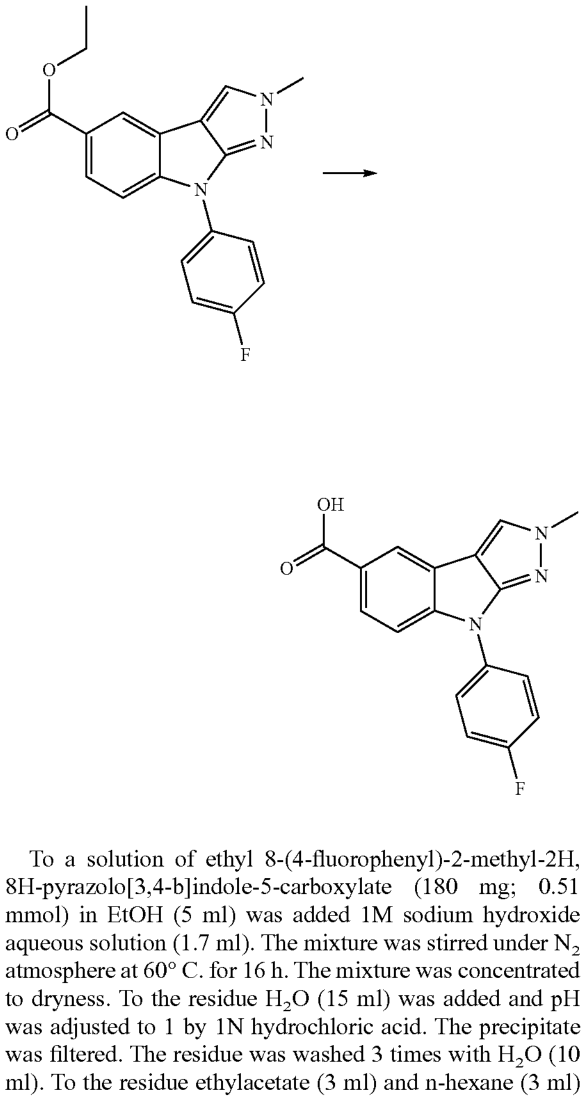

To a solution of ethyl 8-(4-fluorophenyl)-2-methyl-2H,8H-pyrazolo[3,4-b]indole-5-carboxylate (180 mg; 0.51 mmol) in EtOH (5 ml) was added 1M sodium hydroxide aqueous solution (1.7 ml). The mixture was stirred under $N_2$ atmosphere at 60° C. for 16 h. The mixture was concentrated to dryness. To the residue $H_2O$ (15 ml) was added and pH was adjusted to 1 by 1N hydrochloric acid. The precipitate was filtered. The residue was washed 3 times with $H_2O$ (10 ml). To the residue ethylacetate (3 ml) and n-hexane (3 ml) was added and the mixture was stirred 30 min. The suspension was filtered and the residue was dried under vacuum. The purified product could be obtained (100 mg; 62%; white solid).

$^1H$ NMR (400 MHz, DMSO) δ 12.65 (s, 1H), 8.41 (d, J=1.4 Hz, 1H), 8.18 (s, 1H), 7.90 (dd, J=8.7, 1.6 Hz, 1H), 7.83-7.77 (m, 2H), 7.54 (d, J=8.7 Hz, 1H), 7.49-7.42 (m, 2H), 4.01 (s, 3H).

Example 11: 8-(cyclohexylmethyl)-2-methyl-2H, 8H-pyrazolo[3,4-b]indole-5-carboxylic acid Example 11-1: Synthesis of ethyl 8-(cyclohexylmethyl)-2-methyl-2H,8H-pyrazolo[3,4-b]indole-5-carboxylate

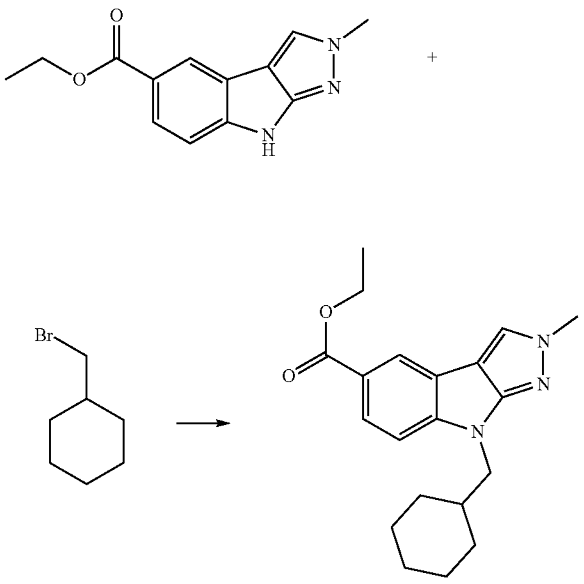

To a suspension of ethyl 2-methyl-2H,8H-pyrazolo[3,4-b]indole-5-carboxylate (200 mg; 0.82 mmol) in propan-2-one (5 ml) was added bromomethyl-cyclohexane (0.14 ml; 0.99 mmol) and KOH (138 mg; 2.47 mmol.). The mixture was stirred at 65° C. under $N_2$ atmosphere for 12 h. The mixture was poured into water (10 ml), and then extracted 3 times with EA (5 ml). The combined organic phase was collected and evaporated under vacuum. The residue was purified by C18 column chromatography ($ACN/H_2O$=5%-95%) and the product could be obtained (170 mg; 57%; yellow gel).

Example 11-2: Synthesis of 8-(cyclohexylmethyl)-2-methyl-2H,8H-pyrazolo[3,4-b]indole-5-carboxylic acid

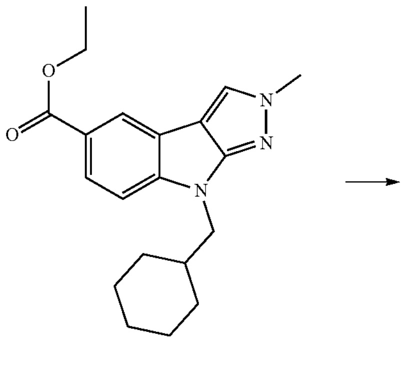

-continued

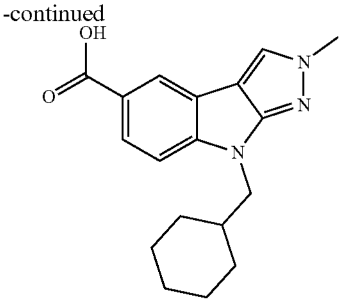

To a suspension of ethyl 8-(cyclohexylmethyl)-2-methyl-2H,8H-pyrazolo[3,4-b]indole-5-carboxylate (170 mg; 0.47 mmol) in EtOH (24 ml) was added Water (8 ml) and sodium hydroxide (320 mg; 8 mmol) The mixture was stirred at 65° C. under $N_2$ atmosphere for 12 h. The mixture was evaporated under vacuum.

The residue was acidified with 1 N HCl solution and evaporated. The residue was purified by C18 column chromatography ($ACN/H_2O$=5%-95%) and the product could be obtained (50 mg; 33%; white solid).

$^1H$ NMR (400 MHz, CDCl3) δ 7.63 (s, 1H), 7.31 C 7.26 (m, 3H), 4.09 (s, 3H), 4.01 (d, J=7.5 Hz, 2H), 2.49 (s, 1H), 2.01 (s, 1H), 1.75-1.63 (m, 5H), 1.26-1.15 (m, 3H), 1.13-1.03 (m, 2H).

Example 12: 8-(Benzyl)-2-methyl-2H,8H-pyrazolo [3,4-b]indole-5-carboxylic acid

Example 12-1: Synthesis of ethyl 8-(cyclohexylmethyl)-2-methyl-2H,8H-pyrazolo[3,4-b]indole-5-carboxylate

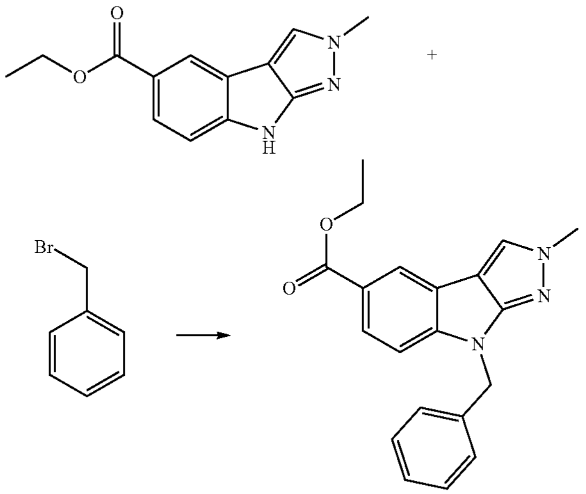

To a suspension of ethyl 2-methyl-2H,8H-pyrazolo[3,4-b]indole-5-carboxylate (300 mg; 1.23 mmol) in propan-2-one (5 ml) was added bromomethylbenzene (0.18 ml; 1.48 mmol) and KOH (208 mg; 3.7 mmol). The mixture was stirred at 65° C. under $N_2$ atmosphere for 12 h. The mixture was poured into water (10 ml), and then extracted 3 times with EA (5 ml). The combined organic phase was collected and evaporated under vacuum. The residue was purified by C18 column chromatography ($ACN/H_2O$=5%-95%) and the product could be obtained (180 mg; 41%; off white powder).

Example 12-2: Synthesis of 8-(benzyl)-2-methyl-2H,8H-pyrazolo[3,4-b]indole-5-carboxylic acid

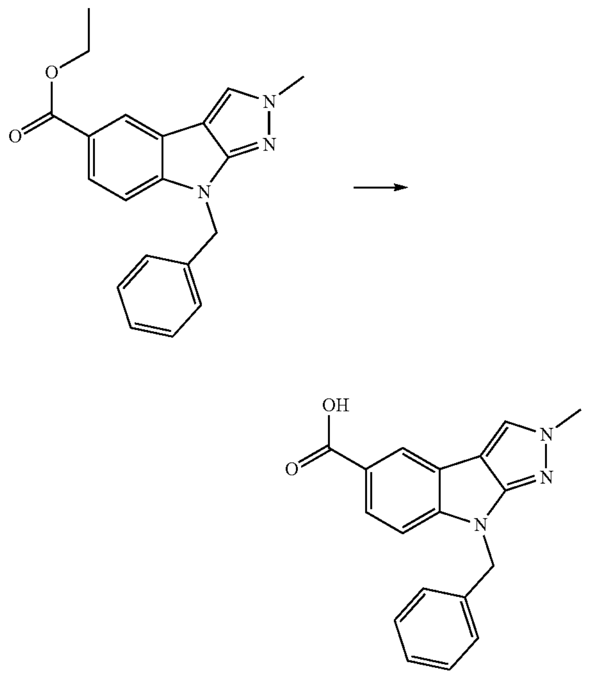

To a suspension of ethyl 8-(benzyl)-2-methyl-2H,8H-pyrazolo[3,4-b]indole-5-carboxylate (170 mg; 0.48 mmol) in EtOH (12 ml) was added sodium hydroxide (320 mg; 8 mmol) and water (4 ml). The mixture was stirred at 65° C. under $N_2$ atmosphere for 12 h. The residue was acidified with 1 N HCl solution and evaporated under vacuum. The residue was purified by C18 column chromatography (ACN/$H_2O$=5%-95%) and the product could be obtained (60 mg; 41%; white solid).

$^1$H NMR (300 MHz, DMSO) δ 12.58-12.44 (m, 1H), 8.35 (d, J=1.4 Hz, 1H), 8.12 (s, 1H), 7.87 (dd, J=8.5, 1.6 Hz, 1H), 7.52 (d, J=8.6 Hz, 1H), 7.39-7.24 (m, 6H), 5.43 (s, 2H), 4.02 (s, 3H).

Example 13: 8-(4-chlorophenyl)-2-methyl-2H,8H-pyrazolo[3,4-b]indole-5-carboxylic acid Example 13-1: Synthesis of ethyl 8-(4-chlorophenyl)-2-methyl-2H,8H-pyrazolo[3,4-b]indole-5-carboxylate

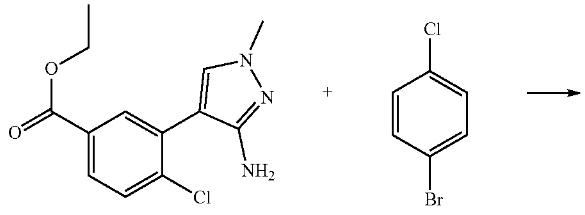

-continued

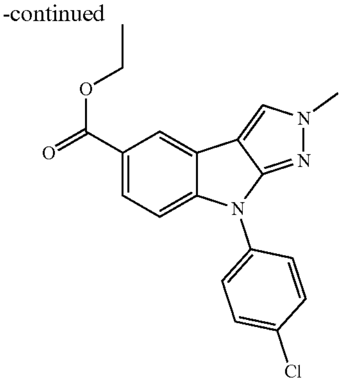

To a suspension of ethyl 3-(3-amino-1-methyl-1H-pyrazol-4-yl)-4-chlorobenzoate (300 mg; 0.97 mmol) in Dioxane-1,4 (10 ml) was added 1-bromo-4-chlorobenzene (222 mg; 1.16 mmol), XPhosPd G2 (84 mg; 0.11 mmol) and $Cs_2CO_3$ (944 mg; 2.90 mmol). The mixture was stirred at 120° C. under $N_2$ atmosphere for 12 h. The mixture was poured into water (10 ml), and then extracted three times with EA (5 ml). The combined organic phase was collected and evaporated under vacuum. The residue was purified by C18 column chromatography (ACN/$H_2O$=5%-95%) and the purified product could be obtained (180 mg; 52%; off-white solid).

Example 13-2: Synthesis of 8-(4-chlorophenyl)-2-methyl-2H,8H-pyrazolo[3,4-b]indole-5-carboxylic acid

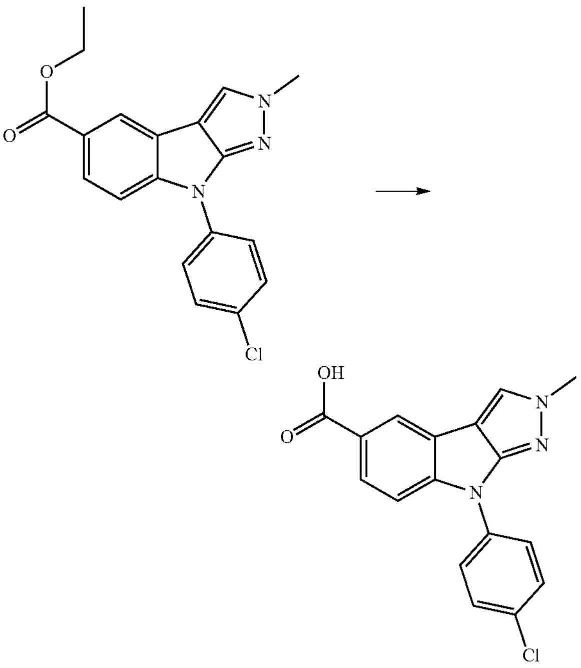

To a suspension of ethyl 8-(4-chlorophenyl)-2-methyl-2H,8H-pyrazolo[3,4-b]indole-5-carboxylate (150 mg; 0.42 mmol) in EtOH (12 ml) was added sodium hydroxide (320 mg; 8 mmol) and Water (4 ml). The mixture was stirred at 65° C. under $N_2$ atmosphere for 12 h. The mixture was evaporated under vacuum. The residue was acidified with 1 N HCl solution and evaporated. The reminder was purified by C18 column chromatography (ACN/$H_2O$=5%-95%) and the purified product could be obtained (30 mg; 21%; white solid).

$^1$H NMR (300 MHz, DMSO) δ 12.70 (s, 1H), 8.44 (d, J=1.4 Hz, 1H), 8.22 (s, 1H), 7.93 (dd, J=8.7, 1.7 Hz, 1H), 7.86 (d, J=8.8 Hz, 2H), 7.72 (d, J=2.9 Hz, 1H), 7.67 (dd, J=7.1, 4.0 Hz, 2H), 4.04 (s, 3H).

Example 14: 8-(4-methoxyphenyl)-2-methyl-2H,8H-pyrazolo[3,4-b]indole-5-carboxylic acid

Example 14-1: Synthesis of ethyl 8-(4-methoxyphenyl)-2-methyl-2H,8H-pyrazolo[3,4-b]indole-5-carboxylate

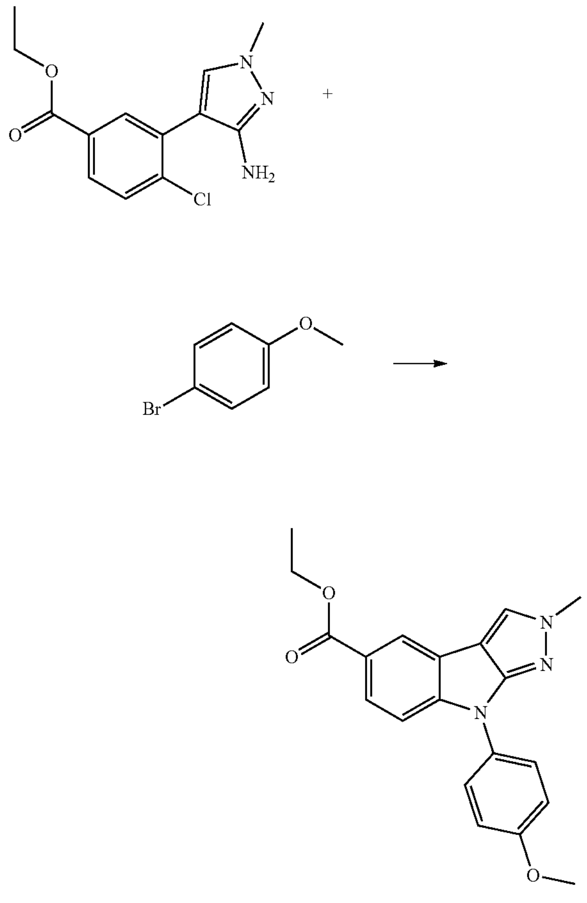

In a microwave vial ethyl 3-(3-amino-1-methyl-1H-pyrazol-4-yl)-4-chlorobenzoate (60 mg; 0.21 mmol) in 1,4-Dioxane (4 ml) was added under argon 4-Bromoanisole (32 μl; 0.26 mmol), Cesium carbonate (206 mg; 0.64 mmol) and XPhos Pd G4 (19 mg; 0.02 mmol). The reaction was stirred for 16 hours at 120° C. The reaction mixture was diluted with EA and extracted 3× with water, dried over $Na_2SO_4$ and evaporated to dryness. The residue was purified by prep. HPLC. The purified product could be obtained. (56 mg, 68%, beige solid).

Example 14-2: Synthesis of 8-(4-methoxyphenyl)-2-methyl-2H,8H-pyrazolo[3,4-b]indole-5-carboxylic acid

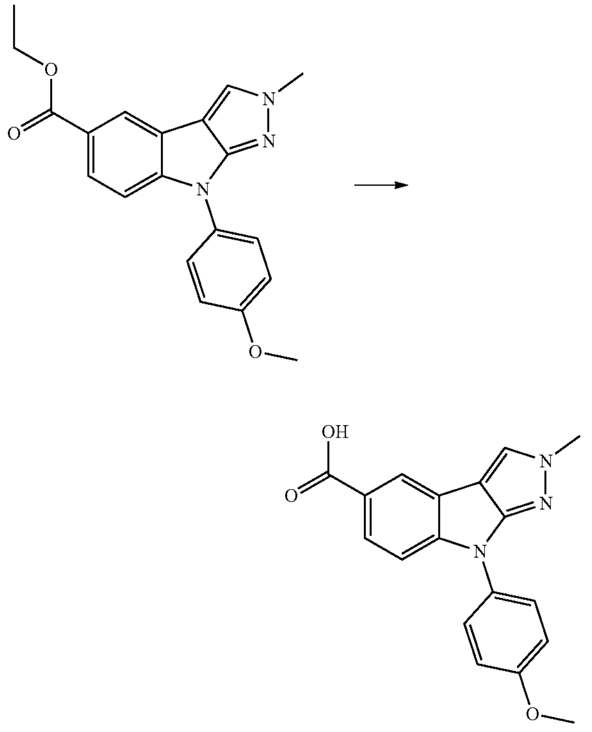

To ethyl 8-(4-methoxyphenyl)-2-methyl-2H,8H-pyrazolo[3,4-b]indole-5-carboxylate (56 mg; 0.15 mmol) in Ethanol (0.3 ml) was added Sodium hydroxide solution c(NaOH)=2 mol/l (0.2 ml) and the mixture was stirred for 16 hours at 60° C. The reaction was evaporated to dryness and the residue was purified by prep. HPLC. The purified product could be obtained (19 mg, 40%, white solid).

$^1$H NMR (500 MHz, DMSO-d6) δ 12.58-12.54 (m, 1H), 8.40-8.38 (m, 1H), 8.15 (s, 1H), 7.87 (dd, J=8.6, 1.8 Hz, 1H), 7.65-7.61 (m, 2H), 7.44 (d, J=8.7 Hz, 1H), 7.18-7.14 (m, 2H), 4.00 (s, 3H), 3.85 (s, 3H).

Example 15: 8-(4-Ethoxyphenyl)-2-methyl-2H,8H-pyrazolo[3,4-b]indole-5-carboxylic acid

Example 15-1: Synthesis of ethyl 3-(3-amino-1-methyl-1H-pyrazol-4-yl)-4-chlorobenzoate

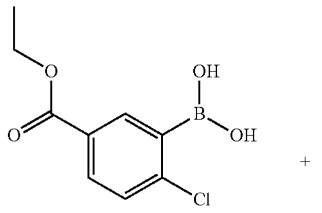

-continued

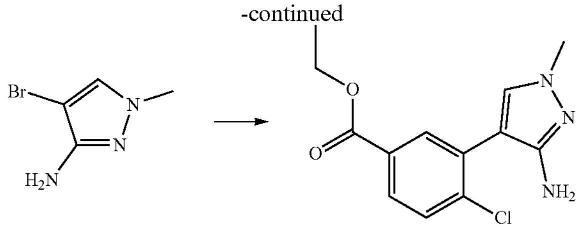

To a suspension of Ethyl 3-borono-4-chlorobenzoate (600 mg; 2.63 mmol) in 1,4-Dioxane (8 ml) and Water (0.8 ml) was added 4-Bromo-1-methyl-1H-pyrazol-3-amine (462 mg; 2.63 mmol), Potassium carbonate (726 mg; 5.25 mmol) and [1,1'-Bis(diphenylphosphino)ferrocene]-dichloropalladium(II), complex with dichloromethane (214 mg) in a microwave vial under argon. The reaction was stirred for 16 hours at 60° C. and then diluted with EA at room temperature. The mixture was extracted 3× with water, dried over $Na_2SO_4$ and evaporated to dryness. The residue was purified by flash chromatopgraphy. The purified product could be obtained as brown oil (273 mg, 36% yield).

Example 15-2: Synthesis of ethyl 8-(4-ethoxyphenyl)-2-methyl-2H,8H-pyrazolo[3,4-b]indole-5-carboxylate

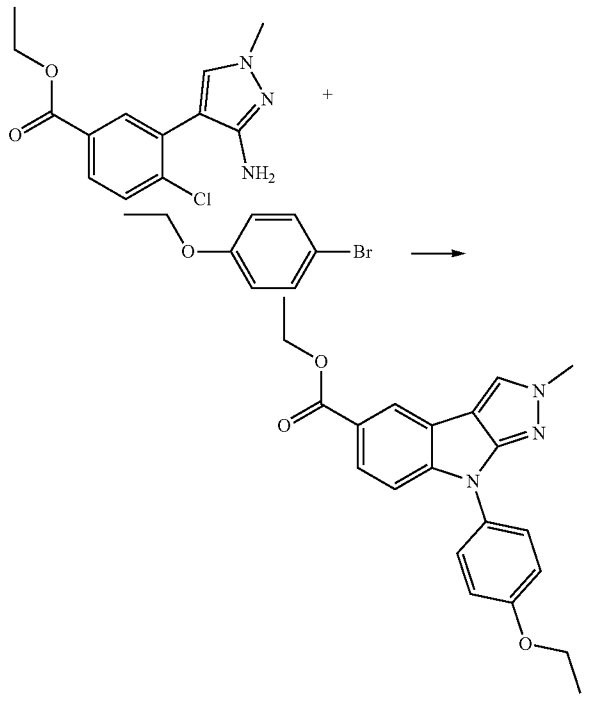

To ethyl 3-(3-amino-1-methyl-1H-pyrazol-4-yl)-4-chlorobenzoate (60 mg; 0.21 mmol) in 1,4-Dioxane (4 ml) was added under argon 4-Bromophenetole (35 µl; 0.25 mmol), Cesium carbonate (0.62 mmol) and XPhos Pd G4 (19 mg; 0.02 mmol) in a microwave vial. The reaction was stirred for 16 hours at 120° C. and diluted with EA at room temperature. The mixture was extracted 3× with water, dried over $Na_2SO_4$ and evaporated to dryness. The residue was purified by prep. HPLC and the purified product could be obtained as yellow solid (10 mg, 12% yield).

Example 15-3: Synthesis of 8-(4-ethoxyphenyl)-2-methyl-2H,8H-pyrazolo[3,4-b]indole-5-carboxylic acid

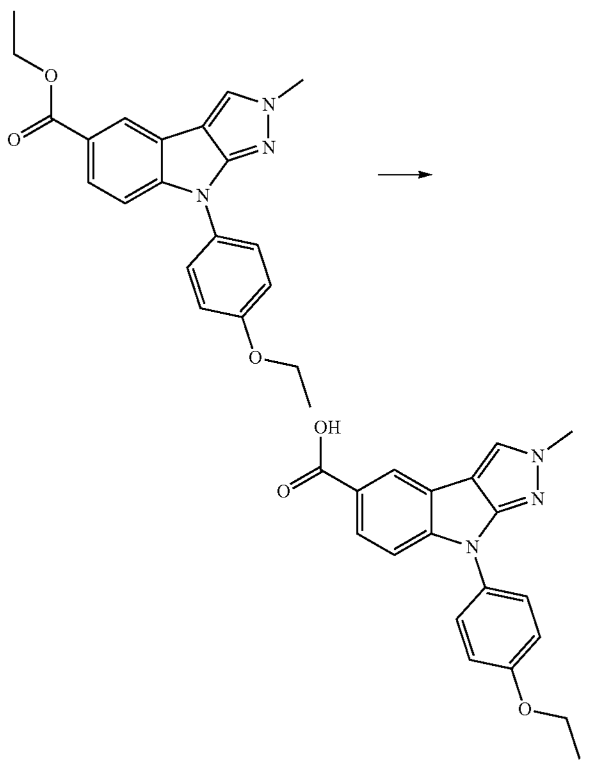

To ethyl 8-(4-ethoxyphenyl)-2-methyl-2H,8H-pyrazolo[3,4-b]indole-5-carboxylate (10 mg; 0.03 mmol) in ethanol (2 ml) was added sodium hydroxide solution c(NaOH)=2 mol/l (2 N) (76 µl; 0.15 mmol) and the mixture was stirred for 16 h at 60° C. As the reaction was not completed more sodium hydroxide solution c(NaOH)=2 mol/l (2 N) (76 µl; 0.15 mmol) was added and the mixture was stirred for additional 16 hours at 60° C. The reaction was evaporated to dryness at room temperature and the residue was purified by prep. HPLC column chromatography. The purified product could be obtained was off white solid (13 mg, 99% yield).

Example 16: Methyl 2-methyl-4-[4-(trifluoromethyl)phenyl]pyrazolo[4,3-b]indole-7-carboxylate

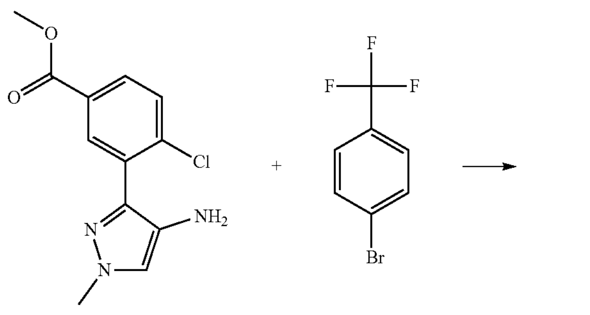

-continued

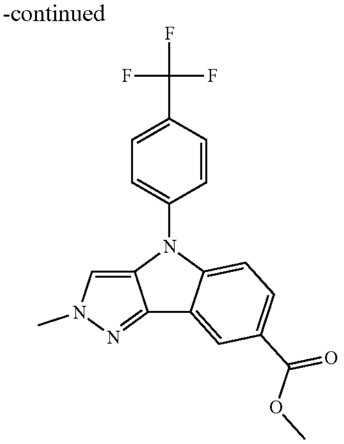

Into a sealed tube were combined methyl 3-(4-amino-1-methylpyrazol-3-yl)-4-chlorobenzoate (330 mg, 1.192 mmol), XPhos Pd G3 (99 mg, 0.115 mmol), $Cs_2CO_3$ (825 mg, 2.481 mmol), dioxane (160 mL) and 1-bromo-4-(trifluoromethyl)benzene (0.19 mL, 0.004 mmol) at room temperature. The resulting mixture was stirred for 24 h at 120° C. under argon atmosphere. The resulting mixture was concentrated under vacuum. The crude product was purified by Prep-HPLC giving the product methyl 2-methyl-4-[4-(trifluoromethyl)phenyl]pyrazolo[4,3-b]indole-7-carboxylate as a white solid (40 mg, 9%).

Example 17: N,2-dimethyl-4-[4-(trifluoromethyl) phenyl]pyrazolo [4,3-b]indole-7-carboxamide

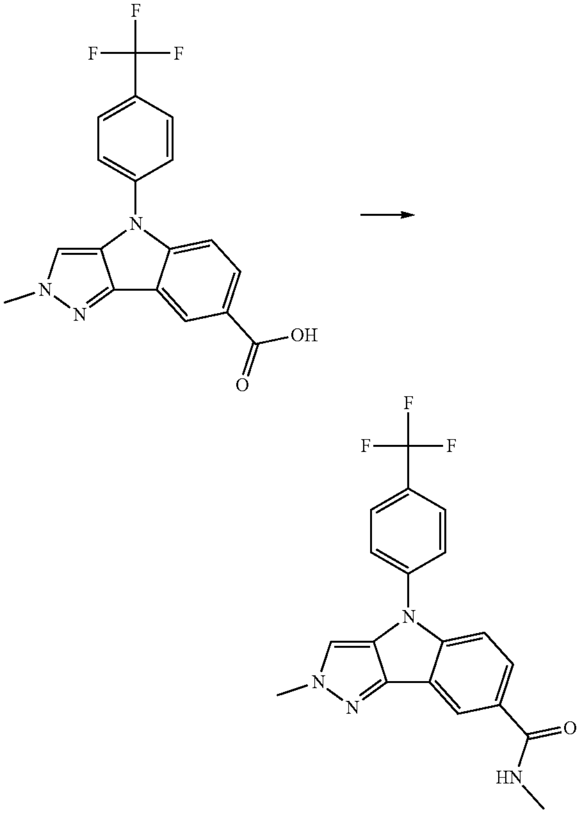

Into a sealed tube were added 2-methyl-4-[4-(trifluoromethyl) phenyl]pyrazolo[4,3-b]indole-7-carboxylic acid (Example 4-4) (70 mg, 0.189 mmol), HATU (153 mg, 0.393 mmol), DCM (6.80 mL), Methylamine, 2M in THF (0.19 mL, 6.248 mmol) and DIEA (0.07 mL, 0.525 mmol) at room temperature. The resulting mixture was stirred for 2 h at 30° C. and concentrated under vacuum afterwards. The crude product was purified by Prep-HPLC giving N,2-dimethyl-4-[4-(trifluoromethyl)phenyl]pyrazolo[4,3-b]indole-7-carboxamide (41 mg, 58%) as a white solid.

$^1H$ NMR (400 MHz, DMSO, ppm) δ 8.52 (d, J=4.6 Hz, 1H), 8.46 (d, J=1.8 Hz, 1H), 8.10 (s, 1H), 7.93 (s, 5H), 7.85 (d, J=8.7 Hz, 1H), 4.10 (s, 3H), 2.83 (d, J=4.4 Hz, 3H).

Example 18: 2-methyl-8-[4-(trifluoromethoxy)phenyl]-2H,8H-pyrazolo[3,4-b]indole-5-carboxylic acid Example 18-1: Synthesis of ethyl 2-methyl-8-[4-(trifluoromethoxy)phenyl]-2H,8H-pyrazolo[3,4-b] indole-5-carboxylate

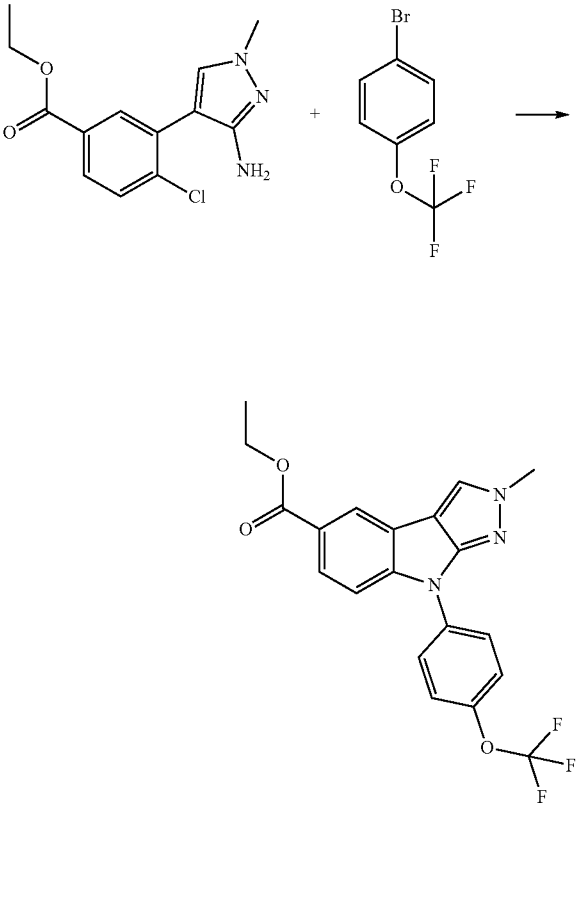

To ethyl 3-(3-amino-1-methyl-1H-pyrazol-4-yl)-4-chlorobenzoate (60 mg; 0.21 mmol) in 1,4-Dioxane (4 ml) was added under argon 1-Brom-4-(trifluormethoxy)-benzene (60 mg; 0.25 mmol), Cesium carbonate (202 mg; 0.62 mmol) and XPhos Pd G4 (18.7 mg; 0.02 mmol) in a microwave vial. The reaction was stirred for 16 hrs at 120° C. At room temperature the reaction mixture was diluted with EA and extracted 3× with water, dried over $Na_2SO_4$ and evaporated to dryness. The residue was purified by prep. HPLC giving the procut as white solid (28 mg; 34%).

$^1$H NMR (500 MHz, DMSO-d6) δ 8.45-8.43 (m, 1H), 8.21 (s, 1H), 7.94-7.90 (m, 3H), 7.68-7.65 (m, 1H), 7.64-7.60 (m, 2H), 4.35 (q, J=7.1 Hz, 2H), 4.02 (s, 3H), 1.36 (t, J=7.1 Hz, 3H).

Example 18-2: Synthesis of 2-methyl-8-[4-(trifluoromethoxy)phenyl]-2H,8H-pyrazolo[3,4-b]indole-5-carboxylic acid

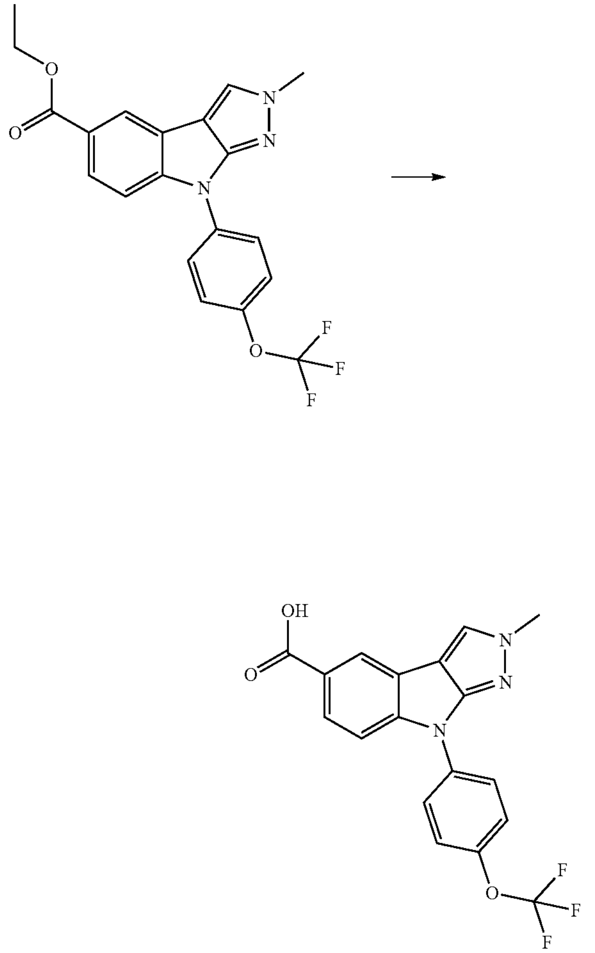

To a solution of ethyl 2-methyl-8-[4-(trifluoromethoxy) phenyl]-2H,8H-pyrazolo[3,4-b]indole-5-carboxylate (28 mg; 0.07 mmol) in Ethanol (2 ml) was added Sodium hydroxide solution c(NaOH)=2 mol/l (2 N) (104 μl; 0.21 mmol) and the mixture was stirred for 16 hrs at 60° C. The reaction was evaporated to dryness and the residue was purified by prep. HPLC giving the product as white solid (20 mg; 76%).

$^1$H NMR (400 MHz, DMSO-d6) δ 12.67-12.62 (m, 1H), 8.41 (d, J=1.7 Hz, 1H), 8.19 (s, 1H), 7.95-7.90 (m, 2H), 7.93-7.88 (m, 1H), 7.65 (d, J=8.7 Hz, 1H), 7.63-7.59 (m, 2H), 4.02 (s, 3H).

Example 19: 2-methyl-4-[4-(trifluoromethyl)phenyl] pyrazolo [4,3-b]indole-7-carbonitrile Example 19-1: Synthesis of 2-methyl-4-[4-(trifluoromethyl)phenyl]pyrazolo [4,3-b]indole-7-carboxamide

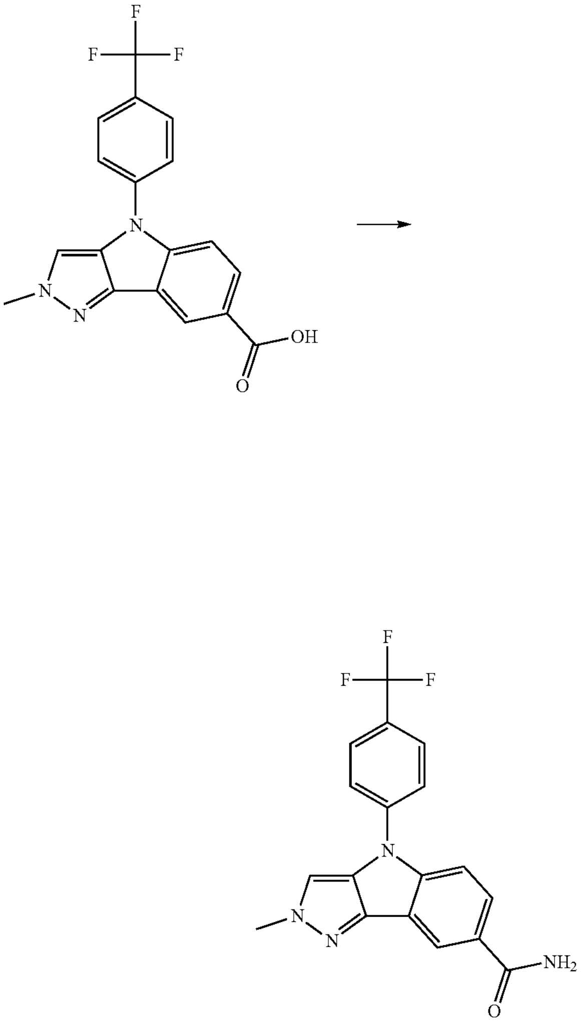

Into a sealed tube were combined 2-methyl-4-[4-(trifluoromethyl)phenyl]pyrazolo[4,3-b]indole-7-carboxylic acid (Example 4-4) (490 mg, 1.324 mmol), THF (25 mL), CDI (344 mg, 2.079 mmol), $NH_4OH$ (30 mL) at room temperature. The resulting mixture was stirred for 3 h at 30° C. The reaction was quenched with water at room temperature. The aqueous layer was extracted with EtOAc (3×100 mL). The resulting mixture was concentrated under vacuum. This resulted in 2-methyl-4-[4-(trifluoromethyl)phenyl]pyrazolo [4,3-b]indole-7-carboxamide (520 mg, 98%) as a white solid.

$^1$H NMR (300 MHz, DMSO, ppm) δ 8.45 (d, J=1.7 Hz, 1H), 8.10 (s, 1H), 8.04-7.95 (m, 1H), 7.93 (s, 4H), 7.86 (d, J=8.8 Hz, 1H), 4.09 (s, 3H), 3.88 (s, 3H).

Example 19-2: Synthesis of 2-methyl-4-[4-(trifluoromethyl)phenyl]pyrazolo [4,3-b]indole-7-carbonitrile

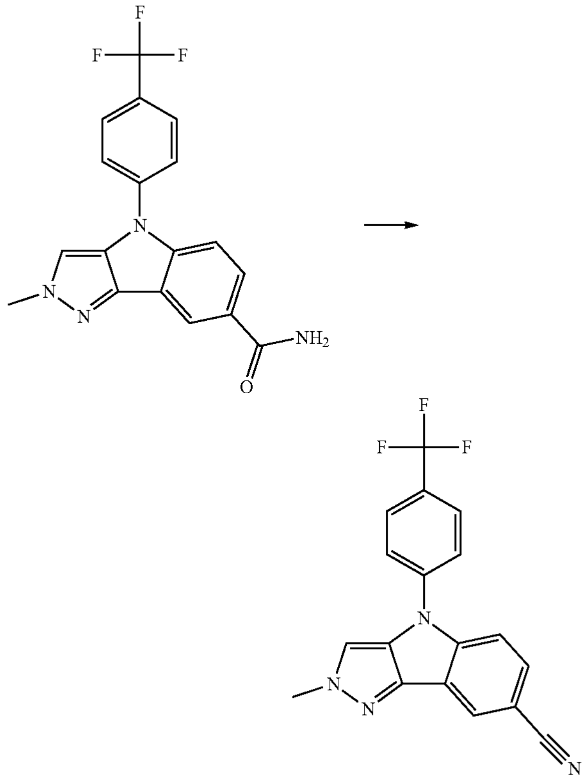

Into a sealed tube were added 2-methyl-4-[4-(trifluoromethyl)phenyl]pyrazolo[4,3-b]indole-7-carboxamide (150 mg, 0.419 mmol), THF (7.5 mL) and $POCl_3$ (0.15 mL) at room temperature. The resulting mixture was stirred for 3 h at room temperature. The reaction was quenched with ice at 0° C. The aqueous layer was extracted with EtOAc (3×50 mL). The resulting mixture was concentrated under vacuum. The crude product was purified by Prep-HPLC. This resulted in 2-methyl-4-[4-(trifluoromethyl)phenyl]pyrazolo[4,3-b]indole-7-carbonitrile (37 mg, 25%) as a white solid.

$^1H$ NMR (300 MHz, DMSO, ppm) δ 8.44 (d, J=1.7 Hz, 1H), 8.15 (s, 1H), 7.95 (s, 4H), 8.02-7.87 (m, 1H), 7.85-7.75 (m, 1H), 4.12 (s, 3H).

Example 20: N-[2-methyl-8-[4-(trifluoromethyl)phenyl]pyrazolo[3,4-b]indol-5-yl]prop-2-enamide Example 20-1: Synthesis of 4-(2-chloro-5-nitrophenyl)-1-methylpyrazol-3-amine

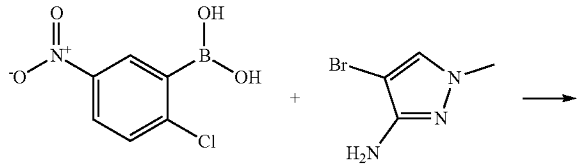

-continued

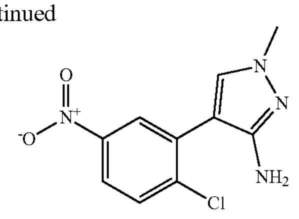

To a solution of 2-chloro-5-nitrophenylboronic acid (1.0 g, 4.718 mmol) and 4-bromo-1-methylpyrazol-3-amine (437 mg, 2.359 mmol) in dioxane (10 mL) and $H_2O$ (2 mL) were added $Pd(dppf)Cl_2$ (363 mg, 0.471 mmol) and $K_2CO_3$ (1.3 g, 8.936 mmol). After stirring for 4 h at 80° C. under a nitrogen atmosphere. The resulting mixture was concentrated under vacuum. The residue was purified by silica gel column chromatography, eluted with PE/EtOAc (1:1) to afford 4-(2-chloro-5-nitrophenyl)-1-methylpyrazol-3-amine (190 mg, 15%) as a yellow solid.

Example 20-2: Synthesis of 2-methyl-5-nitro-8-[4-(trifluoromethyl) phenyl]pyrazolo[3,4-b]indole

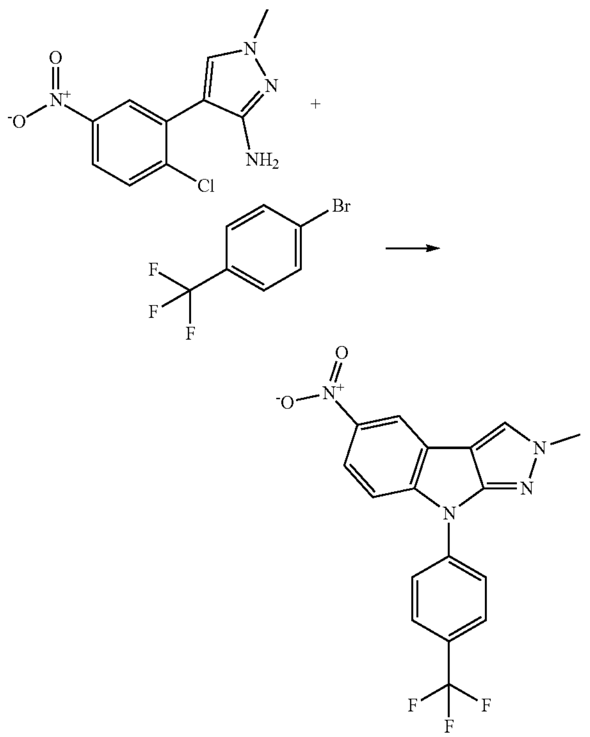

To a stirred solution of 4-(2-chloro-5-nitrophenyl)-1-methylpyrazol-3-amine (330 mg, 1.124 mmol) and 1-bromo-4-(trifluoromethyl)benzene (346 mg, 1.461 mmol) in dioxane (10 mL) was added XPhos Pd G3 (50 mg, 0.056 mmol), $Cs_2CO_3$ (1.16 g, 3.372 mmol) in portions at room temperature under nitrogen atmosphere. The resulting mixture was stirred overnight at 120° C. under nitrogen atmosphere. The resulting mixture was concentrated under vacuum. The residue was purified by silica gel column chromatography, eluted with PE/EtOAc (1:2) to afford 2-methyl-5-nitro-8-[4-(trifluoromethyl) phenyl]-pyrazolo[3,4-b]indole (460 mg, 95%) as a yellow solid.

Example 20-3: Synthesis of 2-methyl-8-[4-(trifluoromethyl) phenyl]pyrazolo [3,4-b]indol-5-amine

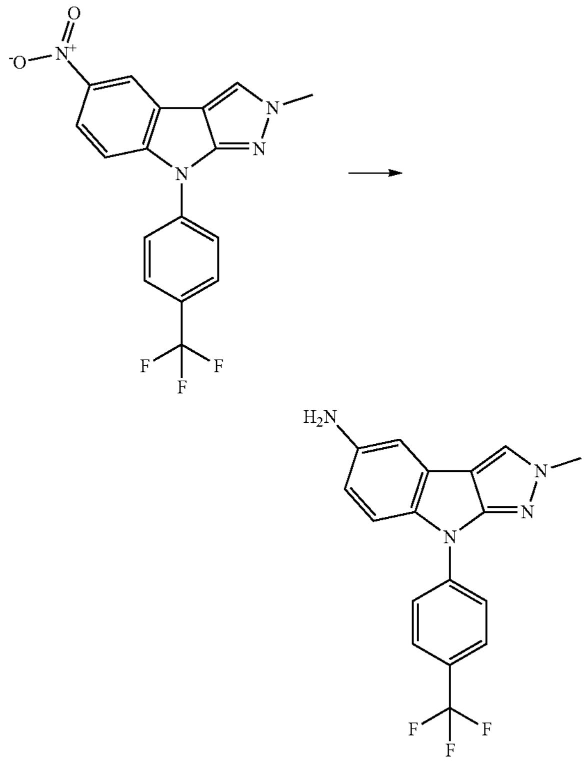

To a solution of 2-methyl-5-nitro-8-[4-(trifluoromethyl) phenyl]pyrazolo[3,4-b]indole (450 mg, 1.048 mmol) in 20 mL MeOH was added Pd/C (10%, 450 mg) under nitrogen atmosphere in a 250 mL round-bottom flask. The mixture was hydrogenated at room temperature for 1 h under hydrogen atmosphere using a hydrogen balloon, filtered through a Celite pad and concentrated under reduced pressure. This resulted in 2-methyl-8-[4-(trifluoromethyl) phenyl]pyrazolo [3,4-b]indol-5-amine (360 mg, 99%) as a yellow solid.

Example 20-4: Synthesis of N-[2-methyl-8-[4-(trifluoromethyl)phenyl]pyrazolo[3,4-b]indol-5-yl]prop-2-enamide

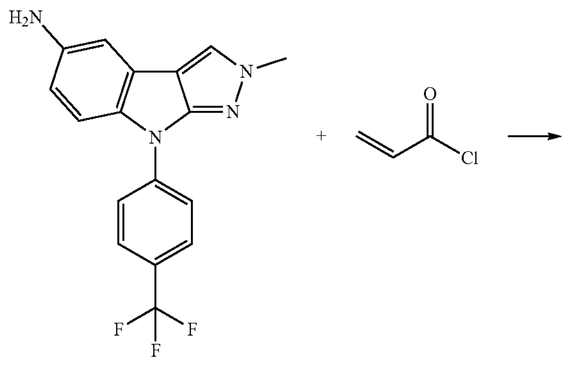

-continued

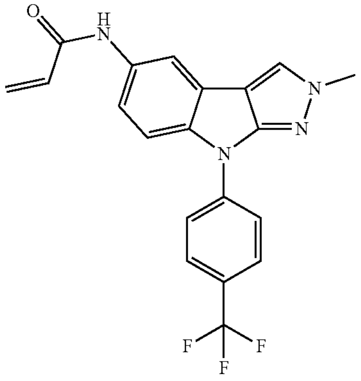

To a stirred solution of 2-methyl-8-[4-(trifluoromethyl) phenyl]pyrazolo[3,4-b]indol-5-amine (160 mg, 0.463 mmol) and TEA (99 mg, 0.929 mmol) in DCM (5 mL) was added acryloyl chloride (52 mg, 0.546 mmol) dropwise at room temperature under nitrogen atmosphere. The resulting mixture was stirred for 2 h at room temperature under nitrogen atmosphere. The reaction was quenched with Water/Ice and the resulting mixture was extracted with $CH_2Cl_2$ (3×30 mL). The combined organic layers were washed with brine (1×30 mL), dried over anhydrous $Na_2SO_4$. After filtration, the filtrate was concentrated under reduced pressure. The residue was purified by silica gel column chromatography and purified by Prep-HPLC giving N-[2-methyl-8-[4-(trifluoromethyl)phenyl]pyrazolo[3,4-b] indol-5-yl]prop-2-enamide as a white solid (45 mg, 25%).

$^1$H-NMR (400 MHz, DMSO, ppm) 10.20 (s, 1H), 8.27 (d, J=2.1 Hz, 1H), 8.17 (s, 1H), 8.08 (d, J=8.5 Hz, 2H), 7.92 (d, J=8.5 Hz, 2H), 7.74 (d, J=8.9 Hz, 1H), 7.47 (dd, J=8.9, 2.1 Hz, 1H), 6.47 (dd, J=16.9, 10.1 Hz, 1H), 6.27 (dd, J=16.9, 2.1 Hz, 1H), 5.75 (dd, J=10.0, 2.1 Hz, 1H), 4.01 (s, 3H).

Example 21: N—([2-methyl-8-[4-(trifluoromethyl) phenyl]pyrazolo [3,4-b]indol-5-yl]methyl)prop-2-enamide Example 21-1: Synthesis of 1-[2-methyl-8-[4-(trifluoromethyl)phenyl]pyrazolo [3,4-b]indol-5-yl] methanamine

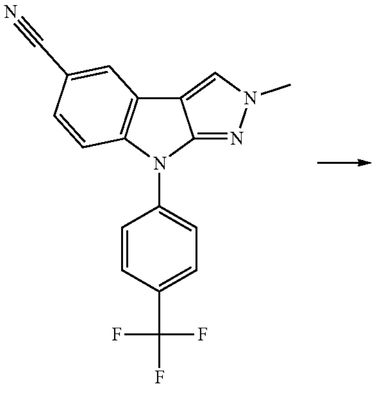

-continued

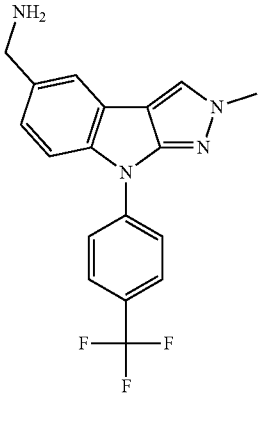

To a stirred mixture of 2-methyl-8-[4-(trifluoromethyl)phenyl]pyrazolo[3,4-b]indole-5-carbonitrile (Example 19) (300 mg, 0.882 mmol) and $NH_3$ (g) in MeOH (15 mL, 13%) in MeOH (30 mL) was added Raney Ni (300 mg, 3.327 mmol) under nitrogen atmosphere. The resulting mixture was stirred for 6 h at room temperature under hydrogen atmosphere, filtered and the filter cake was washed with MeOH (5×15 mL). The filtrate was concentrated under reduced pressure. The residue was purified by silica gel column chromatography, eluted with $CH_2Cl_2$ ($Et_3N$)/MeOH (24:1) to afford 1-[2-methyl-8-[4-(trifluoromethyl)phenyl]pyrazolo[3,4-b]indol-5-yl]methanamine (300 mg, 89%) as a light yellow solid.

Example 21-2: Synthesis of N—([2-methyl-8-[4-(trifluoromethyl)phenyl]pyrazolo [3,4-b]indol-5-yl]methyl)prop-2-enamide

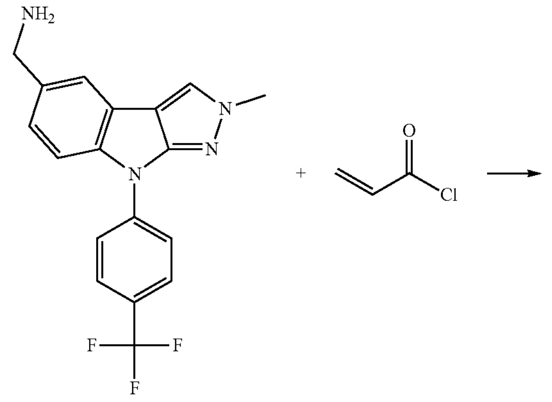

-continued

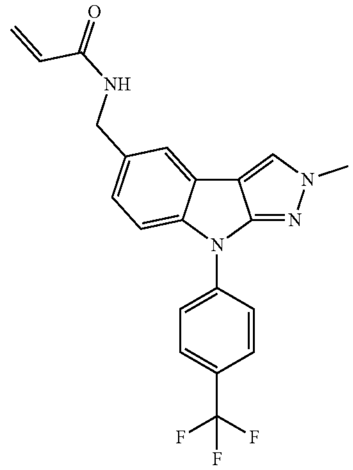

To a stirred solution of 1-[2-methyl-8-[4-(trifluoromethyl)phenyl]pyrazolo[3,4-b]indol-5-yl]methanamine (125 mg, 0.326 mmol) and DIPEA (133 mg, 0.979 mmol) in DCM (20 mL) was added acryloyl chloride (38 mg, 0.399 mmol) in DCM dropwise at 0° C. under nitrogen atmosphere. The resulting mixture was stirred for 1 h at 0° C. under nitrogen atmosphere and then concentrated under reduced pressure. The crude product was purified by Prep-HPLC resulting in N—([2-methyl-8-[4-(trifluoromethyl)phenyl]pyrazolo[3,4-b]indol-5-yl]methyl)prop-2-enamide (62 mg, 48%) as a white solid.

$^1$H-NMR (300 MHz, DMSO-d6) δ 8.64 (t, J=5.8 Hz, 1H), 8.13 (s, 1H), 8.05 (d, J=8.4 Hz, 2H), 7.92 (d, J=8.7 Hz, 2H), 7.75-7.66 (m, 2H), 7.22 (dd, J=8.5, 1.9 Hz, 1H), 6.29 (dd, J=17.1, 10.0 Hz, 1H), 6.13 (dd, J=17.1, 2.4 Hz, 1H), 5.61 (dd, J=10.0, 2.4 Hz, 1H), 4.45 (d, J=5.8 Hz, 2H), 3.99 (s, 3H).

Example 22: 8-(4-cyclopentylphenyl)-2-methyl-2H,8H-pyrazolo [3,4-b]indole-5-carboxylic acid Example 22-1: Synthesis of ethyl 8-(4-cyclopentylphenyl)-2-methyl-2H,8H-pyrazolo[3,4-b]indole-5-carboxylate

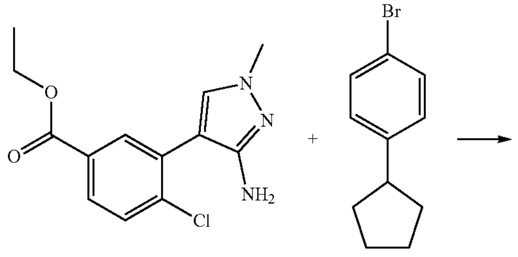

-continued

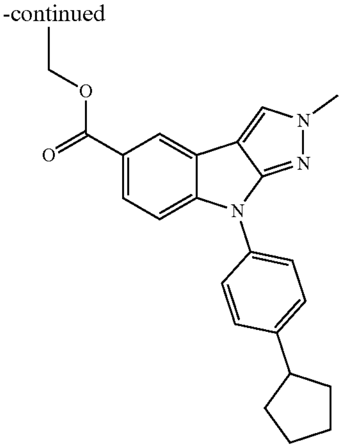

To a mixture of ethyl 3-(3-amino-1-methyl-1H-pyrazol-4-yl)-4-chlorobenzoate (60 mg; 0.21 mmol) in 1,4-dioxane (4 ml) was added under argon 1-Bromo-4-cyclopentylbenzene (56 mg; 0.25 mmol), Cesium carbonate (202 mg; 0.62 mmol) and XPhos Pd G4 (19 mg; 0.02 mmol) in a microwave vial. The reaction was stirred for 16 hrs at 120° C. At room temperature the reaction was diluted with EA and extracted 3× with water, dried over $Na_2SO_4$ and evaporated to dryness. The residue was purified by prep. HPLC giving the product as white solid (15 mg; 18%).

Example 22-2: Synthesis of 8-(4-cyclopentylphenyl)-2-methyl-2H,8H-pyrazolo [3,4-b]indole-5-carboxylic acid

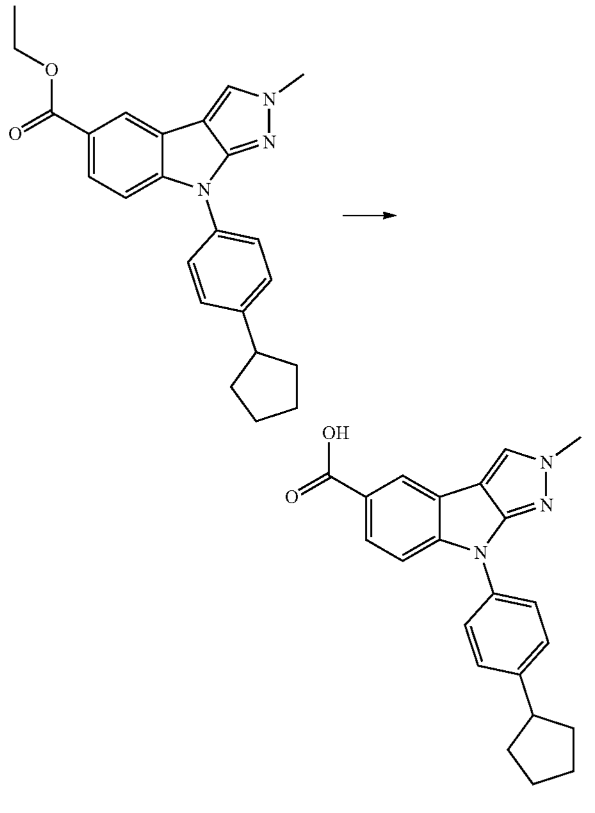

To ethyl 8-(4-cyclopentylphenyl)-2-methyl-2H,8H-pyrazolo[3,4-b]indole-5-carboxylate (15 mg; 0.04 mmol) in Ethanol (2 ml) was added Sodium hydroxide solution c(NaOH)=2 mol/l (2 N) (57 μl; 0.11 mmol) and the mixture was stirred for 2 days at 60° C. The reaction was evaporated to dryness and the residue was purified by prep. HPLC giving 14 mg (quantitative yield) of the desired product as off-white solid.

Example 23: Synthesis of 2-chloro-N-[2-methyl-8-[4-(trifluoromethyl)phenyl]pyrazolo[3,4-b]indol-5-yl]acetamide

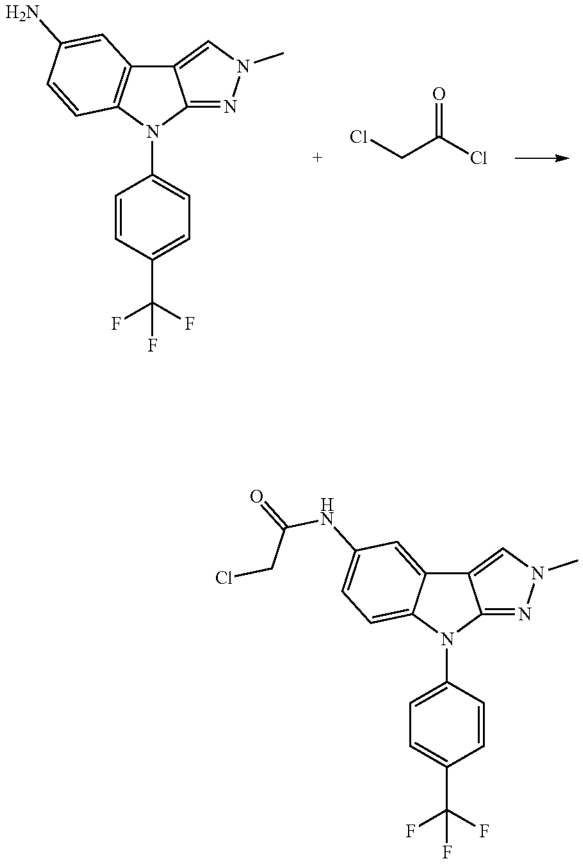

To a stirred solution of 2-methyl-8-[4-(trifluoromethyl)phenyl]pyrazolo[3,4-b]indol-5-amine (Example 20-3) (170 mg, 0.492 mmol) and TEA (122 mg, 1.145 mmol) in DCM (5 mL) was added chloroacetyl chloride (81 mg, 0.681 mmol) dropwise at 0° C. under nitrogen atmosphere. The resulting mixture was stirred for 1 h at room temperature. The reaction was quenched with water/ice and extracted with $CH_2Cl_2$ (3×40 mL). The combined organic layers were washed with brine (1×30 mL) and dried over anhydrous $Na_2SO_4$. After filtration, the filtrate was concentrated under reduced pressure. The residue was purified by silica gel column chromatography, eluted with $CH_2Cl_2$/MeOH (10:1) and the crude product was purified by Prep-HPLC giving 2-chloro-N-[2-methyl-8-[4-(trifluoromethyl)phenyl]pyrazolo[3,4-b]indol-5-yl]acetamide (45 mg, 22%) as an off-white solid.

Example 24: 2-chloro-N—([2-methyl-8-[4-(trifluoromethyl)phenyl]pyrazolo[3,4-b]indol-5-yl]methyl) acetamide

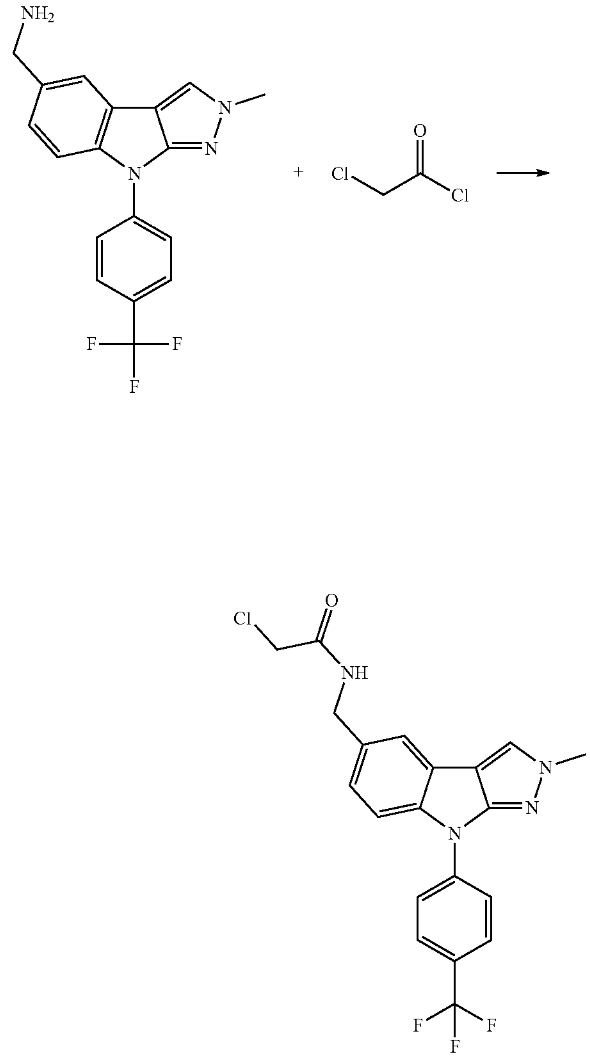

To a stirred solution of 1-[2-methyl-8-[4-(trifluoromethyl) phenyl]pyrazolo[3,4-b]indol-5-yl]methanamine (Example 21-1) (130 mg, 0.339 mmol) and DIPEA (139 mg, 1.022 mmol) in DCM (20 mL) was added chloroacetyl chloride (50 mg, 0.443 mmol) in DCM dropwise at 0° C. under nitrogen atmosphere. The resulting mixture was stirred for 1 h at 0° C. under nitrogen atmosphere and concentrated under reduced pressure. The residue was purified by silica gel column chromatography, eluted with PE/EtOAc (1:1). The crude product was purified by Prep-HPLC giving 2-chloro-N—([2-methyl-8-[4-(trifluoromethyl)-phenyl] pyrazolo[3,4-b]indol-5-yl]methyl)acetamide (75 mg, 52%) as a white solid.

$^1$H NMR (400 MHz, DMSO-d6) δ 8.77 (t, J=5.9 Hz, 1H), 8.15 (s, 1H), 8.08 (d, J=8.4 Hz, 2H), 7.94 (d, J=8.5 Hz, 2H), 7.77-7.69 (m, 2H), 7.25 (dd, J=8.5, 1.9 Hz, 1H), 4.43 (d, J=5.8 Hz, 2H), 4.15 (s, 2H), 4.02 (s, 3H).

Example 25: 2-methyl-4-[4-(trifluoromethyl)phenyl]-[1,3]thiazolo[4,5-b]indole-7-carboxylic acid Example 25-1: Synthesis of methyl 3-bromo-4-[(2-methyl-1,3-thiazol-4-yl)amino]benzoate

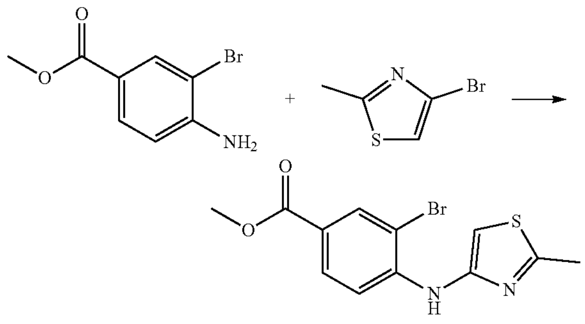

To a solution of methyl 4-amino-3-bromobenzoate (1.03 g, 4.268 mmol) and 4-bromo-2-methyl-1,3-thiazole (0.80 g, 4.268 mmol) in Toluene (16 mL) were added XantPhos (0.39 g, 0.640 mmol), $Pd_2(dba)_3$ (0.21 g, 0.213 mmol) and $Cs_2CO_3$ (2.94 g, 8.580 mmol) at room temperature under nitrogen atmosphere.

The final reaction mixture was irradiated with microwave radiation for 2 h at 130° C. and then concentrated under reduced pressure. The residue was purified by silica gel column chromatography, eluted with PE/EtOAc (8:1) to afford methyl 3-bromo-4-[(2-methyl-1,3-thiazol-4-yl) amino]benzoate (220 mg, 14%) as a light yellow solid.

Example 25-2: Synthesis of 2-methyl-4H-[1,3]thiazolo[4,5-b]indole-7-carboxylate

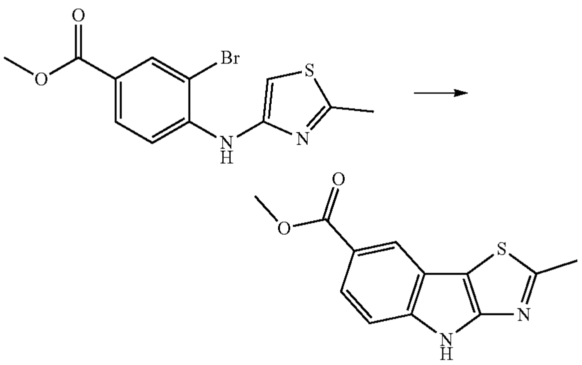

To a mixture of methyl 3-bromo-4-[(2-methyl-1,3-thiazol-4-yl)amino]benzoate (1.01 g, 2.624 mmol) and pivalic acid (285 mg, 2.651 mmol) in xylene (45 mL) were added $PCy_3$·HBF4 (153 mg, 0.395 mmol), $Pd(AcO)_2$ (31 mg, 0.131 mmol) and $Cs_2CO_3$ (2.7 g, 7.872 mmol) at room temperature under nitrogen atmosphere. The resulting mixture was stirred for 2 days at 120° C. under nitrogen atmosphere and then concentrated under reduced pressure. The residue was purified by silica gel column chromatography, eluted with PE/EtOAc (1:1) to afford methyl 2-methyl-4H-[1,3]thiazolo [4,5-b]indole-7-carboxylate (380 mg, 59%) as a light yellow solid.

Example 25-3: Synthesis of methyl 2-methyl-4-[4-(trifluoromethyl)phenyl]-[1,3]thiazolo[4,5-b]indole-7-carboxylate

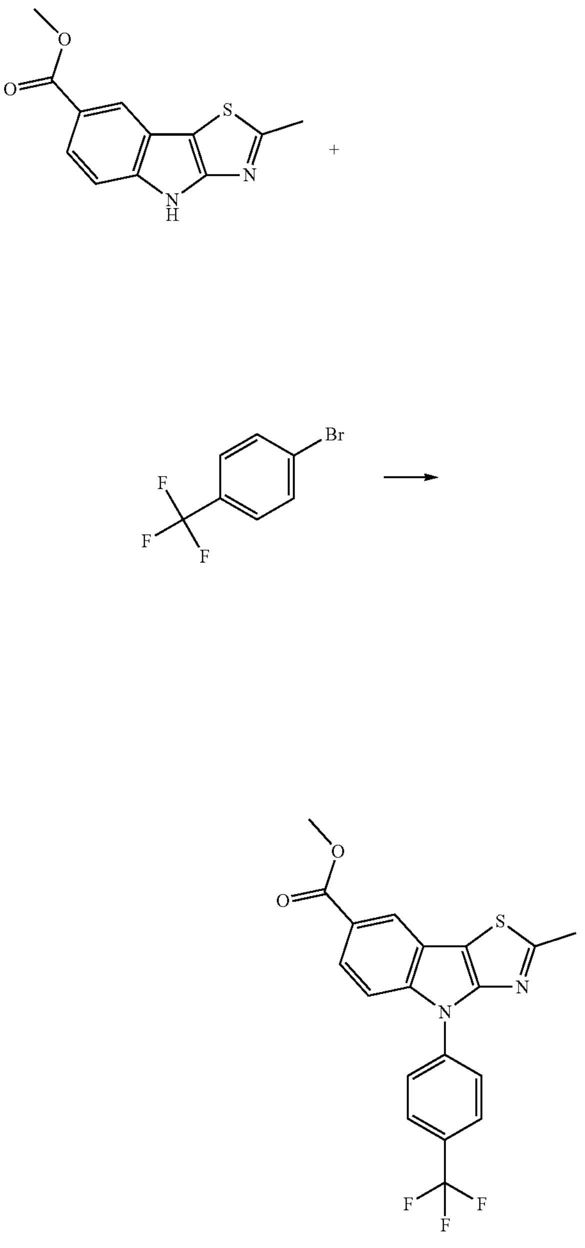

To a stirred mixture of methyl 2-methyl-4H-[1,3]thiazolo[4,5-b]indole-7-carboxylate (230 mg, 0.934 mmol) and 1-bromo-4-(trifluoromethyl)benzene (332 mg, 1.402 mmol) in dioxane (10 mL) was added XPhos Pd G3 (83 mg, 0.093 mmol) and $Cs_2CO_3$ (960 mg, 2.799 mmol) at room temperature under nitrogen atmosphere. The resulting mixture was stirred overnight at 100° C. under nitrogen atmosphere and then concentrated under reduced pressure. The residue was purified by silica gel column chromatography, eluted with PE/EtOAc (1:1) to afford methyl 2-methyl-4-[4-(trifluoromethyl)phenyl]-[1,3]thiazolo[4,5-b]indole-7-carboxylate (230 mg, 63%) as a light yellow solid.

Example 25-4: Synthesis of 2-methyl-4-[4-(trifluoromethyl)phenyl]-[1,3]thiazolo[4,5-b]indole-7-carboxylic acid

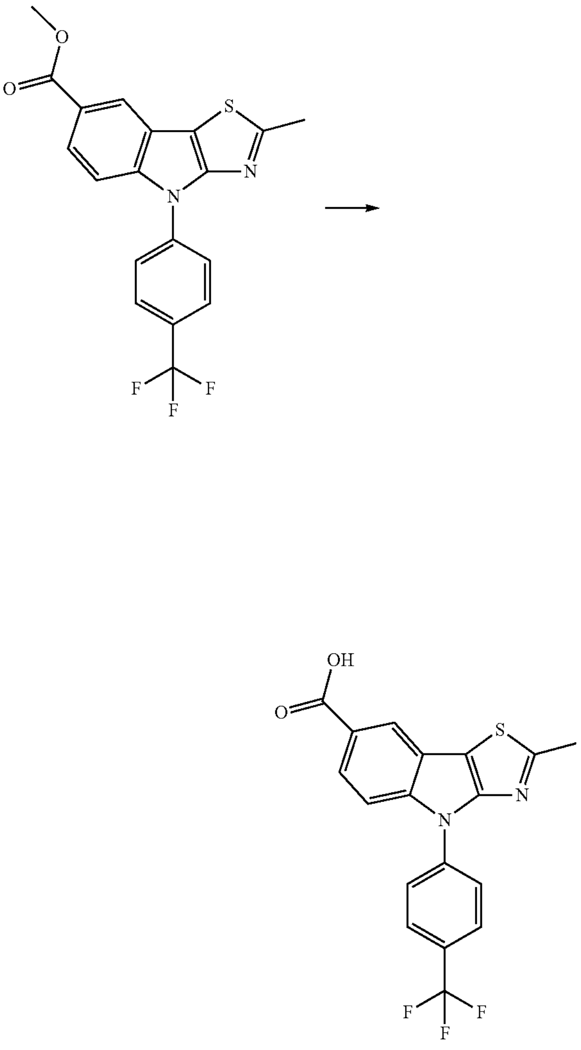

A mixture of methyl 2-methyl-4-[4-(trifluoromethyl)phenyl]-[1,3]thiazolo[4,5-b]indole-7-carboxylate (210 mg, 0.538 mmol) and LiOH (82 mg, 3.253 mmol) in THF (5 mL) and $H_2O$ (5 mL) was stirred for overnight at 50° C. At room temperature THF is removed under reduced pressure. The remainder was acidified to pH 4 with 1 M HCl (aq.) and the resulting mixture was extracted with EtOAc (5×20 mL) and dried over anhydrous $Na_2SO_4$. After filtration, the filtrate was concentrated under reduced pressure and the crude product was purified by Prep-HPLC giving 2-methyl-4-[4-(trifluoromethyl)phenyl]-[1,3]thiazolo[4,5-b]indole-7-carboxylic acid (57 mg, 28%) as a white solid.

$^1$H NMR (300 MHz, DMSO-d6) δ 8.50 (d, J=1.7 Hz, 1H), 7.99 (s, 3H), 7.92 (dd, J=8.8, 1.7 Hz, 2H), 7.70 (d, J=8.8 Hz, 1H), 2.82 (s, 3H).

Example 26: 7-fluoro-2-methyl-4-[4-(trifluoromethyl)phenyl]pyrazolo[4,3-b]indole

Example 26-1: Synthesis of 3-(2-bromo-5-fluorophenyl)-1-methyl-4-nitropyrazole

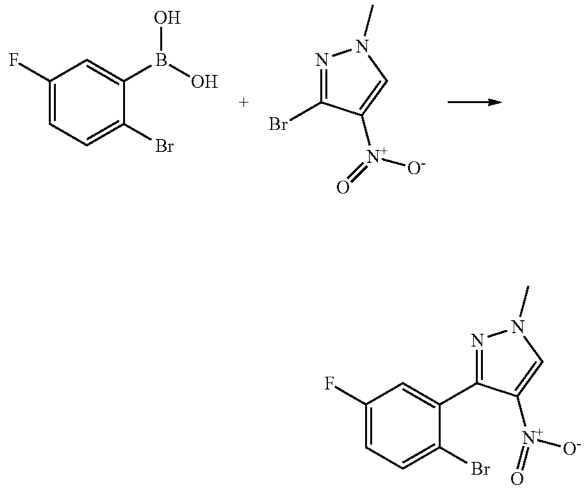

To a stirred mixture of 2-bromo-5-fluorophenylboronic acid (700 mg, 3.039 mmol) and 3-bromo-1-methyl-4-nitropyrazole (700 mg, 3.330 mmol) in dioxane (28 mL) and $H_2O$ (7 mL) were added $NaHCO_3$ (1.40 g, 15.832 mmol) and $Pd(PPh_3)_4$ (350 mg, 0.300 mmol). The resulting mixture was stirred overnight at 110° C. under nitrogen atmosphere and then concentrated under vacuum. The residue was extracted with EtOAc (3x30 mL) and the combined organic layers were washed with brine (1×50 mL) and dried over anhydrous $Na_2SO_4$. After filtration, the filtrate was concentrated under reduced pressure. The residue was purified by silica gel column chromatography, eluted with PE/EtOAc (4:1) to afford 3-(2-bromo-5-fluorophenyl)-1-methyl-4-nitropyrazole (700 mg, 40%) as a white solid.

Example 26-2: Synthesis of 3-(2-bromo-5-fluorophenyl)-1-methylpyrazol-4-amine

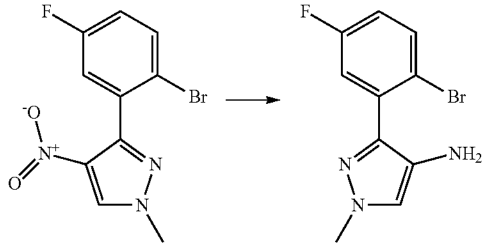

To a stirred solution of 3-(2-bromo-5-fluorophenyl)-1-methyl-4-nitropyrazole (650 mg, 1.133 mmol) and $NH_4Cl$ (580 mg, 10.301 mmol) in MeOH (13 mL) and $H_2O$ (6.5 mL) was added Fe (609 mg, 10.360 mmol) at room temperature under nitrogen atmosphere. The resulting mixture was stirred for 2 h at 70° C. and then diluted with water (20 mL). The resulting mixture was extracted with $CH_2Cl_2$ (3x50 mL). The combined organic layers were washed with brine (1×100 mL) and dried over anhydrous $Na_2SO_4$. After filtration, the filtrate was concentrated under reduced pressure. This resulted in 3-(2-bromo-5-fluorophenyl)-1-methylpyrazol-4-amine (500 mg, 100.00%) as a brown oil.

Example 26-3: Synthesis of 7-fluoro-2-methyl-4-[4-(trifluoromethyl)phenyl]pyrazolo[4,3-b]indole

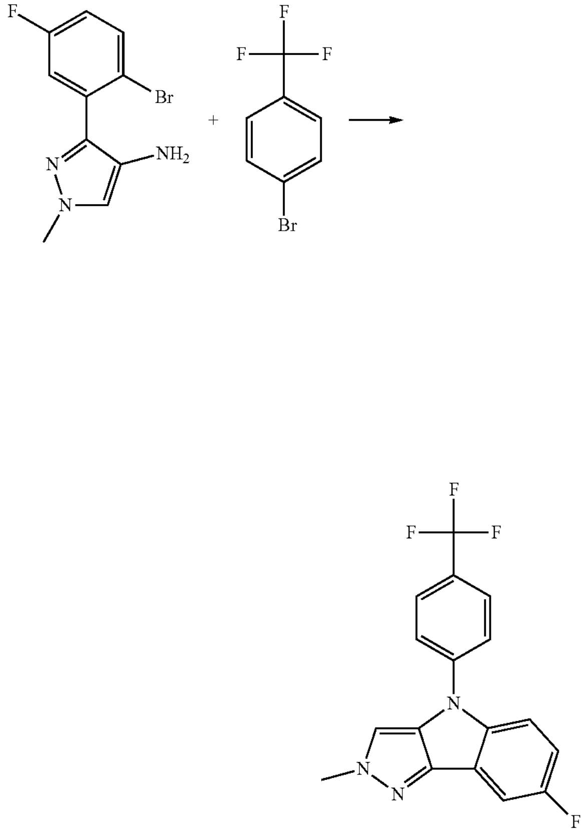

To a stirred solution of 3-(2-bromo-5-fluorophenyl)-1-methylpyrazol-4-amine (500 mg, 1.133 mmol) and 1-bromo-4-(trifluoromethyl)benzene (460 mg, 1.942 mmol) in dioxane (15 mL) were added $Cs_2CO_3$ (1.20 g, 3.499 mmol) and XPhos Pd G3 (161 mg, 0.181 mmol) at room temperature under nitrogen atmosphere. The resulting mixture was stirred overnight at 120° C. and then quenched with water. This mixture was extracted with EtOAc (3x20 mL). The combined organic layers were washed with brine (1×50 mL) and dried over anhydrous $Na_2SO_4$. After filtration, the filtrate was concentrated under reduced pressure. The crude product was purified by Prep-HPLC giving 7-fluoro-2-methyl-4-[4-(trifluoromethyl)phenyl]pyrazolo[4,3-b]indole (26 mg, 7%) as a white solid.

$^1H$ NMR (300 MHz, DMSO-d6, ppm) 8.07 (s, 1H), 7.88 (s, 4H), 7.84-7.78 (m, 1H), 7.76-7.66 (m, 1H), 7.30-7.17 (m, 1H), 4.07 (s, 3H).

Example 27: N-cyclopropyl-2-methyl-8-[6-(trifluoromethyl)pyridin-3-yl]-2H,8H-pyrazolo[3,4-b]indole-5-carboxamide Example 27-1: Synthesis of N-cyclopropyl-2-methyl-8-[6-(trifluoromethyl)pyridin-3-yl]-2H,8H-pyrazolo[3,4-b]indole-5-carboxamide

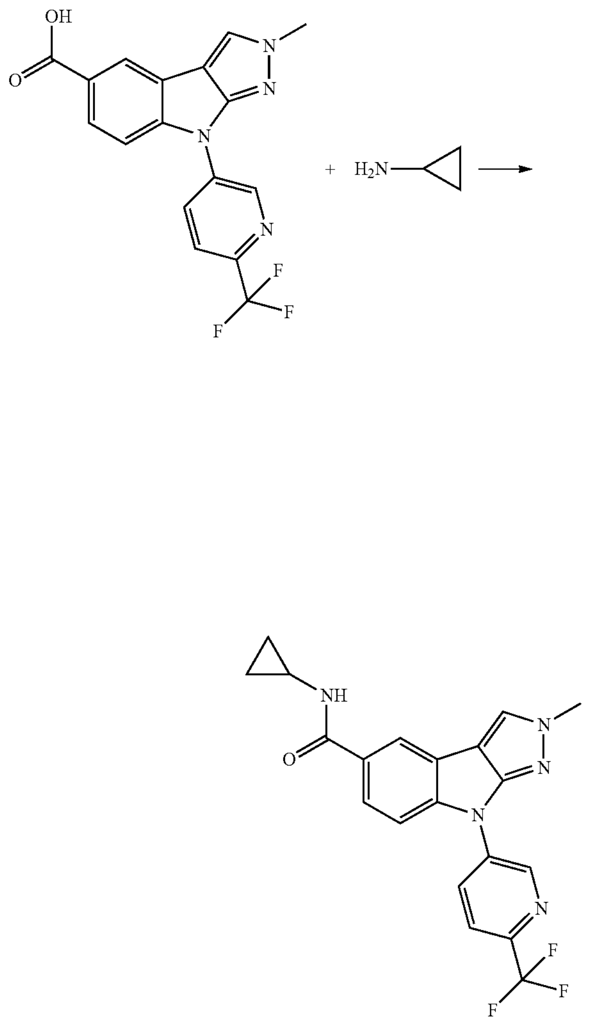

To 2-methyl-8-[6-(trifluoromethyl)pyridin-3-yl]-2H,8H-pyrazolo[3,4-b]indole-5-carboxylic acid (73 mg; 0.20 mmol) in DMF (4 ml) was added cyclopropylamine (21 μl; 0.29 mmol), N-(3-dimethylaminopropyl)-N'-ethylcarbodiimide hydrochloride (75 mg; 0.39 mmol), 1-hydroxybenzotriazole hydrate (30 mg; 0.20 mmol) and 4-methylmorpholine (108 μl; 0.98 mmol). The reaction was stirred for 16 h at RT and directly purified by HPLC giving the product in 72% yield (58 mg) as white solid.

Example 28: 2-methyl-N—[(pyridin-4-yl)methyl]-8-[4-(trifluoromethyl)phenyl]-2H, 8H-pyrazolo[3,4-b]indole-5-carboxamide Example 28-1: Synthesis of 2-methyl-N—[(pyridin-4-yl)methyl]-8-[4-(trifluoromethyl)phenyl]-2H,8H-pyrazolo[3,4-b]indole-5-carboxamide

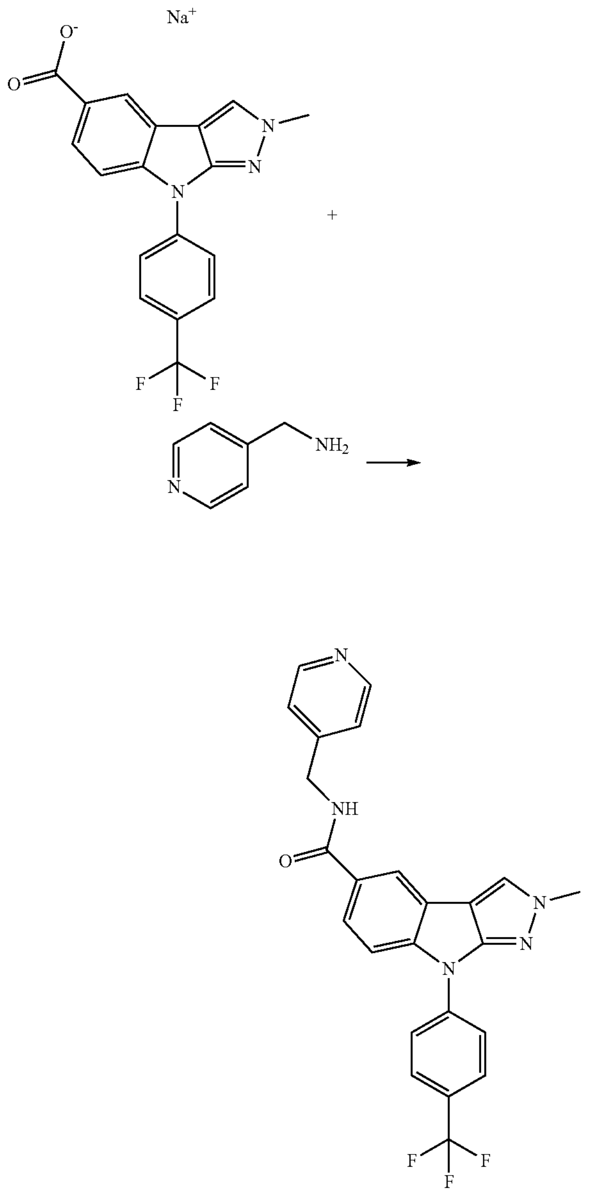

To sodium 2-methyl-8-[4-(trifluoromethyl)phenyl]-2H,8H-pyrazolo[3,4-b]indole-5-carboxylate (50 mg; 0.13 mmol) in DMF (3 ml) was added 4-picolylamine (21 μl; 0.20 mmol), N-(3-dimethylaminopropyl)-N'-ethylcarbodiimide hydro chloride (50 mg; 0.26 mmol), 1-hydroxybenzotriazole hydrate (20 mg; 0.13 mmol) and 4-methylmorpholine (72 μl; 0.65 mmol). The reaction was stirred for 16 h at RT. The reaction was directly purified by HPLC giving the product in 57% (34 mg) yield as off-white solid.

Example 29: N-[2-hydroxy-1-(pyridin-2-yl)ethyl]-2-methyl-8-[4-(trifluoromethyl)phenyl]-2H,8H-pyrazolo[3,4-b]indole-5-carboxamide Example 29-1: Synthesis of N-[2-hydroxy-1-(pyridin-2-yl)ethyl]-2-methyl-8-[4-(trifluoromethyl)phenyl]-2H,8H-pyrazolo[3,4-b]indole-5-carboxamide

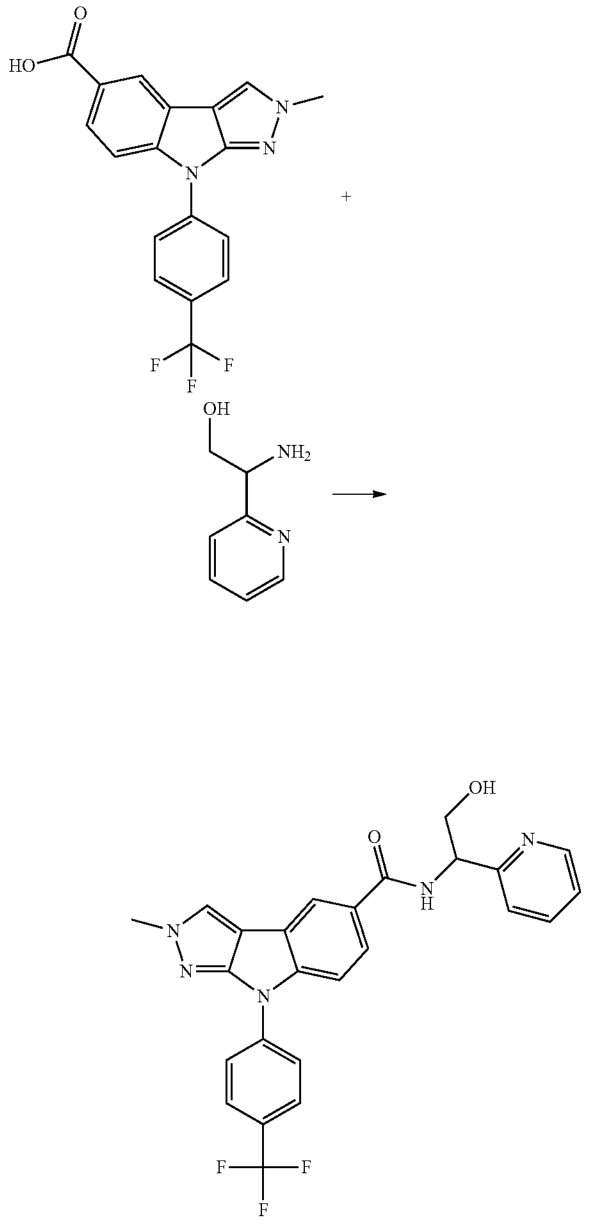

A solution of 2-methyl-8-[4-(trifluoromethyl)phenyl]pyrazolo[3,4-b]indole-5-carboxylic acid (150 mg, 0.42 mmol), DIEA (162 mg, 1.13 mmol) and HATU (191 mg, 0.45 mmol) in DMF (2 mL) was stirred for 1 h at RT. To the above mixture was added 2-amino-2-(pyridin-2-yl)ethanol (87 mg, 0.57 mmol). The resulting mixture was stirred for additional 3 h at RT. The crude product was purified by HPLC giving the product (82 mg, 41%) as white solid.

Example 29-2: Separation of Enantiomers

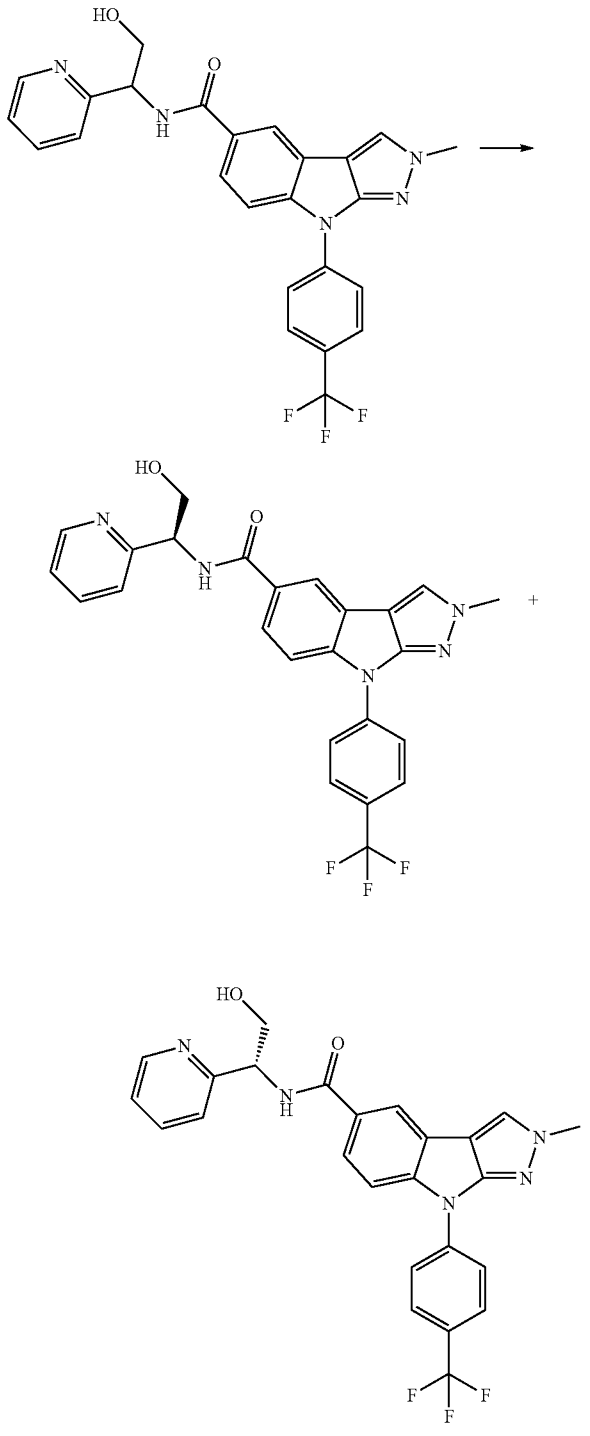

The enantiomers of N-[2-hydroxy-1-(pyridin-2-yl)ethyl]-2-methyl-8-[4-(trifluoromethyl) phenyl]-2H,8H-pyrazolo[3,4-b]indole-5-carboxamide were separated by SCF on a YMC Cellulose-SC column with the eluent of CO2/Methanol=60:40 and a flow of 5 ml/min. 50 mg of the racemic mixture delivered 22 mg and 23 mg of the respective enantiomers.

Example 30: (2S,3S,4S,5R,6S)-3,4,5-trihydroxy-6-{2-methyl-8-[4-(trifluoromethyl)phenyl]-2H,8H-pyrazolo[3,4-b]indole-5-carbonyloxy}oxane-2-carboxylic acid Example 30-1: Synthesis of (2S,3S,4S,5R,6S)-3,4,5-trihydroxy-6-{2-methyl-8-[4-(trifluoromethyl)phenyl]-2H,8H-pyrazolo[3,4-b]indole-5-carbonyloxy}oxane-2-carboxylic acid

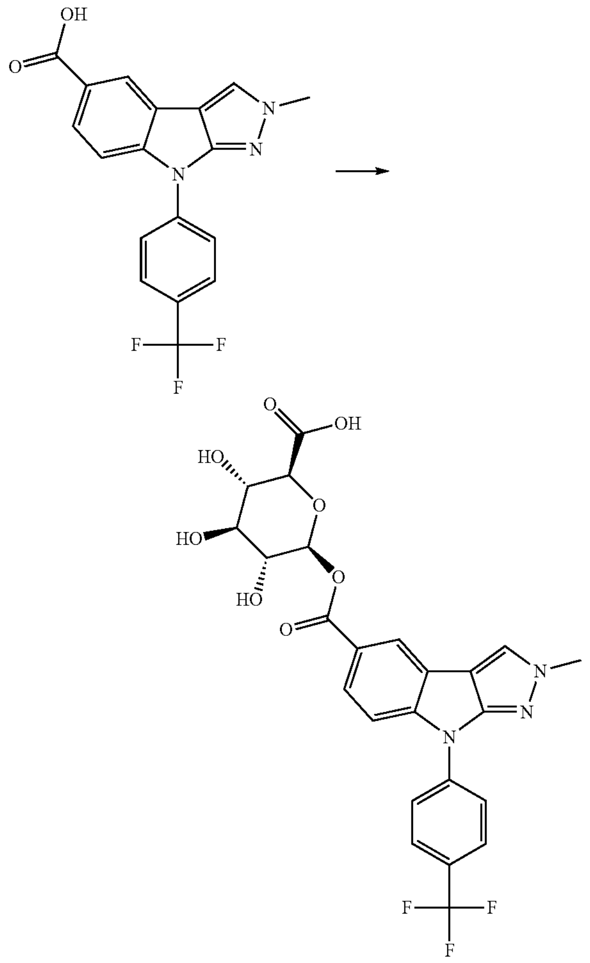

To a DMF (35 ml) solution of (2S,3S,4S,5R,6R)-3,4,5,6-tetrahydroxyoxane-2-carboxylic acid (5 g; 24 mmol) and TBAF in THF (1 Mol/L; 31 ml; 24 mmol) was added BnBr (4.60 g; 25.55 mmol) at 0° C. The resulting mixture was stirred over night at RT under $N_2$ atmosphere. Then the mixture was concentrated under reduced pressure. The residue was purified by silica gel column chromatography to afford benzyl (2S,3S,4S,5R,6R)-3,4,5,6-tetrahydroxyoxane-2-carboxylate (4 g; 13.90 mmol; 57%) as yellow oil.

To a stirred solution of benzyl (2S,3S,4S,5R,6R)-3,4,5,6-tetrahydroxyoxane-2-carboxylate (4 g; 13.90 mmol) and 2-methyl-8-[4-(trifluoromethyl)phenyl]-2H,8H-pyrazolo[3,4-b]indole-5-carboxylic acid (2.50 g; 6.71 mmol) in Dioxane-1,4 (80 ml) were added HATU (4 g; 9.99 mmol) and NMM (2 g; 18.79 mmol) at RT under $N_2$ atmosphere. The resulting mixture was stirred for overnight at RT. For work up the reaction was quenched with water. The resulting mixture was extracted with EtOAc (3x40 ml). The combined organic layers were washed with brine (3x100 ml) and dried over anhydrous $Na_2SO_4$. After filtration, the filtrate was concentrated under reduced pressure and the residue was purified by silica gel column chromatography to afford (2S,3R,4S,5S,6S)-6-[(benzyloxy)carbonyl]-3,4,5-trihydroxyoxan-2-yl 2-methyl-8-[4-(trifluoro-methyl)phenyl]-2H,8H-pyrazolo[3,4-b]indole-5-carboxylate (500 mg; 0.70 mmol; 11%) as yellow solid.

To a stirred solution of (2S,3R,4S,5S,6S)-6-[(benzyloxy)carbonyl]-3,4,5-trihydroxyoxan-2-yl 2-methyl-8-[4-(trifluoromethyl)phenyl]-2H,8H-pyrazolo-[3,4-b]indole-5-carboxylate (500 mg; 0.70 mmol) and tert-butyldimethylsilane (180 mg; 1.47 mmol) in DCE (3 ml) was added triethylamine (0.50 ml; 3.66 mmol) and $Pd(AcO)_2$ (360 mg; 1.52 mmol) at RT under $N_2$ atmosphere. The mixture was stirred for 2 h at 60° C. and then filtered. The filter cake was washed with DCM (3x5 ml) and the filtrate was concentrated under reduced pressure. The residue was treated with TBAF in THF (1M) (4 ml) at RT. The resulting mixture was stirred for 1 h at RT and then acidified to pH 5 with HCl (aq.), extracted with EtOAc (3x20 ml) and dried over anhydrous $Na_2SO_4$. After filtration, the filtrate was concentrated under reduced pressure. The crude was purified by HPLC giving the product (53 mg; 15%) as white solid.

Example 31: 2-methyl-8-(4-methylphenyl)-5-(methylsulfanyl)-2H,8H-pyrazolo[3,4-b]indole Example 31-1: Synthesis of 2-methyl-8-(4-methylphenyl)-5-(methylsulfanyl)-2H,8H-pyrazolo[3,4-b]indole

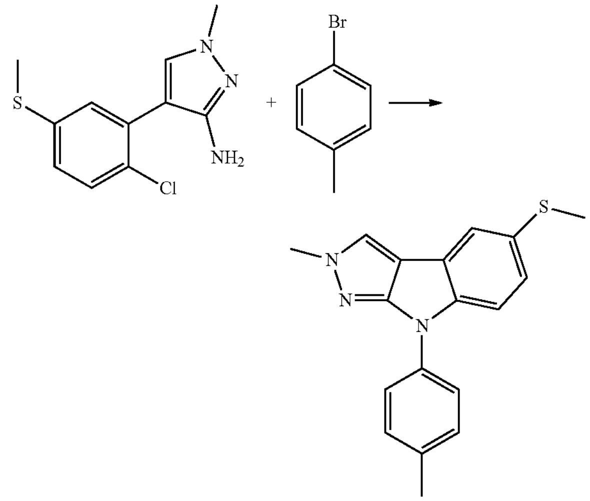

4-[2-chloro-5-(methylsulfanyl)phenyl]-1-methyl-1H-pyrazol-3-amine (500 mg; 1.9 mmol), 4-bromotoluene (661 mg; 3.9 mmol) and cesium carbonate (1.9 g; 5.8 mmol) were suspended in 1,4-Dioxane (30 ml) and flushed with argon, then XPhos Pd G4 (175 mg; 0.2 mmol) was added stirred over weekend at 120° C. Then XPhos Pd G4 (175 mg; 0.2 mmol) was added again and stirred for 2 days at 100° C. The reactions was filtered over Celite and the residue was washed with ethyl acetate and the filtrate was concentrated under the reduced pressure. The crude was purified by chromatography giving the product (385 mg; 62%) as light yellow solid.

Example 32: 7-methanesulfinyl-2-methyl-4-[4-(trifluoromethyl)phenyl]-2H,4H-pyrazolo[4,3-b]indole

Example 32-1: Synthesis of 7-methanesulfinyl-2-methyl-4-[4-(trifluoromethyl)phenyl]-2H,4H-pyrazolo[4,3-b]indole

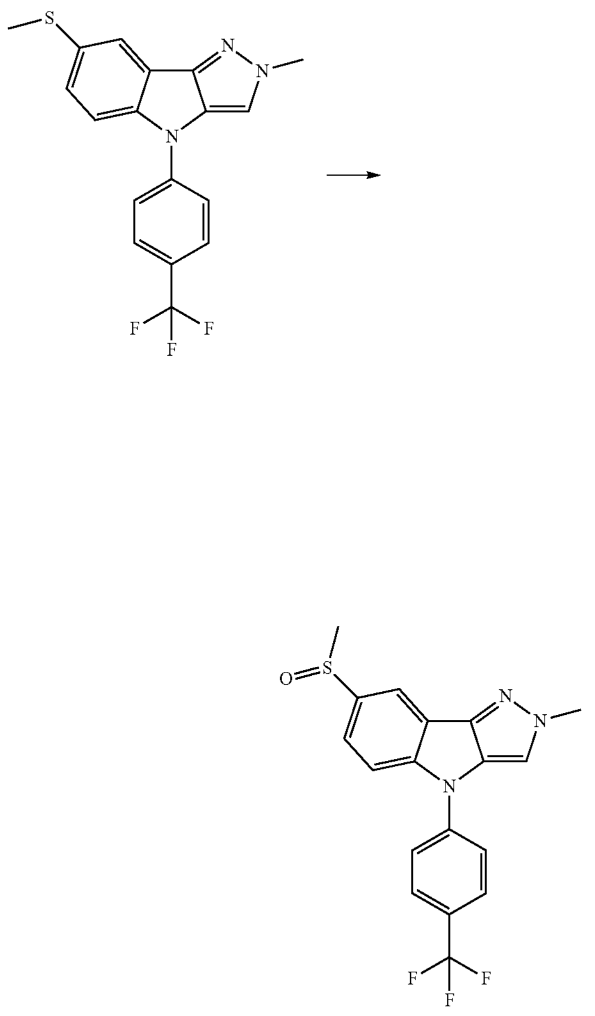

To a solution of 2-methyl-7-(methylsulfanyl)-4-[4-(trifluoromethyl)phenyl]-pyrazolo[4,3-b]indole (400 mg, 0.7 mmol) in AcOH (400 mg) and $CHCl_2$ (20 mL) was added $H_2O_2$ (0.11 mL; 30% in water) at 0° C. The resulting mixture was stirred for 16 h at RT under nitrogen atmosphere. The reaction was quenched by the addition of Water (100 mL) at RT. The resulting mixture was extracted with EtOAc (3×100 mL). The combined organic layers were washed with brine and dried over anhydrous $Na_2SO_4$. After filtration, the filtrate was concentrated under reduced pressure. The crude was purified by HPLC giving the product (23 mg, 8%) as a white solid.

Example 33: 7-methanesulfonyl-2-methyl-4-[4-(trifluoromethyl)phenyl]-2H,4H-pyrazolo[4,3-b]indole

Example 33-1: Synthesis of 7-methanesulfonyl-2-methyl-4-[4-(trifluoromethyl)phenyl]-2H,4H-pyrazolo[4,3-b]indole

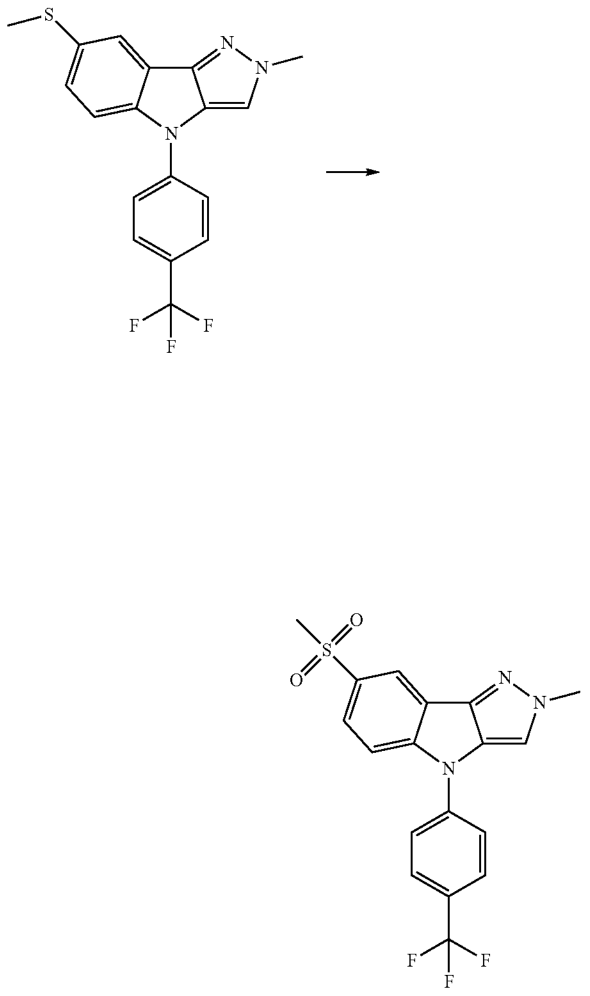

To a stirred mixture of 2-methyl-7-(methylsulfanyl)-4-[4-(trifluoromethyl)-phenyl]pyrazolo[4,3-b]indole (20 mg, 0.036 mmol) in DCM (1 mL) was added MCPBA (22 mg, 0.089 mmol) at RT. The resulting mixture was stirred for 3 h at RT under air atmosphere. The reaction mixture was diluted with water, washed with 10% aqueous sodium sulfite solution and saturated aqueous sodium hydrogen carbonate solution. After phase separation and extraction of the aqueous phase with DCM the combined organic layers were washed with brine (2×100 mL) and dried over anhydrous $Na_2SO_4$. After filtration, the filtrate was concentrated under reduced pressure. The crude was purified by HPLC giving the product (48 mg, 17%) as a yellow solid.

Example 34: 2-methyl-4-[4-(trifluoromethyl)phenyl]-2H,4H-pyrazolo[4,3-b]indole-7-sulfonamide

Example 34-1: Synthesis of 2-methyl-4-[4-(trifluoromethyl)phenyl]-2H,4H-pyrazolo[4,3-b]indole-7-sulfonamide

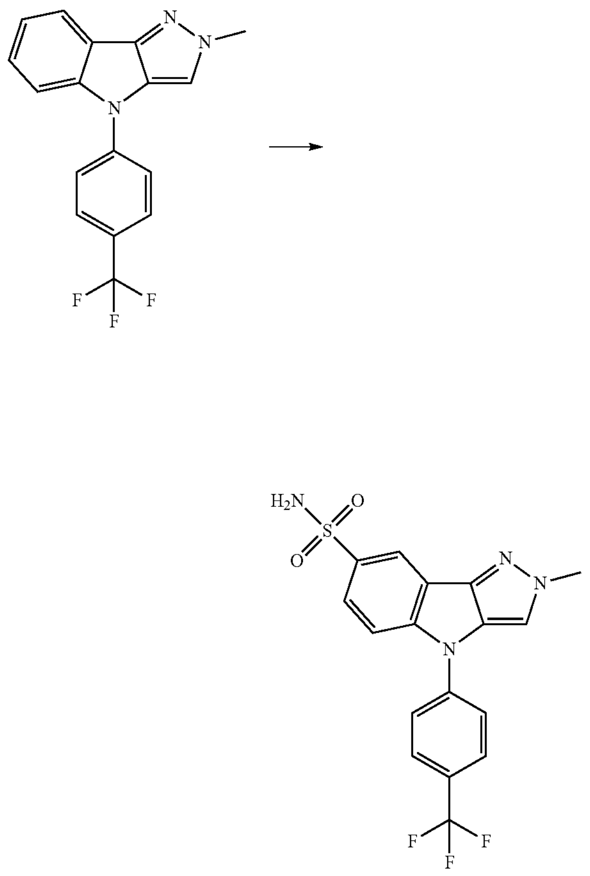

To a stirred $HSO_3Cl$ (25 mL) was added 2-methyl-4-[4-(trifluoromethyl)phenyl]-pyrazolo[4,3-b]indole (1.6 g, 4.8 mmol) at 0° C. under nitrogen atmosphere. The resulting mixture was stirred for 1 h at 0° C. under nitrogen atmosphere. The reaction was quenched by the addition to Water/Ice. The resulting mixture was extracted with $CH_2Cl_2$ (3×100 mL). The combined organic layers were concentrated under reduced pressure. This resulted in crude 2-methyl-4-[4-(trifluoromethyl)phenyl]pyrazolo[4,3-b]indole-7-sulfonyl chloride (900 mg, 24%) as a yellow solid.

To the reactant 2-methyl-4-[4-(trifluoromethyl)phenyl]pyrazolo[4,3-b]indole-7-sulfonyl chloride (140 mg, 0.18 mmol) was added a mixture of $NH_3 \cdot H_2O$ (3 mL) and THF (3 mL) dropwise. The resulting mixture was stirred for 30 min at RT. The mixture was concentrated under reduced pressure. The residue was purified by silica gel column chromatography giving the product (47 mg, 68%) as a white solid.

Example 35: Imino(methyl){2-methyl-4-[4-(trifluoromethyl)phenyl]-2H,4H-pyrazolo[4,3-b]indol-7-yl}-lambda6-sulfanone

Example 35-1: Synthesis of imino(methyl){2-methyl-4-[4-(trifluoromethyl)phenyl]-2H,4H-pyrazolo[4,3-b]indol-7-yl}-lambda6-sulfanone

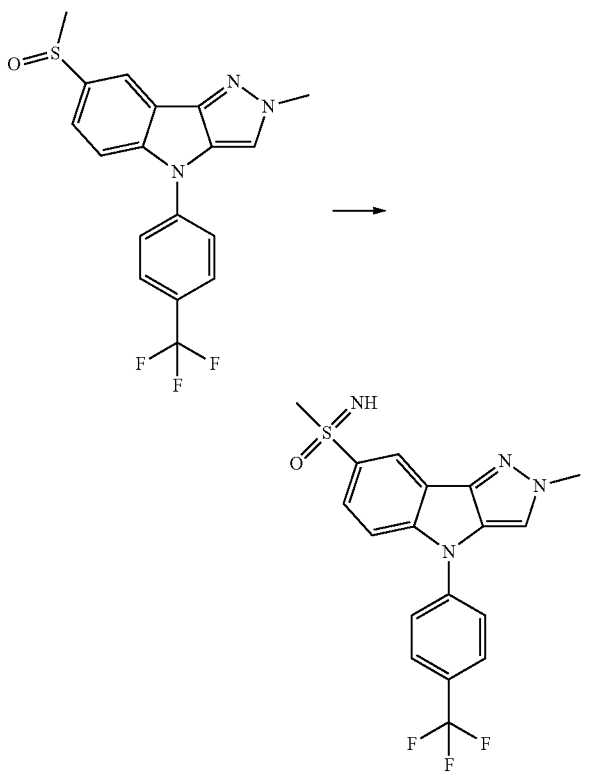

A mixture of 7-methanesulfinyl-2-methyl-4-[4-(trifluoromethyl)phenyl]pyrazolo-[4,3-b]indole (300 mg, 0.674 mmol), MgO (1.14 g, 27 mmol), $Rh_2(OAc)_4$ (9 mg, 0.019 mmol), DIB (347 mg, 1.02 mmol) and $BocNH_2$ (124 mg, 1 mmol) in $CH_2Cl_2$ (15 mL) was stirred for 8 h at 40° C. The reaction was quenched by the addition of Water (100 mL) at RT. The mixture was extracted with EtOAc (3×100 mL). The combined organic layers were washed with brine (2×100 mL), dried over anhydrous $Na_2SO_4$. After filtration, the filtrate was concentrated under reduced pressure. The residue was purified by silica gel column chromatography giving tert-butyl N—[methyl([2-methyl-4-[4-(trifluoromethyl)-phenyl]pyrazolo[4,3-b]indol-7-yl])oxo-lambda6-sulfanylidene]carbamate (45 mg, 7%) as a brown solid.

A mixture of tert-butyl N—[methyl([2-methyl-4-[4-(trifluoromethyl)phenyl]-pyrazolo[4,3-b]indol-7-yl])oxo-lambda6-sulfanylidene]carbamate (40 mg, 0.04 mmol) in HCl (g) in MeOH (8 mL) was stirred for 3 h at RT under air atmosphere. The reaction was quenched by the addition of Water (50 mL) at RT. The resulting mixture was extracted with EtOAc (3×50 mL). The combined organic layers were washed with brine (50 mL) and dried over anhydrous $Na_2SO_4$. After filtration, the filtrate was concentrated under reduced pressure. The crude was purified by HPLC giving the product (10 mg, 65%) as a white solid.

Example 36: N,N,2-Trimethyl-4-[4-(trifluoromethyl)phenyl]-2H,4H-pyrazolo[4,3-b]indole-7-sulfonoimidamide Example 36-1: Synthesis of N,N,2-trimethyl-4-[4-(trifluoromethyl)phenyl]-2H,4H-pyrazolo[4,3-b]indole-7-sulfonoimidamide

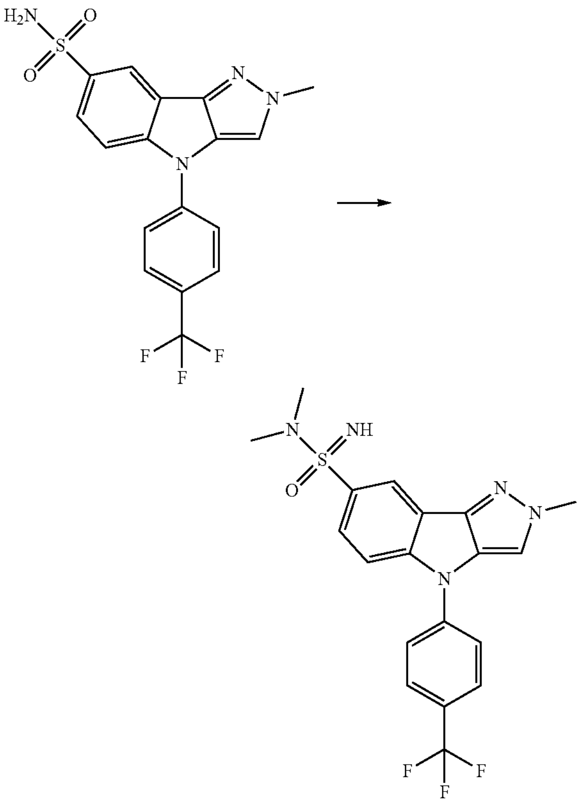

To a stirred solution of 2-methyl-4-[4-(trifluoromethyl)phenyl]pyrazolo[4,3-b]indole-7-sulfonamide (280 mg, 0.68 mmol) in THF (15) was added NaH (42 mg, 1.1 mmol) at 0° C. under nitrogen atmosphere. The resulting mixture was stirred for 1 h at RT under nitrogen atmosphere. To the above mixture was added TBSCl (141 mg, 0.89 mmol) in portions at 0° C. The reaction mixture was stirred for additional 2 h at room temperature and quenched by the addition of sat. $NH_4Cl$ (aq.) at 0° C. The resulting mixture was concentrated under reduced pressure and the residue was purified by silica gel column chromatography to afford N-(tert-butyldimethylsilyl)-2-methyl-4-[4-(trifluoro-methyl)phenyl]pyrazolo[4,3-b]indole-7-sulfonamide (150 mg, 42%) as off-white solid.

In a sealed tube a solution of PPh3 (200 mg, 0.72 mmol) and $CCl_3CCl_3$ (181 mg, 0.73 mmol) in $CHCl_3$ (2 mL) was stirred for 6 h at 70° C. under nitrogen atmosphere. To the mixture was added TEA (52 mg, 0.49 mmol) dropwise at RT and stirred for additional 10 min at RT. To the above mixture was added N-(tert-butyldimethylsilyl)-2-methyl-4-[4-(trifluoromethyl)phenyl]pyrazolo[4,3-b]indole-7-sulfonamide (130 mg, 0.24 mmol) in $CHCl_3$ dropwise at 0° C. The mixture was stirred for 20 min at 0° C. Then dimethylamine (35 mg, 0.74 mmol) in THF (0.37 mL) was added dropwise at 0° C. The resulting mixture was stirred for additional 30 min at 0° C. and overnight at RT. After concentration in vacuum the residue was resolved in ACN (1 mL) and a solution of HCOOH (1 mL) in $H_2O$ (1 mL) was added dropwise at 0° C. The resulting mixture was stirred for 1 h at room temperature and then concentrated under vacuum. The residue was purified by silica gel column chromatography giving the product (46 mg, 40%) as off-white solid.

TABLE 1

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 1 (Ex. 1) | 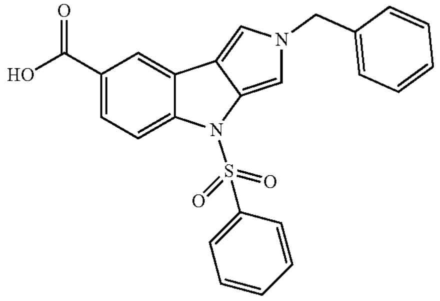 [SMILES: O=C(O)c1ccc2c(c1)c1cn(Cc3ccccc3)cc1n2S(=O)(=O)c1ccccc1] 4-(benzenesulfonyl)-2-benzyl-2H,4H-pyrrolo[3,4-b]indole-7-carboxylic acid | (400 MHz, DMSO-d6) δ 12.86 (br., s, 1H), 8.15 (d, J = 1.6 Hz, 1H), 8.03-8.01 (m, 1H), 7.90-7.87 (m, 1H), 7.80-7.78 (m, 2H), 7.63-7.61 (m, 1H), 7.49-7.45 (m, 2H), 7.38-7.35 (m, 2H), 7.32-7.27 (m, 2H), 7.24-7.22 (m, 3H), 5.31 (s, 2H) | 1 3.496 (431.1) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 2 (Ex. 2) | 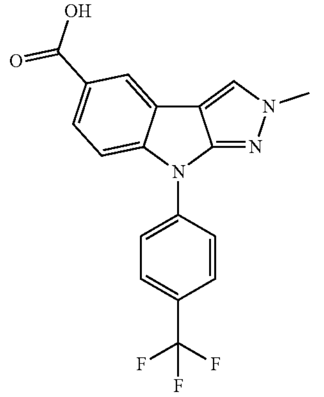 [SMILES: Cn1cc2c3cc(C(=O)O)ccc3n(-c3ccc(C(F)(F)F)cc3)c2n1] 2-methyl-8-[4-(trifluoromethyl)phenyl]-2H,8H-pyrazolo[3,4-b]indole-5-carboxylic acid | (400 MHz, DMSO) δ 12.72 (s, 1H), 8.43 (d, J = 1.6 Hz, 1H), 8.21 (s, 1H), 8.08 (d, J = 8.5 Hz, 2H), 7.97 (d, J = 8.6 Hz, 2H), 7.93 (dd, J = 8.7, 1.7 Hz, 1H), 7.78 (d, J = 8.7 Hz, 1H), 4.03 (s, 3H). | 1 4.067 (360.1) |
| 3 | 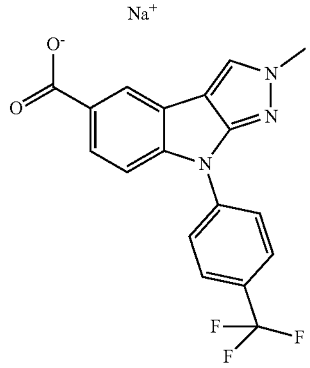 [SMILES: [Na+] ; Cn1cc2c3cc(C(=O)[O-])ccc3n(-c3ccc(C(F)(F)F)cc3)c2n1] Sodium 2-methyl-8-[4-(trifluoromethyl)phenyl]-2H,8H-pyrazolo[3,4-b]indole-5-carboxylate | (400 MHz, DMSO) δ 8.29 (s, 1H), 8.11 (d, J = 5.5 Hz, 2H), 8.09 (s, 1H), 7.93 (d, J = 8.6 Hz, 2H), 7.88 (dd, J = 8.5, 1.2 Hz, 1H), 7.62 (d, J = 8.6 Hz, 1H), 4.01 (s, 3H). | 2 3.954 (360.1) |
| 4 (Ex. 3) | 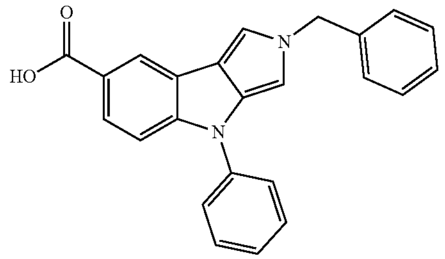 [SMILES: O=C(O)c1ccc2c(c1)c1cn(Cc3ccccc3)cc1n2-c1ccccc1] 2-benzyl-4-phenyl-2H,4H-pyrrolo[3,4-b]indole-7-carboxylic acid | (400 MHz, DMSO-d6) δ 12.48 (s, 1H), 8.33 (d, J = 1.6 Hz, 1H), 7.84-7.82 (m, 1H), 7.68-7.66 (m, 2H), 7.60-7.55 (m, 3H), 7.39-7.27 (m, 7H), 6.98 (d, J = 1.6 Hz, 1H), 5.30 (s, 2H) | 1 3.857 (367.1) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 5 (Ex. 4) | 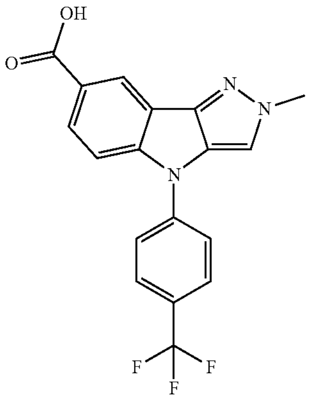 2-methyl-4-[4-(trifluoromethyl)phenyl]-2H,4H-pyrazolo[4,3-b]indole-7-carboxylic acic | (400 MHz, DMSO) 8.44 (d, J = 1.4 Hz, 1H), 8.10 (s, 1H), 7.99 (d, J = 1.7 Hz, 1H), 7.94 (s, 4H), 7.84 (d, J = 8.8 Hz, 1H), 4.10 (s, 3H). | 2<br>3.927<br>(359.8) |
| 6 (Ex. 5) | 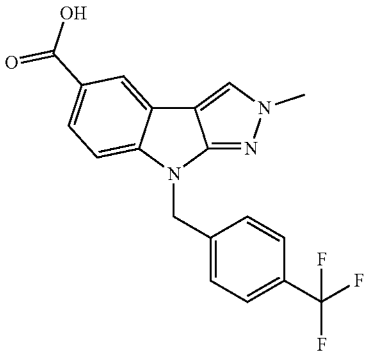 [SMILES: Cn1cc2c3cc(C(=O)O)ccc3n(Cc3ccc(C(F)(F)F)cc3)c2n1] 2-methyl-8-{[4-(trifluoromethyl)phenyl]methyl}-2H,8H-pyrazolo[3,4-b]indole-5-carboxylic acid | (400 MHz, DMSO-d6) δ 12.49 (s, 1H), 8.34 (d, J = 1.6 Hz, 1H), 8.10 (s, 1H), 7.85 (dd, J = 8.8, 1.6 Hz, 1H), 7.68 (d, J = 8.4 Hz, 2H), 7.51-7.43 (m, 3H), 5.52 (s, 2H), 3.99 (s, 3H) | 1<br>3.377<br>(374.1) |
| 7 (Ex. 6) | 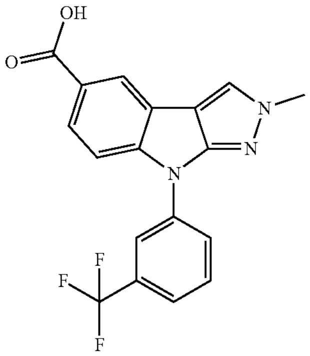 [SMILES: Cn1cc2c3cc(C(=O)O)ccc3n(-c3cccc(C(F)(F)F)c3)c2n1] 2-methyl-8-[3-(trifluoromethyl)phenyl]-2H,8H-pyrazolo[3,4-b]indole-5-carboxylic acid | (400 MHz, DMSO) δ 12.69 (d, J = 0.6 Hz, 1H), 8.43 (d, J = 1.5 Hz, 1H), 8.21 (s, 1H), 8.13 (d, J = 12.1 Hz, 2H), 7.93 (dd, J = 8.7, 1.7 Hz, 1H), 7.86 (t, J = 7.9 Hz, H), 7.76 (d, J = 7.8 Hz, 1H), 7.67 (d, J = 8.7 Hz, 1H), 4.03 (s, 3H). | 2<br>3.587<br>(360.1) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 8 (Ex. 7) | 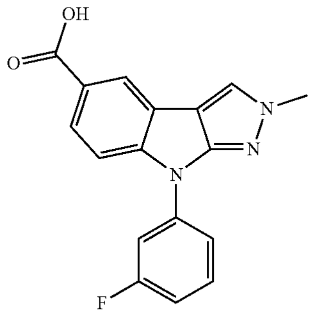 [SMILES: Cn1cc2c3cc(C(=O)O)ccc3n(-c3cccc(F)c3)c2n1] 8-(3-fluorophenyl)-2-methyl-2H,8H-pyrazolo[3,4-b]indole-5-carboxylic acid | (400 MHz, DMSO) δ 12.68 (s, 1H), 8.41 (d, J = 1.4 Hz, 1H), 8.19 (s, 1H), 7.92 (dd, J = 8.7, 1.6 Hz, 1H), 7.72 "C 7.63 (m, 4H), 7.27 "C 7.20 (m, 1H), 4.03 (s, 3H). | 2 2.910 (310.1) |
| 9 (Ex. 8) | 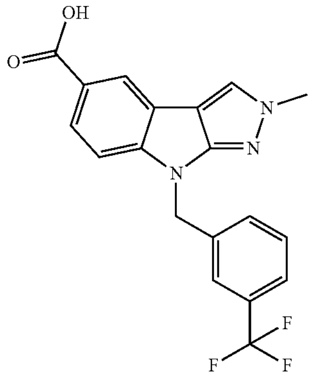 [SMILES: Cn1cc2c3cc(C(=O)O)ccc3n(Cc3cccc(C(F)(F)F)c3)c2n1] 2-methyl-8-{[3-(trifluoromethyl)phenyl]methyl}-2H,8H-pyrazolo[3,4-b]indole-5-carboxylic acid | (400 MHz, DMSO-d6) δ 12.51 (s, 1H), 8.34 (d, J = 1.6 Hz, 1H), 8.10 (s, 1H), 7.85 (dd, J = 8.8, 2.0 Hz, 1H), 7.72 (s, 1H), 7.64-7.62 (m, 1H), 7.56-7.47 (m, 3H), 5.52 (s, 2H), 3.99 (s, 3H) | 2 3.822 (374.1) |
| 10 (Ex. 9) | 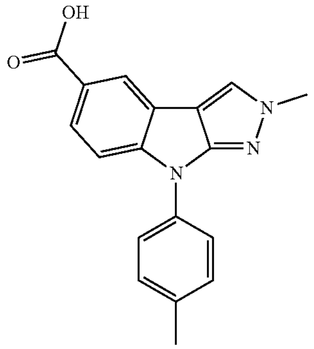 [SMILES: Cc1ccc(-n2c3ccc(C(=O)O)cc3c3cn(C)nc32)cc1] 2-methyl-8-(4-methylphenyl)-2H,8H-pyrazolo[3,4-b]indole-5-carboxylic acid | (400 MHz, DMSO) δ 12.60 (s, 1H), 8.40 (d, J = 1.5 Hz, 1H), 8.17 (s, 1H), 7.89 (dt, J = 5.2, 3.3 Hz, 1H), 7.63 (d, J = 8.3 Hz, 2H), 7.54 (d, J = 8.7 Hz, 1H), 7.41 (d, J = 8.2 Hz, 2H), 4.00 (s, 3H), 2.40 (s, 3H). | 2 3.138 (306.1) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 11 (Ex. 10) | 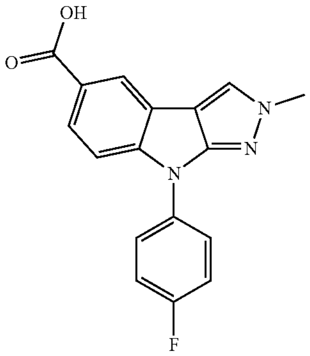 [SMILES: Cn1cc2c3cc(C(=O)O)ccc3n(-c3ccc(F)cc3)c2n1] 8-(4-fluorophenyl)-2-methyl-2H,8H-pyrazolo[3,4-b]indole-5-carboxylic acid | (400 MHz, DMSO) δ 12.65 (s, 1H), 8.41 (d, J = 1.4 Hz, 1H), 8.18 (s, 1H), 7.90 (dd, J = 8.7, 1.6 Hz, 1H), 7.83-7.77 (m, 2H), 7.54 (d, J = 8.7 Hz, 1H), 7.49-7.42 (m, 2H), 4.01 (s, 3H). | 2 3.612 (310.1) |
| 12 (Ex. 11) | 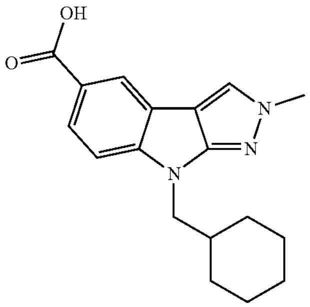 [SMILES: Cn1cc2c3cc(C(=O)O)ccc3n(CC3CCCCC3)c2n1] 8-(cyclohexylmethyl)-2-methyl-2H,8H-pyrazolo[3,4-b]indole-5-carboxylic acid | (400 MHz, CDCl3) δ 7.63 (s, 1H), 7.31-7.26 (m, 3H), 4.09 (s, 3H), 4.01 (d, J = 7.5 Hz, 2H), 2.49 (s, 1H), 2.01 (s, 1H), 1.75-1.63 (m, 5H), 1.26-1.15 (m, 3H), 1.13-1.03 (m, 2H). | 6 3.920 (312.2) |
| 13 (Ex. 12) | 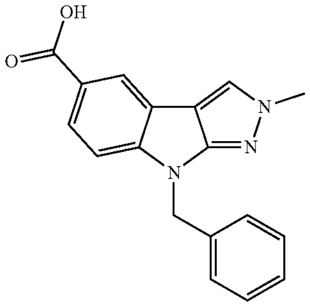 [SMILES: Cn1cc2c3cc(C(=O)O)ccc3n(Cc3ccccc3)c2n1] 8-benzyl-2-methyl-2H,8H-pyrazolo[3,4-b]indole-5-carboxylic acid | (300 MHz, DMSO) δ 12.58-12.44 (m, 1H), 8.35 (d, J = 1.4 Hz, 1H), 8.12 (s, 1H), 7.87 (dd, J = 8.5, 1.6 Hz, 1H), 7.52 (d, J = 8.6 Hz, 1H), 7.39-7.24 (m, 6H), 5.43 (s, 2H), 4.02 (s, 3H). | 6 3.373 (306.1) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 14 (Ex. 13) | 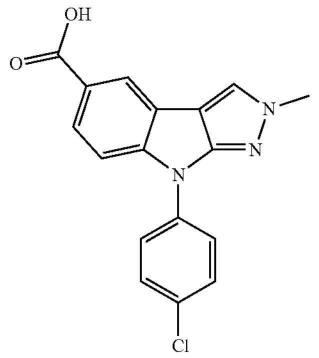 8-(4-chlorophenyl)-2-methyl-2H,8H-pyrazolo[3,4-b]indole-5-carboxylic acid | (300 MHz, DMSO) δ 12.70 (s, 0H), 8.44 (d, J = 1.4 Hz, 1H), 8.22 (s, 1H), 7.93 (dd, J = 8.7, 1.7 Hz, 1H), 7.86 (d, J = 8.8 Hz, 2H), 7.72 (d, J = 2.9 Hz, 1H), 7.67 (dd, J = 7.1, 4.0 Hz, 2H), 4.04 (s, 3H). | 6 4.082 (326.1) |
| 15 (Ex. 16) | 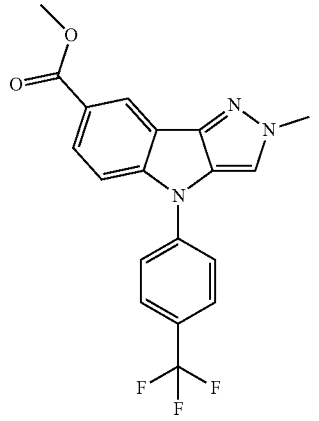 [SMILES: COC(=O)c1ccc2c(c1)c1nn(C)cc1n2-c1ccc(C(F)(F)F)cc1] methyl 2-methyl-4-[4-(trifluoromethyl)phenyl]-2H,4H-pyrazolo[4,3-b]indole-7-carboxylate | (300 MHz, DMSO,) δ 8.45 (d, J = 1.7 Hz, 1 H), 8.10 (s, 1 H), 8.04-7.95 (m, 1 H), 7.93 (s, 4 H), 7.86 (d, J = 8.8 Hz, 1 H), 4.09 (s, 3 H), 3.88 (s, 3 H). | 9 0.782 (374.1) |
| 16 (Ex. 17) | 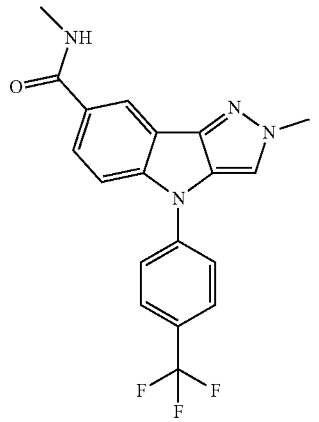 [SMILES: CNC(=O)c1ccc2c(c1)c1nn(C)cc1n2-c1ccc(C(F)(F)F)cc1] N,2-dimethyl-4-[4-(trifluoromethyl)phenyl]-2H,4H-pyrazolo[4,3-b]indole-7-carboxamide | (400 MHz, DMSO) δ 8.52 (d, J = 4.6 Hz, 1 H), 8.46 (d, J = 1.8 Hz, 1 H), 8.10 (s, 1 H), 7.93 (s, 5 H), 7.85 (d, J = 8.7 Hz, 1 H), 4.10 (s, 3 H), 2.83 (d, J = 4.4 Hz, 3 H). | 9 0.627 (373.1) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 17 (Ex. 14) | 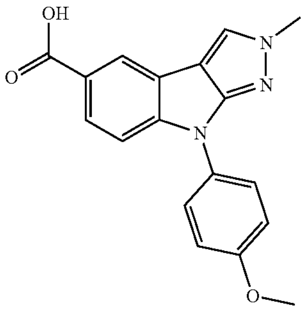 [SMILES: COc1ccc(-n2c3ccc(C(=O)O)cc3c3cn(C)nc32)cc1] 8-(4-methoxyphenyl)-2-methyl-2H,8H-pyrazolo[3,4-b]indole-5-carboxylic acid | (500 MHz, DMSO-d6) δ 12.58-12.54 (m, 1H), 8.40-8.38 (m, 1H), 8.15 (s, 1H), 7.87 (dd, J = 8.6, 1.8 Hz, 1H), 7.65-7.61 (m, 2H), 7.44 (d, J = 8.7 Hz, 1H), 7.18-7.14 (m, 2H), 4.00 (s, 3H), 3.85 (s, 3H). | 8 1.516 (322.0) |
| 18 (Ex. 18) | 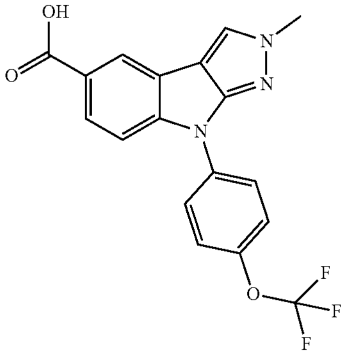 [SMILES: Cn1cc2c3cc(C(=O)O)ccc3n(-c3ccc(OC(F)(F)F)cc3)c2n1] 2-methyl-8-[4-(trifluoromethoxy)phenyl]-2H,8H-pyrazolo[3,4-b]indole-5-carboxylic acid | (400 MHz, DMSO-d6) δ 12.67-12.62 (m, 1H), 8.41 (d, J = 1.7 Hz, 1H), 8.19 (s, 1H), 7.95-7.90 (m, 2H), 7.93-7.88 (m, 1H), 7.65 (d, J = 8.7 Hz, 1H), 7.63-7.59 (m, 2H), 4.02 (s, 3H). | 8 1.752 (376.1) |
| 19 (Ex 19) | 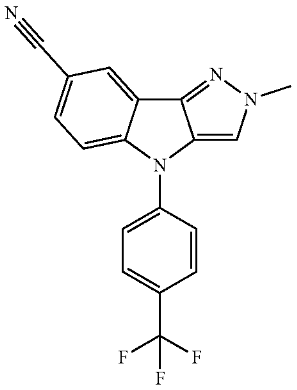 [SMILES: Cn1cc2c(n1)c1cc(C#N)ccc1n2-c1ccc(C(F)(F)F)cc1] 2-methyl-4-[4-(trifluoromethyl)phenyl]-2H,4H-pyrazolo[4,3-b]indole-7-carbonitrile | (300 MHz, DMSO) δ 8.44 (d, J = 1.7 Hz, 1 H), 8.15 (s, 1 H), 7.95 (s, 4 H), 8.02-7.87 (m, 1 H), 7.85-7.75 (m, 1 H), 4.12 (s, 3 H). | 11 (1.298) 341.1 |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 20 (Ex. 20) | 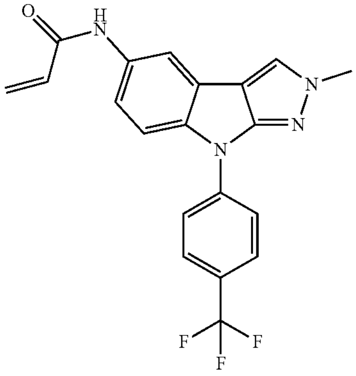 [SMILES: C=CC(=O)Nc1ccc2c(c1)c1cn(C)nc1n2-c1ccc(C(F)(F)F)cc1] N-{2-methyl-8-[4-(trifluoromethyl)phenyl]-2H,8H-pyrazolo[3,4-b]indol-5-yl}prop-2-enamide | (400 MHz, DMSO) δ 10.20 (s, 1 H), 8.27 (d, J = 2.1 Hz, 1 H), 8.17 (s, 1 H), 8.08 (d, J = 8.5 Hz, 2 H), 7.92 (d, J = 8.5 Hz, 2 H), 7.74 (d, J = 8.9 Hz, 1 H), 7.47 (dd, J = 8.9, 2.1 Hz, 1 H), 6.47 (dd, J = 16.9, 10.1 Hz, 1 H), 6.27 (dd, J = 16.9, 2.1 Hz, 1 H), 5.75 (dd, J = 10.0, 2.1 Hz, 1 H), 4.01 (s, 3 H). | 9 (1.585) 385.0 |
| 21 (Ex 21) | 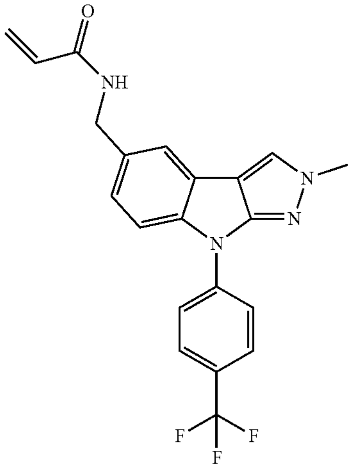 [SMILES: C=CC(=O)NCc1ccc2c(c1)c1cn(C)nc1n2-c1ccc(C(F)(F)F)cc1] N-({2-methyl-8-[4-(trifluoromethyl)-phenyl]-2H,8H-pyrazolo[3,4-b]indol-5-yl}methyl)prop-2-enamide | (300 MHz, DMSO-d6) δ 8.64 (t, J = 5.8 Hz, 1H), 8.13 (s, 1H), 8.05 (d, J = 8.4 Hz, 2H), 7.92 (d, J = 8.7 Hz, 2H), 7.75-7.66 (m, 2H), 7.22 (dd, J = 8.5, 1.9 Hz, 1H), 6.29 (dd, J = 17.1, 10.0 Hz, 1H), 6.13 (dd, J = 17.1, 2.4 Hz, 1H), 5.61 (dd, J = 10.0, 2.4 Hz, 1H), 4.45 (d, J = 5.8 Hz, 2H), 3.99 (s, 3H). | 9 1.548 (399.4) |
| 22 (Ex. 22) | 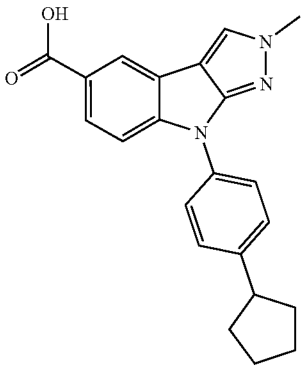 [SMILES: Cn1cc2c3cc(C(=O)O)ccc3n(-c3ccc(C4CCCC4)cc3)c2n1] 8-(4-cyclopentylphenyl)-2-methyl-2H,8H-pyrazolo[3,4-b]indole-5-carboxylic acid | (500 MHz, DMSO-$d_6$) δ 12.58 (s, 1H), 8.40 (d, J = 1.7 Hz, 1H), 8.16 (s, 1H), 7.88 (dd, J = 8.7, 1.8 Hz, 1H), 7.67-7.63 (m, 2H), 7.55 (d, J = 8.7 Hz, 1H), 7.50-7.46 (m, 2H), 4.00 (s, 3H), 3.07 (tt, J = 9.5, 7.4 Hz, 1H), 2.13-2.02 (m, 2H), 1.88-1.77 (m, 2H), 1.76-1.55 (m, 5H). | 8 1.938 (360.1) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 23 | 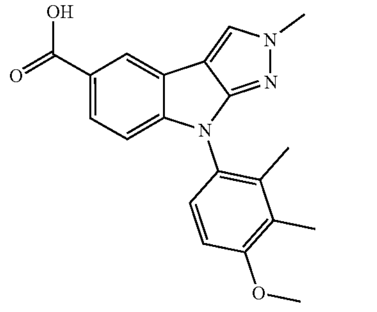 [SMILES: COc1ccc(-n2c3ccc(C(=O)O)cc3c3cn(C)nc32)c(C)c1C] 8-(4-methoxy-2,3-dimethylphenyl)-2-methyl-2H,8H-pyrazolo[3,4-b]indole-5-carboxylic acid | (500 MHz, DMSO-$d_6$) δ 13.02 (br. S, 1H), 8.02 (d, J = 2.2 Hz, 1H), 7.83 (s, 1H), 7.70 (dd, J = 8.3, 2.1 Hz, 1H), 7.55 (d, J = 8.4 Hz, 1H), 6.85 (d, J = 8.8 Hz, 1H), 6.53 (d, J = 8.8 Hz, 1H), 3.74 (s, 3H), 3.64 (s, 3H), 2.05 (d, J = 15.4 Hz, 6H). | 8 1.657 (350.1) |
| 24 (Ex. 23) | 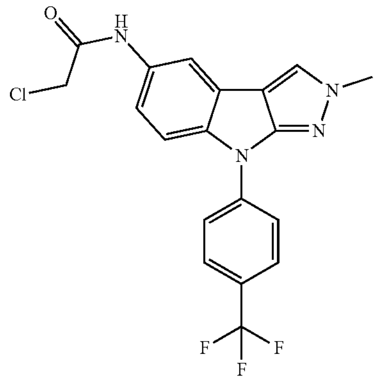 [SMILES: Cn1cc2c3cc(NC(=O)CCl)ccc3n(-c3ccc(C(F)(F)F)cc3)c2n1] 2-chloro-N-{2-methyl-8-[4-(trifluoromethyl)phenyl]-2H,8H-pyrazolo[3,4-b]indol-5-yl}acetamide | (400 MHz, DMSO, ppm) δ 10.35 (s, 1 H), 8.20-8.14 (m, 2 H), 8.07 (d, J = 8.4 Hz, 2 H), 7.92 (d, J = 8.4 Hz, 2 H), 7.74 (d, J = 8.9 Hz, 1 H), 7.41 (dd, J = 8.9, 2.2 Hz, 1 H), 4.28 (s, 2 H), 4.01 (s, 3 H). | 9 1.629 (407.0) |
| 25 (Ex. 24) | 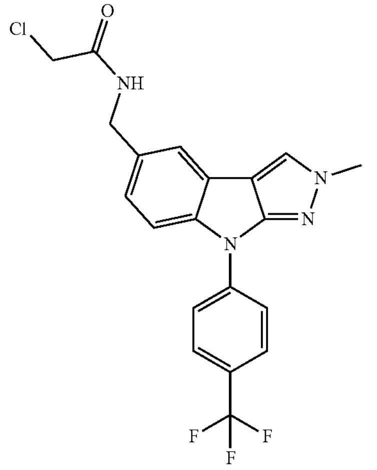 [SMILES: Cn1cc2c3cc(CNC(=O)CCl)ccc3n(-c3ccc(C(F)(F)F)cc3)c2n1] 2-chloro-N-({2-methyl-8-[4-(trifluoromethyl)phenyl]-2H,8H-pyrazolo[3,4-b]indol-5-yl}methyl)acetamide | (400 MHz, DMSO-d6) δ 8.77 (t, J = 5.9 Hz, 1H), 8.15 (s, 1H), 8.08 (d, J = 8.4 Hz, 2H), 7.94 (d, J = 8.5 Hz, 2H), 7.77-7.69 (m, 2H), 7.25 (dd, J = 8.5, 1.9 Hz, 1H), 4.43 (d, J = 5.8 Hz, 2H), 4.15 (s, 2H), 4.02 (s, 3H). | 8 1.618 (421.0) |

TABLE 1-continued

| Compound No. (Example No.) | Structure and Name | $^1$H-NMR | Conditions and elution time (min) LCMS (M + H$^+$) |
|---|---|---|---|
| Table 1 below shows exemplary compounds of the present invention. They have been synthesized as described in the Examples above or similar thereto. | | | |
| 26 (Ex. 15) | 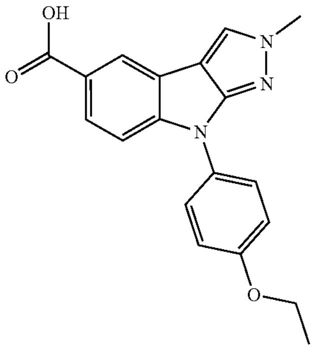 [SMILES: CCOc1ccc(-n2c3ccc(C(=O)O)cc3c3cn(C)nc32)cc1] 8-(4-ethoxyphenyl)-2-methyl-2H,8H-pyrazolo[3,4-b]indole-5-carboxylic acid | (400 MHz, DMSO-d6) δ 12.55 (s, 1H), 8.39 (d, J = 1.7 Hz, 1H), 8.15 (s, 1H), 7.87 (dd, J = 8.7, 1.8 Hz, 1H), 7.65-7.57 (m, 2H), 7.44 (d, J = 8.6 Hz, 1H), 7.18-7.10 (m, 2H), 4.12 (q, J = 7.0 Hz, 2H), 4.00 (s, 3H), 1.38 (t, J = 6.9 Hz, 3H). | 8 1.608 (336.1) |
| 27 (Ex. 25) | 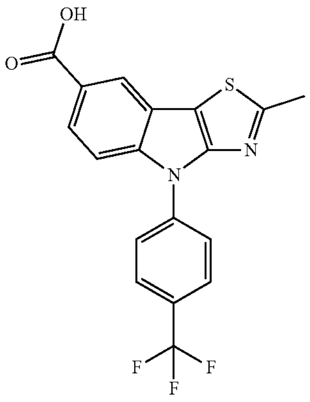 [SMILES: Cc1nc2c(s1)c1cc(C(=O)O)ccc1n2-c1ccc(C(F)(F)F)cc1] 2-methyl-4-[4-(trifluoromethyl)phenyl]-4H-[1,3]thiazolo[4,5-b]indole-7-carboxylic acid | (300 MHz, DMSO-d6) δ 8.50 (d, J = 1.7 Hz, 1H), 7.99 (s, 3H), 7.92 (dd, J = 8.8, 1.7 Hz, 2H), 7.70 (d, J = 8.8 Hz, 1H), 2.82 (s, 3H) | 9 0.782 (377.0) |
| 28 (Ex. 26) | 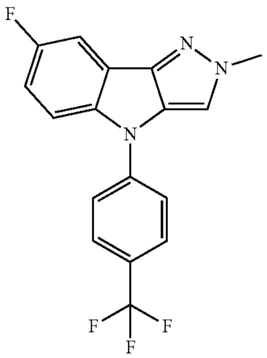 [SMILES: Cn1cc2c(n1)c1cc(F)ccc1n2-c1ccc(C(F)(F)F)cc1] 7-fluoro-2-methyl-4-[4-(trifluoromethyl)phenyl]-2H,4H-pyrazolo[4,3-b]indole | (300 MHz, DMSO-d6) δ 8.07 (s, 1H), 7.88 (s, 4H), 7.84-7.78 (m, 1H), 7.76-7.66 (m, 1H), 7.30-7.17 (m, 1H), 4.07 (s, 3H). | 7 1.99 (334.1) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
| --- | --- | --- | --- |
| 29 | 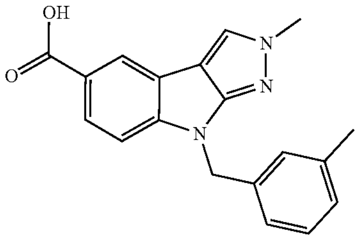 [SMILES: Cc1cccc(Cn2c3ccc(C(=O)O)cc3c3cn(C)nc32)c1] 2-methyl-8-[(3-methylphenyl)methyl]-2H,8H-pyrazolo[3,4-b]indole-5-carboxylic acid | (500 MHz, DMSO-$d_6$) δ 12.45 (br. s, 1H), 8.32 (d, J = 1.7 Hz, 1H), 8.08 (s, 1H), 7.84 (dd, J = 8.6, 1.7 Hz, 1H), 7.46 (d, J = 8.6 Hz, 1H), 7.17 (t, J = 7.6 Hz, 1H), 7.12 (d, J = 1.8 Hz, 1H), 7.08-7.00 (m, 2H), 5.35 (s, 2H), 4.00 (s, 3H), 2.23 (s, 3H). | 8 1.568 (320.1) |
| 30 (Ex. 33) | 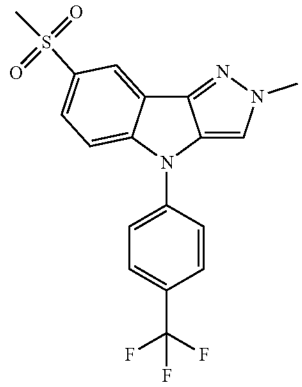 [SMILES: Cn1cc2c(n1)c1cc(S(C)(=O)=O)ccc1n2-c1ccc(C(F)(F)F)cc1] 7-methanesulfonyl-2-methyl-4-[4-(trifluoromethyl)phenyl]-2H,4H-pyrazolo[4,3-b]indole | (300 MHz, DMSO-d6) δ 8.43 (d, J = 1.8 Hz, 1H), 8.15 (s, 1H), 8.01-7.89 (m, 6H), 4.11 (s, 3H) , 3.27 (s, 3H). | 15 1.59 (394.1) |
| 31 | 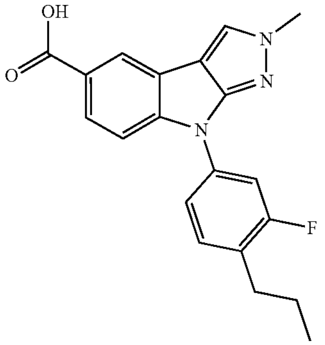 [SMILES: CCCc1ccc(-n2c3ccc(C(=O)O)cc3c3cn(C)nc32)cc1F] 8-(3-fluoro-4-propylphenyl)-2-methyl-2H,8H-pyrazolo[3,4-b]indole-5-carboxylic acid | (500 MHz, DMSO-$d_6$) δ 12.64 (s, 1H), 8.40 (dd, J = 1.8, 0.5 Hz, 2H), 8.18 (s, 2H), 7.90 (dd, J = 8.7, 1.8 Hz, 2H), 7.66 (dd, J = 8.7, 0.6 Hz, 2H), 7.63-7.55 (m, 4H), 7.51 (t, J = 8.3 Hz, 2H), 4.02 (s, 6H), 2.67 (t, J = 7.5 Hz, 4H), 1.71-1.60 (m, 4H), 0.96 (t, J = 7.3 Hz, 6H). | 8 1.868 (352.1) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 32 | 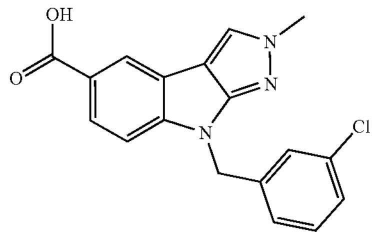 [SMILES: Cn1cc2c3cc(C(=O)O)ccc3n(Cc3cccc(Cl)c3)c2n1] 8-[(3-chlorophenyl)methyl]-2-methyl-2H,8H-pyrazolo[3,4-b]indole-5-carboxylic acid | (500 MHz, DMSO-$d_6$) δ 12.48 (s, 1H), 8.36-8.32 (m, 1H), 8.10 (s, 1H), 7.85 (dd, J = 8.6, 1.8 Hz, 1H), 7.51 (d, J = 8.6 Hz, 1H), 7.37-7.28 (m, 3H), 7.23-7.17 (m, 1H), 5.42 (s, 2H), 4.00 (s, 3H). | 8 1.586 (340.0) |
| 33 | 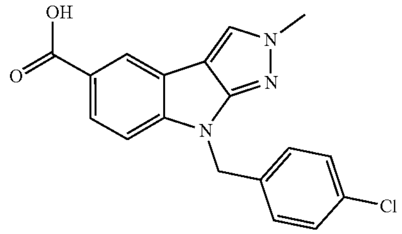 [SMILES: Cn1cc2c3cc(C(=O)O)ccc3n(Cc3ccc(Cl)cc3)c2n1] 8-[(3-chlorophenyl)methyl]-2-methyl-2H,8H-pyrazolo[3,4-b]indole-5-carboxylic acid | (500 MHz, DMSO-$d_6$) δ 12.47 (s, 1H), 8.35-8.31 (m, 1H), 8.09 (s, 1H), 7.84 (dd, J = 8.6, 1.8 Hz, 1H), 7.49 (d, J = 8.6 Hz, 1H), 7.40-7.33 (m, 2H), 7.33-7.25 (m, 2H), 5.40 (s, 2H), 3.99 (s, 3H). | 8 1.599 (340.0) |
| 34 | 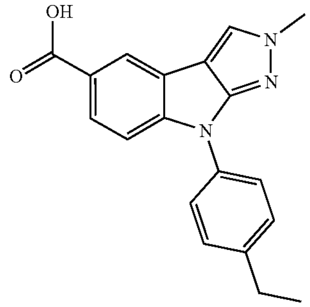 [SMILES: CCc1ccc(-n2c3ccc(C(=O)O)cc3c3cn(C)nc32)cc1] 8-(4-ethylphenyl)-2-methyl-2H,8H-pyrazolo[3,4-b]indole-5-carboxylic acid | (500 MHz, DMSO-$d_6$) δ 12.58 (s, 1H), 8.40 (dd, J = 1.7, 0.5 Hz, 1H), 8.16 (s, 1H), 7.88 (dd, J = 8.7, 1.8 Hz, 1H), 7.70-7.63 (m, 2H), 7.55 (dd, J = 8.7, 0.6 Hz, 1H), 7.47-7.41 (m, 2H), 4.00 (s, 3H), 2.71 (q, J = 7.6 Hz, 2H), 1.26 (t, J = 7.6 Hz, 3H). | 8 1.712 (320.1) |
| 35 | 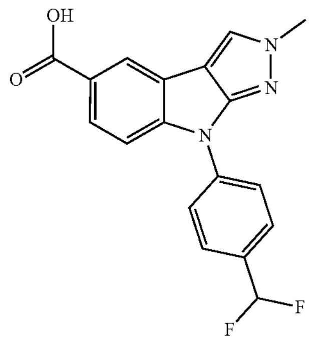 [SMILES: Cn1cc2c3cc(C(=O)O)ccc3n(-c3ccc(C(F)F)cc3)c2n1] 8-[4-(difluoromethyl)phenyl]-2-methyl-2H,8H-pyrazolo[3,4-b]indole-5-carboxylic acid | (500 MHz, DMSO-d6) δ 12.68-12.66 (m, 1H), 8.42-8.41 (m, 1H), 8.20-8.20 (m, 1H), 7.99-7.96 (m, 2H), 7.91 (dd, J = 8.7, 1.8 Hz, 1H), 7.83-7.80 (m, 2H), 7.73-7.70 (m, 1H), 7.14 (t, J = 55.9 Hz, 1H), 4.03 (s, 3H). | 8 1.597 (342.1) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 36 | 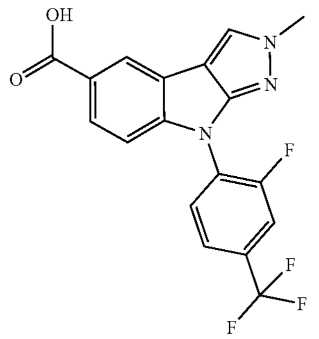 [SMILES: Cn1cc2c3cc(C(=O)O)ccc3n(-c3ccc(C(F)(F)F)cc3F)c2n1] 8-[2-fluoro-4-(trifluoromethyl)phenyl]-2-methyl-2H,8H-pyrazolo[3,4-b]indole-5-carboxylic acid | (500 MHz, DMSO-$d_6$) δ 12.68 (s, 1H), 8.42 (dd, J = 1.7, 0.6 Hz, 1H), 8.19 (s, 1H), 8.08 (dd, J = 10.6, 2.0 Hz, 1H), 8.06-7.99 (m, 1H), 7.89 (dd, J = 8.6, 1.8 Hz, 1H), 7.87-7.81 (m, 1H), 7.29 (dd, J = 8.6, 2.9 Hz, 1H), 3.99 (s, 3H). | 8 1.683 (378.1) |
| 37 | 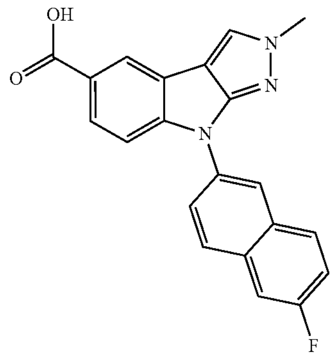 [SMILES: Cn1cc2c3cc(C(=O)O)ccc3n(-c3ccc4cc(F)ccc4c3)c2n1] 8-(6-fluoronaphthalen-2-yl)-2-methyl-2H,8H-pyrazolo[3,4-b]indole-5-carboxylic acid | (700 MHz, DMSO-d6) δ 13.17-12.10 (m, 1H), 8.44 (d, J = 1.7 Hz, 1H), 8.35 (d, J = 2.3 Hz, 1H), 8.22 (s, 1H), 8.17-8.14 (m, 2H), 8.00 (dd, J = 8.9, 2.2 Hz, 1H), 7.92 (dd, J = 8.6, 1.8 Hz, 1H), 7.84 (dd, J = 10.2, 2.7 Hz, 1H), 7.70 (d, J = 8.6 Hz, 1H), 7.53 (td, J = 8.9, 2.7 Hz, 1H), 4.03 (s, 3H). | 8 1.77 (359.9-361) |
| 38 | 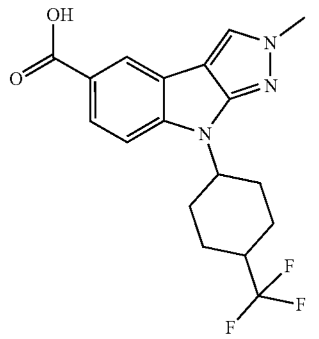 [SMILES: Cn1cc2c3cc(C(=O)O)ccc3n(C3CCC(C(F)(F)F)CC3)c2n1] 2-methyl-8-[4-(trifluoromethyl)cyclohexyl]-2H,8H-pyrazolo[3,4-b]indole-5-carboxylic acid | (400 MHz, DMSO-d6) δ 8.30 (s, 1H), 8.06 (d, J = 4.6 Hz, 1H), 7.86 (d, J = 8.6 Hz, 1H), 7.60-7.48 (m, 1H), 4.51 (d, J = 11.2 Hz, 1H), 3.99 (d, J = 4.3 Hz, 3H), 2.60 (s, 1H), 2.42 (d, J = 12.4 Hz, 1H), 2.33-2.23 (m, 1H), 2.13-1.89 (m, 4H), 1.86-1.77 (m, 1H), 1.68-1.55 (m, 1H). | 9 0.89 (365.95) |

TABLE 1-continued

| Com- pound No. (Example No.) | Structure and Name | $^1$H-NMR | Conditions and elution time (min) LCMS (M + H$^+$) |
|---|---|---|---|
| Table 1 below shows exemplary compounds of the present invention. They have been synthesized as described in the Examples above or similar thereto. | | | |
| 39 | 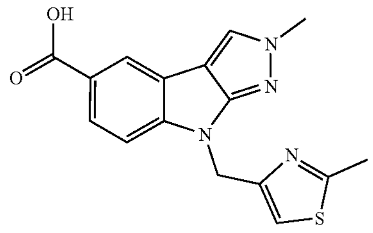 [SMILES: Cc1nc(Cn2c3ccc(C(=O)O)cc3c3cn(C)nc32)cs1]<br>2-methyl-8-[(2-methyl-1,3-thiazol-4-yl)methyl]-2H,8H-pyrazolo[3,4-b]indole-5-carboxylic acid | | |
| 40 | 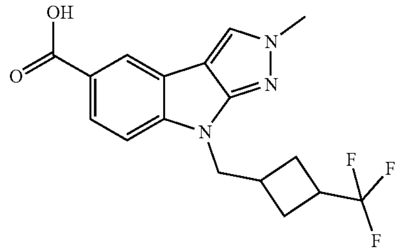 [SMILES: Cn1cc2c3cc(C(=O)O)ccc3n(CC3CC(C(F)(F)F)C3)c2n1]<br>mixture of cis and trans isomers<br>2-methyl-8-{[3-(trifluoromethyl)cyclobutyl]methyl}-2H,8H-pyrazolo[3,4-b]indole-5-carboxylic acid | (700 MHz, DMSO-$d_6$) δ 12.46 (s, 1H), 8.30 (d, J = 1.7 Hz, 1H), 8.05 (d, J = 1.7 Hz, 2H), 7.87 (dt, J = 8.6, 1.6 Hz, 2H), 7.57 (d, J = 8.6 Hz, 1H), 4.30 (d, J = 7.6 Hz, 2H), 4.18 (d, J = 6.9 Hz, 1H), 3.99 (d, J = 1.1 Hz, 5H), 3.07-2.97 (m, 2H), 2.15 (m, 5H), 1.96 (m, 1H). | 8<br>1.554 and 1580<br>(352.1) |
| 41 | 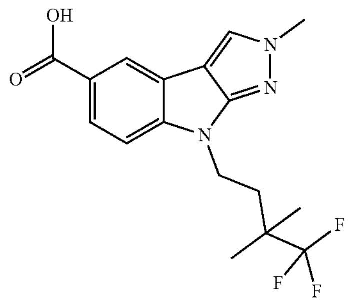 [SMILES: Cn1cc2c3cc(C(=O)O)ccc3n(CCC(C)(C)C(F)(F)F)c2n1]<br>2-methyl-8-(4,4,4-trifluoro-3,3-dimethylbutyl)-2H,8H-pyrazolo[3,4-b]indole-5-carboxylic acid | (400 MHz, DMSO-$d_6$) δ 12.41 (br. s, 1H), 8.32 (d, J = 1.7 Hz, 1H), 8.07 (s, 1H), 7.89 (dd, J = 8.5, 1.8 Hz, 1H), 7.46 (d, J = 8.6 Hz, 1H), 4.30-4.21 (m, 2H), 4.01 (s, 3H), 2.04-1.95 (m, 2H), 1.22 (s, 6H). | 8<br>1.549<br>(354.1) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 42 | 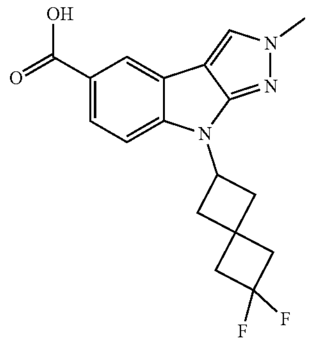 [SMILES: Cn1cc2c3cc(C(=O)O)ccc3n(C3CC4(C3)CC(F)(F)C4)c2n1] 8-{6,6-difluorospiro[3.3]heptan-2-yl}-2-methyl-2H,8H-pyrazolo[3,4-b]indole-5-carboxylic acid | | |
| 43 | 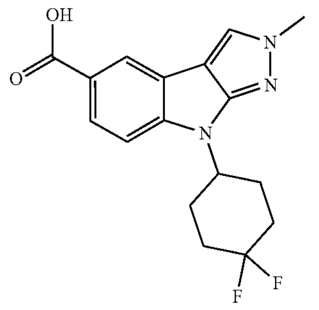 [SMILES: Cn1cc2c3cc(C(=O)O)ccc3n(C3CCC(F)(F)CC3)c2n1] 4-(4,4-difluorocyclohexyl)-2-methyl-2H,4H-pyrazolo[4,3-b]indole-7-carboxylic acid | (300 MHz, DMSO-d6) δ 12.57 (s, 1H), 8.36 (s, 1H), 7.95 (d, J = 8.7 Hz, 1H), 7.89 (s, 1H),7.59 (d, J = 9.0 Hz, 1H), 4.76-4.67 (m, 1H), 4.05 (s, 3H), 2.24-2.10 (m, 4H), 2.08-2.03 (m, 4H) | 9 0.77 (333.95) |
| 44 | 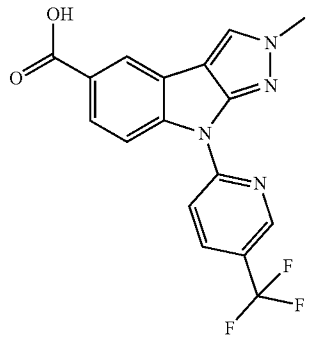 [SMILES: Cn1cc2c3cc(C(=O)O)ccc3n(-c3ccc(C(F)(F)F)cn3)c2n1] 2-methyl-8-[5-(trifluoromethyl)pyridin-2-yl]-2H,8H-pyrazolo[3,4-b]indole-5-carboxylic acid | | |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 45 | 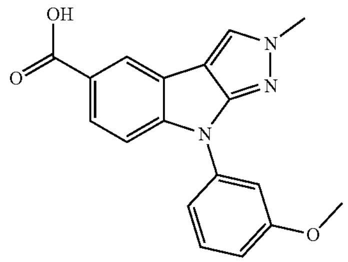 [SMILES: COc1cccc(-n2c3ccc(C(=O)O)cc3c3cn(C)nc32)c1] 8-(3-methoxyphenyl)-2-methyl-2H,8H-pyrazolo[3,4-b]indole-5-carboxylic acid | (500 MHz, DMSO-$d_6$) δ 12.61 (s, 1H), 8.40 (d, J = 1.7 Hz, 1H), 8.17 (s, 1H), 7.90 (dd, J = 8.7, 1.8 Hz, 1H), 7.66-7.61 (m, 1H), 7.52 (t, J = 8.1 Hz, 1H), 7.37-7.30 (m, 2H), 6.98 (ddd, J = 8.4, 2.5, 0.9 Hz, 1H), 4.01 (s, 3H), 3.84 (s, 3H). | 8 1.544 (322.2) |
| 46 | 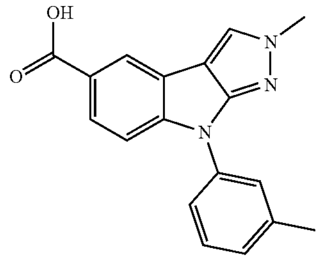 [SMILES: Cc1cccc(-n2c3ccc(C(=O)O)cc3c3cn(C)nc32)c1] 2-methyl-8-(3-methylphenyl)-2H,8H-pyrazolo[3,4-b]indole-5-carboxylic acid | (500 MHz, DMSO-$d_6$) δ 12.59 (s, 1H), 8.42-8.38 (m, 1H), 8.17 (s, 1H), 7.89 (dd, J = 8.7, 1.8 Hz, 1H), 7.60-7.52 (m, 3H), 7.49 (t, J = 7.7 Hz, 1H), 7.22 (ddt, J = 7.5, 1.9, 1.0 Hz, 1H), 4.01 (s, 3H), 2.43 (s, 3H). | 8 1.613 (306.0) |
| 47 | 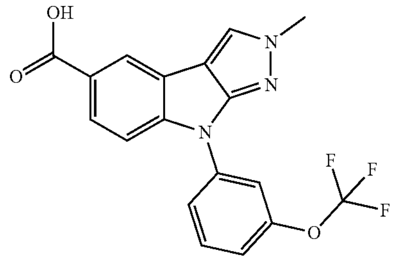 [SMILES: Cn1cc2c3cc(C(=O)O)ccc3n(-c3cccc(OC(F)(F)F)c3)c2n1] 2-methyl-8-[3-(trifluoromethoxy)phenyl]-2H,8H-pyrazolo[3,4-b]indole-5-carboxylic acid | (500 MHz, DMSO-$d_6$) δ 12.59 (s, 1H), 8.42-8.38 (m, 1H), 8.17 (s, 1H), 7.89 (dd, J = 8.7, 1.8 Hz, 1H), 7.60-7.52 (m, 3H), 7.49 (t, J = 7.7 Hz, 1H), 7.22 (ddt, J = 7.5, 1.9, 1.0 Hz, 1H), 4.01 (s, 3H), 2.43 (s, 3H). | 8 1.758 (376.1) |
| 48 | 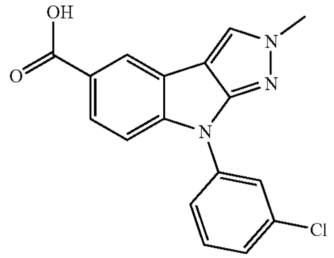 [SMILES: Cn1cc2c3cc(C(=O)O)ccc3n(-c3cccc(Cl)c3)c2n1] 8-(3-chlorophenyl)-2-methyl-2H,8H-pyrazolo[3,4-b]indole-5-carboxylic acid | | |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 49 | 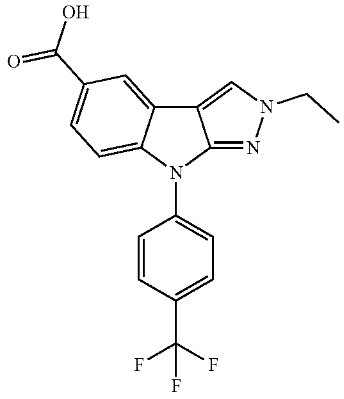 [SMILES: CCn1cc2c3cc(C(=O)O)ccc3n(-c3ccc(C(F)(F)F)cc3)c2n1]<br>2-ethyl-8-[4-(trifluoromethyl)phenyl]-2H,8H-pyrazolo[3,4-b]indole-5-carboxylic acid | (400 MHz, DMSO-d6) δ 8.42 (d, J = 1.8 Hz, 1H), 8.27 (s, 1H), 8.09 (d, J = 8.4 Hz, 2H), 7.98 (d, J = 8.7 Hz, 2H), 7.93 (dd, J = 8.7, 1.8 Hz, 1H), 7.77 (d, J = 8.7 Hz, 1H), 4.32 (q, J = 7.2 Hz, 2H), 1.47 (t, J = 7.2 Hz, 3H). | 12<br>0.754<br>(374.0) |
| 50 | 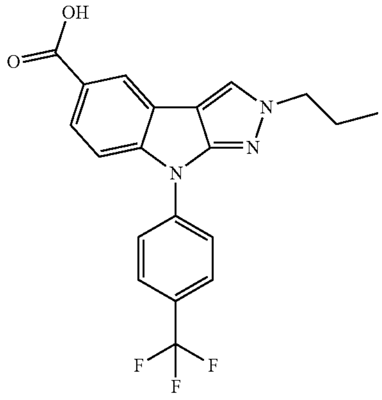 [SMILES: CCCn1cc2c3cc(C(=O)O)ccc3n(-c3ccc(C(F)(F)F)cc3)c2n1]<br>2-propyl-8-[4-(trifluoromethyl)phenyl]-2H,8H-pyrazolo[3,4-b]indole-5-carboxylic acid | (300 MHz, DMSO-d6) δ 8.41 (d, J = 1.8 Hz, 1H), 8.24 (s, 1H), 8.07 (d, J = 8.4 Hz, 2H), 8.00-7.86 (m, 3H), 7.76 (d, J = 8.7 Hz, 1H), 4.22 (t, J = 6.9 Hz, 2H), 1.85 (q, J = 7.2 Hz, 2H), 0.85 (t, J = 7.3 Hz, 3H). | 9<br>1.06<br>(388.1) |
| 51 | 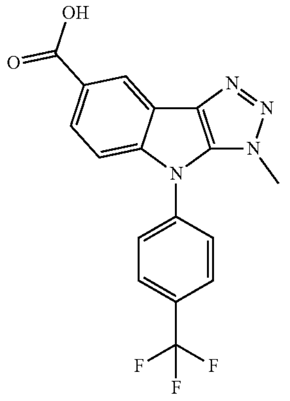 [SMILES: Cn1nnc2c3cc(C(=O)O)ccc3n(-c3ccc(C(F)(F)F)cc3)c21]<br>3-methyl-4-[4-(trifluoromethyl)phenyl]-3H,4H-[1,2,3]triazolo[4,5-b]indole-7-carboxylic acid | (300 MHz, DMSO-d6) δ 8.52 (d, J = 1.7 Hz, 1H), 8.14-7.96 (m, 5H), 7.91 (d, J = 8.8 Hz, 1H), 4.37 (s, 3H). | 12<br>0.797<br>(359.1) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 52 | 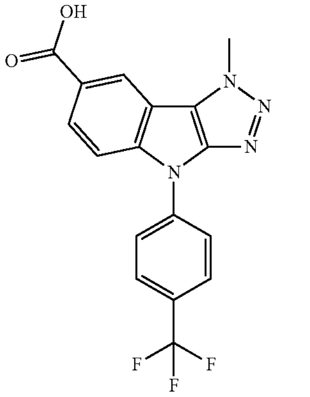 [SMILES: Cn1nnc2c1c1cc(C(=O)O)ccc1n2-c1ccc(C(F)(F)F)cc1]<br>1-methyl-4-[4-(trifluoromethyl)phenyl]-1H,4H-[1,2,3]triazolo[4,5-b]indole-7-carboxylic acid | (400 MHz, DMSO-d6) δ 12.98 (s, 1H), 8.68 (s, 1H), 8.14-8.05 (m, 3H), 8.05-8.00 (m, 2H), 7.98-7.93 (m, 1H), 4.50 (s, 3H). | 7<br>0.73 min<br>(361.2) |
| 53 | 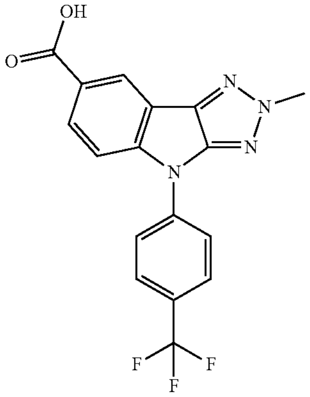 [SMILES: Cn1nc2c3cc(C(=O)O)ccc3n(-c3ccc(C(F)(F)F)cc3)c2n1]<br>2-methyl-4-[4-(trifluoromethyl)phenyl]-2H,4H-[1,2,3]triazolo[4,5-b]indole-7-carboxylic acid | (300 MHz, DMSO-d6) δ 8.51 (d, J = 1.7 Hz, 1H), 8.13-7.95 (m, 5H), 7.89 (d, J = 8.8 Hz, 1H), 4.36 (s, 3H). | 9<br>1.01<br>(359.1) |
| 54 | 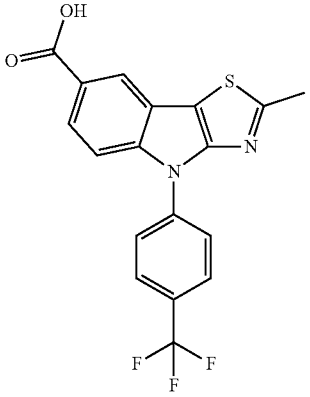<br>2-methyl-4-[4-(trifluoromethyl)phenyl]-4H-[1,3]thiazolo[4,5-b]indole-7-carboxylic acid | (300 MHz, DMSO-d6) δ 8.50 (d, J = 1.7 Hz, 1H), 7.99 (s, 3H), 7.92 (dd, J = 8.8, 1.7 Hz, 2H), 7.70 (d, J = 8.8 Hz, 1H), 2.82 (s, 3H) | 9<br>1.80<br>(377.0) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 55 | 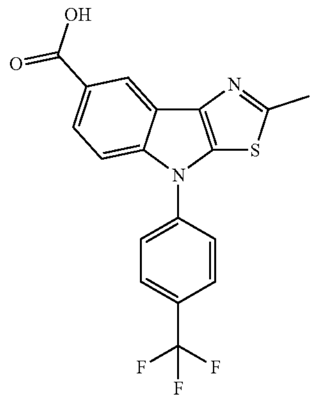 2-methyl-4-[4-(trifluoromethyl)phenyl]-4H-[1,3]thiazolo[5,4-b]indole-7-carboxylic acid | (300 MHz, DMSO-d6) δ 12.87 (s, 1H), 8.48 (d, J = 1.6 Hz, 1H), 8.10-7.89 (m, 5H), 7.80 (d, J = 8.8 Hz, 1H), 2.84 (s, 3H). | 10 0.98 (377.0) |
| 56 | 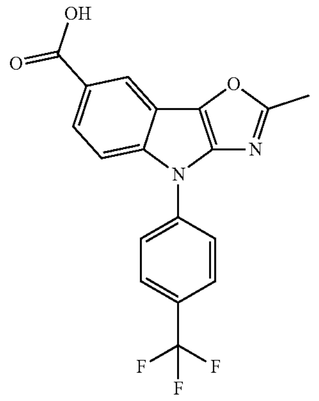 2-methyl-4-[4-(trifluoromethyl)phenyl]-4H-[1,3]oxazolo[4,5-b]indole-7-carboxylic acid | | |
| 57 | 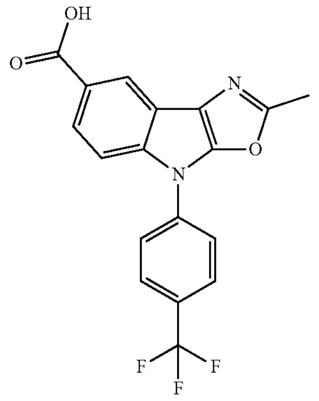 2-methyl-4-[4-(trifluoromethyl)phenyl]-4H-[1,3]oxazolo[5,4-b]indole-7-carboxylic acid | | |

TABLE 1-continued

| Compound No. (Example No.) | Structure and Name | $^1$H-NMR | Conditions and elution time (min) LCMS (M + H$^+$) |
|---|---|---|---|
| Table 1 below shows exemplary compounds of the present invention. They have been synthesized as described in the Examples above or similar thereto. | | | |
| 58 | 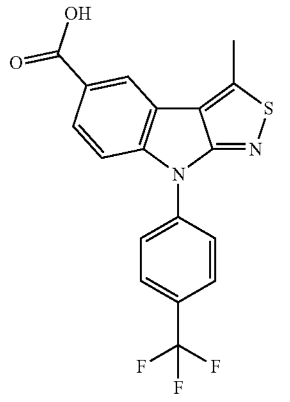 [SMILES: Cc1snc2c1c1cc(C(=O)O)ccc1n2-c1ccc(C(F)(F)F)cc1] 3-methyl-8-[4-(trifluoromethyl)phenyl]-8H-[1,2]thiazolo[3,4-b]indole-5-carboxylic acid | (300 MHz, DMSO-d6) δ 8.48 (s, 1H), 8.20-7.84 (m, 5H), 7.60 (d, J = 8.7 Hz, 1H), 2.96 (s, 3H). | 10<br>6.30<br>(375.0) |
| 59 | 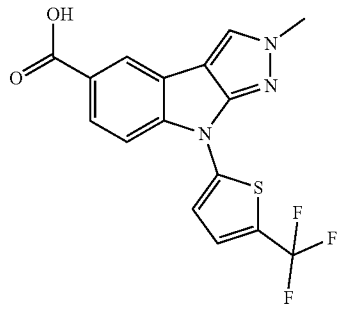 [SMILES: Cn1cc2c3cc(C(=O)O)ccc3n(-c3ccc(C(F)(F)F)s3)c2n1] 2-methyl-8-[5-(trifluoromethyl)thiophen-2-yl]-2H,8H-pyrazolo[3,4-b]indole-5-carboxylic acid | (400 MHz, DMSO-d6) δ 12.82-12.75 (m, 1H), 8.42 (d, J = 1.7 Hz, 1H), 8.22 (s, 1H), 7.98 (dd, J = 8.7, 1.8 Hz, 1H), 7.84 (d, J = 8.7 Hz, 1H), 7.81-7.79 (m, 1H), 7.62-7.59 (m, 1H), 4.05 (s, 3H). | 8<br>1.80<br>(365.00) |
| 60 | 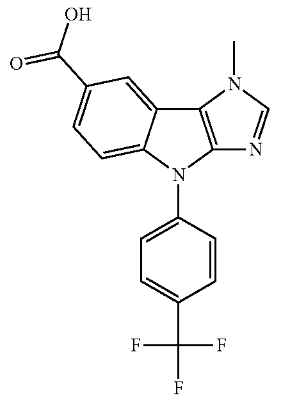 [SMILES: Cn1cnc2c1c1cc(C(=O)O)ccc1n2-c1ccc(C(F)(F)F)cc1] 1-methyl-4-[4-(trifluoromethyl)phenyl]-1H,4H-imidazo[4,5-b]indole-7-carboxylic acid | (300 MHz, DMSO-d6) δ 8.58-8.52 (m, 1H), 8.12-7.98 (m, 6H), 7.84-7.75 (m, 1H), 2.85-2.79 (m, 3H). | 7<br>0.94<br>(360.1) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 61 | 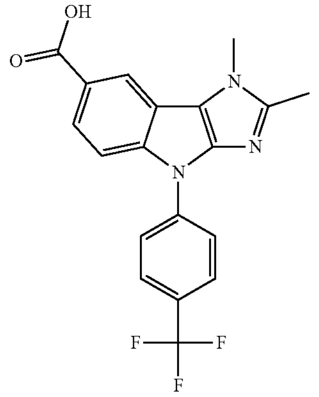 [SMILES: Cc1nc2c(c3cc(C(=O)O)ccc3n2-c2ccc(C(F)(F)F)cc2)n1C] 1,2-dimethyl-4-[4-(trifluoromethyl)phenyl]-1H,4H-imidazo[4,5-b]indole-7-carboxylic acid | (400 MHz, DMSO-d6) δ 8.40 (d, J = 1.5 Hz, 1H), 8.04 (d, J = 8.4 Hz, 2H), 7.95 (d, J = 8.6 Hz, 2H), 7.86-7.76 (m, 2H), 3.99 (s, 3H), 2.50 (s, 3H). | 7 0.83 (374.2) |
| 62 | 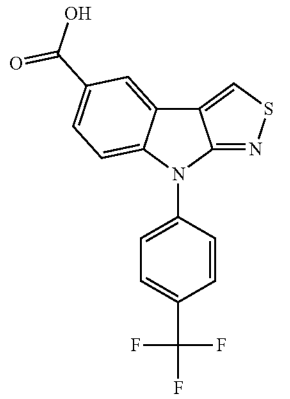 [SMILES: O=C(O)c1ccc2c(c1)c1csnc1n2-c1ccc(C(F)(F)F)cc1] 8-[4-(trifluoromethyl)phenyl]-8H-[1,2]thiazolo[3,4-b]indole-5-carboxylic acid | (300 MHz, DMSO-ppm) δ 12.89 (s, 1H), 9.53 (s, 1H), 8.68 (d, J = 1.7 Hz, 1H), 8.27-7.92 (m, 5H), 7.64 (d, J = 8.7 Hz, 1H). | 11 1.337 min 363.00 (M + H) |
| 63 | 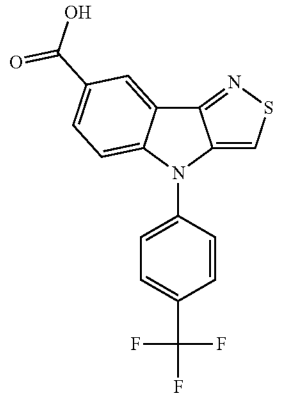 [SMILES: O=C(O)c1ccc2c(c1)c1nscc1n2-c1ccc(C(F)(F)F)cc1] 4-[4-(trifluoromethyl)phenyl]-4H-[1,2]thiazolo[4,3-b]indole-7-carboxylic acid | (300 MHz, DMSO) δ 12.98 (s, 1H), 8.84 (s, 1H), 8.61 (d, J = 1.7 Hz, 1H), 8.20-8.07 (m, 1H), 8.00 (s, 4H), 7.74 (d, J = 8.8 Hz, 1H). | 10 1.75 (362.90) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 64 (Ex. 35) | 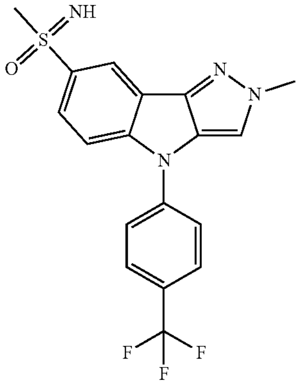 [SMILES: Cn1cc2c(n1)c1cc(S(C)(=N)=O)ccc1n2-c1ccc(C(F)(F)F)cc1]<br>imino(methyl){2-methyl-4-[4-(trifluoromethyl)phenyl]-2H,4H-pyrazolo[4,3-b]indol-7-yl}-??-sulfanone | (300 MHz, DMSO-d6) δ 8.43 (d, J = 1.3 Hz, 1H), 8.14 (s, 1H), 7.95 (d, J = 1.4 Hz, 6H), 4.20 (s, 1H), 4.11 (s, 3H), 3.12 (s, 3H). | 10<br>0.746<br>(393.0) |
| 65 (Ex. 36) | 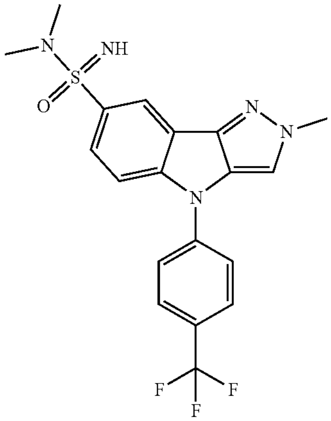<br>N,N,2-trimethyl-4-[4-(trifluoromethyl)phenyl]-2H,4H-pyrazolo[4,3-b]indole-7-sulfonoimidamide | (400 MHz, DMSO-d6) δ 8.29 (d, J = 1.9 Hz, 1H), 8.15 (s, 1H), 7.96 (d, J = 3.4 Hz, 5H), 7.83 (dd, J = 8.9, 1.9 Hz, 1H), 4.37 (s, 1H), 4.12 (s, 3H), 2.59 (s, 6H). | 12<br>1.533<br>(422.1) |
| 66 (Ex. 32) | 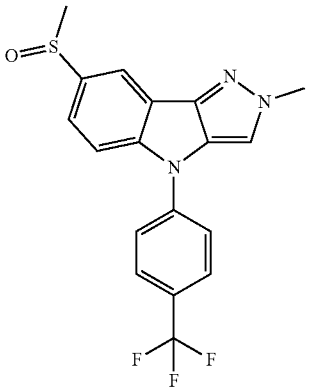 [SMILES: Cn1cc2c(n1)c1cc(S(C)=O)ccc1n2-c1ccc(C(F)(F)F)cc1]<br>7-methanesulfinyl-2-methyl-4-[4-(trifluoromethyl)phenyl]-2H,4H-pyrazolo[4,3-b]indole | (300 MHz, DMSO-d6) δ 8.23 (d, J = 1.8 Hz, 1H), 8.14 (s, 1H), 7.97 (d, J = 8.6 Hz, 5H), 7.73 (dd, J = 8.8, 1.9 Hz, 1H), 4.12 (s, 3H), 2.82 (s, 3H). | 9<br>1.517<br>(378.0) |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 67 | 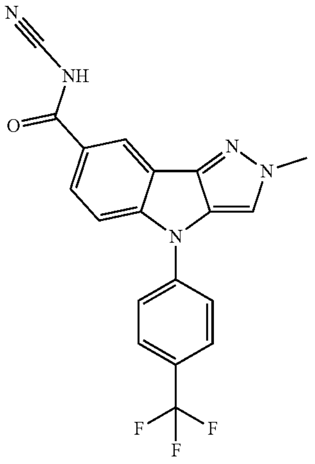 [SMILES: Cn1cc2c(n1)c1cc(C(=O)NC#N)ccc1n2-c1ccc(C(F)(F)F)cc1] N-cyano-2-methyl-4-[4-(trifluoromethyl)phenyl]-2H,4H-pyrazolo[4,3-b]indole-7-carboxamide | (300 MHz, DMSO) δ 8.53 (d, J = 1.8 Hz, 1 H), 8.14 (s, 1 H), 8.02-7.88 (m, 6 H), 4.10 (s, 3 H). | 10 0.662 (384.1) |
| 68 | 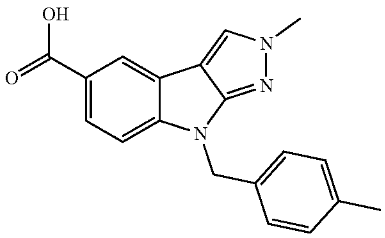 [SMILES: Cc1ccc(Cn2c3ccc(C(=O)O)cc3c3cn(C)nc32)cc1] 2-methyl-8-[(4-methylphenyl)methyl]-2H,8H-pyrazolo[3,4-b]indole-5-carboxylic acid | (400 MHz, DMSO-d6) δ 12.43 (s, 1H), 8.32 (d, J = 1.7 Hz, 1H), 8.07 (s, 1H), 7.83 (dd, J = 8.6, 1.8 Hz, 1H), 7.46 (d, J = 8.6 Hz, 1H), 7.17 (d, J = 8.1 Hz, 2H), 7.09 (d, J = 7.9 Hz, 2H), 5.34 (s, 2H), 3.99 (s, 3H), 2.23 (s, 3H). | 8 1.574 (320.1) |
| 69 (Ex. 34) | 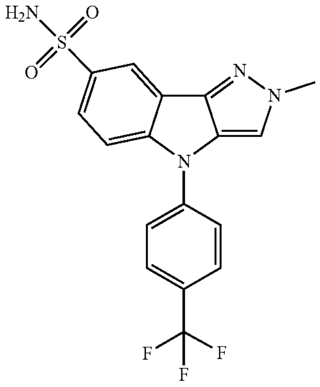 [SMILES: Cn1cc2c(n1)c1cc(S(N)(=O)=O)ccc1n2-c1ccc(C(F)(F)F)cc1] 2-methyl-4-[4-(trifluoromethyl)phenyl]-2H,4H-pyrazolo[4,3-b]indole-7-sulfonamide | (400 MHz, DMSO-d6) δ 8.35 (d, J = 1.9 Hz, 1H), 8.15 (s, 1H), 7.95 (s, 3H), 7.94 (s, 1H), 7.87 (dd, J = 8.8, 1.9 Hz, 1H), 7.37 (s, 2H), 4.12 (s, 3H). | 10 1.505 (395.0) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 70 | 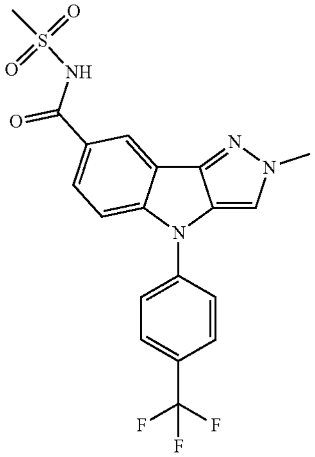 [SMILES: Cn1cc2c(n1)c1cc(C(=O)NS(C)(=O)=O)ccc1n2-c1ccc(C(F)(F)F)cc1] N-methanesulfonyl-2-methyl-4-[4-(trifluoromethyl)phenyl]-2H,4H-pyrazolo[4,3-b]indole-7-carboxamide | (300 MHz, DMSO) δ 12.14 (s, 1 H), 8.57 (d, J = 1.8 Hz, 1 H), 8.11 (s, 1 H), 8.06-8.00 (m, 1 H), 7.94 (s, 4 H), 7.85 (d, J = 8.9 Hz, 1 H), 4.10 (s, 3 H), 3.29(s, 3 H). | 10<br>1.298<br>(434.85) |
| 71 | 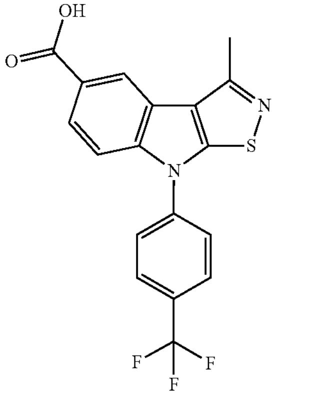 [SMILES: Cc1nsc2c1c1cc(C(=O)O)ccc1n2-c1ccc(C(F)(F)F)cc1] 3-methyl-8-[4-(trifluoromethyl)phenyl]-8H-[1,2]thiazolo[5,4-b]indole-5-carboxylic acid | (300 MHz, DMSO-d6) δ 8.59-8.53 (m, 1H), 8.11-7.97 (m, 5H), 7.85-7.76 (m, 1H), 2.85-2.79 (m, 3H). | 7<br>0.83<br>(377.1) |
| 72 | 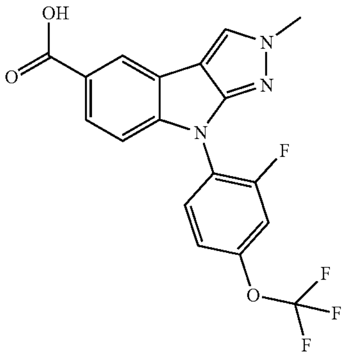 [SMILES: Cn1cc2c3cc(C(=O)O)ccc3n(-c3ccc(OC(F)(F)F)cc3F)c2n1] 8-[2-fluoro-4-(trifluoromethoxy)phenyl]-2-methyl-2H,8H-pyrazolo[3,4-b]indole-5-carboxylic acid | (500 MHz, DMSO-d6) δ 12.68-12.64 (m, 1H), 8.42-8.40 (m, 1H), 8.19 (s, 1H), 7.91 (t, J = 8.7 Hz, 1H), 7.88 (dd, J = 8.6, 1.7 Hz, 1H), 7.81-7.77 (m, 1H), 7.52-7.48 (m, 1H), 7.21 (dd, J = 8.6, 2.3 Hz, 1H), 3.99 (s, 3H). | 8<br>1.662<br>(393.8) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 73 | 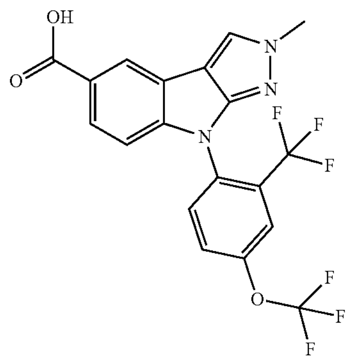 [SMILES: Cn1cc2c3cc(C(=O)O)ccc3n(-c3ccc(OC(F)(F)F)cc3C(F)(F)F)c2n1] 2-methyl-8-[4-(trifluoromethoxy)-2-(trifluoromethyl)phenyl]-2H,8H-pyrazolo[3,4-b]indole-5-carboxylic acid | (400 MHz, DMSO-d6) δ 12.60 (br. s, 1H), 8.39 (d, J = 1.7 Hz, 1H), 8.14 (s, 1H), 8.09 (d, J = 2.8 Hz, 1H), 7.96 (dt, J = 8.8, 1.9 Hz, 1H), 7.85-7.75 (m, 2H), 6.93 (d, J = 8.5 Hz, 1H), 3.95 (s, 3H). | 8 1.732 (444.0) |
| 74 | 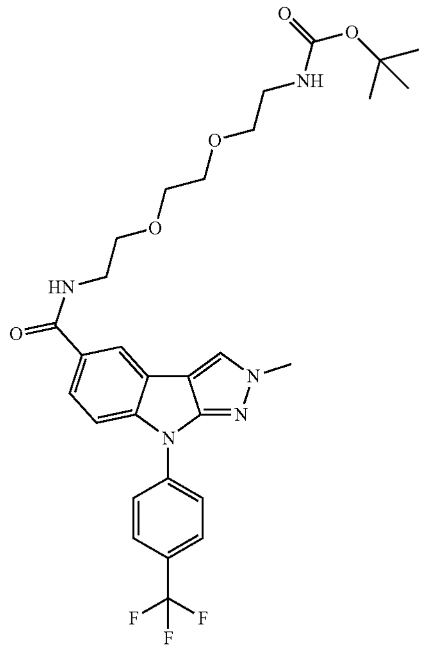 [SMILES: Cn1cc2c3cc(C(=O)NCCOCCOCCNC(=O)OC(C)(C)C)ccc3n(-c3ccc(C(F)(F)F)cc3)c2n1] tert-butyl N-(2-{2-[2-({2-methyl-8-[4-(trifluoromethyl)phenyl]-2H,8H-pyrazolo[3,4-b]indol-5-yl}formamido)-ethoxy]ethoxy}ethyl)carbamate | (300 MHz, DMSO-d6) δ 8.56-8.47 (m, 1H), 8.34 (d, J = 1.8 Hz, 1H), 8.20 (s, 1H), 8.08 (d, J = 8.4 Hz, 2H), 7.96 (d, J = 8.6 Hz, 2H), 7.90-7.81 (m, 1H), 7.76 (d, J = 8.7 Hz, 1H), 6.74 (s, 1H), 4.03 (s, 3H), 3.60-3.42 (m, 8H), 3.37 (d, J = 6.1 Hz, 2H), 3.11-2.99 (m, 2H), 1.35 (s, 9H). | 9 1.12 min (590.3) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 75 | 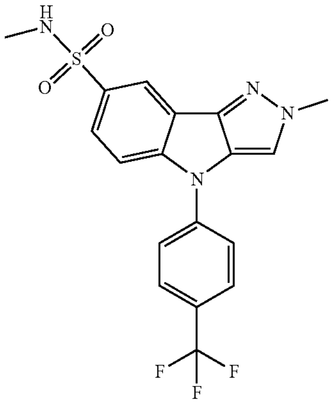<br>N,2-dimethyl-4-[4-(trifluoromethyl)phenyl]-2H,4H-pyrazolo[4,3-b]indole-7-sulfonamide | (400 MHz, DMSO-d6) δ 8.29 (d, J = 1.8 Hz, 1H), 8.15 (s, 1H), 7.96 (s, 5H), 7.81 (dd, J = 8.8, 1.9 Hz, 1H), 7.44 (q, J = 5.0 Hz, 1H), 4.12 (s, 3H), 2.44 (d, J = 5.2 Hz, 3H). | 9<br>0.92<br>(409.0) |
| 76 | 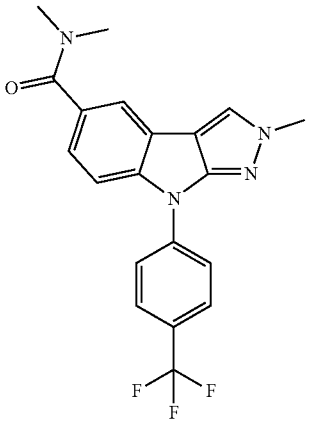 [SMILES: CN(C)C(=O)c1ccc2c(c1)c1cn(C)nc1n2-c1ccc(C(F)(F)F)cc1]<br>N,N,2-trimethyl-8-[4-(trifluoromethyl)phenyl]-2H,8H-pyrazolo[3,4-b]indole-5-carboxamide | (300 MHz, DMSO-d6) δ 8.15 (s, 1H), 8.09 (d, J = 8.5 Hz, 2H), 7.96 (d, J = 8.7 Hz, 2H), 7.90 (d, J = 1.7 Hz, 1H), 7.76 (d, J = 8.5 Hz, 1H), 7.37 (dd, J = 8.5, 1.8 Hz, 1H), 4.03 (s, 3H), 3.02 (s, 6H). | 9<br>0.93 min<br>(387.0) |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 77 | 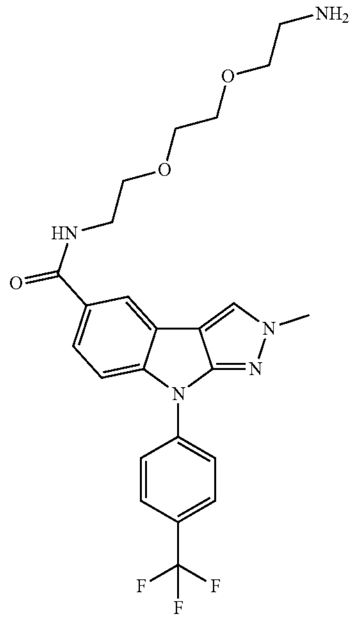 [SMILES: Cn1cc2c3cc(C(=O)NCCOCCOCCN)ccc3n(-c3ccc(C(F)(F)F)cc3)c2n1]<br>N-{2-[2-(2-aminoethoxy)ethoxy]ethyl}-2-methyl-8-[4-(trifluoromethyl)phenyl]-2H,8H-pyrazolo[3,4-b]indole-5-carboxamide | (300 MHz, DMSO-d6) δ 8.54 (t, J = 5.4 Hz, 1H), 8.34 (d, J = 1.8 Hz, 1H), 8.20 (s, 1H), 8.08 (d, J = 8.4 Hz, 2H), 7.96 (d, J = 8.5 Hz, 2H), 7.85 (dd, J = 8.7, 1.8 Hz, 1H), 7.77 (d, J = 8.7 Hz, 1H), 4.03 (s, 3H), 3.67-3.45 (m, 9H), 3.39-3.33 (m, 3H), 2.68-2.60 (m, 2H). | 7<br>0.74 min<br>(490.1) |
| 78 | 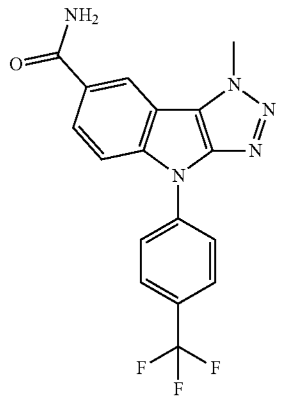 [SMILES: Cn1nnc2c1c1cc(C(N)=O)ccc1n2-c1ccc(C(F)(F)F)cc1]<br>1-methyl-4-[4-(trifluoromethyl)phenyl]-1H,4H-[1,2,3]triazolo[4,5-b]indole-7-carboxamide | (400 MHz, DMSO-d6) δ 8.70 (s, 1H), 8.19-7.88 (m, 7H), 7.45 (s, 1H), 4.50 (s, 3H). | 7<br>1.238<br>(360.2) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 79 | 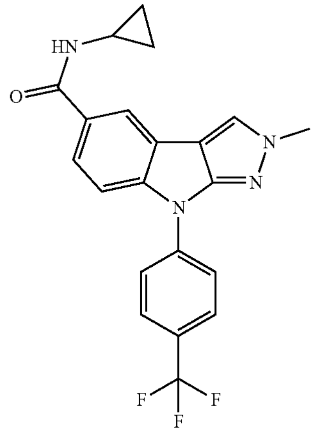 [SMILES: Cn1cc2c3cc(C(=O)NC4CC4)ccc3n(-c3ccc(C(F)(F)F)cc3)c2n1] N-cyclopropyl-2-methyl-8-[4-(trifluoromethyl)phenyl]-2H,8H-pyrazolo[3,4-b]indole-5-carboxamide | (300 MHz, DMSO-d6) δ 8.45 (d, J = 4.2 Hz, 1H), 8.29 (d, J = 1.7 Hz, 1H), 8.18 (s, 1H), 8.06 (d, J = 8.4 Hz, 2H), 7.95 (d, J = 8.5 Hz, 2H), 7.86-7.77 (m, 1H), 7.74 (d, J = 8.7 Hz, 1H), 4.02 (s, 3H), 2.94-2.80 (m, 1H), 0.76-0.62 (m, 2H), 0.62-0.53 (m, 2H). | 7<br>1.42<br>(399.2) |
| 80 | 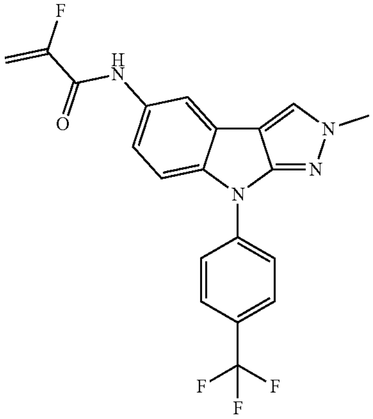 [SMILES: C=C(F)C(=O)Nc1ccc2c(c1)c1cn(C)nc1n2-c1ccc(C(F)(F)F)cc1] 2-fluoro-N-{2-methyl-8-[4-(trifluoromethyl)phenyl]-2H,8H-pyrazolo[3,4-b]indol-5-yl}prop-2-enamide | (300 MHz, DMSO-d6) δ 10.35 (s, 1H), 8.28-8.13 (m, 2H), 8.08 (d, J = 8.4 Hz, 2H), 7.92 (d, J = 8.5 Hz, 2H), 7.75 (d, J = 9.0 Hz, 1H), 7.59 (dd, J = 9.0, 2.2 Hz, 1H), 5.72 (dd, J = 47.7, 3.6 Hz, 1H), 5.42 (dd, J = 15.7, 3.6 Hz, 1H), 4.01 (s, 3H). | 9<br>1.136<br>(403.1) |
| 81 | 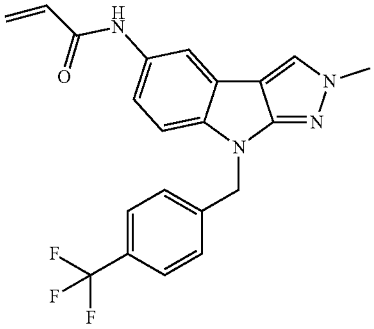 [SMILES: C=CC(=O)Nc1ccc2c(c1)c1cn(C)nc1n2Cc1ccc(C(F)(F)F)cc1] N-(2-methyl-8-{[4-(trifluoromethyl)-phenyl]methyl}-2H,8H-pyrazolo[3,4-b]indol-5-yl)prop-2-enamide | (300 MHz, DMSO-d6) δ 10.04 (s, 1H), 8.16 (d, J = 1.9 Hz, 1H), 8.04 (s, 1H), 7.66 (d, J = 8.0 Hz, 2H), 7.47-7.28 (m, 4H), 6.45 (dd, J = 17.0, 10.0 Hz, 1H), 6.23 (dd, J = 16.9, 2.2 Hz, 1H), 5.71 (dd, J = 10.0, 2.2 Hz, 1H), 5.42 (s, 2H), 3.95 (s, 3H). | 9<br>1.017<br>(399.1) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 82 | 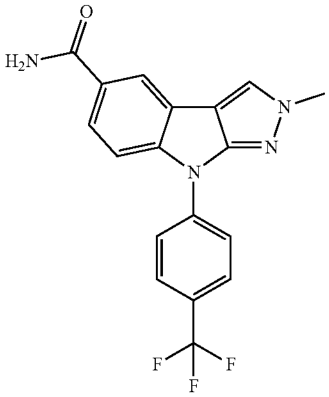 [SMILES: Cn1cc2c3cc(C(N)=O)ccc3n(-c3ccc(C(F)(F)F)cc3)c2n1] 2-methyl-8-[4-(trifluoromethyl)phenyl]-2H,8H-pyrazolo[3,4-b]indole-5-carboxamide | (300 MHz, DMSO-d6) δ 8.37 (d, J = 1.8 Hz, 1H), 8.19 (s, 1H), 8.09 (d, J = 8.4 Hz, 2H), 7.97 (t, J = 7.7 Hz, 3H), 7.93-7.83 (m, 1H), 7.75 (d, J = 8.7 Hz, 1H), 7.26 (s, 1H), 4.03 (s, 3H). | 9 0.84 (359.0) |
| 83 | 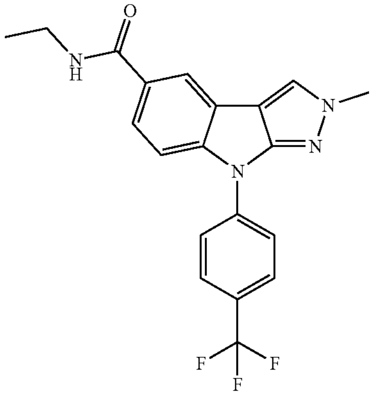 [SMILES: CCNC(=O)c1ccc2c(c1)c1cn(C)nc1n2-c1ccc(C(F)(F)F)cc1] N-ethyl-2-methyl-8-[4-(trifluoromethyl)phenyl]-2H,8H-pyrazolo[3,4-b]indole-5-carboxamide | (300 MHz, DMSO-d6) δ 8.53-8.44 (m, 1H), 8.33 (d, J = 1.8 Hz, 1H), 8.20 (s, 1H), 8.08 (d, J = 8.4 Hz, 2H), 7.96 (d, J = 8.5 Hz, 2H), 7.89-7.80 (m, 1H), 7.76 (d, J = 8.7 Hz, 1H), 4.03 (s, 3H), 3.36 (d, J = 7.1 Hz, 1H), 3.31-3.27 (m, 1H), 1.21-1.10 (m, 3H). | 7 1.43 (387.2) |
| 84 | 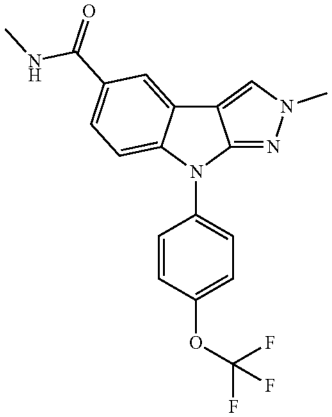 N,2-dimethyl-8-[4-(trifluoromethoxy)phenyl]-2H,8H-pyrazolo[3,4-b]indole-5-carboxamide | (300 MHz, DMSO-d6) δ 8.42 (d, J = 4.7 Hz, 1H), 8.30 (d, J = 1.7 Hz, 1H), 8.17 (s, 1H), 7.97-7.86 (m, 2H), 7.91-7.75 (m, 1H), 7.69-7.55 (m, 3H), 4.00 (s, 3H), 2.80 (d, J = 4.4 Hz, 3H). | 9 0.892 (389.0) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 85 | 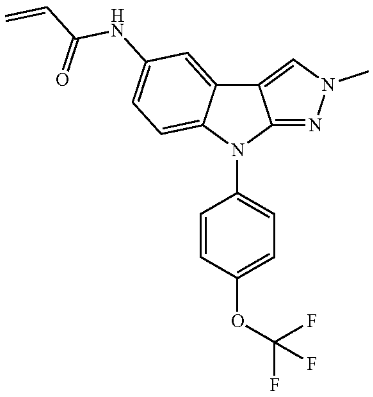 [SMILES: C=CC(=O)Nc1ccc2c(c1)c1cn(C)nc1n2-c1ccc(OC(F)(F)F)cc1] N-{2-methyl-8-[4-(trifluoromethoxy)-phenyl]-2H,8H-pyrazolo[3,4-b]indol-5-yl}prop-2-enamide | (300 MHz, DMSO-d6) δ 10.17 (s, 1H), 8.25 (s, 1H), 8.15 (s, 1H), 7.92 (d, J = 9.0 Hz, 2H), 7.59 (dd, J = 12.2, 8.7 Hz, 3H), 7.44 (d, J = 8.8 Hz, 1H), 6.47 (dd, J = 16.9, 9.9 Hz, 1H), 6.29 (s, 1H), 5.74 (d, J = 11.7 Hz, 1H), 3.99 (s, 3H). | 9 1.742 (401.1) |
| 86 | 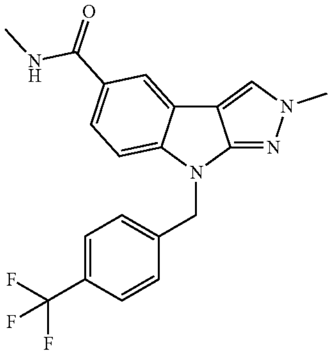 N,2-dimethyl-8-{[4-(trifluoromethyl)-phenyl]methyl}-2H,8H-pyrazolo[3,4-b]indole-5-carboxamide | (300 MHz, DMSO-d6) δ 8.31 (d, J = 4.6 Hz, 1H), 8.23 (d, J = 1.7 Hz, 1H), 8.07 (s, 1H), 7.77-7.70 (m, 1H), 7.66 (d, J = 8.1 Hz, 2H), 7.50-7.38 (m, 3H), 5.49 (s, 2H), 3.97 (s, 3H), 2.78 (d, J = 4.5 Hz, 3H). | 9 0.952 (387.1) |
| 87 | 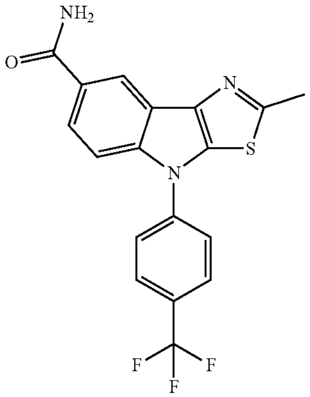 2-methyl-4-[4-(trifluoromethyl)phenyl]-4H-[1,3]thiazolo[5,4-b]indole-7-carboxamide | (300 MHz, DMSO-d6, ppm) δ 8.53 (d, J = 1.7 Hz, 1H), 8.09 (s, 1H), 8.06-7.94 (m, 4H), 7.94-7.85 (m, 1H), 7.76 (d, J = 8.8 Hz, 1H), 7.33 (s, 1H), 2.82 (s, 3H). | 7 0.950 374.0 |

TABLE 1-continued

| Compound No. (Example No.) | Structure and Name | $^1$H-NMR | Conditions and elution time (min) LCMS (M + H$^+$) |
|---|---|---|---|
| | Table 1 below shows exemplary compounds of the present invention. They have been synthesized as described in the Examples above or similar thereto. | | |
| 88 | 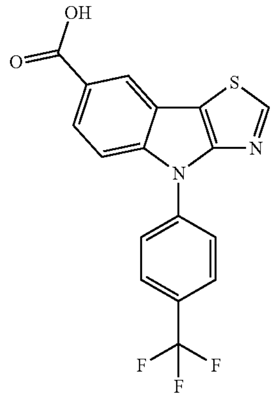 [SMILES: O=C(O)c1ccc2c(c1)c1scnc1n2-c1ccc(C(F)(F)F)cc1] 4-[4-(trifluoromethyl)phenyl]-4H-[1,3]thiazolo[4,5-b]indole-7-carboxylic acid | (400 MHz, DMSO-d6) δ 9.27 (s, 1H), 8.65 (d, J = 1.7 Hz, 1H), 8.10-7.97 (m, 5H), 7.80 (d, J = 8.8 Hz, 1H). | 9 0.972 (363.1) |
| 89 | 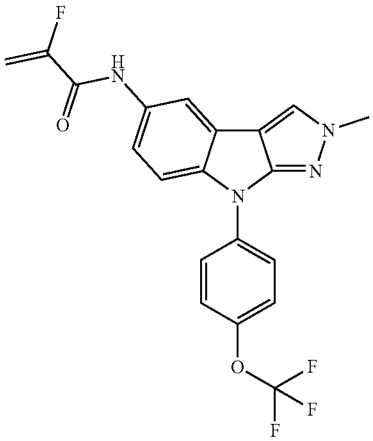 [SMILES: C=C(F)C(=O)Nc1ccc2c(c1)c1cn(C)nc1n2-c1ccc(OC(F)(F)F)cc1] 2-fluoro-N-{2-methyl-8-[4-(trifluoromethoxy)phenyl]-2H,8H-pyrazolo[3,4-b]indol-5-yl}prop-2-enamide | (300 MHz, DMSO-d6) δ 10.32 (s, 1H), 8.21 (d, J = 2.1 Hz, 1H), 8.15 (s, 1H), 7.97-7.88 (m, 2H), 7.67-7.51 (m, 4H), 5.71 (dd, J = 47.7, 3.6 Hz, 1H), 5.41 (dd, J = 15.7, 3.6 Hz, 1H), 3.99 (s, 3H). | 9 1.15 (419.1) |

TABLE 1-continued

| Compound No. (Example No.) | Structure and Name | $^1$H-NMR | Conditions and elution time (min) LCMS (M + H$^+$) |
|---|---|---|---|
| Table 1 below shows exemplary compounds of the present invention. They have been synthesized as described in the Examples above or similar thereto. | | | |
| 90 | 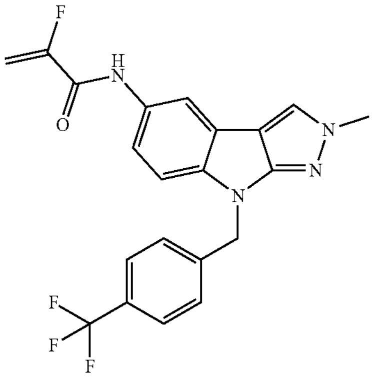 [SMILES: C=C(F)C(=O)Nc1ccc2c(c1)c1cn(C)nc1n2Cc1ccc(C(F)(F)F)cc1] 2-fluoro-N-(2-methyl-8-{[4-(trifluoro-methyl)phenyl]methyl}-2H,8H-pyrazolo[3,4-b]indol-5-yl)prop-2-enamide | (300 MHz, DMSO-d6) δ 10.21 (s, 1H), 8.10 (s, 1H), 8.05 (s, 1H), 7.66 (d, J = 8.0 Hz, 2H), 7.52-7.28 (m, 4H), 5.68 (d, J = 44.1 Hz, 1H), 5.47-5.31 (m, 3H), 3.96 (s, 3H). | 7 1.227 (417.2) |
| 91 | 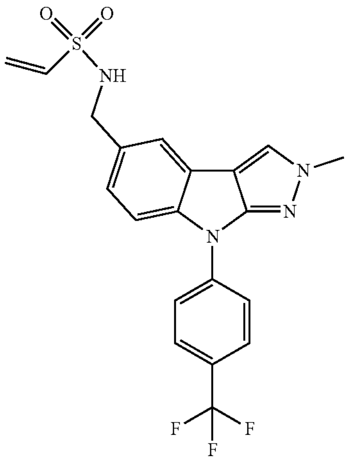 [SMILES: C=CS(=O)(=O)NCc1ccc2c(c1)c1cn(C)nc1n2-c1ccc(C(F)(F)F)cc1] N-({2-methyl-8-[4-(trifluoromethyl)-phenyl]-2H,8H-pyrazolo[3,4-b]indol-5-yl}methyl)ethene-1-sulfonamide | (300 MHz, DMSO-d6) δ 8.15 (s, 1H), 8.06 (d, J = 8.5 Hz, 2H), 7.92 (d, J = 8.6 Hz, 2H), 7.85 (s, 1H), 7.78-7.67 (m, 2H), 7.26 (dd, J = 8.6, 1.9 Hz, 1H), 6.68 (dd, J = 16.5, 10.0 Hz, 1H), 6.04 (d, J = 16.5 Hz, 1H), 5.94 (d, J = 10.0 Hz, 1H), 4.15 (s, 2H), 4.00 (s, 3H). | 9 0.990 (435.1) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 92 | 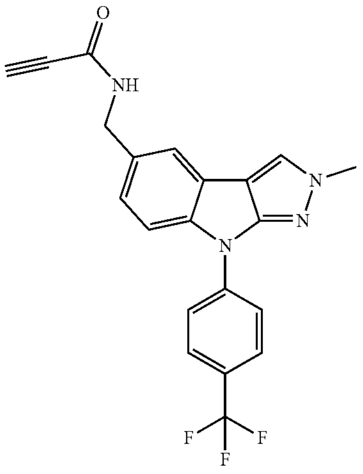 [SMILES: C#CC(=O)NCc1ccc2c(c1)c1cn(C)nc1n2-c1ccc(C(F)(F)F)cc1] N-({2-methyl-8-[4-(trifluoromethyl)-phenyl]-2H,8H-pyrazolo[3,4-b]indol-5-yl}methyl)prop-2-ynamide | (300 MHz, DMSO-d6) δ 9.29 (t, J = 6.0 Hz, 1H), 8.15 (s, 1H), 8.06 (d, J = 8.5 Hz, 2H), 7.92 (d, J = 8.7 Hz, 2H), 7.75-7.63 (m, 2H), 7.20 (dd, J = 8.5, 1.8 Hz, 1H), 4.38 (d, J = 6.0 Hz, 2H), 4.16 (s, 1H), 4.00 (s, 3H). | 9 1.719 (397.0) |
| 93 | 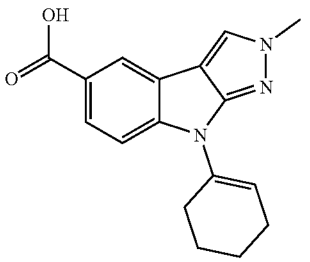 [SMILES: Cn1cc2c3cc(C(=O)O)ccc3n(C3=CCCCC3)c2n1] 8-(cyclohex-1-en-1-yl)-2-methyl-2H,8H-pyrazolo[3,4-b]indole-5-carboxylic acid | | |
| 94 | 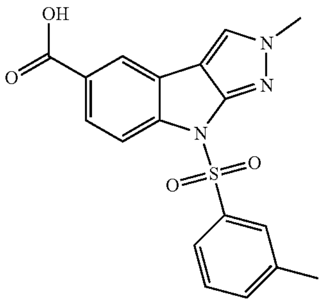 [SMILES: Cc1cccc(S(=O)(=O)n2c3ccc(C(=O)O)cc3c3cn(C)nc32)c1] 2-methyl-8-(3-methylbenzenesulfonyl)-2H,8H-pyrazolo[3,4-b]indole-5-carboxylic acid | | |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + $H^+$) |
|---|---|---|---|
| 95 | 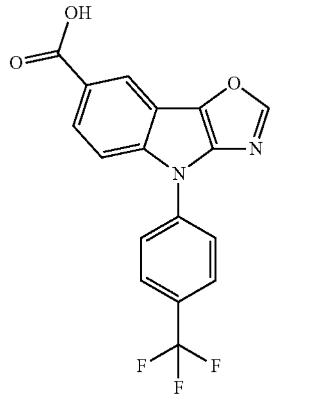 [SMILES: O=C(O)c1ccc2c(c1)c1ocnc1n2-c1ccc(C(F)(F)F)cc1] 4-[4-(trifluoromethyl)phenyl]-4H-[1,3]oxazolo[4,5-b]indole-7-carboxylic acid | (400 MHz, DMSO-d6) δ 8.77 (s, 1H), 8.45 (d, J = 1.6 Hz, 1H), 8.04 (s, 4H), 8.00-7.89 (m, 2H). | 16 1.591 (345.0) |
| 96 | 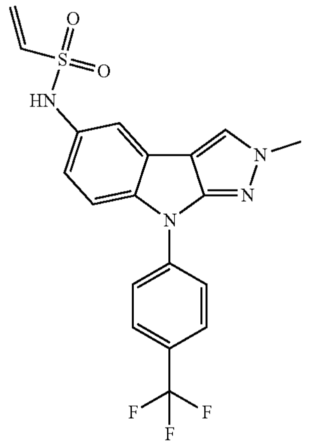 [SMILES: C=CS(=O)(=O)Nc1ccc2c(c1)c1cn(C)nc1n2-c1ccc(C(F)(F)F)cc1] N-{2-methyl-8-[4-(trifluoromethyl)-phenyl]-2H,8H-pyrazolo[3,4-b]indol-5-yl}ethene-1-sulfonamide | (300 MHz, DMSO-d6) δ 9.83 (s, 1H), 8.16 (s, 1H), 8.05 (d, J = 8.5 Hz, 2H), 7.92 (d, J = 8.5 Hz, 2H), 7.70 (d, J = 8.8 Hz, 1H), 7.60 (d, J = 2.2 Hz, 1H), 7.12 (dd, J = 8.8, 2.3 Hz, 1H), 6.76 (dd, J = 16.4, 10.0 Hz, 1H), 6.07 ? 5.95 (m, 2H), 4.00 (s, 3H). | 9 0.962 (421.0) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 97 | 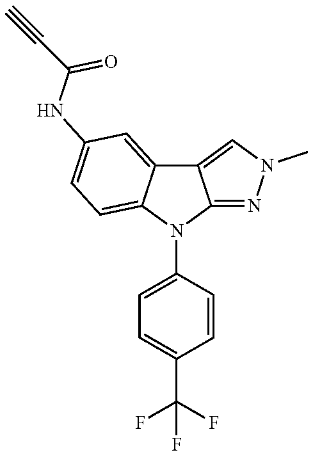 [SMILES: C#CC(=O)Nc1ccc2c(c1)c1cn(C)nc1n2-c1ccc(C(F)(F)F)cc1] N-{2-methyl-8-[4-(trifluoromethyl)-phenyl]-2H,8H-pyrazolo[3,4-b]indol-5-yl}prop-2-ynamide | (300 MHz, DMSO-d6) δ 10.84 (s, 1H), 8.20-8.11 (m, 2H), 8.07 (d, J = 8.4 Hz, 2H), 7.92 (d, J = 8.5 Hz, 2H), 7.73 (d, J = 8.9 Hz, 1H), 7.44 (dd, J = 8.9, 2.2 Hz, 1H), 4.39 (s, 1H), 4.00 (s, 3H). | 9<br>1.08<br>(383.1) |
| 98 | 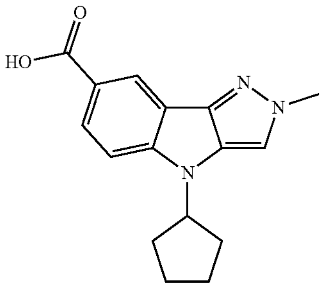 [SMILES: Cn1cc2c(n1)c1cc(C(=O)O)ccc1n2C1CCCC1] 4-cyclopentyl-2-methyl-2H,4H-pyrazolo[4,3-b]indole-7-carboxylic acid | (300 MHz, DMSO-d6) δ 8.35 (d, J = 1.7 Hz, 1H), 7.97-7.88 (m, 1H), 7.86 (s, 1H), 7.53 (d, J = 8.8 Hz, 1H), 5.00-4.87 (m, 1H), 4.06 (s, 3H), 2.10 (d, J = 7.7 Hz, 2H), 1.96-1.83 (m, 4H), 1.71 (d, J = 6.2 Hz, 2H). | 10<br>0.747<br>(284.0) |
| 100 | 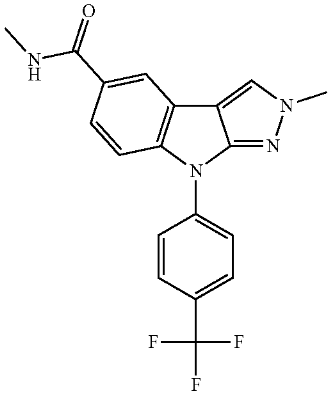 N,2-dimethyl-8-[4-(trifluoromethyl)phenyl]-2H,8H-pyrazolo[3,4-b]indole-5-carboxamide | (500 MHz, DMSO-d6) δ 8.46 (dd, J = 1.8, 0.5 Hz, 1H), 8.22 (s, 1H), 8.05-8.11 (m, 2H), 7.95-8.01 (m, 2H), 7.94 (dd, J = 8.7, 1.8 Hz, 1H), 7.79 (dd, J = 8.7, 0.6 Hz, 1H), 4.03 (s, 3H), 3.89 (s, 3H). | 14<br>0.91 min<br>(374.1) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 101 | 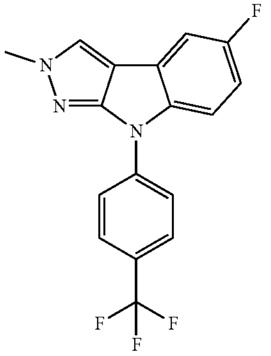 [SMILES: Cn1cc2c3cc(F)ccc3n(-c3ccc(C(F)(F)F)cc3)c2n1] 5-fluoro-2-methyl-8-[4-(trifluoromethyl)phenyl]-2H,8H-pyrazolo[3,4-b]indole | (500 MHz, DMSO-d6) δ 8.13 (s, 1H), 8.03-8.09 (m, 2H), 7.90-7.96 (m, 2H), 7.73 (dd, J = 9.0, 4.3 Hz, 1H), 7.66 (dd, J = 9.1, 2.7 Hz, 1H), 7.13 (td, J = 9.2, 2.8 Hz, 1H), 4.02 (s, 3H). | |
| 102 | 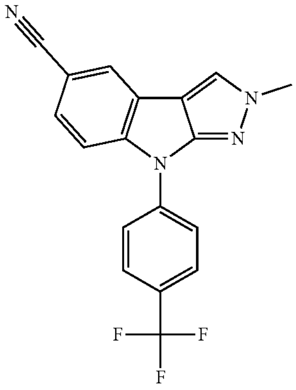 [SMILES: Cn1cc2c3cc(C#N)ccc3n(-c3ccc(C(F)(F)F)cc3)c2n1] 2-methyl-8-[4-(trifluoromethyl)phenyl]-2H,8H-pyrazolo[3,4-b]indole-5-carbonitrile | (500 MHz, DMSO-d6) δ 8.33 (dd, J = 1.7, 0.6 Hz, 1H), 8.22 (s, 1H), 8.03-8.09 (m, 2H), 7.95-8.01 (m, 2H), 7.82 (dd, J = 8.6, 0.6 Hz, 1H), 7.71 (dd, J = 8.6, 1.8 Hz, 1H), 4.04 (s, 3H). | 14 0.88 min (341.1) |
| 103 | 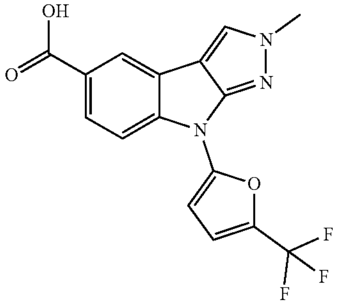 [SMILES: Cn1cc2c3cc(C(=O)O)ccc3n(-c3ccc(C(F)(F)F)o3)c2n1] 2-methyl-8-[5-(trifluoromethyl)furan-2-yl]-2H,8H-pyrazolo[3,4-b]indole-5-carboxylic acid | (500 MHz, DMSO-$d_6$) δ 12.78 (br. s, 1H), 8.41 (d, J = 1.8 Hz, 1H), 8.22 (s, 1H), 7.98 (dd, J = 8.7, 1.8 Hz, 1H), 7.76 (d, J = 8.7 Hz, 1H), 7.49 (dq, J = 3.8, 1 Hz, 1H), 6.79 (dd, J = 3.8, 1 Hz, 1H), 4.05 (s, 3H). | 13 0.77 min (350.0) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 104 | 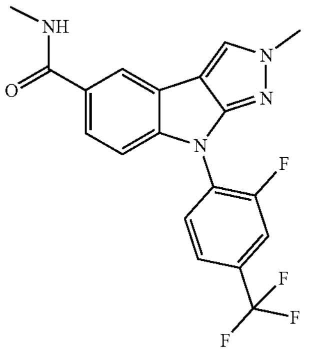 8-[2-fluoro-4-(trifluoromethyl)phenyl]-N,2-dimethyl-2H,8H-pyrazolo[3,4-b]indole-5-carboxamide | (500 MHz, DMSO-$d_6$) δ 8.39 (d, J = 4.6 Hz, 1H), 8.31 (d, J = 1.8 Hz, 1H), 8.17 (s, 1H), 8.08-7.98 (m, 2H), 7.81 (ddd, J = 19.6, 8.5, 1.9 Hz, 2H), 7.26 (dd, J = 8.6, 3.0 Hz, 1H), 3.99 (s, 3H), 2.81 (d, J = 4.5 Hz, 3H) | 8<br>1.5569<br>(391.1) |
| 105 | 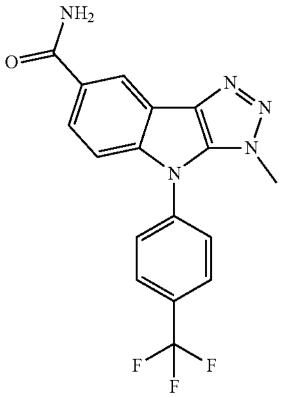 3-methyl-4-[4-(trifluoromethyl)phenyl]-3H,4H-[1,2,3]triazolo[4,5-b]indole-7-carboxamide | (300 MHz, DMSO-d6) δ 8.62-8.52 (m, 1H), 8.18-7.85 (m, 7H), 7.41 (s, 1H), 4.37 (s, 3H). | 9<br>1.618<br>(360.0) |
| 106 | 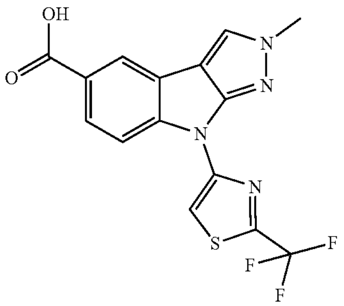 [SMILES: Cn1cc2c3cc(C(=O)O)ccc3n(-c3csc(C(F)(F)F)n3)c2n1] 2-methyl-8-[2-(trifluoromethyl)-1,3-thiazol-4-yl]-2H,8H-pyrazolo[3,4-b]indole-5-carboxylic acid | (500 MHz, DMSO-$d_6$) δ 12.67 (s, 1H), 8.44-8.37 (m, 2H), 8.32 (s, 1H), 8.25 (s, 1H), 7.99 (dd, J = 8.7, 1.8 Hz, 1H), 4.09 (s, 3H) | 13<br>1.775<br>(366.0) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
| --- | --- | --- | --- |
| 107 | 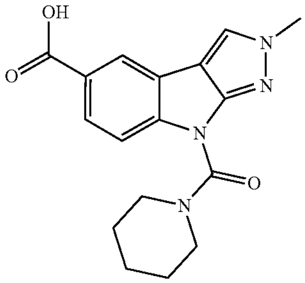 [SMILES: Cn1cc2c3cc(C(=O)O)ccc3n(C(=O)N3CCCCC3)c2n1] 2-methyl-8-(piperidine-1-carbonyl)-2H,8H-pyrazolo[3,4-b]indole-5-carboxylic acid | (500 MHz, DMSO-d6) δ 12.69-12.62 (m, 1H), 8.42-8.40 (m, 1H), 8.19 (s, 1H), 7.90 (dd, J = 8.7, 1.8 Hz, 1H), 7.82-7.79 (m, 2H), 7.65-7.62 (m, 1H), 7.62-7.58 (m, 2H), 4.01 (s, 3H), 3.77 (q, J = 11.6 Hz, 2H). | 8 1.645 (374.0) |
| 108 | 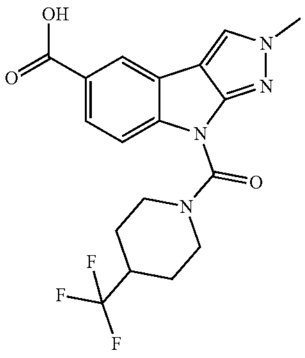 [SMILES: Cn1cc2c3cc(C(=O)O)ccc3n(C(=O)N3CCC(C(F)(F)F)CC3)c2n1] 2-methyl-8-[4-(trifluoromethyl)-piperidine-1-carbonyl]-2H,8H-pyrazolo[3,4-b]indole-5-carboxylic acid | (700 MHz, DMSO-$d_6$) δ 12.75 (s, 1H), 8.33 (d, J = 1.7 Hz, 1H), 8.14 (s, 1H), 7.89 (dd, J = 8.6, 1.8 Hz, 1H), 7.74 (d, J = 8.6 Hz, 1H), 4.11 (d, J = 13.5 Hz, 2H), 4.00 (s, 3H), 3.16 (t, J = 12.9 Hz, 2H), 1.92 (d, J = 12.2 Hz, 2H), 1.70-1.62 (m, 2H). | 8 1.527 (395.1) |
| 109 | 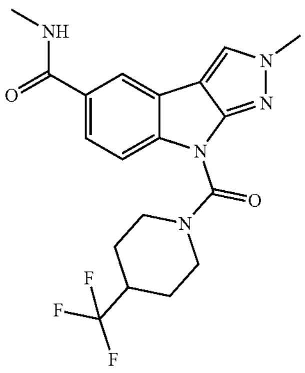 [SMILES: CNC(=O)c1ccc2c(c1)c1cn(C)nc1n2C(=O)N1CCC(C(F)(F)F)CC1] N,2-dimethyl-8-[4-(trifluoromethyl)-piperidine-1-carbonyl]-2H,8H-pyrazolo[3,4-b]indole-5-carboxamide | | |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 110 | 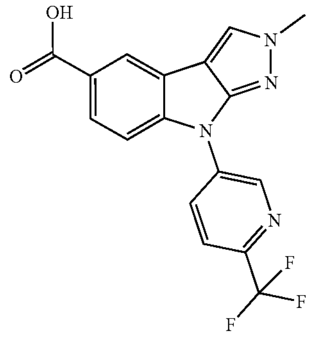 [SMILES: Cn1cc2c3cc(C(=O)O)ccc3n(-c3ccc(C(F)(F)F)nc3)c2n1]<br>2-methyl-8-[6-(trifluoromethyl)pyridin-3-yl]-2H,8H-pyrazolo[3,4-b]indole-5-carboxylic acid | (500 MHz, DMSO-d$_6$) δ 12.80 (s, 1H), 9.33 (d, J = 2.6 Hz, 1H), 8.59-8.53 (m, 1H), 8.46-8.42 (m, 1H), 8.24 (s, 1H), 8.15 (dd, J = 8.6, 0.7 Hz, 1H), 7.94 (dd, J = 8.7, 1.8 Hz, 1H), 7.88-7.83 (m, 1H), 4.04 (s, 3H). | 8<br>1.577<br>(361.0) |
| 111 | 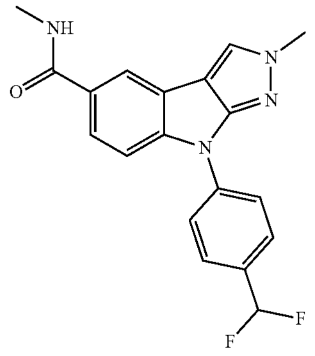 [SMILES: CNC(=O)c1ccc2c(c1)c1cn(C)nc1n2-c1ccc(C(F)F)cc1]<br>8-[4-(difluoromethyl)phenyl]-N,2-dimethyl-2H,8H-pyrazolo[3,4-b]indole-5-carboxamide | (500 MHz, DMSO-d6) δ 8.44 (q, J = 4.4 Hz, 1H), 8.32-8.31 (m, 1H), 8.19 (s, 1H), 8.00-7.96 (m, 2H), 7.84-7.79 (m, 3H), 7.72-7.69 (m, 1H), 7.14 (t, J = 55.9 Hz, 1H), 4.03 (s, 3H), 2.82 (d, J = 4.4 Hz, 3H). | 8<br>1.492<br>(355.0) |
| 112 | 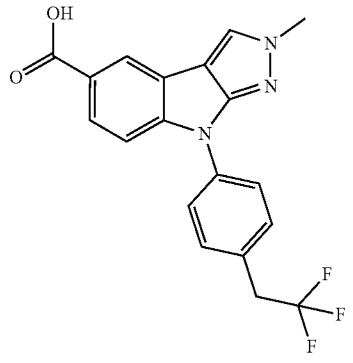<br>2-methyl-8-[4-(2,2,2-trifluoroethyl)phenyl]-2H,8H-pyrazolo[3,4-b]indole-5-carboxylic acid | (500 MHz, DMSO-d6) δ 12.69-12.62 (m, 1H), 8.42-8.40 (m, 1H), 8.19 (s, 1H), 7.90 (dd, J = 8.7, 1.8 Hz, 1H), 7.82-7.79 (m, 2H), 7.65-7.62 (m, 1H), 7.62-7.58 (m, 2H), 4.01 (s, 3H), 3.77 (q, J = 11.6 Hz, 2H). | 8<br>1.645<br>(374.0) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 113 | 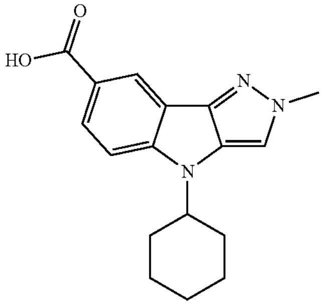 [SMILES: Cn1cc2c(n1)c1cc(C(=O)O)ccc1n2C1CCCCC1] 4-cyclohexyl-2-methyl-2H,4H-pyrazolo[4,3-b]indole-7-carboxylic acid | (300 MHz, DMSO-d6) δ 8.35 (d, J = 1.7 Hz, 1H), 8.01-7.84 (m, 2H), 7.52 (d, J = 8.8 Hz, 1H), 4.37 (d, J = 12.2 Hz, 1H), 4.05 (s, 3H), 2.00-1.68 (m, 6H), 1.63-1.43 (m, 2H), 1.28 (d, J = 21.6 Hz, 2H). | 9<br>0.97<br>(298.1) |
| 114 | 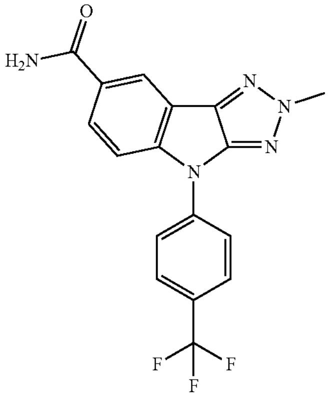 [SMILES: Cn1nc2c3cc(C(N)=O)ccc3n(-c3ccc(C(F)(F)F)cc3)c2n1] 2-methyl-4-[4-(trifluoromethyl)phenyl]-2H,4H-[1,2,3]triazolo[4,5-b]indole-7-carboxamide | (400 MHz, DMSO-d6, ppm) δ 8.58 (d, J = 1.8 Hz, 1H), 8.14 (s, 1H), 8.10-8.03 (m, 3H), 8.01 (d, J = 8.7 Hz, 2H), 7.91 (d, J = 8.8 Hz, 1H), 7.43 (s, 1H), 4.37 (s, 3H). | 9<br>1.04<br>(360.1) |
| 115 | 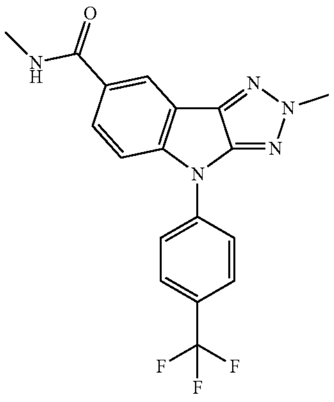 N,2-dimethyl-4-[4-(trifluoromethyl)-phenyl]-2H,4H-[1,2,3]triazolo[4,5-b]indole-7-carboxamide | (300 MHz, DMSO-d6) δ 8.57 (d, J = 4.6 Hz, 1H), 8.50 (d, J = 1.8 Hz, 1H), 8.10-7.94 (m, 5H), 7.89 (d, J = 8.8 Hz, 1H), 4.35 (s, 3H), 2.82 (d, J = 4.4 Hz, 3H). | 7<br>0.91<br>(373.91) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 116 | 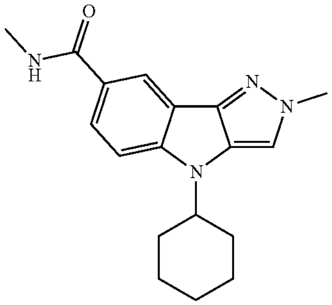 4-cyclohexyl-N,2-dimethyl-2H,4H-pyrazolo[4,3-b]indole-7-carboxamide | (300 MHz, DMSO-d6) δ 8.44-8.22 (m, 2H), 7.86 (d, J = 10.4 Hz, 2H), 7.51 (d, J = 8.8 Hz, 1H), 4.48-4.27 (m, 1H), 4.05 (s, 3H), 2.86-2.71 (m, 3H), 2.00-1.62 (m, 7H), 1.62-1.38 (m, 2H), 1.38-1.17 (m, 1H). | 16 1.29 (311.25) |
| 117 | 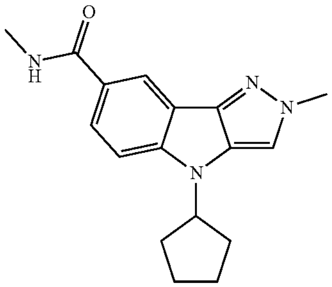 4-cyclopentyl-N,2-dimethyl-2H,4H-pyrazolo[4,3-b]indole-7-carboxamide | (300 MHz, DMSO-d6) δ 8.47-8.16 (m, 2H), 7.96-7.67 (m, 2H), 7.51 (d, J = 8.7 Hz, 1H), 5.02-4.80 (m, 1H), 4.06 (s, 3H), 2.81 (d, J = 4.4 Hz, 3H), 2.10 (d, J = 7.8 Hz, 2H), 1.99-1.79 (m, 4H), 1.72 (s, 2H). | 16 1.20 (297.20) |
| 118 | 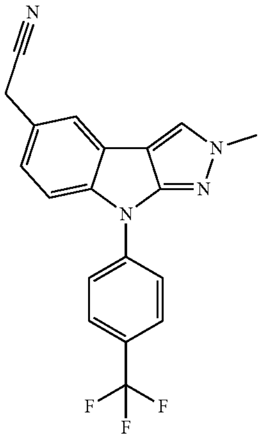 [SMILES: Cn1cc2c3cc(CC#N)ccc3n(-c3ccc(C(F)(F)F)cc3)c2n1] 2-{2-methyl-8-[4-(trifluoromethyl)phenyl]-2H,8H-pyrazolo[3,4-b]indol-5-yl}acetonitrile | (300 MHz, DMSO-d6) δ 8.19 (s, 1H), 8.08 (d, J = 8.4 Hz, 2H), 7.95 (d, J = 8.5 Hz, 2H), 7.90-7.73 (m, 2H), 7.29 (dd, J = 8.6, 1.9 Hz, 1H), 4.14 (s, 2H), 4.03 (s, 3H). | 9 1.01 (355.00) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
| --- | --- | --- | --- |
| 119 (Ex. 30) | 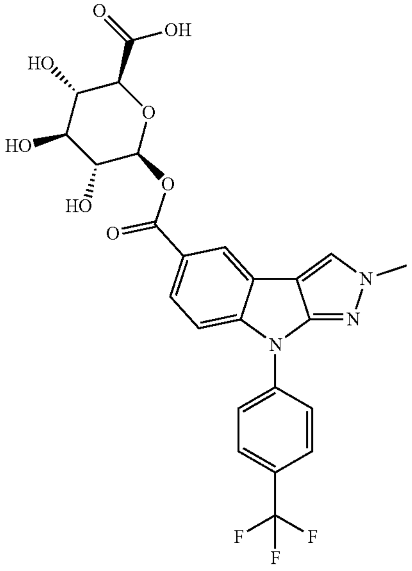 [SMILES: Cn1cc2c3cc(C(=O)O[C@@H]4O[C@H](C(=O)O)[C@@H](O)[C@H](O)[C@H]4O)ccc3n(-c3ccc(C(F)(F)F)cc3)c2n1] (2S,3S,4S,5R,6S)-3,4,5-trihydroxy-6-{2-methyl-8-[4-(trifluoromethyl)phenyl]-2H,8H-pyrazolo[3,4-b]indole-5-carbonyloxy}oxane-2-carboxylic acid | (300 MHz, DMSO-d6) δ 8.57-8.46 (m, 1H), 8.25 (s, 1H), 8.09 (d, J = 8.4 Hz, 2H), 8.00 (d, J = 6.1 Hz, 3H), 7.83 (d, J = 8.8 Hz, 1H), 5.66 (d, J = 7.1 Hz, 1H), 5.51 (s, 1H), 5.29 (s, 1H), 4.05 (s, 3H), 3.76 (s, 1H). | 15 1.16 (536.20) |
| 120 (Ex. 29) | 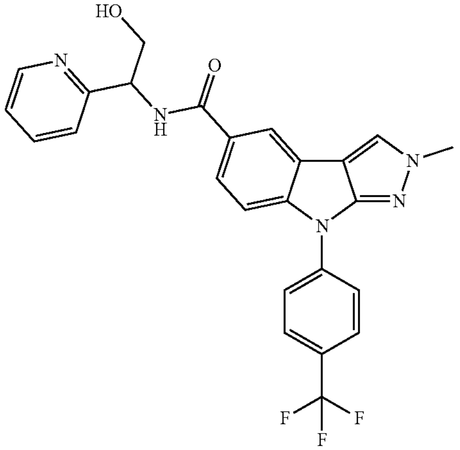 [SMILES: Cn1cc2c3cc(C(=O)NC(CO)c4ccccn4)ccc3n(-c3ccc(C(F)(F)F)cc3)c2n1] N-[2-hydroxy-1-(pyridin-2-yl)ethyl]-2-methyl-8-[4-(trifluoromethyl)phenyl]-2H,8H-pyrazolo[3,4-b]indole-5-carboxamide | (400 MHz, DMSO-d6) δ 8.70 (d, J = 7.8 Hz, 1H), 8.58-8.51 (m, 1H), 8.45 (d, J = 1.8 Hz, 1H), 8.22 (s, 1H), 8.10 (d, J = 8.5 Hz, 2H), 7.98 (d, J = 8.6 Hz, 2H), 7.93 (dd, J = 8.8, 1.9 Hz, 1H), 7.83-7.72 (m, 2H), 7.45 (d, J = 7.9 Hz, 1H), 7.27 (ddd, J = 7.6, 4.8, 1.2 Hz, 1H), 5.20 (q, J = 7.3 Hz, 1H), 4.96 (t, J = 6.0 Hz, 1H), 4.04 (s, 3H), 3.93-3.77 (m, 2H). | 12 0.75 (480.1) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
| --- | --- | --- | --- |
| 121 | 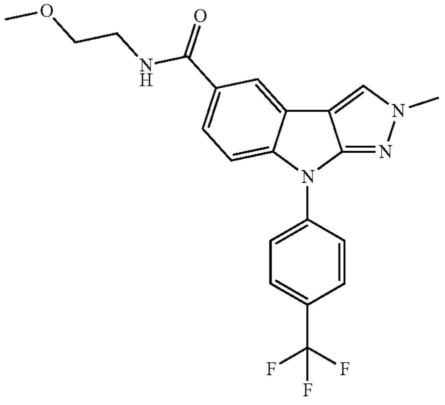 N-(2-methoxyethyl)-2-methyl-8-[4-(trifluoromethyl)phenyl]-2H,8H-pyrazolo[3,4-b]indole-5-carboxamide | (400 MHz, DMSO-d6) δ 8.55 (d, J = 5.3 Hz, 1H), 8.35 (d, J = 1.8 Hz, 1H), 8.21 (s, 1H), 8.09 (d, J = 8.4 Hz, 2H), 7.97 (d, J = 8.5 Hz, 2H), 7.86 (dd, J = 8.7, 1.9 Hz, 1H), 7.77 (d, J = 8.7 Hz, 1H), 4.03 (s, 3H), 3.53-3.43 (m, 4H), 3.29 (s, 3H). | 9 1.69 (417.0) |
| 122 | 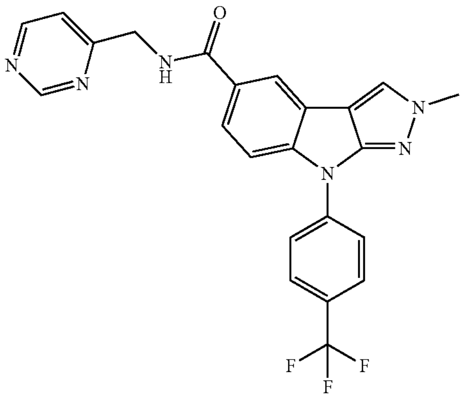 [SMILES: Cn1cc2c3cc(C(=O)NCc4ccncn4)ccc3n(-c3ccc(C(F)(F)F)cc3)c2n1] 2-methyl-N-[(pyrimidin-4-yl)methyl]-8-[4-(trifluoromethyl)phenyl]-2H,8H-pyrazolo[3,4-b]indole-5-carboxamide | (400 MHz, DMSO-d6) δ 9.23 (t, J = 5.9 Hz, 1H), 9.13 (d, J = 1.4 Hz, 1H), 8.74 (d, J = 5.2 Hz, 1H), 8.43 (d, J = 1.8 Hz, 1H), 8.23 (s, 1H), 8.10 (d, J = 8.4 Hz, 2H), 7.98 (d, J = 8.6 Hz, 2H), 7.93 (dd, J = 8.7, 1.9 Hz, 1H), 7.81 (d, J = 8.7 Hz, 1H), 7.46 (dd, J = 5.3, 1.4 Hz, 1H), 4.59 (d, J = 5.8 Hz, 2H), 4.04 (s, 3H). | 9 0.86 (451.1) |
| 123 | 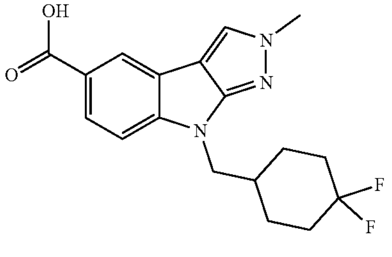 [SMILES: Cn1cc2c3cc(C(=O)O)ccc3n(CC3CCC(F)(F)CC3)c2n1] 8-[(4,4-difluorocyclohexyl)methyl]-2-methyl-2H,8H-pyrazolo[3,4-b]indole-5-carboxylic acid | (700 MHz, DMSO-d6) δ 12.47-12.42 (m, 1H), 8.31 (d, J = 1.7 Hz, 1H), 8.06 (s, 1H), 7.86 (dd, J = 8.6, 1.7 Hz, 1H), 7.52 (d, J = 8.6 Hz, 1H), 4.08 (d, J = 7.3 Hz, 2H), 3.99 (s, 3H), 2.19-2.12 (m, 1H), 2.02-1.96 (m, 2H), 1.80-1.69 (m, 2H), 1.67-1.62 (m, 2H), 1.38-1.31 (m, 2H). | 8 1.53 (348.00) |

TABLE 1-continued

| Compound No. (Example No.) | Structure and Name | $^1$H-NMR | Conditions and elution time (min) LCMS (M + H$^+$) |
| --- | --- | --- | --- |
| Table 1 below shows exemplary compounds of the present invention. They have been synthesized as described in the Examples above or similar thereto. | | | |
| 124 | 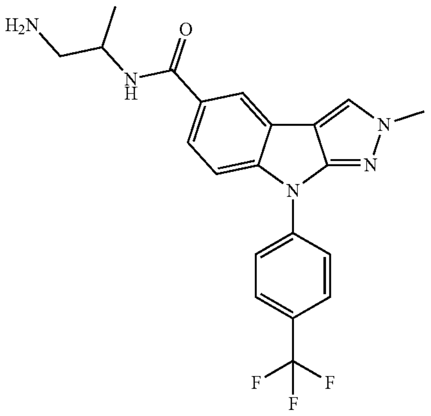 [SMILES: CC(CN)NC(=O)c1ccc2c(c1)c1cn(C)nc1n2-c1ccc(C(F)(F)F)cc1] N-(1-aminopropan-2-yl)-2-methyl-8-[4-(trifluoromethyl)phenyl]-2H,8H-pyrazolo[3,4-b]indole-5-carboxamide | (400 MHz, DMSO-d6) 8.37-8.30 (m, 1H), 8.17 (d, J = 22.5 Hz, 2H), 8.08 (d, J = 8.4 Hz, 2H), 7.97 (d, J = 8.5 Hz, 2H), 7.86 (dd, J = 8.7, 1.9 Hz, 1H), 7.77 (d, J = 8.7 Hz, 1H), 4.04 (s, 3H), 3.12 (d, J = 6.2 Hz, 1H), 2.69 (dd, J = 12.7, 6.6 Hz, 1H), 2.66-2.57 (m, 1H), 1.15 (d, J = 6.6 Hz, 3H). | 9<br>1.53<br>(416.0) |
| 125 | 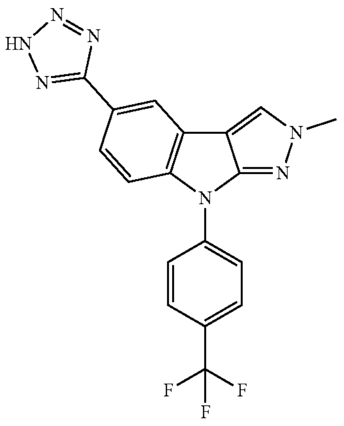 [SMILES: Cn1cc2c3cc(-c4nn[nH]n4)ccc3n(-c3ccc(C(F)(F)F)cc3)c2n1] 5-{2-methyl-8-[4-(trifluoromethyl)-phenyl]-2H,8H-pyrazolo[3,4-b]indol-5-yl}-2H-1,2,3,4-tetrazole | (400 MHz, DMSO) δ 4.05 (s, 3H, 7), 7.93 (d, J = 8.7 Hz, 1H, 13), 7.99 (td, J = 6.2, 3.0 Hz, 3H, 12, 18, 20), 8.11 (d, J = 8.4 Hz, 2H, 15, 17), 8.28 (s, 1H, 5), 8.52 (d, J = 1.7 Hz, 1H, 10), 16.67 (s, 1H, 27). | 14<br>0.77 min<br>(384.20) |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 126 | 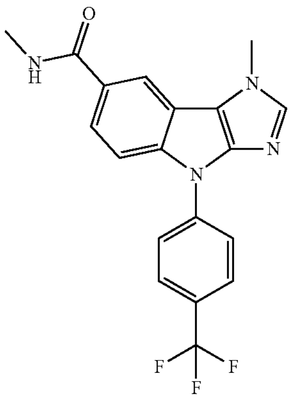 [SMILES: CNC(=O)c1ccc2c(c1)c1c(ncn1C)n2-c1ccc(C(F)(F)F)cc1] N,1-dimethyl-4-[4-(trifluoromethyl)phenyl]-1H,4H-imidazo[4,5-b]indole-7-carboxamide | (400 MHz, DMSO) δ 8.47 (d, J = 4.7 Hz, 1H), 8.40 (d, J = 1.7 Hz, 1H), 8.10 (d, J = 8.4 Hz, 2H), 7.97 (d, J = 8.6 Hz, 2H), 7.91-7.84 (m, 2H), 7.79 (dd, J = 8.9, 1.8 Hz, 1H), 4.12 (s, 3H), 2.85 (d, J = 4.3 Hz, 3H). | 9 1.58 (373.00) |
| 127 | 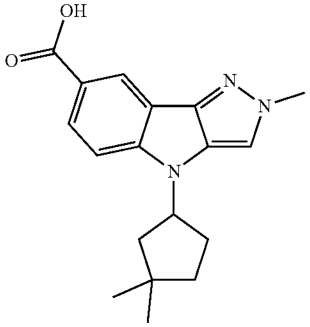 [SMILES: Cn1cc2c(n1)c1cc(C(=O)O)ccc1n2C1CCC(C)(C)C1] 4-(3,3-dimethylcyclopentyl)-2-methyl-2H,4H-pyrazolo[4,3-b]indole-7-carboxylic acid | (300 MHz, DMSO-d6) δ 8.35 (d, J = 1.7 Hz, 1H), 7.97-7.86 (m, 2H), 7.57 (d, J = 8.8 Hz, 1H), 5.20-5.03 (m, 1H), 4.07 (s, 3H), 2.32-2.15 (m, 1H), 2.11-1.97 (m, 1H), 1.97-1.85 (m, 1H), 1.84-1.68 (m, 2H), 1.66-1.51 (m, 1H), 1.15 (d, J = 18.6 Hz, 6H). | 9 0.88 (312.10) |
| 128 | 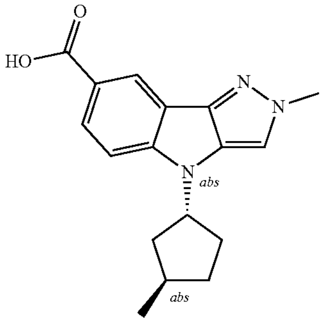 [SMILES: C[C@@H]1CC[C@@H](n2c3ccc(C(=O)O)cc3c3nn(C)cc32)C1] Trans isomer, absolute stereochemistry unknown 2-methyl-4-[(1R,3R)-3-methylcyclopentyl]-2H,4H-pyrazolo[4,3-b]indole-7-carboxylic acid | (400 MHz, DMSO-d6) δ 8.39 (d, J = 28.5 Hz, 1H), 7.98-7.80 (m, 2H), 7.52 (d, J = 8.7 Hz, 1H), 5.12-5.02 (m, 1H), 4.06 (s, 3H), 2.38-2.16 (m, 2H), 2.12-2.01 (m, 2H), 1.98-1.85 (m, 1H), 1.77-1.65 (m, 1H), 1.36-1.21 (m, 1H), 1.07 (d, J = 6.6 Hz, 3H). | 15 0.97 (298.20) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 129 | 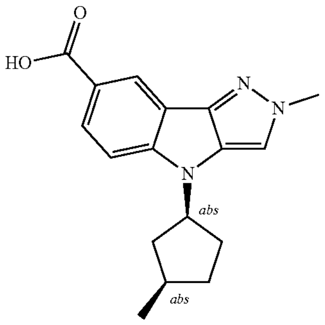 [SMILES: C[C@@H]1CC[C@H](n2c3ccc(C(=O)O)cc3c3nn(C)cc32)C1]<br>Mixture of cis isomers<br>2-methyl-4-[(1S,3R)-3-methylcyclopentyl]-2H,4H-pyrazolo[4,3-b]indole-7-carboxylic acid | (400 MHz, DMSO-d6) δ 8.35 (s, 1H), 7.95-7.84 (m, 2H), 7.53 (d, J = 8.7 Hz, 1H), 5.05-4.92 (m, 1H), 4.07 (d, J = 3.8 Hz, 3H), 2.30-2.19 (m, 1H), 2.14-2.01 (m, 2H), 1.99-1.91 (m, 1H), 1.74-1.44 (m, 2H), 1.36-1.21 (m, 1H), 1.09 (dd, J = 18.1, 6.6 Hz, 3H). | 9<br>0.99<br>(298.10) |
| 130 | 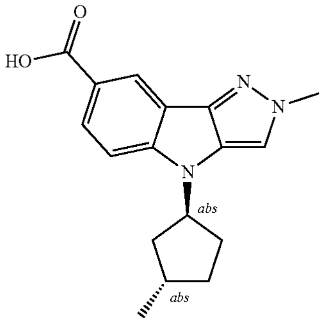 [SMILES: C[C@H]1CC[C@H](n2c3ccc(C(=O)O)cc3c3nn(C)cc32)C1]<br>Trans isomer, absolute stereochemistry unknown<br>2-methyl-4-[(1S,3S)-3-methylcyclopentyl]-2H,4H-pyrazolo[4,3-b]indole-7-carboxylic acid | (300 MHz, DMSO-d6) δ 8.34 (s, 1H), 7.96-7.84 (m, 2H), 7.51 (d, J = 8.7 Hz, 1H), 5.03-4.91 (m, 1H), 2.28-2.04 (m, 3H), 1.99-1.86 (m, 2H), 1.61-1.41 (m, 2H), 1.11 (dd, J = 6.3, 2.2 Hz, 3H). | 15<br>1.00<br>(298.10) |
| 131 | 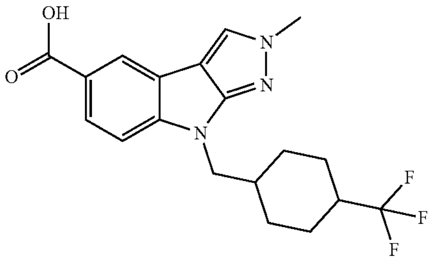 [SMILES: Cn1cc2c3cc(C(=O)O)ccc3n(CC3CCC(C(F)(F)F)CC3)c2n1]<br>Mixture of cis and trans isomers<br>2-methyl-8-{[4-(trifluoromethyl)cyclohexyl]methyl}-2H,8H-pyrazolo[3,4-b]indole-5-carboxylic acid | (400 MHz, DMSO-d6) δ 12.53-12.27 (m, 1H), 8.32-8.29 (m, 1H), 8.05 (s, 1H), 7.88-7.84 (m, 1H), 7.48-7.44 (m, 1H), 4.19-4.00 (m, 2H), 3.99 (s, 3H), 2.44-1.95 (m, 2H), 1.88-1.80 (m, 1H), 1.78-1.59 (m, 3H), 1.53-1.44 (m, 1H), 1.25-1.10 (m, 3H). | 8<br>1.67-1.69<br>(380.00) |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 132 | 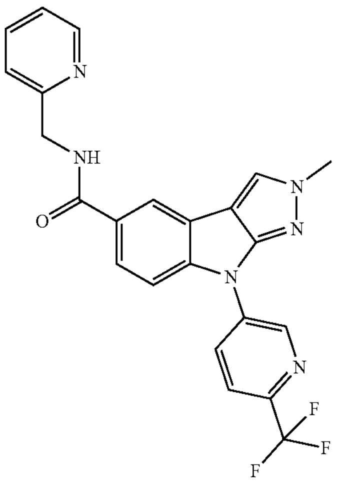 [SMILES: Cn1cc2c3cc(C(=O)NCc4ccccn4)ccc3n(-c3ccc(C(F)(F)F)nc3)c2n1] 2-methyl-N-[(pyridin-2-yl)methyl]-8-[6-(trifluoromethyl)pyridin-3-yl]-2H,8H-pyrazolo[3,4-b]indole-5-carboxamide | (400 MHz, DMSO-d6) δ 9.34 (d, J = 2.6 Hz, 1H), 9.24 (t, J = 5.8 Hz, 1H), 8.68-8.65 (m, 1H), 8.57 (dd, J = 8.5, 2.6 Hz, 1H), 8.44-8.42 (m, 1H), 8.24 (s, 1H), 8.15 (d, J = 8.5 Hz, 1H), 8.12-8.07 (m, 1H), 7.94 (dd, J = 8.8, 1.8 Hz, 1H), 7.89 (d, J = 8.7 Hz, 1H), 7.63 (d, J = 8.0 Hz, 1H), 7.58-7.53 (m, 1H), 4.72 (d, J = 5.7 Hz, 2H), 4.05 (s, 3H). | 8<br>1.38<br>(451.00) |
| 133 | 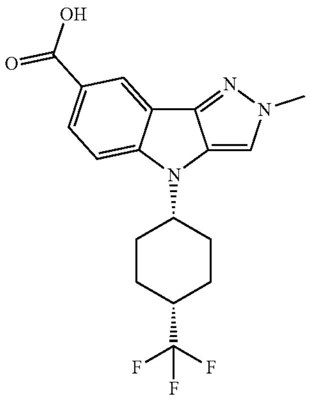 [SMILES: Cn1cc2c(n1)c1cc(C(=O)O)ccc1n2[C@H]1CC[C@@H](C(F)(F)F)CC1] Pure cis isomer<br>2-methyl-4-[(1s,4s)-4-(trifluoromethyl)cyclohexyl]-2H,4H-pyrazolo[4,3-b]indole-7-carboxylic acid | (400 MHz, DMSO-d6) δ 8.36 (d, J = 1.7 Hz, 1H), 7.96-7.89 (m, 2H), 7.59 (d, J = 8.8 Hz, 1H), 4.52 (dd, J = 10.5, 5.5 Hz, 1H), 4.06 (s, 3H), 2.49 (s, 1H), 2.06-1.90 (m, 6H), 1.71-1.58 (m, 2H). | 10<br>1.81<br>(366.20) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 134 | 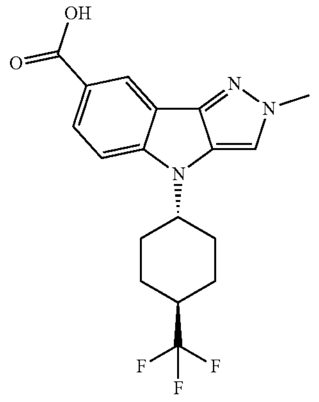 [SMILES: Cn1cc2c(n1)c1cc(C(=O)O)ccc1n2[C@H]1CC[C@H](C(F)(F)F)CC1] Pure trans isomer 2-methyl-4-[(1r,4r)-4-(trifluoromethyl)cyclohexyl]-2H,4H-pyrazolo[4,3-b]indole-7-carboxylic acid | (400 MHz, DMSO-d6) δ 8.37 (s, 1H), 7.94 (d, J = 8.9 Hz, 1H), 7.71 (s, 1H), 7.58 (d, J = 8.8 Hz, 1H), 4.55 (s, 1H), 4.07 (s, 3H), 2.63 (s, 1H), 2.07-1.88 (m, 8H). | 10 0.84 (366.10) |
| 135 | 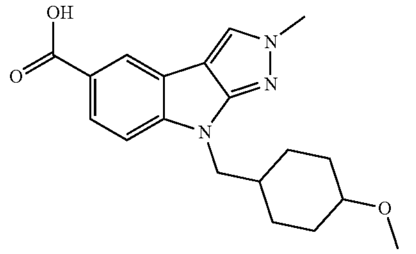 [SMILES: COC1CCC(Cn2c3ccc(C(=O)O)cc3c3cn(C)nc32)CC1] 8-[(4-methoxycyclohexyl)methyl]-2-methyl-2H,8H-pyrazolo[3,4-b]indole-5-carboxylic acid | (400 MHz, DMSO-d6) δ 12.49-12.29 (m, 1H), 8.31-8.29 (m, 1H), 8.04 (s, 1H), 7.87-7.83 (m, 1H), 7.48-7.44 (m, 1H), 4.02-3.98 (m, 2H), 3.99 (s, 3H), 3.36-3.30 (m, 1H), 3.21-3.17 (m, 3H), 2.13-2.01 (m, 1H), 2.00-1.91 (m, 1H), 1.84-1.74 (m, 1H), 1.64-1.56 (m, 1H), 1.37-1.28 (m, 4H), 1.18-0.94 (m, 1H). | 8 1.40-1.44 (342.00) |
| 136 | 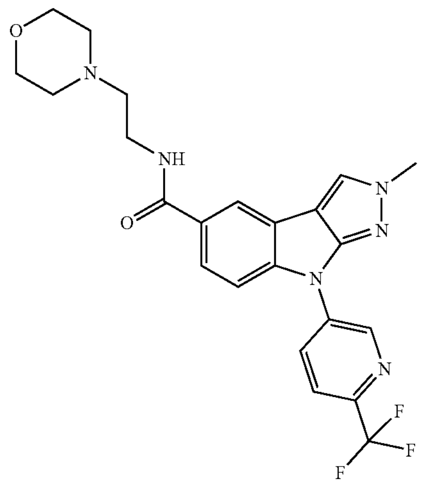 [SMILES: Cn1cc2c3cc(C(=O)NCCN4CCOCC4)ccc3n(-c3ccc(C(F)(F)F)nc3)c2n1] 2-methyl-N-[2-(morpholin-4-yl)ethyl]-8-[6-(trifluoromethyl)pyridin-3-yl]-2H,8H-pyrazolo[3,4-b]indole-5-carboxamide | (400 MHz, DMSO-d6) δ 9.71-9.59 (m, 1H), 9.33 (d, J = 2.6 Hz, 1H), 8.77 (t, J = 5.7 Hz, 1H), 8.56 (dd, J = 8.5, 2.6 Hz, 1H), 8.38-8.36 (m, 1H), 8.24 (s, 1H), 8.15 (d, J = 8.6 Hz, 1H), 7.92-7.86 (m, 2H), 4.05 (s, 3H), 4.06-3.98 (m, 2H), 3.71-3.65 (m, 4H), 3.63-3.59 (m, 2H), 3.39-3.33 (m, 2H), 3.25-3.10 (m, 2H). Compound is protonated | 8 1.27 (473.00) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
| --- | --- | --- | --- |
| 137 | 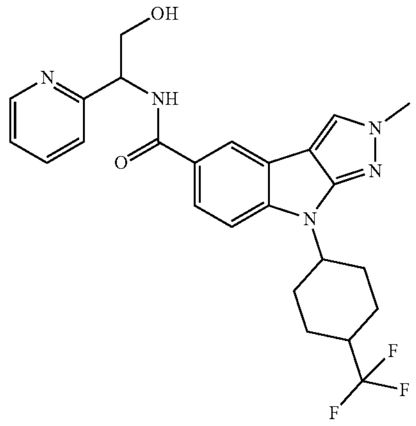 [SMILES: Cn1cc2c3cc(C(=O)NC(CO)c4ccccn4)ccc3n(C3CCC(C(F)(F)F)CC3)c2n1]<br>N-[2-hydroxy-1-(pyridin-2-yl)ethyl]-2-methyl-8-[4-(trifluoromethyl)cyclohexyl]-2H,8H-pyrazolo[3,4-b]indole-5-carboxamide | (400 MHz, Chloroform-d) 8.59 (d, J = 4.9 Hz, 1H), 8.26 (d, J = 1.8 Hz, 1H), 7.93-7.81 (m, 2H), 7.79-7.71 (m, 1H), 7.63 (d, J = 4.7 Hz, 1H), 7.53 (d, J = 7.9 Hz, 1H), 7.31 (d, J = 3.5 Hz, 1H), 7.27 (s, 1H), 5.47-5.40 (m, 1H), 4.60 (s, 1H), 4.36 (d, J = 10.8 Hz, 1H), 4.29-4.12 (m, 2H), 4.07 (d, J = 2.0 Hz, 4H), 2.66-2.55 (m, 1H), 2.49-2.28 (m, 3H), 2.24-2.10 (m, 2H), 1.98-1.81 (m, 2H), 1.61-1.55 (m, 1H). | 15<br>1.46<br>(486.30) |
| 138 | 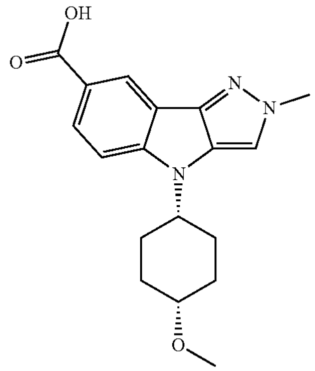 [SMILES: CO[C@H]1CC[C@@H](n2c3ccc(C(=O)O)cc3c3nn(C)cc32)CC1]<br>2-methyl-4-[(1s,4s)-4-methoxycyclohexyl]-2H,4H-pyrazolo[4,3-b]indole-7-carboxylic acid | (300 MHz, DMSO-d6) δ 8.37 (d, J = 1.8 Hz, 1H), 7.98-7.89 (m, 1H), 7.77 (s, 1H), 7.55 (d, J = 8.7 Hz, 1H), 4.44 (d, J = 11.9 Hz, 1H), 4.07 (s, 4H), 3.51 (s, 2H), 2.05 (d, J = 11.6 Hz, 5H), 1.77-1.59 (m, 4H). | 10<br>0.71<br>(328.10) |
| 139 | 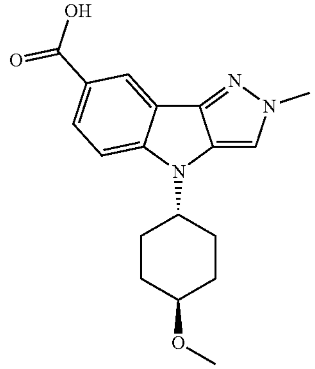 [SMILES: CO[C@H]1CC[C@H](n2c3ccc(C(=O)O)cc3c3nn(C)cc32)CC1]<br>2-methyl-4-[(1r,4r)-4-methoxycyclohexyl]-2H,4H-pyrazolo[4,3-b]indole-7-carboxylic acid | 1H NMR (300 MHz, DMSO-d6) 12.46 (s, 1H), 8.40-8.32 (m, 1H), 7.98-7.87 (m, 2H), 7.63-7.53 (m, 1H), 4.46 (s, 1H), 4.06 (d, J = 2.8 Hz, 3H), 2.14 (d, J = 12.3 Hz, 2H), 1.94 (d, J = 9.1 Hz, 4H), 1.45 (s, 2H), 1.27-1.20 (m, 1H). | 10<br>0.66<br>(328.10) |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 140 | 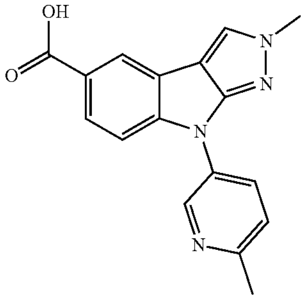 [SMILES: Cc1ccc(-n2c3ccc(C(=O)O)cc3c3cn(C)nc32)cn1] 2-methyl-8-(6-methylpyridin-3-yl)-2H,8H-pyrazolo[3,4-b]indole-5-carboxylic acid | (700 MHz, DMSO-d6) δ 13.48-11.90 (m, 1H), 9.09 (d, J = 2.6 Hz, 1H), 8.58-8.54 (m, 1H), 8.43 (d, J = 1.7 Hz, 1H), 8.23 (s, 1H), 7.93 (dd, J = 8.7, 1.8 Hz, 1H), 7.85 (d, J = 8.5 Hz, 1H), 7.71 (d, J = 8.7 Hz, 1H), 4.03 (s, 3H), 2.72 (s, 3H). | 8 1.157 (307.1) |
| 141 | 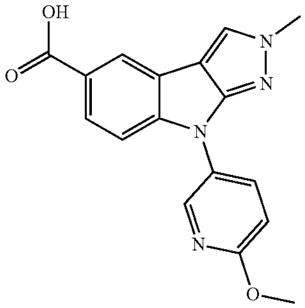 [SMILES: COc1ccc(-n2c3ccc(C(=O)O)cc3c3cn(C)nc32)cn1] 8-(6-methoxypyridin-3-yl)-2-methyl-2H,8H-pyrazolo[3,4-b]indole-5-carboxylic acid | (400 MHz, DMSO-$d_6$) δ 8.54 (d, J = 2.6 Hz, 1H), 8.40 (d, J = 1.7 Hz, 1H), 8.17 (s, 1H), 8.07 (dd, J = 8.8, 2.8 Hz, 1H), 7.88 (dd, J = 8.6, 1.8 Hz, 1H), 7.44 (d, J = 8.6 Hz, 1H), 7.07 (d, J = 8.8 Hz, 1H), 4.00 (s, 3H), 3.95 (s, 3H). | 8 1.418 (323.0) |
| 142 | 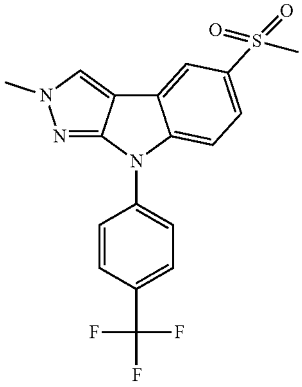 5-methanesulfonyl-2-methyl-8-[4-(trifluoromethyl)phenyl]-2H,8H-pyrazolo[3,4-b]indole | (400 MHz, DMSO-d6) δ 8.42 (dd, J = 2.0, 0.6 Hz, 1H, 6), 8.27 (s, 1H, 11), 8.04-8.11 (m, 2H, 16, 20), 7.99 (d, J = 8.6 Hz, 2H, 17, 19), 7.89 (dd, J = 8.7, 0.6 Hz, 1H, 3), 7.84 (dd, J = 8.7, 1.9 Hz, 1H, 2), 4.05 (s, 3H, 12), 3.23 (s, 3H, 25). | |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 143 | 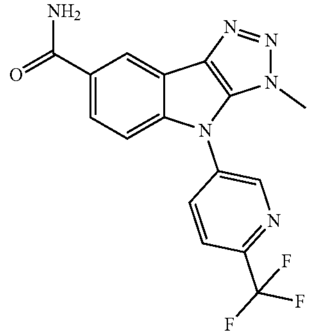 [SMILES: Cn1nnc2c3cc(C(N)=O)ccc3n(-c3ccc(C(F)(F)F)nc3)c21] 3-methyl-4-[6-(trifluoromethyl)pyridin-3-yl]-3H,4H-[1,2,3]triazolo[4,5-b]indole-7-carboxamide | (300 MHz, DMSO-d6) δ 9.33 (d, J = 2.7 Hz, 1H), 8.63-8.52 (m, 2H), 8.19 (d, J = 8.5 Hz, 2H), 8.08 (d, J = 8.8 Hz, 1H), 8.04-7.95 (m, 1H), 7.44 (s, 1H), 4.39 (d, J = 2.5 Hz, 3H). | 9 0.77 (361.00) |
| 144 | 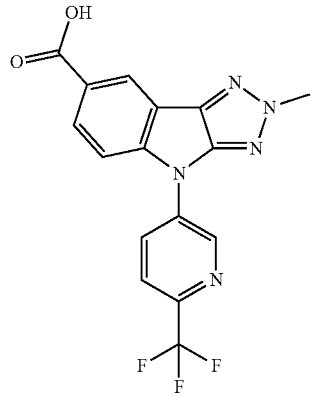 [SMILES: Cn1nc2c3cc(C(=O)O)ccc3n(-c3ccc(C(F)(F)F)nc3)c2n1] 2-methyl-4-[6-(trifluoromethyl)pyridin-3-yl]-2H,4H-[1,2,3]triazolo[4,5-b]indole-7-carboxylic acid | (400 MHz, DMSO-d6) δ 9.39 (d, J = 2.6 Hz, 1H), 8.63 (dd, J = 8.5, 2.5 Hz, 2H), 8.27 (d, J = 8.6 Hz, 1H), 8.22-8.15 (m, 1H), 8.06 (d, J = 8.8 Hz, 1H), 4.47 (s, 3H). | 16 0.97 (359.95) |
| 145 | 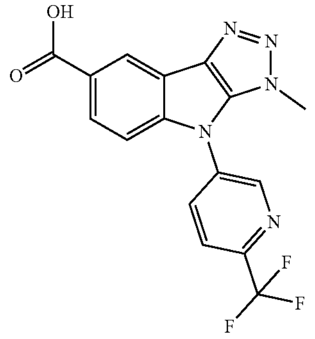 [SMILES: Cn1nnc2c3cc(C(=O)O)ccc3n(-c3ccc(C(F)(F)F)nc3)c21] 3-methyl-4-[6-(trifluoromethyl)pyridin-3-yl]-3H,4H-[1,2,3]triazolo[4,5-b]indole-7-carboxylic acid | (300 MHz, DMSO-d6) δ 9.31 (d, J = 2.5 Hz, 1H), 8.55 (d, J = 8.4 Hz, 2H), 8.19 (d, J = 8.5 Hz, 1H), 8.11 (d, J = 8.8 Hz, 1H), 7.97 (d, J = 8.8 Hz, 1H), 4.39 (s, 3H). | 9 0.85 (362.00) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 146 | 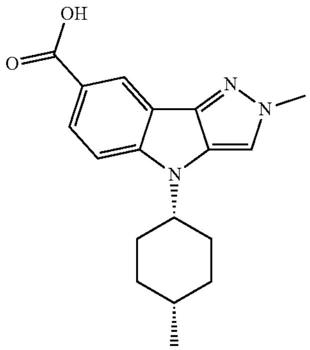 [SMILES: Cn1cc2c(n1)c1cc(C(=O)O)ccc1n2[C@H]1CC[C@@H](C)CC1] 2-methyl-4-[(1s,4s)-4-methylcyclohexyl]-2H,4H-pyrazolo[4,3-b]indole-7-carboxylic acid | (300 MHz, DMSO-d6) δ 12.48 (s, 1H), 8.37 (s, 1H), 7.95-7.92 (m, 2H), 7.55 (d, J = 8.7 Hz, 1H), 4.42-4.35 (m, 1H), 4.08 (s, 3H), 2.09-1.97 (m, 3H), 1.87-1.61 (m, 6H), 1.13 (d, J = 7.2 Hz, 3H) | 9 0.89 (312.05) |
| 147 | 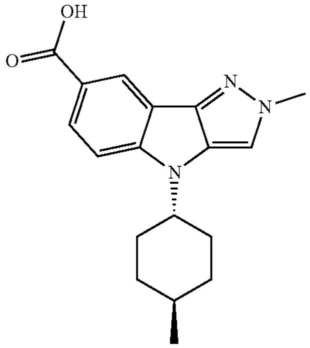 [SMILES: Cn1cc2c(n1)c1cc(C(=O)O)ccc1n2[C@H]1CC[C@H](C)CC1] 2-methyl-4-[(1r,4r)-4-methylcyclohexyl]-2H,4H-pyrazolo[4,3-b]indole-7-carboxylic acid | (300 MHz, DMSO-d6) δ 12.54 (s, 1H), 8.37 (s, 1H), 7.95-7.91 (m, 2H), 7.54 (d, J = 9.0 Hz, 1H), 4.44-4.33 (m, 1H), 4.06 (s, 3H), 1.92-1.80 (m, 6H), 1.67-1.56 (m, 1H), 1.55-1.21 (m, 2H), 0.97 (d, J = 6.6 Hz, 3H) | 9 0.90 (312.00) |
| 148 | 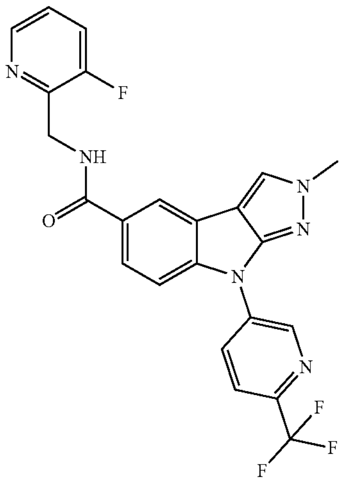 [SMILES: Cn1cc2c3cc(C(=O)NCc4ncccc4F)ccc3n(-c3ccc(C(F)(F)F)nc3)c2n1] N-[(3-fluoropyridin-2-yl)methyl]-2-methyl-8-[6-(trifluoromethyl)pyridin-3-yl]-2H,8H-pyrazolo[3,4-b]indole-5-carboxamide | (400 MHz, DMSO-d6) δ 9.34 (d, J = 2.6 Hz, 1H), 8.98 (t, J = 5.6 Hz, 1H), 8.56 (dd, J = 8.6, 2.6 Hz, 1H), 8.42-8.36 (m, 2H), 8.23 (s, 1H), 8.13 (d, J = 8.5 Hz, 1H), 7.92 (dd, J = 8.7, 1.8 Hz, 1H), 7.86 (d, J = 8.7 Hz, 1H), 7.70 (ddd, J = 10.1, 8.3, 1.3 Hz, 1H), 7.41 (dt, J = 8.5, 4.4 Hz, 1H), 4.69 (dd, J = 5.6, 1.8 Hz, 2H), 4.04 (s, 3H). | 8 1.603 (469.0) |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 149 | 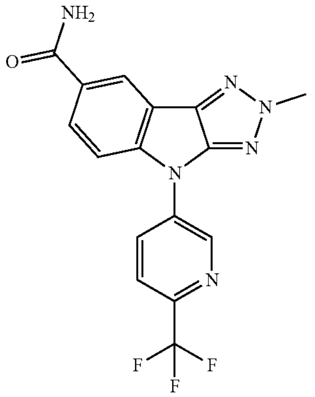 [SMILES: Cn1nc2c3cc(C(N)=O)ccc3n(-c3ccc(C(F)(F)F)nc3)c2n1] 2-methyl-4-[6-(trifluoromethyl)pyridin-3-yl]-2H,4H-[1,2,3]triazolo[4,5-b]indole-7-carboxamide | (300 MHz, DMSO-d6) δ 9.32 (d, J = 2.6 Hz, 1H), 8.63-8.51 (m, 2H), 8.29-7.88 (m, 4H), 7.44 (s, 1H), 4.39 (s, 3H). | 9<br>0.78<br>(361.00) |
| 150 | 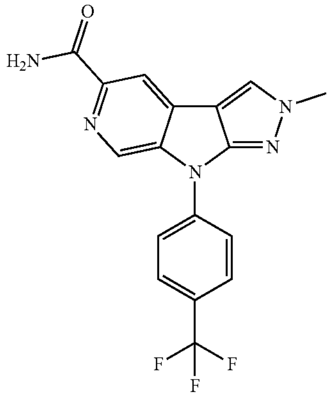 [SMILES: Cn1cc2c3cc(C(N)=O)ncc3n(-c3ccc(C(F)(F)F)cc3)c2n1] 4-methyl-7-[4-(trifluoromethyl)phenyl]-4,5,7,10-tetraazatricyclo[6.4.0.0$^{2,6}$]dodeca-1(8),2,5,9,11-pentaene-11-carboxamide | (300 MHz, DMSO-d6) δ 9.01 (d, J = 0.9 Hz, 1H), 8.52 (d, J = 0.9 Hz, 1H), 8.40 (s, 1H), 8.16 (d, J = 8.4 Hz, 2H), 8.08-8.02 (m, 1H), 7.98 (d, J = 8.6 Hz, 2H), 7.54 (s, 1H), 4.07 (s, 3H). | 9<br>1.47 min<br>(360.00) |
| 151 | 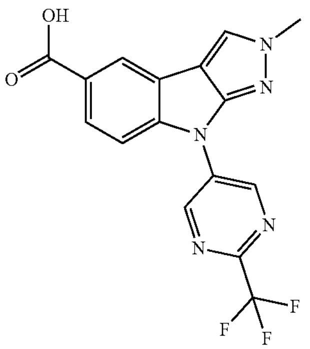 [SMILES: Cn1cc2c3cc(C(=O)O)ccc3n(-c3cnc(C(F)(F)F)nc3)c2n1] 2-methyl-8-[2-(trifluoromethyl)pyrimidin-5-yl]-2H,8H-pyrazolo[3,4-b]indole-5-carboxylic acid | (400 MHz, DMSO-d6) δ 12.92-12.66 (m, 1H), 9.63 (s, 2H), 8.44 (d, J = 1.6 Hz, 1H), 8.25 (s, 1H), 7.98 (d, J = 8.7 Hz, 1H), 7.94 (dd, J = 8.7, 1.7 Hz, 1H), 4.05 (s, 3H). | 8<br>1.581<br>(362.0) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 152 | 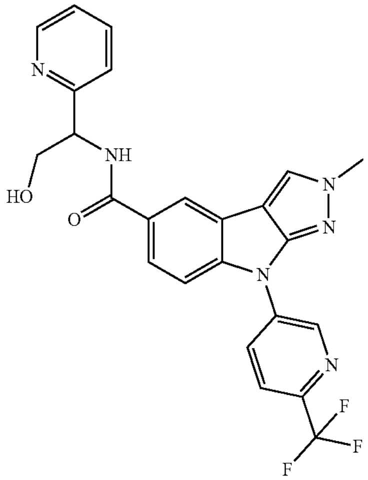 [SMILES: Cn1cc2c3cc(C(=O)NC(CO)c4ccccn4)ccc3n(-c3ccc(C(F)(F)F)nc3)c2n1] N-[2-hydroxy-1-(pyridin-2-yl)ethyl]-2-methyl-8-[6-(trifluoromethyl)pyridin-3-yl]-2H,8H-pyrazolo[3,4-b]indole-5-carboxamide | (700 MHz, DMSO-d6) δ 9.34 (d, J = 2.5 Hz, 1H), 8.86 (d, J = 7.2 Hz, 1H), 8.67 (d, J = 5.0 Hz, 1H), 8.57 (dd, J = 8.5, 2.6 Hz, 1H), 8.45 (d, J = 1.9 Hz, 1H), 8.25 (s, 1H), 8.16 (d, J = 8.5 Hz, 1H), 8.11-8.05 (m, 1H), 7.94 (dd, J = 8.7, 1.9 Hz, 1H), 7.89 (d, J = 8.6 Hz, 1H), 7.75-7.69 (m, 1H), 7.57-7.51 (m, 1H), 5.26 (q, J = 6.6 Hz, 1H), 4.06 (s, 3H), 3.92-3.87 (m, 2H). | 8 1.397 (481.1) |
| 153 | 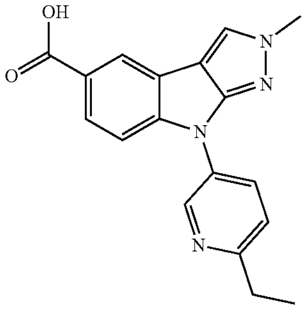 8-(6-ethylpyridin-3-yl)-2-methyl-2H,8H-pyrazolo[3,4-b]indole-5-carboxylic acid | (700 MHz, DMSO-d6) δ 13.37-12.11 (m, 1H), 9.08 (d, J = 2.8 Hz, 1H), 8.54-8.49 (m, 1H), 8.43 (d, J = 1.7 Hz, 1H), 8.23 (s, 1H), 7.93 (dd, J = 8.6, 1.8 Hz, 1H), 7.83 (d, J = 8.5 Hz, 1H), 7.70 (d, J = 8.6 Hz, 1H), 4.03 (s, 3H), 2.99 (q, J = 7.6 Hz, 2H), 1.35 (t, J = 7.6 Hz, 3H). | 8 1.273 (321.1) |
| 154 | 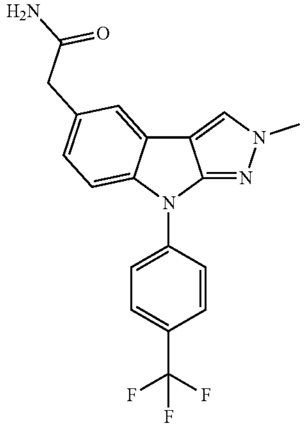 [SMILES: Cn1cc2c3cc(CC(N)=O)ccc3n(-c3ccc(C(F)(F)F)cc3)c2n1] 2-{2-methyl-8-[4-(trifluoromethyl)phenyl]-2H,8H-pyrazolo[3,4-b]indol-5-yl}acetamide | (700 MHz, DMSO-d6) δ 8.13 (s, 1H), 8.09-8.06 (m, 2H), 7.94-7.92 (m, 2H), 7.71-7.69 (m, 1H), 7.69-7.68 (m, 1H), 7.48-7.45 (m, 1H), 7.21 (dd, J = 8.4, 2.0 Hz, 1H), 6.89-6.86 (m, 1H), 4.01 (s, 3H), 3.47 (s, 2H). | 8 1.592 373.1) |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 155 | 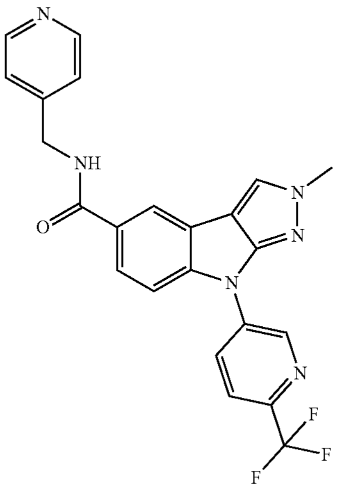 [SMILES: Cn1cc2c3cc(C(=O)NCc4ccncc4)ccc3n(-c3ccc(C(F)(F)F)nc3)c2n1] 2-methyl-N-[(pyridin-4-yl)methyl]-8-[6-(trifluoromethyl)pyridin-3-yl]-2H,8H-pyrazolo[3,4-b]indole-5-carboxamide | (700 MHz, DMSO-d6) δ 9.37 (t, J = 5.8 Hz, 1H), 9.35 (d, J = 2.6 Hz, 1H), 8.81-8.79 (m, 2H), 8.58 (dd, J = 8.5, 2.6 Hz, 1H), 8.44 (d, J = 1.7 Hz, 1H), 8.26 (s, 1H), 8.16 (d, J = 8.5 Hz, 1H), 7.94 (dd, J = 8.7, 1.8 Hz, 1H), 7.91 (d, J = 8.6 Hz, 1H), 7.89-7.86 (m, 2H), 4.74 (d, J = 5.6 Hz, 2H), 4.05 (s, 3H). | 8 1.293 (451.0) |
| 156 (Ex. 27) | 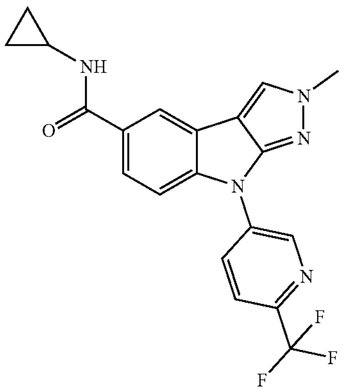 [SMILES: Cn1cc2c3cc(C(=O)NC4CC4)ccc3n(-c3ccc(C(F)(F)F)nc3)c2n1] N-cyclopropyl-2-methyl-8-[6-(trifluoromethyl)pyridin-3-yl]-2H,8H-pyrazolo[3,4-b]indole-5-carboxamide | (400 MHz, DMSO-$d_6$) δ 9.33 (d, J = 2.6 Hz, 1H), 8.55 (dd, J = 8.5, 2.6 Hz, 1H), 8.46 (d, J = 4.2 Hz, 1H), 8.31 (t, J = 1.2 Hz, 1H), 8.21 (s, 1H), 8.13 (d, J = 8.6 Hz, 1H), 7.84 (d, J = 1.3 Hz, 2H), 4.04 (s, 4H), 2.89 (m, 1H), 0.71 (m, 2H), 0.68-0.57 (m, 2H). | 8 1.602 (400.1) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 157 | 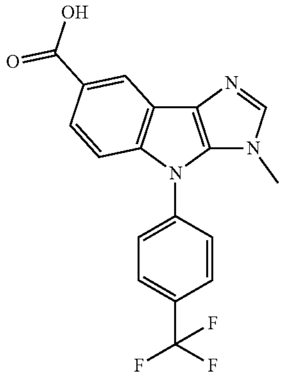 [SMILES: Cn1cnc2c3cc(C(=O)O)ccc3n(-c3ccc(C(F)(F)F)cc3)c21] 3-methyl-4-[4-(trifluoromethyl)phenyl]-3H,4H-imidazo[4,5-b]indole-7-carboxylic acid | (400 MHz, DMSO-d6) δ 8.36 (s, 1H), 8.02 (d, J = 8.4 Hz, 2H), 7.95 (d, J = 8.3 Hz, 2H), 7.80 (d, J = 8.7 Hz, 1H), 7.72 (s, 1H), 7.44 (d, J = 8.7 Hz, 1H), 3.60 (s, 3H). | 10<br>0.69<br>360.00 |
| 158 | 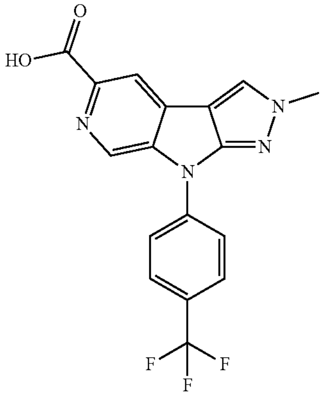 [SMILES: Cn1cc2c3cc(C(=O)O)ncc3n(-c3ccc(C(F)(F)F)cc3)c2n1] 4-methyl-7-[4-(trifluoromethyl)phenyl]-4,5,7,10-tetraaza-tricyclo[6.4.0.0$^{2,6}$]dodeca-1(8),2,5,9,11-pentaene-11-carboxylic acid | (300 MHz, DMSO-d6) δ 9.08 (s, 1H), 8.57 (s, 1H), 8.39 (s, 1H), 8.15 (d, J = 8.5 Hz, 2H), 7.99 (d, J = 8.5 Hz, 2H), 4.07 (s, 3H). | 12<br>0.75 min<br>361.05<br>(M + H) |
| 159 | 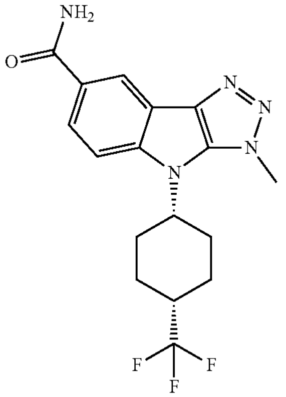 [SMILES: Cn1nnc2c3cc(C(N)=O)ccc3n([C@H]3CC[C@@H](C(F)(F)F)CC3)c21] 3-methyl-4-[(1s,4s)-4-(trifluoromethyl)-cyclohexyl]-3H,4H-[1,2,3]triazolo[4,5-b]indole-7-carboxamide | (300 MHz, DMSO-d6) δ 8.47 (d, J = 1.7 Hz, 1H), 8.00 (dd, J = 8.7, 1.8 Hz, 2H), 7.70 (d, J = 8.8 Hz, 1H), 7.27 (s, 1H), 4.64 (s, 1H), 4.32 (s, 3H), 2.78-2.65 (m, 1H), 2.31 (s, 2H), 2.08 (d, J = 10.1 Hz, 2H), 1.96 (d, J = 14.7 Hz | 10<br>0.83<br>366.00 |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 160 | 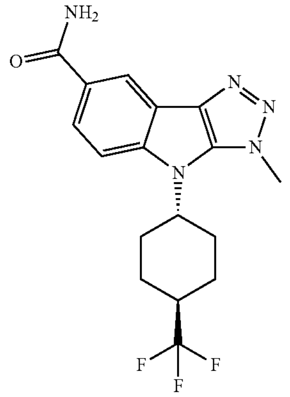 [SMILES: Cn1nnc2c3cc(C(N)=O)ccc3n([C@H]3CC[C@H](C(F)(F)F)CC3)c21]<br>3-methyl-4-[(1r,4r)-4-(trifluoromethyl)-cyclohexyl]-3H,4H-[1,2,3]triazolo[4,5-b]indole-7-carboxamide | (300 MHz, DMSO-d6) δ 8.47 (d, J = 1.7 Hz, 1H), 8.05-7.95 (m, 2H), 7.74 (d, J = 8.8 Hz, 1H), 7.27 (s, 1H), 4.67-4.53 (m, 1H), 4.33 (s, 3H), 4.67-4.53 (m, 1H), 2.52 (s, 1H),2.11 (q, J = 17.0, 14.3 Hz, 6H), 1.73-1.56 (m, 2H). | 10<br>0.85<br>366.00 |
| 161 | 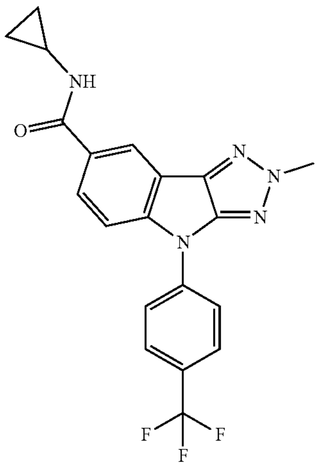 [SMILES: Cn1nc2c3cc(C(=O)NC4CC4)ccc3n(-c3ccc(C(F)(F)F)cc3)c2n1]<br>N-cyclopropyl-2-methyl-4-[4-(trifluoro-methyl)phenyl]-2H,4H-[1,2,3]tri-azolo[4,5-b]indole-7-carboxamide | (400 MHz, DMSO-d6) δ 8.55 (d, J = 4.2 Hz, 1H), 8.53 (d, J = 1.7 Hz, 1H), 8.09-8.04 (m, 2H), 8.03-7.98 (m, 3H), 7.91 (d, J = 8.8 Hz, 1H), 4.37 (s, 3H), 2.95-2.87 (m, 1H), 0.76-0.70 (m, 2H), 0.65-0.60 (m, 2H). | 8<br>1.80<br>400.00 |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 162 | 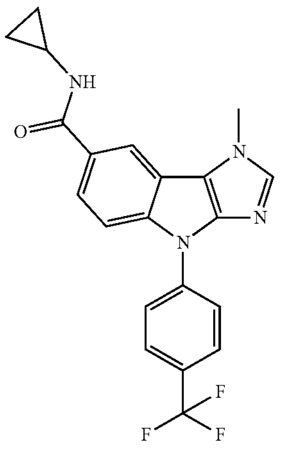 [SMILES: Cn1cnc2c1c1cc(C(=O)NC3CC3)ccc1n2-c1ccc(C(F)(F)F)cc1] N-cyclopropyl-1-methyl-4-[4-(trifluoromethyl)phenyl]-1H,4H-imidazo[4,5-b]indole-7-carboxamide | (700 MHz, DMSO-d6) δ 8.46 (d, J = 4.0 Hz, 1H), 8.37 (d, J = 1.7 Hz, 1H), 8.10-8.08 (m, 2H), 7.98-7.96 (m, 2H), 7.87 (s, 1H), 7.85 (d, J = 8.7 Hz, 1H), 7.78 (dd, J = 8.8, 1.8 Hz, 1H), 4.12 (s, 3H), 2.91-2.86 (m, 1H), 0.75-0.72 (m, 2H), 0.63-0.60 (m, 2H). | 8<br>1.63<br>399.00 |
| 163 | 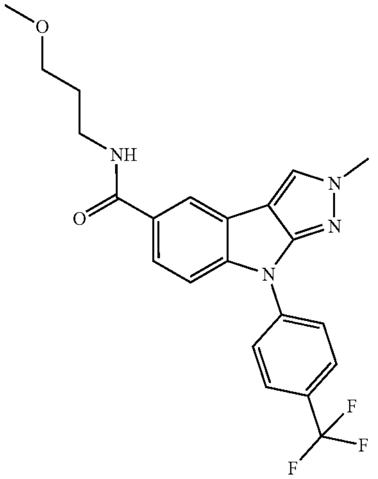 N-(3-methoxypropyl)-2-methyl-8-[4-(trifluoromethyl)phenyl]-2H,8H-pyrazolo[3,4-b]indole-5-carboxamide | (700 MHz, DMSO) δ 8.49 (t, J = 5.7 Hz, 1H), 8.33 (d, J = 1.9 Hz, 1H), 8.21 (s, 1H), 8.09 (d, J = 8.4 Hz, 2H), 7.97 (d, J = 8.3 Hz, 2H), 7.84 (dd, J = 8.7, 1.8 Hz, 1H), 7.77 (d, J = 8.6 Hz, 1H), 4.03 (s, 3H), 3.40 (t, J = 6.3 Hz, 2H), 3.32-3.37 (m, 2H), 3.25 (s, 3H), 1.79 (p, J = 6.6 Hz, 2H). | 8<br>0.79<br>431.30 |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 164 | 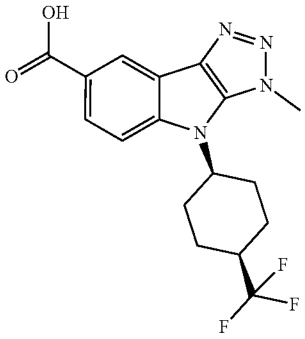 [SMILES: Cn1nnc2c3cc(C(=O)O)ccc3n([C@H]3CC[C@@H](C(F)(F)F)CC3)c21] 3-methyl-4-[(1s,4s)-4-(trifluoromethyl)-cyclohexyl]-3H,4H-[1,2,3]triazolo[4,5-b]indole-7-carboxylic acid | (300 MHz, DMSO-d6) δ 8.45 (d, J = 1.7 Hz, 1H), 8.08-7.99 (m, 1H), 7.72 (d, J = 8.9 Hz, 1H), 4.65 (s, 1H), 4.33 (s, 3H), 2.64 (s, 1H), 2.35-2.21 (m, 2H), 2.09 (d, J = 12.8 Hz, 2H), 1.93 (s, 4H). | 10<br>0.91<br>367.0 |
| 165 | 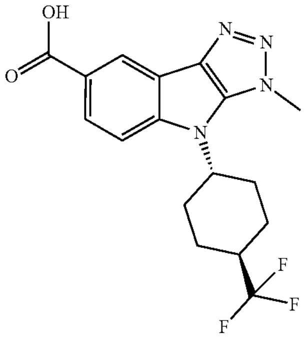 [SMILES: Cn1nnc2c3cc(C(=O)O)ccc3n([C@H]3CC[C@H](C(F)(F)F)CC3)c21] 3-methyl-4-[(1r,4r)-4-(trifluoromethyl)-cyclohexyl]-3H,4H-[1,2,3]triazolo[4,5-b]indole-7-carboxylic acid | (300 MHz, DMSO-d6) δ 8.45 (d, J = 1.7 Hz, 1H), 8.03 (dd, J = 8.8, 1.7 Hz, 1H), 7.77 (d, J = 8.8 Hz, 1H), 4.62 (s, 1H), 4.33 (s, 3H), 2.64 (s, 1H), 2.12 (dd, J = 30.8, 16.4 Hz, 6H), 1.74-1.56 (m, 2H). | 10<br>0.92<br>367.0 |
| 166 | 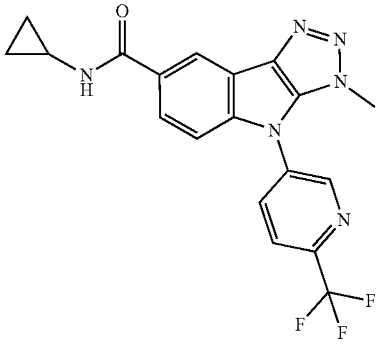 [SMILES: Cn1nnc2c3cc(C(=O)NC4CC4)ccc3n(-c3ccc(C(F)(F)F)nc3)c21] N-cyclopropyl-3-methyl-4-[6-(trifluoromethyl)pyridin-3-yl]-3H,4H-[1,2,3]triazolo[4,5-b]indole-7-carboxamide | (700 MHz, DMSO-d6) δ 9.31 (d, J = 2.5 Hz, 1H), 8.59 (d, J = 4.3 Hz, 1H), 8.56-8.53 (m, 1H), 8.54-8.53 (m, 1H), 8.18 (d, J = 8.5 Hz, 1H), 8.02 (dd, J = 8.8, 1.8 Hz, 1H), 7.98 (d, J = 8.7 Hz, 1H), 4.38 (s, 3H), 2.94-2.89 (m, 1H), 0.74-0.71 (m, 2H), 0.65-0.61 (m, 2H). | 8<br>1.64<br>401.0 |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1H$-NMR | Conditions and elution time (min) LCMS (M + H$^+$) |
| 167 | 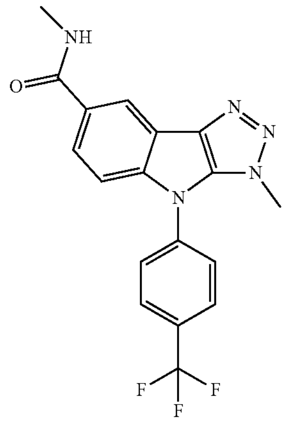 [SMILES: CNC(=O)c1ccc2c(c1)c1nnn(C)c1n2-c1ccc(C(F)(F)F)cc1] N,3-dimethyl-4-[4-(trifluoromethyl)-phenyl]-3H,4H-[1,2,3]triazolo[4,5-b]indole-7-carboxamide | (300 MHz, DMSO-d6) 8.55 (dd, J = 15.7, 3.2 Hz, 2H), 8.12-7.73 (m, 6H), 4.38 (s, 3H), 2.84 (d, J = 4.5 Hz, 3H). | 8<br>1.70<br>374.00 |
| 168 | 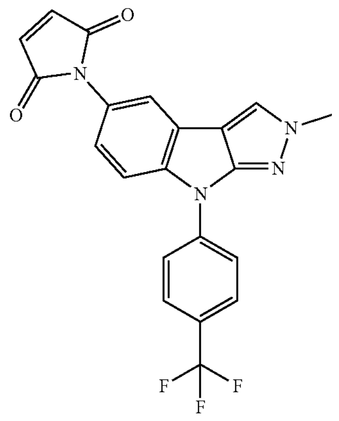 [SMILES: Cn1cc2c3cc(N4C(=O)C=CC4=O)ccc3n(-c3ccc(C(F)(F)F)cc3)c2n1] 1-{2-methyl-8-[4-(trifluoromethyl)-phenyl]-2H,8H-pyrazolo[3,4-b]indol-5-yl}-2,5-dihydro-1H-pyrrole-2,5-dione | (400 MHz, DMSO-d6) δ 8.19 (s, 1H), 8.11 (d, J = 8.4 Hz, 2H), 7.96 (d, J = 8.5 Hz, 2H), 7.83 (d, J = 8.7 Hz, 1H), 7.78 (d, J = 2.1 Hz, 1H), 7.25 (dd, J = 8.8, 2.2 Hz, 1H), 7.21 (s, 2H), 4.04 (s, 3H). | 15<br>1.80<br>411.10 |

TABLE 1-continued

| Com-pound No. (Example No.) | Structure and Name | ¹H-NMR | Conditions and elution time (min) LCMS (M + H⁺) |
|---|---|---|---|
| Table 1 below shows exemplary compounds of the present invention. They have been synthesized as described in the Examples above or similar thereto. | | | |
| 169 | 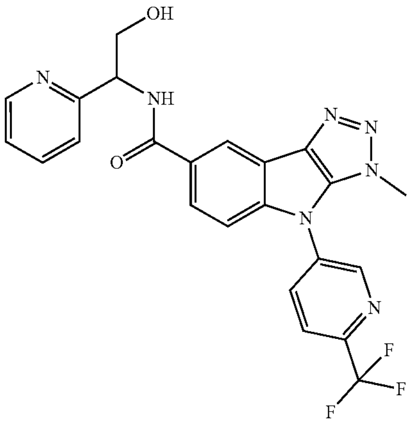 [SMILES: Cn1nnc2c3cc(C(=O)NC(CO)c4ccccn4)ccc3n(-c3ccc(C(F)(F)F)nc3)c21] N-[2-hydroxy-1-(pyridin-2-yl)ethyl]-3-methyl-4-[6-(trifluoromethyl)pyridin-3-yl]-3H,4H-[1,2,3]triazolo[4,5-b]indole-7-carboxamide | (400 MHz, DMSO-d6) δ 9.34 (d, J = 2.6 Hz, 1H), 8.88 (d, J = 7.9 Hz, 1H), 8.72 (d, J = 1.8 Hz, 1H), 8.57 (d, J = 8.7 Hz, 2H), 8.20 (d, J = 8.5 Hz, 1H), 8.11 (dd, J = 9.0, 1.8 Hz, 1H), 8.03 (d, J = 8.8 Hz, 1H), 7.81-7.73 (m, 1H), 7.47 (d, J = 7.9 Hz, 1H), 7.28 (t, J = 6.4 Hz, 1H), 5.25-5.19 (m, 1H), 4.99 (t, J = 5.9 Hz, 1H), 4.40 (s, 3H), 3.87 (q, J = 6.9, 6.4 Hz, 2H). | 10 0.70 482.10 |
| 170 | 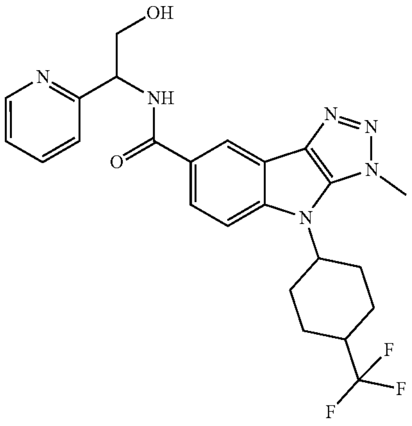 [SMILES: Cn1nnc2c3cc(C(=O)NC(CO)c4ccccn4)ccc3n(C3CCC(C(F)(F)F)CC3)c21] N-[2-hydroxy-1-(pyridin-2-yl)ethyl]-3-methyl-4-[4-(trifluoromethyl)cyclohexyl]-3H,4H-[1,2,3]triazolo[4,5-b]indole-7-carboxamide | (300 MHz, DMSO-d6) δ 8.70 (d, J = 7.8 Hz, 1H), 8.60 (t, J = 2.1 Hz, 1H), 8.55 (dd, J = 5.2, 1.7 Hz, 1H), 8.03 (dt, J = 8.7, 1.5 Hz, 1H), 7.75 (td, J = 8.6, 6.7 Hz, 2H), 7.45 (d, J = 7.9 Hz, 1H), 7.27 (ddd, J = 7.5, 4.8, 1.2 Hz, 1H), 5.20 (q, J = 7.1 Hz, 1H), 4.95 (s, 1H), 4.64 (d, J = 11.0 Hz, 1H), 4.33 (d, J = 1.7 Hz, 3H), 3.86 (s, 2H), 2.32 (s, 1H), 2.13 (dd, J = 24.2, 8.8 Hz, 4H), 1.94 (s, 2H), 1.68 (t, J = 11.7 Hz, 1H). | 10 1.34 487.20 |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 171 | 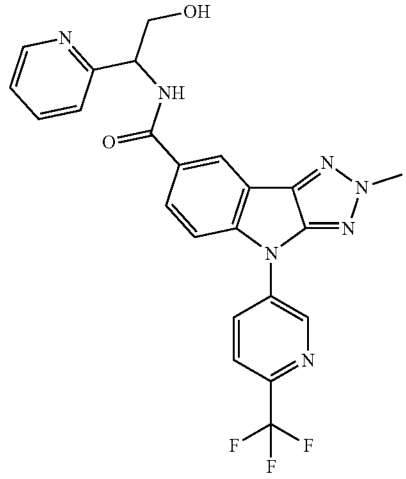 [SMILES: Cn1nc2c3cc(C(=O)NC(CO)c4ccccn4)ccc3n(-c3ccc(C(F)(F)F)nc3)c2n1] N-[2-hydroxy-1-(pyridin-2-yl)ethyl]-2-methyl-4-[6-(trifluoromethyl)pyridin-3-yl]-2H,4H-[1,2,3]triazolo[4,5-b]indole-7-carboxamide | (300 MHz, DMSO-d6) δ 9.21 (d, J = 2.7 Hz, 1H), 8.77 (d, J = 7.8 Hz, 1H), 8.59 (d, J = 2.0 Hz, 1H), 8.43 (dd, J = 6.8, 3.8 Hz, 2H), 8.07 (d, J = 8.5 Hz, 1H), 7.99 (dd, J = 8.8, 1.8 Hz, 1H), 7.90 (d, J = 8.7 Hz, 1H), 7.71-7.59 (m, 1H), 7.34 (d, J = 7.9 Hz, 1H), 7.21-7.10 (m, 1H), 5.16-5.03 (m, 1H), 4.88 (t, J = 6.0 Hz, 1H), 4.27 (d, J = 1.4 Hz, 3H), 3.82-3.68 (m, 2H). | 10<br>0.81<br>482.20 |
| 172 | 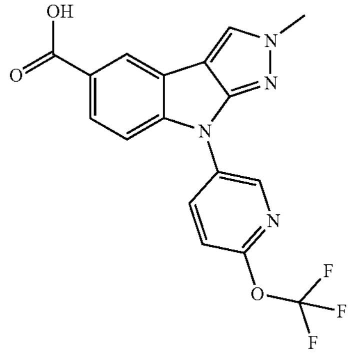 [SMILES: Cn1cc2c3cc(C(=O)O)ccc3n(-c3ccc(OC(F)(F)F)nc3)c2n1] 2-methyl-8-[6-(trifluoromethoxy)-pyridin-3-yl]-2H,8H-pyrazolo[3,4-b]indole-5-carboxylic acid | (400 MHz, DMSO-d6) δ 12.68-12.65 (m, 1H), 8.85 (dd, J = 2.8, 0.5 Hz, 1H), 8.47 (dd, J = 8.8, 2.8 Hz, 1H), 8.42 (dd, J = 1.8, 0.4 Hz, 1H), 8.21 (s, 1H), 7.91 (dd, J = 8.7, 1.8 Hz, 1H), 7.67 (dd, J = 8.7, 0.5 Hz, 1H), 7.56 (dd, J = 8.7, 0.6 Hz, 1H), 4.02 (s, 3H). | 8<br>1.66<br>377.00 |
| 173 | 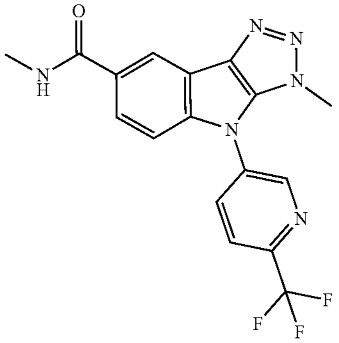 N,3-dimethyl-4-[6-(trifluoromethyl)-pyridin-3-yl]-3H,4H-[1,2,3]triazolo[4,5-b]indole-7-carboxamide | (400 MHz, DMSO-d6) δ 9.32-9.30 (m, 1H), 8.59-8.53 (m, 2H), 8.53 (dd, J = 1.8, 0.7 Hz, 1H), 8.17 (dd, J = 8.7, 0.7 Hz, 1H), 8.03 (dd, J = 8.8, 1.8 Hz, 1H), 7.99 (dd, J = 8.8, 0.7 Hz, 1H), 4.38 (s, 3H), 2.84 (d, J = 4.4 Hz, 3H). | 8<br>1.54<br>375.00 |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 174 | 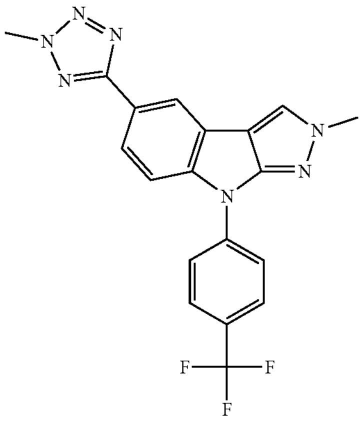<br>2-methyl-5-{2-methyl-8-[4-(trifluoromethyl)phenyl]-2H,8H-pyrazolo[3,4-b]indol-5-yl}-2H-1,2,3,4-tetrazole | (400 MHz, DMSO-$d_6$) δ 8.55-8.50 (m, 1H), 8.23 (s, 1H), 8.10 (d, J = 8.4 Hz, 2H), 8.05-7.94 (m, 3H), 7.88 (dd, J = 8.7, 0.6 Hz, 1H), 4.44 (s, 3H), 4.04 (s, 3H). | 8<br>1.21<br>398.20 |
| 175 | 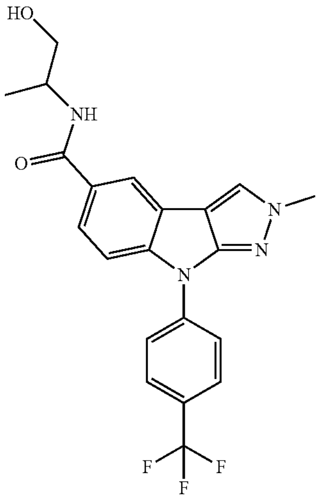 [SMILES: CC(CO)NC(=O)c1ccc2c(c1)c1cn(C)nc1n2-c1ccc(C(F)(F)F)cc1]<br>N-(1-hydroxypropan-2-yl)-2-methyl-8-[4-(trifluoromethyl)phenyl]-2H,8H-pyrazolo[3,4-b]indole-5-carboxamide | (700 MHz, DMSO-d6) δ 8.35 (d, J = 1.8 Hz, 1H), 8.20 (s, 1H), 8.12 (d, J = 7.9 Hz, 1H), 8.10-8.07 (m, 2H), 7.99-7.96 (m, 2H), 7.86 (dd, J = 8.6, 1.9 Hz, 1H), 7.77 (d, J = 8.7 Hz, 1H), 4.10-4.04 (m, 1H), 4.04 (s, 3H), 3.50 (dd, J = 10.7, 5.7 Hz, 1H), 3.37 (dd, J = 10.6, 6.4 Hz, 1H), 1.17 (d, J = 6.7 Hz, 3H). | 8<br>1.59<br>417.00 |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 176 | 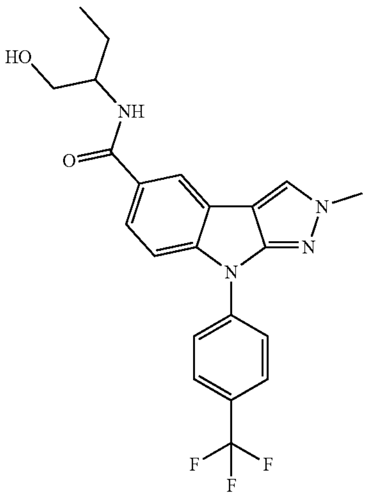 [SMILES: CCC(CO)NC(=O)c1ccc2c(c1)c1cn(C)nc1n2-c1ccc(C(F)(F)F)cc1] N-(1-hydroxybutan-2-yl)-2-methyl-8-[4-(trifluoromethyl)phenyl]-2H,8H-pyrazolo[3,4-b]indole-5-carboxamide | (700 MHz, DMSO-d6) δ 8.36 (d, J = 1.8 Hz, 1H), 8.20 (s, 1H), 8.10-8.07 (m, 2H), 8.03 (d, J = 8.4 Hz, 1H), 7.99-7.96 (m, 2H), 7.87 (dd, J = 8.7, 1.8 Hz, 1H), 7.77 (d, J = 8.6 Hz, 1H), 4.04 (s, 3H), 3.95-3.89 (m, 1H), 3.50 (dd, J = 10.8, 5.6 Hz, 1H), 3.42 (dd, J = 10.8, 6.2 Hz, 1H), 1.73-1.66 (m, 1H), 1.53-1.46 (m, 1H), 0.90 (t, J = 7.4 Hz, 3H). | 8<br>1.65<br>431.00 |
| 177 | 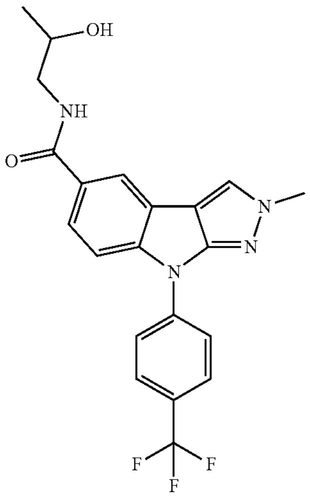 [SMILES: CC(O)CNC(=O)c1ccc2c(c1)c1cn(C)nc1n2-c1ccc(C(F)(F)F)cc1] N-(2-hydroxypropyl)-2-methyl-8-[4-(trifluoromethyl)phenyl]-2H,8H-pyrazolo[3,4-b]indole-5-carboxamide | (400 MHz, DMSO-d6) δ 8.39 (t, J = 5.8 Hz, 1H), 8.35 (d, J = 1.8 Hz, 1H), 8.20 (s, 1H), 8.11-8.06 (m, 2H), 7.99-7.94 (m, 2H), 7.86 (dd, J = 8.7, 1.8 Hz, 1H), 7.77 (d, J = 8.7 Hz, 1H), 4.04 (s, 3H), 3.87-3.78 (m, 1H), 3.30-3.19 (m, 2H), 1.09 (d, J = 6.2 Hz, 3H). | 8<br>1.58<br>417.00 |

TABLE 1-continued

| Compound No. (Example No.) | Structure and Name | $^1$H-NMR | Conditions and elution time (min) LCMS (M + H$^+$) |
|---|---|---|---|
| Table 1 below shows exemplary compounds of the present invention. They have been synthesized as described in the Examples above or similar thereto. | | | |
| 178 | 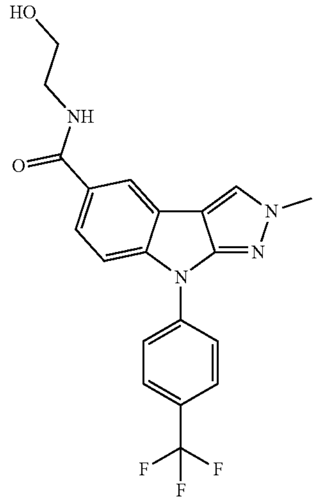 [SMILES: Cn1cc2c3cc(C(=O)NCCO)ccc3n(-c3ccc(C(F)(F)F)cc3)c2n1] N-(2-hydroxyethyl)-2-methyl-8-[4-(trifluoromethyl)phenyl]-2H,8H-pyrazolo[3,4-b]indole-5-carboxamide | (400 MHz, DMSO-d6) δ 8.41 (t, J = 5.6 Hz, 1H), 8.35 (d, J = 1.8 Hz, 1H), 8.19 (s, 1H), 8.11-8.06 (m, 2H), 7.99-7.94 (m, 2H), 7.86 (dd, J = 8.7, 1.9 Hz, 1H), 7.76 (d, J = 8.7 Hz, 1H), 4.03 (s, 3H), 3.55 (t, J = 6.3 Hz, 2H), 3.38 (q, J = 6.0 Hz, 2H). | 8 1.54 403.00 |
| 179 | 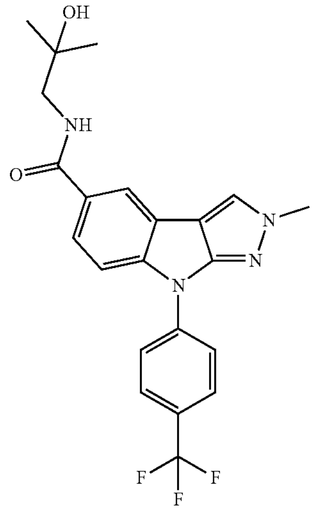 [SMILES: Cn1cc2c3cc(C(=O)NCC(C)(C)O)ccc3n(-c3ccc(C(F)(F)F)cc3)c2n1] N-(2-hydroxy-2-methylpropyl)-2-methyl-8-[4-(trifluoromethyl)phenyl]-2H,8H-pyrazolo[3,4-b]indole-5-carboxamide | (400 MHz, DMSO-d6) δ 8.37 (d, J = 1.8 Hz, 1H), 8.23 (t, J = 6.1 Hz, 1H), 8.19 (s, 1H), 8.11-8.06 (m, 2H), 7.99-7.94 (m, 2H), 7.87 (dd, J = 8.7, 1.9 Hz, 1H), 7.77 (d, J = 8.7 Hz, 1H), 4.04 (s, 3H), 3.31 (d, J = 6.0 Hz, 2H), 1.14 (s, 6H). | 8 1.63 431.00 |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 180 | 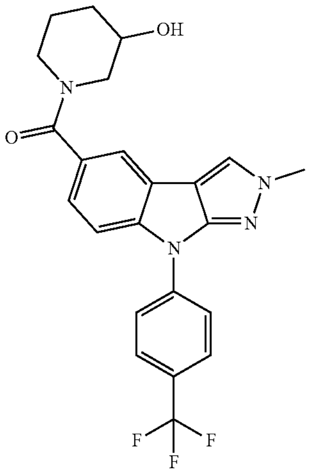 [SMILES: Cn1cc2c3cc(C(=O)N4CCCC(O)C4)ccc3n(-c3ccc(C(F)(F)F)cc3)c2n1] 1-{2-methyl-8-[4-(trifluoromethyl)-phenyl]-2H,8H-pyrazolo[3,4-b]indole-5-carbonyl}piperidin-3-ol | (700 MHz, DMSO-d6/TFA) δ 8.14 (s, 1H), 8.13-8.10 (m, 2H), 7.96-7.93 (m, 2H), 7.93-7.89 (m, 1H), 7.79 (d, J = 8.5 Hz, 1H), 7.39 (d, J = 8.5 Hz, 1H), 4.35-3.59 (m, 2H), 4.06 (s, 3H), 3.63-3.54 (m, 1H), 3.31-2.91 (m, 2H), 1.97-1.88 (m, 1H), 1.87-1.66 (m, 1H), 1.55-1.42 (m, 2H). | 8<br>1.62<br>443.00 |
| 181 | 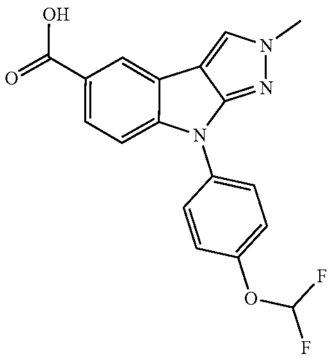 [SMILES: Cn1cc2c3cc(C(=O)O)ccc3n(-c3ccc(OC(F)F)cc3)c2n1] 8-[4-(difluoromethoxy)phenyl]-2-methyl-2H,8H-pyrazolo[3,4-b]indole-5-carboxylic acid | (400 MHz, DMSO-d6) δ 12.65-12.58 (m, 1H), 8.41 (d, J = 1.7 Hz, 1H), 8.18 (s, 1H), 7.90 (dd, J = 8.7, 1.8 Hz, 1H), 7.85-7.80 (m, 2H), 7.57 (d, J = 8.6 Hz, 1H), 7.45-7.40 (m, 2H), 7.31 (t, J = 73.9 Hz, 1H), 4.01 (s, 3H). | 8<br>1.61<br>358.00 |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 182 | 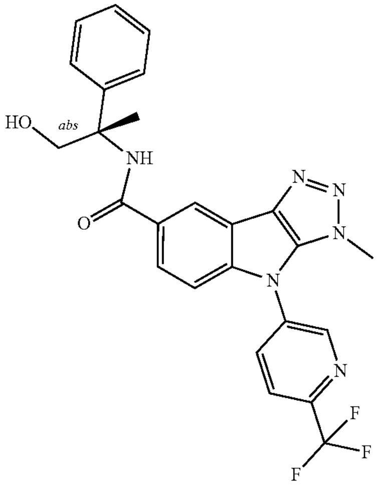 [SMILES: Cn1nnc2c3cc(C(=O)N[C@](C)(CO)c4ccccc4)ccc3n(-c3ccc(C(F)(F)F)nc3)c21] Absolute configuration known/assigned N-[(2S)-1-hydroxy-2-phenylpropan-2-yl]-3-methyl-4-[6-(trifluoromethyl)pyridin-3-yl]-3H,4H-[1,2,3]triazolo[4,5-b]indole-7-carboxamide | (300 MHz, DMSO-d6) 9.33 (d, J = 2.6 Hz, 1H), 8.65 (s, 1H), 8.56 (d, J = 8.6 Hz, 1H), 8.29 (s, 1H), 8.20 (d, J = 8.6 Hz, 1H), 8.02 (s, 2H), 7.30 (ddd, J = 31.0, 24.7, 7.3 Hz, 5H), 5.16 (t, J = 6.0 Hz, 1H), 4.40 (s, 3H), 3.83 (dd, J = 11.0, 6.0 Hz, 1H), 3.60 (dd, J = 11.1, 6.3 Hz, 1H), 1.77 (s, 3H). | 8 0.91 (495.1) |
| 183 | 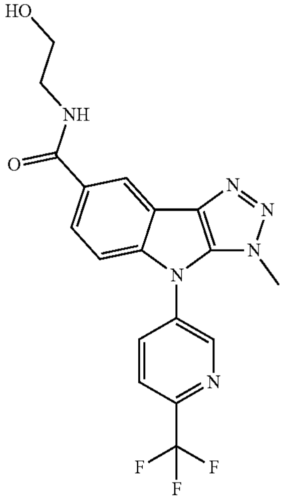 N-(2-hydroxyethyl)-3-methyl-4-[6-(trifluoromethyl)pyridin-3-yl]-3H,4H-[1,2,3]triazolo[4,5-b]indole-7-carboxamide | (400 MHz, DMSO-d6) 9.32 (d, J = 2.7 Hz, 1H), 8.57 (ddd, J = 13.8, 10.9, 4.5 Hz, 3H), 8.19 (d, J = 8.5 Hz, 1H), 8.09-8.03 (m, 1H), 8.00 (d, J = 8.8 Hz, 1H), 4.76 (t, J = 5.6 Hz, 1H), 4.39 (s, 3H), 3.57 (q, J = 6.0 Hz, 2H), 3.39 (d, J = 6.0 Hz, 2H). | 8 0.75 (405.00) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 184 | 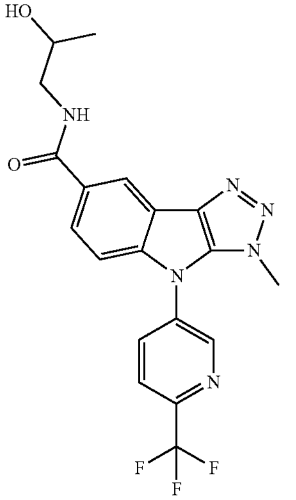 [SMILES: CC(O)CNC(=O)c1ccc2c(c1)c1nnn(C)c1n2-c1ccc(C(F)(F)F)nc1] N-(2-hydroxypropyl)-3-methyl-4-[6-(trifluoromethyl)pyridin-3-yl]-3H,4H-[1,2,3]triazolo[4,5-b]indole-7-carboxamide | (400 MHz, DMSO-d6) 9.32 (d, J = 2.7 Hz, 1H), 8.62-8.52 (m, 3H), 8.19 (d, J = 8.5 Hz, 1H), 8.06 (dd, J = 8.8, 1.9 Hz, 1H), 8.00 (d, J = 8.7 Hz, 1H), 4.78 (s, 1H), 4.39 (s, 3H), 3.84 (s, 1H), 3.28-3.24 (m, 2H), 1.10 (d, J = 6.2 Hz, 3H). | 8 0.78 (419.10) |
| 185 | 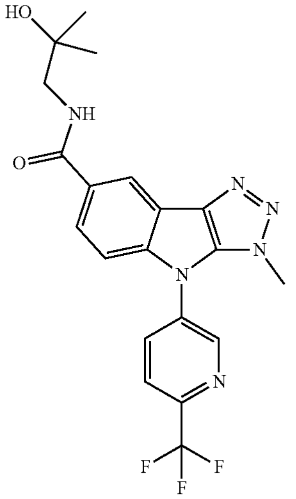 [SMILES: Cn1nnc2c3cc(C(=O)NCC(C)(C)O)ccc3n(-c3ccc(C(F)(F)F)nc3)c21] N-(2-hydroxy-2-methylpropyl)-3-methyl-4-[6-(trifluoromethyl)pyridin-3-yl]-3H,4H-[1,2,3]triazolo[4,5-b]indole-7-carboxamide | (300 MHz, DMSO-d6) 9.32 (d, J = 2.6 Hz, 1H), 8.64-8.50 (m, 2H), 8.43 (t, J = 6.1 Hz, 1H), 8.19 (d, J = 8.6 Hz, 1H), 8.11-7.93 (m, 2H), 4.60 (s, 1H), 4.39 (s, 3H), 1.15 (s, 6H). | 8 0.80 (433.10) |

TABLE 1-continued

| Com-pound No. (Example No.) | Structure and Name | $^1$H-NMR | Conditions and elution time (min) LCMS (M + H$^+$) |
|---|---|---|---|
| Table 1 below shows exemplary compounds of the present invention. They have been synthesized as described in the Examples above or similar thereto. | | | |
| 186 | 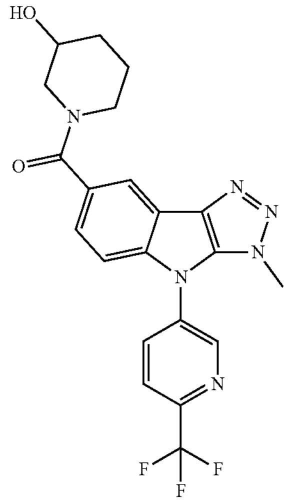 [SMILES: Cn1nnc2c3cc(C(=O)N4CCCC(O)C4)ccc3n(-c3ccc(C(F)(F)F)nc3)c21] 1-{3-methyl-4-[6-(trifluoromethyl)-pyridin-3-yl]-3H,4H-[1,2,3]triazolo[4,5-b]indole-7-carbonyl}piperidin-3-ol | (300 MHz, DMSO-d6) δ 9.32 (s, 1H), 8.55 (d, J = 8.6 Hz, 1H), 8.22-7.97 (m, 3H), 7.55 (d, J = 8.8 Hz, 1H), 4.90 (s, 1H), 4.38 (s, 3H), 3.57 (s, 2H), 3.14 (s, 3H), 1.87 (s, 2H), 1.46 (s, 2H). | 8 0.79 (445.10) |
| 187 | 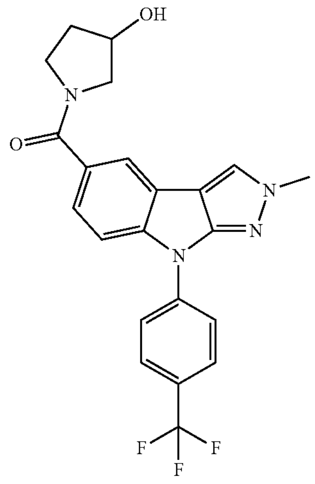 [SMILES: Cn1cc2c3cc(C(=O)N4CCC(O)C4)ccc3n(-c3ccc(C(F)(F)F)cc3)c2n1] 1-{2-methyl-8-[4-(trifluoromethyl)-phenyl]-2H,8H-pyrazolo[3,4-b]indole-5-carbonyl}pyrrolidin-3-ol | (400 MHz, DMSO-d6) δ 8.15 (s, 1H), 8.12-8.06 (m, 2H), 8.05-8.00 (m, 1H), 7.98-7.93 (m, 2H), 7.75 (d, J = 8.5 Hz, 1H), 7.52-7.47 (m, 1H), 4.38-4.22 (m, 1H), 4.03 (s, 3H), 3.74-3.43 (m, 3H), 3.39-3.27 (m, 1H), 2.04-1.76 (m, 2H). | 8 1.55 429.10 |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 188 | 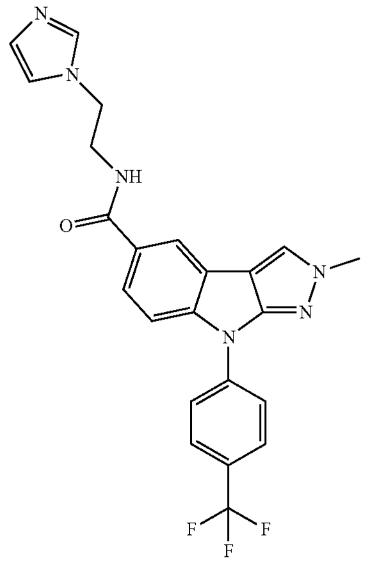 [SMILES: Cn1cc2c3cc(C(=O)NCCn4ccnc4)ccc3n(-c3ccc(C(F)(F)F)cc3)c2n1]<br>N-[2-(1H-imidazol-1-yl)ethyl]-2-methyl-8-[4-(trifluoromethyl)phenyl]-2H,8H-pyrazolo[3,4-b]indole-5-carboxamide | (400 MHz, DMSO-d6) δ 9.09-9.07 (m, 1H), 8.65 (t, J = 5.7 Hz, 1H), 8.28-8.27 (m, 1H), 8.19 (s, 1H), 8.10-8.05 (m, 2H), 7.99-7.95 (m, 2H), 7.78-7.76 (m, 2H), 7.75 (t, J = 1.7 Hz, 1H), 7.64 (t, J = 1.7 Hz, 1H), 4.42-4.38 (m, 2H), 4.04 (s, 3H), 3.75 (q, J = 5.6 Hz, 2H). | 8<br>1.34-1.35<br>453.00 |
| 189 | 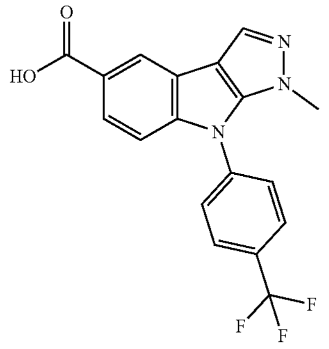 [SMILES: Cn1ncc2c3cc(C(=O)O)ccc3n(-c3ccc(C(F)(F)F)cc3)c21]<br>1-methyl-8-[4-(trifluoromethyl)phenyl]-1H,8H-pyrazolo[3,4-b]indole-5-carboxylic acid | (400 MHz, DMSO-d6) δ 12.70-12.59 (m, 1H), 8.40 (d, J = 1.6 Hz, 1H), 8.07-8.01 (m, 2H), 7.99-7.94 (m, 2H), 7.92 (s, 1H), 7.83 (dd, J = 8.7, 1.7 Hz, 1H), 7.30 (d, J = 8.7 Hz, 1H), 3.65 (s, 3H). | 8<br>1.65<br>360.00 |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 190 | 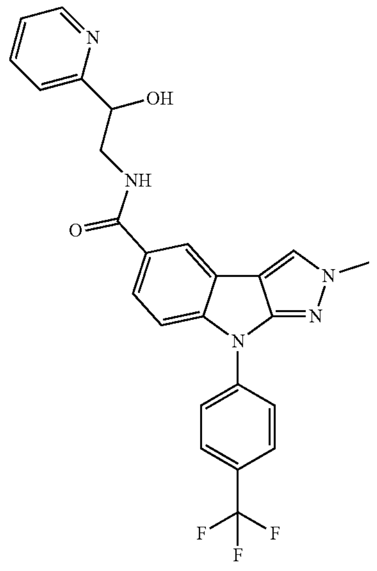 [SMILES: Cn1cc2c3cc(C(=O)NCC(O)c4ccccn4)ccc3n(-c3ccc(C(F)(F)F)cc3)c2n1]<br>N-[2-hydroxy-2-(pyridin-2-yl)ethyl]-2-methyl-8-[4-(trifluoromethyl)phenyl]-2H,8H-pyrazolo[3,4-b]indole-5-carboxamide | (400 MHz, DMSO-d6) δ 8.66-8.62 (m, 1H), 8.56 (t, J = 5.7 Hz, 1H), 8.31 (d, J = 1.7 Hz, 1H), 8.20 (s, 1H), 8.15-8.09 (m, 1H), 8.10-8.06 (m, 2H), 7.99-7.94 (m, 2H), 7.81 (dd, J = 8.7, 1.8 Hz, 1H), 7.78-7.75 (m, 1H), 7.76 (d, J = 8.7 Hz, 1H), 7.59-7.54 (m, 1H), 5.03-4.98 (m, 1H), 4.04 (s, 3H), 3.78-3.71 (m, 1H), 3.62-3.54 (m, 1H). | 8<br>1.41<br>480.00 |
| 191 | 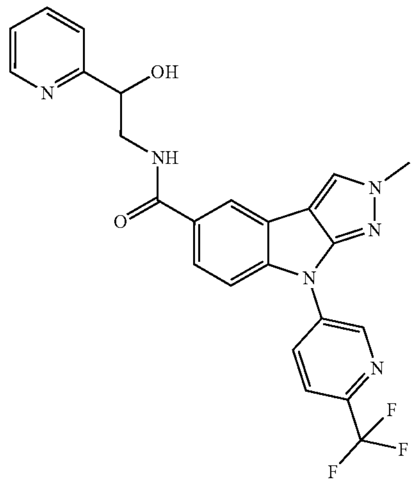 [SMILES: Cn1cc2c3cc(C(=O)NCC(O)c4ccccn4)ccc3n(-c3ccc(C(F)(F)F)nc3)c2n1]<br>N-[2-hydroxy-2-(pyridin-2-yl)ethyl]-2-methyl-8-[6-(trifluoromethyl)pyridin-3-yl]-2H,8H-pyrazolo[3,4-b]indole-5-carboxamide | (400 MHz, DMSO-d6) δ 9.33 (d, J = 2.6 Hz, 1H), 8.66-8.63 (m, 1H), 8.61-8.56 (m, 1H), 8.56 (dd, J = 8.2, 2.5 Hz, 1H), 8.33-8.30 (m, 1H), 8.22 (s, 1H), 8.14 (d, J = 8.6 Hz, 1H), 8.14-8.08 (m, 1H), 7.86-7.80 (m, 2H), 7.77 (d, J = 8.0 Hz, 1H), 7.59-7.54 (m, 1H), 5.01 (dd, J = 6.9, 5.1 Hz, 1H), 4.05 (s, 3H), 3.79-3.70 (m, 1H), 3.63-3.55 (m, 1H). | 8<br>1.28<br>481.00 |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 193 | 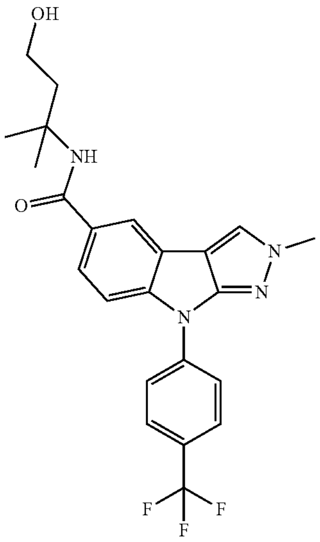 [SMILES: Cn1cc2c3cc(C(=O)NC(C)(C)CCO)ccc3n(-c3ccc(C(F)(F)F)cc3)c2n1] N-(4-hydroxy-2-methylbutan-2-yl)-2-methyl-8-[4-(trifluoromethyl)phenyl]-2H,8H-pyrazolo[3,4-b]indole-5-carboxamide | (400 MHz, DMSO-d6) δ 8.24 (t, J = 1.2 Hz, 1H), 8.18 (s, 1H), 8.10-8.06 (m, 2H), 7.98-7.96 (m, 1H), 7.98-7.94 (m, 2H), 7.74 (s, 1H), 7.74 (s, 1H), 4.03 (s, 3H), 3.61 (t, J = 6.6 Hz, 2H), 1.93 (t, J = 6.6 Hz, 2H), 1.43 (s, 6H). | 8 1.72 445.00 |
| 194 | 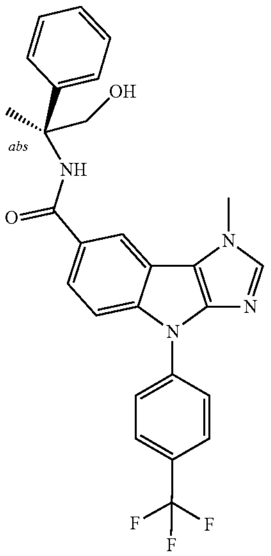 [SMILES: Cn1cnc2c1c1cc(C(=O)N[C@](C)(CO)c3ccccc3)ccc1n2-c1ccc(C(F)(F)F)cc1] Absolute configuration known/assigned N-[(2S)-1-hydroxy-2-phenylpropan-2-yl]-1-methyl-4-[4-(trifluoromethyl)phenyl]-1H,4H-imidazo[4,5-b]indole-7-carboxamide | (400 MHz, DMSO-d6) δ 8.38 (d, J = 1.8 Hz, 1H), 8.14-8.07 (m, 3H), 7.98 (d, J = 8.4 Hz, 2H), 7.91-7.81 (m, 3H), 7.43-7.36 (m, 2H), 7.30 (t, J = 7.6 Hz, 2H), 7.19 (t, J = 7.2 Hz, 1H), 5.21 (t, J = 6.0 Hz, 1H), 4.13 (s, 3H), 3.82 (dd, J = 10.9, 6.1 Hz, 1H), 3.60 (dd, J = 11.0, 6.1 Hz, 1H), 1.77 (s, 3H). | 8 0.94 (493.20) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 195 | 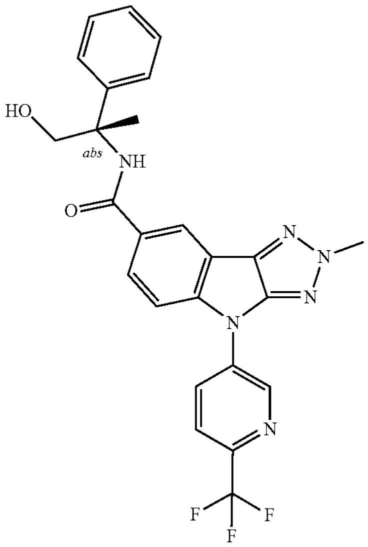 [SMILES: Cn1nc2c3cc(C(=O)N[C@](C)(CO)c4ccccc4)ccc3n(-c3ccc(C(F)(F)F)nc3)c2n1]<br>Absolute configuration known/assgined<br>N-[(2S)-1-hydroxy-2-phenylpropan-2-yl]-2-methyl-4-[6-(trifluoromethyl)pyridin-3-yl]-2H,4H-[1,2,3]triazolo[4,5-b]indole-7-carboxamide | (300 MHz, DMSO-d6, ppm) δ 9.32 (s, 1H), 8.68-8.49 (m, 2H), 8.35-8.14 (m, 2H), 8.01 (s, 2H), 7.45-7.19 (m, 5H), 5.17 (t, J = 6.1 Hz, 1H), 4.39 (s, 3H), 3.86-3.80 (m, 1H), 3.59 (t, J = 9.0 Hz, 1H), 1.77 (s, 3H). | 10<br>1.07<br>495.2 |
| 196 | 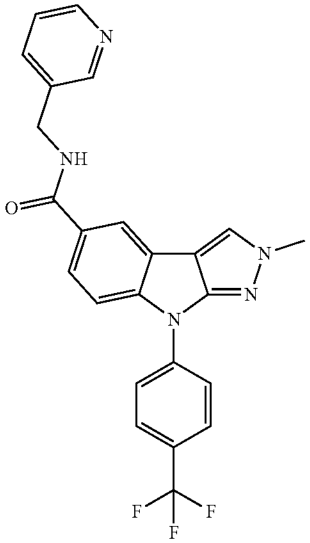 [SMILES: Cn1cc2c3cc(C(=O)NCc4cccnc4)ccc3n(-c3ccc(C(F)(F)F)cc3)c2n1]<br>2-methyl-N-[(pyridin-3-yl)methyl]-8-[4-(trifluoromethyl)phenyl]-2H,8H-pyrazolo[3,4-b]indole-5-carboxamide | (700 MHz, DMSO-d6) δ 9.21 (t, J = 5.8 Hz, 1H), 8.76-8.75 (m, 1H), 8.66-8.64 (m, 1H), 8.39 (d, J = 1.8 Hz, 1H), 8.21 (s, 1H), 8.15 (d, J = 7.9 Hz, 1H), 8.10-8.07 (m, 2H), 7.99-7.96 (m, 2H), 7.89 (dd, J = 8.7, 1.9 Hz, 1H), 7.80 (d, J = 8.6 Hz, 1H), 7.71 (dd, J = 8.0, 5.2 Hz, 1H), 4.62 (d, J = 5.7 Hz, 2H), 4.04 (s, 3H). | 8<br>1.39<br>450.00 |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 197 | 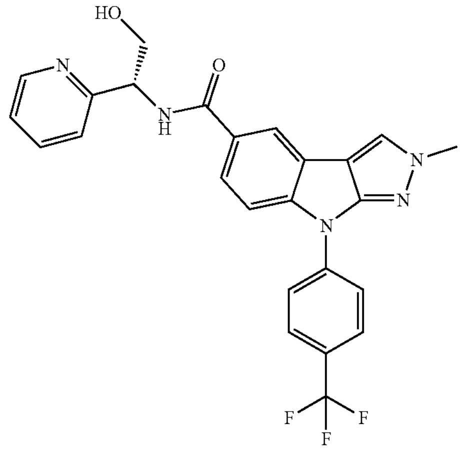 TFA<br>Absolute configuration known/assigned N-[(1R)-2-hydroxy-1-(pyridin-2-yl)ethyl]-2-methyl-8-[4-(trifluoromethyl)phenyl]-2H,8H-pyrazolo[3,4-b]indole-5-carboxamide | (700 MHz, DMSO-$d_6$) δ 8.85 (d, J = 7.0 Hz, 1H), 8.68 (d, J = 6.3 Hz, 1H), 8.44 (d, J = 1.8 Hz, 1H), 8.09 (d, J = 8.4 Hz, 3H), 7.98 (d, J = 8.4 Hz, 2H), 7.92 (dd, J = 8.7, 1.9 Hz, 1H), 7.81 (d, J = 8.6 Hz, 1H), 5.26 (q, J = 6.5 Hz, 1H), 4.05 (s, 3H), 3.90 (t, J = 5.8 Hz, 2H). | |
| 198 | 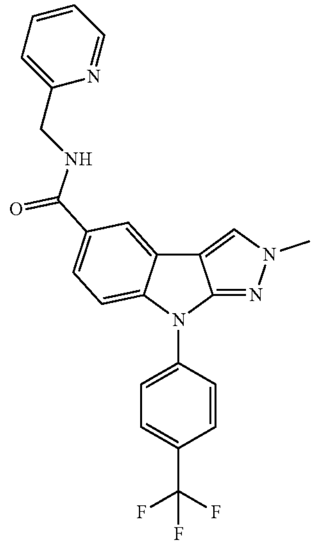 [SMILES: Cn1cc2c3cc(C(=O)NCc4ccccn4)ccc3n(-c3ccc(C(F)(F)F)cc3)c2n1]<br>2-methyl-N-[(pyridin-2-yl)methyl]-8-[4-(trifluoromethyl)phenyl]-2H,8H-pyrazolo[3,4-b]indole-5-carboxamide | (700 MHz, DMSO-d6) δ 9.26 (t, J = 5.8 Hz, 1H), 8.67-8.65 (m, 1H), 8.43 (d, J = 1.8 Hz, 1H), 8.23 (s, 1H), 8.11-8.08 (m, 2H), 8.09-8.06 (m, 1H), 8.00-7.96 (m, 2H), 7.93 (dd, J = 8.7, 1.9 Hz, 1H), 7.81 (d, J = 8.7 Hz, 1H), 7.62 (d, J = 8.0 Hz, 1H), 7.56-7.53 (m, 1H), 4.71 (d, J = 5.6 Hz, 2H), 4.04 (s, 3H). | 8<br>1.50<br>450.00 |

TABLE 1-continued

| Compound No. (Example No.) | Structure and Name | $^1$H-NMR | Conditions and elution time (min) LCMS (M + H$^+$) |
|---|---|---|---|
| Table 1 below shows exemplary compounds of the present invention. They have been synthesized as described in the Examples above or similar thereto. | | | |
| 199 | 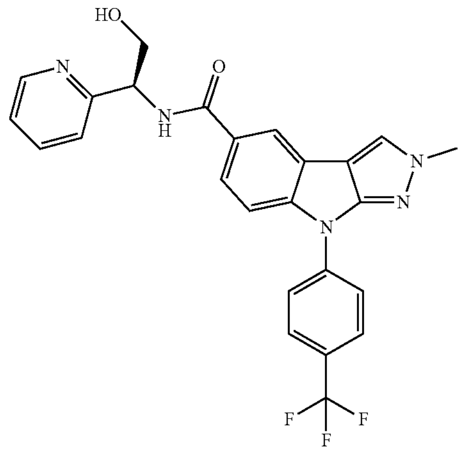 [SMILES: Cn1cc2c3cc(C(=O)N[C@H](CO)c4ccccn4)ccc3n(-c3ccc(C(F)(F)F)cc3)c2n1] Absolute configuration known/assigned N-[(1S)-2-hydroxy-1-(pyridin-2-yl)ethyl]-2-methyl-8-[4-(trifluoromethyl)phenyl]-2H,8H-pyrazolo[3,4-b]indole-5-carboxamide | | |
| 200 | 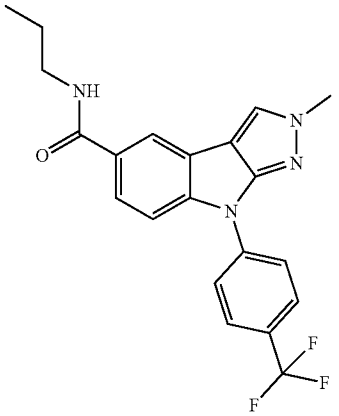 [SMILES: CCCNC(=O)c1ccc2c(c1)c1cn(C)nc1n2-c1ccc(C(F)(F)F)cc1] 2-methyl-N-propyl-8-[4-(trifluoromethyl)phenyl]-2H,8H-pyrazolo[3,4-b]indole-5-carboxamide | (700 MHz, DMSO-d6) δ 0.92 (t, J = 7.4 Hz, 3H, 29), 1.57 (h, J = 7.4 Hz, 2H, 28), 2.55 (t, J = 5.6 Hz, 2H), 3.23-3.29 (m, 2H, 27), 4.04 (s, 3H, 16), 7.77 (d, J = 8.7 Hz, 1H, 3), 7.85 (dd, J = 8.7, 1.8 Hz, 1H, 2), 7.95 (s, 0H), 7.97 (d, J = 8.6 Hz, 2H, 19, 21), 8.09 (d, J = 8.5 Hz, 2H, 18, 22), 8.21 (s, 1H, 12), 8.33 (d, J = 1.8 Hz, 1H, 4), 8.48 (t, J = 5.6 Hz, 1H, 14). | 8 0.83 401.20 |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 201 | 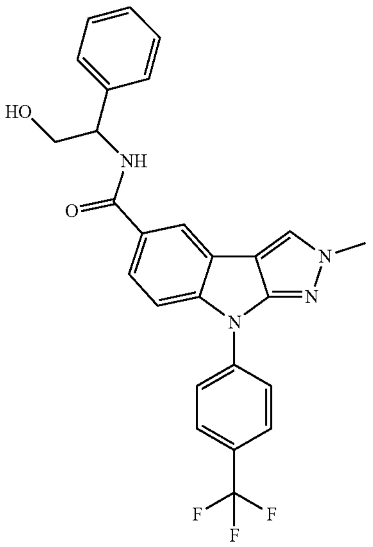 [SMILES: Cn1cc2c3cc(C(=O)NC(CO)c4ccccc4)ccc3n(-c3ccc(C(F)(F)F)cc3)c2n1]<br>N-(2-hydroxy-1-phenylethyl)-2-methyl-8-[4-(trifluoromethyl)phenyl]-2H,8H-pyrazolo[3,4-b]indole-5-carboxamide | (700 MHz, DMSO-d$_6$) δ 8.73 (d, J = 8.0 Hz, 0H), 8.42 (d, J = 1.8 Hz, 0H), 8.22 (s, 0H), 8.09 (d, J = 8.5 Hz, 1H), 7.97 (d, J = 8.5 Hz, 1H), 7.91 (dd, J = 8.7, 1.9 Hz, 0H), 7.79 (d, J = 8.6 Hz, 0H), 7.45-7.41 (m, 1H), 7.33 (t, J = 7.7 Hz, 1H), 7.26-7.21 (m, 0H), 5.13 (td, J = 8.1, 5.4 Hz, 1H), 4.04 (s, 2H), 3.76 (dd, J = 11.2, 8.2 Hz, 0H), 3.69 (dd, J = 11.2, 5.4 Hz, 1H). | 8<br>1.76<br>478.90 |
| 202 (Ex. 28) | 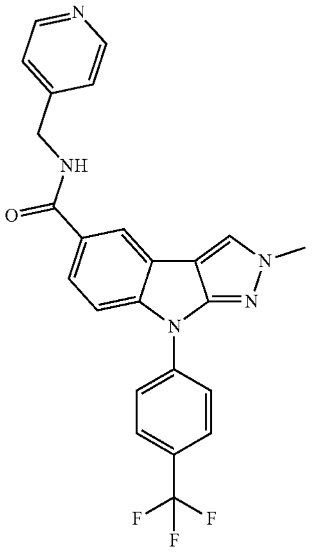 [SMILES: Cn1cc2c3cc(C(=O)NCc4ccncc4)ccc3n(-c3ccc(C(F)(F)F)cc3)c2n1]<br>2-methyl-N-[(pyridin-4-yl)methyl]-8-[4-(trifluoromethyl)phenyl]-2H,8H-pyrazolo[3,4-b]indole-5-carboxamide | (400 MHz, DMSO-d6) δ 9.28 (t, J = 5.9 Hz, 1H), 8.74-8.71 (m, 2H), 8.42 (d, J = 1.8 Hz, 1H), 8.22 (s, 1H), 8.12-8.07 (m, 2H), 8.00-7.96 (m, 2H), 7.92 (dd, J = 8.8, 1.9 Hz, 1H), 7.81 (d, J = 8.7 Hz, 1H), 7.76-7.72 (m, 2H), 4.69 (d, J = 5.7 Hz, 2H), 4.04 (s, 3H). | 8<br>1.37<br>450.00 |

TABLE 1-continued

| Com-pound No. (Example No.) | Structure and Name | ¹H-NMR | Conditions and elution time (min) LCMS (M + H⁺) |
|---|---|---|---|
| 203 | 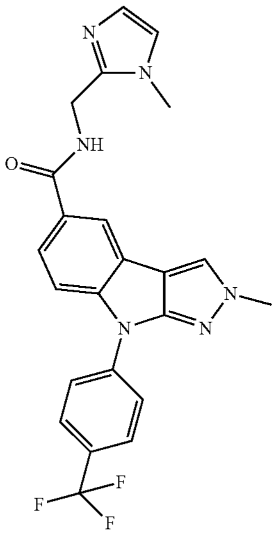 [SMILES: Cn1cc2c3cc(C(=O)NCc4nccn4C)ccc3n(-c3ccc(C(F)(F)F)cc3)c2n1] 2-methyl-N-[(1-methyl-1H-imidazol-2-yl)methyl]-8-[4-(trifluoromethyl)phenyl]-2H,8H-pyrazolo[3,4-b]indole-5-carboxamide | (400 MHz, DMSO-$d_6$) δ 8.92 (t, J = 5.5 Hz, 1H), 8.40 (d, J = 1.9 Hz, 1H), 8.18 (d, J = 7.5 Hz, 1H), 8.08 (d, J = 8.4 Hz, 2H), 7.90 (dd, J = 8.8, 1.9 Hz, 1H), 7.08 (d, J = 1.2 Hz, 1H), 6.81 (d, J = 1.2 Hz, 1H), 4.57 (d, J = 5.4 Hz, 2H), 4.03 (s, 3H), 3.68 (s, 3H). | 8 1.35-1.37 453.00 |
| 204 | 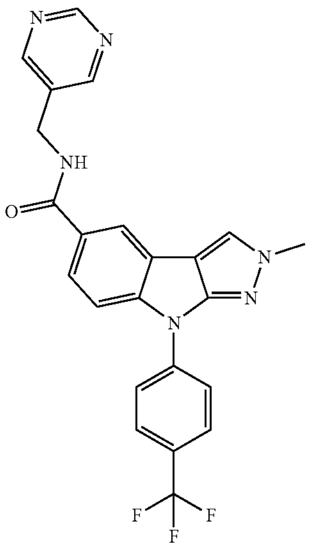 [SMILES: Cn1cc2c3cc(C(=O)NCc4cncnc4)ccc3n(-c3ccc(C(F)(F)F)cc3)c2n1] 2-methyl-N-[(pyrimidin-5-yl)methyl]-8-[4-(trifluoromethyl)phenyl]-2H,8H-pyrazolo[3,4-b]indole-5-carboxamide | (700 MHz, DMSO-d6) δ 9.16 (t, J = 5.8 Hz, 1H), 9.10 (s, 1H), 8.81 (s, 2H), 8.38 (d, J = 1.8 Hz, 1H), 8.21 (s, 1H), 8.10-8.07 (m, 2H), 7.99-7.96 (m, 2H), 7.88 (dd, J = 8.7, 1.8 Hz, 1H), 7.79 (d, J = 8.6 Hz, 1H), 4.54 (d, J = 5.7 Hz, 2H), 4.04 (s, 3H). | 8 1.60 450.9 |

Table 1 below shows exemplary compounds of the present invention. They have been synthesized as described in the Examples above or similar thereto.

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 205 | 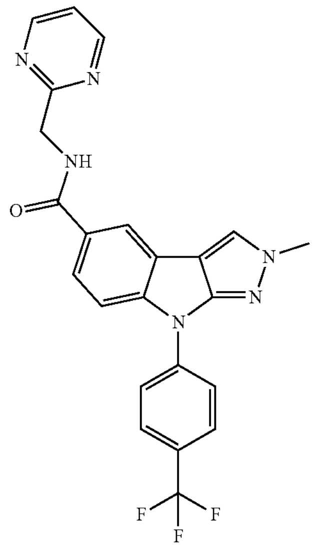 [SMILES: Cn1cc2c3cc(C(=O)NCc4ncccn4)ccc3n(-c3ccc(C(F)(F)F)cc3)c2n1] 2-methyl-N-[(pyrimidin-2-yl)methyl]-8-[4-(trifluoromethyl)phenyl]-2H,8H-pyrazolo[3,4-b]indole-5-carboxamide | (700 MHz, DMSO-d6) δ 9.07 (t, J = 5.9 Hz, 1H), 8.78 (d, J = 4.9 Hz, 2H), 8.42 (d, J = 1.8 Hz, 1H), 8.23 (s, 1H), 8.12-8.09 (m, 2H), 7.99-7.96 (m, 2H), 7.92 (dd, J = 8.7, 1.8 Hz, 1H), 7.81 (d, J = 8.7 Hz, 1H), 7.40 (t, J = 4.9 Hz, 1H), 4.70 (d, J = 5.7 Hz, 2H), 4.04 (s, 3H). | 8<br>1.62<br>450.90 |
| 206 | 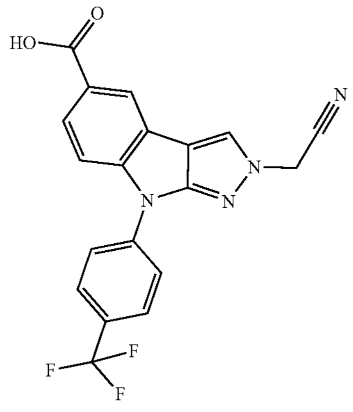 [SMILES: N#CCn1cc2c3cc(C(=O)O)ccc3n(-c3ccc(C(F)(F)F)cc3)c2n1] 2-(cyanomethyl)-8-[4-(trifluoromethyl)phenyl]-2H,8H-pyrazolo[3,4-b]indole-5-carboxylic acid | (300 MHz, DMSO-d6) δ 8.54 (s, 1H), 8.38 (s, 1H), 8.10-7.97 (m, 5H), 7.78 (d, J = 8.7 Hz, 1H), 5.71 (s, 2H) | 10<br>0.80<br>383.00 |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 207 | 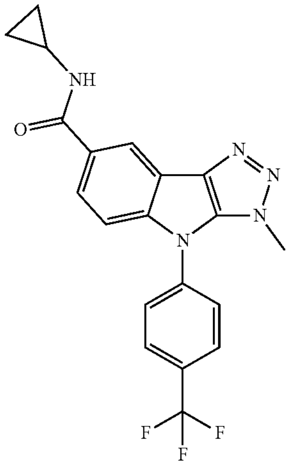 [SMILES: Cn1nnc2c3cc(C(=O)NC4CC4)ccc3n(-c3ccc(C(F)(F)F)cc3)c21] N-cyclopropyl-3-methyl-4-[4-(trifluoromethyl)phenyl]-3H,4H-[1,2,3]triazolo[4,5-b]indole-7-carboxamide | (400 MHz, DMSO-d6) δ 8.57 (d, J = 4.2 Hz, 1H), 8.53 (d, J = 1.8 Hz, 1H), 8.06 (d, J = 8.5 Hz, 2H), 8.04-7.97 (m, 3H), 7.91 (d, J = 8.8 Hz, 1H), 4.37 (s, 3H), 2.90-2.93 (m, J = 7.2, 3.7 Hz, 1H), 0.77-0.66 (m, 2H), 0.62-0.65 (m, J = 3.8 Hz, 2H). | |
| 208 | 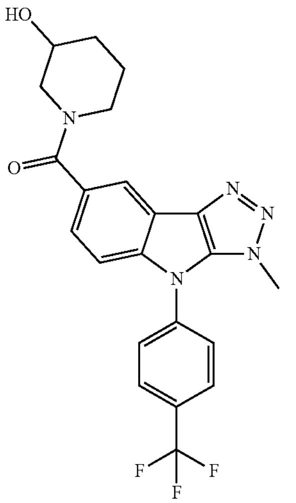 [SMILES: Cn1nnc2c3cc(C(=O)N4CCCC(O)C4)ccc3n(-c3ccc(C(F)(F)F)cc3)c21] 1-{3-methyl-4-[4-(trifluoromethyl)phenyl]-3H,4H-[1,2,3]triazolo[4,5-b]indole-7-carbonyl}piperidin-3-ol | (400 MHz, DMSO-d6) δ 8.07 (d, J = 8.4 Hz, 3H), 8.04-7.98 (m, 2H), 7.92 (d, J = 8.6 Hz, 1H), 7.54 (d, J = 8.6 Hz, 1H), 4.89 (s, 1H), 4.37 (s, 3H), 3.56 (s, 1H), 3.33 (s, 2H), 3.11 (s, 2H), 1.81 (d, J = 50.3 Hz, 2H), 1.45 (s, 2H). | 12 0.89 (444.05) |

TABLE 1-continued

| Compound No. (Example No.) | Structure and Name | ¹H-NMR | Conditions and elution time (min) LCMS (M + H⁺) |
|---|---|---|---|
| Table 1 below shows exemplary compounds of the present invention. They have been synthesized as described in the Examples above or similar thereto. | | | |
| 209 | 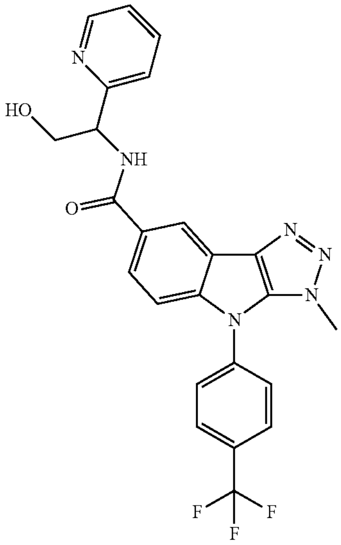 [SMILES: Cn1nnc2c3cc(C(=O)NC(CO)c4ccccn4)ccc3n(-c3ccc(C(F)(F)F)cc3)c21] N-[2-hydroxy-1-(pyridin-2-yl)ethyl]-3-methyl-4-[4-(trifluoromethyl)phenyl]-3H,4H-[1,2,3]triazolo[4,5-b]indole-7-carboxamide | (400 MHz, DMSO-d6) δ 8.86 (d, J = 7.8 Hz, 1H), 8.71 (s, 1H), 8.55 (d, J = 4.9 Hz, 1H), 8.08 (d, J = 8.7 Hz, 3H), 8.02 (d, J = 8.3 Hz, 2H), 7.95 (d, J = 8.9 Hz, 1H), 7.77 (t, J = 7.6 Hz, 1H), 7.46 (d, J = 7.9 Hz, 1H), 7.27 (t, J = 6.2 Hz, 1H), 5.21 (d, J = 6.7 Hz, 1H), 4.98 (t, J = 5.8 Hz, 1H), 4.38 (s, 3H), 3.87 (p, J = 7.1, 6.4 Hz, 2H). | 12 1.30 481.20 |
| 210 | 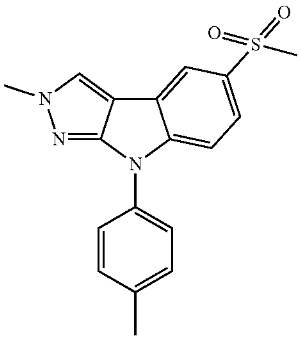 5-methanesulfonyl-2-methyl-8-(4-methylphenyl)-2H,8H-pyrazolo[3,4-b]indole | (700 MHz, DMSO-d6) δ 2.41 (s, 3H, 21), 3.21 (s, 3H, 22), 4.03 (s, 3H, 12), 7.40-7.45 (m, 2H, 17, 19), 7.60-7.66 (m, 3H, 3, 16, 20), 7.79 (dd, J = 8.6, 1.9 Hz, 1H, 2), 8.23 (s, 1H, 11), 8.38 (d, J = 1.9 Hz, 1H, 6). | 8 0.74 340.10 |

TABLE 1-continued

| Com-pound No. (Example No.) | Structure and Name | $^1$H-NMR | Conditions and elution time (min) LCMS (M + H$^+$) |
|---|---|---|---|
| | Table 1 below shows exemplary compounds of the present invention. They have been synthesized as described in the Examples above or similar thereto. | | |
| 211 | 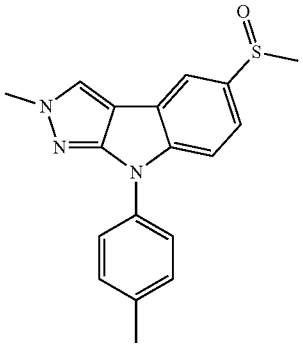 5-methanesulfinyl-2-methyl-8-(4-methylphenyl)-2H,8H-pyrazolo[3,4-b]indole | (700 MHz, DMSO-d6) δ 2.40 (s, 3H, 21), 2.77 (s, 3H, 22), 4.01 (s, 3H, 12), 7.39-7.43 (m, 2H, 17, 19), 7.55 (dd, J = 8.6, 1.9 Hz, 1H, 2), 7.61-7.65 (m, 3H, 3, 16, 20), 8.14 (d, J = 1.8 Hz, 1H, 6), 8.18 (s, 1H, 11). | 8 0.68 324.10 |
| 212 | 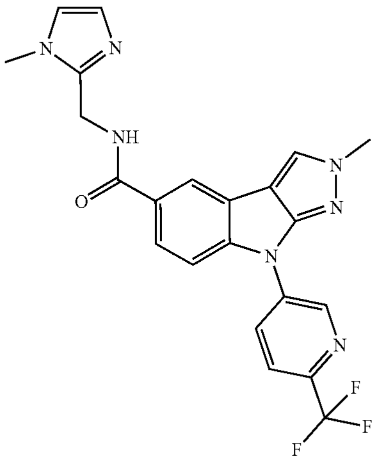 2-methyl-N-[(1-methyl-1H-imidazol-2-yl)methyl]-8-[6-(trifluoromethyl)pyridin-3-yl]-2H,8H-pyrazolo[3,4-b]indole-5-carboxamide | (400 MHz, DMSO-$d_6$) δ 9.33 (d, J = 2.6 Hz, 1H), 8.94 (t, J = 5.5 Hz, 1H), 8.56 (dd, J = 8.5, 2.6 Hz, 1H), 8.40 (d, J = 1.7 Hz, 1H), 8.21 (s, 1H), 8.13 (dd, J = 8.7, 0.7 Hz, 1H), 7.92 (dd, J = 8.7, 1.8 Hz, 1H), 7.84 (d, J = 8.7 Hz, 1H), 7.08 (d, J = 1.2 Hz, 1H), 6.81 (d, J = 1.2 Hz, 1H), 4.57 (d, J = 5.5 Hz, 2H), 4.04 (s, 3H), 3.68 (s, 3H). | 8 1.22 454.00 |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 213 | 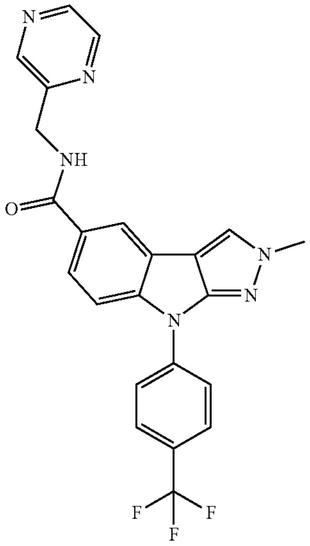 [SMILES: Cn1cc2c3cc(C(=O)NCc4cnccn4)ccc3n(-c3ccc(C(F)(F)F)cc3)c2n1] 2-methyl-N-[(pyrazin-2-yl)methyl]-8-[4-(trifluoromethyl)phenyl]-2H,8H-pyrazolo[3,4-b]indole-5-carboxamide | (700 MHz, DMSO-$d_6$) δ 9.21 (t, J = 5.8 Hz, 1H), 8.67 (d, J = 1.5 Hz, 1H), 8.61 (dd, J = 2.6, 1.5 Hz, 1H), 8.55 (d, J = 2.6 Hz, 1H), 8.41 (d, J = 1.8 Hz, 1H), 8.22 (s, 1H), 8.10 (d, J = 8.3 Hz, 2H), 7.98 (d, J = 8.6 Hz, 2H), 7.91 (dd, J = 8.6, 1.8 Hz, 1H), 7.80 (d, J = 8.6 Hz, 1H), 4.66 (d, J = 5.7 Hz, 2H), 4.04 (s, 3H). | 8 1.63 450.90 |
| 214 | 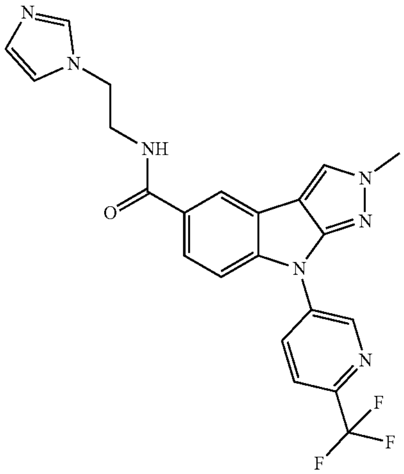 [SMILES: Cn1cc2c3cc(C(=O)NCCn4ccnc4)ccc3n(-c3ccc(C(F)(F)F)nc3)c2n1] N-[2-(1H-imidazol-1-yl)ethyl]-2-methyl-8-[6-(trifluoromethyl)pyridin-3-yl]-2H,8H-pyrazolo[3,4-b]indole-5-carboxamide | (700 MHz, DMSO-d6) δ 9.32 (d, J = 2.5 Hz, 1H), 9.11-9.09 (m, 1H), 8.70 (t, J = 5.8 Hz, 1H), 8.56 (dd, J = 8.5, 2.6 Hz, 1H), 8.29 (d, J = 1.9 Hz, 1H), 8.23 (s, 1H), 8.15 (d, J = 8.4 Hz, 1H), 7.86 (d, J = 8.7 Hz, 1H), 7.80 (dd, J = 8.7, 1.8 Hz, 1H), 7.77 (t, J = 1.7 Hz, 1H), 7.66 (t, J = 1.7 Hz, 1H), 4.41-4.38 (m, 2H), 4.05 (s, 3H), 3.75 (q, J = 5.7 Hz, 2H). | 8 1.21 454.0 |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 215 | 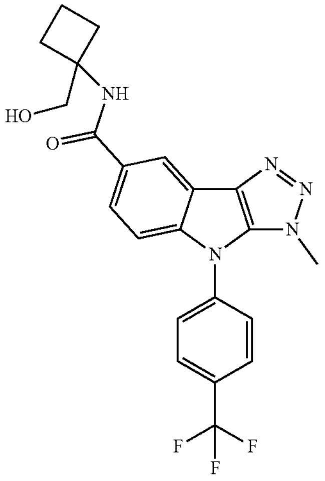 [SMILES: Cn1nnc2c3cc(C(=O)NC4(CO)CCC4)ccc3n(-c3ccc(C(F)(F)F)cc3)c21] N-[1-(hydroxymethyl)cyclobutyl]-3-methyl-4-[4-(trifluoromethyl)phenyl]-3H,4H-[1,2,3]triazolo[4,5-b]indole-7-carboxamide | (400 MHz, DMSO-d6) δ 8.61 (d, J = 2.3 Hz, 1H), 8.42 (d, J = 2.3 Hz, 1H), 8.10-8.04 (m, 2H), 8.04-7.97 (m, 3H), 7.91 (dd, J = 8.8, 2.4 Hz, 1H), 4.87 (dt, J = 5.9, 2.9 Hz, 1H), 4.37 (d, J = 2.4 Hz, 3H), 3.69 (dd, J = 6.1, 2.3 Hz, 2H), 2.30 (q, J = 10.1 Hz, 2H), 2.16 (s, 2H), 1.87-1.72 (m, 2H). | 15 1.45 (444.15) |
| 216 | 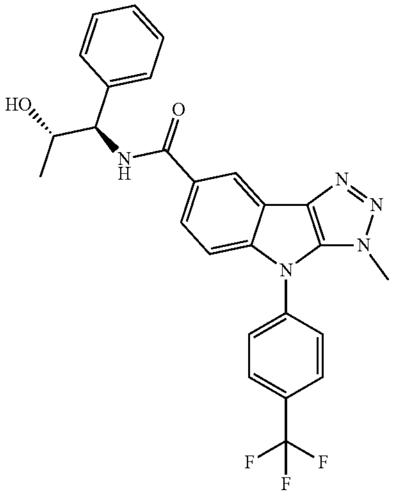 [SMILES: C[C@H](O)[C@H](NC(=O)c1ccc2c(c1)c1nnn(C)c1n2-c1ccc(C(F)(F)F)cc1)c1ccccc1] Absolute configuration known/assigned N-[(1R,2S)-2-hydroxy-1-phenylpropyl]-3-methyl-4-[4-(trifluoromethyl)phenyl]-3H,4H-[1,2,3]triazolo[4,5-b]indole-7-carboxamide | (400 MHz, DMSO-d6) δ 8.76 (d, J = 8.8 Hz, 1H), 8.63 (d, J = 2.1 Hz, 1H), 8.10-8.04 (m, 2H), 8.00 (dd, J = 8.8, 2.1 Hz, 3H), 7.93 (dd, J = 8.8, 2.2 Hz, 1H), 7.50-7.43 (m, 2H), 7.35-7.27 (m, 2H), 7.22 (dd, J = 8.3, 6.2 Hz, 1H), 4.93 (t, J = 7.9 Hz, 1H), 4.77 (dd, J = 5.9, 2.2 Hz, 1H), 4.37 (d, J = 2.2 Hz, 3H), 4.06 (q, J = 6.3 Hz, 1H), 1.16 (dd, J = 6.4, 2.2 Hz, 3H). | 15 1.58 (494.20) |

TABLE 1-continued

| Compound No. (Example No.) | Structure and Name | $^1$H-NMR | Conditions and elution time (min) LCMS (M + H$^+$) |
|---|---|---|---|
| Table 1 below shows exemplary compounds of the present invention. They have been synthesized as described in the Examples above or similar thereto. | | | |
| 217 | 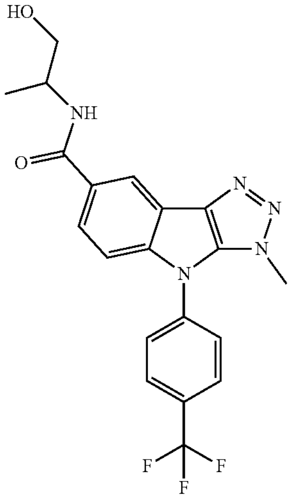 [SMILES: CC(CO)NC(=O)c1ccc2c(c1)c1nnn(C)c1n2-c1ccc(C(F)(F)F)cc1] N-(1-hydroxypropan-2-yl)-3-methyl-4-[4-(trifluoromethyl)phenyl]-3H,4H-[1,2,3]triazolo[4,5-b]indole-7-carboxamide | (300 MHz, DMSO-d6) δ 8.60 (d, J = 1.8 Hz, 1H), 8.25 (d, J = 7.9 Hz, 1H), 8.13-7.88 (m, 6H), 4.74 (t, J = 5.8 Hz, 1H), 4.38 (s, 3H), 4.08 (p, J = 6.6 Hz, 1H), 3.57-3.35 (m, 2H), 1.18 (d, J = 6.7 Hz, 3H). | 12 1.17 (418.10) |
| 218 | 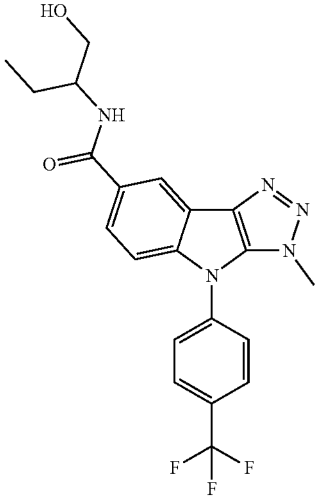 [SMILES: CCC(CO)NC(=O)c1ccc2c(c1)c1nnn(C)c1n2-c1ccc(C(F)(F)F)cc1] N-(1-hydroxybutan-2-yl)-3-methyl-4-[4-(trifluoromethyl)phenyl]-3H,4H-[1,2,3]triazolo[4,5-b]indole-7-carboxamide | (300 MHz, DMSO-d6) δ 8.62 (d, J = 1.8 Hz, 1H), 8.19-7.90 (m, 7H), 4.69 (t, J = 5.7 Hz, 1H), 4.38 (s, 3H), 3.93 (d, J = 5.3 Hz, 1H), 3.58-3.37 (m, 2H), 1.71 (dt, J = 12.8, 6.1 Hz, 1H), 1.50 (dt, J = 14.4, 7.8 Hz, 1H), 0.91 (t, J = 7.4 Hz, 3H). | 12 1.22 (432.10) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 219 | 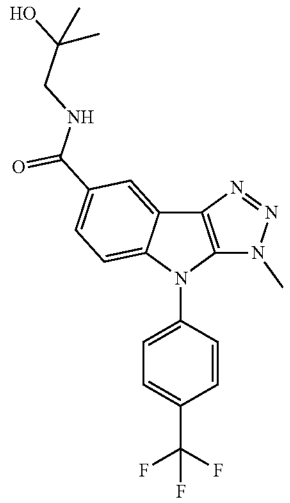 N-(2-hydroxy-2-methylpropyl)-3-methyl-4-[4-(trifluoromethyl)phenyl]-3H,4H-[1,2,3]triazolo[4,5-b]indole-7-carboxamide | (300 MHz, DMSO-d6) δ 8.61 (d, J = 1.7 Hz, 1H), 8.42 (t, J = 6.1 Hz, 1H), 8.12-7.89 (m, 6H), 4.60 (s, 1H), 4.38 (s, 3H), 3.33 (s, 2H), 1.15 (s, 6H). | 12 1.51 (432.20) |
| 220 | 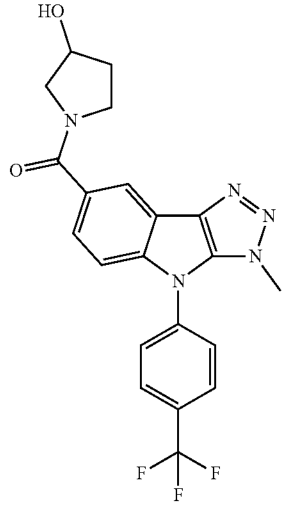 [SMILES: Cn1nnc2c3cc(C(=O)N4CCC(O)C4)ccc3n(-c3ccc(C(F)(F)F)cc3)c21] 1-{3-methyl-4-[4-(trifluoromethyl)-phenyl]-3H,4H-[1,2,3]triazolo[4,5-b]indole-7-carbonyl}pyrrolidin-3-ol | (300 MHz, DMSO-d6) δ 8.58-7.87 (m, 6H), 7.68 (d, J = 9.0 Hz, 1H), 4.99 (d, J = 25.7 Hz, 1H), 4.37 (d, J = 1.9 Hz, 4H), 3.96-3.45 (m, 4H), 1.90 (d, J = 36.5 Hz, 2H). | 12 0.85 (430.00) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 221 | 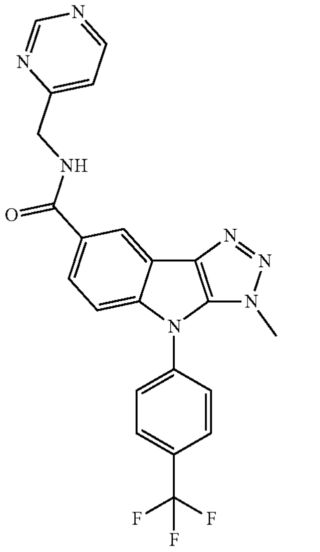 [SMILES: Cn1nnc2c3cc(C(=O)NCc4ccncn4)ccc3n(-c3ccc(C(F)(F)F)cc3)c21] 3-methyl-N-[(pyrimidin-4-yl)methyl]-4-[4-(trifluoromethyl)phenyl]-3H,4H-[1,2,3]triazolo[4,5-b]indole-7-carboxamide | (400 MHz, DMSO-d6) δ 9.35 (t, J = 5.9 Hz, 1H), 9.13 (d, J = 1.4 Hz, 1H), 8.75 (d, J = 5.2 Hz, 1H), 8.65 (d, J = 1.8 Hz, 1H), 8.13-8.06 (m, 3H), 8.02 (d, J = 8.7 Hz, 2H), 7.97 (d, J = 8.8 Hz, 1H), 7.49 (dd, J = 5.3, 1.4 Hz, 1H), 4.61 (d, J = 5.8 Hz, 2H), 4.38 (s, 3H). | 12 0.88 (452.00) |
| 222 | 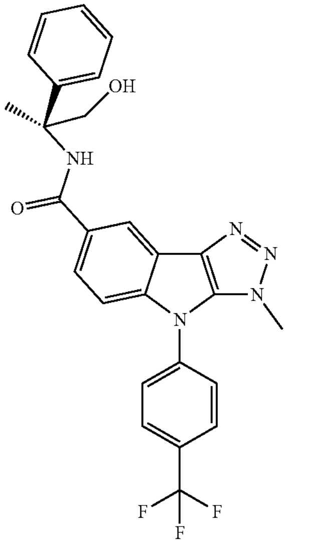 [SMILES: Cn1nnc2c3cc(C(=O)N[C@](C)(CO)c4ccccc4)ccc3n(-c3ccc(C(F)(F)F)cc3)c21] Absolute configuration known/assigned N-[(2S)-1-hydroxy-2-phenylpropan-2-yl]-3-methyl-4-[4-(trifluoromethyl)phenyl]-3H,4H-[1,2,3]triazolo[4,5-b]indole-7-carboxamide | (400 MHz, DMSO-d6) δ 8.65 (s, 1H), 8.27 (d, J = 3.4 Hz, 1H), 8.06 (d, J = 3.3 Hz, 2H), 8.04-7.96 (m, 3H), 7.93 (dd, J = 8.7, 3.5 Hz, 1H), 7.39 (t, J = 5.5 Hz, 2H), 7.30 (t, J = 5.3 Hz, 2H), 7.19 (s, 1H), 5.17 (d, J = 3.7 Hz, 1H), 4.38 (d, J = 3.4 Hz, 3H), 3.84-3.79 (m, 1H), 3.32 (s, 1H), 1.77 (d, J = 3.5 Hz, 3H). | 12 1.00 (494.10) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 223 | 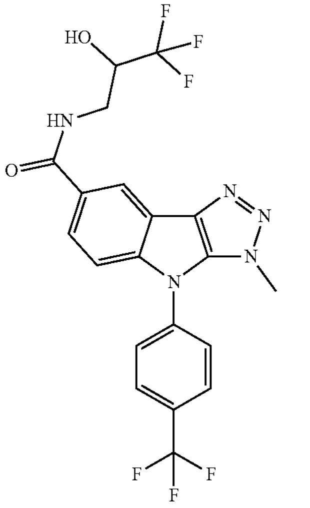 [SMILES: Cn1nnc2c3cc(C(=O)NCC(O)C(F)(F)F)ccc3n(-c3ccc(C(F)(F)F)cc3)c21] 3-methyl-N-(3,3,3-trifluoro-2-hydroxypropyl)-4-[4-(trifluoromethyl)phenyl]-3H,4H-[1,2,3]triazolo[4,5-b]indole-7-carboxamide | (400 MHz, DMSO-d6) δ 8.88 (t, J = 5.6 Hz, 1H), 8.58 (d, J = 1.8 Hz, 1H), 8.07 (d, J = 8.7 Hz, 2H), 8.06-7.98 (m, 3H), 7.95 (d, J = 8.8 Hz, 1H), 6.54 (d, J = 6.4 Hz, 1H), 4.38 (s, 3H), 4.25 (t, J = 6.3 Hz, 1H), 3.667-3.676 (m, 1H), 3.42-3.34 (m, 1H). | 12 0.94 (472.00) |
| 224 | 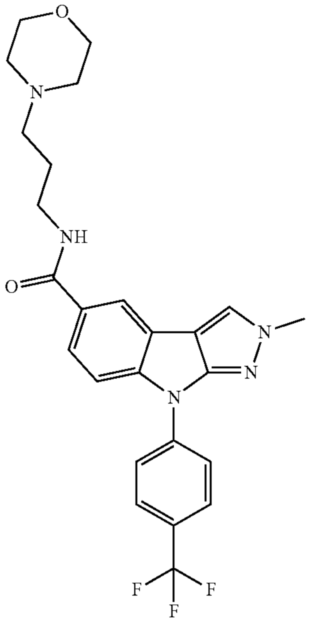 [SMILES: Cn1cc2c3cc(C(=O)NCCCN4CCOCC4)ccc3n(-c3ccc(C(F)(F)F)cc3)c2n1] 2-methyl-N-[3-(morpholin-4-yl)propyl]-8-[4-(trifluoromethyl)phenyl]-2H,8H-pyrazolo[3,4-b]indole-5-carboxamide | (400 MHz, DMSO-d6) δ 9.71-9.59 (m, 1H), 9.33 (d, J = 2.6 Hz, 1H), 8.77 (t, J = 5.7 Hz, 1H), 8.56 (dd, J = 8.5, 2.6 Hz, 1H), 8.38-8.36 (m, 1H), 8.24 (s, 1H), 8.15 (d, J = 8.6 Hz, 1H), 7.92-7.86 (m, 2H), 4.05 (s, 3H), 4.06-3.98 (m, 2H), 3.71-3.65 (m, 4H), 3.63-3.59 (m, 2H), 3.39-3.33 (m, 2H), 3.25-3.10 (m, 2H). | 8 1.27 473 |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 225 | 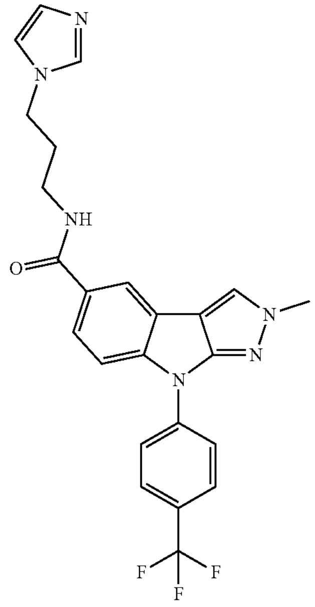 [SMILES: Cn1cc2c3cc(C(=O)NCCCn4ccnc4)ccc3n(-c3ccc(C(F)(F)F)cc3)c2n1] N-[3-(1H-imidazol-1-yl)propyl]-2-methyl-8-[4-(trifluoromethyl)phenyl]-2H,8H-pyrazolo[3,4-b]indole-5-carboxamide | (700 MHz, DMSO-d6) δ 9.15 (d, J = 1.5 Hz, 1H), 8.62 (t, J = 5.7 Hz, 1H), 8.34 (d, J = 1.9 Hz, 1H), 8.21 (s, 1H), 8.09 (d, J = 8.5 Hz, 2H), 7.98 (d, J = 8.4 Hz, 2H), 7.87-7.83 (m, 2H), 7.79 (d, J = 8.6 Hz, 1H), 7.71 (t, J = 1.7 Hz, 1H), 4.28 (t, J = 7.0 Hz, 2H), 4.04 (s, 3H), 3.33 (q, J = 6.3 Hz, 2H), 2.12 (p, J = 6.8 Hz, 2H). | 8 1.333 (466.9) |
| 226 | 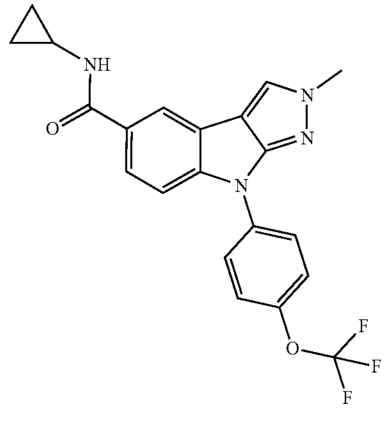 [SMILES: Cn1cc2c3cc(C(=O)NC4CC4)ccc3n(-c3ccc(OC(F)(F)F)cc3)c2n1] N-cyclopropyl-2-methyl-8-[4-(trifluoromethoxy)phenyl]-2H,8H-pyrazolo[3,4-b]indole-5-carboxamide | (700 MHz, DMSO-$d_6$) δ 8.44 (d, J = 4.2 Hz, 1H), 8.29 (d, J = 1.7 Hz, 1H), 8.17 (s, 1H), 7.95-7.90 (m, 2H), 7.80 (dd, J = 8.7, 1.8 Hz, 1H), 7.66-7.59 (m, 3H), 4.02 (s, 4H), 2.88 (tt, J = 7.9, 3.9 Hz, 1H), 0.73-0.67 (m, 2H), 0.63-0.58 (m, 2H). | 8 1.755 (414.9) |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 227 | 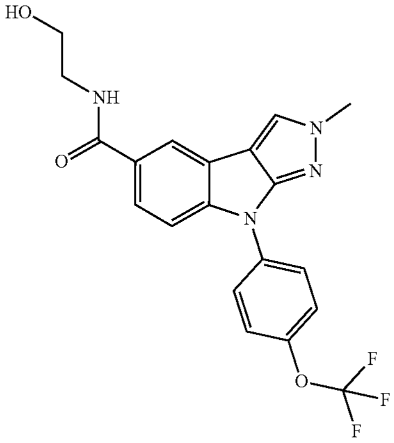 [SMILES: Cn1cc2c3cc(C(=O)NCCO)ccc3n(-c3ccc(OC(F)(F)F)cc3)c2n1]<br>N-(2-hydroxyethyl)-2-methyl-8-[4-(trifluoromethoxy)phenyl]-2H,8H-pyrazolo[3,4-b]indole-5-carboxamide | (400 MHz, DMSO-d$_6$) δ 8.40 (t, J = 5.6 Hz, 1H), 8.34 (d, J = 1.8 Hz, 1H), 8.18 (s, 1H), 7.98-7.89 (m, 2H), 7.83 (dd, J = 8.7, 1.9 Hz, 1H), 7.67-7.57 (m, 3H), 3.54 (t, J = 6.3 Hz, 13H), 3.37 (q, J = 6.1 Hz, 2H). | 8<br>1.562<br>(418.9) |
| 228 | 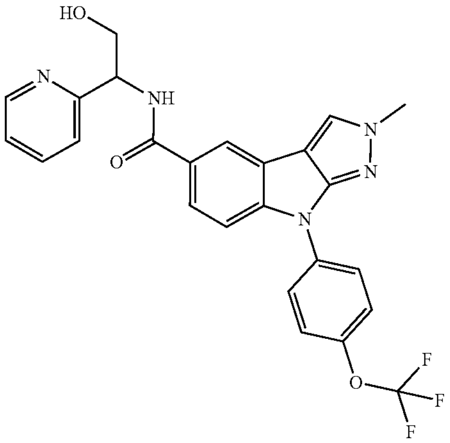 [SMILES: Cn1cc2c3cc(C(=O)NC(CO)c4ccccn4)ccc3n(-c3ccc(OC(F)(F)F)cc3)c2n1]<br>N-[2-hydroxy-1-(pyridin-2-yl)ethyl]-2-methyl-8-[4-(trifluoromethoxy)phenyl]-2H,8H-pyrazolo[3,4-b]indole-5-carboxamide | (400 MHz, DMSO-d$_6$) δ 8.78 (d, J = 7.2 Hz, 1H), 8.66 (dt, J = 5.1, 1.3 Hz, 1H), 8.43 (d, J = 1.8 Hz, 1H), 8.19 (s, 1H), 8.06 (t, J = 7.8 Hz, 1H), 7.98-7.89 (m, 2H), 7.64-7.58 (m, 2H), 5.25 (q, J = 6.4 Hz, 1H), 4.03 (s, 3H), 3.96-3.86 (m, 2H). | 8<br>1.526<br>(495.9) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
| --- | --- | --- | --- |
| 229 | 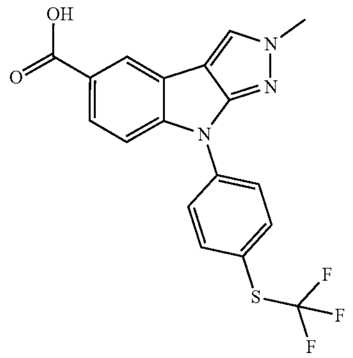 [SMILES: Cn1cc2c3cc(C(=O)O)ccc3n(-c3ccc(SC(F)(F)F)cc3)c2n1] 2-methyl-8-{4-[(trifluoro-methyl)sulfanyl]phenyl}-2H,8H-pyrazolo[3,4-b]indole-5-carboxylic acid | (400 MHz, DMSO-$d_6$) δ 8.45-8.40 (m, 1H), 8.21 (s, 1H), 8.07-7.99 (m, 2H), 7.99-7.89 (m, 3H), 7.80-7.73 (m, 1H), 4.03 (s, 3H). | 8 1.871 (391.8) |
| 230 | 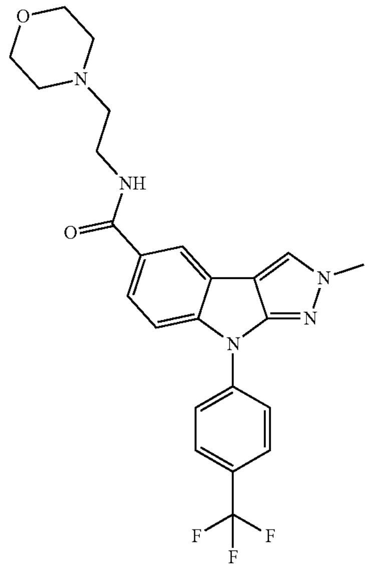 [SMILES: Cn1cc2c3cc(C(=O)NCCN4CCOCC4)ccc3n(-c3ccc(C(F)(F)F)cc3)c2n1] 2-methyl-N-[2-(morpholin-4-yl)ethyl]-8-[4-(trifluoromethyl)phenyl]-2H,8H-pyrazolo[3,4-b]indole-5-carboxamide | (700 MHz, DMSO-d6) δ 9.74-9.67 (m, 1H), 8.80-8.76 (m, 1H), 8.36 (d, J = 1.8 Hz, 1H), 8.23 (s, 1H), 8.10-8.07 (m, 2H), 8.00-7.97 (m, 2H), 7.87 (dd, J = 8.7, 1.9 Hz, 1H), 7.82 (d, J = 8.6 Hz, 1H), 4.04 (s, 3H), 4.05-4.00 (m, 2H), 3.71-3.65 (m, 4H), 3.62-3.56 (m, 2H), 3.39-3.33 (m, 2H), 3.21-3.13 (m, 2H). | 8 1.32-1.33 (472.00) |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 231 | 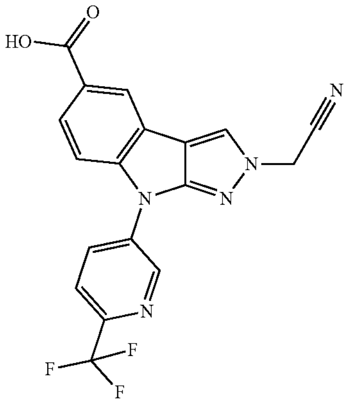 [SMILES: N#CCn1cc2c3cc(C(=O)O)ccc3n(-c3ccc(C(F)(F)F)nc3)c2n1] 2-(cyanomethyl)-8-[6-(trifluoromethyl)pyridin-3-yl]-2H,8H-pyrazolo[3,4-b]indole-5-carboxylic acid | (300 MHz, DMSO-d6) δ 9.32 (s, 1H), 8.58-8.55 (s, 2H), 8.40 (s, 1H), 8.19 (d, J = 8.4 Hz, 1H), 8.00 (d, J = 8.7 Hz, 1H), 7.85 (d, J = 8.7 Hz, 1H), 5.72 (s, 2H) | 12 0.73 (384.00) |
| 232 | 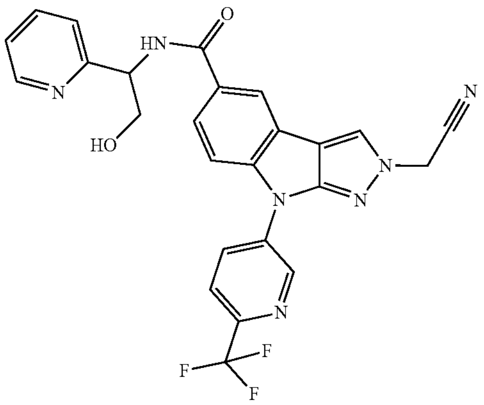 [SMILES: N#CCn1cc2c3cc(C(=O)NC(CO)c4ccccn4)ccc3n(-c3ccc(C(F)(F)F)nc3)c2n1] 2-(cyanomethyl)-N-[2-hydroxy-1-(pyridin-2-yl)ethyl]-8-[6-(trifluoromethyl)pyridin-3-yl]-2H,8H-pyrazolo[3,4-b]indole-5-carboxamide | (300 MHz, DMSO-d6) δ 9.34 (s, 1H), 8.72 (d, J = 7.8 Hz, 1H), 8.59-8.55 (m, 3H), 8.43 (s, 1H), 8.20 (d, J = 8.7 Hz, 1H), 8.05-7.99 (m, 1H), 7.88 (d, J = 8.7 Hz, 1H), 7.82-7.74 (m, 1H), 7.47 (d, J = 7.8 Hz, 1H), 7.32-7.25 (m, 1H), 5.72 (s, 2H), 5.30-5.16 (m, 1H), 5.02-4.93 (m, 1H), 3.96-3.79 (m, 2H) | 12 0.71 (506.10) |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 233 | 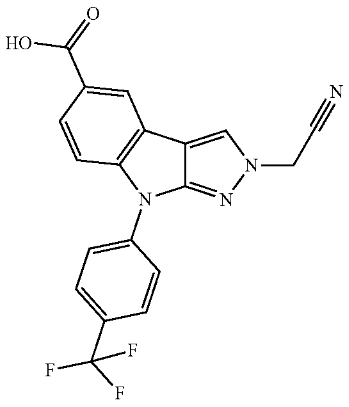 [SMILES: N#CCn1cc2c3cc(C(=O)O)ccc3n(-c3ccc(C(F)(F)F)cc3)c2n1] 2-(prop-2-yn-1-yl)-8-[4-(trifluoromethyl)phenyl]-2H,8H-pyrazolo[3,4-b]indole-5-carboxylic acid | (300 MHz, DMSO-d6) δ 8.33 (d, J = 1.6 Hz, 1H), 8.22 (s, 1H), 8.06 (d, J = 8.5 Hz, 2H), 7.98-7.88 (m, 3H), 7.62 (d, J = 8.7 Hz, 1H), 5.16 (d, J = 2.5 Hz, 2H), 3.43 (t, J = 2.5 Hz, 1H). | 16 1.05 (382.00) |
| 234 | 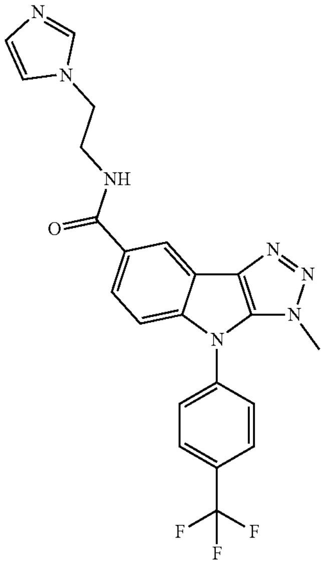 [SMILES: Cn1nnc2c3cc(C(=O)NCCn4ccnc4)ccc3n(-c3ccc(C(F)(F)F)cc3)c21] N-[2-(1H-imidazol-1-yl)ethyl]-3-methyl-4-[4-(trifluoromethyl)phenyl]-3H,4H-[1,2,3]triazolo[4,5-b]indole-7-carboxamide | (300 MHz, DMSO-d6) δ 8.74 (s, 1H), 8.51 (s, 1H), 8.00 (dd, J = 22.5, 12.2 Hz, 6H), 7.62 (s, 1H), 7.19 (s, 1H), 6.89 (s, 1H), 4.37 (s, 3H), 4.21 (d, J = 6.3 Hz, 2H), 3.67-3.58 (m, 2H). | 12 0.78 (454.00) |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 235 | 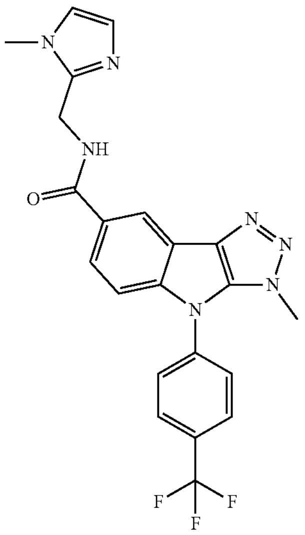 3-methyl-N-[(1-methyl-1H-imidazol-2-yl)methyl]-4-[4-(trifluoromethyl)-phenyl]-3H,4H-[1,2,3]triazolo[4,5-b]indole-7-carboxamide | (300 MHz, DMSO-d6) δ 9.12-9.06 (m, 1H), 8.61 (d, J = 1.8 Hz, 1H), 8.12-7.93 (m, 6H), 7.09 (s, 1H), 6.81 (s, 1H), 4.58 (d, J = 5.4 Hz, 2H), 4.37 (s, 3H), 3.69 (s, 3H). | 12 0.79 (454.00) |
| 236 | 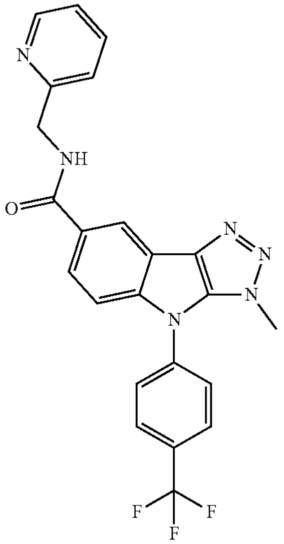 [SMILES: Cn1nnc2c3cc(C(=O)NCc4ccccn4)ccc3n(-c3ccc(C(F)(F)F)cc3)c21] 3-methyl-N-[(pyridin-2-yl)methyl]-4-[4-(trifluoromethyl)phenyl]-3H,4H-[1,2,3]triazolo[4,5-b]indole-7-carboxamide | (300 MHz, DMSO-d6) 9.27 (t, J = 5.9 Hz, 1H), 8.64 (d, J = 1.8 Hz, 1H), 8.53 (dt, J = 4.7, 1.4 Hz, 1H), 8.15-7.91 (m, 6H), 7.77 (td, J = 7.7, 1.8 Hz, 1H), 7.38 (d, J = 7.8 Hz, 1H), 7.33-7.23 (m, 1H), 4.64 (d, J = 5.8 Hz, 2H), 4.38 (s, 3H). | 12 0.80 (451.00) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 237 | 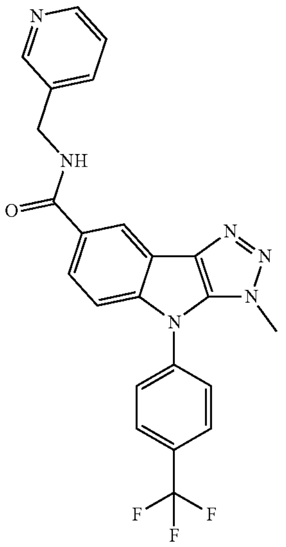 [SMILES: Cn1nnc2c3cc(C(=O)NCc4cccnc4)ccc3n(-c3ccc(C(F)(F)F)cc3)c21] 3-methyl-N-[(pyridin-3-yl)methyl]-4-[4-(trifluoromethyl)phenyl]-3H,4H-[1,2,3]triazolo[4,5-b]indole-7-carboxamide | (300 MHz, DMSO-d6) δ 9.24 (t, J = 5.8 Hz, 1H), 8.60 (d, J = 2.0 Hz, 2H), 8.47 (dd, J = 4.8, 1.7 Hz, 1H), 8.12-7.89 (m, 6H), 7.78 (dt, J = 7.9, 2.0 Hz, 1H), 7.38 (dd, J = 7.8, 4.8 Hz, 1H), 4.56 (d, J = 5.8 Hz, 2H), 4.37 (s, 3H). | |
| 238 | 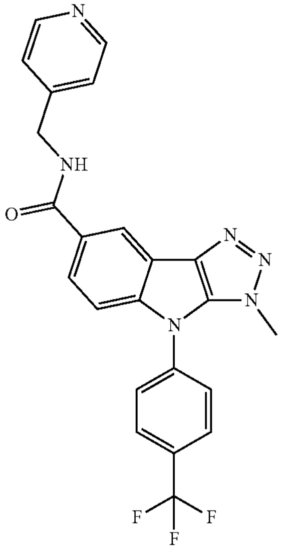 3-methyl-N-[(pyridin-4-yl)methyl]-4-[4-(trifluoromethyl)phenyl]-3H,4H-[1,2,3]triazolo[4,5-b]indole-7-carboxamide | (300 MHz, DMSO-d6) δ 9.28 (t, J = 5.9 Hz, 1H), 8.63 (d, J = 1.8 Hz, 1H), 8.56-8.48 (m, 2H), 8.13-7.91 (m, 6H), 7.40-7.32 (m, 2H), 4.56 (d, J = 5.8 Hz, 2H), 4.38 (s, 3H). | |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 239 | 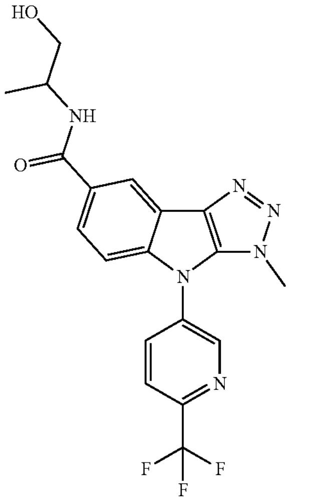 [SMILES: CC(CO)NC(=O)c1ccc2c(c1)c1nnn(C)c1n2-c1ccc(C(F)(F)F)nc1] N-(1-hydroxypropan-2-yl)-3-methyl-4-[6-(trifluoromethyl)pyridin-3-yl]-3H,4H-[1,2,3]triazolo[4,5-b]indole-7-carboxamide | (300 MHz, DMSO-d6) δ 9.32 (d, J = 2.6 Hz, 1H), 8.60 (d, J = 1.7 Hz, 1H), 8.58-8.52 (m, 1H), 8.29 (d, J = 7.9 Hz, 1H), 8.19 (d, J = 8.6 Hz, 1H), 8.11-7.95 (m, 2H), 4.77 (t, J = 5.8 Hz, 1H), 4.39 (s, 3H), 4.16-4.01 (m, 1H), 3.59-3.46 (m, 1H), 3.46-3.34 (m, 1H), 1.18 (d, J = 6.7 Hz, 3H). | |
| 240 | 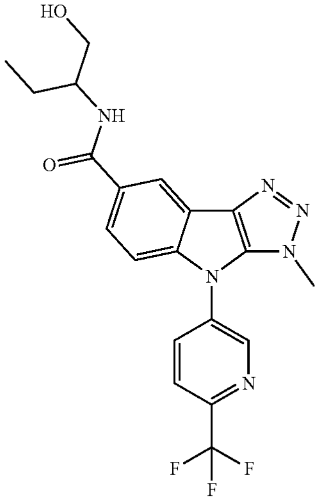 [SMILES: CCC(CO)NC(=O)c1ccc2c(c1)c1nnn(C)c1n2-c1ccc(C(F)(F)F)nc1] N-(1-hydroxybutan-2-yl)-3-methyl-4-[6-(trifluoromethyl)pyridin-3-yl]-3H,4H-[1,2,3]triazolo[4,5-b]indole-7-carboxamide | (300 MHz, DMSO-d6) δ 9.33 (d, J = 2.6 Hz, 1H), 8.62 (d, J = 1.7 Hz, 1H), 8.59-8.54 (m, 1H), 8.23-8.18 (m, 2H), 8.10-7.99 (m, 2H), 4.72 (t, J = 5.7 Hz, 1H), 4.40 (s, 3H), 3.93 (s, 1H), 3.55-3.40 (m, 2H), 1.66 (s, 1H), 1.58-1.44 (m, 1H), 0.91 (t, J = 7.5 Hz, 3H). | |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 241 | 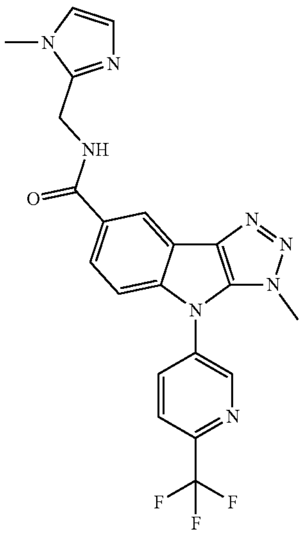 3-methyl-N-[(1-methyl-1H-imidazol-2-yl)methyl]-4-[6-(trifluoromethyl)pyridin-3-yl]-3H,4H-[1,2,3]triazolo[4,5-b]indole-7-carboxamide | (300 MHz, DMSO-d6) δ 9.32 (d, J = 2.6 Hz, 1H), 9.13 (t, J = 5.5 Hz, 1H), 8.62 (d, J = 1.8 Hz, 1H), 8.59-8.51 (m, 1H), 8.19 (d, J = 8.6 Hz, 1H), 8.14-8.05 (m, 1H), 8.00 (d, J = 8.8 Hz, 1H), 7.10 (d, J = 1.1 Hz, 1H), 6.82 (d, J = 1.2 Hz, 1H), 4.59 (d, J = 5.3 Hz, 2H), 4.39 (s, 3H), 3.69 (s, 3H). | |
| 242 | 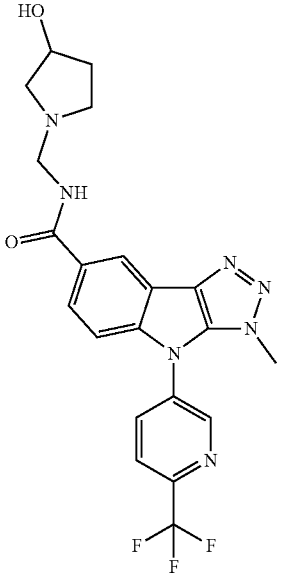 [SMILES: Cn1nnc2c3cc(C(=O)NCN4CCC(O)C4)ccc3n(-c3ccc(C(F)(F)F)nc3)c21] 1-{3-methyl-4-[6-(trifluoromethyl)-pyridin-3-yl]-3H,4H-[1,2,3]triazolo[4,5-b]indole-7-carbonyl}pyrrolidin-3-ol | (300 MHz, DMSO-d6) δ 9.32 (d, J = 2.6 Hz, 1H), 8.63-8.50 (m, 1H), 8.28-8.13 (m, 2H), 7.98 (d, J = 8.7 Hz, 1H), 7.75-7.63 (m, 1H), 5.12-4.90 (m, 1H), 4.39 (s, 3H), 4.27 (s, 1H), 3.80-3.47 (m, 3H), 3.43 (d, J = 12.8 Hz, 1H), 2.11-1.74 (m, 2H). | |

TABLE 1-continued

| Com-pound No. (Example No.) | Structure and Name | $^1$H-NMR | Conditions and elution time (min) LCMS (M + H$^+$) |
|---|---|---|---|
| | Table 1 below shows exemplary compounds of the present invention. They have been synthesized as described in the Examples above or similar thereto. | | |
| 243 | 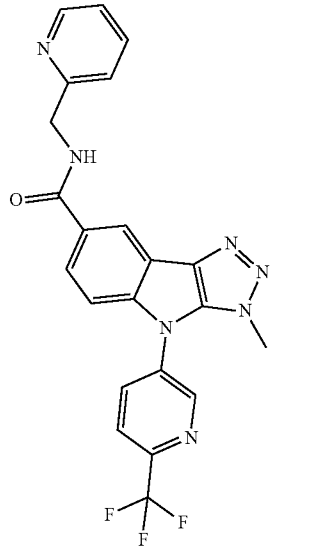 [SMILES: Cn1nnc2c3cc(C(=O)NCc4ccccn4)ccc3n(-c3ccc(C(F)(F)F)nc3)c21] 3-methyl-N-[(pyridin-2-yl)methyl]-4-[6-(trifluoromethyl)pyridin-3-yl]-3H,4H-[1,2,3]triazolo[4,5-b]indole-7-carboxamide | (300 MHz, DMSO-d6) δ 9.36-9.24 (m, 2H), 8.64 (d, J = 1.7 Hz, 1H), 8.60-8.50 (m, 2H), 8.19 (d, J = 8.6 Hz, 1H), 8.15-8.07 (m, 1H), 8.03 (d, J = 8.8 Hz, 1H), 7.78 (m, J = 7.7, 1.8 Hz, 1H), 7.42-7.33 (m, 1H), 7.33-7.23 (m, 1H), 4.64 (d, J = 5.8 Hz, 2H), 4.39 (s, 3H). | |
| 244 | 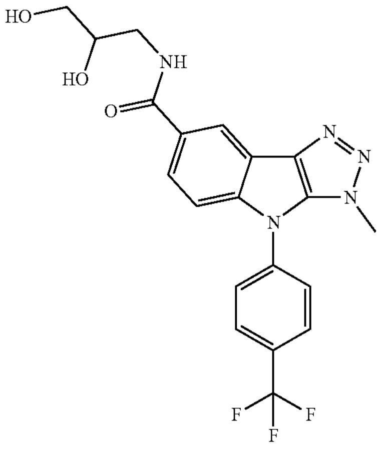 [SMILES: Cn1nnc2c3cc(C(=O)NCC(O)CO)ccc3n(-c3ccc(C(F)(F)F)cc3)c21] N-(2,3-dihydroxypropyl)-3-methyl-4-[4-(trifluoromethyl)phenyl]-3H,4H-[1,2,3]triazolo[4,5-b]indole-7-carboxamide | (300 MHz, DMSO-d6) δ 8.57 (q, J = 5.0, 3.9 Hz, 2H), 8.13-7.98 (m, 5H), 7.93 (d, J = 8.8 Hz, 1H), 4.85 (d, J = 5.1 Hz, 1H), 4.59 (t, J = 5.5 Hz, 1H), 4.38 (d, J = 2.1 Hz, 3H), 3.70 (d, J = 7.1 Hz, 1H), 3.53-3.37 (m, 3H). | |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 245 | 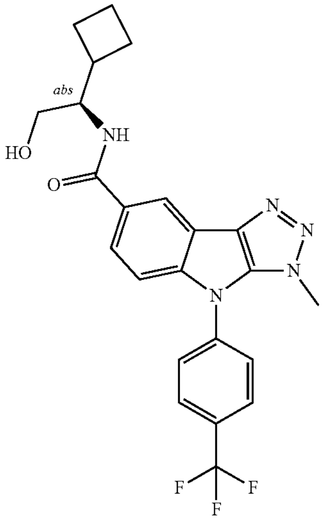 [SMILES: Cn1nnc2c3cc(C(=O)N[C@@H](CO)C4CCC4)ccc3n(-c3ccc(C(F)(F)F)cc3)c21] Absolute configuration known/assigned N-[(1R)-1-cyclobutyl-2-hydroxyethyl]-3-methyl-4-[4-(trifluoromethyl)phenyl]-3H,4H-[1,2,3]triazolo[4,5-b]indole-7-carboxamide | (300 MHz, DMSO-d6) δ 8.62 (d, J = 1.7 Hz, 1H), 8.17-7.84 (m, 7H), 4.58 (s, 1H), 4.38 (s, 3H), 4.07 (s, 1H), 3.46 (d, J = 5.8 Hz, 2H), 1.99-1.74 (m, 6H). | |
| 246 | 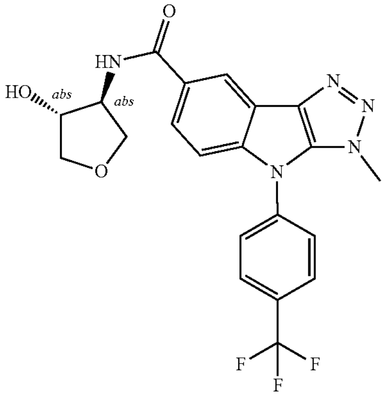 [SMILES: Cn1nnc2c3cc(C(=O)N[C@H]4COC[C@@H]4O)ccc3n(-c3ccc(C(F)(F)F)cc3)c21] Absolute configuration known/assigned N-[(3S,4R)-4-hydroxyoxolan-3-yl]-3-methyl-4-[4-(trifluoromethyl)phenyl]-3H,4H-[1,2,3]triazolo[4,5-b]indole-7-carboxamide | (300 MHz, DMSO-d6) δ 8.62 (d, J = 6.3 Hz, 2H), 8.12-7.79 (m, 6H), 5.30 (d, J = 3.7 Hz, 1H), 4.38 (s, 3H), 4.28 (s, 2H), 4.00 (ddd, J = 23.8, 9.3, 5.2 Hz, 2H), 3.63 (ddd, J = 35.7, 9.5, 2.8 Hz, 2H). | |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 247 | 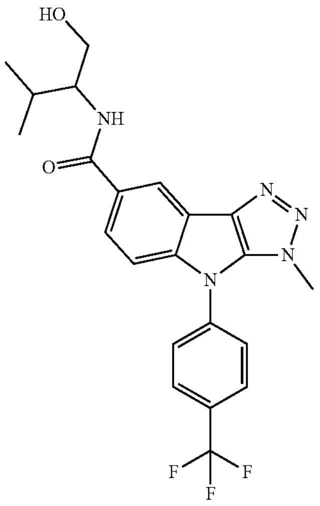 [SMILES: CC(C)C(CO)NC(=O)c1ccc2c(c1)c1nnn(C)c1n2-c1ccc(C(F)(F)F)cc1] N-(1-hydroxy-3-methylbutan-2-yl)-3-methyl-4-[4-(trifluoromethyl)phenyl]-3H,4H-[1,2,3]triazolo[4,5-b]indole-7-carboxamide | (400 MHz, DMSO-d6) 8.63 (d, J = 1.8 Hz, 1H), 8.16-7.98 (m, 6H), 7.92 (d, J = 8.8 Hz, 1H), 4.60 (t, J = 5.6 Hz, 1H), 4.38 (s, 3H), 3.92-3.84 (m, 1H), 3.60-3.50 (m, 2H), 2.00-1.90 (m, 1H), 1.00-0.80 (m, 6H). | 11 1.21 min 446.15 (M + H) |
| 248 | 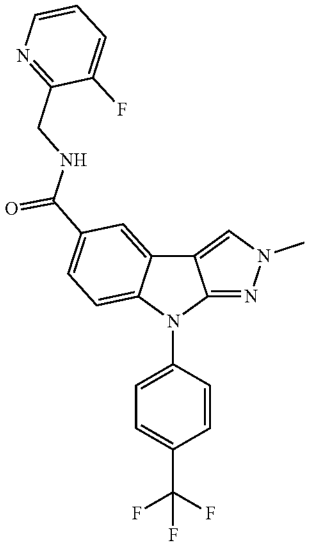 [SMILES: Cn1cc2c3cc(C(=O)NCc4ncccc4F)ccc3n(-c3ccc(C(F)(F)F)cc3)c2n1] N-[(3-fluoropyridin-2-yl)methyl]-2-methyl-8-[4-(trifluoromethyl)phenyl]-2H,8H-pyrazolo[3,4-b]indole-5-carboxamide | (400 MHz, DMSO-d6) δ 8.96 (t, J = 5.6 Hz, 1H), 8.41-8.38 (m, 2H), 8.20 (s, 1H), 8.11-8.07 (m, 2H), 7.99-7.94 (m, 2H), 7.90 (dd, J = 8.7, 1.8 Hz, 1H), 7.78 (d, J = 8.7 Hz, 1H), 7.73-7.68 (m, 1H), 7.43-7.38 (m, 1H), 4.71-4.68 (m, 2H), 4.03 (s, 3H). | |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 249 | 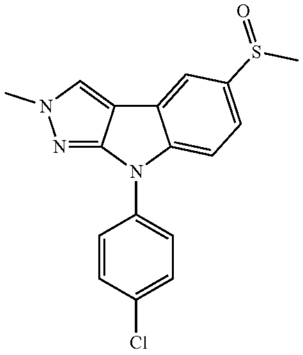 8-(4-chlorophenyl)-5-methanesulfinyl-2-methyl-2H,8H-pyrazolo[3,4-b]indole | (700 MHz, DMSO-d6) δ 2.77 (s, 3H, 22), 4.03 (s, 3H, 12), 7.58 (dd, J = 8.6, 1.9 Hz, 1H, 2), 7.64-7.69 (m, 2H, 17, 19), 7.73 (d, J = 8.5 Hz, 1H, 3), 7.81-7.85 (m, 2H, 16, 20), 8.15 (d, J = 1.8 Hz, 1H, 6), 8.20 (s, 1H, 11). | |
| 250 | 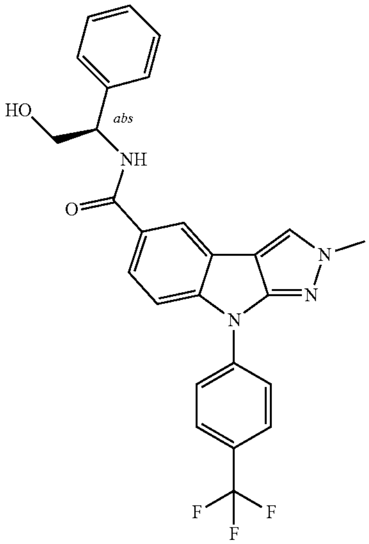 [SMILES: Cn1cc2c3cc(C(=O)N[C@@H](CO)c4ccccc4)ccc3n(-c3ccc(C(F)(F)F)cc3)c2n1] Absolute configuration assigned arbitrarily N-[(1R)-2-hydroxy-1-phenylethyl]-2-methyl-8-[4-(trifluoromethyl)phenyl]-2H,8H-pyrazolo[3,4-b]indole-5-carboxamide | | $^b$ 2.84 min |

TABLE 1-continued

| Com-pound No. (Example No.) | Structure and Name | $^1$H-NMR | Conditions and elution time (min) LCMS (M + H$^+$) |
|---|---|---|---|
| | Table 1 below shows exemplary compounds of the present invention. They have been synthesized as described in the Examples above or similar thereto. | | |
| 251 | 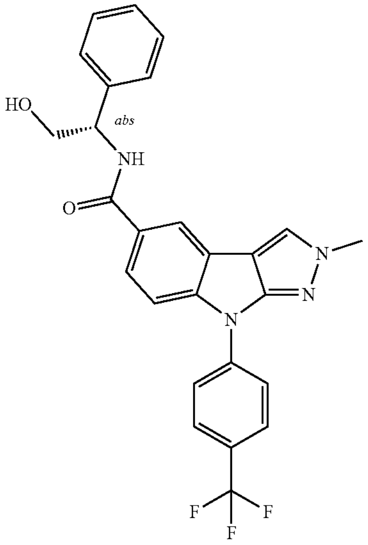 [SMILES: Cn1cc2c3cc(C(=O)N[C@H](CO)c4ccccc4)ccc3n(-c3ccc(C(F)(F)F)cc3)c2n1] Absolute configuration assigned arbitrarily N-[(1S)-2-hydroxy-1-phenylethyl]-2-methyl-8-[4-(trifluoromethyl)phenyl]-2H,8H-pyrazolo[3,4-b]indole-5-carboxamide | | $^b$ 3.86 min |
| 252 | 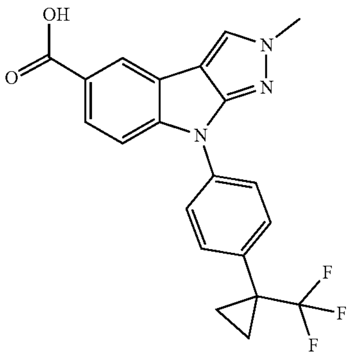 [SMILES: Cn1cc2c3cc(C(=O)O)ccc3n(-c3ccc(C4(C(F)(F)F)CC4)cc3)c2n1] 2-methyl-8-{4-[1-(trifluoromethyl)-cyclopropyl]phenyl}-2H,8H-pyrazolo[3,4-b]indole-5-carboxylic acid | (400 MHz, DMSO-d6) δ 12.66-12.57 (m, 1H), 8.42-8.40 (m, 1H), 8.18 (s, 1H), 7.90 (dd, J = 8.7, 1.8 Hz, 1H), 7.84-7.79 (m, 2H), 7.71-7.67 (m, 2H), 7.65-7.62 (m, 1H), 4.01 (s, 3H), 1.43-1.38 (m, 2H), 1.24-1.19 (m, 2H). | |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 253 | 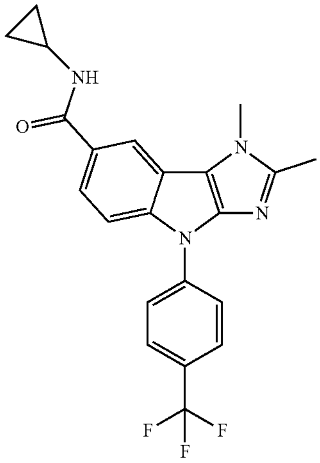 [SMILES: Cc1nc2c(c3cc(C(=O)NC4CC4)ccc3n2-c2ccc(C(F)(F)F)cc2)n1C] N-cyclopropyl-1,2-dimethyl-4-[4-(trifluoromethyl)phenyl]-1H,4H-imidazo[4,5-b]indole-7-carboxamide | (400 MHz, DMSO-d6) δ 8.42 (d, J = 4.0 Hz, 1H), 8.34 (d, J = 1.7 Hz, 1H), 8.07 (d, J = 8.4 Hz, 2H), 7.96 (d, J = 8.6 Hz, 2H), 7.82 (d, J = 8.7 Hz, 1H), 7.73 (d, J = 8.8, 1H), 4.02 (s, 3H), 2.89 (m, 1H), 2.53 (s, 3H), 0.74 (m, 2H), 0.70-0.58 (m, 2H). | 9 0.73 min 413.00 (M + H) |
| 254 | 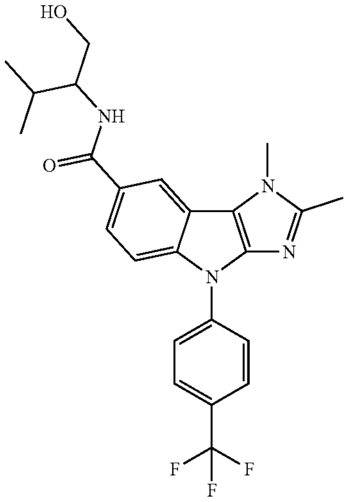 [SMILES: Cc1nc2c(c3cc(C(=O)NC(CO)C(C)C)ccc3n2-c2ccc(C(F)(F)F)cc2)n1C] N-(1-hydroxy-3-methylbutan-2-yl)-1,2-dimethyl-4-[4-(trifluoromethyl)phenyl]-1H,4H-imidazo[4,5-b]indole-7-carboxamide | (400 MHz, DMSO-d6) δ 8.40 (d, J = 1.8 Hz, 1H), 8.08 (d, J = 8.4 Hz, 2H), 8.00-7.91 (m, 3H), 7.84 (d, J = 8.8 Hz, 1H), 7.78 (d, J = 8.7, 1H), 4.62 (t, J = 5.5 Hz, 1H), 4.04 (s, 3H), 3.92-3.84 (m, 1H), 3.58 (t, J = 5.5 Hz, 2H), 2.54 (s, 3H), 1.99 (m, 1H), 0.95 (dd, J = 9.2, 6.8 Hz, 6H). | 9 0.74 min 459.05 (M + H) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 255 | 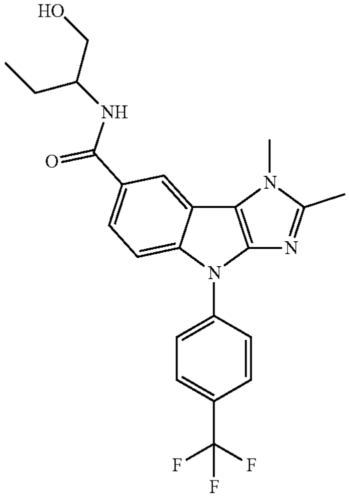 [SMILES: CCC(CO)NC(=O)c1ccc2c(c1)c1c(nc(C)n1C)n2-c1ccc(C(F)(F)F)cc1] N-(1-hydroxybutan-2-yl)-1,2-dimethyl-4-[4-(trifluoromethyl)phenyl]-1H,4H-imidazo[4,5-b]indole-7-carboxamide | (400 MHz, DMSO-d6) δ 8.39 (d, J = 1.8 Hz, 1H), 8.08 (d, J = 8.4 Hz, 2H), 7.98 (t, J = 8.0 Hz, 3H), 7.84 (d, J = 8.8 Hz, 1H), 7.77 (m, 1H), 4.70 (t, J = 5.7 Hz, 1H), 4.04 (s, 3H), 3.53 (m, 1H), 3.45 (m , 1H), 2.54 (s, 3H), 1.78-1.67 (m, 1H), 1.52 (m,1H), 0.92 (t, J = 7.4 Hz, 3H). | 9 0.70 min 445.00 (M + H) |
| 256 | 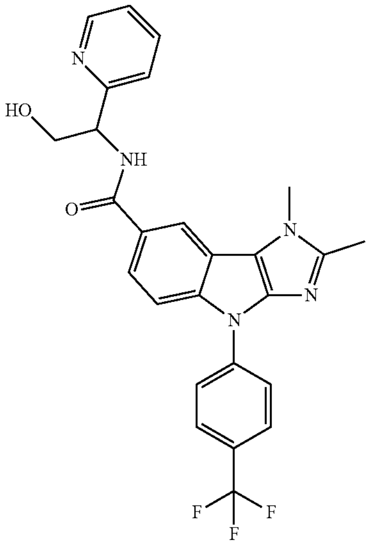 [SMILES: Cc1nc2c(c3cc(C(=O)NC(CO)c4ccccn4)ccc3n2-c2ccc(C(F)(F)F)cc2)n1C] N-[2-hydroxy-1-(pyridin-2-yl)ethyl]-1,2-dimethyl-4-[4-(trifluoromethyl)phenyl]-1H,4H-imidazo[4,5-b]indole-7-carboxamide | (400 MHz, DMSO-d6) δ 8.66 (d, J = 7.9 Hz, 1H), 8.59-8.53 (m, 1H), 8.49 (d, J = 1.7 Hz, 1H), 8.09 (d, J = 8.5 Hz, 2H), 7.97 (d, J = 8.6 Hz, 2H), 7.90-7.73 (m, 3H), 7.47 (d, J = 7.9 Hz, 1H), 7.28 (m, 1H), 5.24 (td, J = 7.5, 5.3 Hz, 1H), 4.97 (t, J = 5.9 Hz, 1H), 4.05 (s, 3H), 3.97-3.81 (m, 2H), 2.54 (s, 3H). | 9 0.63 min 494.05 (M + H) |

TABLE 1-continued

| Compound No. (Example No.) | Structure and Name | $^1$H-NMR | Conditions and elution time (min) LCMS (M + H$^+$) |
|---|---|---|---|
| Table 1 below shows exemplary compounds of the present invention. They have been synthesized as described in the Examples above or similar thereto. | | | |
| 257 | 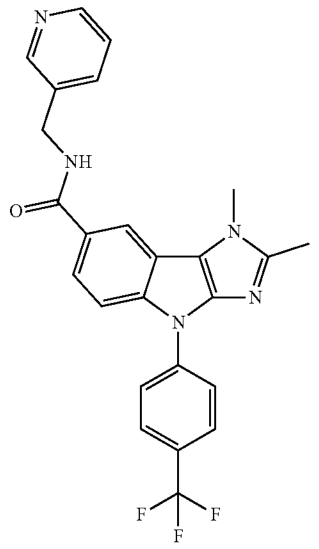 [SMILES: Cc1nc2c(c3cc(C(=O)NCc4cccnc4)ccc3n2-c2ccc(C(F)(F)F)cc2)n1C] 1,2-dimethyl-N-[(pyridin-3-yl)methyl]-4-[4-(trifluoromethyl)phenyl]-1H,4H-imidazo[4,5-b]indole-7-carboxamide | (400 MHz, DMSO-d6) δ 9.09 (t, J = 5.9 Hz, 1H), 8.61 (d, J = 2.3 Hz, 1H), 8.51-8.41 (m, 2H), 8.08 (d, J = 8.4 Hz, 2H), 7.97 (d, J = 8.4 Hz, 2H), 7.86 (d, J = 8.8 Hz, 1H), 7.83-7.73 (m, 2H), 7.38 (m, 1H), 4.57 (d, J = 5.8 Hz, 2H), 4.02 (s, 3H), 2.54 (s, 3H). | 9 0.63 min 464.00 (M + H) |
| 258 | 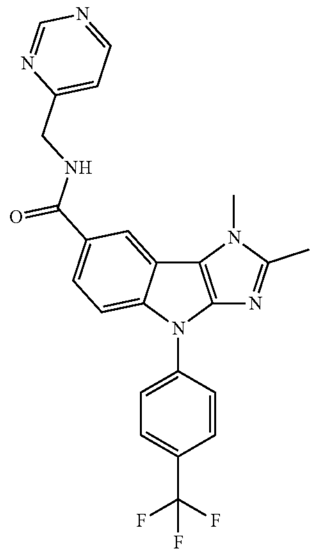 [SMILES: Cc1nc2c(c3cc(C(=O)NCc4ccncn4)ccc3n2-c2ccc(C(F)(F)F)cc2)n1C] 1,2-dimethyl-N-[(pyrimidin-4-yl)methyl]-4-[4-(trifluoromethyl)phenyl]-1H,4H-imidazo[4,5-b]indole-7-carboxamide | (400 MHz, DMSO-d6) δ 9.20 (t, J = 5.9 Hz, 1H), 9.14 (d, J = 1.4 Hz, 1H), 8.76 (d, J = 5.2 Hz, 1H), 8.49 (d, J = 1.8 Hz, 1H), 8.09 (d, J = 8.4 Hz, 2H), 7.97 (d, J = 8.6 Hz, 2H), 7.88 (d, J = 8.8 Hz, 1H), 7.82 (dd, J = 8.8, 1.8 Hz, 1H), 7.48 (dd, J = 5.2, 1.4 Hz, 1H), 4.62 (d, J = 5.8 Hz, 2H), 4.03 (s, 3H), 2.54 (s, 3H). | 9 0.68 min 465.00 (M + H) |

TABLE 1-continued

| Compound No. (Example No.) | Structure and Name | $^1$H-NMR | Conditions and elution time (min) LCMS (M + H$^+$) |
|---|---|---|---|
| Table 1 below shows exemplary compounds of the present invention. They have been synthesized as described in the Examples above or similar thereto. | | | |
| 259 | 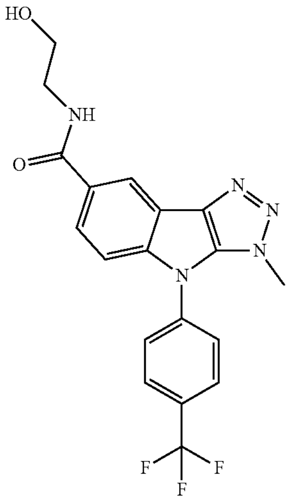 [SMILES: Cn1nnc2c3cc(C(=O)NCCO)ccc3n(-c3ccc(C(F)(F)F)cc3)c21] N-(2-hydroxyethyl)-3-methyl-4-[4-(trifluoromethyl)phenyl]-3H,4H-[1,2,3]triazolo[4,5-b]indole-7-carboxamide | (300 MHz, DMSO-d6) δ 8.58 (t, J = 4.0 Hz, 2H), 8.12-7.90 (m, 6H), 4.75 (t, J = 5.6 Hz, 1H), 4.38 (s, 3H), 3.57 (q, J = 6.0 Hz, 2H), 3.40 (q, J = 6.0 Hz, 2H). | |
| 260 | 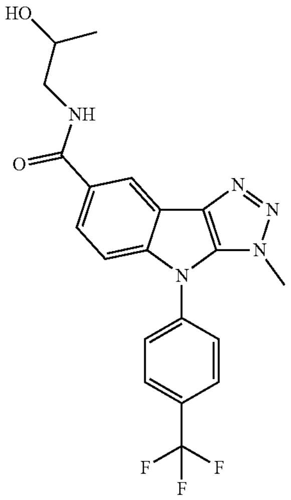 [SMILES: CC(O)CNC(=O)c1ccc2c(c1)c1nnn(C)c1n2-c1ccc(C(F)(F)F)cc1] N-(2-hydroxypropyl)-3-methyl-4-[4-(trifluoromethyl)phenyl]-3H,4H-[1,2,3]triazolo[4,5-b]indole-7-carboxamide | (400 MHz, DMSO-d6) δ 8.61-8.52 (m, 2H), 8.10-7.97 (m, 5H), 7.92 (d, J = 8.8 Hz, 1H), 4.77 (d, J = 4.7 Hz, 1H), 4.37 (s, 3H), 3.84 (dt, J = 11.5, 6.0 Hz, 1H), 3.26 (td, J = 6.0, 2.3 Hz, 2H), 1.10 (d, J = 6.2 Hz, 3H). | 11 1.05 min 418.10 (M + H) |

TABLE 1-continued

| Compound No. (Example No.) | Structure and Name | $^1$H-NMR | Conditions and elution time (min) LCMS (M + H$^+$) |
|---|---|---|---|
| | Table 1 below shows exemplary compounds of the present invention. They have been synthesized as described in the Examples above or similar thereto. | | |
| 261 | 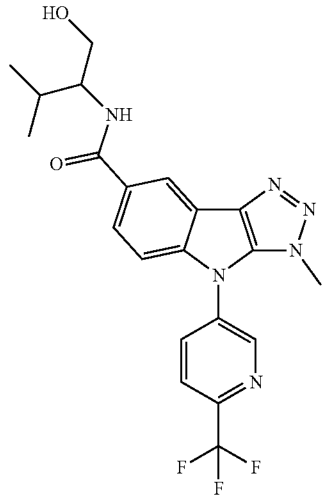 [SMILES: CC(C)C(CO)NC(=O)c1ccc2c(c1)c1nnn(C)c1n2-c1ccc(C(F)(F)F)nc1] N-(1-hydroxy-3-methylbutan-2-yl)-3-methyl-4-[6-(trifluoromethyl)pyridin-3-yl]-3H,4H-[1,2,3]triazolo[4,5-b]indole-7-carboxamide | 1H NMR (300 MHz, DMSO, ppm) 9.33 (d, J = 2.5 Hz, 1H), 8.64 (d, J = 1.7 Hz, 1H), 8.61-8.51 (m, 1H), 8.18 (t, J = 8.5 Hz, 2H), 8.12-8.04 (m, 1H), 8.01 (d, J = 8.8 Hz, 1H), 4.62 (t, J = 5.6 Hz, 1H), 4.39 (s, 3H), 3.94-3.81 (m, 1H), 3.57 (t, J = 6.2 Hz, 2H), 2.06-1.89 (m, 1H), 0.94 (t, J = 6.5 Hz, 6H). | |
| 262 | 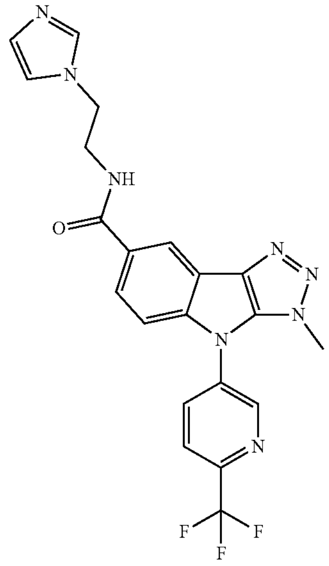 [SMILES: Cn1nnc2c3cc(C(=O)NCCn4ccnc4)ccc3n(-c3ccc(C(F)(F)F)nc3)c21] N-[2-(1H-imidazol-1-yl)ethyl]-3-methyl-4-[6-(trifluoromethyl)pyridin-3-yl]-3H,4H-[1,2,3]triazolo[4,5-b]indole-7-carboxamide | | |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 263 | 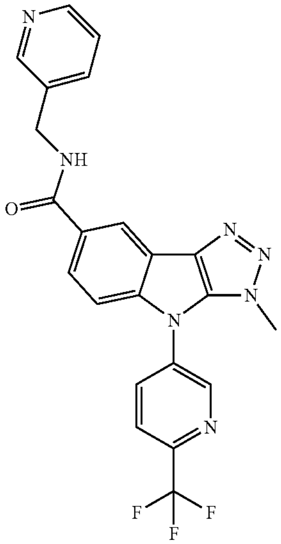 [SMILES: Cn1nnc2c3cc(C(=O)NCc4cccnc4)ccc3n(-c3ccc(C(F)(F)F)nc3)c21]<br>3-methyl-N-[(pyridin-3-yl)methyl]-4-[6-(trifluoromethyl)pyridin-3-yl]-3H,4H-[1,2,3]triazolo[4,5-b]indole-7-carboxamide | (300 MHz, DMSO-d6) δ 9.32 (d, J = 2.6 Hz, 1H), 9.28 (t, J = 5.9 Hz, 1H), 8.65-8.59 (m, 2H), 8.59-8.52 (m, 1H), 8.52-8.42 (m, 1H), 8.19 (d, J = 8.6 Hz, 1H), 8.13-7.95 (m, 2H), 7.82-7.71 (m, 1H), 7.44-7.31 (m, 1H), 4.56 (d, J = 5.8 Hz, 2H), 4.39 (s, 3H). | |
| 264 | 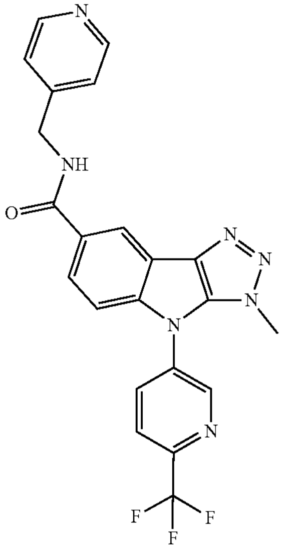 [SMILES: Cn1nnc2c3cc(C(=O)NCc4ccncc4)ccc3n(-c3ccc(C(F)(F)F)nc3)c21]<br>3-methyl-N-[(pyridin-4-yl)methyl]-4-[6-(trifluoromethyl)pyridin-3-yl]-3H,4H-[1,2,3]triazolo[4,5-b]indole-7-carboxamide | (300 MHz, DMSO-d6) δ 9.36-9.26 (m, 2H), 8.63 (d, J = 1.7 Hz, 1H), 8.61-8.49 (m, 3H), 8.19 (d, J = 8.6 Hz, 1H), 8.15-8.06 (m, 1H), 8.03 (d, J = 8.8 Hz, 1H), 7.40-7.32 (m, 2H), 4.57 (d, J = 5.8 Hz, 2H), 4.39 (s, 3H). | |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 265 | 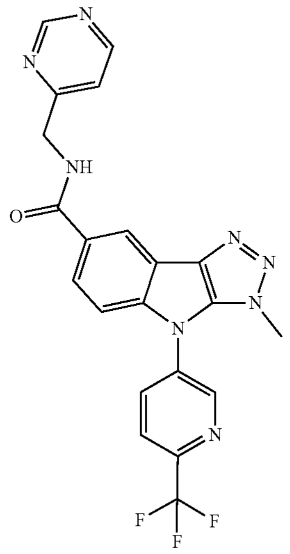 [SMILES: Cn1nnc2c3cc(C(=O)NCc4ccncn4)ccc3n(-c3ccc(C(F)(F)F)nc3)c21] 3-methyl-N-[(pyrimidin-4-yl)methyl]-4-[6-(trifluoromethyl)pyridin-3-yl]-3H,4H-[1,2,3]triazolo[4,5-b]indole-7-carboxamide | (300 MHz, DMSO-d6) δ 9.40-9.23 (m, 2H), 8.63 (d, J = 1.7 Hz, 1H), 8.59-8.45 (m, 3H), 8.19 (d, J = 8.6 Hz, 1H), 8.15-7.97 (m, 2H), 7.44-7.28 (m, 2H), 4.57 (d, J = 5.8 Hz, 2H), 4.39 (s, 3H). | |
| 266 | 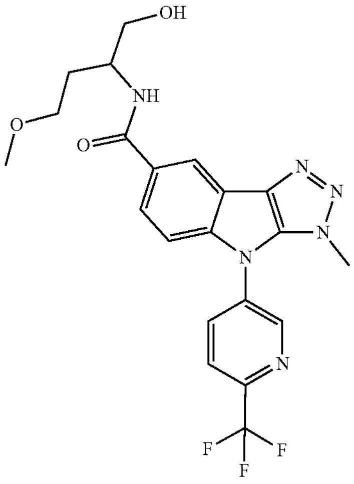 N-(1-hydroxy-4-methoxybutan-2-yl)-3-methyl-4-[4-(trifluoromethyl)phenyl]-3H,4H-[1,2,3]triazolo[4,5-b]indole-7-carboxamide | (400 MHz, DMSO-d6) δ 8.60 (d, J = 1.8 Hz, 1H), 8.22 (d, J = 8.3 Hz, 1H), 8.11-7.98 (m, 5H), 7.93 (d, J = 8.8 Hz, 1H), 4.74 (t, J = 5.8 Hz, 1H), 4.37-4.72 (s, 3H), 4.08 (m, 1H), 3.29 (s, 4H), 3.22 (s, 3H), 1.904-1.92 (m, 1H), 1.82-1.69 (m, 1H). | 11 0.93 min 462.00 (M + H) |

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 267 | 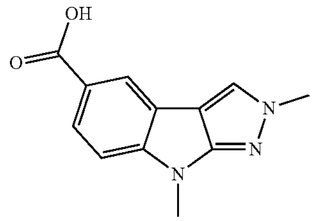 [SMILES: Cn1cc2c3cc(C(=O)O)ccc3n(C)c2n1] 2,8-dimethyl-2H,8H-pyrazolo[3,4-b]indole-5-carboxylic acid | (500 MHz, DMSO-d6) δ 12.43 (s, 1H), 8.31 (d, J = 1.7 Hz, 1H), 8.05 (s, 1H), 7.88 (dd, J = 8.5, 1.8 Hz, 1H), 7.42 (d, J = 8.6 Hz, 1H), 4.00 (s, 3H), 3.71 (s, 3H). | 8 1.201 (230.1) |
| 268 | 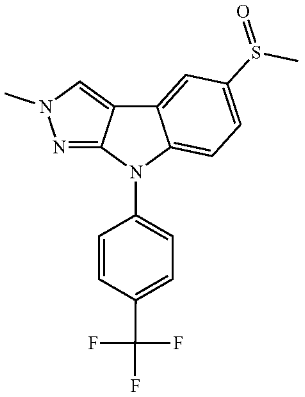 5-methanesulfinyl-2-methyl-8-[4-(trifluoromethyl)phenyl]-2H,8H-pyrazolo[3,4-b]indole | (400 MHz, DMSO-d6) δ 2.78 (s, 3H, 25), 4.04 (s, 3H, 12), 7.60 (dd, J = 8.6, 1.9 Hz, 1H, 2), 7.88 (d, J = 8.6 Hz, 1H, 3), 7.97 (d, J = 8.5 Hz, 2H, 17, 19), 8.08 (d, J = 8.4 Hz, 2H, 16, 20), 8.17 (d, J = 1.8 Hz, 1H, 6), 8.22 (s, 1H, 11). | |
| 269 | 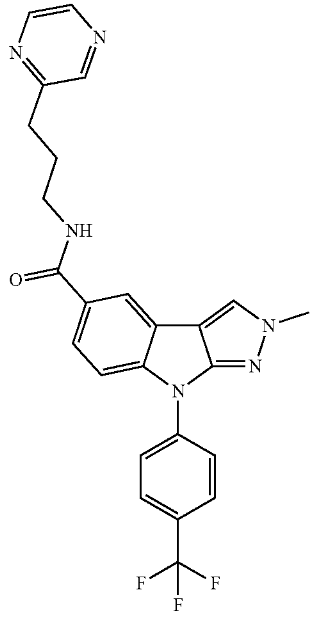 [SMILES: Cn1cc2c3cc(C(=O)NCCCc4cnccn4)ccc3n(-c3ccc(C(F)(F)F)cc3)c2n1] 2-methyl-N-[3-(pyrazin-2-yl)propyl]-8-[4-(trifluoromethyl)phenyl]-2H,8H-pyrazolo[3,4-b]indole-5-carboxamide | (400 MHz, DMSO-d6) δ 8.61 (d, J = 1.5 Hz, 1H), 8.56 (dd, J = 2.6, 1.5 Hz, 1H), 8.52 (t, J = 5.6 Hz, 1H), 8.47 (d, J = 2.6 Hz, 1H), 8.32 (d, J = 1.8 Hz, 1H), 8.20 (s, 1H), 8.11-8.06 (m, 2H), 7.99-7.94 (m, 2H), 7.84 (dd, J = 8.7, 1.8 Hz, 1H), 7.77 (d, J = 8.7 Hz, 1H), 4.04 (s, 3H), 3.37 (q, J = 6.6 Hz, 2H), 2.87 (t, J = 7.6 Hz, 2H), 2.00 (quint , J = 7.2 Hz, 2H). | |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 270 | 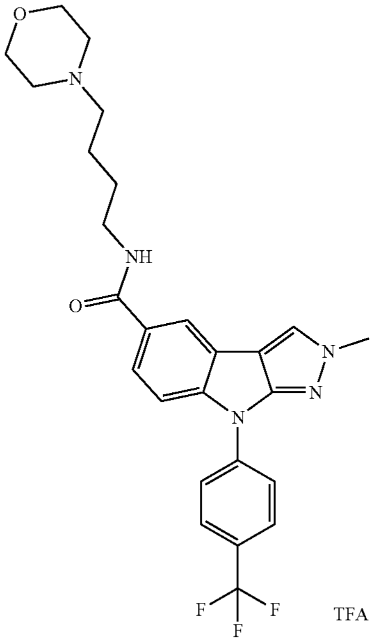 [SMILES: Cn1cc2c3cc(C(=O)NCCCCN4CCOCC4)ccc3n(-c3ccc(C(F)(F)F)cc3)c2n1 ; "TFA"] TFA<br>2-methyl-N-[4-(morpholin-4-yl)butyl]-8-[4-(trifluoromethyl)phenyl]-2H,8H-pyrazolo[3,4-b]indole-5-carboxamide | (700 MHz, DMSO-d6) δ 9.59-9.53 (m, 1H), 8.56 (t, J = 5.7 Hz, 1H), 8.34 (d, J = 1.9 Hz, 1H), 8.21 (s, 1H), 8.10-8.07 (m, 2H), 7.99-7.96 (m, 2H), 7.85 (dd, J = 8.7, 1.8 Hz, 1H), 7.78 (d, J = 8.6 Hz, 1H), 4.04 (s, 3H), 4.01-3.96 (m, 2H), 3.66-3.61 (m, 2H), 3.45-3.41 (m, 2H), 3.35 (q, J = 6.6 Hz, 2H), 3.19-3.14 (m, 2H), 3.09-3.03 (m, 2H), 1.74-1.68 (m, 2H), 1.63-1.57 (m, 2H). | |
| 271 | 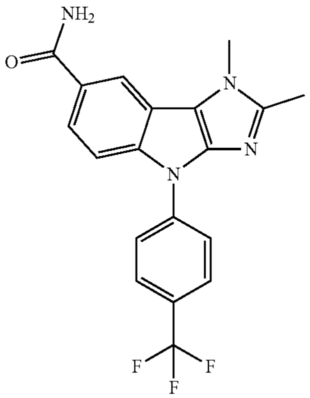 [SMILES: Cc1nc2c(c3cc(C(N)=O)ccc3n2-c2ccc(C(F)(F)F)cc2)n1C]<br>1,2-dimethyl-4-[4-(trifluoromethyl)phenyl]-1H,4H-imidazo[4,5-b]indole-7-carboxamide | (400 MHz, DMSO-d6) 8.44 (d, J = 1.7 Hz, 1H), 8.09 (d, J = 8.4 Hz, 2H), 7.96 (d, J = 8.6 Hz, 3H), 7.83 (d, J = 8.8 Hz, 1H), 7.78 (dd, J = 8.8, 1.8 Hz, 1H), 7.28 (s, 1H), 4.02 (s, 3H), 2.53 (s, 3H). | 9<br>0.66 min<br>372.90<br>(M + H) |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 272 | 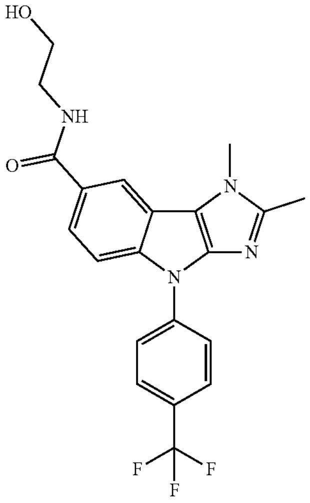 [SMILES: Cc1nc2c(c3cc(C(=O)NCCO)ccc3n2-c2ccc(C(F)(F)F)cc2)n1C]<br>N-(2-hydroxyethyl)-1,2-dimethyl-4-[4-(trifluoromethyl)phenyl]-1H,4H-imidazo[4,5-b]indole-7-carboxamide | (400 MHz, DMSO-d6) 8.45 (t, J = 5.6 Hz, 1H), 8.41 (d, J = 1.7 Hz, 1H), 8.08 (d, J = 8.4 Hz, 2H), 7.96 (d, J = 8.6 Hz, 2H), 7.84 (d, J = 8.8 Hz, 1H), 7.76 (dd, J = 8.7, 1.8 Hz, 1H), 4.77 (t, J = 5.5 Hz, 1H), 4.02 (s, 3H), 3.57 (q, J = 6.1 Hz, 2H), 3.40 (q, J = 6.1 Hz, 2H), 2.53 (s, 3H). | 9<br>0.66 min<br>416.95<br>(M + H) |
| 273 | 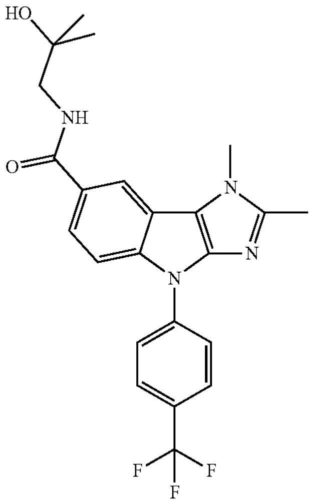 [SMILES: Cc1nc2c(c3cc(C(=O)NCC(C)(C)O)ccc3n2-c2ccc(C(F)(F)F)cc2)n1C]<br>N-(2-hydroxy-2-methylpropyl)-1,2-dimethyl-4-[4-(trifluoromethyl)phenyl]-1H,4H-imidazo[4,5-b]indole-7-carboxamide | (400 MHz, DMSO-d6) δ 8.43 (d, J = 1.8 Hz, 1H), 8.29 (t, J = 6.1 Hz, 1H), 8.08 (d, J = 8.4 Hz, 2H), 7.97 (d, J = 8.6 Hz, 2H), 7.84 (d, J = 8.8 Hz, 1H), 7.78 (dd, J = 8.8, 1.8 Hz, 1H), 4.62 (s, 1H), 4.03 (s, 3H), 3.3-3.34 (d, 2H), 2.53 (s, 3H), 1.15 (s, 6H). | 9<br>0.70 min<br>444.95<br>(M + H) |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 274 | 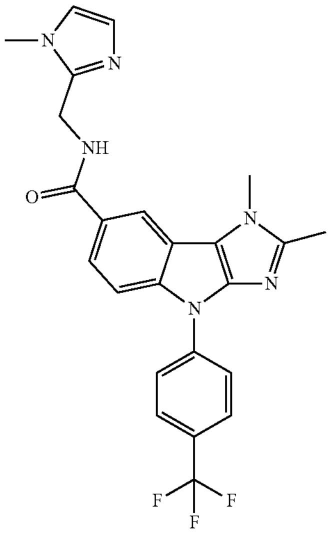 1,2-dimethyl-N-[(1-methyl-1H-imidazol-2-yl)methyl]-4-[4-(trifluoromethyl)-phenyl]-1H,4H-imidazo[4,5-b]indole-7-carboxamide | (400 MHz, DMSO-d6) δ 8.94 (t, J = 5.7 Hz, 1H), 8.47 (d, J = 1.6 Hz, 1H), 8.08 (d, J = 8.4 Hz, 2H), 7.96 (d, J = 8.5 Hz, 2H), 7.88-7.77 (m, 2H), 7.09 (d, J = 1.2 Hz, 1H), 6.82 (d, J = 1.2 Hz, 1H), 4.60 (d, J = 5.5 Hz, 2H), 4.01 (s, 3H), 3.70 (s, 3H), 2.53 (s, 3H). | 9 0.64 min 467.00 (M + H) |
| 275 | 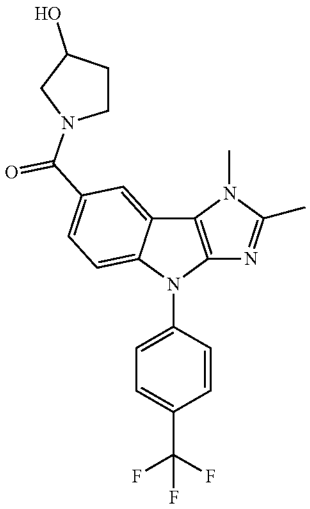 [SMILES: Cc1nc2c(c3cc(C(=O)N4CCC(O)C4)ccc3n2-c2ccc(C(F)(F)F)cc2)n1C] 1-{1,2-dimethyl-4-[4-(trifluoromethyl)-phenyl]-1H,4H-imidazo[4,5-b]indole-7-carbonyl}pyrrolidin-3-ol | (400 MHz, DMSO-d6) δ 8.08 (d, J = 8.4 Hz, 2H), 8.02 (d, J = 1.6 Hz, 1H), 7.96 (d, J = 8.5 Hz, 2H), 7.83 (d, J = 8.6 Hz, 1H), 7.38 (d, J = 8.7 Hz, 1H), 4.98 (dd, J = 39.8, 3.2 Hz, 1H), 4.31 (d, J = 42.5 Hz, 1H), 4.00 (s, 3H), 3.74-3.38 (m, 4H), 2.53 (s, 3H), 2.03-1.77 (m, 2H). | 9 0.66 min 442.95 (M + H) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 276 | 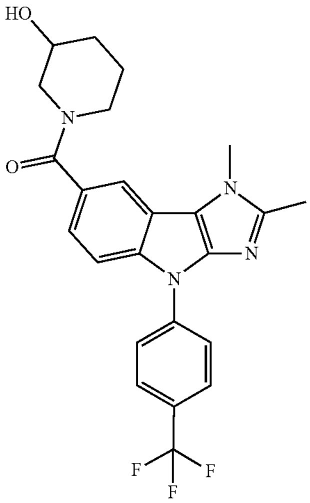 1-{1,2-dimethyl-4-[4-(trifluoromethyl)-phenyl]-1H,4H-imidazo[4,5-b]indole-7-carbonyl}piperidin-3-ol | (400 MHz, DMSO-d6) δ 8.08 (d, J = 8.4 Hz, 2H), 7.99-7.89 (m, 3H), 7.83 (d, J = 8.6 Hz, 1H), 7.23 (d, J = 8.5 Hz, 1H), 4.90 (s, 1H), 3.99 (s, 3H), 3.55 (s, 2H), 3.15 (s, 2H), 2.53 (s, 3H), 2.46 (s, 1H), 1.90 (s, 1H), 1.73 (s, 1H), 1.44 (s, 2H). | 9 0.69 min 457.00 (M + H) |
| 277 | 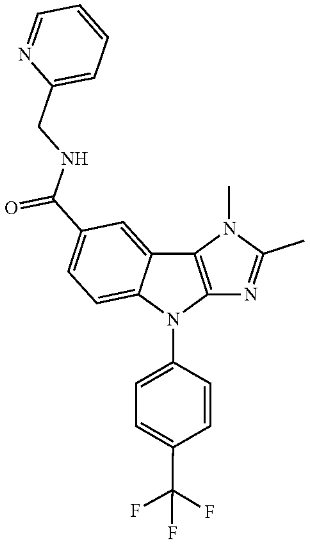 [SMILES: Cc1nc2c(c3cc(C(=O)NCc4ccccn4)ccc3n2-c2ccc(C(F)(F)F)cc2)n1C] 1,2-dimethyl-N-[(pyridin-2-yl)methyl]-4-[4-(trifluoromethyl)phenyl]-1H,4H-imidazo[4,5-b]indole-7-carboxamide | (400 MHz, DMSO-d6) δ 9.12 (t, J = 6.0 Hz, 1H), 8.57-8.47 (m, 2H), 8.09 (d, J = 8.4 Hz, 2H), 7.97 (d, J = 8.5 Hz, 2H), 7.91-7.73 (m, 3H), 7.38 (d, J = 7.9 Hz, 1H), 7.32-7.24 (m, 1H), 4.65 (d, J = 5.9 Hz, 2H), 4.03 (s, 3H), 2.54 (s, 3H). | 9 0.64 min 463.95 (M + H) |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 278 | 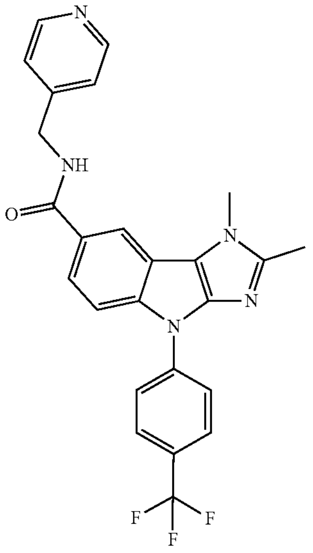 [SMILES: Cc1nc2c(c3cc(C(=O)NCc4ccncc4)ccc3n2-c2ccc(C(F)(F)F)cc2)n1C] 1,2-dimethyl-N-[(pyridin-4-yl)methyl]-4-[4-(trifluoromethyl)phenyl]-1H,4H-imidazo[4,5-b]indole-7-carboxamide | (400 MHz, DMSO-d6) δ 9.14 (t, J = 6.0 Hz, 1H), 8.56-8.50 (m, 2H), 8.47 (d, J = 1.7 Hz, 1H), 8.09 (d, J = 8.4 Hz, 2H), 7.97 (d, J = 8.5 Hz, 2H), 7.88 (d, J = 8.8 Hz, 1H), 7.82 (dd, J = 8.8, 1.8 Hz, 1H), 7.38-7.32 (m, 2H), 4.58 (d, J = 5.8 Hz, 2H), 4.02 (s, 3H), 2.54 (s, 3H). | 9 0.63 min 464.00 (M + H) |
| 279 | 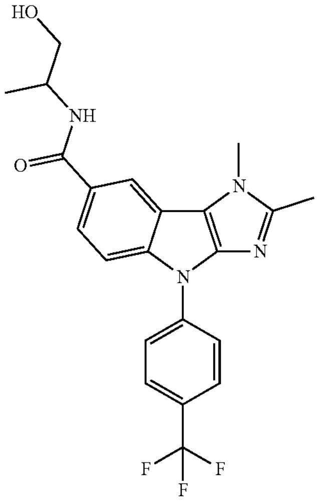 [SMILES: Cc1nc2c(c3cc(C(=O)NC(C)CO)ccc3n2-c2ccc(C(F)(F)F)cc2)n1C] N-(1-hydroxypropan-2-yl)-1,2-dimethyl-4-[4-(trifluoromethyl)phenyl]-1H,4H-imidazo[4,5-b]indole-7-carboxamide | (400 MHz, DMSO-d6) δ 8.38 (d, J = 1.8 Hz, 1H), 8.08 (dd, J = 8.3, 4.0 Hz, 3H), 7.97 (d, J = 8.5 Hz, 2H), 7.83 (d, J = 8.8 Hz, 1H), 7.76 (dd, J = 8.8, 1.8 Hz, 1H), 4.76 (t, J = 5.7 Hz, 1H), 4.04 (m, 4H), 3.53 (dt, J = 11.0, 5.6 Hz, 1H), 3.40 (dt, J = 10.6, 6.1 Hz, 1H), 2.54 (s, 3H), 1.20 (d, J = 6.7 Hz, 3H). | 9 0.67 min 430.99 (M + H) |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 280 | 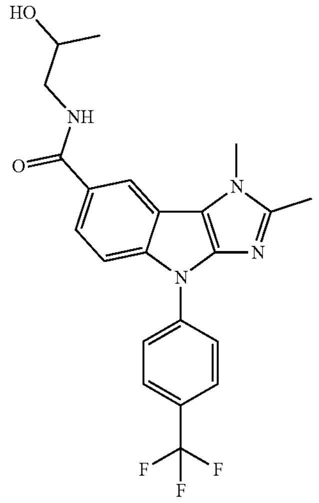 [SMILES: Cc1nc2c(c3cc(C(=O)NCC(C)O)ccc3n2-c2ccc(C(F)(F)F)cc2)n1C]<br>N-(2-hydroxypropyl)-1,2-dimethyl-4-[4-(trifluoromethyl)phenyl]-1H,4H-imidazo[4,5-b]indole-7-carboxamide | (400 MHz, DMSO-d6) δ 8.47-8.39 (m, 2H), 8.08 (d, J = 8.4 Hz, 2H), 7.96 (d, J = 8.5 Hz, 2H), 7.84 (d, J = 8.8 Hz, 1H), 7.76 (m, 1H), 4.79 (d, J = 4.7 Hz, 1H), 4.03 (s, 3H), 3.84 (m, 1H), 3.31-3.19 (m, 2H), 2.53 (s, 3H), 1.11 (d, J = 6.2 Hz, 3H). | 9<br>0.67 min<br>431.00<br>(M + H) |
| 281 | 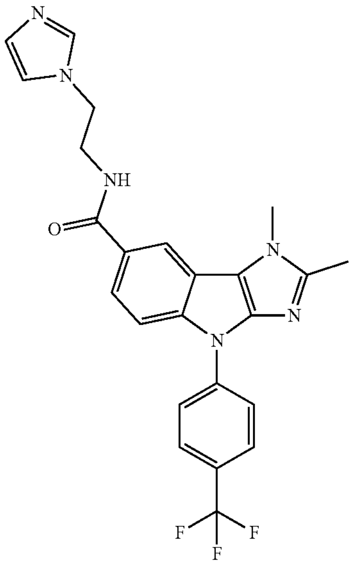 [SMILES: Cc1nc2c(c3cc(C(=O)NCCn4ccnc4)ccc3n2-c2ccc(C(F)(F)F)cc2)n1C]<br>N-[2-(1H-imidazol-1-yl)ethyl]-1,2-dimethyl-4-[4-(trifluoromethyl)phenyl]-1H,4H-imidazo[4,5-b]indole-7-carboxamide | (400 MHz, DMSO-d6) δ 8.60 (t, J = 5.5 Hz, 1H), 8.34 (d, J = 1.9 Hz, 1H), 8.08 (d, J = 8.4 Hz, 2H), 7.96 (d, J = 8.4 Hz, 2H), 7.85 (d, J = 8.8 Hz, 1H), 7.72 (dd, J = 8.8, 1.8 Hz, 1H), 7.62 (t, J = 1.1 Hz, 1H), 7.19 (d, J = 1.3 Hz, 1H), 6.89 (d, J = 1.2 Hz, 1H), 4.22 (t, J = 6.1 Hz, 2H), 4.01 (s, 3H), 3.64 (q, J = 5.9 Hz, 2H), 2.53 (s, 3H). | 9<br>0.66 min<br>467.00<br>(M + H) |

TABLE 1-continued

| Compound No. (Example No.) | Structure and Name | $^1$H-NMR | Conditions and elution time (min) LCMS (M + H$^+$) |
|---|---|---|---|
| | Table 1 below shows exemplary compounds of the present invention. They have been synthesized as described in the Examples above or similar thereto. | | |
| 282 | 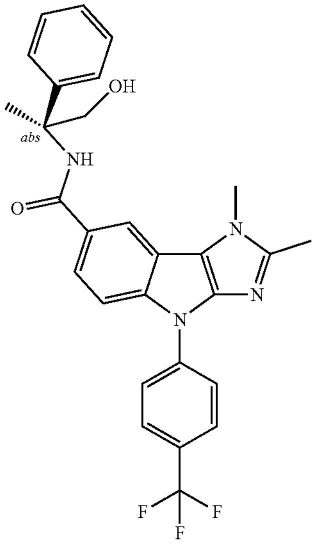 [SMILES: Cc1nc2c(c3cc(C(=O)N[C@](C)(CO)c4ccccc4)ccc3n2-c2ccc(C(F)(F)F)cc2)n1C] Absolute configuration known/assigned N-[(2S)-1-hydroxy-2-phenylpropan-2-yl]-1,2-dimethyl-4-[4-(trifluoromethyl)phenyl]-1H,4H-imidazo[4,5-b]indole-7-carboxamide | (400 MHz, DMSO-d6) δ 8.37 (d, J = 1.8 Hz, 1H), 8.09 (d, J = 8.1 Hz, 3H), 7.98 (d, J = 8.5 Hz, 2H), 7.86 (d, J = 8.8 Hz, 1H), 7.75 (dd, J = 8.8, 1.8 Hz, 1H), 7.44-7.37 (m, 2H), 7.30 (dd, J = 8.5, 6.9 Hz, 2H), 7.24-7.16 (m, 1H), 5.21 (t, J = 6.1 Hz, 1H), 4.04 (s, 3H), 3.83 (dd, J = 11.0, 6.1 Hz, 1H), 3.62 (dd, J = 11.0, 6.1 Hz, 1H), 2.54 (s, 3H), 1.78 (s, 3H). | 9 0.79 min 507.00 (M + H) |
| 283 | 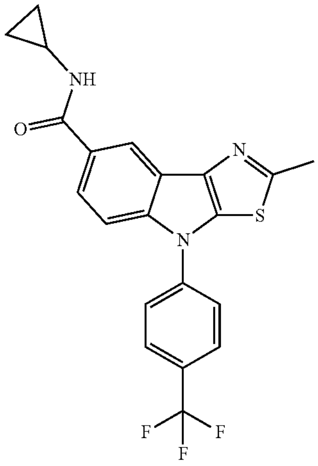 [SMILES: Cc1nc2c3cc(C(=O)NC4CC4)ccc3n(-c3ccc(C(F)(F)F)cc3)c2s1] N-cyclopropyl-2-methyl-4-[4-(trifluoromethyl)phenyl]-4H-[1,3]thiazolo[5,4-b]indole-7-carboxamide | (300 MHz, DMSO, ppm) δ 8.53 (dd, J = 11.7, 3.0 Hz, 2H), 8.09-7.95 (m, 4H), 7.88 (dd, J = 8.8, 1.7 Hz, 1H), 7.78 (d, J = 8.8 Hz, 1H), 2.85 (s, 4H), 0.76-0.56 (m, 4H). | 9 0.96 min 415.90 (M + H) |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 284 | 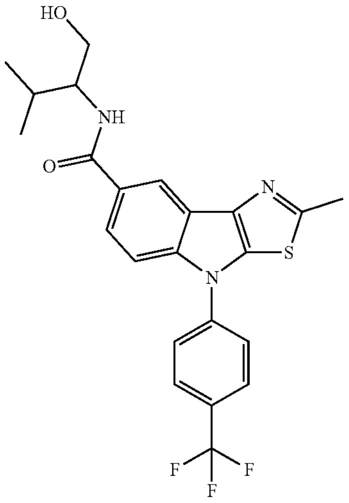 [SMILES: Cc1nc2c3cc(C(=O)NC(CO)C(C)C)ccc3n(-c3ccc(C(F)(F)F)cc3)c2s1] N-(1-hydroxy-3-methylbutan-2-yl)-2-methyl-4-[4-(trifluoromethyl)phenyl]-4H-[1,3]thiazolo[5,4-b]indole-7-carboxamide | (300 MHz, DMSO, ppm) δ 8.60 (d, J = 1.7 Hz, 1H), 8.07 (dd, J = 23.8, 6.9 Hz, 5H), 7.91 (dd, J = 8.8, 1.7 Hz, 1H), 7.80 (d, J = 8.8 Hz, 1H), 4.58 (t, J = 5.6 Hz, 1H), 3.89 (t, J = 7.3 Hz, 1H), 3.58 (t, J = 5.2 Hz, 2H), 2.85 (s, 3H), 1.98 (q, J = 6.9 Hz, 1H), 0.94 (t, J = 6.2 Hz, 6H). | 9<br>0.96 min<br>461.90<br>(M + H) |
| 285 | 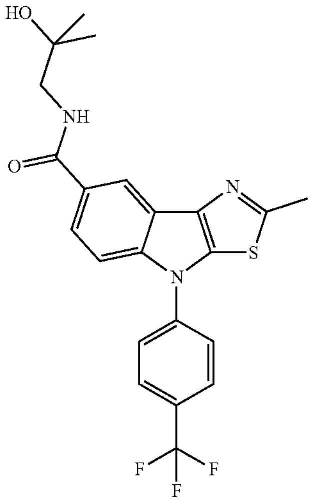 [SMILES: Cc1nc2c3cc(C(=O)NCC(C)(C)O)ccc3n(-c3ccc(C(F)(F)F)cc3)c2s1] N-(2-hydroxy-2-methylpropyl)-2-methyl-4-[4-(trifluoromethyl)phenyl]-4H-[1,3]thiazolo[5,4-b]indole-7-carboxamide | (300 MHz, DMSO, ppm) δ 8.57 (d, J = 1.7 Hz, 1H), 8.37 (d, J = 6.1 Hz, 1H), 8.10-7.96 (m, 4H), 7.91 (dd, J = 8.8, 1.9 Hz, 1H), 7.80 (d, J = 8.8 Hz, 1H), 4.61 (s, 1H), 3.34 (s, 2H), 2.85 (s, 3H), 1.15 (s, 6H). | 9<br>0.91 min<br>448.20<br>(M + H) |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 286 | 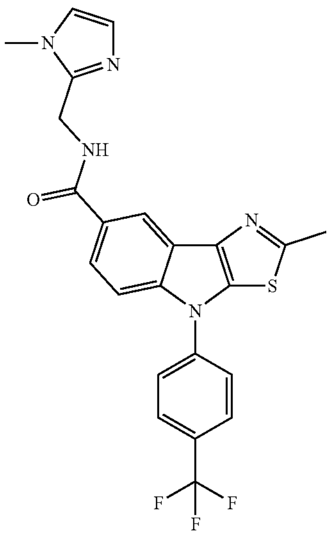<br>2-methyl-N-[(1-methyl-1H-imidazol-2-yl)methyl]-4-[4-(trifluoromethyl)-phenyl]-4H-[1,3]thiazolo[5,4-b]indole-7-carboxamide | (300 MHz, DMSO, ppm) δ 9.05 (d, J = 6.0 Hz, 1H), 8.57 (d, J = 1.8 Hz, 1H), 8.09-7.90 (m, 5H), 7.80 (d, J = 8.8 Hz, 1H), 7.10 (s, 1H), 6.82 (s, 1H), 4.58 (d, J = 5.3 Hz, 2H), 3.70 (s, 3H), 2.85 (s, 3H). | 9<br>0.76 min<br>469.90<br>(M + H) |
| 287 | 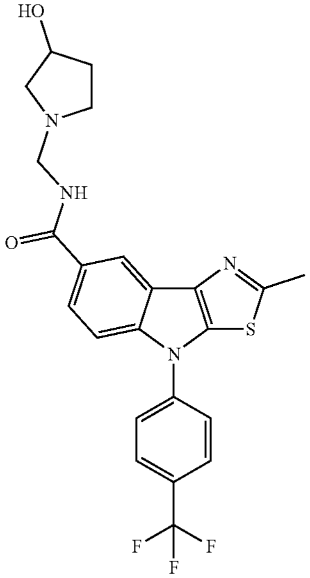<br>1-{2-methyl-4-[4-(trifluoromethyl)-phenyl]-4H-[1,3]thiazolo[5,4-b]indole-7-carbonyl}pyrrolidin-3-ol | 1H NMR (300 MHz, DMSO, ppm) 8.10-7.96 (m, 5H), 7.79 (d, J = 8.7 Hz, 1H), 7.58-7.49 (m, 1H), 4.98 (d, J = 24.3 Hz, 1H), 4.31 (d, J = 28.8 Hz, 1H), 3.74-3.38 (m, 4H), 2.85 (s, 3H), 1.90 (d, J = 39.2 Hz, 2H). | 9<br>0.85 min<br>445.80<br>(M + H) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 288 | 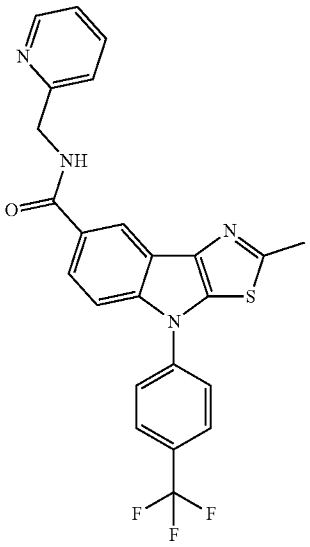 [SMILES: Cc1nc2c3cc(C(=O)NCc4ccccn4)ccc3n(-c3ccc(C(F)(F)F)cc3)c2s1] 2-methyl-N-[(pyridin-2-yl)methyl]-4-[4-(trifluoromethyl)phenyl]-4H-[1,3]thiazolo[5,4-b]indole-7-carboxamide | (300 MHz, DMSO, ppm) δ 9.25 (t, J = 5.9 Hz, 1H), 8.61 (d, J = 1.7 Hz, 1H), 8.54 (d, J = 4.9 Hz, 1H), 8.10-7.99 (m, 4H), 7.96 (dd, J = 8.8, 1.7 Hz, 1H), 7.87-7.72 (m, 2H), 7.38 (d, J = 7.9 Hz, 1H), 7.33-7.23 (m, 1H), 4.64 (d, J = 5.8 Hz, 2H), 2.85 (s, 3H). | 9<br>1.47 min<br>467.00<br>(M + H) |
| 289 | 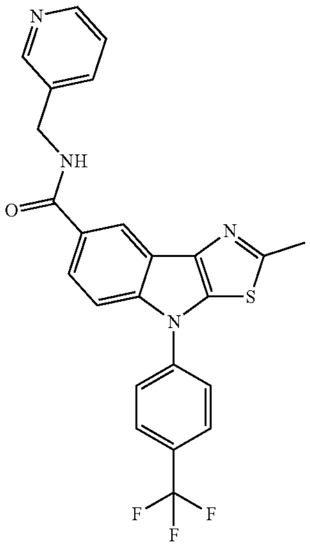 [SMILES: Cc1nc2c3cc(C(=O)NCc4cccnc4)ccc3n(-c3ccc(C(F)(F)F)cc3)c2s1] 2-methyl-N-[(pyridin-3-yl)methyl]-4-[4-(trifluoromethyl)phenyl]-4H-[1,3]thiazolo[5,4-b]indole-7-carboxamide | (300 MHz, DMSO, ppm) δ 9.23 (t, J = 5.9 Hz, 1H), 8.59 (dd, J = 9.4, 2.0 Hz, 2H), 8.48 (dd, J = 4.8, 1.7 Hz, 1H), 8.09-7.97 (m, 4H), 7.93 (dd, J = 8.8, 1.7 Hz, 1H), 7.86-7.73 (m, 2H), 7.38 (dd, J = 7.9, 4.8 Hz, 1H), 4.56 (d, J = 5.8 Hz, 2H), 2.85 (s, 3H). | 9<br>1.44 min<br>466.90<br>(M + H) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 290 | 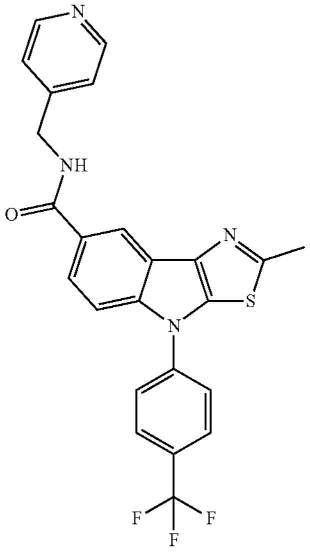 [SMILES: Cc1nc2c3cc(C(=O)NCc4ccncc4)ccc3n(-c3ccc(C(F)(F)F)cc3)c2s1] 2-methyl-N-[(pyridin-4-yl)methyl]-4-[4-(trifluoromethyl)phenyl]-4H-[1,3]thiazolo[5,4-b]indole-7-carboxamide | (300 MHz, DMSO. ppm) δ 9.26 (t, J = 6.0 Hz, 1H), 8.64-8.49 (m, 3H), 8.10-7.81 (m, 6H), 7.40-7.32 (m, 2H), 4.56 (d, J = 5.8 Hz, 2H), 2.85 (s, 3H). | 9 0.76 min 466.70 (M * H) |
| 291 | 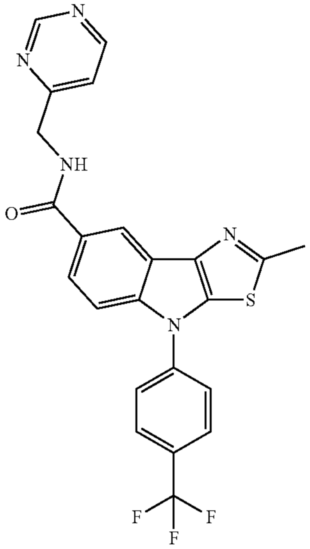 [SMILES: Cc1nc2c3cc(C(=O)NCc4ccncn4)ccc3n(-c3ccc(C(F)(F)F)cc3)c2s1] 2-methyl-N-[(pyrimidin-4-yl)methyl]-4-[4-(trifluoromethyl)phenyl]-4H-[1,3]thiazolo[5,4-b]indole-7-carboxamide | (400 MHz, DMSO, ppm) δ 9.33 (t, J = 5.9 Hz, 1H), 9.14 (d, J = 1.4 Hz, 1H), 8.75 (d, J = 5.2 Hz, 1H), 8.62 (d, J = 1.8 Hz, 1H), 8.09-7.98 (m, 4H), 7.95 (dd, J = 8.8, 1.8 Hz, 1H), 7.84 (d, J = 8.8 Hz, 1H), 7.49 (d, J = 5.3 Hz, 1H), 4.61 (d, J = 5.8 Hz, 2H), 2.85 (s, 3H). | 9 1.61 min 467.90 (M + H) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 292 | 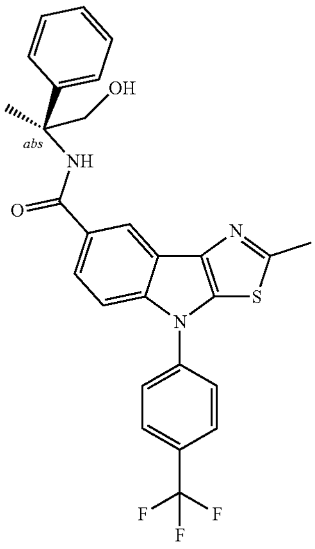 [SMILES: Cc1nc2c3cc(C(=O)N[C@](C)(CO)c4ccccc4)ccc3n(-c3ccc(C(F)(F)F)cc3)c2s1] Absolute configuration known/assigned N-[(2S)-1-hydroxy-2-phenylpropan-2-yl]-2-methyl-4-[4-(trifluoromethyl)phenyl]-4H-[1,3]thiazolo[5,4-b]indole-7-carboxamide | (400 MHz, DMSO-d6) δ 8.61 (d, J = 1.7 Hz, 1H), 8.24 (s, 1H), 8.03-8.01 (m, J = 8.8 Hz, 4H), 7.88-7.77 (m, 2H), 7.43-7.36 (m, 2H), 7.31-7.28 (m, J = 8.4, 6.8 Hz, 2H), 7.24-7.15 (m, 1H), 5.21 (t, J = 6.2 Hz, 1H), 3.83-3.79 (m, J = 11.1, 6.1 Hz, 1H), 3.58 (t, J = 11.0, 6.4 Hz, 1H), 2.86 (s, 3H), 1.77 (s, 3H). | 16 1.77 min 510.25 (M + H) |
| 293 | 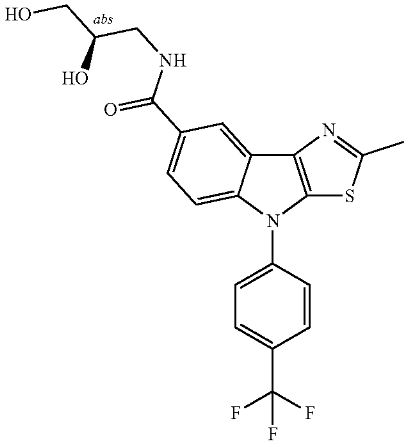 [SMILES: Cc1nc2c3cc(C(=O)NC[C@@H](O)CO)ccc3n(-c3ccc(C(F)(F)F)cc3)c2s1] Absolute configuration known/assigned N-[(2R)-2,3-dihydroxypropyl]-2-methyl-4-[4-(trifluoromethyl)phenyl]-4H-[1,3]thiazolo[5,4-b]indole-7-carboxamide | (300 MHz, DMSO, ppm) δ 8.58-8.47 (m, 2H), 8.09-7.96 (m, 4H), 7.90 (dd, J = 8.8, 1.8 Hz, 1H), 7.80 (d, J = 8.8 Hz, 1H), 4.84 (d, J = 4.9 Hz, 1H), 4.59 (t, J = 5.8 Hz, 1H), 3.70 (q, J = 5.5 Hz, 1H), 3.42 (dt, J = 11.3, 5.8 Hz, 4H), 2.85 (s, 3H). | 9 0.81 min 449.90 (M + H) |

TABLE 1-continued

| Compound No. (Example No.) | Structure and Name | $^1$H-NMR | Conditions and elution time (min) LCMS (M + H$^+$) |
|---|---|---|---|
| Table 1 below shows exemplary compounds of the present invention. They have been synthesized as described in the Examples above or similar thereto. | | | |
| 294 | 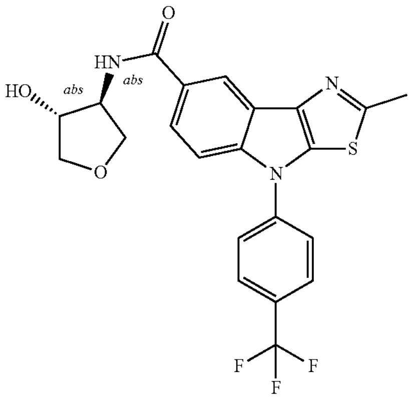 [SMILES: Cc1nc2c3cc(C(=O)N[C@H]4COC[C@@H]4O)ccc3n(-c3ccc(C(F)(F)F)cc3)c2s1] Absolute configuration known/assigned N-[(3S,4R)-4-hydroxyoxolan-3-yl]-2-methyl-4-[4-(trifluoromethyl)phenyl]-4H-[1,3]thiazolo[5,4-b]indole-7-carboxamide | (400 MHz, DMSO-d6) δ 8.64-8.57 (m, 2H), 8.02 (q, J = 8.7 Hz, 4H), 7.91 (dd, J = 8.8, 1.8 Hz, 1H), 7.79 (d, J = 8.8 Hz, 1H), 5.29 (s, 1H), 4.31-4.22 (m, 2H), 4.04 (dd, J = 9.0, 5.8 Hz, 1H), 3.96 (dd, J = 9.3, 4.6 Hz, 1H), 3.69 (dd, J = 9.0, 3.4 Hz, 1H), 3.57 (dd, J = 9.2, 2.4 Hz, 1H), 2.84 (s, 3H). | 16 1.46 min 462.20 (M + H) |
| 295 | 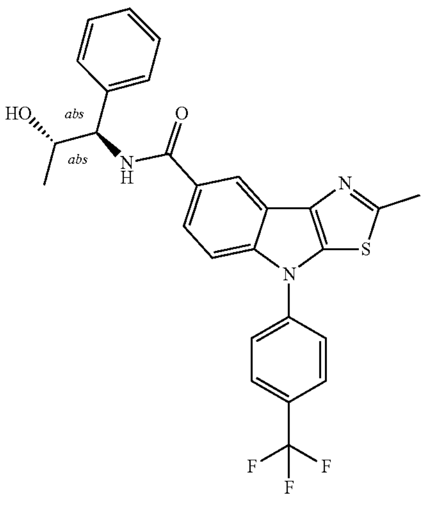 [SMILES: Cc1nc2c3cc(C(=O)N[C@H](c4ccccc4)[C@H](C)O)ccc3n(-c3ccc(C(F)(F)F)cc3)c2s1] Absolute configuration known/assigned N-[(1R,2S)-2-hydroxy-1-phenylpropyl]-2-methyl-4-[4-(trifluoromethyl)phenyl]-4H-[1,3]thiazolo[5,4-b]indole-7-carboxamide | (400 MHz, DMSO-d6) δ 8.74 (dd, J = 8.4, 2.4 Hz, 1H), 8.59 (d, J = 2.3 Hz, 1H), 8.07-7.96 (m, 4H), 7.92-7.84 (m, 1H), 7.79 (dd, J = 8.8, 2.8 Hz, 1H), 7.50-7.43 (m, 2H), 7.36-7.27 (m, 2H), 7.23 (d, J = 8.0 Hz, 1H), 4.93 (t, J = 7.6 Hz, 1H), 4.75 (d, J = 3.6 Hz, 1H), 4.06 (s, 1H), 2.87-2.82 (m, 3H), 1.17 (dd, J = 6.3, 2.7 Hz, 3H). | 16 1.72 min 510.20 (M + H) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 296 | 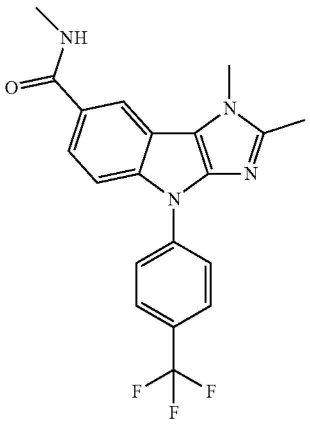 [SMILES: CNC(=O)c1ccc2c(c1)c1c(nc(C)n1C)n2-c1ccc(C(F)(F)F)cc1] N,1,2-trimethyl-4-[4-(trifluoromethyl)phenyl]-1H,4H-imidazo[4,5-b]indole-7-carboxamide | (400 MHz, DMSO-d6) δ 8.42 (q, J = 4.4 Hz, 1H), 8.37 (d, J = 1.7 Hz, 1H), 8.08 (d, J = 8.4 Hz, 2H), 7.96 (d, J = 8.5 Hz, 2H), 7.84 (d, J = 8.7 Hz, 1H), 7.73 (dd, J = 8.8, 1.8 Hz, 1H), 4.02 (s, 3H), 2.85 (d, J = 4.4 Hz, 3H), 2.53 (s, 3H). | 9<br>0.70 min<br>386.90<br>(M * H) |
| 297 | 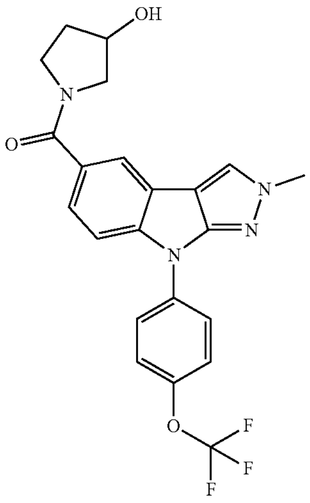 [SMILES: Cn1cc2c3cc(C(=O)N4CCC(O)C4)ccc3n(-c3ccc(OC(F)(F)F)cc3)c2n1] 1-{2-methyl-8-[4-(trifluoromethoxy)-phenyl]-2H,8H-pyrazolo[3,4-b]indole-5-carbonyl}pyrrolidin-3-ol | (700 MHz, DMSO-d6) δ 8.13 (s, 1H), 8.04-8.00 (m, 1H), 7.95-7.92 (m, 2H), 7.63 (d, J = 8.5 Hz, 1H), 7.62-7.59 (m, 2H), 7.50-7.46 (m, 1H), 4.37-4.23 (m, 1H), 4.01 (s, 3H), 3.73-3.58 (m, 2H), 3.56-3.49 (m, 1H), 3.41-3.30 (m, 1H), 2.01-1.87 (m, 1H), 1.86-1.77 (m, 1H). | |

TABLE 1-continued

| Compound No. (Example No.) | Structure and Name | $^1$H-NMR | Conditions and elution time (min) LCMS (M + H$^+$) |
|---|---|---|---|
| Table 1 below shows exemplary compounds of the present invention. They have been synthesized as described in the Examples above or similar thereto. | | | |
| 298 | 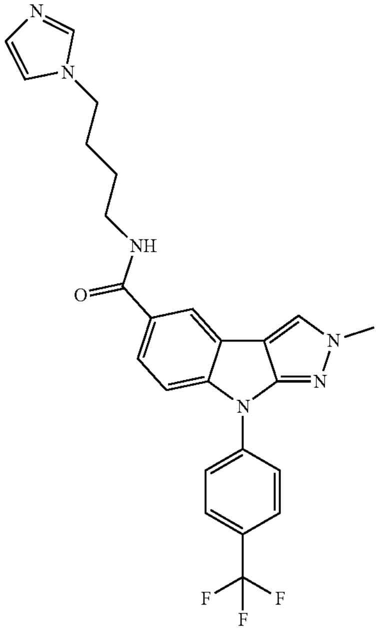 [SMILES: Cn1cc2c3cc(C(=O)NCCCCn4ccnc4)ccc3n(-c3ccc(C(F)(F)F)cc3)c2n1] N-[4-(1H-imidazol-1-yl)butyl]-2-methyl-8-[4-(trifluoromethyl)phenyl]-2H,8H-pyrazolo[3,4-b]indole-5-carboxamide | (700 MHz, DMSO-d6) δ 14.38-14.28 (m, 1H), 9.15-9.14 (m, 1H), 8.55 (t, J = 5.7 Hz, 1H), 8.32 (d, J = 1.9 Hz, 1H), 8.20 (s, 1H), 8.09-8.07 (m, 2H), 7.99-7.96 (m, 2H), 7.84 (dd, J = 8.7, 1.9 Hz, 1H), 7.82 (t, J = 1.7 Hz, 1H), 7.77 (d, J = 8.7 Hz, 1H), 7.71 (t, J = 1.7 Hz, 1H), 4.26 (t, J = 7.2 Hz, 2H), 4.04 (s, 3H), 3.35-3.32 (m, 2H), 1.91-1.85 (m, 2H), 1.55-1.50 (m, 2H). | |
| 299 | 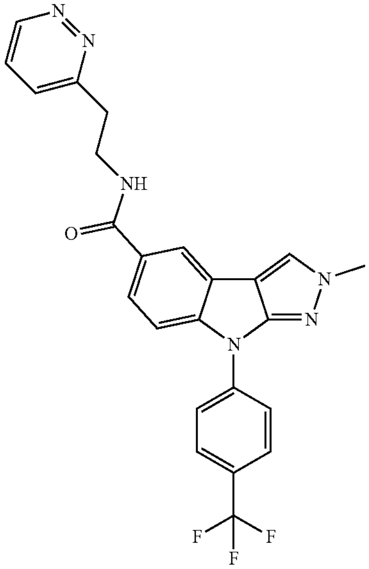 [SMILES: Cn1cc2c3cc(C(=O)NCCc4cccnn4)ccc3n(-c3ccc(C(F)(F)F)cc3)c2n1] 2-methyl-N-[2-(pyridazin-3-yl)ethyl]-8-[4-(trifluoromethyl)phenyl]-2H,8H-pyrazolo[3,4-b]indole-5-carboxamide | (700 MHz, DMSO-d6) δ 9.17-9.16 (m, 1H), 8.65 (t, J = 5.7 Hz, 1H), 8.29 (d, J = 1.8 Hz, 1H), 8.21 (s, 1H), 8.10-8.07 (m, 2H), 7.98-7.95 (m, 2H), 7.80 (dd, J = 8.7, 1.8 Hz, 1H), 7.77-7.75 (m, 2H), 7.76-7.73 (m, 1H), 4.03 (s, 3H), 3.75-3.71 (m, 2H), 3.25 (t, J = 7.1 Hz, 2H). | |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 300 | 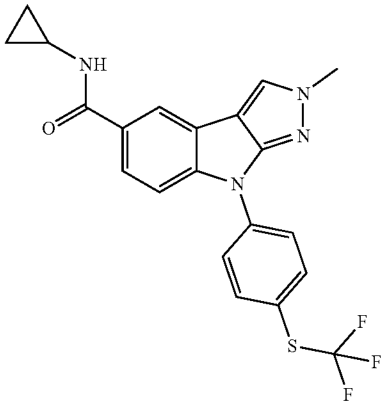 [SMILES: Cn1cc2c3cc(C(=O)NC4CC4)ccc3n(-c3ccc(SC(F)(F)F)cc3)c2n1] N-cyclopropyl-2-methyl-8-{4-[(trifluoromethyl)sulfanyl]phenyl}-2H,8H-pyrazolo[3,4-b]indole-5-carboxamide | (700 MHz, DMSO-d6) δ 8.46 (d, J = 4.3 Hz, 1H), 8.30 (d, J = 1.9 Hz, 1H), 8.19 (s, 1H), 8.04-8.01 (m, 2H), 7.96-7.93 (m, 2H), 7.82 (dd, J = 8.7, 1.8 Hz, 1H), 7.74 (d, J = 8.6 Hz, 1H), 4.03 (s, 3H), 2.91-2.87 (m, 1H), 0.72-0.69 (m, 2H), 0.62-0.59 (m, 2H). | |
| 301 | 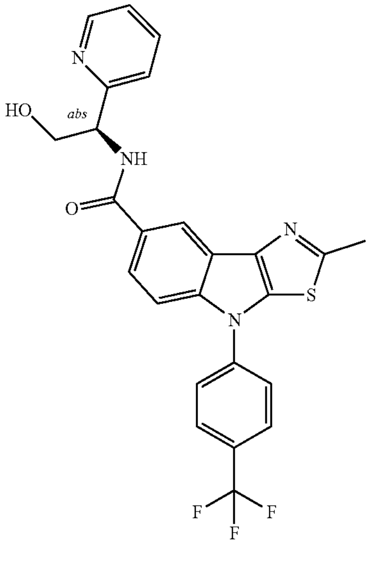 [SMILES: Cc1nc2c3cc(C(=O)N[C@@H](CO)c4ccccn4)ccc3n(-c3ccc(C(F)(F)F)cc3)c2s1] Absolute configuration known/assigned N-[(1R)-2-hydroxy-1-(pyridin-2-yl)ethyl]-2-methyl-4-[4-(trifluoromethyl)phenyl]-4H-[1,3]thiazolo[5,4-b]indole-7-carboxamide | (300 MHz, DMSO, ppm) δ 8.81 (d, J = 7.8 Hz, 1H), 8.68 (d, J = 1.7 Hz, 1H), 8.60-8.51 (m, 1H), 8.10-7.90 (m, 5H), 7.86-7.71 (m, 2H), 7.47 (d, J = 7.9 Hz, 1H), 7.33-7.23 (m, 1H), 5.29-5.16 (m, 1H), 4.96 (t, J = 6.0 Hz, 1H), 3.86 (tt, J = 11.0, 6.2 Hz, 2H), 2.86 (s, 3H). | 9 0.76 min 496.90 (M + H) |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 302 | 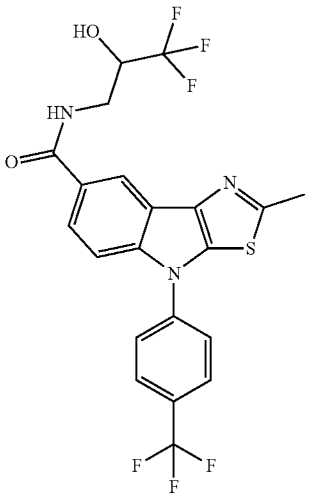 [SMILES: Cc1nc2c3cc(C(=O)NCC(O)C(F)(F)F)ccc3n(-c3ccc(C(F)(F)F)cc3)c2s1]<br>2-methyl-N-(3,3,3-trifluoro-2-hydroxy-propyl)-4-[4-(trifluoromethyl)phenyl]-4H-[1,3]thiazolo[5,4-b]indole-7-carboxamide | (400 MHz, DMSO-d6) δ 8.83 (t, J = 5.7 Hz, 1H), 8.54 (d, J = 1.7 Hz, 1H), 8.07-7.97 (m, 4H), 7.94-7.87 (m, 1H), 7.81 (d, J = 8.8 Hz, 1H), 6.52 (s, 1H), 4.26 (s, 1H), 3.73-3.62 (m, 1H), 3.43-3.35 (m, 1H), 2.85 (s, 3H). | 16<br>1.41 min<br>488.05<br>(M + H) |
| 303 | 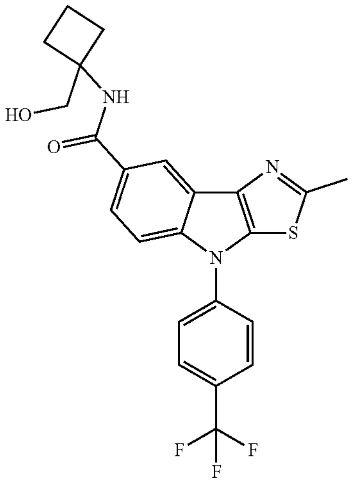 [SMILES: Cc1nc2c3cc(C(=O)NC4(CO)CCC4)ccc3n(-c3ccc(C(F)(F)F)cc3)c2s1]<br>N-[1-(hydroxymethyl)cyclobutyl]-2-methyl-4-[4-(trifluoromethyl)phenyl]-4H-[1,3]thiazolo[5,4-b]indole-7-carboxamide | (400 MHz, DMSO-d6) δ 8.58 (d, J = 1.9 Hz, 1H), 8.38 (s, 1H), 8.07-7.96 (m, 4H), 7.93-7.86 (m, 1H), 7.78 (d, J = 8.7 Hz, 1H), 4.87 (t, J = 5.9 Hz, 1H), 3.69 (d, J = 5.9 Hz, 2H), 2.85 (d, J = 2.1 Hz, 3H), 2.29 (d, J = 9.7 Hz, 2H), 2.19-2.11 (m, 2H), 1.88-1.71 (m, 2H). | 16<br>1.63 min<br>460.20<br>(M + H) |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 304 | 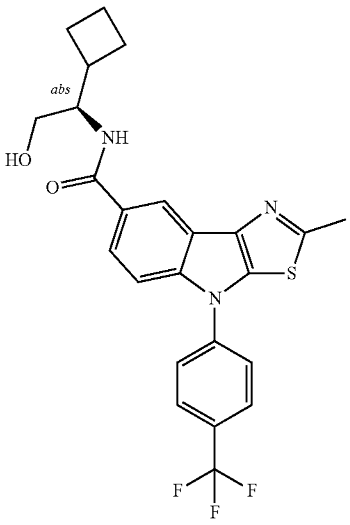 [SMILES: Cc1nc2c3cc(C(=O)N[C@@H](CO)C4CCC4)ccc3n(-c3ccc(C(F)(F)F)cc3)c2s1] Absolute configuration known/assigned N-[(1R)-1-cyclobutyl-2-hydroxyethyl]-2-methyl-4-[4-(trifluoromethyl)phenyl]-4H-[1,3]thiazolo[5,4-b]indole-7-carboxamide | (300 MHz, DMSO, ppm) δ 8.58 (d, J = 1.7 Hz, 1H), 8.10 (d, J = 8.7 Hz, 1H), 8.07-7.89 (m, 5H), 7.79 (d, J = 8.8 Hz, 1H), 4.57 (t, J = 5.7 Hz, 1H), 4.20-4.01 (m, 1H), 3.45 (t, J = 5.6 Hz, 2H), 2.85 (s, 3H), 2.53 (s, 1H), 2.00-1.74 (m, 6H). | 9 0.97 min 373.90 (M + H) |
| 305 | 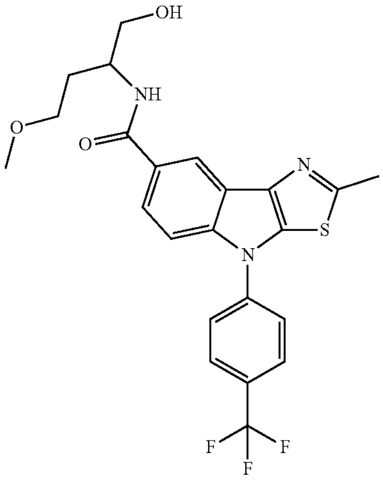 N-(1-hydroxy-4-methoxybutan-2-yl)-2-methyl-4-[4-(trifluoromethyl)phenyl]-4H-[1,3]thiazolo[5,4-b]indole-7-carboxamide | (400 MHz, DMSO-d6) δ 8.57 (d, J = 1.9 Hz, 1H), 8.21 (d, J = 8.3 Hz, 1H), 8.02 (dt, J = 10.3, 7.5 Hz, 4H), 7.89 (dd, J = 8.9, 1.9 Hz, 1H), 7.79 (d, J = 8.8 Hz, 1H), 4.74 (t, J = 5.8 Hz, 1H), 4.09 (s, 1H), 3.51 (dt, J = 10.9, 5.6 Hz, 1H), 3.42 (dt, J = 17.9, 6.3 Hz, 3H), 2.85 (d, J = 2.0 Hz, 3H), 2.50 (d, J = 1.9 Hz, 3H), 1.91 (dq, J = 9.8, 4.1, 3.0 Hz, 1H), 1.76 (s, 1H). | 16 1.51 min 478.25 (M + H) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 306 | 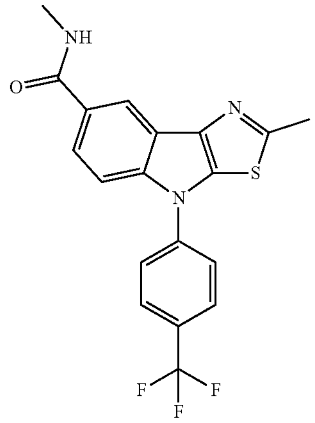 [SMILES: CNC(=O)c1ccc2c(c1)c1nc(C)sc1n2-c1ccc(C(F)(F)F)cc1]<br>N,2-dimethyl-4-[4-(trifluoromethyl)-phenyl]-4H-[1,3]thiazolo[5,4-b]indole-7-carboxamide | (400 MHz, DMSO-d6) δ 8.56 (q, J = 4.5 Hz, 1H), 8.49 (d, J = 1.7 Hz, 1H), 8.01 (q, J = 8.7 Hz, 4H), 7.87 (dd, J = 8.8, 1.8 Hz, 1H), 7.79 (d, J = 8.8 Hz, 1H), 2.83 (d, J = 4.4 Hz, 6H). | 16<br>1.56 min<br>390.15<br>(M + H) |
| 307 | 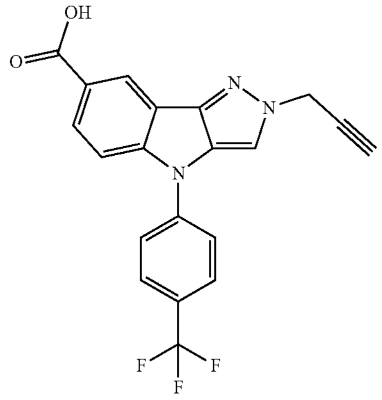 [SMILES: C#CCn1cc2c(n1)c1cc(C(=O)O)ccc1n2-c1ccc(C(F)(F)F)cc1]<br>2-(prop-2-yn-1-yl)-4-[4-(trifluoromethyl)phenyl]-2H,4H-pyrazolo[4,3-b]indole-7-carboxylic acid | (400 MHz, DMSO-d6) δ 12.83 (s, 1H), 8.49 (d, J = 1.8 Hz, 1H), 8.19 (s, 1H), 8.04-8.01 (m, 1H), 7.95 (s, 4H), 7.86 (s, 1H), 5.28 (s, 2H), 3.56 (d, J = 2.6 Hz, 1H). | 16<br>1.03 min<br>384.20<br>(M + H) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 308 | 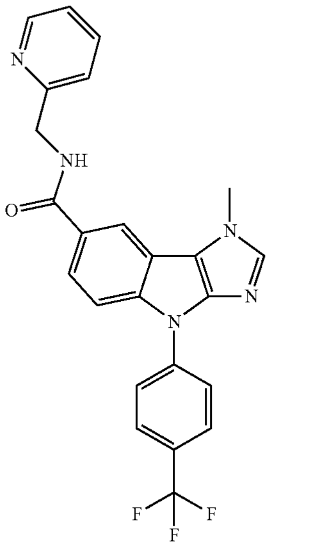 [SMILES: Cn1cnc2c1c1cc(C(=O)NCc3ccccn3)ccc1n2-c1ccc(C(F)(F)F)cc1] 1-methyl-N-[(pyridin-2-yl)methyl]-4-[4-(trifluoromethyl)phenyl]-1H,4H-imidazo[4,5-b]indole-7-carboxamide | (300 MHz, DMSO-d6) δ 9.31 (t, J = 5.6 Hz, 1H), 8.79-8.71 (m, 1H), 8.51 (d, J = 1.6 Hz, 1H), 8.28 (t, J = 7.4 Hz, 1H), 8.11 (d, J = 8.4 Hz, 2H), 7.99 (d, J = 8.6 Hz, 2H), 7.97-7.83 (m, 3H), 7.82-7.68 (m, 2H), 4.79 (d, J = 5.5 Hz, 2H), 4.13 (s, 3H) | 9 0.69 min 450.00 (M + H) |
| 309 | 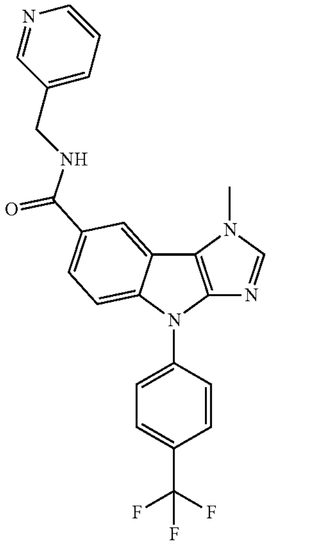 [SMILES: Cn1cnc2c1c1cc(C(=O)NCc3cccnc3)ccc1n2-c1ccc(C(F)(F)F)cc1] 1-methyl-N-[(pyridin-3-yl)methyl]-4-[4-(trifluoromethyl)phenyl]-1H,4H-imidazo[4,5-b]indole-7-carboxamide | (300 MHz, DMSO-d6) δ 9.12 (t, J = 6.0 Hz, 1H), 8.61 (d, J = 2.3 Hz, 1H), 8.52-8.43 (m, 2H), 8.11 (d, J = 8.4 Hz, 2H), 8.01-7.75 (m, 6H), 7.39 (dd, J = 7.9, 4.8 Hz, 1H), 4.58 (d, J = 5.8 Hz, 2H), 4.12 (s, 3H). | 9 0.66 min 449.90 (M + H) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 310 | 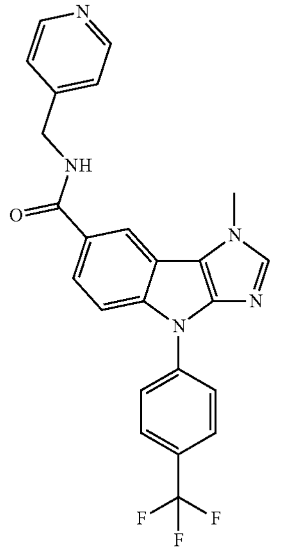 [SMILES: Cn1cnc2c1c1cc(C(=O)NCc3ccncc3)ccc1n2-c1ccc(C(F)(F)F)cc1]<br>1-methyl-N-[(pyridin-4-yl)methyl]-4-[4-(trifluoromethyl)phenyl]-1H,4H-imidazo[4,5-b]indole-7-carboxamide | (300 MHz, DMSO-d6) δ 9.16 (t, J = 6.0 Hz, 1H), 8.57-8.48 (m, 3H), 8.12 (d, J = 8.4 Hz, 2H), 8.02-7.85 (m, 5H), 7.39-7.34 (m, 2H), 4.58 (d, J = 5.9 Hz, 2H), 4.13 (s, 3H). | 9<br>0.64 min<br>449.90<br>(M + H) |
| 311 | 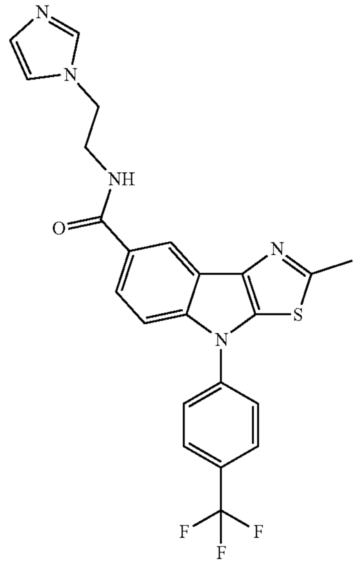 [SMILES: Cc1nc2c3cc(C(=O)NCCn4ccnc4)ccc3n(-c3ccc(C(F)(F)F)cc3)c2s1]<br>N-[2-(1H-imidazol-1-yl)ethyl]-2-methyl-4-[4-(trifluoromethyl)phenyl]-4H-[1,3]thiazolo[5,4-b]indole-7-carboxamide | (300 MHz, DMSO, ppm) δ 8.73 (d, J = 7.0 Hz, 1H), 8.48 (s, 1H), 8.09-7.96 (m, 4H), 7.83 (dt, J = 11.4, 8.6 Hz, 2H), 7.65 (s, 1H), 7.21 (s, 1H), 6.91 (s, 1H), 4.28-4.14 (m, 2H), 3.64 (s, 2H), 2.85 (d, J = 2.5 Hz, 3H). | 9<br>0.74 min<br>469.90<br>(M + H) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 312 | 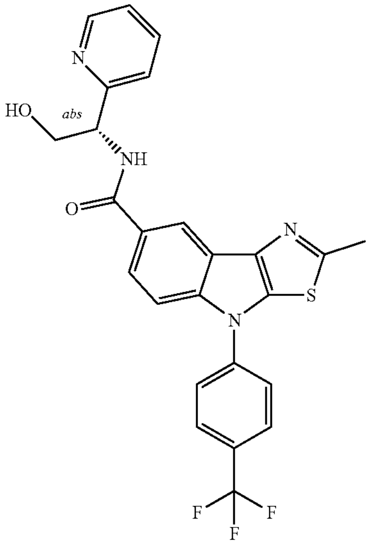 [SMILES: Cc1nc2c3cc(C(=O)N[C@H](CO)c4ccccn4)ccc3n(-c3ccc(C(F)(F)F)cc3)c2s1]<br>Absolute configuration known/assigned N-[(1S)-2-hydroxy-1-(pyridin-2-yl)ethyl]-2-methyl-4-[4-(trifluoromethyl)phenyl]-4H-[1,3]thiazolo[5,4-b]indole-7-carboxamide | 1H NMR (400 MHz, DMSO-d6) δ.83 (d, J = 7.9 Hz, 1H), 8.68 (d, J = 1.7 Hz, 1H), 8.55 (dt, J = 4.7, 1.6 Hz, 1H), 8.08-7.98 (m, 4H), 7.94 (dd, J = 8.8, 1.8 Hz, 1H), 7.82 (d, J = 8.8 Hz, 1H), 7.77 (td, J = 7.7, 1.8 Hz, 1H), 7.46 (d, J = 7.9 Hz, 1H), 7.27 (ddd, J = 7.5, 4.8, 1.2 Hz, 1H), 5.21 (td, J = 7.6, 5.1 Hz, 1H), 4.97 (t, J = 6.0 Hz, 1H), 3.93-3.78 (m, 2H), 2.85 (s, 3H). | 16<br>1.54 min<br>497.20<br>(M + H) |
| 313 | 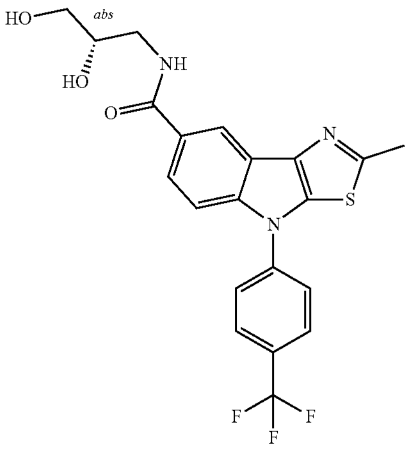 [SMILES: Cc1nc2c3cc(C(=O)NC[C@H](O)CO)ccc3n(-c3ccc(C(F)(F)F)cc3)c2s1]<br>Absolute configuration known/assigned N-[(2S)-2,3-dihydroxypropyl]-2-methyl-4-[4-(trifluoromethyl)phenyl]-4H-[1,3]thiazolo[5,4-b]indole-7-carboxamide | (300 MHz, DMSO-d6) δ 8.52 (d, J = 1.7 Hz, 2H), 8.07-7.94 (m, 4H), 7.88 (dd, J = 8.8, 1.8 Hz, 1H), 7.78 (d, J = 8.8 Hz, 1H), 4.83 (d, J = 5.0 Hz, 1H), 4.58 (t, J = 5.9 Hz, 1H), 3.67 (q, J = 5.7 Hz, 1H), 3.50-3.35 (m, 3H), 3.31 (s, 1H), 2.83 (s, 3H). | 16<br>1.38 min<br>450.20<br>(M + H) |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 314 | 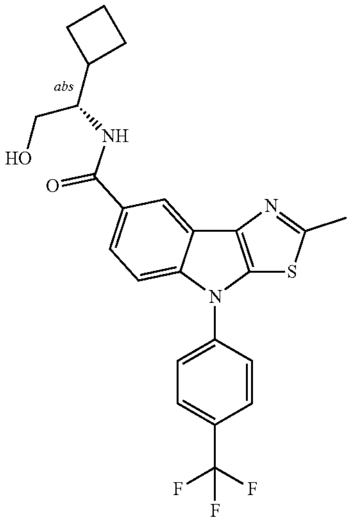 [SMILES: Cc1nc2c3cc(C(=O)N[C@H](CO)C4CCC4)ccc3n(-c3ccc(C(F)(F)F)cc3)c2s1] Absolute configuration known/assigned N-[(1S)-1-cyclobutyl-2-hydroxyethyl]-2-methyl-4-[4-(trifluoromethyl)phenyl]-4H-[1,3]thiazolo[5,4-b]indole-7-carboxamide | (300 MHz, DMSO-d6) δ 8.56 (s, 1H), 8.10 (d, J = 8.6 Hz, 1H), 8.07-7.94 (m, 4H), 7.88 (d, J = 9.1 Hz, 1H), 7.77 (d, J = 8.8 Hz, 1H), 4.56 (t, J = 5.8 Hz, 1H), 4.05 (s, 1H), 3.42 (t, J = 5.7 Hz, 2H), 2.83 (s, 3H), 1.95 (s, 1H), 1.76 (d, J = 6.2 Hz, 6H). | 16 1.67 min 474.25 (M + H) |
| 315 | 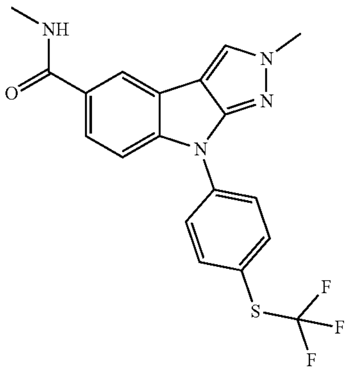 [SMILES: CNC(=O)c1ccc2c(c1)c1cn(C)nc1n2-c1ccc(SC(F)(F)F)cc1] N,2-dimethyl-8-{4-[(trifluoromethyl)-sulfanyl]phenyl}-2H,8H-pyrazolo[3,4-b]indole-5-carboxamide | (700 MHz, DMSO-d6) δ 8.45 (q, J = 4.5 Hz, 1H), 8.32 (d, J = 1.8 Hz, 1H), 8.20 (s, 1H), 8.05-8.02 (m, 2H), 7.96-7.93 (m, 2H), 7.83 (dd, J = 8.6, 1.9 Hz, 1H), 7.76 (d, J = 8.7 Hz, 1H), 4.03 (s, 3H), 2.82 (d, J = 4.5 Hz, 3H). | |

TABLE 1-continued

| Table 1 below shows exemplary compounds of the present invention. They have been synthesized as described in the Examples above or similar thereto. | | | |
|---|---|---|---|
| Com-pound No. (Example No.) | Structure and Name | $^1$H-NMR | Conditions and elution time (min) LCMS (M + H$^+$) |
| 316 | 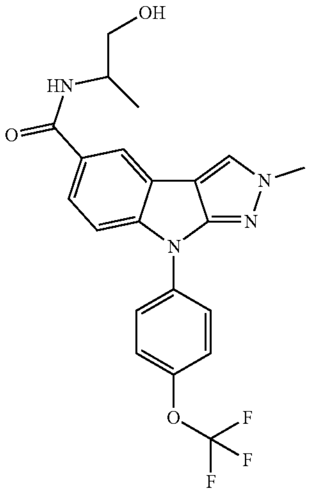 [SMILES: CC(CO)NC(=O)c1ccc2c(c1)c1cn(C)nc1n2-c1ccc(OC(F)(F)F)cc1] N-(1-hydroxypropan-2-yl)-2-methyl-8-[4-(trifluoromethoxy)phenyl]-2H,8H-pyrazolo[3,4-b]indole-5-carboxamide | (700 MHz, DMSO-d6) δ 8.34 (d, J = 1.8 Hz, 1H), 8.18 (s, 1H), 8.09 (d, J = 7.9 Hz, 1H), 7.95-7.91 (m, 2H), 7.84 (dd, J = 8.6, 1.8 Hz, 1H), 7.64 (d, J = 8.7 Hz, 1H), 7.63-7.60 (m, 2H), 4.09-4.03 (m, 1H), 4.02 (s, 3H), 3.50 (dd, J = 10.6, 5.7 Hz, 1H), 3.36 (dd, J = 10.6, 6.5 Hz, 1H), 1.17 (d, J = 6.7 Hz, 3H). | 8<br>1.65<br>432.90<br>(M + H) |
| 317 (Ex. 31) | 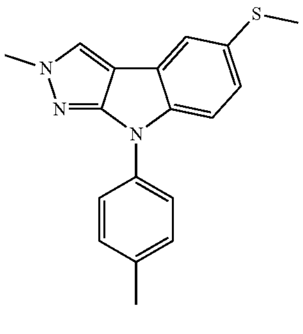 2-methyl-8-(4-methylphenyl)-5-(methylsulfanyl)-2H,8H-pyrazolo[3,4-b]indole | (700 MHz, DMSO) δ 8.06 (s, 1H, 11), 7.76 (d, J = 2.0 Hz, 1H), 7.59-7.64 (m, 2H, 16), 7.48 (d, J = 8.5 Hz, 1H), 7.36-7.40 (m, 2H), 2.38 (s, 3H), 7.22 (dd, J = 8.6, 2.0 Hz, 1H), 3.99 (s, 3H), 2.52 (s, 3H). | 8<br>0.93 min<br>308.20<br>(M + H) |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 318 | 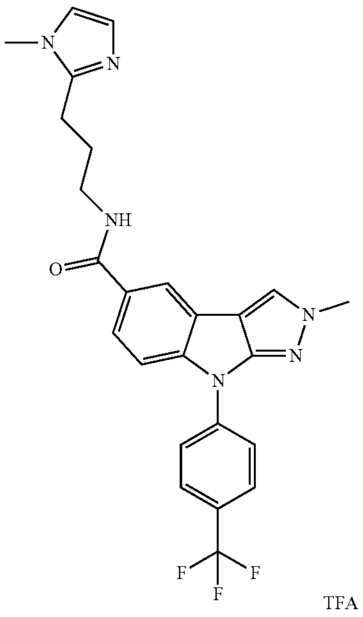 2-methyl-N-[3-(1-methyl-1H-imidazol-2-yl)propyl]-8-[4-(trifluoromethyl)phenyl]-2H,8H-pyrazolo[3,4-b]indole-5-carboxamide | (700 MHz, DMSO-d6) δ 14.01-13.98 (m, 1H), 8.63 (t, J = 5.7 Hz, 1H), 8.32 (d, J = 1.9 Hz, 1H), 8.21 (s, 1H), 8.10-8.07 (m, 2H), 7.99-7.97 (m, 2H), 7.84 (dd, J = 8.7, 1.9 Hz, 1H), 7.79 (d, J = 8.6 Hz, 1H), 7.60 (d, J = 2.0 Hz, 1H), 7.57 (d, J = 2.0 Hz, 1H), 4.04 (s, 3H), 3.78 (s, 3H), 3.38 (q, J = 6.5 Hz, 2H), 3.02 (t, J = 7.7 Hz, 2H), 2.02-1.97 (m, 2H). | $^g$ 1.39 min 480.00-480.90 (M; M + H) |
| 319 | 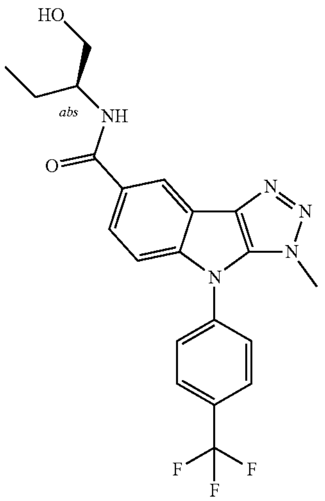 [SMILES: CC[C@@H](CO)NC(=O)c1ccc2c(c1)c1nnn(C)c1n2-c1ccc(C(F)(F)F)cc1] Absolute configuration assigned arbitrarily N-[(2S)-1-hydroxybutan-2-yl]-3-methyl-4-[4-(trifluoromethyl)phenyl]-3H,4H-[1,2,3]triazolo[4,5-b]indole-7-carboxamide | | $^c$ 2.29 min |

TABLE 1-continued

| Compound No. (Example No.) | Structure and Name | $^1$H-NMR | Conditions and elution time (min) LCMS (M + H$^+$) |
|---|---|---|---|
| Table 1 below shows exemplary compounds of the present invention. They have been synthesized as described in the Examples above or similar thereto. | | | |
| 320 | 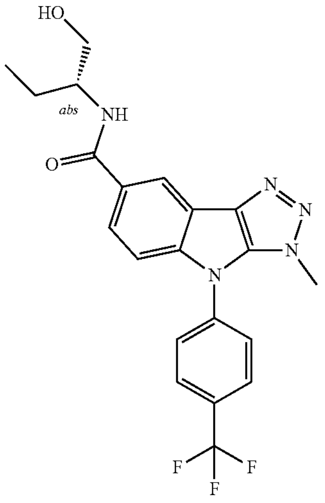 [SMILES: CC[C@H](CO)NC(=O)c1ccc2c(c1)c1nnn(C)c1n2-c1ccc(C(F)(F)F)cc1] Absolute configuration assigned arbitrarily N-[(2R)-1-hydroxybutan-2-yl]-3-methyl-4-[4-(trifluoromethyl)phenyl]-3H,4H-[1,2,3]triazolo[4,5-b]indole-7-carboxamide | | $^c$ 4.85 min |
| 321 | 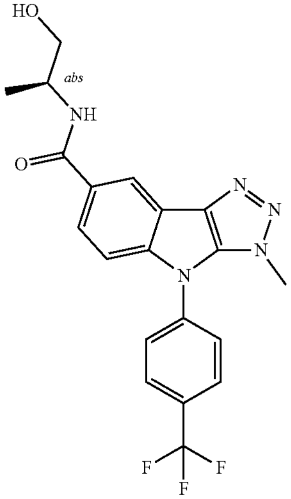 [SMILES: C[C@@H](CO)NC(=O)c1ccc2c(c1)c1nnn(C)c1n2-c1ccc(C(F)(F)F)cc1] Absolute configuration known/assigned N-[(2S)-1-hydroxypropan-2-yl]-3-methyl-4-[4-(trifluoromethyl)phenyl]-3H,4H-[1,2,3]triazolo[4,5-b]indole-7-carboxamide | | |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 322 | 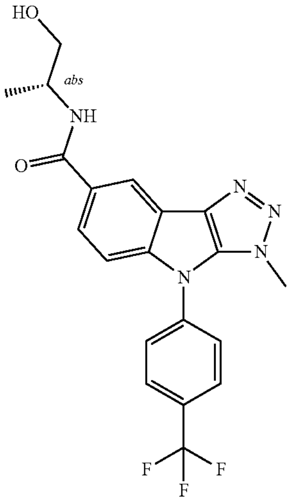 [SMILES: C[C@H](CO)NC(=O)c1ccc2c(c1)c1nnn(C)c1n2-c1ccc(C(F)(F)F)cc1] Absolute configuration known/assigned N-[(2R)-1-hydroxypropan-2-yl]-3-methyl-4-[4-(trifluoromethyl)phenyl]-3H,4H-[1,2,3]triazolo[4,5-b]indole-7-carboxamide | | |
| 323 | 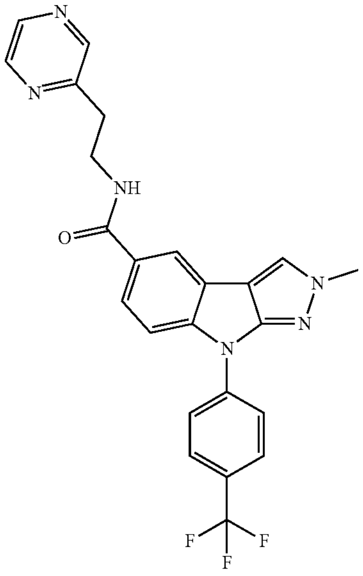 [SMILES: Cn1cc2c3cc(C(=O)NCCc4cnccn4)ccc3n(-c3ccc(C(F)(F)F)cc3)c2n1] 2-methyl-N-[2-(pyrazin-2-yl)ethyl]-8-[4-(trifluoromethyl)phenyl]-2H,8H-pyrazolo[3,4-b]indole-5-carboxamide | (700 MHz, DMSO-d6) δ 8.62 (t, J = 5.7 Hz, 1H), 8.59-8.58 (m, 1H), 8.58-8.57 (m, 1H), 8.49 (d, J = 2.6 Hz, 1H), 8.29 (d, J = 1.8 Hz, 1H), 8.21 (s, 1H), 8.10-8.07 (m, 2H), 7.98-7.95 (m, 2H), 7.80 (dd, J = 8.7, 1.8 Hz, 1H), 7.76 (d, J = 8.6 Hz, 1H), 4.03 (s, 3H), 3.70-3.67 (m, 2H), 3.09 (t, J = 7.1 Hz, 2H). | 8 1.67 464.90 (M + H) |

TABLE 1-continued

| Compound No. (Example No.) | Structure and Name | $^1$H-NMR | Conditions and elution time (min) LCMS (M + H$^+$) |
|---|---|---|---|
| | Table 1 below shows exemplary compounds of the present invention. They have been synthesized as described in the Examples above or similar thereto. | | |
| 324 | 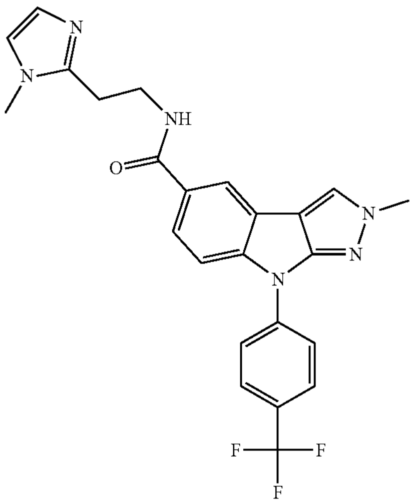 2-methyl-N-[2-(1-methyl-1H-imidazol-2-yl)ethyl]-8-[4-(trifluoromethyl)phenyl]-2H,8H-pyrazolo[3,4-b]indole-5-carboxamide | (700 MHz, DMSO-d6) δ 14.08-14.05 (m, 1H), 8.77 (t, J = 5.9 Hz, 1H), 8.28-8.27 (m, 1H), 8.21 (s, 1H), 8.09-8.06 (m, 2H), 7.99-7.96 (m, 2H), 7.78-7.77 (m, 2H), 7.61 (d, J = 2.0 Hz, 1H), 7.57 (d, J = 2.1 Hz, 1H), 4.04 (s, 3H), 3.80 (s, 3H), 3.67 (q, J = 6.4 Hz, 2H), 3.23 (t, J = 6.6 Hz, 2H). | 8 1.37-1.38 min 467.00-467.90 (M; M + H) |
| 325 | 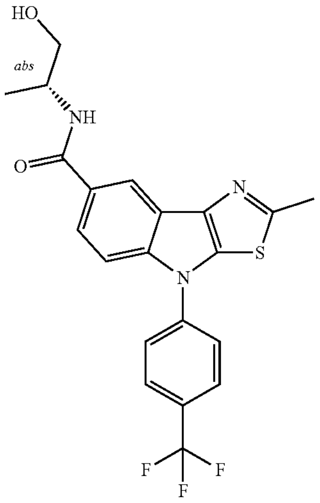 [SMILES: Cc1nc2c3cc(C(=O)N[C@H](C)CO)ccc3n(-c3ccc(C(F)(F)F)cc3)c2s1] Absolute configuration known/assigned N-[(2R)-1-hydroxypropan-2-yl]-2-methyl-4-[4-(trifluoromethyl)phenyl]-4H-[1,3]thiazolo[5,4-b]indole-7-carboxamide | (300 MHz, DMSO, ppm) δ 8.57 (d, J = 1.7 Hz, 1H), 8.23 (d, J = 7.9 Hz, 1H), 8.09-7.95 (m, 4H), 7.90 (dd, J = 8.8, 1.8 Hz, 1H), 7.79 (d, J = 8.8 Hz, 1H), 4.73 (t, J = 5.8 Hz, 1H), 4.09 (p, J = 6.8 Hz, 1H), 3.68-3.36 (m, 2H), 2.85 (s, 3H), 1.18 (d, J = 6.7 Hz, 3H). | 9 0.88 min 434.00 (M + H) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 326 | 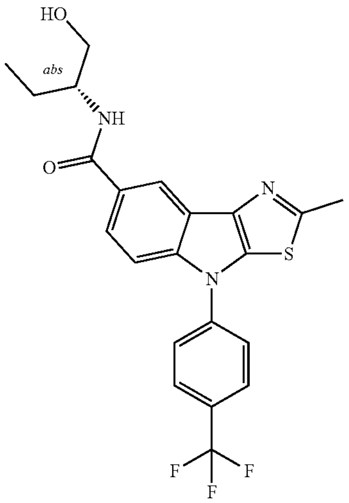 [SMILES: CC[C@H](CO)NC(=O)c1ccc2c(c1)c1nc(C)sc1n2-c1ccc(C(F)(F)F)cc1]<br>Absolute configuration known/assigned N-[(2R)-1-hydroxybutan-2-yl]-2-methyl-4-[4-(trifluoromethyl)phenyl]-4H-[1,3]thiazolo[5,4-b]indole-7-carboxamide | (300 MHz, DMSO, ppm) δ 8.58 (s, 1H), 8.22-7.88 (m, 6H), 7.79 (d, J = 8.9 Hz, 1H), 4.68 (t, J = 5.8 Hz, 1H), 3.93 (s, 1H), 3.56-3.43 (m, 2H), 2.85 (s, 3H), 1.71-1.48 (m, 2H), 0.92 (t, J = 7.4 Hz, 3H). | 9<br>0.91 min<br>447.90<br>(M + H) |
| 327 | 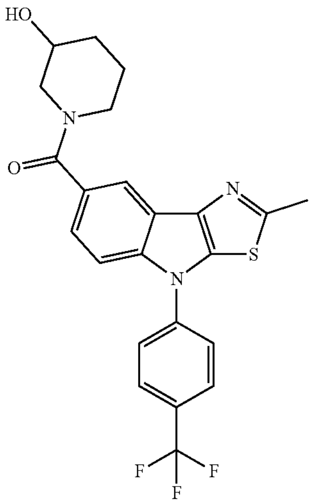 [SMILES: Cc1nc2c3cc(C(=O)N4CCCC(O)C4)ccc3n(-c3ccc(C(F)(F)F)cc3)c2s1]<br>1-{2-methyl-4-[4-(trifluoromethyl)-phenyl]-4H-[1,3]thiazolo[5,4-b]indole-7-carbonyl}piperidin-3-ol | (300 MHz, DMSO, ppm) δ 8.09-7.92 (m, 5H), 7.79 (d, J = 8.6 Hz, 1H), 7.39 (d, J = 8.8 Hz, 1H), 4.89 (s, 1H), 3.56 (s, 3H), 3.25-2.96 (m, 2H), 2.84 (s, 3H), 1.89 (s, 2H), 1.45 (s, 2H). | 9<br>0.90 min<br>460.00<br>(M + H) |

TABLE 1-continued

| Com-pound No. (Example No.) | Structure and Name | $^1$H-NMR | Conditions and elution time (min) LCMS (M + H$^+$) |
|---|---|---|---|
| | Table 1 below shows exemplary compounds of the present invention. They have been synthesized as described in the Examples above or similar thereto. | | |
| 328 | 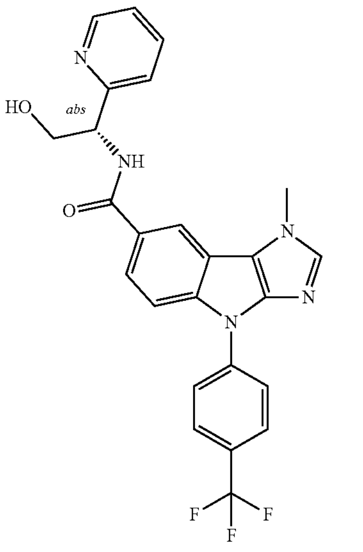 [SMILES: Cn1cnc2c1c1cc(C(=O)N[C@H](CO)c3ccccn3)ccc1n2-c1ccc(C(F)(F)F)cc1] Absolute configuration known/assigned N-[(1S)-2-hydroxy-1-(pyridin-2-yl)ethyl]-1-methyl-4-[4-(trifluoromethyl)phenyl]-1H,4H-imidazo[4,5-b]indole-7-carboxamide | (300 MHz, DMSO-d6) δ 8.73 (d, J = 7.6 Hz, 1H), 8.64-8.55 (m, 1H), 8.50 (s, 1H), 8.11 (d, J = 8.4 Hz, 2H), 7.99 (d, J = 8.6 Hz, 2H), 7.89 (d, J = 3.9 Hz, 4H), 7.54 (d, J = 7.9 Hz, 1H), 7.37 (t, J = 6.3 Hz, 1H), 5.25 (q, J = 6.9 Hz, 1H), 4.15 (s, 3H), 3.91 (q, J = 6.5, 5.9 Hz, 2H). | 9 0.70 min 480.00 (M + H) |
| 329 | 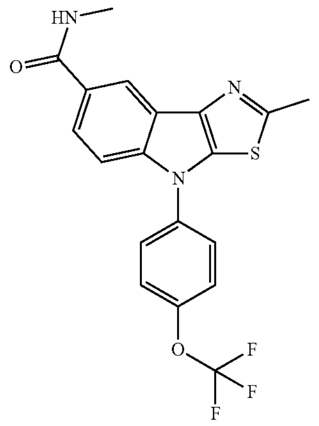 [SMILES: CNC(=O)c1ccc2c(c1)c1nc(C)sc1n2-c1ccc(OC(F)(F)F)cc1] N,2-dimethyl-4-[4-(trifluoromethoxy)-phenyl]-4H-[1,3]thiazolo[5,4-b]indole-7-carboxamide | (300 MHz, DMSO, ppm) δ 8.52 (dd, J = 18.2, 3.2 Hz, 2H), 7.95-7.81 (m, 3H), 7.68 (dd, J = 8.8, 4.5 Hz, 3H), 2.84 (d, J = 2.5 Hz, 6H). | 16 0.92 min 406.00 (M + H) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
| --- | --- | --- | --- |
| 330 | 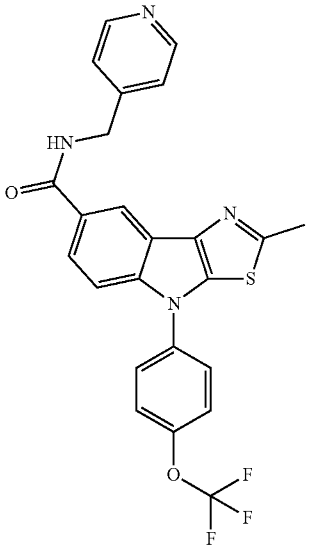 [SMILES: Cc1nc2c3cc(C(=O)NCc4ccncc4)ccc3n(-c3ccc(OC(F)(F)F)cc3)c2s1] 2-methyl-N-[(pyridin-4-yl)methyl]-4-[4-(trifluoromethoxy)phenyl]-4H-[1,3]thiazolo[5,4-b]indole-7-carboxamide | (400 MHz, DMSO-d6) δ 9.25 (t, J = 6.0 Hz, 1H), 8.59 (d, J = 1.7 Hz, 1H), 8.55-8.49 (m, 2H), 7.95-7.87 (m, 3H), 7.75-7.67 (m, 3H), 7.38-7.32 (m, 2H), 4.55 (d, J = 5.9 Hz, 2H), 2.84 (s, 3H). | 16 1.54 min 483.20 (M + H) |
| 331 | 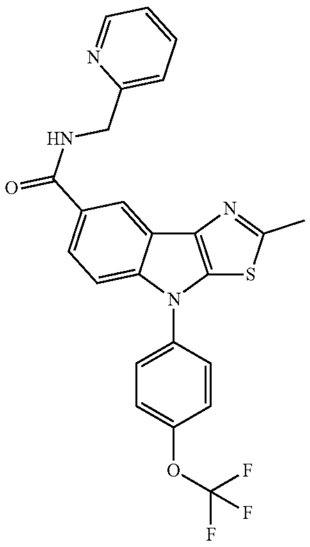 [SMILES: Cc1nc2c3cc(C(=O)NCc4ccccn4)ccc3n(-c3ccc(OC(F)(F)F)cc3)c2s1] 2-methyl-N-[(pyridin-2-yl)methyl]-4-[4-(trifluoromethoxy)phenyl]-4H-[1,3]thiazolo[5,4-b]indole-7-carboxamide | (400 MHz, DMSO-d6) 9.23 (t, J = 5.8 Hz, 1H), 8.59 (d, J = 1.8 Hz, 1H), 8.53 (dt, J = 4.6, 1.6 Hz, 1H), 7.97-7.88 (m, 3H), 7.77 (td, J = 7.7, 1.9 Hz, 1H), 7.73-7.56 (m, 3H), 7.37 (d, J = 7.8 Hz, 1H), 7.27 (dd, J = 7.5, 5.4 Hz, 1H), 4.63 (d, J = 5.9 Hz, 2H), 2.84 (s, 3H). | 16 1.65 min 483.20 (M + H) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 332 | 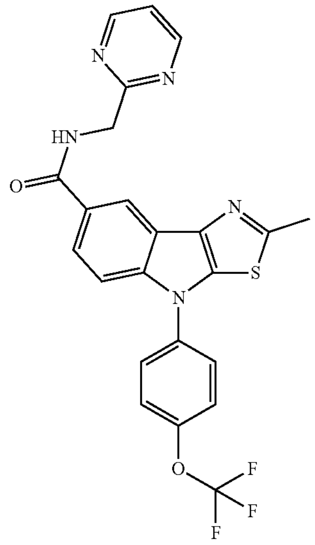 [SMILES: Cc1nc2c3cc(C(=O)NCc4ncccn4)ccc3n(-c3ccc(OC(F)(F)F)cc3)c2s1] 2-methyl-N-[(pyrimidin-2-yl)methyl]-4-[4-(trifluoromethoxy)phenyl]-4H-[1,3]thiazolo[5,4-b]indole-7-carboxamide | (300 MHz, DMSO, ppm) δ 9.17 (t, J = 5.9 Hz, 1H), 8.79 (d, J = 4.9 Hz, 2H), 8.59 (d, J = 1.7 Hz, 1H), 7.93 (dd, J = 9.0, 2.5 Hz, 3H), 7.70 (dd, J = 12.2, 8.6 Hz, 3H), 7.41 (t, J = 4.9 Hz, 1H), 4.72 (d, J = 5.8 Hz, 2H), 2.85 (s, 3H). | 16 0.91 min 484.00 (M + H) |
| 333 | 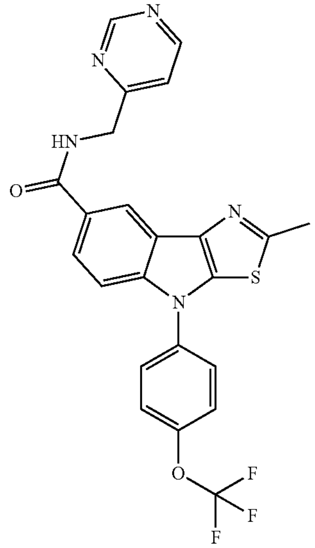 [SMILES: Cc1nc2c3cc(C(=O)NCc4ccncn4)ccc3n(-c3ccc(OC(F)(F)F)cc3)c2s1] 2-methyl-N-[(pyrimidin-4-yl)methyl]-4-[4-(trifluoromethoxy)phenyl]-4H-[1,3]thiazolo[5,4-b]indole-7-carboxamide | (300 MHz, DMSO, ppm) δ 9.31 (t, J = 5.8 Hz, 1H), 9.13 (s, 1H), 8.75 (d, J = 5.3 Hz, 1H), 8.61 (d, J = 1.8 Hz, 1H), 7.98-7.88 (m, 3H), 7.71 (dd, J = 14.6, 8.7 Hz, 3H), 7.48 (d, J = 5.3 Hz, 1H), 4.61 (d, J = 5.8 Hz, 2H), 2.85 (s, 3H). | 16 0.89 min 484.00 (M + H) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 334 | 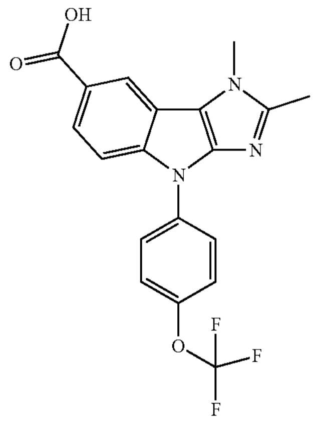 [SMILES: Cc1nc2c(c3cc(C(=O)O)ccc3n2-c2ccc(OC(F)(F)F)cc2)n1C] 1,2-dimethyl-4-[4-(trifluoromethoxy)-phenyl]-1H,4H-imidazo[4,5-b]indole-7-carboxylic acid | (400 MHz, DMSO-d6) δ 12.66 (s, 1H), 8.42 (d, J = 1.7 Hz, 1H), 7.96-7.87 (m, 2H), 7.81 (m, 1H), 7.73 (d, J = 8.7 Hz, 1H), 7.62 (d, J = 8.5 Hz, 2H), 4.01 (s, 3H), 2.52 (S, 3H). | 9 0.72 min 389.95 (M + H) |
| 335 | 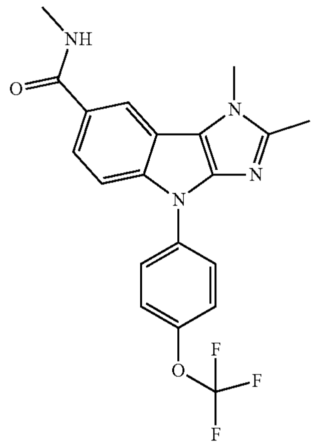 [SMILES: CNC(=O)c1ccc2c(c1)c1c(nc(C)n1C)n2-c1ccc(OC(F)(F)F)cc1] N,1,2-trimethyl-4-[4-(trifluoromethoxy)phenyl]-1H,4H-imidazo[4,5-b]indole-7-carboxamide | (400 MHz, DMSO-d6) δ 8.44-8.34 (m, 2H), 7.96-7.88 (m, 2H), 7.72 (d, J = 1.2 Hz, 2H), 7.61 (d, J = 8.5 Hz, 2H), 4.01 (s, 3H), 2.85 (d, J = 4.5 Hz, 3H), 2.52(s, 3H). | 9 0.68 min 403.00 (M + H) |

TABLE 1-continued

| Com-pound No. (Example No.) | Structure and Name | $^1$H-NMR | Conditions and elution time (min) LCMS (M + H$^+$) |
|---|---|---|---|
| Table 1 below shows exemplary compounds of the present invention. They have been synthesized as described in the Examples above or similar thereto. | | | |
| 336 | 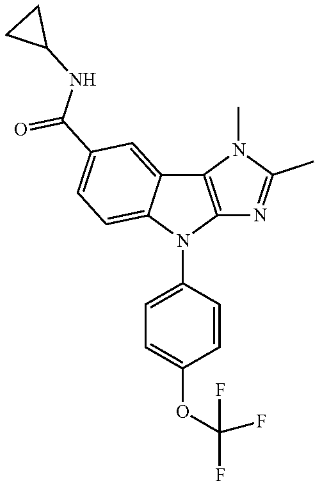 [SMILES: Cc1nc2c(c3cc(C(=O)NC4CC4)ccc3n2-c2ccc(OC(F)(F)F)cc2)n1C] N-cyclopropyl-1,2-dimethyl-4-[4-(trifluoromethoxy)phenyl]-1H,4H-imidazo[4,5-b]indole-7-carboxamide | (400 MHz, DMSO-d6) δ 8.41 (d, J = 4.0 Hz, 1H), 8.33 (d, J = 1.3 Hz, 1H), 7.95-7.87 (m, 2H), 7.71 (d, J = 1.2 Hz, 2H), 7.61 (d, J = 8.5 Hz, 2H), 4.01 (d, J = 1.3 Hz, 3H), 2.89 (m, 1H), 2.52(s, 3H), 0.73 (m, 2H), 0.71-0.57 (m, 2H). | 9 0.72 min 429.00 (M + H) |
| 337 | 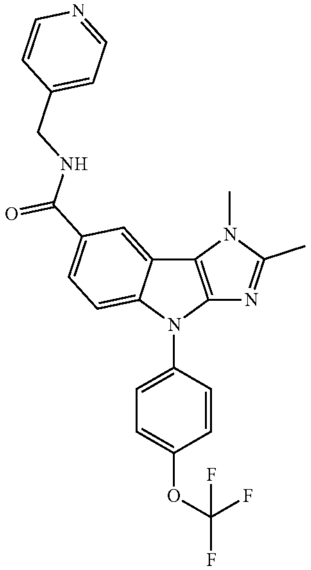 [SMILES: Cc1nc2c(c3cc(C(=O)NCc4ccncc4)ccc3n2-c2ccc(OC(F)(F)F)cc2)n1C] 1,2-dimethyl-N-[(pyridin-4-yl)methyl]-4-[4-(trifluoromethoxy)phenyl]-1H,4H-imidazo[4,5-b]indole-7-carboxamide | (400 MHz, DMSO-d6) δ 9.11 (t, J = 6.0 Hz, 1H), 8.56-8.50 (m, 2H), 8.46 (d, J = 1.7 Hz, 1H), 7.97-7.89 (m, 2H), 7.83-7.72 (m, 2H), 7.66-7.59 (m, 2H), 7.38-7.32 (m, 2H), 4.57 (d, J = 5.9 Hz, 2H), 4.02 (s, 3H), 2.52 (s, 3H). | 9 0.61 min 480.00 (M + H) |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 338 | 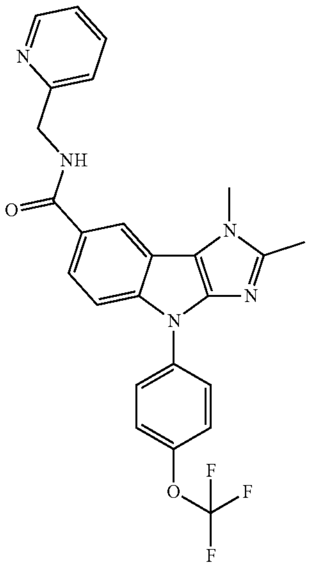 [SMILES: Cc1nc2c(c3cc(C(=O)NCc4ccccn4)ccc3n2-c2ccc(OC(F)(F)F)cc2)n1C]<br>1,2-dimethyl-N-[(pyridin-2-yl)methyl]-4-[4-(trifluoromethoxy)phenyl]-1H,4H-imidazo[4,5-b]indole-7-carboxamide | (400 MHz, DMSO-d6) δ 9.10 (t, J = 6.0 Hz, 1H), 8.53 (m,1H), 8.49 (d, J = 1.7 Hz, 1H), 7.97-7.89 (m, 2H), 7.85-7.72 (m, 3H), 7.62 (d, J = 8.5 Hz, 2H), 7.37 (d, J = 7.9 Hz, 1H), 7.32-7.24 (m, 1H), 4.64 (d, J = 5.9 Hz, 2H), 4.02 (s, 3H), 2.52 (s, 3H). | 9<br>0.62 min<br>480.00<br>(M + H) |
| 339 | 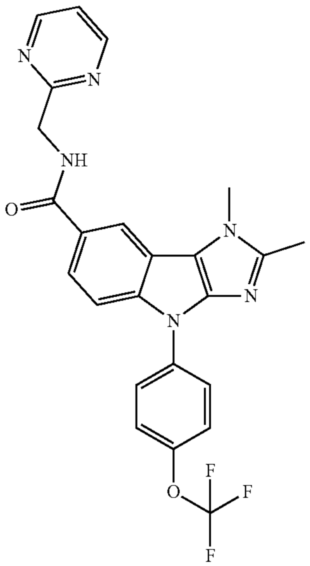 [SMILES: Cc1nc2c(c3cc(C(=O)NCc4ncccn4)ccc3n2-c2ccc(OC(F)(F)F)cc2)n1C]<br>1,2-dimethyl-N-[(pyrimidin-2-yl)methyl]-4-[4-(trifluoromethoxy)phenyl]-1H,4H-imidazo[4,5-b]indole-7-carboxamide | (400 MHz, DMSO-d6) δ 9.04 (t, J = 5.9 Hz, 1H), 8.79 (d, J = 4.9 Hz, 2H), 8.48 (d, J = 1.7 Hz, 1H), 7.98-7.89 (m, 2H), 7.80 (m 1H), 7.75 (d, J = 8.8 Hz, 1H), 7.62 (d, J = 8.5 Hz, 2H), 7.41 (t, J = 4.9 Hz, 1H), 4.73 (d, J = 5.8 Hz, 2H), 4.02 (s, 3H), 2.53 (s, 3H). | 9<br>0.67 min<br>481.00<br>(M + H) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 340 | 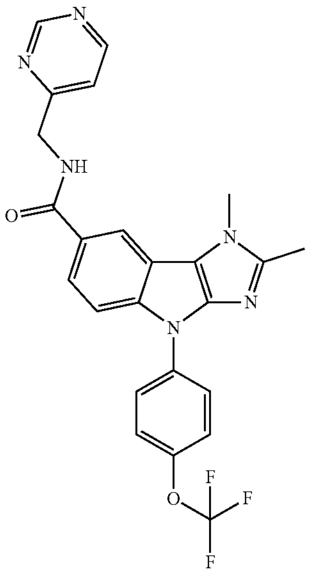 [SMILES: Cc1nc2c(c3cc(C(=O)NCc4ccncn4)ccc3n2-c2ccc(OC(F)(F)F)cc2)n1C] 1,2-dimethyl-N-[(pyrimidin-4-yl)methyl]-4-[4-(trifluoromethoxy)phenyl]-1H,4H-imidazo[4,5-b]indole-7-carboxamide | (400 MHz, DMSO-d6) δ 9.22-9.10 (m, 2H), 8.75 (d, J = 5.2 Hz, 1H), 8.48 (d, J = 1.7 Hz, 1H), 7.97-7.89 (m, 2H), 7.84-7.73 (m, 2H), 7.62 (d, J = 8.5 Hz, 2H), 7.47 (m, 1H), 4.62 (d, J = 5.8 Hz, 2H), 4.02 (s, 3H), 2.53 (s, 3H). | 9 0.67 min 481.00 (M + H) |
| 341 | 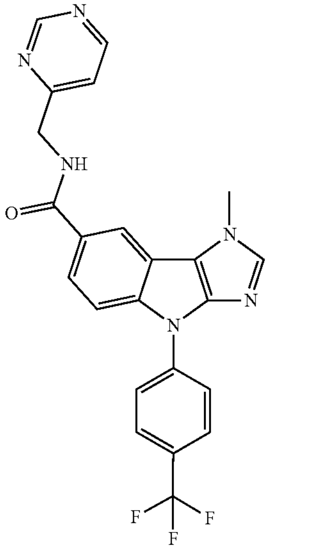 1-methyl-N-[(pyrimidin-4-yl)methyl]-4-[4-(trifluoromethyl)phenyl]-1H,4H-imidazo[4,5-b]indole-7-carboxamide | (400 MHz, DMSO-d6) δ 9.22-9.10 (m, 2H), 8.75 (d, J = 5.2 Hz, 1H), 8.48 (d, J = 1.7 Hz, 1H), 7.97-7.89 (m, 2H), 7.84-7.73 (m, 2H), 7.62 (d, J = 8.5 Hz, 2H), 7.47 (m, 1H), 4.62 (d, J = 5.8 Hz, 2H), 4.02 (s, 3H), 2.53 (s, 3H). | 9 0.67 min 481.00 (M + H) |

TABLE 1-continued

| Compound No. (Example No.) | Structure and Name | $^1$H-NMR | Conditions and elution time (min) LCMS (M + H$^+$) |
| --- | --- | --- | --- |
| Table 1 below shows exemplary compounds of the present invention. They have been synthesized as described in the Examples above or similar thereto. | | | |
| 342 | 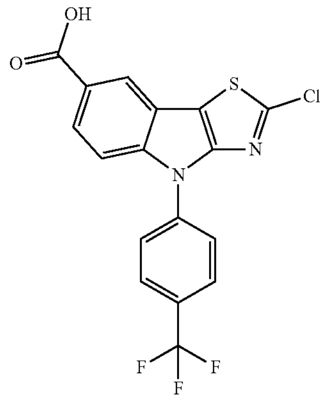 [SMILES: O=C(O)c1ccc2c(c1)c1sc(Cl)nc1n2-c1ccc(C(F)(F)F)cc1] 2-chloro-4-[4-(trifluoromethyl)phenyl]-4H-[1,3]thiazolo[4,5-b]indole-7-carboxylic acid | (300 MHz, DMSO-d6, ppm) δ 8.70 (s, 1H), 8.05-7.98 (m, 5H), 7.73-7.70 (m, 1H) | 9 0.89 min 394.85 (M − H) |
| 343 | 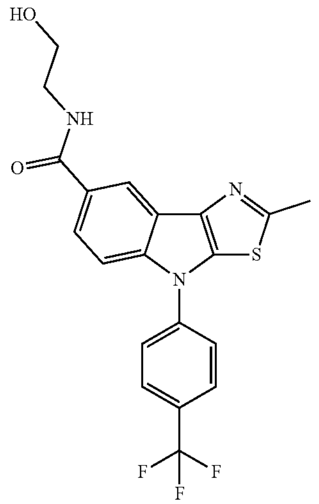 [SMILES: Cc1nc2c3cc(C(=O)NCCO)ccc3n(-c3ccc(C(F)(F)F)cc3)c2s1] N-(2-hydroxyethyl)-2-methyl-4-[4-(trifluoromethyl)phenyl]-4H-[1,3]thiazolo[5,4-b]indole-7-carboxamide | (300 MHz, DMSO, ppm) δ 8.61-8.51 (m, 2H), 8.09-7.95 (m, 4H), 7.90 (dd, J = 8.8, 1.8 Hz, 1H), 7.80 (d, J = 8.8 Hz, 1H), 4.75 (t, J = 5.6 Hz, 1H), 3.57 (q, J = 6.0 Hz, 2H), 3.39 (q, J = 6.0 Hz, 2H), 2.85 (s, 3H). | 9 0.84 min 420.00 (M + H) |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 344 | 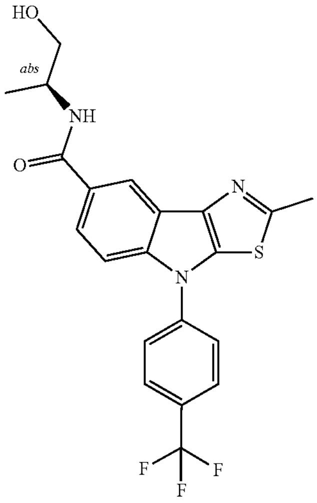 [SMILES: Cc1nc2c3cc(C(=O)N[C@@H](C)CO)ccc3n(-c3ccc(C(F)(F)F)cc3)c2s1] Absolute confiugration known/assigned N-[(2S)-1-hydroxypropan-2-yl]-2-methyl-4-[4-(trifluoromethyl)phenyl]-4H-[1,3]thiazolo[5,4-b]indole-7-carboxamide | (400 MHz, DMSO-d6) δ 8.56 (d, J = 2.1 Hz, 1H), 8.23 (d, J = 7.9 Hz, 1H), 8.02 (qd, J = 8.8, 2.2 Hz, 4H), 7.90 (dt, J = 8.8, 2.2 Hz, 1H), 7.79 (dd, J = 8.8, 2.1 Hz, 1H), 4.74 (s, 1H), 4.08 (p, J = 6.9 Hz, 1H), 3.52 (dd, J = 11.2, 5.6 Hz, 1H), 3.39 (t, J = 5.6 Hz, 1H), 2.84 (d, J = 2.1 Hz, 3H), 1.18 (dd, J = 6.7, 2.1 Hz, 3H). | 16 1.50 min 434.20 (M + H) |
| 345 | 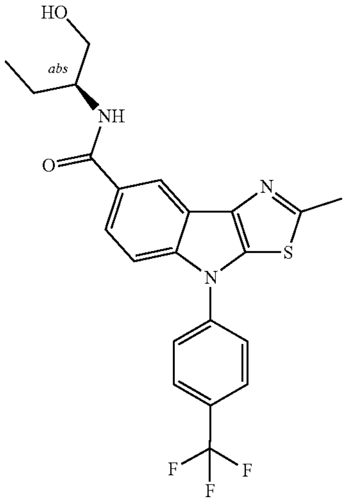 [SMILES: CC[C@@H](CO)NC(=O)c1ccc2c(c1)c1nc(C)sc1n2-c1ccc(C(F)(F)F)cc1] Absolute configuration known/assigned N-[(2S)-1-hydroxybutan-2-yl]-2-methyl-4-[4-(trifluoromethyl)phenyl]-4H-[1,3]thiazolo[5,4-b]indole-7-carboxamide | (400 MHz, DMSO-d6) δ 8.58 (d, J = 1.8 Hz, 1H), 8.14 (d, J = 8.3 Hz, 1H), 8.02 (q, J = 8.7 Hz, 4H), 7.90 (dd, J = 8.9, 1.8 Hz, 1H), 7.79 (d, J = 8.8 Hz, 1H), 4.68 (t, J = 5.8 Hz, 1H), 3.93 (d, J = 5.5 Hz, 1H), 3.52 (dt, J = 11.0, 5.6 Hz, 1H), 3.43 (dt, J = 11.3, 6.1 Hz, 1H), 2.85 (s, 3H), 1.76-1.65 (m, 1H), 1.51 (dt, J = 14.2, 7.8 Hz, 1H), 0.91 (t, J = 7.4 Hz, 3H). | 16 1.56 min 448.20 (M + H) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 346 | 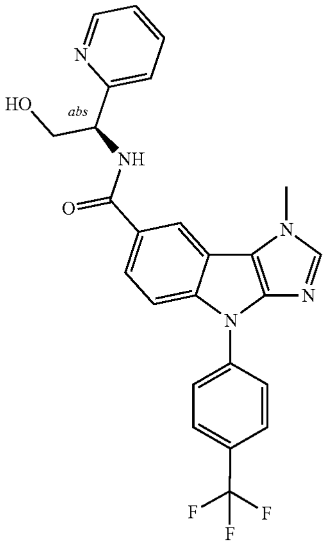 [SMILES: Cn1cnc2c1c1cc(C(=O)N[C@@H](CO)c3ccccn3)ccc1n2-c1ccc(C(F)(F)F)cc1] Absolute configuration known/assigned N-[(1R)-2-hydroxy-1-(pyridin-2-yl)ethyl]-1-methyl-4-[4-(trifluoromethyl)phenyl]-1H,4H-imidazo[4,5-b]indole-7-carboxamide | (300 MHz, DMSO-d6) δ 8.96 (d, J = 6.3 Hz, 1H), 8.80 (d, J = 5.7 Hz, 1H), 8.48 (d, J = 1.6 Hz, 1H), 8.38 (d, J = 8.3 Hz, 1H), 8.10 (d, J = 8.5 Hz, 2H), 8.03-7.76 (m, 7H), 5.32 (q, J = 6.1 Hz, 1H), 4.16 (s, 3H), 3.97 (d, J = 6.1 Hz, 2H). | 9 0.70 min 480.00 (M + H) |
| 347 | 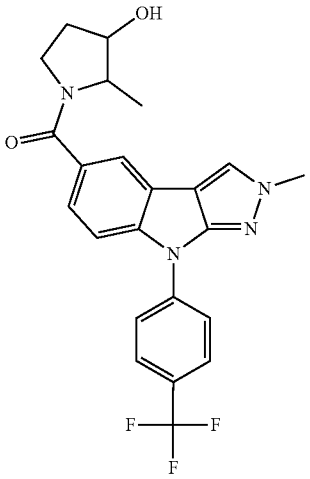 [SMILES: CC1C(O)CCN1C(=O)c1ccc2c(c1)c1cn(C)nc1n2-c1ccc(C(F)(F)F)cc1] Mixtures of 4 isomers 2-methyl-1-{2-methyl-8-[4-(trifluoromethyl)phenyl]-2H,8H-pyrazolo[3,4-b]indole-5-carbonyl}pyrrolidin-3-ol | (700 MHz, DMSO-d6) δ delta 8.20-8.12 (m, 1H), 8.11-8.07 (m, 2H), 8.03-7.86 (m, 1H), 7.98-7.95 (m, 2H), 7.80-7.73 (m, 1H), 7.50-7.35 (m, 1H), 4.25-4.18 (m, 1H), 4.10-4.01 (m, 1H), 4.02-3.87 (m, 3H), 3.65-3.32 (m, 2H), 2.14-1.68 (m, 2H), 1.30-0.74 (m, 3H). | 8 1.62 min 442.90 (M + H) |

TABLE 1-continued

| Compound No. (Example No.) | Structure and Name | $^1$H-NMR | Conditions and elution time (min) LCMS (M + H$^+$) |
|---|---|---|---|
| Table 1 below shows exemplary compounds of the present invention. They have been synthesized as described in the Examples above or similar thereto. | | | |
| 348 | 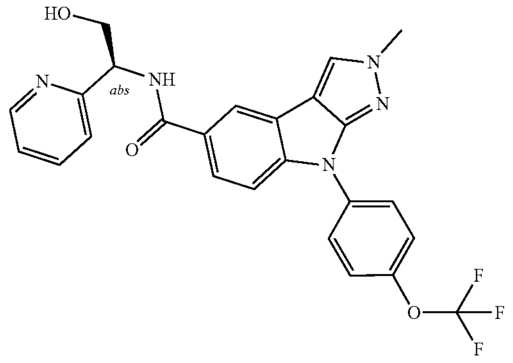 [SMILES: Cn1cc2c3cc(C(=O)N[C@H](CO)c4ccccn4)ccc3n(-c3ccc(OC(F)(F)F)cc3)c2n1] Absolute configuration known/assigned N-[(1S)-2-hydroxy-1-(pyridin-2-yl)ethyl]-2-methyl-8-[4-(trifluoromethoxy)-phenyl]-2H,8H-pyrazolo[3,4-b]indole-5-carboxamide | | |
| 349 | 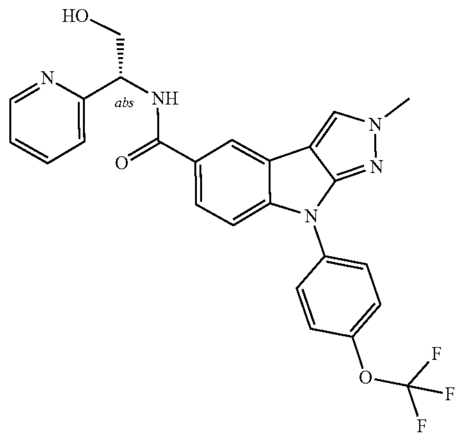 [SMILES: Cn1cc2c3cc(C(=O)N[C@@H](CO)c4ccccn4)ccc3n(-c3ccc(OC(F)(F)F)cc3)c2n1] Absolute configuration known/assigned N-[(1R)-2-hydroxy-1-(pyridin-2-yl)ethyl]-2-methyl-8-[4-(trifluoromethoxy)-phenyl]-2H,8H-pyrazolo[3,4-b]indole-5-carboxamide | | |

TABLE 1-continued

| Compound No. (Example No.) | Structure and Name | $^1$H-NMR | Conditions and elution time (min) LCMS (M + H$^+$) |
|---|---|---|---|
| Table 1 below shows exemplary compounds of the present invention. They have been synthesized as described in the Examples above or similar thereto. | | | |
| 350 | 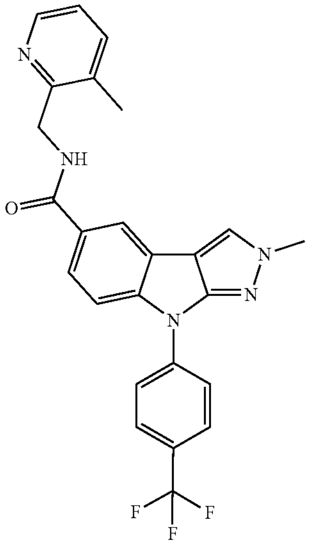 [SMILES: Cc1cccnc1CNC(=O)c1ccc2c(c1)c1cn(C)nc1n2-c1ccc(C(F)(F)F)cc1] 2-methyl-N-[(3-methylpyridin-2-yl)methyl]-8-[4-(trifluoromethyl)-phenyl]-2H,8H-pyrazolo[3,4-b]indole-5-carboxamide | (700 MHz, DMSO-d6) δ 9.15-9.11 (m, 1H), 8.58-8.56 (m, 1H), 8.41 (d, J = 1.8 Hz, 1H), 8.22 (s, 1H), 8.15-8.10 (m, 1H), 8.10-8.08 (m, 2H), 7.99-7.96 (m, 2H), 7.91 (dd, J = 8.7, 1.9 Hz, 1H), 7.81 (d, J = 8.6 Hz, 1H), 7.68-7.63 (m, 1H), 4.76 (d, J = 5.2 Hz, 2H), 4.04 (s, 3H), 2.48 (s, 3H). | 8 1.45 min 463.90 (M + H) |
| 351 | 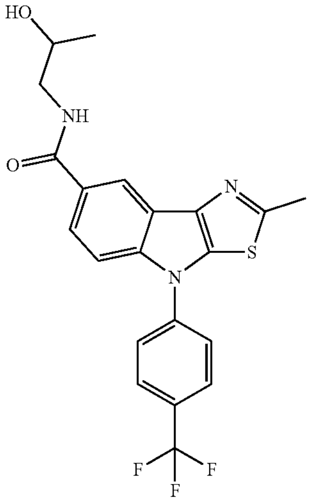 [SMILES: Cc1nc2c3cc(C(=O)NCC(C)O)ccc3n(-c3ccc(C(F)(F)F)cc3)c2s1] N-(2-hydroxypropyl)-2-methyl-4-[4-(trifluoromethyl)phenyl]-4H-[1,3]thiazolo[5,4-b]indole-7-carboxamide | (300 MHz, DMSO, ppm) δ 8.58-8.47 (m, 2H), 8.09-7.78 (m, 6H), 4.77 (s, 1H), 3.85 (s, 1H), 3.25 (s, 2H), 2.85 (s, 3H), 1.11 (d, J = 6.2 Hz, 3H). | 9 0.84 min 434.00 (M + H) |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 352 | 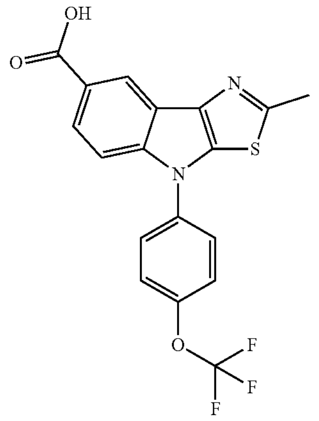 [SMILES: Cc1nc2c3cc(C(=O)O)ccc3n(-c3ccc(OC(F)(F)F)cc3)c2s1] 2-methyl-4-[4-(trifluoromethoxy)-phenyl]-4H-[1,3]thiazolo[5,4-b]indole-7-carboxylic acid | (300 MHz, DMSO, ppm) δ 8.48 (s, 1H), 7.92 (t, J = 8.5 Hz, 3H), 7.68 (d, J = 8.3 Hz, 3H), 2.83 (s, 3H). | 9 0.98 min 393.10 (M + H) |
| 353 | 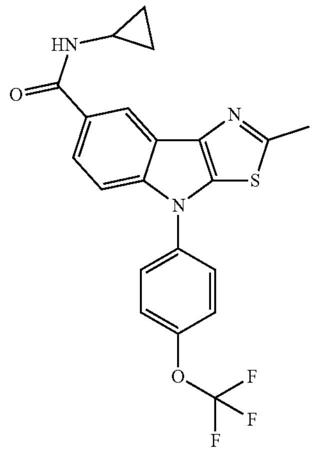 [SMILES: Cc1nc2c3cc(C(=O)NC4CC4)ccc3n(-c3ccc(OC(F)(F)F)cc3)c2s1] N-cyclopropyl-2-methyl-4-[4-(trifluoro-methoxy)phenyl]-4H-[1,3]thiazolo[5,4-b]indole-7-carboxamide | (400 MHz, DMSO-d6) δ 8.53 (d, J = 4.3 Hz, 1H), 8.49 (d, J = 1.8 Hz, 1H), 7.93-7.78 (m, 3H), 7.67 (dd, J = 8.7, 1.9 Hz, 3H), 2.92 (tt, J = 7.3, 3.9 Hz, 1H), 2.83 (s, 3H), 0.76-0.67 (m, 2H), 0.63 (qd, J = 6.3, 5.5, 3.5 Hz, 2H). | 16 1.0 min 431.85 (M + H) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 354 | 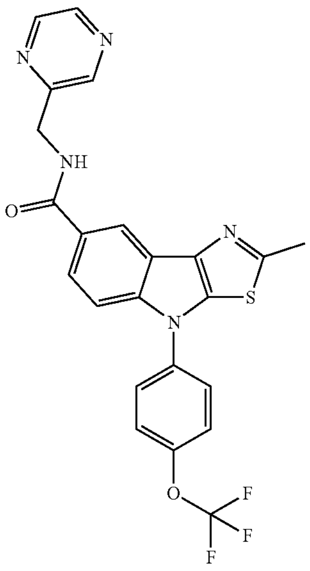 [SMILES: Cc1nc2c3cc(C(=O)NCc4cnccn4)ccc3n(-c3ccc(OC(F)(F)F)cc3)c2s1] 2-methyl-N-[(pyrazin-2-yl)methyl]-4-[4-(trifluoromethoxy)phenyl]-4H-[1,3]thiazolo[5,4-b]indole-7-carboxamide | (400 MHz, DMSO-d6) δ 9.29 (t, J = 5.8 Hz, 1H), 8.68 (d, J = 1.5 Hz, 1H), 8.61 (dd, J = 2.6, 1.5 Hz, 1H), 8.58 (d, J = 1.8 Hz, 1H), 8.55 (d, J = 2.6 Hz, 1H), 7.95-7.86 (m, 3H), 7.70 (dd, J = 15.7, 8.6 Hz, 3H), 4.67 (d, J = 5.7 Hz, 2H), 2.84 (s, 3H). | 16 1.51 min 484.15 (M + H) |
| 355 | 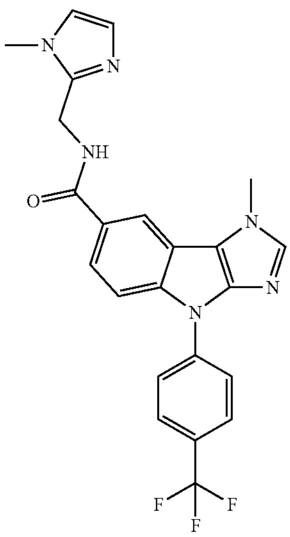 [SMILES: Cn1ccnc1CNC(=O)c1ccc2c(c1)c1c(ncn1C)n2-c1ccc(C(F)(F)F)cc1] 1-methyl-N-[(1-methyl-1H-imidazol-2-yl)methyl]-4-[4-(trifluoromethyl)-phenyl]-1H,4H-imidazo[4,5-b]indole-7-carboxamide | (300 MHz, DMSO-d6, ppm) δ 8.99-8.97 (m, 1H), 8.51 (s, 1H), 8.11 (d, J = 8.4 Hz, 2H), 7.98 (d, J = 8.4 Hz, 2H), 7.87 (s, 3H), 7.10 (s, 1H), 6.83 (s, 1H), 4.61 (d, J = 5.4 Hz, 2H), 4.12 (s, 3H), 3.71 (s, 3H) | 9 1.32 min 453.20 (M + H) |

TABLE 1-continued

| Compound No. (Example No.) | Structure and Name | $^1$H-NMR | Conditions and elution time (min) LCMS (M + H$^+$) |
|---|---|---|---|
| Table 1 below shows exemplary compounds of the present invention. They have been synthesized as described in the Examples above or similar thereto. | | | |
| 356 | 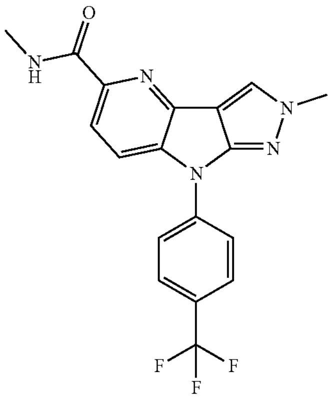 N,4-dimethyl-7-[4-(trifluoromethyl)phenyl]-4,5,7,12-tetraazatricyclo[6.4.0.0$^{2,6}$]dodeca-1(8),2,5,9,11-pentaene-11-carboxamide | 1H NMR (400 MHz, Methanol-d4, ppm) 8.15 (s, 1H), 8.14-8.07 (m, 1H), 8.07-8.00 (m, 3H), 7.92 (d, J = 8.3 Hz, 2H), 4.11 (s, 3H), 3.03 (s, 3H). | |
| 357 | 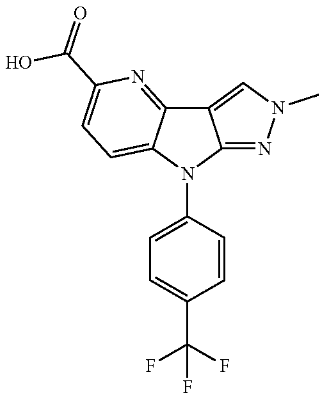 4-methyl-7-[4-(trifluoromethyl)phenyl]-4,5,7,12-tetraazatricyclo[6.4.0.0$^{2,6}$]dodeca-1(8),2,5,9,11-pentaene-11-carboxylic acid | 1H NMR (300 MHz, DMSO-d6, ppm ) 8.42 (s, 1H), 8.22-7.70 (m, 6H), 4.07 (s, 3H). | |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 358 | 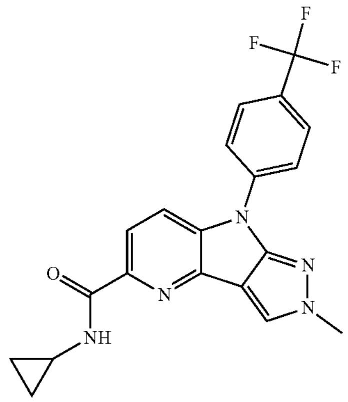 [SMILES: Cn1cc2c3nc(C(=O)NC4CC4)ccc3n(-c3ccc(C(F)(F)F)cc3)c2n1] N-cyclopropyl-4-methyl-7-[4-(trifluoromethyl)phenyl]-4,5,7,12-tetraazatricyclo[6.4.0.0$^{2,6}$]dodeca-1(8),2,5,9,11-pentaene-11-carboxamide | 1H NMR (400 MHz, DMSO-d6) 8.65 (d, J = 4.9 Hz, 1H), 8.35 (s, 1H), 8.23 (d, J = 8.7 Hz, 1H), 8.11 (d, J = 8.4 Hz, 2H), 8.04-7.97 (m, 3H), 4.09 (s, 3H), 2.99-2.90 (m, 1H), 0.76-0.69 (m, 4H). | *A* 2.14 min, (M + H) 400 |
| 359 | 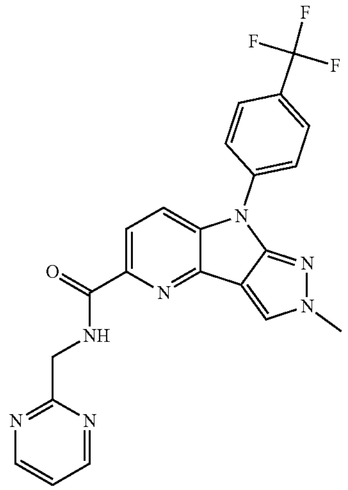 [SMILES: Cn1cc2c3nc(C(=O)NCc4ncccn4)ccc3n(-c3ccc(C(F)(F)F)cc3)c2n1] 4-methyl-N-[(pyrimidin-2-yl)methyl]-7-[4-(trifluoromethyl)phenyl]-4,5,7,12-tetraazatricyclo [6.4.0.0$^{2,6}$]dodeca-1(8),2,5,9,11-pentaene-11-carboxamide | 1H NMR (400 MHz, DMSO-d6) 9.27 (t, J = 5.9 Hz, 1H), 8.87 (d, J = 4.9 Hz, 2H), 8.50 (s, 1H), 8.32 (d, J = 8.6 Hz, 1H), 8.19 (d, J = 8.4 Hz, 2H), 8.11 (d, J = 8.6 Hz, 1H), 8.06 (d, J = 8.6 Hz, 2H), 7.49 (t, J = 4.9 Hz, 1H), 4.85 (d, J = 5.9 Hz, 2H), 4.17 (s, 3H). | *A* 2.02 min, (M + H) 452 |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 360 | 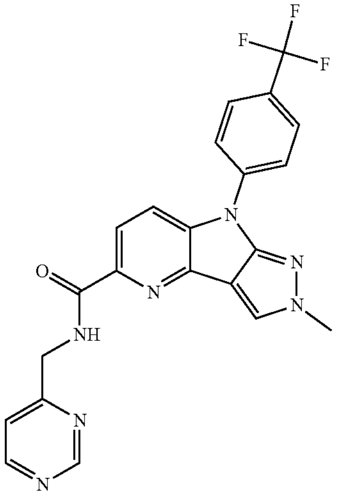 [SMILES: Cn1cc2c3nc(C(=O)NCc4ccncn4)ccc3n(-c3ccc(C(F)(F)F)cc3)c2n1] 4-methyl-N-[(pyrimidin-4-yl)methyl]-7-[4-(trifluoromethyl)phenyl]-4,5,7,12-tetraazatricyclo[6.4.0.0$^{2,6}$]dodeca-1(12),2,5,8,10-pentaene-11-carboxamide | 1H NMR (700 MHz, DMSO-d6) delta 9.22 (t, J = 5.9 Hz, 1H), 9.13 (d, J = 1.3 Hz, 1H), 8.75 (d, J = 5.3 Hz, 1H), 8.43 (d, J = 1.8 Hz, 1H), 8.23 (s, 1H), 8.12-8.09 (m, 2H), 7.99-7.97 (m, 2H), 7.93 (dd, J = 8.7, 1.8 Hz, 1H), 7.82 (d, J = 8.6 Hz, 1H), 7.47-7.46 (m, 1H), 4.59 (d, J = 5.7 Hz, 2H), 4.04 (s, 3H). | |
| 361 | 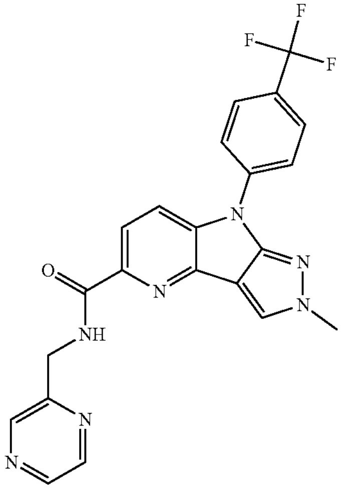 [SMILES: Cn1cc2c3nc(C(=O)NCc4cnccn4)ccc3n(-c3ccc(C(F)(F)F)cc3)c2n1] 4-methyl-N-[(pyrazin-2-yl)methyl]-7-[4-(trifluoromethyl)phenyl]-4,5,7,12-tetra-azatricyclo[6.4.0.0$^{2,6}$]dodeca-1(12),2,5,8,10-pentaene-11-carboxamide | 1H NMR (700 MHz, DMSO-d6) delta 9.21 (t, J = 5.8 Hz, 1H), 8.67 (d, J = 1.5 Hz, 1H), 8.61 (dd, J = 2.6, 1.5 Hz, 1H), 8.55 (d, J = 2.6 Hz, 1H), 8.41 (d, J = 1.8 Hz, 1H), 8.22 (s, 1H), 8.11-8.08 (m, 2H), 7.99-7.96 (m, 2H), 7.91 (dd, J = 8.6, 1.8 Hz, 1H), 7.80 (d, J = 8.6 Hz, 1H), 4.66 (d, J = 5.7 Hz, 2H), 4.04 (s, 3H). | |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 362 2736641 | 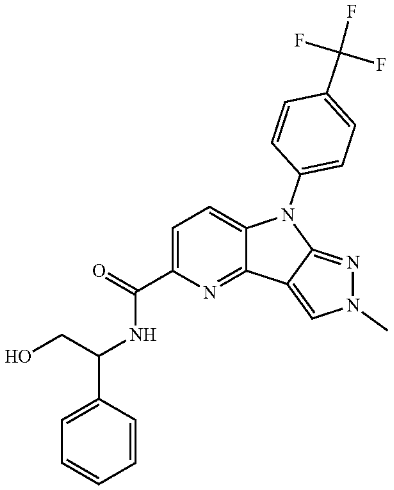 [SMILES: Cn1cc2c3nc(C(=O)NC(CO)c4ccccc4)ccc3n(-c3ccc(C(F)(F)F)cc3)c2n1] N-(2-hydroxy-1-phenylethyl)-4-methyl-7-[4-(trifluoromethyl)phenyl]-4,5,7,12-tetraazatricyclo[6.4.0.0$^{2,6}$]dodeca-1(12),2,5,8,10-pentaene-11-carboxamide | $^1$H NMR (700 MHz, DMSO-d$_6$) δ 8.73 (d, J = 8.0 Hz, 0H), 8.42 (d, J = 1.8 Hz, 0H), 8.22 (s, 0H), 8.09 (d, J = 8.5 Hz, 1H), 7.97 (d, J = 8.5 Hz, 1H), 7.91 (dd, J = 8.7, 1.9 Hz, 0H), 7.79 (d, J = 8.6 Hz, 0H), 7.45-7.41 (m, 1H), 7.33 (t, J = 7.7 Hz, 1H), 7.26-7.21 (m, 0H), 5.13 (td, J = 8.1, 5.4 Hz, 1H), 4.04 (s, 2H), 3.76 (dd, J = 11.2, 8.2 Hz, 0H), 3.69 (dd, J = 11.2, 5.4 Hz, 1H). | |
| 363 | 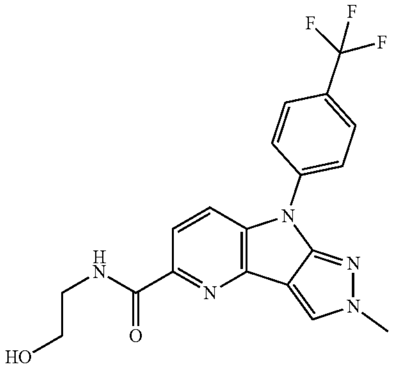 [SMILES: Cn1cc2c3nc(C(=O)NCCO)ccc3n(-c3ccc(C(F)(F)F)cc3)c2n1] N-(2-hydroxyethyl)-4-methyl-7-[4-(trifluoromethyl)phenyl]-4,5,7,12-tetraazatricyclo[6.4.0.0$^{2,6}$]dodeca-1(8),2,5,9,11-pentaene-11-carboxamide | | |

TABLE 1-continued

| Compound No. (Example No.) | Structure and Name | $^1$H-NMR | Conditions and elution time (min) LCMS (M + H$^+$) |
|---|---|---|---|
| | Table 1 below shows exemplary compounds of the present invention. They have been synthesized as described in the Examples above or similar thereto. | | |
| 364 | 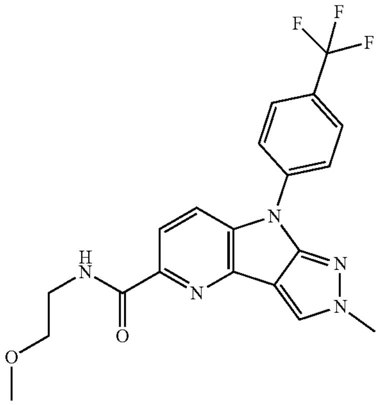 [SMILES: COCCNC(=O)c1ccc2c(n1)c1cn(C)nc1n2-c1ccc(C(F)(F)F)cc1] N-(2-methoxyethyl)-4-methyl-7-[4-(trifluoromethyl)phenyl]-4,5,7,12-tetraazatricyclo[6.4.0.0$^{2,6}$]dodeca-1(8),2,5,9,11-pentaene-11-carboxamide | | |
| 365 | 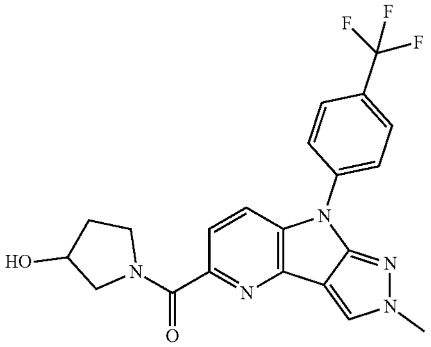 [SMILES: Cn1cc2c3nc(C(=O)N4CCC(O)C4)ccc3n(-c3ccc(C(F)(F)F)cc3)c2n1] 1-{4-methyl-7-[4-(trifluoromethyl)-phenyl]-4,5,7,12-tetraazatri-cyclo[6.4.0.0$^{2,6}$]dodeca-1(8),2,5,9,11-pentaene-11-carbonyl}pyrrolidin-3-ol | | |
| 366 | 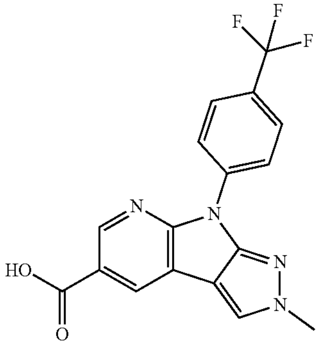 [SMILES: Cn1cc2c3cc(C(=O)O)cnc3n(-c3ccc(C(F)(F)F)cc3)c2n1] 4-methyl-7-[4-(trifluoromethyl)phenyl]-4,5,7,9-tetraazatricyclo[6.4.0.0$^{2,6}$]do-deca-1(8),2,5,9,11-pentaene-11-carboxylic acid | | |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 367 | 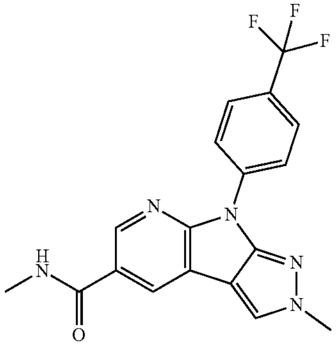 N,4-dimethyl-7-[4-(trifluoromethyl)-phenyl]-4,5,7,9-tetraazatricyclo[6.4.0.0$^{2,6}$]dodeca-1(8),2,5,9,11-pentaene-11-carboxamide | | |
| 368 | 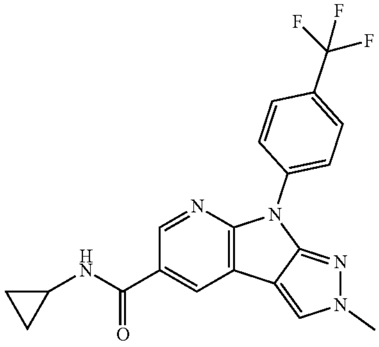 [SMILES: Cn1cc2c3cc(C(=O)NC4CC4)cnc3n(-c3ccc(C(F)(F)F)cc3)c2n1] N-cyclopropyl-4-methyl-7-[4-(trifluoromethyl)phenyl]-4,5,7,9-tetraazatricyclo[6.4.0.0$^{2,6}$]dodeca-1(8),2,5,9,11-pentaene-11-carboxamide | | |
| 369 | 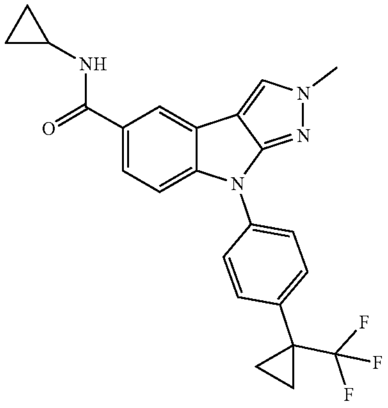 [SMILES: Cn1cc2c3cc(C(=O)NC4CC4)ccc3n(-c3ccc(C4(C(F)(F)F)CC4)cc3)c2n1] N-cyclopropyl-2-methyl-8-{4-[1-(trifluoromethyl)cyclopropyl]phenyl}-2H,8H-pyrazolo[3,4-b]indole-5-carboxamide | (700 MHz, DMSO-d6) δ 8.43 (d, J = 4.2 Hz, 1H), 8.28 (d, J = 1.8 Hz, 1H), 8.16 (s, 1H), 7.83-7.80 (m, 2H), 7.79 (dd, J = 8.6, 1.9 Hz, 1H), 7.70-7.67 (m, 2H), 7.62 (d, J = 8.6 Hz, 1H), 4.01 (s, 3H), 2.91-2.86 (m, 1H), 1.42-1.39 (m, 2H), 1.23-1.19 (m, 2H), 0.72-0.68 (m, 2H), 0.62-0.58 (m, 2H). | 8<br>1.80 min<br>438.90 |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 370 | 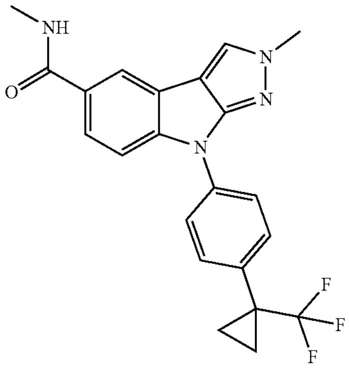 [SMILES: CNC(=O)c1ccc2c(c1)c1cn(C)nc1n2-c1ccc(C2(C(F)(F)F)CC2)cc1] N,2-dimethyl-8-{4-[1-(trifluoromethyl)-cyclopropyl]phenyl}-2H,8H-pyrazolo[3,4-b]indole-5-carboxamide | (700 MHz, DMSO-d6) δ 8.42 (q, J = 4.5 Hz, 1H), 8.31 (d, J = 1.8 Hz, 1H), 8.17 (s, 1H), 7.84-7.81 (m, 2H), 7.82-7.79 (m, 1H), 7.70-7.67 (m, 2H), 7.63 (d, J = 8.6 Hz, 1H), 4.01 (s, 3H), 2.82 (d, J = 4.4 Hz, 3H), 1.42-1.39 (m, 2H), 1.23-1.19 (m, 2H). | |
| 371 | 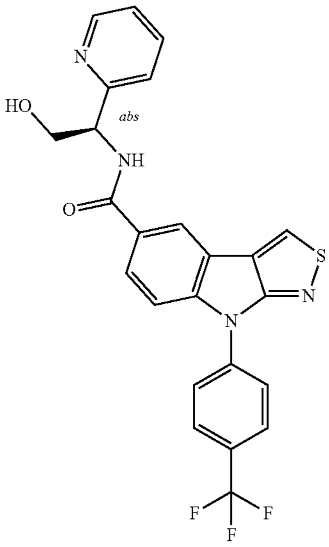 [SMILES: O=C(N[C@@H](CO)c1ccccn1)c1ccc2c(c1)c1csnc1n2-c1ccc(C(F)(F)F)cc1] Absolute configuration assgined/known N-[(1R)-2-hydroxy-1-(pyridin-2-yl)ethyl]-8-[4-(trifluoromethyl)phenyl]-8H-[1,2]thiazolo[3,4-b]indole-5-carboxamide | (400 MHz, DMSO-d6) δ 9.49 (s, 1H), 8.74 (d, J = 7.8 Hz, 1H), 8.68 (d, J = 1.8 Hz, 1H), 8.60-8.50 (m, 1H), 8.12-8.05 (m, 3H), 8.02 (d, J = 8.7 Hz, 2H), 7.88-7.70 (m, 1H), 7.67 (d, J = 8.7 Hz, 1H), 7.46 (d, J = 7.8 Hz, 1H), 7.45-7.33 (m, 1H), 5.30-5.20 (m, 1H), 4.96 (t, J = 6.0 Hz, 1H), 3.90-3.80 (m, 2H). | 16 1.55 min 483.20 |

TABLE 1-continued

| Compound No. (Example No.) | Structure and Name | $^1$H-NMR | Conditions and elution time (min) LCMS (M + H$^+$) |
|---|---|---|---|
| Table 1 below shows exemplary compounds of the present invention. They have been synthesized as described in the Examples above or similar thereto. | | | |
| 372 | 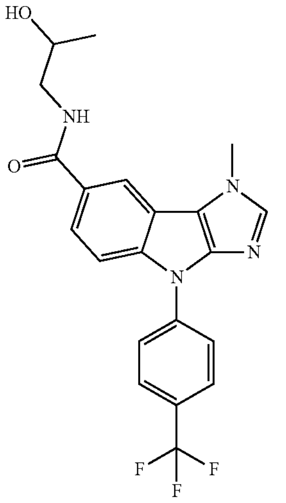 [SMILES: CC(O)CNC(=O)c1ccc2c(c1)c1c(ncn1C)n2-c1ccc(C(F)(F)F)cc1] N-(2-hydroxypropyl)-1-methyl-4-[4-(trifluoromethyl)phenyl]-1H,4H-imidazo[4,5-b]indole-7-carboxamide | (300 MHz, DMSO-d6, ppm) δ 8.48-8.45 (m, 2H), 8.10 (d, J = 8.4 Hz, 2H), 7.98 (d, J = 8.4 Hz, 2H), 7.90-7.81 (m, 3H), 4.81 (s, 1H), 4.13 (s, 3H), 3.87-3.83 (m, 1H), 3.01-3.25 (m, 2H), 1.10 (d, J = 6.3 Hz, 3H) | 12 0.69 min 417.20 |
| 373 | 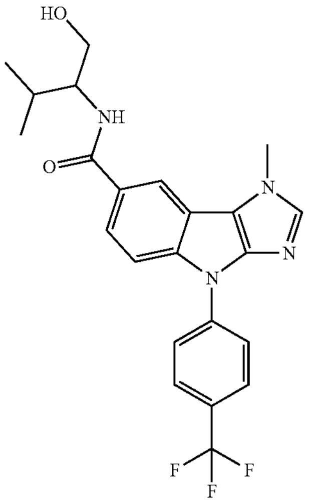 [SMILES: CC(C)C(CO)NC(=O)c1ccc2c(c1)c1c(ncn1C)n2-c1ccc(C(F)(F)F)cc1] N-(1-hydroxy-3-methylbutan-2-yl)-1-methyl-4-[4-(trifluoromethyl)phenyl]-1H,4H-imidazo[4,5-b]indole-7-carboxamide | (300 MHz, DMSO-d6, ppm) δ 8.43 (s, 1H), 8.10 (d, J = 8.4 Hz, 2H), 8.00-7.96 (m, 3H), 7.89-7.81 (m, 3H), 4.65-4.61 (m, 1H), 4.13 (s, 3H), 3.91-3.84 (m, 1H), 3.59-3.56(m, 2H), 2.02-1.95 (m, 1H), 0.94 (t, J = 7.2 Hz, 6H) | 12 1.59 445.20 |

TABLE 1-continued

| Compound No. (Example No.) | Structure and Name | $^1$H-NMR | Conditions and elution time (min) LCMS (M + H$^+$) |
|---|---|---|---|
| Table 1 below shows exemplary compounds of the present invention. They have been synthesized as described in the Examples above or similar thereto. | | | |
| 374 | 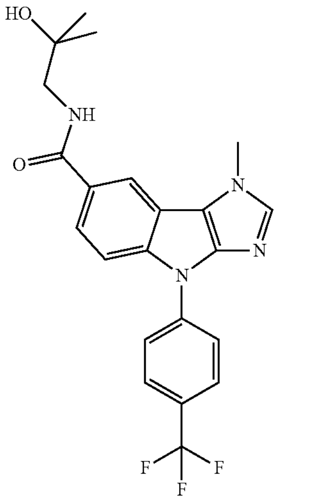 [SMILES: Cn1cnc2c1c1cc(C(=O)NCC(C)(C)O)ccc1n2-c1ccc(C(F)(F)F)cc1] N-(2-hydroxy-2-methylpropyl)-1-methyl-4-[4-(trifluoromethyl)phenyl]-1H,4H-imidazo[4,5-b]indole-7-carboxamide | (300 MHz, DMSO-d6, ppm): δ 8.46 (s, 1H), 8.35-8.31 (m, 1H), 8.05 (d, J = 8.4 Hz, 2H), 7.98 (d, J = 8.4 Hz, 2H), 7.90-7.82 (m, 3H), 4.64 (s, 1H), 4.14 (s, 3H), 3.33 (s, 2H), 1.15 (s, 6H) | 12 0.90 431.20 |
| 375 | 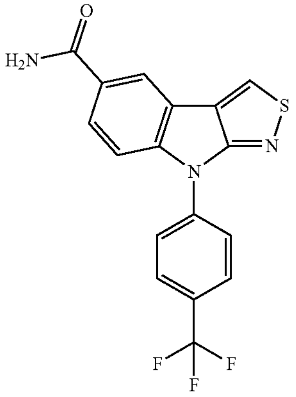 [SMILES: NC(=O)c1ccc2c(c1)c1csnc1n2-c1ccc(C(F)(F)F)cc1] 8-[4-(trifluoromethyl)phenyl]-8H-[1,2]thiazolo[3,4-b]indole-5-carboxamide | (400 MHz, DMSO-d6) δ 9.46 (s, 1H), 8.60 (d, J = 1.8 Hz, 1H), 8.11-7.97 (m, 6H), 7.63 (d, J = 8.6 Hz, 1H), 7.35 (s, 1H). | 16 0.90 362.05 |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 376 | 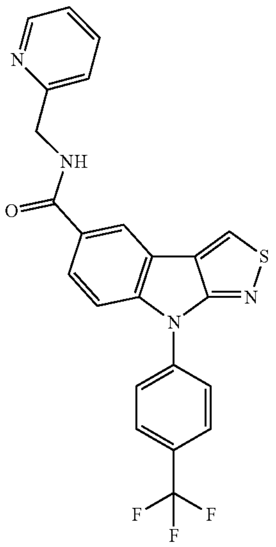 [SMILES: O=C(NCc1ccccn1)c1ccc2c(c1)c1csnc1n2-c1ccc(C(F)(F)F)cc1] N-[(pyridin-2-yl)methyl]-8-[4-(trifluoromethyl)phenyl]-8H-[1,2]thiazolo[3,4-b]indole-5-carboxamide | (400 MHz, DMSO-d6) δ 9.49 (s, 1H), 9.19 (t, J = 5.9 Hz, 1H), 8.66 (d, J = 1.8 Hz, 1H), 8.55-8.45 (m, 1H), 8.12-8.04 (m, 3H), 8.02 (d, J = 8.6 Hz, 2H), 7.80-7.70 (m, 1H), 7.67 (d, J = 8.7 Hz, 1H), 7.37 (d, J = 7.8 Hz, 1H), 7.30-7.20 (m, 1H), 4.63 (d, J = 5.9 Hz, 2H). | 16 1.64 min 453.20 |
| 377 | 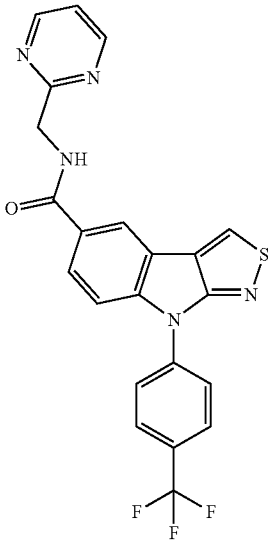 [SMILES: O=C(NCc1ncccn1)c1ccc2c(c1)c1csnc1n2-c1ccc(C(F)(F)F)cc1] N-[(pyrimidin-2-yl)methyl]-8-[4-(trifluoromethyl)phenyl]-8H-[1,2]thiazolo[3,4-b]indole-5-carboxamide | (400 MHz, DMSO-d6) δ 9.49 (s, 1H), 9.12 (t, J = 5.9 Hz, 1H), 8.79 (d, J = 4.9 Hz, 2H), 8.64 (d, J = 1.8 Hz, 1H), 8.13-7.98 (m, 5H), 7.68 (d, J = 8.7 Hz, 1H), 7.41 (t, J = 4.9 Hz, 1H), 4.72 (d, J = 5.8 Hz, 2H). | 16 1.55 min 454.15 |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 378 | 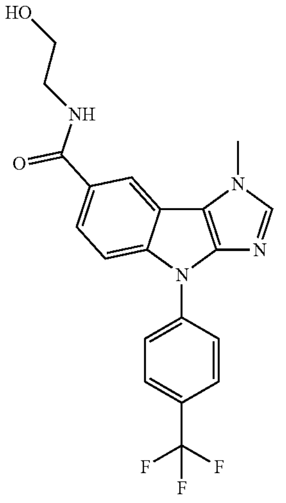 [SMILES: Cn1cnc2c1c1cc(C(=O)NCCO)ccc1n2-c1ccc(C(F)(F)F)cc1]<br>N-(2-hydroxyethyl)-1-methyl-4-[4-(trifluoromethyl)phenyl]-1H,4H-imidazo[4,5-b]indole-7-carboxamide | (300 MHz, DMSO-d6, ppm) δ 8.51-8.48 (m, 1H), 8.45 (s, 1H), 8.11 (d, J = 8.1 Hz, 2H), 7.98 (d, J = 8.4 Hz, 2H), 7.88 (d, J = 7.8 Hz, 2H), 7.81 (d, J = 8.7 Hz, 1H), 4.78 (t, J = 5.4 Hz, 1H), 4.13 (s, 3H), 3.60-3.54 (m, 2H), 3.44-3.33 (m, 2H) | 12<br>0.83<br>403.20 |
| 379 | 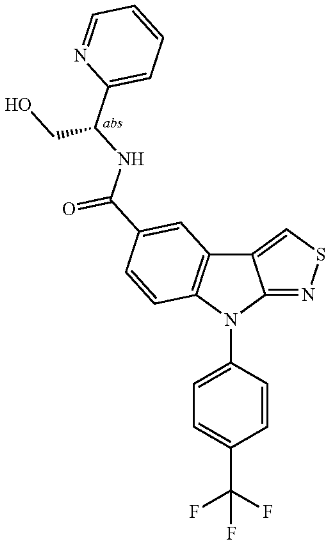 [SMILES: O=C(N[C@H](CO)c1ccccn1)c1ccc2c(c1)c1csnc1n2-c1ccc(C(F)(F)F)cc1]<br>Absolute configuration known/assigned<br>N-[(1S)-2-hydroxy-1-(pyridin-2-yl)ethyl]-8-[4-(trifluoromethyl)phenyl]-8H-[1,2]thiazolo[3,4-b]indole-5-carboxamide | (400 MHz, DMSO-d6) δ 9.49 (s, 1H), 8.74 (d, J = 7.9 Hz, 1H), 8.68 (d, J = 1.8 Hz, 1H), 8.60-8.50 (m, 1H), 8.12-8.05 (m, 3H), 8.02 (d, J = 8.7 Hz, 2H), 7.80-7.70 (m, 1H), 7.67 (d, J = 8.7 Hz, 1H), 7.50-7.40 (m, 1H), 7.30-7.20 (m, 1H), 5.30-5.18 (m, 1H), 4.96 (t, J = 5.9 Hz, 1H), 3.94-3.78 (m, 2H). | 12<br>1.56 min<br>483.15 |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 380 | 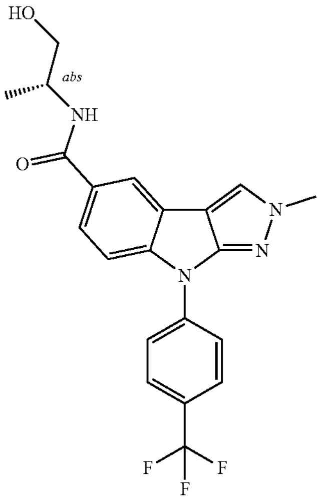 [SMILES: C[C@H](CO)NC(=O)c1ccc2c(c1)c1cn(C)nc1n2-c1ccc(C(F)(F)F)cc1] Absolute configuration known/assigned N-[(2R)-1-hydroxypropan-2-yl]-2-methyl-8-[4-(trifluoromethyl)phenyl]-2H,8H-pyrazolo[3,4-b]indole-5-carboxamide | (700 MHz, DMSO-d6) δ 8.35 (d, J = 1.8 Hz, 1H), 8.20 (s, 1H), 8.12 (d, J = 8.0 Hz, 1H), 8.10-8.07 (m, 2H), 7.99-7.95 (m, 2H), 7.86 (dd, J = 8.7, 1.8 Hz, 1H), 7.77 (d, J = 8.7 Hz, 1H), 4.74 (t, J = 5.8 Hz, 1H), 4.10-4.05 (m, 1H), 4.04 (s, 3H), 3.53-3.49 (m, 1H), 3.40-3.35 (m, 1H), 1.17 (d, J = 6.7 Hz, 3H). | 8<br>1.58 min<br>416.90 |
| 381 | 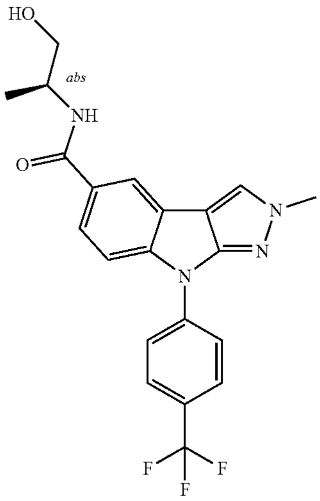 [SMILES: C[C@@H](CO)NC(=O)c1ccc2c(c1)c1cn(C)nc1n2-c1ccc(C(F)(F)F)cc1] Absolute configuration known/assigned N-[(2S)-1-hydroxypropan-2-yl]-2-methyl-8-[4-(trifluoromethyl)phenyl]-2H,8H-pyrazolo[3,4-b]indole-5-carboxamide | (400 MHz, DMSO-d6) δ 8.35 (d, J = 1.8 Hz, 1H), 8.19 (s, 1H), 8.12-8.06 (m, 3H), 7.99-7.94 (m, 2H), 7.86 (dd, J = 8.8, 1.9 Hz, 1H), 7.76 (d, J = 8.7 Hz, 1H), 4.71 (t, J = 5.8 Hz, 1H), 4.11-4.03 (m, 1H), 4.04 (s, 3H), 3.54-3.47 (m, 1H), 3.41-3.34 (m, 1H), 1.17 (d, J = 6.7 Hz, 3H). | 8<br>1.58 min<br>416.90 |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 382 | 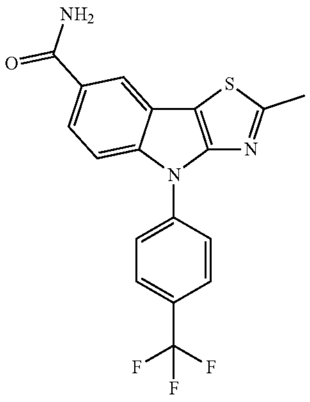 [SMILES: Cc1nc2c(s1)c1cc(C(N)=O)ccc1n2-c1ccc(C(F)(F)F)cc1] 2-methyl-4-[4-(trifluoromethyl)phenyl]-4H-[1,3]thiazolo[4,5-b]indole-7-carboxamide | (400 MHz, DMSO-$d_6$) δ 8.45 (d, J = 1.7 Hz, 1H), 8.01 (m, 5H), 7.89 (dd, J = 8.8, 1.8 Hz, 1H), 7.73 (d, J = 8.8 Hz, 1H), 7.28 (s, 1H), 2.85 (s, 3H) | 16<br>1.386<br>376 M + H<br>398 M + Na<br>773 2M + Na |
| 383 | 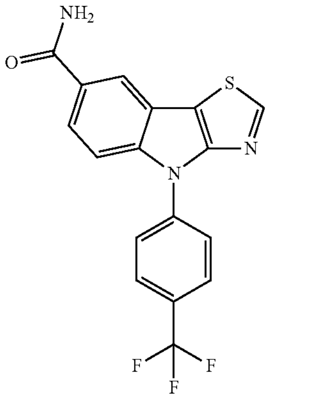 4-[4-(trifluoromethyl)phenyl]-4H-[1,3]thiazolo[4,5-b]indole-7-carboxamide | ((400 MHz, DMSO-$d_6$) δ 9.27 (s, 1H), 8.55 (d, J = 1.6 Hz, 1H), 8.07-8.00 (m, 5H), 7.95 (dd, J = 8.8, 1.8 Hz, 1H), 7.79 (d, J = 8.8 Hz, 1H), 7.30 (s, 1H) | 16<br>1.326<br>362 M + H<br>384 + Na<br>745 2M + Na |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 384 | 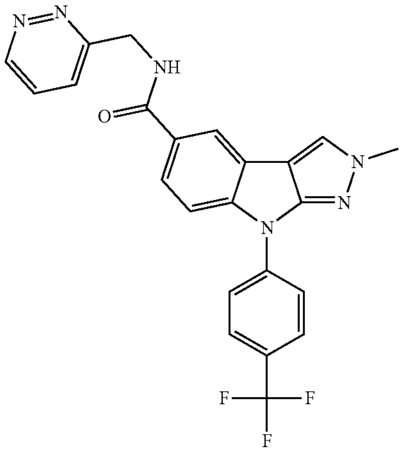 [SMILES: Cn1cc2c3cc(C(=O)NCc4cccnn4)ccc3n(-c3ccc(C(F)(F)F)cc3)c2n1] 2-methyl-N-[(pyridazin-3-yl)methyl]-8-[4-(trifluoromethyl)phenyl]-2H,8H-pyrazolo[3,4-b]indole-5-carboxamide | (700 MHz, DMSO-d6) δ 9.27 (t, J = 5.9 Hz, 1H), 9.17 (dd, J = 4.7, 1.8 Hz, 1H), 8.42 (d, J = 1.7 Hz, 1H), 8.22 (s, 1H), 8.11-8.08 (m, 2H), 7.99-7.96 (m, 2H), 7.92 (dd, J = 8.7, 1.9 Hz, 1H), 7.81 (d, J = 8.6 Hz, 1H), 7.72 (dd, J = 8.6, 4.7 Hz, 1H), 7.69 (dd, J = 8.6, 1.8 Hz, 1H), 4.81 (d, J = 5.7 Hz, 2H), 4.04 (s, 3H). | 8 1.57 450.90 M + H |
| 385 | 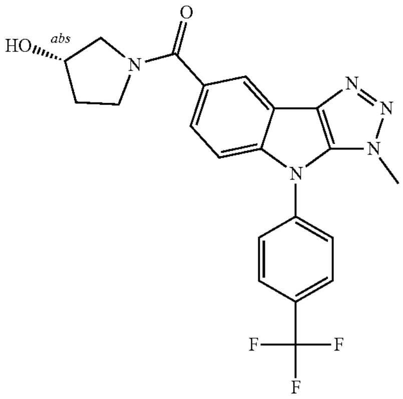 [SMILES: Cn1nnc2c3cc(C(=O)N4CC[C@H](O)C4)ccc3n(-c3ccc(C(F)(F)F)cc3)c21] Absolute configuration known/assigned (3S)-1-{3-methyl-4-[4-(trifluoromethyl)-phenyl]-3H,4H-[1,2,3]triazolo[4,5-b]indole-7-carbonyl}pyrrolidin-3-ol | (700 MHz, DMSO-d6) δ 8.18-8.16 (m, 1H), 8.09-8.06 (m, 2H), 8.02-7.99 (m, 2H), 7.91 (d, J = 8.7 Hz, 1H), 7.70-7.66 (m, 1H), 4.37 (s, 3H), 4.37-4.24 (m, 1H), 3.73-3.60 (m, 2H), 3.59-3.50 (m, 1H), 3.44-3.30 (m, 1H), 2.02-1.89 (m, 1H), 1.88-1.78 (m, 1H). | 8 1.58 429.90 M + h |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 386 | 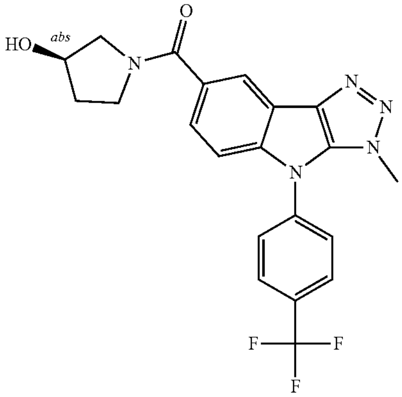 [SMILES: Cn1nnc2c3cc(C(=O)N4CC[C@@H](O)C4)ccc3n(-c3ccc(C(F)(F)F)cc3)c21] Absolute configuration known/assigned (3R)-1-{3-methyl-4-[4-(trifluoromethyl)-phenyl]-3H,4H-[1,2,3]triazolo[4,5-b]indole-7-carbonyl}pyrrolidin-3-ol | (400 MHz, DMSO-d6) δ 8.17 (d, J = 1.7 Hz, 1H), 8.10-8.05 (m, 2H), 8.03-7.98 (m, 2H), 7.91 (d, J = 8.7 Hz, 1H), 7.70-7.65 (m, 1H), 4.37 (s, 3H), 4.37-4.23 (m, 1H), 3.74-3.51 (m, 3H), 3.46-3.27 (m, 1H), 2.05-1.75 (m, 2H). | 8 1.58 429.90 M + H |
| 387 | 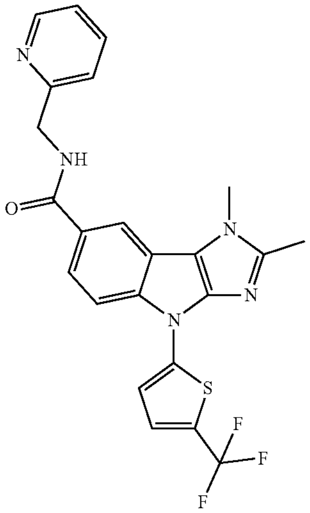 [SMILES: Cc1nc2c(c3cc(C(=O)NCc4ccccn4)ccc3n2-c2ccc(C(F)(F)F)s2)n1C] 1,2-dimethyl-N-[(pyridin-2-yl)methyl]-4-[5-(trifluoromethyl)thiophen-2-yl]-1H,4H-imidazo[4,5-b]indole-7-carboxamide | (400 MHz, DMSO-d6) δ 9.15 (t, J = 6.0 Hz, 1H), 8.54 (m, 1H), 8.47 (d, J = 1.7 Hz, 1H), 7.94-7.83 (m, 2H), 7.82-7.73 (m, 2H), 7.60 (m, 1H), 7.38 (m, 1H), 7.28 (m, 1H), 4.65 (d, J = 5.9 Hz, 2H), 4.00 (s, 3H), 2.54 (s, 3H). | 9 0.75 470.10 M + H |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 388 | 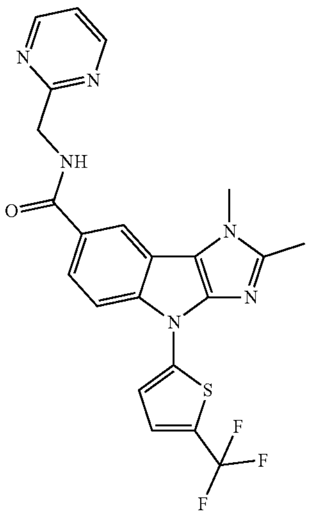<br>1,2-dimethyl-N-[(pyrimidin-2-yl)methyl]-4-[5-(trifluoromethyl)thiophen-2-yl]-1H,4H-imidazo[4,5-b]indole-7-carboxamide | (400 MHz, DMSO-d6) δ 9.09 (t, J = 5.9 Hz, 1H), 8.79 (d, J = 4.9 Hz, 2H), 8.46 (d, J = 1.9 Hz, 1H), 7.88 (m, 2H), 7.78 (m, 1H), 7.60 (d, J = 4.4 Hz, 1H), 7.41 (t, J = 4.9 Hz, 1H), 4.74 (d, J = 5.8 Hz, 2H), 4.00 (d, J = 1.9 Hz, 3H), 2.54 (d, J = 1.2 Hz, 3H). | 9<br>0.81 min<br>471.10<br>M + H |
| 389 | 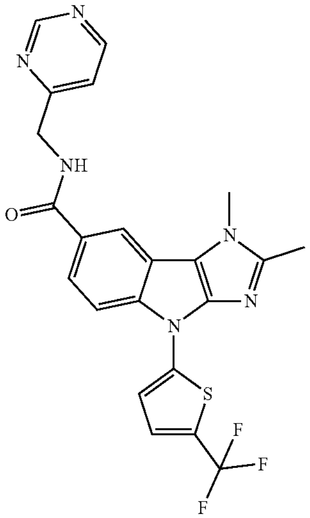 [SMILES: Cc1nc2c(c3cc(C(=O)NCc4ccncn4)ccc3n2-c2ccc(C(F)(F)F)s2)n1C]<br>1,2-dimethyl-N-[(pyrimidin-4-yl)methyl]-4-[5-(trifluoromethyl)thiophen-2-yl]-1H,4H-imidazo[4,5-b]indole-7-carboxamide | (400 MHz, DMSO-d6) δ 9.23 (t, J = 5.9 Hz, 1H), 9.14 (d, J = 1.4 Hz, 1H), 8.76 (d, J = 5.2 Hz, 1H), 8.47 (d, J = 1.7 Hz, 1H), 7.93 (d, J = 8.7 Hz, 1H), 7.87 (m, 1H), 7.80 (m, 1H), 7.61 (d, J = 4.1 Hz, 1H), 7.48 (m, 1H), 4.62 (d, J = 5.8 Hz, 2H), 4.02 (s, 3H), 2.55 (s, 3H). | 9<br>0.81 min<br>471.10<br>M + H |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 390 | 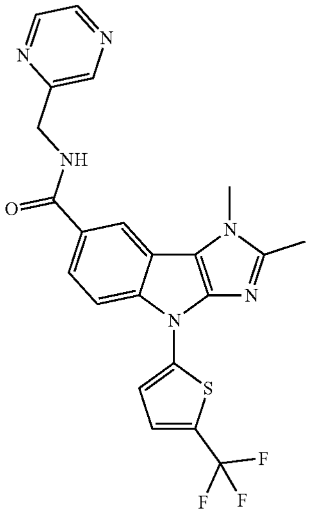 [SMILES: Cc1nc2c(c3cc(C(=O)NCc4cnccn4)ccc3n2-c2ccc(C(F)(F)F)s2)n1C]<br>1,2-dimethyl-N-[(pyrazin-2-yl)methyl]-4-[5-(trifluoromethyl)thiophen-2-yl]-1H,4H-imidazo[4,5-b]indole-7-carboxamide | (400 MHz, DMSO-d6) δ 9.22 (t, J = 5.9 Hz, 1H), 8.69 (d, J = 1.5 Hz, 1H), 8.62 (d, J = 2.6, 1H), 8.56 (d, J = 2.6 Hz, 1H), 8.45 (d, J = 1.7 Hz, 1H), 7.91 (d, J = 8.8 Hz, 1H), 7.85 (d, J = 8.7, 1H), 7.82-7.76 (m, 1H), 7.60 (d, J = 4.1 Hz, 1H), 4.69 (d, J = 5.7 Hz, 2H), 4.01 (s, 3H), 2.54 (s, 3H). | 9<br>0.82 min<br>471.10<br>M + H |
| 391 | 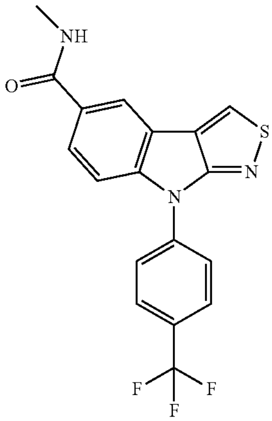 [SMILES: CNC(=O)c1ccc2c(c1)c1csnc1n2-c1ccc(C(F)(F)F)cc1]<br>N-methyl-8-[4-(trifluoromethyl)phenyl]-8H-[1,2]thiazolo[3,4-b]indole-5-carboxamide | (400 MHz, DMSO-d6) δ 9.47 (s, 1H), 8.56 (d, J = 1.8 Hz, 1H), 8.51 (d, J = 4.4 Hz, 1H), 8.08 (d, J = 8.4 Hz, 2H), 8.04-7.92 (m, 3H), 7.64 (d, J = 8.7 Hz, 1H), 2.83 (d, J = 4.4 Hz, 3H). | 16<br>1.59 min<br>376.10<br>M + H |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 392 | 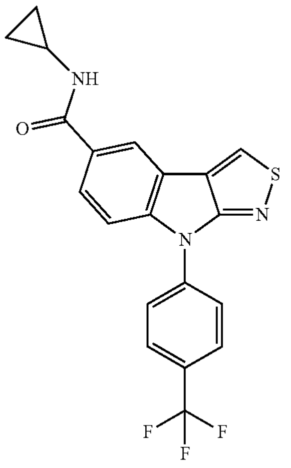 [SMILES: O=C(NC1CC1)c1ccc2c(c1)c1csnc1n2-c1ccc(C(F)(F)F)cc1] N-cyclopropyl-8-[4-(trifluoromethyl)-phenyl]-8H-[1,2]thiazolo[3,4-b]indole-5-carboxamide | (400 MHz, DMSO-d6) δ 9.46 (s, 1H), 8.56-8.49 (m, 2H), 8.07 (d, J = 8.5 Hz, 2H), 8.01-7.91 (m, 2H), 7.62 (d, J = 8.7 Hz, 1H), 2.95-2.85 (m, 1H), 0.77-0.68 (m, 2H), 0.68-0.59 (m, 2H). | 16 1.68 min 402.15 M + H |
| 393 | 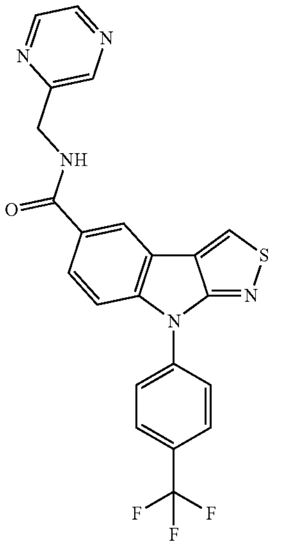 [SMILES: O=C(NCc1cnccn1)c1ccc2c(c1)c1csnc1n2-c1ccc(C(F)(F)F)cc1] N-[(pyrazin-2-yl)methyl]-8-[4-(trifluoromethyl)phenyl]-8H-[1,2]thiazolo[3,4-b]indole-5-carboxamide | (400 MHz, DMSO-d6) δ 9.49 (s, 1H), 9.26 (t, J = 5.8 Hz, 1H), 8.68 (d, J =1.5 Hz, 1H), 8.66-8.59 (m, 2H), 8.55 (d, J = 2.6 Hz, 1H), 8.12-7.98 (m, 5H), 7.67 (d, J = 8.7 Hz, 1H), 4.67 (d, J = 5.7 Hz, 2H). | 16 1.57 min 454.15 M + H |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 394 | 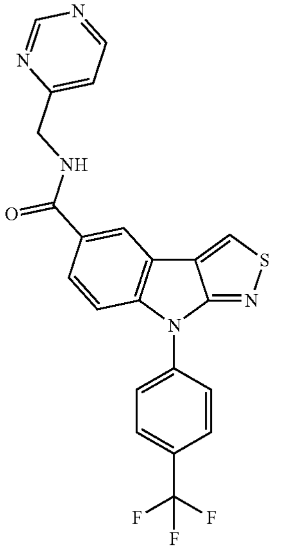 [SMILES: O=C(NCc1ccncn1)c1ccc2c(c1)c1csnc1n2-c1ccc(C(F)(F)F)cc1] N-[(pyrimidin-4-yl)methyl]-8-[4-(trifluoromethyl)phenyl]-8H-[1,2]thiazolo[3,4-b]indole-5-carboxamide | (400 MHz, DMSO-d6) δ 9.50 (s, 1H), 9.27 (t, J = 5.9 Hz, 1H), 9.13 (d, J = 1.4 Hz, 1H), 8.75 (d, J = 5.2 Hz, 1H), 8.66 (d, J = 1.8 Hz, 1H), 8.12-7.98 (m, 5H), 7.68 (d, J = 8.7 Hz, 1H), 7.51-7.44 (m, 1H), 4.61 (d, J = 5.8 Hz, 2H). | 16<br>2.05<br>454.15<br>(M + H) |
| 395 | 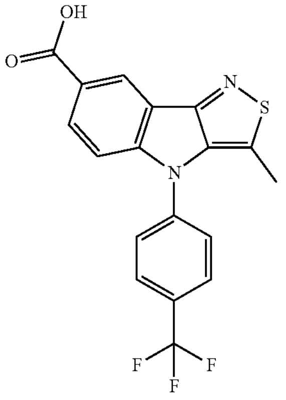 [SMILES: Cc1snc2c3cc(C(=O)O)ccc3n(-c3ccc(C(F)(F)F)cc3)c12] 3-methyl-4-[4-(trifluoromethyl)phenyl]-4H-[1,2]thiazolo[4,3-b]indole-7-carboxylic acid | (300 MHz, DMSO-d6) δ 12.93 (s, 1H), 8.57 (s, 1H), 8.06 (dd, J = 12.3, 8.6 Hz, 3H), 7.93 (d, J = 8.3 Hz, 2H), 7.45 (d, J = 8.8 Hz, 1H), 2.38 (s, 3H). | 16<br>1.05 min<br>377.10<br>(M + H) |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
| --- | --- | --- | --- |
| 396 | 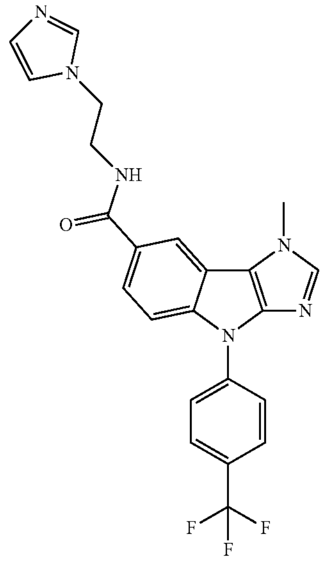 [SMILES: Cn1cnc2c1c1cc(C(=O)NCCn3ccnc3)ccc1n2-c1ccc(C(F)(F)F)cc1] N-[2-(1H-imidazol-1-yl)ethyl]-1-methyl-4-[4-(trifluoromethyl)phenyl]-1H,4H-imidazo[4,5-b]indole-7-carboxamide | (300 MHz, DMSO-d6) δ 8.67 (s, 2H), 8.34 (s, 1H), 8.10 (d, J = 8.4 Hz, 2H), 7.98 (d, J = 8.5 Hz, 2H), 7.88 (t, J = 4.5 Hz, 2H), 7.74 (d, J = 8.9 Hz, 1H), 7.61 (s, 1H), 7.44 (s, 1H), 4.36 (t, J = 5.8 Hz, 2H), 4.11 (s, 3H), 3.73 (d, J = 5.8 Hz, 2H). | 9<br>0.69 min<br>453.20<br>(M + H) |
| 397 | 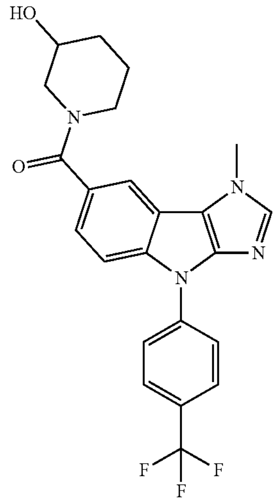 [SMILES: Cn1cnc2c1c1cc(C(=O)N3CCCC(O)C3)ccc1n2-c1ccc(C(F)(F)F)cc1] 1-{1-methyl-4-[4-(trifluoromethyl)-phenyl]-1H,4H-imidazo[4,5-b]indole-7-carbonyl}piperidin-3-ol | 1H NMR (300 MHz, DMSO-d6, ppm): 8.10 (d, J = 6.3 Hz, 2H), 7.98-7.85 (m, 5H), 7.29 (d, J = 6.3 Hz, 1H), 5.15-4.87 (m, 1H), 4.09 (s, 3H), 3.92-3.40 (m, 3H), 3.16-3.68 (m, 2H), 2.08-1.74 (m, 2H), 1.08-1.04 (m, 2H) | 9<br>0.74 min<br>443.20<br>(M + H) |

TABLE 1-continued

| Com-pound No. (Example No.) | Structure and Name | $^1$H-NMR | Conditions and elution time (min) LCMS (M + H$^+$) |
|---|---|---|---|
| | Table 1 below shows exemplary compounds of the present invention. They have been synthesized as described in the Examples above or similar thereto. | | |
| 398 | 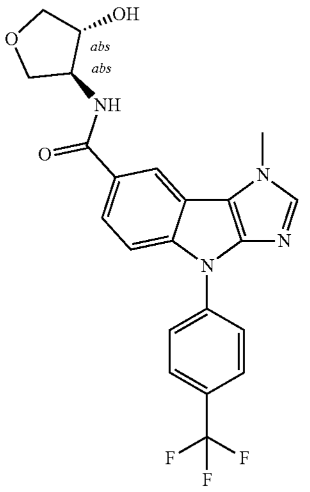 [SMILES: Cn1cnc2c1c1cc(C(=O)N[C@H]3COC[C@@H]3O)ccc1n2-c1ccc(C(F)(F)F)cc1] Absolute configuration known/assigned N-[(3S,4R)-4-hydroxyoxolan-3-yl]-1-methyl-4-[4-(trifluoromethyl)phenyl]-1H,4H-imidazo[4,5-b]indole-7-carboxamide | (400 MHz, DMSO-d6) δ 8.48 (d, J = 6.4 Hz, 1H), 8.42 (s, 1H), 8.10 (d, J = 8.5 Hz, 2H), 7.98 (d, J = 8.5 Hz, 2H), 7.91-7.80 (m, 3H), 5.32 (s, 1H), 4.32-4.25 (m, 2H), 4.13 (s, 3H), 4.06 (dd, J = 9.0, 5.6 Hz, 1H), 3.97 (dd, J = 9.3, 4.4 Hz, 1H), 3.71 (dd, J = 9.1, 3.1 Hz, 1H), 3.58 (dd, J = 9.3, 2.3 Hz, 1H). | 9 0.72 445.20 (M + H) |
| 399 | 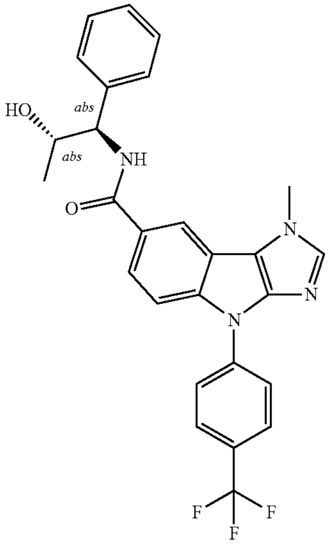 [SMILES: C[C@H](O)[C@H](NC(=O)c1ccc2c(c1)c1c(ncn1C)n2-c1ccc(C(F)(F)F)cc1)c1ccccc1] Absolute configuration known/assigned N-[(1R,2S)-2-hydroxy-1-phenylpropyl]-1-methyl-4-[4-(trifluoromethyl)phenyl]-1H,4H-imidazo[4,5-b]indole-7-carboxamide | (400 MHz, DMSO-d6) δ 8.61 (d, J = 8.8 Hz, 1H), 8.39 (s, 1H), 8.10 (d, J = 8.5 Hz, 2H), 7.98 (d, J = 8.6 Hz, 2H), 7.90-7.78 (m, 3H), 7.50-7.44 (m, 2H), 7.32 (dd, J = 8.3, 6.8 Hz, 2H), 7.26-7.17 (m, 1H), 4.95 (dd, J = 8.8, 7.1 Hz, 1H), 4.78 (d, J = 5.8 Hz, 1H), 4.13 (s, 3H), 4.10-4.04 (m, 1H), 1.18 (d, J = 6.2 Hz, 3H). | 9 0.86 min 493.20 (M + H) |

TABLE 1-continued

| Compound No. (Example No.) | Structure and Name | $^1$H-NMR | Conditions and elution time (min) LCMS (M + H$^+$) |
|---|---|---|---|
| | Table 1 below shows exemplary compounds of the present invention. They have been synthesized as described in the Examples above or similar thereto. | | |
| 400 | 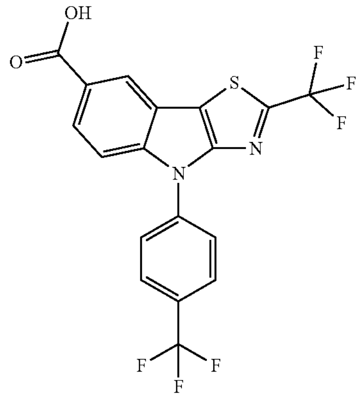 [SMILES: O=C(O)c1ccc2c(c1)c1sc(C(F)(F)F)nc1n2-c1ccc(C(F)(F)F)cc1] 2-(trifluoromethyl)-4-[4-(trifluoro-methyl)phenyl]-4H-[1,3]thiazolo[4,5-b]indole-7-carboxylic acid | (300 MHz, DMSO-d6) δ 12.93 (br, 1H), 8.93 (d, J = 1.6 Hz, 1H), 8.19-7.92 (m, 5H), 7.79 (d, J = 9.0 Hz, 1H). | 10 1.07 429.0 (M − H) |
| 401 | 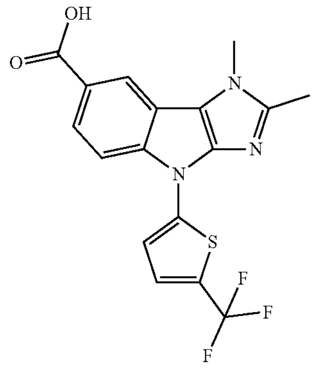 [SMILES: Cc1nc2c(c3cc(C(=O)O)ccc3n2-c2ccc(C(F)(F)F)s2)n1C] 1,2-dimethyl-4-[5-(trifluoromethyl)-thiophen-2-yl]-1H,4H-imidazo[4,5-b]indole-7-carboxylic acid | 1H NMR (400 MHz, DMSO-d6) 12.80 (s, 1H), 8.39 (s, 1H), 7.92-7.83 (m, 2H), 7.79 (m, 1H), 7.60 (d, J = 4.1 Hz, 1H), 3.99 (s, 3H), 2.54 (s, 3H). | 9 0.87 380.0 (M + H) |
| 402 | 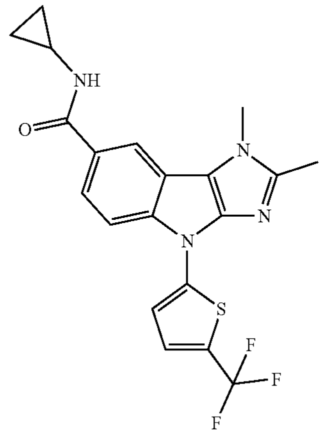 [SMILES: Cc1nc2c(c3cc(C(=O)NC4CC4)ccc3n2-c2ccc(C(F)(F)F)s2)n1C] N-cyclopropyl-1,2-dimethyl-4-[5-(trifluoromethyl)thiophen-2-yl]-1H,4H-imidazo[4,5-b]indole-7-carboxamide | 1H NMR (400 MHz, DMSO-d6) 8.46 (d, J = 4.0 Hz, 1H), 8.33 (d, J = 1.7 Hz, 1H), 7.87 (d, J = 8.7 Hz, 1H), 7.82-7.74 (m, 2H), 7.59 (m, 1H), 4.01 (s, 3H), 2.89 (m, 1H), 2.54 (s, 3H), 0.74 (td, J = 7.1, 4.7 Hz, 2H), 0.66-0.58 (m, 2H). | 9 0.87 419.10 (M + H) |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 403 | 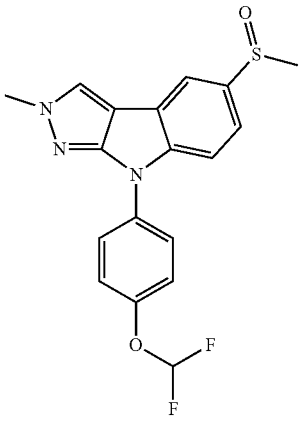 8-[4-(difluoromethoxy)phenyl]-5-methanesulfinyl-2-methyl-2H,8H-pyrazolo[3,4-b]indole | (400 MHz, DMSO-d6) δ 8.19 (s, 1H), 8.15 (d, J = 1.8 Hz, 1H), 7.84-7.80 (m, 2H), 7.67 (d, J = 8.6 Hz, 1H), 7.57 (dd, J = 8.6, 1.8 Hz, 1H), 7.44-7.40 (m, 2H), 7.31 (t, J = 74.0 Hz, 1H), 4.02 (s, 3H), 2.77 (s, 3H). | 8 1.510 min 375.9 (M + H) |
| 404 | 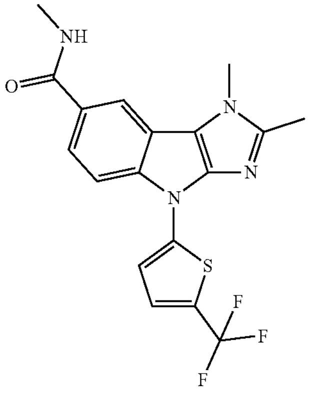 [SMILES: CNC(=O)c1ccc2c(c1)c1c(nc(C)n1C)n2-c1ccc(C(F)(F)F)s1] N,1,2-trimethyl-4-[5-(trifluoromethyl)thiophen-2-yl]-1H,4H-imidazo[4,5-b]indole-7-carboxamide | 1H NMR (400 MHz, DMSO-d6) 8.46 (d, J = 4.7 Hz, 1H), 8.36 (d, J = 1.8 Hz, 1H), 7.88 (d, J = 8.7 Hz, 1H), 7.78 (m, 2H), 7.60 (m, 1H), 4.01 (s, 3H), 2.85 (d, J = 4.4 Hz, 3H), 2.54 (s, 3H). | |

TABLE 1-continued

| Compound No. (Example No.) | Structure and Name | $^1$H-NMR | Conditions and elution time (min) LCMS (M + H$^+$) |
|---|---|---|---|
| Table 1 below shows exemplary compounds of the present invention. They have been synthesized as described in the Examples above or similar thereto. | | | |
| 405 | 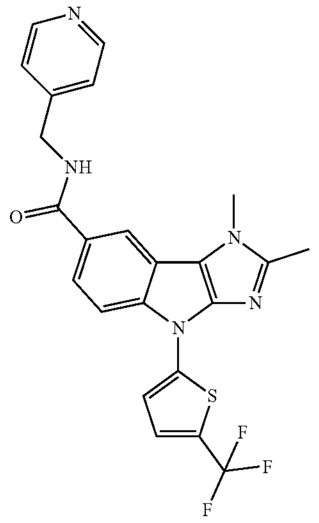 [SMILES: Cc1nc2c(c3cc(C(=O)NCc4ccncc4)ccc3n2-c2ccc(C(F)(F)F)s2)n1C] 1,2-dimethyl-N-[(pyridin-4-yl)methyl]-4-[5-(trifluoromethyl)thiophen-2-yl]-1H,4H-imidazo[4,5-b]indole-7-carboxamide | 1H NMR (400 MHz, DMSO-d6) 9.17 (t, J = 6.0 Hz, 1H), 8.57-8.51 (m, 2H), 8.45 (d, J = 1.7 Hz, 1H), 7.92 (d, J = 8.8 Hz, 1H), 7.86 (dd, J = 8.8, 1.8 Hz, 1H), 7.80 (m,, 1H), 7.61 (m, 1H), 7.40-7.34 (m, 2H), 4.58 (d, J = 5.8 Hz, 2H), 4.01 (s, 3H), 2.54 (s, 3H). | |
| 406 | 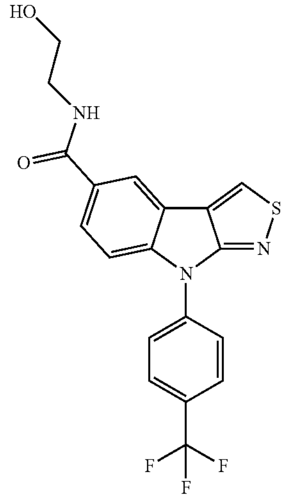 [SMILES: O=C(NCCO)c1ccc2c(c1)c1csnc1n2-c1ccc(C(F)(F)F)cc1] N-(2-hydroxyethyl)-8-[4-(trifluoro-methyl)phenyl]-8H-[1,2]thiazolo[3,4-b]indole-5-carboxamide | 1H NMR (400 MHz, DMSO-d6) 9.47 (s, 1H), 8.59 (d, J = 1.8 Hz, 1H), 8.51 (t, J = 5.6 Hz, 1H), 8.08 (d, J = 8.5 Hz, 2H), 8.04-7.96 (m, 3H), 7.64 (d, J = 8.7 Hz, 1H), 4.76 (t, J = 5.6 Hz, 1H), 3.60-3.51 (m, 2H), 3.43-3.34 (m, 2H). | |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 407 | 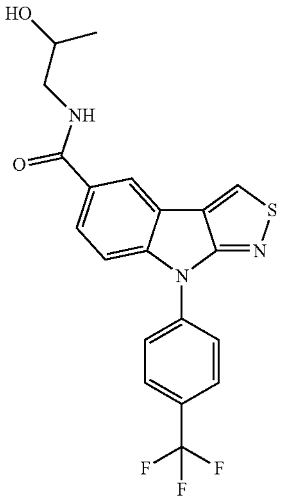 [SMILES: CC(O)CNC(=O)c1ccc2c(c1)c1csnc1n2-c1ccc(C(F)(F)F)cc1] N-(2-hydroxypropyl)-8-[4-(trifluoromethyl)phenyl]-8H-[1,2]thiazolo[3,4-b]indole-5-carboxamide | 1H NMR (400 MHz, DMSO-d6) 9.47 (s, 1H), 8.59 (d, J = 1.8 Hz, 1H), 8.47 (t, J = 5.7 Hz, 1H), 8.07 (d, J = 8.5 Hz, 2H), 8.04-7.96 (m, 3H), 7.64 (d, J = 8.7 Hz, 1H), 4.77 (d, J = 4.7 Hz, 1H), 3.88-3.76 (m, 1H), 3.30 (d, J = 15.4 Hz, 2H), 1.10 (d, J = 6.2 Hz, 3H). | |
| 408 | 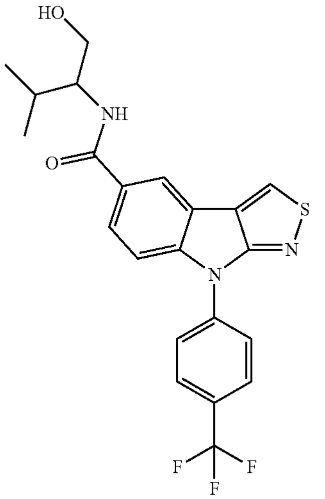 [SMILES: CC(C)C(CO)NC(=O)c1ccc2c(c1)c1csnc1n2-c1ccc(C(F)(F)F)cc1] N-(1-hydroxy-3-methylbutan-2-yl)-8-[4-(trifluoromethyl)phenyl]-8H-[1,2]thiazolo[3,4-b]indole-5-carboxamide | 1H NMR (400 MHz, DMSO-d6) 9.47 (s, 1H), 8.60 (d, J = 1.8 Hz, 1H), 8.08 (d, J = 8.4 Hz, 2H), 8.05-7.98 (m, 4H), 7.64 (d, J = 8.7 Hz, 1H), 4.59 (t, J = 5.6 Hz, 1H), 3.92-3.82 (m, 1H), 3.56 (t, J = 6.0 Hz, 2H),2.04-1.90 (m, 1H), 0.98-0.89 (m, 6H). | |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 409 | 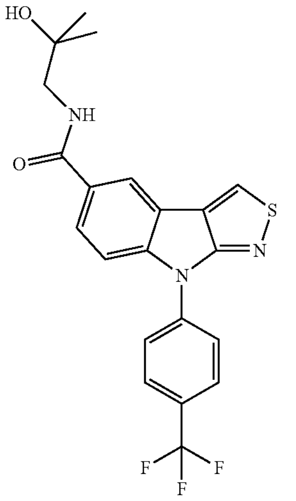 [SMILES: CC(C)(O)CNC(=O)c1ccc2c(c1)c1csnc1n2-c1ccc(C(F)(F)F)cc1] N-(2-hydroxy-2-methylpropyl)-8-[4-(trifluoromethyl)phenyl]-8H-[1,2]thiazolo[3,4-b]indole-5-carboxamide | 1H NMR (400 MHz, DMSO-d6) 9.48 (s, 1H), 8.61 (d, J = 1.8 Hz, 1H), 8.31 (t, J = 6.1 Hz, 1H), 8.08 (d, J = 8.5 Hz, 2H), 8.05-7.98 (m, 3H), 7.64 (d, J = 8.7 Hz, 1H), 4.59 (s, 1H), 3.31 (d, J = 6.1 Hz, 2H), 1.14 (s, 6H). | |
| 410 | 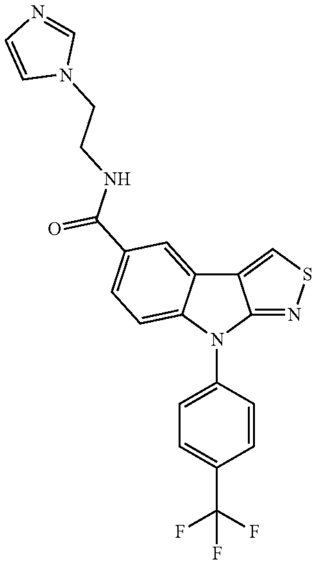 [SMILES: O=C(NCCn1ccnc1)c1ccc2c(c1)c1csnc1n2-c1ccc(C(F)(F)F)cc1] N-[2-(1H-imidazol-1-yl)ethyl]-8-[4-(trifluoromethyl)phenyl]-8H-[1,2]thiazolo[3,4-b]indole-5-carboxamide | 1H NMR (400 MHz, DMSO-d6) 9.48 (s, 1H), 8.68 (t, J = 5.6 Hz, 1H), 8.53 (d, J = 1.8 Hz, 1H), 8.07 (d, J = 8.4 Hz, 2H), 8.01 (d, J = 8.8 Hz, 2H), 7.98-7.91 (m, 1H), 7.68-7.59 (m, 2H), 7.18 (s, 1H), 6.88 (s, 1H), 4.21 (t, J = 6.0 Hz, 2H), 3.68-3.58 (m, 2H). | |

TABLE 1-continued

| Compound No. (Example No.) | Structure and Name | $^1$H-NMR | Conditions and elution time (min) LCMS (M + H$^+$) |
|---|---|---|---|
| 411 | 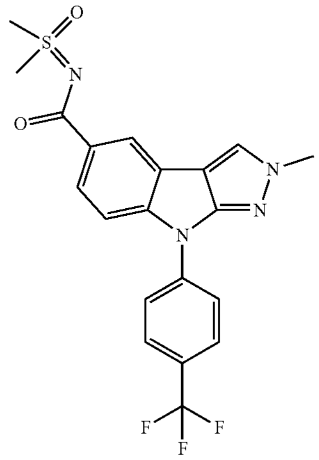 N-[dimethyl(oxo)-$\lambda^6$-sulfanylidene]-2-methyl-8-[4-(trifluoromethyl)phenyl]-2H,8H-pyrazolo[3,4-b]indole-5-carboxamide | (700 MHz, DMSO) δ 3.49 (s, 2H), 4.03 (s, 1H), 7.75 (d, J = 8.7 Hz, 1H), 7.94-8.01 (m, 1H), 8.08 (d, J = 8.4 Hz, 1H), 8.22 (s, 1H), 8.46 (d, J = 1.8 Hz, 1H). | 8 1.69 min 434.90 (M + H) |
| 412 | 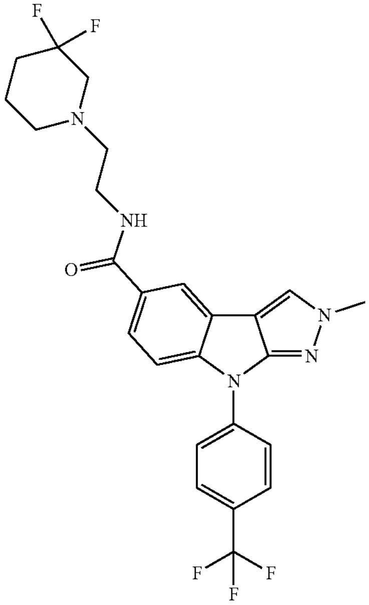 [SMILES: Cn1cc2c3cc(C(=O)NCCN4CCCC(F)(F)C4)ccc3n(-c3ccc(C(F)(F)F)cc3)c2n1] N-[2-(3,3-difluoropiperidin-1-yl)ethyl]-2-methyl-8-[4-(trifluoromethyl)phenyl]-2H,8H-pyrazolo[3,4-b]indole-5-carboxamide | (400 MHz, DMSO-d6) δ 8.83-8.75 (m, 1H), 8.35 (d, J = 1.8 Hz, 1H), 8.22 (s, 1H), 8.12-8.05 (m, 2H), 8.01-7.95 (m, 2H), 7.86 (dd, J = 8.7, 1.8 Hz, 1H), 7.81 (d, J = 8.7 Hz, 1H), 4.04 (s, 3H), 3.74-3.61 (m, 2H), 3.94-2.93 (m, 4H), 3.43-3.25 (m, 2H), 2.28-1.78 (m, 4H). | 8 1.43 min 505.90 (M + H) |

Table 1 below shows exemplary compounds of the present invention. They have been synthesized as described in the Examples above or similar thereto.

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 413 | 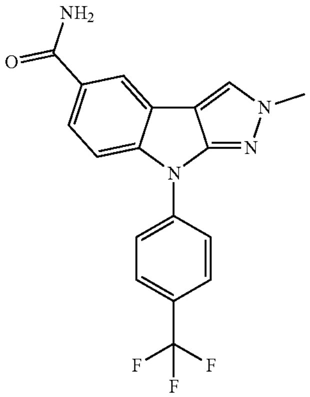 2-methyl-4-[4-(trifluoromethyl)phenyl]-2H,4H-pyrazolo[4,3-b]indole-7-carboxamide | (400 MHz, DMSO) δ 8.50 (d, J = 1.8 Hz, 1H), 8.10 (s, 1H), 8.05 (s, 1H), 7.97 (dd, J = 8.8, 1.9 Hz, 1H), 7.93 (s, 4H), 7.84 (d, J = 8.8 Hz, 1H), 7.28 (s, 1H), 4.09 (s, 3H). | 16 1.29 min 359.10 (M + H); 381.00 (M + Na); 739.10 (2M + Na) |
| 414 | 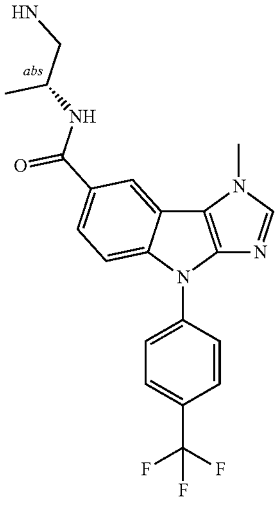 [SMILES: C[C@H](CN)NC(=O)c1ccc2c(c1)c1c(ncn1C)n2-c1ccc(C(F)(F)F)cc1] Absolute configuration assigned/known N-[(2R)-1-hydroxypropan-2-yl]-1-methyl-4-[4-(trifluoromethyl)phenyl]-1H,4H-imidazo[4,5-b]indole-7-carboxamide | 1H NMR (300 MHz, DMSO-d6) 8.42 (d, J = 1.6 Hz, 1H), 8.12 (dd, J = 8.4, 3.0 Hz, 3H), 7.99 (d, J = 8.6 Hz, 2H), 7.91-7.79 (m, 3H), 4.78 (s, 1H), 4.14 (s, 4H), 3.59-3.47 (m, 1H), 3.46-3.37 (m, 1H), 1.20 (d, J = 6.7 Hz, 3H). | |

TABLE 1-continued

| Com-pound No. (Example No.) | Structure and Name | $^1$H-NMR | Conditions and elution time (min) LCMS (M + H$^+$) |
|---|---|---|---|
| Table 1 below shows exemplary compounds of the present invention. They have been synthesized as described in the Examples above or similar thereto. | | | |
| 415 | 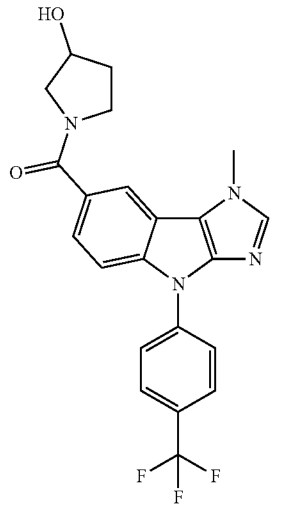 [SMILES: Cn1cnc2c1c1cc(C(=O)N3CCC(O)C3)ccc1n2-c1ccc(C(F)(F)F)cc1] 1-{1-methyl-4-[4-(trifluoro-methyl)phenyl]-1H,4H-imidazo[4,5-b]indole-7-carbonyl}pyrrolidin-3-ol | 1H NMR (300 MHz, DMSO-d6) 8.11 (d, J = 8.4 Hz, 2H), 8.05 (s, 1H), 7.98 (d, J = 8.6 Hz, 2H), 7.87 (d, J = 7.9 Hz, 2H), 7.44 (d, J = 8.7 Hz, 1H), 5.05 (s, 1H), 4.32 (d, J = 31.8 Hz, 1H), 4.11 (s, 3H), 3.46-3.37 (m, 1H), 3.76-3.50 (m, 3H), 2.08-1.73 (m, 2H). | |
| 416 | 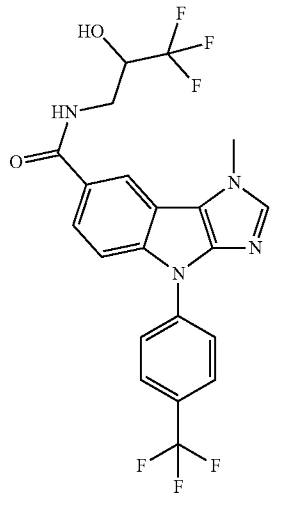 [SMILES: Cn1cnc2c1c1cc(C(=O)NCC(O)C(F)(F)F)ccc1n2-c1ccc(C(F)(F)F)cc1] 1-methyl-N-(3,3,3-trifluoro-2-hydroxypropyl)-4-[4-(trifluoro-methyl)phenyl]-1H,4H-imidazo[4,5-b]indole-7-carboxamide | 1H NMR (300 MHz, DMSO-d6, ppm): 8.87 (s, 1H), 8.78 (s, 1H), 8.10 (d, J = 6.3 Hz, 2H), 7.98 (d, J = 6.3 Hz, 2H), 7.91-7.82 (m, 3H), 6.57-6.55 (m, 1H), 4.26-4.24 (m, 1H), 4.13 (s, 3H), 3.73-3.69 (m, 1H) | |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 417 | 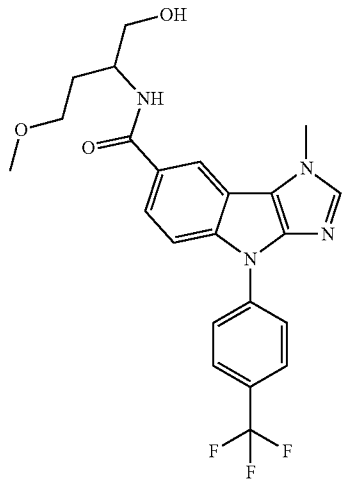 [SMILES: COCCC(CO)NC(=O)c1ccc2c(c1)c1c(ncn1C)n2-c1ccc(C(F)(F)F)cc1] N-(1-hydroxy-4-methoxybutan-2-yl)-1-methyl-4-[4-(trifluoromethyl)phenyl]-1H,4H-imidazo[4,5-b]indole-7-carboxamide | 1H NMR (300 MHz, DMSO-d6) 8.42 (d, J = 1.6 Hz, 1H), 8.11 (d, J = 8.3 Hz, 3H), 7.99 (d, J = 8.5 Hz, 2H), 7.91-7.76 (m, 3H), 4.14 (s, 5H), 3.58-3.35 (m, 4H), 3.24(s, 3H), 1.94 (dt, J = 12.1, 6.6 Hz, 1H), 1.84-1.71 (m,1H) | |
| 418 | 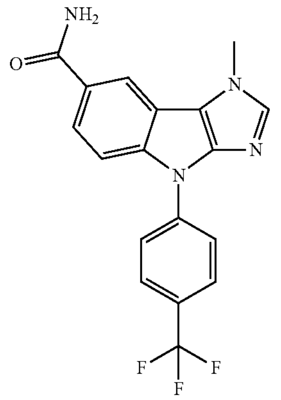 [SMILES: Cn1cnc2c1c1cc(C(N)=O)ccc1n2-c1ccc(C(F)(F)F)cc1] 1-methyl-4-[4-(trifluoromethyl)phenyl]-1H,4H-imidazo[4,5-b]indole-7-carboxamide | 1H NMR (300 MHz, DMSO-d6) 8.47 (d, J = 1.5 Hz, 1H), 8.11 (d, J = 8.4 Hz, 2H), 8.00 (t, J = 10.2 Hz, 3H), 7.86 (dd, J = 4.2, 2.2 Hz, 3H), 7.33 (s, 1H), 4.12 (s, 3H). | |

TABLE 1-continued

| Com-pound No. (Example No.) | Structure and Name | $^1$H-NMR | Conditions and elution time (min) LCMS (M + H$^+$) |
|---|---|---|---|
| | Table 1 below shows exemplary compounds of the present invention. They have been synthesized as described in the Examples above or similar thereto. | | |
| 419 | 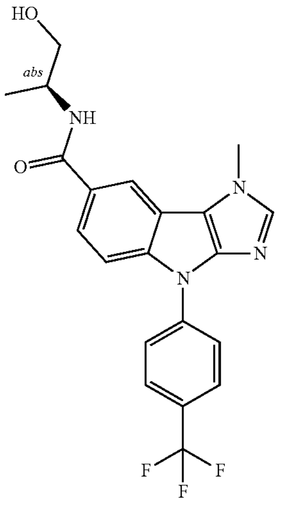 [SMILES: C[C@@H](CO)NC(=O)c1ccc2c(c1)c1c(ncn1C)n2-c1ccc(C(F)(F)F)cc1] Absolute configuration known/assigned N-[(2S)-1-hydroxypropan-2-yl]-1-methyl-4-[4-(trifluoromethyl)phenyl]-1H,4H-imidazo[4,5-b]indole-7-carboxamide | 1H NMR (300 MHz, DMSO-d6) 8.42 (d, J = 1.7 Hz, 1H), 8.17-8.07 (m, 3H), 7.98 (d, J = 8.5 Hz, 2H), 7.89-7.78 (m, 3H), 4.81 (s, 1H), 4.14 (s, 4H), 3.53 (dd, J = 10.8, 5.7 Hz, 1H), 3.40 (dd, J = 10.5, 6.4 Hz, 1H), 1.20 (d, J = 6.7 Hz, 3H). | |
| 420 | 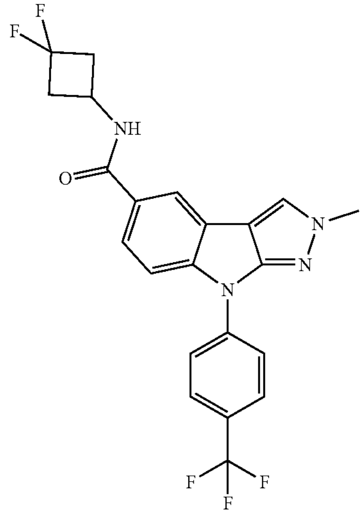 [SMILES: Cn1cc2c3cc(C(=O)NC4CC(F)(F)C4)ccc3n(-c3ccc(C(F)(F)F)cc3)c2n1] N-(3,3-difluorocyclobutyl)-2-methyl-8-[4-(trifluoromethyl)phenyl]-2H,8H-pyrazolo[3,4-b]indole-5-carboxamide | 1H NMR (400 MHz, DMSO) d 8.83 (d, J = 6.6 Hz, 1H), 8.34 (d, J = 1.8 Hz, 1H), 8.20 (s, 1H), 8.12-8.05 (m, 2H), 7.97 (d, J = 8.5 Hz, 2H), 7.86 (dd, J = 8.7, 1.8 Hz, 1H), 7.78 (d, J = 8.7 Hz, 1H), 4.33 (p, J = 7.4 Hz, 1H), 4.04 (s, 3H), 3.05-2.90 (m, 1H), 2.88-2.70 (m, 1H). | 18 1.43 449.1 |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 421 | 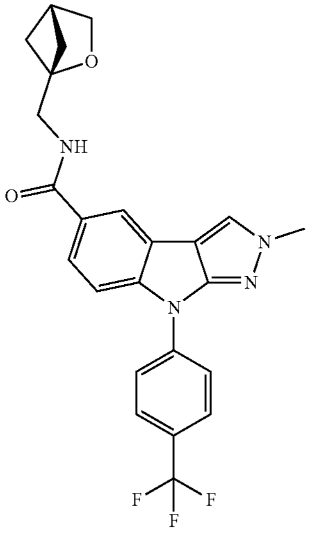 [SMILES: Cn1cc2c3cc(C(=O)NC[C@]45C[C@H](CO4)C5)ccc3n(-c3ccc(C(F)(F)F)cc3)c2n1] 2-methyl-N-({2-oxabicyclo[2.1.1]hexan-1-yl}methyl)-8-[4-(trifluoromethyl)phenyl]-2H,8H-pyrazolo[3,4-b]indole-5-carboxamide | 1H NMR (700 MHz, DMSO) d 8.56 (t, J = 6.0 Hz, 1H), 8.37 (d, J = 1.8 Hz, 1H), 8.21 (s, 1H), 8.09 (d, J = 8.3 Hz, 2H), 7.97 (d, J = 8.3 Hz, 2H), 7.87 (dd, J = 8.7, 1.8 Hz, 1H), 7.77 (d, J = 8.7 Hz, 1H), 4.04 (s, 3H), 3.67 (s, 2H), 3.62 (d, J = 6.0 Hz, 2H), 2.84 (t, J = 3.2 Hz, 1H), 1.76 (ddd, J = 4.8, 3.1, 1.8 Hz, 2H), 1.34 (dd, J = 4.6, 1.8 Hz, 2H). | 18<br>1.39<br>455.1 |
| 422 | 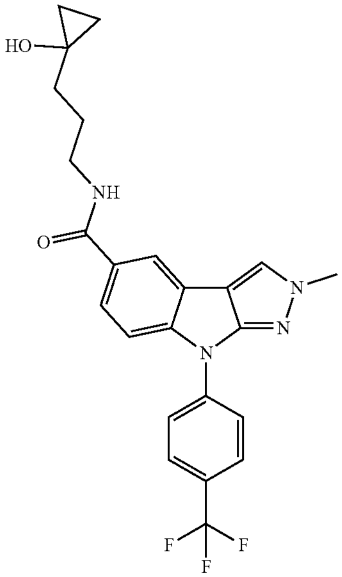 [SMILES: Cn1cc2c3cc(C(=O)NCCCC4(O)CC4)ccc3n(-c3ccc(C(F)(F)F)cc3)c2n1] N-[3-(1-hydroxycyclopropyl)propyl]-2-methyl-8-[4-(trifluoromethyl)phenyl]-2H,8H-pyrazolo[3,4-b]indole-5-carboxamide | 1H NMR (700 MHz, DMSO) d 8.46 (t, J = 5.6 Hz, 1H), 8.33 (d, J = 1.8 Hz, 1H), 8.20 (s, 1H), 8.09 (d, J = 8.5 Hz, 2H), 7.97 (d, J = 8.5 Hz, 2H), 7.84 (dd, J = 8.6, 1.9 Hz, 1H), 7.77 (d, J = 8.6 Hz, 1H), 5.02 (s, 1H), 4.03 (s, 3H), 3.34 (dd, J = 7.1, 5.5 Hz, 1H), 1.74 (p, J = 7.4 Hz, 2H), 1.53-1.49 (m, 2H), 0.55-0.51 (m, 2H), 0.36-0.32 (m, 2H). | 18<br>1.36<br>457.2 |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
| --- | --- | --- | --- |
| 423 | 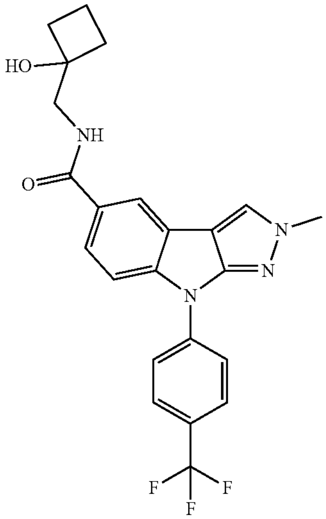 [SMILES: Cn1cc2c3cc(C(=O)NCC4(O)CCC4)ccc3n(-c3ccc(C(F)(F)F)cc3)c2n1] N-[(1-hydroxycyclobutyl)methyl]-2-methyl-8-[4-(trifluoromethyl)phenyl]-2H,8H-pyrazolo[3,4-b]indole-5-carboxamide | 1H NMR (700 MHz, DMSO) d 8.38 (d, J = 1.9 Hz, 1H), 8.36 (t, J = 5.9 Hz, 1H), 8.21 (s, 1H), 8.09 (d, J = 8.4 Hz, 2H), 7.97 (d, J = 8.5 Hz, 2H), 7.88 (dd, J = 8.6, 1.9 Hz, 1H), 7.78 (d, J = 8.6 Hz, 1H), 5.24 (s, 1H), 4.04 (s, 3H), 3.47 (d, J = 5.8 Hz, 2H), 2.08 (tt, J = 8.8, 3.0 Hz, 2H), 1.93 (qd, J = 9.6, 2.8 Hz, 2H), 1.69-1.61 (m, 1H), 1.54-1.46 (m, 1H). | 18<br>1.35<br>443.1 |
| 424 | 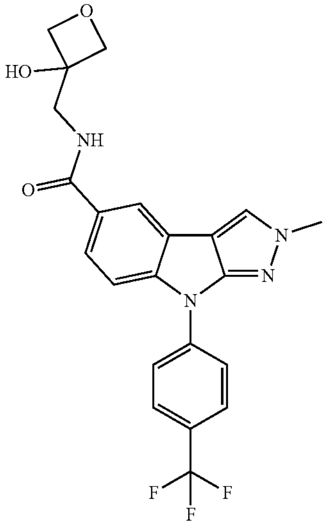 [SMILES: Cn1cc2c3cc(C(=O)NCC4(O)COC4)ccc3n(-c3ccc(C(F)(F)F)cc3)c2n1] N-[(3-hydroxyoxetan-3-yl)methyl]-2-methyl-8-[4-(trifluoromethyl)phenyl]-2H,8H-pyrazolo[3,4-b]indole-5-carboxamide | 1H NMR (700 MHz, DMSO) d 8.65 (t, J = 6.0 Hz, 1H), 8.38 (d, J = 1.9 Hz, 1H), 8.22 (s, 1H), 8.09 (d, J = 8.5 Hz, 2H), 7.97 (d, J = 8.4 Hz, 2H), 7.89 (dd, J = 8.7, 1.8 Hz, 1H), 7.79 (d, J = 8.6 Hz, 1H), 5.90 (s, 1H), 4.56-4.52 (m, 2H), 4.41 (d, J = 6.5 Hz, 2H), 4.34 (t, J = 5.1 Hz, 0H), 4.04 (s, 3H), 3.61 (d, J = 6.0 Hz, 2H). | 18<br>1.27<br>445.1 |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 425 | 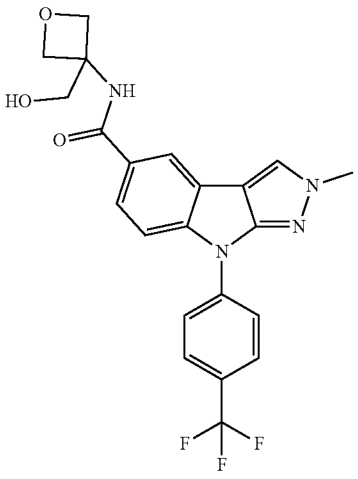 [SMILES: Cn1cc2c3cc(C(=O)NC4(CO)COC4)ccc3n(-c3ccc(C(F)(F)F)cc3)c2n1] N-[3-(hydroxymethyl)oxetan-3-yl]-2-methyl-8-[4-(trifluoromethyl)phenyl]-2H,8H-pyrazolo[3,4-b]indole-5-carboxamide | 1H NMR (400 MHz, DMSO) d 8.85 (s, 1H), 8.38 (d, J = 1.8 Hz, 1H), 8.20 (s, 1H), 8.09 (d, J = 8.4 Hz, 2H), 7.97 (d, J = 8.6 Hz, 2H), 7.88 (dd, J = 8.8, 1.9 Hz, 1H), 7.78 (d, J = 8.7 Hz, 1H), 5.12 (t, J = 5.9 Hz, 1H), 4.67 (d, J = 6.5 Hz, 2H), 4.57 (d, J = 6.5 Hz, 2H), 4.04 (s, 3H), 3.78 (d, J = 5.9 Hz, 2H). | 18 1.26 445.3 |
| 426 | 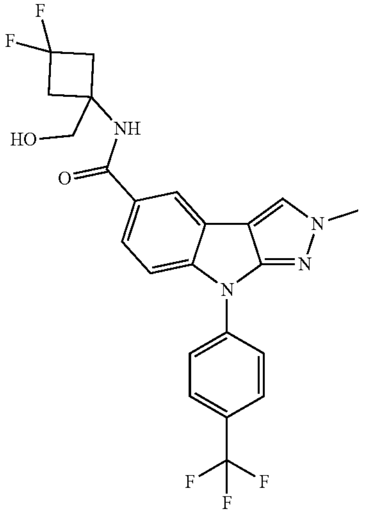 [SMILES: Cn1cc2c3cc(C(=O)NC4(CO)CC(F)(F)C4)ccc3n(-c3ccc(C(F)(F)F)cc3)c2n1] N-[3,3-difluoro-1-(hydroxymethyl)cyclobutyl]-2-methyl-8-[4-(trifluoromethyl)phenyl]-2H,8H-pyrazolo[3,4-b]indole-5-carboxamide | 1H NMR (700 MHz, DMSO) d 8.66 (s, 1H), 8.37 (d, J = 1.8 Hz, 1H), 8.22 (s, 1H), 8.09 (d, J = 8.5 Hz, 2H), 7.97 (d, J = 8.5 Hz, 2H), 7.87 (dd, J = 8.7, 1.9 Hz, 1H), 7.78 (d, J = 8.6 Hz, 1H), 5.17 (t, J = 5.9 Hz, 1H), 4.34 (t, J = 5.1 Hz, 0H), 4.14 (s, 0H), 4.09 (q, J = 5.3 Hz, 0H), 4.04 (s, 3H), 3.65 (d, J = 5.8 Hz, 2H), 2.88 (dd, J = 14.4, 10.3 Hz, 4H). | 18 1.37 479.1 |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 427 | 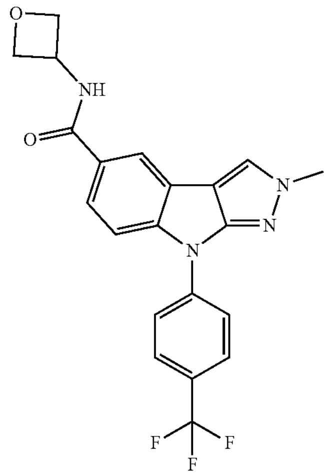 [SMILES: Cn1cc2c3cc(C(=O)NC4COC4)ccc3n(-c3ccc(C(F)(F)F)cc3)c2n1] 2-methyl-N-(oxetan-3-yl)-8-[4-(trifluoromethyl)phenyl]-2H,8H-pyrazolo[3,4-b]indole-5-carboxamide | 1H NMR (700 MHz, DMSO) d 9.13 (d, J = 6.4 Hz, 1H), 8.39 (d, J = 1.8 Hz, 1H), 8.22 (s, 1H), 8.09 (d, J = 8.4 Hz, 2H), 7.97 (d, J = 8.4 Hz, 2H), 7.89 (dd, J = 8.7, 1.9 Hz, 1H), 7.79 (d, J = 8.7 Hz, 1H), 5.06 (h, J = 6.8 Hz, 1H), 4.80 (dd, J = 7.6, 6.3 Hz, 2H), 4.64 (t, J = 6.5 Hz, 2H), 4.04 (s, 3H). | 18 1.32 415.1 |
| 428 | 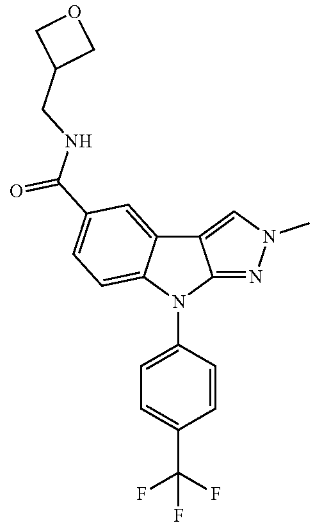 [SMILES: Cn1cc2c3cc(C(=O)NCC4COC4)ccc3n(-c3ccc(C(F)(F)F)cc3)c2n1] 2-methyl-N-[(oxetan-3-yl)methyl]-8-[4-(trifluoromethyl)phenyl]-2H,8H-pyrazolo[3,4-b]indole-5-carboxamide | 1H NMR (700 MHz, DMSO) d 8.65 (t, J = 5.7 Hz, 1H), 8.33 (d, J = 1.9 Hz, 1H), 8.21 (s, 1H), 8.08 (d, J = 8.3 Hz, 2H), 7.97 (d, J = 8.6 Hz, 2H), 7.84 (dd, J = 8.7, 1.9 Hz, 1H), 7.78 (d, J = 8.6 Hz, 1H), 4.66 (dd, J = 7.8, 6.0 Hz, 2H), 4.38 (t, J = 5.9 Hz, 2H), 4.04 (s, 3H), 3.58 (dd, J = 7.1, 5.6 Hz, 2H), 3.20 (ddd, J = 13.3, 7.5, 5.9 Hz, 1H). | 18 1.32 429.1 |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 429 | 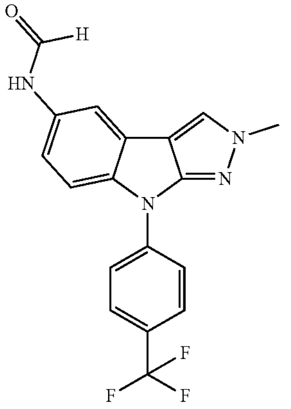 [SMILES: Cn1cc2c3cc(NC=O)ccc3n(-c3ccc(C(F)(F)F)cc3)c2n1] N-{2-methyl-8-[4-(trifluoromethyl)phenyl]-2H,8H-pyrazolo[3,4-b]indol-5-yl}formamide | 1H NMR (400 MHz, DMSO-d6) 10.26-10.14 (m, 1H), 8.30 (d, J = 1.9 Hz, 1H), 8.19-8.10 (m, 2H), 8.11-8.03 (m, 2H), 7.92 (d, J = 8.6 Hz, 2H), 7.76-7.69 (m, 1H), 7.45-7.38 (m, 1H), 4.01 (d, J = 2.2 Hz, 3H). | |
| 430 | 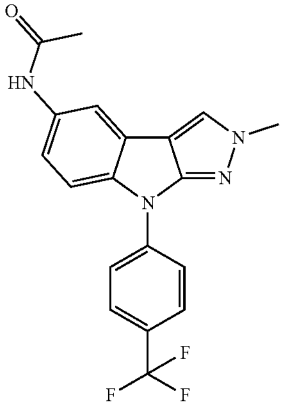 [SMILES: CC(=O)Nc1ccc2c(c1)c1cn(C)nc1n2-c1ccc(C(F)(F)F)cc1] N-{2-methyl-8-[4-(trifluoromethyl)phenyl]-2H,8H-pyrazolo[3,4-b]indol-5-yl}acetamide | 1H NMR (400 MHz, DMSO-d6) 2.07 (s, 3H), 4.00 (s, 3H), 7.34-7.41 (m, 1H), 7.71 (d, J = 8.9 Hz, 1H), 7.92 (d, J = 8.6 Hz, 2H), 8.07 (d, J = 8.4 Hz, 2H), 8.17 (d, J = 2.5 Hz, 2H), 9.98 (s, 1H). | |
| 431 | 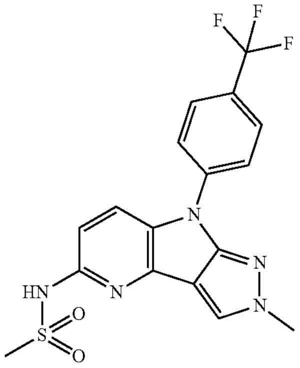 N-{4-methyl-7-[4-(trifluoromethyl)-phenyl]-4,5,7,12-tetraazatricyclo[6.4.0.0$^{2,6}$]dodeca-1(8),2,5,9,11-pentaen-11-yl}methanesulfonamide | 1H NMR (300 MHz, DMSO, ppm) 9.57 (s, 1H), 8.18 (s, 1H), 8.07 (d, J = 8.4 Hz, 2H), 7.93 (d, J = 8.5 Hz, 2H), 7.74 (d, J = 8.8 Hz, 1H), 7.67 (d, J = 2.2 Hz, 1H), 7.19 (dd, J = 8.8, 2.3 Hz, 1H), 4.01 (s, 3H), 2.95 (s, 3H). | |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 432 | 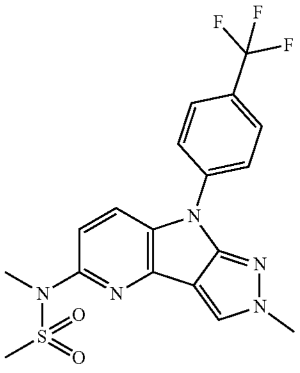 N-methyl-N-{4-methyl-7-[4-(trifluoromethyl)phenyl]-4,5,7,12-tetraazatricyclo[6.4.0.0$^{2,6}$]dodeca-1(8),2,5,9,11-pentaen-11-yl}methanesulfonamide | | |
| 433 | 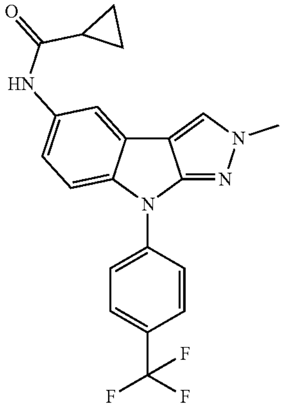 [SMILES: Cn1cc2c3cc(NC(=O)C4CC4)ccc3n(-c3ccc(C(F)(F)F)cc3)c2n1] N-{2-methyl-8-[4-(trifluoromethyl)-phenyl]-2H,8H-pyrazolo[3,4-b]indol-5-yl}cyclopropanecarboxamide | 1H NMR (400 MHz, DMSO-d6) 0.75-0.89 (m, 4H), 1.75-1.87 (m, 1H), 4.01 (s, 3H), 7.36-7.44 (m, 1H), 7.71 (d, J = 8.9 Hz, 1H), 7.92 (d, J = 8.6 Hz, 2H), 8.08 (d, J = 8.4 Hz, 2H), 8.12-8.2 (m, 2H), 10.23 (s, 1H). | |
| 434 | 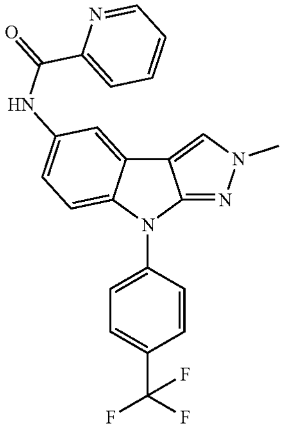 [SMILES: Cn1cc2c3cc(NC(=O)c4ccccn4)ccc3n(-c3ccc(C(F)(F)F)cc3)c2n1] N-{2-methyl-8-[4-(trifluoromethyl)-phenyl]-2H,8H-pyrazolo[3,4-b]indol-5-yl}pyridine-2-carboxamide | 1H NMR (400 MHz, DMSO-d6) 4.02 (s, 3H), 7.66-7.72 (m, 1H), 7.77 (s, 2H), 7.93 (d, J = 8.7 Hz, 2H), 8.10 (d, J = 8.9 Hz, 3H), 8.19 (d, J = 7.0 Hz, 2H), 8.45 (s, 1H), 8.76 (d, J = 4.5 Hz, 1H), 10.69 (s, 1H). | |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 435 | 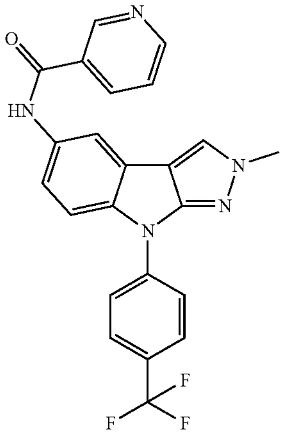 [SMILES: Cn1cc2c3cc(NC(=O)c4cccnc4)ccc3n(-c3ccc(C(F)(F)F)cc3)c2n1] N-{2-methyl-8-[4-(trifluoromethyl)-phenyl]-2H,8H-pyrazolo[3,4-b]indol-5-yl}pyridine-3-carboxamide | 1H NMR (400 MHz, DMSO-d6) 4.03 (s, 3H), 7.55-7.68 (m, 2H), 7.79 (d, J = 8.8 Hz, 1H), 7.94 (d, J = 8.4 Hz, 2H), 8.11 (d, J = 8.3 Hz, 2H), 8.20 (s, 1H), 8.3-8.38 (m, 2H), 8.74-8.81 (m, 1H), 9.13-9.18 (m, 1H), 10.50 (s, 1H). | |
| 436 | 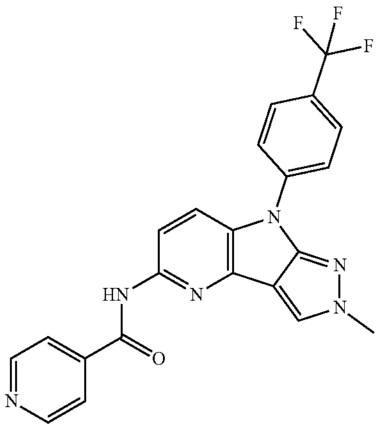 [SMILES: Cn1cc2c3nc(NC(=O)c4ccncc4)ccc3n(-c3ccc(C(F)(F)F)cc3)c2n1] N-{4-methyl-7-[4-(trifluoromethyl)-phenyl]-4,5,7,12-tetraazatri-cyclo[6.4.0.0$^{2,6}$]dodeca-1(8),2,5,9,11-pentaen-11-yl}pyridine-4-carboxamide | | |

TABLE 1-continued

| Com-pound No. (Example No.) | Structure and Name | $^1$H-NMR | Conditions and elution time (min) LCMS (M + H$^+$) |
|---|---|---|---|
| | Table 1 below shows exemplary compounds of the present invention. They have been synthesized as described in the Examples above or similar thereto. | | |
| 437 | 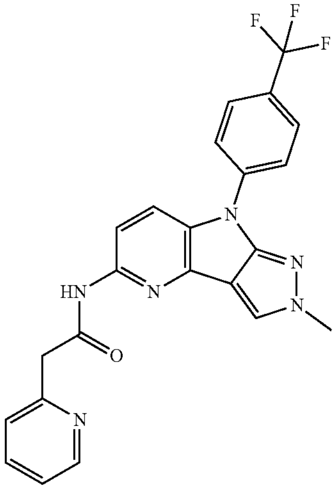 [SMILES: Cn1cc2c3nc(NC(=O)Cc4ccccn4)ccc3n(-c3ccc(C(F)(F)F)cc3)c2n1] N-{4-methyl-7-[4-(trifluoromethyl)-phenyl]-4,5,7,12-tetraazatri-cyclo[6.4.0.0$^{2,6}$]dodeca-1(8),2,5,9,11-pentaen-11-yl}-2-(pyridin-2-yl)acetamide | | |
| 438 | 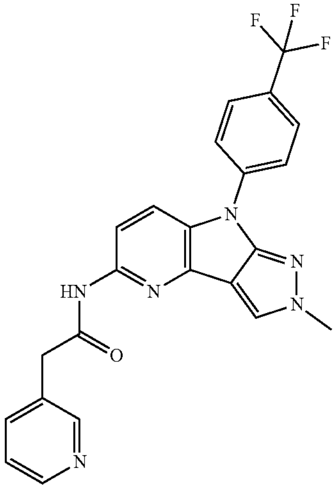 [SMILES: Cn1cc2c3nc(NC(=O)Cc4cccnc4)ccc3n(-c3ccc(C(F)(F)F)cc3)c2n1] N-{4-methyl-7-[4-(trifluoromethyl)-phenyl]-4,5,7,12-tetraazatri-cyclo[6.4.0.0$^{2,6}$]dodeca-1(8),2,5,9,11-pentaen-11-yl}-2-(pyridin-3-yl)acetamide | | |

TABLE 1-continued

| Compound No. (Example No.) | Structure and Name | $^1$H-NMR | Conditions and elution time (min) LCMS (M + H$^+$) |
|---|---|---|---|
| Table 1 below shows exemplary compounds of the present invention. They have been synthesized as described in the Examples above or similar thereto. | | | |
| 439 | 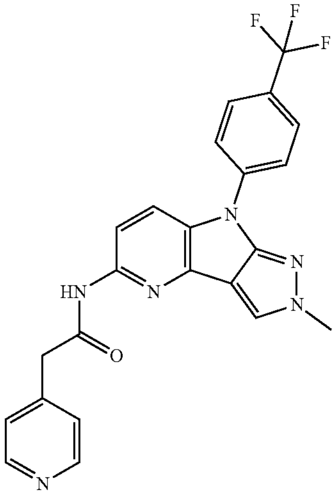 [SMILES: Cn1cc2c3nc(NC(=O)Cc4ccncc4)ccc3n(-c3ccc(C(F)(F)F)cc3)c2n1] N-{4-methyl-7-[4-(trifluoromethyl)phenyl]-4,5,7,12-tetraazatricyclo[6.4.0.0$^{2,6}$]dodeca-1(8),2,5,9,11-pentaen-11-yl}-2-(pyridin-4-yl)acetamide | | |
| 440 | 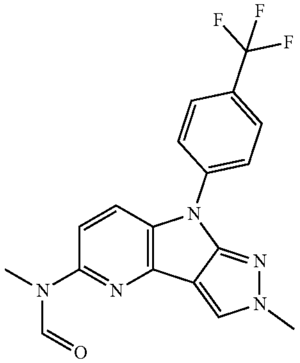 N-methyl-N-{4-methyl-7-[4-(trifluoromethyl)phenyl]-4,5,7,12-tetraazatricyclo[6.4.0.0$^{2,6}$]dodeca-1(8),2,5,9,11-pentaen-11-yl}formamide | 1H NMR (400 MHz, DMSO-d6) 8.49 (s, 1H), 8.13 (s, 1H), 8.08 (d, J = 8.4 Hz, 2H), 7.94 (d, J = 8.3 Hz, 2H), 7.83-7.75 (m, 2H), 7.28 (dd, J = 8.9, 2.4 Hz, 1H), 4.03 (s, 3H), 3.31 (d, J = 1.2 Hz, 5H). | |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 441 | 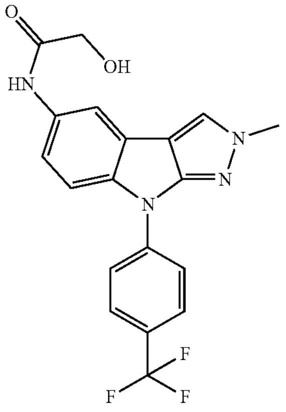 [SMILES: Cn1cc2c3cc(NC(=O)CO)ccc3n(-c3ccc(C(F)(F)F)cc3)c2n1] 2-hydroxy-N-{2-methyl-8-[4-(trifluoromethyl)phenyl]-2H,8H-pyrazolo[3,4-b]indol-5-yl}acetamide | 1H NMR (400 MHz, DMSO-d6) 4.02 (d, J = 8.0 Hz, 5H), 5.66 (t, J = 5.9 Hz, 1H), 7.51-7.60 (m, 1H), 7.72 (d, J = 8.9 Hz, 1H), 7.92 (d, J = 8.4 Hz, 2H), 8.08 (d, J = 8.4 Hz, 2H), 8.16 (s, 1H), 8.24 (d, J = 2.1 Hz, 1H), 9.69 (s, 1H). | |
| 442 | 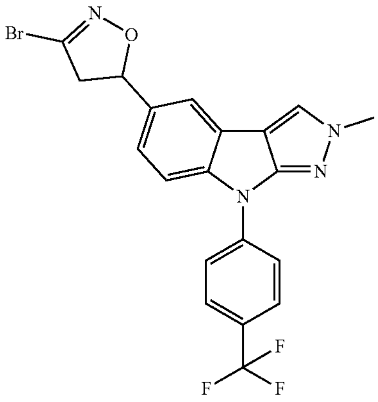 3-bromo-5-{2-methyl-8-[4-(trifluoromethyl)phenyl]-2H,8H-pyrazolo[3,4-b]indol-5-yl}-4,5-dihydro-1,2-oxazole | 1H NMR (400 MHz, Chloroform-d) 7.94 (d, J = 8.3 Hz, 2H), 7.86-7.76 (m, 3H), 7.69-7.61 (m, 2H), 7.31-7.24 (m, 1H), 5.88-5.79 (m, 1H), 4.09 (s, 3H), 3.75-3.68 (m, 1H), 3.39-3.30 (m, 1H). | |
| 443 | 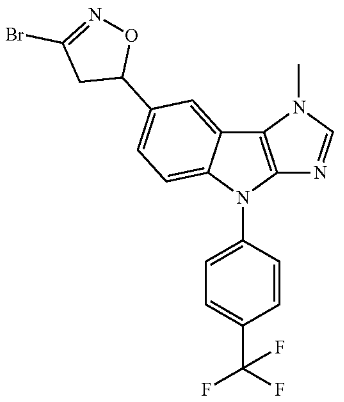 [SMILES: Cn1cnc2c1c1cc(C3CC(Br)=NO3)ccc1n2-c1ccc(C(F)(F)F)cc1] 3-bromo-5-{1-methyl-4-[4-(trifluoromethyl)phenyl]-1H,4H-imidazo[4,5-b]indol-7-yl}-4,5-dihydro-1,2-oxazole | | |

TABLE 1-continued

| Compound No. (Example No.) | Structure and Name | $^1$H-NMR | Conditions and elution time (min) LCMS (M + H$^+$) |
|---|---|---|---|
| Table 1 below shows exemplary compounds of the present invention. They have been synthesized as described in the Examples above or similar thereto. | | | |
| 444 | 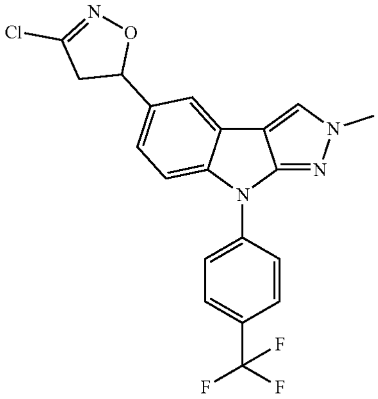 [SMILES: Cn1cc2c3cc(C4CC(Cl)=NO4)ccc3n(-c3ccc(C(F)(F)F)cc3)c2n1] 3-chloro-5-{2-methyl-8-[4-(trifluoromethyl)phenyl]-2H,8H-pyrazolo[3,4-b]indol-5-yl}-4,5-dihydro-1,2-oxazole | | |
| 445 | 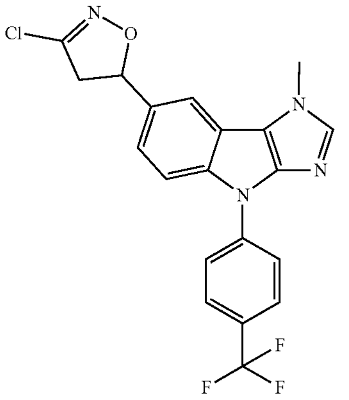 [SMILES: Cn1cnc2c1c1cc(C3CC(Cl)=NO3)ccc1n2-c1ccc(C(F)(F)F)cc1] 3-chloro-5-{1-methyl-4-[4-(trifluoromethyl)phenyl]-1H,4H-imidazo[4,5-b]indol-7-yl}-4,5-dihydro-1,2-oxazole | | |

TABLE 1-continued
| Com-pound No. (Example No.) | Structure and Name | $^1$H-NMR | Conditions and elution time (min) LCMS (M + H$^+$) |
|---|---|---|---|
| 446 | 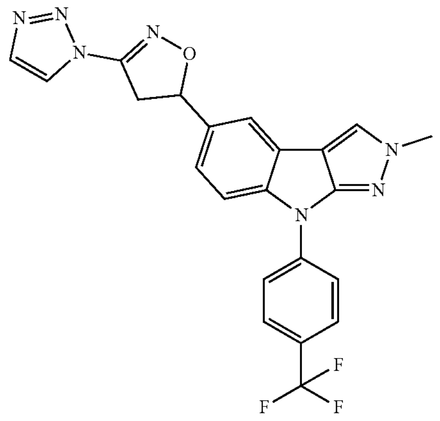 [SMILES: Cn1cc2c3cc(C4CC(n5ccnn5)=NO4)ccc3n(-c3ccc(C(F)(F)F)cc3)c2n1] 1-(5-{2-methyl-8-[4-(trifluoromethyl)-phenyl]-2H,8H-pyrazolo[3,4-b]indol-5-yl}-4,5-dihydro-1,2-oxazol-3-yl)-1H-1,2,3-triazole | | |
| 447 | 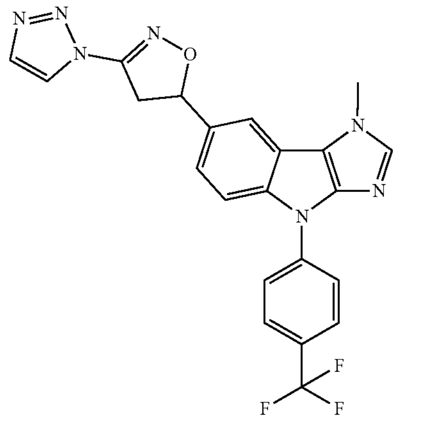 1-(5-{1-methyl-4-[4-(trifluoromethyl)phenyl]-1H,4H-imidazo[4,5-b]indol-7-yl}-4,5-dihydro-1,2-oxazol-3-yl)-1H-1,2,3-triazole | | |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 448 | 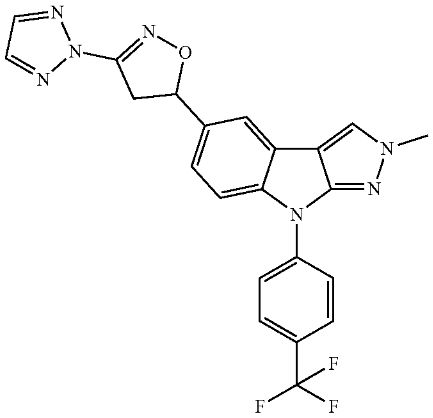 [SMILES: Cn1cc2c3cc(C4CC(n5nccn5)=NO4)ccc3n(-c3ccc(C(F)(F)F)cc3)c2n1] 2-(5-{2-methyl-8-[4-(trifluoromethyl)phenyl]-2H,8H-pyrazolo[3,4-b]indol-5-yl}-4,5-dihydro-1,2-oxazol-3-yl)-2H-1,2,3-triazole | | |
| 449 | 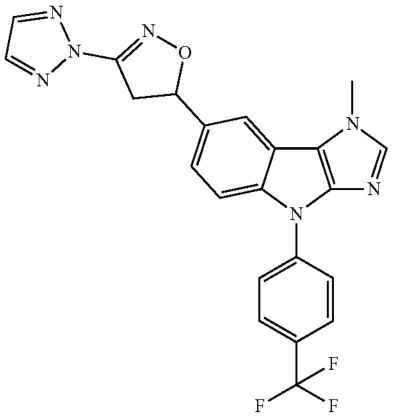 2-(5-{1-methyl-4-[4-(trifluoromethyl)phenyl]-1H,4H-imidazo[4,5-b]indol-7-yl}-4,5-dihydro-1,2-oxazol-3-yl)-2H-1,2,3-triazole | | |
| 450 | 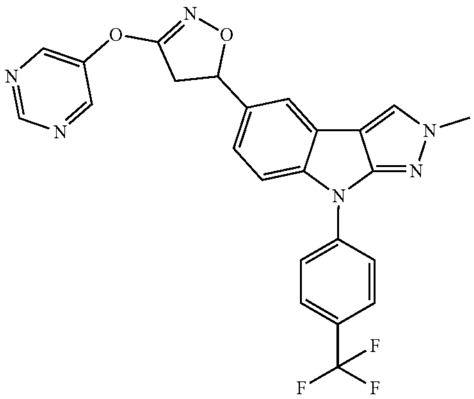 [SMILES: Cn1cc2c3cc(C4CC(Oc5cncnc5)=NO4)ccc3n(-c3ccc(C(F)(F)F)cc3)c2n1] | | |

TABLE 1-continued

| Com-pound No. (Example No.) | Structure and Name | $^1$H-NMR | Conditions and elution time (min) LCMS (M + H$^+$) |
|---|---|---|---|
| | 5-[(5-{2-methyl-8-[4-(trifluoromethyl)-phenyl]-2H,8H-pyrazolo[3,4-b]indol-5-yl}-4,5-dihydro-1,2-oxazol-3-yl)oxy]pyrimidine | | |
| 451 | 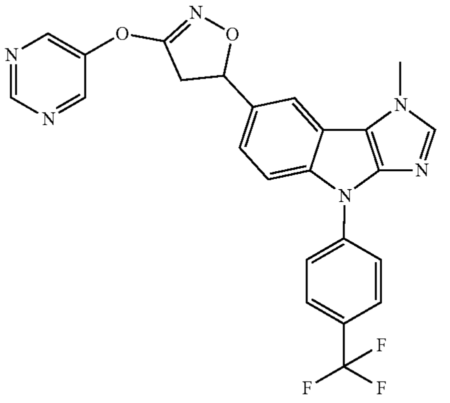 [SMILES: Cn1cnc2c1c1cc(C3CC(Oc4cncnc4)=NO3)ccc1n2-c1ccc(C(F)(F)F)cc1] 5-[(5-{1-methyl-4-[4-(trifluoromethyl)-phenyl]-1H,4H-imidazo[4,5-b]indol-7-yl}-4,5-dihydro-1,2-oxazol-3-yl)oxy]pyrimidine | | |
| 452 | 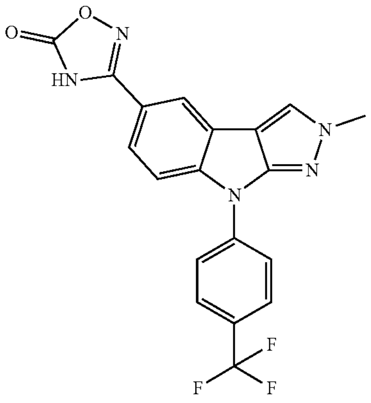 [SMILES: Cn1cc2c3cc(-c4noc(=O)[nH]4)ccc3n(-c3ccc(C(F)(F)F)cc3)c2n1] 3-{2-methyl-8-[4-(trifluoromethyl)phenyl]-2H,8H-pyrazolo[3,4-b]indol-5-yl}-4,5-dihydro-1,2,4-oxadiazol-5-one | 1H NMR (300 MHz, DMSO-d6) 8.33-8.24 (m, 2H), 8.10 (d, J = 8.4 Hz, 2H), 7.98 (d, J = 8.5 Hz, 2H), 7.88 (d, J = 8.8 Hz, 1H), 7.76 (d, J = 8.5 Hz, 1H), 4.05 (s, 3H). | |

Table 1 below shows exemplary compounds of the present invention. They have been synthesized as described in the Examples above or similar thereto.

TABLE 1-continued

| Compound No. (Example No.) | Structure and Name | ¹H-NMR | Conditions and elution time (min) LCMS (M + H⁺) |
|---|---|---|---|
| Table 1 below shows exemplary compounds of the present invention. They have been synthesized as described in the Examples above or similar thereto. | | | |
| 453 | 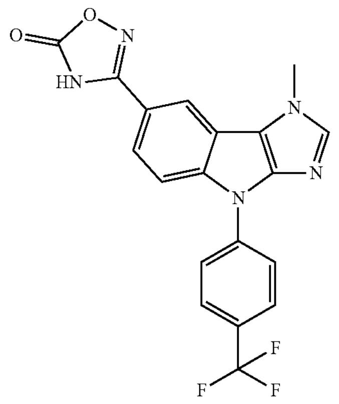 [SMILES: Cn1cnc2c1c1cc(-c3noc(=O)[nH]3)ccc1n2-c1ccc(C(F)(F)F)cc1] 3-{1-methyl-4-[4-(trifluoromethyl)phenyl]-1H,4H-imidazo[4,5-b]indol-7-yl}-4,5-dihydro-1,2,4-oxadiazol-5-one | | |
| 454 | 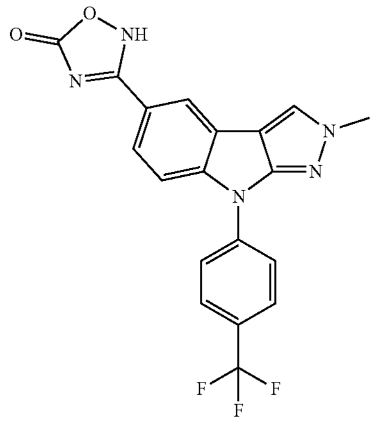 [SMILES: Cn1cc2c3cc(-c4nc(=O)o[nH]4)ccc3n(-c3ccc(C(F)(F)F)cc3)c2n1] 3-{2-methyl-8-[4-(trifluoromethyl)phenyl]-2H,8H-pyrazolo[3,4-b]indol-5-yl}-2,5-dihydro-1,2,4-oxadiazol-5-one | | |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 455 | 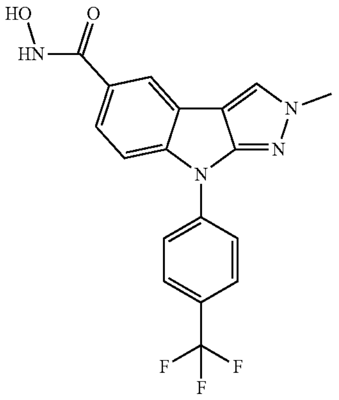 [SMILES: Cn1cc2c3cc(C(=O)NO)ccc3n(-c3ccc(C(F)(F)F)cc3)c2n1] N-hydroxy-2-methyl-8-[4-(trifluoromethyl)phenyl]-2H,8H-pyrazolo[3,4-b]indole-5-carboxamide | | |
| 456 | 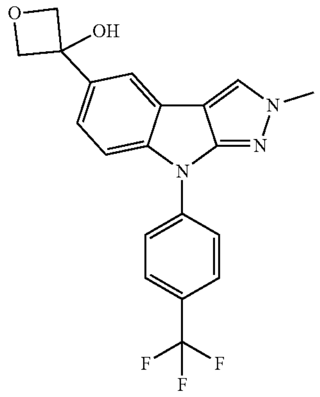 [SMILES: Cn1cc2c3cc(C4(O)COC4)ccc3n(-c3ccc(C(F)(F)F)cc3)c2n1] 3-{2-methyl-8-[4-(trifluoromethyl)phenyl]-2H,8H-pyrazolo[3,4-b]indol-5-yl}oxetan-3-ol | | |
| 457 | 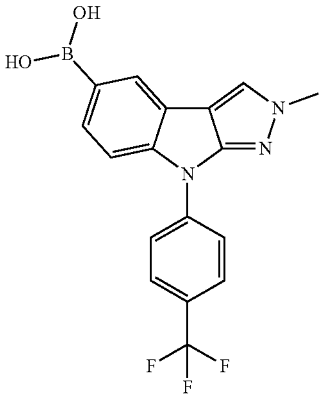 [SMILES: Cn1cc2c3cc(B(O)O)ccc3n(-c3ccc(C(F)(F)F)cc3)c2n1] {2-methyl-8-[4-(trifluoromethyl)phenyl]-2H,8H-pyrazolo[3,4-b]indol-5-yl}boronic acid | | |

TABLE 1-continued

| Com-pound No. (Example No.) | Structure and Name | $^1$H-NMR | Conditions and elution time (min) LCMS (M + H$^+$) |
|---|---|---|---|
| Table 1 below shows exemplary compounds of the present invention. They have been synthesized as described in the Examples above or similar thereto. | | | |
| 458 | 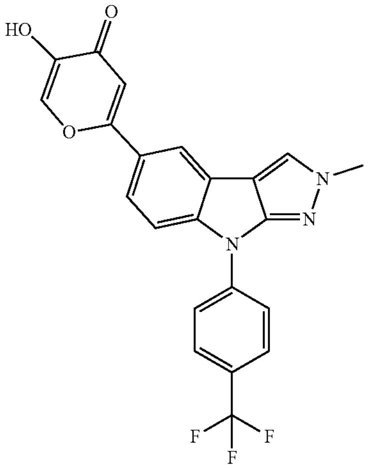 [SMILES: Cn1cc2c3cc(-c4cc(=O)c(O)co4)ccc3n(-c3ccc(C(F)(F)F)cc3)c2n1] 5-hydroxy-2-{2-methyl-8-[4-(trifluoromethyl)phenyl]-2H,8H-pyrazolo[3,4-b]indol-5-yl}-4H-pyran-4-one | | |
| 459 | 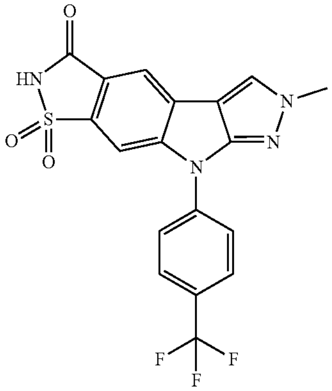 [SMILES: Cn1cc2c3cc4c(cc3n(-c3ccc(C(F)(F)F)cc3)c2n1)S(=O)(=O)NC4=O] 12-methyl-15-[4-(trifluoromethyl)-phenyl]-4-$\lambda^6$-thia-5,12,13,15-tetraazatetra-cyclo[7.6.0.0$^{3,7}$.0$^{10,14}$]pentadeca-1,3(7),8,10,13-pentaene-4,4,6-trione | | |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 460 | 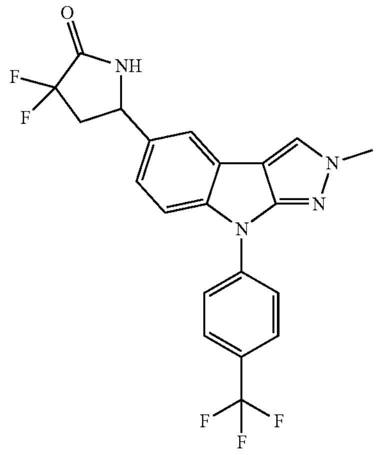 [SMILES: Cn1cc2c3cc(C4CC(F)(F)C(=O)N4)ccc3n(-c3ccc(C(F)(F)F)cc3)c2n1] 3,3-difluoro-5-{2-methyl-8-[4-(trifluoromethyl)phenyl]-2H,8H-pyrazolo[3,4-b]indol-5-yl}pyrrolidin-2-one | | |
| 461 | 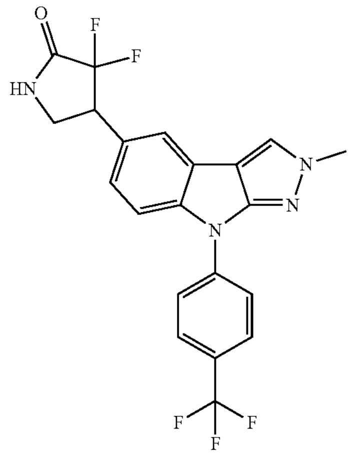 [SMILES: Cn1cc2c3cc(C4CNC(=O)C4(F)F)ccc3n(-c3ccc(C(F)(F)F)cc3)c2n1] 3,3-difluoro-4-{2-methyl-8-[4-(trifluoromethyl)phenyl]-2H,8H-pyrazolo[3,4-b]indol-5-yl}pyrrolidin-2-one | | |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 462 | 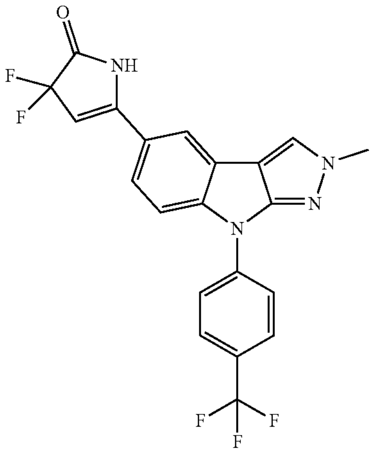 [SMILES: Cn1cc2c3cc(C4=CC(F)(F)C(=O)N4)ccc3n(-c3ccc(C(F)(F)F)cc3)c2n1] 3,3-difluoro-5-{2-methyl-8-[4-(trifluoromethyl)phenyl]-2H,8H-pyrazolo[3,4-b]indol-5-yl}-2,3-dihydro-1H-pyrrol-2-one | | |
| 463 | 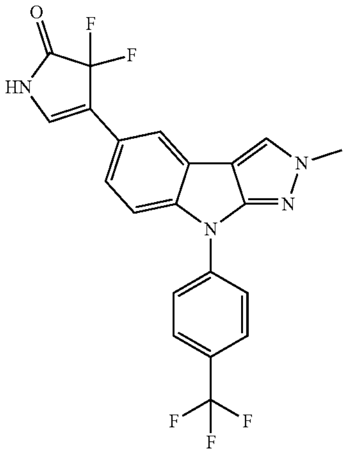 [SMILES: Cn1cc2c3cc(C4=CNC(=O)C4(F)F)ccc3n(-c3ccc(C(F)(F)F)cc3)c2n1] 3,3-difluoro-4-{2-methyl-8-[4-(trifluoromethyl)phenyl]-2H,8H-pyrazolo[3,4-b]indol-5-yl}-2,3-dihydro-1H-pyrrol-2-one | | |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 465 | 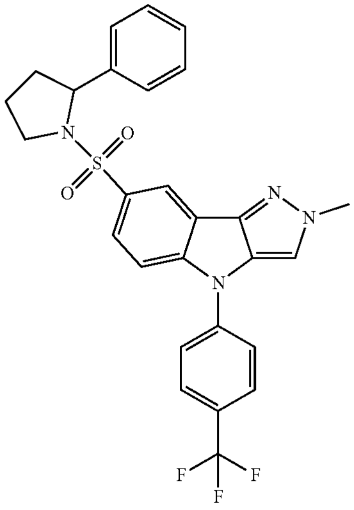 [SMILES: Cn1cc2c(n1)c1cc(S(=O)(=O)N3CCCC3c3ccccc3)ccc1n2-c1ccc(C(F)(F)F)cc1] 1-({2-methyl-4-[4-(trifluoromethyl)-phenyl]-2H,4H-pyrazolo[4,3-b]indol-7-yl}sulfonyl)-2-phenylpyrrolidine | | |
| 466 | 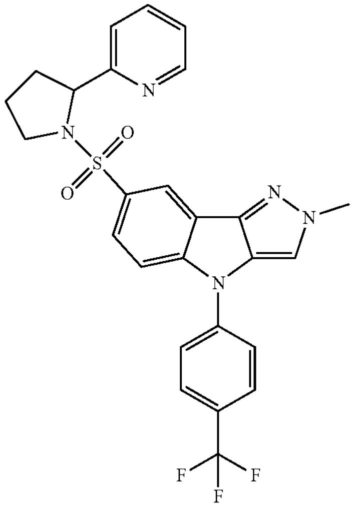 [SMILES: Cn1cc2c(n1)c1cc(S(=O)(=O)N3CCCC3c3ccccn3)ccc1n2-c1ccc(C(F)(F)F)cc1] 2-[1-{{2-methyl-4-[4-(trifluoromethyl)-phenyl]-2H,4H-pyrazolo[4,3-b]indol-7-yl}sulfonyl)pyrrolidin-2-yl]pyridine | | |

TABLE 1-continued

| Compound No. (Example No.) | Structure and Name | ¹H-NMR | Conditions and elution time (min) LCMS (M + H⁺) |
|---|---|---|---|
| | Table 1 below shows exemplary compounds of the present invention. They have been synthesized as described in the Examples above or similar thereto. | | |
| 467 | 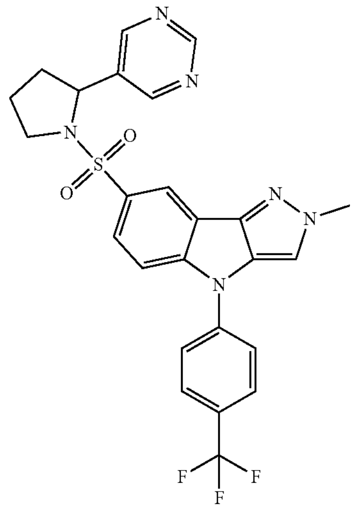 [SMILES: Cn1cc2c(n1)c1cc(S(=O)(=O)N3CCCC3c3cncnc3)ccc1n2-c1ccc(C(F)(F)F)cc1] 5-[1-({2-methyl-4-[4-(trifluoromethyl)-phenyl]-2H,4H-pyrazolo[4,3-b]indol-7-yl}sulfonyl)pyrrolidin-2-yl]pyrimidine | | |
| 468 | 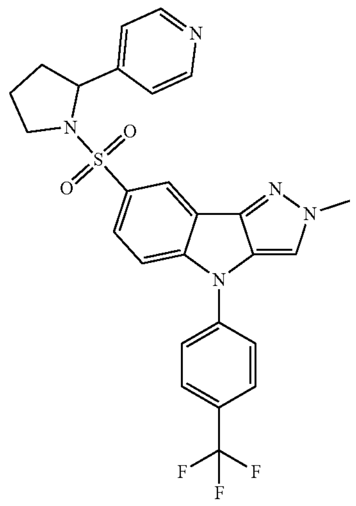 [SMILES: Cn1cc2c(n1)c1cc(S(=O)(=O)N3CCCC3c3ccncc3)ccc1n2-c1ccc(C(F)(F)F)cc1] 4-[1-({2-methyl-4-[4-(trifluoromethyl)-phenyl]-2H,4H-pyrazolo[4,3-b]indol-7-yl}sulfonyl)pyrrolidin-2-yl]pyridine | | |

TABLE 1-continued
| Com-pound No. (Example No.) | Structure and Name | $^1$H-NMR | Conditions and elution time (min) LCMS (M + H$^+$) |
|---|---|---|---|
| 469 | 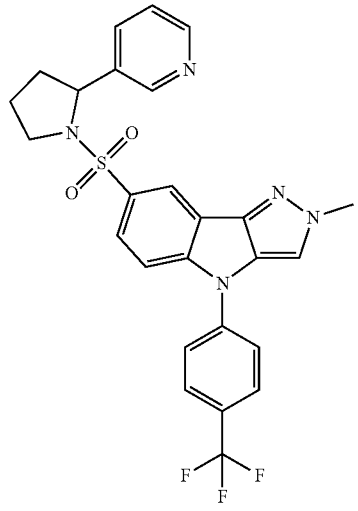 [SMILES: Cn1cc2c(n1)c1cc(S(=O)(=O)N3CCCC3c3cccnc3)ccc1n2-c1ccc(C(F)(F)F)cc1] 3-[1-({2-methyl-4-[4-(trifluoromethyl)-phenyl]-2H,4H-pyrazolo[4,3-b]indol-7-yl}sulfonyl)pyrrolidin-2-yl]pyridine | | |
| 470 | 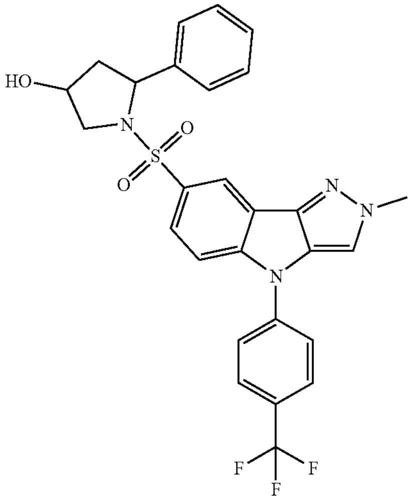 [SMILES: Cn1cc2c(n1)c1cc(S(=O)(=O)N3CC(O)CC3c3ccccc3)ccc1n2-c1ccc(C(F)(F)F)cc1] 1-({2-methyl-4-[4-(trifluoromethyl)-phenyl]-2H,4H-pyrazolo[4,3-b]indol-7-yl}sulfonyl)-5-phenylpyrrolidin-3-ol | | |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 472 | 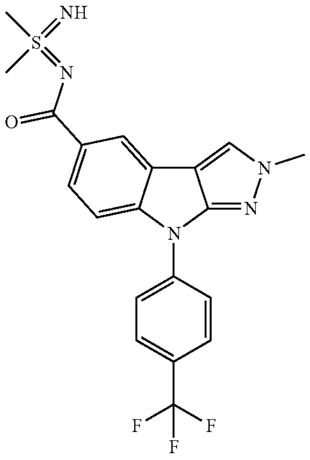 N-(iminodimethyl-λ$^6$-sulfanylidene)-2-methyl-8-[4-(trifluoromethyl)phenyl]-2H,8H-pyrazolo[3,4-b]indole-5-carboxamide | | |
| 473 | 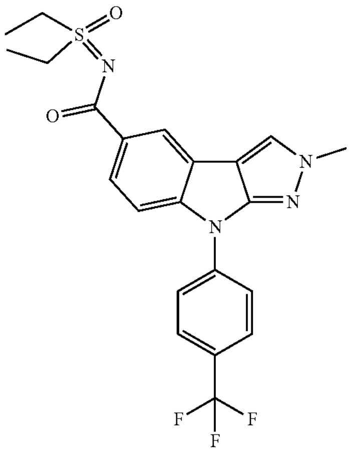 [SMILES: CCS(=O)(CC)=NC(=O)c1ccc2c(c1)c1cn(C)nc1n2-c1ccc(C(F)(F)F)cc1] N-[diethyl(oxo)-λ$^6$-sulfanylidene]-2-methyl-8-[4-(trifluoromethyl)phenyl]-2H,8H-pyrazolo[3,4-b]indole-5-carboxamide | 1H NMR (700 MHz, DMSO) d 8.47 (d, J = 1.9 Hz, 1H), 8.22 (s, 1H), 8.09 (d, J = 8.4 Hz, 2H), 8.01 (dd, J = 8.7, 1.8 Hz, 1H), 7.97 (d, J = 8.6 Hz, 2H), 7.75 (d, J = 8.7 Hz, 1H), 4.03 (s, 3H), 3.62 (dp, J = 26.2, 7.2 Hz, 4H), 1.35 (t, J = 7.4 Hz, 6H). | 18 1.41 463.1 |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 474 | 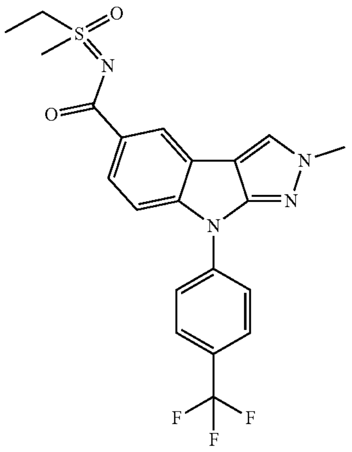 [SMILES: CCS(C)(=O)=NC(=O)c1ccc2c(c1)c1cn(C)nc1n2-c1ccc(C(F)(F)F)cc1]<br>Racemate<br>N-[ethyl(methyl)oxo-λ$^6$-sulfanylidene]-2-methyl-8-[4-(trifluoromethyl)phenyl]-2H,8H-pyrazolo[3,4-b]indole-5-carboxamide | 1H NMR (700 MHz, DMSO) d 8.46 (d, J = 1.7 Hz, 1H), 8.22 (s, 1H), 8.08 (d, J = 8.4 Hz, 2H), 8.00 (dd, J = 8.6, 1.8 Hz, 1H), 7.97 (d, J = 8.4 Hz, 2H), 7.75 (d, J = 8.7 Hz, 1H), 4.03 (s, 3H), 3.63 (ddt, J = 17.4, 14.1, 7.1 Hz, 2H), 3.44 (s, 3H), 1.37 (t, J = 7.4 Hz, 3H). | 18<br>1.38<br>449.0 |
| 475 | 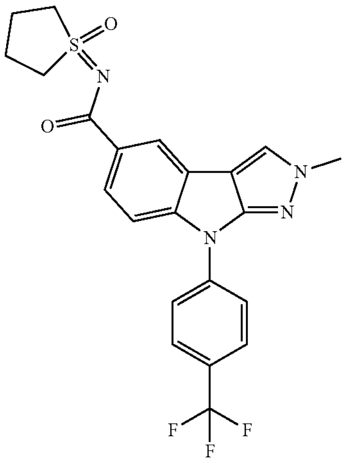 [SMILES: Cn1cc2c3cc(C(=O)N=S4(=O)CCCC4)ccc3n(-c3ccc(C(F)(F)F)cc3)c2n1]<br>2-methyl-N-(1-oxo-1λ$^6$-thiolan-1-ylidene)-8-[4-(trifluoromethyl)phenyl]-2H,8H-pyrazolo[3,4-b]indole-5-carboxamide | 1H NMR (700 MHz, DMSO) d 8.48 (d, J = 1.7 Hz, 1H), 8.22 (s, 1H), 8.08 (d, J = 8.3 Hz, 2H), 8.01 (dd, J = 8.7, 1.8 Hz, 1H), 7.97 (d, J = 8.4 Hz, 2H), 7.76 (d, J = 8.7 Hz, 1H), 4.03 (s, 3H), 3.72-3.65 (m, 2H), 3.50-3.42 (m, 2H), 2.31-2.22 (m, 2H), 2.21-2.12 (m, 2H). | 18<br>1.39<br>461.0 |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 476 | 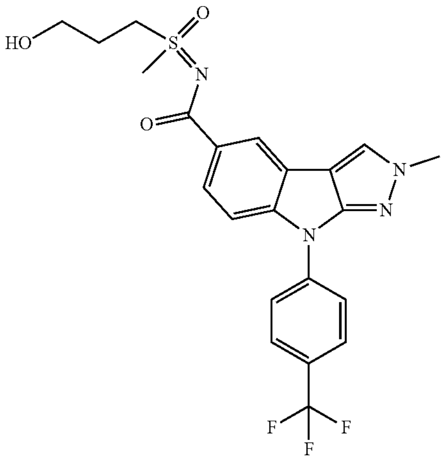 [SMILES: Cn1cc2c3cc(C(=O)N=S(C)(=O)CCCO)ccc3n(-c3ccc(C(F)(F)F)cc3)c2n1] Racemate N-[(3-hydroxypropyl)(methyl)oxo-$\lambda^6$-sulfanylidene]-2-methyl-8-[4-(trifluoromethyl)phenyl]-2H,8H-pyrazolo[3,4-b]indole-5-carboxamide | 1H NMR (700 MHz, DMSO) d 8.45 (d, J = 1.7 Hz, 1H), 8.22 (s, 1H), 8.09 (d, J = 8.4 Hz, 2H), 7.99 (dd, J = 8.7, 1.8 Hz, 1H), 7.97 (d, J = 8.3 Hz, 2H), 7.75 (d, J = 8.7 Hz, 1H), 4.78 (t, J = 5.2 Hz, 1H), 4.03 (s, 3H), 3.69-3.59 (m, 2H), 3.57-3.55 (m, 2H), 3.47 (s, 3H), 2.03-1.91 (m, 2H). | 18<br>1.30<br>479.0 |
| 477 | 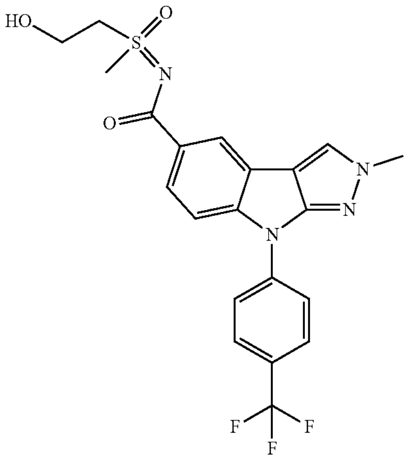 [SMILES: Cn1cc2c3cc(C(=O)N=S(C)(=O)CCO)ccc3n(-c3ccc(C(F)(F)F)cc3)c2n1] Racemate N-[(2-hydroxyethyl)(methyl)oxo-$\lambda^6$-sulfanylidene]-2-methyl-8-[4-(trifluoromethyl)phenyl]-2H,8H-pyrazolo[3,4-b]indole-5-carboxamide | 1H NMR (700 MHz, DMSO) d 8.46 (d, J = 1.7 Hz, 1H), 8.22 (s, 1H), 8.08 (d, J = 8.3 Hz, 2H), 8.00 (dd, J = 8.6, 1.7 Hz, 1H), 7.97 (d, J = 8.4 Hz, 2H), 7.75 (d, J = 8.7 Hz, 1H), 5.30 (t, J = 5.0 Hz, 1H), 4.09 (q, J = 5.3 Hz, 0H), 4.03 (s, 3H), 3.94 (tdd, J = 11.8, 9.4, 6.1 Hz, 2H), 3.85-3.74 (m, 2H), 3.47 (s, 3H), 0.85 (t, J = 7.0 Hz, 0H). | 18<br>1.30<br>465.1 |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 478 | 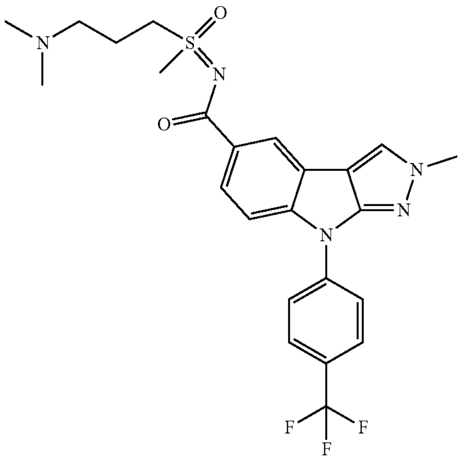<br>Racemate<br>N-{[3-(dimethylamino)propyl](methyl)oxo-λ$^6$-sulfanylidene}-2-methyl-8-[4-(trifluoromethyl)phenyl]-2H,8H-pyrazolo[3,4-b]indole-5-carboxamide | 1H NMR (400 MHz, DMSO) d 8.45 (d, J = 1.7 Hz, 1H), 8.20 (s, 1H), 8.08 (d, J = 8.4 Hz, 2H), 8.03-7.93 (m, 3H), 7.74 (d, J = 8.7 Hz, 1H), 4.03 (s, 3H), 3.72-3.52 (m, 2H), 3.47 (s, 3H), 2.38 (t, J = 6.8 Hz, 2H), 2.16 (s, 6H), 1.96 (dtd, J = 16.4, 13.7, 6.8 Hz, 2H). | 18<br>1.17<br>506.1 |
| 479 | 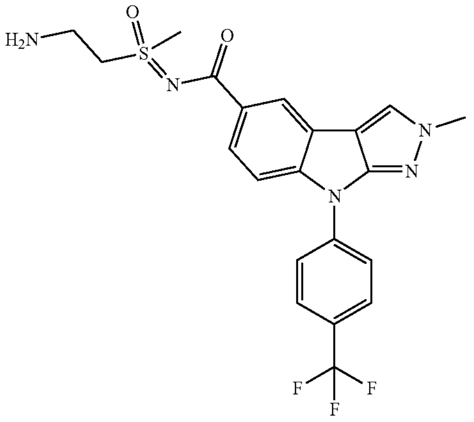 [SMILES: Cn1cc2c3cc(C(=O)N=S(C)(=O)CCN)ccc3n(-c3ccc(C(F)(F)F)cc3)c2n1]<br>Racemate<br>N-[(2-aminoethyl)(methyl)oxo-λ$^6$-sulfanylidene]-2-methyl-8-[4-(trifluoromethyl)phenyl]-2H,8H-pyrazolo[3,4-b]indole-5-carboxamide | | |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 480 | 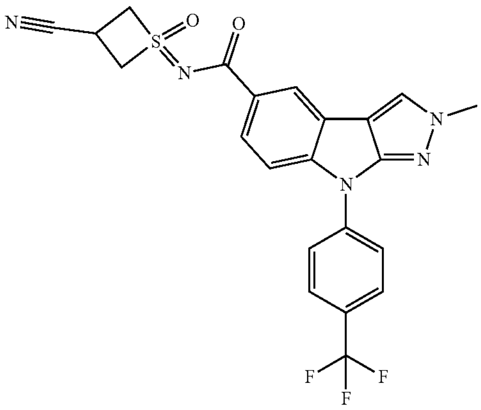 [SMILES: Cn1cc2c3cc(C(=O)N=S4(=O)CC(C#N)C4)ccc3n(-c3ccc(C(F)(F)F)cc3)c2n1] N-(3-cyano-1-oxo-1-λ$^6$-thietan-1-ylidene)-2-methyl-8-[4-(trifluoromethyl)phenyl]-2H,8H-pyrazolo[3,4-b]indole-5-carboxamide | | |
| 481 | 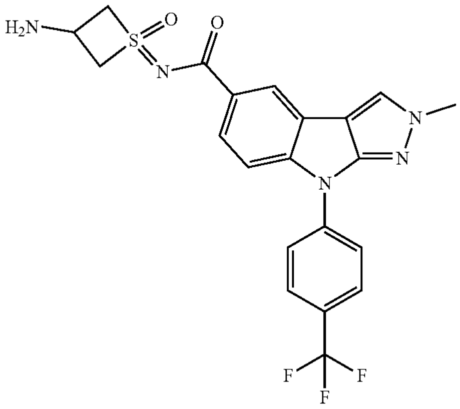 [SMILES: Cn1cc2c3cc(C(=O)N=S4(=O)CC(N)C4)ccc3n(-c3ccc(C(F)(F)F)cc3)c2n1] N-(3-amino-1-oxo-1λ$^6$-thietan-1-ylidene)-2-methyl-8-[4-(trifluoromethyl)phenyl]-2H,8H-pyrazolo[3,4-b]indole-5-carboxamide | | |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 482 | 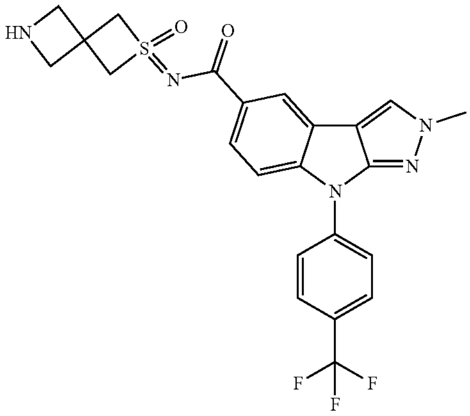 [SMILES: Cn1cc2c3cc(C(=O)N=S4(=O)CC5(CNC5)C4)ccc3n(-c3ccc(C(F)(F)F)cc3)c2n1] 2-methyl-N-{2-oxo-2λ$^6$-thia-6-azaspiro[3.3]heptan-2-ylidene}-8-[4-(trifluoromethyl)phenyl]-2H,8H-pyrazolo[3,4-b]indole-5-carboxamide | | |
| 483 | 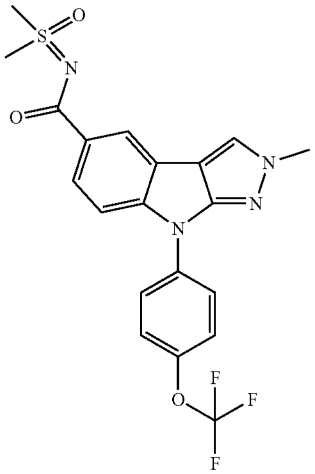 N-[dimethyl(oxo)-λ$^6$-sulfanylidene]-2-methyl-8-[4-(trifluoromethoxy)phenyl]-2H,8H-pyrazolo[3,4-b]indole-5-carboxamide | 1H NMR (400 MHz, DMSO) d 3.48 (s, 6H), 3.84 (s, 11H), 4.01 (s, 3H), 7.57-7.65 (m, 3H), 7.89-7.95 (m, 2H), 7.97 (dd, J = 8.7, 1.8 Hz, 1H), 8.19 (s, 1H), 8.45 (d, J = 1.7 Hz, 1H). | 8<br>1.71<br>451.1 |

TABLE 1-continued

| Com-pound No. (Example No.) | Structure and Name | $^1$H-NMR | Conditions and elution time (min) LCMS (M + H$^+$) |
|---|---|---|---|
| 484 | 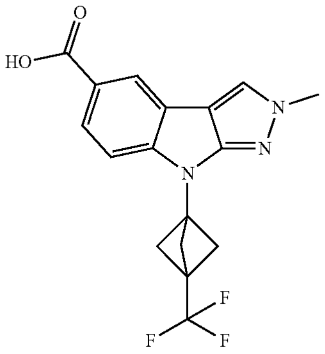 [SMILES: Cn1cc2c3cc(C(=O)O)ccc3n(C34CC(C(F)(F)F)(C3)C4)c2n1] 2-methyl-8-[3-(trifluoromethyl)-bicyclo[1.1.1]pentan-1-yl]-2H,8H-pyrazolo[3,4-b]indole-5-carboxylic acid | | |
| 485 | 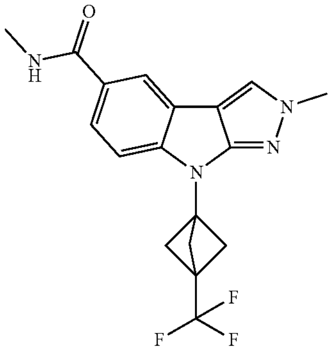 N,2-dimethyl-8-[3-(trifluoromethyl)-bicyclo[1.1.1]pentan-1-yl]-2H,8H-pyrazolo[3,4-b]indole-5-carboxamide | | |
| 486 | 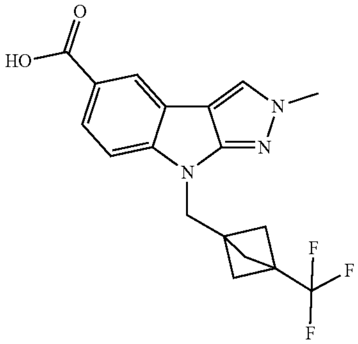 [SMILES: Cn1cc2c3cc(C(=O)O)ccc3n(CC34CC(C(F)(F)F)(C3)C4)c2n1] 2-methyl-8-{[3-(trifluoromethyl)-bicyclo[1.1.1]pentan-1-yl]methyl}-2H,8H-pyrazolo[3,4-b]indole-5-carboxylic acid | | |

Table 1 below shows exemplary compounds of the present invention. They have been synthesized as described in the Examples above or similar thereto.

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 487 | 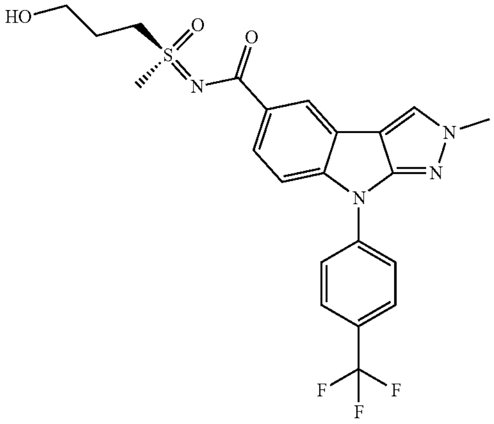 [SMILES: Cn1cc2c3cc(C(=O)N=[S@](C)(=O)CCCO)ccc3n(-c3ccc(C(F)(F)F)cc3)c2n1]<br>Absolute configuration assigned arbitrarily | | 17<br>0.93<br>478.8<br>a) 3.29 min |
| 488 | 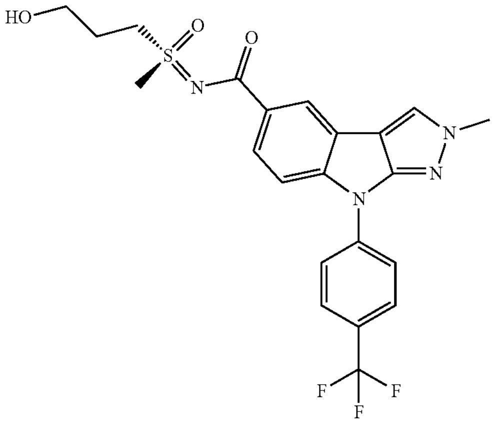 [SMILES: Cn1cc2c3cc(C(=O)N=[S@@](C)(=O)CCCO)ccc3n(-c3ccc(C(F)(F)F)cc3)c2n1]<br>Absolute configuration assigned arbitrarily | | 17<br>0.93<br>478.8<br>a 4.46 min |

TABLE 1-continued

| Compound No. (Example No.) | Structure and Name | $^1$H-NMR | Conditions and elution time (min) LCMS (M + H$^+$) |
|---|---|---|---|
| Table 1 below shows exemplary compounds of the present invention. They have been synthesized as described in the Examples above or similar thereto. | | | |
| 489 | 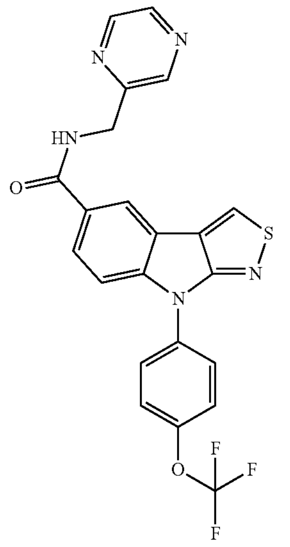 [SMILES: O=C(NCc1cnccn1)c1ccc2c(c1)c1csnc1n2-c1ccc(OC(F)(F)F)cc1] N-[(pyrazin-2-yl)methyl]-8-[4-(trifluoro-methoxy)phenyl]-8H-[1,2]thiazolo[3,4-b]indole-5-carboxamide | 1H NMR (300 MHz, DMSO, ppm) 9.48 (s, 1H), 9.27 (t, J = 5.9 Hz, 1H), 8.72-8.53 (m, 4H), 8.06-7.89 (m, 3H), 7.61 (dd, J = 30.6, 8.6 Hz, 3H), 4.68 (d, J = 5.7 Hz, 2H). | |
| 490 | 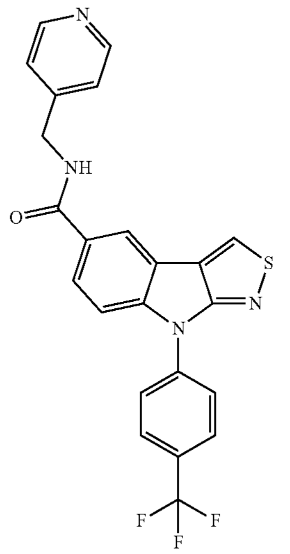 [SMILES: O=C(NCc1ccncc1)c1ccc2c(c1)c1csnc1n2-c1ccc(C(F)(F)F)cc1] N-[(pyridin-4-yl)methyl]-8-[4-(trifluoromethyl)phenyl]-8H-[1,2]thiazolo[3,4-b]indole-5-carboxamide | 1H NMR (400 MHz, DMSO-d6) 9.49 (d, J = 1.1 Hz, 1H), 9.22 (t, J = 6.1 Hz, 1H), 8.64 (d, J = 1.8 Hz, 1H), 8.52 (d, J = 5.1 Hz, 2H), 8.12-7.98 (m, 5H), 7.67 (d, J = 8.7 Hz, 1H), 7.34 (d, J = 5.2 Hz, 2H), 4.55 (d, J = 5.9 Hz, 2H). | |

TABLE 1-continued

| Compound No. (Example No.) | Structure and Name | 1H-NMR | Conditions and elution time (min) LCMS (M + H+) |
|---|---|---|---|
| Table 1 below shows exemplary compounds of the present invention. They have been synthesized as described in the Examples above or similar thereto. | | | |
| 491 | 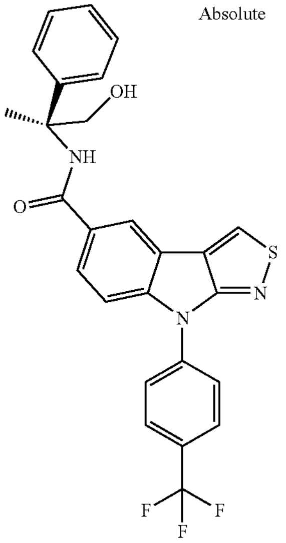 [SMILES: C[C@](CO)(NC(=O)c1ccc2c(c1)c1csnc1n2-c1ccc(C(F)(F)F)cc1)c1ccccc1] Absolute<br>N-[(2S)-1-hydroxy-2-phenylpropan-2-yl]-8-[4-(trifluoromethyl)phenyl]-8H-[1,2]thiazolo[3,4-b]indole-5-carboxamide | 1H NMR (400 MHz, DMSO-d6) 9.49 (s, 1H), 8.60 (d, J = 1.8 Hz, 1H), 8.19 (s, 1H), 8.11-7.92 (m, 5H), 7.65 (d, J = 8.6 Hz, 1H), 7.39 (d, J = 7.8 Hz, 2H), 7.30 (t, J = 7.6 Hz, 2H), 7.19 (t, J = 7.2 Hz, 1H), 5.18 (t, J = 6.1 Hz, 1H), 3.82-3.80 (m, 1H), 3.60-3.58 (m, 1H), 1.76 (s, 3H). | |
| 492 | 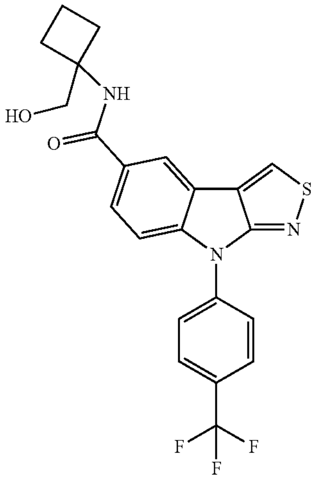 [SMILES: O=C(NC1(CO)CCC1)c1ccc2c(c1)c1csnc1n2-c1ccc(C(F)(F)F)cc1]<br>N-[1-(hydroxymethyl)cyclobutyl]-8-[4-(trifluoromethyl)phenyl]-8H-[1,2]thiazolo[3,4-b]indole-5-carboxamide | 1H NMR (400 MHz, DMSO-d6) 9.45 (s, 1H), 8.59 (d, J = 1.8 Hz, 1H), 8.33 (s, 1H), 8.11-7.98 (m, 5H), 7.63 (d, J = 8.7 Hz, 1H), 4.87 (t, J = 5.8 Hz, 1H), 3.68 (d, J = 5.8 Hz, 2H), 2.31-2.28 (m, 2H), 2.23-2.12 (m, 2H), 1.89-1.71 (m, 2H). | |

TABLE 1-continued

| Compound No. (Example No.) | Structure and Name | $^1$H-NMR | Conditions and elution time (min) LCMS (M + H$^+$) |
|---|---|---|---|
| Table 1 below shows exemplary compounds of the present invention. They have been synthesized as described in the Examples above or similar thereto. | | | |
| 493 | 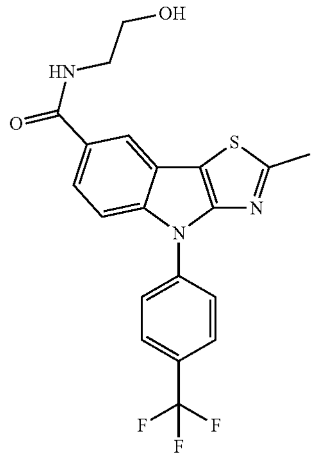 [SMILES: Cc1nc2c(s1)c1cc(C(=O)NCCO)ccc1n2-c1ccc(C(F)(F)F)cc1] N-(2-hydroxyethyl)-2-methyl-4-[4-(trifluoromethyl)phenyl]-4H-[1,3]thiazolo[4,5-b]indole-7-carboxamide | 1H NMR (300 MHz, DMSO-d6) 8.52-8.42 (m, 2H), 8.03 (s, 4H), 7.88 (d, J = 8.8 , 1H), 7.75 (d, J = 8.8 Hz, 1H), 4.76 (t, J = 5.6 Hz, 1H), 3.56 (q, J = 6.1 Hz, 2H), 3.40 (t, J = 5.9 Hz, 2H), 2.86 (s, 3H). | |
| 494 | 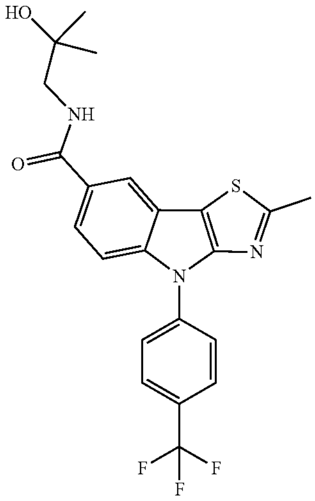 [SMILES: Cc1nc2c(s1)c1cc(C(=O)NCC(C)(C)O)ccc1n2-c1ccc(C(F)(F)F)cc1] N-(2-hydroxy-2-methylpropyl)-2-methyl-4-[4-(trifluoromethyl)phenyl]-4H-[1,3]thiazolo[4,5-b]indole-7-carboxamide | 1H NMR (300 MHz, DMSO-d6) 8.49 (d, J = 1.7 Hz, 1H), 8.29 (t, J = 6.1 Hz, 1H), 8.03 (s, 4H), 7.89 (d, J = 8.8, , 1H), 7.76 (d, J = 8.8 Hz, 1H), 4.61 (s, 1H), 3.32 (d, J = 5.9 Hz, 2H), 2.86 (s, 3H), 1.15 (s, 6H). | |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 495 | 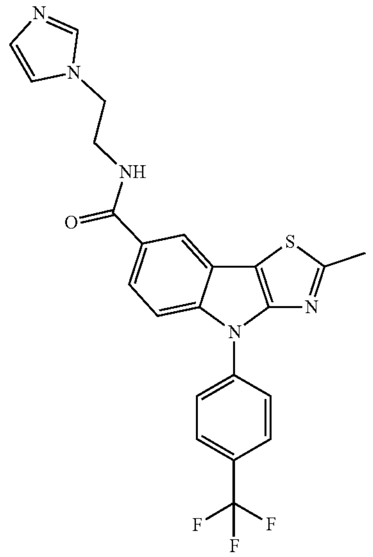 [SMILES: Cc1nc2c(s1)c1cc(C(=O)NCCn3ccnc3)ccc1n2-c1ccc(C(F)(F)F)cc1] N-[2-(1H-imidazol-1-yl)ethyl]-2-methyl-4-[4-(trifluoromethyl)phenyl]-4H-[1,3]thiazolo[4,5-b]indole-7-carboxamide | 1H NMR (300 MHz, DMSO-d6) 8.65 (t, J = 5.5 Hz, 1H), 8.39 (d, J = 1.7 Hz, 1H), 8.03 (s, 4H), 7.83 (m, 1H), 7.79-7.68 (m, 2H), 7.23 (t, J = 1.2 Hz, 1H), 6.93 (d, J = 1.1 Hz, 1H), 4.22 (t, J = 6.0 Hz, 2H), 3.64 (q, J = 5.9 Hz, 2H), 2.86 (s, 3H). | |
| 496 | 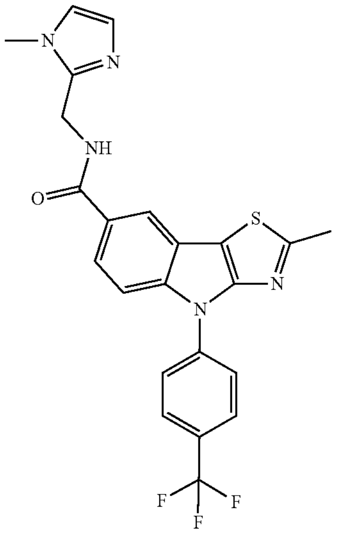 2-methyl-N-[(1-methyl-1H-imidazol-2-yl)methyl]-4-[4-(trifluoromethyl)phenyl]-4H-[1,3]thiazolo[4,5-b]indole-7-carboxamide | 1H NMR (300 MHz, DMSO-d6) 9.08 (s, 1H), 8.50 (d, J = 1.7 Hz, 1H), 8.03 (d, J = 1.7 Hz, 4H), 7.91 (m, 1H), 7.77 (d, J = 8.8 Hz, 1H), 7.28 (d, J = 4.0 Hz, 1H), 7.07 (d, J = 5.5 Hz, 1H), 4.65 (d, J = 5.2 Hz, 2H), 3.75 (d, J = 1.3 Hz, 3H), 2.86 (s, 3H). | |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 497 | 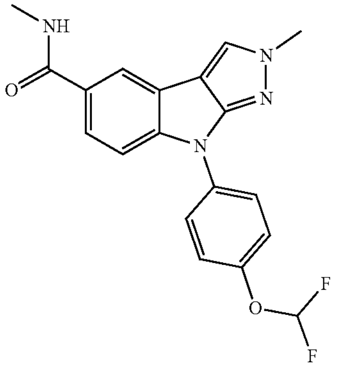 [SMILES: CNC(=O)c1ccc2c(c1)c1cn(C)nc1n2-c1ccc(OC(F)F)cc1] 8-[4-(difluoromethoxy)phenyl]-N,2-dimethyl-2H,8H-pyrazolo[3,4-b]indole-5-carboxamide | 1H NMR (700 MHz, DMSO) d 2.81 (d, J = 4.4 Hz, 3H), 4.01 (s, 3H), 7.21 (s, 0H), 7.31 (s, 1H), 7.39-7.44 (m, 2H), 7.56 (d, J = 8.6 Hz, 1H), 7.80 (dd, J = 8.6, 1.9 Hz, 1H), 7.80-7.85 (m, 2H), 8.17 (s, 1H), 8.31 (d, J = 1.8 Hz, 1H), 8.41 (q, J = 4.5 Hz, 1H) | |
| 498 | 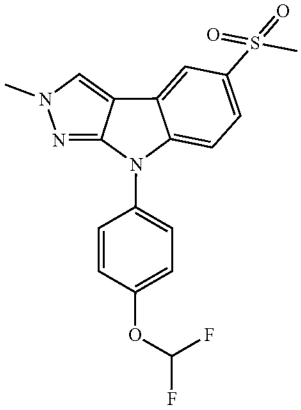 8-[4-(difluoromethoxy)phenyl]-5-methanesulfonyl-2-methyl-2H,8H-pyrazolo[3,4-b]indole | 1H NMR (700 MHz, DMSO) d 3.22 (s, 3H), 4.03 (s, 3H), 7.34 (t, 1H), 7.41-7.48 (m, 2H), 7.67 (d, J = 8.6 Hz, 1H), 7.79-7.82 (dd, 1H), 7.82-7.85 (m, 2H), 8.24 (s, 1H), 8.40 (d, J = 1.9 Hz, 1H). | |
| 499 | 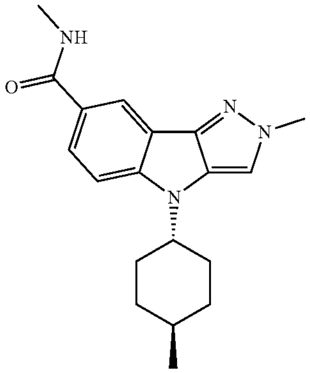 [SMILES: CNC(=O)c1ccc2c(c1)c1nn(C)cc1n2[C@H]1CC[C@H](C)CC1] Absolute configuration assigned arbitrarily N,2-dimethyl-4-[(1r,4r)-4-methylcyclohexyl]-2H,4H-pyrazolo[4,3-b]indole-7-carboxamide | 1H NMR (700 MHz, DMSO) d 8.35 (q, J = 4.5 Hz, 1H), 8.33 (d, J = 1.8 Hz, 1H), 7.85 (s, 1H), 7.84 (dd, J = 8.7, 1.9 Hz, 1H), 7.50 (d, J = 8.7 Hz, 1H), 4.35 (tt, J = 11.5, 4.2 Hz, 1H), 4.04 (s, 3H), 2.80 (d, J = 4.5 Hz, 3H), 1.93-1.83 (m, 4H), 1.83-1.78 (m, 2H), 1.52 (tdd, J = 11.7, 6.6, 3.4 Hz, 1H), 1.25 (qd, J = 12.7, 5.3 Hz, 2H), 0.96 (d, J = 6.5 Hz, 3H). Spectra | |

TABLE 1-continued

| Compound No. (Example No.) | Structure and Name | $^1$H-NMR | Conditions and elution time (min) LCMS (M + H$^+$) |
|---|---|---|---|
| Table 1 below shows exemplary compounds of the present invention. They have been synthesized as described in the Examples above or similar thereto. | | | |
| 500 | 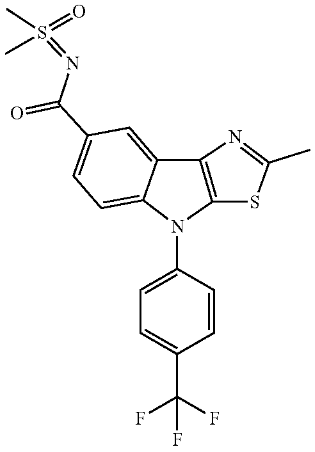 N-[dimethyl(oxo)-λ$^6$-sulfanylidene]-2-methyl-4-[4-(trifluoromethyl)phenyl]-4H-[1,3]thiazolo[5,4-b]indole-7-carboxamide | 1H NMR (400 MHz, DMSO) d 2.84 (s, 3H), 3.50 (s, 6H), 7.77 (d, J = 8.8, 0.7 Hz, 1H), 7.96-8.07 (m, 5H), 8.60 (dd, J = 1.7, 0.6 Hz, 1H). Spektrum | |
| 501 | 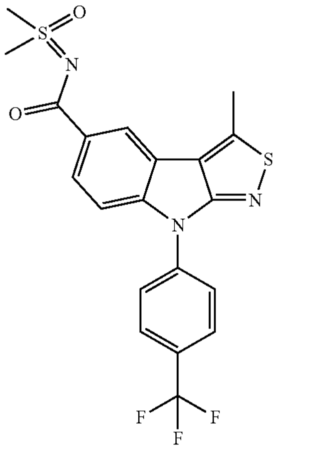 [SMILES: Cc1snc2c1c1cc(C(=O)N=S(C)(C)=O)ccc1n2-c1ccc(C(F)(F)F)cc1] N-[dimethyl(oxo)-λ$^6$-sulfanylidene]-3-methyl-8-[4-(trifluoromethyl)phenyl]-8H-[1,2]thiazolo[3,4-b]indole-5-carboxamide | 1H NMR (400 MHz, DMSO) d 2.07 (s, 1H), 2.97 (s, 3H), 3.50 (s, 6H), 7.59 (d, 1H), 7.99 (d, J = 8.7 Hz, 2H), 8.04 (d, J = 8.6 Hz, 2H), 8.11 (dd, J = 8.7, 1.7 Hz, 1H), 8.54 (d, J = 1.6 Hz, 1H)- | |

TABLE 1-continued

| Com-pound No. (Example No.) | Structure and Name | ¹H-NMR | Conditions and elution time (min) LCMS (M + H⁺) |
|---|---|---|---|
| | Table 1 below shows exemplary compounds of the present invention. They have been synthesized as described in the Examples above or similar thereto. | | |
| 502 | 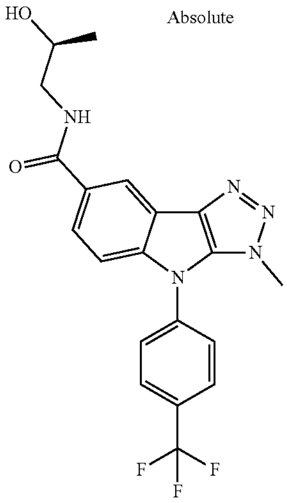 [SMILES: C[C@H](O)CNC(=O)c1ccc2c(c1)c1nnn(C)c1n2-c1ccc(C(F)(F)F)cc1] Absolute configuration assigned arbitrarily N-[(2S)-2-hydroxypropyl]-3-methyl-4-[4-(trifluoromethyl)phenyl]-3H,4H-[1,2,3]triazolo[4,5-b]indole-7-carboxamide | | |
| 503 | 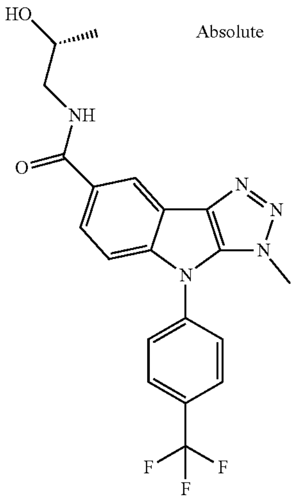 [SMILES: C[C@@H](O)CNC(=O)c1ccc2c(c1)c1nnn(C)c1n2-c1ccc(C(F)(F)F)cc1] Absolute configuration assigned arbitrarily N-[(2R)-2-hydroxypropyl]-3-methyl-4-[4-(trifluoromethyl)phenyl]-3H,4H-[1,2,3]triazolo[4,5-b]indole-7-carboxamide | | |

TABLE 1-continued

| Compound No. (Example No.) | Structure and Name | $^1$H-NMR | Conditions and elution time (min) LCMS (M + H$^+$) |
|---|---|---|---|
| | Table 1 below shows exemplary compounds of the present invention. They have been synthesized as described in the Examples above or similar thereto. | | |
| 504 | 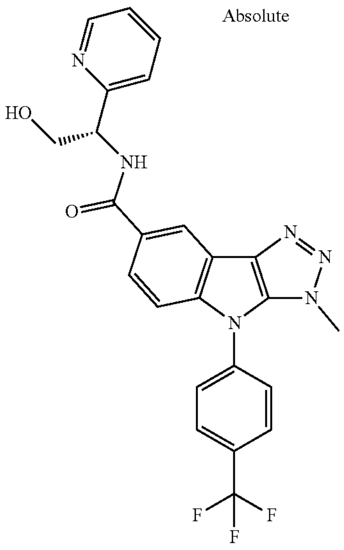 [SMILES: Cn1nnc2c3cc(C(=O)N[C@H](CO)c4ccccn4)ccc3n(-c3ccc(C(F)(F)F)cc3)c21] Absolute configuration assigned arbitrarily N-[(1S)-2-hydroxy-1-(pyridin-2-yl)ethyl]-3-methyl-4-[4-(trifluoromethyl)phenyl]-3H,4H-[1,2,3]triazolo[4,5-b]indole-7-carboxamide | | |
| 505 | 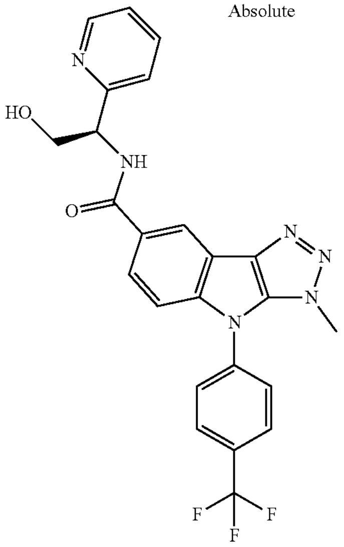 [SMILES: Cn1nnc2c3cc(C(=O)N[C@@H](CO)c4ccccn4)ccc3n(-c3ccc(C(F)(F)F)cc3)c21] Absolute configuration assigned arbitrarily N-[(1R)-2-hydroxy-1-(pyridin-2-yl)ethyl]-3-methyl-4-[4-(trifluoromethyl)phenyl]-3H,4H-[1,2,3]triazolo[4,5-b]indole-7-carboxamide | | |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 506 | 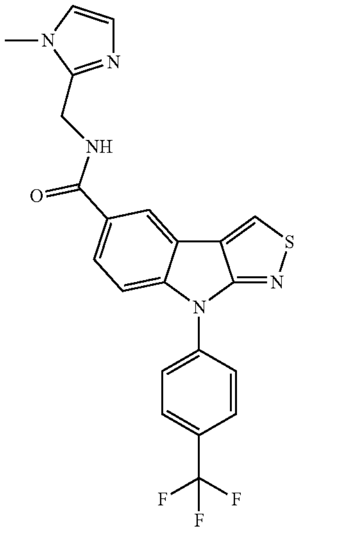 [SMILES: Cn1ccnc1CNC(=O)c1ccc2c(c1)c1csnc1n2-c1ccc(C(F)(F)F)cc1] N-[(1-methyl-1H-imidazol-2-yl)methyl]-8-[4-(trifluoromethyl)phenyl]-8H-[1,2]thiazolo[3,4-b]indole-5-carboxamide | 1H NMR (400 MHz, DMSO-d6) 9.47 (d, J = 2.9 Hz, 1H), 9.01 (s, 1H), 8.63 (d, J = 1.9 Hz, 1H), 8.10-7.98 (m, 5H), 7.64 (d, J = 8.8 Hz, 1H), 7.09 (d, J = 1.3 Hz, 1H), 6.81 (d, J = 1.3 Hz, 1H), 4.58 (d, J = 5.3 Hz, 2H), 3.68 (d, J = 3.1 Hz, 3H). | |
| 507 | 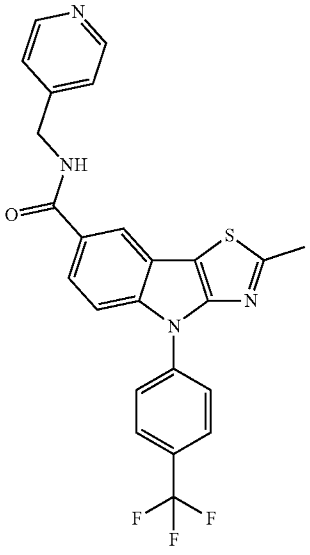 [SMILES: Cc1nc2c(s1)c1cc(C(=O)NCc3ccncc3)ccc1n2-c1ccc(C(F)(F)F)cc1] 2-methyl-N-[(pyridin-4-yl)methyl]-4-[4-(trifluoromethyl)phenyl]-4H-[1,3]thiazolo[4,5-b]indole-7-carboxamide | 1H NMR (300 MHz, DMSO-d6) 9.19 (t, J = 6.0 Hz, 1H), 8.57-8.49 (m, 3H), 8.04 (s, 4H), 7.93 (dd, J = 8.8, 1.8 Hz, 1H), 7.79 (d, J = 8.8 Hz, 1H), 7.40-7.32 (m, 2H), 4.56 (d, J = 5.8 Hz, 2H), 2.86 (s, 3H). | |

TABLE 1-continued

| Com-pound No. (Example No.) | Structure and Name | ¹H-NMR | Conditions and elution time (min) LCMS (M + H⁺) |
|---|---|---|---|
| | Table 1 below shows exemplary compounds of the present invention. They have been synthesized as described in the Examples above or similar thereto. | | |
| 508 | 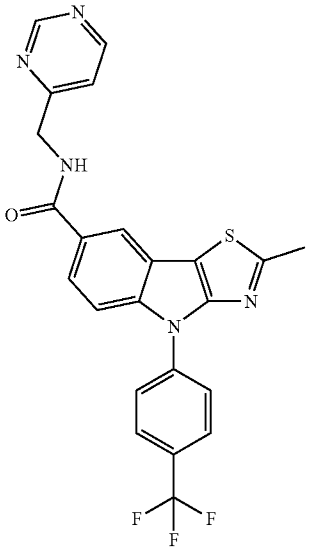 2-methyl-N-[(pyrimidin-4-yl)methyl]-4-[4-(trifluoromethyl)phenyl]-4H-[1,3]thiazolo[4,5-b]indole-7-carboxamide | 1H NMR (300 MHz, DMSO-d6) 9.25 (t, J = 5.8 Hz, 1H), 9.14 (d, J = 1.4 Hz, 1H), 8.76 (d, J = 5.2 Hz, 1H), 8.54 (d, J = 1.7 Hz, 1H), 8.04 (s, 4H), 7.94 (d, J = 8.8, 1H), 7.80 (d, J = 8.8 Hz, 1H), 7.52-7.44 (m, 1H), 4.61 (d, J = 5.8 Hz, 2H), 2.87 (s, 3H). | |
| 509 | 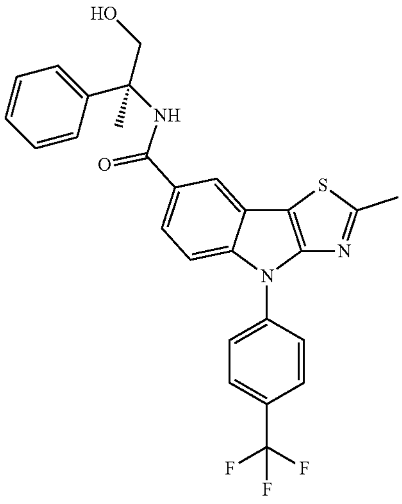 [SMILES: Cc1nc2c(s1)c1cc(C(=O)N[C@](C)(CO)c3ccccc3)ccc1n2-c1ccc(C(F)(F)F)cc1] N-[(2S)-1-hydroxy-2-phenylpropan-2-yl]-2-methyl-4-[4-(trifluoromethyl)phenyl]-4H-[1,3]thiazolo[4,5-b]indole-7-carboxamide | 1H NMR (300 MHz, DMSO-d6) 8.53 (d, J = 1.7 Hz, 1H), 8.17 (s, 1H), 8.03 (s, 4H), 7.83 (, J = 8.8, 1H), 7.76 (d, J = 8.8 Hz, 1H), 7.45-7.36 (m, 2H), 7.30 (dd, J = 8.5, 6.7 Hz, 2H), 7.25-7.15 (m, 1H), 5.20 (t, J = 6.1 Hz, 1H), 3.81 (dd, J = 11.0, 6.1 Hz, 1H), 3.59 (dd, J = 11.0, 6.3 Hz, 1H), 2.87 (s, 3H), 1.78 (s, 3H). | |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 510 | 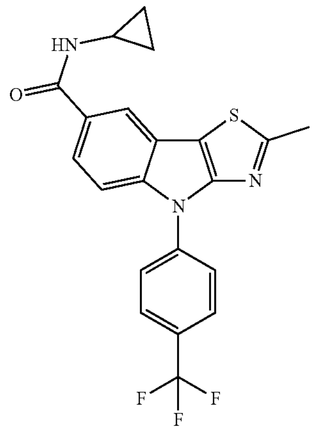 [SMILES: Cc1nc2c(s1)c1cc(C(=O)NC3CC3)ccc1n2-c1ccc(C(F)(F)F)cc1] N-cyclopropyl-2-methyl-4-[4-(trifluoromethyl)phenyl]-[1,3]thiazolo[4,5-b]indole-7-carboxamide | 1H NMR (300 MHz, DMSO-d6) 8.48 (d, J = 4.2 Hz, 1H), 8.39 (s, 1H), 8.02 (s, 4H), 7.85 (d, J = 9.0, 1H), 7.74 (d, J = 8.8 Hz, 1H), 2.92 (m, 1H), 2.86 (s, 3H), 0.71 (m, 2H), 0.68-0.56 (m, 2H). | |
| 511 | 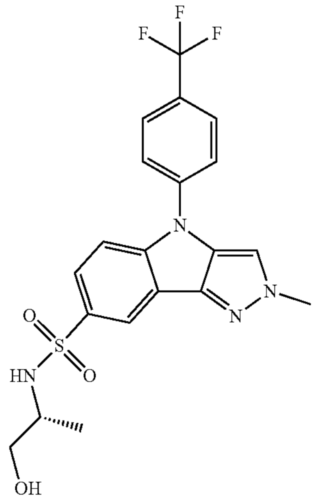 [SMILES: C[C@H](CO)NS(=O)(=O)c1ccc2c(c1)c1nn(C)cc1n2-c1ccc(C(F)(F)F)cc1] N-[(2R)-1-hydroxypropan-2-yl]-2-methyl-4-[4-(trifluoromethyl)phenyl]-2H,4H-pyrazolo[4,3-b]indole-7-sulfonamide | 1H NMR (400 MHz, DMSO-d6) 8.33 (d, J = 1.8 Hz, 1H), 8.16 (s, 1H), 7.96 (s, 5H), 7.84 (dd, J = 8.9, 1.9 Hz, 1H), 7.51 (d, J = 6.7 Hz, 1H), 4.12 (s, 3H), 3.31 (q, J = 3.4 Hz, 1H), 3.22-3.04 (m, 2H), 0.89 (d, J = 5.9 Hz, 3H). | |

TABLE 1-continued

| Compound No. (Example No.) | Structure and Name | $^1$H-NMR | Conditions and elution time (min) LCMS (M + H$^+$) |
|---|---|---|---|
| Table 1 below shows exemplary compounds of the present invention. They have been synthesized as described in the Examples above or similar thereto. | | | |
| 512 | 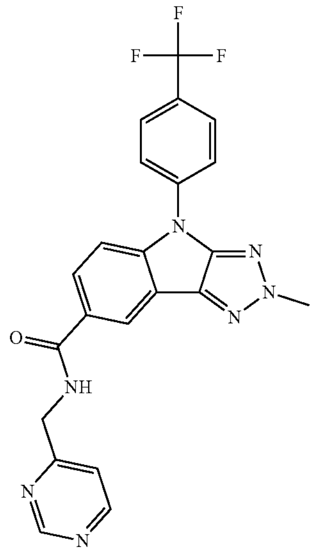 [SMILES: Cn1nc2c3cc(C(=O)NCc4ccncn4)ccc3n(-c3ccc(C(F)(F)F)cc3)c2n1] 2-methyl-N-[(pyrimidin-4-yl)methyl]-4-[4-(trifluoromethyl)phenyl]-2H,4H-[1,2,3]triazolo[4,5-b]indole-7-carboxamide | 1H NMR (300 MHz, DMSO-d6) 9.36 (s, 0H), 9.14 (d, J = 1.5 Hz, 1H), 8.76 (d, J = 5.3 Hz, 1H), 8.66 (d, J = 1.9 Hz, 1H), 8.10 (d, J = 8.9 Hz, 3H), 8.00 (dd, J = 14.4, 8.6 Hz, 3H), 7.49 (d, J = 5.8 Hz, 1H). | |
| 513 | 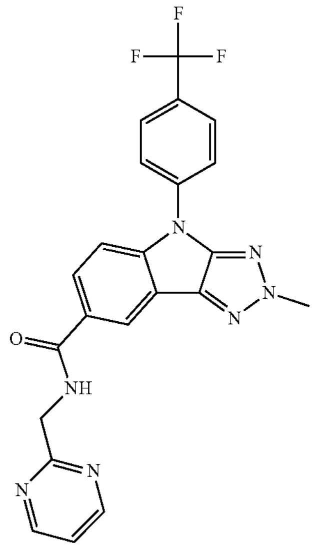 [SMILES: Cn1nc2c3cc(C(=O)NCc4ncccn4)ccc3n(-c3ccc(C(F)(F)F)cc3)c2n1] 2-methyl-N-[(pyrimidin-2-yl)methyl]-4-[4-(trifluoromethyl)phenyl]-2H,4H-[1,2,3]triazolo[4,5-b]indole-7-carboxamide | 1H NMR (300 MHz, DMSO-d6) 9.25 (d, J = 5.9 Hz, 1H), 8.79 (d, J = 4.9 Hz, 2H), 8.64 (d, J = 1.7 Hz, 1H), 8.10 (d, J = 8.7 Hz, 3H), 8.00 (dd, J = 16.4, 8.8 Hz, 3H), 7.42 (t, J = 4.8 Hz, 1H), 4.73 (d, J = 5.8 Hz, 2H), 4.39 (s, 3H). | |

TABLE 1-continued

| Com-pound No. (Example No.) | Structure and Name | $^1$H-NMR | Conditions and elution time (min) LCMS (M + H$^+$) |
|---|---|---|---|
| Table 1 below shows exemplary compounds of the present invention. They have been synthesized as described in the Examples above or similar thereto. | | | |
| 514 | Absolute 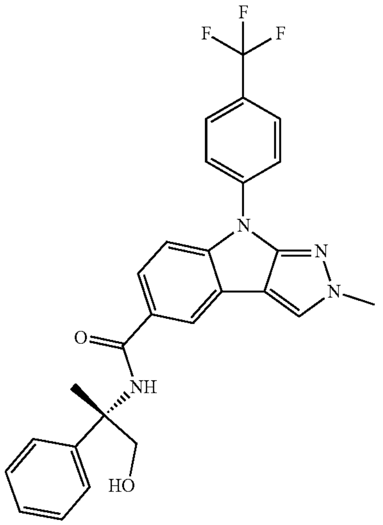 N-[(2S)-1-hydroxy-2-phenylpropan-2-yl]-2-methyl-8-[4-(trifluoromethyl)phenyl]-2H,8H-pyrazolo[3,4-b]indole-5-carboxamide | 1H NMR (300 MHz, DMSO-d6) 8.38 (d, J = 1.7 Hz, 1H), 8.23 (s, 1H), 8.19-8.06 (m, 3H), 7.99 (d, J = 8.6 Hz, 2H), 7.89-7.75 (m, 2H), 7.44-7.35 (m, 2H), 7.30 (dd, J = 8.4, 6.7 Hz, 2H), 7.26-7.15 (m, 1H), 5.21 (t, J = 6.1 Hz, 1H), 4.05 (s, 3H), 3.80 (dd, J = 11.0, 6.1 Hz, 1H), 3.59 (dd, J = 11.0, 6.2 Hz, 1H), 1.77 (s, 3H). | |
| 515 | 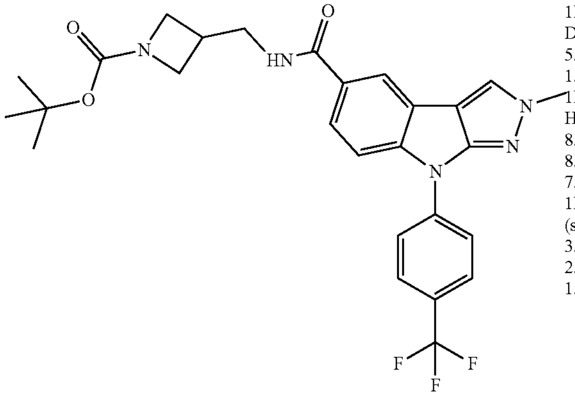 tert-butyl 3-[{{2-methyl-8-[4-(trifluoro-methyl)phenyl]-2H,8H-pyrazolo[3,4-b]indol-5-yl}formamido)methyl]azetidine-1-carboxylate | 1H NMR (700 MHz, DMSO) d 8.66 (t, J = 5.8 Hz, 1H), 8.33 (d, J = 1.9 Hz, 1H), 8.21 (s, 1H), 8.08 (d, J = 8.4 Hz, 2H), 7.97 (d, J = 8.4 Hz, 2H), 7.84 (dd, J = 8.6, 1.9 Hz, 1H), 7.78 (d, J = 8.6 Hz, 1H), 4.04 (s, 3H), 3.90 (s, 2H), 3.65 (s, 2H), 3.51-3.47 (m, 2H), 2.80-2.72 (m, 1H), 1.36 (s, 9H). Spectra | |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 516 | 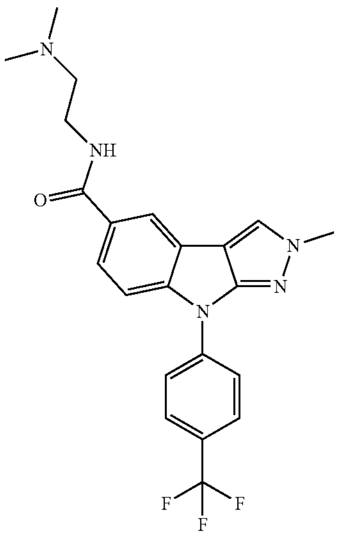 N-[2-(dimethylamino)ethyl]-2-methyl-8-[4-(trifluoromethyl)phenyl]-2H,8H-pyrazolo[3,4-b]indole-5-carboxamide trifluoroacetate | 1H NMR (400 MHz, DMSO) d 9.39 (t, 1H), 8.71 (t, J = 5.7 Hz, 1H), 8.35 (d, J = 1.8 Hz, 1H), 8.21 (s, 1H), 8.08 (d, J = 8.4 Hz, 2H), 7.98 (d, J = 8.7 Hz, 2H), 7.87 (dd, J = 8.7, 1.8 Hz, 1H), 7.80 (d, J = 8.7 Hz, 1H), 4.04 (s, 3H), 3.65 (q, J = 5.9 Hz, 2H), 3.31 (q, J = 5.7 Hz, 2H), 2.88 (d, J = 4.5 Hz, 6H). | |
| 517 | 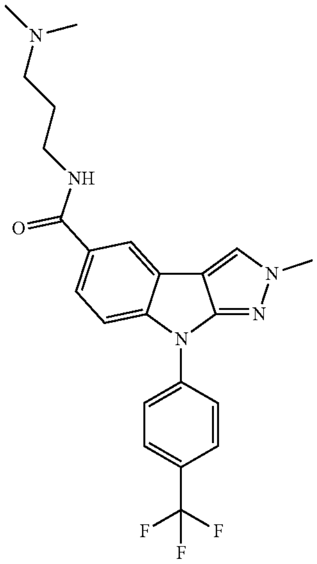 N-[3-(dimethylamino)propyl]-2-methyl-8-[4-(trifluoromethyl)phenyl]-2H,8H-pyrazolo[3,4-b]indole-5-carboxamide trifluoracetate | 1H NMR (400 MHz, DMSO) d 1.91 (p, J = 6.7 Hz, 2H), 2.80 (d, J = 4.7 Hz, 6H), 3.13 (dt, J = 10.0, 5.4 Hz, 2H), 3.38 (q, J = 6.4 Hz, 2H), 4.04 (s, 3H), 7.78 (d, J = 8.7 Hz, 1H), 7.85 (dd, J = 8.7, 1.8 Hz, 1H), 7.97 (d, J = 8.6 Hz, 2H), 8.08 (d, J = 8.4 Hz, 2H), 8.20 (s, 1H), 8.34 (d, J = 1.8 Hz, 1H), 8.63 (t, J = 5.8 Hz, 1H), 9.26 (s, 1H). | |

TABLE 1-continued

| Compound No. (Example No.) | Structure and Name | ¹H-NMR | Conditions and elution time (min) LCMS (M + H⁺) |
|---|---|---|---|
| Table 1 below shows exemplary compounds of the present invention. They have been synthesized as described in the Examples above or similar thereto. | | | |
| 518 | 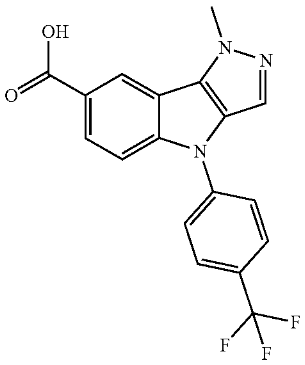 [SMILES: Cn1ncc2c1c1cc(C(=O)O)ccc1n2-c1ccc(C(F)(F)F)cc1] 1-methyl-4-[4-(trifluoromethyl)phenyl]-1H,4H-pyrazolo[4,3-b]indole-7-carboxylic acid | 1H NMR (400 MHz, DMSO) d 12.85 (s, 1H), 8.59 (d, J = 1.6 Hz, 1H), 8.00 (dd, J = 8.9, 1.7 Hz, 1H), 7.96 (s, 4H), 7.89 (d, J = 8.9 Hz, 1H), 7.76 (s, 1H), 4.26 (s, 3H). | |
| 519 | 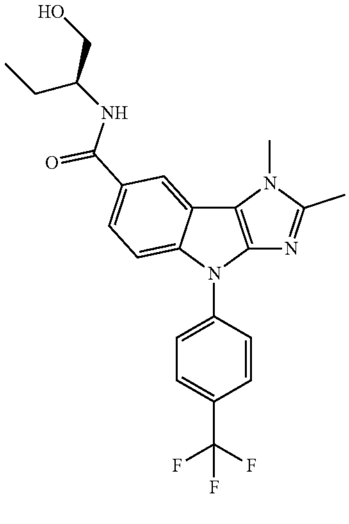 [SMILES: CC[C@@H](CO)NC(=O)c1ccc2c(c1)c1c(nc(C)n1C)n2-c1ccc(C(F)(F)F)cc1] Absolute configuration assigned arbitrarily N-[(2S)-1-hydroxybutan-2-yl]-1,2-dimethyl-4-[4-(trifluoromethyl)phenyl]-1H,4H-imidazo[4,5-b]indole-7-carboxamide | | |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 520 | 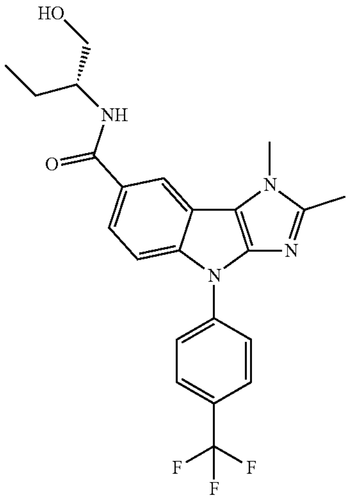 Absolute configuration assigned arbitrarily N-[(2R)-1-hydroxybutan-2-yl]-1,2-dimethyl-4-[4-(trifluoromethyl)phenyl]-1H,4H-imidazo[4,5-b]indole-7-carboxamide | | |
| 521 | 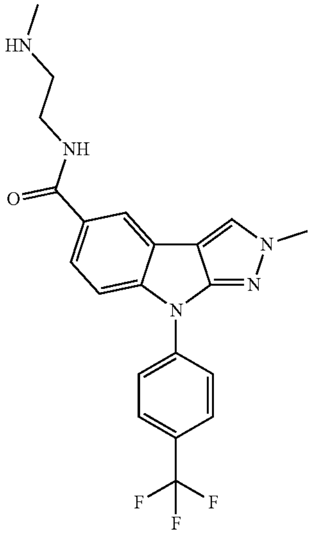 [SMILES: CNCCNC(=O)c1ccc2c(c1)c1cn(C)nc1n2-c1ccc(C(F)(F)F)cc1] 2-methyl-N-[2-(methylamino)ethyl]-8-[4-(trifluoromethyl)phenyl]-2H,8H-pyrazolo[3,4-b]indole-5-carboxamide | 1H NMR (400 MHz, DMSO) d 8.40 (t, J = 5.6 Hz, 1H), 8.34 (d, J = 1.8 Hz, 1H), 8.20 (s, 1H), 8.09 (d, J = 8.4 Hz, 2H), 7.96 (d, J = 8.5 Hz, 2H), 7.85 (dd, J = 8.7, 1.8 Hz, 1H), 7.76 (d, J = 8.7 Hz, 1H), 4.03 (s, 3H), 3.39 (q, J = 6.2 Hz, 2H), 2.67 (t, J = 6.5 Hz, 2H), 2.32 (s, 3H). | |

TABLE 1-continued

| Compound No. (Example No.) | Structure and Name | $^1$H-NMR | Conditions and elution time (min) LCMS (M + H$^+$) |
|---|---|---|---|
| Table 1 below shows exemplary compounds of the present invention. They have been synthesized as described in the Examples above or similar thereto. | | | |
| 522 | 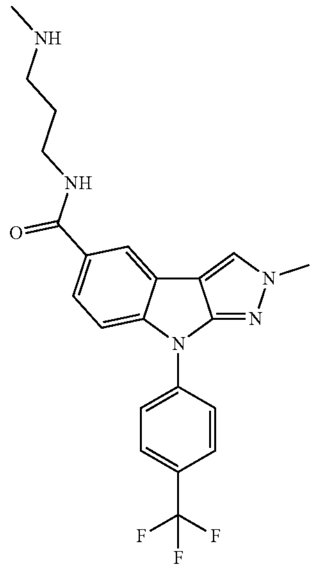 2-methyl-N-[3-(methylamino)propyl]-8-[4-(trifluoromethyl)phenyl]-2H,8H-pyrazolo[3,4-b]indole-5-carboxamide | 1H NMR (400 MHz, DMSO) d 8.55 (t, J = 5.6 Hz, 1H), 8.32 (d, J = 1.8 Hz, 1H), 8.20 (s, 1H), 8.09 (d, J = 8.4 Hz, 2H), 7.96 (d, J = 8.5 Hz, 2H), 7.83 (dd, J = 8.7, 1.8 Hz, 1H), 7.77 (d, J = 8.7 Hz, 1H), 4.03 (s, 3H), 3.34 (q, J = 6.5 Hz, 2H), 2.57 (t, J = 6.8 Hz, 2H), 2.31 (s, 3H), 1.70 (p, J = 6.9 Hz, 2H). | |
| 523 | 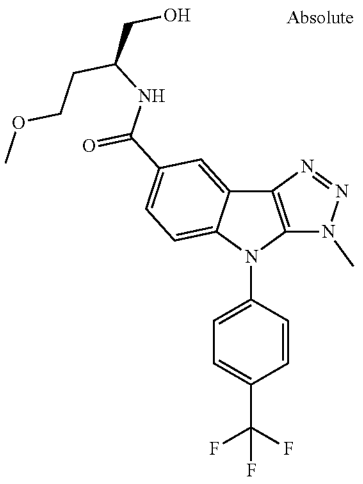 Absolute configuration assigned arbitrarily N-[(2S)-1-hydroxy-4-methoxybutan-2-yl]-3-methyl-4-[4-(trifluoromethyl)phenyl]-3H,4H-[1,2,3]triazolo[4,5-b]indole-7-carboxamide | | |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 524 | 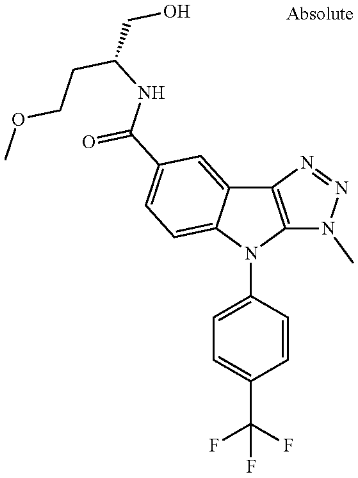 Absolute<br>Absolute configuration assigned arbitrarily N-[(2R)-1-hydroxy-4-methoxybutan-2-yl]-3-methyl-4-[4-(trifluoromethyl)phenyl]-3H,4H-[1,2,3]triazolo[4,5-b]indole-7-carboxamide | | |
| 525 | 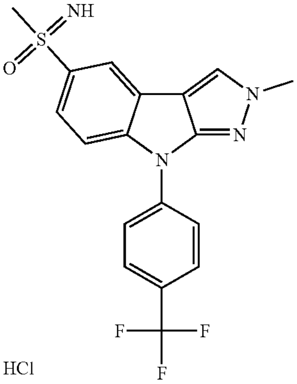 [SMILES: Cl ; Cn1cc2c3cc(S(C)(=N)=O)ccc3n(-c3ccc(C(F)(F)F)cc3)c2n1] HCl<br>imino(methyl){2-methyl-8-[4-(trifluoromethyl)phenyl]-2H,8H-pyrazolo[3,4-b]indol-5-yl}-$\lambda^6$-sulfanone | 1H NMR (700 MHz, DMSO) d 10.19 (s, 2H), 8.67 (d, J = 1.4 Hz, 1H), 8.58 (d, J = 2.1 Hz, 0H), 8.36 (s, 1H), 8.33 (s, 0H), 8.08 (d, J = 8.6 Hz, 2H), 8.05-8.01 (m, 5H), 7.98 (d, J = 8.8 Hz, 0H), 7.94 (dd, J = 8.8, 2.1 Hz, 0H), 4.08 (s, 3H), 4.01 (s, 3H), 3.90 (s, 0H). | |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 526 | 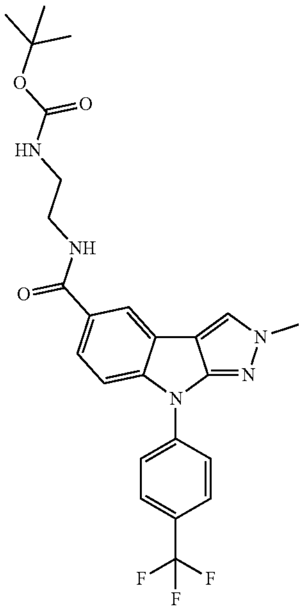 [SMILES: Cn1cc2c3cc(C(=O)NCCNC(=O)OC(C)(C)C)ccc3n(-c3ccc(C(F)(F)F)cc3)c2n1] tert-butyl N-[2-({2-methyl-8-[4-(trifluoromethyl)phenyl]-2H,8H-pyrazolo[3,4-b]indol-5-yl}formamido)ethyl]carbamate | (700 MHz, DMSO-$d_6$) δ 8.48 (t, J = 5.7 Hz, 1H), 8.33 (d, J = 1.9 Hz, 1H), 8.20 (s, 1H), 8.09 (d, J = 8.4 Hz, 2H), 7.97 (d, J = 8.4 Hz, 2H), 7.84 (dd, J = 8.7, 1.9 Hz, 1H), 7.77 (d, J = 8.6 Hz, 1H), 6.93 (t, J = 5.8 Hz, 1H), 4.04 (s, 3H), 3.34 (m, 2H), 3.14 (m, 2H), 1.39 (s, 9H). | |
| 527 | 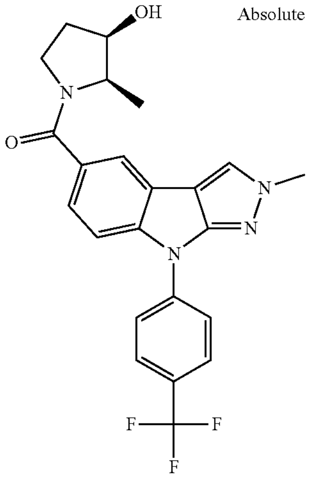 [SMILES: C[C@@H]1[C@H](O)CCN1C(=O)c1ccc2c(c1)c1cn(C)nc1n2-c1ccc(C(F)(F)F)cc1] Absolute<br>Absolute configuration assigned arbitrarily (2R,3R)-2-methyl-1-{2-methyl-8-[4-(trifluoromethyl)phenyl]-2H,8H-pyrazolo[3,4-b]indole-5-carbonyl}pyrrolidin-3-ol | | |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 528 | 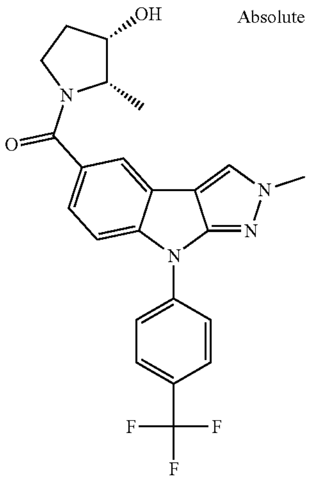 [SMILES: C[C@H]1[C@@H](O)CCN1C(=O)c1ccc2c(c1)c1cn(C)nc1n2-c1ccc(C(F)(F)F)cc1] Absolute configuration assigned arbitrarily (2S,3S)-2-methyl-1-{2-methyl-8-[4-(trifluoromethyl)phenyl]-2H,8H-pyrazolo[3,4-b]indole-5-carbonyl}pyrrolidin-3-ol | | |
| 529 | 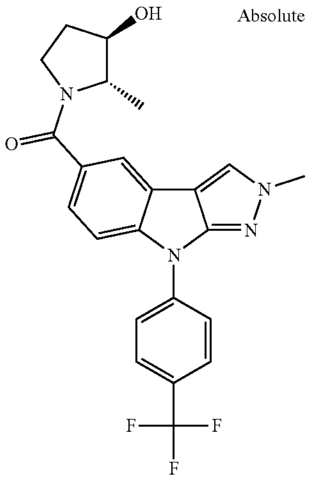 [SMILES: C[C@H]1[C@H](O)CCN1C(=O)c1ccc2c(c1)c1cn(C)nc1n2-c1ccc(C(F)(F)F)cc1] Absolute configuration assigned arbitrarily (2S,3R)-2-methyl-1-{2-methyl-8-[4-(trifluoromethyl)phenyl]-2H,8H-pyrazolo[3,4-b]indole-5-carbonyl}pyrrolidin-3-ol | | |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 530 | 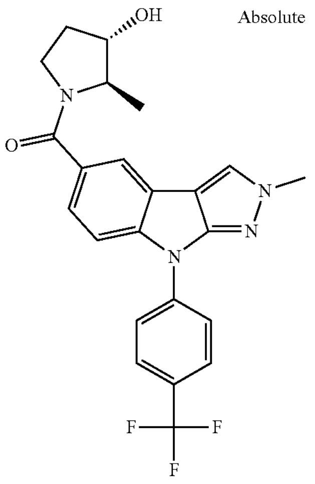 [SMILES: C[C@@H]1[C@@H](O)CCN1C(=O)c1ccc2c(c1)c1cn(C)nc1n2-c1ccc(C(F)(F)F)cc1] Absolute<br>Absolute configuration assigned arbitrarily (2R,3S)-2-methyl-1-{2-methyl-8-[4-(trifluoromethyl)phenyl]-2H,8H-pyrazolo[3,4-b]indole-5-carbonyl}pyrrolidin-3-ol | | |
| 531 | 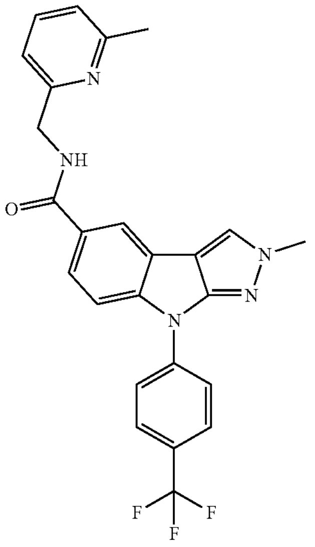 [SMILES: Cc1cccc(CNC(=O)c2ccc3c(c2)c2cn(C)nc2n3-c2ccc(C(F)(F)F)cc2)n1]<br>2-methyl-N-[(6-methylpyridin-2-yl)methyl]-8-[4-(trifluoromethyl)phenyl]-2H,8H-pyrazolo[3,4-b]indole-5-carboxamide | 1H NMR (700 MHz, DMSO) d 9.41-9.19 (m, 1H), 8.42 (d, J = 1.8 Hz, 1H), 8.23 (s, 1H), 8.14 (s, 1H), 8.09 (d, J = 8.3 Hz, 2H), 7.98 (d, J = 8.6 Hz, 2H), 7.92 (dd, J = 8.7, 1.9 Hz, 1H), 7.82 (d, J = 8.6 Hz, 1H), 7.55 (s, 2H), 4.71 (d, J = 5.6 Hz, 2H), 4.04 (s, 3H), 2.65 (s, 3H). | |

TABLE 1-continued

| Compound No. (Example No.) | Structure and Name | $^1$H-NMR | Conditions and elution time (min) LCMS (M + H$^+$) |
|---|---|---|---|
| Table 1 below shows exemplary compounds of the present invention. They have been synthesized as described in the Examples above or similar thereto. | | | |
| 532 | 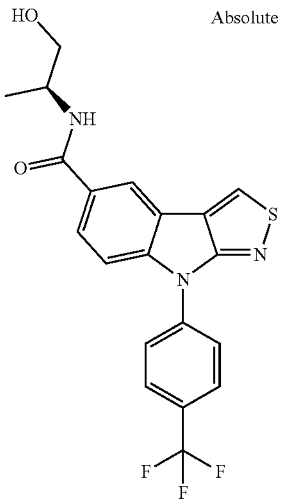 [SMILES: C[C@@H](CO)NC(=O)c1ccc2c(c1)c1csnc1n2-c1ccc(C(F)(F)F)cc1] N-[(2S)-1-hydroxypropan-2-yl]-8-[4-(trifluoromethyl)phenyl]-8H-[1,2]thiazolo[3,4-b]indole-5-carboxamide | 1H NMR (400 MHz, DMSO-d6) 9.47 (s, 1H), 8.58 (d, J = 1.8 Hz, 1H), 8.17 (d, J = 8.0 Hz, 1H), 8.11-7.96 (m, 5H), 7.64 (d, J = 8.7 Hz, 1H), 4.74 (t, J = 5.8 Hz, 1H), 4.14-4.02 (m, 1H), 3.56-3.47 (m, 1H), 3.41-3.33 (m, 1H), 1.18 (d, J = 6.7 Hz, 3H). | |
| 533 | 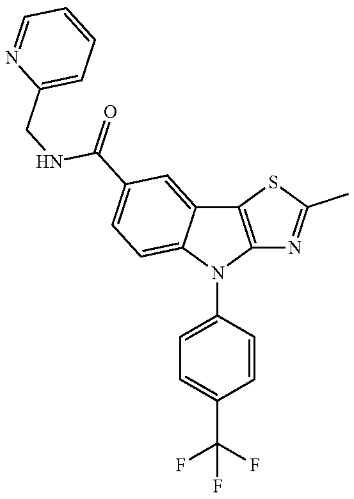 [SMILES: Cc1nc2c(s1)c1cc(C(=O)NCc3ccccn3)ccc1n2-c1ccc(C(F)(F)F)cc1] 2-methyl-N-[(pyridin-2-yl)methyl]-4-[4-(trifluoromethyl)phenyl]-4H-[1,3]thiazolo[4,5-b]indole-7-carboxamide | 1H NMR (300 MHz, DMSO-d6) 9.16 (t, J = 6.0 Hz, 1H), 8.58-8.50 (m, 2H), 8.04 (s, 4H), 7.95 (d, J = 8.9, 1H), 7.84-7.72 (m, 2H), 7.38 (d, J = 7.8 Hz, 1H), 7.34-7.23 (m, 1H), 4.63 (d, J = 5.8 Hz, 2H), 2.86 (s, 3H). | |

TABLE 1-continued

| Compound No. (Example No.) | Structure and Name | $^1$H-NMR | Conditions and elution time (min) LCMS (M + H$^+$) |
|---|---|---|---|
| | Table 1 below shows exemplary compounds of the present invention. They have been synthesized as described in the Examples above or similar thereto. | | |
| 534 | 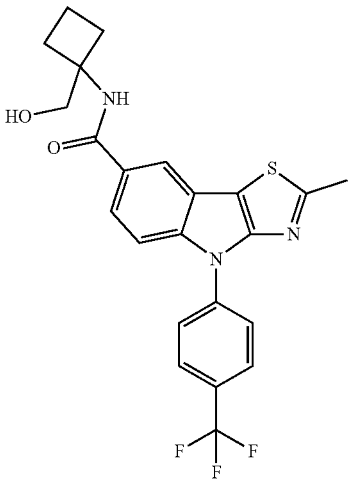 [SMILES: Cc1nc2c(s1)c1cc(C(=O)NC3(CO)CCC3)ccc1n2-c1ccc(C(F)(F)F)cc1] N-[1-(hydroxymethyl)cyclobutyl]-2-methyl-4-[4-(trifluoromethyl)phenyl]-4H-[1,3]thiazolo[4,5-b]indole-7-carboxamide | 1H NMR (300 MHz, DMSO-d6) 8.48 (s, 1H), 8.29 (s, 1H), 8.03 (s, 4H), 7.88 (d, J = 8.8, 1H), 7.74 (d, J = 8.8 Hz, 1H), 4.87 (t, J = 5.8 Hz, 1H), 3.69 (d, J = 5.8 Hz, 2H), 2.86 (s, 3H), 2.30 (m, 9.5 Hz, 2H), 2.23-2.14 (m, 2H), 1.92-1.73 (m, 2H). | |
| 535 | 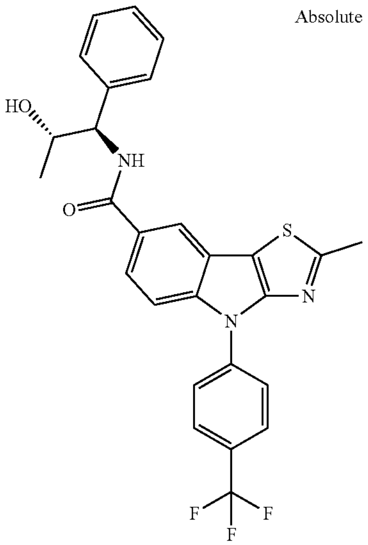 [SMILES: Cc1nc2c(s1)c1cc(C(=O)N[C@H](c3ccccc3)[C@H](C)O)ccc1n2-c1ccc(C(F)(F)F)cc1] N-[(1R,2S)-2-hydroxy-1-phenylpropyl]-2-methyl-4-[4-(trifluoromethyl)phenyl]-4H-[1,3]thiazolo[4,5-b]indole-7-carboxamide | 1H NMR (300 MHz, DMSO-d6) 8.64 (d, J = 8.8 Hz, 1H), 8.50 (d, J = 1.7 Hz, 1H), 8.03 (d, J = 1.6 Hz, 4H), 7.87 (d, J = 8.8, 1H), 7.76 (d, J = 8.8 Hz, 1H), 7.51-7.43 (m, 2H), 7.32 (t, J = 7.4 Hz, 2H), 7.23 (t, J = 7.2 Hz, 1H), 4.94 (dd, J = 8.7, 7.1 Hz, 1H), 4.78 (d, J = 5.8 Hz, 1H), 4.07 (m, 1H), 2.86 (s, 3H), 1.16 (d, J = 6.2 Hz, 3H). | |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 536 | 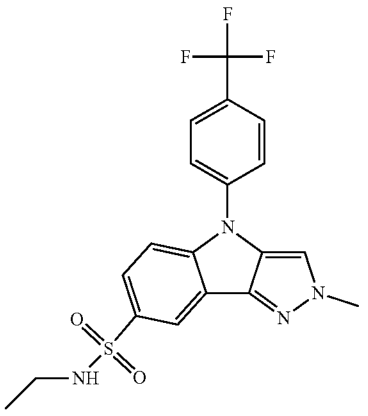 [SMILES: CCNS(=O)(=O)c1ccc2c(c1)c1nn(C)cc1n2-c1ccc(C(F)(F)F)cc1] N-ethyl-2-methyl-4-[4-(trifluoromethyl)phenyl]-2H,4H-pyrazolo[4,3-b]indole-7-sulfonamide | 1H NMR (300 MHz, DMSO-d6) 8.17 (d, J = 2.0 Hz, 1H), 8.03 (s, 1H), 7.84 (d, J = 2.3 Hz, 5H), 7.69 (dd, J = 9.0, 1.9 Hz, 1H), 7.41 (t, J = 5.5 Hz, 1H), 3.99 (s, 3H), 2.83-2.64 (m, 2H), 0.85 (t, J = 7.2 Hz, 3H). | |
| 537 | 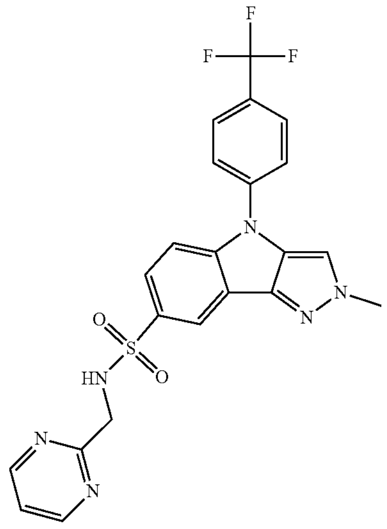 [SMILES: Cn1cc2c(n1)c1cc(S(=O)(=O)NCc3ncccn3)ccc1n2-c1ccc(C(F)(F)F)cc1] 2-methyl-N-[(pyrimidin-2-yl)methyl]-4-[4-(trifluoromethyl)phenyl]-2H,4H-pyrazolo[4,3-b]indole-7-sulfonamide | 1H NMR (400 MHz, DMSO-d6) 8.65 (d, J = 4.9 Hz, 2H), 8.33-8.22 (m, 2H), 8.15 (s, 1H), 8.00-7.91 (m, 4H), 7.88 (d, J = 8.8 Hz, 1H), 7.78 (dd, J = 8.8, 1.9 Hz, 1H), 7.28 (t, J = 4.9 Hz, 1H), 4.24 (d, J = 6.1 Hz, 2H), 4.12 (s, 3H). | |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 538 | 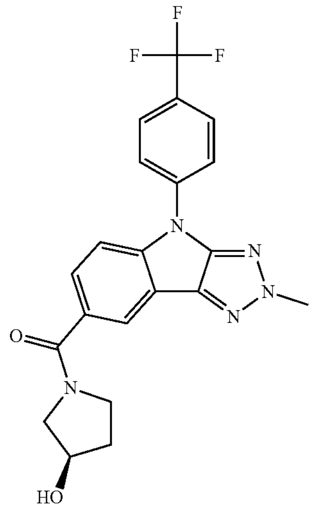 [SMILES: Cn1nc2c3cc(C(=O)N4CC[C@@H](O)C4)ccc3n(-c3ccc(C(F)(F)F)cc3)c2n1] (3R)-1-{2-methyl-4-[4-(trifluoromethyl)phenyl]-2H,4H-[1,2,3]triazolo[4,5-b]indole-7-carbonyl}pyrrolidin-3-ol | 1H NMR (300 MHz, DMSO-d6, ppm): 8.18 (s, 1H), 8.08 (d, J = 9.0 Hz, 2H), 8.01 (d, J = 9.0 Hz, 2H), 7.92 (d, J = 9.0 Hz, 1H), 7.69 (d, J = 9.0 Hz, 1H), 5.08-4.94 (m, 1H), 4.43-4.23 (m, 4H), 3.77-3.71 (m, 4H), 2.06-1.75 (m, 2H) | |
| 539 | 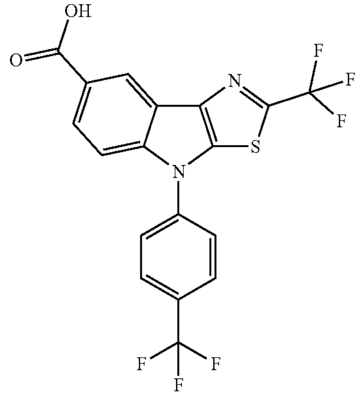 [SMILES: O=C(O)c1ccc2c(c1)c1nc(C(F)(F)F)sc1n2-c1ccc(C(F)(F)F)cc1] 2-(trifluoromethyl)-4-[4-(trifluoromethyl)phenyl]-4H-[1,3]thiazolo[5,4-b]indole-7-carboxylic acid | 1H NMR (300 MHz, DMSO-d6) 8.62 (s, 1H), 8.19-7.96 (m, 5H), 7.70 (d, J = 8.8 Hz, 1H). | |

| Com-pound No. (Example No.) | Structure and Name | $^1$H-NMR | Conditions and elution time (min) LCMS (M + H$^+$) |
|---|---|---|---|
| | Table 1 below shows exemplary compounds of the present invention. They have been synthesized as described in the Examples above or similar thereto. | | |
| 540 | Absolute 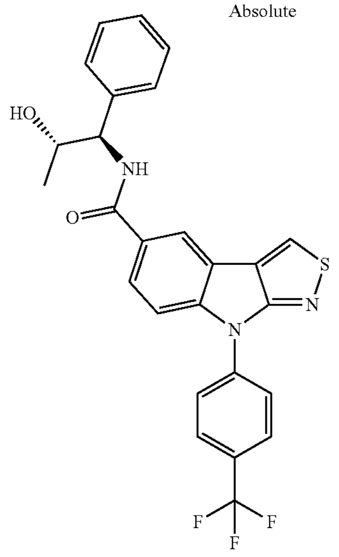 [SMILES: C[C@H](O)[C@H](NC(=O)c1ccc2c(c1)c1csnc1n2-c1ccc(C(F)(F)F)cc1)c1ccccc1] N-[(1R,2S)-2-hydroxy-1-phenylpropyl]-8-[4-(trifluoromethyl)phenyl]-8H-[1,2]thiazolo[3,4-b]indole-5-carboxamide | 1H NMR (400 MHz, DMSO-d6) 9.49 (s, 1H), 8.68 (d, J = 8.8 Hz, 1H), 8.59 (d, J = 1.8 Hz, 1H), 8.10-7.96 (m, 5H), 7.65 (d, J = 8.7 Hz, 1H), 7.49-7.43 (m, 2H), 7.31 (t, J = 7.5 Hz, 2H), 7.23 (t, J = 7.3 Hz, 1H), 4.93 (t, J = 7.9 Hz, 1H), 4.76 (d, J = 5.8 Hz, 1H), 4.06-4.03 (m, 1H), 1.16 (d, J = 6.2 Hz, 3H). | |
| 541 | Absolute 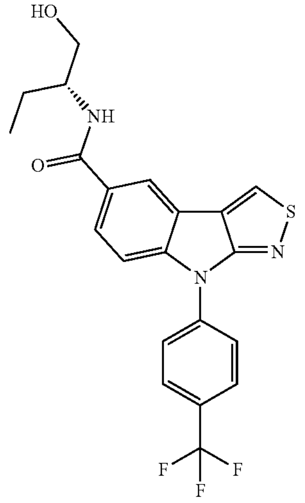 N-[(2R)-1-hydroxybutan-2-yl]-8-[4-(trifluoromethyl)phenyl]-8H-[1,2]thiazolo[3,4-b]indole-5-carboxamide | 1H NMR (400 MHz, DMSO-d6) 9.47 (d, J = 1.7 Hz, 1H), 8.59 (s, 1H), 8.07 (d, J = 7.6 Hz, 3H), 8.01 (d, J = 8.6 Hz, 3H), 7.64 (d, J = 8.7 Hz, 1H), 4.69 (t, J = 5.7 Hz, 1H), 3.92 (s, 1H), 3.55-3.50 (m, 1H), 3.46-3.37 (m, 1H), 1.74-1.65 (m, 1H), 1.55-1.43 (m, 1H), 0.91 (t, J = 7.4 Hz, 3H). | |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 542 | 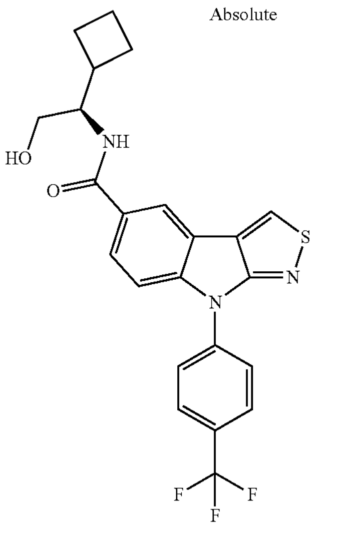 [SMILES: O=C(N[C@@H](CO)C1CCC1)c1ccc2c(c1)c1csnc1n2-c1ccc(C(F)(F)F)cc1] N-[(1R)-1-cyclobutyl-2-hydroxyethyl]-8-[4-(trifluoromethyl)phenyl]-8H-[1,2]thiazolo[3,4-b]indole-5-carboxamide | 1H NMR (400 MHz, DMSO-d6) 9.47 (s, 1H), 8.59 (d, J = 1.8 Hz, 1H), 8.20-7.85 (m, 6H), 7.64 (d, J = 8.7 Hz, 1H), 4.58 (t, J = 5.7 Hz, 1H), 4.13-4.00 (m, 1H), 3.44 (t, J = 6.0 Hz, 2H), 2.62-2.54 (m, 1H), 2.05-1.68 (m, 6H). | |
| 543 | 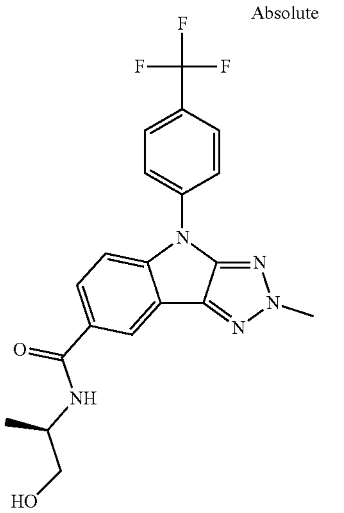 [SMILES: C[C@H](CO)NC(=O)c1ccc2c(c1)c1nn(C)nc1n2-c1ccc(C(F)(F)F)cc1] N-[(2R)-1-hydroxypropan-2-yl]-2-methyl-4-[4-(trifluoromethyl)phenyl]-2H,4H-[1,2,3]triazolo[4,5-b]indole-7-carboxamide | 1H NMR (300 MHz, DMSO-d6, ppm): 8.61 (s, 1H), 8.27 (d, J = 6.0 Hz, 1H), 8.11-7.98 (m, 5H), 7.93 (d, J = 6.0 Hz, 1H), 4.76(t, J = 6.0 Hz, 1H), 4.38 (s, 3H), 4.16-4.04 (m, 1H), 3.58-3.47 (m, 1H), 3.45-3.35 (m, 1H), 1.18 (d, J = 6.0 Hz, 3H) | |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 544 | 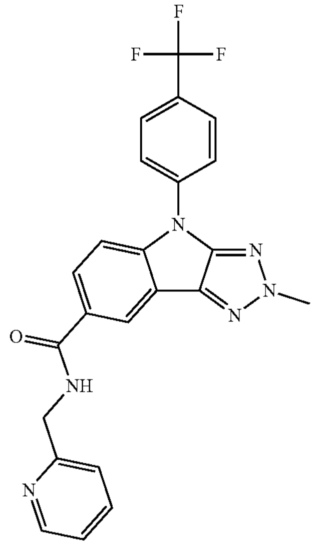 [SMILES: Cn1nc2c3cc(C(=O)NCc4ccccn4)ccc3n(-c3ccc(C(F)(F)F)cc3)c2n1] 2-methyl-N-[(pyridin-2-yl)methyl]-4-[4-(trifluoromethyl)phenyl]-2H,4H-[1,2,3]triazolo[4,5-b]indole-7-carboxamide | 1H NMR (300 MHz, DMSO-d6) 9.29 (t, J = 6.0 Hz, 1H), 8.65 (d, J = 1.8 Hz, 1H), 8.56-8.52 (m, 1H), 8.18-7.90 (m, 6H), 7.84-7.74 (m, 1H), 7.39 (d, J = 7.9 Hz, 1H), 7.32-7.24 (m, 1H), 4.64 (d, J = 5.8 Hz, 2H), 4.39 (s, 3H). | |
| 545 | Absolute 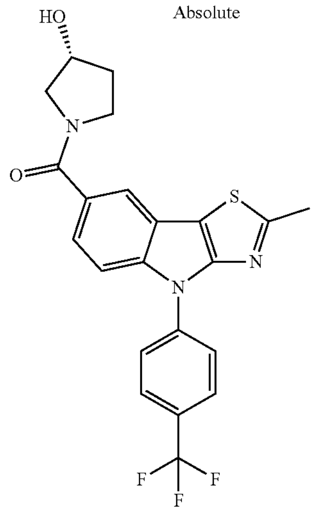 [SMILES: Cc1nc2c(s1)c1cc(C(=O)N3CC[C@@H](O)C3)ccc1n2-c1ccc(C(F)(F)F)cc1] (3R)-1-{2-methyl-4-[4-(trifluoromethyl)phenyl]-4H-[1,3]thiazolo[4,5-b]indole-7-carbonyl}pyrrolidin-3-ol | 1H NMR (300 MHz, DMSO-d6) 8.17 (d, J = 8.3 Hz, 1H), 8.02 (s, 4H), 7.73 (d, J = 8.7 Hz, 1H), 7.52 (d, J = 8.7 Hz, 1H), 5.00 (dd, J = 26.0, 3.2 Hz, 1H), 4.31 (d, J = 29.4 Hz, 1H), 3.82-3.28 (m, 4H), 2.85 (s, 3H), 2.03-1.75 (m, 2H). | |

TABLE 1-continued

| Com-pound No. (Example No.) | Structure and Name | $^1$H-NMR | Conditions and elution time (min) LCMS (M + H$^+$) |
|---|---|---|---|
| Table 1 below shows exemplary compounds of the present invention. They have been synthesized as described in the Examples above or similar thereto. | | | |
| 546 | 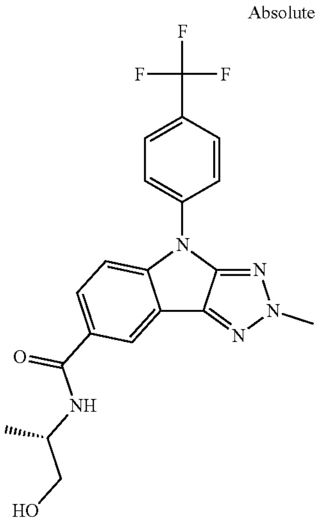 [SMILES: C[C@@H](CO)NC(=O)c1ccc2c(c1)c1nn(C)nc1n2-c1ccc(C(F)(F)F)cc1] N-[(2S)-1-hydroxypropan-2-yl]-2-methyl-4-[4-(trifluoromethyl)phenyl]-2H,4H-[1,2,3]triazolo[4,5-b]indole-7-carboxamide | 1H NMR (300 MHz, DMSO-d6, ppm): 8.61 (s, 1H), 8.27 (d, J = 6.0 Hz, 1H), 8.11-7.98 (m, 5H), 7.93 (d, J = 6.0 Hz, 1H), 4.76 (t, J = 6.0 Hz, 1H), 4.38 (s, 3H), 4.16-4.04 (m, 1H), 3.58-3.47 (m, 1H), 3.45-3.35 (m, 1H), 1.18 (d, J = 6.0 Hz, 3H) | |
| 547 | 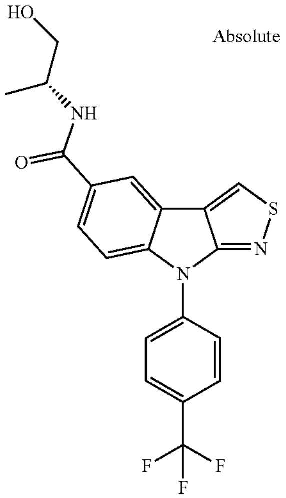 [SMILES: C[C@H](CO)NC(=O)c1ccc2c(c1)c1csnc1n2-c1ccc(C(F)(F)F)cc1] N-[(2R)-1-hydroxypropan-2-yl]-8-[4-(trifluoromethyl)phenyl]-8H-[1,2]thiazolo[3,4-b]indole-5-carboxamide | 1H NMR (400 MHz, DMSO-d6) 9.47 (d, J = 3.2 Hz, 1H), 8.55-8.60 (m, 1H), 8.24-8.16 (m, 1H), 8.11-8.04 (m, 2H), 8.04-7.95 (m, 3H), 8.04-7.95 (m, 1H), 4.71-4.80 (m, 1H), 4.11-4.03 (m, 1H), 3.56-3.46 (m, 1H), 3.42-3.36 (m, 1H), 1.20-1.13 (m, 3H). | |

TABLE 1-continued

| Compound No. (Example No.) | Structure and Name | $^1$H-NMR | Conditions and elution time (min) LCMS (M + H$^+$) |
|---|---|---|---|
| Table 1 below shows exemplary compounds of the present invention. They have been synthesized as described in the Examples above or similar thereto. | | | |
| 548 | 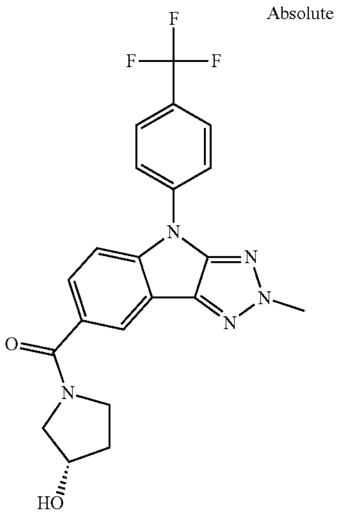 [SMILES: Cn1nc2c3cc(C(=O)N4CC[C@H](O)C4)ccc3n(-c3ccc(C(F)(F)F)cc3)c2n1] (3S)-1-{2-methyl-4-[4-(trifluoro-methyl)phenyl]-2H,4H-[1,2,3]triazolo[4,5-b]indole-7-carbonyl}pyrrolidin-3-ol | 1H NMR (300 MHz, DMSO-d6, ppm): 8.18 (s, 1H), 8.08 (d, J = 9.0 Hz, 2H), 8.01 (d, J = 9.0 Hz, 2H), 7.92 (d, J = 9.0 Hz, 1H), 7.69 (d, J = 9.0 Hz, 1H), 5.08-4.94 (m, 1H), 4.43-4.23 (m, 4H), 3.77-3.71 (m, 4H), 2.06-1.75 (m, 2H) | |
| 549 | 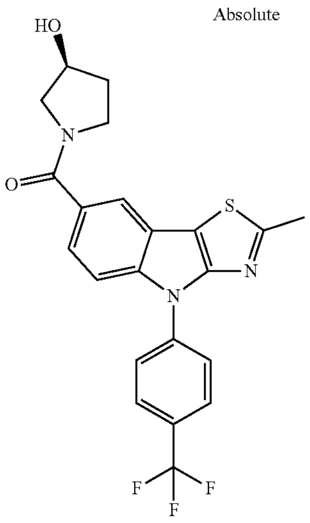 [SMILES: Cc1nc2c(s1)c1cc(C(=O)N3CC[C@H](O)C3)ccc1n2-c1ccc(C(F)(F)F)cc1] (3S)-1-{2-methyl-4-[4-(trifluoro-methyl)phenyl]-4H-[1,3]thiazolo[4,5-b]indole-7-carbonyl}pyrrolidin-3-ol | 1H NMR (300 MHz, DMSO-d6) 8.17 (d, J = 8.2 Hz, 1H), 8.03 (s, 4H), 7.73 (d, J = 8.6 Hz, 1H), 7.52 (d, J = 8.8 Hz, 1H), 5.07-4.91 (m, 1H), 4.31 (d, J = 29.5 Hz, 1H), 3.73-3.38 (m, 4H), 2.85 (s, 3H), 1.90 (d, J = 40.3 Hz, 2H). | |

TABLE 1-continued

| Compound No. (Example No.) | Structure and Name | $^1$H-NMR | Conditions and elution time (min) LCMS (M + H$^+$) |
|---|---|---|---|
| | Table 1 below shows exemplary compounds of the present invention. They have been synthesized as described in the Examples above or similar thereto. | | |
| 550 | 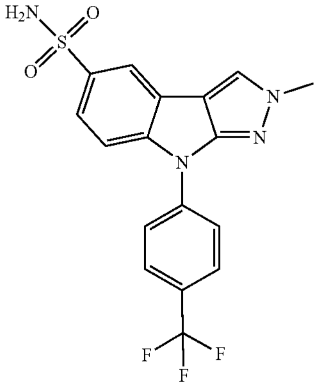 [SMILES: Cn1cc2c3cc(S(N)(=O)=O)ccc3n(-c3ccc(C(F)(F)F)cc3)c2n1] 2-methyl-8-[4-(trifluoromethyl)phenyl]-2H,8H-pyrazolo[3,4-b]indole-5-sulfonamide | 1H NMR (300 MHz, DMSO-d6) ¦8.34 "C 8.26 (m, 1H), 8.09 (d, J = 8.4 Hz, 1H), 7.99 (d, J = 8.6 Hz, 1H), 7.91 "C 7.73 (m, 1H), 7.31 (s, 1H), 4.05 (s, 1H). | |
| 551 | 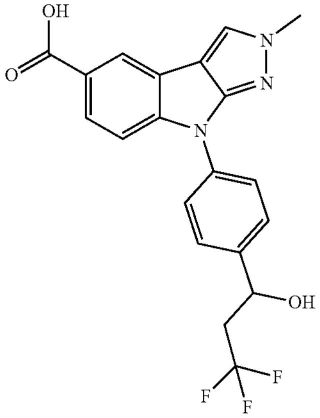 [SMILES: Cn1cc2c3cc(C(=O)O)ccc3n(-c3ccc(C(O)CC(F)(F)F)cc3)c2n1] 2-methyl-8-[4-(3,3,3-trifluoro-1-hydroxypropyl)phenyl]-2H,8H-pyrazolo[3,4-b]indole-5-carboxylic acid | 1H NMR (700 MHz, DMSO) d 12.63 (s, 1H), 8.41 (d, J = 1.8 Hz, 1H), 8.18 (s, 1H), 7.90 (dd, J = 8.7, 1.8 Hz, 1H), 7.75 (d, 2H), 7.64 (d, 2H), 7.58 (d, J = 8.6 Hz, 1H), 5.77 (s, 1H), 4.98 (t, J = 7.4, 5.6 Hz, 1H), 4.01 (s, 3H), 2.73-2.63 (m, 2H). | |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 552 | 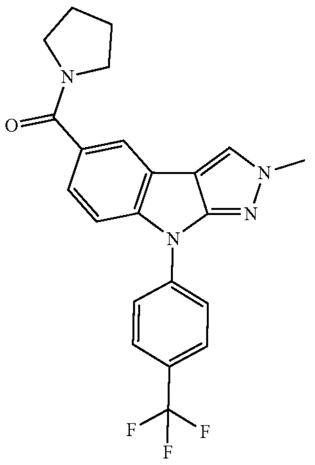 [SMILES: Cn1cc2c3cc(C(=O)N4CCCC4)ccc3n(-c3ccc(C(F)(F)F)cc3)c2n1] 1-{2-methyl-8-[4-(trifluoromethyl)phenyl]-2H,8H-pyrazolo[3,4-b]indole-5-carbonyl}pyrrolidine | 1H NMR (400 MHz, DMSO) d 8.14 (s, 1H), 8.11-8.06 (m, 2H), 8.02 (dd, J = 1.8, 0.6 Hz, 1H), 7.98-7.93 (m, 2H), 7.75 (dd, J = 8.6, 0.6 Hz, 1H), 7.50 (dd, J = 8.6, 1.8 Hz, 1H), 4.03 (s, 3H), 3.51 (t, J = 6.6 Hz, 4H), 3.26 (s, 4H), 1.86 (s, 4H). | |
| 553 | 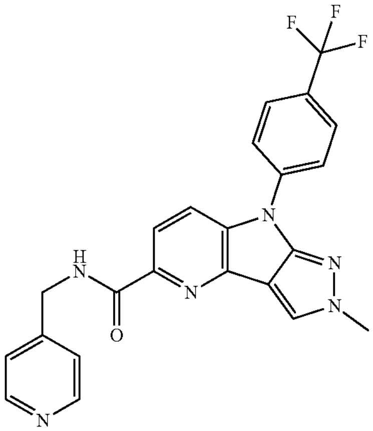 [SMILES: Cn1cc2c3nc(C(=O)NCc4ccncc4)ccc3n(-c3ccc(C(F)(F)F)cc3)c2n1] 4-methyl-N-[(pyridin-4-yl)methyl]-7-[4-(trifluoromethyl)phenyl]-4,5,7,12-tetraazatricyclo [6.4.0.0$^{2,6}$]dodeca-1(8),2,5,9,11-pentaene-11-carboxamide | 1H NMR (400 MHz, DMSO-d6) 9.42 (t, J = 6.4 Hz, 1H), 8.55-8.47 (m, 2H), 8.37 (s, 1H), 8.26 (d, J = 8.7 Hz, 1H), 8.12 (d, J = 8.4 Hz, 2H), 8.05 (d, J = 8.6 Hz, 1H), 8.00 (d, J = 8.6 Hz, 2H), 7.37-7.30 (m, 2H), 4.57 (d, J = 6.3 Hz, 2H), 4.10 (s, 3H). | B 4.47 min, (M + H) 451 |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 554 | 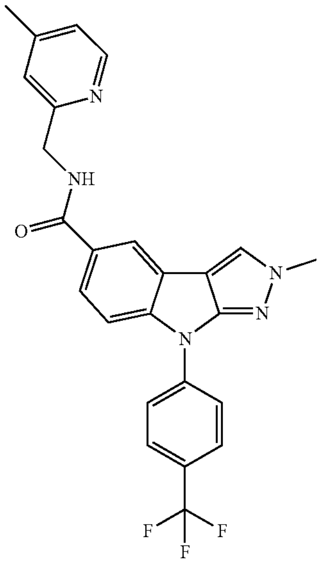 2-methyl-N-[(4-methylpyridin-2-yl)methyl]-8-[4-(trifluoromethyl)phenyl]-2H,8H-pyrazolo[3,4-b]indole-5-carboxamide | 1H NMR (700 MHz, DMSO) d 9.25 (t, J = 5.7 Hz, 1H), 8.57 (d, J = 5.6 Hz, 1H), 8.43 (d, J = 1.8 Hz, 1H), 8.23 (s, 1H), 8.09 (d, J = 8.4 Hz, 2H), 7.98 (d, J = 8.3 Hz, 2H), 7.92 (dd, J = 8.7, 1.9 Hz, 1H), 7.82 (d, J = 8.6 Hz, 1H), 7.55 (s, 1H), 7.49 (s, 1H), 4.70 (d, J = 5.6 Hz, 2H), 4.04 (s, 3H), 2.46 (s, 3H). | |
| 555 | 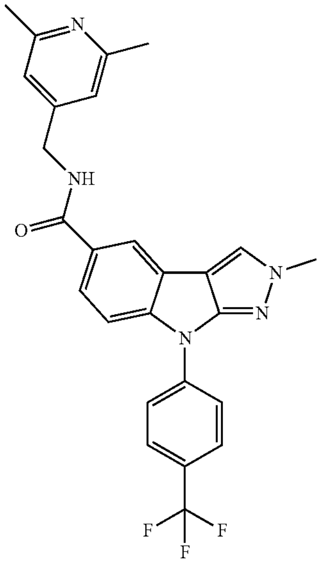 N-[(2,6-dimethylpyridin-4-yl)methyl]-2-methyl-8-[4-(trifluoromethyl)phenyl]-2H,8H-pyrazolo[3,4-b]indole-5-carboxamide | 1H NMR (700 MHz, DMSO) d 9.33 (t, J = 5.7 Hz, 1H), 8.43 (d, J = 1.8 Hz, 1H), 8.23 (s, 1H), 8.09 (d, J = 8.4 Hz, 2H), 7.98 (d, J = 8.6 Hz, 2H), 7.92 (dd, J = 8.7, 1.9 Hz, 1H), 7.82 (d, J = 8.6 Hz, 1H), 7.58 (s, 1H), 7.54 (s, 1H), 4.73 (d, J = 5.6 Hz, 2H), 4.05 (s, 3H), 2.67 (s, 3H), 2.49 (s, 3H). | |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 556 | Absolute 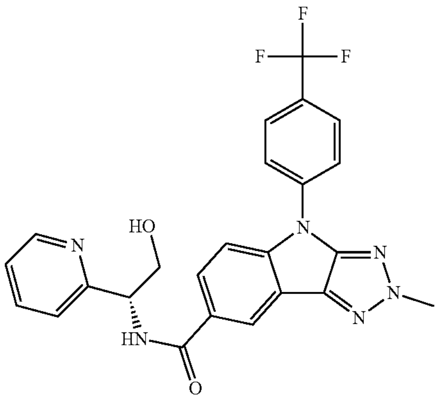 N-[(1R)-2-hydroxy-1-(pyridin-2-yl)ethyl]-2-methyl-4-[4-(trifluoromethyl)phenyl]-2H,4H-[1,2,3]triazolo[4,5-b]indole-7-carboxamide | 1H NMR (300 MHz, DMSO-d6) 8.87 (d, J = 7.8 Hz, 1H), 8.73 (s, 1H), 8.62-8.48 (m, 1H), 8.14-7.92 (m, 6H), 7.83-7.72 (m, 1H), 7.48 (d, J = 7.8 Hz, 1H), 7.32-7.24 (m, 1H), 5.27-5.16 (m, 1H), 5.00 (t, J = 6.0 Hz, 1H), 4.39 (s, 3H), 3.94-3.80 (m, 2H). | |
| 557 | Absolute 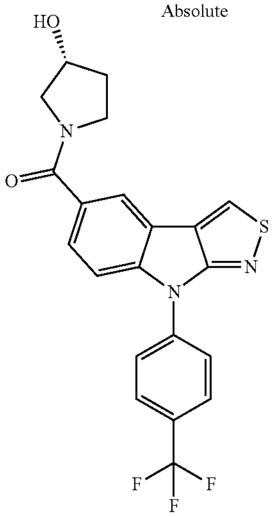 [SMILES: O=C(c1ccc2c(c1)c1csnc1n2-c1ccc(C(F)(F)F)cc1)N1CC[C@@H](O)C1] (3R)-1-{8-[4-(trifluoromethyl)phenyl]-8H-[1,2]thiazolo[3,4-b]indole-5-carbonyl}pyrrolidin-3-ol | 1H NMR (300 MHz, DMSO-d6) 9.43 (s, 1H), 8.29 (d, J = 8.4 Hz, 1H), 8.07 (d, J = 8.4 Hz, 2H), 7.99 (d, J = 8.3 Hz, 2H), 7.62 (s, 2H), 5.02 (s, 1H), 4.95 (s, 1H), 4.25 (s, 1H), 3.64-3.49 (m, 3H), 1.95 (s, 1H), 1.83 (s, 1H). | |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 558 | Absolute 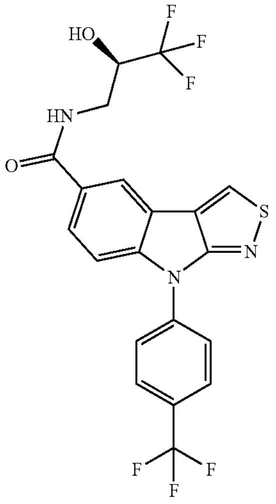 N-[(2R)-3,3,3-trifluoro-2-hydroxypropyl]-8-[4-(trifluoromethyl)phenyl]-8H-[1,2]thiazolo[3,4-b]indole-5-carboxamide | 1H NMR (300 MHz, DMSO-d6) 9.48 (s, 1H), 8.78 (t, J = 5.7 Hz, 1H), 8.58 (d, J = 1.8 Hz, 1H), 8.11-7.94 (m, 5H), 7.65 (d, J = 8.7 Hz, 1H), 6.52 (d, J = 6.4 Hz, 1H), 4.28-4.18 (m, 1H), 3.72-3.58 (m, 1H), 3.42-3.31 (m, 1H). | |
| 559 | 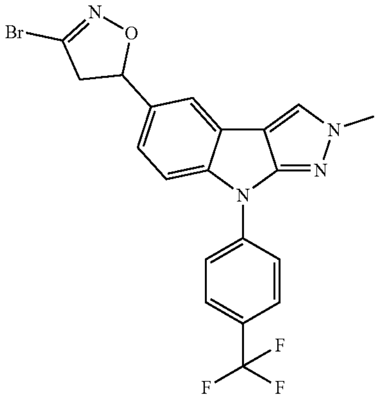 3-bromo-5-{2-methyl-8-[4-(trifluoromethyl)phenyl]-2H,8H-pyrazolo[3,4-b]indol-5-yl}-4,5-dihydro-1,2-oxazole | 1H NMR (400 MHz, Chloroform-d) 7.94 (d, J = 8.3 Hz, 2H), 7.86-7.76 (m, 3H), 7.69-7.61 (m, 2H), 7.31-7.24 (m, 1H), 5.88-5.79 (m, 1H), 4.09 (s, 3H), 3.75-3.68 (m, 1H), 3.39-3.30 (m, 1H). | |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 560 | 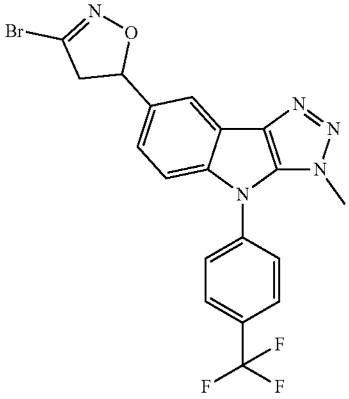 [SMILES: Cn1nnc2c3cc(C4CC(Br)=NO4)ccc3n(-c3ccc(C(F)(F)F)cc3)c21] 3-bromo-5-{3-methyl-4-[4-(trifluoromethyl)phenyl]-3H,4H-[1,2,3]triazolo[4,5-b]indol-7-yl}-4,5-dihydro-1,2-oxazole | 1H NMR (300 MHz, DMSO-d6) 8.11-7.97 (m, 6H), 7.55 (m, 1H), 5.91 (t, J = 10.1 Hz, 1H), 4.37 (s, 3H), 3.84 (m, 1H), 3.47 (m, 1H). | |
| 561 | 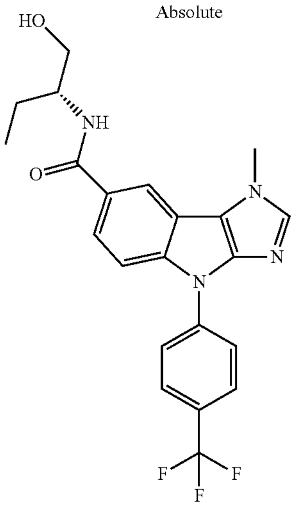 [SMILES: CC[C@H](CO)NC(=O)c1ccc2c(c1)c1c(ncn1C)n2-c1ccc(C(F)(F)F)cc1] N-[(2R)-1-hydroxybutan-2-yl]-1-methyl-4-[4-(trifluoromethyl)phenyl]-1H,4H-imidazo[4,5-b]indole-7-carboxamide | 1H NMR (300 MHz, DMSO-d6) 8.44 (s, 1H), 8.08 (dd, J = 17.8, 8.4 Hz, 3H), 7.99 (d, J = 8.5 Hz, 2H), 7.90-7.80 (m, 3H),4.96-4.63 (m, 1H),4.14 (s, 3H), 3.95 (d, J = 5.9 Hz, 1H), 3.61-3.39 (m, 2H), 1.81-1.65 (m, 1H), 1.52 (dt, J = 14.4, 7.7 Hz, 1H), 0.93 (t, J = 7.3 Hz, 3H). | |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 562 | 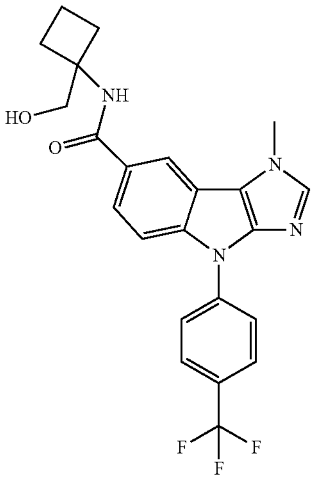 [SMILES: Cn1cnc2c1c1cc(C(=O)NC3(CO)CCC3)ccc1n2-c1ccc(C(F)(F)F)cc1] N-[1-(hydroxymethyl)cyclobutyl]-1-methyl-4-[4-(trifluoromethyl)phenyl]-1H,4H-imidazo[4,5-b]indole-7-carboxamide | 1H NMR (300 MHz, DMSO-d6) 8.45 (d, J = 1.6 Hz, 1H), 8.31 (s, 1H), 8.11 (d, J = 8.5 Hz, 2H), 7.98 (d, J = 8.5 Hz, 2H), 7.91-7.79 (m, 3H), 4.91 (t, J = 5.7 Hz, 1H), 4.14 (s, 3H), 3.71 (d, J = 5.8 Hz, 2H), 2.37-2.14 (m, 4H), 1.95-1.70 (m, 2H). | |
| 563 | Absolute 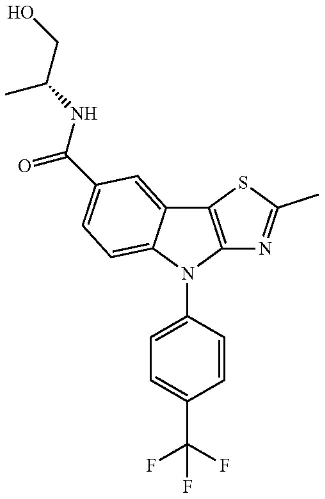 N-[(2R)-1-hydroxypropan-2-yl]-2-methyl-4-[4-(trifluoromethyl)phenyl]-4H-[1,3]thiazolo[4,5-b]indole-7-carboxamide | 1H NMR (300 MHz, DMSO-d6) 8.46 (s, 1H), 8.14 (d, J = 8.0 Hz, 1H), 8.03 (s, 4H), 7.93-7.84 (m, 1H), 7.75 (d, J = 8.8 Hz, 1H), 4.75 (t, J = 5.8 Hz, 1H), 4.13-4.03 (m, 1H), 3.52 (m, 1H), 3.41 (d, J = 6.3 Hz, 1H), 2.86 (s, 3H), 1.18 (d, J = 6.7 Hz, 3H). | |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 564 | 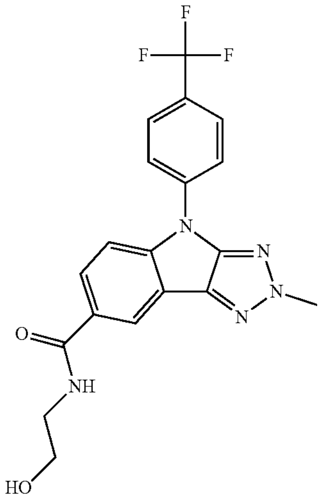 [SMILES: Cn1nc2c3cc(C(=O)NCCO)ccc3n(-c3ccc(C(F)(F)F)cc3)c2n1] N-(2-hydroxyethyl)-2-methyl-4-[4-(trifluoromethyl)phenyl]-2H,4H-[1,2,3]triazolo[4,5-b]indole-7-carboxamide | 1H NMR (300 MHz, DMSO-d6) 8.64-8.53 (m, 2H), 8.12-7.99 (m, 5H), 7.93 (d, J = 8.8 Hz, 1H), 4.78 (t, J = 5.6 Hz, 1H), 4.38 (s, 3H), 3.62-3.53 (m, 2H), 3.45-3.34 (m, 2H). | |
| 565 | 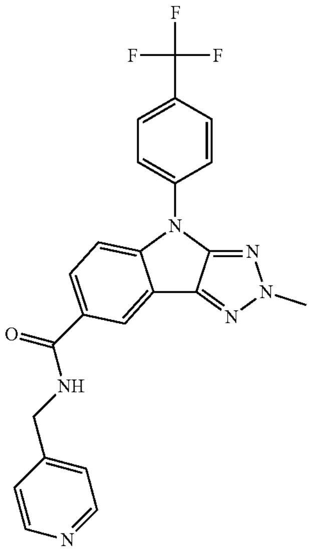 [SMILES: Cn1nc2c3cc(C(=O)NCc4ccncc4)ccc3n(-c3ccc(C(F)(F)F)cc3)c2n1] 2-methyl-N-[(pyridin-4-yl)methyl]-4-[4-(trifluoromethyl)phenyl]-2H,4H-[1,2,3]triazolo[4,5-b]indole-7-carboxamide | 1H NMR (300 MHz, DMSO-d6) 9.30 (t, J = 6.0 Hz, 1H), 8.64 (d, J = 1.8 Hz, 1H), 8.58-8.47 (m, 2H), 8.14-7.91 (m, 6H), 7.41-7.32 (m, 2H), 4.57 (d, J = 5.9 Hz, 2H), 4.39 (s, 3H). | |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 566 | Absolute 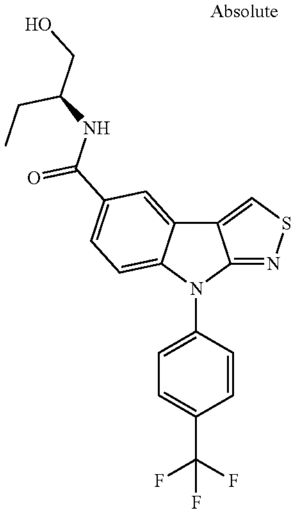 [SMILES: CC[C@@H](CO)NC(=O)c1ccc2c(c1)c1csnc1n2-c1ccc(C(F)(F)F)cc1] N-[(2S)-1-hydroxybutan-2-yl]-8-[4-(trifluoromethyl)phenyl]-8H-[1,2]thiazolo[3,4-b]indole-5-carboxamide | 1H NMR (300 MHz, DMSO-d6) 9.46 (d, J = 1.4 Hz, 1H), 8.57 (s, 1H), 8.06 (d, J = 8.7 Hz, 3H), 7.99 (d, J = 9.1 Hz, 3H), 7.62 (d, J = 8.7 Hz, 1H), 4.68 (t, J = 5.7 Hz, 1H), 3.90 (s, 1H), 3.42 (t, J = 5.8 Hz, 2H), 3.26 (s, 1H), 1.68 (s, 1H), 0.89 (t, J = 7.5 Hz, 3H). | |
| 567 | Absolute 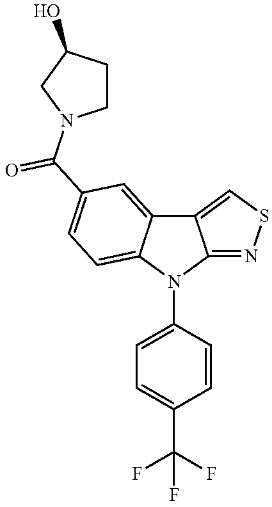 (3S)-1-{8-[4-(trifluoromethyl)phenyl]-8H-[1,2]thiazolo[3,4-b]indole-5-carbonyl}pyrrolidin-3-ol | 1H NMR (400 MHz, DMSO-d6) 9.45 (d, J = 2.5 Hz, 1H), 8.30 (d, J = 11.8 Hz, 1H), 8.08 (d, J = 8.5 Hz, 2H), 8.00 (d, J = 8.4 Hz, 2H), 7.63 (d, J = 5.2 Hz, 2H), 5.07-4.93 (m, 1H), 4.31 (d, J = 37.6 Hz, 1H), 3.77-3.68 (m, 1H), 3.61-3.49 (m, 2H), 3.33 (s, 1H), 1.88 (d, J = 38.5 Hz, 2H). | |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 568 | Absolute 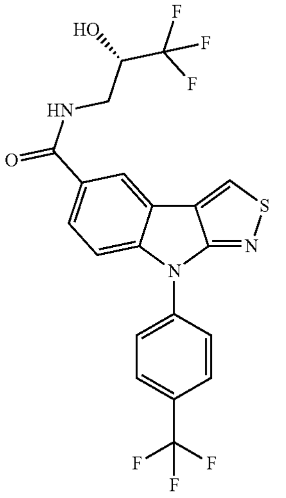 N-[(2S)-3,3,3-trifluoro-2-hydroxypropyl]-8-[4-(trifluoromethyl)phenyl]-8H-[1,2]thiazolo[3,4-b]indole-5-carboxamide | 1H NMR (300 MHz, DMSO-d6) 9.48 (s, 1H), 8.78 (t, J = 5.7 Hz, 1H), 8.58 (d, J = 1.8 Hz, 1H), 8.06 (d, J = 8.5 Hz, 2H), 8.03-7.94 (m, 3H), 7.64 (d, J = 8.7 Hz, 1H), 6.52 (d, J = 6.4 Hz, 1H), 4.31-4.18 (m, 1H), 3.73-3.58 (m, 1H), 3.42-3.31 (m, 1H). | |
| 569 | Absolute 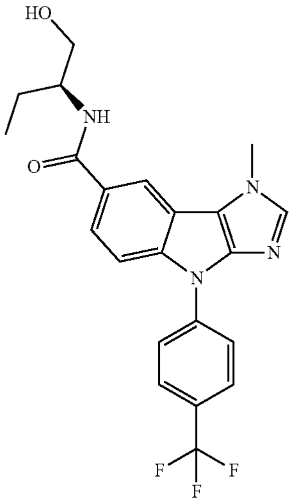 N-[(2S)-1-hydroxybutan-2-yl]-1-methyl-4-[4-(trifluoromethyl)phenyl]-1H,4H-imidazo[4,5-b]indole-7-carboxamide | 1H NMR (300 MHz, DMSO-d6) 8.43 (s, 1H), 8.08 (dd, J = 18.3, 8.4 Hz, 3H), 7.99 (d, J = 8.5 Hz, 2H), 7.91-7.80 (m, 3H), 4.96-4.63 (m, 1H),4.14 (s, 3H), 3.95 (d, J = 5.4 Hz, 1H), 3.58-3.42 (m, 2H), 1.81-1.65 (m, 1H), 1.63-1.45 (m, 1H), 0.93 (t, J = 7.4 Hz, 3H). | |

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 570 | Absolute 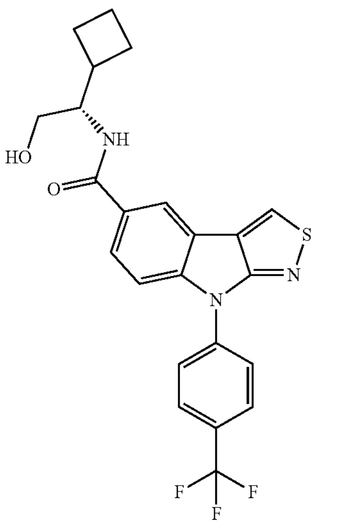 N-[(1S)-1-cyclobutyl-2-hydroxyethyl]-8-[4-(trifluoromethyl)phenyl]-8H-[1,2]thiazolo[3,4-b]indole-5-carboxamide | 1H NMR (300 MHz, DMSO-d6) 9.46 (s, 1H), 8.58 (s, 1H), 8.14-7.86 (m, 6H), 7.62 (d, J = 8.5 Hz, 1H), 4.56 (d, J = 5.7 Hz, 1H), 4.05 (s, 1H), 3.43 (d, J = 5.7 Hz, 3H), 1.78 (s, 6H). | |
| 571 | Absolute 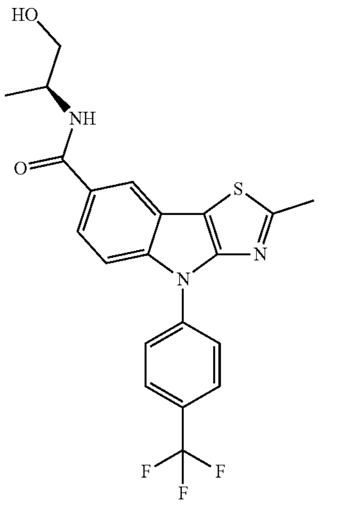 N-[(2S)-1-hydroxypropan-2-yl]-2-methyl-4-[4-(trifluoromethyl)phenyl]-4H-[1,3]thiazolo[4,5-b]indole-7-carboxamide | 1H NMR (300 MHz, DMSO-d6) 8.46 (d, J = 1.7 Hz, 1H), 8.14 (d, J = 7.9 Hz, 1H), 8.03 (d, J = 1.4 Hz, 4H), 7.88 (d, J = 8.7, 1H), 7.75 (d, J = 8.8 Hz, 1H), 4.76 (t, J = 5.8 Hz, 1H), 4.08 (m, 1H), 3.52 (m, 1H), 3.43-3.35 (m, 1H), 2.86 (s, 3H), 1.18 (d, J = 6.7 Hz, 3H). | |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 572 | Absolute 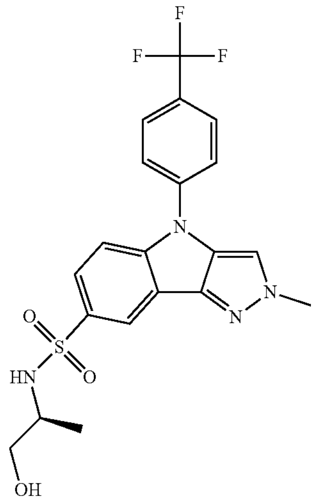 N-[(2S)-1-hydroxypropan-2-yl]-2-methyl-4-[4-(trifluoromethyl)phenyl]-2H,4H-pyrazolo[4,3-b]indole-7-sulfonamide | 1H NMR (400 MHz, DMSO-d6) 8.33 (d, J = 1.9 Hz, 1H), 8.16 (s, 1H), 7.96 (d, J = 5.0 Hz, 5H), 7.84 (dd, J = 8.8, 1.9 Hz, 1H), 7.52 (d, J = 6.9 Hz, 1H), 4.12 (s, 3H), 3.31 (d, J = 5.6 Hz, 0H), 3.20-3.01 (m, 2H), 0.89 (d, J = 6.2 Hz, 3H). | |
| 573 | 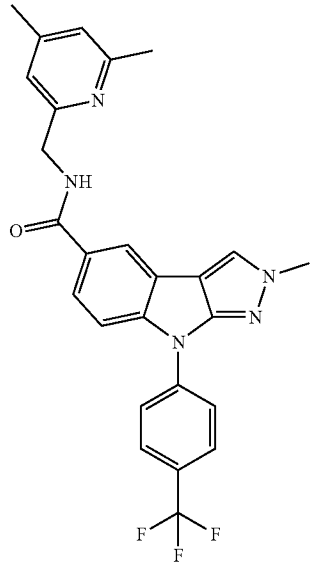 N-[(4,6-dimethylpyridin-2-yl)methyl]-2-methyl-8-[4-(trifluoromethyl)phenyl]-2H,8H-pyrazolo[3,4-b]indole-5-carboxamide | 1H NMR (400 MHz, DMSO) d 9.26 (t, J = 5.6 Hz, 1H), 8.42 (d, J = 1.8 Hz, 1H), 8.22 (s, 1H), 8.12-8.06 (m, 2H), 8.02-7.95 (m, 2H), 7.92 (dd, J = 8.7, 1.9 Hz, 1H), 7.81 (d, J = 8.8 Hz, 1H), 7.51 (s, 1H), 7.48 (s, 1H), 4.72 (s, 1H), 4.71 (s, 1H), 4.04 (s, 3H), 2.64 (s, 3H), 2.47 (s, 3H), . | |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 574 | 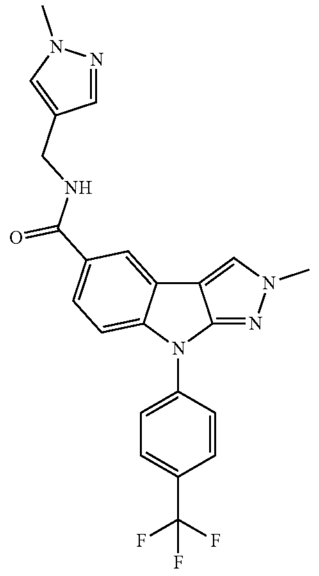 2-methyl-N-[(1-methyl-1H-pyrazol-4-yl)methyl]-8-[4-(trifluoromethyl)phenyl]-2H,8H-pyrazolo[3,4-b]indole-5-carboxamide | 1H NMR (700 MHz, DMSO) d 8.83 (t, J = 5.7 Hz, 1H), 8.35 (d, J = 1.8 Hz, 1H), 8.20 (s, 1H), 8.08 (d, J = 8.5 Hz, 2H), 7.97 (d, J = 8.5 Hz, 2H), 7.86 (dd, J = 8.7, 1.9 Hz, 1H), 7.77 (d, J = 8.7 Hz, 1H), 7.62 (s, 1H), 7.38 (s, 1H), 4.33 (d, J = 5.6 Hz, 2H), 4.03 (s, 3H), 3.79 (s, 3H). Spektrum | |
| 575 | Absolute 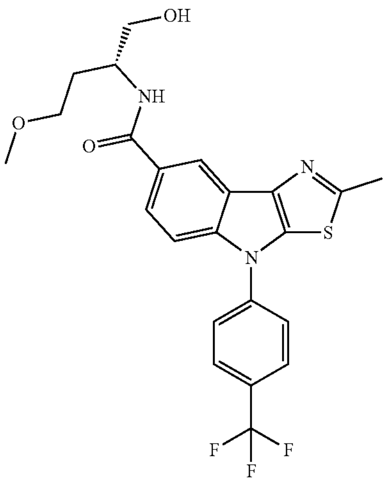 Absolute configuration assigned arbitrarily N-[(2R)-1-hydroxy-4-methoxybutan-2-yl]-2-methyl-4-[4-(trifluoromethyl)phenyl]-4H-[1,3]thiazolo[5,4-b]indole-7-carboxamide | | |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 576 | Absolute 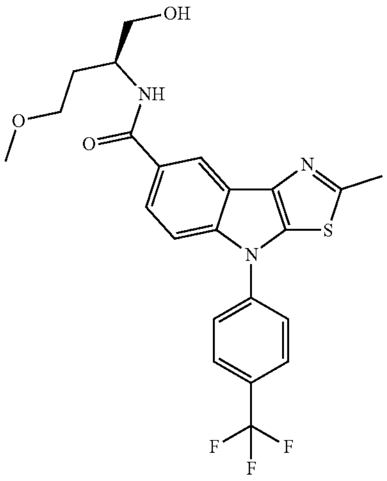 Absolute configuratin assigned arbitrarily N-[(2S)-1-hydroxy-4-methoxybutan-2-yl]-2-methyl-4-[4-(trifluoromethyl)phenyl]-4H-[1,3]thiazolo[5,4-b]indole-7-carboxamide | | |
| 577 | Absolute 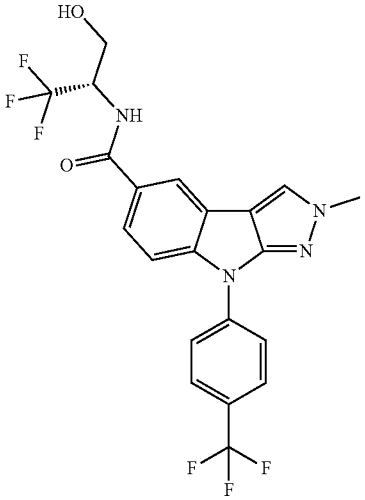 2-methyl-N-[(2S)-1,1,1-trifluoro-3-hydroxypropan-2-yl]-8-[4-(trifluoromethyl)phenyl]-2H,8H-pyrazolo[3,4-b]indole-5-carboxamide | 1H NMR (700 MHz, DMSO) d 8.79 (d, J = 8.9 Hz, 1H), 8.43 (d, J = 1.9 Hz, 1H), 8.23 (s, 1H), 8.09 (d, J = 8.4 Hz, 2H), 7.98 (d, J = 8.6 Hz, 2H), 7.92 (dd, J = 8.6, 1.9 Hz, 1H), 7.81 (d, J = 8.7 Hz, 1H), 5.19 (t, J = 6.0 Hz, 1H), 4.86 (qd, J = 8.4, 5.3 Hz, 1H), 4.04 (s, 3H), 3.84 (dt, J = 11.2, 5.4 Hz, 1H), 3.77 (dt, J = 11.6, 6.9 Hz, 1H). | |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 578 | 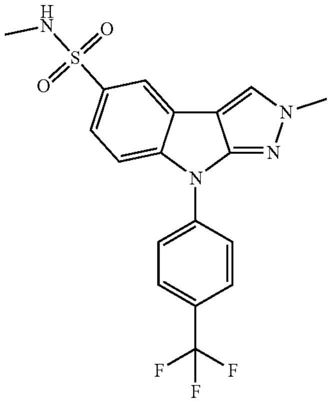 N,2-dimethyl-8-[4-(trifluoromethyl)phenyl]-2H,8H-pyrazolo[3,4-b]indole-5-sulfonamide | 1H NMR (300 MHz, DMSO-d6) 8.27 (d, J = 2.2 Hz, 2H), 8.09 (d, J = 8.5 Hz, 2H), 7.99 (d, J = 8.6 Hz, 2H), 7.89 (d, J = 8.7 Hz, 1H), 7.77-7.68 (m, 1H), 7.36 (d, J = 5.1 Hz, 1H), 4.05 (s, 3H), 2.43 (d, J = 5.1 Hz, 3H). | |
| 579 | 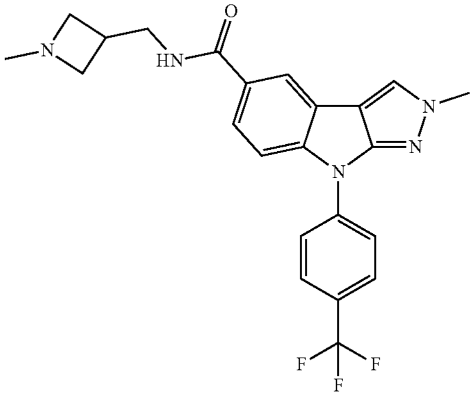 2-methyl-N-[(1-methylazetidin-3-yl)methyl]-8-[4-(trifluoromethyl)phenyl]-2H,8H-pyrazolo[3,4-b]indole-5-carboxamide | 1H NMR (400 MHz, DMSO) d 8.53 (t, J = 5.7 Hz, 1H), 8.32 (d, J = 1.8 Hz, 1H), 8.21 (s, 0H), 8.20 (s, 1H), 8.08 (d, J = 8.5 Hz, 2H), 8.01-7.93 (m, 2H), 7.89-7.80 (m, 1H), 7.76 (d, J = 8.7 Hz, 1H), 4.04 (d, J = 5.0 Hz, 3H), 3.60-3.42 (m, 3H), 3.19 (q, J = 6.9 Hz, 2H), 2.99 (s, 1H), 2.89 (dd, J = 7.0, 5.6 Hz, 1H), 2.64-2.51 (m, 1H), 2.24 (s, 1H), 2.17 (s, 2H). | |

TABLE 1-continued

| Compound No. (Example No.) | Structure and Name | ¹H-NMR | Conditions and elution time (min) LCMS (M + H⁺) |
|---|---|---|---|
| | Table 1 below shows exemplary compounds of the present invention. They have been synthesized as described in the Examples above or similar thereto. | | |
| 580 | 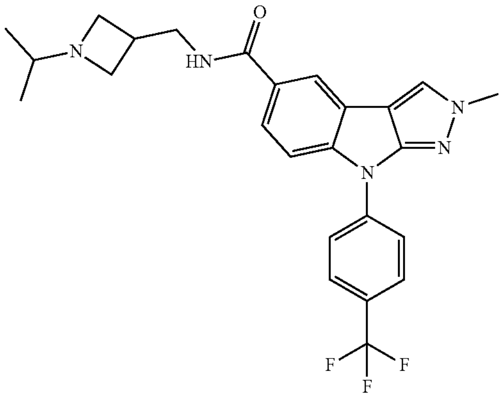 [SMILES: CC(C)N1CC(CNC(=O)c2ccc3c(c2)c2cn(C)nc2n3-c2ccc(C(F)(F)F)cc2)C1] 2-methyl-N-{[1-(propan-2-yl)azetidin-3-yl]methyl}-8-[4-(trifluoromethyl)phenyl]-2H,8H-pyrazolo[3,4-b]indole-5-carboxamide | 1H NMR (400 MHz, DMSO) d 8.60 (s, 1H), 8.33 (d, J = 1.8 Hz, 1H), 8.20 (s, 1H), 8.08 (d, J = 8.4 Hz, 2H), 8.02-7.89 (m, 2H), 7.85 (dd, J = 8.7, 1.8 Hz, 1H), 7.77 (d, J = 8.7 Hz, 1H), 4.04 (s, 2H), 3.69-3.63 (m, 2H), 3.50 (s, 2H), 2.70 (s, 1H), 1.19 (d, J = 6.6 Hz, 1H), 0.95 (s, 5H). | |
| 581 | 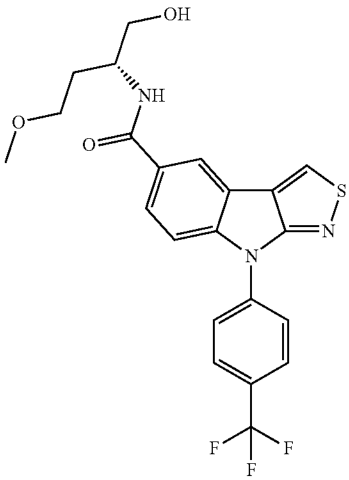 [SMILES: COCC[C@H](CO)NC(=O)c1ccc2c(c1)c1csnc1n2-c1ccc(C(F)(F)F)cc1] Absolute configuration assigned arbitrarily N-[(2R)-1-hydroxy-4-methoxybutan-2-yl]-8-[4-(trifluorosmethyl)phenyl]-8H-[1,2]thiazolo[3,4-b]indole-5-carboxamide | | |

TABLE 1-continued

| Compound No. (Example No.) | Structure and Name | $^1$H-NMR | Conditions and elution time (min) LCMS (M + H$^+$) |
|---|---|---|---|
| | Table 1 below shows exemplary compounds of the present invention. They have been synthesized as described in the Examples above or similar thereto. | | |
| 582 | 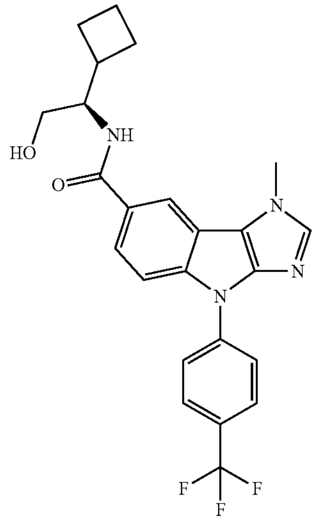 [SMILES: Cn1cnc2c1c1cc(C(=O)N[C@@H](CO)C3CCC3)ccc1n2-c1ccc(C(F)(F)F)cc1] N-[(1R)-1-cyclobutyl-2-hydroxyethyl]-1-methyl-4-[4-(trifluoromethyl)phenyl]-1H,4H-imidazo[4,5-b]indole-7-carboxamide | 1H NMR (300 MHz, DMSO-d6) 8.42 (s, 1H), 8.11 (d, J = 8.4 Hz, 2H), 7.98 (d, J = 8.8 Hz, 3H), 7.92-7.79 (m, 3H), 4.14 (s, 4H), 3.46 (d, J = 5.4 Hz, 2H), 2.31 (s, 1H), 2.00-1.76 (m, 6H). | |
| 583 | 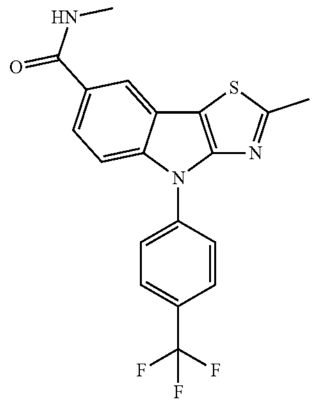 [SMILES: CNC(=O)c1ccc2c(c1)c1sc(C)nc1n2-c1ccc(C(F)(F)F)cc1] N,2-dimethyl-4-[4-(trifluoromethyl)phenyl]-4H-[1,3]thiazolo[4,5-b]indole-7-carboxamide | 1H NMR (300 MHz, DMSO-d6) 8.49 (d, J = 4.7 Hz, 1H), 8.41 (d, J = 1.7 Hz, 1H), 8.03 (s, 4H), 7.86 (d, J = 8, 1H), 7.75 (d, J = 8.8 Hz, 1H), 2.89-2.80 (m, 6H). | |

TABLE 1-continued

| Compound No. (Example No.) | Structure and Name | $^1$H-NMR | Conditions and elution time (min) LCMS (M + H$^+$) |
|---|---|---|---|
| Table 1 below shows exemplary compounds of the present invention. They have been synthesized as described in the Examples above or similar thereto. | | | |
| 584 | Absolute 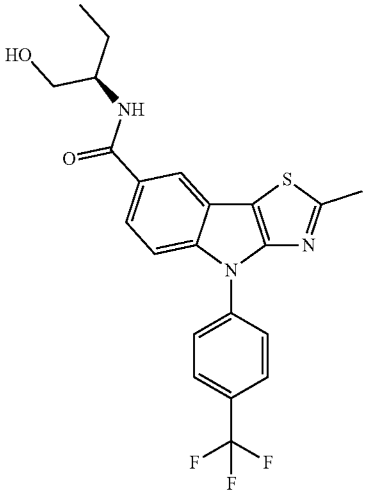 N-[(2R)-1-hydroxybutan-2-yl]-2-methyl-4-[4-(trifluoromethyl)phenyl]-4H-[1,3]thiazolo[4,5-b]indole-7-carboxamide | 1H NMR (300 MHz, DMSO-d6) 8.47 (d, J = 1.7 Hz, 1H), 8.05 (m, 5H), 7.94-7.85 (m, 1H), 7.75 (d, J = 8.7 Hz, 1H), 4.70 (t, J = 5.7 Hz, 1H), 3.93 (d, J = 5.4 Hz, 1H), 3.48 (m, 2H), 2.86 (s, 3H), 1.77-1.66 (m, 1H), 1.51 (m, 1H), 0.91 (t, J = 7.4 Hz, 3H). | |
| 585 | Absolute 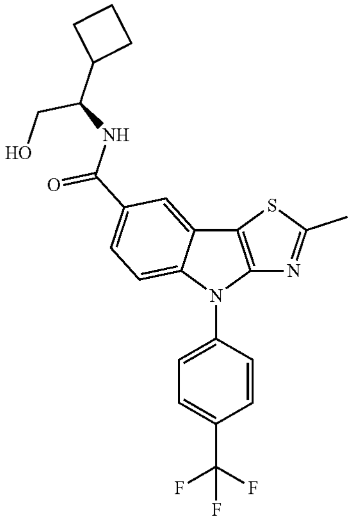 N-[(1R)-1-cyclobutyl-2-hydroxyethyl]-2-methyl-4-[4-(trifluoromethyl)phenyl]-4H-[1,3]thiazolo[4,5-b]indole-7-carboxamide | 1H NMR (300 MHz, DMSO-d6) 8.48 (d, J = 1.7 Hz, 1H), 8.03 (s, 4H), 7.99 (d, J = 3.5 Hz, 1H), 7.90 (d, J = 8.9, 1H), 7.75 (d, J = 8.8 Hz, 1H), 4.59 (t, J = 5.7 Hz, 1H), 4.13-3.99 (m, 1H), 3.45 (t, J = 5.6 Hz, 2H), 2.86 (s, 3H), 2.02-1.74 (m, 6H). | |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 586 | 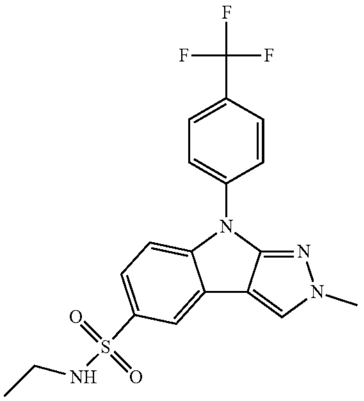 [SMILES: CCNS(=O)(=O)c1ccc2c(c1)c1cn(C)nc1n2-c1ccc(C(F)(F)F)cc1] N-ethyl-2-methyl-8-[4-(trifluoromethyl)phenyl]-2H,8H-pyrazolo[3,4-b]indole-5-sulfonamide | 1H NMR (400 MHz, DMSO-d6) 8.28 (d, J = 2.5 Hz, 2H), 8.09 (d, J = 8.3 Hz, 2H), 7.99 (d, J = 8.5 Hz, 2H), 7.88 (d, J = 8.7 Hz, 1H), 7.73 (d, J = 8.7 Hz, 1H), 7.47 (t, J = 5.8 Hz, 1H), 4.05 (s, 3H), 2.80 (p, J = 6.9 Hz, 2H), 0.99 (t, J = 7.2 Hz, 3H). | |
| 587 | 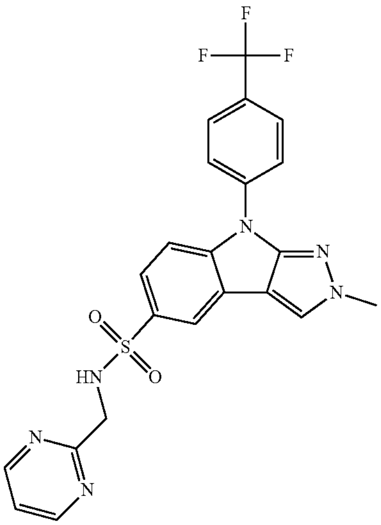 [SMILES: Cn1cc2c3cc(S(=O)(=O)NCc4ncccn4)ccc3n(-c3ccc(C(F)(F)F)cc3)c2n1] 2-methyl-N-[(pyrimidin-2-yl)methyl]-8-[4-(trifluoromethyl)phenyl]-2H,8H-pyrazolo[3,4-b]indole-5-sulfonamide | 1H NMR (300 MHz, DMSO-d6) ¦ 8.64 (d, J = 4.9 Hz, 2H), 8.30 "C 8.13 (m, 3H), 8.11 "C 7.95 (m, 5H), 7.78 (d, J = 8.6 Hz, 1H), 7.69 (d, J = 8.2 Hz, 1H), 7.28 (t, J = 5.0 Hz, 1H), 4.24 (d, J = 6.1 Hz, 2H), 4.05 (s, 3H). | |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 588 | 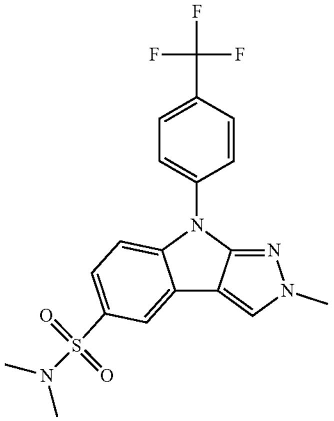 N,N,2-trimethyl-8-[4-(trifluoromethyl)phenyl]-2H,8H-pyrazolo[3,4-b]indole-5-sulfonamide | 1H NMR (300 MHz, DMSO-d6) 8.31 "C 8.23 (m, 3H), 8.09 (d, J = 8.4 Hz, 3H), 8.00 (d, J = 8.7 Hz, 3H), 7.91 (d, J = 8.7 Hz, 1H), 7.68 (dd, J = 8.7, 2.0 Hz, 1H), 4.06 (s, 4H), 2.64 (s, 7H). | |
| 589 | Absolute 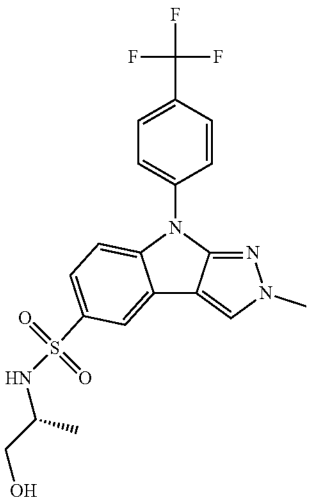 N-[(2R)-1-hydroxypropan-2-yl]-2-methyl-8-[4-(trifluoromethyl)phenyl]-2H,8H-pyrazolo[3,4-b]indole-5-sulfonamide | 1H NMR (300 MHz, DMSO-d6) 8.33-8.18 (m, 2H), 8.09 (d, J = 8.5 Hz, 2H), 7.99 (d, J = 8.6 Hz, 2H), 7.87 (d, J = 8.8 Hz, 1H), 7.76 (dd, J = 8.8, 2.0 Hz, 1H), 7.43 (d, J = 6.8 Hz, 1H), 4.67 (d, J = 6.2 Hz, 1H), 4.05 (s, 3H), 3.11 (q, J = 7.1, 6.2 Hz, 2H), 0.89 (d, J = 6.1 Hz, 3H). | |

TABLE 1-continued

| Compound No. (Example No.) | Structure and Name | $^1$H-NMR | Conditions and elution time (min) LCMS (M + H$^+$) |
|---|---|---|---|
| | Table 1 below shows exemplary compounds of the present invention. They have been synthesized as described in the Examples above or similar thereto. | | |
| 590 | Absolute 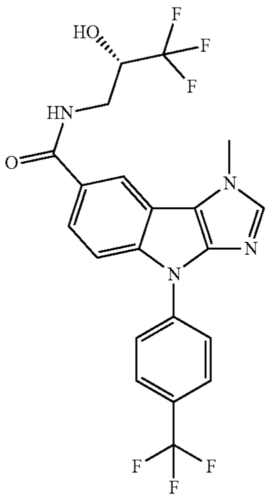 1-methyl-N-[(2S)-3,3,3-trifluoro-2-hydroxypropyl]-4-[4-(trifluoromethyl)phenyl]-1H,4H-imidazo[4,5-b]indole-7-carboxamide | 1H NMR (300 MHz, DMSO-d6) 8.77 (t, J = 5.6 Hz, 1H), 8.47 (s, 1H), 8.11 (d, J = 8.4 Hz, 2H), 7.98 (d, J = 8.4 Hz, 2H), 7.93-7.77 (m, 3H), 6.56 (d, J = 6.4 Hz, 1H), 4.25 (s, 1H), 4.13 (s, 3H), 3.70 (dd, J = 12.0, 6.8 Hz, 1H), 3.38 (d, J = 7.2 Hz, 1H). | |
| 591 | 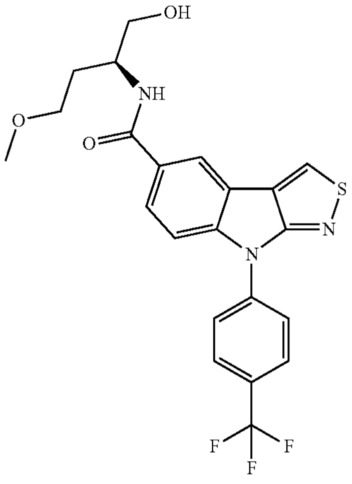 [SMILES: COCC[C@@H](CO)NC(=O)c1ccc2c(c1)c1csnc1n2-c1ccc(C(F)(F)F)cc1] Absolute configuration assigned arbitrarily N-[(2S)-1-hydroxy-4-methoxybutan-2-yl]-8-[4-(trifluoromethyl)phenyl]-8H-[1,2]thiazolo[3,4-b]indole-5-carboxamide | | |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 592 | Absolute 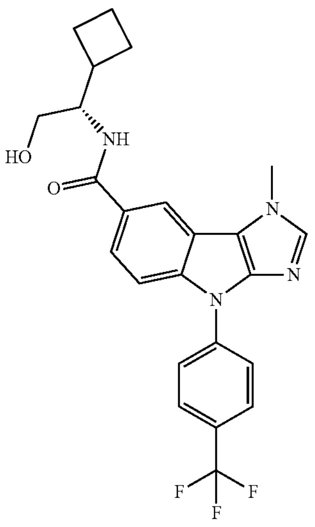 N-[(1S)-1-cyclobutyl-2-hydroxyethyl]-1-methyl-4-[4-(trifluoromethyl)phenyl]-1H,4H-imidazo[4,5-b]indole-7-carboxamide | 1H NMR (300 MHz, DMSO-d6) 8.42 (d, J = 1.5 Hz, 1H), 8.11 (d, J = 8.4 Hz, 2H), 7.98 (d, J = 8.5 Hz, 3H), 7.89-7.81 (m, 3H), 4.63 (s, 1H), 4.14 (s, 4H), 3.46 (d, J = 5.4 Hz, 2H), 2.61 (d, J = 8.4 Hz, 1H), 2.02-1.75 (m, 6H). | |
| 593 | Absolute 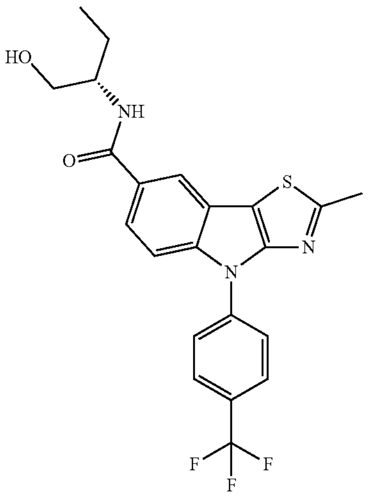 N-[(2S)-1-hydroxybutan-2-yl]-2-methyl-4-[4-(trifluoromethyl)phenyl]-4H-[1,3]thiazolo[4,5-b]indole-7-carboxamide | 1H NMR (300 MHz, DMSO-d6) 8.47 (d, J = 1.7 Hz, 1H), 8.07 (s, 1H), 8.03 (s, 4H), 7.89 (d, J = 8.8, 1H), 7.75 (d, J = 8.8 Hz, 1H), 4.70 (t, J = 5.7 Hz, 1H), 3.93 (d, J = 5.1 Hz, 1H), 3.48 (m, 2H), 2.86 (s, 3H), 1.79-1.64 (m, 1H), 1.50 (m, 1H), 0.91 (t, J = 7.4 Hz, 3H). | |

TABLE 1-continued

| Compound No. (Example No.) | Structure and Name | $^1$H-NMR | Conditions and elution time (min) LCMS (M + H$^+$) |
|---|---|---|---|
| | Table 1 below shows exemplary compounds of the present invention. They have been synthesized as described in the Examples above or similar thereto. | | |
| 594 | Absolute 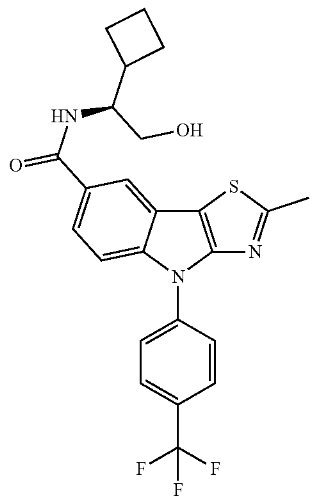 N-[(1S)-1-cyclobutyl-2-hydroxyethyl]-2-methyl-4-[4-(trifluoromethyl)phenyl]-4H-[1,3]thiazolo[4,5-b]indole-7-carboxamide | 1H NMR (300 MHz, DMSO-d6) 8.48 (d, J = 1.7 Hz, 1H), 8.09-7.96 (m, 5H), 7.90 (d, J = 8.8 , 1H), 7.75 (d, J = 8.8 Hz, 1H), 4.59 (t, J = 5.7 Hz, 1H), 4.13-4.01 (m, 1H), 3.44 (t, J = 5.7 Hz, 2H), 2.86 (s, 3H), 2.59 (d, J = 8.1 Hz, 1H), 2.07-1.72 (m, 6H). | |
| 595 | Absolute 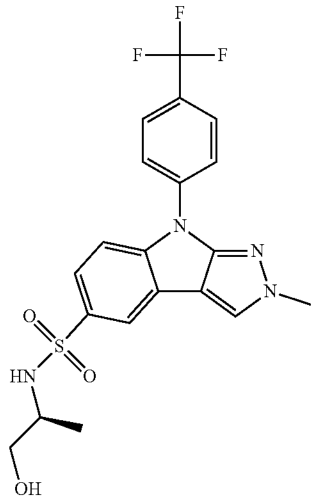 N-[(2S)-1-hydroxypropan-2-yl]-2-methyl-8-[4-(trifluoromethyl)phenyl]-2H,8H-pyrazolo[3,4-b]indole-5-sulfonamide | | |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 596 | Absolute 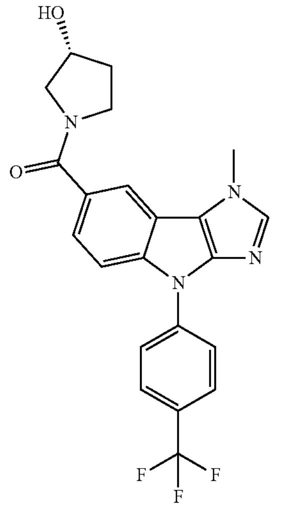 (3R)-1-{1-methyl-4-[4-(trifluoromethyl)phenyl]-1H,4H-imidazo[4,5-b]indole-7-carbonyl}pyrrolidin-3-ol | 1H NMR (300 MHz, DMSO-d6) 8.11 (d, J = 8.4 Hz, 2H), 8.05 (s, 1H), 7.97 (d, J = 8.5 Hz, 2H), 7.86 (d, J = 8.4 Hz, 2H), 7.44 (d, J = 8.7 Hz, 1H), 5.07 (s, 1H), 4.31 (d, J = 31.5 Hz, 1H), 4.10 (s, 3H), 3.75-3.50 (m, 3H), 3.42 (d, J = 12.9 Hz, 1H), 2.01-1.78 (m, 2H). | |
| 597 | Absolute 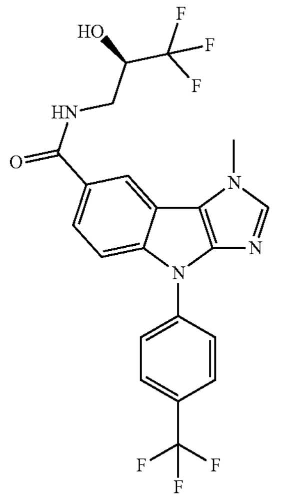 1-methyl-N-[(2R)-3,3,3-trifluoro-2-hydroxypropyl]-4-[4-(trifluoromethyl)phenyl]-1H,4H-imidazo[4,5-b]indole-7-carboxamide | 1H NMR (300 MHz, DMSO-d6) 8.77 (s, 1H), 8.47 (s, 1H), 8.11 (d, J = 8.4 Hz, 2H), 7.98 (d, J = 8.6 Hz, 2H), 7.87 (d, J = 11.8 Hz, 3H), 6.64-6.47 (m, 1H),4.24 (s, 1H), 4.13 (s, 3H), 3.69 (s, 1H), 3.35 (s, 1H). | |

TABLE 1-continued

| Compound No. (Example No.) | Structure and Name | ¹H-NMR | Conditions and elution time (min) LCMS (M + H⁺) |
|---|---|---|---|
| Table 1 below shows exemplary compounds of the present invention. They have been synthesized as described in the Examples above or similar thereto. | | | |
| 598 | Absolute 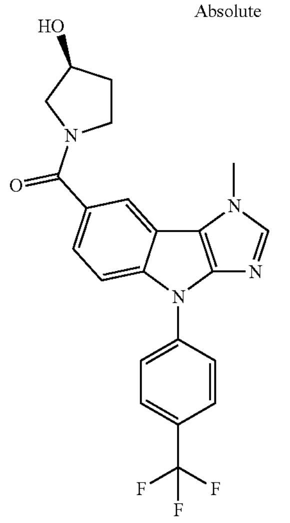 [SMILES: Cn1cnc2c1c1cc(C(=O)N3CC[C@H](O)C3)ccc1n2-c1ccc(C(F)(F)F)cc1] (3S)-1-{1-methyl-4-[4-(trifluoro-methyl)phenyl]-1H,4H-imidazo[4,5-b]indole-7-carbonyl}pyrrolidin-3-ol | 1H NMR (300 MHz, DMSO-d6) 8.11 (d, J = 8.4 Hz, 2H), 8.05 (d, J = 1.5 Hz, 1H), 7.97 (d, J = 8.5 Hz, 2H), 7.86 (d, J = 8.4 Hz, 2H), 7.44 (d, J = 8.5 Hz, 1H), 5.07 (s, 1H), 4.31 (d, J = 31.5 Hz, 1H), 4.10 (s, 3H), 3.75-3.40 (m, 4H), 1.90 (dd, J = 31.1, 15.3 Hz, 2H). | |
| 599 | Absolute 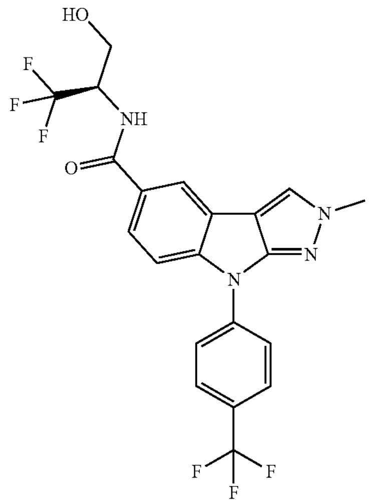 2-methyl-N-[(2R)-1,1,1-trifluoro-3-hydroxypropan-2-yl]-8-[4-(trifluoromethyl)phenyl]-2H,8H-pyrazolo[3,4-b]indole-5-carboxamide | 1H NMR (700 MHz, DMSO) d 8.79 (d, J = 8.8 Hz, 1H), 8.43 (d, J = 1.8 Hz, 1H), 8.23 (s, 1H), 8.09 (d, J = 8.4 Hz, 2H), 7.98 (d, J = 8.6 Hz, 2H), 7.92 (dd, J = 8.6, 1.9 Hz, 1H), 7.81 (d, J = 8.6 Hz, 1H), 5.19 (t, J = 6.0 Hz, 1H), 4.86 (qd, J = 8.2, 5.1 Hz, 1H), 4.04 (s, 3H), 3.84 (dt, J = 11.1, 5.4 Hz, 1H), 3.80-3.73 (m, 1H). | |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 600 | 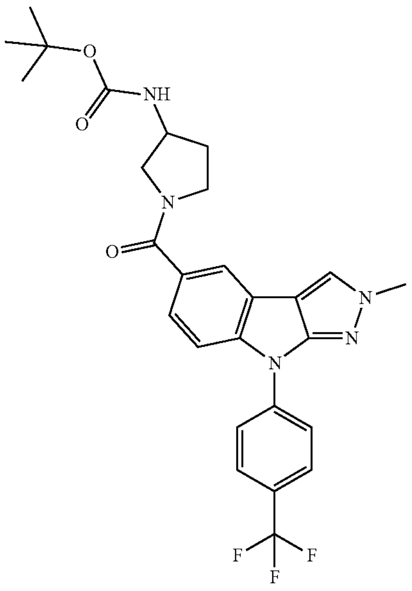 [SMILES: Cn1cc2c3cc(C(=O)N4CCC(NC(=O)OC(C)(C)C)C4)ccc3n(-c3ccc(C(F)(F)F)cc3)c2n1] tert-butyl N-(1-{2-methyl-8-[4-(trifluoromethyl)phenyl]-2H,8H-pyrazolo[3,4-b]indole-5-carbonyl}pyrrolidin-3-yl)carbamate | (700 MHz, DMSO-d6) δ 8.16 (s, 1H), 8.09 (d, J = 8.4 Hz, 2H), 8.01 (d, J = 27.4 Hz, 1H), 7.96 (d, J = 8.3 Hz, 2H), 7.76 (d, J = 8.4 Hz, 1H), 7.49 (m, 1H), 7.24 (m, 1H), 4.03 (s, 3H), 3.94 (m, 1H), 3.76-3.67 (m, 1H), 3.64 (m, 1H), 3.52 (m, 1H), 3.35 (m, 1H), 2.13-1.98 (m, 1H), 1.85-1.75 (m, 1H), 1.37 (s, 9H). | |
| 601 | 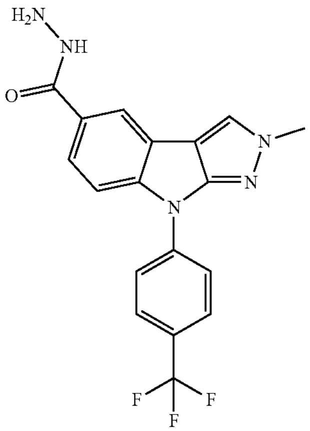 [SMILES: Cn1cc2c3cc(C(=O)NN)ccc3n(-c3ccc(C(F)(F)F)cc3)c2n1] 2-methyl-8-[4-(trifluoromethyl)phenyl]-2H,8H-pyrazolo[3,4-b]indole-5-carbohydrazide | $^1$H NMR (400 MHz, DMSO-$d_6$) δ 11.63 (s, 1H), 8.45 (d, J = 1.8 Hz, 1H), 8.25 (s, 1H), 8.12-8.05 (m, 2H), 7.98 (d, J = 8.7 Hz, 2H), 7.94 (dd, J = 8.8, 1.9 Hz, 1H), 7.83 (d, J = 8.7 Hz, 1H), 4.05 (s, 3H), 3.57 (s, 1H). | |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 602 | 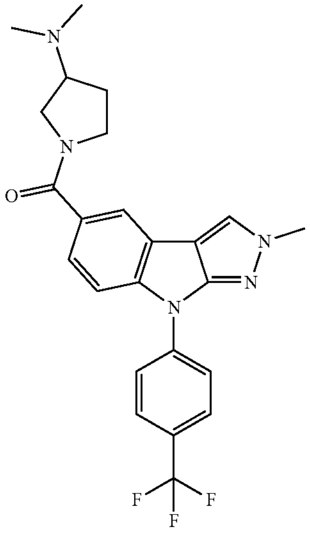 [SMILES: CN(C)C1CCN(C(=O)c2ccc3c(c2)c2cn(C)nc2n3-c2ccc(C(F)(F)F)cc2)C1] N,N-dimethyl-1-{2-methyl-8-[4-(trifluoromethyl)phenyl]-2H,8H-pyrazolo[3,4-b]indole-5-carbonyl}pyrrolidin-3-amine | $^1$H NMR (700 MHz, DMSO-$d_6$) δ 8.15 (d, J = 6.2 Hz, 1H), 8.09 (d, J = 8.2 Hz, 2H), 8.03 (d, J = 7.1 Hz, 1H), 7.96 (d, J = 8.4 Hz, 2H), 7.76 (d, J = 8.5 Hz, 1H), 7.50 (t, J = 9.1 Hz, 1H), 4.03 (s, 3H), 3.74-3.62 (m, 2H), 3.51-3.41 (m, 1H), 3.30-3.20 (m, 1H), 2.73 (m, 1H), 2.64 (m, 1H), 2.20 (s, 3H), 2.10 (s, 3H), 1.74 (m, 1H) | |
| 603 | Absolute 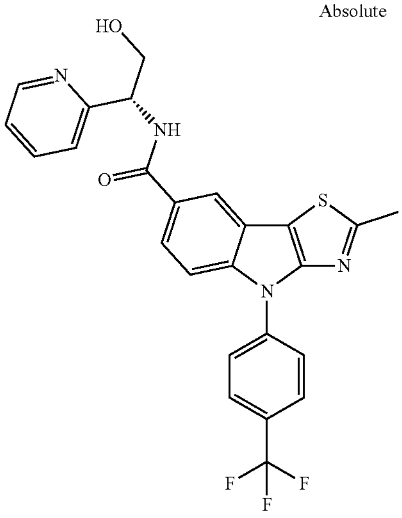 [SMILES: Cc1nc2c(s1)c1cc(C(=O)N[C@@H](CO)c3ccccn3)ccc1n2-c1ccc(C(F)(F)F)cc1] N-[(1R)-2-hydroxy-1-(pyridin-2-yl)ethyl]-2-methyl-4-[4-(trifluoromethyl)phenyl]-4H-[1,3]thiazolo[4,5-b]indole-7-carboxamide | 1H NMR (300 MHz, DMSO-d6) 8.89 (d, J = 7.2 Hz, 1H), 8.64 (m, 2H), 8.04 (m, 5H), 7.94 (d, J = 8.8, 1H), 7.78 (d, J = 8.8 Hz, 1H), 7.71 (d, J = 8.0 Hz, 1H), 7.53 (s, 1H), 5.27 (q, J = 6.4 Hz, 1H), 3.99-3.82 (m, 3H), 2.87(s, 3H). | |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 604 | Absolute 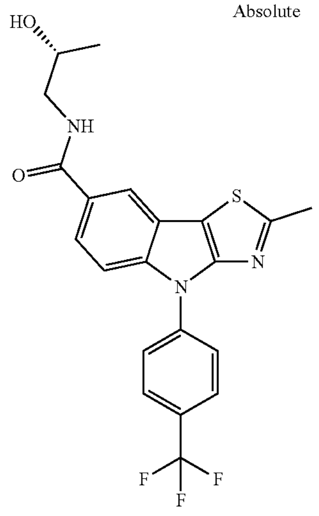 [SMILES: Cc1nc2c(s1)c1cc(C(=O)NC[C@@H](C)O)ccc1n2-c1ccc(C(F)(F)F)cc1] N-[(2R)-2-hydroxypropyl]-2-methyl-4-[4-(trifluoromethyl)phenyl]-4H-[1,3]thiazolo[4,5-b]indole-7-carboxamide | 1H NMR (300 MHz, DMSO-d6) 8.50-8.40 (m, 2H), 8.03 (s, 4H), 7.89 (d, J = 8.7, 1H), 7.76 (d, J = 8.8 Hz, 1H), 4.78 (d, J = 4.7 Hz, 1H), 3.83 (m, 1H), 3.26 (t, J = 5.9 Hz, 2H), 2.86 (s, 3H), 1.10 (d, J = 6.2 Hz, 3H). | |
| 605 | Absolute 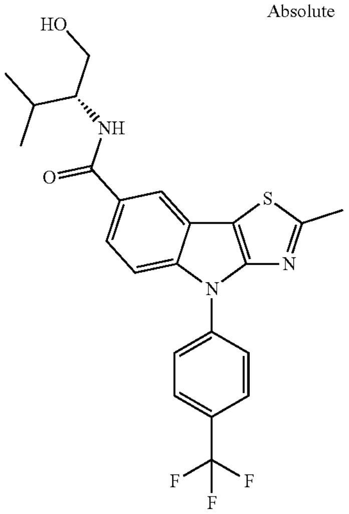 [SMILES: Cc1nc2c(s1)c1cc(C(=O)N[C@@H](CO)C(C)C)ccc1n2-c1ccc(C(F)(F)F)cc1] N-[(2R)-1-hydroxy-3-methylbutan-2-yl]-2-methyl-4-[4-(trifluoromethyl)phenyl]-4H-[1,3]thiazolo[4,5-b]indole-7-carboxamide | 1H NMR (300 MHz, DMSO-d6) 8.49 (d, J = 1.7 Hz, 1H), 8.09-7.95 (m, 5H), 7.90 (d, J = 8.8, 1H), 7.76 (d, J = 8.8 Hz, 1H), 4.61 (t, J = 5.6 Hz, 1H), 3.88 (t, J = 7.3 Hz, 1H), 3.56 (t, J = 5.6 Hz, 2H), 2.86 (s, 3H), 1.97 (m, 1H), 0.94 (t, J = 6.7 Hz, 6H). | |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 606 | Absolute 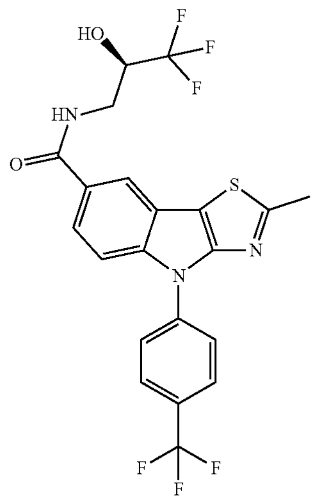 2-methyl-N-[(2R)-3,3,3-trifluoro-2-hydroxypropyl]-4-[4-(trifluoromethyl)phenyl]-4H-[1,3]thiazolo[4,5-b]indole-7-carboxamide | 1H NMR (300 MHz, DMSO-d6) 8.76 (t, J = 5.7 Hz, 1H), 8.47 (d, J = 1.7 Hz, 1H), 8.03 (s, 4H), 7.89 (dd, J = 8.8, 1.7 Hz, 1H), 7.77 (d, J = 8.8 Hz, 1H), 6.54 (d, J = 6.4 Hz, 1H), 4.25 (dt, J = 12.3, 7.0 Hz, 1H), 3.67 (dt, J = 13.5, 5.0 Hz, 1H), 3.44-3.36 (m, 1H), 2.86 (s, 3H). | |
| 607 | 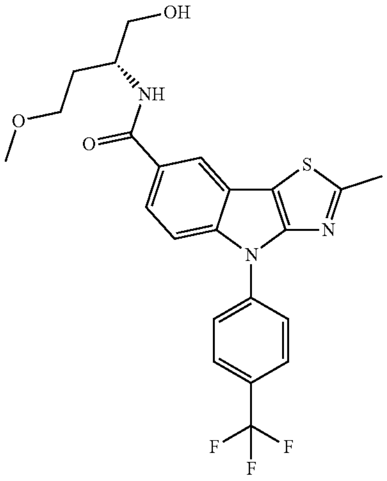 Absolute configuration assigned arbitrarily N-[(2R)-1-hydroxy-4-methoxybutan-2-yl]-2-methyl-4-[4-(trifluoromethyl)phenyl]-4H-[1,3]thiazolo[4,5-b]indole-7-carboxamide | | |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 608 | 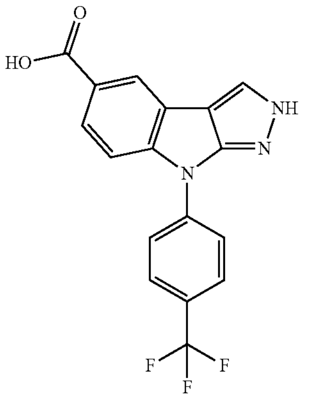 [SMILES: O=C(O)c1ccc2c(c1)c1c[nH]nc1n2-c1ccc(C(F)(F)F)cc1] 8-[4-(trifluoromethyl)phenyl]-2H,8H-pyrazolo[3,4-b]indole-5-carboxylic acid | 1H NMR (300 MHz, DMSO) 7.79 (d, J = 8.7 Hz, 1H), 7.89-8.02 (m, 3H), 8.13 (d, J = 8.4 Hz, 2H), 8.25 (s, 1H), 8.44 (d, J = 1.7 Hz, 1H), 13.01 (s, 1H). | |
| 609 | 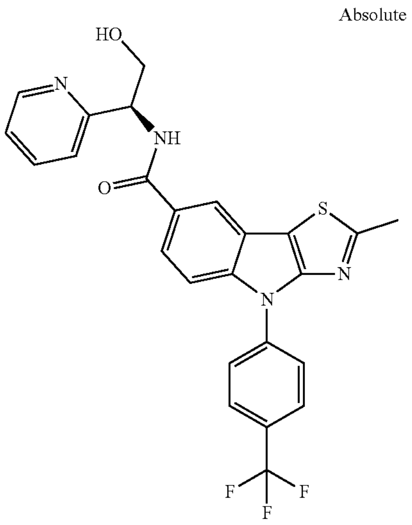 [SMILES: Cc1nc2c(s1)c1cc(C(=O)N[C@H](CO)c3ccccn3)ccc1n2-c1ccc(C(F)(F)F)cc1] N-[(1S)-2-hydroxy-1-(pyridin-2-yl)ethyl]-2-methyl-4-[4-(trifluoromethyl)phenyl]-4H-[1,3]thiazolo[4,5-b]indole-7-carboxamide | 1H NMR (300 MHz, DMSO-d6) 8.71 (d, J = 7.9 Hz, 1H), 8.62-8.52 (m, 2H), 8.09-7.89 (m, 5H), 7.83-7.72 (m, 2H), 7.47 (d, J = 7.9 Hz, 1H), 7.28 (m , 1H), 5.22 (m, 1H), 4.98 (t, J = 6.0 Hz, 1H), 3.85 (m, 2H), 2.87 (s, 3H). | |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 610 | Absolute 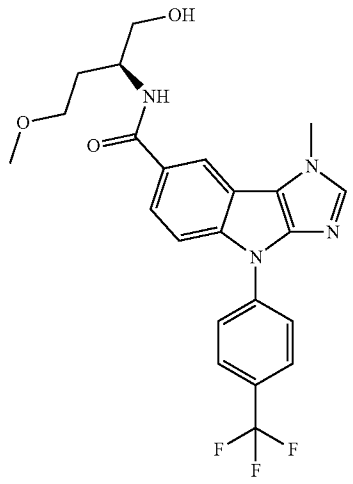 N-[(2S)-1-hydroxy-4-methoxybutan-2-yl]-1-methyl-4-[4-(trifluoromethyl)phenyl]-1H,4H-imidazo[4,5-b]indole-7-carboxamide | | |
| 611 | Absolute 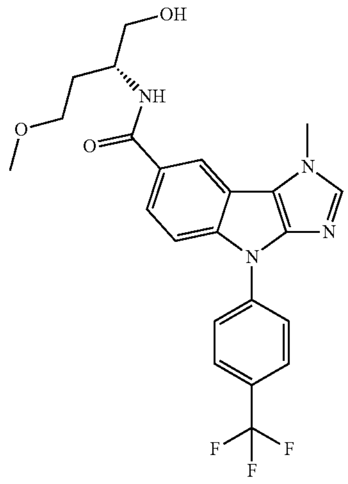 N-[(2R)-1-hydroxy-4-methoxybutan-2-yl]-1-methyl-4-[4-(trifluoromethyl)phenyl]-1H,4H-imidazo[4,5-b]indole-7-carboxamide | | |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^{1}$H-NMR | Conditions and elution time (min) LCMS (M + H$^{+}$) |
| 612 | Absolute 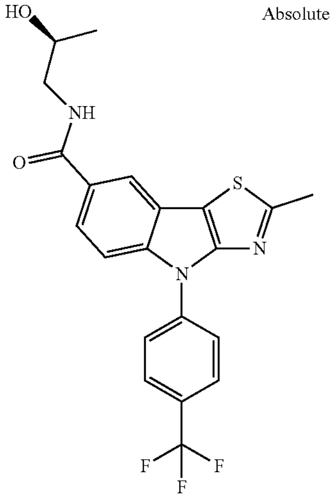 [SMILES: Cc1nc2c(s1)c1cc(C(=O)NC[C@H](C)O)ccc1n2-c1ccc(C(F)(F)F)cc1] N-[(2S)-2-hydroxypropyl]-2-methyl-4-[4-(trifluoromethyl)phenyl]-4H-[1,3]thiazolo[4,5-b]indole-7-carboxamide | 1H NMR (300 MHz, DMSO-d6) 8.50-8.40 (m, 2H), 8.03 (s, 4H), 7.89 (d, J = 8.8, 1H), 7.75 (d, J = 8.8 Hz, 1H), 4.79 (d, J = 4.7 Hz, 1H), 3.84 (m, 1H), 3.26 (s, 2H), 2.86 (s, 3H), 1.11 (d, J = 6.2 Hz, 3H). | |
| 613 | Absolute 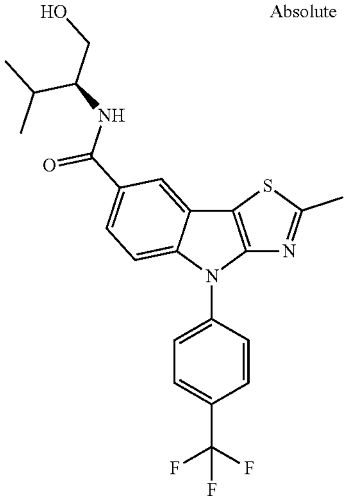 [SMILES: Cc1nc2c(s1)c1cc(C(=O)N[C@H](CO)C(C)C)ccc1n2-c1ccc(C(F)(F)F)cc1] N-[(2S)-1-hydroxy-3-methylbutan-2-yl]-2-methyl-4-[4-(trifluoromethyl)phenyl]-4H-[1,3]thiazolo[4,5-b]indole-7-carboxamide | 1H NMR (300 MHz, DMSO-d6) 8.48 (d, J = 1.7 Hz, 1H), 8.09-7.96 (m, 5H), 7.90 (d, J = 8.8 , 1H), 7.75 (d, J = 8.8 Hz, 1H), 4.59 (t, J = 5.7 Hz, 1H), 4.13-4.01 (m, 1H), 3.44 (t, J = 5.7 Hz, 2H), 2.86 (s, 3H), 2.59 (d, J = 8.1 Hz, 1H), 2.07-1.72 (m, 6H). | |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 614 | Absolute 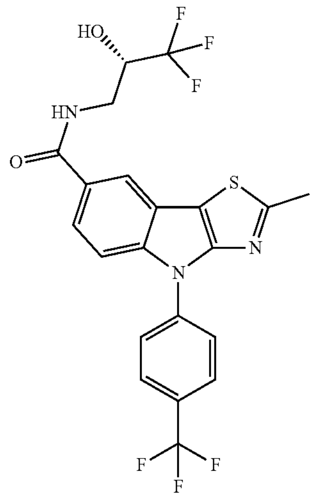 2-methyl-N-[(2S)-3,3,3-trifluoro-2-hydroxypropyl]-4-[4-(trifluoromethyl)-phenyl]-4H-[1,3]thiazolo[4,5-b]indole-7-carboxamide | 1H NMR (300 MHz, DMSO-d6) ¦Ä 8.76 (t, J = 5.7 Hz, 1H), 8.47 (d, J = 1.7 Hz, 1H), 8.03 (s, 4H), 7.89 (dd, J = 8.8, 1.8 Hz, 1H), 7.78 (d, J = 8.8 Hz, 1H), 6.53 (d, J = 6.4 Hz, 1H), 4.24 (d, J = 6.6 Hz, 1H), 3.67 (dt, J = 13.7, 5.2 Hz, 1H), 3.38 (d, J = 7.1 Hz, 1H), 2.86 (s, 3H). | |
| 615 | 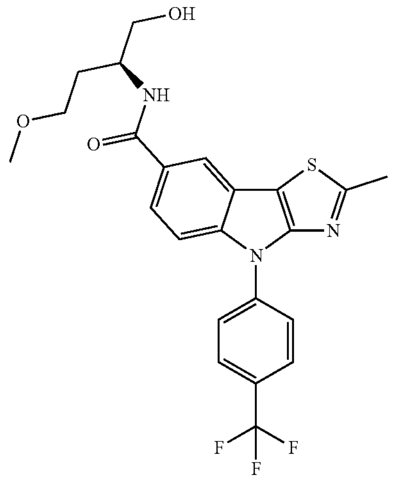 Absolute configuration assigned arbitrarily N-[(2S)-1-hydroxy-4-methoxybutan-2-yl]-2-methyl-4-[4-(trifluoromethyl)phenyl]-4H-[1,3]thiazolo[4,5-b]indole-7-carboxamide | | |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 616 | 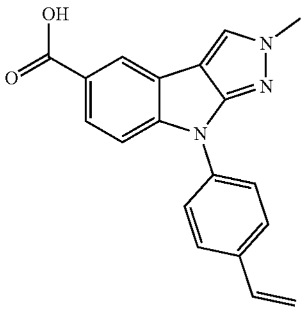 [SMILES: C=Cc1ccc(-n2c3ccc(C(=O)O)cc3c3cn(C)nc32)cc1] 8-(4-ethenylphenyl)-2-methyl-2H,8H-pyrazolo[3,4-b]indole-5-carboxylic acid | 1H NMR (400 MHz, DMSO) d 12.59 (s, 1H), 8.40 (d, J = 1.7 Hz, 1H), 8.18 (s, 1H), 7.90 (dd, J = 8.7, 1.8 Hz, 1H), 7.81-7.74 (m, 2H), 7.74-7.66 (m, 2H), 7.63 (d, J = 8.7 Hz, 1H), 6.83 (dd, J = 17.6, 11.0 Hz, 1H), 5.90 (dd, J = 17.7, 1.0 Hz, 1H), 5.33 (dd, J = 10.9, 0.9 Hz, 1H), 4.02 (s, 3H) | |
| 617 | 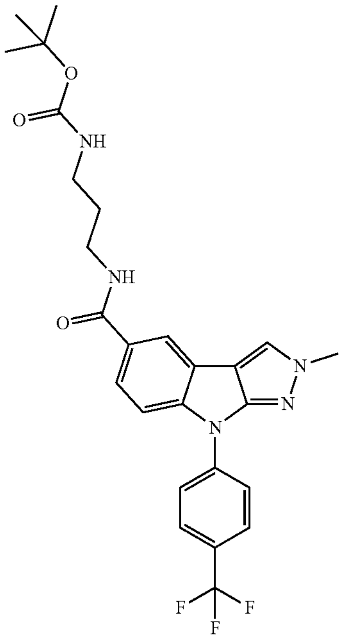 [SMILES: Cn1cc2c3cc(C(=O)NCCCNC(=O)OC(C)(C)C)ccc3n(-c3ccc(C(F)(F)F)cc3)c2n1] tert-butyl N-[3-({2-methyl-8-[4-(trifluoromethyl)phenyl]-2H,8H-pyrazolo[3,4-b]indol-5-yl}formamido)propyl]carbamate | 1H NMR (700 MHz, DMSO) d 8.47 (t, J = 5.7 Hz, 1H), 8.33 (d, J = 1.8 Hz, 1H), 8.20 (s, 1H), 8.09 (d, J = 8.3 Hz, 2H), 7.97 (d, J = 8.5 Hz, 2H), 7.84 (dd, J = 8.7, 1.8 Hz, 1H), 7.77 (d, J = 8.7 Hz, 1H), 6.83 (t, J = 5.8 Hz, 1H), 4.04 (s, 3H), 3.29 (d, J = 6.2 Hz, 2H), 3.00 (q, J = 6.7 Hz, 2H), 1.66 (p, J = 7.0 Hz, 2H), 1.38 (s, 9H), 1.37 (s, 1H). Spektrum | |

TABLE 1-continued

| Compound No. (Example No.) | Structure and Name | $^1$H-NMR | Conditions and elution time (min) LCMS (M + H$^+$) |
|---|---|---|---|
| Table 1 below shows exemplary compounds of the present invention. They have been synthesized as described in the Examples above or similar thereto. | | | |
| 618 | 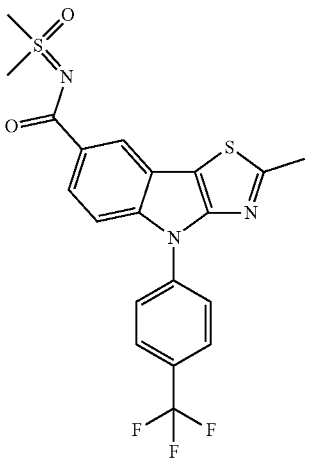 N-[dimethyl(oxo)-λ$^6$-sulfanylidene]-2-methyl-4-[4-(trifluoromethyl)phenyl]-4H-[1,3]thiazolo[4,5-b]indole-7-carboxamide | 1H NMR (400 MHz, DMSO) d 8.54 (d, J = 1.7 Hz, 1H), 8.01 (d, J = 1.6 Hz, 4H), 7.99 (d, J = 1.7 Hz, 1H), 7.75-7.68 (m, 1H), 3.49 (s, 6H), 2.84 (s, 3H). | |
| 619 | 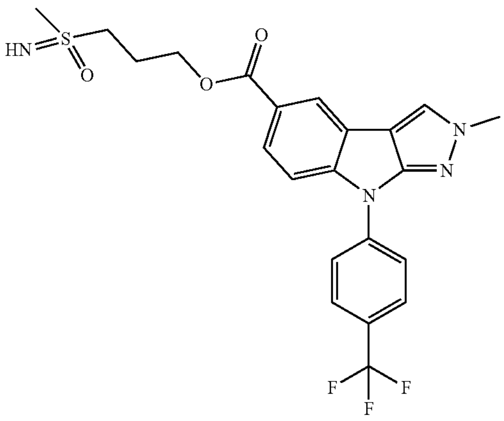 [SMILES: Cn1cc2c3cc(C(=O)OCCCS(C)(=N)=O)ccc3n(-c3ccc(C(F)(F)F)cc3)c2n1] 3-[imino(methyl)oxo-λ$^6$-sulfanyl]propyl 2-methyl-8-[4-(trifluoromethyl)phenyl]-2H,8H-pyrazolo[3,4-b]indole-5-carboxylate | 1H NMR (700 MHz, DMSO) d 8.45 (d, J = 1.7 Hz, 1H), 8.22 (s, 1H), 8.09 (d, J = 8.4 Hz, 2H), 7.99 (dd, J = 8.7, 1.8 Hz, 1H), 7.97 (d, J = 8.3 Hz, 2H), 7.75 (d, J = 8.7 Hz, 1H), 4.78 (t, J = 5.2 Hz, 1H), 4.03 (s, 3H), 3.64 (dddd, J = 40.2, 13.9, 10.2, 5.6 Hz, 2H), 3.56 (q, J = 6.0 Hz, 2H), 3.47 (s, 3H), 2.03-1.91 (m, 2H). | |

TABLE 1-continued

| Compound No. (Example No.) | Structure and Name | $^1$H-NMR | Conditions and elution time (min) LCMS (M + H$^+$) |
|---|---|---|---|
| Table 1 below shows exemplary compounds of the present invention. They have been synthesized as described in the Examples above or similar thereto. | | | |
| 620 | 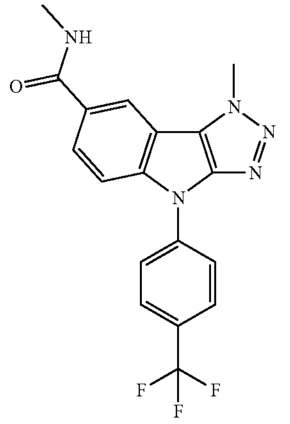 [SMILES: CNC(=O)c1ccc2c(c1)c1c(nnn1C)n2-c1ccc(C(F)(F)F)cc1] N,1-dimethyl-4-[4-(trifluoromethyl)-phenyl]-1H,4H-[1,2,3]triazolo[4,5-b]indole-7-carboxamide | 1H NMR (400 MHz, DMSO) d 2.86 (d, J = 4.5 Hz, 3H), 4.50 (s, 3H), 7.96 (d, J = 8.8 Hz, 1H), 7.98-8.05 (m, 3H), 8.13 (d, J = 8.4 Hz, 2H), 8.55 (d, J = 4.7 Hz, 1H), 8.64 (d, J = 1.8 Hz, 1H). | |
| 621 | 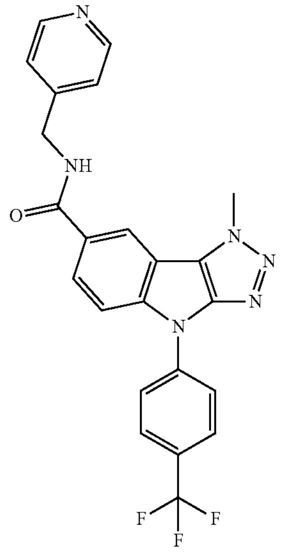 [SMILES: Cn1nnc2c1c1cc(C(=O)NCc3ccncc3)ccc1n2-c1ccc(C(F)(F)F)cc1] 1-methyl-N-[(pyridin-4-yl)methyl]-4-[4-(trifluoromethyl)phenyl]-1H,4H-[1,2,3]triazolo[4,5-b]indole-7-carboxamide | 1H NMR (400 MHz, DMSO) d 4.50 (s, 3H), 4.59 (d, J = 5.9 Hz, 2H), 7.32-7.38 (m, 2H), 7.99 (d, J = 8.9 Hz, 1H), 8.02 (d, J = 8.6 Hz, 2H), 8.09 (dd, J = 8.9, 1.8 Hz, 1H), 8.14 (d, J = 8.3 Hz, 2H), 8.49-8.55 (m, 2H), 8.72 (d, J = 1.8 Hz, 1H), 9.22 (t, J = 6.0 Hz, 1H). | |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 622 | 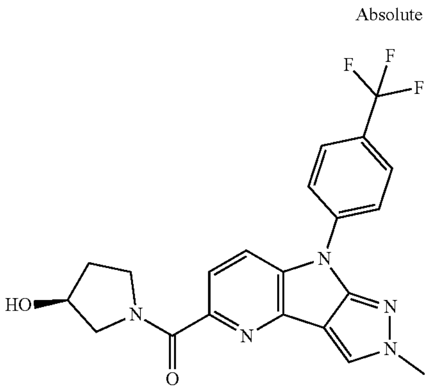 [SMILES: Cn1cc2c3nc(C(=O)N4CC[C@H](O)C4)ccc3n(-c3ccc(C(F)(F)F)cc3)c2n1] (3S)-1-{4-methyl-7-[4-(trifluoromethyl)phenyl]-4,5,7,12-tetraazatricyclo[6.4.0.0Â$^2$,?]dodeca-1(8),2,5,9,11-pentaene-11-carbonyl}pyrrolidin-3-ol | 1H NMR (400 MHz, DMSO-d6) 8.41 (d, J = 6.2 Hz, 1H), 8.21 (d, J = 8.7 Hz, 1H), 8.12 (d, J = 8.5 Hz, 2H), 7.99 (d, J = 8.6 Hz, 2H), 7.72 (dd, J = 9.6, 8.6 Hz, 1H), 4.98 (d, J = 27.9 Hz, 1H), 4.33 (d, J = 13.7 Hz, 1H), 4.08 (s, 3H), 3.95-3.81 (m, 1H), 3.68-3.57 (m, 2H), 3.49 (d, J = 12.7 Hz, 1H), 1.95 (ddt, J = 14.5, 9.8, 5.1 Hz, 1H), 1.85 (s, 1H). | *A* 1.72 min 430 (M + H) |
| 623 | 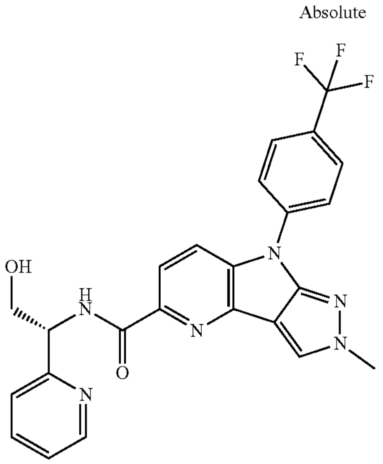 [SMILES: Cn1cc2c3nc(C(=O)N[C@@H](CO)c4ccccn4)ccc3n(-c3ccc(C(F)(F)F)cc3)c2n1] N-[(1R)-2-hydroxy-1-(pyridin-2-yl)ethyl]-4-methyl-7-[4-(trifluoromethyl)phenyl]-4,5,7,12-tetraazatricyclo[6.4.0.0$^{2,6}$]dodeca-1(8),2,5,9,11-pentaene-11-carboxamide | 1H NMR (400 MHz, DMSO-d6) 9.03 (d, J = 8.3 Hz, 1H), 8.61 (dt, J = 4.7, 1.6 Hz, 1H), 8.53 (s, 1H), 8.26 (d, J = 8.6 Hz, 1H), 8.13 (d, J = 8.4 Hz, 2H), 8.05 (d, J = 8.6 Hz, 1H), 8.00 (d, J = 8.6 Hz, 2H), 7.79 (td, J = 7.6, 1.8 Hz, 1H), 7.45 (dd, J = 7.9, 1.2 Hz, 1H), 7.32 (ddd, J = 7.5, 4.8, 1.1 Hz, 1H), 5.22-5.16 (m, 1H), 5.11 (t, J = 5.6 Hz, 1H), 4.10 (s, 3H), 3.92 (dt, J = 10.9, 5.3 Hz, 1H), 3.81 (dt, J = 10.9, 5.5 Hz, 1H). | *A* 1.77 min, (M + H) 481 |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 624 | Absolute 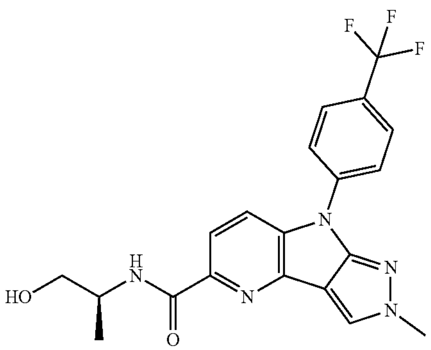 N-[(2S)-1-hydroxypropan-2-yl]-4-methyl-7-[4-(trifluoromethyl)phenyl]-4,5,7,12-tetraazatricyclo[6.4.0.0Â$^2$,?]dodeca-1(8),2,5,9,11-pentaene-11-carboxamide | 1H NMR (400 MHz, DMSO-d6) 8.44 (s, 1H), 8.36 (d, J = 8.5 Hz, 1H), 8.25 (d, J = 8.6 Hz, 1H), 8.12 (d, J = 8.4 Hz, 2H), 8.04 (d, J = 8.7 Hz, 1H), 7.99 (d, J = 8.6 Hz, 2H), 4.91 (t, J = 5.5 Hz, 1H), 4.09 (s, 3H), 3.58-3.45 (m, 2H), 3.30-3.29 (m, 1H), 1.21 (d, J = 6.7 Hz, 3H). | *A* 1.88 min, (M + H) 418 |
| 625 | Absolute 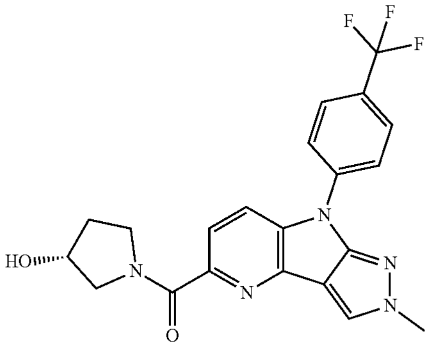 (3R)-1-{4-methyl-7-[4-(trifluoromethyl)phenyl]-4,5,7,12-tetraazatricyclo[6.4.0.0$^{2,6}$]dodeca-1(8),2,5,9,11-pentaene-11-carbonyl}pyrrolidin-3-ol | 1H NMR (400 MHz, DMSO-d6) 8.41 (d, J = 6.2 Hz, 1H), 8.21 (d, J = 8.7 Hz, 1H), 8.12 (d, J = 8.5 Hz, 2H), 7.99 (d, J = 8.6 Hz, 2H), 7.72 (dd, J = 9.6, 8.6 Hz, 1H), 4.98 (d, J = 27.9 Hz, 1H), 4.33 (d, J = 13.7 Hz, 1H), 4.08 (s, 3H), 3.95-3.81 (m, 1H), 3.68-3.57 (m, 2H), 3.49 (d, J = 12.7 Hz, 1H), 1.95 (ddt, J = 14.5, 9.8, 5.1 Hz, 1H), 1.85 (s, 1H). | *A* 1.73 min, (M + H) 430 |

TABLE 1-continued

| Compound No. (Example No.) | Structure and Name | $^1$H-NMR | Conditions and elution time (min) LCMS (M + H$^+$) |
|---|---|---|---|
| | Table 1 below shows exemplary compounds of the present invention. They have been synthesized as described in the Examples above or similar thereto. | | |
| 626 | Absolute 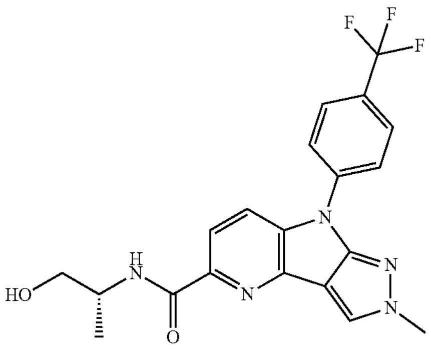 N-[(2R)-1-hydroxypropan-2-yl]-4-methyl-7-[4-(trifluoromethyl)phenyl]-4,5,7,12-tetraazatricyclo [6.4.0.0$^{2,6}$]dodeca-1(8),2,5,9,11-pentaene-11-carboxamide | 1H NMR (400 MHz, DMSO-d6) 8.45 (s, 1H), 8.36 (d, J = 8.5 Hz, 1H), 8.25 (d, J = 8.7 Hz, 1H), 8.12 (d, J = 8.4 Hz, 2H), 8.03 (d, J = 8.7 Hz, 1H), 7.99 (d, J = 8.6 Hz, 2H), 4.93 (t, J = 5.5 Hz, 1H), 4.09 (s, 3H), 3.55-3.48 (m, 2H), 3.31-3.29 (m, 1H), 1.21 (d, J = 6.7 Hz, 3H). | *A* 1.89 min, (M + H) 418 |
| 627 | 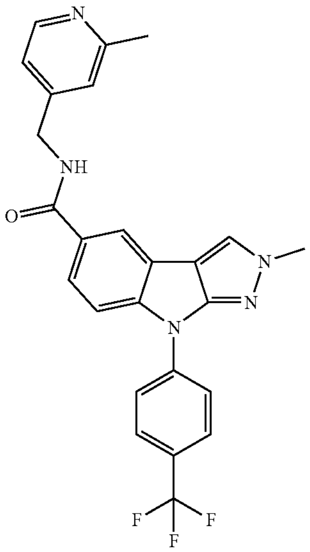 [SMILES: Cc1cc(CNC(=O)c2ccc3c(c2)c2cn(C)nc2n3-c2ccc(C(F)(F)F)cc2)ccn1] 2-methyl-N-[(2-methylpyridin-4-yl)methyl]-8-[4-(trifluoromethyl)phenyl]-2H,8H-pyrazolo[3,4-b]indole-5-carboxamide | 1H NMR (700 MHz, DMSO) d 9.33 (t, J = 5.9 Hz, 1H), 8.70 (d, J = 6.2 Hz, 1H), 8.43 (d, J = 1.8 Hz, 1H), 8.23 (s, 1H), 8.09 (d, J = 8.4 Hz, 2H), 7.99 (d, J = 8.4 Hz, 2H), 7.92 (dd, J = 8.7, 1.9 Hz, 1H), 7.83 (d, J = 8.7 Hz, 1H), 7.81 (s, 1H), 7.76 (d, J = 6.0 Hz, 1H), 4.71 (d, J = 5.6 Hz, 2H), 4.05 (s, 3H), 2.69 (s, 3H). | |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 628 | 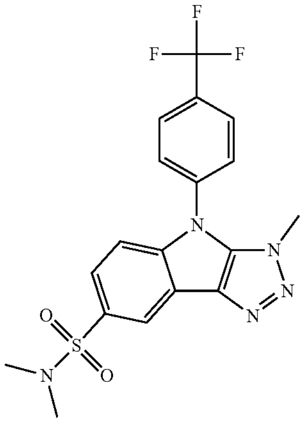 N,N,3-trimethyl-4-[4-(trifluoromethyl)-phenyl]-3H,4H-[1,2,3]triazolo[4,5-b]indole-7-sulfonamide | 1H NMR (400 MHz, DMSO) 2.60 (s, 6H), 4.36 (s, 3H), 7.7" C. 7.81 (m, 2H), 8.09 (d, J = 1.7 Hz, 1H), 8.15 (d, J = 8.4 Hz, 2H), 8.20 (d, J = 8.2 Hz, 2H). | |
| 629 | Absolute 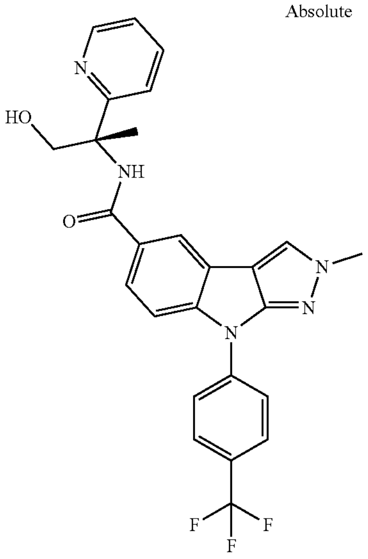 [SMILES: Cn1cc2c3cc(C(=O)N[C@](C)(CO)c4ccccn4)ccc3n(-c3ccc(C(F)(F)F)cc3)c2n1] Absolute configuration assigned arbitrarily N-[(2S)-1-hydroxy-2-(pyridin-2-yl)propan-2-yl]-2-methyl-8-[4-(trifluoromethyl)-phenyl]-2H,8H-pyrazolo[3,4-b]indole-5-carboxamide | 1H NMR (400 MHz, DMSO-d6) 1.74 (s, 3H), 3.82-3.96 (m, 2H), 4.04 (s, 3H), 5.02-5.10 (m, 1H), 7.19-7.28 (m, 1H), 7.46 (d, J = 8.0 Hz, 1H), 7.68-7.78 (m, 1H), 7.78-7.87 (m, 2H), 7.98 (d, J = 8.5 Hz, 2H), 8.10 (d, J = 8.4 Hz, 2H), 8.22 (s, 1H), 8.34-8.41 (m, 2H), 8.5-8.56 (m, 1H). | |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 630 | 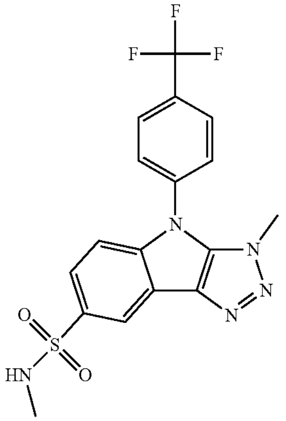 [SMILES: CNS(=O)(=O)c1ccc2c(c1)c1nnn(C)c1n2-c1ccc(C(F)(F)F)cc1] N,3-dimethyl-4-[4-(trifluoromethyl)-phenyl]-3H,4H-[1,2,3]triazolo[4,5-b]indole-7-sulfonamide | 1H NMR (300 MHz, DMSO) 2.35 (3H, d), 4.35 (3H, s), 7.30 (1H, t), 7.7" C. 7.83 (2H, m), 8.1" C. 8.24 (5H, m). | |
| 631 | 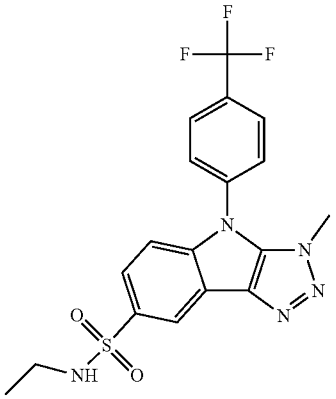 [SMILES: CCNS(=O)(=O)c1ccc2c(c1)c1nnn(C)c1n2-c1ccc(C(F)(F)F)cc1] N-ethyl-3-methyl-4-[4-(trifluoromethyl)phenyl]-3H,4H-[1,2,3]triazolo[4,5-b]indole-7-sulfonamide | 1H NMR (300 MHz, DMSO) 0.94 (3H, t), 2.74 (2H, q), 4.36 (3H, s), 7.73 (1H, d), 7.81 (1H, dd), 8.18 (5H, q). | |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 632 | 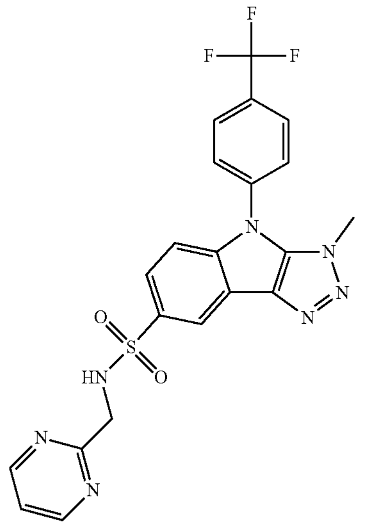 [SMILES: Cn1nnc2c3cc(S(=O)(=O)NCc4ncccn4)ccc3n(-c3ccc(C(F)(F)F)cc3)c21] 3-methyl-N-[(pyrimidin-2-yl)methyl]-4-[4-(trifluoromethyl)phenyl]-3H,4H-[1,2,3]triazolo[4,5-b]indole-7-sulfonamide | 1H NMR 400 MHz, DMSO, 4.17 (d, J = 5.5 Hz, 2H), 4.35 (s, 3H), 7.19 (t, J = 4.9 Hz, 1H), 7.63 (d, J = 9.0 Hz, 1H), 7.75 (dd, J = 9.0, 1.8 Hz, 1H), 8.22 (m, 6H), 8.51 (d, J = 4.9 Hz, 2H). | |
| 633 | Absolute 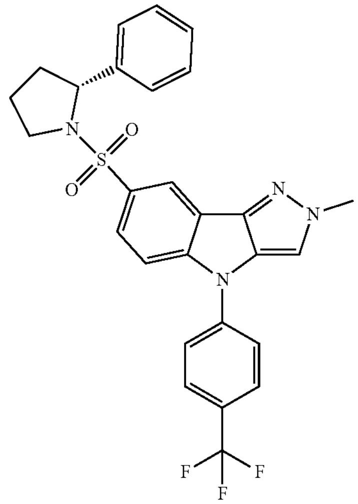 (2R)-1-({2-methyl-4-[4-(trifluoromethyl)phenyl]-2H,4H-pyrazolo[4,3-b]indol-7-yl}sulfonyl)-2-phenylpyrrolidine | 1H NMR (400 MHz, DMSO) 1.50 (dt, J = 12.0, 6.8 Hz, 1H), 1.59-1.8 (m, 2H), 1.87 (dt, J = 11.9, 7.7 Hz, 1H), 3.39 (dt, J = 10.4, 7.1 Hz, 1H), 3.60 (dt, J = 11.0, 5.8 Hz, 1H), 4.13 (s, 3H), 4.83 (dd, J = 8.0, 4.0 Hz, 1H), 7.22-7.31 (m, 1H), 7.32-7.44 (m, 4H), 7.87 (dd, J = 8.9, 1.9 Hz, 1H), 7.97 (d, J = 4.4 Hz, 5H), 8.18 (s, 1H), 8.32 (d, J = 1.9 Hz, 1H). | |

TABLE 1-continued

| Table 1 below shows exemplary compounds of the present invention. They have been synthesized as described in the Examples above or similar thereto. | | | |
|---|---|---|---|
| Compound No. (Example No.) | Structure and Name | $^1$H-NMR | Conditions and elution time (min) LCMS (M + H$^+$) |
| 634 | Absolute 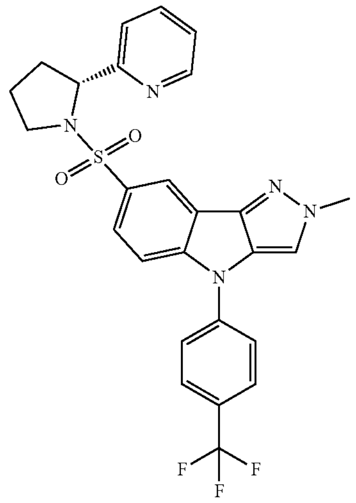 2-[(2R)-1-({2-methyl-4-[4-(trifluoromethyl)phenyl]-2H,4H-pyrazolo[4,3-b]indol-7-yl}sulfonyl)pyrrolidin-2-yl]pyridine | 1H NMR (400 MHz, DMSO) 1.53 (dt, J = 12.0, 6.0 Hz, 1H), 1.75-1.84 (m, 1H), 1.88 (q, J = 6.5, 6.0 Hz, 2H), 3.39 (dt, J = 10.4, 7.3 Hz, 1H), 3.61 (dt, J = 11.5, 6.0 Hz, 1H), 4.14 (s, 3H), 4.79 (t, J = 6.1 Hz, 1H), 7.28 (ddd, J = 7.5, 4.8, 1.2 Hz, 1H), 7.57 (d, J = 7.9 Hz, 1H), 7.77-7.92 (m, 2H), 7.98 (d, J = 3.0 Hz, 5H), 8.18 (s, 1H), 8.31 (d, J = 1.9 Hz, 1H), 8.43-8.61 (m, 1H). | |
| 635 | Absolute 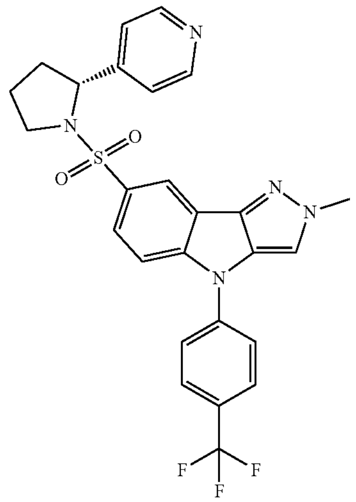 4-[(2R)-1-({2-methyl-4-[4-(trifluoromethyl)phenyl]-2H,4H-pyrazolo[4,3-b]indol-7-yl}sulfonyl)pyrrolidin-2-yl]pyridine | 1H NMR (400 MHz, DMSO) 1.42-1.6 (m, 1H), 1.69 (ddt, J = 13.6, 9.9, 6.1 Hz, 2H), 1.93 (dq, J = 11.9, 9.4, 8.2 Hz, 1H), 3.27-3.47 (m, 2H), 3.61 (dt, J = 10.1, 6.3 Hz, 1H), 4.13 (s, 3H), 4.85 (dd, J = 8.2, 3.9 Hz, 1H), 7.36-7.48 (m, 2H), 7.89 (dd, J = 8.8, 2.0 Hz, 1H), 7.97 (d, J = 2.7 Hz, 5H), 8.18 (s, 1H), 8.35 (d, J = 1.9 Hz, 1H), 8.49-8.62 (m, 2H). | |

TABLE 1-continued

| Compound No. (Example No.) | Structure and Name | $^1$H-NMR | Conditions and elution time (min) LCMS (M + H$^+$) |
|---|---|---|---|
| | Table 1 below shows exemplary compounds of the present invention. They have been synthesized as described in the Examples above or similar thereto. | | |
| 636 | Absolute 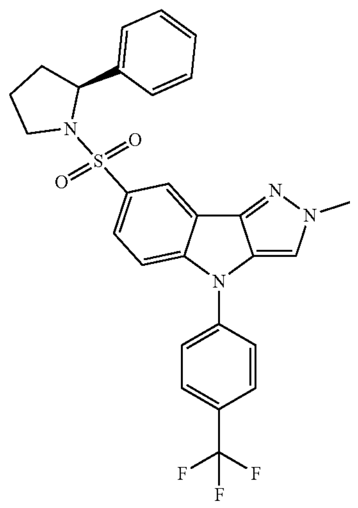 (2S)-1-({2-methyl-4-[4-(trifluoro-methyl)phenyl]-2H,4H-pyrazolo[4,3-b]indol-7-yl}sulfonyl)-2-phenylpyrrolidine | 1H NMR (400 MHz, DMSO) 1.49 (dd, J = 11.2, 5.9 Hz, 1H), 1.61-1.81 (m, 2H), 1.87 (dt, J = 11.7, 7.7 Hz, 1H), 3.39 (dt, J = 10.4, 7.1 Hz, 1H), 3.60 (dt, J = 11.0, 5.9 Hz, 1H), 4.83 (dd, J = 8.0, 3.9 Hz, 1H), 7.2-7.3 (m, 1H), 7.31-7.44 (m, 4H), 7.87 (dd, J = 8.9, 2.0 Hz, 1H), 7.97 (d, J = 4.5 Hz, 5H), 8.18 (s, 1H), 8.32 (d, J = 1.9 Hz, 1H). | |
| 637 | Absolute 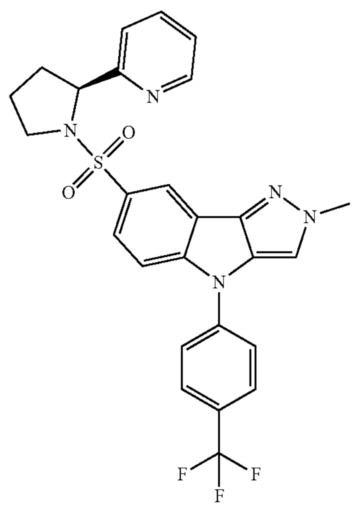 2-[(2S)-1-({2-methyl-4-[4-(trifluoro-methyl)phenyl]-2H,4H-pyrazolo[4,3-b]indol-7-yl}sulfonyl)pyrrolidin-2-yl]pyridine | 1H NMR (400 MHz, DMSO) 1.51 (dd, J = 12.6, 6.8 Hz, 1H), 1.88 (ddq, J = 19.3, 13.3, 6.8, 6.3 Hz, 2H), 1.98-2.16 (m, 1H), 3.40 (dt, J = 10.0, 6.9 Hz, 1H), 3.69 (dt, J = 11.9, 6.1 Hz, 1H), 4.14 (s, 4H), 4.94 (dd, J = 8.3, 4.6 Hz, 1H), 7.71 (s, 1H), 7.84-8.09 (m, 7H), 8.19 (s, 1H), 8.28 (d, J = 8.3 Hz, 1H), 8.40 (d, J = 1.8 Hz, 1H), 8.75 (d, J = 5.4 Hz, 1H). | |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 638 | Absolute 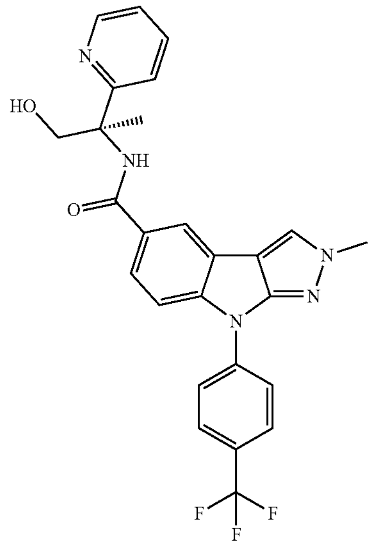 N-[(2R)-1-hydroxy-2-(pyridin-2-yl)propan-2-yl]-2-methyl-8-[4-(trifluoromethyl)-phenyl]-2H,8H-pyrazolo[3,4-b]indole-5-carboxamide | 1H NMR (400 MHz, DMSO-d6) 1.74 (d, J = 5.7 Hz, 3H), 3.84-3.93 (m, 2H), 4.01-4.07 (m, 3H), 5.02-5.13 (m, 1H), 7.2-7.27 (m, 1H), 7.46 (t, J = 7.0 Hz, 1H), 7.70-7.77 (m, 1H), 7.77-7.86 (m, 2H), 7.94-8.02 (m, 2H), 8.06-8.13 (m, 2H), 8.22 (d, J = 6.0 Hz, 1H), 8.34-8.42 (m, 2H), 8.49-8.56 (m, 1H). | |
| 639 | Absolute 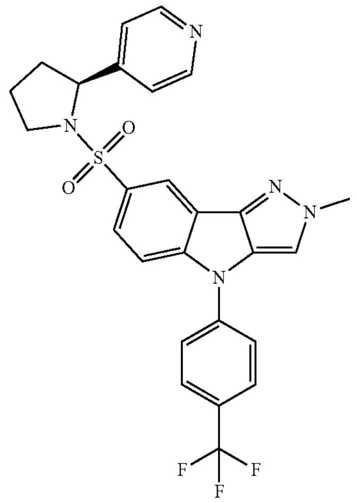 4-[(2S)-1-({2-methyl-4-[4-(trifluoro-methyl)phenyl]-2H,4H-pyrazolo[4,3-b]indol-7-yl}sulfonyl)pyrrolidin-2-yl]pyridine | 1H NMR (400 MHz, DMSO) 1.42-1.6 (m, 1H), 1.69 (ddt, J = 13.6, 9.9, 6.1 Hz, 2H), 1.93 (dq, J = 11.9, 9.4, 8.2 Hz, 1H), 3.27-3.47 (m, 2H), 3.61 (dt, J = 10.1, 6.3 Hz, 1H), 4.13 (s, 3H), 4.85 (dd, J = 8.2, 3.9 Hz, 1H), 7.36-7.48 (m, 2H), 7.89 (dd, J = 8.8, 2.0 Hz, 1H), 7.97 (d, J = 2.7 Hz, 5H), 8.18 (s, 1H), 8.35 (d, J = 1.9 Hz, 1H), 8.49-8.62 (m, 2H). | |

TABLE 1-continued

Table 1 below shows exemplary compounds of the present invention. They have been synthesized as described in the Examples above or similar thereto.

| Compound No. (Example No.) | Structure and Name | $^1$H-NMR | Conditions and elution time (min) LCMS (M + H$^+$) |
|---|---|---|---|
| 640 | 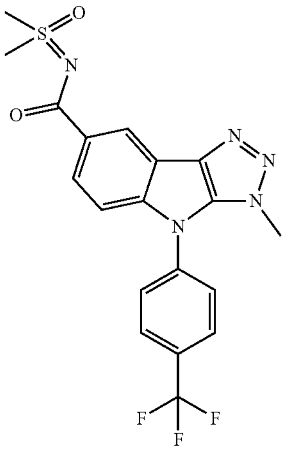 N-[dimethyl(oxo)-λ6-sulfanylidene]-3-methyl-4-[4-(trifluoromethyl)phenyl]-3H,4H-[1,2,3]triazolo[4,5-b]indole-7-carboxamide | 1H NMR (400 MHz, DMSO) d 8.61 (d, J = 1.7 Hz, 1H), 8.15 (dd, J = 8.8, 1.8 Hz, 1H), 8.07 (d, J = 8.6 Hz, 2H), 8.01 (d, J = 8.8 Hz, 2H), 7.90 (d, J = 8.8 Hz, 1H), 4.37 (s, 3H), 3.50 (s, 6H). | |

TFA = trifluoroacetate

LC-MS conditions:

[1] Column: Waters XBridge C18 3.5 µm, 50 * 4.6 mm; 5-95%: Flow Rate: 1.5 mL/min; Analysis Time: 6.5 min; MS scan range: 100-1000; Mobil Phase A: 0.02% NH4OAc in water; Mobil Phase B: acetonitrile; Gradient: 0.15 min: 5% B, 4.5 min: 95% B, 6.0 min: 95% B, 6.1 min: 5% B, 6.5 min: 5% B.

[2] 24Column: Waters XBridge C18 3.5 um, 50 * 4.6 mm; Solvent A: water + 0.1% TFA; Solvent: ACN; Flow: 1.5 ml/min; Time: 6.5 min; Gradient: 0.15 min: 10% B, 4.5 min: 80% B, 4.6 min: 95% B, 6.0 min: 95% B, 6.1 min: 5% B, 6.5 min: 5% B.

[3] Column: Waters XBridge C18 3.5 µm, 50 * 4.6 mm; 20-70%: Flow Rate: 1.5 mL/min; Analysis Time: 6.5 min; MS scan range: 100-1000; Mobil Phase A: 0.1% TFA in water; Mobil Phase B: acetonitrile; Gradient: 0.15 min: 20% B, 4.5 min: 70% B, 4.6 min: 95% B, 6.0 min: 95% B, 6.1 min: 5% B, 6.5 min: 5% B

[4] Column: Waters XBridge C18 3.5 µm, 50 * 4.6 mm; 30-95%: Flow Rate: 1.5 mL/min; Analysis Time: 6.5 min; MS scan range: 100-1000; Mobil Phase A: 0.1% TFA in water; Mobil Phase B: acetonitrile; Gradient: 0.15 min: 30% B, 4.5 min: 95% B, 4.6 min: 95% B, 6.0 min: 95% B, 6.1 min: 5% B, 6.5 min: 5% B

[5] Column: waters XBridge C18 5 um, 50 * 4.6 mm; Solvent A: water + 0.1% TFA; Solvent: ACN; Flow: 1.5 ml/min; Time: 6.5 min; Gradient :0.15 min: 10 % B, 4.5 min£°80 % BE-4.6 min: 95% B, 6.0 min: 95% B, 6.1 min: 5% B, 6.5 min: 5% B

[6] Column: XBridge C18, 3.5 µm, 3.0 * 30 mm; Solvent A: water + 0.1% TFA; Solvent B: ACN + 0.1% TFA; Flow: 2 ml/min; Gradient: 0 min: 5% B, 8 min: 100% B, 8.1 min: 100% B, 8.5 min: 5% B, 10 min 5% B.

[7] Column: Titank C18 1.8 µm, 30 * 2.1 mm; Column Oven: 40 C.; Mobile Phase A: 0.04% NH4OH, Mobile Phase B: ACN; Flow rate: 0.8 mL/min; Gradient: 10% B to 95% B in 2.1 min, hold 0.6 min; 254 nm

[8] Agilent 1200 Series; Chromolith RP-18e 50-4.6 mm; 3.3 ml/min; solvent A: Water + 0.05% HCOOH; solvent B: Acetonitrile + 0.04% HCOOH; 220 nm; 0 to 2.0 min: 0% B to 100% B; 2.0 to 2.5 min: 100% B

[9] Column: HALO, 3.0 * 30 mm, 2 um; Column Oven: 40° C.; Mobile Phase A: Water/0.05% TFA, Mobile Phase B: ACN/0.05% TFA; Flow rate: 1.5 ml/min; Gradient: 5% B to 100% B in 1.2 min, hold 0.5 min

[10] Column: HALO C18, 3.0 * 30 mm, 2.0 um; Column Oven: 40° C.; Mobile phase A: Water/0.1% FA; Mobile phase B: Acetonitrile/0.1% FA; Flow rate: 1.5 mL/min; Gradient: 5% B to 100% B in 1.2 min, hold 0.6 min

[11] Column: Shim-pack XR-ODS, 3.0 * 50 mm, 2.2 um; Mobile Phase A: Water/0.05% TFA, Mobile Phase B: ACN/0.05% TFA; Flow rate: 1.2 mL/min; Gradient: 5% B to 100% B in 2.0 min, hold 0.7 min

[12] Column: HALO C18, 3.0 * 30 mm, 2.0 um; Column Oven: 40° C.; Mobile phase A: Water/0.1% FA, Mobile phase B: Acetonitrile/0.1% TFA; Flow rate: 1.5 mL/min; Gradient: 5% B to 100% B in 1.2 min, hold 0.5 min; 254 nm

[13] Column: Chromolith RP-18e 50-4.6 mm; A: H2O + 0.05% HCOOH | B: MeCN + 0.04% HCOOH/4%->100% B: 0->2.8 min | 100% B: 2.8->3.3 min

[14] Waters Acquity UPLC; A: H2O + 0.05% HCOOH | B: MeCN + 0.04% HCOOH + 1% H2O T: 40° C. | Flow: 0.9 ml/min | Column: Kinetex EVO-C18 1.7 µm 50-2.1 mm 1%->99% B: 0->1.0 min | 99% B: 1.0->1.3 min

[15] Column: Poroshell HPH-C18 2.7 um, 3.0 * 50 mm; Column Oven: 40° C.; Mobile Phase A: water/5 mM NH4HCO3, Mobile Phase B: Acetonitrile; Flow rate: 1.2 mL/min; Gradient: 10% B to 95% B in 2.1 min, hold 0.6 min; 254 nm

[16] Column: Kinetex EVO 2.6 um, 3.0 * 50 mm; Column Oven: 40° C.; Mobile Phase A: water/5 mM NH4HCO3, Mobile Phase B: Acetonitrile; Flow rate: 1.2 mL/min; Gradient: 10% B to 95% B in 2.1 min, hold 0.6 min; 254 nm

[17] Column: Kinetex ® EVO C18 5.0 µm 50-4.6 mm; A: H2O + 0.05% HCOOH; B: MeCN + 0.04% HCOOH + 1% H2O; 1%->99% B: 0->0.8 min; 99% B: 0.8->1.1 min; T: 40° C.; Flow: 3.3 mL/min; MS: 61-1000 amu positive

[18] Kinetex EVO C18 5.0 µm 50-4.6 mm; A: H2O + 0.1% TFA B: MeCN + 0.1% TFA ; 1%->99% B: 0->1.8 min ; 99% B: 1.8->2.1 min ; T: 40° C.; Flow: 3.3 mL/min; MS: 61-1000 amu positive

[A] Column: Waters Cortecs C18 2.1 * 50 mm, 1.6 micron particle size, column oven 45° C.; Mobile phase A: Water/0.1% FA, Mobile phase B: Acetonitrile/0.1% FA; Flow rate: 0.8 mL/min; Gradient: 5% B to 95% B in 3 min, hold 0.8 min, 254 nm

[B] Column: Waters Xbridge C18 4.6 * 50 mm, 5.0 micron particle size, column oven room temperature; Mobile phase A: Water/0.1% ammonium hydroxide, Mobile phase B: Acetonitrile/0.1% ammonium hydroxide; Flow rate: 1.5 mL/min; Gradient: 5% B to 95% B in 5.5 min, hold 1 min, 254 nm Chiral HPLC/SFC:

[a] SFC; column: ChiralPak IC; eluent: $CO_2$: ethanol (55:45); wave length: 220 nm; flow: 5 mL/min.

[b] SFC: Column: YMC Cellulose-SC, eluent $CO_2$: Methanol 65:35, wavelength 254, flow: 5 mL/min.

[c] SFC: Column: Lux Cellulose-2, Eluent $CO_2$: Methanol 65:35, Wavelength 270 nm, Flow: 5 ml/min.

Melting point of selected compounds of Table 1 were determined by using a Tianjin Analytical Instrument RY-1 meting point detector and are depicted in Table 1a below:

TABLE 1a

| Compound No. | Melting Point [° C.] | Compound No. | Melting Point [° C.] |
|---|---|---|---|
| 15 | 179-181 | 16 | 111-112 |
| 19 | 208-210 | 20 | 223-224 |
| 21 | 185-187 | 24 | 221-222 |
| 25 | 169-171 | 27 | 300 |
| 28 | 181-185 | 30 | 110-111 |
| 38 | 232-234 | 43 | 256-258 |
| 49 | 184-186 | 50 | 240-242 |
| 51 | 252-254 | 52 | 188-190 |
| 53 | 228-230 | 55 | 300 |
| 58 | 300 | 60 | 264-265 |
| 61 | 290-291 | 63 | 278-280 |
| 64 | 120-121 | 65 | 130-132 |
| 66 | 102-103 | 67 | 169-171 |
| 69 | 288-290 | 70 | 160-162 |
| 75 | 238-240 | 78 | 278-280 |
| 79 | 228-230 | 80 | 90-91 |
| 81 | 201-202 | 82 | 218-220 |
| 83 | 218-220 | 84 | 182-184 |
| 85 | 187-188 | 86 | 198-200 |
| 87 | 248-250 | 88 | 262-264 |
| 89 | 62-63 | 90 | 179-180 |
| 91 | 176-178 | 92 | 194-196 |
| 95 | 246-248 | 96 | 200-201 |

TABLE 1a-continued

| Compound No. | Melting Point [° C.] | Compound No. | Melting Point [° C.] |
|---|---|---|---|
| 97 | 109-110 | 98 | 229-231 |
| | | 105 | 222-224 |
| 113 | 218-218 | 114 | 226-228 |
| 115 | 160-162 | 116 | 146-148 |
| 117 | 88-90 | 118 | 137-139 |
| 119 | 147-149 | 120 | 145-150 |
| 121 | 188-190 | 122 | 235-240 |
| 124 | 200-205 | 126 | 264-267 |
| 127 | 276-278 | 128 | 225-227 |
| 129 | 228-230 | 130 | 224-226 |
| 133 | 225-227 | 134 | 223-225 |
| 137 | 208-210 | 138 | 221-223 |
| 139 | 208-210 | 143 | 211-213 |
| 144 | 201-203 | 145 | 271-273 |
| 146 | 287-288 | 147 | 274-275 |
| 149 | 213-215 | 150 | 195-197 |
| 157 | 300 | 159 | 240-241 |
| 160 | 299-300 | 164 | 259-260 |
| 165 | 259-260 | 168 | 183-185 |
| 169 | 246-248 | 170 | 101-102 |
| 171 | 209-211 | 206 | 220-222 |

Table 1b below shows further exemplary compounds of the present invention. They can be synthesized by adapting the methods and procedures described in the Examples above. LC-MS and Chiral HPLC/SFC conditions are as defined above for Table 1.

TABLE 1b

| Compound No. | Structure and Name | $^1$H-NMR | Conditions and elution time (min) LCMS (M + H$^+$) |
|---|---|---|---|
| B1 | 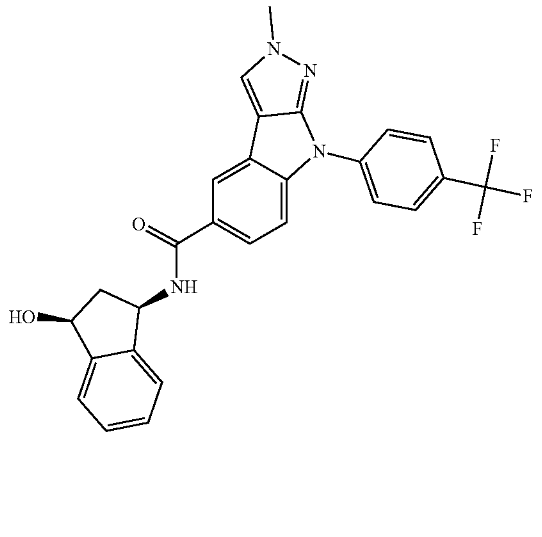 [SMILES: Cn1cc2c3cc(C(=O)N[C@@H]4C[C@H](O)c5ccccc54)ccc3n(-c3ccc(C(F)(F)F)cc3)c2n1] racemic diastereomer with known relative stereochemistry, cis N-[(1R,3S)-3-hydroxy-2,3-dihydro-1H-inden-1-yl]-2-methyl-8-[4-(trifluoromethyl)phenyl]-2H,8H-pyrazolo[3,4-b]indole-5-carboxamide | | |

TABLE 1b-continued

| Compound No. | Structure and Name | $^1$H-NMR | Conditions and elution time (min) LCMS (M + H$^+$) |
| --- | --- | --- | --- |
| B2 | 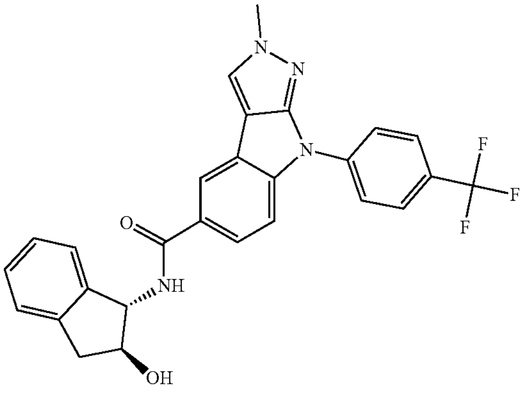 [SMILES: Cn1cc2c3cc(C(=O)N[C@H]4c5ccccc5C[C@@H]4O)ccc3n(-c3ccc(C(F)(F)F)cc3)c2n1]<br>stereochemistry assigned/known; single diastereomer<br>N-[(1S,2S)-2-hydroxy-2,3-dihydro-1H-inden-1-yl]-2-methyl-8-[4-(trifluoromethyl)phenyl]-2H,8H-pyrazolo[3,4-b]indole-5-carboxamide | | |
| B3 | 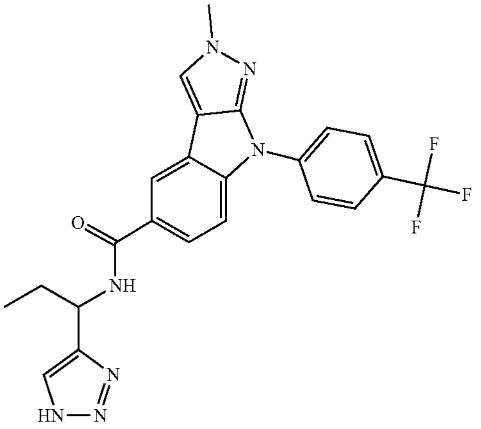 [SMILES: CCC(NC(=O)c1ccc2c(c1)c1cn(C)nc1n2-c1ccc(C(F)(F)F)cc1)c1c[nH]nn1]<br>2-methyl-N-[1-(1H-1,2,3-triazol-4-yl)propyl]-8-[4-(trifluoromethyl)phenyl]-2H,8H-pyrazolo[3,4-b]indole-5-carboxamide | | 18<br>1.33<br>468.1 |
| B4 | 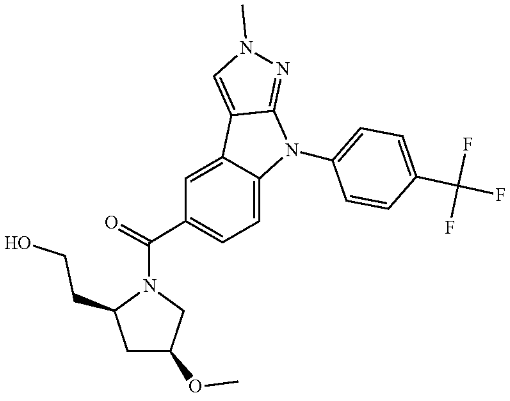 [SMILES: CO[C@H]1C[C@@H](CCO)N(C(=O)c2ccc3c(c2)c2cn(C)nc2n3-c2ccc(C(F)(F)F)cc2)C1]<br>stereochemistry assigned/known; single diastereomer<br>2-[(2R,4S)-4-methoxy-1-{2-methyl-8-[4-(trifluoromethyl)phenyl]-2H,8H-pyrazolo[3,4-b]indole-5-carbonyl}pyrrolidin-2-yl]ethan-1-ol | | |

TABLE 1b-continued

| Compound No. | Structure and Name | ¹H-NMR | Conditions and elution time (min) LCMS (M + H⁺) |
|---|---|---|---|
| B5 | 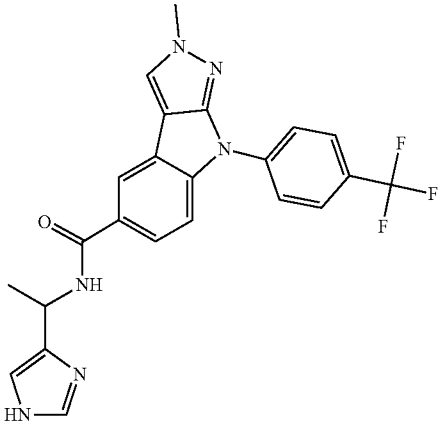 [SMILES: CC(NC(=O)c1ccc2c(c1)c1cn(C)nc1n2-c1ccc(C(F)(F)F)cc1)c1c[nH]cn1] N-[1-(1H-imidazol-4-yl)ethyl]-2-methyl-8-[4-(trifluoro-methyl)phenyl]-2H,8H-pyrazolo[3,4-b]indole-5-carboxamide | | |
| B6 | 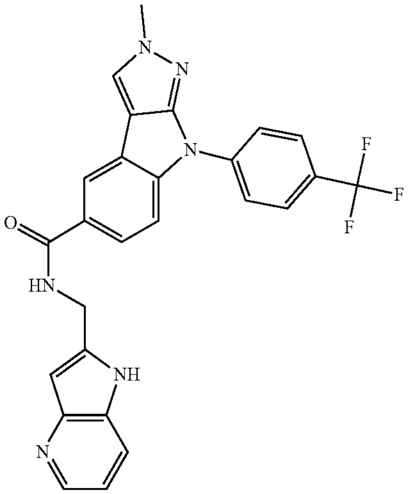 [SMILES: Cn1cc2c3cc(C(=O)NCc4cc5ncccc5[nH]4)ccc3n(-c3ccc(C(F)(F)F)cc3)c2n1] 2-methyl-N-({1H-pyrrolo[3,2-b]pyridin-2-yl}methyl)-8-[4-(trifluoromethyl)phenyl]-2H,8H-pyrazolo[3,4-b]indole-5-carboxamide | | |
| B7 | 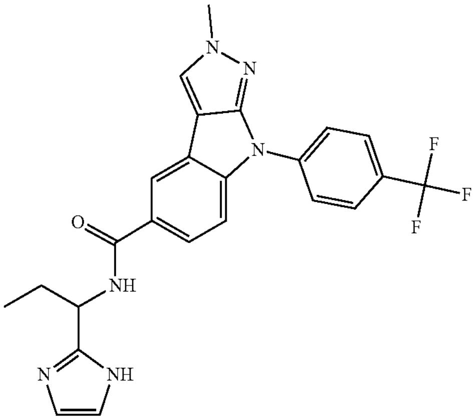 [SMILES: CCC(NC(=O)c1ccc2c(c1)c1cn(C)nc1n2-c1ccc(C(F)(F)F)cc1)c1ncc[nH]1] N-[1-(1H-imidazol-2-yl)propyl]-2-methyl-8-[4-(trifluoro-methyl)phenyl]-2H,8H-pyrazolo[3,4-b]indole-5-carboxamide | | |

TABLE 1b-continued

| Compound No. | Structure and Name | $^1$H-NMR | Conditions and elution time (min) LCMS (M + H$^+$) |
|---|---|---|---|
| B8 | 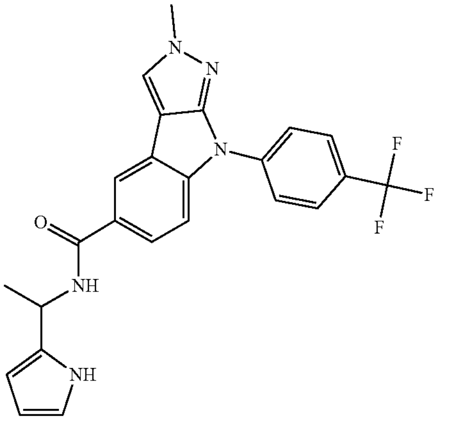 [SMILES: CC(NC(=O)c1ccc2c(c1)c1cn(C)nc1n2-c1ccc(C(F)(F)F)cc1)c1ccc[nH]1] 2-methyl-N-[1-(1H-pyrrol-2-yl)ethyl]-8-[4-(trifluoro-methyl)phenyl]-2H,8H-pyrazolo[3,4-b]indole-5-carboxamide | | |
| B9 | 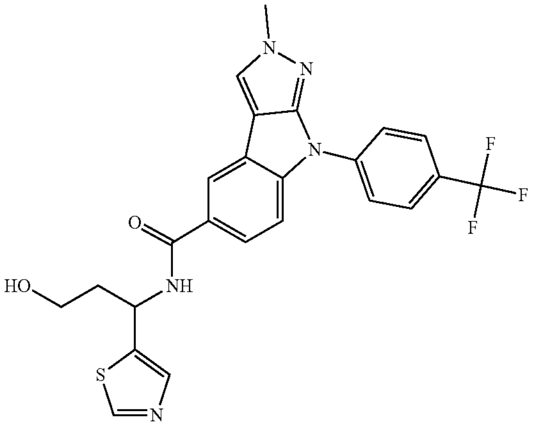 [SMILES: Cn1cc2c3cc(C(=O)NC(CCO)c4cncs4)ccc3n(-c3ccc(C(F)(F)F)cc3)c2n1] N-[3-hydroxy-1-(1,3-thiazol-5-yl)propyl]-2-methyl-8-[4-(trifluo-romethyl)phenyl]-2H,8H-pyrazolo[3,4-b]indole-5-carboxamide | | 18<br>1.26<br>500.1 |
| B10 | 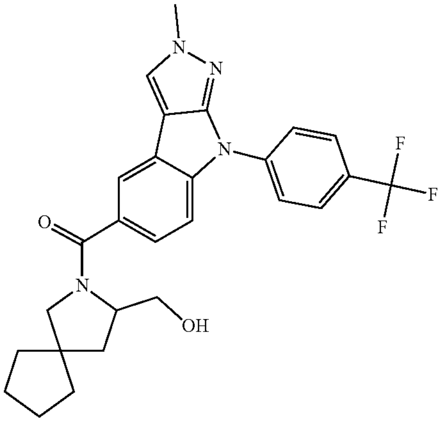 [SMILES: Cn1cc2c3cc(C(=O)N4CC5(CCCC5)CC4CO)ccc3n(-c3ccc(C(F)(F)F)cc3)c2n1] (2-{2-methyl-8-[4-(trifluoromethyl)phenyl]-2H,8H-pyrazolo[3,4-b]indole-5-carbonyl}-2-azaspiro[4.4]nonan-3-yl)methanol | | |

TABLE 1b-continued

| Compound No. | Structure and Name | ¹H-NMR | Conditions and elution time (min) LCMS (M + H⁺) |
|---|---|---|---|
| B11 | 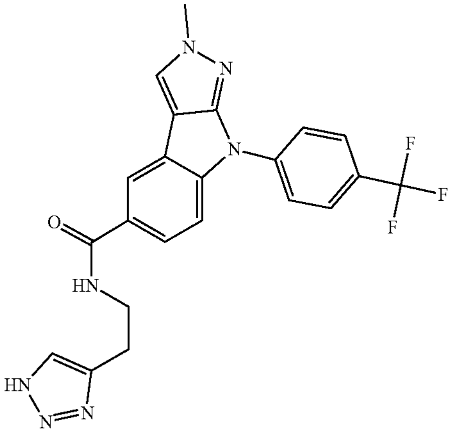 [SMILES: Cn1cc2c3cc(C(=O)NCCc4c[nH]nn4)ccc3n(-c3ccc(C(F)(F)F)cc3)c2n1] 2-methyl-N-[2-(1H-1,2,3-triazol-4-yl)ethyl]-8-[4-(trifluoromethyl)phenyl]-2H,8H-pyrazolo[3,4-b]indole-5-carboxamide | | 18<br>1.27<br>454.1 |
| B12 | 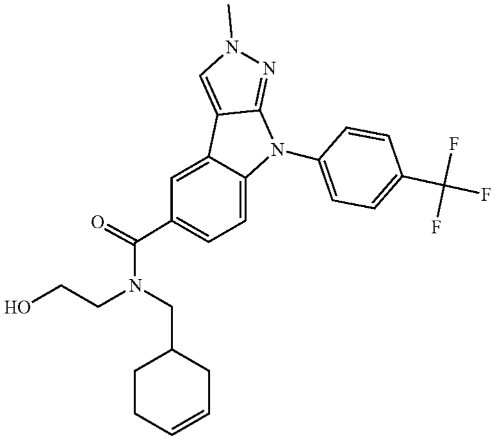 [SMILES: Cn1cc2c3cc(C(=O)N(CCO)CC4CC=CCC4)ccc3n(-c3ccc(C(F)(F)F)cc3)c2n1] N-[(cyclohex-3-en-1-yl)methyl]-N-(2-hydroxyethyl)-2-methyl-8-[4-(trifluoromethyl)phenyl]-2H,8H-pyrazolo[3,4-b]indole-5-carboxamide | | |
| B13 | 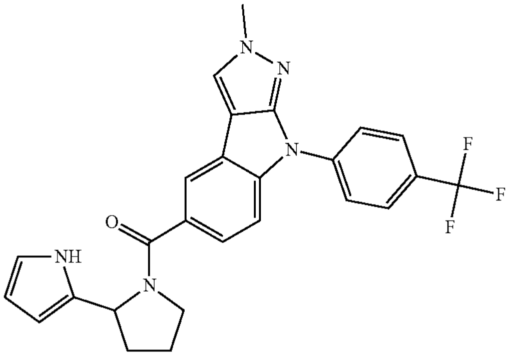 [SMILES: Cn1cc2c3cc(C(=O)N4CCCC4c4ccc[nH]4)ccc3n(-c3ccc(C(F)(F)F)cc3)c2n1] 2-(1-{2-methyl-8-[4-(trifluoromethyl)-phenyl]-2H,8H-pyrazolo[3,4-b]indole-5-carbonyl}pyrrolidin-2-yl)-1H-pyrrole | | |

TABLE 1b-continued
| Compound No. | Structure and Name | ¹H-NMR | Conditions and elution time (min) LCMS (M + H⁺) |
|---|---|---|---|
| B14 | 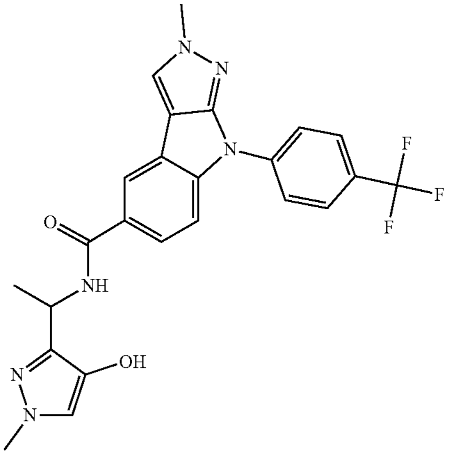 [SMILES: CC(NC(=O)c1ccc2c(c1)c1cn(C)nc1n2-c1ccc(C(F)(F)F)cc1)c1nn(C)cc1O] N-[1-(4-hydroxy-1-methyl-1H-pyrazol-3-yl)ethyl]-2-methyl-8-[4-(trifluoromethyl)phenyl]-2H,8H-pyrazolo[3,4-b]indole-5-carboxamide | | |
| B15 | 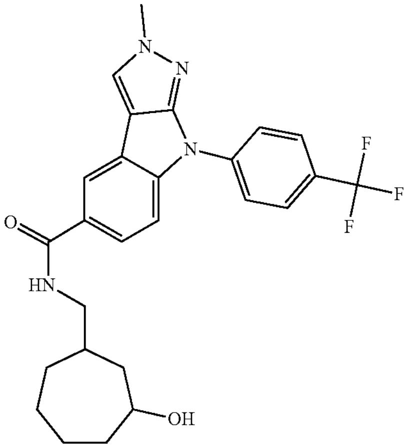 [SMILES: Cn1cc2c3cc(C(=O)NCC4CCCCC(O)C4)ccc3n(-c3ccc(C(F)(F)F)cc3)c2n1] diastereomeric mixture N-[(3-hydroxycycloheptyl)methyl]-2-methyl-8-[4-(trifluoromethyl)phenyl]-2H,8H-pyrazolo[3,4-b]indole-5-carboxamide | | |
| B16 | 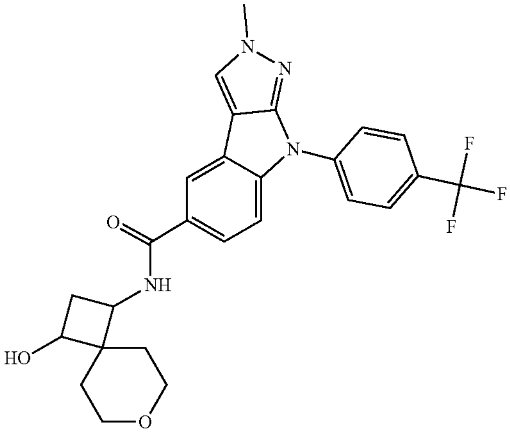 [SMILES: Cn1cc2c3cc(C(=O)NC4CC(O)C45CCOCC5)ccc3n(-c3ccc(C(F)(F)F)cc3)c2n1] | | |

TABLE 1b-continued

| Compound No. | Structure and Name | $^1$H-NMR | Conditions and elution time (min) LCMS (M + H$^+$) |
| --- | --- | --- | --- |
| | diastereomeric mixture N-{3-hydroxy-7-oxaspiro[3.5]nonan-1-yl}-2-methyl-8-[4-(trifluoromethyl)phenyl]-2H,8H-pyrazolo[3,4-b]indole-5-carboxamide | | |
| B17 | 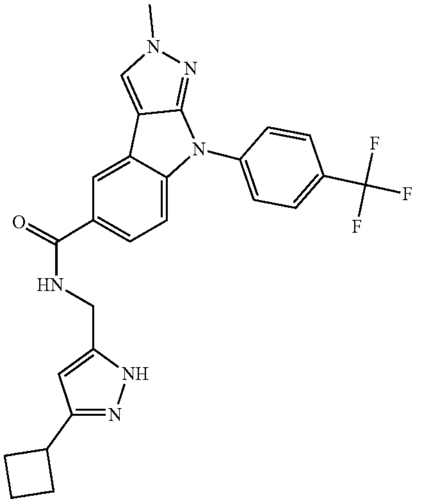 [SMILES: Cn1cc2c3cc(C(=O)NCc4cc(C5CCC5)n[nH]4)ccc3n(-c3ccc(C(F)(F)F)cc3)c2n1] N-[(3-cyclobutyl-1H-pyrazol-5-yl)methyl]-2-methyl-8-[4-(trifluoro-methyl)phenyl]-2H,8H-pyrazolo[3,4-b]indole-5-carboxamide | | |
| B18 stereo-chemistry assinged; single enantiomer | 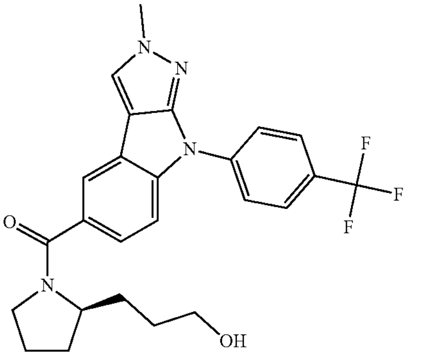 [SMILES: Cn1cc2c3cc(C(=O)N4CCC[C@@H]4CCCO)ccc3n(-c3ccc(C(F)(F)F)cc3)c2n1] stereochemistry assigned/known; single enantiomer 3-[(2R)-1-{2-methyl-8-[4-(trifluoromethyl)phenyl]-2H,8H-pyrazolo[3,4-b]indole-5-carbonyl}pyrrolidin-2-yl]propan-1-ol | | |

TABLE 1b-continued
| Compound No. | Structure and Name | ¹H-NMR | Conditions and elution time (min) LCMS (M + H⁺) |
|---|---|---|---|
| B19 | 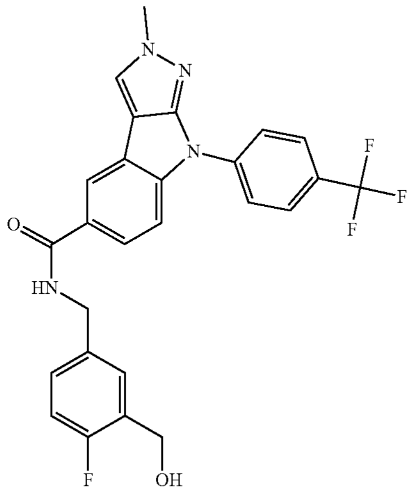 [SMILES: Cn1cc2c3cc(C(=O)NCc4ccc(F)c(CO)c4)ccc3n(-c3ccc(C(F)(F)F)cc3)c2n1] N-{[4-fluoro-3-(hydroxymethyl)-phenyl]methyl}-2-methyl-8-[4-(trifluoromethyl)phenyl]-2H,8H-pyrazolo[3,4-b]indole-5-carboxamide | | 18<br>1.38<br>497.1 |
| B20 | 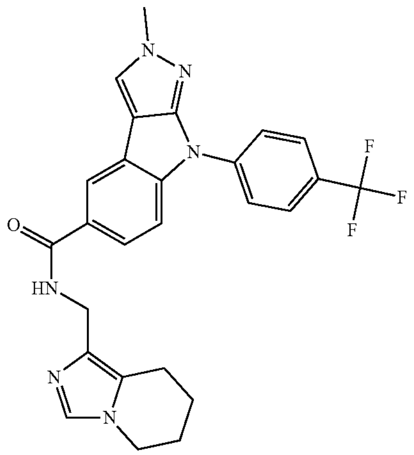 [SMILES: Cn1cc2c3cc(C(=O)NCc4ncn5c4CCCC5)ccc3n(-c3ccc(C(F)(F)F)cc3)c2n1] N-({5H,6H,7H,8H-imidazo[1,5-a]pyridin-1-yl}methyl)-2-methyl-8-[4-(trifluoromethyl)phenyl]-2H,8H-pyrazolo[3,4-b]indole-5-carboxamide | | |

TABLE 1b-continued

| Compound No. | Structure and Name | ¹H-NMR | Conditions and elution time (min) LCMS (M + H⁺) |
|---|---|---|---|
| B21 | 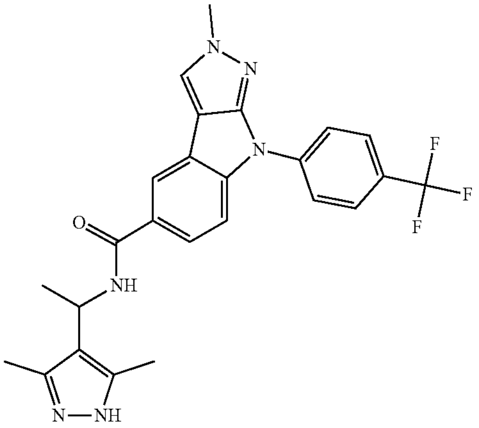 [SMILES: Cc1n[nH]c(C)c1C(C)NC(=O)c1ccc2c(c1)c1cn(C)nc1n2-c1ccc(C(F)(F)F)cc1] N-[1-(3,5-dimethyl-1H-pyrazol-4-yl)ethyl]-2-methyl-8-[4-(trifluoromethyl)phenyl]-2H,8H-pyrazolo[3,4-b]indole-5-carboxamide | | 17<br>0.91<br>480.80 |
| B22 | 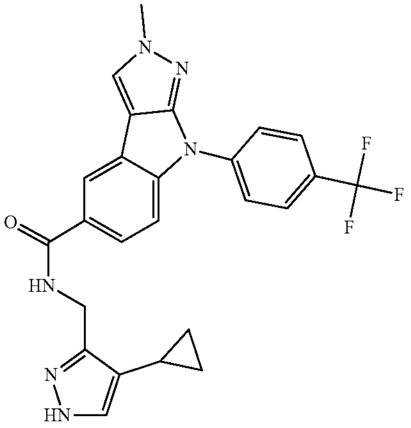 [SMILES: Cn1cc2c3cc(C(=O)NCc4n[nH]cc4C4CC4)ccc3n(-c3ccc(C(F)(F)F)cc3)c2n1] N-[(4-cyclopropyl-1H-pyrazol-3-yl)methyl]-2-methyl-8-[4-(trifluoromethyl)phenyl]-2H,8H-pyrazolo[3,4-b]indole-5-carboxamide | 1H NMR (400 MHz, DMSO-d6) δ 0.41-0.49 (m, 2H), 0.67-0.78 (m, 2H), 1.72 (tt, J = 8.4, 5.1 Hz, 1H), 4.03 (s, 3H), 4.58 (d, J = 5.5 Hz, 2H), 7.23 (s, 1H), 7.76 (d, J = 8.7 Hz, 1H), 7.90 (dd, J = 8.7, 1.9 Hz, 1H), 7.96 (d, J = 8.6 Hz, 2H), 8.05-8.12 (m, 2H), 8.18 (s, 1H), 8.39 (d, J = 1.8 Hz, 1H), 8.73 (s, 1H), 12.33 (s, 1H). | 17<br>0.98<br>478.8 |
| B23 | 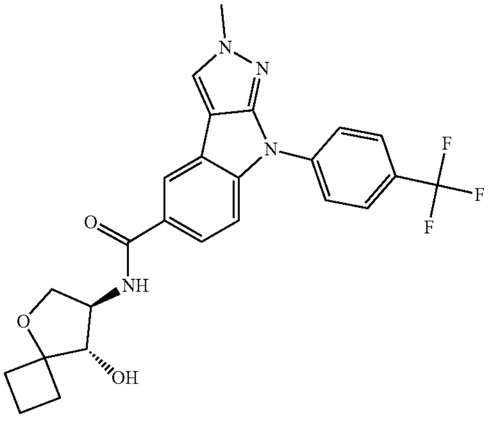 [SMILES: Cn1cc2c3cc(C(=O)N[C@@H]4COC5(CCC5)[C@H]4O)ccc3n(-c3ccc(C(F)(F)F)cc3)c2n1] racemic diastereomer with known relative stereochemistry, trans N-[(7R,8S)-8-hydroxy-5-oxaspiro[3.4]octan-7-yl]-2-methyl-8-[4-(trifluoromethyl)phenyl]-2H,8H-pyrazolo[3,4-b]indole-5-carboxamide | | |

TABLE 1b-continued

| Compound No. | Structure and Name | $^1$H-NMR | Conditions and elution time (min) LCMS (M + H$^+$) |
|---|---|---|---|
| B24 | 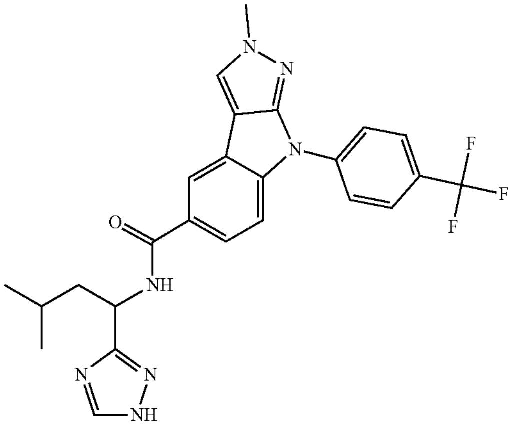 [SMILES: CC(C)CC(NC(=O)c1ccc2c(c1)c1cn(C)nc1n2-c1ccc(C(F)(F)F)cc1)c1nc[nH]n1] 2-methyl-N-[3-methyl-1-(1H-1,2,4-triazol-3-yl)butyl]-8-[4-(trifluoromethyl)phenyl]-2H,8H-pyrazolo[3,4-b]indole-5-carboxamide | | |
| B25 | 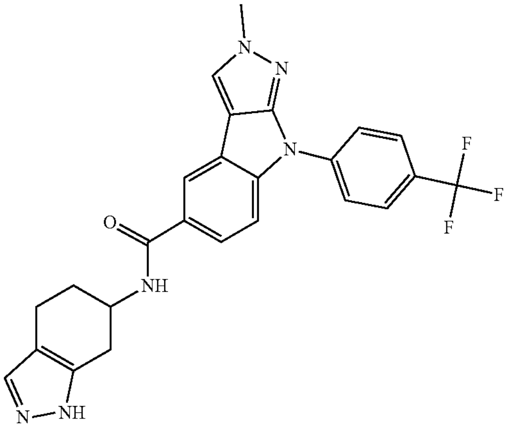 [SMILES: Cn1cc2c3cc(C(=O)NC4CCc5cn[nH]c5C4)ccc3n(-c3ccc(C(F)(F)F)cc3)c2n1] 2-methyl-N-(4,5,6,7-tetrahydro-1H-indazol-6-yl)-8-[4-(trifluoromethyl)phenyl]-2H,8H-pyrazolo[3,4-b]indole-5-carboxamide | | |
| B26 | 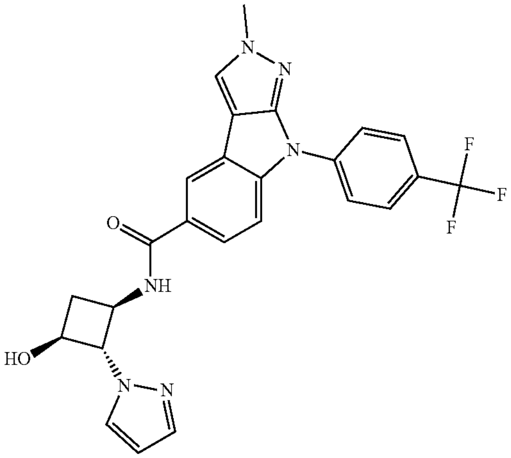 [SMILES: Cn1cc2c3cc(C(=O)N[C@@H]4C[C@H](O)[C@H]4n4cccn4)ccc3n(-c3ccc(C(F)(F)F)cc3)c2n1] racemic diastereomer with known relative stereochemistry N-[(1R,2S,3S)-3-hydroxy-2-(1H-pyrazol-1-yl)cyclobutyl]-2-methyl-8-[4-(trifluoromethyl)phenyl]-2H,8H-pyrazolo[3,4-b]indole-5-carboxamide | | |

TABLE 1b-continued

| Compound No. | Structure and Name | $^1$H-NMR | Conditions and elution time (min) LCMS (M + H$^+$) |
|---|---|---|---|
| B27 | 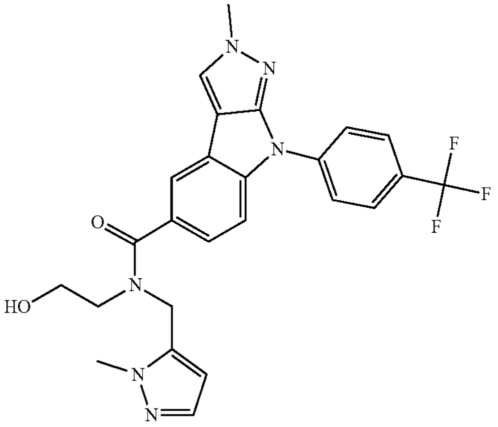 [SMILES: Cn1cc2c3cc(C(=O)N(CCO)Cc4ccnn4C)ccc3n(-c3ccc(C(F)(F)F)cc3)c2n1]<br>N-(2-hydroxyethyl)-2-methyl-N-[(1-methyl-1H-pyrazol-5-yl)methyl]-8-[4-(trifluoromethyl)phenyl]-2H,8H-pyrazolo[3,4-b]indole-5-carboxamide | | 18<br>1.27<br>497.1 |
| B28 | 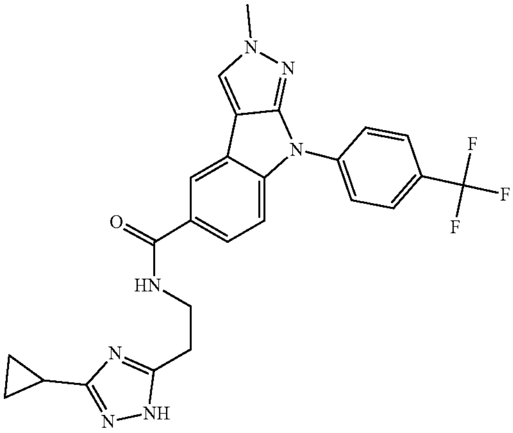 [SMILES: Cn1cc2c3cc(C(=O)NCCc4nc(C5CC5)n[nH]4)ccc3n(-c3ccc(C(F)(F)F)cc3)c2n1]<br>N-[2-(3-cyclopropyl-1H-1,2,4-triazol-5-yl)ethyl]-2-methyl-8-[4-(trifluoro-methyl)phenyl]-2H,8H-pyrazolo[3,4-b]indole-5-carboxamide | | |
| B29 | 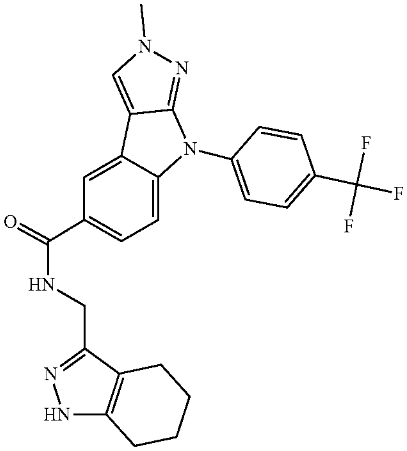 [SMILES: Cn1cc2c3cc(C(=O)NCc4n[nH]c5c4CCCC5)ccc3n(-c3ccc(C(F)(F)F)cc3)c2n1]<br>2-methyl-N-[(4,5,6,7-tetrahydro-1H-indazol-3-yl)methyl]-8-[4-(trifluoromethyl)phenyl]-2H,8H-pyrazolo[3,4-b]indole-5-carboxamide | | |

TABLE 1b-continued

| Compound No. | Structure and Name | $^1$H-NMR | Conditions and elution time (min) LCMS (M + H$^+$) |
|---|---|---|---|
| B30 | 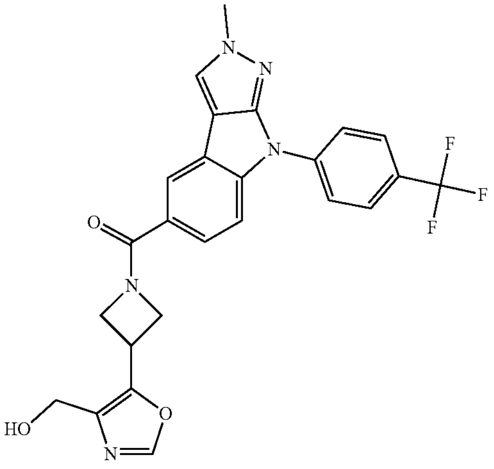 [SMILES: Cn1cc2c3cc(C(=O)N4CC(c5ocnc5CO)C4)ccc3n(-c3ccc(C(F)(F)F)cc3)c2n1] [5-(1-{2-methyl-8-[4-(trifluoro-methyl)phenyl]-2H,8H-pyrazolo[3,4-b]indole-5-carbonyl}azetidin-3-yl)-1,3-oxazol-4-yl]methanol | | |
| B31 | 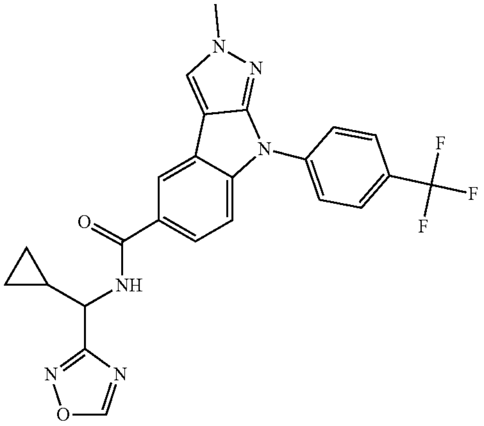 [SMILES: Cn1cc2c3cc(C(=O)NC(c4ncon4)C4CC4)ccc3n(-c3ccc(C(F)(F)F)cc3)c2n1] N-[cyclopropyl(1,2,4-oxadiazol-3-yl)methyl]-2-methyl-8-[4-(trifluoromethyl)phenyl]-2H,8H-pyrazolo[3,4-b]indole-5-carboxamide | | 18<br>1.40<br>481.1 |
| B32 | 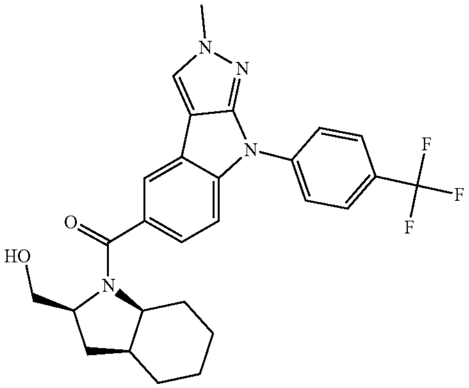 [SMILES: Cn1cc2c3cc(C(=O)N4[C@H](CO)C[C@@H]5CCCC[C@@H]54)ccc3n(-c3ccc(C(F)(F)F)cc3)c2n1] stereochemistry assigned/known; single enantiomer [(2S,3aS,7aS)-1-(2-methyl-8-[4-(trifluoromethyl)phenyl]-2H,8H-pyrazolo[3,4-b]indole-5-carbonyl}-octahydro-1H-indol-2-yl]methanol | | |

TABLE 1b-continued
| Compound No. | Structure and Name | $^1$H-NMR | Conditions and elution time (min) LCMS (M + H$^+$) |
|---|---|---|---|
| B33 | 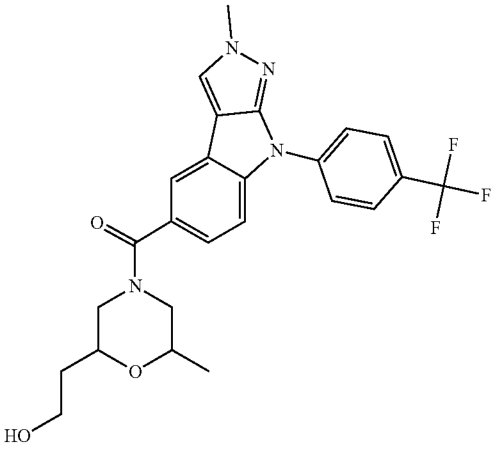 [SMILES: CC1CN(C(=O)c2ccc3c(c2)c2cn(C)nc2n3-c2ccc(C(F)(F)F)cc2)CC(CCO)O1]<br>diastereomeric mixture<br>2-(6-methyl-4-{2-methyl-8-[4-(trifluoromethyl)phenyl]-2H,8H-pyrazolo[3,4-b]indole-5-carbonyl}morpholin-2-yl)ethan-1-ol | | |
| B34 | 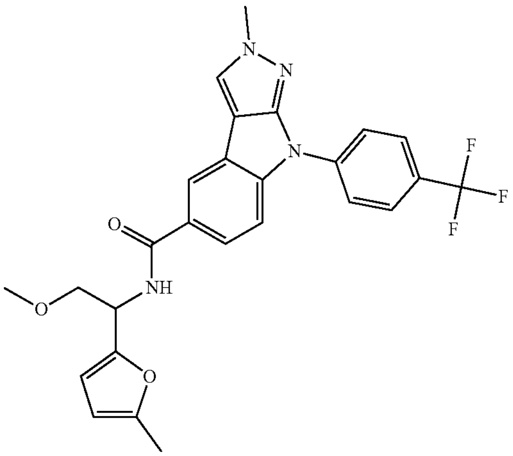 [SMILES: COCC(NC(=O)c1ccc2c(c1)c1cn(C)nc1n2-c1ccc(C(F)(F)F)cc1)c1ccc(C)o1]<br>N-[2-methoxy-1-(5-methylfuran-2-yl)ethyl]-2-methyl-8-[4-(trifluoromethyl)phenyl]-2H,8H-pyrazolo[3,4-b]indole-5-carboxamide | | 18<br>1.48<br>497.1 |

TABLE 1b-continued

| Compound No. | Structure and Name | ¹H-NMR | Conditions and elution time (min) LCMS (M + H⁺) |
|---|---|---|---|
| B35 | 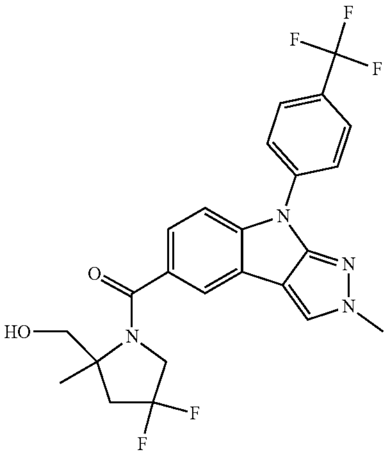 [SMILES: Cn1cc2c3cc(C(=O)N4CC(F)(F)CC4(C)CO)ccc3n(-c3ccc(C(F)(F)F)cc3)c2n1]<br>(4,4-difluoro-2-methyl-1-{2-methyl-8-[4-(trifluoro-methyl)phenyl]-2H,8H-pyrazolo[3,4-b]indole-5-carbonyl}pyrrolidin-2-yl)methanol | | |
| B36 | 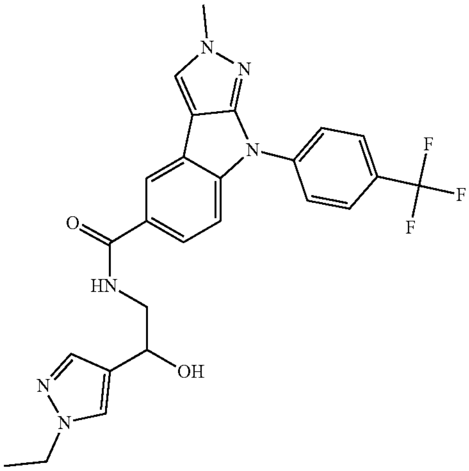 [SMILES: CCn1cc(C(O)CNC(=O)c2ccc3c(c2)c2cn(C)nc2n3-c2ccc(C(F)(F)F)cc2)cn1]<br>N-[2-(1-ethyl-1H-pyrazol-4-yl)-2-hydroxyethyl]-2-methyl-8-[4-(trifluoromethyl)phenyl]-2H,8H-pyrazolo[3,4-b]indole-5-carboxamide | 1H NMR (400 MHz, DMSO-d6) d 1.35 (t, J = 7.3 Hz, 3H), 3.41 (ddd, J = 13.1, 7.8, 5.3 Hz, 1H), 3.55 (dt, J = 13.2, 5.7 Hz, 1H), 4.03 (s, 3H), 4.08 (q, J = 7.2 Hz, 2H), 4.78 (dt, J = 7.9, 4.9 Hz, 1H), 5.23 (d, J = 4.8 Hz, 1H), 7.38 (s, 1H), 7.64 (s, 1H), 7.77 (d, J = 8.7 Hz, 1H), 7.86 (dd, J = 8.7, 1.9 Hz, 1H), 7.96 (d, J = 8.6 Hz, 2H), 8.09 (d, J = 8.5 Hz, 2H), 8.20 (s, 1H), 8.35 (d, J = 1.8 Hz, 1H), 8.45 (t, J = 5.6 Hz, 1H). | 17<br>0.93<br>478.8 |
| B37 | 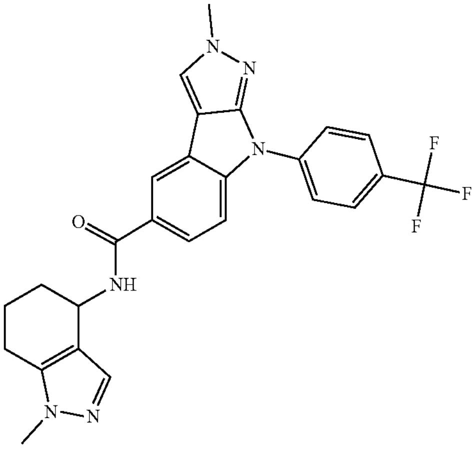 [SMILES: Cn1cc2c3cc(C(=O)NC4CCCc5c4cnn5C)ccc3n(-c3ccc(C(F)(F)F)cc3)c2n1] | | |

TABLE 1b-continued

| Compound No. | Structure and Name | $^1$H-NMR | Conditions and elution time (min) LCMS (M + H$^+$) |
|---|---|---|---|
| | 2-methyl-N-(1-methyl-4,5,6,7-tetrahydro-1H-indazol-4-yl)-8-[4-(trifluoromethyl)phenyl]-2H,8H-pyrazolo[3,4-b]indole-5-carboxamide | | |
| B38 | 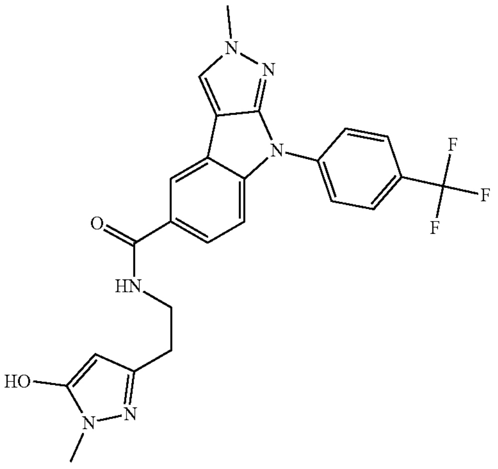 [SMILES: Cn1cc2c3cc(C(=O)NCCc4cc(O)n(C)n4)ccc3n(-c3ccc(C(F)(F)F)cc3)c2n1] N-[2-(5-hydroxy-1-methyl-1H-pyrazol-3-yl)ethyl]-2-methyl-8-[4-(trifluoromethyl)phenyl]-2H,8H-pyrazolo[3,4-b]indole-5-carboxamide | | |
| B39 | 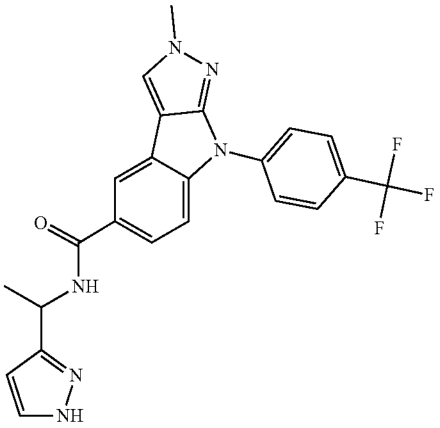 [SMILES: CC(NC(=O)c1ccc2c(c1)c1cn(C)nc1n2-c1ccc(C(F)(F)F)cc1)c1cc[nH]n1] 2-methyl-N-[1-(lH-pyrazol-5-yl)ethyl]-8-[4-(trifluoromethyl)phenyl]-2H,8H-pyrazolo[3,4-b]indole-5-carboxamide | 1H NMR (400 MHz, DMSO-d6) δ 1.52 (d, J = 7.0 Hz, 3H), 4.03 (s, 3H), 5.34 (p, J = 7.2 Hz, 1H), 6.22 (d, J = 2.1 Hz, 1H), 7.54 (s, 1H), 7.76 (d, J = 8.8 Hz, 1H), 7.89 (dd, J = 8.7, 1.9 Hz, 1H), 7.96 (d, J = 8.6 Hz, 2H), 8.05-8.12 (m, 2H), 8.19 (s, 1H), 8.39 (d, J = 1.8 Hz, 1H), 8.65 (d, J = 8.3 Hz, 1H), 12.55 (s, 1H). | 17 0.95 452.8 |
| B40 | 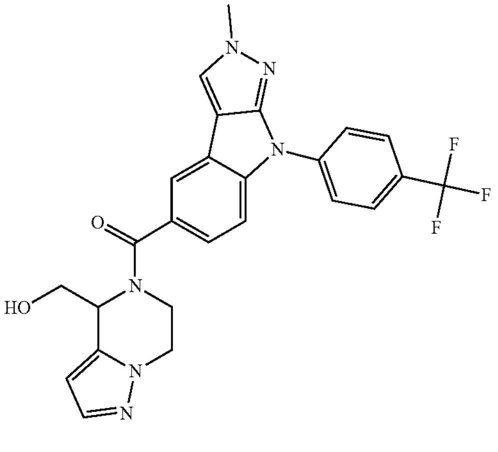 [SMILES: Cn1cc2c3cc(C(=O)N4CCn5nccc5C4CO)ccc3n(-c3ccc(C(F)(F)F)cc3)c2n1] | | |

TABLE 1b-continued

| Compound No. | Structure and Name | ¹H-NMR | Conditions and elution time (min) LCMS (M + H⁺) |
|---|---|---|---|
| | (5-{2-methyl-8-[4-(trifluoro-methyl)phenyl]-2H,8H-pyrazolo[3,4-b]indole-5-carbonyl)-4H,5H,6H,7H-pyrazolo[1,5-a]pyrazin-4-yl)methanol | | |
| B41 | 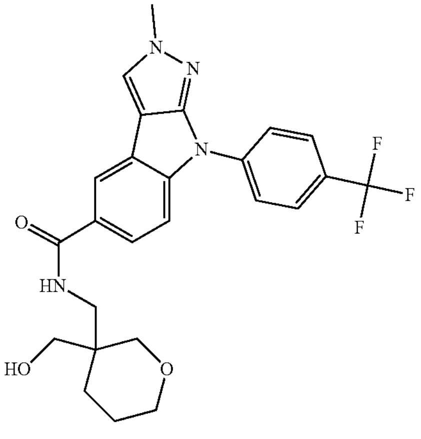 [SMILES: Cn1cc2c3cc(C(=O)NCC4(CO)CCCOC4)ccc3n(-c3ccc(C(F)(F)F)cc3)c2n1] N-{[3-(hydroxymethyl)oxan-3-yl]methyl}-2-methyl-8-[4-(trifluoromethyl)phenyl]-2H,8H-pyrazolo[3,4-b]indole-5-carboxamide | | |
| B42 | 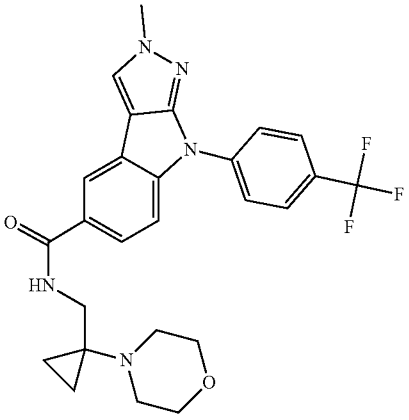 [SMILES: Cn1cc2c3cc(C(=O)NCC4(N5CCOCC5)CC4)ccc3n(-c3ccc(C(F)(F)F)cc3)c2n1] 2-methyl-N-{[1-(morpholin-4-yl)cyclopropyl]methyl}-8-[4-(trifluoromethyl)phenyl]-2H,8H-pyrazolo[3,4-b]indole-5-carboxamide | | |
| B43 | 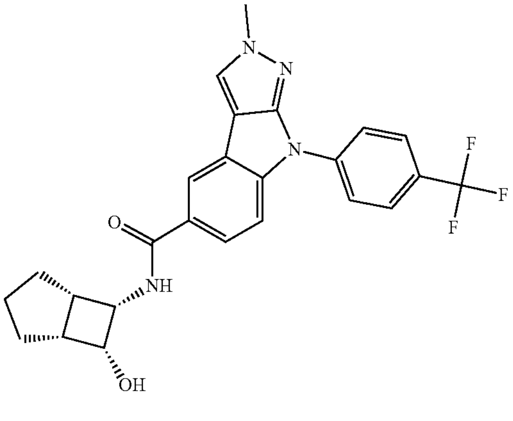 [SMILES: Cn1cc2c3cc(C(=O)N[C@@H]4[C@H](O)[C@@H]5CCC[C@@H]54)ccc3n(-c3ccc(C(F)(F)F)cc3)c2n1] | | |

TABLE 1b-continued

| Compound No. | Structure and Name | $^1$H-NMR | Conditions and elution time (min) LCMS (M + H$^+$) |
|---|---|---|---|
| | racemic diastereomer with known relative stereochemistry N-[(1R,5S,6S,7R)-7-hydroxy-bicyclo[3.2.0]heptan-6-yl]-2-methyl-8-[4-(trifluoromethyl)phenyl]-2H,8H-pyrazolo[3,4-b]indole-5-carboxamide | | |
| B44 | 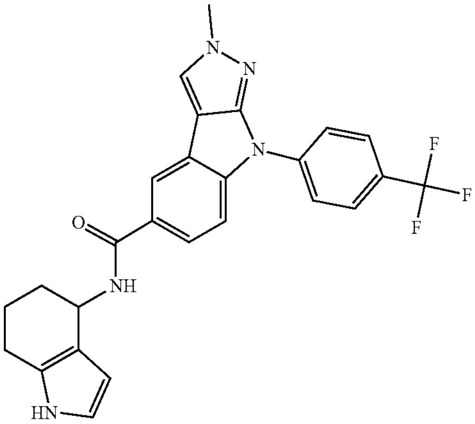 [SMILES: Cn1cc2c3cc(C(=O)NC4CCCc5[nH]ccc54)ccc3n(-c3ccc(C(F)(F)F)cc3)c2n1] 2-methyl-N-(4,5,6,7-tetrahydro-1H-indol-4-yl)-8-[4-(trifluoromethyl)phenyl]-2H,8H-pyrazolo[3,4-b]indole-5-carboxamide | | |
| B45 | 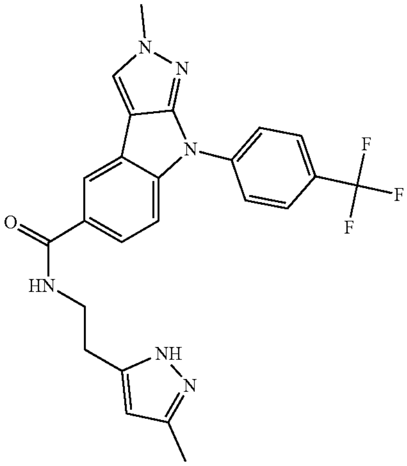 [SMILES: Cc1cc(CCNC(=O)c2ccc3c(c2)c2cn(C)nc2n3-c2ccc(C(F)(F)F)cc2)[nH]n1] 2-methyl-N-[2-(3-methyl-1H-pyrazol-5-yl)ethyl]-8-[4-(trifluoromethyl)phenyl]-2H,8H-pyrazolo[3,4-b]indole-5-carboxamide | | |
| B46 | 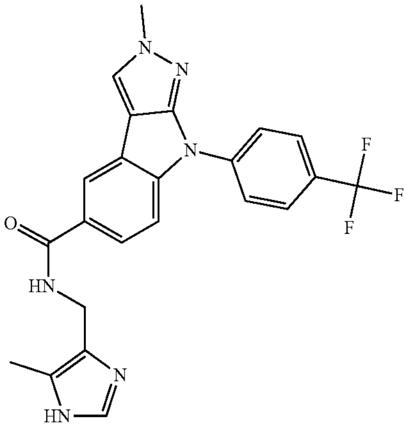 [SMILES: Cc1[nH]cnc1CNC(=O)c1ccc2c(c1)c1cn(C)nc1n2-c1ccc(C(F)(F)F)cc1] | | |

TABLE 1b-continued

| Compound No. | Structure and Name | $^1$H-NMR | Conditions and elution time (min) LCMS (M + H+) |
|---|---|---|---|
| | 2-methyl-N-[(5-methyl-1H-imidazol-4-yl)methyl]-8-[4-(trifluoromethyl)phenyl]-2H,8H-pyrazolo[3,4-b]indole-5-carboxamide | | |
| B47 | 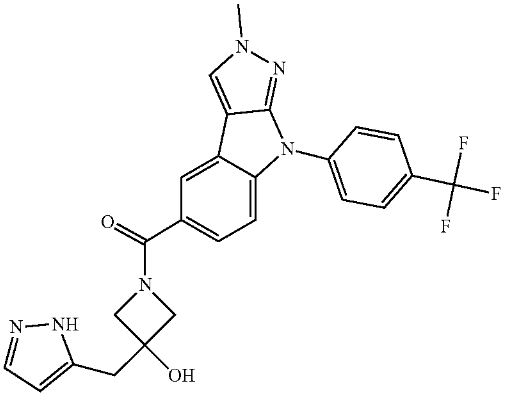 [SMILES: Cn1cc2c3cc(C(=O)N4CC(O)(Cc5ccn[nH]5)C4)ccc3n(-c3ccc(C(F)(F)F)cc3)c2n1]<br>1-{2-methyl-8-[4-(trifluoromethyl)-phenyl]-2H,8H-pyrazolo[3,4-b]indole-5-carbonyl}-3-[(1H-pyrazol-5-yl)methyl]azetidin-3-ol | | |
| B48 | 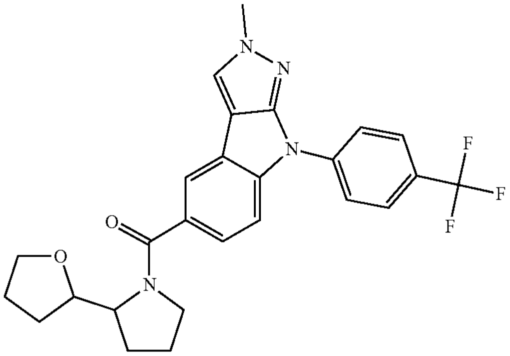 [SMILES: Cn1cc2c3cc(C(=O)N4CCCC4C4CCCO4)ccc3n(-c3ccc(C(F)(F)F)cc3)c2n1]<br>diastereomeric mixture<br>1-{2-methyl-8-[4-(trifluoromethyl)phenyl]-2H,8H-pyrazolo[3,4-b]indole-5-carbonyl}-2-(oxolan-2-yl)pyrrolidine | | |
| B49 | 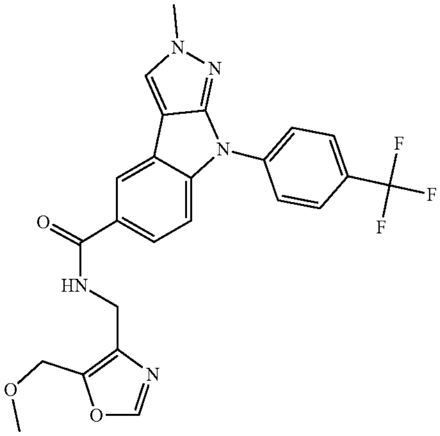 [SMILES: COCc1ocnc1CNC(=O)c1ccc2c(c1)c1cn(C)nc1n2-c1ccc(C(F)(F)F)cc1]<br>N-{[5-(methoxymethyl)-1,3-oxazol-4-yl]methyl}-2-methyl-8-[4-(trifluoromethyl)phenyl]-2H,8H-pyrazolo[3,4-b]indole-5-carboxamide | | 18<br>1.35<br>484.1 |

TABLE 1b-continued

| Compound No. | Structure and Name | $^1$H-NMR | Conditions and elution time (min) LCMS (M + H$^+$) |
|---|---|---|---|
| B50 | 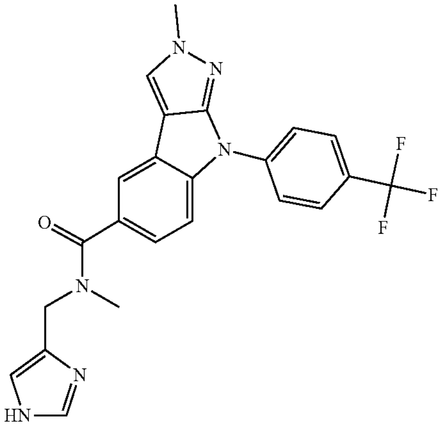 [SMILES: CN(Cc1c[nH]cn1)C(=O)c1ccc2c(c1)c1cn(C)nc1n2-c1ccc(C(F)(F)F)cc1] N-[(1H-imidazol-4-yl)methyl]-N,2-dimethyl-8-[4-(trifluoromethyl)phenyl]-2H,8H-pyrazolo[3,4-b]indole-5-carboxamide | | |
| B51 | 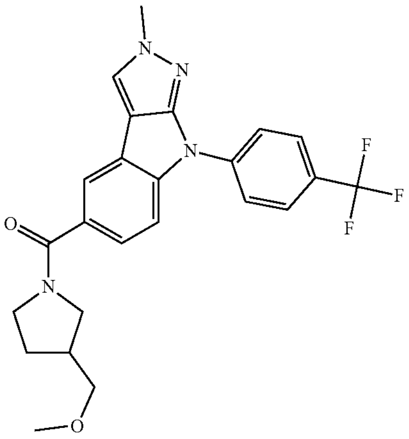 [SMILES: COCC1CCN(C(=O)c2ccc3c(c2)c2cn(C)nc2n3-c2ccc(C(F)(F)F)cc2)C1] 3-(methoxymethyl)-1-{2-methyl-8-[4-(trifluoromethyl)phenyl]-2H,8H-pyrazolo[3,4-b]indole-5-carbonyl}pyrrolidine | | |
| B52 | 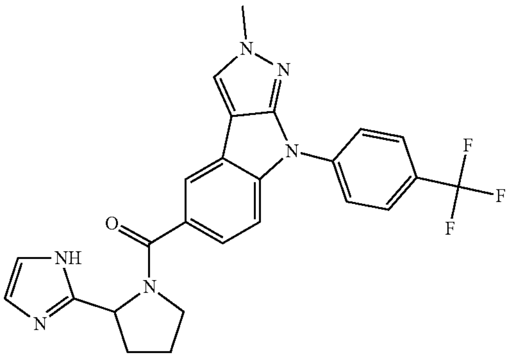 [SMILES: Cn1cc2c3cc(C(=O)N4CCCC4c4ncc[nH]4)ccc3n(-c3ccc(C(F)(F)F)cc3)c2n1] 2-(1-{2-methyl-8-[4-(trifluoromethyl)phenyl]-2H,8H-pyrazolo[3,4-b]indole-5-carbonyl}pyrrolidin-2-yl)-1H-imidazole | | |

TABLE 1b-continued

| Compound No. | Structure and Name | ¹H-NMR | Conditions and elution time (min) LCMS (M + H⁺) |
|---|---|---|---|
| B53 | 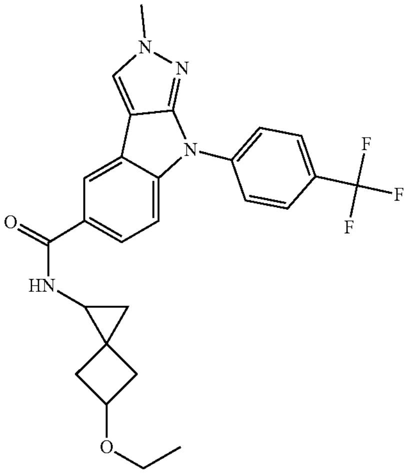 [SMILES: CCOC1CC2(C1)CC2NC(=O)c1ccc2c(c1)c1cn(C)nc1n2-c1ccc(C(F)(F)F)cc1] diastereomeric mixture N-{5-ethoxyspiro[2.3]hexan-1-yl}-2-methyl-8-[4-(trifluoromethyl)phenyl]-2H,8H-pyrazolo[3,4-b]indole-5-carboxamide | | |
| B54 | 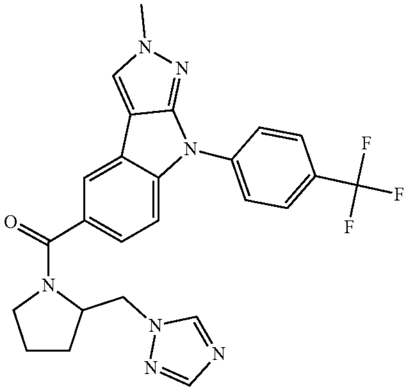 [SMILES: Cn1cc2c3cc(C(=O)N4CCCC4Cn4cncn4)ccc3n(-c3ccc(C(F)(F)F)cc3)c2n1] 1-[(1-{2-methyl-8-[4-(trifluoromethyl)phenyl]-2H,8H-pyrazolo[3,4-b]indole-5-carbonyl}pyrrolidin-2-yl)methyl]-1H-1,2,4-triazole | | |
| B55 | 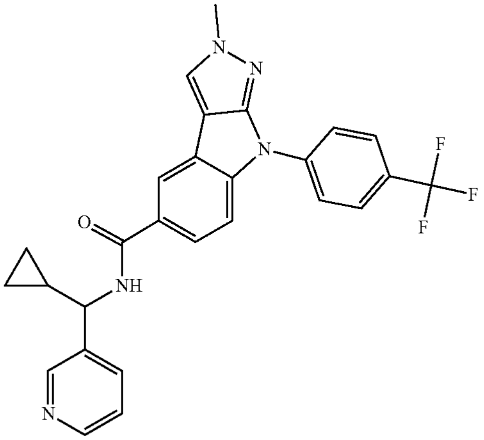 [SMILES: Cn1cc2c3cc(C(=O)NC(c4cccnc4)C4CC4)ccc3n(-c3ccc(C(F)(F)F)cc3)c2n1] N-[cyclopropyl(pyridin-3-yl)methyl]-2-methyl-8-[4-(trifluoromethyl)phenyl]-2H,8H-pyrazolo[3,4-b]indole-5-carboxamide | | 17<br>0.87<br>489.8 |

TABLE 1b-continued

| Compound No. | Structure and Name | ¹H-NMR | Conditions and elution time (min) LCMS (M + H⁺) |
|---|---|---|---|
| B56 | 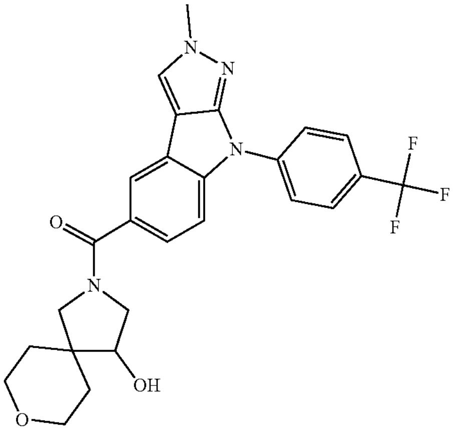 [SMILES: Cn1cc2c3cc(C(=O)N4CC(O)C5(CCOCC5)C4)ccc3n(-c3ccc(C(F)(F)F)cc3)c2n1]<br>2-(2-methyl-8-[4-(trifluoromethyl)phenyl]-2H,8H-pyrazolo[3,4-b]indole-5-carbonyl}-8-oxa-2-azaspiro[4.5]decan-4-ol | | |
| B57 | 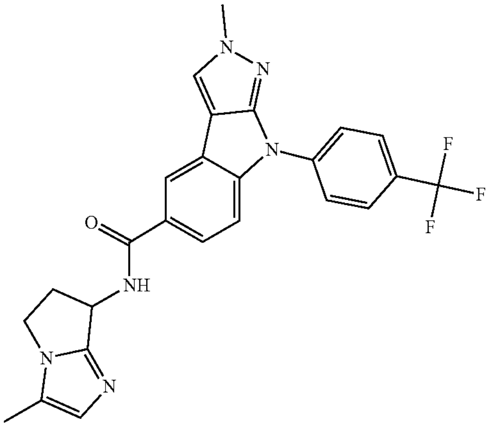 [SMILES: Cc1cnc2n1CCC2NC(=O)c1ccc2c(c1)c1cn(C)nc1n2-c1ccc(C(F)(F)F)cc1]<br>2-methyl-N-(3-methyl-5H,6H,7H-pyrrolo[1,2-a]imidazol-7-yl}-8-[4-(trifluoromethyl)phenyl]-2H,8H-pyrazolo[3,4-b]indole-5-carboxamide | | |
| B58 | 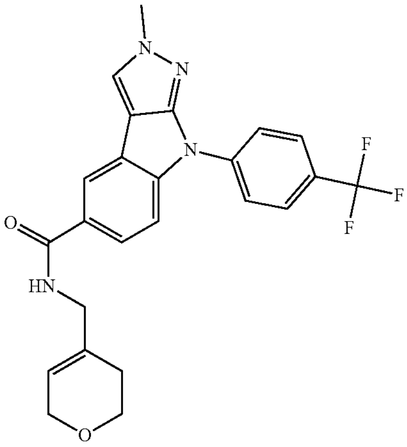 [SMILES: Cn1cc2c3cc(C(=O)NCC4=CCOCC4)ccc3n(-c3ccc(C(F)(F)F)cc3)c2n1]<br>N-[(3,6-dihydro-2H-pyran-4-yl)methyl]-2-methyl-8-[4-(trifluoromethyl)phenyl]-2H,8H-pyrazolo[3,4-b]indole-5-carboxamide | | 18<br>1.38<br>455.1 |

TABLE 1b-continued
| Compound No. | Structure and Name | $^1$H-NMR | Conditions and elution time (min) LCMS (M + H$^+$) |
|---|---|---|---|
| B59 | 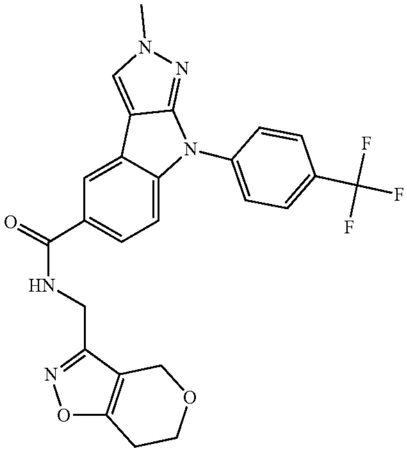 [SMILES: Cn1cc2c3cc(C(=O)NCc4noc5c4COCC5)ccc3n(-c3ccc(C(F)(F)F)cc3)c2n1] 2-methyl-N-({4H,6H,7H-pyrano[3,4-d][1,2]oxazol-3-yl}methyl)-8-[4-(trifluoromethyl)phenyl]-2H,8H-pyrazolo[3,4-b]indole-5-carboxamide | | |
| B60 | 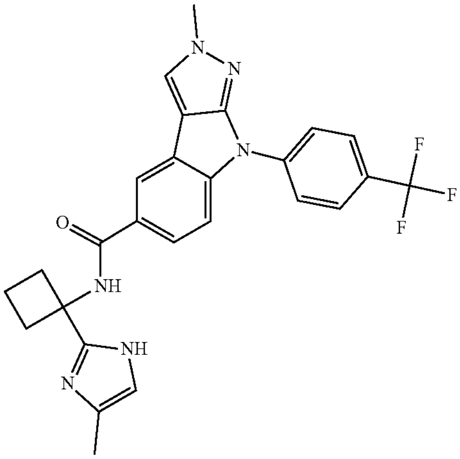 [SMILES: Cc1c[nH]c(C2(NC(=O)c3ccc4c(c3)c3cn(C)nc3n4-c3ccc(C(F)(F)F)cc3)CCC2)n1] 2-methyl-N-[1-(4-methyl-1H-imidazol-2-yl)cyclobutyl]-8-[4-(trifluoromethyl)phenyl]-2H,8H-pyrazolo[3,4-b]indole-5-carboxamide | | |
| B61 | 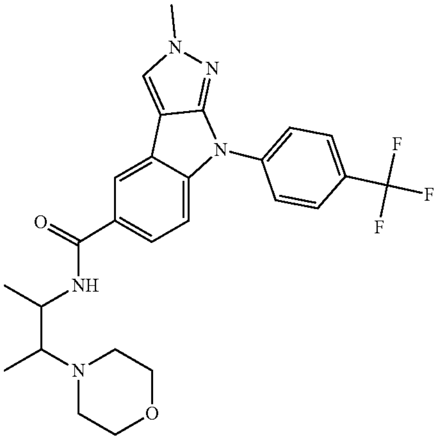 [SMILES: CC(NC(=O)c1ccc2c(c1)c1cn(C)nc1n2-c1ccc(C(F)(F)F)cc1)C(C)N1CCOCC1] | | |

TABLE 1b-continued

| Compound No. | Structure and Name | $^1$H-NMR | Conditions and elution time (min) LCMS (M + H$^+$) |
|---|---|---|---|
| | diastereomeric mixture 2-methyl-N-[3-(morpholin-4-yl)butan-2-yl]-8-[4-(trifluoromethyl)phenyl]-2H,8H-pyrazolo[3,4-b]indole-5-carboxamide | | |
| B62 | 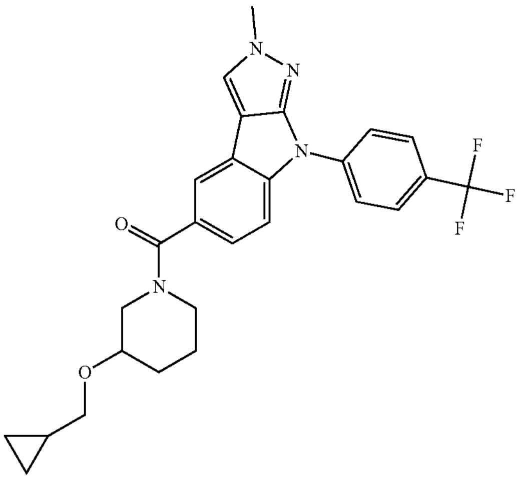 [SMILES: Cn1cc2c3cc(C(=O)N4CCCC(OCC5CC5)C4)ccc3n(-c3ccc(C(F)(F)F)cc3)c2n1] 3-(cyclopropylmethoxy)-1-{2-methyl-8-[4-(trifluoromethyl)phenyl]-2H,8H-pyrazolo[3,4-b]indole-5-carbonyl}piperidine | | |
| B63 | 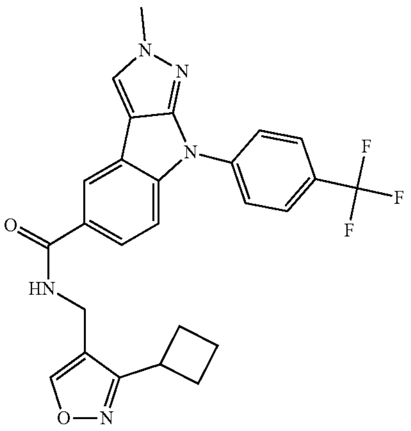 [SMILES: Cn1cc2c3cc(C(=O)NCc4conc4C4CCC4)ccc3n(-c3ccc(C(F)(F)F)cc3)c2n1] N-[(3-cyclobutyl-1,2-oxazol-4-yl)methyl]-2-methyl-8-[4-(trifluoromethyl)phenyl]-2H,8H-pyrazolo[3,4-b]indole-5-carboxamide | | |

TABLE 1b-continued

| Compound No. | Structure and Name | $^1$H-NMR | Conditions and elution time (min) LCMS (M + H$^+$) |
|---|---|---|---|
| B64 | 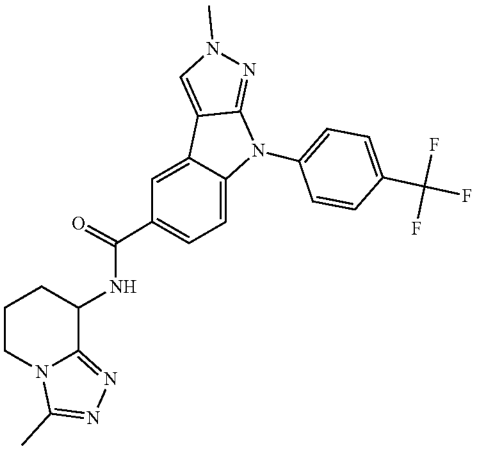 [SMILES: Cc1nnc2n1CCCC2NC(=O)c1ccc2c(c1)c1cn(C)nc1n2-c1ccc(C(F)(F)F)cc1] 2-methyl-N-(3-methyl-5H,6H,7H,8H-[1,2,4]triazolo[4,3-a]pyridin-8-yl}-8-[4-(trifluoromethyl)phenyl]-2H,8H-pyrazolo[3,4-b]indole-5-carboxamide | | |
| B65 | 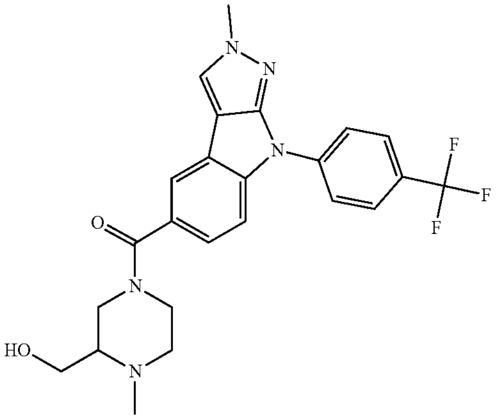 [SMILES: CN1CCN(C(=O)c2ccc3c(c2)c2cn(C)nc2n3-c2ccc(C(F)(F)F)cc2)CC1CO] (1-methyl-4-{2-methyl-8-[4-(trifluoromethyl)phenyl]-2H,8H-pyrazolo[3,4-b]indole-5-carbonyl}piperazin-2-yl)methanol | | |
| B66 | 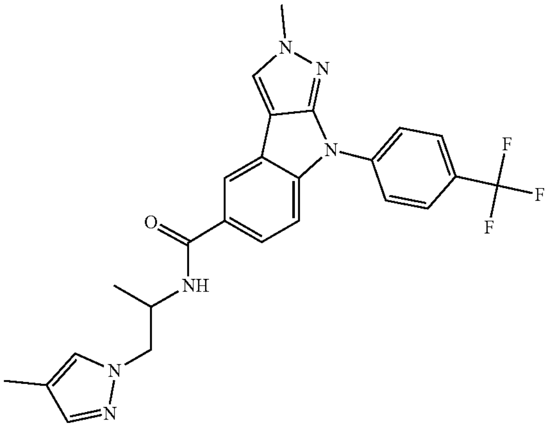 [SMILES: Cc1cnn(CC(C)NC(=O)c2ccc3c(c2)c2cn(C)nc2n3-c2ccc(C(F)(F)F)cc2)c1] 2-methyl-N-[1-(4-methyl-1H-pyrazol-1-yl)propan-2-yl]-8-[4-(trifluoromethyl)phenyl]-2H,8H-pyrazolo[3,4-b]indole-5-carboxamide | | |

TABLE 1b-continued

| Compound No. | Structure and Name | $^1$H-NMR | Conditions and elution time (min) LCMS (M + H$^+$) |
|---|---|---|---|
| B67 | 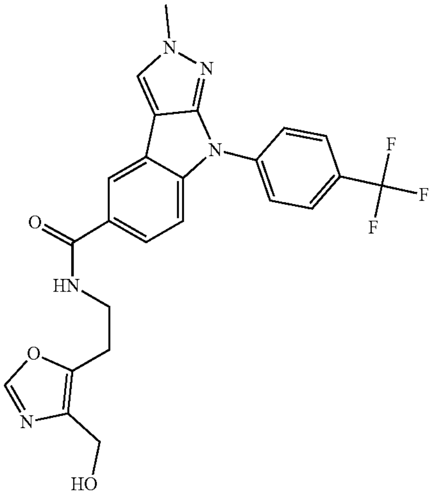 [SMILES: Cn1cc2c3cc(C(=O)NCCc4ocnc4CO)ccc3n(-c3ccc(C(F)(F)F)cc3)c2n1] N-{2-[4-(hydroxymethyl)-1,3-oxazol-5-yl]ethyl}-2-methyl-8-[4-(trifluoromethyl)phenyl]-2H,8H-pyrazolo[3,4-b]indole-5-carboxamide | | 18<br>1.28<br>484.1 |
| B68 | 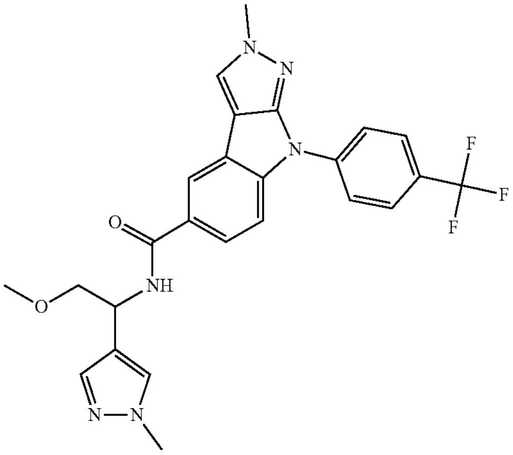 [SMILES: COCC(NC(=O)c1ccc2c(c1)c1cn(C)nc1n2-c1ccc(C(F)(F)F)cc1)c1cnn(C)c1] N-[2-methoxy-1-(1-methyl-1H-pyrazol-4-yl)ethyl]-2-methyl-8-[4-(trifluoromethyl)phenyl]-2H,8H-pyrazolo[3,4-b]indole-5-carboxamide | 1H NMR (400 MHz, DMSO-d6) δ 3.32 (s, 3H), 3.58 (dd, J = 9.8, 5.9 Hz, 1H), 3.68 (dd, J = 9.8, 7.9 Hz, 1H), 3.80 (s, 3H), 4.04 (s, 3H), 5.32 (td, J = 8.1, 5.8 Hz, 1H), 7.41 (d, J = 0.8 Hz, 1H), 7.64 (s, 1H), 7.77 (d, J = 8.7 Hz, 1H), 7.88 (dd, J = 8.7, 1.8 Hz, 1H), 7.97 (d, J = 8.6 Hz, 2H), 8.05-8.12 (m, 2H), 8.20 (s, 1H), 8.37 (d, J = 1.8 Hz, 1H), 8.58 (d, J = 8.5 Hz, 1H). | 17<br>0.95<br>496.8 |
| B69 | 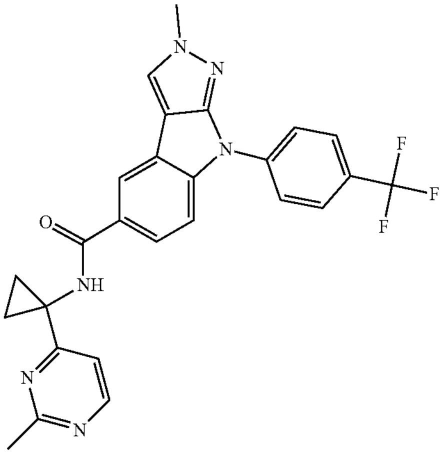 [SMILES: Cc1nccc(C2(NC(=O)c3ccc4c(c3)c3cn(C)nc3n4-c3ccc(C(F)(F)F)cc3)CC2)n1] | | |

TABLE 1b-continued

| Compound No. | Structure and Name | ¹H-NMR | Conditions and elution time (min) LCMS (M + H⁺) |
|---|---|---|---|
| | 2-methyl-N-[1-(2-methylpyrimidin-4-yl)cyclopropyl]-8-[4-(trifluoromethyl)phenyl]-2H,8H-pyrazolo[3,4-b]indole-5-carboxamide | | |
| B70 | 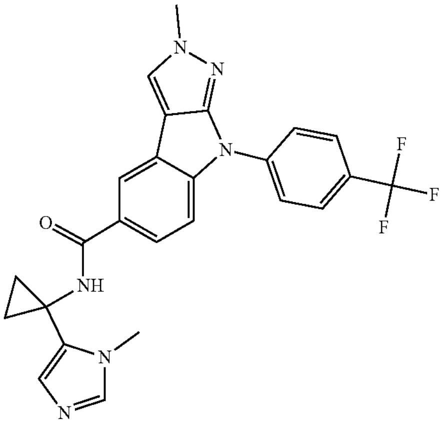 [SMILES: Cn1cc2c3cc(C(=O)NC4(c5cncn5C)CC4)ccc3n(-c3ccc(C(F)(F)F)cc3)c2n1] 2-methyl-N-[1-(1-methyl-1H-imidazol-5-yl)cyclopropyl]-8-[4-(trifluoromethyl)phenyl]-2H,8H-pyrazolo[3,4-b]indole-5-carboxamide | | |
| B71 | 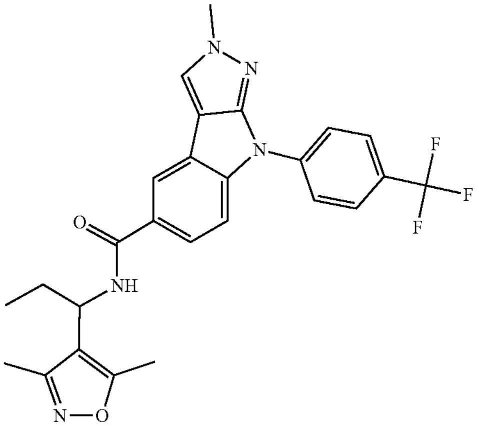 [SMILES: CCC(NC(=O)c1ccc2c(c1)c1cn(C)nc1n2-c1ccc(C(F)(F)F)cc1)c1c(C)noc1C] N-[1-(3,5-dimethyl-1,2-oxazol-4-yl)propyl]-2-methyl-8-[4-(trifluoromethyl)phenyl]-2H,8H-pyrazolo[3,4-b]indole-5-carboxamide | | 18 1.46 496.1 |
| B72 | 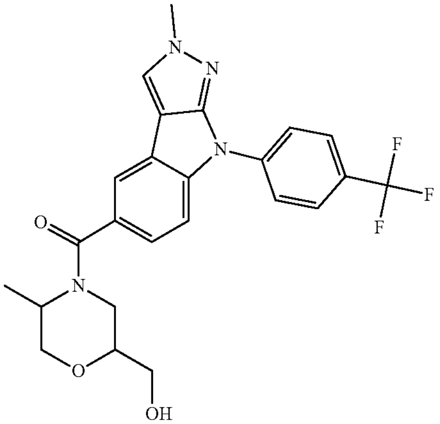 [SMILES: CC1COC(CO)CN1C(=O)c1ccc2c(c1)c1cn(C)nc1n2-c1ccc(C(F)(F)F)cc1] | | |

TABLE 1b-continued

| Compound No. | Structure and Name | $^1$H-NMR | Conditions and elution time (min) LCMS (M + H$^+$) |
|---|---|---|---|
| | diastereomeric mixture (5-methyl-4-{2-methyl-8-[4-(trifluoromethyl)phenyl]-2H,8H-pyrazolo[3,4-b]indole-5-carbonyl}morpholin-2-yl)methanol | | |
| B73 | 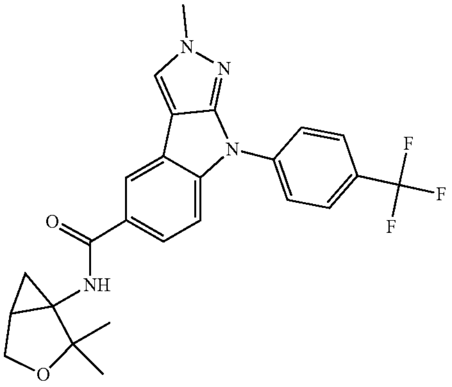 [SMILES: Cn1cc2c3cc(C(=O)NC45CC4COC5(C)C)ccc3n(-c3ccc(C(F)(F)F)cc3)c2n1] diastereomeric mixture N-(2,2-dimethyl-3-oxabicyclo[3.1.0]hexan-1-yl}-2-methyl-8-[4-(trifluoromethyl)phenyl]-2H,8H-pyrazolo[3,4-b]indole-5-carboxamide | | |
| B74 | 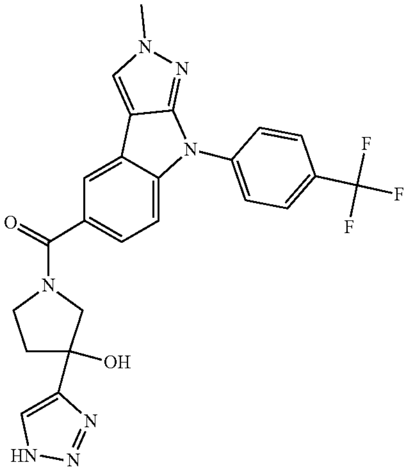 [SMILES: Cn1cc2c3cc(C(=O)N4CCC(O)(c5c[nH]nn5)C4)ccc3n(-c3ccc(C(F)(F)F)cc3)c2n1] 1-(2-methyl-8-[4-(trifluoromethyl)phenyl]-2H,8H-pyrazolo[3,4-b]indole-5-carbonyl}-3-(1H-1,2,3-triazol-4-yl)pyrrolidin-3-ol | | |

TABLE 1b-continued
| Compound No. | Structure and Name | $^1$H-NMR | Conditions and elution time (min) LCMS (M + H$^+$) |
|---|---|---|---|
| B75 | 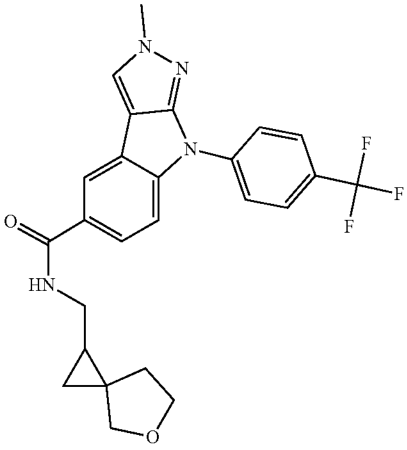 [SMILES: Cn1cc2c3cc(C(=O)NCC4CC45CCOC5)ccc3n(-c3ccc(C(F)(F)F)cc3)c2n1] diastereomeric mixture 2-methyl-N-({5-oxaspiro[2.4]heptan-1-yl}methyl)-8-[4-(trifluoromethyl)phenyl]-2H,8H-pyrazolo[3,4-b]indole-5-carboxamide | | |
| B76 | 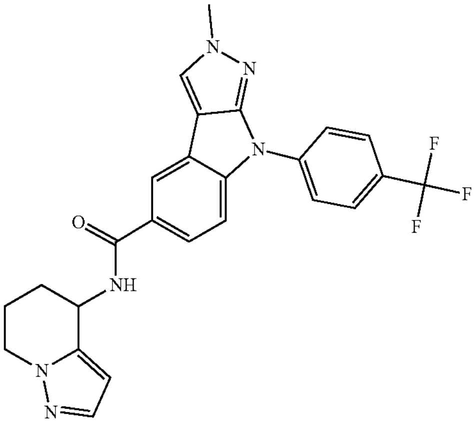 [SMILES: Cn1cc2c3cc(C(=O)NC4CCCn5nccc54)ccc3n(-c3ccc(C(F)(F)F)cc3)c2n1] 2-methyl-N-(4H,5H,6H,7H-pyrazolo[1,5-a]pyridin-4-yl}-8-[4-(trifluoromethyl)phenyl]-2H,8H-pyrazolo[3,4-b]indole-5-carboxamide | | 18<br>1.37<br>479.1 |
| B77 | 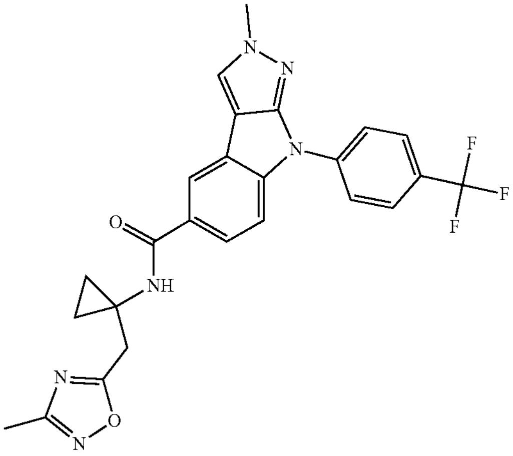 [SMILES: Cc1noc(CC2(NC(=O)c3ccc4c(c3)c3cn(C)nc3n4-c3ccc(C(F)(F)F)cc3)CC2)n1] | | |

TABLE 1b-continued

| Compound No. | Structure and Name | $^1$H-NMR | Conditions and elution time (min) LCMS (M + H$^+$) |
|---|---|---|---|
| | 2-methyl-N-{1-[(3-methyl-1,2,4-oxadiazol-5-yl)methyl]cyclo-propyl}-8-[4-(trifluoromethyl)phenyl]-2H,8H-pyrazolo[3,4-b]indole-5-carboxamide | | |
| B78 | 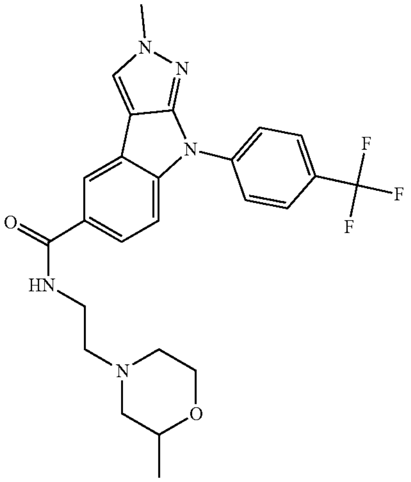 [SMILES: CC1CN(CCNC(=O)c2ccc3c(c2)c2cn(C)nc2n3-c2ccc(C(F)(F)F)cc2)CCO1] 2-methyl-N-[2-(2-methylmorpholin-4-yl)ethyl]-8-[4-(trifluoromethyl)phenyl]-2H,8H-pyrazolo[3,4-b]indole-5-carboxamide | | |
| B79 | 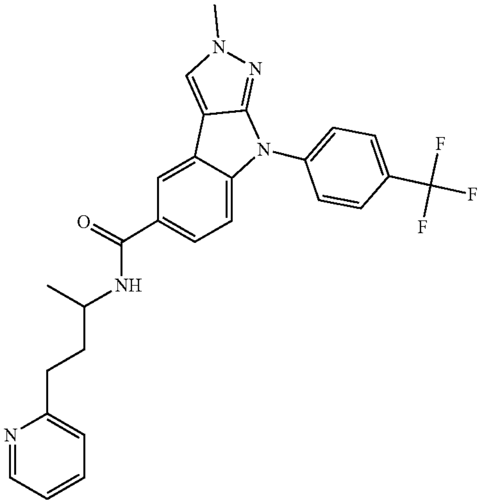 [SMILES: CC(CCc1ccccn1)NC(=O)c1ccc2c(c1)c1cn(C)nc1n2-c1ccc(C(F)(F)F)cc1] 2-methyl-N-[4-(pyridin-2-yl)butan-2-yl]-8-[4-(trifluoro-methyl)phenyl]-2H,8H-pyrazolo[3,4-b]indole-5-carboxamide | | |

TABLE 1b-continued

| Compound No. | Structure and Name | $^1$H-NMR | Conditions and elution time (min) LCMS (M + H$^+$) |
|---|---|---|---|
| B80 | 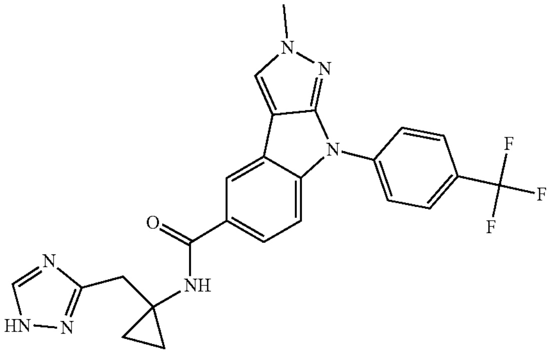 [SMILES: Cn1cc2c3cc(C(=O)NC4(Cc5nc[nH]n5)CC4)ccc3n(-c3ccc(C(F)(F)F)cc3)c2n1]<br>2-methyl-N-{1-[(1H-1,2,4-triazol-3-yl)methyl]cyclopropyl}-8-[4-(trifluoromethyl)phenyl]-2H,8H-pyrazolo[3,4-b]indole-5-carboxamide | | 18<br>1.20<br>480.1 |
| B81 | 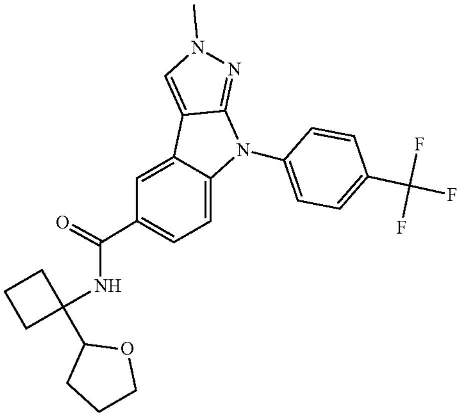 [SMILES: Cn1cc2c3cc(C(=O)NC4(C5CCCO5)CCC4)ccc3n(-c3ccc(C(F)(F)F)cc3)c2n1]<br>2-methyl-N-[1-(oxolan-2-yl)cyclobutyl]-8-[4-(trifluoro-methyl)phenyl]-2H,8H-pyrazolo[3,4-b]indole-5-carboxamide | | |
| B82 | 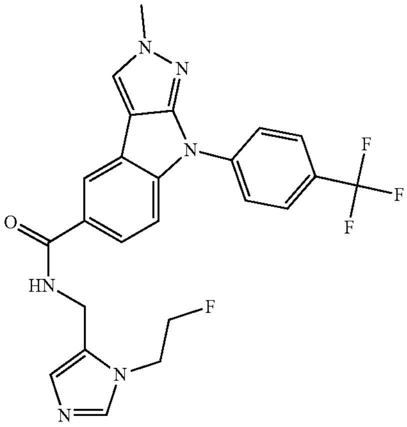 [SMILES: Cn1cc2c3cc(C(=O)NCc4cncn4CCF)ccc3n(-c3ccc(C(F)(F)F)cc3)c2n1]<br>N-{[1-(2-fluoroethyl)-1H-imidazol-5-yl]methyl}-2-methyl-8-[4-(trifluoromethyl)phenyl]-2H,8H-pyrazolo[3,4-b]indole-5-carboxamide | | |

TABLE 1b-continued
| Compound No. | Structure and Name | $^1$H-NMR | Conditions and elution time (min) LCMS (M + H$^+$) |
|---|---|---|---|
| B83 | 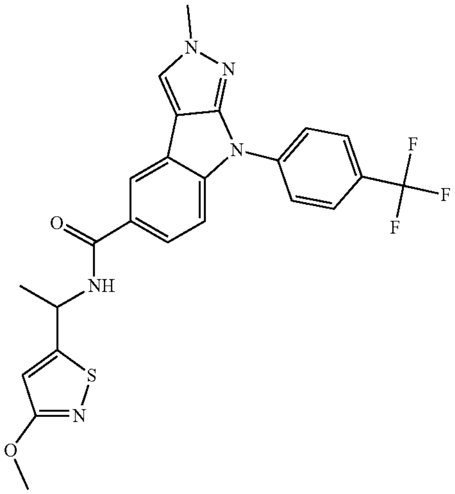 [SMILES: COc1cc(C(C)NC(=O)c2ccc3c(c2)c2cn(C)nc2n3-c2ccc(C(F)(F)F)cc2)sn1] N-[1-(3-methoxy-1,2-thiazol-5-yl)ethyl]-2-methyl-8-[4-(trifluoromethyl)phenyl]-2H,8H-pyrazolo[3,4-b]indole-5-carboxamide | | |
| B84 | 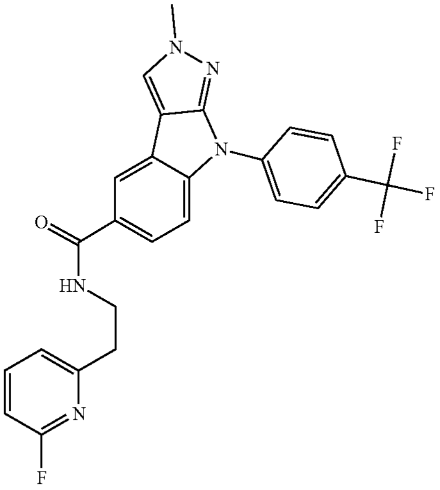 [SMILES: Cn1cc2c3cc(C(=O)NCCc4cccc(F)n4)ccc3n(-c3ccc(C(F)(F)F)cc3)c2n1] N-[2-(6-fluoropyridin-2-yl)ethyl]-2-methyl-8-[4-(trifluoromethyl)phenyl]-2H,8H-pyrazolo[3,4-b]indole-5-carboxamide | | |

TABLE 1b-continued
| Compound No. | Structure and Name | ¹H-NMR | Conditions and elution time (min) LCMS (M + H⁺) |
|---|---|---|---|
| B85 | 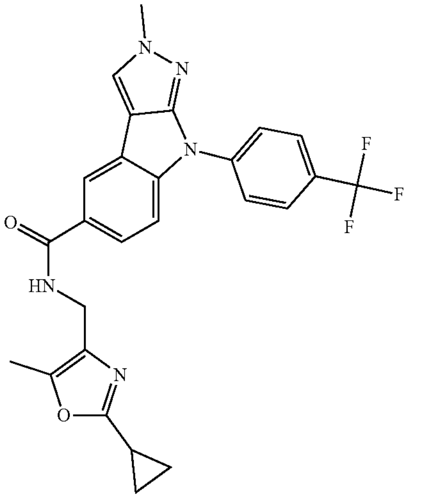 [SMILES: Cc1oc(C2CC2)nc1CNC(=O)c1ccc2c(c1)c1cn(C)nc1n2-c1ccc(C(F)(F)F)cc1]<br>N-[(2-cyclopropyl-5-methyl-1,3-oxazol-4-yl)methyl]-2-methyl-8-[4-(trifluoromethyl)phenyl]-2H,8H-pyrazolo[3,4-b]indole-5-carboxamide | | 18<br>1.42<br>494.1 |
| B86 | 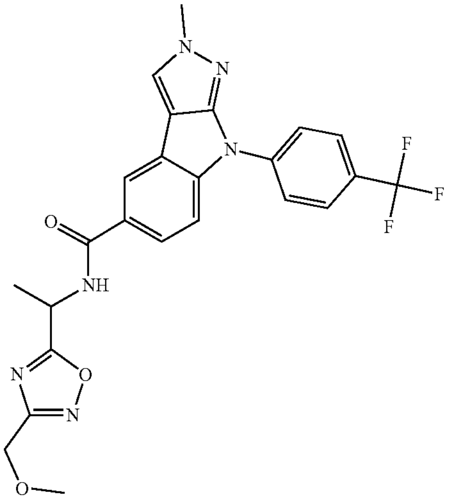 [SMILES: COCc1noc(C(C)NC(=O)c2ccc3c(c2)c2cn(C)nc2n3-c2ccc(C(F)(F)F)cc2)n1]<br>N-{1-[3-(methoxymethyl)-1,2,4-oxadiazol-5-yl]ethyl}-2-methyl-8-[4-(trifluoromethyl)phenyl]-2H,8H-pyrazolo[3,4-b]indole-5-carboxamide | | |
| B87 | 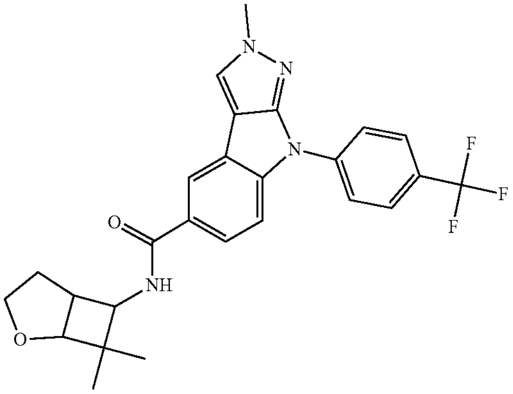 [SMILES: Cn1cc2c3cc(C(=O)NC4C5CCOC5C4(C)C)ccc3n(-c3ccc(C(F)(F)F)cc3)c2n1] | | |

TABLE 1b-continued

| Compound No. | Structure and Name | $^1$H-NMR | Conditions and elution time (min) LCMS (M + H$^+$) |
|---|---|---|---|
| | diastereomeric mixture N-(7,7-dimethyl-2-oxabicyclo[3.2.0]heptan-6-yl}-2-methyl-8-[4-(trifluoromethyl)phenyl]-2H,8H-pyrazolo[3,4-b]indole-5-carboxamide | | |
| B88 | 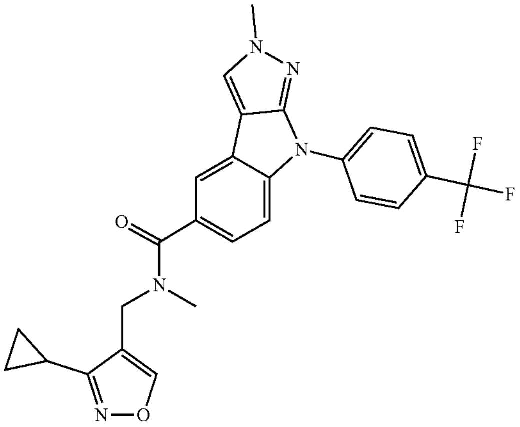 [SMILES: CN(Cc1conc1C1CC1)C(=O)c1ccc2c(c1)c1cn(C)nc1n2-c1ccc(C(F)(F)F)cc1] N-[(3-cyclopropyl-1,2-oxazol-4-yl)methyl]-N,2-dimethyl-8-[4-(trifluoromethyl)phenyl]-2H,8H-pyrazolo[3,4-b]indole-5-carboxamide | | |
| B89 | 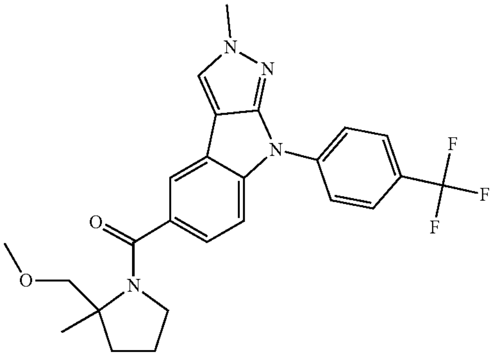 [SMILES: COCC1(C)CCCN1C(=O)c1ccc2c(c1)c1cn(C)nc1n2-c1ccc(C(F)(F)F)cc1] 2-(methoxymethyl)-2-methyl-1-{2-methyl-8-[4-(trifluoromethyl)phenyl]-2H,8H-pyrazolo[3,4-b]indole-5-carbonyl}pyrrolidine | | |
| B90 | 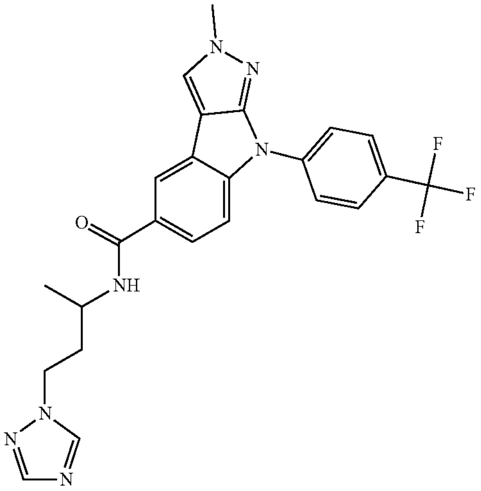 [SMILES: CC(CCn1cncn1)NC(=O)c1ccc2c(c1)c1cn(C)nc1n2-c1ccc(C(F)(F)F)cc1] | | 18 1.29 482.1 |

TABLE 1b-continued

| Compound No. | Structure and Name | $^1$H-NMR | Conditions and elution time (min) LCMS (M + H$^+$) |
|---|---|---|---|
| | 2-methyl-N-[4-(1H-1,2,4-triazol-1-yl)butan-2-yl]-8-[4-(trifluoromethyl)phenyl]-2H,8H-pyrazolo[3,4-b]indole-5-carboxamide | | |
| B91 | 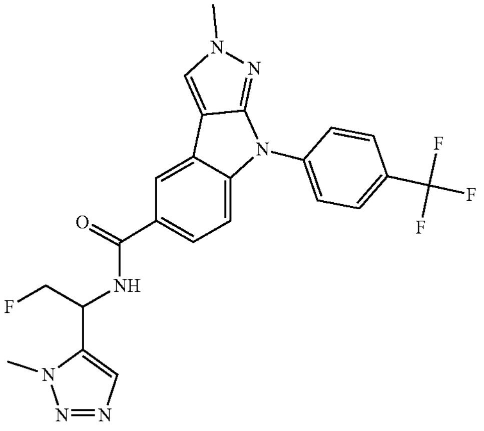 [SMILES: Cn1cc2c3cc(C(=O)NC(CF)c4cnnn4C)ccc3n(-c3ccc(C(F)(F)F)cc3)c2n1] N-[2-fluoro-1-(1-methyl-1H-1,2,3-triazol-5-yl)ethyl]-2-methyl-8-[4-(trifluoromethyl)phenyl]-2H,8H-pyrazolo[3,4-b]indole-5-carboxamide | | 18<br>1.38<br>486.1 |
| B92 | 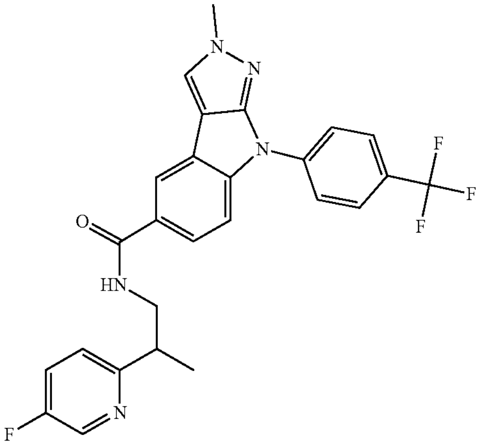 [SMILES: CC(CNC(=O)c1ccc2c(c1)c1cn(C)nc1n2-c1ccc(C(F)(F)F)cc1)c1ccc(F)cn1] N-[2-(5-fluoropyridin-2-yl)propyl]-2-methyl-8-[4-(trifluoromethyl)phenyl]-2H,8H-pyrazolo[3,4-b]indole-5-carboxamide | | |
| B93 | 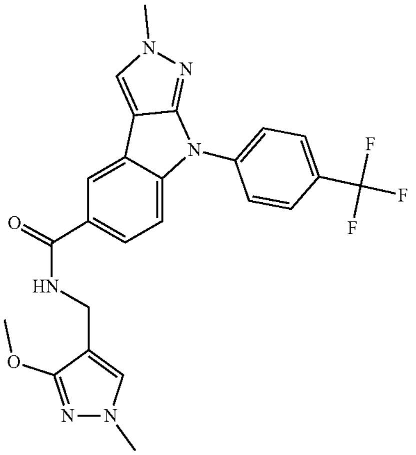 [SMILES: COc1nn(C)cc1CNC(=O)c1ccc2c(c1)c1cn(C)nc1n2-c1ccc(C(F)(F)F)cc1] | | 18<br>1.37<br>483.1 |

TABLE 1b-continued

| Compound No. | Structure and Name | $^1$H-NMR | Conditions and elution time (min) LCMS (M + H$^+$) |
|---|---|---|---|
| | N-[(3-methoxy-1-methyl-1H-pyrazol-4-yl)methyl]-2-methyl-8-[4-(trifluoromethyl)phenyl]-2H,8H-pyrazolo[3,4-b]indole-5-carboxamide | | |
| B94 | 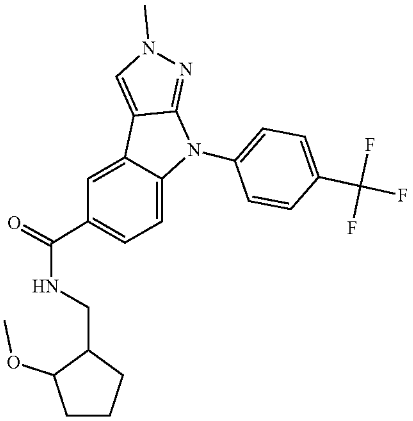 [SMILES: COC1CCCC1CNC(=O)c1ccc2c(c1)c1cn(C)nc1n2-c1ccc(C(F)(F)F)cc1] diastereomeric mixture N-[(2-methoxycyclopentyl)methyl]-2-methyl-8-[4-(trifluoromethyl)phenyl]-2H,8H-pyrazolo[3,4-b]indole-5-carboxamide | | |
| B95 2742775 | 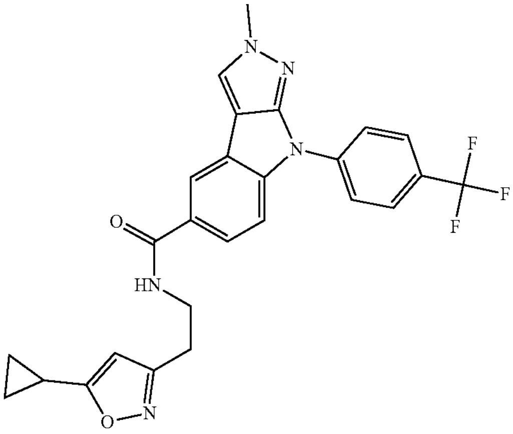 [SMILES: Cn1cc2c3cc(C(=O)NCCc4cc(C5CC5)on4)ccc3n(-c3ccc(C(F)(F)F)cc3)c2n1] N-[2-(5-cyclopropyl-1,2-oxazol-3-yl)ethyl]-2-methyl-8-[4-(trifluoromethyl)phenyl]-2H,8H-pyrazolo[3,4-b]indole-5-carboxamide | | |
| B96 2742746 | 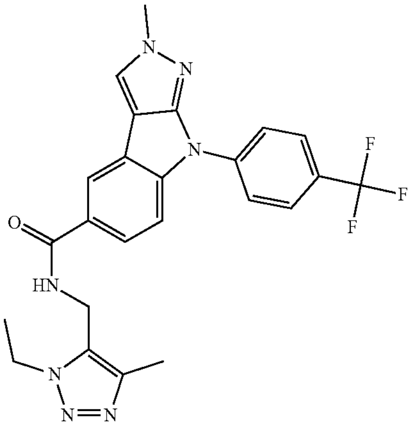 [SMILES: CCn1nnc(C)c1CNC(=O)c1ccc2c(c1)c1cn(C)nc1n2-c1ccc(C(F)(F)F)cc1] | | |

TABLE 1b-continued

| Compound No. | Structure and Name | $^1$H-NMR | Conditions and elution time (min) LCMS (M + H$^+$) |
| --- | --- | --- | --- |
| | N-[(1-ethyl-4-methyl-1H-1,2,3-triazol-5-yl)methyl]-2-methyl-8-[4-(trifluoromethyl)phenyl]-2H,8H-pyrazolo[3,4-b]indole-5-carboxamide | | |
| B97 | 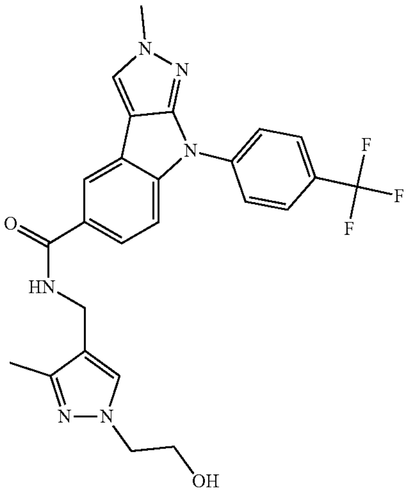 [SMILES: Cc1nn(CCO)cc1CNC(=O)c1ccc2c(c1)c1cn(C)nc1n2-c1ccc(C(F)(F)F)cc1] N-{[1-(2-hydroxyethyl)-3-methyl-1H-pyrazol-4-yl]methyl}-2-methyl-8-[4-(trifluoromethyl)phenyl]-2H,8H-pyrazolo[3,4-b]indole-5-carboxamide | | |
| B98 | 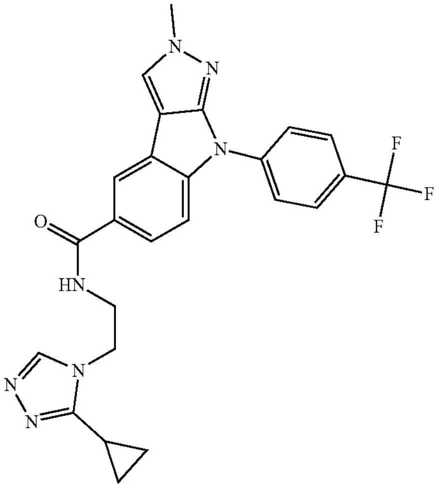 [SMILES: Cn1cc2c3cc(C(=O)NCCn4cnnc4C4CC4)ccc3n(-c3ccc(C(F)(F)F)cc3)c2n1] N-[2-(3-cyclopropyl-4H-1,2,4-triazol-4-yl)ethyl]-2-methyl-8-[4-(trifluoromethyl)phenyl]-2H,8H-pyrazolo[3,4-b]indole-5-carboxamide | | |

TABLE 1b-continued

| Compound No. | Structure and Name | ¹H-NMR | Conditions and elution time (min) LCMS (M + H⁺) |
|---|---|---|---|
| B99 | 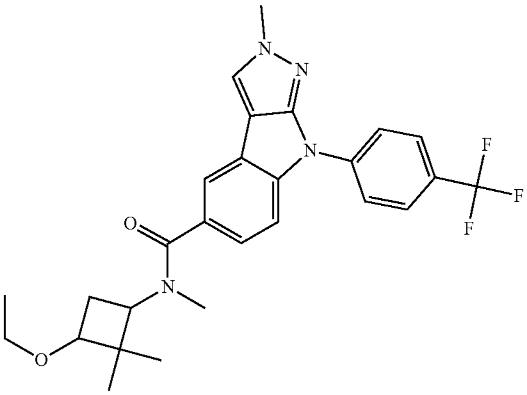 [SMILES: CCOC1CC(N(C)C(=O)c2ccc3c(c2)c2cn(C)nc2n3-c2ccc(C(F)(F)F)cc2)C1(C)C] diastereomeric mixture N-(3-ethoxy-2,2-dimethylcyclobutyl)-N,2-dimethyl-8-[4-(trifluoromethyl)phenyl]-2H,8H-pyrazolo[3,4-b]indole-5-carboxamide | | |
| B100 | 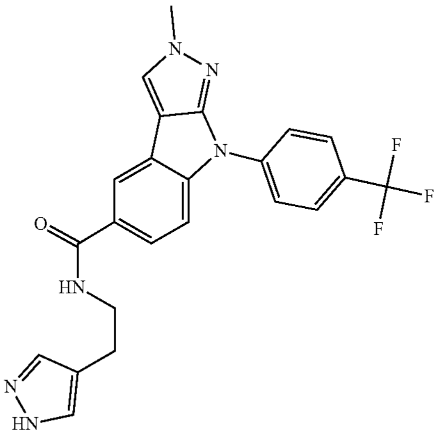 [SMILES: Cn1cc2c3cc(C(=O)NCCc4cn[nH]c4)ccc3n(-c3ccc(C(F)(F)F)cc3)c2n1] 2-methyl-N-[2-(1H-pyrazol-4-yl)ethyl]-8-[4-(trifluoromethyl)phenyl]-2H,8H-pyrazolo[3,4-b]indole-5-carboxamide | | 18<br>1.23<br>453.1 |
| B101 | 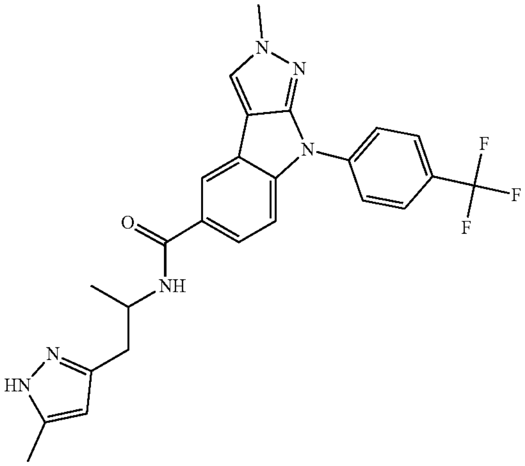 [SMILES: Cc1cc(CC(C)NC(=O)c2ccc3c(c2)c2cn(C)nc2n3-c2ccc(C(F)(F)F)cc2)n[nH]1] 2-methyl-N-[1-(5-methyl-1H-pyrazol-3-yl)propan-2-yl]-8-[4-(trifluoromethyl)phenyl]-2H,8H-pyrazolo[3,4-b]indole-5-carboxamide | | |

TABLE 1b-continued
| Compound No. | Structure and Name | ¹H-NMR | Conditions and elution time (min) LCMS (M + H⁺) |
| --- | --- | --- | --- |
| B102 | 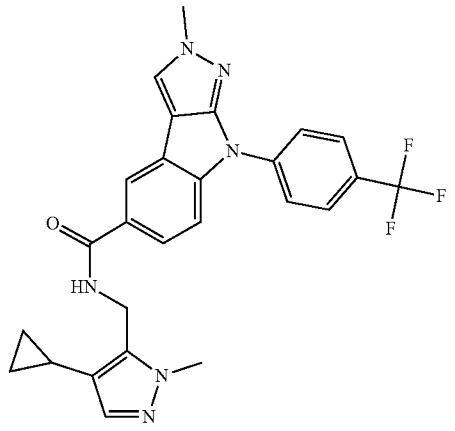 [SMILES: Cn1cc2c3cc(C(=O)NCc4c(C5CC5)cnn4C)ccc3n(-c3ccc(C(F)(F)F)cc3)c2n1] N-[(4-cyclopropyl-1-methyl-1H-pyrazol-5-yl)methyl]-2-methyl-8-[4-(trifluoromethyl)phenyl]-2H,8H-pyrazolo[3,4-b]indole-5-carboxamide | | 18<br>1.40<br>493.1 |
| B103 | 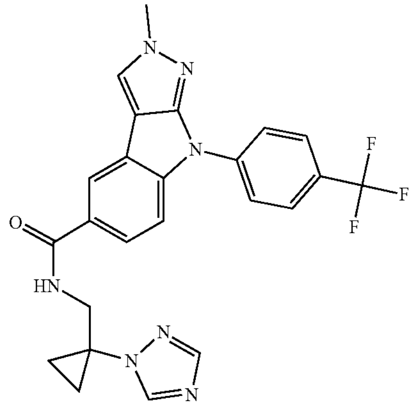 [SMILES: Cn1cc2c3cc(C(=O)NCC4(n5cncn5)CC4)ccc3n(-c3ccc(C(F)(F)F)cc3)c2n1] 2-methyl-N-{[1-(1H-1,2,4-triazol-1-yl)cyclopropyl]methyl}-8-[4-(trifluoromethyl)phenyl]-2H,8H-pyrazolo[3,4-b]indole-5-carboxamide | | |
| B104 | 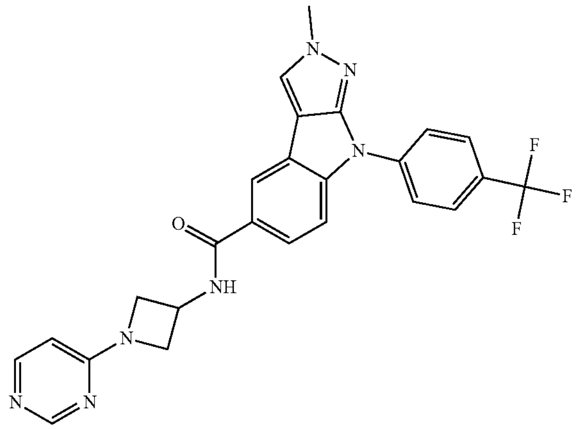 [SMILES: Cn1cc2c3cc(C(=O)NC4CN(c5ccncn5)C4)ccc3n(-c3ccc(C(F)(F)F)cc3)c2n1] | | |

TABLE 1b-continued

| Compound No. | Structure and Name | ¹H-NMR | Conditions and elution time (min) LCMS (M + H⁺) |
|---|---|---|---|
| | 2-methyl-N-[1-(pyrimidin-4-yl)azetidin-3-yl]-8-[4-(trifluoro-methyl)phenyl]-2H,8H-pyrazolo[3,4-b]indole-5-carboxamide | | |
| B105 | 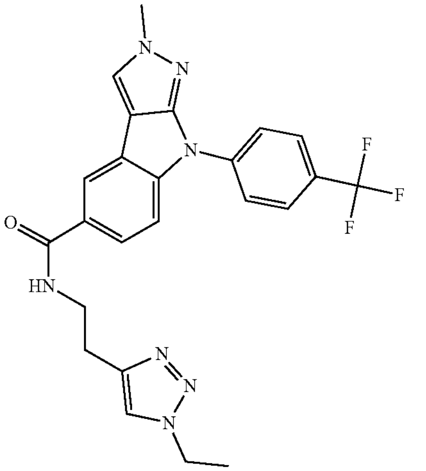 [SMILES: CCn1cc(CCNC(=O)c2ccc3c(c2)c2cn(C)nc2n3-c2ccc(C(F)(F)F)cc2)nn1] N-[2-(1-ethyl-1H-1,2,3-triazol-4-yl)ethyl]-2-methyl-8-[4-(trifluoromethyl)phenyl]-2H,8H-pyrazolo[3,4-b]indole-5-carboxamide | | |
| B106 | 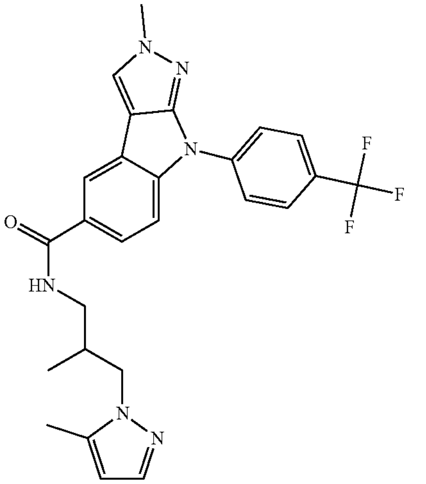 [SMILES: Cc1ccnn1CC(C)CNC(=O)c1ccc2c(c1)c1cn(C)nc1n2-c1ccc(C(F)(F)F)cc1] 2-methyl-N-{2-[(5-methyl-1H-pyrazol-1-yl)methyl]propyl}-8-[4-(trifluoromethyl)phenyl]-2H,8H-pyrazolo[3,4-b]indole-5-carboxamide | | |

TABLE 1b-continued
| Compound No. | Structure and Name | ¹H-NMR | Conditions and elution time (min) LCMS (M + H⁺) |
|---|---|---|---|
| B107 | 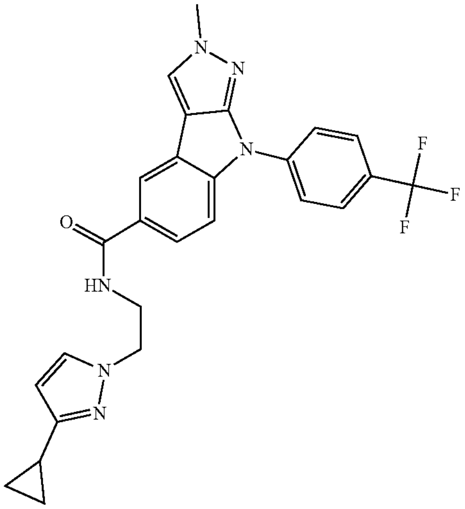 [SMILES: Cn1cc2c3cc(C(=O)NCCn4ccc(C5CC5)n4)ccc3n(-c3ccc(C(F)(F)F)cc3)c2n1] N-[2-(3-cyclopropyl-1H-pyrazol-1-yl)ethyl]-2-methyl-8-[4-(trifluoromethyl)phenyl]-2H,8H-pyrazolo[3,4-b]indole-5-carboxamide | | |
| B108 | 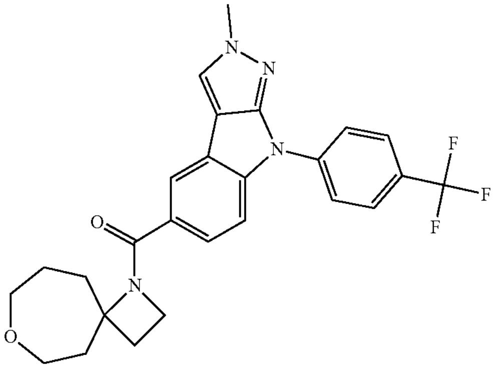 [SMILES: Cn1cc2c3cc(C(=O)N4CCC45CCCOCC5)ccc3n(-c3ccc(C(F)(F)F)cc3)c2n1] 1-{2-methyl-8-[4-(trifluoromethyl)-phenyl]-2H,8H-pyrazolo[3,4-b]indole-5-carbonyl}-7-oxa-1-azaspiro[3.6]decane | | |
| B109 | 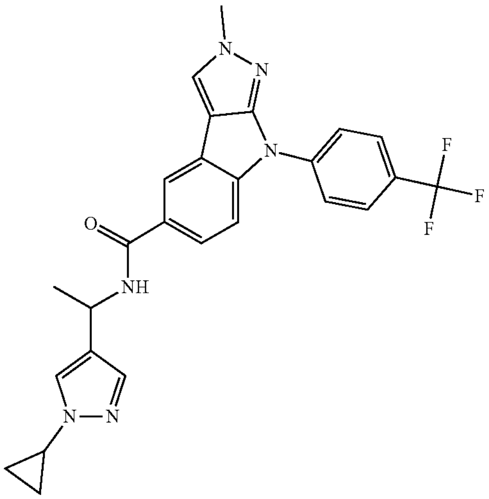 [SMILES: CC(NC(=O)c1ccc2c(c1)c1cn(C)nc1n2-c1ccc(C(F)(F)F)cc1)c1cnn(C2CC2)c1] | | |

TABLE 1b-continued

| Compound No. | Structure and Name | 1H-NMR | Conditions and elution time (min) LCMS (M + H+) |
| --- | --- | --- | --- |
| | Racemate N-[1-(1-cyclopropyl-1H-pyrazol-4-yl)ethyl]-2-methyl-8-[4-(trifluoromethyl)phenyl]-2H,8H-pyrazolo[3,4-b]indole-5-carboxamide | | |
| B110 | 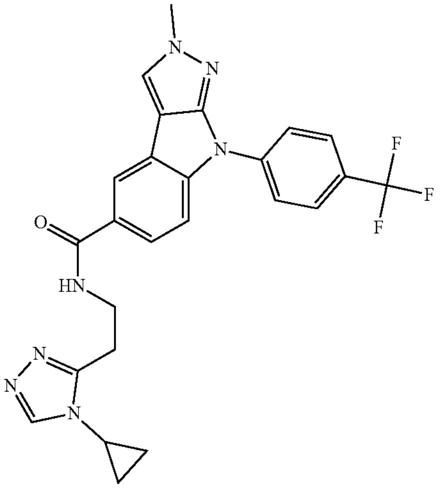 [SMILES: Cn1cc2c3cc(C(=O)NCCc4nncn4C4CC4)ccc3n(-c3ccc(C(F)(F)F)cc3)c2n1] N-[2-(4-cyclopropyl-4H-1,2,4-triazol-3-yl)ethyl]-2-methyl-8-[4-(trifluoromethyl)-phenyl]-2H,8H-pyrazolo[3,4-b]indole-5-carboxamide | | |
| B111 | 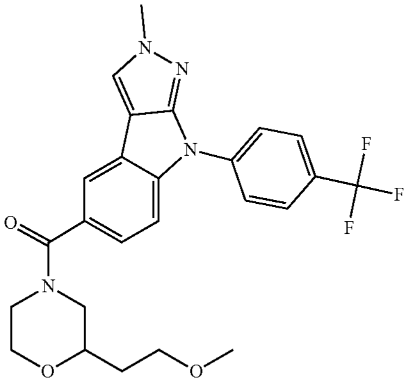 [SMILES: COCCC1CN(C(=O)c2ccc3c(c2)c2cn(C)nc2n3-c2ccc(C(F)(F)F)cc2)CCO1] 2-(2-methoxyethyl)-4-{2-methyl-8-[4-(trifluoro-methyl)phenyl]-2H,8H-pyrazolo[3,4-b]indole-5-carbonyl}morpholine | | |
| B112 | 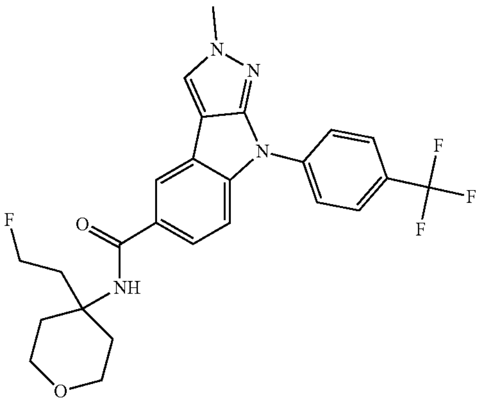 [SMILES: Cn1cc2c3cc(C(=O)NC4(CCF)CCOCC4)ccc3n(-c3ccc(C(F)(F)F)cc3)c2n1] | | |

TABLE 1b-continued

| Compound No. | Structure and Name | $^1$H-NMR | Conditions and elution time (min) LCMS (M + H$^+$) |
|---|---|---|---|
| | N-[4-(2-fluoroethyl)oxan-4-yl]-2-methyl-8-[4-(trifluoromethyl)phenyl]-2H,8H-pyrazolo[3,4-b]indole-5-carboxamide | | |
| B113 | 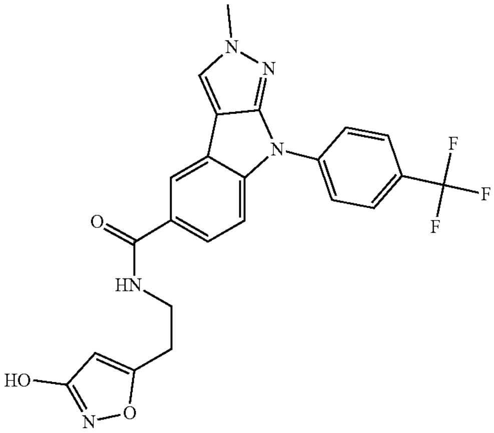 [SMILES: Cn1cc2c3cc(C(=O)NCCc4cc(O)no4)ccc3n(-c3ccc(C(F)(F)F)cc3)c2n1] N-[2-(3-hydroxy-1,2-oxazol-5-yl)ethyl]-2-methyl-8-[4-(trifluoromethyl)phenyl]-2H,8H-pyrazolo[3,4-b]indole-5-carboxamide | | |
| B114 | 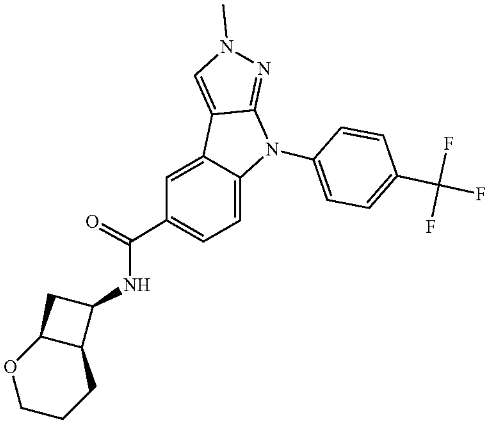 [SMILES: Cn1cc2c3cc(C(=O)N[C@@H]4C[C@@H]5OCCC[C@@H]54)ccc3n(-c3ccc(C(F)(F)F)cc3)c2n1] racemic diastereomer with known relative stereochemistry 2-methyl-N-[(1S,6R,7R)-2-oxabicyclo[4.2.0]octan-7-yl]-8-[4-(trifluoromethyl)phenyl]-2H,8H-pyrazolo[3,4-b]indole-5-carboxamide | | |
| B115 | 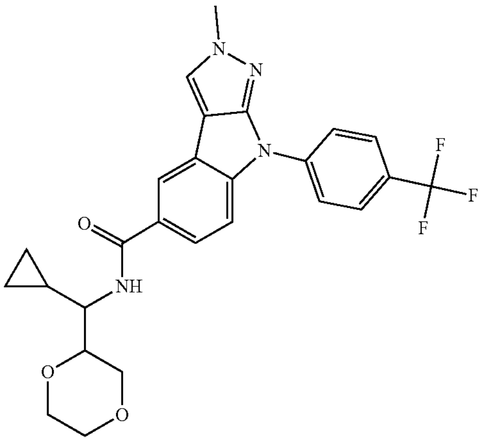 [SMILES: Cn1cc2c3cc(C(=O)NC(C4CC4)C4COCCO4)ccc3n(-c3ccc(C(F)(F)F)cc3)c2n1] | | |

TABLE 1b-continued

| Compound No. | Structure and Name | $^1$H-NMR | Conditions and elution time (min) LCMS (M + H$^+$) |
|---|---|---|---|
| | diastereomeric mixture N-[cyclopropyl(1,4-dioxan-2-yl)methyl]-2-methyl-8-[4-(trifluoromethyl)phenyl]-2H,8H-pyrazolo[3,4-b]indole-5-carboxamide | | |
| B116 | 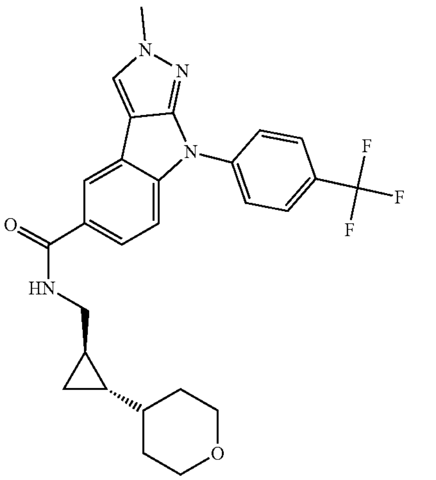 [SMILES: Cn1cc2c3cc(C(=O)NC[C@@H]4C[C@H]4C4CCOCC4)ccc3n(-c3ccc(C(F)(F)F)cc3)c2n1] racemic diastereomer with known relative stereochemistry, trans 2-methyl-N-{[(1R,2S)-2-(oxan-4-yl)cyclopropyl]methyl}-8-[4-(trifluoromethyl)phenyl]-2H,8H-pyrazolo[3,4-b]indole-5-carboxamide | | |
| B117 2742791 | 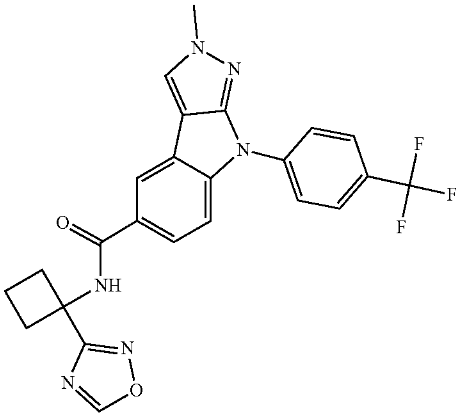 [SMILES: Cn1cc2c3cc(C(=O)NC4(c5ncon5)CCC4)ccc3n(-c3ccc(C(F)(F)F)cc3)c2n1] 2-methyl-N-[1-(1,2,4-oxadiazol-3-yl)cyclobutyl]-8-[4-(trifluoromethyl)phenyl]-2H,8H-pyrazolo[3,4-b]indole-5-carboxamide | 1H NMR (400 MHz, DMSO-d6) δ 2.00-2.13 (m, 2H), 2.57-2.69 (m, 4H), 4.04 (s, 3H), 7.78 (d, J = 8.7 Hz, 1H), 7.87 (dd, J = 8.7, 1.9 Hz, 1H), 7.97 (d, J = 8.7 Hz, 2H), 8.09 (d, J = 8.5 Hz, 2H), 8.21 (s, 1H), 8.38 (d, J = 1.8 Hz, 1H), 9.22 (s, 1H), 9.47 (s, 1H). | 17 0.99 480.8 |

TABLE 1b-continued
| Compound No. | Structure and Name | $^1$H-NMR | Conditions and elution time (min) LCMS (M + H$^+$) |
|---|---|---|---|
| B118 | 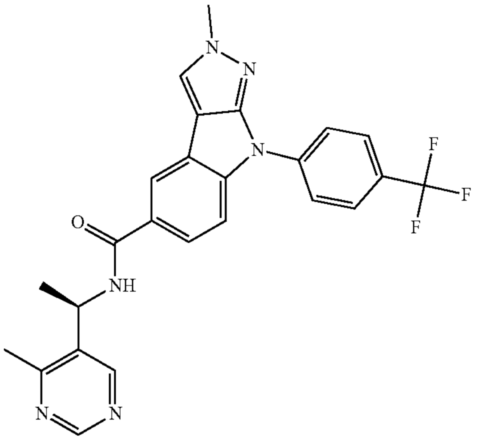 [SMILES: Cc1ncncc1[C@@H](C)NC(=O)c1ccc2c(c1)c1cn(C)nc1n2-c1ccc(C(F)(F)F)cc1] stereochemistry assigned/known; single enantiomer 2-methyl-N-[(1R)-1-(4-methylpyrimidin-5-yl)ethyl]-8-[4-(trifluoromethyl)phenyl]-2H,8H-pyrazolo[3,4-b]indole-5-carboxamide | | |
| B119 | 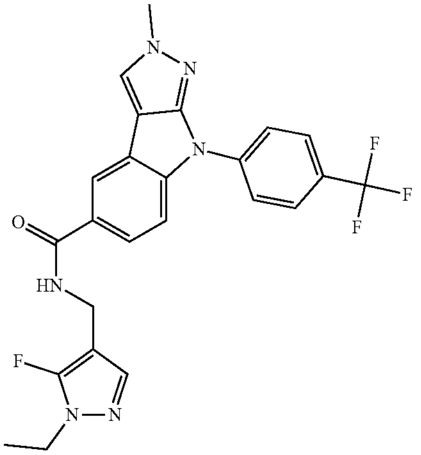 [SMILES: CCn1ncc(CNC(=O)c2ccc3c(c2)c2cn(C)nc2n3-c2ccc(C(F)(F)F)cc2)c1F] N-[(1-ethyl-5-fluoro-1H-pyrazol-4-yl)methyl]-2-methyl-8-[4-(trifluoromethyl)phenyl]-2H,8H-pyrazolo[3,4-b]indole-5-carboxamide | | |
| B120 | 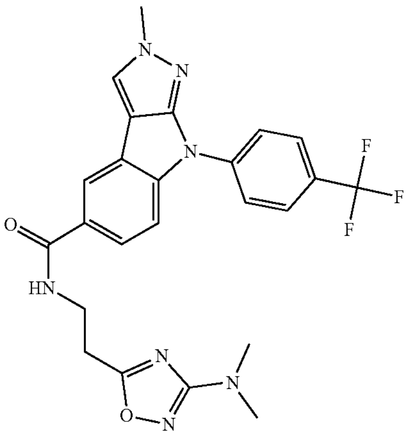 [SMILES: CN(C)c1noc(CCNC(=O)c2ccc3c(c2)c2cn(C)nc2n3-c2ccc(C(F)(F)F)cc2)n1] | | |

TABLE 1b-continued

| Compound No. | Structure and Name | $^1$H-NMR | Conditions and elution time (min) LCMS (M + H$^+$) |
|---|---|---|---|
| | N-{2-[3-(dimethylamino)-1,2,4-oxadiazol-5-yl]ethyl}-2-methyl-8-[4-(trifluoromethyl)phenyl]-2H,8H-pyrazolo[3,4-b]indole-5-carboxamide | | |
| B121 | 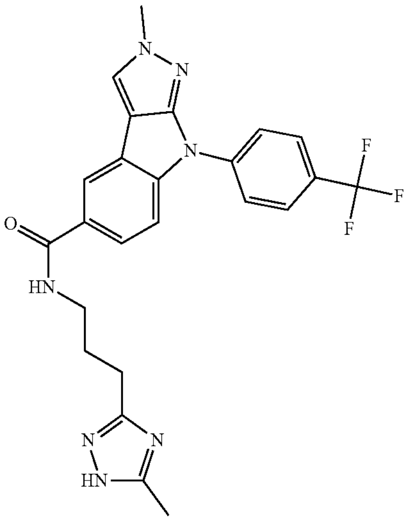 [SMILES: Cc1nc(CCCNC(=O)c2ccc3c(c2)c2cn(C)nc2n3-c2ccc(C(F)(F)F)cc2)n[nH]1] 2-methyl-N-[3-(5-methyl-1H-1,2,4-triazol-3-yl)propyl]-8-[4-(trifluoromethyl)phenyl]-2H,8H-pyrazolo[3,4-b]indole-5-carboxamide | | |
| B122 | 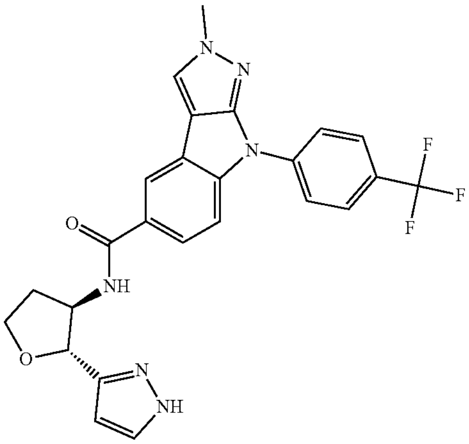 [SMILES: Cn1cc2c3cc(C(=O)N[C@@H]4CCO[C@H]4c4cc[nH]n4)ccc3n(-c3ccc(C(F)(F)F)cc3)c2n1] racemic diastereomer with known relative stereochemistry, trans 2-methyl-N-[(2R,3R)-2-(1H-pyrazol-3-yl)oxolan-3-yl]-8-[4-(trifluoromethyl)phenyl]-2H,8H-pyrazolo[3,4-b]indole-5-carboxamide | | 18 1.29 495.1 |

TABLE 1b-continued

| Compound No. | Structure and Name | $^1$H-NMR | Conditions and elution time (min) LCMS (M + H$^+$) |
|---|---|---|---|
| B123 | 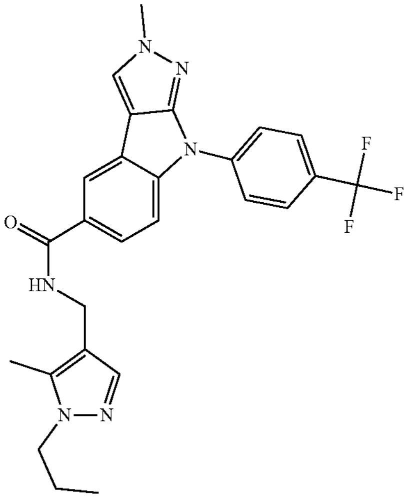 [SMILES: CCCn1ncc(CNC(=O)c2ccc3c(c2)c2cn(C)nc2n3-c2ccc(C(F)(F)F)cc2)c1C] 2-methyl-N-[(5-methyl-1-propyl-1H-pyrazol-4-yl)methyl]-8-[4-(trifluoromethyl)phenyl]-2H,8H-pyrazolo[3,4-b]indole-5-carboxamide | 1H NMR (400 MHz, DMSO-d6) δ 0.84 (t, J = 7.4 Hz, 3H), 1.71 (h, J = 7.4 Hz, 2H), 2.27 (s, 3H), 3.94 (t, J = 7.7, 6.6 Hz, 2H), 4.03 (s, 3H), 4.29 (d, J = 5.5 Hz, 2H), 7.33 (s, 1H), 7.75 (d, J = 8.7 Hz, 1H), 7.85 (dd, J = 8.7, 1.8 Hz, 1H), 7.96 (d, J = 8.7 Hz, 2H), 8.08 (d, J = 8.4 Hz, 2H), 8.18 (s, 1H), 8.34 (d, J = 1.8 Hz, 1H), 8.70 (t, J = 5.6 Hz, 1H). | 17<br>1.00<br>494.9 |
| B124 | 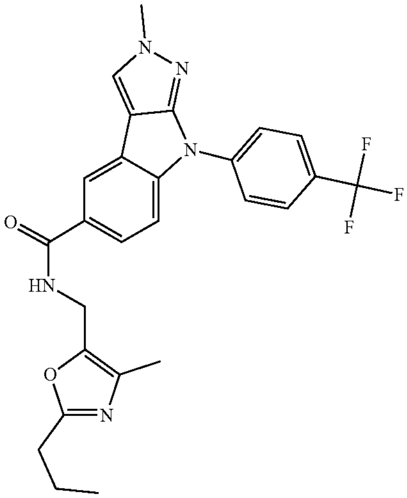 [SMILES: CCCc1nc(C)c(CNC(=O)c2ccc3c(c2)c2cn(C)nc2n3-c2ccc(C(F)(F)F)cc2)o1] 2-methyl-N-[(4-methyl-2-propyl-1,3-oxazol-5-yl)methyl]-8-[4-(trifluoromethyl)phenyl]-2H,8H-pyrazolo[3,4-b]indole-5-carboxamide | | 18<br>1.40<br>496.2 |

TABLE 1b-continued

| Compound No. | Structure and Name | ¹H-NMR | Conditions and elution time (min) LCMS (M + H⁺) |
|---|---|---|---|
| B125 | 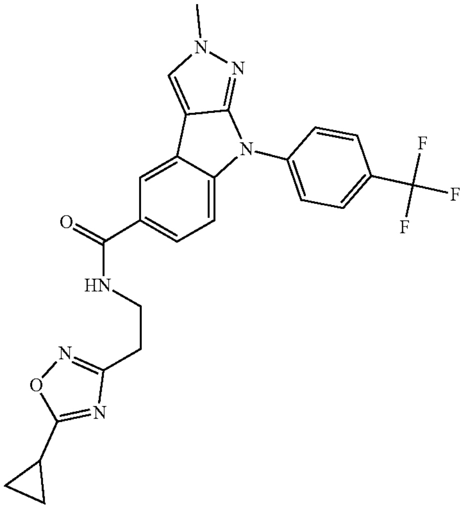 [SMILES: Cn1cc2c3cc(C(=O)NCCc4noc(C5CC5)n4)ccc3n(-c3ccc(C(F)(F)F)cc3)c2n1] N-[2-(5-cyclopropyl-1,2,4-oxadiazol-3-yl)ethyl]-2-methyl-8-[4-(trifluoromethyl)phenyl]-2H,8H-pyrazolo[3,4-b]indole-5-carboxamide | | |
| B126 | 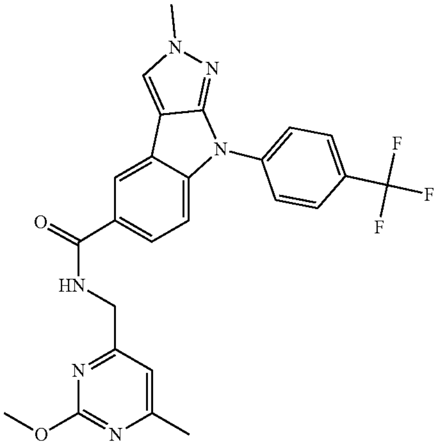 [SMILES: COc1nc(C)cc(CNC(=O)c2ccc3c(c2)c2cn(C)nc2n3-c2ccc(C(F)(F)F)cc2)n1] N-[(2-methoxy-6-methylpyrimidin-4-yl)methyl]-2-methyl-8-[4-(trifluoromethyl)phenyl]-2H,8H-pyrazolo[3,4-b]indole-5-carboxamide | 1H NMR (400 MHz, DMSO-d6) δ 2.37 (s, 3H), 3.89 (s, 3H), 4.04 (s, 3H), 4.48 (d, J = 5.8 Hz, 2H), 6.93 (s, 1H), 7.81 (d, J = 8.7 Hz, 1H), 7.93 (dd, J = 8.8, 1.9 Hz, 1H), 7.97 (d, J = 8.6 Hz, 2H), 8.10 (d, J = 8.4 Hz, 2H), 8.22 (s, 1H), 8.42 (d, J = 1.8 Hz, 1H), 9.11 (t, J = 5.9 Hz, 1H). | 17 0.99 494.8 |
| B127 | 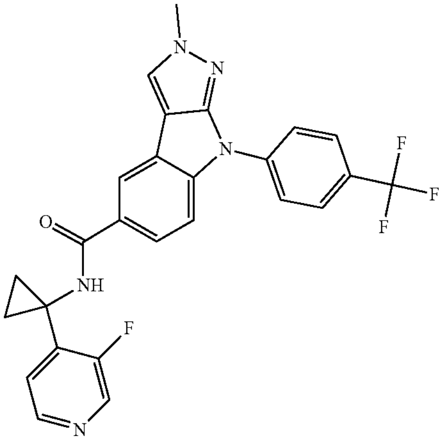 [SMILES: Cn1cc2c3cc(C(=O)NC4(c5ccncc5F)CC4)ccc3n(-c3ccc(C(F)(F)F)cc3)c2n1] | | |

TABLE 1b-continued

| Compound No. | Structure and Name | $^1$H-NMR | Conditions and elution time (min) LCMS (M + H$^+$) |
|---|---|---|---|
| | N-[1-(3-fluoropyridin-4-yl)cyclopropyl]-2-methyl-8-[4-(trifluoromethyl)phenyl]-2H,8H-pyrazolo[3,4-b]indole-5-carboxamide | | |
| B128 | 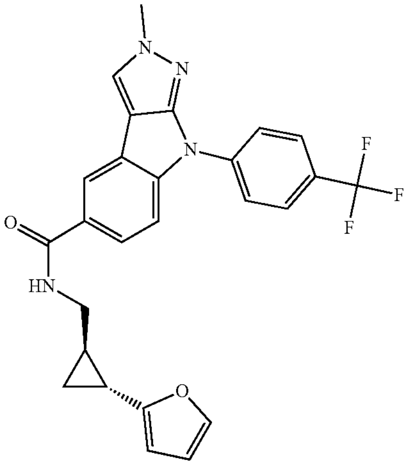 [SMILES: Cn1cc2c3cc(C(=O)NC[C@@H]4C[C@H]4c4ccco4)ccc3n(-c3ccc(C(F)(F)F)cc3)c2n1] racemic diastereomer with known relative stereochemistry, trans N-{[(1R,2R)-2-(furan-2-yl)cyclopropyl]methyl}-2-methyl-8-[4-(trifluoromethyl)phenyl]-2H,8H-pyrazolo[3,4-b]indole-5-carboxamide | | |
| B129 | 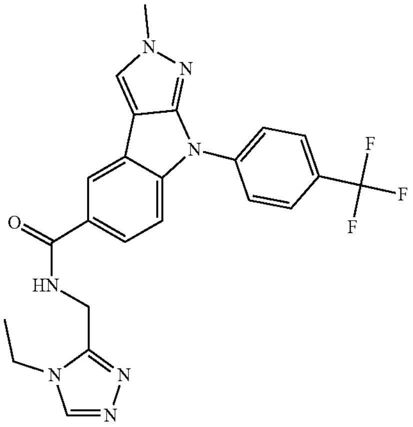 [SMILES: CCn1cnnc1CNC(=O)c1ccc2c(c1)c1cn(C)nc1n2-c1ccc(C(F)(F)F)cc1] N-[(4-ethyl-4H-1,2,4-triazol-3-yl)methyl]-2-methyl-8-[4-(trifluoromethyl)phenyl]-2H,8H-pyrazolo[3,4-b]indole-5-carboxamide | | |

TABLE 1b-continued
| Compound No. | Structure and Name | $^1$H-NMR | Conditions and elution time (min) LCMS (M + H$^+$) |
|---|---|---|---|
| B130 | 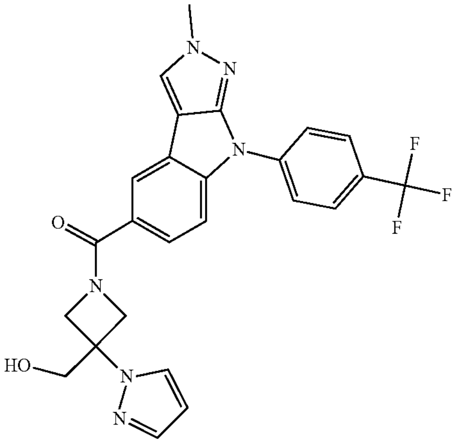 [SMILES: Cn1cc2c3cc(C(=O)N4CC(CO)(n5cccn5)C4)ccc3n(-c3ccc(C(F)(F)F)cc3)c2n1] (1-{2-methyl-8-[4-(trifluoromethyl)phenyl]-2H,8H-pyrazolo[3,4-b]indole-5-carbonyl}-3-(1H-pyrazol-1-yl)azetidin-3-yl)methanol | | |
| B131 | 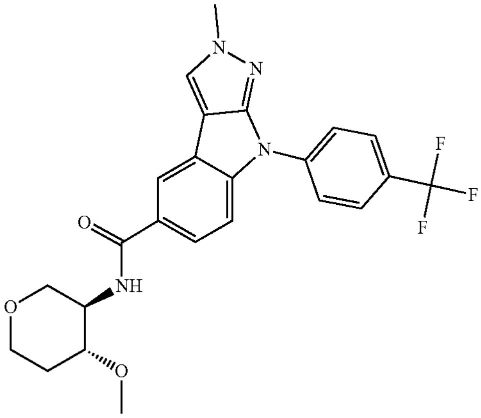 [SMILES: CO[C@@H]1CCOC[C@H]1NC(=O)c1ccc2c(c1)c1cn(C)nc1n2-c1ccc(C(F)(F)F)cc1] racemic diastereomer with known relative stereochemistry, trans N-[(3R,4R)-4-methoxyoxan-3-yl]-2-methyl-8-[4-(trifluoromethyl)phenyl]-2H,8H-pyrazolo[3,4-b]indole-5-carboxamide | | |
| B132 | 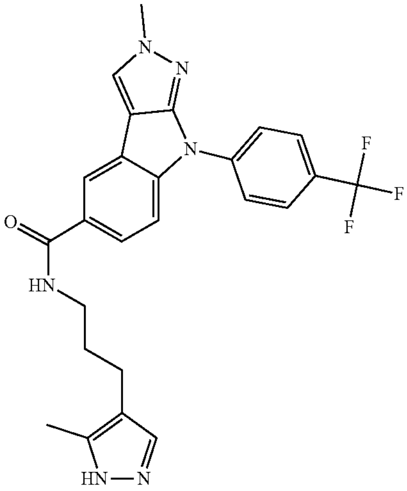 [SMILES: Cc1[nH]ncc1CCCNC(=O)c1ccc2c(c1)c1cn(C)nc1n2-c1ccc(C(F)(F)F)cc1] | | |

TABLE 1b-continued

| Compound No. | Structure and Name | $^1$H-NMR | Conditions and elution time (min) LCMS (M + H$^+$) |
|---|---|---|---|
| | 2-methyl-N-[3-(5-methyl-1H-pyrazol-4-yl)propyl]-8-[4-(trifluoromethyl)phenyl]-2H,8H-pyrazolo[3,4-b]indole-5-carboxamide | | |
| B133 | 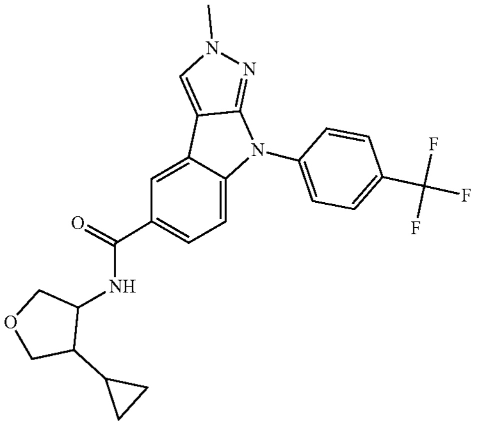 [SMILES: Cn1cc2c3cc(C(=O)NC4COCC4C4CC4)ccc3n(-c3ccc(C(F)(F)F)cc3)c2n1] diastereomeric mixture N-(4-cyclopropyloxolan-3-yl)-2-methyl-8-[4-(trifluoromethyl)phenyl]-2H,8H-pyrazolo[3,4-b]indole-5-carboxamide | | 18 1.43 469.1 |
| B134 | 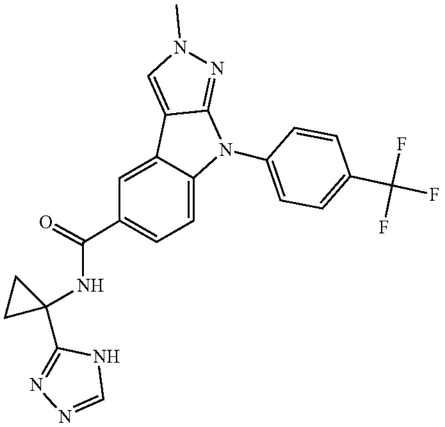 [SMILES: Cn1cc2c3cc(C(=O)NC4(c5nnc[nH]5)CC4)ccc3n(-c3ccc(C(F)(F)F)cc3)c2n1] 2-methyl-N-[1-(4H-1,2,4-triazol-3-yl)cyclopropyl]-8-[4-(trifluoromethyl)phenyl]-2H,8H-pyrazolo[3,4-b]indole-5-carboxamide | | |

TABLE 1b-continued
| Compound No. | Structure and Name | $^1$H-NMR | Conditions and elution time (min) LCMS (M + H$^+$) |
| --- | --- | --- | --- |
| B135 | 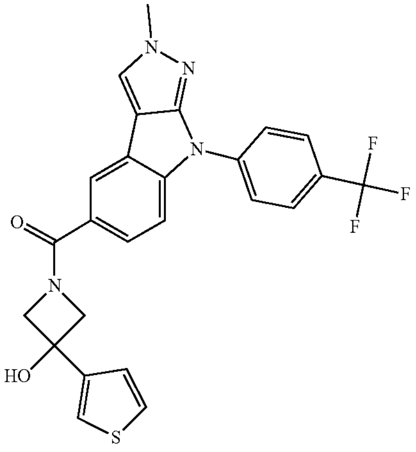 [SMILES: Cn1cc2c3cc(C(=O)N4CC(O)(c5ccsc5)C4)ccc3n(-c3ccc(C(F)(F)F)cc3)c2n1] 1-(2-methyl-8-[4-(trifluoromethyl)phenyl]-2H,8H-pyrazolo[3,4-b]indole-5-carbonyl}-3-(thiophen-3-yl)azetidin-3-ol | | |
| B136 | 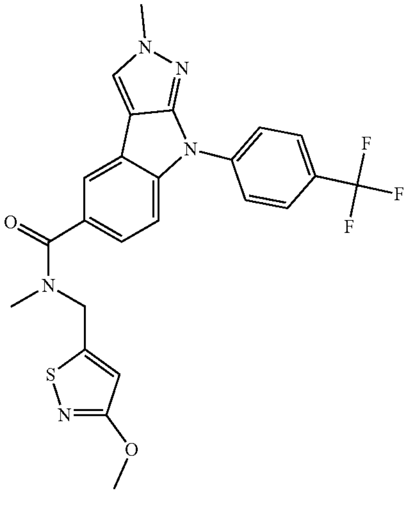 [SMILES: COc1cc(CN(C)C(=O)c2ccc3c(c2)c2cn(C)nc2n3-c2ccc(C(F)(F)F)cc2)sn1] N-[(3-methoxy-1,2-thiazol-5-yl)methyl]-N,2-dimethyl-8-[4-(trifluoromethyl)phenyl]-2H,8H-pyrazolo[3,4-b]indole-5-carboxamide | | |

TABLE 1b-continued
| Compound No. | Structure and Name | $^1$H-NMR | Conditions and elution time (min) LCMS (M + H$^+$) |
| --- | --- | --- | --- |
| B137 | 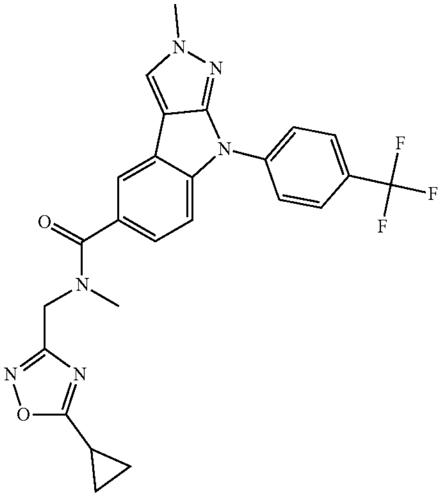 [SMILES: CN(Cc1noc(C2CC2)n1)C(=O)c1ccc2c(c1)c1cn(C)nc1n2-c1ccc(C(F)(F)F)cc1] N-[(5-cyclopropyl-1,2,4-oxadiazol-3-yl)methyl]-N,2-dimethyl-8-[4-(trifluoromethyl)phenyl]-2H,8H-pyrazolo[3,4-b]indole-5-carboxamide | | |
| B138 | 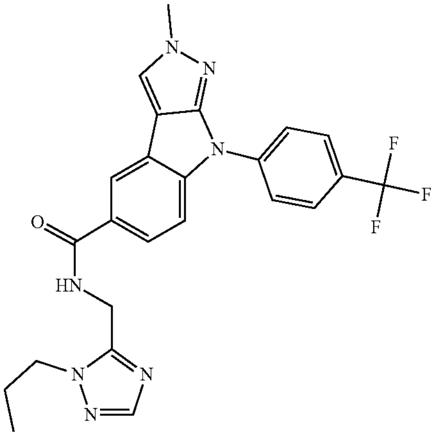 [SMILES: CCCn1ncnc1CNC(=O)c1ccc2c(c1)c1cn(C)nc1n2-c1ccc(C(F)(F)F)cc1] 2-methyl-N-[(1-propyl-1H-1,2,4-triazol-5-yl)methyl]-8-[4-(trifluoromethyl)phenyl]-2H,8H-pyrazolo[3,4-b]indole-5-carboxamide | | |

TABLE 1b-continued
| Compound No. | Structure and Name | $^1$H-NMR | Conditions and elution time (min) LCMS (M + H$^+$) |
|---|---|---|---|
| B139 | 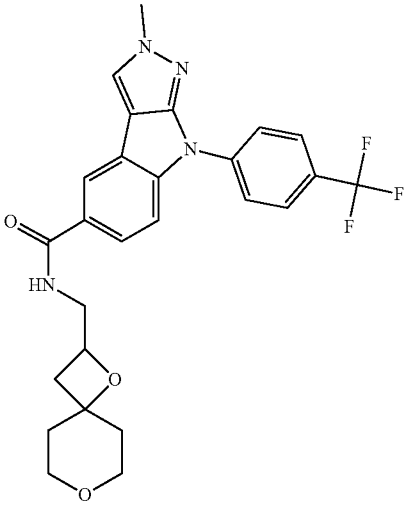 [SMILES: Cn1cc2c3cc(C(=O)NCC4CC5(CCOCC5)O4)ccc3n(-c3ccc(C(F)(F)F)cc3)c2n1] N-({1,7-dioxaspiro[3.5]nonan-2-yl}methyl)-2-methyl-8-[4-(trifluoromethyl)phenyl]-2H,8H-pyrazolo[3,4-b]indole-5-carboxamide | | |
| B140 | 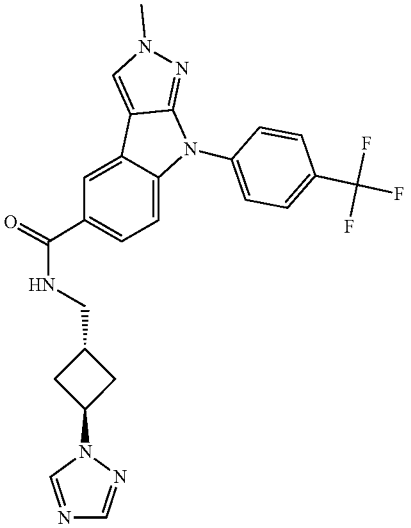 [SMILES: Cn1cc2c3cc(C(=O)NC[C@H]4C[C@H](n5cncn5)C4)ccc3n(-c3ccc(C(F)(F)F)cc3)c2n1] Relative configuration known, trans 2-methyl-N-{[(1r,3r)-3-(1H-1,2,4-triazol-1-yl)cyclobutyl]methyl}-8-[4-(trifluoromethyl)phenyl]-2H,8H-pyrazolo[3,4-b]indole-5-carboxamide | | |

TABLE 1b-continued
| Compound No. | Structure and Name | $^1$H-NMR | Conditions and elution time (min) LCMS (M + H$^+$) |
|---|---|---|---|
| B141 2742806 | 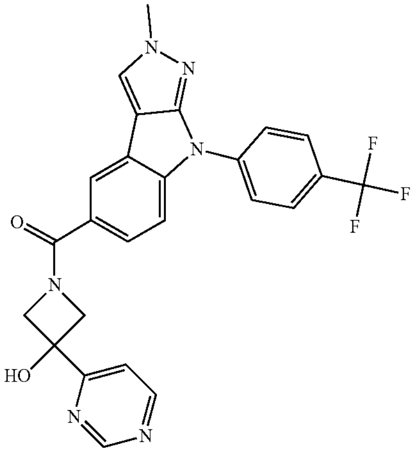 [SMILES: Cn1cc2c3cc(C(=O)N4CC(O)(c5ccncn5)C4)ccc3n(-c3ccc(C(F)(F)F)cc3)c2n1] 1-(2-methyl-8-[4-(trifluoromethyl)phenyl]-2H,8H-pyrazolo[3,4-b]indole-5-carbonyl}-3-(pyrimidin-4-yl)azetidin-3-ol | | |
| B142 | 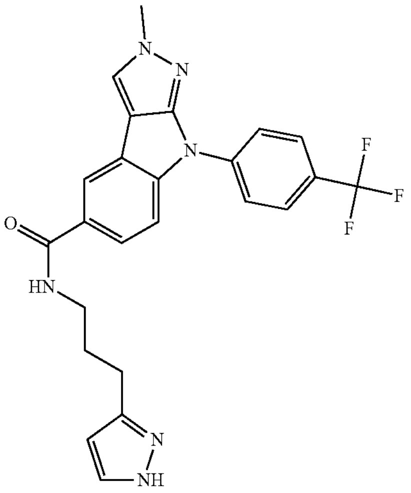 [SMILES: Cn1cc2c3cc(C(=O)NCCCc4cc[nH]n4)ccc3n(-c3ccc(C(F)(F)F)cc3)c2n1] 2-methyl-N-[3-(1H-pyrazol-3-yl)propyl]-8-[4-(trifluoromethyl)phenyl]-2H,8H-pyrazolo[3,4-b]indole-5-carboxamide | | |

TABLE 1b-continued
| Compound No. | Structure and Name | ¹H-NMR | Conditions and elution time (min) LCMS (M + H⁺) |
|---|---|---|---|
| B143 | 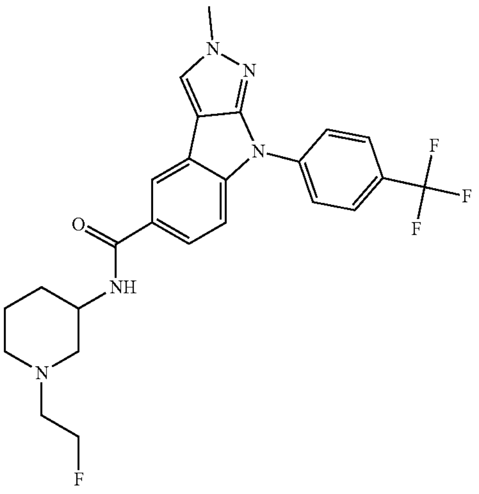 [SMILES: Cn1cc2c3cc(C(=O)NC4CCCN(CCF)C4)ccc3n(-c3ccc(C(F)(F)F)cc3)c2n1] N-[1-(2-fluoroethyl)piperidin-3-yl]-2-methyl-8-[4-(trifluoromethyl)phenyl]-2H,8H-pyrazolo[3,4-b]indole-5-carboxamide | | |
| B144 | 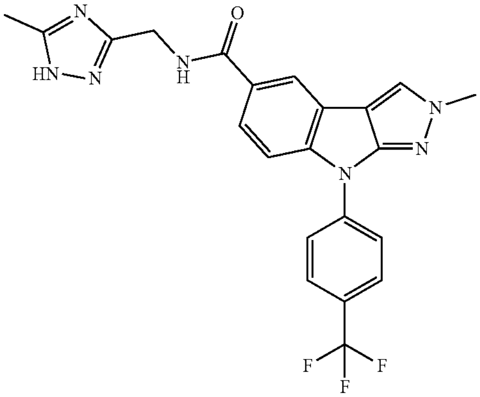 2-methyl-N-[(5-methyl-1H-1,2,4-triazol-3-yl)methyl]-8-[4-(trifluoromethyl)phenyl]-2H,8H-pyrazolo[3,4-b]indole-5-carboxamide | | 18 1.16 454.1 |

TABLE 1b-continued

| Compound No. | Structure and Name | $^1$H-NMR | Conditions and elution time (min) LCMS (M + H$^+$) |
| --- | --- | --- | --- |
| B145 | 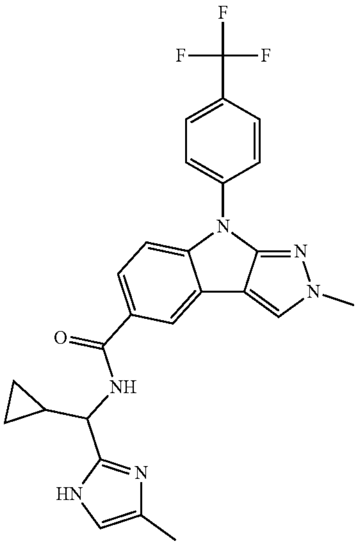 [SMILES: Cc1c[nH]c(C(NC(=O)c2ccc3c(c2)c2cn(C)nc2n3-c2ccc(C(F)(F)F)cc2)C2CC2)n1] N-[cyclopropyl(4-methyl-1H-imidazol-2-yl)methyl]-2-methyl-8-[4-(trifluoromethyl)phenyl]-2H,8H-pyrazolo[3,4-b]indole-5-carboxamide | | |

Biological Activity

SK-HEP-1 Reporter Assay

To identify inhibitors of YAP-TEAD interaction, 8×TEAD responsive elements driving the NanoLuc® luciferase gene were stably integrated into SK-HEP-1 cells (ECACC #: 91091816).

For the assay, cells were treated in duplicates with the test compounds in a 10-point dose, with the top concentration starting at 30 μM (final concentration in assay). After a 24 hour incubation at 37° C., 95% rH, and 5% $CO_2$, a luciferase substrate/lysis reagent mix (NanoGlo™, Promega) was added to the cells, allowing the quantification of cellular luciferase activity.

Cell Media: The cells were cultured in the following media: MEM, +10% FBS, +1× GlutaMAX, +1 mM Sodium-Pyruvate, +100 μM Non-essential amino acids, +0.1 mg/ml Hygromycin. The media used for the assay was: MEM (w/o Phenol Red), +10% FBS, +1× GlutaMAX, +1 mM Sodium-Pyruvate, +100 μM Non-essential amino acids, +0.5% Pen/Strep Reagents: The reagents used are listed below:

| Reagent | Manufacturer | Order No. |
| --- | --- | --- |
| MEM | Sigma | 2279-500 ml |
| MEM (w/o Phenol Red) | Gibco | 51200-046 |
| FBS | PAN Biotech | P30-1502 |
| GlutaMAX | Gibco | 35050-038 |
| Sodium Pyruvate | Gibco | 11360 |
| NEAA | Gibco | 11140 |
| Hygromycin | Sigma | 10687-010 |
| NanoGlo ® Luciferase Assay System | Promega | N1150 |
| Penicillin/Streptomycin | Invitrogen | 15140 |
| DPBS (1x) | Gibco | 14190 |
| Accutase | PAN Biotech | P10-21500 |

Cell culture: The cells were examined using an inverted microscope to check for health and cell density. To dissociate adherent cells, the monolayer of cells was washed once with pre-warmed PBS. After removing the PBS, 3 ml pre-warmed Accutase® was added to a F75 flask, dispersed evenly and the flask was allowed to sit in incubator for ~4-5 minutes.

When a single cell suspension was obtained, 7 ml of prewarmed growth media was added and resuspended with the cells. The cell suspension was transferred to a sterile 15 ml conical centrifuge tube, and spun for 5 min at 300×g, RT. The supernatant was discarded and the pellet was resuspended in 10 ml of pre-warmed growth media.

The total cell count was determined, and 20 μl of the desired cell number was added to each well of a 384 well plate using a Multidrop Combi. The plates were then incubated for 24 hours at 37° C., 95% rH, and 5% $CO_2$.

Compound treatment: 24 hours after seeding, the cells were treated with compounds.

A 1:333 dilution of compounds, diluted in DMSO, was made to get a final concentration of 0.3% DMSO per well. To transfer the compounds to the assay plate, 120 nl was shot from Labcyte low dead volume plates to the cell plates containing 20 μl media/well with the ECHO 555 liquid handling system.

After treatment, the cells were fed with 20 μl fresh pre-warmed assay media using a Multidrop combi.

The assay plates were then incubated for another 24 h at 37° C., 95% rH, and 5% $CO_2$.

Luciferase readout: 24 h after treatment, the plates were taken out of the incubator and were allowed to equilibrate to RT. 30 μl of NanoGlo® reagent was added to the plates in the dark. Plates were shaken for 20 min on a Teleshake (~1500 rpm) in the dark. The luminescence was then measured using an EnVision microplate reader. The IC50 values were generated using Genedata Screener®.

Viability Assay in NCI-H226 (Yap-Dependent) and SW620 Yap KO (Yap Independent) Cells The ability of YAP-TEAD inhibitors to inhibit tumor cell growth was evaluated using two different cell lines: NCI-H226, which is a YAP dependent cell line, and SW620 cells, where YAP and TAZ were knocked out using CRISPR to generate a YAP independent cell line.

For the assay, cells were treated in duplicates with the test compounds in a 10-point dose, 1:3 dilution steps, with the top concentration starting at 30 μM (final concentration in assay). After a 96 hour incubation at 37° C., 95% rH, and 5% $CO_2$, a cell-permeant DNA-binding dye that stains only healthy cells (CyQUANT®, Promega) was added to the cells, allowing the quantification of cell viability.

Cell Media: The NCI-H226 cells were cultured in the following media: RPMI 1640, +10% FBS, +1× GlutaMAX, +10 mM HEPES, +0.5% Pen/Strep. The SW620-KO cells were cultured in the following media: DMEM/F-12, +10% FBS, +1× GlutaMAX, +10 mM HEPES, +0.5% Pen/Strep.

Reagents: The reagents used are listed below:

| Reagent | Manufacturer | Order No. |
|---|---|---|
| DMEM/F12 | Gibco | 21331 |
| RPMI 1640 | Gibco | 31870 |
| FBS | PAN Biotech | P30-1502 |
| GlutaMAX | Gibco | 35050-038 |
| HEPES | Gibco | 15630 |
| CyQuant ® | Promega | C35012 |
| Penicillin/Streptomycin | Invitrogen | 15140 |
| DPBS (1x) | Gibco | 14190 |
| Accutase | PAN Biotech | P10-21500 |

Cell culture: The cells were examined using an inverted microscope to check for health, cell density, etc. To dissociate adherent cells, the monolayer of cells was washed once with pre-warmed PBS. After removing the PBS, 3 ml pre-warmed Accutase was added to a F75 flask, dispersed evenly and the flask was allowed to sit in incubator for ~4-5 minutes.

When a single cell suspension was obtained, 7 ml of prewarmed growth media was added and resuspended with the cells. The cell suspension was transferred to a sterile 15 ml conical centrifuge tube, and spun for 5 min at 300×g, RT. The supernatant was discarded and the pellet was resuspended in 10 ml of pre-warmed growth media.

The total cell count was determined, and 20 μl of the desired cell number was added to each well of a 384 well plate using a Multidrop Combi. The plates were then incubated for 24 hours at 37° C., 95% rH, and 5% $CO_2$.

Compound treatment: 24 hours after seeding, the cells were treated with compounds.

A 1:333 dilution of compounds, diluted in DMSO, was made to get a final concentration of 0.3% DMSO per well. To transfer the compounds to the assay plate, 120 nl was shot from Labcyte low dead volume plates to the cell plates containing 20 μl media/well with the ECHO 555 liquid handling system.

After treatment, the cells were fed with 20 μl fresh pre-warmed assay media using a Multidrop combi.

The assay plates were then incubated for 96 h at 37° C., 95% rH, and 5% $CO_2$.

CyQuant® Measurement 96 h after treatment 30 μl of CyQuant® reagent was added to the assay plates using a Multidrop combi in the dark. The plates were then incubated for 1 hour at 37° C., 95% rH and 5% $CO_2$. Thereafter, the assay plates were removed from the incubator and allowed to equilibrate to RT for 30 min in the dark without lid. Finally, they were measured using an EnVision microplate reader with a FITC bottom read program.

Experimental data in SK-HEP-1 reporter assay of the compounds shown in Table 1 are shown in Table 2 below and classified in the following groups:

| | |
|---|---|
| Group A | $IC_{50}$ is in the range of 1 nM to 10 nM |
| Group B | $IC_{50}$ is in the range of >10 nM to 100 nM |
| Group C | $IC_{50}$ is in the range of >100 nM to 10000 nM |
| Group D | $IC_{50}$ is in the range >10000 nM |

Experimental data in the Viability assay of the compounds shown in Table 1 are shown in Table 2 below and classified in the following groups: For the viability assay in NCI-H226 cells:

| | |
|---|---|
| Group A | $IC_{50}$ is in the range of 1 nM to 100 nM |
| Group B | $IC_{50}$ is in the range of >100 nM to 1000 nM |
| Group C | $IC_{50}$ is in the range of >1000 nM to 10000 nM |
| Group D | $IC_{50}$ is in the range >10000 nM |

For the viability assay in SW620 Yap KO cells:

| | |
|---|---|
| Group A | $IC_{50}$ is in the range of 0.1 μM to 1 μM |
| Group B | $IC_{50}$ is in the range of >1 μM to 10 μM |
| Group C | $IC_{50}$ is in the range of >10 μM to 30 μM |
| Group D | $IC_{50}$ is in the range >30 μM |

ND=Not determinable within the entire range

TABLE 2

| Compound No. (Example No.) | SK-HEP-1 reporter $IC_{50}$ (nM) | NCI-H226 viability $IC_{50}$ (nM) | SW620 viability $IC_{50}$ (μM) |
|---|---|---|---|
| 1 (Ex. 1) | C | | |
| 2 (Ex. 2) | A | A | D |
| 3 | A | | |
| 4 (Ex, 3) | C | | |
| 5 (Ex. 4) | B | A | D |
| 6 (Ex. 5) | B | B | D |
| 7 (Ex. 6) | B | | |
| 8 (Ex. 7) | C | | |
| 9 (Ex. 8) | C | | |
| 10 (Ex. 9) | B | B | D |
| 11 (Ex. 10) | C | | |
| 12 (Ex. 11) | B | B | D |
| 13 (Ex. 12) | C | | |
| 14 (Ex. 13) | B | B | D |
| 15 (Ex. 16) | B | B | D |
| 16 (Ex. 17) | B | A | B |
| 17 (Ex. 14) | B | B | D |
| 18 (Ex. 18) | A | B | D |
| 19 (Ex. 19) | D | D | D |
| 20 (Ex. 20) | A | B | C |
| 21 (Ex. 21) | A | C | C |
| 22 (Ex. 22) | B | B | D |
| 23 | D | | |
| 24 (Ex. 23) | C | B | B |
| 25 (Ex. 24) | B | B | B |
| 26 (Ex. 15) | B | D | C |
| 27 (Ex. 25) | A | A | D |
| 28 (Ex. 26) | D | | |
| 29 | C | | |
| 30 | C | C | D |
| 31 | B | D | D |
| 32 | C | D | |
| 33 | C | | |
| 34 | B | D | D |

TABLE 2-continued

| Compound No. (Example No.) | SK-HEP-1 reporter $IC_{50}$ (nM) | NCI-H226 viability $IC_{50}$ (nM) | SW620 viability $IC_{50}$ (μM) |
|---|---|---|---|
| 35 | A | B | D |
| 36 | A | A | D |
| 37 | | | |
| 46 | C | B | D |
| 45 | C | D | D |
| 47 | B | D | D |
| 66 | B | B | C |
| 67 | C | D | D |
| 60 | A | A | D |
| 61 | A | A | |
| 68 | C | D | D |
| 69 | B | B | B |
| 70 | C | D | D |
| 71 | B | C | D |
| 72 | B | D | D |
| 73 | C | D | D |
| 74 | C | B | B |
| 52 | B | B | D |
| 64 | C | C | C |
| 267 | D | | |
| 55 | A | A | D |
| 75 | B | A | D |
| 49 | A | A | D |
| 50 | A | A | D |
| 76 | B | B | |
| 77 | D | | |
| 78 | C | C | |
| 9 | B | A | C |
| 80 | A | A | C |
| 81 | A | D | C |
| 82 | B | B | |
| 83 | B | A | C |
| 65 | C | C | |
| 84 | B | A | C |
| 85 | A | B | B |
| 86 | B | C | |
| 87 | B | A | D |
| 51 | A | A | D |
| 88 | A | A | D |
| 89 | B | B | C |
| 90 | A | C | B |
| 91 | C | C | D |
| 92 | B | B | A |
| 100 | B | A | B |
| 101 | D | | |
| 102 | C | | |
| 103 | C | C | |
| 41 | B | D | D |
| 40 | B | D | D |
| 97 | B | | A |
| 96 | C | C | B |
| 95 | A | A | D |
| 106 | C | B | |
| 98 | D | C | |
| 105 | B | A | |
| 110 | B | B | |
| 111 | B | B | |
| 112 | B | D | |
| 107 | C | | |
| 53 | A | A | |
| 113 | C | D | D |
| 114 | A | A | B |
| 115 | A | A | |
| 116 | D | | |
| 117 | | | |
| 118 | C | B | |
| 119 | B | B | |
| 120 | B | A | D |
| 121 | B | A | |
| 122 | A | A | |
| 108 | C | D | D |
| 123 | C | D | D |
| 124 | C | B | C |
| 125 | B | B | |
| 126 | B | A | A |
| 127 | C | D | D |

TABLE 2-continued

| Compound No. (Example No.) | SK-HEP-1 reporter $IC_{50}$ (nM) | NCI-H226 viability $IC_{50}$ (nM) | SW620 viability $IC_{50}$ (μM) |
|---|---|---|---|
| 128 | C | D | D |
| 129 | C | | |
| 130 | C | | |
| 38 | B | D | D |
| 131 | B | D | D |
| 132 | A | C | |
| 133 | B | B | |
| 134 | C | | |
| 135 | C | | |
| 136 | D | D | |
| 137 | C | B | |
| 43 | C | | |
| 138 | D | | |
| 139 | D | | |
| 140 | C | D | |
| 141 | C | C | |
| 142 | B | B | D |
| 143 | C | B | |
| 144 | B | A | |
| 145 | B | C | |
| 146 | C | A | D |
| 147 | B | A | |
| 148 | C | B | D |
| 149 | C | B | |
| 150 | D | C | |
| 151 | C | C | |
| 152 | B | A | |
| 153 | C | C | |
| 154 | C | B | |
| 155 | B | B | |
| 268 | B | A | D |
| 156 | C | B | |
| 58 | A | A | |
| 157 | C | D | |
| 158 | B | B | |
| 159 | C | C | |
| 160 | C | C | |
| 161 | B | A | |
| 162 | B | A | B |
| 163 | B | A | |
| 164 | C | D | |
| 165 | B | D | |
| 59 | A | A | |
| 166 | C | C | |
| 167 | B | A | B |
| 168 | D | C | |
| 169 | B | B | |
| 170 | B | B | |
| 171 | B | B | |
| 172 | A | C | |
| 173 | C | C | |
| 174 | D | D | |
| 175 | B | A | |
| 176 | B | A | |
| 177 | B | A | |
| 178 | B | A | |
| 179 | B | B | |
| 180 | C | C | |
| 181 | A | A | |
| 182 | C | B | |
| 183 | C | B | |
| 184 | D | B | D |
| 185 | D | C | |
| 186 | D | C | |
| 187 | B | B | |
| 188 | C | A | D |
| 189 | D | D | |
| 190 | B | B | |
| 191 | | C | |
| 63 | A | A | |
| 193 | C | A | B |
| 194 | B | A | |
| 195 | | B | |
| 196 | B | A | |
| 197 | B | A | C |
| 198 | A | A | |

TABLE 2-continued

| Compound No. (Example No.) | SK-HEP-1 reporter $IC_{50}$ (nM) | NCI-H226 viability $IC_{50}$ (nM) | SW620 viability $IC_{50}$ (μM) |
|---|---|---|---|
| 199 | C | B | D |
| 200 | A | A | |
| 201 | B | A | B |
| 202 | A | A | |
| 203 | A | B | |
| 204 | B | B | |
| 205 | A | A | |
| 62 | A | A | |
| 206 | B | C | |
| 207 | A | A | |
| 208 | C | B | |
| 209 | B | A | |
| 214 | C | C | D |
| 211 | C | B | D |
| 212 | D | C | |
| 213 | B | A | |
| 214 | D | C | |
| 215 | | A | |
| 216 | B | A | |
| 217 | B | A | |
| 218 | B | A | |
| 219 | B | A | |
| 220 | B | A | |
| 221 | A | A | |
| 222 | C | A | |
| 223 | B | B | |
| 224 | D | C | |
| 225 | C | B | |
| 226 | C | A | |
| 227 | C | A | |
| 228 | B | A | |
| 229 | B | A | |
| 230 | D | B | |
| 231 | | D | |
| 232 | | C | |
| 233 | | A | |
| 234 | | B | |
| 235 | | B | |
| 236 | | A | |
| 237 | | A | |
| 238 | | A | |
| 239 | | B | |
| 240 | | B | |
| 241 | | C | |
| 242 | D | C | |
| 243 | | A | |
| 244 | B | B | |
| 245 | B | A | |
| 246 | C | B | |
| 247 | B | B | |
| 248 | B | B | |
| 249 | C | C | D |
| 250 | A | A | |
| 251 | C | B | |
| 252 | B | B | |
| 253 | A | A | |
| 254 | C | B | |
| 255 | B | A | |
| 256 | B | A | |
| 257 | B | A | |
| 258 | A | A | |
| 259 | A | A | |
| 260 | B | A | |
| 261 | C | C | |
| 262 | C | C | |
| 263 | D | B | |
| 264 | B | C | |
| 265 | B | B | |
| 266 | B | A | |
| 37 | A | D | |
| 269 | C | B | |
| 270 | C | B | |
| 271 | | B | |
| 272 | C | A | |
| 273 | B | A | |
| 274 | | B | |

TABLE 2-continued

| Compound No. (Example No.) | SK-HEP-1 reporter $IC_{50}$ (nM) | NCI-H226 viability $IC_{50}$ (nM) | SW620 viability $IC_{50}$ (μM) |
|---|---|---|---|
| 275 | C | B | |
| 276 | C | C | |
| 277 | B | A | |
| 278 | A | B | |
| 297 | B | B | |
| 298 | B | B | |
| 299 | C | B | |
| 300 | C | B | |
| 315 | C | B | |
| 316 | C | A | |
| 356 | B | A | D |
| 357 | B | B | |
| 318 | | C | |
| 319 | | A | D |
| 320 | | A | D |
| 321 | | A | D |
| 322 | | A | D |
| 323 | B | A | |
| 324 | C | B | |
| 325 | B | | |
| 326 | B | | |
| 327 | C | | |
| 328 | C | | |
| 329 | A | A | C |
| 330 | A | A | D |
| 331 | D | | |
| 332 | A | A | B |
| 333 | A | A | D |
| 334 | A | | |
| 335 | B | A | D |
| 336 | C | | |
| 337 | B | A | B |
| 338 | B | A | D |
| 339 | C | | |
| 340 | C | | |
| 341 | B | A | D |
| 342 | A | | |
| 343 | B | A | D |
| 344 | B | B | D |
| 345 | B | B | D |
| 346 | B | A | D |
| 347 | B | A | |
| 348 | D | B | |
| 349 | B | A | |
| 350 | B | B | D |
| 351 | B | | |
| 352 | A | A | D |
| 353 | B | B | B |
| 354 | B | A | B |
| 355 | C | | |
| 369 | C | | |
| 370 | C | | |
| 371 | B | | |
| 372 | C | | |
| 373 | C | | |
| 374 | C | | |
| 375 | C | | |
| 376 | B | | |
| 377 | C | | |
| 378 | C | | |
| 379 | C | | |
| 380 | B | A | D |
| 381 | B | | |
| 382 | B | | |
| 383 | B | | |
| 384 | B | | |
| 385 | B | A | D |
| 386 | B | A | D |
| 387 | B | | |
| 388 | B | | |
| 389 | A | | |
| 390 | B | | |
| 391 | B | | |
| 392 | B | | |
| 393 | B | | |
| 394 | C | | |

TABLE 2-continued

| Compound No. (Example No.) | SK-HEP-1 reporter $IC_{50}$ (nM) | NCI-H226 viability $IC_{50}$ (nM) | SW620 viability $IC_{50}$ (μM) |
|---|---|---|---|
| 395 | C | | |
| 396 | B | | |
| 397 | C | | |
| 398 | C | | |
| 399 | B | | |
| 400 | B | | |
| 401 | A | | |
| 402 | B | | |
| 403 | C | | |
| 404 | C | | |
| 405 | C | | |
| 406 | B | A | D |
| 407 | B | A | ND |
| 408 | C | | |
| 409 | C | | |
| 410 | C | B | ND |
| 411 | B | A | D |
| 412 | D | | |
| 413 | B | B | ND |
| 414 | B | A | D |
| 415 | C | | |
| 416 | C | | |
| 417 | C | | |
| 418 | B | A | ND |
| 419 | B | A | D |
| 421 | C | | |
| 422 | B | | |
| 424 | C | | |
| 427 | B | | |
| 471 | B | A | D |
| 473 | B | | |
| 474 | C | | |
| 475 | C | | |
| 476 | A | A | B |
| 477 | A | A | ND |
| 483 | C | A | ND |
| 489 | C | | |
| 490 | C | | |
| 491 | B | A | B |
| 492 | C | | |
| 493 | C | | |
| 494 | C | | |
| 495 | C | | |
| 496 | B | B | B |
| 497 | C | B | B |
| 498 | C | | |
| 499 | B | B | D |
| 500 | B | A | B |
| 501 | A | A | B |
| 502 | B | A | B |
| 503 | B | B | D |
| 504 | C | | |
| 505 | B | A | B |
| 506 | C | | |
| 507 | A | | |
| 508 | A | | |
| 509 | C | | |
| 510 | B | | |
| 511 | D | | |
| 512 | A | | |
| 513 | B | | |
| 514 | C | | |
| 515 | C | | |
| 516 | C | C | B |
| 517 | C | C | B |
| 518 | B | C | D |
| 519 | B | A | D |
| 520 | B | A | D |
| 521 | C | | |
| 522 | C | | |
| 523 | B | | |
| 524 | C | | |
| 525 | B | B | D |
| 526 | C | | |
| 527 | C | | |
| 528 | C | | |

TABLE 2-continued

| Compound No. (Example No.) | SK-HEP-1 reporter $IC_{50}$ (nM) | NCI-H226 viability $IC_{50}$ (nM) | SW620 viability $IC_{50}$ (μM) |
|---|---|---|---|
| 529 | C | | |
| 530 | B | | |
| 531 | A | | |
| 532 | B | | |
| 533 | B | | |
| 534 | B | | |
| 535 | B | | |
| 536 | B | | |
| 537 | D | | |
| 538 | B | | |
| 539 | B | | |
| 540 | B | | |
| 541 | B | | |
| 542 | B | | |
| 543 | B | | |
| 544 | A | | |
| 545 | B | | |
| 546 | B | | |
| 547 | B | | |
| 548 | B | | |
| 549 | C | | |
| 550 | B | B | D |
| 551 | D | | |
| 552 | B | B | ND |
| 553 | B | | |
| 554 | B | A | ND |
| 555 | C | | |
| 556 | B | | |
| 557 | C | | |
| 558 | B | | |
| 559 | B | | |
| 560 | B | | |
| 561 | B | | |
| 562 | C | | |
| 563 | B | | |
| 564 | B | | |
| 565 | A | | |
| 566 | B | | |
| 567 | C | | |
| 568 | C | | |
| 569 | B | | |
| 570 | C | | |
| 571 | B | | |
| 572 | C | | |
| 573 | B | D | D |
| 574 | B | D | D |
| 575 | C | | |
| 576 | B | D | D |
| 577 | B | A | D |
| 578 | A | A | D |
| 579 | C | | |
| 580 | C | | |
| 581 | B | | |
| 582 | B | | |
| 583 | B | | |
| 584 | B | | |
| 585 | B | | |
| 586 | A | | |
| 587 | D | | |
| 588 | B | | |
| 589 | B | | |
| 590 | C | | |
| 591 | C | | |
| 592 | C | | |
| 593 | B | | |
| 594 | D | | |
| 595 | C | | |
| 596 | C | | |
| 597 | B | | |
| 598 | C | | |
| 599 | C | | |
| 600 | C | | |
| 601 | C | | |
| 602 | C | | |
| 616 | A | | |
| 617 | C | | |

TABLE 2-continued

| Compound No. (Example No.) | SK-HEP-1 reporter $IC_{50}$ (nM) | NCI-H226 viability $IC_{50}$ (nM) | SW620 viability $IC_{50}$ (μM) |
|---|---|---|---|
| 618 | C | | |
| 622 | C | | |
| 623 | B | | |
| 624 | C | | |
| 625 | C | | |
| 626 | C | | |
| B136 | D | | |
| B142 | C | | |
| B120 | C | | |
| B67 | B | | |
| B87 | C | | |
| B124 | B | | |
| B28 | C | | |
| B143 | D | | |
| B52 | D | | |
| B3 | B | | |
| B34 | B | | |
| B33 | C | | |
| B82 | C | | |
| B11 | B | | |
| B38 | D | | |
| B83 | C | | |
| B9 | B | | |
| B56 | D | | |
| B21 | B | | |
| B133 | B | | |
| B76 | B | | |
| B16 | C | | |
| B107 | C | | |
| B97 | ND | | |
| B32 | C | | |
| B59 | ND | | |
| B119 | D | | |
| B129 | C | | |
| B118 | C | | |
| B2 | C | | |
| B51 | C | | |
| B121 | C | | |
| B17 | C | | |
| B88 | D | | |
| B135 | C | | |
| B53 | ND | | |
| B137 | D | | |
| B89 | C | | |
| B68 | B | B | D |
| B108 | D | | |
| B25 | C | | |
| B91 | B | | |
| B80 | B | | |
| B12 | C | | |
| B112 | C | | |
| B5 | C | | |
| B64 | D | | |
| B95 | C | | |
| B113 | C | | |
| B69 | D | | |
| B19 | A | | |
| B46 | C | | |
| B63 | C | | |
| B42 | C | | |
| B94 | ND | | |
| B85 | A | | |
| B36 | B | A | D |
| B70 | C | | |
| B30 | D | | |
| B72 | C | | |
| B54 | D | | |
| B57 | C | | |
| B103 | C | | |
| B117 | B | | |
| B47 | C | | |
| B71 | B | | |
| B90 | B | | |
| B44 | C | | |
| B65 | D | | |
| B27 | B | | |

TABLE 2-continued

| Compound No. (Example No.) | SK-HEP-1 reporter $IC_{50}$ (nM) | NCI-H226 viability $IC_{50}$ (nM) | SW620 viability $IC_{50}$ (μM) |
|---|---|---|---|
| B15 | ND | | |
| B31 | B | | |
| B29 | D | | |
| B134 | C | | |
| B104 | D | | |
| B92 | C | | |
| B141 | ND | | |
| B14 | C | | |
| B41 | ND | | |
| B35 | D | | |
| B126 | B | A | D |
| B84 | D | | |
| B144 | B | | |
| B100 | A | | |
| B86 | C | | |
| B123 | B | B | ND |
| B79 | C | | |
| B18 | C | | |
| B60 | C | | |
| B78 | C | | |
| B93 | B | | |
| B66 | C | | |
| B130 | C | | |
| B99 | D | | |
| B127 | C | | |
| B6 | C | | |
| B73 | C | | |
| B139 | ND | | |
| B138 | C | | |
| B125 | C | | |
| B132 | C | | |
| B75 | C | | |
| B98 | C | | |
| B77 | D | | |
| B13 | C | | |
| B8 | C | | |
| B110 | D | | |
| B96 | C | | |
| B101 | D | | |
| B22 | B | A | D |
| B49 | B | | |
| B109 | D | | |
| B74 | C | | |
| B37 | C | | |
| B105 | C | | |
| B50 | C | | |
| B4 | D | | |
| B81 | C | | |
| B7 | D | | |
| B62 | D | | |
| B40 | D | | |
| B102 | B | | |
| B111 | D | | |
| B48 | C | | |
| B61 | C | | |
| B115 | C | | |
| B58 | A | | |
| B10 | C | | |
| B106 | D | | |
| B20 | D | | |
| B24 | C | | |
| B55 | B | | |
| B122 | B | | |
| B116 | D | | |
| B128 | C | | |
| B1 | C | | |
| B43 | C | | |
| B23 | C | | |
| B26 | C | | |
| B131 | C | | |
| B114 | D | | |
| B140 | D | | |
| B39 | B | | |
| B145 | D | | |

NCI-H226 In Vivo Efficacy Study 7-9-week-old H2d Rag2 female mice (own breeding, Taconic-Denmark) were inoculated subcutaneously with 5×10^6 NCI-H226 human mesothelioma tumor cells in the right flank. Tumor growth and body weight was measured twice weekly using caliper. Tumor volume was calculated using the formula TV=L×W×W/2.

Figure 2:
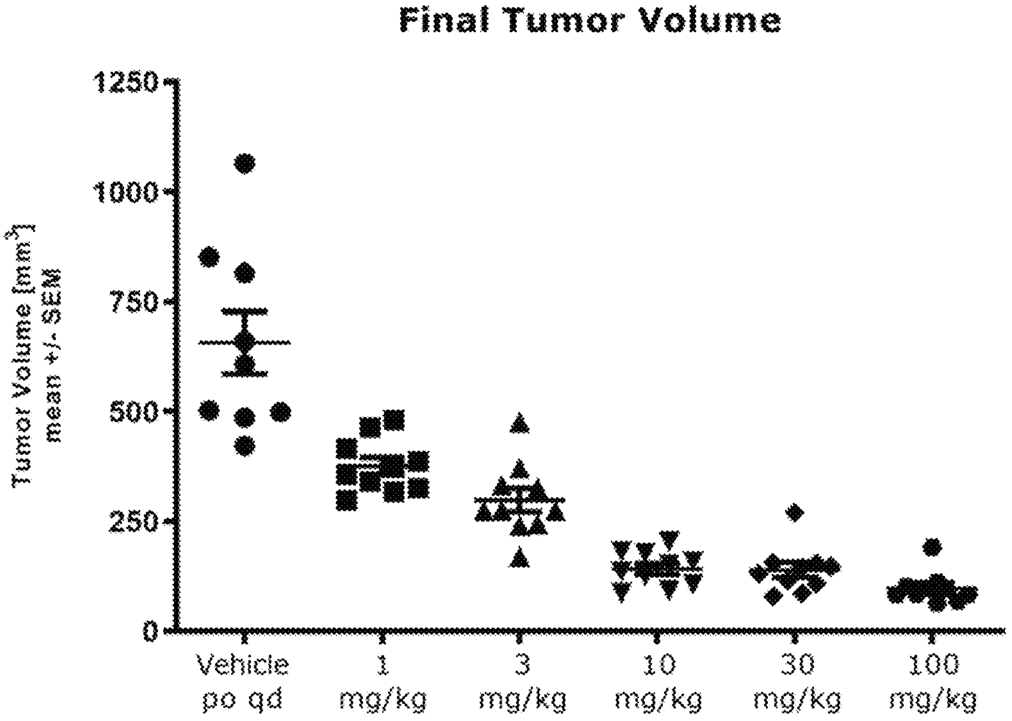
FIG. 2 shows final tumor volume of a vehicle group and each dosage group.

When tumor volume reached approximately 75-150 $mm^3$, animals were randomized (Day 0) into treatment groups (n=9-10/group) and treated perorally (po) once daily (qd) for 29 days with either vehicle (20% hydroxypropyl β-cyclodextrin in 50 mM PBS pH 7.4) or Compound no. 2. Compound no. 2 was tested at dosing levels of 1, 3, 10, 30, and 100 mg/kg, respectively. Results are depicted in FIG. 1 (tumor growth over time for vehicle group and each dosage group) and FIG. 2 (final tumor volume of vehicle group and each dosage group).

Significant tumor growth inhibition was achieved compared to vehicle treated group for all tested dosing levels (FIG. 1—graphs b and c; p-value <0.001) showing maximal inhibition at dosing levels >10 mg/kg. Statistical analysis of tumor volumes between treatment groups was done using repeated measures analysis of covariance (RM-ANCOVA) in a linear mixed effects model followed by least-squares means pairwise comparisons.

The animal experiment was performed under regulation of the German animal welfare act and in accordance with the EU laboratory animal directive for the area of animal experiments.

The following examples relate to medicaments:

Example A: Injection Vials

A solution of 100 g of an active ingredient of the formula I or I-A and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

Example B: Suppositories

A mixture of 20 g of an active ingredient of the formula I or I-A with 100 g of soya lecithin and 1400 g of cocoa butter is melted, poured into moulds and allowed to cool. Each suppository contains 20 mg of active ingredient.

Example C: Solution

A solution is prepared from 1 g of an active ingredient of the formula I or I-A, 9.38 g of $NaH_2PO_4 \cdot 2\ H_2O$, 28.48 g of $Na_2HPO_4 \cdot 12\ H_2O$ and 0.1 g of benzalkonium chloride in 940 mL of bidistilled water. The pH is adjusted to 6.8, and the solution is made up to 1 l and sterilised by irradiation. This solution can be used in the form of eye drops.

Example D: Ointment 500 mg of an active ingredient of the formula I or I-A are mixed with 99.5 g of Vaseline under aseptic conditions.

Example E: Tablets

A mixture of 1 kg of active ingredient of the formula I or I-A, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

Example F: Dragees

Tablets are pressed analogously to Example E and subsequently coated in a conventional manner with a coating of sucrose, potato starch, talc, tragacanth and dye.

Example G: Capsules 2 kg of active ingredient of the formula I or I-A are introduced into hard gelatine capsules in a conventional manner in such a way that each capsule contains 20 mg of the active ingredient.

Example H: Ampoules

A solution of 1 kg of active ingredient of the formula I or I-A in 60 l of bidistilled water is sterile filtered, transferred into ampoules, lyophilised under sterile conditions and sealed under sterile conditions. Each ampoule contains 10 mg of active ingredient.

The invention claimed is:

1. A compound of formula I-A

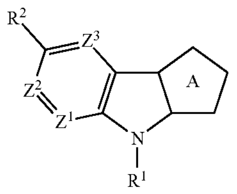

I-A wherein

Ring A represents a five-membered heteroaromatic ring moiety selected from the group consisting of:

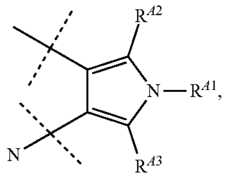

A-1

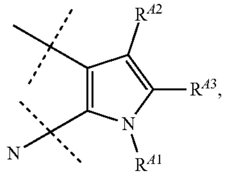

A-2

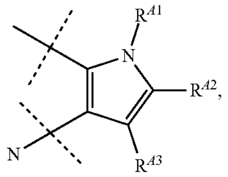

A-3

-continued
A-4
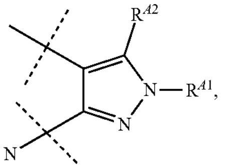
A-5
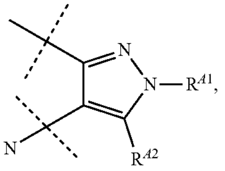
A-6
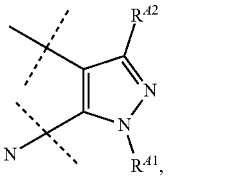
A-7
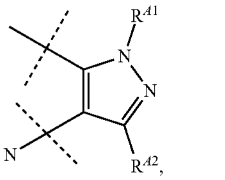
A-8
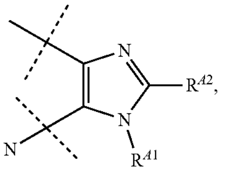
A-9
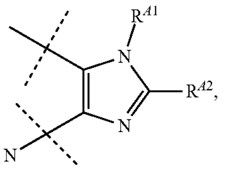
A-10
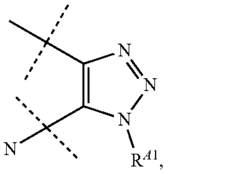
A-11
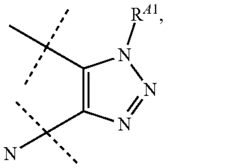
A-12
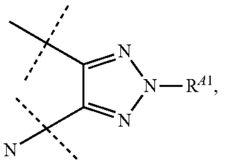
-continued
A-13
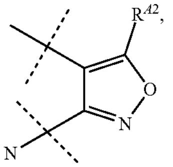
A-14
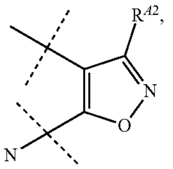
A-15
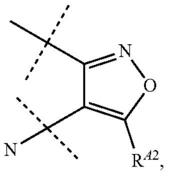
A-16
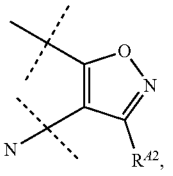
A-17
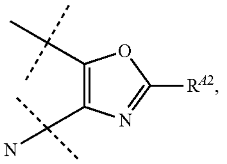
A-18
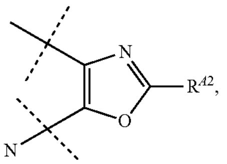
A-19
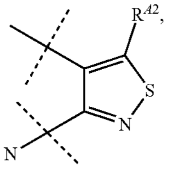
A-20
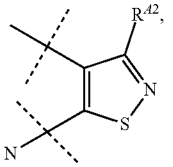
A-21
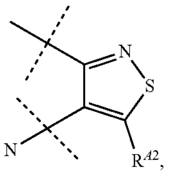

-continued

A-22

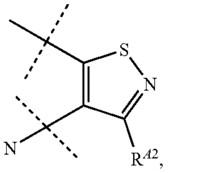

A-23

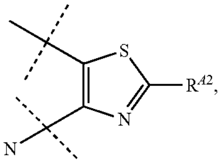

A-24

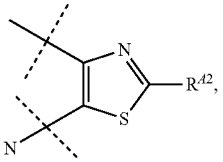

A-25

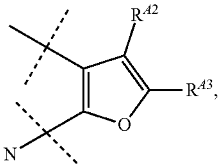

A-26

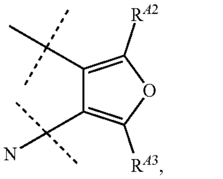

A-27

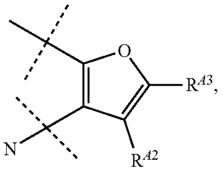

A-28

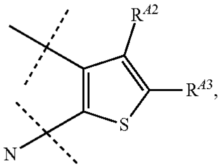

A-29

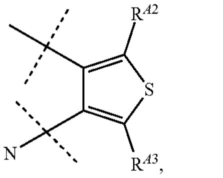

A-30

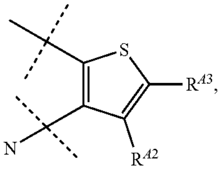

-continued

A-31

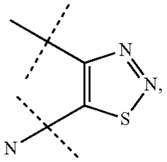

A-32

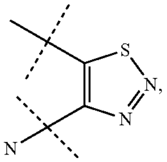 and

A-33

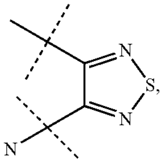

wherein $R^{A1}$ represents H, D, $C_{1-6}$-aliphatic, —$CH_2$—$Ar^{A1}$, or —$CH_2$—$CH_2$—$Ar^{A1}$;

$R^{A2}$ represents H, D, halogen, $C_{1-6}$-aliphatic, —$CH_2$—$Ar^{A2}$, or —$CH_2$—$CH_2$—$Ar^{A2}$;

$R^{A3}$ represents H, D, $C_{1-6}$-aliphatic, —$CH_2$—$Ar^{A3}$, or —$CH_2$—$CH_2$—$Ar^{A3}$;

$Z^1$ is $CR^{Z1}$ or N;

$Z^2$ is $CR^{Z2}$ or N;

$Z^3$ is $CR^{Z3}$ or N;

wherein at least two of $Z^1$, $Z^2$ and $Z^3$, are not N;

$R^1$ is selected from the group consisting of:

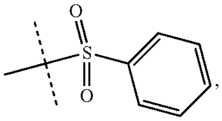, 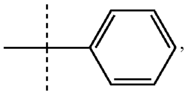,

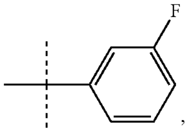, 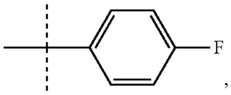,

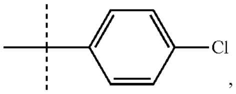, 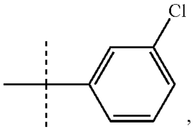,

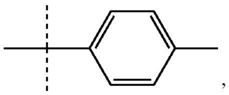, 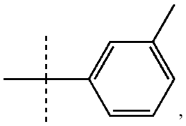,

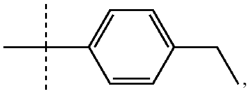, 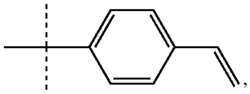,

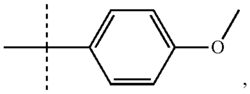, 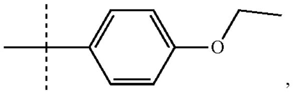,

-continued
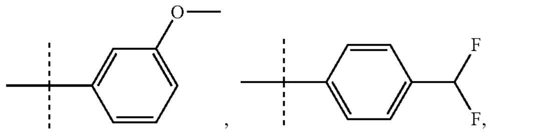
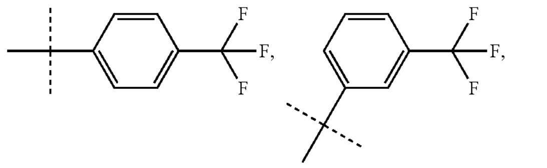
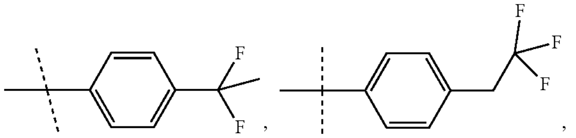
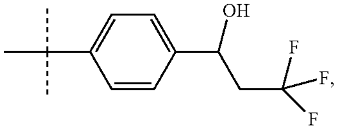
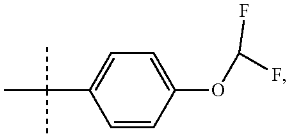
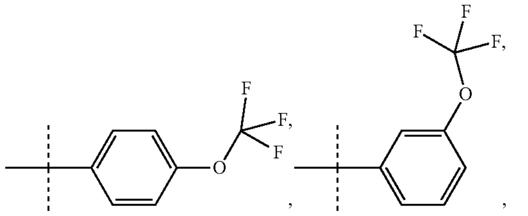
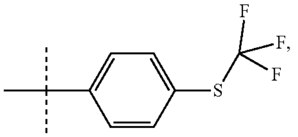
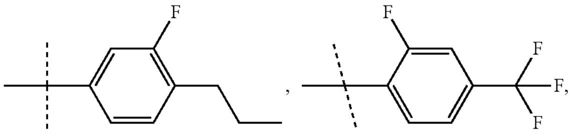
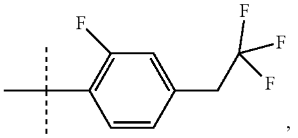
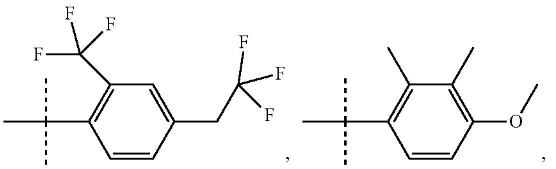
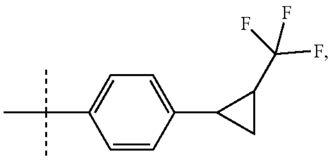
-continued
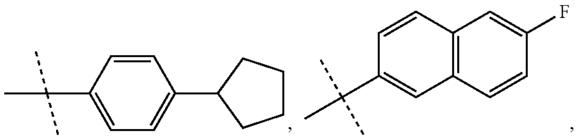
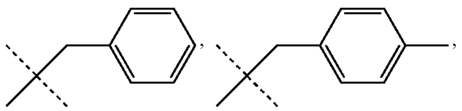
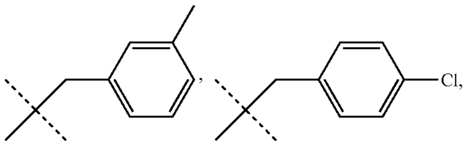
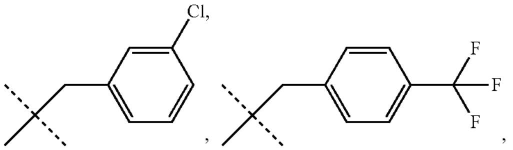
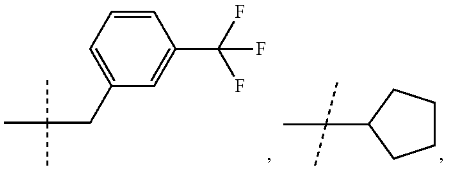
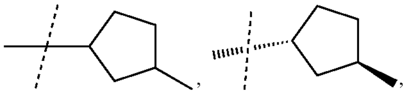
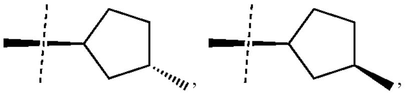
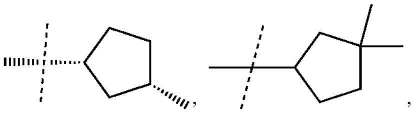
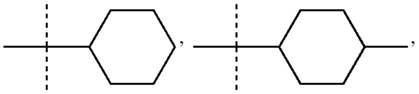
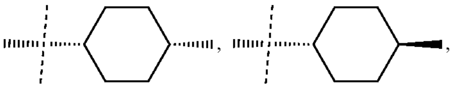
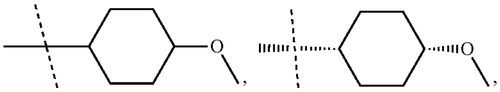
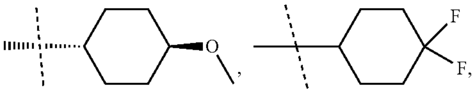
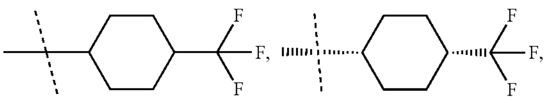
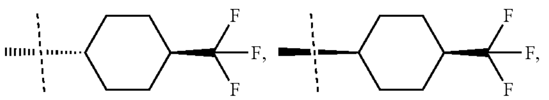
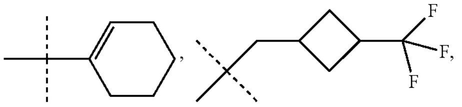

-continued

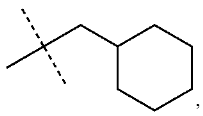,
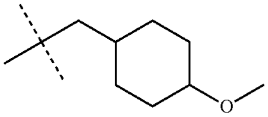,
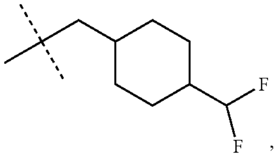,
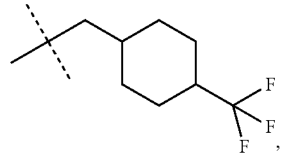,
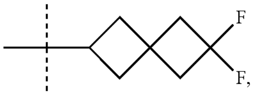
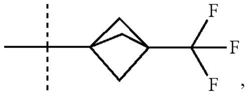,
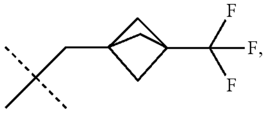
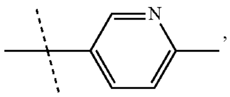,
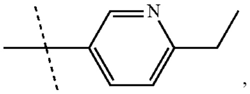,
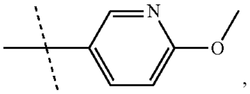,
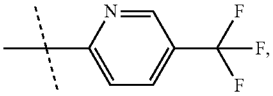
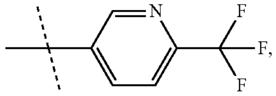
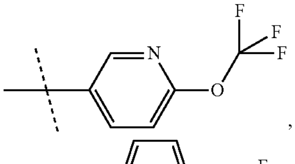,
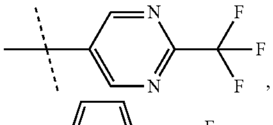,
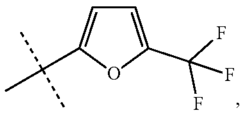,
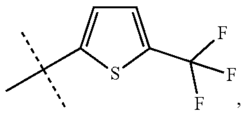,
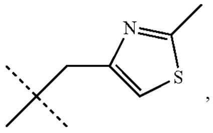,
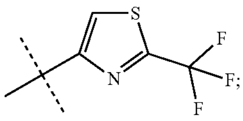;

$R^2$ represents —C(=O)—$OR^{2a}$, —C(=O)—$NR^{2b}R^{2c}$, —$(CH_2)_w$—C(=O)—$NR^{2b}R^{2c}$, —$(CH_2)_x$—$NR^{2d}$—C(=O)—$R^{2e}$, —S—$R^{2f}$, —S(=O)—$R^{2f}$, —S(=O)$_2$—$R^{2g}$, —S(=O)$_2$—$NR^{2h}R^{2i}$, —S(=O)$_2$—OH, —S(=O)(=$NR^{2j}$)—OH, —S(=O)(=$NR^{2j}$)—$R^{2g}$, —S(=O)(=$NR^{2k}$)—$NR^{2l}R^{2m}$, $(CH_2)_y$—CN, —P(=O)($OR^{2o}$)($OR^{2p}$), —$(CH_2)_z$—$NR^{2d}$—S(=O)$_2$—$R^{2g}$, —C(=O)—N=S(=O)—$R^{2s}R^{2t}$, —C(=O)—N=S(=N—$R^{2u}$)—$R^{2s}R^{2t}$, —$B(OH)_2$, or $Hetcyc^X$;

$Ar^{A1}$, $Ar^{A2}$, $Ar^{A3}$ represent independently from each other phenyl which may be unsubstituted or mono- or di-substituted with independently from each other $R^{A11}$ and/or $R^{A12}$;

$R^{Z1}$ represents H or halogen;

$R^{Z2}$ represents H; or forms together with $R^2$ a divalent radical —S(=O)$_2$—N(H)—C(=O)—;

$R^{Z3}$ represents H or halogen;

$R^{2a}$ represents H, un-substituted or substituted $C_{1-8}$-aliphatic, aryl, heteroaryl, saturated or partially unsaturated heterocyclyl, or carbohydrate derived radical, or Cat;

Cat represents a monovalent cation;

$R^{2b}$, $R^{2c}$, $R^{2q}$, $R^{2r}$ represent independently from each other H, un-substituted or substituted $C_{1-8}$-aliphatic including $C_{3-7}$-cycloaliphatic; or form together with the nitrogen atom to which they are attached to an unsubstituted or substituted saturated, partially unsaturated or aromatic heterocycle with 3, 4, 5, 6, 7 ring atoms wherein 1 of said ring atoms is said nitrogen atom and no or one further ring atom is a hetero atom selected from N, O, or S and the remaining are carbon atoms; wherein said heterocycle may optionally be fused with $Hetar^Z$; or one of $R^{2b}$ and $R^{2c}$ represents —CN, —$NH_2$, —OH, —O—$C_{1-6}$-alkyl, —S(=O)$_2$—$R^{2g}$, $Ar^2$, $Hetar^2$, $Cyc^2$, or $Hetcyc^2$, while an other of $R^{2b}$ and $R^{2c}$ represents H or un-substituted or substituted $C_{1-8}$-aliphatic;

$R^{2d}$, $R^{2j}$, $R^{2k}$, $R^{2o}$, $R^{2p}$ represent independently from each other H, un-substituted or substituted $C_{1-8}$-aliphatic;

$R^{2e}$ represents H, halogen, un-substituted or substituted $C_{1-8}$-aliphatic, heteroaryl;

$R^{2f}$, $R^{2g}$ represent independently from each other un-substituted or substituted $C_{1-8}$-aliphatic;

$R^{2h}$, $R^{2i}$ represent independently from each other H, un-substituted or substituted $C_{1-8}$-aliphatic, aryl, heterocyclyl, heteroaryl; or form together with the nitrogen atom to which they are attached to an unsubstituted or substituted saturated, partially unsaturated or aromatic heterocycle with 3, 4, 5, 6, 7 ring atoms wherein 1 of said ring atoms is said nitrogen atom and no or one further ring atom is a hetero atom selected from N, O, or S and the remaining are carbon atoms;

$R^{2l}$, $R^{2m}$ represent independently from each other H, un-substituted or substituted $C_{1-8}$-aliphatic; or form together with the nitrogen atom to which they are attached to an unsubstituted or substituted saturated, partially unsaturated or aromatic heterocycle with 3, 4, 5, 6, 7 ring atoms wherein 1 of said ring atoms is said nitrogen atom and no or one further ring atom is a hetero atom selected from N, O, or S and the remaining are carbon atoms;

$R^{2s}$, $R^{2t}$ represent independently from each other unsubstituted or substituted $C_{1-8}$-aliphatic; or form together an unsubstituted or substituted divalent $C_{3-6}$-alkylene radical;

$R^{2u}$ represents hydrogen or unsubstituted or substituted $C_{1-6}$-aliphatic;

$R^{A11}$, $R^{A12}$ represent independently from each other halogen or un-substituted or substituted, straight-chain or branched $C_{1-6}$-aliphatic;

$Ar^2$ is a mono- or bicyclic aryl with 5, 6, 7, 8, 9, 10 ring carbon atoms, wherein that aryl may be unsubstituted or substituted with substituents $R^{D1}$, $R^{D2}$, $R^{D3}$, $R^{D4}$, and/or $R^{D5}$ which may be the same or different;

$Hetar^2$ is a mono- or bicyclic heteroaryl with 5, 6, 7, 8, 9, 10 ring atoms wherein 1, 2, 3, 4, 5 of said ring atoms is/are a hetero atom(s) selected from N, O, and/or S and the remaining are carbon atoms, wherein that heteroaryl may be unsubstituted or substituted with substituents $R^{D1}$, $R^{D2}$, $R^{D3}$, $R^{D4}$, and/or $R^{D5}$ which may be the same or different;

$Cyc^2$ is a saturated or partially unsaturated monocyclic carbocycle with 3, 4, 5, 6, or 7 ring carbon atoms, wherein that carbocycle may be unsubstituted or substituted with $R^{D6}$, $R^{D7}$, $R^{D8}$, $R^{D9}$, and/or $R^{D10}$ which may be the same or different; wherein that carbocycle may optionally be fused to $Ar^Z$ or $Hetar^Z$ via 2 adjacent ring atoms of said $Ar^Z$ or $Hetar^Z$ and wherein that fused carbocycle may further be unsubstituted or substituted with $R^{C1}$, $R^{C2}$, $R^{C3}$, $R^{C4}$, $R^{C5}$, $R^{C6}$ which may be the same or different;

$Hetcyc^2$ is a saturated or partially unsaturated, monocyclic heterocycle with 3, 4, 5, 6, 7 ring atoms wherein 1 or 2 of said ring atoms is/are a hetero atom(s) selected from N, O, and/or S and the remaining are carbon atoms, wherein that heterocycle may be unsubstituted or substituted with $R^{D6}$, $R^{D7}$, $R^{D8}$, $R^{D9}$, and/or $R^{D10}$ which may be the same or different;

wherein that heterocycle may optionally be fused to $Ar^Z$ or $Hetar^Z$ via 2 adjacent ring atoms of said $Ar^Z$ or $Hetar^Z$ and wherein that fused heterocycle may further be unsubstituted or substituted with $R^{C1}$, $R^{C2}$, $R^{C3}$, $R^{C4}$, $R^{C5}$, $R^{C6}$ which may be the same or different;

$Ar^X$, $Ar^Z$ are independently from each other an un-substituted or substituted benzo ring;

$Ar^Y$ is an un-substituted or mono- or di-substituted phenyl;

$Hetar^{Y1}$ is a 5 or 6 membered monocyclic heteroaryl wherein 1, 2, 3, 4 ring atoms are hetero atoms selected from N, O, and/or S and the remaining are carbon atoms, wherein that heteroaryl may be unsubstituted or substituted with halogen, $C_{1-4}$-alkyl which may optionally be substituted with OH;

$Hetar^Z$ is an unsubstituted or substituted 5 or 6 membered heteroaryl ring selected from the group consisting of pyrrole, furan, thiophene, pyrazole, imidazole, oxazole, isoxazole, thiazole, oxadiazole, triazole, tetrazole, pyridine, pyrimidine, pyrazine, pyrane;

$Cyc^{Y1}$ is a saturated monocyclic carbocycle with 3, 4, 5, 6, or 7 ring carbon atoms, wherein that carbocycle may be unsubstituted or substituted with halogen, OH, $C_{1-4}$-alkyl;

$Hetcyc^X$ is a saturated, partially unsaturated or aromatic, monocyclic heterocycle with 3, 4, 5, 6, 7 ring atoms wherein 1, 2, 3, 4 of said ring atoms is/are a hetero atom(s) selected from N, O, and/or S and the remaining are carbon atoms, wherein said heterocycle may be unsubstituted or substituted with $R^{X1}$, $R^{X2}$, $R^{X3}$, $R^{X4}$, $R^{X5}$, $R^{X6}$, $R^{X7}$, and/or $R^{X8}$ which may be the same or different, and wherein that heterocycle is optionally a carboxylic acid bioisostere;

$Hetcyc^Y$ is a saturated, partially unsaturated or aromatic, monocyclic heterocycle with 3, 4, 5, 6, 7 ring atoms wherein 1, 2, 3, 4 of said ring atoms is/are a hetero atom(s) selected from N, O, and/or S and the remaining are carbon atoms;

$Hetcyc^{Y1}$ is a saturated or partially unsaturated monocyclic heterocycle with 5 or 6 ring atoms wherein 1 or 2 of said ring atoms are heteroatoms selected from N, O, and/or S and the remaining are carbon atoms;

$R^{C1}$, $R^{C2}$, $R^{C3}$, $R^{C4}$, $R^{C5}$, $R^{C6}$ represent independently from each other un-substituted or substituted $C_{1-6}$-aliphatic;

$R^{D1}$, $R^{D2}$, $R^{D3}$, $R^{D4}$, $R^{D5}$ represent independently from each other un-substituted or substituted $C_{1-6}$-aliphatic;

$R^{D6}$, $R^{D7}$, $R^{D8}$, $R^{D9}$, $R^{D10}$ represent independently from each other un-substituted or substituted $C_{1-6}$-aliphatic, unsubstituted or substituted $C_{1-6}$-aliphatoxy, halogen, hydroxy;

$Hetar^{Y1}$, $CH_2$-$Hetar^{Y1}$, $Cyc^{Y1}$, $Hetcyc^{Y1}$, $-CH_2$-$Hetcyc^{Y1}$; and/or two of $R^{D6}$, $R^{D7}$, $R^{D8}$, $R^{D9}$, $R^{D10}$ which are attached to the same ring atom of said carbocycle or heterocycle may form a divalent $C_{2-6}$-alkylene radical, wherein one or two non-adjacent carbon units of said alkylene radical may optionally be replaced by independently from each other O, N—H, or N—$C_{1-4}$-alkyl, and wherein that alkylene radical may optionally be substituted with OH, $C_{1-4}$-alkyl, or —O—$C_{1-4}$-alkyl; and/or two of $R^{D6}$, $R^{D7}$, $R^{D8}$, $R^{D9}$, $R^{D10}$ which are attached to different ring atoms of said carbocycle or heterocycle may form a divalent $C_{1-6}$-alkylene radical, wherein one or two non-adjacent carbon units of said alkylene radical may optionally be replaced by independently from each other O, N—H, or N—$C_{1-4}$-alkyl;

$R^{X1}$, $R^{X2}$, $R^{X3}$, $R^{X4}$, $R^{X5}$, $R^{X6}$, $R^{X7}$, $R^{X8}$ represent independently from each other un-substituted or substituted $C_{1-6}$-aliphatic, $C_{1-6}$-aliphatoxy, halogen, —OH, —$NR^{2d}$—$S(=O)_2$—$R^{2g}$, $Hetcyc^Y$, O-$Hetcyc^Y$; and/or two of $R^{X1}$, $R^{X2}$, $R^{X3}$, $R^{X4}$, $R^{X5}$, $R^{X6}$, $R^{X7}$, $R^{X8}$ which are attached to the same carbon atom of said heterocycle form a divalent oxo (=O) group; and/or two of $R^{X1}$, $R^{X2}$, $R^{X3}$, $R^{X4}$, $R^{X5}$, $R^{X6}$, $R^{X7}$, $R^{X8}$ or four of $R^{X1}$, $R^{X2}$, $R^{X3}$, $R^{X4}$, $R^{X5}$, $R^{X6}$, $R^{X7}$, $R^{X8}$ which are attached to the same sulfur atom of said heterocycle form a divalent oxo (=O) group thereby forming either an —S(=O)— or an —$S(=O)_2$— moiety;

halogen is F, Cl, Br, I;

v is 1 or 2;

w is 1 or 2;

x is 0, 1 or 2;

y is 0, 1 or 2;

z is 0, 1 or 2;

or any N-oxide, tautomer or stereoisomer thereof and/or any pharmaceutically acceptable salt of each of the foregoing, including mixtures thereof in all ratios, with the proviso that Ring A represents a five-membered heteroaromatic ring moiety selected from the group consisting of A-1, A-4, A-5, A-6, A-7, A-9, A-10, A-11, A-12, A-13, A-15, A-17, A-19, A-20, A-21, A-23, and A-24;

$R^{A1}$ represents $C_{1-6}$-aliphatic, —$CH_2$—$Ar^{A1}$;

$R^{A2}$ represents H, $C_{1-6}$-aliphatic;

$R^{A3}$ represents H, $C_{1-6}$-aliphatic;

$Ar^{A1}$ represents phenyl which may be unsubstituted or mono-substituted with $R^{A11}$; and $R^{A11}$ represents halogen.

2. The compound according to claim 1, or any N-oxide, tautomer or stereoisomer thereof and/or any pharmaceutically acceptable salt of each of the foregoing, including mixtures thereof in all ratios, wherein $Z^1$ is $CR^{Z1}$;

$Z^2$ is $CR^{Z2}$;

$Z^3$ is $CR^{Z3}$ or N;

$R^{Z1}$ is H or F;

$R^{Z2}$ is H; or forms together with $R^2$ a divalent radical —$S(=O)_2$—N(H)—C(=O)—; and $R^{Z3}$ is H or F.

3. A compound of formula I

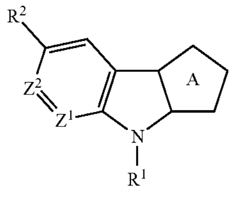

I wherein

Ring A represents a five-membered heteroaromatic ring moiety selected from the group consisting:

-continued
A-1
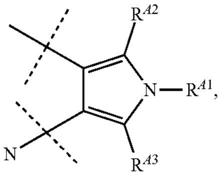
A-2
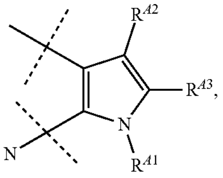
A-3
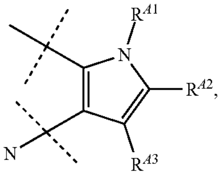
A-4
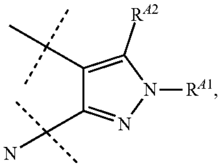
A-5
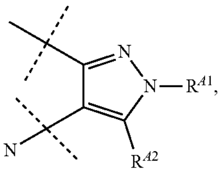
A-6
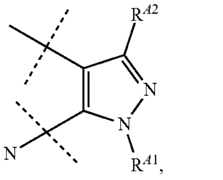
A-7
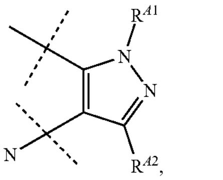
A-8
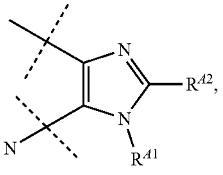
A-9
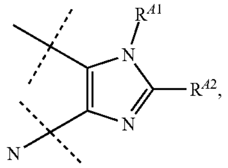
A-10
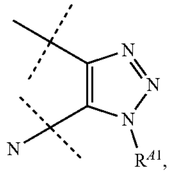
A-11
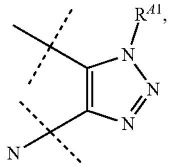
A-12
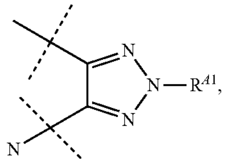
A-13
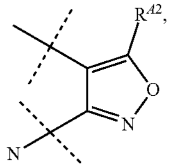
A-14
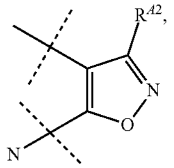
A-15
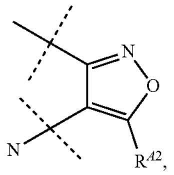
A-16
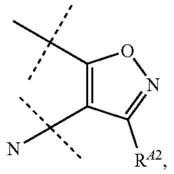
A-17
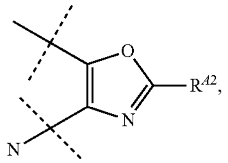

-continued
A-18
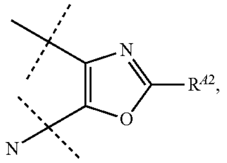
A-19
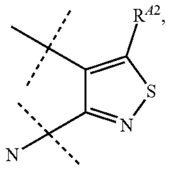
A-20
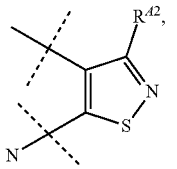
A-21
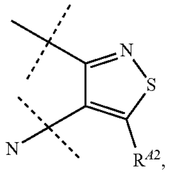
A-22
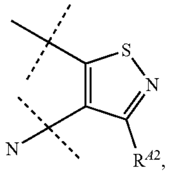
A-23
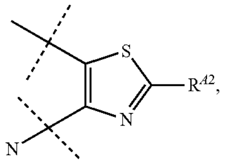
A-24
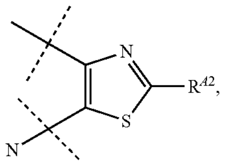
A-25
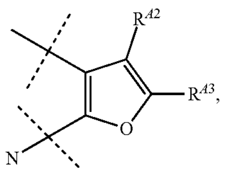
A-26
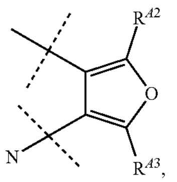
-continued
A-27
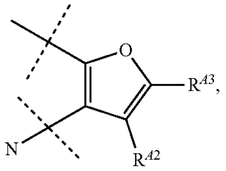
A-28
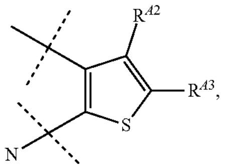
A-29
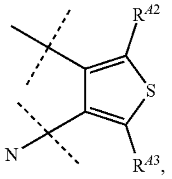
A-30
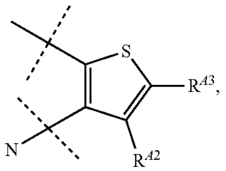
A-31
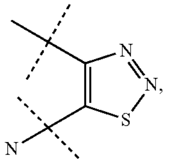
A-32
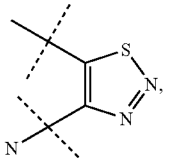
A-33
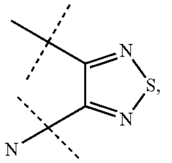
and
wherein
$R^{A1}$ represents H, $C_{1-6}$-aliphatic, —$CH_2$—$Ar^{A1}$, or —$CH_2$—$CH_2$—$Ar^{A1}$;
$R^{A2}$ represents H, halogen, $C_{1-6}$-aliphatic, —$CH_2$—$Ar^{A2}$, or —$CH_2$—$CH_2$—$Ar^{A2}$;
$R^{A3}$ represents H, $C_{1-6}$-aliphatic, —$CH_2$—$Ar^{A3}$, or —$CH_2$—$CH_2$—$Ar^{A3}$;
$Z^1$ is $CR^{Z1}$ or N;
$Z^2$ is $CR^{Z2}$ or N;
wherein at least one of $Z^1$ and $Z^2$ is not N;

R[1] is selected from the group consisting of:
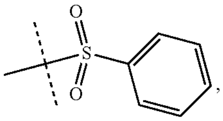,
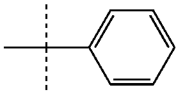,
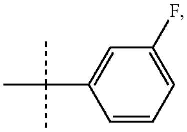
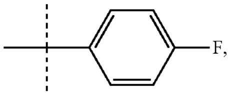
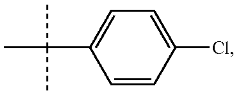
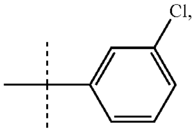
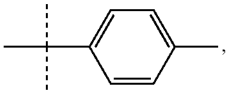,
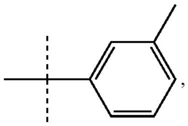,
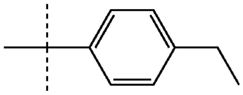,
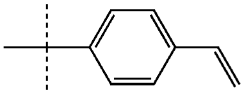,
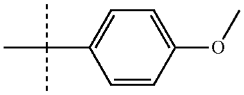,
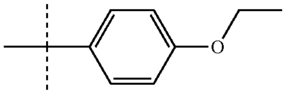,
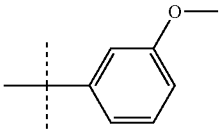,
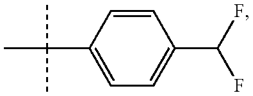
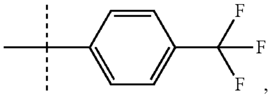,
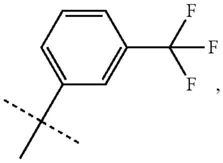,
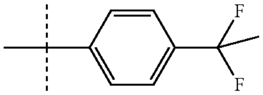,
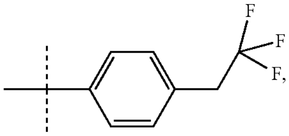
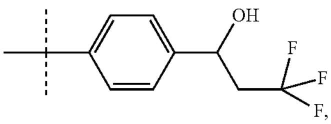
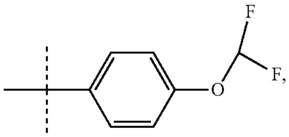
-continued
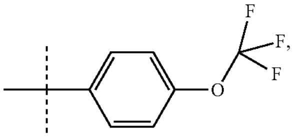
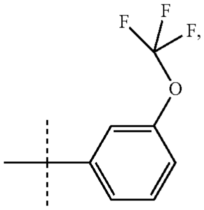
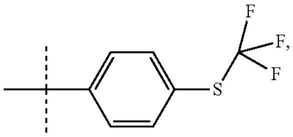
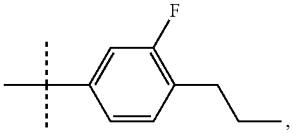,
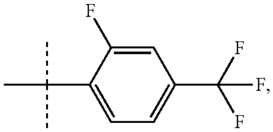
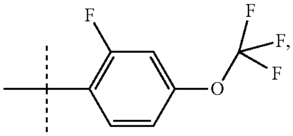
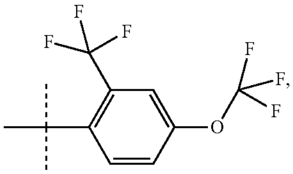
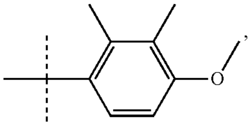,
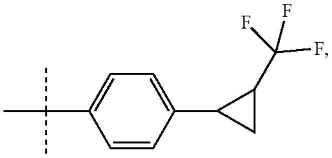
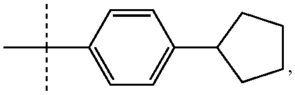,
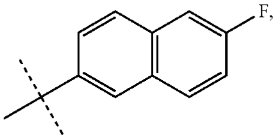,
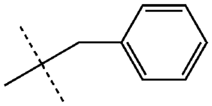
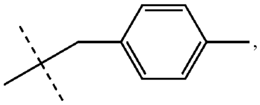,
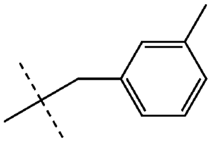,
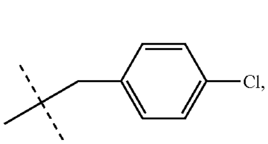
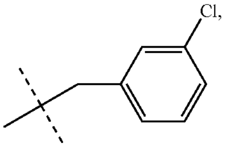
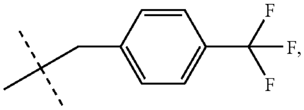

-continued

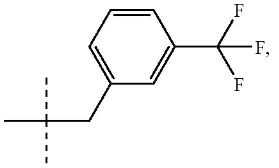

,

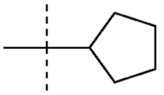

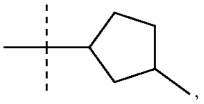

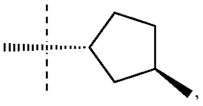

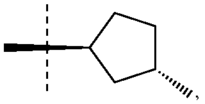

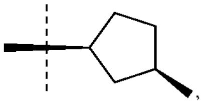

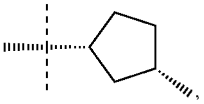

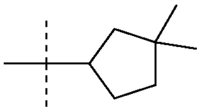

,

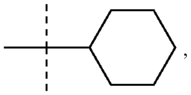

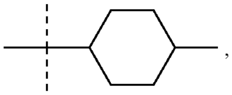

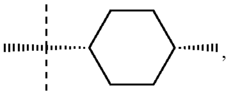

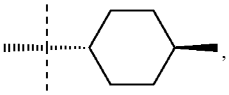

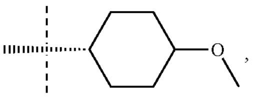

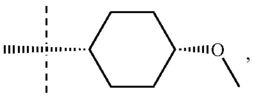

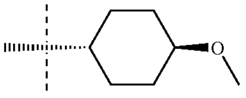

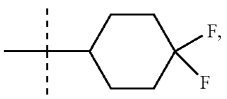

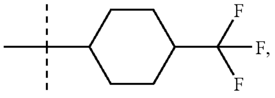

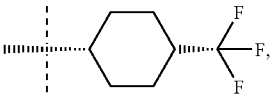

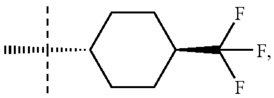

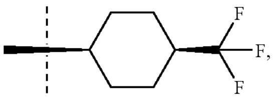

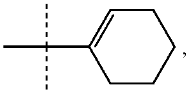

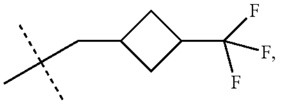

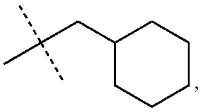

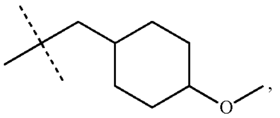

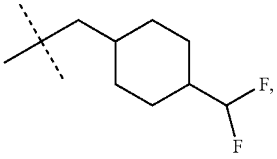

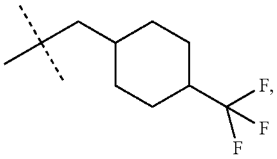

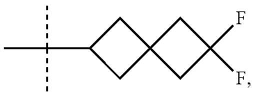

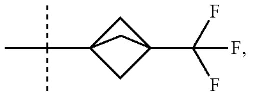

-continued

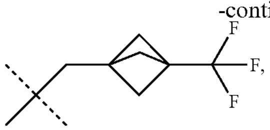

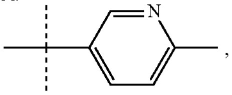

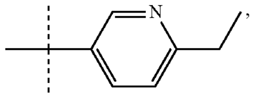

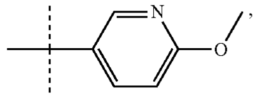

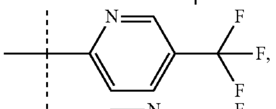

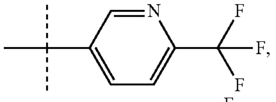

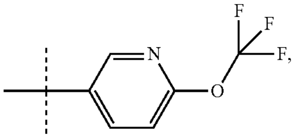

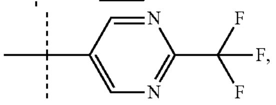

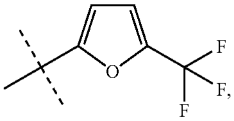

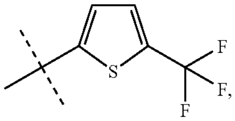

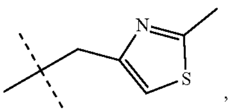

,

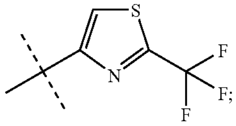

$R^2$ represents —C(═O)—$OR^{2a}$, —C(═O)—$NR^{2b}R^{2c}$, —$(CH_2)_w$—C(═O)—$NR^{2b}R^{2c}$, —$(CH_2)_x$—$NR^{2d}$—C(═O)—$R^{2e}$, —S—$R^{2f}$, —S(═O)—$R^{2f}$, —S(═O)$_2$—$R^{2g}$, —S(═O)$_2$—$NR^{2h}R^{2i}$, —S(═O)$_2$—OH, —S(═O)(═$NR^{2j}$)—OH, —S(═O)(═$NR^{2j}$)—$R^{2g}$, —S(═O)(═$NR^{2k}$)—$NR^{2l}R^{2m}$, —CN, —$(CH_2)_v$—CN, —P(═O)($OR^{2o}$)($OR^{2p}$), —$(CH_2)_z$—$NR^{2d}$—S(═O)$_2$—$R^{2g}$, —C(═O)—N═S(═O)—$R^{2s}R^{2t}$, —C(═O)—N═S(═N—$R^{2u}$)—$R^{2s}R^{2t}$, —B(OH)$_2$, or $Hetcyc^X$;

$Ar^{A1}$, $Ar^{A2}$, $Ar^{A3}$ represent independently from each other phenyl which may be unsubstituted or mono- or di-substituted with independently from each other $R^{A11}$ and/or $R^{A12}$;

$R^{Z1}$ represents H or halogen;

$R^{Z2}$ represents H; or forms together with $R^2$ a divalent radical —S(═O)$_2$—N(H)—C(═O)—;

$R^{2a}$ represents H, un-substituted or substituted $C_{1-8}$-aliphatic, aryl, heteroaryl, saturated or partially unsaturated heterocyclyl, or carbohydrate derived radical, or Cat;

Cat represents a monovalent cation;

$R^{2b}$, $R^{2c}$, $R^{2q}$, $R^{2r}$ represent independently from each other H, un-substituted or substituted $C_{1-8}$-aliphatic including $C_{3-7}$-cycloaliphatic; or form together with the nitrogen atom to which they are attached to an unsubstituted or substituted saturated, partially unsaturated or aromatic heterocycle with 3, 4, 5, 6, 7 ring atoms wherein 1 of said ring atoms is said nitrogen atom and no or one further ring atom is a hetero atom selected from N, O, or S and the remaining are carbon atoms; wherein said heterocycle may optionally be fused with $Hetar^Z$; or one of $R^{2b}$ and $R^{2c}$ represents —CN, —$NH_2$, —OH, —O—$C_{1-6}$-alkyl, —S(═O)$_2$—$R^{2g}$, $Ar^2$, $Hetar^2$, $Cyc^2$, or $Hetcyc^2$, while the other represents H or un-substituted or substituted $C_{1-8}$-aliphatic;

$R^{2d}$, $R^{2j}$, $R^{2k}$, $R^{2o}$, $R^{2p}$ represent independently from each other H, un-substituted or substituted $C_{1-8}$-aliphatic;

$R^{2e}$ represents H, halogen, un-substituted or substituted $C_{1-8}$-aliphatic, heteroaryl;

$R^{2f}$, $R^{2g}$ represent independently from each other un-substituted or substituted $C_{1-8}$-aliphatic;

$R^{2h}$, $R^{2i}$ represent independently from each other H, un-substituted or substituted $C_{1-8}$-aliphatic, aryl, heterocyclyl, heteroaryl; or form together with the nitrogen atom to which they are attached to an unsubstituted or substituted saturated, partially unsaturated or aromatic heterocycle with 3, 4, 5, 6, 7 ring atoms wherein 1 of said ring atoms is said nitrogen atom and no or one further ring atom is a hetero atom selected from N, O, or S and the remaining are carbon atoms;

$R^{2l}$, $R^{2m}$ represent independently from each other H, un-substituted or substituted $C_{1-8}$-aliphatic; or form together with the nitrogen atom to which they are attached to an unsubstituted or substituted saturated, partially unsaturated or aromatic heterocycle with 3, 4, 5, 6, 7 ring atoms wherein 1 of said ring atoms is said nitrogen atom and no or one further ring atom is a hetero atom selected from N, O, or S and the remaining are carbon atoms;

$R^{2s}$, $R^{2t}$ represent independently from each other unsubstituted or substituted $C_{1-8}$-aliphatic; or form together an unsubstituted or substituted divalent $C_{3-6}$-alkylene radical;

$R^{2u}$ represents hydrogen or unsubstituted or substituted $C_{1-6}$-aliphatic;

$R^{A11}$, $R^{A12}$ represent independently from each other halogen or un-substituted or substituted, straight-chain or branched $C_{1-6}$-aliphatic;

$Ar^2$ is a mono- or bicyclic aryl with 5, 6, 7, 8, 9, 10 ring carbon atoms, wherein that aryl may be unsubstituted or substituted with substituents $R^{D1}$, $R^{D2}$, $R^{D3}$, $R^{D4}$, and/or $R^{D5}$ which may be the same or different;

$Hetar^2$ is a mono- or bicyclic heteroaryl with 5, 6, 7, 8, 9, 10 ring atoms wherein 1, 2, 3, 4, 5 of said ring atoms is/are a hetero atom(s) selected from N, O, and/or S and the remaining are carbon atoms, wherein that heteroaryl may be unsubstituted or substituted with substituents $R^{D1}$, $R^{D2}$, $R^{D3}$, $R^{D4}$, and/or $R^{D5}$ which may be the same or different;

$Cyc^2$ is a saturated or partially unsaturated monocyclic carbocycle with 3, 4, 5, 6, or 7 ring carbon atoms, wherein that carbocycle may be unsubstituted or substituted with $R^{D6}$, $R^{D7}$, $R^{D8}$, $R^{D9}$, and/or $R^{D10}$ which may be the same or different; wherein that carbocycle may optionally be fused to $Ar^Z$ or $Hetar^Z$ via 2 adjacent ring atoms of said $Ar^Z$ or $Hetar^Z$ and wherein that fused carbocycle may further be unsubstituted or substituted with $R^{C1}$, $R^{C2}$, $R^{C3}$, $R^{C4}$, $R^{C5}$, $R^{C6}$ which may be the same or different;

$Hetcyc^2$ is a saturated or partially unsaturated, monocyclic heterocycle with 3, 4, 5, 6, 7 ring atoms wherein 1 or 2 of said ring atoms is/are a hetero atom(s) selected from N, O, and/or S and the remaining are carbon atoms, wherein that heterocycle may be unsubstituted or substituted with $R^{D6}$, $R^{D7}$, $R^{D8}$, $R^{D9}$, and/or $R^{D10}$ which may be the same or different;

wherein that heterocycle may optionally be fused to $Ar^Z$ or $Hetar^Z$ via 2 adjacent ring atoms of said $Ar^Z$ or $Hetar^Z$ and wherein that fused heterocycle may further be unsubstituted or substituted with $R^{C1}$, $R^{C2}$, $R^{C3}$, $R^{C4}$, $R^{C5}$, $R^{C6}$ which may be the same or different;

$Ar^X$, $Ar^Z$ are independently from each other an un-substituted or substituted benzo ring;

$Ar^Y$ is an un-substituted or mono- or di-substituted phenyl;

$Hetar^{Y1}$ is a 5 or 6 membered monocyclic heteroaryl wherein 1, 2, 3, 4 ring atoms are hetero atoms selected from N, O, and/or S and the remaining are carbon atoms, wherein that heteroaryl may be unsubstituted or substituted with halogen, $C_{1-4}$-alkyl which may optionally be substituted with OH;

$Hetar^Z$ is an unsubstituted or substituted 5 or 6 membered heteroaryl ring selected from the group consisting of pyrrole, furan, thiophene, pyrazole, imidazole, oxazole, isoxazole, thiazole, oxadiazole, triazole, tetrazole, pyridine, pyrimidine, pyrazine, and pyrane;

$Cyc^{Y1}$ is a saturated monocyclic carbocycle with 3, 4, 5, 6, or 7 ring carbon atoms, wherein that carbocycle may be unsubstituted or substituted with halogen, OH, $C_{1-4}$-alkyl;

$Hetcyc^X$ is a saturated, partially unsaturated or aromatic, monocyclic heterocycle with 3, 4, 5, 6, 7 ring atoms wherein 1, 2, 3, 4 of said ring atoms is/are a hetero atom(s) selected from N, O, and/or S and the remaining are carbon atoms, wherein said heterocycle may be unsubstituted or substituted with $R^{X1}$, $R^{X2}$, $R^{X3}$, $R^{X4}$, $R^{X5}$, $R^{X6}$, $R^{X7}$, and/or $R^{X8}$ which may be the same or different, and wherein that heterocycle is optionally a carboxylic acid bioisostere;

$Hetcyc^Y$ is a saturated, partially unsaturated or aromatic, monocyclic heterocycle with 3, 4, 5, 6, 7 ring atoms wherein 1, 2, 3, 4 of said ring atoms is/are a hetero atom(s) selected from N, O, and/or S and the remaining are carbon atoms;

$Hetcyc^{Y1}$ is a saturated or partially unsaturated monocyclic heterocycle with 5 or 6 ring atoms wherein 1 or 2 of said ring atoms are heteroatoms selected from N, O, and/or S and the remaining are carbon atoms;

$R^{C1}$, $R^{C2}$, $R^{C3}$, $R^{C4}$, $R^{C5}$, $R^{C6}$ represent independently from each other un-substituted or substituted $C_{1-6}$-aliphatic;

$R^{D1}$, $R^{D2}$, $R^{D3}$, $R^{D4}$, $R^{D5}$ represent independently from each other un-substituted or substituted $C_{1-6}$-aliphatic;

$R^{D6}$, $R^{D7}$, $R^{D8}$, $R^{D9}$, $R^{D10}$ represent independently from each other un-substituted or substituted $C_{1-6}$-aliphatic, unsubstituted or substituted $C_{1-6}$-aliphatoxy, halogen, hydroxy;

$Hetar^{Y1}$, $CH_2$-$Hetar^{Y1}$, $Cyc^{Y1}$, $Hetcyc^{Y1}$, —$CH_2$-$Hetcyc^{Y1}$; and/or two of $R^{D6}$, $R^{D7}$, $R^{D8}$, $R^{D9}$, $R^{D10}$ which are attached to the same ring atom of said carbocycle or heterocycle may form a divalent $C_{2-6}$-alkylene radical, wherein one or two non-adjacent carbon units of said alkylene radical may optionally be replaced by independently from each other O, N—H, or N—$C_{1-4}$-alkyl, and wherein that alkylene radical may optionally be substituted with OH, $C_{1-4}$-alkyl, or —O—$C_{1-4}$-alkyl; and/or two of $R^{D6}$, $R^{D7}$, $R^{D8}$, $R^{D9}$, $R^{D10}$ which are attached to different ring atoms of said carbocycle or heterocycle may form a divalent $C_{1-6}$-alkylene radical, wherein one or two non-adjacent carbon units of said alkylene radical may optionally be replaced by independently from each other O, N—H, or N—$C_{1-4}$-alkyl;

$R^{X1}$, $R^{X2}$, $R^{X3}$, $R^{X4}$, $R^{X5}$, $R^{X6}$, $R^{X7}$, $R^{X8}$ represent independently from each other un-substituted or substituted $C_{1-6}$-aliphatic, $C_{1-6}$-aliphatoxy, halogen, —OH, —$NR^{2d}$—S(═O)$_2$—$R^{2g}$, Hetcyc$^Y$, O-Hetcyc$^Y$; and/or two of $R^{X1}$, $R^{X2}$, $R^{X3}$, $R^{X4}$, $R^{X5}$, $R^{X6}$, $R^{X7}$, $R^{X8}$ which are attached to the same carbon atom of said heterocycle form a divalent oxo (═O) group; and/or two of $R^{X1}$, $R^{X2}$, $R^{X3}$, $R^{X4}$, $R^{X5}$, $R^{X6}$, $R^{X7}$, $R^{X8}$ or four of $R^{X1}$, $R^{X2}$, $R^{X3}$, $R^{X4}$, $R^{X5}$, $R^{X6}$, $R^{X7}$, $R^{X8}$ which are attached to the same sulfur atom of said heterocycle form a divalent oxo (═O) group thereby forming either an —S(═O)— or an —S(═O)$_2$-moiety;

halogen is F, Cl, Br, I;

v is 1 or 2;

w is 1 or 2;

x is 0, 1 or 2;

y is 0, 1 or 2;

z is 0, 1 or 2;

or any N-oxide, tautomer or stereoisomer thereof and/or any pharmaceutically acceptable salt of each of the foregoing, including mixtures thereof in all ratios, with the proviso that Ring A represents a five-membered heteroaromatic ring moiety selected from the group consisting of A-1, A-4, A-5, A-6, A-7, A-9, A-10, A-11, A-12, A-13, A-15, A-17, A-19, A-20, A-21, A-23, and A-24;

$R^{A1}$ represents $C_{1-6}$-aliphatic, —$CH_2$—$Ar^{A1}$;

$R^{A2}$ represents H, $C_{1-6}$-aliphatic;

$R^{A3}$ represents H, $C_{1-6}$-aliphatic;

$Ar^{A1}$ represents phenyl which may be unsubstituted or mono-substituted with $R^{A11}$; and $R^{A11}$ represents halogen.

4. The compound according to claim 3, or any N-oxide, tautomer or stereoisomer thereof and/or any pharmaceutically acceptable salt of each of the foregoing, including mixtures thereof in all ratios, wherein $Z^1$ is $CR^{Z1}$;

$Z^2$ is $CR^{Z2}$;

$R^{Z1}$ is H; and $R^{Z2}$ is H; or forms together with $R^2$ a divalent radical —S(═O)$_2$—N(H)—C(═O)—.

5. The compound according to claim 1, or any N-oxide, tautomer or stereoisomer thereof and/or any pharmaceutically acceptable salt of each of the foregoing, including mixtures thereof in all ratios, wherein $R^1$ is selected from the group consisting of:

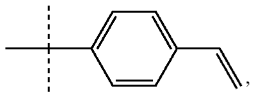

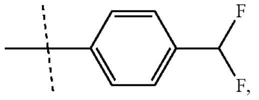

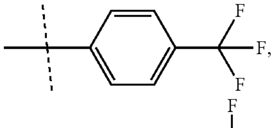

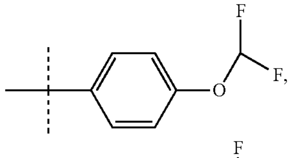

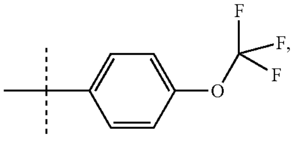

-continued

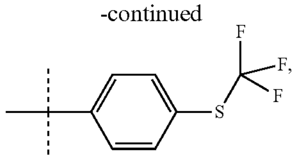

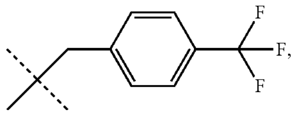

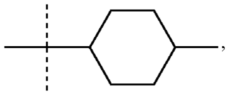

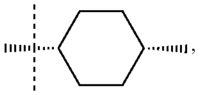

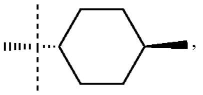

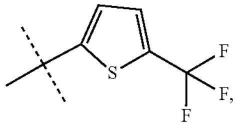

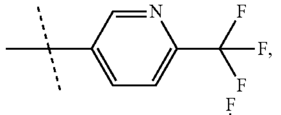

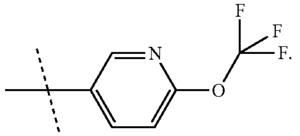

6. The compound according to claim 1, or any N-oxide, tautomer or stereoisomer thereof and/or any pharmaceutically acceptable salt of each of the foregoing, including mixtures thereof in all ratios, wherein $R^2$ represents —C(═O)—$OR^{2a}$, or Hetcyc$^X$;

$R^{2a}$ represents H, straight-chain or branched, unsubstituted or substituted $C_{1-4}$-alkyl or Cat;

Cat represents a monovalent cation selected from the group consisting of lithium (Li), sodium (Na) and potassium (K); and Hetcyc$^X$ represents 1H-1,2,3,4-tetrazol-5-yl, 2H-1,2,3,4-tetrazol-5-yl, 2-methyl-2H-1,2,3,4-tetrazol-5-yl, 5-oxo-2,5-dihydro-1,2,4-oxadiazol-3-yl (2H-1,2,4-oxadiazol-5-on-3-yl), 5-oxo-4,5-dihydro-1,2,4-oxadiazol-3-yl (4H-1,2,4-oxadiazol-5-on-3-yl), 3-bromo-4,5-dihydro-1,2-oxazol-5-yl, 3-chloro-4,5-dihydro-1,2-oxazol-5-yl, 3-(1H-1,2,3-triazol-1-yl)-4,5-dihydro-1,2-oxazol-5-yl, 3-(2H-1,2,3-triazol-2-yl)-4,5-dihydro-1,2-oxazol-5-yl, 3-(pyrimidin-5-yloxy)-4,5-dihydro-1,2-oxazol-5-yl, 3-hydroxy-oxetan-3-yl, 5-hydroxy-4H-pyran-4-on-2-yl, 3,3-difluoropyrrolidin-2-on-4-yl, 3,3-difluoropyrrolidin-2-on-5-yl, 3,3-difluoro-2,3-dihydro-1H-pyrrol-2-on-4-yl, 3,3-difluoro-2,3-dihydro-1H-pyrrol-2-on-5-yl.

7. The compound according to claim 1, or any N-oxide, tautomer or stereoisomer thereof and/or any pharmaceutically acceptable salt of each of the foregoing, including mixtures thereof in all ratios, wherein $R^2$ represents —C(═O)—$NR^{2b}R^{2c}$;

$R^{2b}$ and $R^{2c}$ represent independently from each other H or straight-chain or branched $C_{1-8}$-aliphatic which may be unsubstituted or substituted with 1, 2, 3, 4, or 5 substituents which may be the same or different;

or form together with the nitrogen atom to which they are attached to an unsubstituted or substituted saturated, partially unsaturated or aromatic heterocycle with 3, 4, 5, 6, 7 ring atoms wherein 1 of said ring atoms is said nitrogen atom and no or one further ring atom is a hetero atom selected from N, O, or S and the remaining are carbon atoms; wherein said heterocycle may optionally be fused with $Hetar^Z$; and or one of $R^{2b}$ and $R^{2c}$ represents H and the other represents $Cyc^2$ or $Hetcyc^2$.

8. The compound according to claim 7, or any N-oxide, tautomer or stereoisomer thereof and/or any pharmaceutically acceptable salt of each of the foregoing, including mixtures thereof in all ratios, wherein (a)

$R^{2b}$ represents hydrogen, $R^{2c}$ represents hydrogen; straight-chain or branched $C_{1-8}$-alkyl which may be unsubstituted or substituted with $R^{E1}$, $R^{E2}$, $R^{E3}$, $R^{E4}$, and/or $R^{E5}$ which may be the same or different, $Cyc^2$ or $Hetcyc^2$, wherein $R^{E1}$, $R^{E2}$, $R^{E3}$, $R^{E4}$, and/or $R^{E5}$ represent independently from each other halogen; —$NR^{Ea}R^{Eb}$, —OH, $OR^{Ec}$, $Ar^E$, $Hetar^E$, $Cyc^E$, $Hetcyc^E$;

$Ar^E$ is a mono- or bicyclic aryl with 6 or 10 ring carbon atoms, wherein that aryl may be unsubstituted or substituted with substituents $R^{F1}$, $R^{F2}$, and/or $R^{F3}$ which may be the same or different;

$Hetar^E$ is a monocyclic heteroaryl with 5 or 6 ring atoms or a bicyclic heteroaryl with 9 or 10 ring atoms wherein 1, 2, 3, or 4 of said ring atoms is/are a hetero atom(s) selected from N, O, and/or S and the remaining are carbon atoms, wherein that heteroaryl may be unsubstituted or substituted with substituents $R^{F1}$, $R^{F2}$, and/or $R^{F3}$ which may be the same or different;

$Cyc^E$ is a saturated or partially unsaturated, mono- or bicyclic carbocycle with 3, 4, 5, 6, 7 or 8 ring carbon atoms, wherein that carbocycle may be unsubstituted or substituted with $R^{G1}$ and/or $R^{G2}$ which may be the same or different;

$Hetcyc^E$ is a saturated or partially unsaturated, monocyclic heterocycle with 4, 5, or 6 ring atoms wherein 1 or 2 of said ring atoms is/are a hetero atom(s) selected from N, O, and/or S and the remaining are carbon atoms, wherein that heterocycle may be unsubstituted or substituted with $R^{G1}$ and/or $R^{G2}$ which may be the same or different;

$R^{Ea}$, $R^{Eb}$ represent independently from each other H, $C_{1-4}$-alkyl, —C(=O)—$OC_{1-4}$-alkyl;

$R^{Ec}$ represents H or $C_{1-4}$-alkyl;

$R^{F1}$, $R^{F2}$, and/or $R^{F3}$ represent independently from each other straight-chain or branched $C_{1-6}$-alkyl, which $C_{1-6}$-alkyl may be unsubstituted or monosubstituted with —CN, OH, —O—$C_{1-4}$-alkyl or substituted with 1, 2, or 3 halogen; straight-chain or branched $C_{1-4}$-alkoxy, which $C_{1-4}$-alkoxy may be unsubstituted or substituted with 1, 2, or 3 halogen; straight-chain or branched —S—$C_{1-4}$-alkyl, which —S—$C_{1-4}$-alkyl may be unsubstituted or substituted with 1, 2, or 3 halogen; $C_{3-7}$-cyclopropyl optionally substituted with halogen, OH, and/or $C_{1-4}$-alkyl; F, Cl, Br, —CN, —S(—O)—$C_{1-3}$-alkyl, S(=O)$_2$—$C_{1-3}$-alkyl, —$NH_2$, —NH ($C_{1-3}$-alkyl), —N($C_{1-3}$-alkyl)$_2$, —OH;

and/or two of $R^{F1}$, $R^{F2}$, $R^{F3}$ which are attached to two different ring atoms of that aryl or heteroaryl form a divalent $C_{1-6}$-alkylene radical wherein optionally one or two non-adjacent carbon units of that alkylene radical may be replaced by independently from each other O, NH, N—$C_{1-4}$-alkyl;

$R^{G1}$ and/or $R^{G2}$ represent independently from each other halogen, hydroxy, unsubstituted or substituted $C_{1-6}$-aliphatic;

and/or $R^{G1}$ and $R^{G2}$ which are attached to the same ring atom of that carbocycle or heterocycle form a divalent $C_{2-6}$-alkylene radical wherein optionally one or two non-adjacent carbon units of that alkylene radical may be replaced by independently from each other O, NH, N—$C_{1-4}$-alkyl, and wherein that alkylene radical may optionally be substituted with OH, $C_{1-4}$-alkyl, or —O—$C_{1-4}$-alkyl;

and/or $R^{G1}$ and $R^{G2}$ which are attached to two different ring atoms of that carbocycle or heterocycle form a divalent $C_{1-6}$-alkylene radical wherein optionally one or two non-adjacent carbon units of that alkylene radical may be replaced by independently from each other O, NH, N—$C_{1-4}$-alkyl;

$Cyc^2$ is a saturated monocyclic carbocycle with 3, 4, 5, 6, or 7 ring carbon atoms, wherein that carbocycle may be unsubstituted or substituted independently from each other with $R^{D6}$, $R^{D7}$, $R^{D8}$, $R^{D9}$, and/or $R^{D10}$ wherein that carbocycle may optionally be fused to $Ar^Z$ or $Hetar^Z$ via 2 adjacent ring atoms and wherein that fused carbocycle may optionally further be substituted with independently from each other $R^{C1}$, $R^{C2}$, and/or $R^{C3}$;

$Hetcyc^2$ is a saturated monocyclic heterocycle with 4, 5, or 6 ring atoms wherein 1 or 2 of said ring atoms is/are a hetero atom(s) selected from N, O, and/or S and the remaining are carbon atoms, wherein that heterocycle may be unsubstituted or substituted independently from each other with $R^{D6}$, $R^{D7}$, $R^{D8}$, $R^{D9}$, and/or $R^{D10}$ wherein that heterocycle may optionally be fused to $Ar^Z$ or $Hetar^Z$ and wherein that fused heterocycle may optionally further be substituted with independently from each other $R^{C1}$, $R^{C2}$, and/or $R^{C3}$;

$R^{C1}$, $R^{C2}$, $R^{C3}$ represent $C_{1-4}$-alkyl;

$R^{D6}$, $R^{D7}$, $R^{D8}$, $R^{D9}$, $R^{D10}$ represent independently from each other halogen; hydroxy; $C_{1-4}$-alkyl optionally substituted with —OH and/or halogen; —O—$C_{1-4}$-alkyl; $Hetar^{Y1}$, —$CH_2$-$Hetar^{Y1}$, $Cyc^{Y1}$, $Hetcyc^{Y1}$, —$CH_2$-$Hetcyc^{Y1}$;

and/or two of $R^{D6}$, $R^{D7}$, $R^{D8}$, $R^{D9}$, $R^{D10}$ which are attached to the same ring atom of that carbocycle or heterocycle form a divalent $C_{2-6}$-alkylene radical wherein optionally one or two non-adjacent carbon units of that alkylene radical may be replaced by independently from each other O, NH, N—$C_{1-4}$-alkyl, and wherein that alkylene radical may optionally be substituted with OH, $C_{1-4}$-alkyl, or —O—$C_{1-4}$-alkyl;

and/or two of $R^{D6}$, $R^{D7}$, $R^{D8}$, $R^{D9}$, $R^{D10}$ which are attached to two different ring atoms of that carbocycle or heterocycle form a divalent $C_{1-6}$-alkylene radical wherein optionally one or two non-adjacent carbon units of that alkylene radical may be replaced by independently from each other O, NH, N—$C_{1-4}$-alkyl;

$Ar^Z$ is benzo;

$Hetar^{Y1}$ is a 5 or 6 membered monocyclic heteroaryl wherein 1, 2, 3, 4 ring atoms are hetero atoms selected from N, O, and/or S and the remaining are carbon atoms, wherein that heteroaryl may be unsubstituted or substituted with F, $C_{1-4}$-alkyl which may optionally be substituted with OH;

$Hetar^{Y2}$ is a 5 or 6 membered monocyclic heteroaryl wherein 1, 2, 3, 4 ring atoms are hetero atoms selected from N, O, and/or S and the remaining are carbon atoms, wherein that heteroaryl may be unsubstituted or substituted with halogen, $C_{1-4}$-alkyl which may optionally be substituted with OH;

$Hetar^Z$ is pyrrole, N-methyl-pyrrole, pyrazole, imidazole, triazole;

$Cyc^{Y1}$ is a saturated monocyclic carbocycle with 3, 4, 5, 6, or 7 ring carbon atoms, wherein that carbocycle may be unsubstituted or substituted with halogen, OH, $C_{1-4}$-alkyl;

$Hetcyc^{Y1}$ is a saturated or partially unsaturated monocyclic heterocycle with 5 or 6 ring atoms wherein 1 or 2 of said ring atoms are heteroatoms selected from N, O, and/or S and the remaining are carbon atoms;

$Hetcyc^{Y2}$ is a saturated or partially unsaturated monocyclic heterocycle with 5 or 6 ring atoms wherein 1 or 2 of said ring atoms are heteroatoms selected from N, O, and/or S and the remaining are carbon atoms;

or (b)

$R^{2b}$ and $R^{2c}$ form together with the nitrogen atom to which they are attached a saturated or partially unsaturated heterocycle optionally substituted with independently from each other $R^{Y1}$, $R^{Y2}$, $R^{Y3}$, $R^{Y4}$, and/or $R^{Y5}$; wherein that heterocycle may optionally be fused with $Hetar^Z$; and wherein that heterocycle is selected from the group consisting of: azetidine, pyrrolidine, piperidine, piperazine, morpholine;

$R^{Y1}$, $R^{Y2}$, $R^{Y3}$, $R^{Y4}$, $R^{Y5}$ represent independently from each other halogen; —$NH_2$, —N(H)—$C_{1-4}$-alkyl, —N(H)—C(═O)—O—$C_{1-4}$-alkyl, —N($C_{1-4}$-alkyl)$_2$; —OH; $C_{1-4}$-alkyl optionally substituted with —OH, —O—$C_{1-4}$-alkyl, —O—$C_{3-7}$-cycloalkyl, —O—$CH_2C_{3-7}$-cycloalkyl, —O—$C_{1-4}$-alkyl; $Hetar^{Y2}$; —$CH_2$-$Hetar^{Y2}$; $Hetcyc^{Y2}$;

and/or two of $R^{Y1}$, $R^{Y2}$, $R^{Y3}$, $R^{Y4}$, $R^{Y5}$ which are attached to the same ring atom of that heterocycle form a divalent $C_{2-6}$-alkylene radical wherein optionally one or two non-adjacent carbon units of that alkylene radical may be replaced by independently from each other O, NH, N—$C_{1-4}$-alkyl;

and/or two of $R^{Y1}$, $R^{Y2}$, $R^{Y3}$, $R^{Y4}$, $R^{Y5}$ which are attached to two different ring atoms of that heterocycle form a divalent $C_{1-6}$-alkylene radical wherein optionally one or two non-adjacent carbon units of that alkylene radical may be replaced by independently from each other O, NH, N—$C_{1-4}$-alkyl;

$Hetar^{Y2}$ is a 5 or 6 membered monocyclic heteroaryl wherein 1, 2, 3, 4 ring atoms are hetero atoms selected from N, O, and/or S and the remaining are carbon atoms, wherein that heteroaryl may be unsubstituted or substituted with halogen, $C_{1-4}$-alkyl which may optionally be substituted with OH;

$Hetar^Z$ is pyrrole, N-methyl-pyrrole, pyrazole, imidazole, triazole;

$Hetcyc^{Y2}$ is a saturated or partially unsaturated monocyclic heterocycle with 5 or 6 ring atoms wherein 1 or 2 of said ring atoms are heteroatoms selected from N, O, and/or S and the remaining are carbon atoms;

or (c)

$R^{2b}$ represents a straight-chain of branched $C_{1-4}$-alkyl optionally substituted with OH; and $R^{2c}$ represents $Cyc^2$, $Hetcyc^2$ or straight-chain or branched $C_{1-8}$-alkyl which may be unsubstituted or substituted with independently from each other $R^{E1}$, $R^{E2}$, $R^{E3}$, $R^{E4}$, and/or $R^{E5}$ which may be the same or different.

9. The compound according to claim 8, or any N-oxide, tautomer or stereoisomer thereof and/or any pharmaceutically acceptable salt of each of the foregoing, including mixtures thereof in all ratios, wherein (a)

$R^{2b}$ represents hydrogen, $R^{2c}$ represents hydrogen; straight-chain or branched $C_{1-8}$-alkyl which may be unsubstituted or substituted with $R^{E1}$, $R^{E2}$, $R^{E3}$, $R^{E4}$, and/or $R^{E5}$ which may be the same or different, $Cyc^2$ or $Hetcyc^2$, wherein $R^{E1}$, $R^{E2}$, $R^{E3}$, $R^{E4}$, and/or $R^{E5}$ represent independently from each other halogen; —$NR^{Ea}R^{Eb}$, —OH, $OR^{Ec}$, $Ar^E$, $Hetar^E$, $Cyc^E$, $Hetcyc^E$;

$Ar^E$ is a mono- or bicyclic aryl with 6 or 10 ring carbon atoms, wherein that aryl may be unsubstituted or substituted with substituents $R^{F1}$, $R^{F2}$, and/or $R^{F3}$ which may be the same or different;

$Hetar^E$ is a monocyclic heteroaryl with 5 or 6 ring atoms or a bicyclic heteroaryl with 9 or 10 ring atoms wherein 1, 2, 3, or 4 of said ring atoms is/are a hetero atom(s) selected from N, O, and/or S and the remaining are carbon atoms, wherein that heteroaryl may be unsubstituted or substituted with substituents $R^{F1}$, $R^{F2}$, and/or $R^{F3}$ which may be the same or different;

$Cyc^E$ is a saturated or partially unsaturated, mono- or bicyclic carbocycle with 3, 4, 5, 6, 7 or 8 ring carbon atoms, wherein that carbocycle may be unsubstituted or substituted with $R^{G1}$ and/or $R^{G2}$ which may be the same or different;

$Hetcyc^E$ is a saturated or partially unsaturated, monocyclic heterocycle with 5 or 6 ring atoms wherein 1 or 2 of said ring atoms is/are a hetero atom(s) selected from N, O, and/or S and the remaining are carbon atoms, wherein that heterocycle may be unsubstituted or substituted with $R^{G1}$ and/or $R^{G2}$ which may be the same or different;

$R^{Ea}$, $R^{Eb}$ represent independently from each other H, $C_{1-4}$-alkyl, —C(═O)—$OC_{1-4}$-alkyl;

$R^{Ec}$ represents H or $C_{1-4}$-alkyl;

$R^{F1}$, $R^{F2}$, and/or $R^{F3}$ represent independently from each other straight-chain or branched $C_{1-6}$-alkyl, which $C_{1-6}$-alkyl may be unsubstituted or monosubstituted with-CN OH, —O—$C_{1-4}$-alkyl or substituted with 1, 2, or 3 halogen, straight-chain or branched $C_{1-4}$-alkoxy, which $C_{1-4}$-alkoxy may be unsubstituted or substituted with 1, 2, or 3 halogen, straight-chain or branched —S—$C_{1-4}$-alkyl, which —S—$C_{1-4}$-alkyl may be unsubstituted or substituted with 1, 2, or 3 halogen, $C_{3-7}$-cyclopropyl optionally substituted with halogen, OH and/or $C_{1-4}$-alkyl, F, Cl, Br, —CN, —S(═O)—$C_{1-3}$-alkyl, S(═O)$_2$—$C_{1-3}$-alkyl, —$NH_2$, —NH($C_{1-3}$-alkyl), —N($C_{1-3}$-alkyl)$_2$, —OH;

$R^{G1}$ and/or $R^{G2}$ represent independently from each other halogen, hydroxy, unsubstituted or substituted $C_{1-4}$-alkyl, —O—$C_{1-4}$-alkyl;

$Cyc^2$ is a saturated monocyclic carbocycle with 3, 4, 5, 6, or 7 ring carbon atoms, wherein that carbocycle may be unsubstituted or mono-substituted with $R^{D6}$, wherein $R^{D6}$ is $C_{1-4}$-alkyl which is unsubstituted or mono-substituted with —OH;

$Hetcyc^2$ is a saturated monocyclic heterocycle with 5 or 6 ring atoms wherein 1 or 2 of said ring atoms is/are a hetero atom(s) selected from N, O, and/or S and the remaining are carbon atoms, wherein that heterocycle may be unsubstituted or mono-substituted with hydroxy;

or (b)

$R^{2b}$ and $R^{2c}$ form together with the nitrogen atom to which they are attached a 3-hydroxypyrrolidinyl, 2-methyl-3-hydroxypyrrolidinyl, or 3-hydroxypiperidinyl ring.

10. The compound according to claim 1, or any N-oxide, tautomer or stereoisomer thereof and/or any pharmaceutically acceptable salt of each of the foregoing, including mixtures thereof in all ratios, wherein $R^2$ represents $-(CH_2)_x-NR^{2d}-C(=O)-R^{2e}$, $-S-R^{2f}$, $-S(=O)-R^{2f}$, $-S(=O)_2-R^{2g}$, $-S(=O)_2-NR^{2h}R^{2i}$, $-S(=O)_2-OH$, $-S(=O)(=NR^{2j})-OH$, $-S(=O)(=NR^{2j})-R^{2g}$, $-S(=O)(=NR^{2k})-NR^{2l}R^{2m}$, $-(CH_2)_z-NR^{2d}-S(=O)_2-R^{2g}$;

$R^{2e}$ represents H, $C_{1-6}$-alkyl optionally substituted with —OH or a monocyclic 5- or 6-membered heteroaryl; $C_{3-7}$-cycloalkyl, monocyclic 5- or 6-membered heteroaryl;

$R^{2f}$, $R^{2g}$ represent independently from each other un-substituted or substituted $C_{1-8}$-aliphatic;

$R^{2h}$, $R^{2i}$ represent independently from each other H, un-substituted or substituted $C_{1-8}$-aliphatic, aryl, heterocyclyl, heteroaryl; or form together with the nitrogen atom to which they are attached to an unsubstituted or substituted saturated, partially unsaturated or aromatic heterocycle with 3, 4, 5, 6, 7 ring atoms wherein 1 of said ring atoms is said nitrogen atom and no or one further ring atom is a hetero atom selected from N, O, or S and the remaining are carbon atoms;

$R^{2d}$, $R^{2j}$, $R^{2k}$ represent independently from each other H, un-substituted or substituted $C_{1-8}$-aliphatic;

$R^{2l}$, $R^{2m}$ represent independently from each other H, un-substituted or substituted $C_{1-8}$-aliphatic; or form together with the nitrogen atom to which they are attached to an unsubstituted or substituted saturated, partially unsaturated or aromatic heterocycle with 3, 4, 5, 6, 7 ring atoms wherein 1 of said ring atoms is said nitrogen atom and no or one further ring atom is a hetero atom selected from N, O, or S and the remaining are carbon atoms;

$R^{2s}$, $R^{2t}$ represent independently from each other $C_{1-6}$-alkyl which may optionally be substituted with —OH, O—$C_{1-4}$-alkyl, $NH_2$, $NHC_{1-4}$-alkyl, $N(C_{1-4}\text{-alkyl})_2$, pyrrolidinyl, piperidinyl, morpholinyl, piperazinyl; or form together a divalent $C_{3-4}$-alkylene radical which may optionally be substituted with —$NH_2$, —CN, or a divalent $C_{2-5}$-alkylene radical wherein optionally one of the carbon units of said $C_{2-5}$-alkylene radical may be replaced by O, NH, or N—$C_{1-4}$-alkyl;

$R^{2u}$ represents hydrogen or $C_{1-4}$-alkyl;

x represents 0 or 1; and z represents 0 or 1.

11. The compound according to claim 1, or any N-oxide, tautomer or stereoisomer thereof and/or any pharmaceutically acceptable salt of each of the foregoing, including mixtures thereof in all ratios, wherein Ring A represents a five-membered heteroaromatic ring moiety selected from the group consisting of:

A-1a

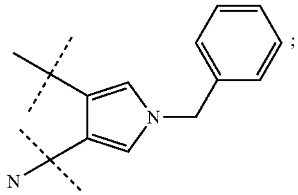

;

A-4a

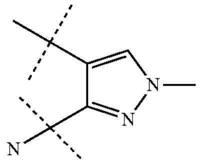

,

A-4b

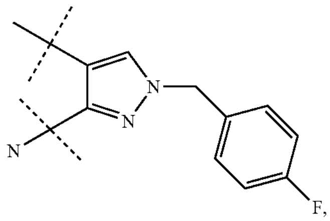

,

A-4c

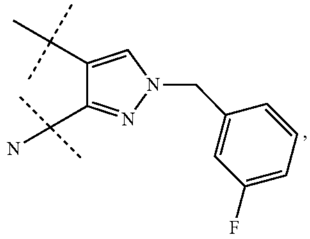

,

A-4d

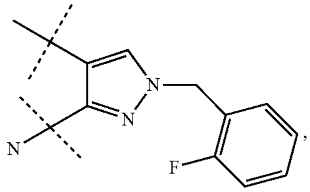

,

A-4e

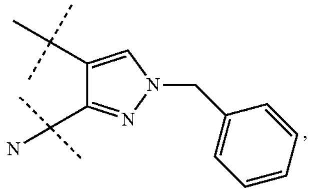

,

A-4f

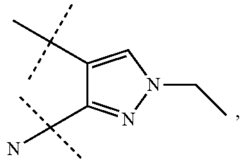

,

A-4g

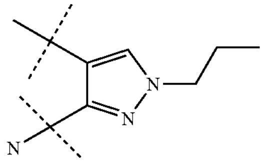

,

-continued
A-4h
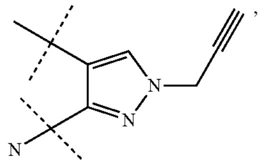
A-4i
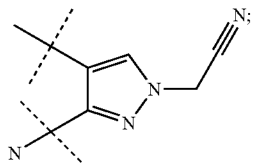
A-5a
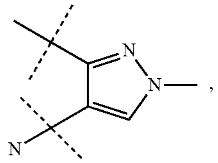
A-5b
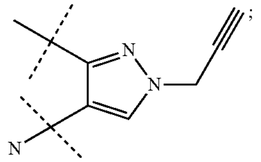
A-7a
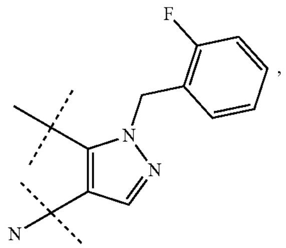
A-7b
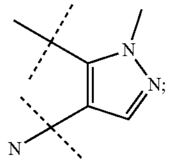
A-9a
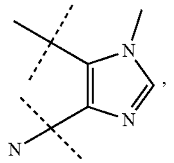
A-9b
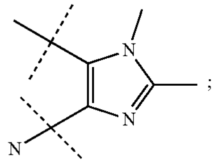
-continued
A-10a
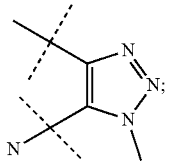
A-12a
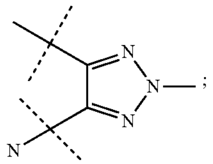
A-13a
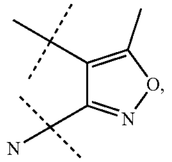
A-13b
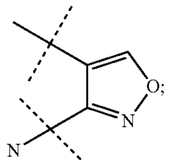
A-15a
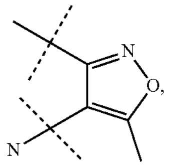
A-15b
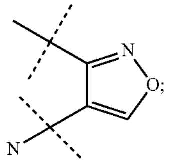
A-17a
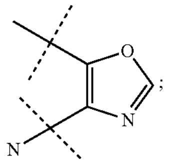
A-19a
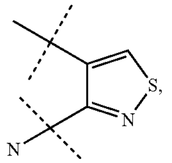
A-19b
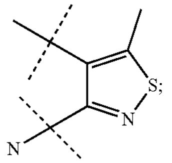

-continued

A-21a

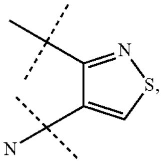

A-21b

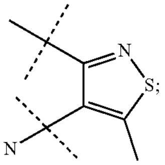

A-23a

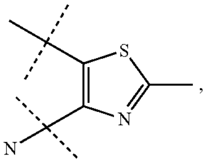

A-23b

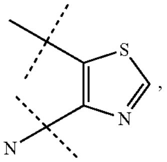

A-23c

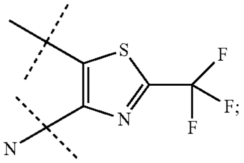

A-24a

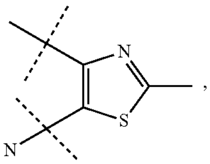

and

A-24b

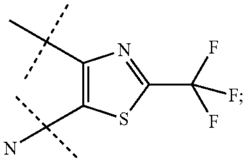

$Z^1$ is CH;

$Z^2$ is CH;

$Z^3$ is CH or N;

$R^1$ represents phenyl, 3-fluorophenyl, 4-fluorophenyl, 4-chlorophenyl, 4-methylphenyl, 4-ethylphenyl, 4-difluoromethylphenyl, 3-trifluoromethylphenyl, 4-trifluoromethylphenyl, 4-(1,1-difluorethyl) phenyl, 4-(2,2,2-trifluorethyl) phenyl, 4-(1-trifluoromethylcyclopropyl)-phen-1-yl, 4-cyclopentylphenyl, 4-ethoxyphenyl, 4-difluormethoxyphenyl, 4-trifluoromethoxyphenyl, 4-(trifluoromethyl) sulfanylphenyl, 2-fluoro-4-trifluoromethylphenyl, 2-fluoro-4-trifluoromethoxyphenyl, 3-fluoro-4-(n-propyl) phenyl, 2,3-dimethyl-4-methoxyphenyl, 6-fluoronaphth-2-yl; 5-trifluoromethylfuran-2-yl; 5-trifluoromethylthiophen-2-yl, 2-trifluoromethyl-1,3-thiazol-4-yl 6-methylpyridin-3-yl, 6-methoxypyridin-3-yl, 6-ethylpyridin-3-yl, 4-trifluoromethylpyridin-2-yl, 6-trifluoromethylpyridin-3-yl (2-trifluoromethylpyridin-5-yl), 6-trifluoromethoxypyridin-3-yl (2-trifluoromethoxypyridin-5-yl), cyclopentyl, 3-methylcyclopentyl, 3,3-dimethylcyclopentyl, 3-trifluoromethylbicyclo[1.1.1]petan-1-yl, cyclohexyl, 4-methylcyclohexyl, 4-(trifluoromethyl) cyclohexyl, 4,4-difluorocyclohexyl, cyclohex-1-enyl, 6,6-difluorospiro[3.3]heptan-2-yl, benzenesulfonyl (phenylsulfonyl), benzyl, 3-chlorophenylmethyl, 4-chlorophenylmethyl, 3-methylphenylmethyl, 4-methylphenylmethyl, cyclohexylmethyl, 4-trifluoromethylcyclohexylmethyl, 4-methoxycyclohexylmethyl, 3-trifluoromethyl-bicyclo[1.1.1]petan-1-ylmethyl; and $R^2$ represents —C(═O)—OH, —C(═O)—ONa, —C(═O)—$OCH_3$, —C(═O)—$NH_2$, —C(═O)—$NHCH_3$, —C(═O)—$NHCH_2CH_3$, —C(═O)—NH$(CH_2)_2CH_3$, —C(═O)—N(H)-cyclopropyl, —C(═O)—N(H)-(1-hydroxymethyl) cyclobutan-1-yl, —C(═O)—N(H)—$CH_2CH_2$—OH, —C(═O)—N(H)—$CH_2CH_2$—$OCH_3$, —C(═O)—N(H)—$CH_2$—C(H)(OH)—$CH_3$, —C(═O)—N(H)—$CH_2C(CH_3)_2OH$, —C(═O)—N(H)—C(H)($CH_3$)—$CH_2OH$, —C(═O)—N(H)—C(H)($CH_2CH_3$)—$CH_2OH$, —C(═O)—N(H)—C(H)($CH_2OH$)—$CH_2CH_2$—O—$CH_3$, —C(═O)—N(H)—$C(CH_3)_2CH_2CH_2OH$, —C(═O)—N(H)—C(H)($CH_2OH$)-phenyl, —C(═O)—N(H)—C($CH_3$)($CH_2OH$)-phenyl, —C(═O)—N(H)—C(H)(CH(OH) $CH_3$)-phenyl, —C(═O)—N(H)—$CH_2$-1H-1-methylimidazol-2-yl, —C(═O)—N(H)—$(CH_2)_2$-1H-imidazol-1-yl, —C(═O)—N(H)—$CH_2$-pyridin-2-yl, —C(═O)—N(H)—$CH_2$-pyridin-3-yl, —C(═O)—N(H)—$CH_2$-pyridin-4-yl, —C(═O)—N(H)—C(H)($CH_2OH$)-pyridin-2-yl, —C(═O)—N(H)—$CH_2$-1,3-pyrimidin-2-yl, —C(═O)—N(H)—$CH_2$-1,3-pyrimidin-4-yl, —C(═O)—N(H)—$CH_2$-pyridazin-2-yl, —C(═O)—NH—C($CH_2OH$)-cyclobutyl, —C(═O)-3-hydroxy-pyrrolidin-1-yl, —NH—C(═O)—CH═$CH_2$, —NH—C(═O)—CF═$CH_2$, —NH—C(═O)—$CH_2Cl$, —NH—C(═O)—C≡CH, —$CH_2$—NH—C(═O)—CH—$CH_2$, —$CH_2$—NH—C(═O)—$CH_2Cl$, —$CH_2$—NH—C(═O)—C≡CH, —S(═O)—$CH_3$, —$S(═O)_2$—$CH_3$, —$S(═O)_2$—OH, —$S(═O)_2$—$NH_2$, —$S(═O)_2$—$NHCH_3$, —S(═O)(═NH)—N$(CH_3)_2$, —S(═O)(═N—$CH_3$)—N$(CH_3)_2$, —S(═O)(═N—$CH_3$)—OH, —S(═O)(═NH)—$CH_3$, —P(═O)$(OH)_2$.

12. The compound according to claim 3, or any N-oxide, tautomer or stereoisomer thereof and/or any pharmaceutically acceptable salt of each of the foregoing, including mixtures thereof in all ratios, wherein Ring A represents a five-membered heteroaromatic ring moiety selected from the group consisting of:

A-1a

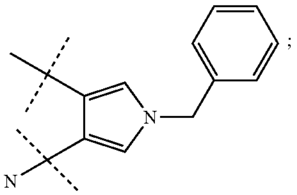

-continued
A-4a
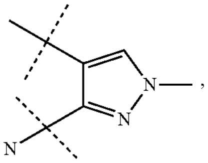
A-4b
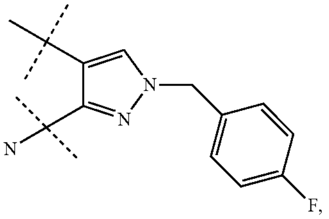
A-4c
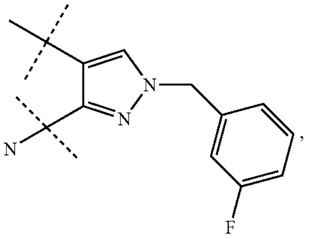
A-4d
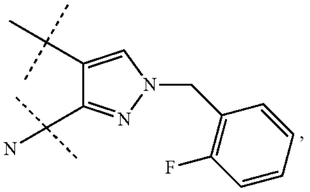
A-4e
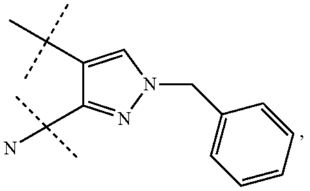
A-4f
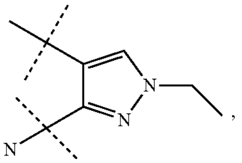
A-4g
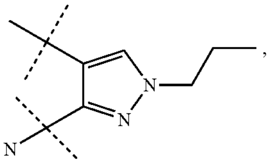
A-4h
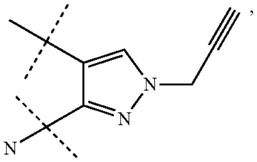
-continued
A-4i
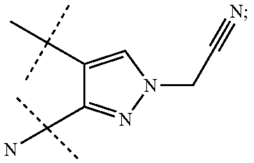
A-5a
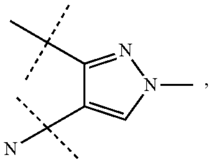
A-5b
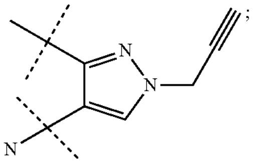
A-7a
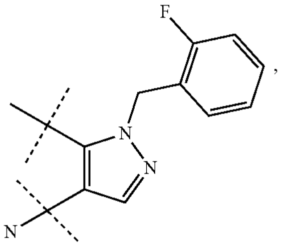
A-7b
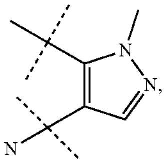
A-9a
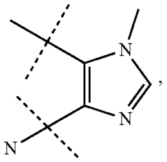
A-9b
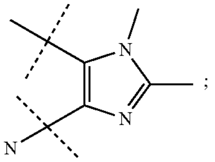
A-10a
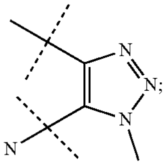

-continued

A-12a

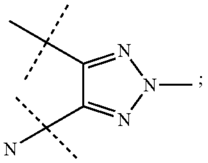

A-13a

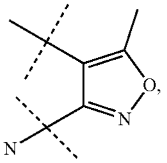

A-13b

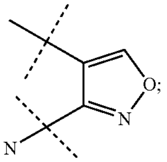

A-15a

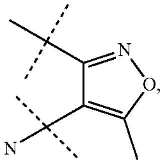

A-15b

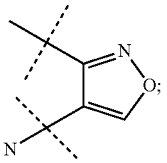

A-17a

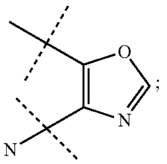

A-19a

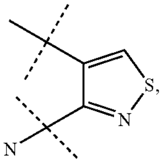

A-19b

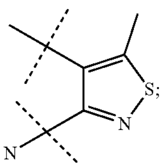

A-21a

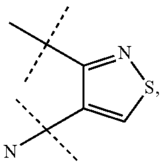

-continued

A-21b

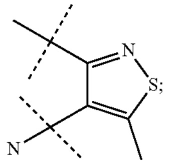

A-23a

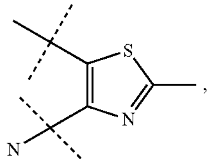

A-23b

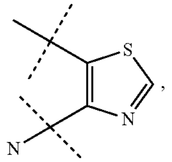

A-23c

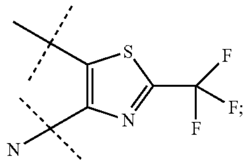

A-24a

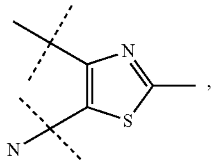

and

A-24b

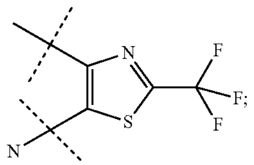

$Z^1$ is CH;

$Z^2$ is CH;

$R^1$ represents phenyl, 3-fluorophenyl, 4-fluorophenyl, 4-chlorophenyl, 4-methylphenyl, 4-ethylphenyl, 4-difluoromethylphenyl, 3-trifluoromethylphenyl, 4-trifluoromethylphenyl, 4-(1,1-difluorethyl) phenyl, 4-(2,2,2-trifluorethyl) phenyl, 4-(1-trifluoromethylcyclopropyl)-phen-1-yl, 4-cyclopentylphenyl, 4-ethoxyphenyl, 4-difluormethoxyphenyl, 4-trifluoromethoxyphenyl, 4-(trifluoromethyl) sulfanylphenyl, 2-fluoro-4-trifluoromethylphenyl, 2-fluoro-4-trifluoromethoxyphenyl, 3-fluoro-4-(n-propyl) phenyl, 2,3-dimethyl-4-methoxyphenyl, 6-fluoronaphth-2-yl; 5-trifluoromethylfuran-2-yl; 5-trifluoromethylthiophen-2-yl, 2-trifluoromethyl-1,3-thiazol-4-yl, 6-methylpyridin-3-yl, 6-methoxypyridin-3-yl, 6-ethylpyridin-3-yl, 4-trifluoromethylpyridin-2-yl, 6-trifluoromethylpyridin-3-yl (2-trifluoromethylpyridin-5-yl), 6-trifluoromethoxypyridin-3-yl (2-trifluoromethoxypyridin-5-yl), cyclopentyl, 3-methylcyclopentyl, 3,3-dimethylcyclopentyl, 3-trifluoromethylbicyclo[1.1.1]petan-1-yl, cyclohexyl, 4-methylcyclohexyl, 4-(trifluoromethyl) cyclohexyl, 4,4-difluorocyclohexyl, cyclohex-1-enyl, 6,6-difluorospiro[3.3]heptan-2-yl, benzenesulfonyl (phenylsulfonyl), benzyl, 3-chlorophenylmethyl, 4-chlorophenylmethyl, 3-methylphenylmethyl, 4-methylphenylmethyl, cyclohexylmethyl, 4-trifluoromethylcyclohexylmethyl, 4-methoxycyclohexylmethyl, 3-trifluoromethyl-bicyclo[1.1.1]petan-1-ylmethyl; and $R^2$ represents —C(═O)—OH, —C(═O)—ONa, —C(═O)—$OCH_3$, —C(═O)—$NH_2$, —C(═O)—$NHCH_3$, —C(═O)—$NHCH_2CH_3$, —C(═O)—NH$(CH_2)_2CH_3$, —C(═O)—N(H)-cyclopropyl, —C(═O)—N(H)-(1-hydroxymethyl) cyclobutan-1-yl, —C(═O)—N(H)—$CH_2CH_2$—OH, —C(═O)—N(H)—$CH_2CH_2$—$OCH_3$, —C(═O)—N(H)—$CH_2$—C(H)(OH)—$CH_3$, —C(═O)—N(H)—$CH_2C(CH_3)_2OH$, —C(═O)—N(H)—C(H)($CH_3$)—$CH_2OH$, —C(═O)—N(H)—C(H)($CH_2CH_3$)—$CH_2OH$, —C(═O)—N(H)—C(H)($CH_2OH$)—$CH_2CH_2$—O—$CH_3$, —C(═O)—N(H)—$C(CH_3)_2CH_2CH_2OH$, —C(═O)—N(H)—C(H)($CH_2OH$)-phenyl, —C(═O)—N(H)—C($CH_3$)($CH_2OH$)-phenyl, —C(═O)—N(H)—C(H)(CH(OH) $CH_3$)-phenyl, —C(═O)—N(H)—$CH_2$-1H-1-methylimidazol-2-yl, —C(═O)—N(H)—$(CH_2)_2$-1H-imidazol-1-yl, —C(═O)—N(H)—$CH_2$-pyridin-2-yl, —C(═O)—N(H)—$CH_2$-pyridin-3-yl, —C(═O)—N(H)—$CH_2$-pyridin-4-yl, —C(═O)—N(H)—C(H)($CH_2OH$)-pyridin-2-yl, —C(═O)—N(H)—$CH_2$-1,3-pyrimidin-2-yl, —C(═O)—N(H)—$CH_2$-1,3-pyrimidin-4-yl, —C(═O)—N(H)—$CH_2$-pyridazin-2-yl, —C(═O)—NH—C($CH_2OH$)-cyclobutyl, —C(═O)-3-hydroxy-pyrrolidin-1-yl, —NH—C(═O)—CH═$CH_2$, —NH—C(═O)—CF═$CH_2$, —NH—C(═O)—$CH_2Cl$, —NH—C(═O)—C≡CH, —$CH_2$—NH—C(═O)—CH═$CH_2$, —$CH_2$—NH—C(═O)—$CH_2Cl$, —$CH_2$—NH—C(═O)—C≡CH, —S(═O)—$CH_3$, —$S(═O)_2$—$CH_3$, —$S(═O)_2$—OH, —$S(═O)_2$—$NH_2$, —$S(═O)_2$—$NHCH_3$, —S(═O)(═NH)—N$(CH_3)_2$, —S(═O)(═N—$CH_3$)—$N(CH_3)_2$, —S(═O)(═N—$CH_3$)—OH, —S(═O)(═NH)—$CH_3$, —P(═O)$(OH)_2$.

13. The compound according to claim 1, wherein $R^1$ is

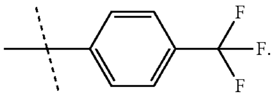

14. A compound, or any N-oxide, tautomer or stereoisomer thereof and/or any pharmaceutically acceptable salt of each of the foregoing, including mixtures thereof in all ratios, selected from the table below

| Compound No. | Structure and Name |
|---|---|
| 1 | 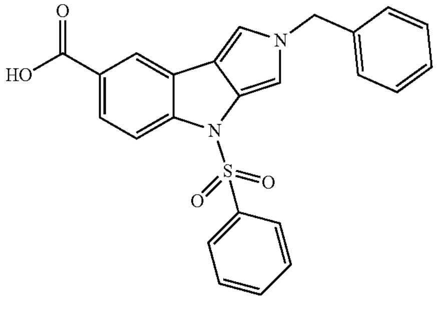 [SMILES: O=C(O)c1ccc2c(c1)c1cn(Cc3ccccc3)cc1n2S(=O)(=O)c1ccccc1] 4-(benzenesulfonyl)-2-benzyl-2H,4H-pyrrolo[3,4-b]indole-7-carboxylic acid |
| 2 | 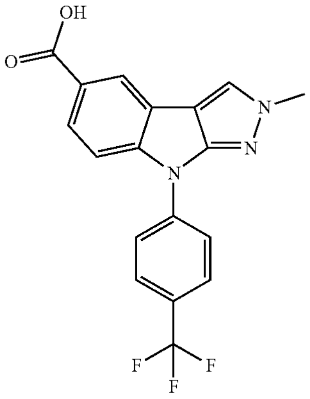 [SMILES: Cn1cc2c3cc(C(=O)O)ccc3n(-c3ccc(C(F)(F)F)cc3)c2n1] 2-methyl-8-[4-(trifluoromethyl)phenyl]-2H,8H-pyrazolo[3,4-b]indole-5-carboxylic acid |
| 3 | 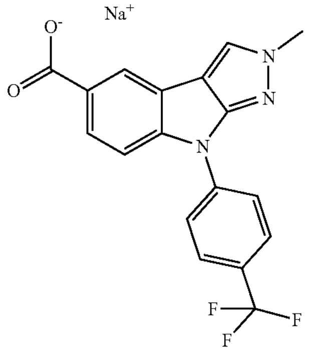 [SMILES: [Na+] ; Cn1cc2c3cc(C(=O)[O-])ccc3n(-c3ccc(C(F)(F)F)cc3)c2n1] Sodium 2-methyl-8-[4-(trifluoromethyl)phenyl]-2H,8H-pyrazolo[3,4-b]indole-5-carboxylate |
| 4 | 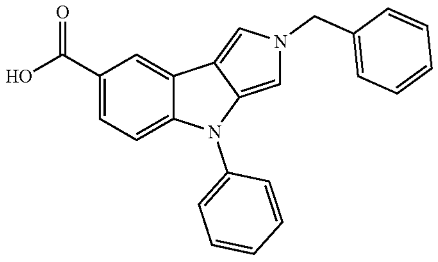 [SMILES: O=C(O)c1ccc2c(c1)c1cn(Cc3ccccc3)cc1n2-c1ccccc1] 2-benzyl-4-phenyl-2H,4H-pyrrolo[3,4-b]indole-7-carboxylic acid |

-continued

| Compound No. | Structure and Name |
|---|---|
| 5 | 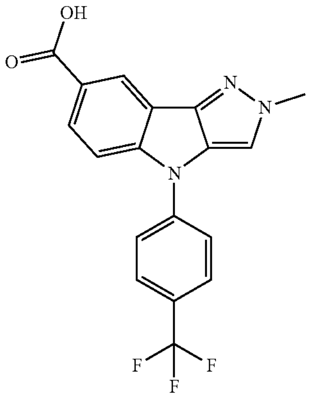 [SMILES: Cn1cc2c(n1)c1cc(C(=O)O)ccc1n2-c1ccc(C(F)(F)F)cc1] 2-methyl-4-[4-(trifluoromethyl)phenyl]-2H,4H-pyrazolo[4,3-b]indole-7-carboxylic acid |
| 6 | 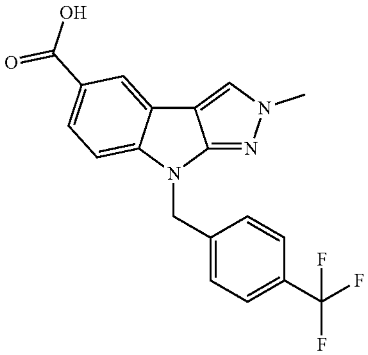 [SMILES: Cn1cc2c3cc(C(=O)O)ccc3n(Cc3ccc(C(F)(F)F)cc3)c2n1] 2-methyl-8-{[4-(trifluoromethyl)phenyl]methyl}-2H,8H-pyrazolo[3,4-b]indole-5-carboxylic acid |
| 7 | 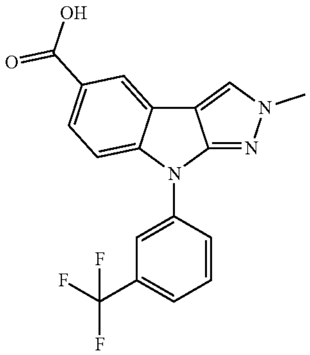 [SMILES: Cn1cc2c3cc(C(=O)O)ccc3n(-c3cccc(C(F)(F)F)c3)c2n1] 2-methyl-8-[3-(trifluoromethyl)phenyl]-2H,8H-pyrazolo[3,4-b]indole-5-carboxylic acid |

-continued

| Compound No. | Structure and Name |
|---|---|
| 8 | 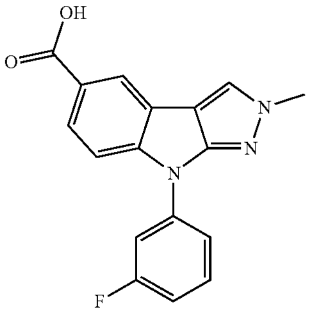 [SMILES: Cn1cc2c3cc(C(=O)O)ccc3n(-c3cccc(F)c3)c2n1] 8-(3-fluorophenyl)-2-methyl-2H,8H-pyrazolo[3,4-b]indole-5-carboxylic acid |
| 9 | 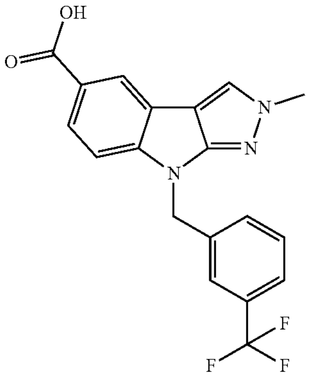 [SMILES: Cn1cc2c3cc(C(=O)O)ccc3n(Cc3cccc(C(F)(F)F)c3)c2n1] 2-methyl-8-{[3-(trifluoromethyl)phenyl]methyl}-2H,8H-pyrazolo[3,4-b]indole-5-carboxylic acid |
| 10 | 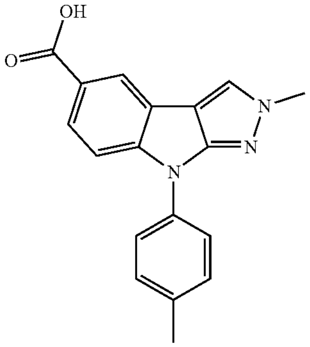 [SMILES: Cc1ccc(-n2c3ccc(C(=O)O)cc3c3cn(C)nc32)cc1] 2-methyl-8-(4-methylphenyl)-2H,8H-pyrazolo[3,4-b]indole-5-carboxylic acid |

-continued

| Compound No. | Structure and Name |
| --- | --- |
| 11 | 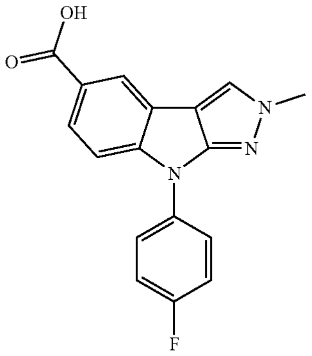 [SMILES: Cn1cc2c3cc(C(=O)O)ccc3n(-c3ccc(F)cc3)c2n1] 8-(4-fluorophenyl)-2-methyl-2H,8H-pyrazolo[3,4-b]indole-5-carboxylic acid |
| 12 | 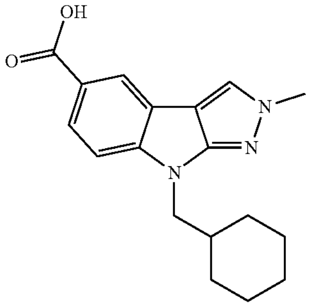 [SMILES: Cn1cc2c3cc(C(=O)O)ccc3n(CC3CCCCC3)c2n1] 8-(cyclohexylmethyl)-2-methyl-2H,8H-pyrazolo[3,4-b]indole-5-carboxylic acid |
| 13 | 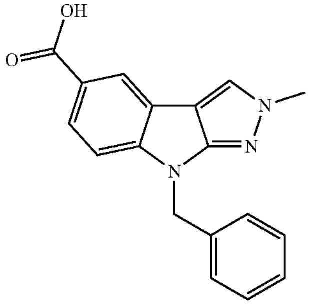 [SMILES: Cn1cc2c3cc(C(=O)O)ccc3n(Cc3ccccc3)c2n1] 8-benzyl-2-methyl-2H,8H-pyrazolo[3,4-b]indole-5-carboxylic acid |
| 14 | 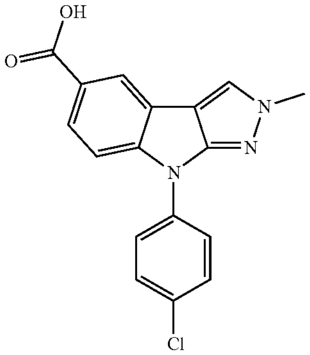 8-(4-chlorophenyl)-2-methyl-2H,8H-pyrazolo[3,4-b]indole-5-carboxylic acid |
| 15 | 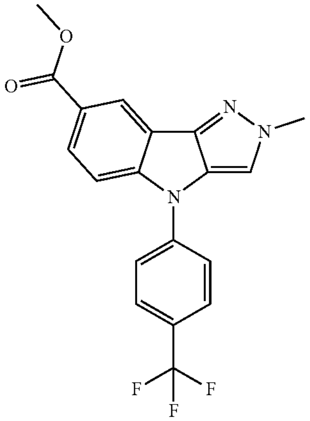 [SMILES: COC(=O)c1ccc2c(c1)c1nn(C)cc1n2-c1ccc(C(F)(F)F)cc1] methyl 2-methyl-4-[4-(trifluoromethyl)phenyl]-2H,4H-pyrazolo[4,3-b]indole-7-carboxylate |
| 16 | 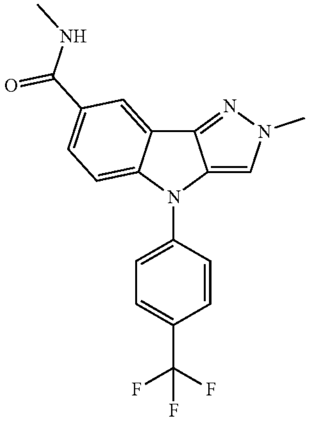 [SMILES: CNC(=O)c1ccc2c(c1)c1nn(C)cc1n2-c1ccc(C(F)(F)F)cc1] N,2-dimethyl-4-[4-(trifluoromethyl)phenyl]-2H,4H-pyrazolo[4,3-b]indole-7-carboxamide |

-continued

| Compound No. | Structure and Name |
| --- | --- |
| 17 | 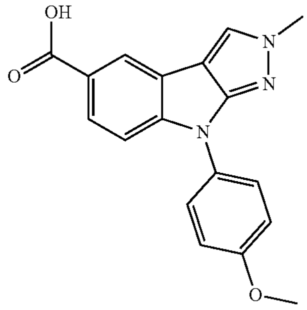 8-(4-methoxyphenyl)-2-methyl-2H,8H-pyrazolo[3,4-b]indole-5-carboxylic acid |
| 18 | 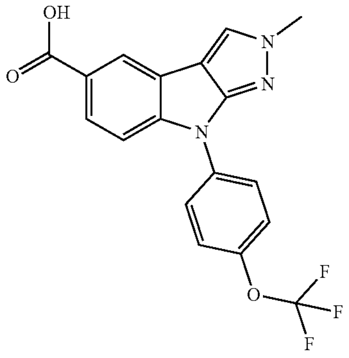 [SMILES: Cn1cc2c3cc(C(=O)O)ccc3n(-c3ccc(OC(F)(F)F)cc3)c2n1] 2-methyl-8-[4-(trifluoromethoxy)phenyl]-2H,8H-pyrazolo[3,4-b]indole-5-carboxylic acid |
| 19 | 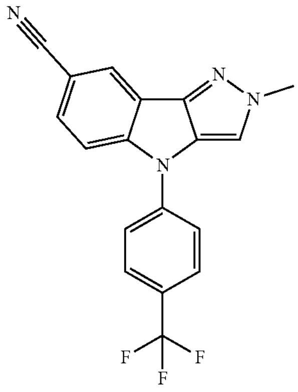 [SMILES: Cn1cc2c(n1)c1cc(C#N)ccc1n2-c1ccc(C(F)(F)F)cc1] 2-methyl-4-[4-(trifluoromethyl)phenyl]-2H,4H-pyrazolo[4,3-b]indole-7-carbonitrile |

-continued

| Compound No. | Structure and Name |
| --- | --- |
| 20 | 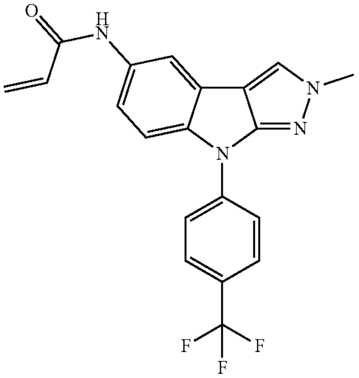 [SMILES: C=CC(=O)Nc1ccc2c(c1)c1cn(C)nc1n2-c1ccc(C(F)(F)F)cc1] N-{2-methyl-8-[4-(trifluoromethyl)phenyl]-2H,8H-pyrazolo[3,4-b]indol-5-yl}prop-2-enamide |
| 21 | 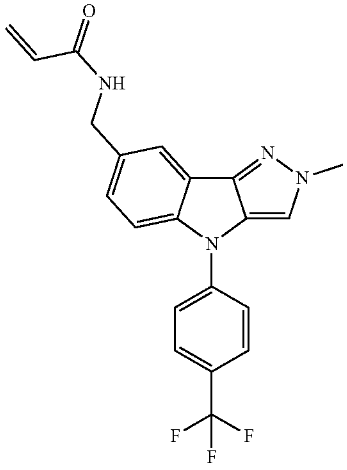 [SMILES: C=CC(=O)NCc1ccc2c(c1)c1nn(C)cc1n2-c1ccc(C(F)(F)F)cc1] N-({2-methyl-8-[4-(trifluoromethyl)phenyl]-2H,8H-pyrazolo[3,4-b]indol-5-yl}methyl)prop-2-enamide |
| 22 | 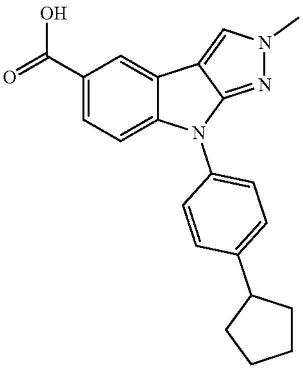 [SMILES: Cn1cc2c3cc(C(=O)O)ccc3n(-c3ccc(C4CCCC4)cc3)c2n1] 8-(4-cyclopentylphenyl)-2-methyl-2H,8H-pyrazolo[3,4-b]indole-5-carboxylic acid |

-continued

| Compound No. | Structure and Name |
|---|---|
| 23 | 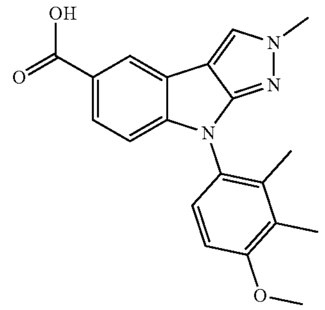 [SMILES: COc1ccc(-n2c3ccc(C(=O)O)cc3c3cn(C)nc32)c(C)c1C]<br>8-(4-methoxy-2,3-dimethylphenyl)-2-methyl-2H,8H-pyrazolo[3,4-b]indole-5-carboxylic acid |
| 24 | 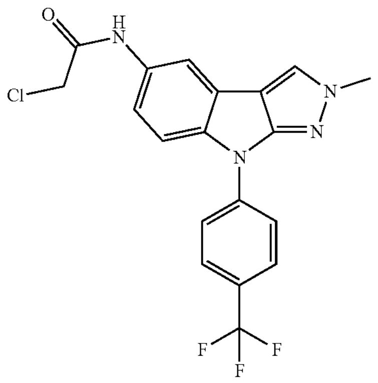 [SMILES: Cn1cc2c3cc(NC(=O)CCl)ccc3n(-c3ccc(C(F)(F)F)cc3)c2n1]<br>2-chloro-N-{2-methyl-8-[4-(trifluoromethyl)phenyl]-2H,8H-pyrazolo[3,4-b]indol-5-yl}acetamide |
| 25 | 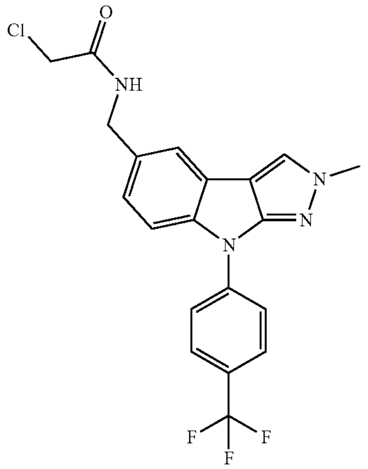 [SMILES: Cn1cc2c3cc(CNC(=O)CCl)ccc3n(-c3ccc(C(F)(F)F)cc3)c2n1]<br>2-chloro-N-({2-methyl-8-[4-(trifluoromethyl)phenyl]-2H,8H-pyrazolo[3,4-b]indol-5-yl}methyl)acetamide |

-continued

| Compound No. | Structure and Name |
|---|---|
| 26 | 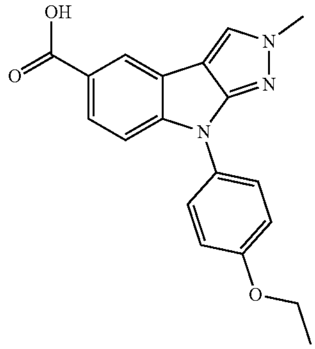 [SMILES: CCOc1ccc(-n2c3ccc(C(=O)O)cc3c3cn(C)nc32)cc1]<br>8-(4-ethoxyphenyl)-2-methyl-2H,8H-pyrazolo[3,4-b]indole-5-carboxylic acid |
| 27 | 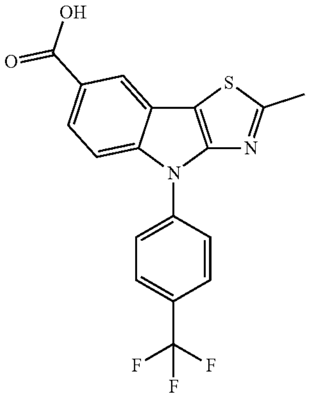 [SMILES: Cc1nc2c(s1)c1cc(C(=O)O)ccc1n2-c1ccc(C(F)(F)F)cc1]<br>2-methyl-4-[4-(trifluoromethyl)phenyl]-4H-[1,3]thiazolo[4,5-b]indole-7-carboxylic acid |
| 28 | 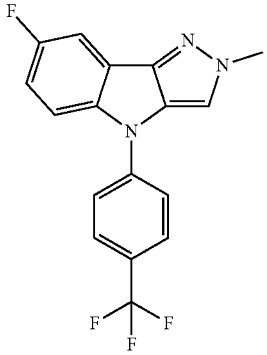 [SMILES: Cn1cc2c(n1)c1cc(F)ccc1n2-c1ccc(C(F)(F)F)cc1]<br>7-fluoro-2-methyl-4-[4-(trifluoromethyl)phenyl]-2H,4H-pyrazolo[4,3-b]indole |
| 29 | 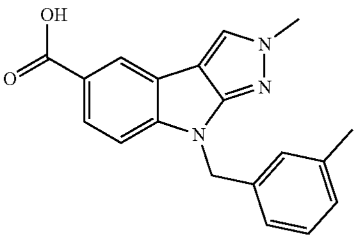 [SMILES: Cc1cccc(Cn2c3ccc(C(=O)O)cc3c3cn(C)nc32)c1] |

-continued

| Compound No. | Structure and Name |
| --- | --- |
| | 2-methyl-8-[(3-methylphenyl)methyl]-2H,8H-pyrazolo[3,4-b]indole-5-carboxylic acid |
| 30 | 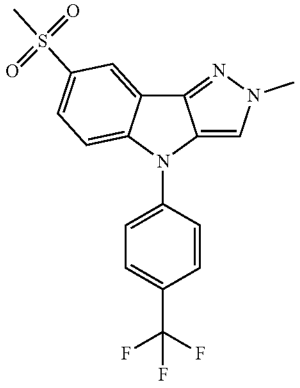 [SMILES: Cn1cc2c(n1)c1cc(S(C)(=O)=O)ccc1n2-c1ccc(C(F)(F)F)cc1]<br>7-methanesulfonyl-2-methyl-4-[4-(trifluoromethyl)phenyl]-2H,4H-pyrazolo[4,3-b]indole |
| 31 | 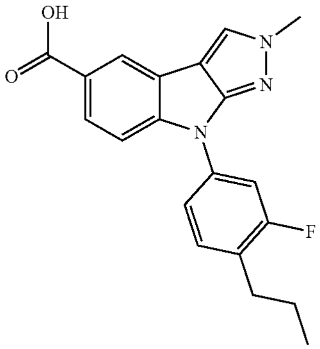 [SMILES: CCCc1ccc(-n2c3ccc(C(=O)O)cc3c3cn(C)nc32)cc1F]<br>8-(3-fluoro-4-propylphenyl)-2-methyl-2H,8H-pyrazolo[3,4-b]indole-5-carboxylic acid |
| 32 | 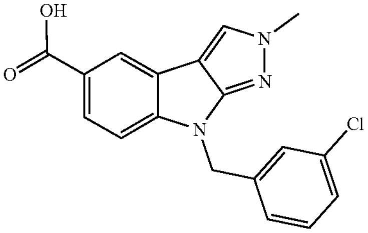 [SMILES: Cn1cc2c3cc(C(=O)O)ccc3n(Cc3cccc(Cl)c3)c2n1]<br>8-[(3-chlorophenyl)methyl]-2-methyl-2H,8H-pyrazolo[3,4-b]indole-5-carboxylic acid |
| 33 | 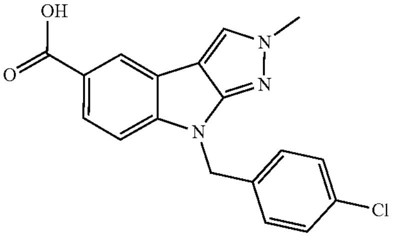 [SMILES: Cn1cc2c3cc(C(=O)O)ccc3n(Cc3ccc(Cl)cc3)c2n1]<br>8-[(3-chlorophenyl)methyl]-2-methyl-2H,8H-pyrazolo[3,4-b]indole-5-carboxylic acid |

-continued

| Compound No. | Structure and Name |
| --- | --- |
| 34 | 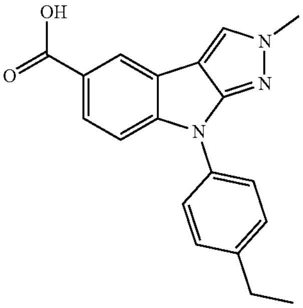<br>8-(4-ethylphenyl)-2-methyl-2H,8H-pyrazolo[3,4-b]indole-5-carboxylic acid |
| 35 | 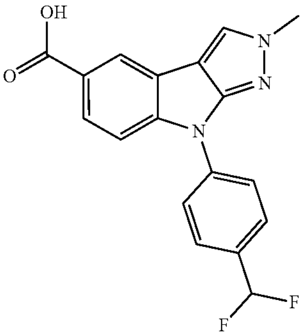 [SMILES: Cn1cc2c3cc(C(=O)O)ccc3n(-c3ccc(C(F)F)cc3)c2n1]<br>8-[4-(difluoromethyl)phenyl]-2-methyl-2H,8H-pyrazolo[3,4-b]indole-5-carboxylic acid |
| 36 | 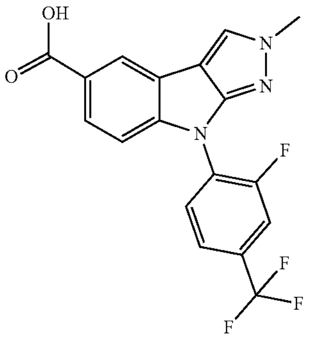 [SMILES: Cn1cc2c3cc(C(=O)O)ccc3n(-c3ccc(C(F)(F)F)cc3F)c2n1]<br>8-[2-fluoro-4-(trifluoromethyl)phenyl]-2-methyl-2H,8H-pyrazolo[3,4-b]indole-5-carboxylic acid |
| 37 | 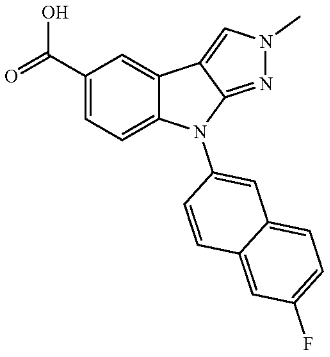 [SMILES: Cn1cc2c3cc(C(=O)O)ccc3n(-c3ccc4cc(F)ccc4c3)c2n1] |

-continued

| Compound No. | Structure and Name |
|---|---|
| | 8-(6-fluoronaphthalen-2-yl)-2-methyl-2H,8H-pyrazolo[3,4-b]indole-5-carboxylic acid |
| 38 | 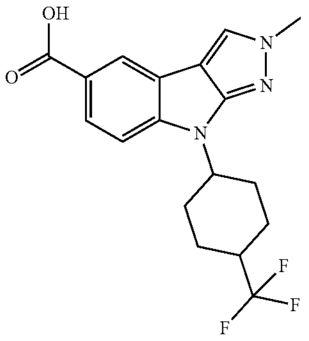 [SMILES: Cn1cc2c3cc(C(=O)O)ccc3n(C3CCC(C(F)(F)F)CC3)c2n1] 2-methyl-8-[4-(trifluoromethyl)cyclohexyl]-2H,8H-pyrazolo[3,4-b]indole-5-carboxylic acid |
| 39 | 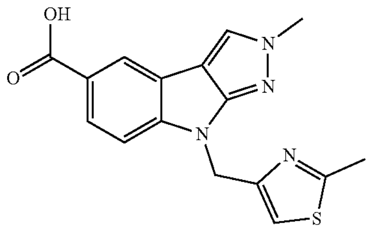 [SMILES: Cc1nc(Cn2c3ccc(C(=O)O)cc3c3cn(C)nc32)cs1] 2-methyl-8-[(2-methyl-1,3-thiazol-4-yl)methyl]-2H,8H-pyrazolo[3,4-b]indole-5-carboxylic acid |
| 40 | 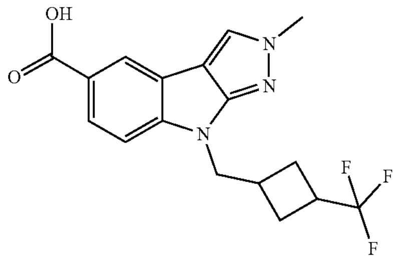 [SMILES: Cn1cc2c3cc(C(=O)O)ccc3n(CC3CC(C(F)(F)F)C3)c2n1] mixture of cis and trans isomers 2-methyl-8-{[3-(trifluoromethyl)cyclobutyl]methyl}-2H,8H-pyrazolo[3,4-b]indole-5-carboxylic acid |
| 42 | 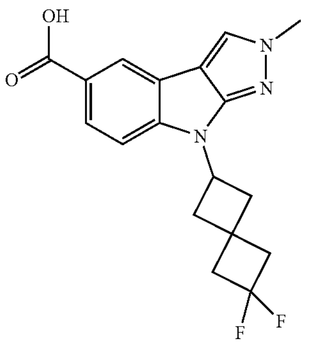 [SMILES: Cn1cc2c3cc(C(=O)O)ccc3n(C3CC4(C3)CC(F)(F)C4)c2n1] 8-{6,6-difluorospiro[3.3]heptan-2-yl}-2-methyl-2H,8H-pyrazolo[3,4-b]indole-5-carboxylic acid |

-continued

| Compound No. | Structure and Name |
|---|---|
| 43 | 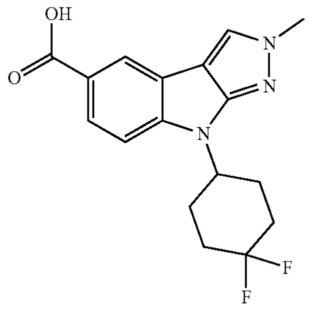 [SMILES: Cn1cc2c3cc(C(=O)O)ccc3n(C3CCC(F)(F)CC3)c2n1] 4-(4,4-difluorocyclohexyl)-2-methyl-2H,4H-pyrazolo[4,3-b]indole-7-carboxylic acid |
| 44 | 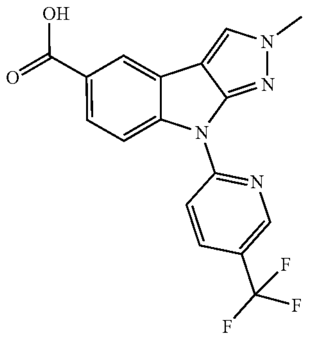 [SMILES: Cn1cc2c3cc(C(=O)O)ccc3n(-c3ccc(C(F)(F)F)cn3)c2n1] 2-methyl-8-[5-(trifluoromethyl)pyridin-2-yl]-2H,8H-pyrazolo[3,4-b]indole-5-carboxylic acid |
| 45 | 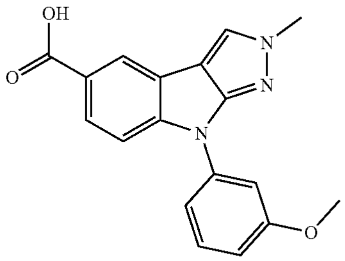 [SMILES: COc1cccc(-n2c3ccc(C(=O)O)cc3c3cn(C)nc32)c1] 8-(3-methoxyphenyl)-2-methyl-2H,8H-pyrazolo[3,4-b]indole-5-carboxylic acid |
| 46 | 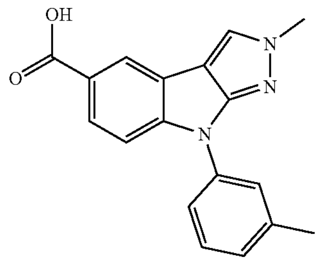 [SMILES: Cc1cccc(-n2c3ccc(C(=O)O)cc3c3cn(C)nc32)c1] 2-methyl-8-(3-methylphenyl)-2H,8H-pyrazolo[3,4-b]indole-5-carboxylic acid |

-continued

| Compound No. | Structure and Name |
|---|---|
| 47 | 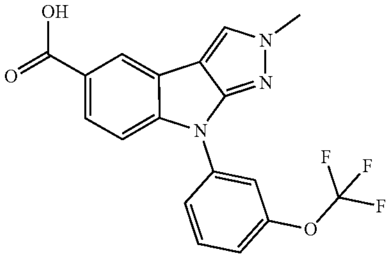 [SMILES: Cn1cc2c3cc(C(=O)O)ccc3n(-c3cccc(OC(F)(F)F)c3)c2n1] 2-methyl-8-[3-(trifluoromethoxy)phenyl]-2H,8H-pyrazolo[3,4-b]indole-5-carboxylic acid |
| 48 | 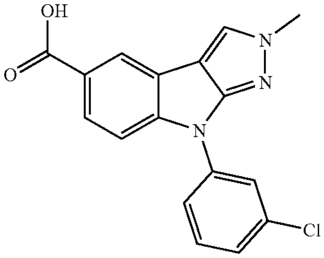 [SMILES: Cn1cc2c3cc(C(=O)O)ccc3n(-c3cccc(Cl)c3)c2n1] 8-(3-chlorophenyl)-2-methyl-2H,8H-pyrazolo[3,4-b]indole-5-carboxylic acid |
| 49 | 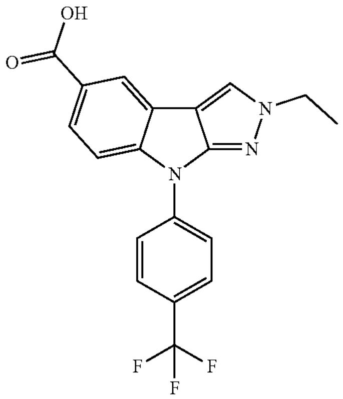 [SMILES: CCn1cc2c3cc(C(=O)O)ccc3n(-c3ccc(C(F)(F)F)cc3)c2n1] 2-ethyl-8-[4-(trifluoromethyl)phenyl]-2H,8H-pyrazolo[3,4-b]indole-5-carboxylic acid |
| 50 | 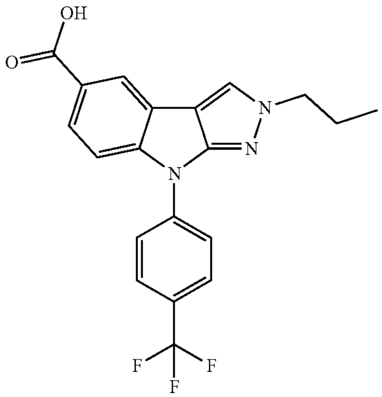 [SMILES: CCCn1cc2c3cc(C(=O)O)ccc3n(-c3ccc(C(F)(F)F)cc3)c2n1] 2-propyl-8-[4-(trifluoromethyl)phenyl]-2H,8H-pyrazolo[3,4-b]indole-5-carboxylic acid |
| 51 | 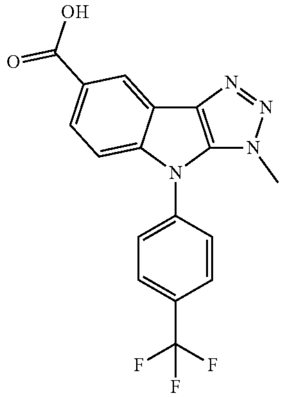 [SMILES: Cn1nnc2c3cc(C(=O)O)ccc3n(-c3ccc(C(F)(F)F)cc3)c21] 3-methyl-4-[4-(trifluoromethyl)phenyl]-3H,4H-[1,2,3]triazolo[4,5-b]indole-7-carboxylic acid |
| 52 | 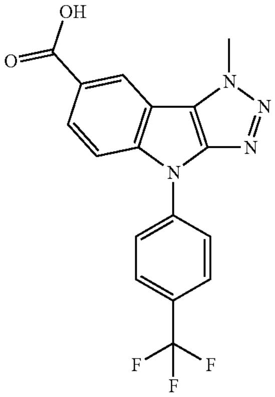 [SMILES: Cn1nnc2c1c1cc(C(=O)O)ccc1n2-c1ccc(C(F)(F)F)cc1] 1-methyl-4-[4-(trifluoromethyl)phenyl]-1H,4H-[1,2,3]triazolo[4,5-b]indole-7-carboxylic acid |
| 53 | 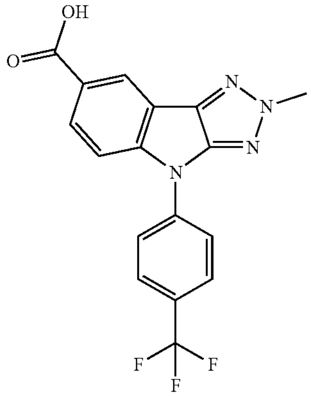 [SMILES: Cn1nc2c3cc(C(=O)O)ccc3n(-c3ccc(C(F)(F)F)cc3)c2n1] 2-methyl-4-[4-(trifluoromethyl)phenyl]-2H,4H-[1,2,3]triazolo[4,5-b]indole-7-carboxylic acid |

-continued

| Compound No. | Structure and Name |
|---|---|
| 54 | 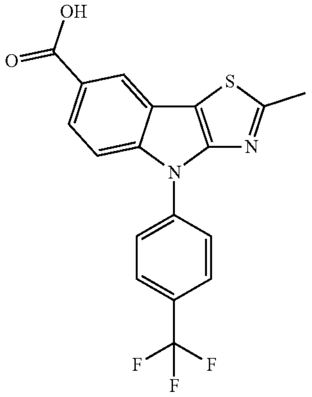 [SMILES: Cc1nc2c(s1)c1cc(C(=O)O)ccc1n2-c1ccc(C(F)(F)F)cc1] 2-methyl-4-[4-(trifluoromethyl)phenyl]-4H-[1,3]thiazolo[4,5-b]indole-7-carboxylic acid |
| 55 | 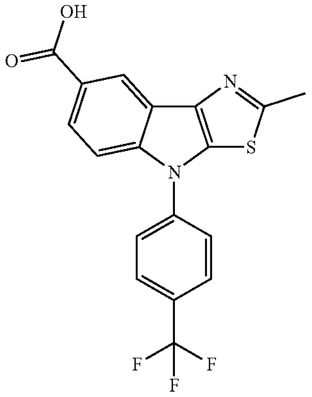 2-methyl-4-[4-(trifluoromethyl)phenyl]-4H-[1,3]thiazolo[5,4-b]indole-7-carboxylic acid |
| 56 | 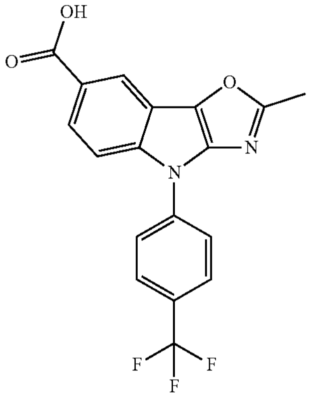 2-methyl-4-[4-(trifluoromethyl)phenyl]-4H-[1,3]oxazolo[4,5-b]indole-7-carboxylic acid |

-continued

| Compound No. | Structure and Name |
|---|---|
| 57 | 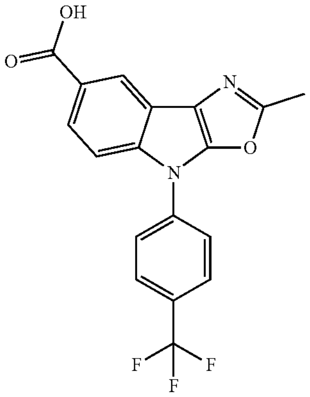 [SMILES: Cc1nc2c3cc(C(=O)O)ccc3n(-c3ccc(C(F)(F)F)cc3)c2o1] 2-methyl-4-[4-(trifluoromethyl)phenyl]-4H-[1,3]oxazolo[5,4-b]indole-7-carboxylic acid |
| 58 | 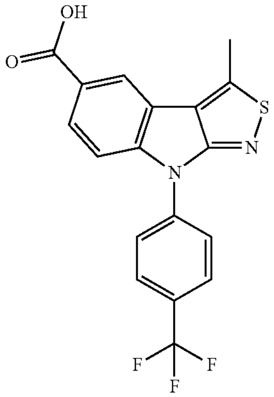 [SMILES: Cc1snc2c1c1cc(C(=O)O)ccc1n2-c1ccc(C(F)(F)F)cc1] 3-methyl-8-[4-(trifluoromethyl)phenyl]-8H-[1,2]thiazolo[3,4-b]indole-5-carboxylic acid |
| 59 | 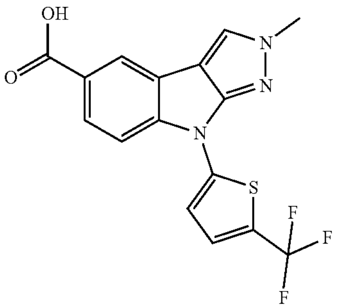 [SMILES: Cn1cc2c3cc(C(=O)O)ccc3n(-c3ccc(C(F)(F)F)s3)c2n1] 2-methyl-8-[5-(trifluoromethyl)thiophen-2-yl]-2H,8H-pyrazolo[3,4-b]indole-5-carboxylic acid |

-continued

| Compound No. | Structure and Name |
|---|---|
| 60 | 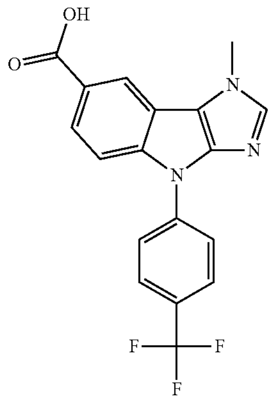 [SMILES: Cn1cnc2c1c1cc(C(=O)O)ccc1n2-c1ccc(C(F)(F)F)cc1]<br>1-methyl-4-[4-(trifluoromethyl)phenyl]-1H,4H-imidazo[4,5-b]indole-7-carboxylic acid |
| 61 | 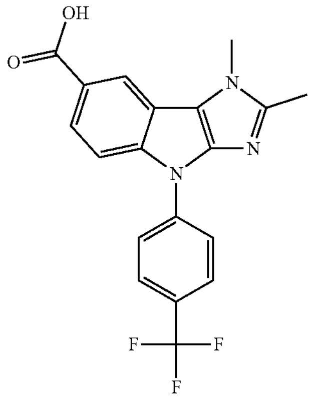 [SMILES: Cc1nc2c(c3cc(C(=O)O)ccc3n2-c2ccc(C(F)(F)F)cc2)n1C]<br>1,2-dimethyl-4-[4-(trifluoromethyl)phenyl]-1H,4H-imidazo[4,5-b]indole-7-carboxylic acid |
| 62 | 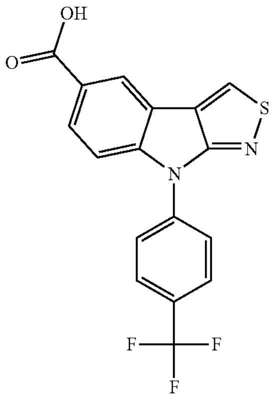 [SMILES: O=C(O)c1ccc2c(c1)c1csnc1n2-c1ccc(C(F)(F)F)cc1]<br>8-[4-(trifluoromethyl)phenyl]-8H-[1,2]thiazolo[3,4-b]indole-5-carboxylic acid |

-continued

| Compound No. | Structure and Name |
|---|---|
| 63 | 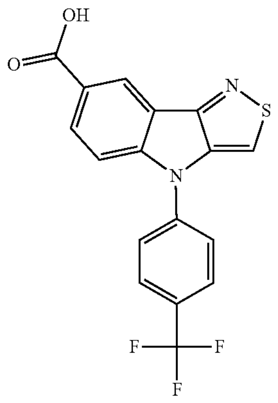 [SMILES: O=C(O)c1ccc2c(c1)c1nscc1n2-c1ccc(C(F)(F)F)cc1]<br>4-[4-(trifluoromethyl)phenyl]-4H-[1,2]thiazolo[4,3-b]indole-7-carboxylic acid |
| 64 | 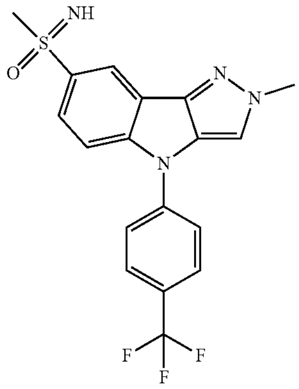<br>imino(methyl){2-methyl-4-[4-(trifluoromethyl)phenyl]-2H,4H-pyrazolo[4,3-b]indol-7-yl}-??-sulfanone |
| 65 | 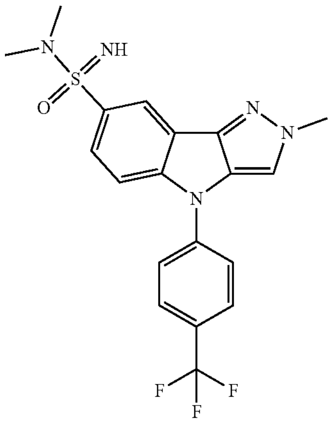<br>N,N,2-trimethyl-4-[4-(trifluoromethyl)phenyl]-2H,4H-pyrazolo[4,3-b]indole-7-sulfonoimidamide |

-continued

| Compound No. | Structure and Name |
|---|---|
| 66 | 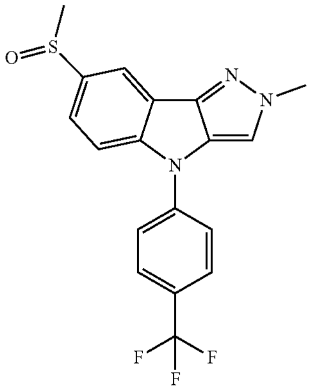 [SMILES: Cn1cc2c(n1)c1cc(S(C)=O)ccc1n2-c1ccc(C(F)(F)F)cc1] 7-methanesulfinyl-2-methyl-4-[4-(trifluoromethyl)phenyl]-2H,4H-pyrazolo[4,3-b]indole |
| 67 | 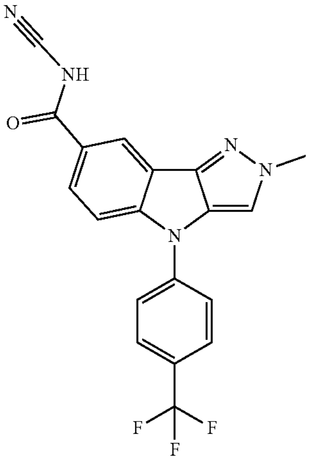 [SMILES: Cn1cc2c(n1)c1cc(C(=O)NC#N)ccc1n2-c1ccc(C(F)(F)F)cc1] N-cyano-2-methyl-4-[4-(trifluoromethyl)phenyl]-2H,4H-pyrazolo[4,3-b]indole-7-carboxamide |
| 68 | 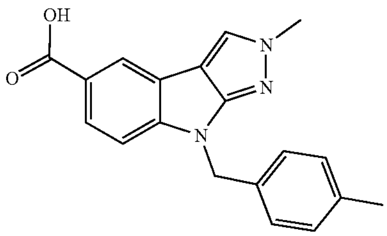 [SMILES: Cc1ccc(Cn2c3ccc(C(=O)O)cc3c3cn(C)nc32)cc1] 2-methyl-8-[(4-methylphenyl)methyl]-2H,8H-pyrazolo[3,4-b]indole-5-carboxylic acid |

-continued

| Compound No. | Structure and Name |
|---|---|
| 69 | 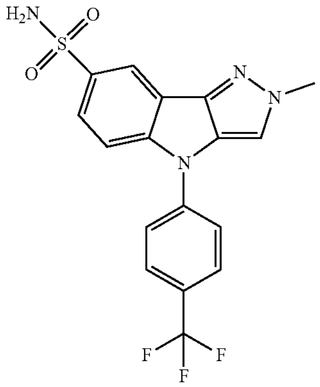 2-methyl-4-[4-(trifluoromethyl)phenyl]-2H,4H-pyrazolo[4,3-b]indole-7-sulfonamide |
| 70 | 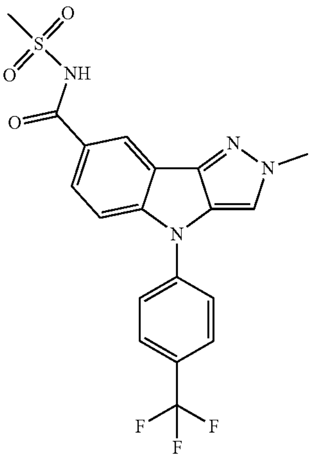 N-methanesulfonyl-2-methyl-4-[4-(trifluoromethyl)phenyl]-2H,4H-pyrazolo[4,3-b]indole-7-carboxamide |
| 71 | 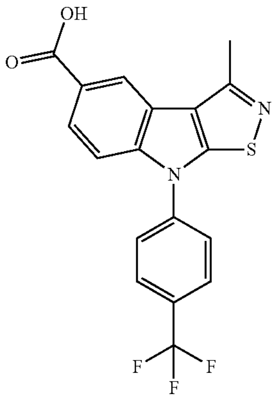 [SMILES: Cc1nsc2c1c1cc(C(=O)O)ccc1n2-c1ccc(C(F)(F)F)cc1] 3-methyl-8-[4-(trifluoromethyl)phenyl]-8H-[1,2]thiazolo[5,4-b]indole-5-carboxylic acid |

-continued

| Compound No. | Structure and Name |
|---|---|
| 72 | 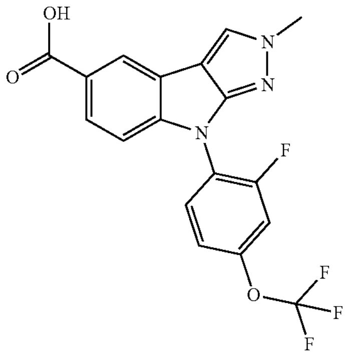 [SMILES: Cn1cc2c3cc(C(=O)O)ccc3n(-c3ccc(OC(F)(F)F)cc3F)c2n1] 8-[2-fluoro-4-(trifluoromethoxy)phenyl]-2-methyl-2H,8H-pyrazolo[3,4-b]indole-5-carboxylic acid |
| 73 | 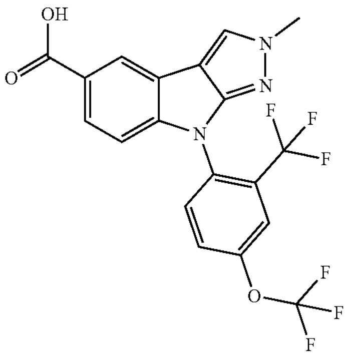 [SMILES: Cn1cc2c3cc(C(=O)O)ccc3n(-c3ccc(OC(F)(F)F)cc3C(F)(F)F)c2n1] 2-methyl-8-[4-(trifluoromethoxy)-2-(trifluoromethyl)phenyl]-2H,8H-pyrazolo[3,4-b]indole-5-carboxylic acid |
| 74 | 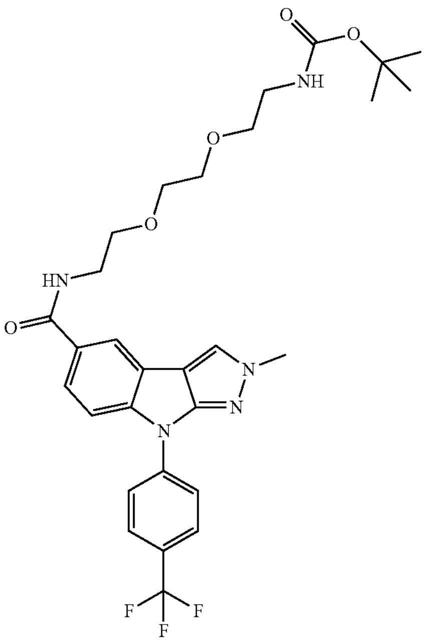 [SMILES: Cn1cc2c3cc(C(=O)NCCOCCOCCNC(=O)OC(C)(C)C)ccc3n(-c3ccc(C(F)(F)F)cc3)c2n1] tert-butyl N-(2-{2-[2-({2-methyl-8-[4-(trifluoromethyl)phenyl]-2H,8H-pyrazolo[3,4-b]indol-5-yl}formamido)ethoxy]ethoxy}ethyl)carbamate |

-continued

| Compound No. | Structure and Name |
|---|---|
| 75 | 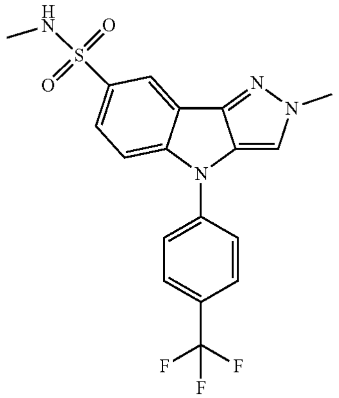 N,2-dimethyl-4-[4-(trifluoromethyl)phenyl]-2H,4H-pyrazolo[4,3-b]indole-7-sulfonamide |
| 76 | 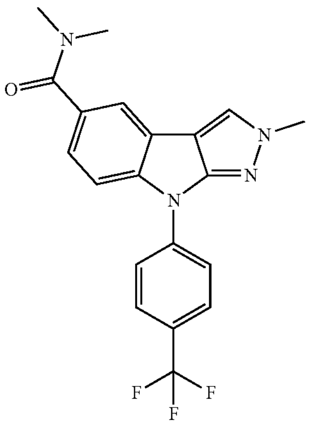 [SMILES: CN(C)C(=O)c1ccc2c(c1)c1cn(C)nc1n2-c1ccc(C(F)(F)F)cc1] N,N,2-trimethyl-8-[4-(trifluoromethyl)phenyl]-2H,8H-pyrazolo[3,4-b]indole-5-carboxamide |
| 77 | 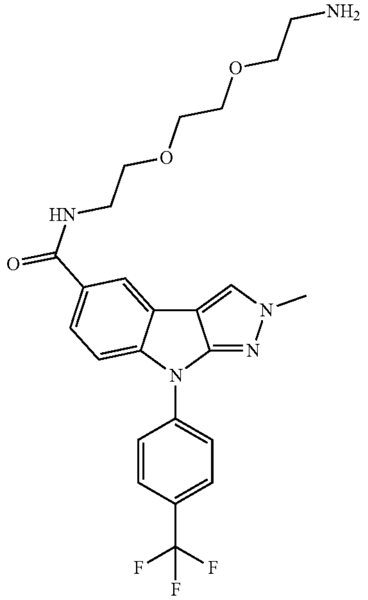 [SMILES: Cn1cc2c3cc(C(=O)NCCOCCOCCN)ccc3n(-c3ccc(C(F)(F)F)cc3)c2n1] |

| Compound No. | Structure and Name |
|---|---|
| | N-{2-[2-(2-aminoethoxy)ethoxy]ethyl}-2-methyl-8-[4-(trifluoromethyl)phenyl]-2H,8H-pyrazolo[3,4-b]indole-5-carboxamide |
| 78 | 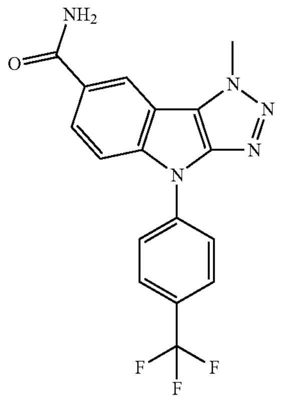<br>1-methyl-4-[4-(trifluoromethyl)phenyl]-1H,4H-[1,2,3]triazolo[4,5-b]indole-7-carboxamide |
| 79 | 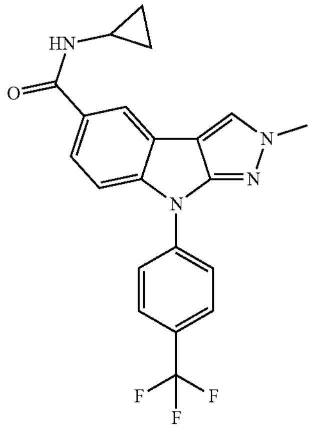 [SMILES: Cn1cc2c3cc(C(=O)NC4CC4)ccc3n(-c3ccc(C(F)(F)F)cc3)c2n1]<br>N-cyclopropyl-2-methyl-8-[4-(trifluoromethyl)phenyl]-2H,8H-pyrazolo[3,4-b]indole-5-carboxamide |
| 80 | 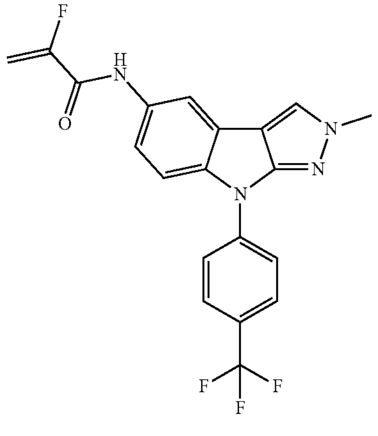 [SMILES: C=C(F)C(=O)Nc1ccc2c(c1)c1cn(C)nc1n2-c1ccc(C(F)(F)F)cc1]<br>2-fluoro-N-{2-methyl-8-[4-(trifluoromethyl)phenyl]-2H,8H-pyrazolo[3,4-b]indol-5-yl}prop-2-enamide |

| Compound No. | Structure and Name |
|---|---|
| 81 | 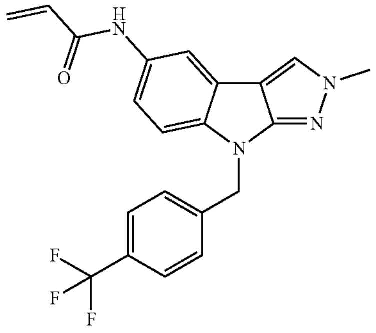 [SMILES: C=CC(=O)Nc1ccc2c(c1)c1cn(C)nc1n2Cc1ccc(C(F)(F)F)cc1]<br>N-(2-methyl-8-{[4-(trifluoromethyl)phenyl]methyl}-2H,8H-pyrazolo[3,4-b]indol-5-yl)prop-2-enamide |
| 82 | 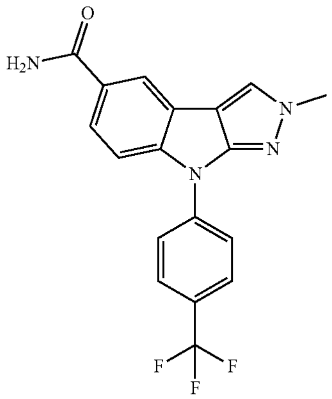 [SMILES: Cn1cc2c3cc(C(N)=O)ccc3n(-c3ccc(C(F)(F)F)cc3)c2n1]<br>2-methyl-8-[4-(trifluoromethyl)phenyl]-2H,8H-pyrazolo[3,4-b]indole-5-carboxamide |
| 83 | 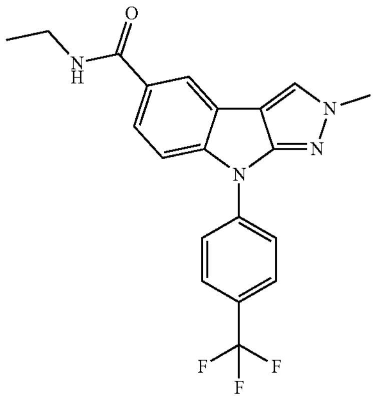 [SMILES: CCNC(=O)c1ccc2c(c1)c1cn(C)nc1n2-c1ccc(C(F)(F)F)cc1]<br>N-ethyl-2-methyl-8-[4-(trifluoromethyl)phenyl]-2H,8H-pyrazolo[3,4-b]indole-5-carboxamide |

-continued

| Compound No. | Structure and Name |
|---|---|
| 84 | 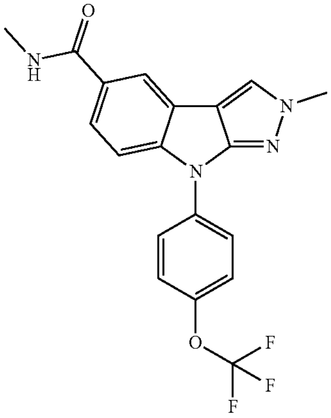 N,2-dimethyl-8-[4-(trifluoromethoxy)phenyl]-2H,8H-pyrazolo[3,4-b]indole-5-carboxamide |
| 85 | 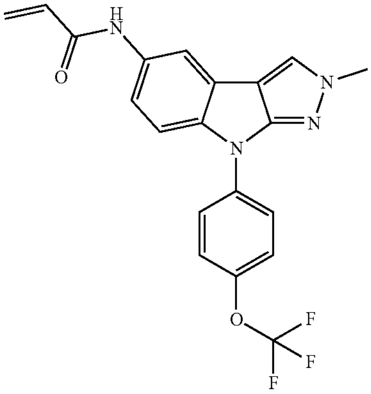 [SMILES: C=CC(=O)Nc1ccc2c(c1)c1cn(C)nc1n2-c1ccc(OC(F)(F)F)cc1] N-{2-methyl-8-[4-(trifluoromethoxy)phenyl]-2H,8H-pyrazolo[3,4-b]indol-5-yl}prop-2-enamide |
| 86 | 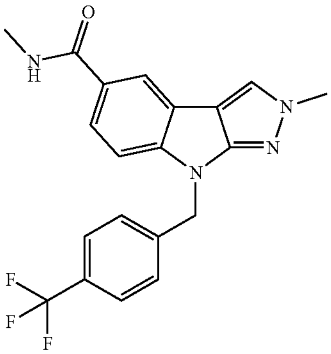 N,2-dimethyl-8-{[4-(trifluoromethyl)phenyl]methyl}-2H,8H-pyrazolo[3,4-b]indole-5-carboxamide |

-continued

| Compound No. | Structure and Name |
|---|---|
| 87 | 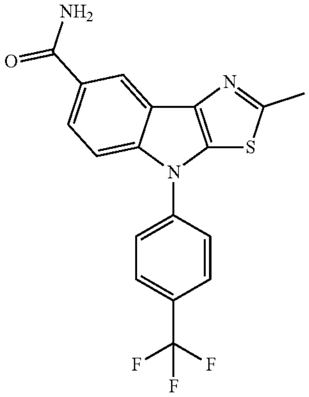 2-methyl-4-[4-(trifluoromethyl)phenyl]-4H-[1,3]thiazolo[5,4-b]indole-7-carboxamide |
| 88 | 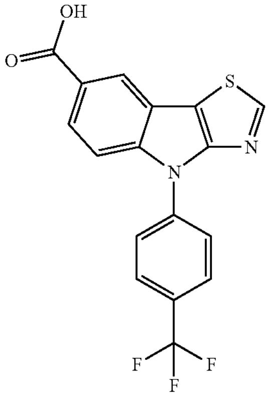 4-[4-(trifluoromethyl)phenyl]-4H-[1,3]thiazolo[4,5-b]indole-7-carboxylic acid |
| 89 | 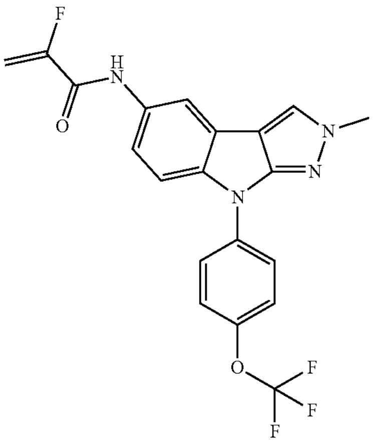 [SMILES: C=C(F)C(=O)Nc1ccc2c(c1)c1cn(C)nc1n2-c1ccc(OC(F)(F)F)cc1] 2-fluoro-N-{2-methyl-8-[4-(trifluoromethoxy)phenyl]-2H,8H-pyrazolo[3,4-b]indol-5-yl}prop-2-enamide |

-continued

| Compound No. | Structure and Name |
|---|---|
| 90 | 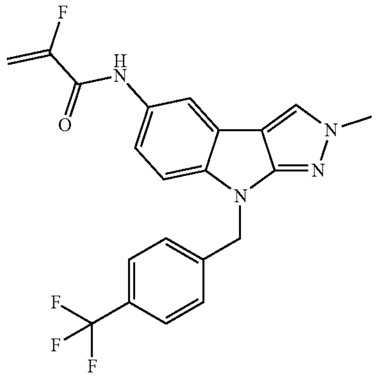 [SMILES: C=C(F)C(=O)Nc1ccc2c(c1)c1cn(C)nc1n2Cc1ccc(C(F)(F)F)cc1] 2-fluoro-N-(2-methyl-8-{[4-(trifluoromethyl)phenyl]methyl}-2H,8H-pyrazolo[3,4-b]indol-5-yl)prop-2-enamide |
| 91 | 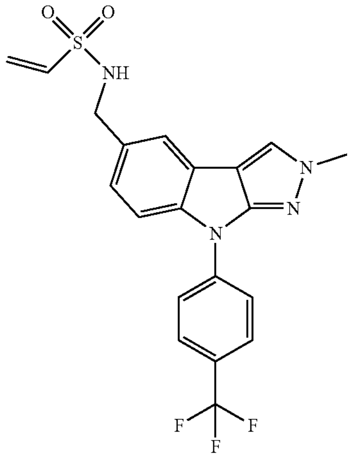 [SMILES: C=CS(=O)(=O)NCc1ccc2c(c1)c1cn(C)nc1n2-c1ccc(C(F)(F)F)cc1] N-({2-methyl-8-[4-(trifluoromethyl)phenyl]-2H,8H-pyrazolo[3,4-b]indol-5-yl}methyl)ethene-1-sulfonamide |
| 92 | 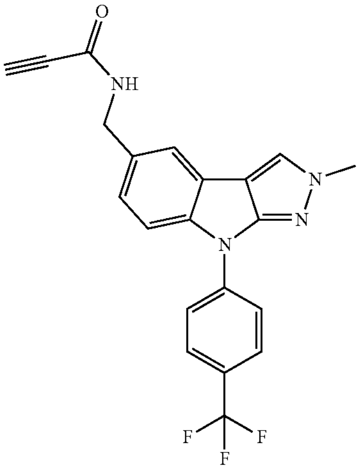 [SMILES: C#CC(=O)NCc1ccc2c(c1)c1cn(C)nc1n2-c1ccc(C(F)(F)F)cc1] N-({2-methyl-8-[4-(trifluoromethyl)phenyl]-2H,8H-pyrazolo[3,4-b]indol-5-yl}methyl)prop-2-ynamide |

-continued

| Compound No. | Structure and Name |
|---|---|
| 93 | 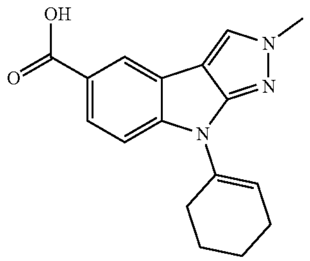 [SMILES: Cn1cc2c3cc(C(=O)O)ccc3n(C3=CCCCC3)c2n1] 8-(cyclohex-1-en-1-yl)-2-methyl-2H,8H-pyrazolo[3,4-b]indole-5-carboxylic acid |
| 94 | 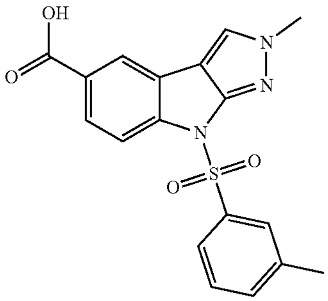 [SMILES: Cc1cccc(S(=O)(=O)n2c3ccc(C(=O)O)cc3c3cn(C)nc32)c1] 2-methyl-8-(3-methylbenzenesulfonyl)-2H,8H-pyrazolo[3,4-b]indole-5-carboxylic acid |
| 95 | 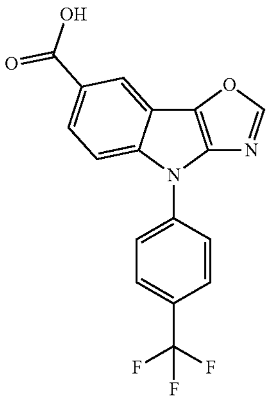 [SMILES: O=C(O)c1ccc2c(c1)c1ocnc1n2-c1ccc(C(F)(F)F)cc1] 4-[4-(trifluoromethyl)phenyl]-4H-[1,3]oxazolo[4,5-b]indole-7-carboxylic acid |

-continued

| Compound No. | Structure and Name |
|---|---|
| 96 | 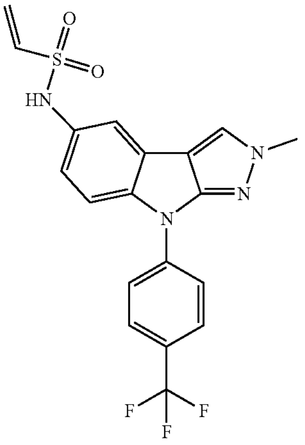 [SMILES: C=CS(=O)(=O)Nc1ccc2c(c1)c1cn(C)nc1n2-c1ccc(C(F)(F)F)cc1] N-{2-methyl-8-[4-(trifluoromethyl)phenyl]-2H,8H-pyrazolo[3,4-b]indol-5-yl}ethene-1-sulfonamide |
| 97 | 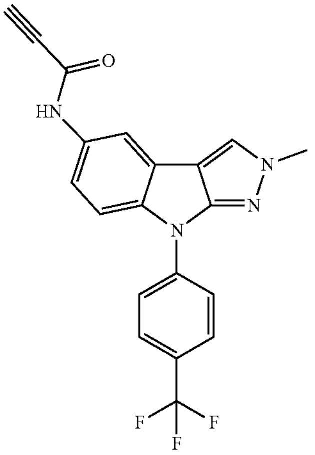 [SMILES: C#CC(=O)Nc1ccc2c(c1)c1cn(C)nc1n2-c1ccc(C(F)(F)F)cc1] N-{2-methyl-8-[4-(trifluoromethyl)phenyl]-2H,8H-pyrazolo[3,4-b]indol-5-yl}prop-2-ynamide |
| 98 | 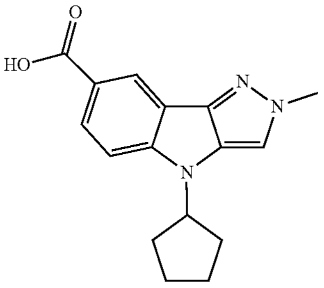 [SMILES: Cn1cc2c(n1)c1cc(C(=O)O)ccc1n2C1CCCC1] 4-cyclopentyl-2-methyl-2H,4H-pyrazolo[4,3-b]indole-7-carboxylic acid |

-continued

| Compound No. | Structure and Name |
|---|---|
| 100 | 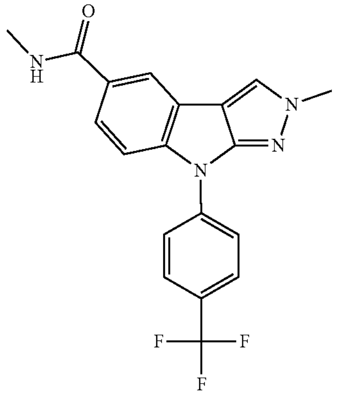 N,2-dimethyl-8-[4-(trifluoromethyl)phenyl]-2H,8H-pyrazolo[3,4-b]indole-5-carboxamide |
| 101 | 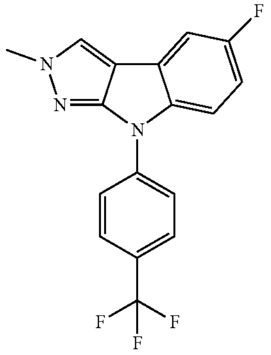 [SMILES: Cn1cc2c3cc(F)ccc3n(-c3ccc(C(F)(F)F)cc3)c2n1] 5-fluoro-2-methyl-8-[4-(trifluoromethyl)phenyl]-2H,8H-pyrazolo[3,4-b]indole |
| 102 | 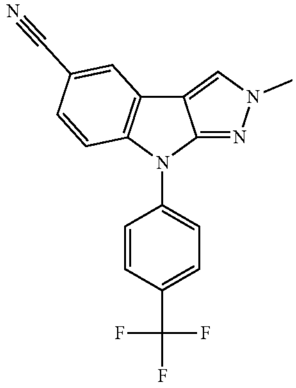 [SMILES: Cn1cc2c3cc(C#N)ccc3n(-c3ccc(C(F)(F)F)cc3)c2n1] 2-methyl-8-[4-(trifluoromethyl)phenyl]-2H,8H-pyrazolo[3,4-b]indole-5-carbonitrile |

| Compound No. | Structure and Name |
|---|---|
| 103 | 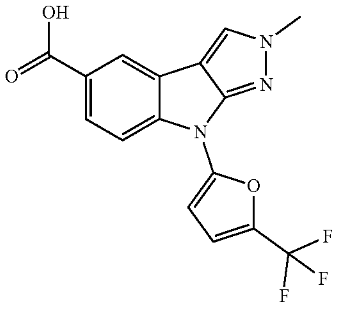 [SMILES: Cn1cc2c3cc(C(=O)O)ccc3n(-c3ccc(C(F)(F)F)o3)c2n1] 2-methyl-8-[5-(trifluoromethyl)furan-2-yl]-2H,8H-pyrazolo[3,4-b]indole-5-carboxylic acid |
| 104 | 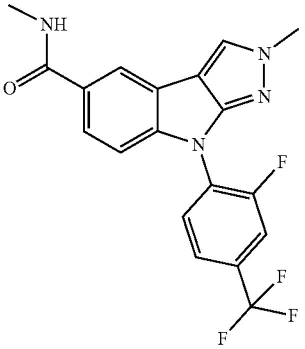 8-[2-fluoro-4-(trifluoromethyl)phenyl]-N,2-dimethyl-2H,8H-pyrazolo[3,4-b]indole-5-carboxamide |
| 105 | 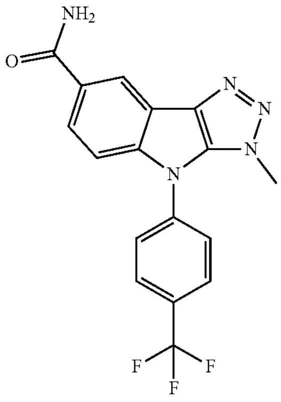 [SMILES: Cn1nnc2c3cc(C(N)=O)ccc3n(-c3ccc(C(F)(F)F)cc3)c21] 3-methyl-4-[4-(trifluoromethyl)phenyl]-3H,4H-[1,2,3]triazolo[4,5-b]indole-7-carboxamide |
| 106 | 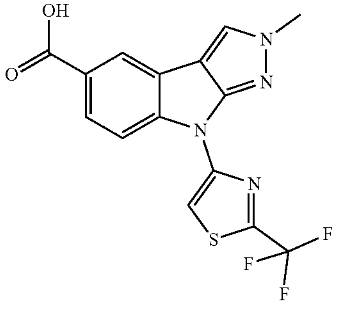 [SMILES: Cn1cc2c3cc(C(=O)O)ccc3n(-c3csc(C(F)(F)F)n3)c2n1] |

-continued

| Compound No. | Structure and Name |
|---|---|
| | 2-methyl-8-[2-(trifluoromethyl)-1,3-thiazol-4-yl]-2H,8H-pyrazolo[3,4-b]indole-5-carboxylic acid |
| 110 | 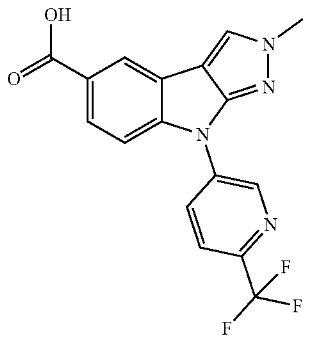 [SMILES: Cn1cc2c3cc(C(=O)O)ccc3n(-c3ccc(C(F)(F)F)nc3)c2n1] 2-methyl-8-[6-(trifluoromethyl)pyridin-3-yl]-2H,8H-pyrazolo[3,4-b]indole-5-carboxylic acid |
| 111 | 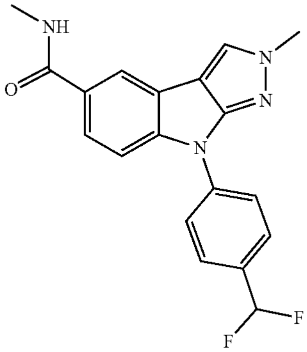 [SMILES: CNC(=O)c1ccc2c(c1)c1cn(C)nc1n2-c1ccc(C(F)F)cc1] 8-[4-(difluoromethyl)phenyl]-N,2-dimethyl-2H,8H-pyrazolo[3,4-b]indole-5-carboxamide |
| 112 | 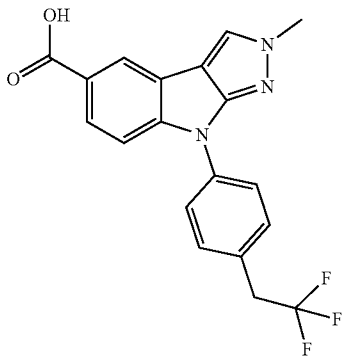 [SMILES: Cn1cc2c3cc(C(=O)O)ccc3n(-c3ccc(CC(F)(F)F)cc3)c2n1] 2-methyl-8-[4-(2,2,2-trifluoroethyl)phenyl]-2H,8H-pyrazolo[3,4-b]indole-5-carboxylic acid |

-continued

| Compound No. | Structure and Name |
|---|---|
| 113 | 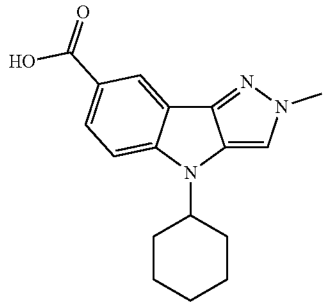 [SMILES: Cn1cc2c(n1)c1cc(C(=O)O)ccc1n2C1CCCCC1] 4-cyclohexyl-2-methyl-2H,4H-pyrazolo[4,3-b]indole-7-carboxylic acid |
| 114 | 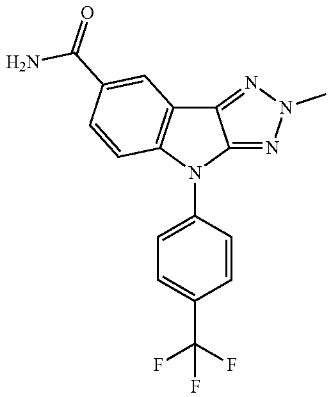 [SMILES: Cn1nc2c3cc(C(N)=O)ccc3n(-c3ccc(C(F)(F)F)cc3)c2n1] 2-methyl-4-[4-(trifluoromethyl)phenyl]-2H,4H-[1,2,3]triazolo[4,5-b]indole-7-carboxamide |
| 115 | 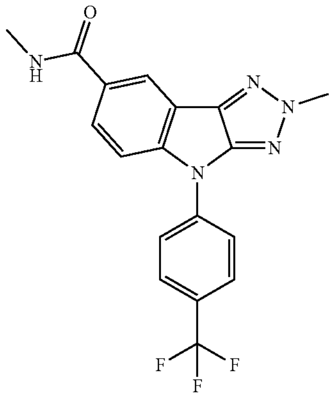 N,2-dimethyl-4-[4-(trifluoromethyl)phenyl]-2H,4H-[1,2,3]triazolo[4,5-b]indole-7-carboxamide |

-continued

| Compound No. | Structure and Name |
|---|---|
| 116 | 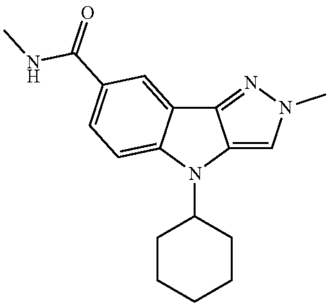 4-cyclohexyl-N,2-dimethyl-2H,4H-pyrazolo[4,3-b]indole-7-carboxamide |
| 117 | 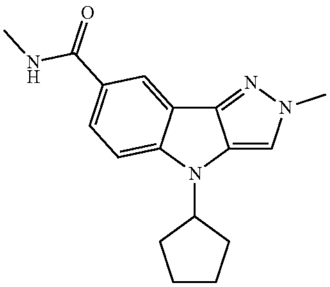 4-cyclopentyl-N,2-dimethyl-2H,4H-pyrazolo[4,3-b]indole-7-carboxamide |
| 118 | 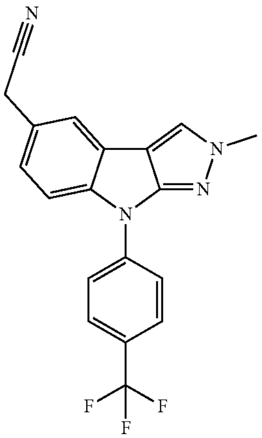 [SMILES: Cn1cc2c3cc(CC#N)ccc3n(-c3ccc(C(F)(F)F)cc3)c2n1] 2-{2-methyl-8-[4-(trifluoromethyl)phenyl]-2H,8H-pyrazolo[3,4-b]indol-5-yl}acetonitrile |

| Compound No. | Structure and Name |
|---|---|
| 119 | 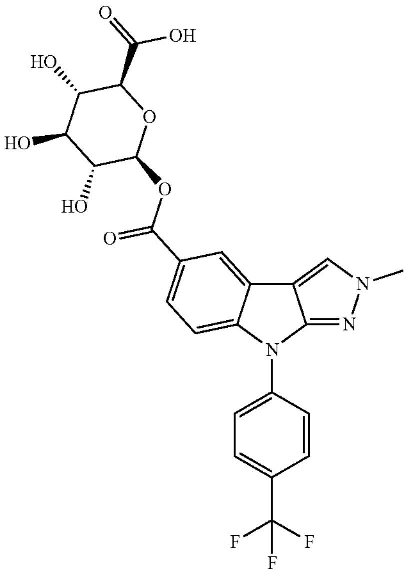 [SMILES: Cn1cc2c3cc(C(=O)O[C@@H]4O[C@H](C(=O)O)[C@@H](O)[C@H](O)[C@H]4O)ccc3n(-c3ccc(C(F)(F)F)cc3)c2n1]<br>(2S,3S,4S,5R,6S)-3,4,5-trihydroxy-6-{2-methyl-8-[4-(trifluoromethyl)phenyl]-2H,8H-pyrazolo[3,4-b]indole-5-carbonyloxy}oxane-2-carboxylic acid |
| 120 | 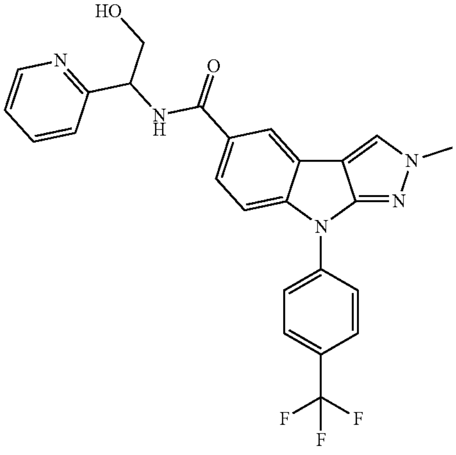 [SMILES: Cn1cc2c3cc(C(=O)NC(CO)c4ccccn4)ccc3n(-c3ccc(C(F)(F)F)cc3)c2n1]<br>N-[2-hydroxy-1-(pyridin-2-yl)ethyl]-2-methyl-8-[4-(trifluoromethyl)phenyl]-2H,8H-pyrazolo[3,4-b]indole-5-carboxamide |

| Compound No. | Structure and Name |
|---|---|
| 121 | 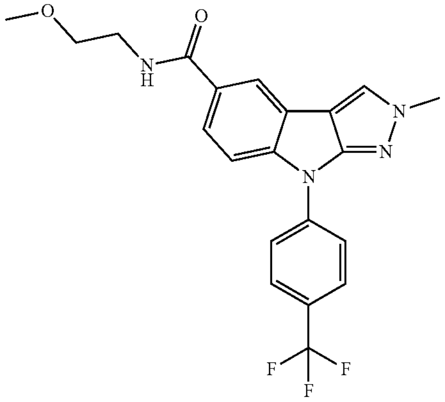<br>N-(2-methoxyethyl)-2-methyl-8-[4-(trifluoromethyl)phenyl]-2H,8H-pyrazolo[3,4-b]indole-5-carboxamide |
| 122 | 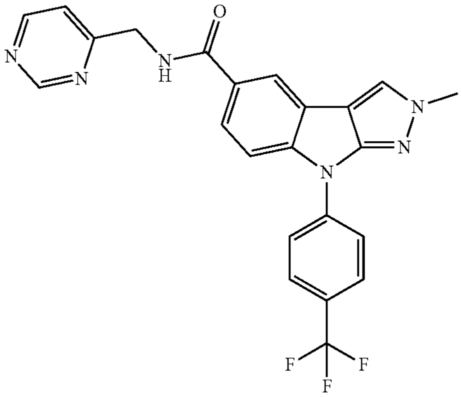 [SMILES: Cn1cc2c3cc(C(=O)NCc4ccncn4)ccc3n(-c3ccc(C(F)(F)F)cc3)c2n1]<br>2-methyl-N-[(pyrimidin-4-yl)methyl]-8-[4-(trifluoromethyl)phenyl]-2H,8H-pyrazolo[3,4-b]indole-5-carboxamide |
| 123 | 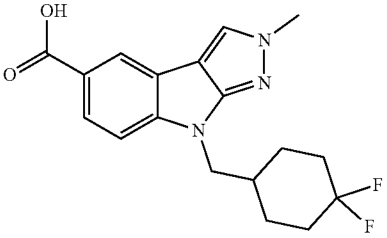 [SMILES: Cn1cc2c3cc(C(=O)O)ccc3n(CC3CCC(F)(F)CC3)c2n1]<br>8-[(4,4-difluorocyclohexyl)methyl]-2-methyl-2H,8H-pyrazolo[3,4-b]indole-5-carboxylic acid |

-continued

| Compound No. | Structure and Name |
|---|---|
| 124 | 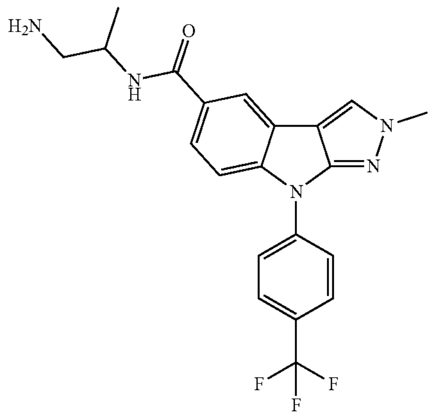 [SMILES: CC(CN)NC(=O)c1ccc2c(c1)c1cn(C)nc1n2-c1ccc(C(F)(F)F)cc1]<br>N-(1-aminopropan-2-yl)-2-methyl-8-[4-(trifluoromethyl)phenyl]-2H,8H-pyrazolo[3,4-b]indole-5-carboxamide |
| 125 | 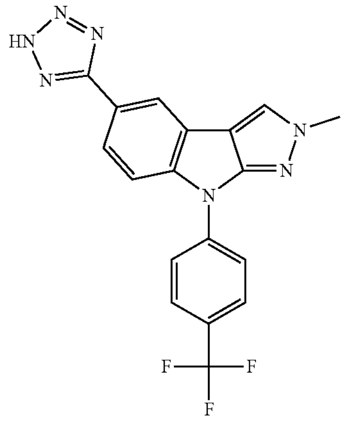 [SMILES: Cn1cc2c3cc(-c4nn[nH]n4)ccc3n(-c3ccc(C(F)(F)F)cc3)c2n1]<br>5-{2-methyl-8-[4-(trifluoromethyl)phenyl]-2H,8H-pyrazolo[3,4-b]indol-5-yl}-2H-1,2,3,4-tetrazole |
| 126 | 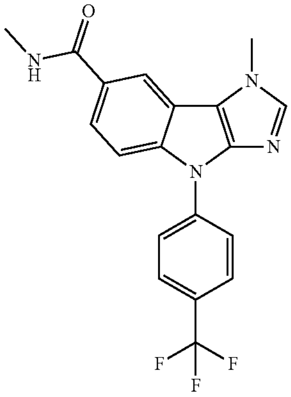 [SMILES: CNC(=O)c1ccc2c(c1)c1c(ncn1C)n2-c1ccc(C(F)(F)F)cc1]<br>N,1-dimethyl-4-[4-(trifluoromethyl)phenyl]-1H,4H-imidazo[4,5-b]indole-7-carboxamide |
| 127 | 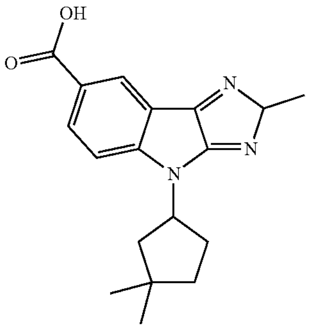 [SMILES: CC1N=c2c(n(C3CCC(C)(C)C3)c3ccc(C(=O)O)cc23)=N1]<br>4-(3,3-dimethylcyclopentyl)-2-methyl-2H,4H-pyrazolo[4,3-b]indole-7-carboxylic acid |
| 128 | 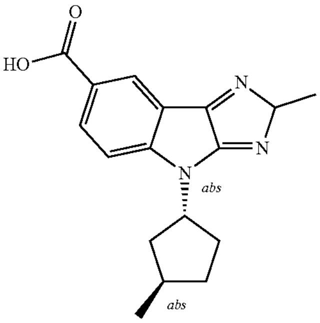 [SMILES: CC1N=c2c(n([C@@H]3CC[C@@H](C)C3)c3ccc(C(=O)O)cc23)=N1]<br>Trans isomer, absolute stereochemistry unknown<br>2-methyl-4-[(1R,3R)-3-methylcyclopentyl]-2H,4H-pyrazolo[4,3-b]indole-7-carboxylic acid |
| 129 | 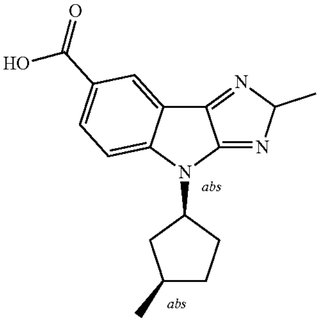 [SMILES: CC1N=c2c(n([C@H]3CC[C@@H](C)C3)c3ccc(C(=O)O)cc23)=N1]<br>Mixture of cis isomers<br>2-methyl-4-[(1S,3R)-3-methylcyclopentyl]-2H,4H-pyrazolo[4,3-b]indole-7-carboxylic acid |
| 130 | 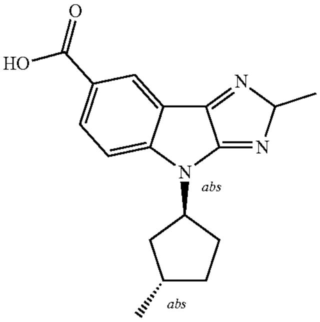 [SMILES: CC1N=c2c(n([C@H]3CC[C@H](C)C3)c3ccc(C(=O)O)cc23)=N1] |

| Compound No. | Structure and Name |
|---|---|
| | Trans isomer, absolute stereochemistry unknown 2-methyl-4-[(1S,3S)-3-methylcyclopentyl]-2H,4H-pyrazolo[4,3-b]indole-7-carboxylic acid |
| 131 | 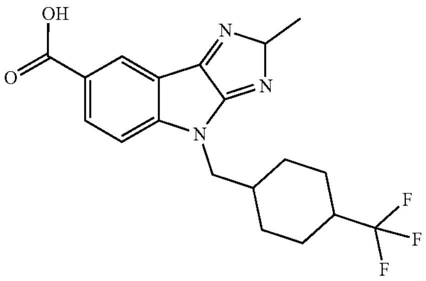 [SMILES: CC1N=c2c(n(CC3CCC(C(F)(F)F)CC3)c3ccc(C(=O)O)cc23)=N1] Mixture of cis and trans isomers 2-methyl-8-{[4-(trifluoromethyl)cyclohexyl]methyl}-2H,8H-pyrazolo[3,4-b]indole-5-carboxylic acid |
| 132 | 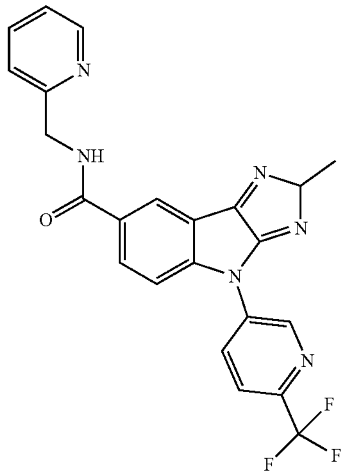 [SMILES: CC1N=c2c(n(-c3ccc(C(F)(F)F)nc3)c3ccc(C(=O)NCc4ccccn4)cc23)=N1] 2-methyl-N-[(pyridin-2-yl)methyl]-8-[6-(trifluoromethyl)pyridin-3-yl]-2H,8H-pyrazolo[3,4-b]indole-5-carboxamide |
| 133 | 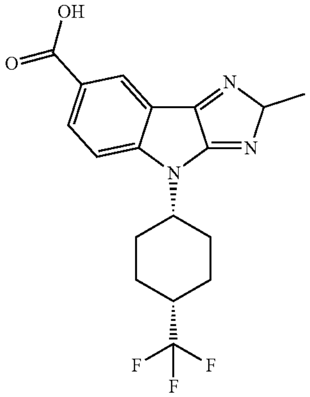 [SMILES: CC1N=c2c(n([C@H]3CC[C@@H](C(F)(F)F)CC3)c3ccc(C(=O)O)cc23)=N1] Pure cis isomer 2-methyl-4-[(1s,4s)-4-(trifluoromethyl)cyclohexyl]-2H,4H-pyrazolo[4,3-b]indole-7-carboxylic acid |

| Compound No. | Structure and Name |
|---|---|
| 134 | 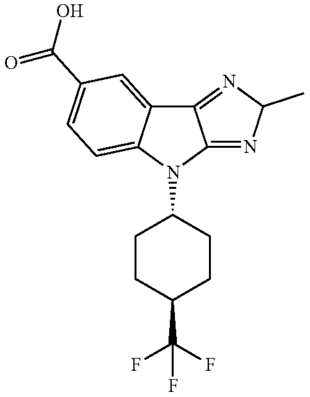 [SMILES: CC1N=c2c(n([C@H]3CC[C@H](C(F)(F)F)CC3)c3ccc(C(=O)O)cc23)=N1] Pure trans isomer 2-methyl-4-[(1r,4r)-4-(trifluoromethyl)cyclohexyl]-2H,4H-pyrazolo[4,3-b]indole-7-carboxylic acid |
| 135 | 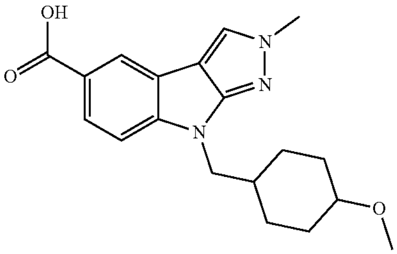 [SMILES: COC1CCC(Cn2c3ccc(C(=O)O)cc3c3cn(C)nc32)CC1] 8-[(4-methoxycyclohexyl)methyl]-2-methyl-2H,8H-pyrazolo[3,4-b]indole-5-carboxylic acid |
| 136 | 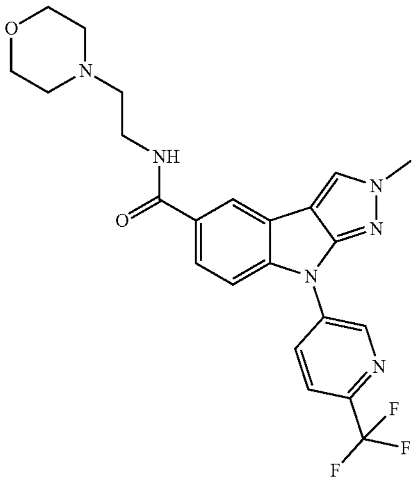 [SMILES: Cn1cc2c3cc(C(=O)NCCN4CCOCC4)ccc3n(-c3ccc(C(F)(F)F)nc3)c2n1] 2-methyl-N-[2-(morpholin-4-yl)ethyl]-8-[6-(trifluoromethyl)pyridin-3-yl]-2H,8H-pyrazolo[3,4-b]indole-5-carboxamide |

| Compound No. | Structure and Name |
|---|---|
| 137 | 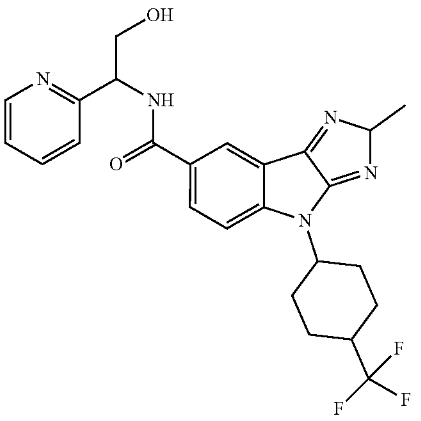 [SMILES: CC1N=c2c(n(C3CCC(C(F)(F)F)CC3)c3ccc(C(=O)NC(CO)c4ccccn4)cc23)=N1] N-[2-hydroxy-1-(pyridin-2-yl)ethyl]-2-methyl-8-[4-(trifluoromethyl)cyclohexyl]-2H,8H-pyrazolo[3,4-b]indole-5-carboxamide |
| 138 | 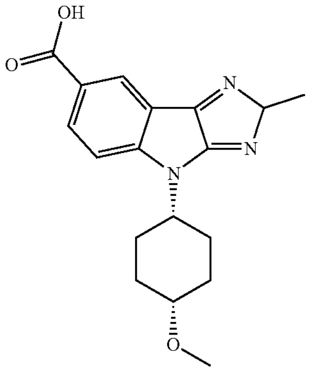 [SMILES: CO[C@H]1CC[C@@H](n2c3c(c4cc(C(=O)O)ccc42)=NC(C)N=3)CC1] 2-methyl-4-[(1s,4s)-4-methoxycyclohexyl]-2H,4H-pyrazolo[4,3-b]indole-7-carboxylic acid |
| 139 | 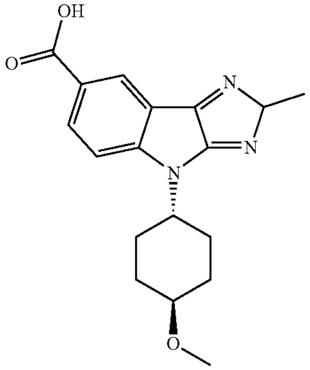 [SMILES: CO[C@H]1CC[C@H](n2c3c(c4cc(C(=O)O)ccc42)=NC(C)N=3)CC1] 2-methyl-4-[(1r,4r)-4-methoxycyclohexyl]-2H,4H-pyrazolo[4,3-b]indole-7-carboxylic acid |

| Compound No. | Structure and Name |
|---|---|
| 140 | 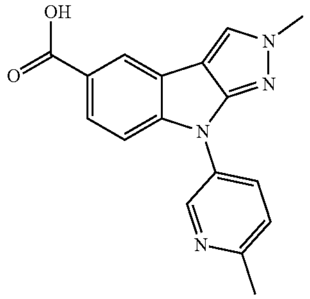 [SMILES: Cc1ccc(-n2c3ccc(C(=O)O)cc3c3cn(C)nc32)cn1] 2-methyl-8-(6-methylpyridin-3-yl)-2H,8H-pyrazolo[3,4-b]indole-5-carboxylic acid |
| 141 | 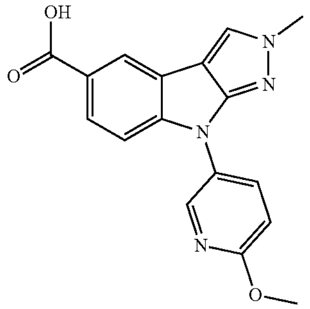 8-(6-methoxypyridin-3-yl)-2-methyl-2H,8H-pyrazolo[3,4-b]indole-5-carboxylic acid |
| 142 | 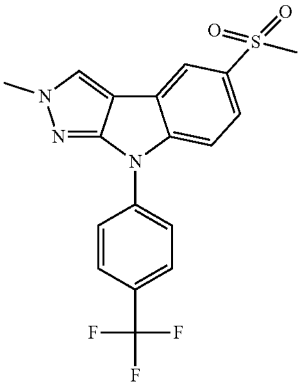 5-methanesulfonyl-2-methyl-8-[4-(trifluoromethyl)phenyl]-2H,8H-pyrazolo[3,4-b]indole |
| 143 | 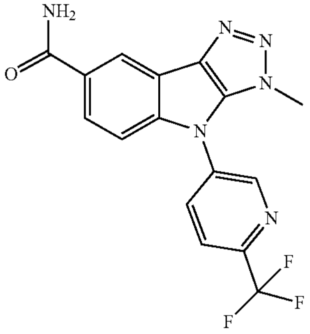 [SMILES: Cn1nnc2c3cc(C(N)=O)ccc3n(-c3ccc(C(F)(F)F)nc3)c21] |

-continued

| Compound No. | Structure and Name |
|---|---|
| | 3-methyl-4-[6-(trifluoromethyl)pyridin-3-yl]-3H,4H-[1,2,3]triazolo[4,5-b]indole-7-carboxamide |
| 144 | 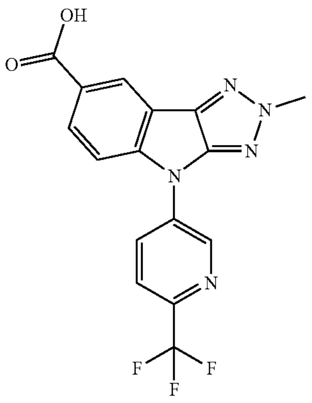 2-methyl-4-[6-(trifluoromethyl)pyridin-3-yl]-2H,4H-[1,2,3]triazolo[4,5-b]indole-7-carboxylic acid |
| 145 | 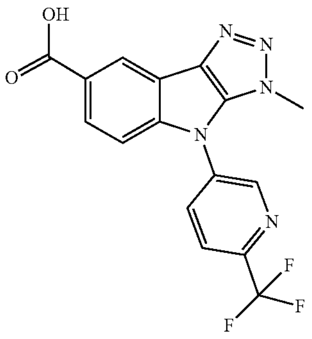 [SMILES: Cn1nnc2c3cc(C(=O)O)ccc3n(-c3ccc(C(F)(F)F)nc3)c21] 3-methyl-4-[6-(trifluoromethyl)pyridin-3-yl]-3H,4H-[1,2,3]triazolo[4,5-b]indole-7-carboxylic acid |
| 146 | 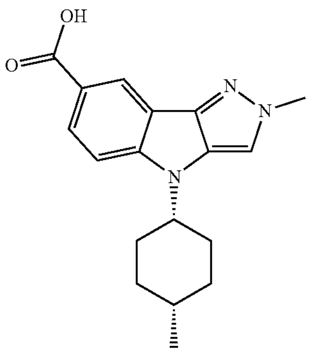 [SMILES: Cn1cc2c(n1)c1cc(C(=O)O)ccc1n2[C@H]1CC[C@@H](C)CC1] 2-methyl-4-[(1s,4s)-4-methylcyclohexyl]-2H,4H-pyrazolo[4,3-b]indole-7-carboxylic acid |

-continued

| Compound No. | Structure and Name |
|---|---|
| 147 | 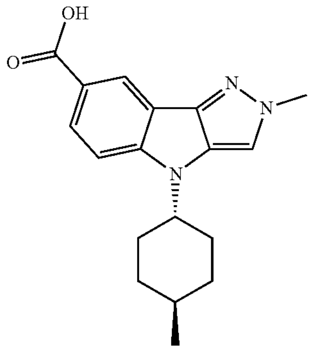 [SMILES: Cn1cc2c(n1)c1cc(C(=O)O)ccc1n2[C@H]1CC[C@H](C)CC1] 2-methyl-4-[(1r,4r)-4-methylcyclohexyl]-2H,4H-pyrazolo[4,3-b]indole-7-carboxylic acid |
| 148 | 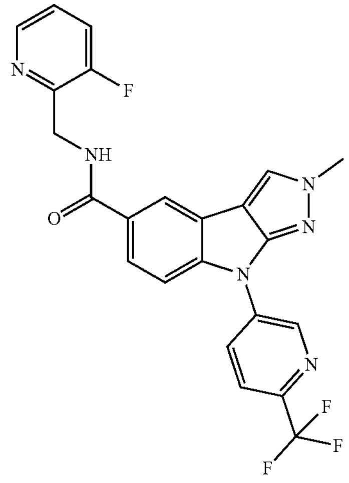 [SMILES: Cn1cc2c3cc(C(=O)NCc4ncccc4F)ccc3n(-c3ccc(C(F)(F)F)nc3)c2n1] N-[(3-fluoropyridin-2-yl)methyl]-2-methyl-8-[6-(trifluoromethyl)pyridin-3-yl]-2H,8H-pyrazolo[3,4-b]indole-5-carboxamide |
| 149 | 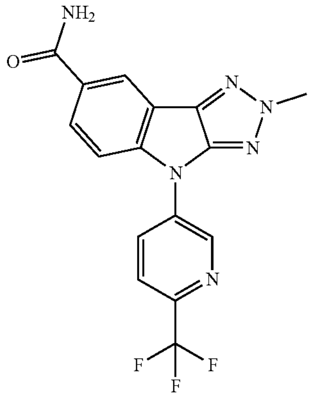 [SMILES: Cn1nc2c3cc(C(N)=O)ccc3n(-c3ccc(C(F)(F)F)nc3)c2n1] 2-methyl-4-[6-(trifluoromethyl)pyridin-3-yl]-2H,4H-[1,2,3]triazolo[4,5-b]indole-7-carboxamide |

-continued

| Compound No. | Structure and Name |
|---|---|
| 150 | 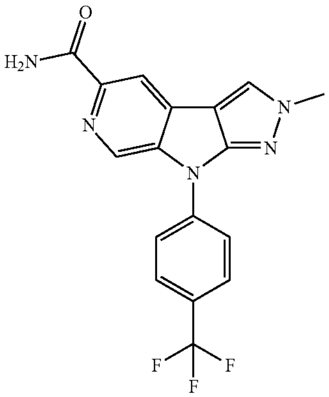 [SMILES: Cn1cc2c3cc(C(N)=O)ncc3n(-c3ccc(C(F)(F)F)cc3)c2n1] 4-methyl-7-[4-(trifluoromethyl)phenyl]-4,5,7,10-tetraazatricyclo[6.4.0.0$^{2,6}$]dodeca-1(8),2,5,9,11-pentaene-11-carboxamide |
| 151 | 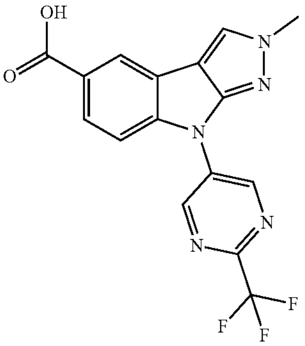 [SMILES: Cn1cc2c3cc(C(=O)O)ccc3n(-c3cnc(C(F)(F)F)nc3)c2n1] 2-methyl-8-[2-(trifluoromethyl)pyrimidin-5-yl]-2H,8H-pyrazolo[3,4-b]indole-5-carboxylic acid |
| 152 | 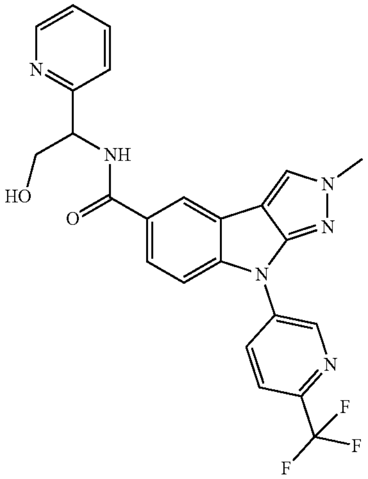 [SMILES: Cn1cc2c3cc(C(=O)NC(CO)c4ccccn4)ccc3n(-c3ccc(C(F)(F)F)nc3)c2n1] N-[2-hydroxy-1-(pyridin-2-yl)ethyl]-2-methyl-8-[6-(trifluoromethyl)pyridin-3-yl]-2H,8H-pyrazolo[3,4-b]indole-5-carboxamide |

-continued

| Compound No. | Structure and Name |
|---|---|
| 153 | 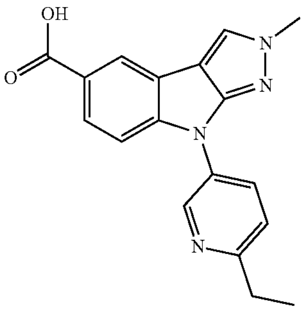 [SMILES: CCc1ccc(-n2c3ccc(C(=O)O)cc3c3cn(C)nc32)cn1] 8-(6-ethylpyridin-3-yl)-2-methyl-2H,8H-pyrazolo[3,4-b]indole-5-carboxylic acid |
| 154 | 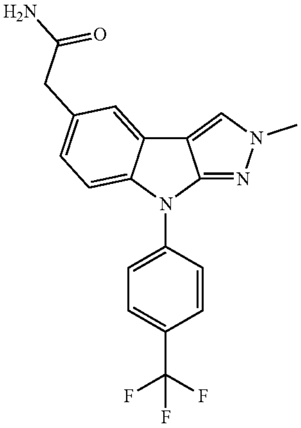 [SMILES: Cn1cc2c3cc(CC(N)=O)ccc3n(-c3ccc(C(F)(F)F)cc3)c2n1] 2-{2-methyl-8-[4-(trifluoromethyl)phenyl]-2H,8H-pyrazolo[3,4-b]indol-5-yl}acetamide |
| 155 | 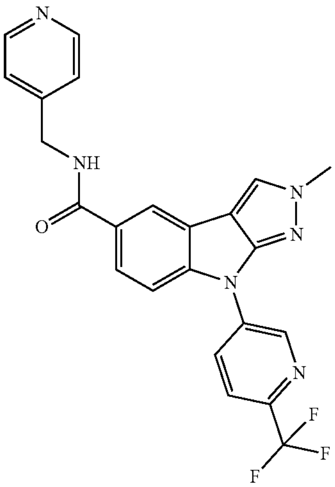 [SMILES: Cn1cc2c3cc(C(=O)NCc4ccncc4)ccc3n(-c3ccc(C(F)(F)F)nc3)c2n1] 2-methyl-N-[(pyridin-4-yl)methyl]-8-[6-(trifluoromethyl)pyridin-3-yl]-2H,8H-pyrazolo[3,4-b]indole-5-carboxamide |

-continued

| Compound No. | Structure and Name |
|---|---|
| 156 | 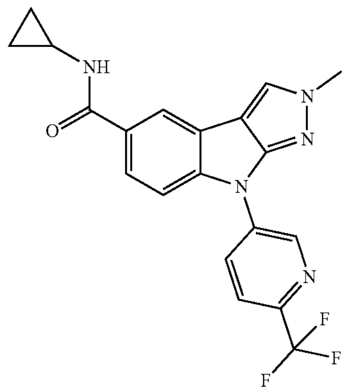 [SMILES: Cn1cc2c3cc(C(=O)NC4CC4)ccc3n(-c3ccc(C(F)(F)F)nc3)c2n1] N-cyclopropyl-2-methyl-8-[6-(trifluoromethyl)pyridin-3-yl]-2H,8H-pyrazolo[3,4-b]indole-5-carboxamide |
| 157 | 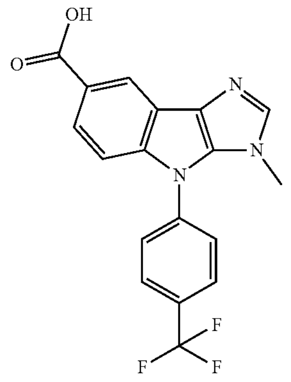 [SMILES: Cn1cnc2c3cc(C(=O)O)ccc3n(-c3ccc(C(F)(F)F)cc3)c21] 3-methyl-4-[4-(trifluoromethyl)phenyl]-3H,4H-imidazo[4,5-b]indole-7-carboxylic acid |
| 158 | 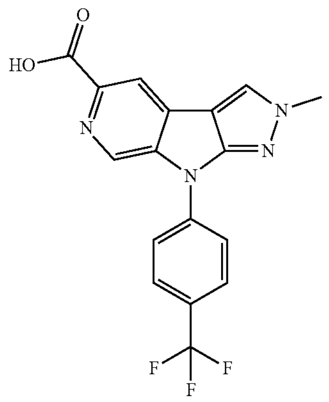 [SMILES: Cn1cc2c3cc(C(=O)O)ncc3n(-c3ccc(C(F)(F)F)cc3)c2n1] 4-methyl-7-[4-(trifluoromethyl)phenyl]-4,5,7,10-tetraaza-tricyclo[6.4.0.0$^{2,6}$]dodeca-1(8),2,5,9,11-pentaene-11-carboxylic acid |

-continued

| Compound No. | Structure and Name |
|---|---|
| 159 | 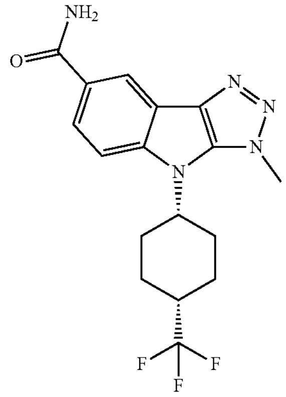 [SMILES: Cn1nnc2c3cc(C(N)=O)ccc3n([C@H]3CC[C@@H](C(F)(F)F)CC3)c21] 3-methyl-4-[(1s,4s)-4-(trifluoromethyl)cyclohexyl]-3H,4H-[1,2,3]triazolo[4,5-b]indole-7-carboxamide |
| 160 | 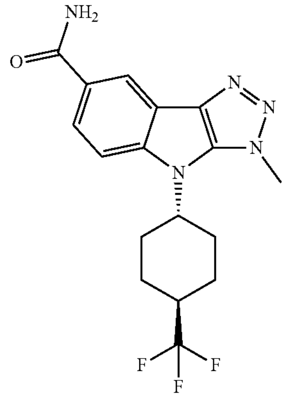 [SMILES: Cn1nnc2c3cc(C(N)=O)ccc3n([C@H]3CC[C@H](C(F)(F)F)CC3)c21] 3-methyl-4-[(1r,4r)-4-(trifluoromethyl)cyclohexyl]-3H,4H-[1,2,3]triazolo[4,5-b]indole-7-carboxamide |
| 161 | 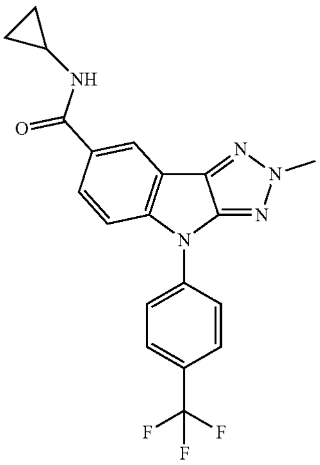 [SMILES: Cn1nc2c3cc(C(=O)NC4CC4)ccc3n(-c3ccc(C(F)(F)F)cc3)c2n1] N-cyclopropyl-2-methyl-4-[4-(trifluoromethyl)phenyl]-2H,4H-[1,2,3]triazolo[4,5-b]indole-7-carboxamide |

-continued

| Compound No. | Structure and Name |
|---|---|
| 162 | 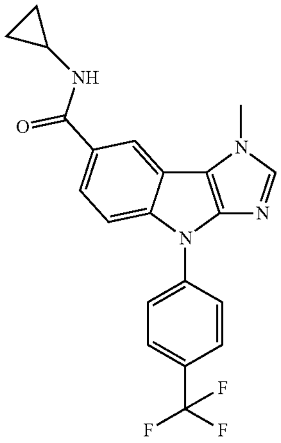 [SMILES: Cn1cnc2c1c1cc(C(=O)NC3CC3)ccc1n2-c1ccc(C(F)(F)F)cc1] N-cyclopropyl-1-methyl-4-[4-(trifluoromethyl)phenyl]-1H,4H-imidazo[4,5-b]indole-7-carboxamide |
| 163 | 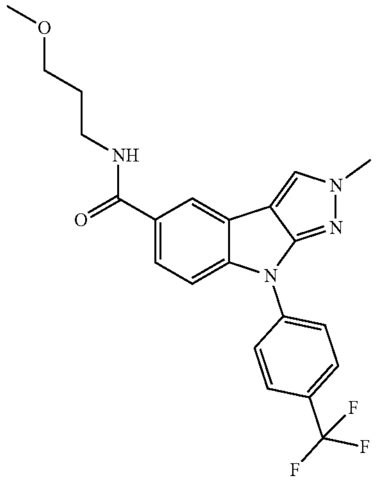 N-(3-methoxypropyl)-2-methyl-8-[4-(trifluoromethyl)phenyl]-2H,8H-pyrazolo[3,4-b]indole-5-carboxamide |
| 164 | 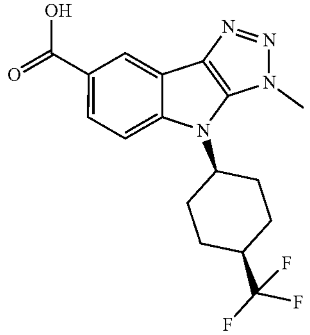 [SMILES: Cn1nnc2c3cc(C(=O)O)ccc3n([C@H]3CC[C@@H](C(F)(F)F)CC3)c21] 3-methyl-4-[(1s,4s)-4-(trifluoromethyl)cyclohexyl]-3H,4H-[1,2,3]triazolo[4,5-b]indole-7-carboxylic acid |

-continued

| Compound No. | Structure and Name |
|---|---|
| 165 | 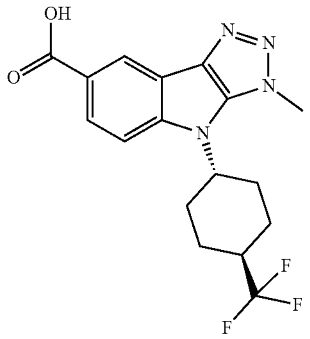 [SMILES: Cn1nnc2c3cc(C(=O)O)ccc3n([C@H]3CC[C@H](C(F)(F)F)CC3)c21] 3-methyl-4-[(1r,4r)-4-(trifluoromethyl)cyclohexyl]-3H,4H-[1,2,3]triazolo[4,5-b]indole-7-carboxylic acid |
| 166 | 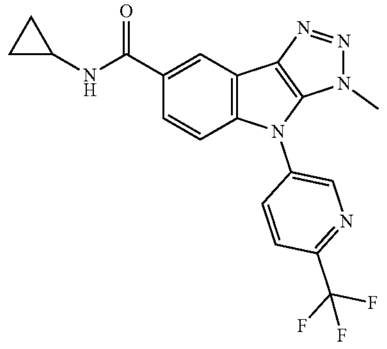 [SMILES: Cn1nnc2c3cc(C(=O)NC4CC4)ccc3n(-c3ccc(C(F)(F)F)nc3)c21] N-cyclopropyl-3-methyl-4-[6-(trifluoromethyl)pyridin-3-yl]-3H,4H-[1,2,3]triazolo[4,5-b]indole-7-carboxamide |
| 167 | 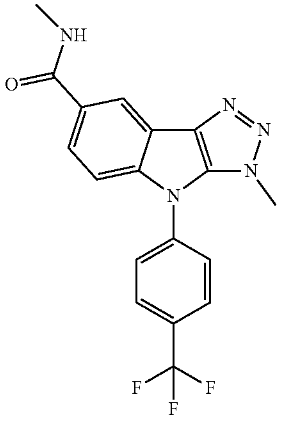 [SMILES: CNC(=O)c1ccc2c(c1)c1nnn(C)c1n2-c1ccc(C(F)(F)F)cc1] N,3-dimethyl-4-[4-(trifluoromethyl)phenyl]-3H,4H-[1,2,3]triazolo[4,5-b]indole-7-carboxamide |

-continued

| Compound No. | Structure and Name |
|---|---|
| 168 | 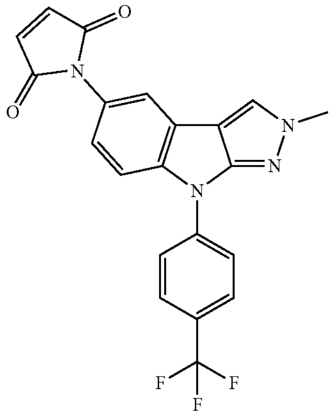 [SMILES: Cn1cc2c3cc(N4C(=O)C=CC4=O)ccc3n(-c3ccc(C(F)(F)F)cc3)c2n1] 1-{2-methyl-8-[4-(trifluoromethyl)phenyl]-2H,8H-pyrazolo[3,4-b]indol-5-yl}-2,5-dihydro-1H-pyrrole-2,5-dione |
| 169 | 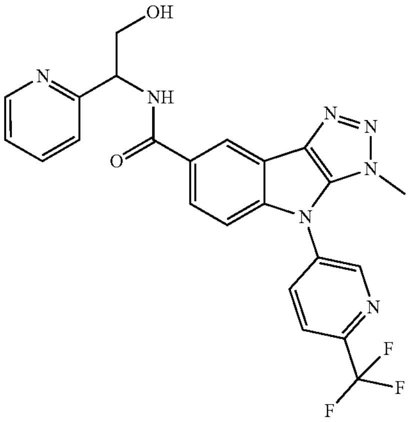 [SMILES: Cn1nnc2c3cc(C(=O)NC(CO)c4ccccn4)ccc3n(-c3ccc(C(F)(F)F)nc3)c21] N-[2-hydroxy-1-(pyridin-2-yl)ethyl]-3-methyl-4-[6-(trifluoromethyl)pyridin-3-yl]-3H,4H-[1,2,3]triazolo[4,5-b]indole-7-carboxamide |
| 170 | 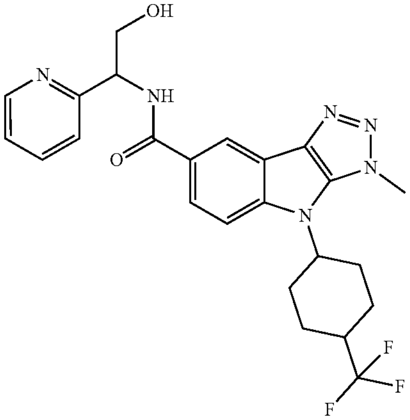 [SMILES: Cn1nnc2c3cc(C(=O)NC(CO)c4ccccn4)ccc3n(C3CCC(C(F)(F)F)CC3)c21] N-[2-hydroxy-1-(pyridin-2-yl)ethyl]-3-methyl-4-[4-(trifluoromethyl)cyclohexyl]-3H,4H-[1,2,3]triazolo[4,5-b]indole-7-carboxamide |

-continued

| Compound No. | Structure and Name |
|---|---|
| 171 | 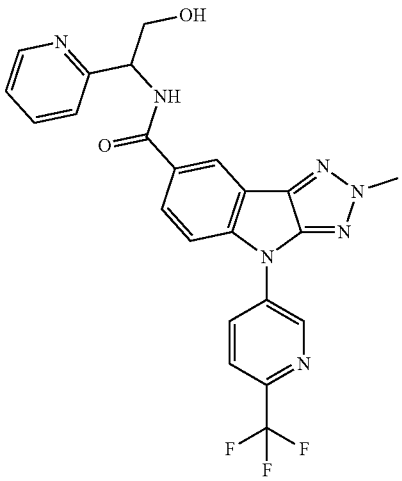 [SMILES: Cn1nc2c3cc(C(=O)NC(CO)c4ccccn4)ccc3n(-c3ccc(C(F)(F)F)nc3)c2n1] N-[2-hydroxy-1-(pyridin-2-yl)ethyl]-2-methyl-4-[6-(trifluoromethyl)pyridin-3-yl]-2H,4H-[1,2,3]triazolo[4,5-b]indole-7-carboxamide |
| 172 | 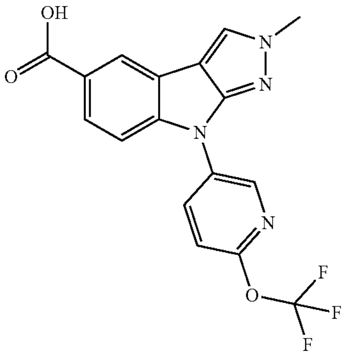 [SMILES: Cn1cc2c3cc(C(=O)O)ccc3n(-c3ccc(OC(F)(F)F)nc3)c2n1] 2-methyl-8-[6-(trifluoromethoxy)pyridin-3-yl]-2H,8H-pyrazolo[3,4-b]indole-5-carboxylic acid |
| 173 | 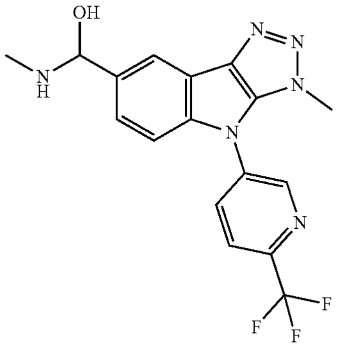 N,3-dimethyl-4-[6-(trifluoromethyl)pyridin-3-yl]-3H,4H-[1,2,3]triazolo[4,5-b]indole-7-carboxamide |

-continued

| Compound No. | Structure and Name |
|---|---|
| 174 | 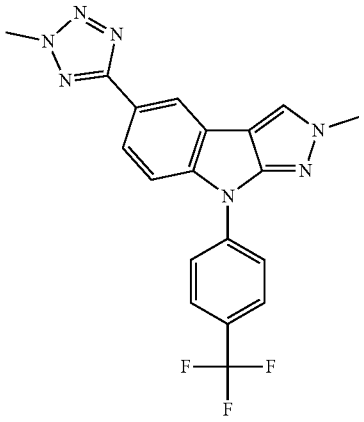<br>2-methyl-5-{2-methyl-8-[4-(trifluoromethyl)phenyl]-2H,8H-pyrazolo[3,4-b]indol-5-yl}-2H-1,2,3,4-tetrazole |
| 175 | 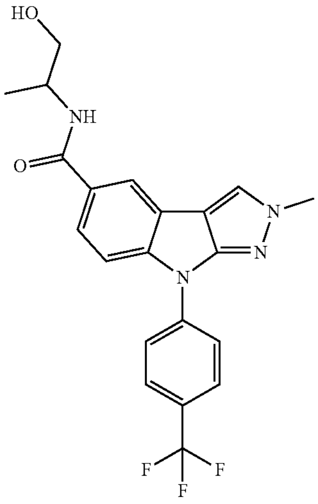 [SMILES: CC(CO)NC(=O)c1ccc2c(c1)c1cn(C)nc1n2-c1ccc(C(F)(F)F)cc1]<br>N-(1-hydroxypropan-2-yl)-2-methyl-8-[4-(trifluoromethyl)phenyl]-2H,8H-pyrazolo[3,4-b]indole-5-carboxamide |
| 176 | 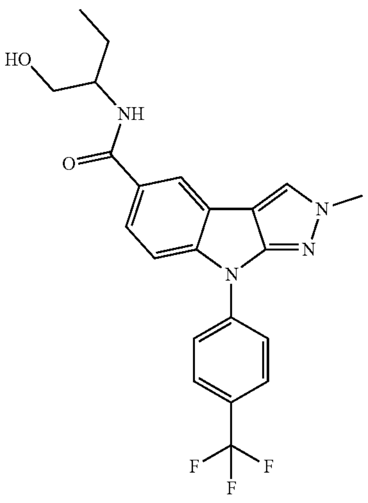 [SMILES: CCC(CO)NC(=O)c1ccc2c(c1)c1cn(C)nc1n2-c1ccc(C(F)(F)F)cc1]<br>N-(1-hydroxybutan-2-yl)-2-methyl-8-[4-(trifluoromethyl)phenyl]-2H,8H-pyrazolo[3,4-b]indole-5-arboxamide |
| 177 | 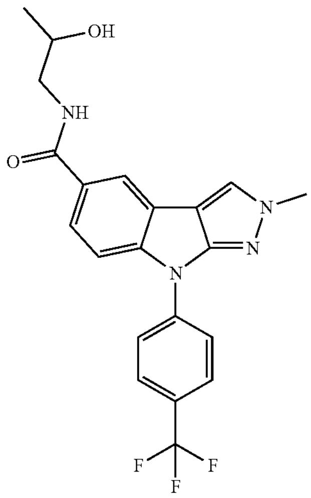 [SMILES: CC(O)CNC(=O)c1ccc2c(c1)c1cn(C)nc1n2-c1ccc(C(F)(F)F)cc1]<br>N-(2-hydroxypropyl)-2-methyl-8-[4-(trifluoromethyl)phenyl]-2H,8H-pyrazolo[3,4-b]indole-5-carboxamide |
| 178 | 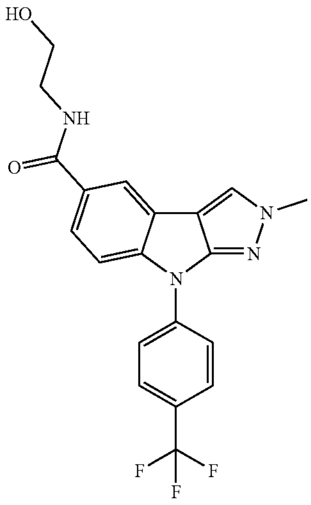 [SMILES: Cn1cc2c3cc(C(=O)NCCO)ccc3n(-c3ccc(C(F)(F)F)cc3)c2n1]<br>N-(2-hydroxyethyl)-2-methyl-8-[4-(trifluoromethyl)phenyl]-2H,8H-pyrazolo[3,4-b]indole-5-carboxamide |

-continued

| Compound No. | Structure and Name |
| --- | --- |
| 179 | 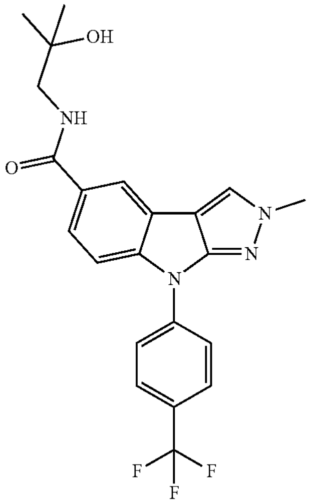 [SMILES: Cn1cc2c3cc(C(=O)NCC(C)(C)O)ccc3n(-c3ccc(C(F)(F)F)cc3)c2n1]<br>N-(2-hydroxy-2-methylpropyl)-2-methyl-8-[4-(trifluoromethyl)phenyl]-2H,8H-pyrazolo[3,4-b]indole-5-carboxamide |
| 180 | 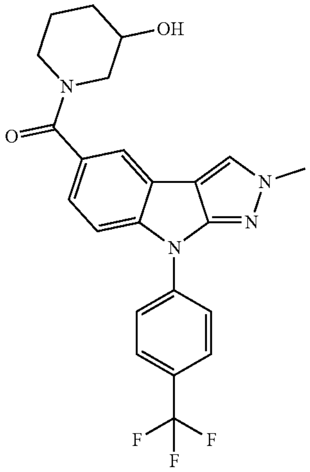 [SMILES: Cn1cc2c3cc(C(=O)N4CCCC(O)C4)ccc3n(-c3ccc(C(F)(F)F)cc3)c2n1]<br>1-{2-methyl-8-[4-(trifluoromethyl)phenyl]-2H,8H-pyrazolo[3,4-b]indole-5-carbonyl}piperidin-3-ol |
| 181 | 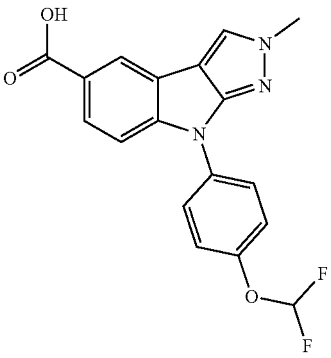 [SMILES: Cn1cc2c3cc(C(=O)O)ccc3n(-c3ccc(OC(F)F)cc3)c2n1]<br>8-[4-(difluoromethoxy)phenyl]-2-methyl-2H,8H-pyrazolo[3,4-b]indole-5-carboxylic acid |

-continued

| Compound No. | Structure and Name |
| --- | --- |
| 182 | 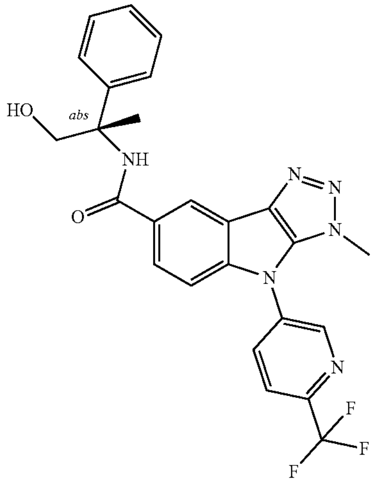 [SMILES: Cn1nnc2c3cc(C(=O)N[C@](C)(CO)c4ccccc4)ccc3n(-c3ccc(C(F)(F)F)nc3)c21]<br>Absolute configuration known/assigned<br>N-[(2S)-1-hydroxy-2-phenylpropan-2-yl]-3-methyl-4-[6-(trifluoromethyl)pyridin-3-yl]-3H,4H-[1,2,3]triazolo[4,5-b]indole-7-carboxamide |
| 183 | 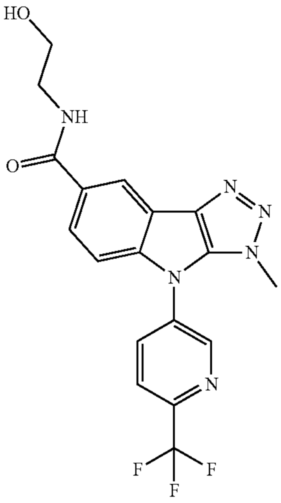 [SMILES: Cn1nnc2c3cc(C(=O)NCCO)ccc3n(-c3ccc(C(F)(F)F)nc3)c21]<br>N-(2-hydroxyethyl)-3-methyl-4-[6-(trifluoromethyl)pyridin-3-yl]-3H,4H-[1,2,3]triazolo[4,5-b]indole-7-carboxamide |

-continued

| Compound No. | Structure and Name |
|---|---|
| 184 | 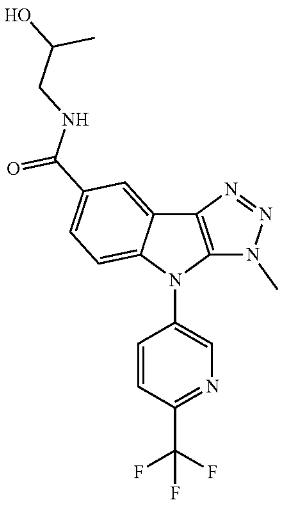 [SMILES: CC(O)CNC(=O)c1ccc2c(c1)c1nnn(C)c1n2-c1ccc(C(F)(F)F)nc1]<br>N-(2-hydroxypropyl)-3-methyl-4-[6-(trifluoromethyl)pyridin-3-yl]-3H,4H-[1,2,3]triazolo[4,5-b]indole-7-carboxamide |
| 185 | 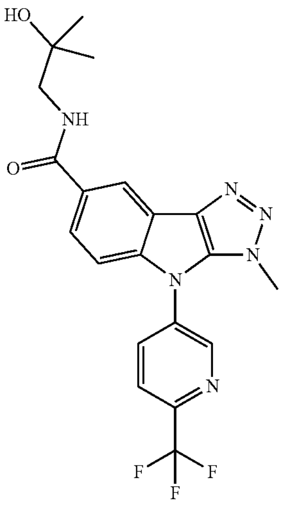 [SMILES: Cn1nnc2c3cc(C(=O)NCC(C)(C)O)ccc3n(-c3ccc(C(F)(F)F)nc3)c21]<br>N-(2-hydroxy-2-methylpropyl)-3-methyl-4-[6-(trifluoromethyl)pyridin-3-yl]-3H,4H-[1,2,3]triazolo[4,5-b]indole-7-carboxamide |

-continued

| Compound No. | Structure and Name |
|---|---|
| 186 | 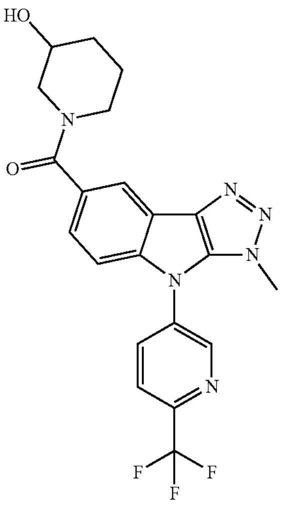 [SMILES: Cn1nnc2c3cc(C(=O)N4CCCC(O)C4)ccc3n(-c3ccc(C(F)(F)F)nc3)c21]<br>1-{3-methyl-4-[6-(trifluoromethyl)pyridin-3-yl]-3H,4H-[1,2,3]triazolo[4,5-b]indole-7-carbonyl}piperidin-3-ol |
| 187 | 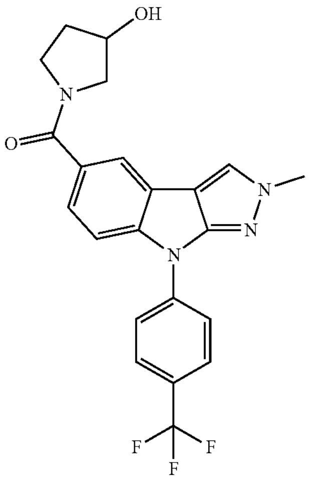 [SMILES: Cn1cc2c3cc(C(=O)N4CCC(O)C4)ccc3n(-c3ccc(C(F)(F)F)cc3)c2n1]<br>1-{2-methyl-8-[4-(trifluoromethyl)phenyl]-2H,8H-pyrazolo[3,4-b]indole-5-carbonyl}pyrrolidin-3-ol |

-continued

| Compound No. | Structure and Name |
|---|---|
| 188 | 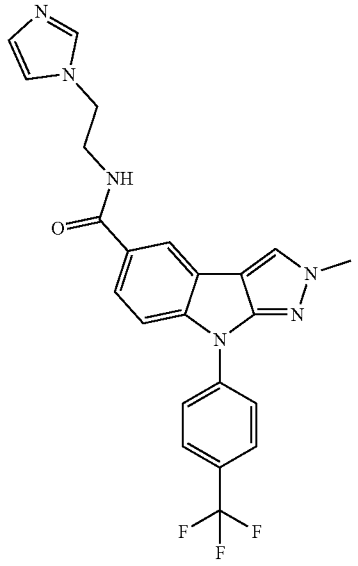 [SMILES: Cn1cc2c3cc(C(=O)NCCn4ccnc4)ccc3n(-c3ccc(C(F)(F)F)cc3)c2n1] N-[2-(1H-imidazol-1-yl)ethyl]-2-methyl-8-[4-(trifluoromethyl)phenyl]-2H,8H-pyrazolo[3,4-b]indole-5-carboxamide |
| 189 | 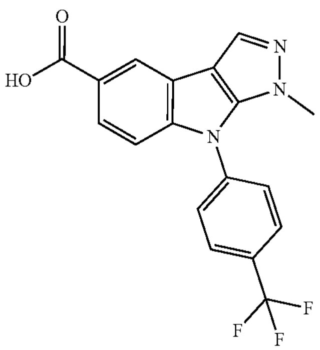 [SMILES: Cn1ncc2c3cc(C(=O)O)ccc3n(-c3ccc(C(F)(F)F)cc3)c21] 1-methyl-8-[4-(trifluoromethyl)phenyl]-1H,8H-pyrazolo[3,4-b]indole-5-carboxylic acid |

-continued

| Compound No. | Structure and Name |
|---|---|
| 190 | 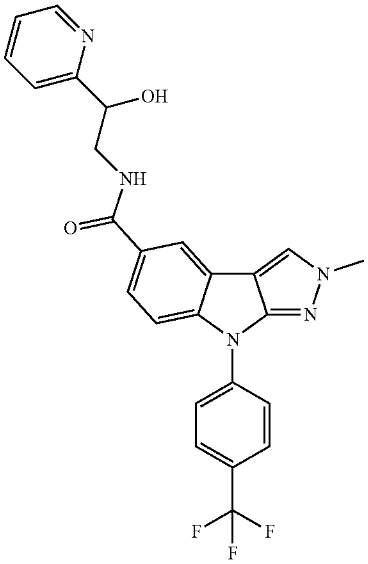 [SMILES: Cn1cc2c3cc(C(=O)NCC(O)c4ccccn4)ccc3n(-c3ccc(C(F)(F)F)cc3)c2n1] N-[2-hydroxy-2-(pyridin-2-yl)ethyl]-2-methyl-8-[4-(trifluoromethyl)phenyl]-2H,8H-pyrazolo[3,4-b]indole-5-carboxamide |
| 191 | 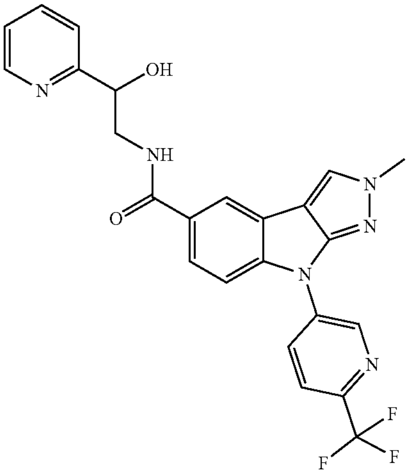 [SMILES: Cn1cc2c3cc(C(=O)NCC(O)c4ccccn4)ccc3n(-c3ccc(C(F)(F)F)nc3)c2n1] N-[2-hydroxy-2-(pyridin-2-yl)ethyl]-2-methyl-8-[6-(trifluoromethyl)pyridin-3-yl]-2H,8H-pyrazolo[3,4-b]indole-5-carboxamide |

-continued

| Compound No. | Structure and Name |
| --- | --- |
| 193 | 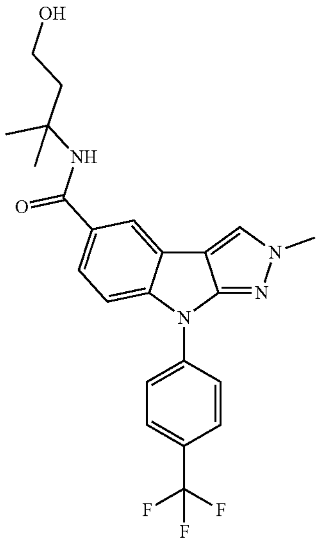 [SMILES: Cn1cc2c3cc(C(=O)NC(C)(C)CCO)ccc3n(-c3ccc(C(F)(F)F)cc3)c2n1] N-(4-hydroxy-2-methylbutan-2-yl)-2-methyl-8-[4-(trifluoromethyl)phenyl]-2H,8H-pyrazolo[3,4-ib]ndole-5-carboxamide |
| 194 | 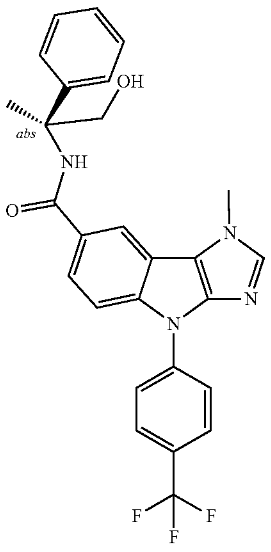 [SMILES: Cn1cnc2c1c1cc(C(=O)N[C@](C)(CO)c3ccccc3)ccc1n2-c1ccc(C(F)(F)F)cc1] Absolute configuration known/assigned N-[(2S)-1-hydroxy-2-phenylpropan-2-yl]-1-methyl-4-[4-(trifluoromethyl)phenyl]-1H,4H-imidazo[4,5-b]indole-7-carboxamide |

-continued

| Compound No. | Structure and Name |
| --- | --- |
| 195 | 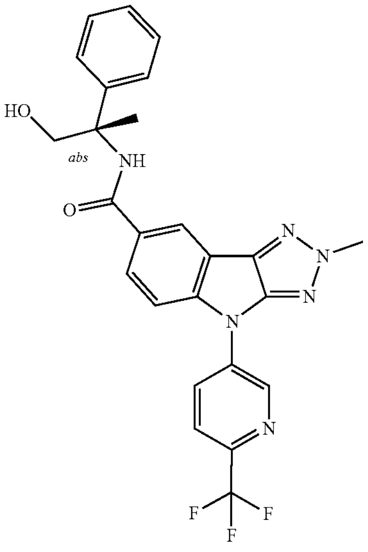 [SMILES: Cn1nc2c3cc(C(=O)N[C@](C)(CO)c4ccccc4)ccc3n(-c3ccc(C(F)(F)F)nc3)c2n1] Absolute configuration known/assgined N-[(2S)-1-hydroxy-2-phenylpropan-2-yl]-2-methyl-4-[6-(trifluoromethyl)pyridin-3-yl]-2H,4H-[1,2,3]triazolo[4,5-b]indole-7-carboxamide |
| 196 | 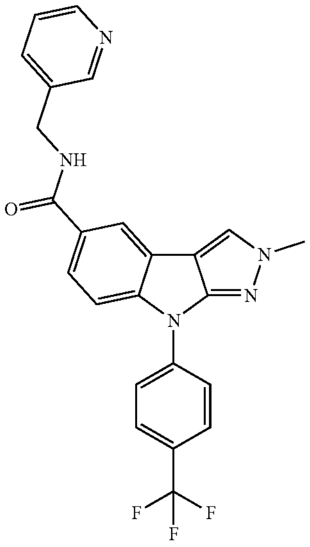 [SMILES: Cn1cc2c3cc(C(=O)NCc4cccnc4)ccc3n(-c3ccc(C(F)(F)F)cc3)c2n1] 2-methyl-N-[(pyridin-3-yl)methyl]-8-[4-(trifluoromethyl)phenyl]-2H,8H-pyrazolo[3,4-b]indole-5-carboxamide |

-continued

| Compound No. | Structure and Name |
| --- | --- |
| 197 | 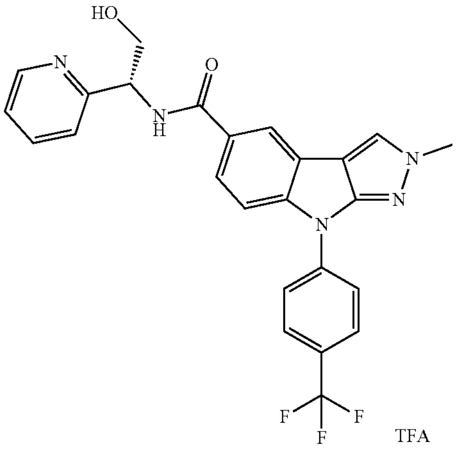 [SMILES: Cn1cc2c3cc(C(=O)N[C@@H](CO)c4ccccn4)ccc3n(-c3ccc(C(F)(F)F)cc3)c2n1] TFA<br>Absolute configuration known/assigned<br>N-[(1R)-2-hydroxy-1-(pyridin-2-yl)ethyl]-2-methyl-8-[4-(trifluoromethyl)phenyl]-2H,8H-pyrazolo[3,4-b]indole-5-carboxamide |
| 198 | 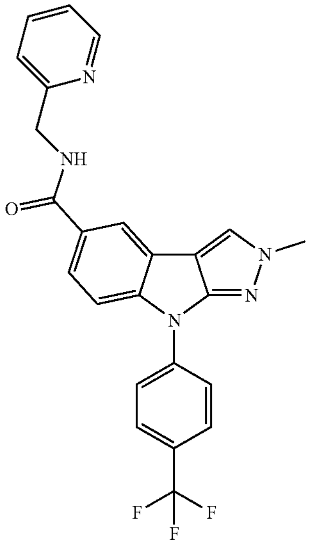 [SMILES: Cn1cc2c3cc(C(=O)NCc4ccccn4)ccc3n(-c3ccc(C(F)(F)F)cc3)c2n1]<br>2-methyl-N-[(pyridin-2-yl)methyl]-8-[4-(trifluoromethyl)phenyl]-2H,8H-pyrazolo[3,4-b]indole-5-carboxamide |

-continued

| Compound No. | Structure and Name |
| --- | --- |
| 199 | 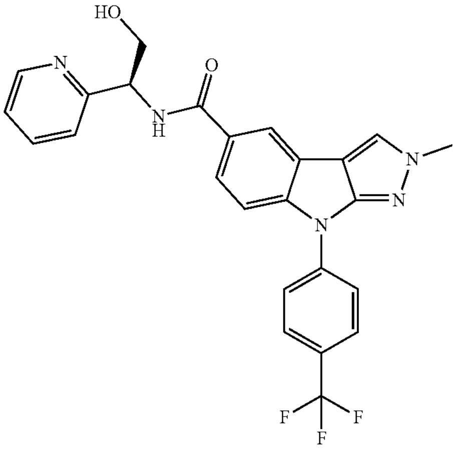 [SMILES: Cn1cc2c3cc(C(=O)N[C@H](CO)c4ccccn4)ccc3n(-c3ccc(C(F)(F)F)cc3)c2n1]<br>Absolute configuration known/assigned<br>N-[(1S)-2-hydroxy-1-(pyridin-2-yl)ethyl]-2-methyl-8-[4-(trifluoromethyl)phenyl]-2H,8H-pyrazolo[3,4-b]indole-5-carboxamide |
| 200 | 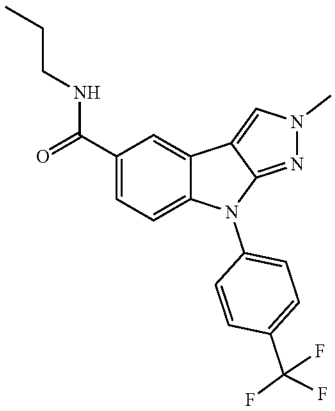 [SMILES: CCCNC(=O)c1ccc2c(c1)c1cn(C)nc1n2-c1ccc(C(F)(F)F)cc1]<br>2-methyl-N-propyl-8-[4-(trifluoromethyl)phenyl]-2H,8H-pyrazolo[3,4-b]indole-5-carboxamide |
| 201 | 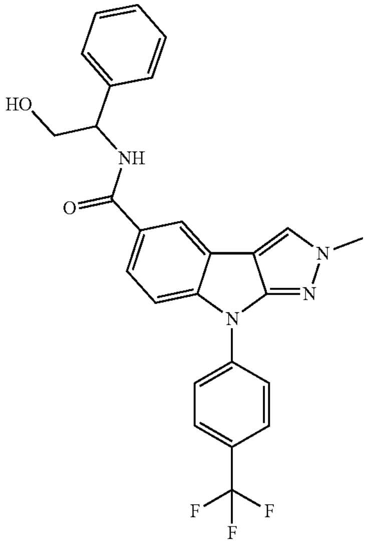 [SMILES: Cn1cc2c3cc(C(=O)NC(CO)c4ccccc4)ccc3n(-c3ccc(C(F)(F)F)cc3)c2n1] |

-continued

| Compound No. | Structure and Name |
|---|---|
| | N-(2-hydroxy-1-phenylethyl)-2-methyl-8-[4-(trifluoromethyl)phenyl]-2H,8H-pyrazolo[3,4-b]indole-5-carboxamide |
| 202 | 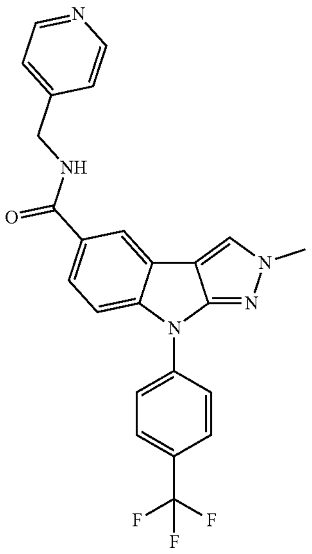 [SMILES: Cn1cc2c3cc(C(=O)NCc4ccncc4)ccc3n(-c3ccc(C(F)(F)F)cc3)c2n1] 2-methyl-N-[(pyridin-4-yl)methyl]-8-[4-(trifluoromethyl)phenyl]-2H,8H-pyrazolo[3,4-b]indole-5-carboxamide |
| 203 | 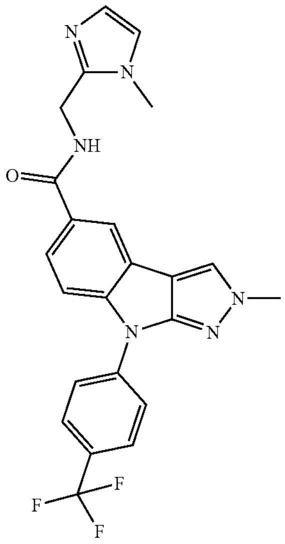 [SMILES: Cn1cc2c3cc(C(=O)NCc4nccn4C)ccc3n(-c3ccc(C(F)(F)F)cc3)c2n1] 2-methyl-N-[(1-methyl-1H-imidazol-2-yl)methyl]-8-[4-(trifluoromethyl)phenyl]-2H,8H-pyrazolo[3,4-b]indole-5-carboxamide |

-continued

| Compound No. | Structure and Name |
|---|---|
| 204 | 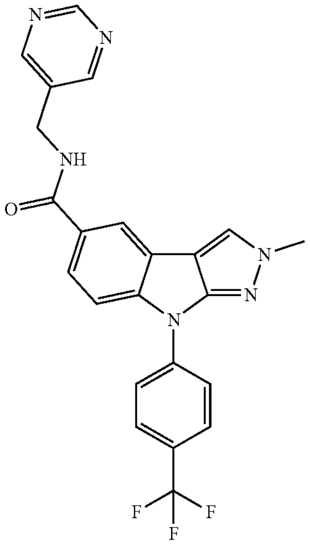 [SMILES: Cn1cc2c3cc(C(=O)NCc4cncnc4)ccc3n(-c3ccc(C(F)(F)F)cc3)c2n1] 2-methyl-N-[(pyrimidin-5-yl)methyl]-8-[4-(trifluoromethyl)phenyl]-2H,8H-pyrazolo[3,4-b]indole-5-carboxamide |
| 205 | 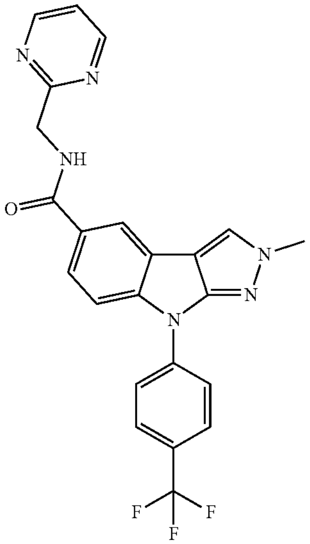 [SMILES: Cn1cc2c3cc(C(=O)NCc4ncccn4)ccc3n(-c3ccc(C(F)(F)F)cc3)c2n1] 2-methyl-N-[(pyrimidin-2-yl)methyl]-8-[4-(trifluoromethyl)phenyl]-2H,8H-pyrazolo[3,4-b]indole-5-carboxamide |

-continued

| Compound No. | Structure and Name |
|---|---|
| 206 | 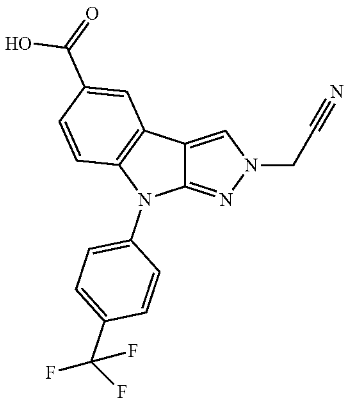 [SMILES: N#CCn1cc2c3cc(C(=O)O)ccc3n(-c3ccc(C(F)(F)F)cc3)c2n1] 2-(cyanomethyl)-8-[4-(trifluoromethyl)phenyl]-2H,8H-pyrazolo[3,4-b]indole-5-carboxylic acid |
| 207 | 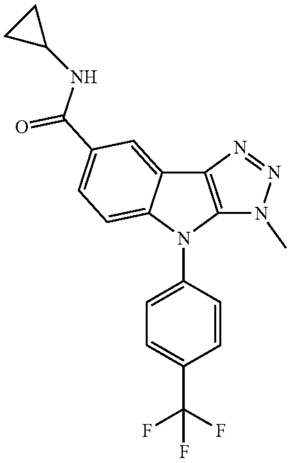 [SMILES: Cn1nnc2c3cc(C(=O)NC4CC4)ccc3n(-c3ccc(C(F)(F)F)cc3)c21] N-cyclopropyl-3-methyl-4-[4-(trifluoromethyl)phenyl]-3H,4H-[1,2,3]triazolo[4,5-b]indole-7-carboxamide |
| 208 | 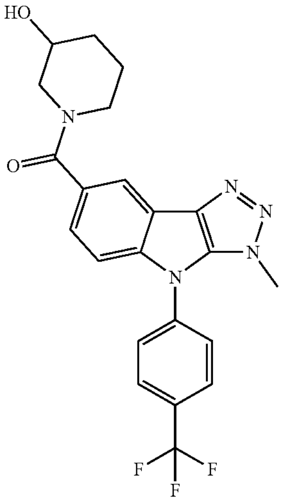 [SMILES: Cn1nnc2c3cc(C(=O)N4CCCC(O)C4)ccc3n(-c3ccc(C(F)(F)F)cc3)c21] 1-{3-methyl-4-[4-(trifluoromethyl)phenyl]-3H,4H-[1,2,3]triazolo[4,5-b]indole-7-carbonyl}piperidin-3-ol |

-continued

| Compound No. | Structure and Name |
|---|---|
| 209 | 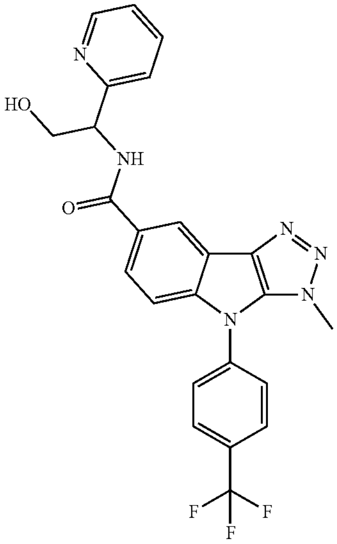 [SMILES: Cn1nnc2c3cc(C(=O)NC(CO)c4ccccn4)ccc3n(-c3ccc(C(F)(F)F)cc3)c21] N-[2-hydroxy-1-(pyridin-2-yl)ethyl]-3-methyl-4-[4-(trifluoromethyl)phenyl]-3H,4H-[1,2,3]triazolo[4,5-b]indole-7-carboxamide |
| 210 | 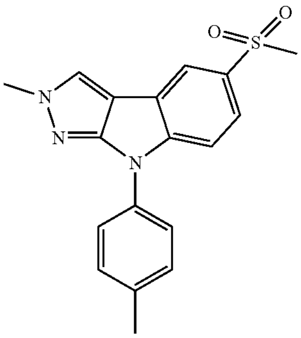 5-methanesulfonyl-2-methyl-8-(4-methylphenyl)-2H,8H-pyrazolo[3,4-b]indole |
| 211 | 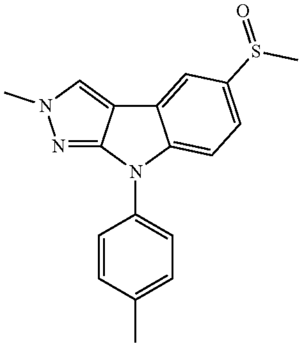 5-methanesulfinyl-2-methyl-8-(4-methylphenyl)-2H,8H-pyrazolo[3,4-b]indole |

-continued

| Compound No. | Structure and Name |
|---|---|
| 212 | 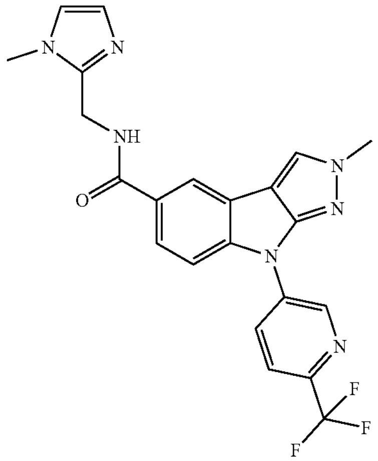<br>2-methyl-N-[(1-methyl-1H-imidazol-2-yl)methyl]-8-[6-(trifluoromethyl)pyridin-3-yl]-2H,8H-pyrazolo[3,4-b]indole-5-carboxamide |
| 213 | 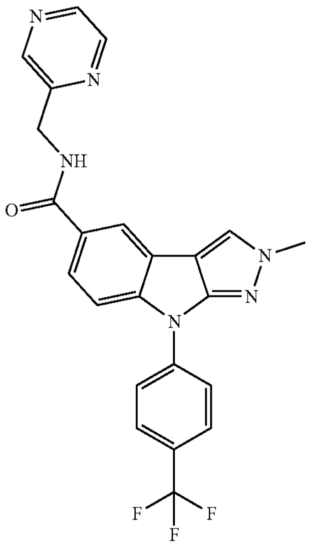 [SMILES: Cn1cc2c3cc(C(=O)NCc4cnccn4)ccc3n(-c3ccc(C(F)(F)F)cc3)c2n1]<br>2-methyl-N-[(pyrazin-2-yl)methyl]-8-[4-(trifluoromethyl)phenyl]-2H,8H-pyrazolo[3,4-b]indole-5-carboxamide |

-continued

| Compound No. | Structure and Name |
|---|---|
| 214 | 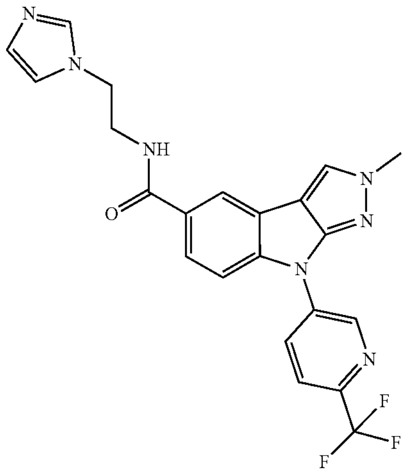 [SMILES: Cn1cc2c3cc(C(=O)NCCn4ccnc4)ccc3n(-c3ccc(C(F)(F)F)nc3)c2n1]<br>N-[2-(1H-imidazol-1-yl)ethyl]-2-methyl-8-[6-(trifluoromethyl)pyridin-3-yl]-2H,8H-pyrazolo[3,4-b]indole-5-carboxamide |
| 215 | 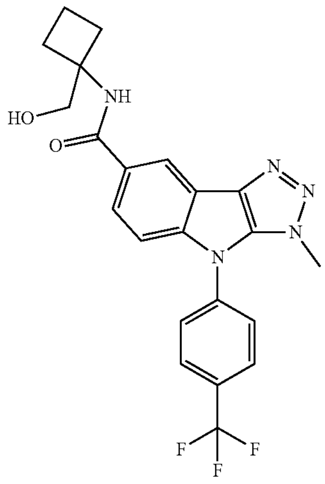 [SMILES: Cn1nnc2c3cc(C(=O)NC4(CO)CCC4)ccc3n(-c3ccc(C(F)(F)F)cc3)c21]<br>N-[1-(hydroxymethyl)cyclobutyl]-3-methyl-4-[4-(trifluoromethyl)phenyl]-3H,4H-[1,2,3]triazolo[4,5-b]indole-7-carboxamide |

-continued

| Compound No. | Structure and Name |
|---|---|
| 216 | 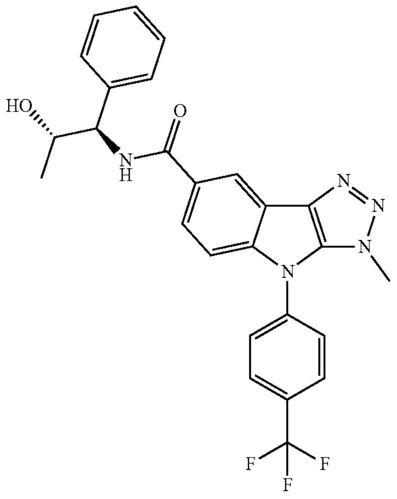 [SMILES: C[C@H](O)[C@H](NC(=O)c1ccc2c(c1)c1nnn(C)c1n2-c1ccc(C(F)(F)F)cc1)c1ccccc1] Absolute configuration known/assigned N-[(1R,2S)-2-hydroxy-1-phenylpropyl]-3-methyl-4-[4-(trifluoromethyl)phenyl]-3H,4H-[1,2,3]triazolo[4,5-b]indole-7-carboxamide |
| 217 | 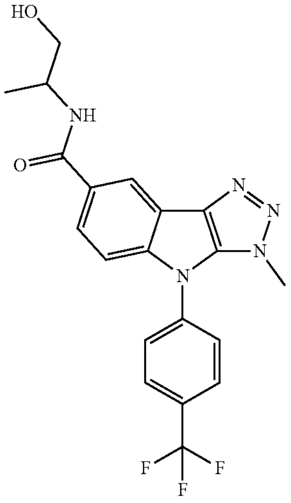 [SMILES: CC(CO)NC(=O)c1ccc2c(c1)c1nnn(C)c1n2-c1ccc(C(F)(F)F)cc1] N-(1-hydroxypropan-2-yl)-3-methyl-4-[4-(trifluoromethyl)phenyl]-3H,4H-[1,2,3]triazolo[4,5-b]indole-7-carboxamide |

-continued

| Compound No. | Structure and Name |
|---|---|
| 218 | 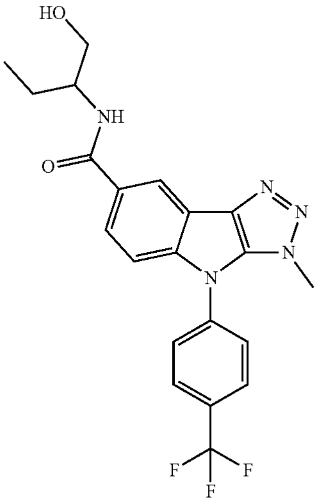 [SMILES: CCC(CO)NC(=O)c1ccc2c(c1)c1nnn(C)c1n2-c1ccc(C(F)(F)F)cc1] N-(1-hydroxybutan-2-yl)-3-methyl-4-[4-(trifluoromethyl)phenyl]-3H,4H-[1,2,3]triazolo[4,5-b]indole-7-carboxamide |
| 219 | 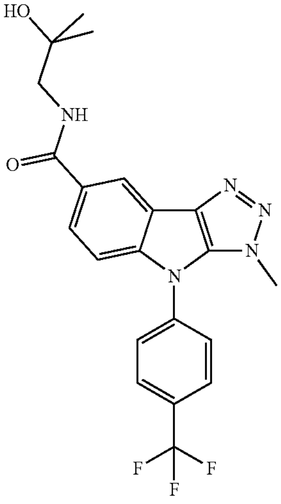 N-(2-hydroxy-2-methylpropyl)-3-methyl-4-[4-(trifluoromethyl)phenyl]-3H,4H-[1,2,3]triazolo[4,5-b]indole-7-carboxamide |

| Compound No. | Structure and Name |
|---|---|
| 220 | 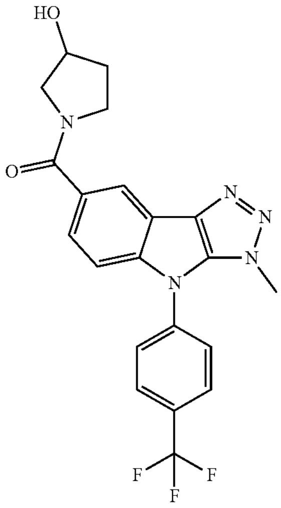 [SMILES: Cn1nnc2c3cc(C(=O)N4CCC(O)C4)ccc3n(-c3ccc(C(F)(F)F)cc3)c21]<br>1-{3-methyl-4-[4-(trifluoromethyl)phenyl]-3H,4H-[1,2,3]triazolo[4,5-b]indole-7-carbonyl}pyrrolidin-3-ol |
| 221 | 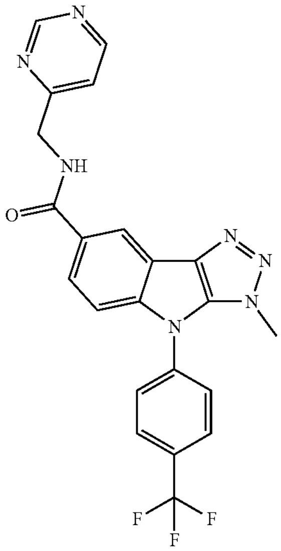 [SMILES: Cn1nnc2c3cc(C(=O)NCc4ccncn4)ccc3n(-c3ccc(C(F)(F)F)cc3)c21]<br>3-methyl-N-[(pyrimidin-4-yl)methyl]-4-[4-(trifluoromethyl)phenyl]-3H,4H-[1,2,3]triazolo[4,5-b]indole-7-carboxamide |

| Compound No. | Structure and Name |
|---|---|
| 222 | 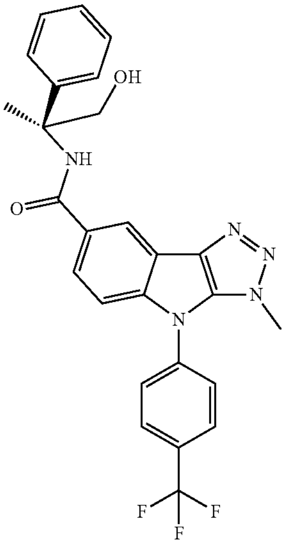 [SMILES: Cn1nnc2c3cc(C(=O)N[C@](C)(CO)c4ccccc4)ccc3n(-c3ccc(C(F)(F)F)cc3)c21]<br>Absolute configuration known/assigned<br>N-[(2S)-1-hydroxy-2-phenylpropan-2-yl]-3-methyl-4-[4-(trifluoromethyl)phenyl]-3H,4H-[1,2,3]triazolo[4,5-b]indole-7-carboxamide |
| 223 | 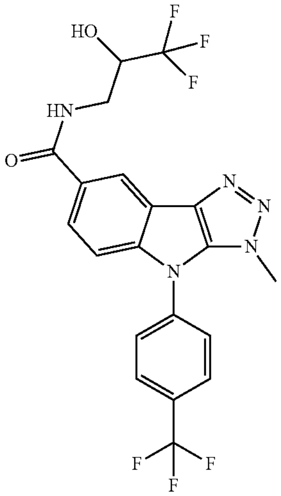 [SMILES: Cn1nnc2c3cc(C(=O)NCC(O)C(F)(F)F)ccc3n(-c3ccc(C(F)(F)F)cc3)c21]<br>3-methyl-N-(3,3,3-trifluoro-2-hydroxypropyl)-4-[4-(trifluoromethyl)phenyl]-3H,4H-[1,2,3]triazolo[4,5-b]indole-7-carboxamide |

-continued

| Compound No. | Structure and Name |
|---|---|
| 224 | 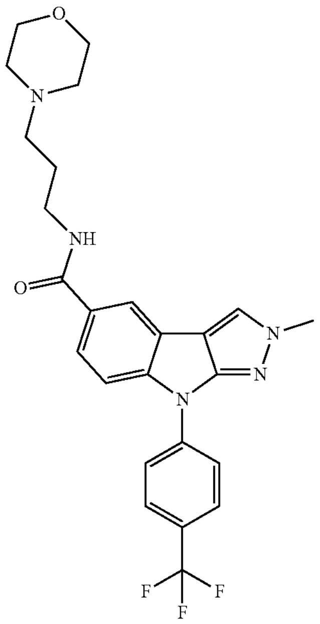 [SMILES: Cn1cc2c3cc(C(=O)NCCCN4CCOCC4)ccc3n(-c3ccc(C(F)(F)F)cc3)c2n1] 2-methyl-N-[3-(morpholin-4-yl)propyl]-8-[4-(trifluoromethyl)phenyl]-2H,8H-pyrazolo[3,4-b]indole-5-carboxamide |
| 225 | 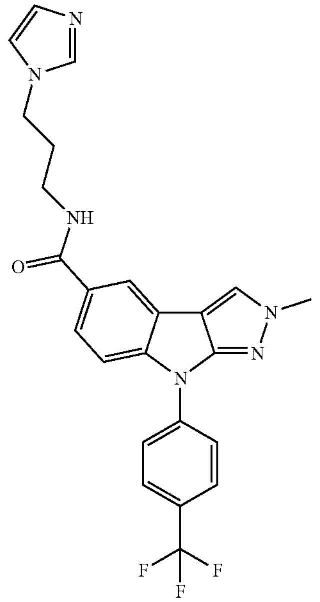 [SMILES: Cn1cc2c3cc(C(=O)NCCCn4ccnc4)ccc3n(-c3ccc(C(F)(F)F)cc3)c2n1] N-[3-(1H-imidazol-1-yl)propyl]-2-methyl-8-[4-(trifluoromethyl)phenyl]-2H,8H-pyrazolo[3,4-b]indole-5-carboxamide |

-continued

| Compound No. | Structure and Name |
|---|---|
| 226 | 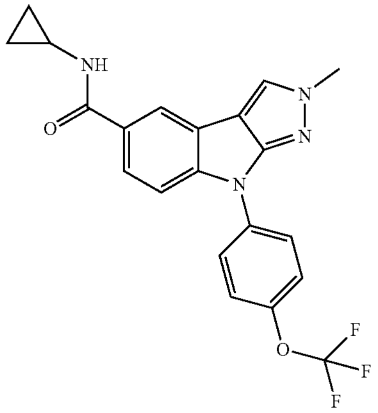 [SMILES: Cn1cc2c3cc(C(=O)NC4CC4)ccc3n(-c3ccc(OC(F)(F)F)cc3)c2n1] N-cyclopropyl-2-methyl-8-[4-(trifluoromethoxy)phenyl]-2H,8H-pyrazolo[3,4-b]indole-5-carboxamide |
| 227 | 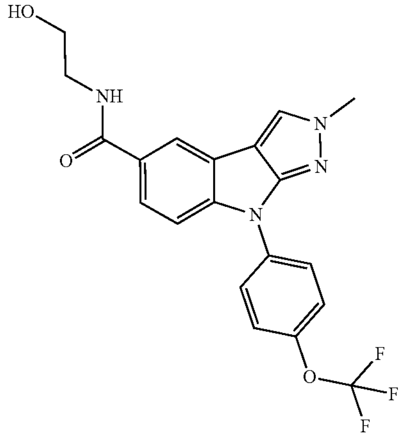 [SMILES: Cn1cc2c3cc(C(=O)NCCO)ccc3n(-c3ccc(OC(F)(F)F)cc3)c2n1] N-(2-hydroxyethyl)-2-methyl-8-[4-(trifluoromethoxy)phenyl]-2H,8H-pyrazolo[3,4-b]indole-5-carboxamide |
| 228 | 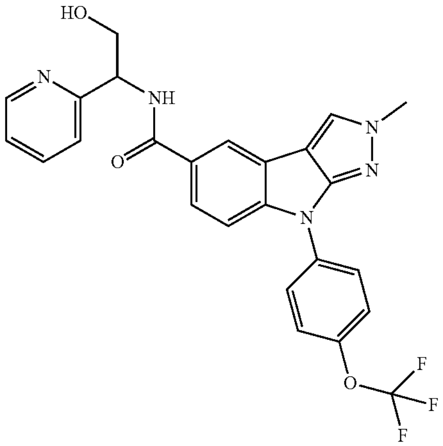 [SMILES: Cn1cc2c3cc(C(=O)NC(CO)c4ccccn4)ccc3n(-c3ccc(OC(F)(F)F)cc3)c2n1] N-[2-hydroxy-1-(pyridin-2-yl)ethyl]-2-methyl-8-[4-(trifluoromethoxy)phenyl]-2H,8H-pyrazolo[3,4-b]indole-5-carboxamide |

-continued

| Compound No. | Structure and Name |
|---|---|
| 229 | 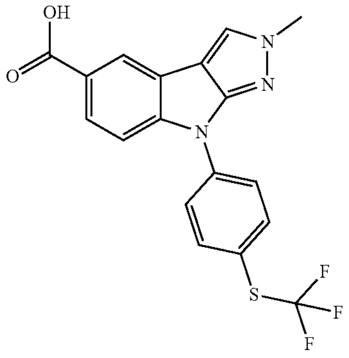 [SMILES: Cn1cc2c3cc(C(=O)O)ccc3n(-c3ccc(SC(F)(F)F)cc3)c2n1] 2-methyl-8-{4-[(trifluoromethyl)sulfanyl]phenyl}-2H,8H-pyrazolo[3,4-b]indole-5-carboxylic acid |
| 230 | 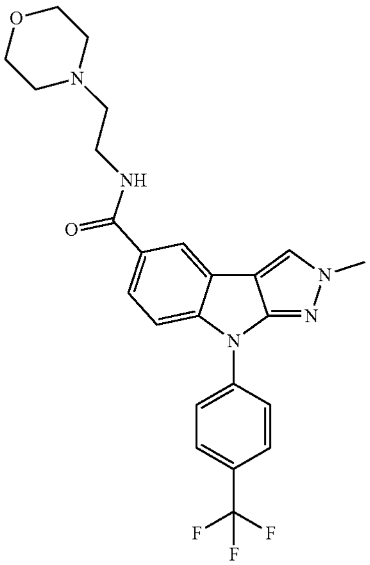 [SMILES: Cn1cc2c3cc(C(=O)NCCN4CCOCC4)ccc3n(-c3ccc(C(F)(F)F)cc3)c2n1] 2-methyl-N-[2-(morpholin-4-yl)ethyl]-8-[4-(trifluoromethyl)phenyl]-2H,8H-pyrazolo[3,4-b]indole-5-carboxamide |
| 231 | 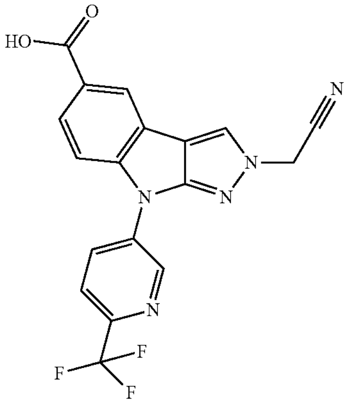 [SMILES: N#CCn1cc2c3cc(C(=O)O)ccc3n(-c3ccc(C(F)(F)F)nc3)c2n1] 2-(cyanomethyl)-8-[6-(trifluoromethyl)pyridin-3-yl]-2H,8H-pyrazolo[3,4-b]indole-5-carboxylic acid |

-continued

| Compound No. | Structure and Name |
|---|---|
| 232 | 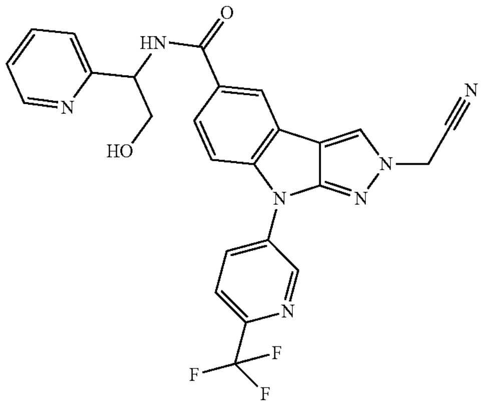 [SMILES: N#CCn1cc2c3cc(C(=O)NC(CO)c4ccccn4)ccc3n(-c3ccc(C(F)(F)F)nc3)c2n1] 2-(cyanomethyl)-N-[2-hydroxy-1-(pyridin-2-yl)ethyl]-8-[6-(trifluoromethyl)pyridin-3-yl]-2H,8H-pyrazolo[3,4-b]indole-5-carboxamide |
| 233 | 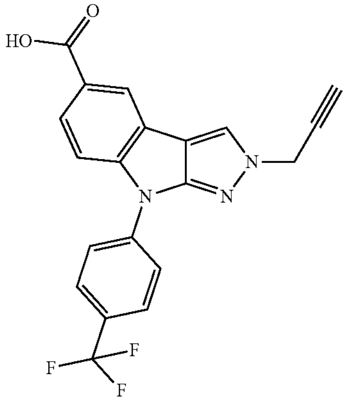 [SMILES: C#CCn1cc2c3cc(C(=O)O)ccc3n(-c3ccc(C(F)(F)F)cc3)c2n1] 2-(prop-2-yn-1-yl)-8-[4-(trifluoromethyl)phenyl]-2H,8H-pyrazolo[3,4-b]indole-5-carboxylic acid |
| 234 | 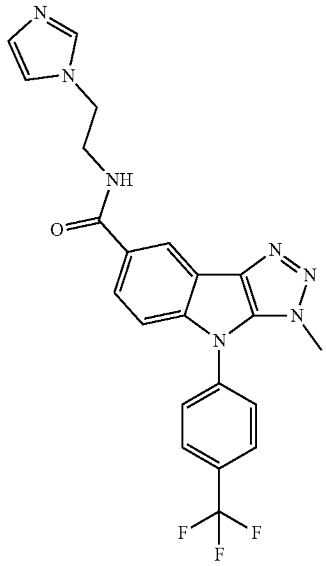 [SMILES: Cn1nnc2c3cc(C(=O)NCCn4ccnc4)ccc3n(-c3ccc(C(F)(F)F)cc3)c21] N-[2-(1H-imidazol-1-yl)ethyl]-3-methyl-4-[4-(trifluoromethyl)phenyl]-3H,4H-[1,2,3]triazolo[4,5- |

-continued

| Compound No. | Structure and Name |
| --- | --- |
| | b]indole-7-carboxamide |
| 235 | 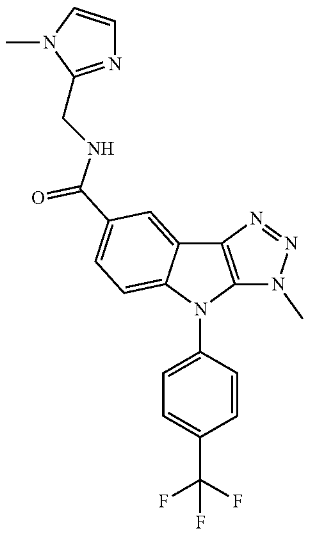 3-methyl-N-[(1-methyl-1H-imidazol-2-yl)methyl]-4-[4-(trifluoromethyl)phenyl]-3H,4H-[1,2,3]triazolo[4,5-b]indole-7-carboxamide |
| 236 | 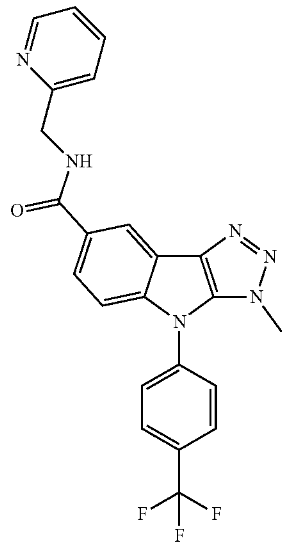 [SMILES: Cn1nnc2c3cc(C(=O)NCc4ccccn4)ccc3n(-c3ccc(C(F)(F)F)cc3)c21] 3-methyl-N-[(pyridin-2-yl)methyl]-4-[4-(trifluoromethyl)phenyl]-3H,4H-[1,2,3]triazolo[4,5-b]indole-7-carboxamide |

-continued

| Compound No. | Structure and Name |
| --- | --- |
| 237 | 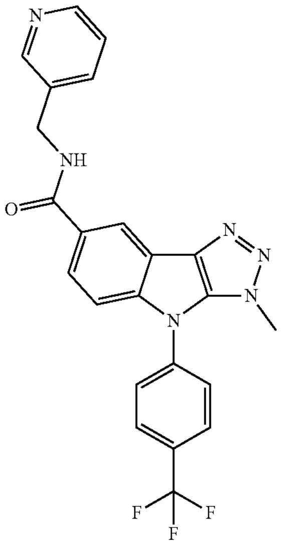 [SMILES: Cn1nnc2c3cc(C(=O)NCc4cccnc4)ccc3n(-c3ccc(C(F)(F)F)cc3)c21] 3-methyl-N-[(pyridin-3-yl)methyl]-4-[4-(trifluoromethyl)phenyl]-3H,4H-[1,2,3]triazolo[4,5-b]indole-7-carboxamide |
| 238 | 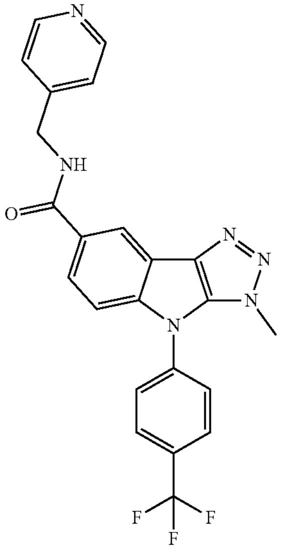 3-methyl-N-[(pyridin-4-yl)methyl]-4-[4-(trifluoromethyl)phenyl]-3H,4H-[1,2,3]triazolo[4,5-b]indole-7-carboxamide |

-continued

| Compound No. | Structure and Name |
|---|---|
| 239 | 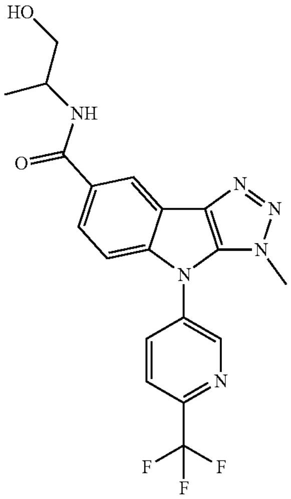 [SMILES: CC(CO)NC(=O)c1ccc2c(c1)c1nnn(C)c1n2-c1ccc(C(F)(F)F)nc1]<br>N-(1-hydroxypropan-2-yl)-3-methyl-4-[6-(trifluoromethyl)pyridin-3-yl]-3H,4H-[1,2,3]triazolo[4,5-b]indole-7-carboxamide |
| 240 | 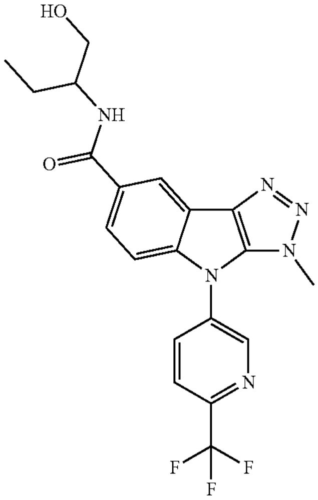 [SMILES: CCC(CO)NC(=O)c1ccc2c(c1)c1nnn(C)c1n2-c1ccc(C(F)(F)F)nc1]<br>N-(1-hydroxybutan-2-yl)-3-methyl-4-[6-(trifluoromethyl)pyridin-3-yl]-3H,4H-[1,2,3]triazolo[4,5-b]indole-7-carboxamide |

-continued

| Compound No. | Structure and Name |
|---|---|
| 241 | 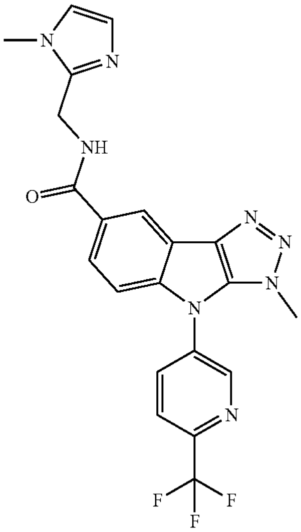<br>3-methyl-N-[(1-methyl-1H-imidazol-2-yl)methyl]-4-[6-(trifluoromethyl)pyridin-3-yl]-3H,4H-[1,2,3]triazolo[4,5-b]indole-7-carboxamide |
| 242 | 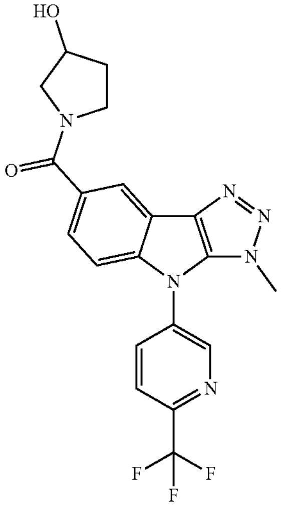 [SMILES: Cn1nnc2c3cc(C(=O)N4CCC(O)C4)ccc3n(-c3ccc(C(F)(F)F)nc3)c21]<br>1-{3-methyl-4-[6-(trifluoromethyl)pyridin-3-yl]-3H,4H-[1,2,3]triazolo[4,5-b]indole-7-carbonyl}pyrrolidin-3-ol |

-continued

| Compound No. | Structure and Name |
|---|---|
| 243 | 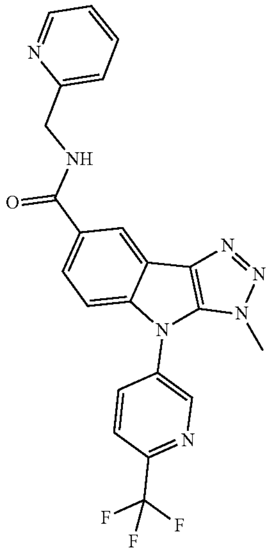 [SMILES: Cn1nnc2c3cc(C(=O)NCc4ccccn4)ccc3n(-c3ccc(C(F)(F)F)nc3)c21] 3-methyl-N-[(pyridin-2-yl)methyl]-4-[6-(trifluoromethyl)pyridin-3-yl]-3H,4H-[1,2,3]triazolo[4,5-b]indole-7-carboxamide |
| 244 | 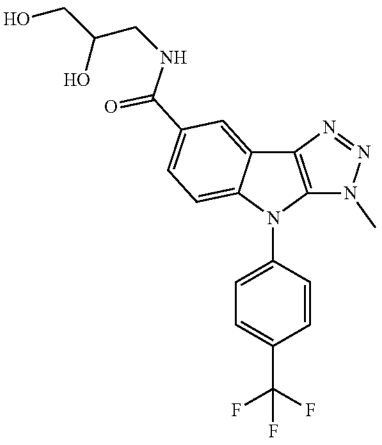 [SMILES: Cn1nnc2c3cc(C(=O)NCC(O)CO)ccc3n(-c3ccc(C(F)(F)F)cc3)c21] N-(2,3-dihydroxypropyl)-3-methyl-4-[4-(trifluoromethyl)phenyl]-3H,4H-[1,2,3]triazolo[4,5-b]indole-7-carboxamide |

-continued

| Compound No. | Structure and Name |
|---|---|
| 245 | 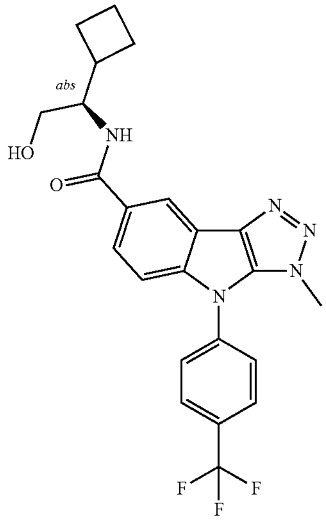 [SMILES: Cn1nnc2c3cc(C(=O)N[C@@H](CO)C4CCC4)ccc3n(-c3ccc(C(F)(F)F)cc3)c21] Absolute configuration known/assigned N-[(1R)-1-cyclobutyl-2-hydroxyethyl]-3-methyl-4-[4-(trifluoromethyl)phenyl]-3H,4H-[1,2,3]triazolo[4,5-b]indole-7-carboxamide |
| 246 | 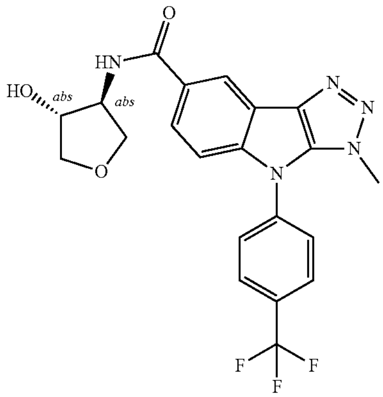 [SMILES: Cn1nnc2c3cc(C(=O)N[C@H]4COC[C@@H]4O)ccc3n(-c3ccc(C(F)(F)F)cc3)c21] Absolute configuration known/assigned N-[(3S,4R)-4-hydroxyoxolan-3-yl]-3-methyl-4-[4-(trifluoromethyl)phenyl]-3H,4H-[1,2,3]triazolo[4,5-b]indole-7-carboxamide |

-continued

| Compound No. | Structure and Name |
|---|---|
| 247 | 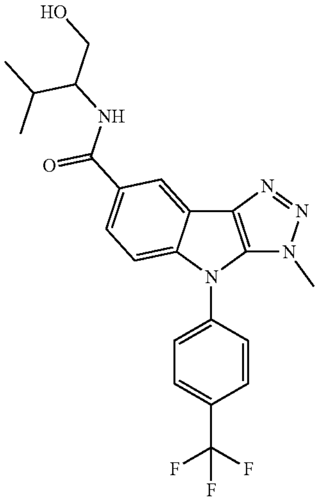 [SMILES: CC(C)C(CO)NC(=O)c1ccc2c(c1)c1nnn(C)c1n2-c1ccc(C(F)(F)F)cc1] N-(1-hydroxy-3-methylbutan-2-yl)-3-methyl-4-[4-(trifluoromethyl)phenyl]-3H,4H-[1,2,3]triazolo[4,5-b]indole-7-carboxamide |
| 248 | 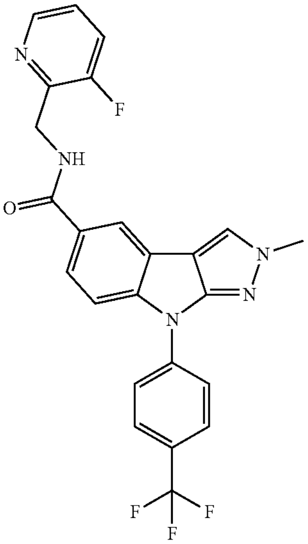 [SMILES: Cn1cc2c3cc(C(=O)NCc4ncccc4F)ccc3n(-c3ccc(C(F)(F)F)cc3)c2n1] N-[(3-fluoropyridin-2-yl)methyl]-2-methyl-8-[4-(trifluoromethyl)phenyl]-2H,8H-pyrazolo[3,4-b]indole-5-carboxamide |
| 249 | 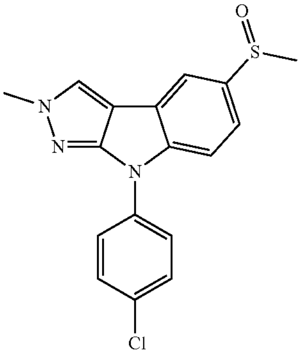 |

-continued

| Compound No. | Structure and Name |
|---|---|
| | 8-(4-chlorophenyl)-5-methanesulfinyl-2-methyl-2H,8H-pyrazolo[3,4-b]indole |
| 250 | 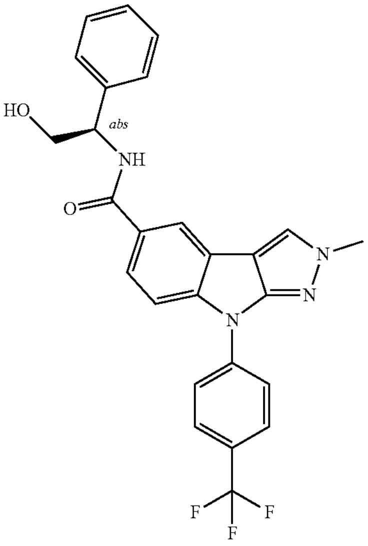 [SMILES: Cn1cc2c3cc(C(=O)N[C@@H](CO)c4ccccc4)ccc3n(-c3ccc(C(F)(F)F)cc3)c2n1] Absolute configuration assigned arbitrarily N-[(1R)-2-hydroxy-1-phenylethyl]-2-methyl-8-[4-(trifluoromethyl)phenyl]-2H,8H-pyrazolo[3,4-b]indole-5-carboxamide |
| 251 | 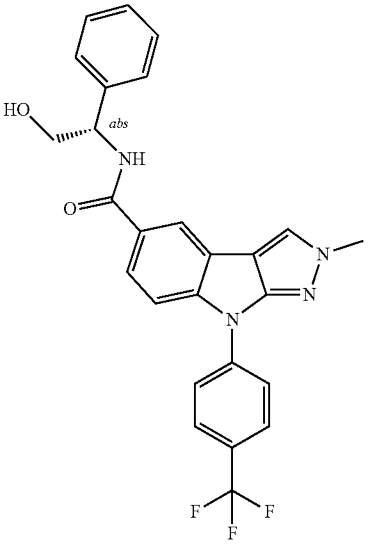 [SMILES: Cn1cc2c3cc(C(=O)N[C@H](CO)c4ccccc4)ccc3n(-c3ccc(C(F)(F)F)cc3)c2n1] Absolute configuration assigned arbitrarily N-[(1S)-2-hydroxy-1-phenylethyl]-2-methyl-8-[4-(trifluoromethyl)phenyl]-2H,8H-pyrazolo[3,4-b]indole-5-carboxamide |

-continued

| Compound No. | Structure and Name |
|---|---|
| 252 | 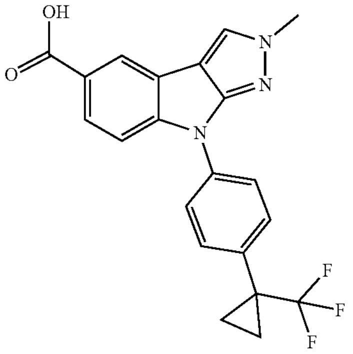 [SMILES: Cn1cc2c3cc(C(=O)O)ccc3n(-c3ccc(C4(C(F)(F)F)CC4)cc3)c2n1] 2-methyl-8-{4-[1-(trifluoromethyl)cyclopropyl]phenyl}-2H,8H-pyrazolo[3,4-b]indole-5-carboxylic acid |
| 253 | 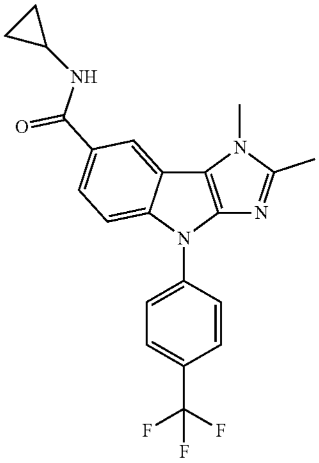 [SMILES: Cc1nc2c(c3cc(C(=O)NC4CC4)ccc3n2-c2ccc(C(F)(F)F)cc2)n1C] N-cyclopropyl-1,2-dimethyl-4-[4-(trifluoromethyl)phenyl]-1H,4H-imidazo[4,5-b]indole-7-carboxamide |
| 254 | 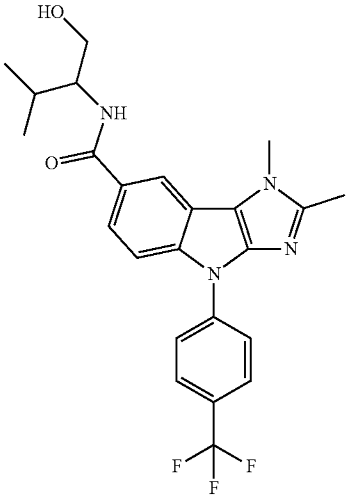 [SMILES: Cc1nc2c(c3cc(C(=O)NC(CO)C(C)C)ccc3n2-c2ccc(C(F)(F)F)cc2)n1C] N-(1-hydroxy-3-methylbutan-2-yl)-1,2-dimethyl-4-[4-(trifluoromethyl)phenyl]-1H,4H-imidazo[4,5-b]indole-7-carboxamide |

-continued

| Compound No. | Structure and Name |
|---|---|
| 255 | 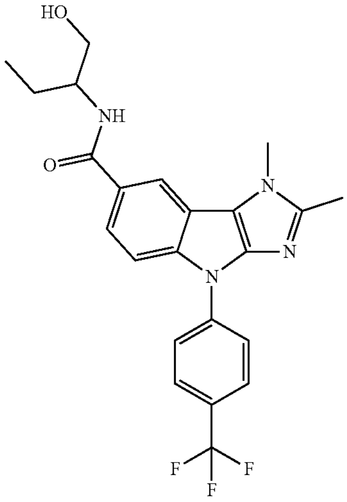 [SMILES: CCC(CO)NC(=O)c1ccc2c(c1)c1c(nc(C)n1C)n2-c1ccc(C(F)(F)F)cc1] N-(1-hydroxybutan-2-yl)-1,2-dimethyl-4-[4-(trifluoromethyl)phenyl]-1H,4H-imidazo[4,5-b]indole-7-carboxamide |
| 256 | 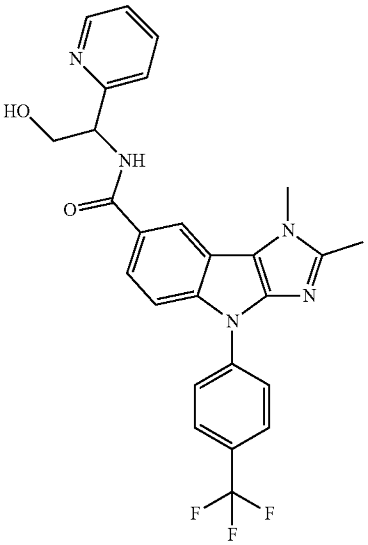 [SMILES: Cc1nc2c(c3cc(C(=O)NC(CO)c4ccccn4)ccc3n2-c2ccc(C(F)(F)F)cc2)n1C] N-[2-hydroxy-1-(pyridin-2-yl)ethyl]-1,2-dimethyl-4-[4-(trifluoromethyl)phenyl]-1H,4H-imidazo[4,5-b]indole-7-carboxamide |

-continued

| Compound No. | Structure and Name |
|---|---|
| 257 | 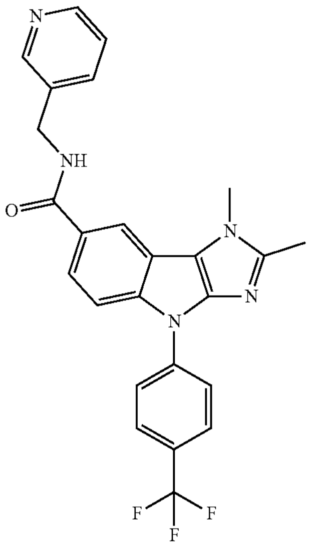 [SMILES: Cc1nc2c(c3cc(C(=O)NCc4cccnc4)ccc3n2-c2ccc(C(F)(F)F)cc2)n1C] 1,2-dimethyl-N-[(pyridin-3-yl)methyl]-4-[4-(trifluoromethyl)phenyl]-1H,4H-imidazo[4,5-b]indole-7-carboxamide |
| 258 | 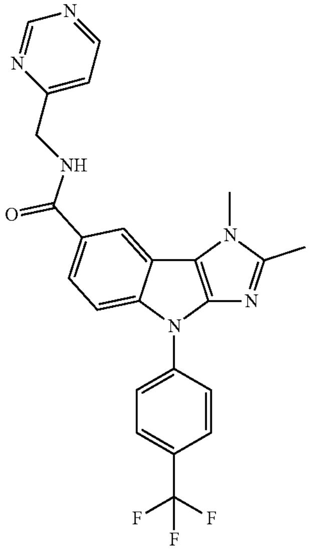 1,2-dimethyl-N-[(pyrimidin-4-yl)methyl]-4-[4-(trifluoromethyl)phenyl]-1H,4H-imidazo[4,5-b]indole-7-carboxamide |

-continued

| Compound No. | Structure and Name |
|---|---|
| 259 | 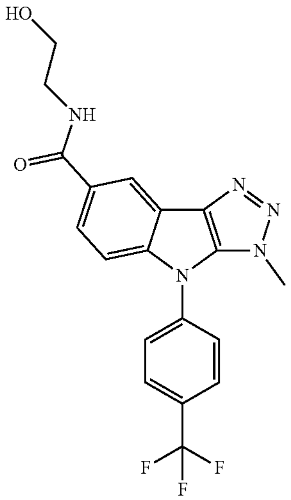 [SMILES: Cn1nnc2c3cc(C(=O)NCCO)ccc3n(-c3ccc(C(F)(F)F)cc3)c21] N-(2-hydroxyethyl)-3-methyl-4-[4-(trifluoromethyl)phenyl]-3H,4H-[1,2,3]triazolo[4,5-b]indole-7-carboxamide |
| 260 | 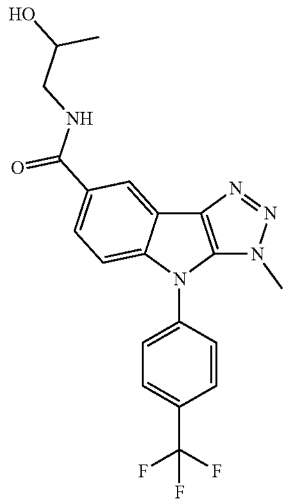 [SMILES: CC(O)CNC(=O)c1ccc2c(c1)c1nnn(C)c1n2-c1ccc(C(F)(F)F)cc1] N-(2-hydroxypropyl)-3-methyl-4-[4-(trifluoromethyl)phenyl]-3H,4H-[1,2,3]triazolo[4,5-b]indole-7-carboxamide |

-continued

| Compound No. | Structure and Name |
| --- | --- |
| 261 | 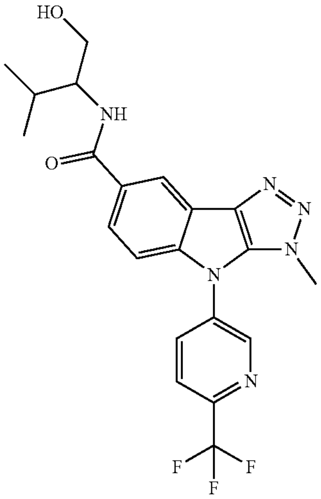 [SMILES: CC(C)C(CO)NC(=O)c1ccc2c(c1)c1nnn(C)c1n2-c1ccc(C(F)(F)F)nc1] N-(1-hydroxy-3-methylbutan-2-yl)-3-methyl-4-[6-(trifluoromethyl)pyridin-3-yl]-3H,4H-[1,2,3]triazolo[4,5-b]indole-7-carboxamide |
| 262 | 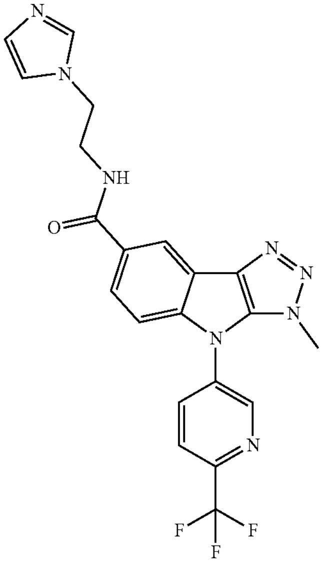 [SMILES: Cn1nnc2c3cc(C(=O)NCCn4ccnc4)ccc3n(-c3ccc(C(F)(F)F)nc3)c21] N-[2-(1H-imidazol-1-yl)ethyl]-3-methyl-4-[6-(trifluoromethyl)pyridin-3-yl]-3H,4H-[1,2,3]triazolo[4,5-b]indole-7-carboxamide |

-continued

| Compound No. | Structure and Name |
| --- | --- |
| 263 | 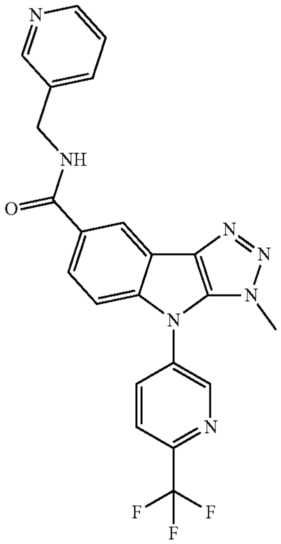 [SMILES: Cn1nnc2c3cc(C(=O)NCc4cccnc4)ccc3n(-c3ccc(C(F)(F)F)nc3)c21] 3-methyl-N-[(pyridin-3-yl)methyl]-4-[6-(trifluoromethyl)pyridin-3-yl]-3H,4H-[1,2,3]triazolo[4,5-b]indole-7-carboxamide |
| 264 | 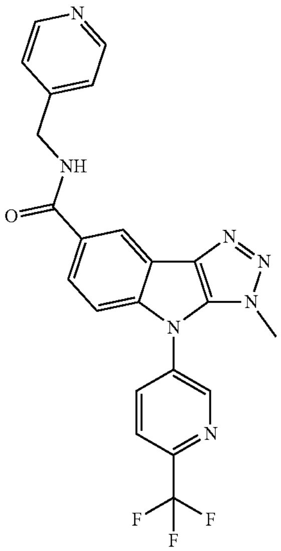 [SMILES: Cn1nnc2c3cc(C(=O)NCc4ccncc4)ccc3n(-c3ccc(C(F)(F)F)nc3)c21] 3-methyl-N-[(pyridin-4-yl)methyl]-4-[6-(trifluoromethyl)pyridin-3-yl]-3H,4H-[1,2,3]triazolo[4,5-b]indole-7-carboxamide |

-continued

| Compound No. | Structure and Name |
|---|---|
| 265 | 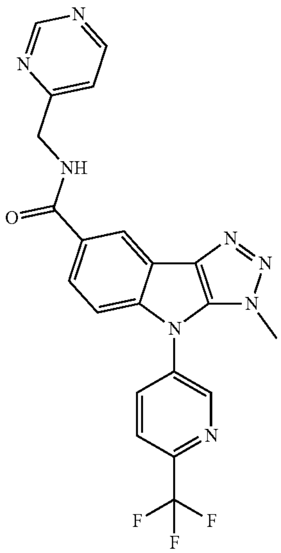 [SMILES: Cn1nnc2c3cc(C(=O)NCc4ccncn4)ccc3n(-c3ccc(C(F)(F)F)nc3)c21]<br>3-methyl-N-[(pyrimidin-4-yl)methyl]-4-[6-(trifluoromethyl)pyridin-3-yl]-3H,4H-[1,2,3]triazolo[4,5-b]indole-7-carboxamide |
| 266 | 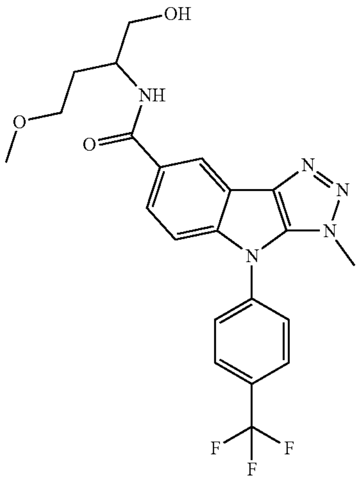<br>N-(1-hydroxy-4-methoxybutan-2-yl)-3-methyl-4-[4-(trifluoromethyl)phenyl]-3H,4H-[1,2,3]triazolo[4,5-b]indole-7-carboxamide |

-continued

| Compound No. | Structure and Name |
|---|---|
| 268 | 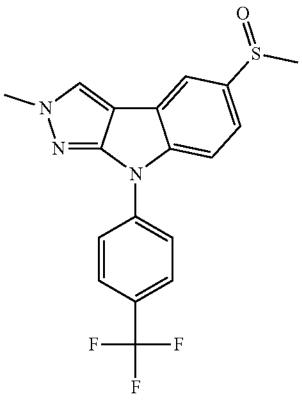<br>5-methanesulfinyl-2-methyl-8-[4-(trifluoromethyl)phenyl]-2H,8H-pyrazolo[3,4-b]indole |
| 269 | 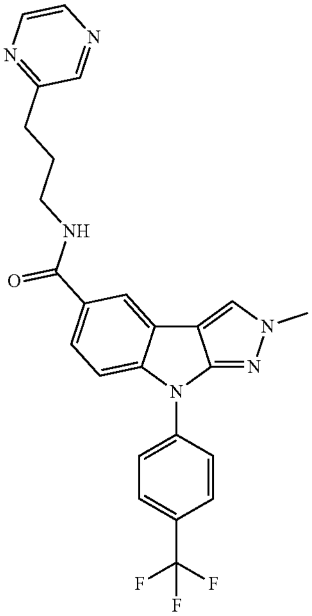 [SMILES: Cn1cc2c3cc(C(=O)NCCCc4cnccn4)ccc3n(-c3ccc(C(F)(F)F)cc3)c2n1]<br>2-methyl-N-[3-(pyrazin-2-yl)propyl]-8-[4-(trifluoromethyl)phenyl]-2H,8H-pyrazolo[3,4-b]indole-5-carboxamide |

| Compound No. | Structure and Name |
|---|---|
| 270 | 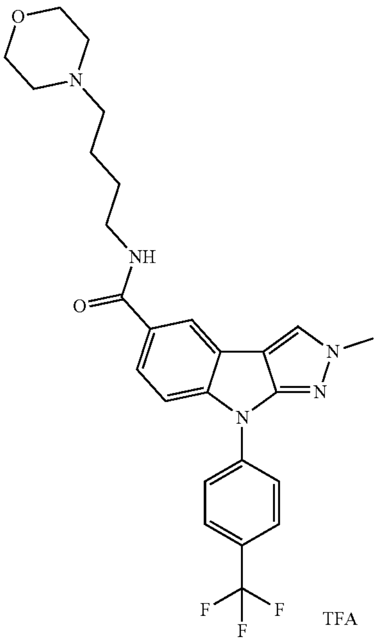 [SMILES: Cn1cc2c3cc(C(=O)NCCCCN4CCOCC4)ccc3n(-c3ccc(C(F)(F)F)cc3)c2n1] TFA 2-methyl-N-[4-(morpholin-4-yl)butyl]-8-[4-(trifluoromethyl)phenyl]-2H,8H-pyrazolo[3,4-b]indole-5-carboxamide |
| 271 | 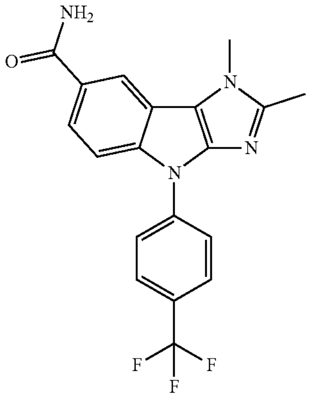 [SMILES: Cc1nc2c(c3cc(C(N)=O)ccc3n2-c2ccc(C(F)(F)F)cc2)n1C] 1,2-dimethyl-4-[4-(trifluoromethyl)phenyl]-1H,4H-imidazo[4,5-b]indole-7-carboxamide |
| 272 | 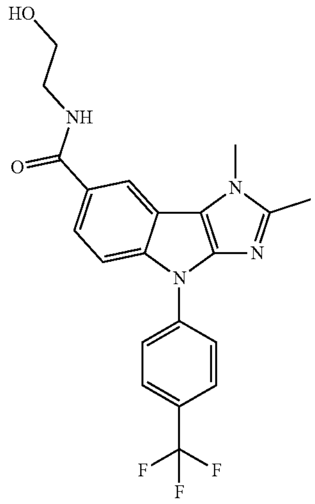 N-(2-hydroxyethyl)-1,2-dimethyl-4-[4-(trifluoromethyl)phenyl]-1H,4H-imidazo[4,5-b]indole-7-carboxamide |
| 273 | 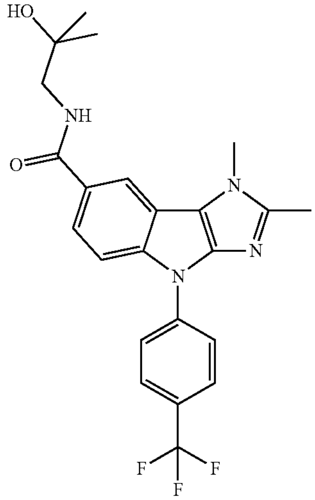 [SMILES: Cc1nc2c(c3cc(C(=O)NCC(C)(C)O)ccc3n2-c2ccc(C(F)(F)F)cc2)n1C] N-(2-hydroxy-2-methylpropyl)-1,2-dimethyl-4-[4-(trifluoromethyl)phenyl]-1H,4H-imidazo[4,5-b]indole-7-carboxamide |

-continued

| Compound No. | Structure and Name |
| --- | --- |
| 274 | 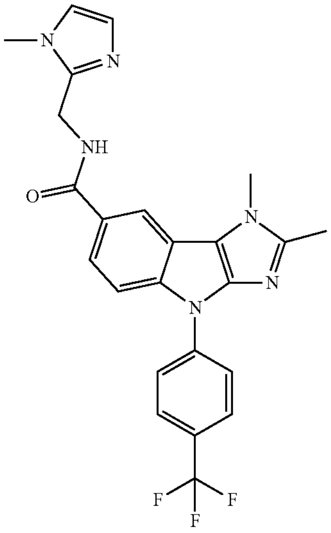 1,2-dimethyl-N-[(1-methyl-1H-imidazol-2-yl)methyl]-4-[4-(trifluoromethyl)phenyl]-1H,4H-imidazo[4,5-b]indole-7-carboxamide |
| 275 | 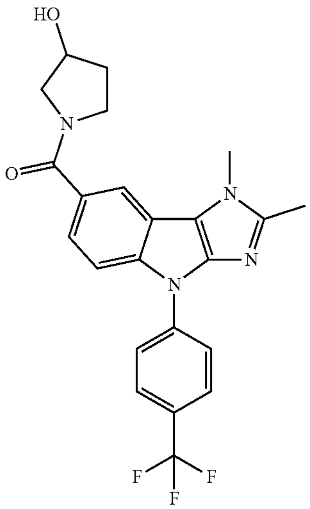 [SMILES: Cc1nc2c(c3cc(C(=O)N4CCC(O)C4)ccc3n2-c2ccc(C(F)(F)F)cc2)n1C] 1-{1,2-dimethyl-4-[4-(trifluoromethyl)phenyl]-1H,4H-imidazo[4,5-b]indole-7-carbonyl}pyrrolidin-3-ol |

-continued

| Compound No. | Structure and Name |
| --- | --- |
| 276 | 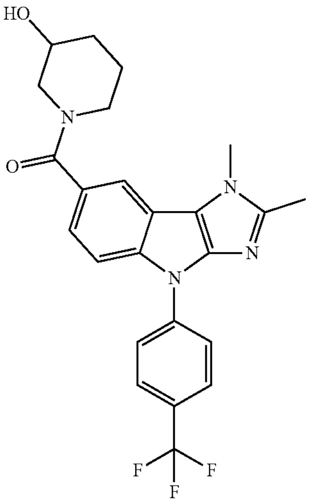 [SMILES: Cc1nc2c(c3cc(C(=O)N4CCCC(O)C4)ccc3n2-c2ccc(C(F)(F)F)cc2)n1C] 1-{1,2-dimethyl-4-[4-(trifluoromethyl)phenyl]-1H,4H-imidazo[4,5-b]indole-7-carbonyl}piperidin-3-ol |
| 277 | 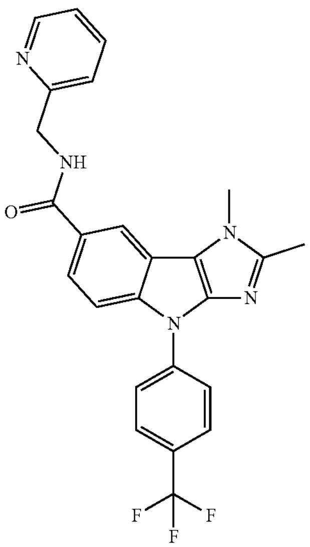 [SMILES: Cc1nc2c(c3cc(C(=O)NCc4ccccn4)ccc3n2-c2ccc(C(F)(F)F)cc2)n1C] 1,2-dimethyl-N-[(pyridin-2-yl)methyl]-4-[4-(trifluoromethyl)phenyl]-1H,4H-imidazo[4,5-b]indole-7-carboxamide |

| Compound No. | Structure and Name |
|---|---|
| 278 | 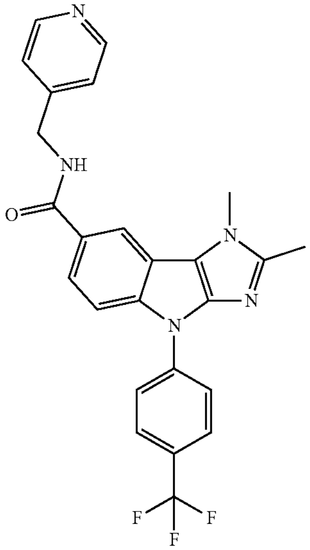 1,2-dimethyl-N-[(pyridin-4-yl)methyl]-4-[4-(trifluoromethyl)phenyl]-1H,4H-imidazo[4,5-b]indole-7-carboxamide |
| 279 | 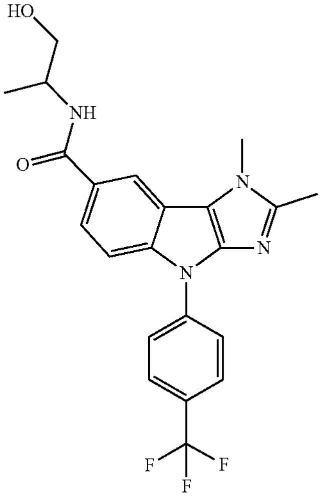 [SMILES: Cc1nc2c(c3cc(C(=O)NC(C)CO)ccc3n2-c2ccc(C(F)(F)F)cc2)n1C] N-(1-hydroxypropan-2-yl)-1,2-dimethyl-4-[4-(trifluoromethyl)phenyl]-1H,4H-imidazo[4,5-b]indole-7-carboxamide |

| Compound No. | Structure and Name |
|---|---|
| 280 | 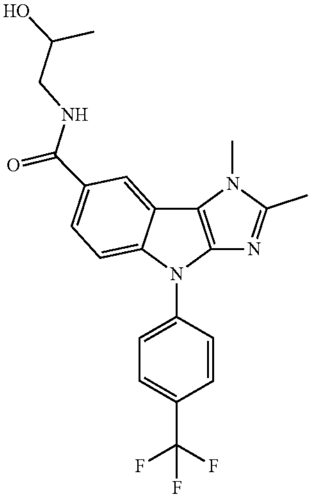 [SMILES: Cc1nc2c(c3cc(C(=O)NCC(C)O)ccc3n2-c2ccc(C(F)(F)F)cc2)n1C] N-(2-hydroxypropyl)-1,2-dimethyl-4-[4-(trifluoromethyl)phenyl]-1H,4H-imidazo[4,5-b]indole-7-carboxamide |
| 281 | 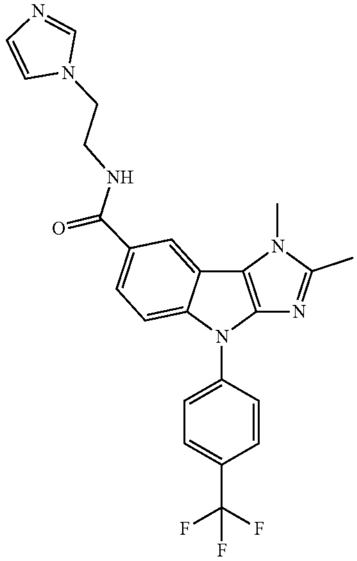 [SMILES: Cc1nc2c(c3cc(C(=O)NCCn4ccnc4)ccc3n2-c2ccc(C(F)(F)F)cc2)n1C] N-[2-(1H-imidazol-1-yl)ethyl]-1,2-dimethyl-4-[4-(trifluoromethyl)phenyl]-1H,4H-imidazo[4,5-b]indole-7-carboxamide |

| Compound No. | Structure and Name |
|---|---|
| 282 | 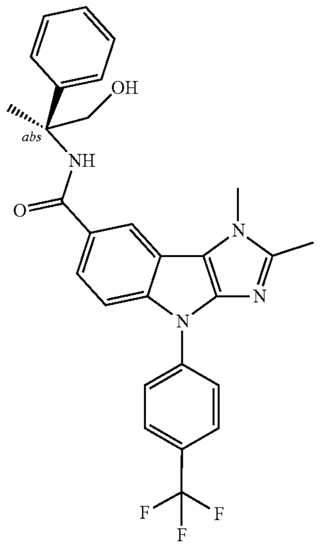 [SMILES: Cc1nc2c(c3cc(C(=O)N[C@](C)(CO)c4ccccc4)ccc3n2-c2ccc(C(F)(F)F)cc2)n1C] Absolute configuration known/assigned N-[(2S)-1-hydroxy-2-phenylpropan-2-yl]-1,2-dimethyl-4-[4-(trifluoromethyl)phenyl]-1H,4H-imidazo[4,5-b]indole-7-carboxamide |
| 283 | 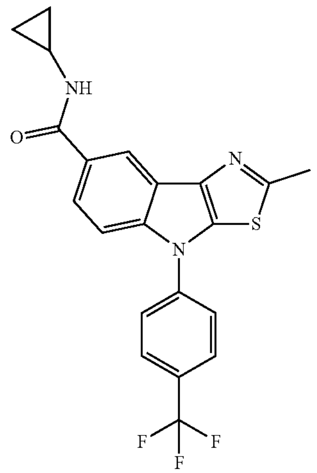 [SMILES: Cc1nc2c3cc(C(=O)NC4CC4)ccc3n(-c3ccc(C(F)(F)F)cc3)c2s1] N-cyclopropyl-2-methyl-4-[4-(trifluoromethyl)phenyl]-4H-[1,3]thiazolo[5,4-b]indole-7-carboxamide |

| Compound No. | Structure and Name |
|---|---|
| 284 | 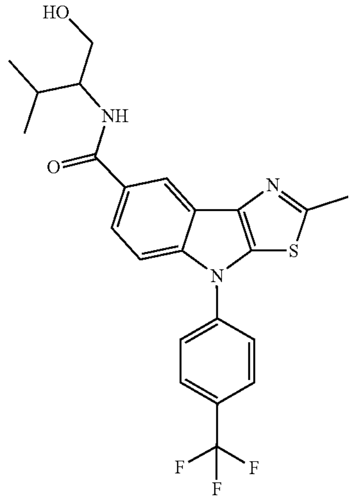 [SMILES: Cc1nc2c3cc(C(=O)NC(CO)C(C)C)ccc3n(-c3ccc(C(F)(F)F)cc3)c2s1] N-(1-hydroxy-3-methylbutan-2-yl)-2-methyl-4-[4-(trifluoromethyl)phenyl]-4H-[1,3]thiazolo[5,4-b]indole-7-carboxamide |
| 285 | 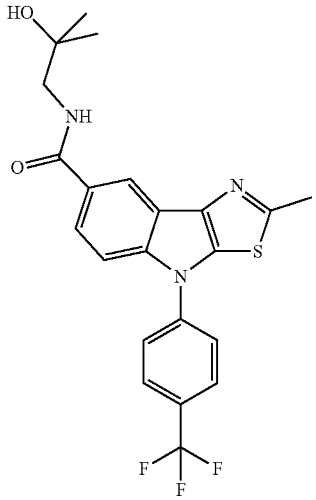 [SMILES: Cc1nc2c3cc(C(=O)NCC(C)(C)O)ccc3n(-c3ccc(C(F)(F)F)cc3)c2s1] N-(2-hydroxy-2-methylpropyl)-2-methyl-4-[4-(trifluoromethyl)phenyl]-4H-[1,3]thiazolo[5,4-b]indole-7-carboxamide |

| Compound No. | Structure and Name |
| --- | --- |
| 286 | 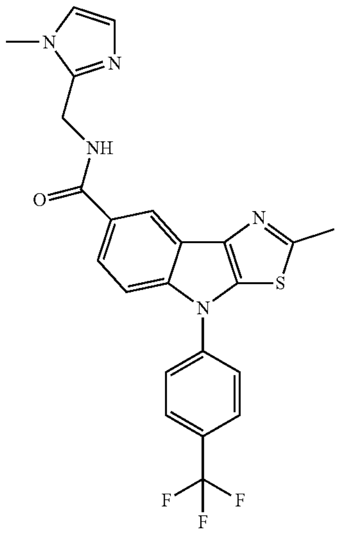 2-methyl-N-[(1-methyl-1H-imidazol-2-yl)methyl]-4-[4-(trifluoromethyl)phenyl]-4H-[1,3]thiazolo[5,4-b]indole-7-carboxamide |
| 287 | 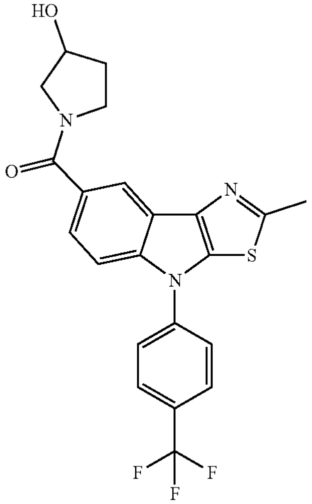 [SMILES: Cc1nc2c3cc(C(=O)N4CCC(O)C4)ccc3n(-c3ccc(C(F)(F)F)cc3)c2s1] 1-{2-methyl-4-[4-(trifluoromethyl)phenyl]-4H-[1,3]thiazolo[5,4-b]indole-7-carbonyl}pyrrolidin-3-ol |

| Compound No. | Structure and Name |
| --- | --- |
| 288 | 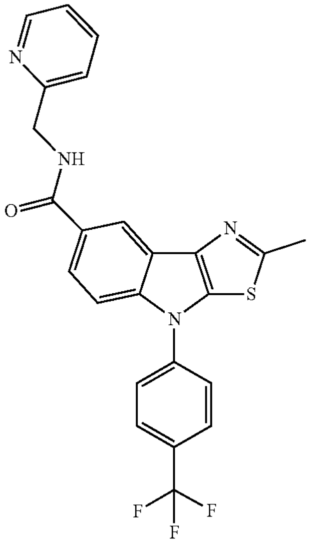 [SMILES: Cc1nc2c3cc(C(=O)NCc4ccccn4)ccc3n(-c3ccc(C(F)(F)F)cc3)c2s1] 2-methyl-N-[(pyridin-2-yl)methyl]-4-[4-(trifluoromethyl)phenyl]-4H-[1,3]thiazolo[5,4-b]indole-7-carboxamide |
| 289 | 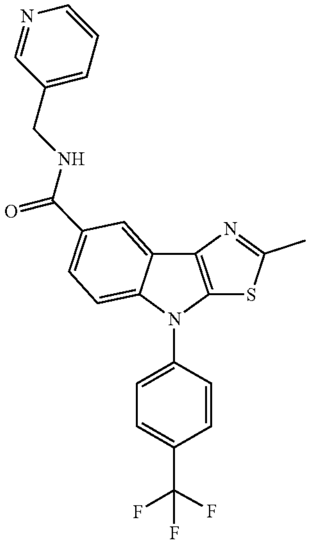 [SMILES: Cc1nc2c3cc(C(=O)NCc4cccnc4)ccc3n(-c3ccc(C(F)(F)F)cc3)c2s1] 2-methyl-N-[(pyridin-3-yl)methyl]-4-[4-(trifluoromethyl)phenyl]-4H-[1,3]thiazolo[5,4-b]indole-7-carboxamide |

| Compound No. | Structure and Name |
|---|---|
| 290 | 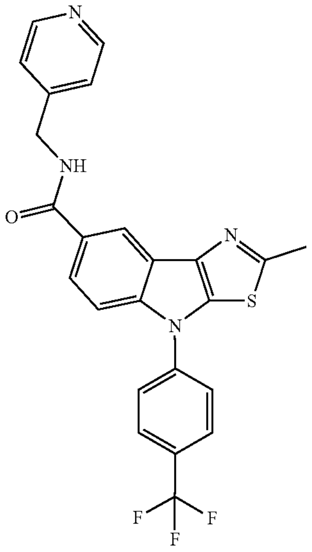 [SMILES: Cc1nc2c3cc(C(=O)NCc4ccncc4)ccc3n(-c3ccc(C(F)(F)F)cc3)c2s1]<br>2-methyl-N-[(pyridin-4-yl)methyl]-4-[4-(trifluoromethyl)phenyl]-4H-[1,3]thiazolo[5,4-b]indole-7-carboxamide |
| 291 | 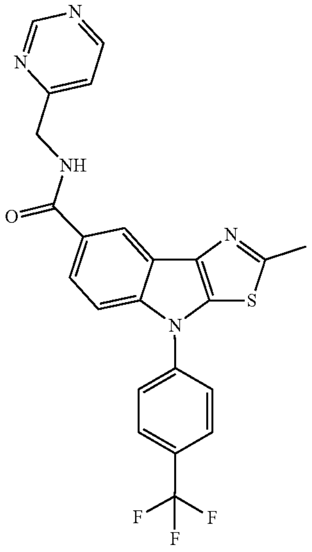 [SMILES: Cc1nc2c3cc(C(=O)NCc4ccncn4)ccc3n(-c3ccc(C(F)(F)F)cc3)c2s1]<br>2-methyl-N-[(pyrimidin-4-yl)methyl]-4-[4-(trifluoromethyl)phenyl]-4H-[1,3]thiazolo[5,4-b]indole-7-carboxamide |

| Compound No. | Structure and Name |
|---|---|
| 292 | 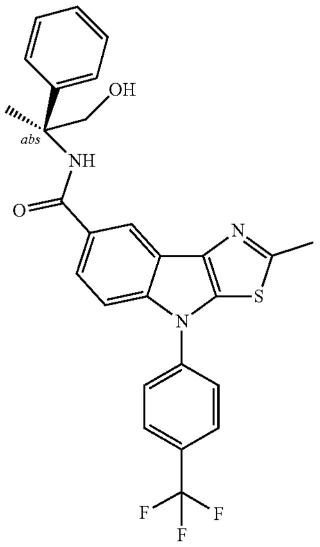 [SMILES: Cc1nc2c3cc(C(=O)N[C@](C)(CO)c4ccccc4)ccc3n(-c3ccc(C(F)(F)F)cc3)c2s1]<br>Absolute configuration known/assigned<br>N-[(2S)-1-hydroxy-2-phenylpropan-2-yl]-2-methyl-4-[4-(trifluoromethyl)phenyl]-4H-[1,3]thiazolo[5,4-b]indole-7-carboxamide |
| 293 | 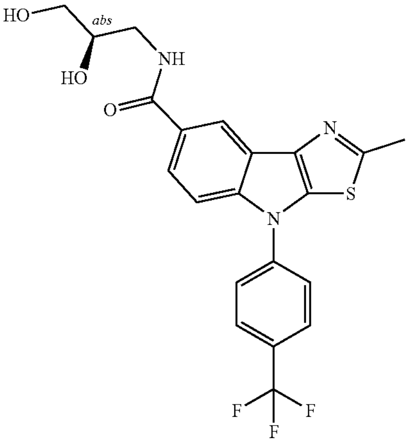 [SMILES: Cc1nc2c3cc(C(=O)NC[C@@H](O)CO)ccc3n(-c3ccc(C(F)(F)F)cc3)c2s1]<br>Absolute configuration known/assigned<br>N-[(2R)-2,3-dihydroxypropyl]-2-methyl-4-[4-(trifluoromethyl)phenyl]-4H-[1,3]thiazolo[5,4-b]indole-7-carboxamide |

| Compound No. | Structure and Name |
|---|---|
| 294 | 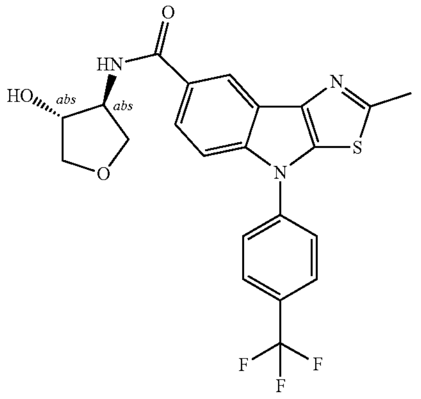 [SMILES: Cc1nc2c3cc(C(=O)N[C@H]4COC[C@@H]4O)ccc3n(-c3ccc(C(F)(F)F)cc3)c2s1]<br>Absolute configuration known/assigned<br>N-[(3S,4R)-4-hydroxyoxolan-3-yl]-2-methyl-4-[4-(trifluoromethyl)phenyl]-4H-[1,3]thiazolo[5,4-b]indole-7-carboxamide |
| 295 | 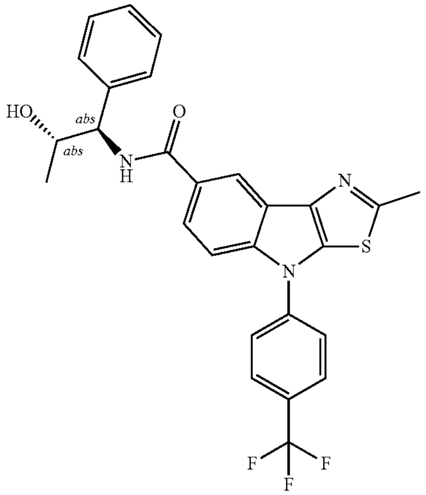 [SMILES: Cc1nc2c3cc(C(=O)N[C@H](c4ccccc4)[C@H](C)O)ccc3n(-c3ccc(C(F)(F)F)cc3)c2s1]<br>Absolute configuration known/assigned<br>N-[(1R,2S)-2-hydroxy-1-phenylpropyl]-2-methyl-4-[4-(trifluoromethyl)phenyl]-4H-[1,3]thiazolo[5,4-b]indole-7-carboxamide |
| 296 | 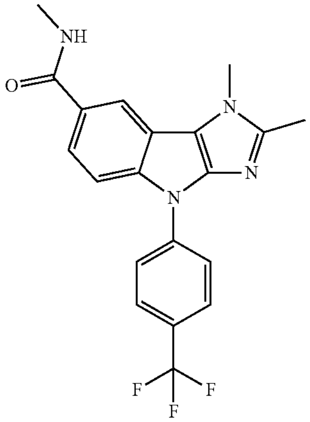 [SMILES: CNC(=O)c1ccc2c(c1)c1c(nc(C)n1C)n2-c1ccc(C(F)(F)F)cc1] |

-continued

| Compound No. | Structure and Name |
|---|---|
| | N,1,2-trimethyl-4-[4-(trifluoromethyl)phenyl]-1H,4H-imidazo[4,5-b]indole-7-carboxamide |
| 297 | 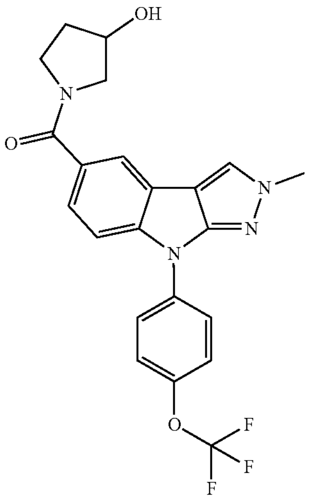 [SMILES: Cn1cc2c3cc(C(=O)N4CCC(O)C4)ccc3n(-c3ccc(OC(F)(F)F)cc3)c2n1]<br>1-{2-methyl-8-[4-(trifluoromethoxy)phenyl]-2H,8H-pyrazolo[3,4-b]indole-5-carbonyl}pyrrolidin-3-ol |
| 298 | 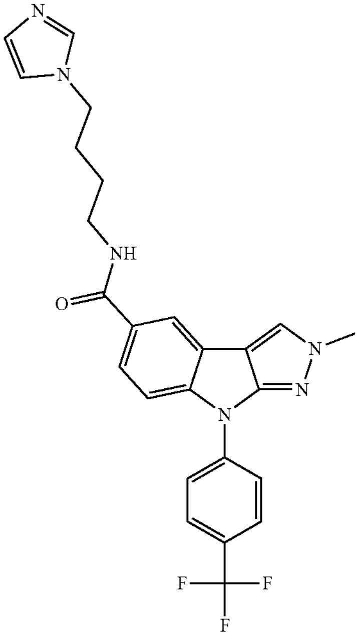 [SMILES: Cn1cc2c3cc(C(=O)NCCCCn4ccnc4)ccc3n(-c3ccc(C(F)(F)F)cc3)c2n1]<br>N-[4-(1H-imidazol-1-yl)butyl]-2-methyl-8-[4-(trifluoromethyl)phenyl]-2H,8H-pyrazolo[3,4-b]indole-5-carboxamide |

-continued

| Compound No. | Structure and Name |
|---|---|
| 299 | 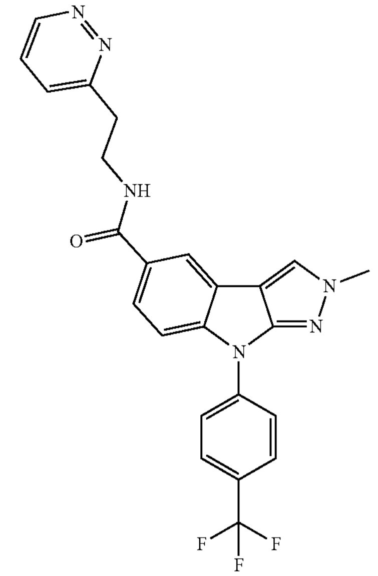 [SMILES: Cn1cc2c3cc(C(=O)NCCc4cccnn4)ccc3n(-c3ccc(C(F)(F)F)cc3)c2n1] 2-methyl-N-[2-(pyridazin-3-yl)ethyl]-8-[4-(trifluoromethyl)phenyl]-2H,8H-pyrazolo[3,4-b]indole-5-carboxamide |
| 300 | 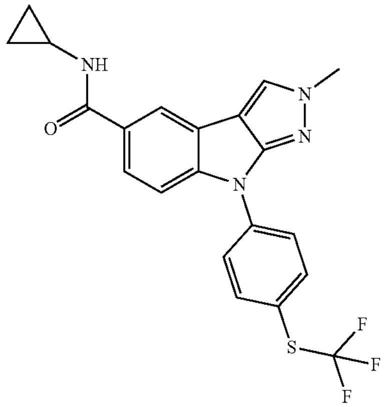 [SMILES: Cn1cc2c3cc(C(=O)NC4CC4)ccc3n(-c3ccc(SC(F)(F)F)cc3)c2n1] N-cyclopropyl-2-methyl-8-{4-[(trifluoromethyl)sulfanyl]phenyl}-2H,8H-pyrazolo[3,4-b]indole-5-carboxamide |

-continued

| Compound No. | Structure and Name |
|---|---|
| 301 | 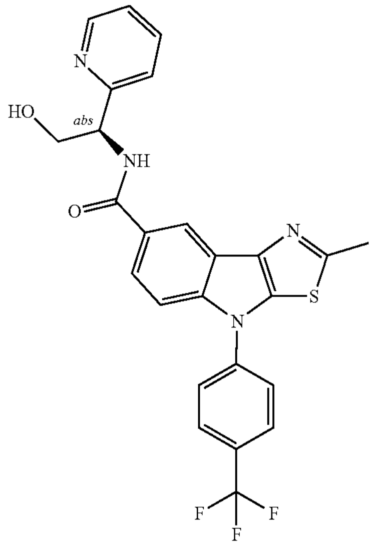 [SMILES: Cc1nc2c3cc(C(=O)N[C@@H](CO)c4ccccn4)ccc3n(-c3ccc(C(F)(F)F)cc3)c2s1] Absolute configuration known/assigned N-[(1R)-2-hydroxy-1-(pyridin-2-yl)ethyl]-2-methyl-4-[4-(trifluoromethyl)phenyl]-4H-[1,3]thiazolo[5,4-b]indole-7-carboxamide |
| 302 | 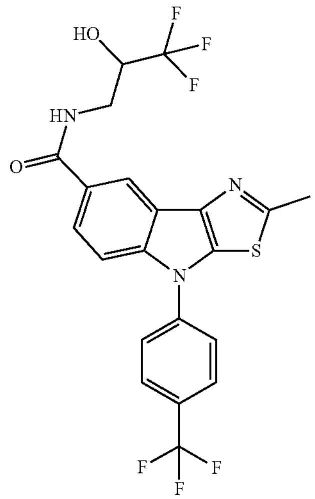 [SMILES: Cc1nc2c3cc(C(=O)NCC(O)C(F)(F)F)ccc3n(-c3ccc(C(F)(F)F)cc3)c2s1] 2-methyl-N-(3,3,3-trifluoro-2-hydroxypropyl)-4-[4-(trifluoromethyl)phenyl]-4H-[1,3]thiazolo[5,4-b]indole-7-carboxamide |

-continued

| Compound No. | Structure and Name |
|---|---|
| 303 | 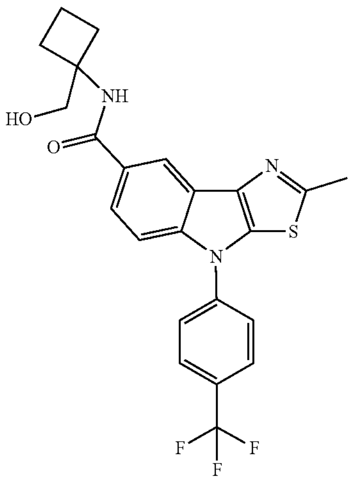 [SMILES: Cc1nc2c3cc(C(=O)NC4(CO)CCC4)ccc3n(-c3ccc(C(F)(F)F)cc3)c2s1] N-[1-(hydroxymethyl)cyclobutyl]-2-methyl-4-[4-(trifluoromethyl)phenyl]-4H-[1,3]thiazolo[5,4-b]indole-7-carboxamide |
| 304 | 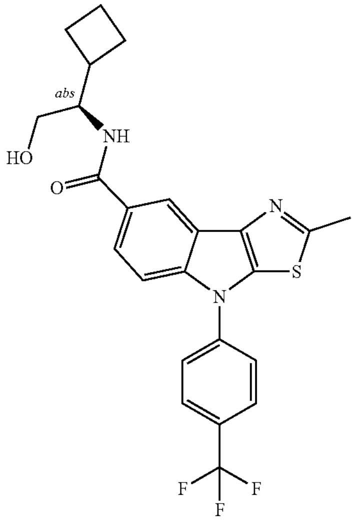 [SMILES: Cc1nc2c3cc(C(=O)N[C@@H](CO)C4CCC4)ccc3n(-c3ccc(C(F)(F)F)cc3)c2s1] Absolute configuration known/assigned N-[(1R)-1-cyclobutyl-2-hydroxyethyl]-2-methyl-4-[4-(trifluoromethyl)phenyl]-4H-[1,3]thiazolo[5,4-b]indole-7-carboxamide |

-continued

| Compound No. | Structure and Name |
|---|---|
| 305 | 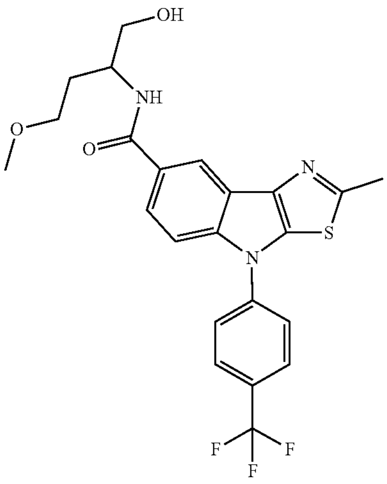 N-(1-hydroxy-4-methoxybutan-2-yl)-2-methyl-4-[4-(trifluoromethyl)phenyl]-4H-[1,3]thiazolo[5,4-b]indole-7-carboxamide |
| 306 | 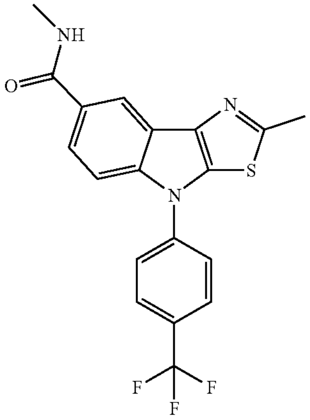 [SMILES: CNC(=O)c1ccc2c(c1)c1nc(C)sc1n2-c1ccc(C(F)(F)F)cc1] N,2-dimethyl-4-[4-(trifluoromethyl)phenyl]-4H-[1,3]thiazolo[5,4-b]indole-7-carboxamide |
| 307 | 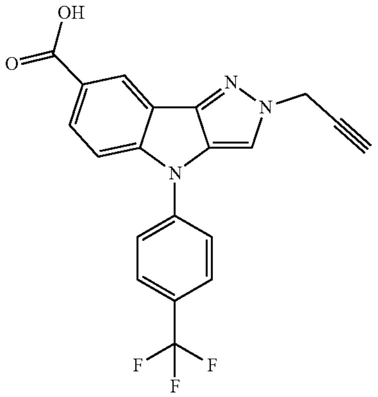 [SMILES: C#CCn1cc2c(n1)c1cc(C(=O)O)ccc1n2-c1ccc(C(F)(F)F)cc1] 2-(prop-2-yn-1-yl)-4-[4-(trifluoromethyl)phenyl]-2H,4H-pyrazolo[4,3-b]indole-7-carboxylic acid |

-continued

| Compound No. | Structure and Name |
|---|---|
| 308 | 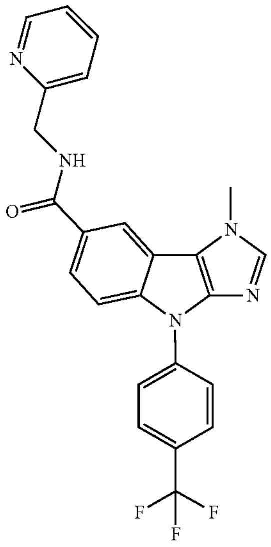 [SMILES: Cn1cnc2c1c1cc(C(=O)NCc3ccccn3)ccc1n2-c1ccc(C(F)(F)F)cc1] 1-methyl-N-[(pyridin-2-yl)methyl]-4-[4-(trifluoromethyl)phenyl]-1H,4H-imidazo[4,5-b]indole-7-carboxamide |
| 309 | 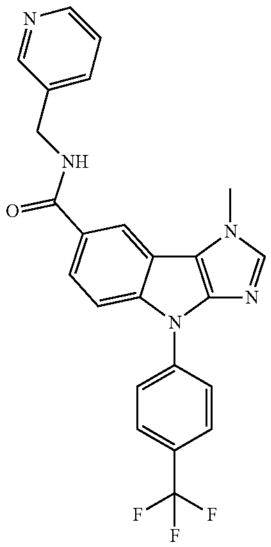 [SMILES: Cn1cnc2c1c1cc(C(=O)NCc3cccnc3)ccc1n2-c1ccc(C(F)(F)F)cc1] 1-methyl-N-[(pyridin-3-yl)methyl]-4-[4-(trifluoromethyl)phenyl]-1H,4H-imidazo[4,5-b]indole-7-carboxamide |

-continued

| Compound No. | Structure and Name |
|---|---|
| 310 | 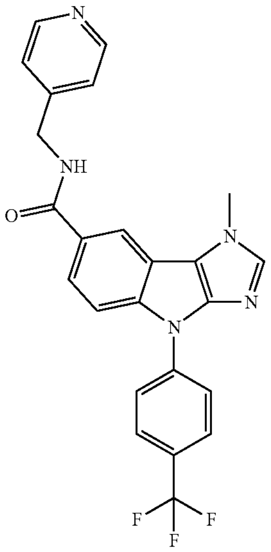 [SMILES: Cn1cnc2c1c1cc(C(=O)NCc3ccncc3)ccc1n2-c1ccc(C(F)(F)F)cc1] 1-methyl-N-[(pyridin-4-yl)methyl]-4-[4-(trifluoromethyl)phenyl]-1H,4H-imidazo[4,5-b]indole-7-carboxamide |
| 311 | 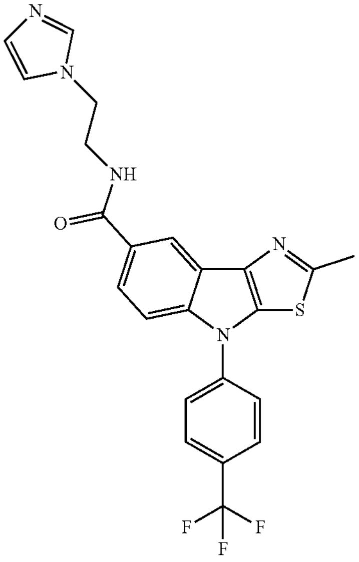 [SMILES: Cc1nc2c3cc(C(=O)NCCn4ccnc4)ccc3n(-c3ccc(C(F)(F)F)cc3)c2s1] N-[2-(1H-imidazol-1-yl)ethyl]-2-methyl-4-[4-(trifluoromethyl)phenyl]-4H-[1,3]thiazolo[5,4-b]indole-7-carboxamide |

| Compound No. | Structure and Name |
|---|---|
| 312 | 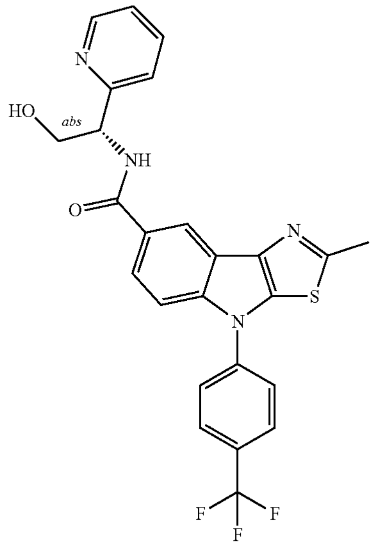 [SMILES: Cc1nc2c3cc(C(=O)N[C@H](CO)c4ccccn4)ccc3n(-c3ccc(C(F)(F)F)cc3)c2s1]<br>Absolute configuration known/assigned<br>N-[(1S)-2-hydroxy-1-(pyridin-2-yl)ethyl]-2-methyl-4-[4-(trifluoromethyl)phenyl]-4H-[1,3]thiazolo[5,4-b]indole-7-carboxamide |
| 313 | 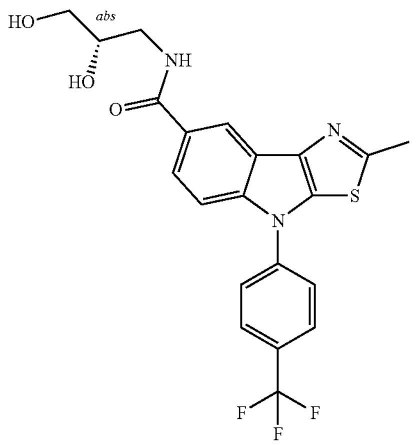 [SMILES: Cc1nc2c3cc(C(=O)NC[C@H](O)CO)ccc3n(-c3ccc(C(F)(F)F)cc3)c2s1]<br>Absolute configuration known/assigned<br>N-[(2S)-2,3-dihydroxypropyl]-2-methyl-4-[4-(trifluoromethyl)phenyl]-4H-[1,3]thiazolo[5,4-b]indole-7-carboxamide |

| Compound No. | Structure and Name |
|---|---|
| 314 | 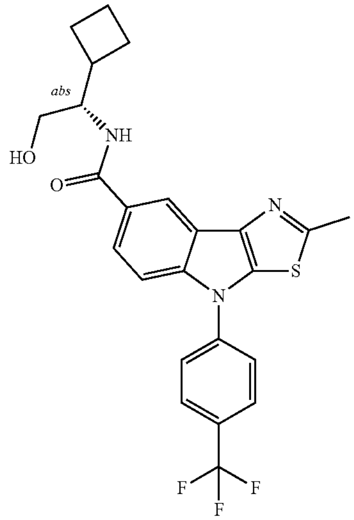 [SMILES: Cc1nc2c3cc(C(=O)N[C@H](CO)C4CCC4)ccc3n(-c3ccc(C(F)(F)F)cc3)c2s1]<br>Absolute configuration known/assigned<br>N-[(1S)-1-cyclobutyl-2-hydroxyethyl]-2-methyl-4-[4-(trifluoromethyl)phenyl]-4H-[1,3]thiazolo[5,4-b]indole-7-carboxamide |
| 315 | 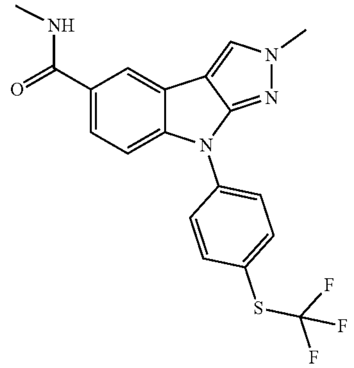 [SMILES: CNC(=O)c1ccc2c(c1)c1cn(C)nc1n2-c1ccc(SC(F)(F)F)cc1]<br>N,2-dimethyl-8-{4-[(trifluoromethyl)sulfanyl]phenyl}-2H,8H-pyrazolo[3,4-b]indole-5-carboxamide |
| 316 | 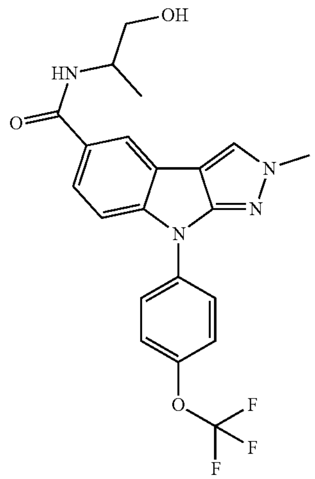 [SMILES: CC(CO)NC(=O)c1ccc2c(c1)c1cn(C)nc1n2-c1ccc(OC(F)(F)F)cc1] |

-continued

| Compound No. | Structure and Name |
|---|---|
| | N-(1-hydroxypropan-2-yl)-2-methyl-8-[4-(trifluoromethoxy)phenyl]-2H,8H-pyrazolo[3,4-b]indole-5-carboxamide |
| 317 | 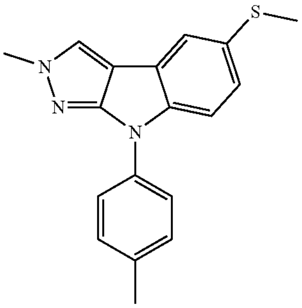 2-methyl-8-(4-methylphenyl)-5-(methylsulfanyl)-2H,8H-pyrazolo[3,4-b]indole |
| 318 | 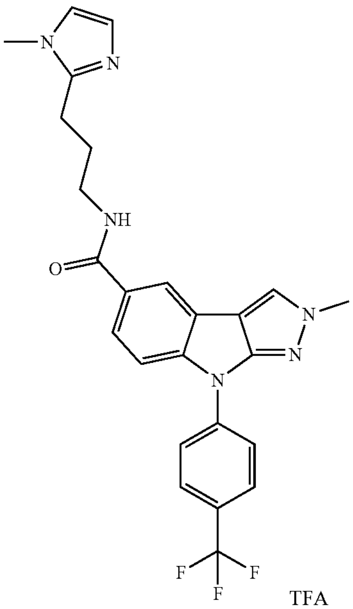 TFA 2-methyl-N-[3-(1-methyl-1H-imidazol-2-yl)propyl]-8-[4-(trifluoromethyl)phenyl]-2H,8H-pyrazolo[3,4-b]indole-5-carboxamide |

-continued

| Compound No. | Structure and Name |
|---|---|
| 319 | 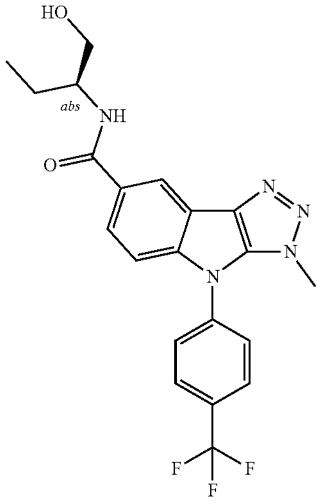 [SMILES: CC[C@@H](CO)NC(=O)c1ccc2c(c1)c1nnn(C)c1n2-c1ccc(C(F)(F)F)cc1] Absolute configuration assigned arbitrarily N-[(2S)-1-hydroxybutan-2-yl]-3-methyl-4-[4-(trifluoromethyl)phenyl]-3H,4H-[1,2,3]triazolo[4,5-b]indole-7-carboxamide |
| 320 | 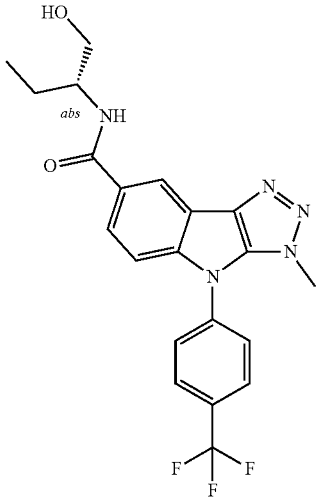 [SMILES: CC[C@H](CO)NC(=O)c1ccc2c(c1)c1nnn(C)c1n2-c1ccc(C(F)(F)F)cc1] Absolute configuration assigned arbitrarily N-[(2R)-1-hydroxybutan-2-yl]-3-methyl-4-[4-(trifluoromethyl)phenyl]-3H,4H-[1,2,3]triazolo[4,5-b]indole-7-carboxamide |

-continued

| Compound No. | Structure and Name |
|---|---|
| 321 | 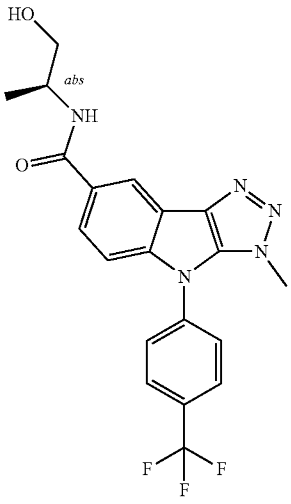 [SMILES: C[C@@H](CO)NC(=O)c1ccc2c(c1)c1nnn(C)c1n2-c1ccc(C(F)(F)F)cc1] Absolute configuration known/assigned N-[(2S)-1-hydroxypropan-2-yl]-3-methyl-4-[4-(trifluoromethyl)phenyl]-3H,4H-[1,2,3]triazolo[4,5-b]indole-7-carboxamide |
| 322 | 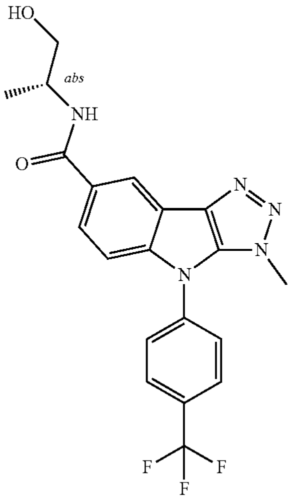 [SMILES: C[C@H](CO)NC(=O)c1ccc2c(c1)c1nnn(C)c1n2-c1ccc(C(F)(F)F)cc1] Absolute configuration known/assigned N-[(2R)-1-hydroxypropan-2-yl]-3-methyl-4-[4-(trifluoromethyl)phenyl]-3H,4H-[1,2,3]triazolo[4,5-b]indole-7-carboxamide |

-continued

| Compound No. | Structure and Name |
|---|---|
| 323 | 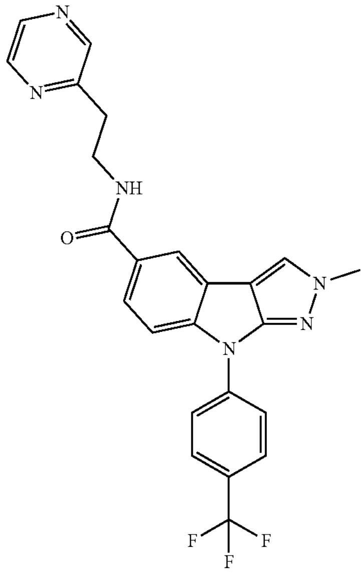 [SMILES: Cn1cc2c3cc(C(=O)NCCc4cnccn4)ccc3n(-c3ccc(C(F)(F)F)cc3)c2n1] 2-methyl-N-[2-(pyrazin-2-yl)ethyl]-8-[4-(trifluoromethyl)phenyl]-2H,8H-pyrazolo[3,4-b]indole-5-carboxamide |
| 324 | 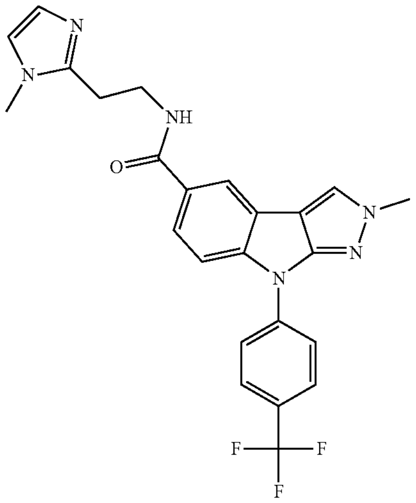 2-methyl-N-[2-(1-methyl-1H-imidazol-2-yl)ethyl]-8-[4-(trifluoromethyl)phenyl]-2H,8H-pyrazolo[3,4-b]indole-5-carboxamide |

-continued

| Compound No. | Structure and Name |
|---|---|
| 325 | 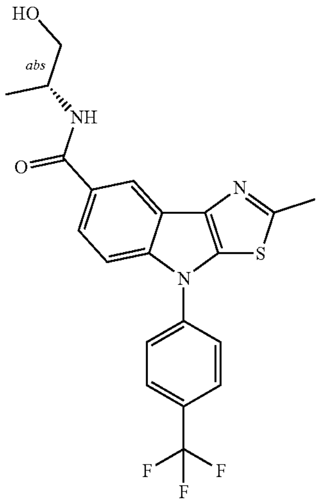 [SMILES: Cc1nc2c3cc(C(=O)N[C@H](C)CO)ccc3n(-c3ccc(C(F)(F)F)cc3)c2s1]<br>Absolute configuration known/assigned<br>N-[(2R)-1-hydroxypropan-2-yl]-2-methyl-4-[4-(trifluoromethyl)phenyl]-4H-[1,3]thiazolo[5,4-b]indole-7-carboxamide |
| 326 | 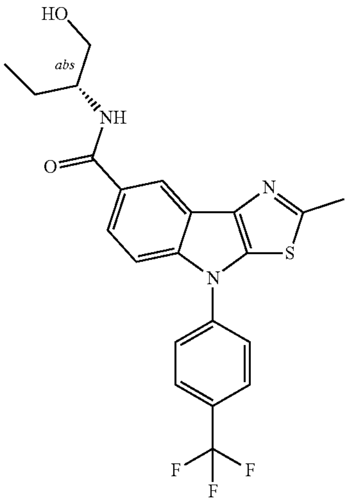 [SMILES: CC[C@H](CO)NC(=O)c1ccc2c(c1)c1nc(C)sc1n2-c1ccc(C(F)(F)F)cc1]<br>Absolute configuration known/assigned<br>N-[(2R)-1-hydroxybutan-2-yl]-2-methyl-4-[4-(trifluoromethyl)phenyl]-4H-[1,3]thiazolo[5,4-b]indole-7-carboxamide |

-continued

| Compound No. | Structure and Name |
|---|---|
| 327 | 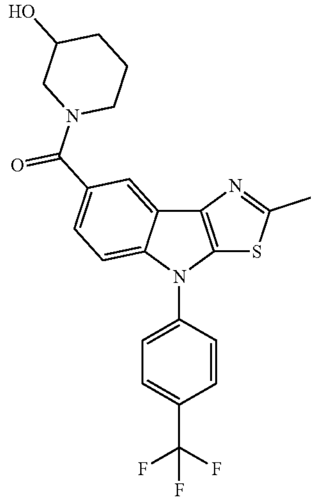<br>1-{2-methyl-4-[4-(trifluoromethyl)phenyl]-4H-[1,3]thiazolo[5,4-b]indole-7-carbonyl}piperidin-3-ol |
| 328 | 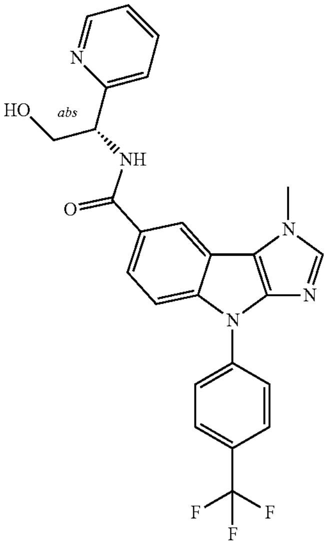 [SMILES: Cn1cnc2c1c1cc(C(=O)N[C@H](CO)c3ccccn3)ccc1n2-c1ccc(C(F)(F)F)cc1]<br>Absolute configuration known/assigned<br>N-[(1S)-2-hydroxy-1-(pyridin-2-yl)ethyl]-1-methyl-4-[4-(trifluoromethyl)phenyl]-1H,4H-imidazo[4,5-b]indole-7-carboxamide |

-continued

| Compound No. | Structure and Name |
|---|---|
| 329 | 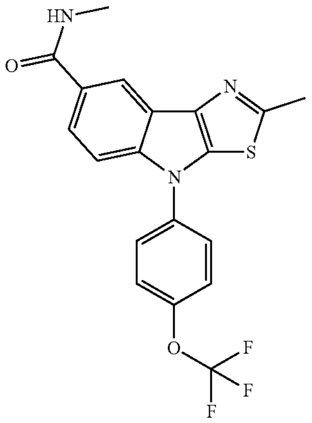 [SMILES: CNC(=O)c1ccc2c(c1)c1nc(C)sc1n2-c1ccc(OC(F)(F)F)cc1] N,2-dimethyl-4-[4-(trifluoromethoxy)phenyl]-4H-[1,3]thiazolo[5,4-b]indole-7-carboxamide |
| 330 | 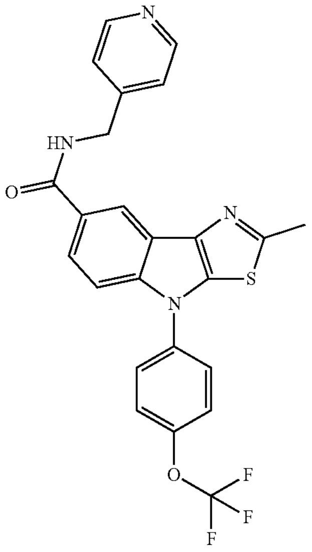 2-methyl-N-[(pyridin-4-yl)methyl]-4-[4-(trifluoromethoxy)phenyl]-4H-[1,3]thiazolo[5,4-b]indole-7-carboxamide |

-continued

| Compound No. | Structure and Name |
|---|---|
| 331 | 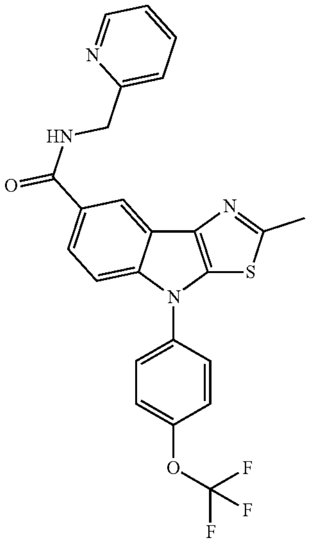 [SMILES: Cc1nc2c3cc(C(=O)NCc4ccccn4)ccc3n(-c3ccc(OC(F)(F)F)cc3)c2s1] 2-methyl-N-[(pyridin-2-yl)methyl]-4-[4-(trifluoromethoxy)phenyl]-4H-[1,3]thiazolo[5,4-b]indole-7-carboxamide |
| 332 | 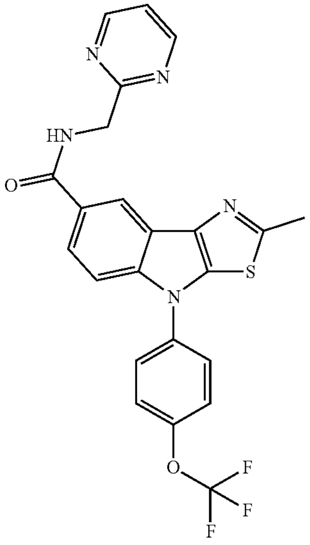 2-methyl-N-[(pyrimidin-2-yl)methyl]-4-[4-(trifluoromethoxy)phenyl]-4H-[1,3]thiazolo[5,4-b]indole-7-carboxamide |

-continued

| Compound No. | Structure and Name |
| --- | --- |
| 333 | 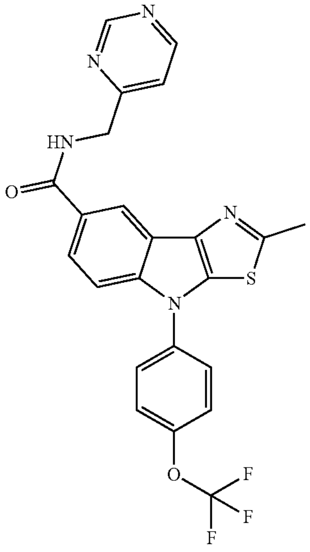 2-methyl-N-[(pyrimidin-4-yl)methyl]-4-[4-(trifluoromethoxy)phenyl]-4H-[1,3]thiazolo[5,4-b]indole-7-carboxamide |
| 334 | 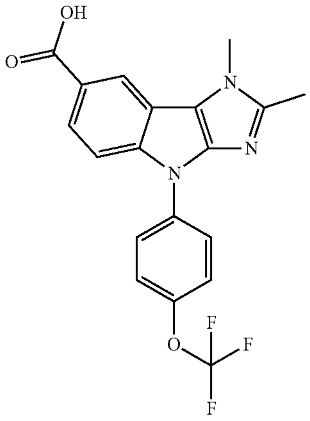 [SMILES: Cc1nc2c(c3cc(C(=O)O)ccc3n2-c2ccc(OC(F)(F)F)cc2)n1C] 1,2-dimethyl-4-[4-(trifluoromethoxy)phenyl]-1H,4H-imidazo[4,5-b]indole-7-carboxylic acid |
| 335 | 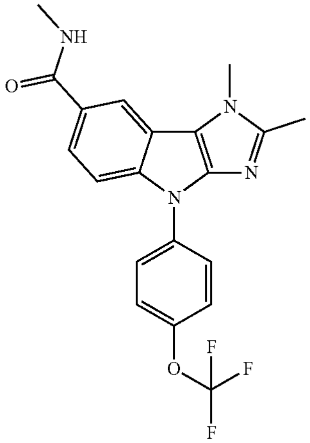 [SMILES: CNC(=O)c1ccc2c(c1)c1c(nc(C)n1C)n2-c1ccc(OC(F)(F)F)cc1] N,1,2-trimethyl-4-[4-(trifluoromethoxy)phenyl]-1H,4H-imidazo[4,5-b]indole-7-carboxamide |
| 336 | 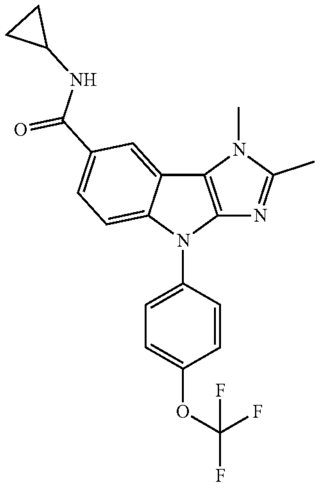 [SMILES: Cc1nc2c(c3cc(C(=O)NC4CC4)ccc3n2-c2ccc(OC(F)(F)F)cc2)n1C] N-cyclopropyl-1,2-dimethyl-4-[4-(trifluoromethoxy)phenyl]-1H,4H-imidazo[4,5-b]indole-7-carboxamide |
| 337 | 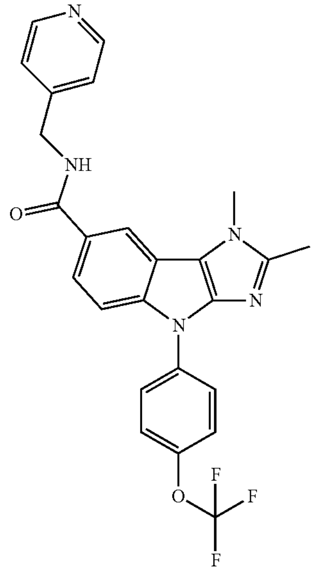 [SMILES: Cc1nc2c(c3cc(C(=O)NCc4ccncc4)ccc3n2-c2ccc(OC(F)(F)F)cc2)n1C] 1,2-dimethyl-N-[(pyridin-4-yl)methyl]-4-[4-(trifluoromethoxy)phenyl]-1H,4H-imidazo[4,5-b]indole-7-carboxamide |

-continued

| Compound No. | Structure and Name |
|---|---|
| 338 | 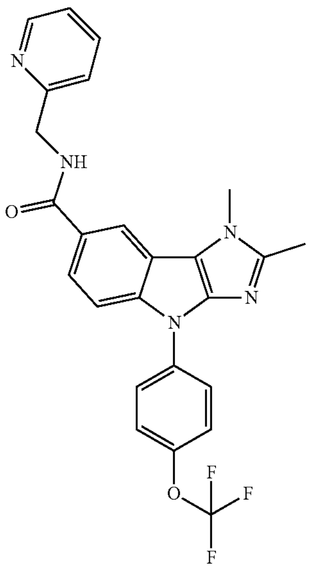 1,2-dimethyl-N-[(pyridin-2-yl)methyl]-4-[4-(trifluoromethoxy)phenyl]-1H,4H-imidazo[4,5-b]indole-7-carboxamide |
| 339 | 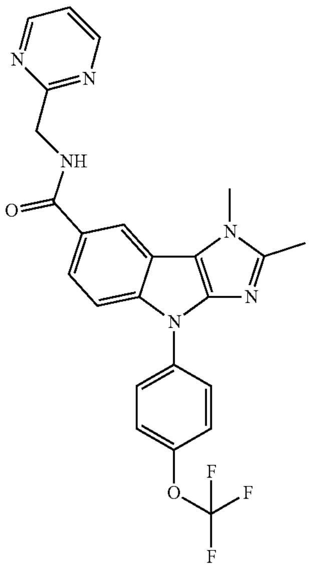 [SMILES: Cc1nc2c(c3cc(C(=O)NCc4ncccn4)ccc3n2-c2ccc(OC(F)(F)F)cc2)n1C] 1,2-dimethyl-N-[(pyrimidin-2-yl)methyl]-4-[4-(trifluoromethoxy)phenyl]-1H,4H-imidazo[4,5-b]indole-7-carboxamide |

-continued

| Compound No. | Structure and Name |
|---|---|
| 340 | 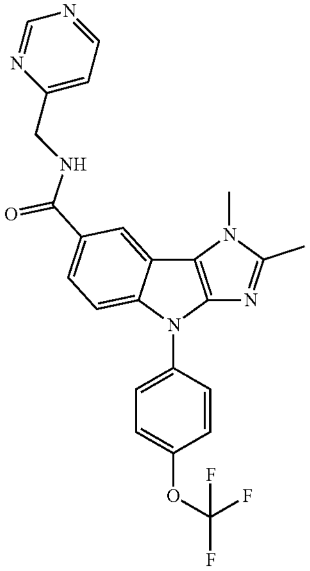 [SMILES: Cc1nc2c(c3cc(C(=O)NCc4ccncn4)ccc3n2-c2ccc(OC(F)(F)F)cc2)n1C] 1,2-dimethyl-N-[(pyrimidin-4-yl)methyl]-4-[4-(trifluoromethoxy)phenyl]-1H,4H-imidazo[4,5-b]indole-7-carboxamide |
| 341 | 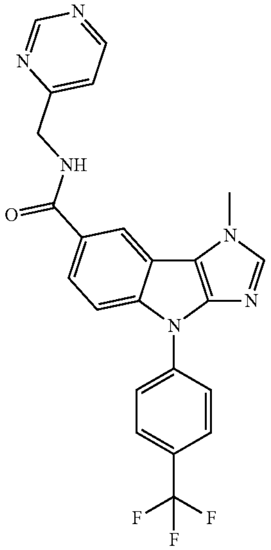 [SMILES: Cn1cnc2c1c1cc(C(=O)NCc3ccncn3)ccc1n2-c1ccc(C(F)(F)F)cc1] 1-methyl-N-[(pyrimidin-4-yl)methyl]-4-[4-(trifluoromethyl)phenyl]-1H,4H-imidazo[4,5-b]indole-7-carboxamide |

-continued

| Compound No. | Structure and Name |
|---|---|
| 342 | 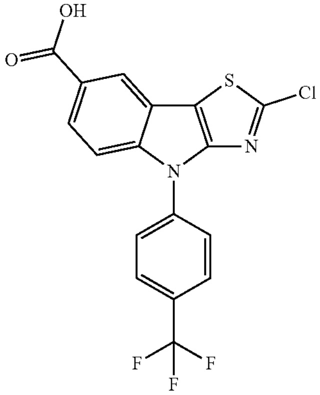 [SMILES: O=C(O)c1ccc2c(c1)c1sc(Cl)nc1n2-c1ccc(C(F)(F)F)cc1]<br>2-chloro-4-[4-(trifluoromethyl)phenyl]-4H-[1,3]thiazolo[4,5-b]indole-7-carboxylic acid |
| 343 | 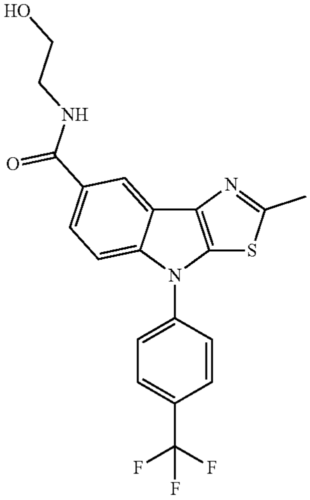<br>N-(2-hydroxyethyl)-2-methyl-4-[4-(trifluoromethyl)phenyl]-4H-[1,3]thiazolo[5,4-b]indole-7-carboxamide |
| 344 | 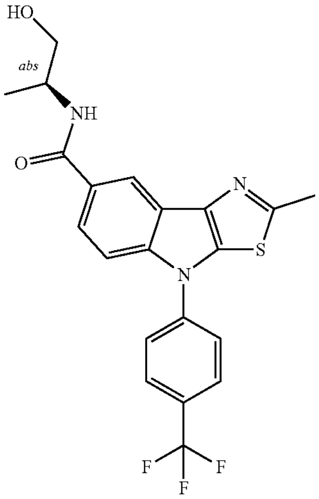 [SMILES: Cc1nc2c3cc(C(=O)N[C@@H](C)CO)ccc3n(-c3ccc(C(F)(F)F)cc3)c2s1] |

-continued

| Compound No. | Structure and Name |
|---|---|
| | Absolute confiugration known/assigned<br>N-[(2S)-1-hydroxypropan-2-yl]-2-methyl-4-[4-(trifluoromethyl)phenyl]-4H-[1,3]thiazolo[5,4-b]indole-7-carboxamide |
| 345 | 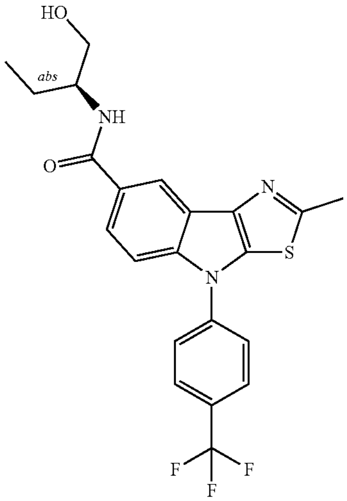 [SMILES: CC[C@@H](CO)NC(=O)c1ccc2c(c1)c1nc(C)sc1n2-c1ccc(C(F)(F)F)cc1]<br>Absolute configuration known/assigned<br>N-[(2S)-1-hydroxybutan-2-yl]-2-methyl-4-[4-(trifluoromethyl)phenyl]-4H-[1,3]thiazolo[5,4-b]indole-7-carboxamide |
| 346 | 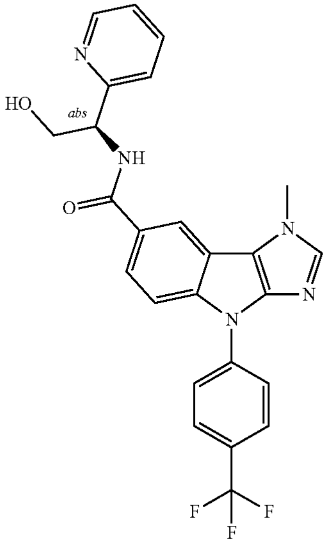 [SMILES: Cn1cnc2c1c1cc(C(=O)N[C@@H](CO)c3ccccn3)ccc1n2-c1ccc(C(F)(F)F)cc1]<br>Absolute configuration known/assigned<br>N-[(1R)-2-hydroxy-1-(pyridin-2-yl)ethyl]-1-methyl-4-[4-(trifluoromethyl)phenyl]-1H,4H-imidazo[4,5-b]indole-7-carboxamide |

-continued

| Compound No. | Structure and Name |
|---|---|
| 347 | 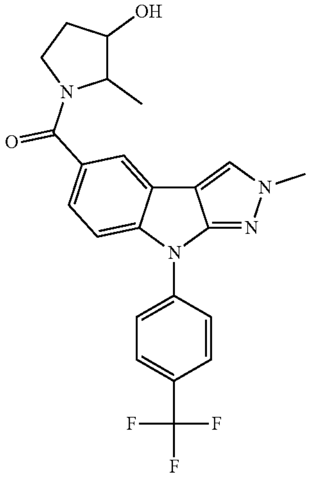 [SMILES: CC1C(O)CCN1C(=O)c1ccc2c(c1)c1cn(C)nc1n2-c1ccc(C(F)(F)F)cc1] Mixtures of 4 isomers 2-methyl-1-{2-methyl-8-[4-(trifluoromethyl)phenyl]-2H,8H-pyrazolo[3,4-b]indole-5-carbonyl}pyrrolidin-3-ol |
| 348 | 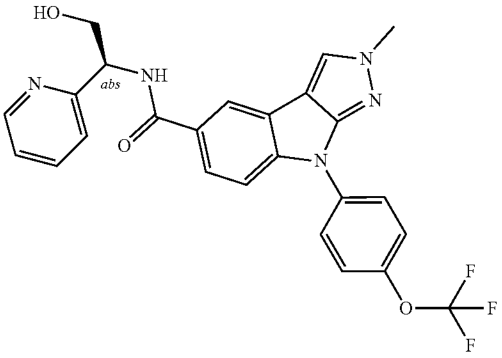 [SMILES: Cn1cc2c3cc(C(=O)N[C@H](CO)c4ccccn4)ccc3n(-c3ccc(OC(F)(F)F)cc3)c2n1] Absolute configuration known/assigned N-[(1S)-2-hydroxy-1-(pyridin-2-yl)ethyl]-2-methyl-8-[4-(trifluoromethoxy)phenyl]-2H,8H-pyrazolo[3,4-b]indole-5-carboxamide |
| 349 | 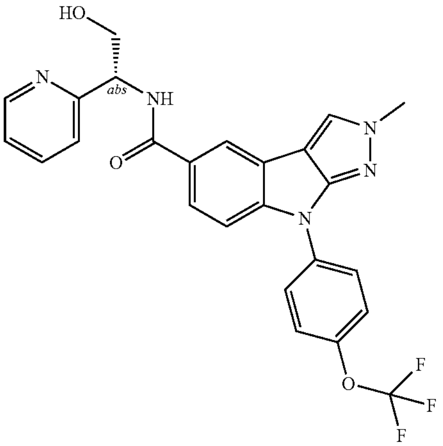 [SMILES: Cn1cc2c3cc(C(=O)N[C@@H](CO)c4ccccn4)ccc3n(-c3ccc(OC(F)(F)F)cc3)c2n1] Absolute configuration known/assigned N-[(1R)-2-hydroxy-1-(pyridin-2-yl)ethyl]-2-methyl-8-[4-(trifluoromethoxy)phenyl]-2H,8H-pyrazolo[3,4-b]indole-5-carboxamide |

-continued

| Compound No. | Structure and Name |
|---|---|
| 350 | 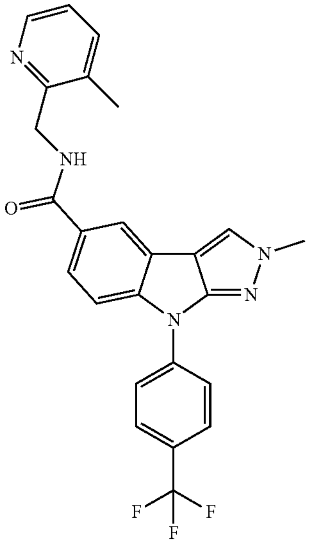 [SMILES: Cc1cccnc1CNC(=O)c1ccc2c(c1)c1cn(C)nc1n2-c1ccc(C(F)(F)F)cc1] 2-methyl-N-[(3-methylpyridin-2-yl)methyl]-8-[4-(trifluoromethyl)phenyl]-2H,8H-pyrazolo[3,4-b]indole-5-carboxamide |
| 351 | 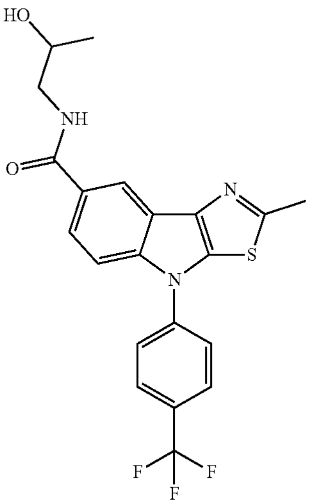 N-(2-hydroxypropyl)-2-methyl-4-[4-(trifluoromethyl)phenyl]-4H-[1,3]thiazolo[5,4-b]indole-7-carboxamide |

-continued

| Compound No. | Structure and Name |
|---|---|
| 352 | 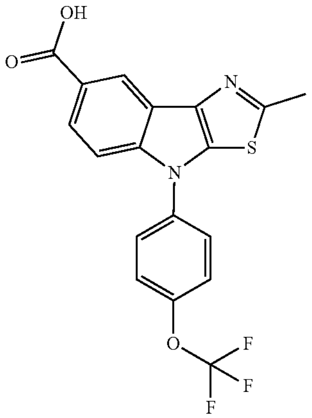 [SMILES: Cc1nc2c3cc(C(=O)O)ccc3n(-c3ccc(OC(F)(F)F)cc3)c2s1]<br>2-methyl-4-[4-(trifluoromethoxy)phenyl]-4H-[1,3]thiazolo[5,4-b]indole-7-carboxylic acid |
| 353 | 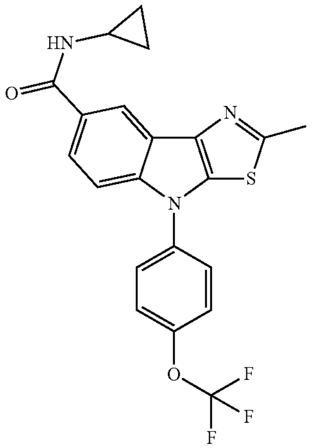 [SMILES: Cc1nc2c3cc(C(=O)NC4CC4)ccc3n(-c3ccc(OC(F)(F)F)cc3)c2s1]<br>N-cyclopropyl-2-methyl-4-[4-(trifluoromethoxy)phenyl]-4H-[1,3]thiazolo[5,4-b]indole-7-carboxamide |
| 354 | 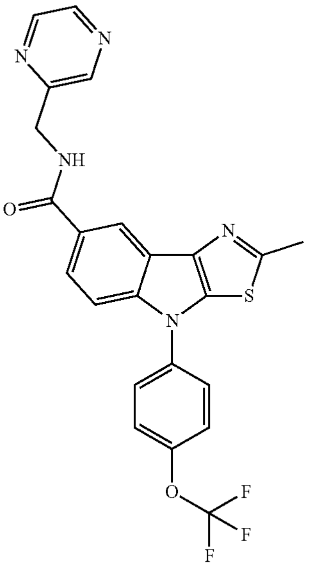 [SMILES: Cc1nc2c3cc(C(=O)NCc4cnccn4)ccc3n(-c3ccc(OC(F)(F)F)cc3)c2s1] |

-continued

| Compound No. | Structure and Name |
|---|---|
| | 2-methyl-N-[(pyrazin-2-yl)methyl]-4-[4-(trifluoromethoxy)phenyl]-4H-[1,3]thiazolo[5,4-b]indole-7-carboxamide |
| 355 | 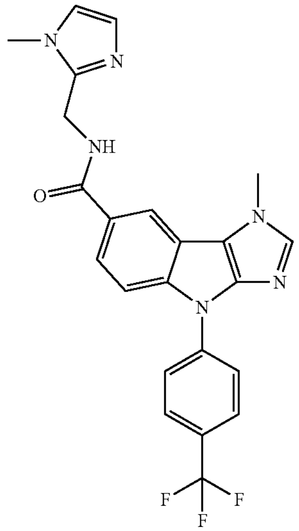 [SMILES: Cn1ccnc1CNC(=O)c1ccc2c(c1)c1c(ncn1C)n2-c1ccc(C(F)(F)F)cc1]<br>1-methyl-N-[(1-methyl-1H-imidazol-2-yl)methyl]-4-[4-(trifluoromethyl)phenyl]-1H,4H-imidazo[4,5-b]indole-7-carboxamide |
| 356 | 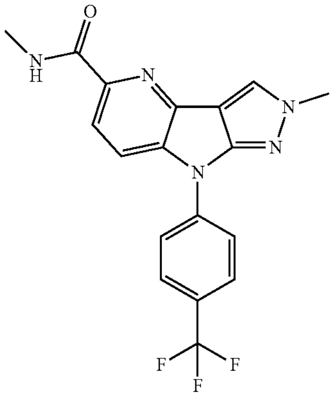<br>N,4-dimethyl-7-[4-(trifluoromethyl)phenyl]-4,5,7,12-tetraazatricyclo[6.4.0.0$^{2,6}$]dodeca-1(8),2,5,9,11-pentaene-11-carboxamide |
| 357 | 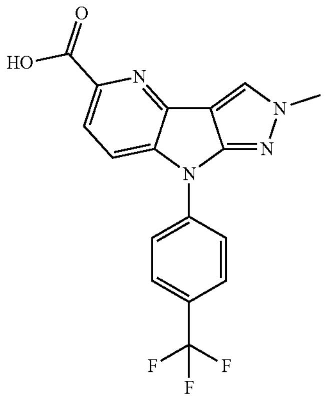 [SMILES: Cn1cc2c3nc(C(=O)O)ccc3n(-c3ccc(C(F)(F)F)cc3)c2n1] |

| Compound No. | Structure and Name |
| --- | --- |
| | 4-methyl-7-[4-(trifluoromethyl)phenyl]-4,5,7,12-tetraazatricyclo[6.4.0.0$^{2,6}$]dodeca-1(8),2,5,9,11-pentaene-11-carboxylic acid |
| 358 | 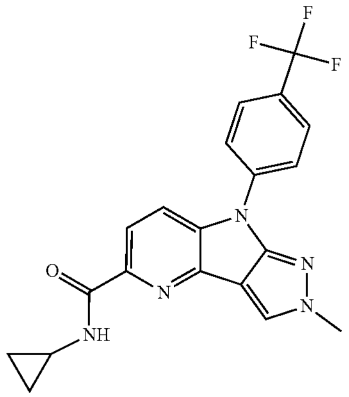 [SMILES: Cn1cc2c3nc(C(=O)NC4CC4)ccc3n(-c3ccc(C(F)(F)F)cc3)c2n1] N-cyclopropyl-4-methyl-7-[4-(trifluoromethyl)phenyl]-4,5,7,12-tetraazatricyclo[6.4.0.0$^{2,6}$]dodeca-1(8),2,5,9,11-pentaene-11-carboxamide |
| 359 | 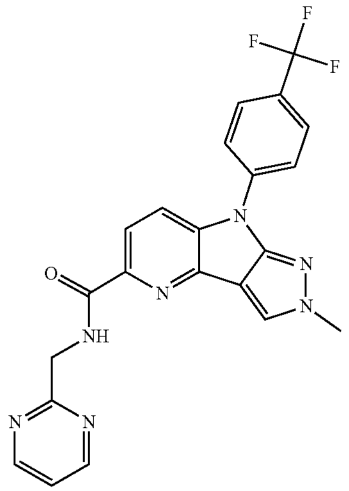 4-methyl-N-[(pyrimidin-2-yl)methyl]-7-[4-(trifluoromethyl)phenyl]-4,5,7,12-tetraazatricyclo[6.4.0.0$^{2,6}$]dodeca-1(8),2,5,9,11-pentaene-11-carboxamide |

| Compound No. | Structure and Name |
| --- | --- |
| 360 | 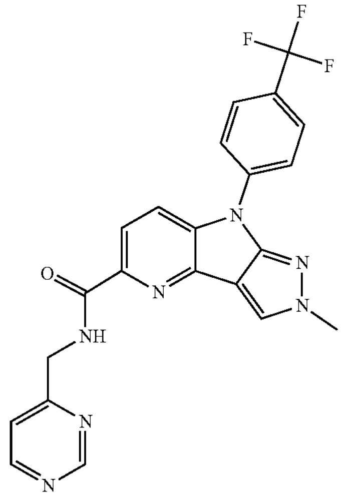 [SMILES: Cn1cc2c3nc(C(=O)NCc4ccncn4)ccc3n(-c3ccc(C(F)(F)F)cc3)c2n1] 4-methyl-N-[(pyrimidin-4-yl)methyl]-7-[4-(trifluoromethyl)phenyl]-4,5,7,12-tetraazatricyclo[6.4.0.0$^{2,6}$]dodeca-1(12),2,5,8,10-pentaene-11-carboxamide |
| 361 | 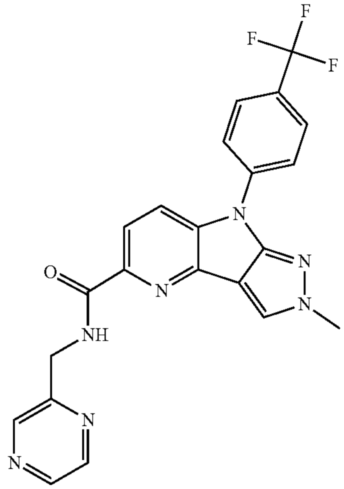 [SMILES: Cn1cc2c3nc(C(=O)NCc4cnccn4)ccc3n(-c3ccc(C(F)(F)F)cc3)c2n1] 4-methyl-N-[(pyrazin-2-yl)methyl]-7-[4-(trifluoromethyl)phenyl]-4,5,7,12-tetraazatricyclo[6.4.0.0$^{2,6}$]dodeca-1(12),2,5,8,10-pentaene-11-carboxamide |

-continued

| Compound No. | Structure and Name |
| --- | --- |
| 362 | 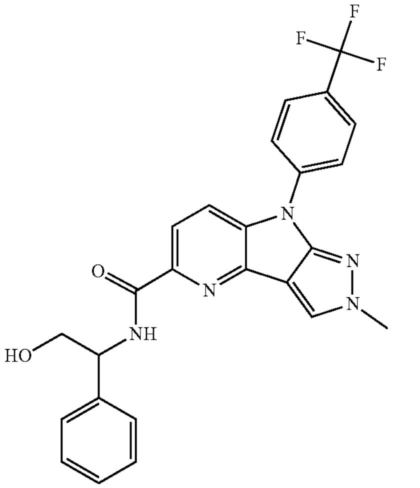 [SMILES: Cn1cc2c3nc(C(=O)NC(CO)c4ccccc4)ccc3n(-c3ccc(C(F)(F)F)cc3)c2n1] N-(2-hydroxy-1-phenylethyl)-4-methyl-7-[4-(trifluoromethyl)phenyl]-4,5,7,12-tetraazatricyclo[6.4.0.$0^{2,6}$]dodeca-1(12),2,5,8,10-pentaene-11-carboxamide |
| 363 | 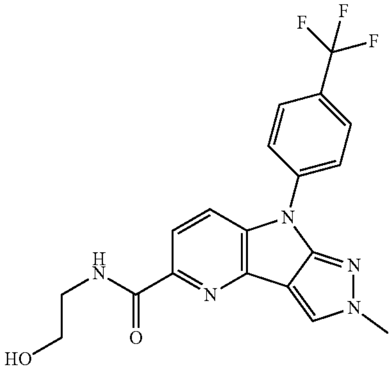 [SMILES: Cn1cc2c3nc(C(=O)NCCO)ccc3n(-c3ccc(C(F)(F)F)cc3)c2n1] N-(2-hydroxyethyl)-4-methyl-7-[4-(trifluoromethyl)phenyl]-4,5,7,12-tetraazatricyclo[6.4.0.$0^{2,6}$]dodeca-1(8),2,5,9,11-pentaene-11-carboxamide |
| 364 | 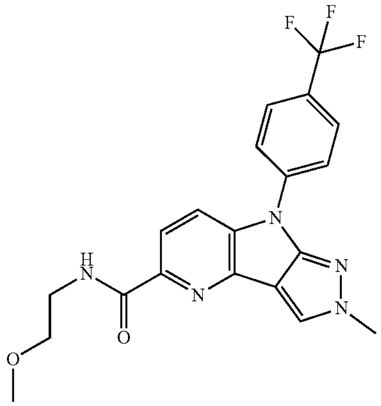 [SMILES: COCCNC(=O)c1ccc2c(n1)c1cn(C)nc1n2-c1ccc(C(F)(F)F)cc1] N-(2-methoxyethyl)-4-methyl-7-[4-(trifluoromethyl)phenyl]-4,5,7,12-tetraazatricyclo[6.4.0.$0^{2,6}$]dodeca-1(8),2,5,9,11-pentaene-11-carboxamide |
| 365 | 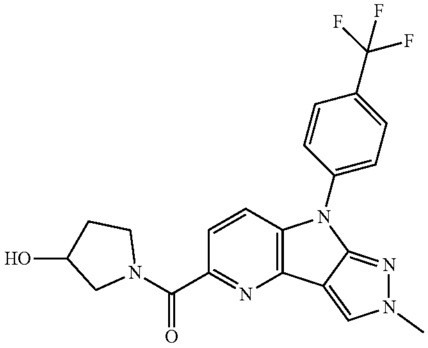 [SMILES: Cn1cc2c3nc(C(=O)N4CCC(O)C4)ccc3n(-c3ccc(C(F)(F)F)cc3)c2n1] 1-{4-methyl-7-[4-(trifluoromethyl)phenyl]-4,5,7,12-tetraazatricyclo[6.4.0.$0^{2,6}$]dodeca-1(8),2,5,9,11-pentaene-11-carbonyl}pyrrolidin-3-ol |
| 366 | 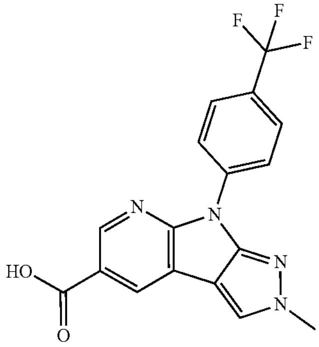 [SMILES: Cn1cc2c3cc(C(=O)O)cnc3n(-c3ccc(C(F)(F)F)cc3)c2n1] 4-methyl-7-[4-(trifluoromethyl)phenyl]-4,5,7,9-tetraazatricyclo[6.4.0.$0^{2,6}$]dodeca-1(8),2,5,9,11-pentaene-11-carboxylic acid |
| 367 | 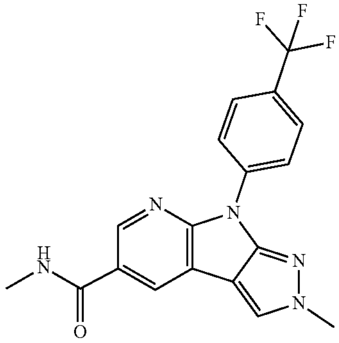 |

-continued

| Compound No. | Structure and Name |
|---|---|
| | N,4-dimethyl-7-[4-(trifluoromethyl)phenyl]-4,5,7,9-tetraazatricyclo[$6.4.0.0^{2,6}$]dodeca-1(8),2,5,9,11-pentaene-11-carboxamide |
| 368 | 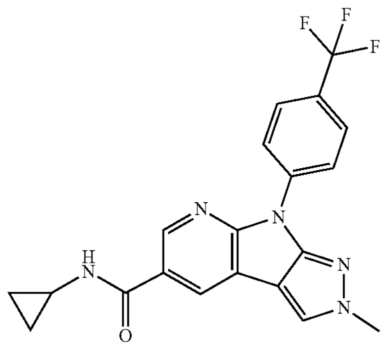 [SMILES: Cn1cc2c3cc(C(=O)NC4CC4)cnc3n(-c3ccc(C(F)(F)F)cc3)c2n1] N-cyclopropyl-4-methyl-7-[4-(trifluoromethyl)phenyl]-4,5,7,9-tetraazatricyclo[$6.4.0.0^{2,6}$]dodeca-1(8),2,5,9,11-pentaene-11-carboxamide |
| 369 | 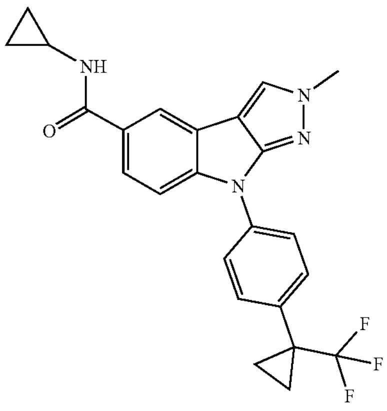 [SMILES: Cn1cc2c3cc(C(=O)NC4CC4)ccc3n(-c3ccc(C4(C(F)(F)F)CC4)cc3)c2n1] N-cyclopropyl-2-methyl-8-{4-[1-(tri-fluoromethyl)cyclopropyl]phenyl}-2H,8H-pyrazolo[3,4-b]indole-5-carboxamide |
| 370 | 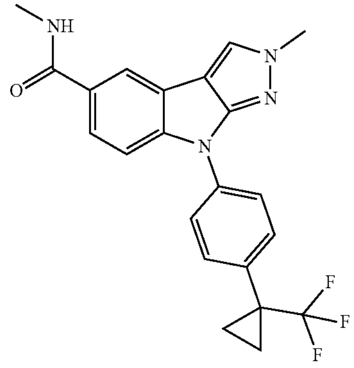 [SMILES: CNC(=O)c1ccc2c(c1)c1cn(C)nc1n2-c1ccc(C2(C(F)(F)F)CC2)cc1] N,2-dimethyl-8-{4-[1-(trifluoromethyl)-cyclopropyl]phenyl}-2H,8H-pyrazolo[3,4-b]indole-5-carboxamide |

-continued

| Compound No. | Structure and Name |
|---|---|
| 371 | 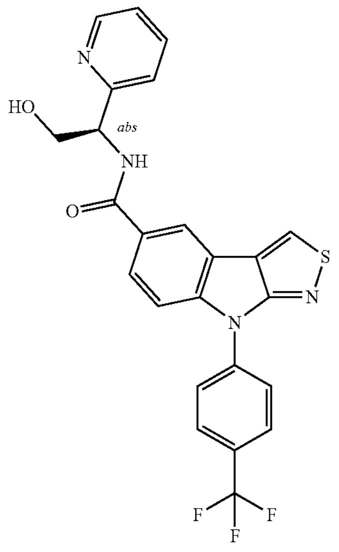 [SMILES: O=C(N[C@@H](CO)c1ccccn1)c1ccc2c(c1)c1csnc1n2-c1ccc(C(F)(F)F)cc1] Absolute configuration assgined/known N-[(1R)-2-hydroxy-1-(pyridin-2-yl)ethyl]-8-[4-(trifluoromethyl)phenyl]-8H-[1,2]thiazolo[3,4-b]indole-5-carboxamide |
| 372 | 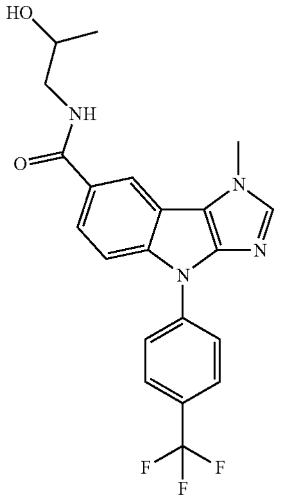 [SMILES: CC(O)CNC(=O)c1ccc2c(c1)c1c(ncn1C)n2-c1ccc(C(F)(F)F)cc1] N-(2-hydroxypropyl)-1-methyl-4-[4-(trifluoromethyl)phenyl]-1H,4H-imidazo[4,5-b]indole-7-carboxamide |

-continued

| Compound No. | Structure and Name |
|---|---|
| 373 | 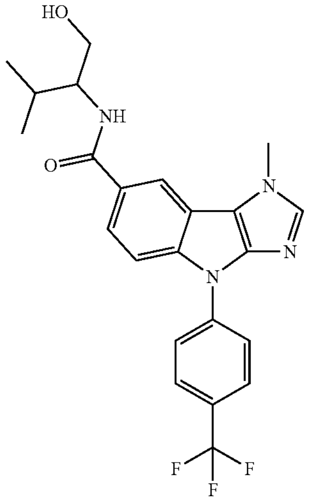 [SMILES: CC(C)C(CO)NC(=O)c1ccc2c(c1)c1c(ncn1C)n2-c1ccc(C(F)(F)F)cc1] N-(1-hydroxy-3-methylbutan-2-yl)-1-methyl-4-[4-(trifluoromethyl)phenyl]-1H,4H-imidazo[4,5-b]indole-7-carboxamide |
| 374 | 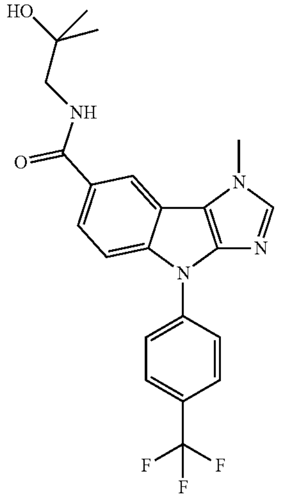 [SMILES: Cn1cnc2c1c1cc(C(=O)NCC(C)(C)O)ccc1n2-c1ccc(C(F)(F)F)cc1] N-(2-hydroxy-2-methylpropyl)-1-methyl-4-[4-(trifluoromethyl)phenyl]-1H,4H-imidazo[4,5-b]indole-7-carboxamide |
| 375 | 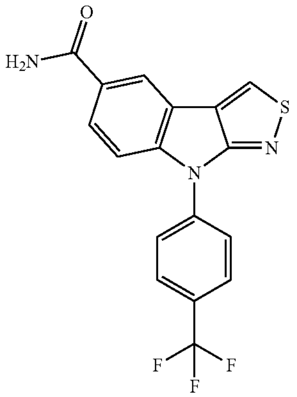 [SMILES: NC(=O)c1ccc2c(c1)c1csnc1n2-c1ccc(C(F)(F)F)cc1] |

-continued

| Compound No. | Structure and Name |
|---|---|
| | 8-[4-(trifluoromethyl)phenyl]-8H-[1,2]thiazolo[3,4-b]indole-5-carboxamide |
| 376 | 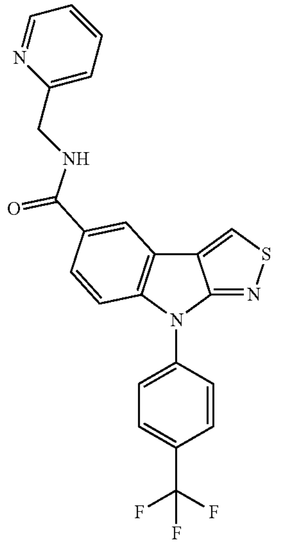 [SMILES: O=C(NCc1ccccn1)c1ccc2c(c1)c1csnc1n2-c1ccc(C(F)(F)F)cc1] N-[(pyridin-2-yl)methyl]-8-[4-(trifluoromethyl)phenyl]-8H-[1,2]thiazolo[3,4-b]indole-5-carboxamide |
| 377 | 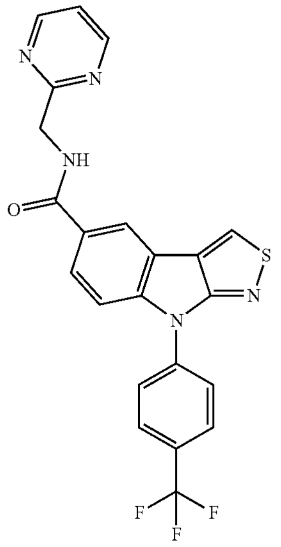 [SMILES: O=C(NCc1ncccn1)c1ccc2c(c1)c1csnc1n2-c1ccc(C(F)(F)F)cc1] N-[(pyrimidin-2-yl)methyl]-8-[4-(trifluoromethyl)phenyl]-8H-[1,2]thiazolo[3,4-b]indole-5-carboxamide |

| Compound No. | Structure and Name |
|---|---|
| 378 | 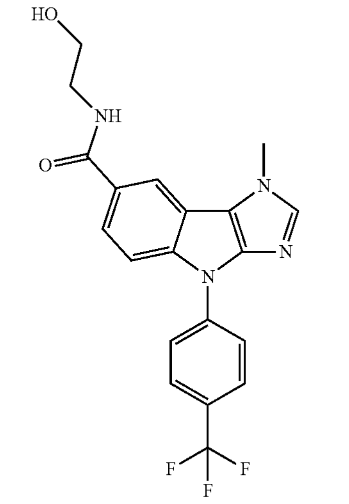 [SMILES: Cn1cnc2c1c1cc(C(=O)NCCO)ccc1n2-c1ccc(C(F)(F)F)cc1] N-(2-hydroxyethyl)-1-methyl-4-[4-(trifluoromethyl)phenyl]-1H,4H-imidazo[4,5-b]indole-7-carboxamide |
| 379 | 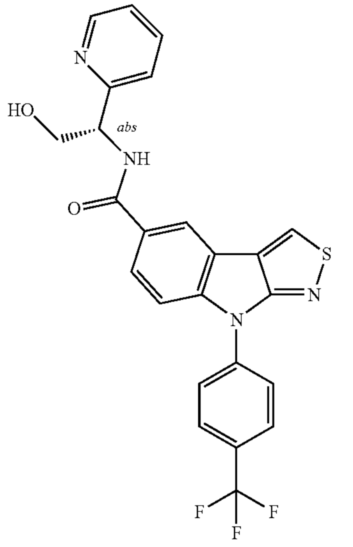 [SMILES: O=C(N[C@H](CO)c1ccccn1)c1ccc2c(c1)c1csnc1n2-c1ccc(C(F)(F)F)cc1] Absolute configuration known/assigned N-[(1S)-2-hydroxy-1-(pyridin-2-yl)ethyl]-8-[4-(trifluoromethyl)phenyl]-8H-[1,2]thiazolo[3,4-b]indole-5-carboxamide |

| Compound No. | Structure and Name |
|---|---|
| 380 | 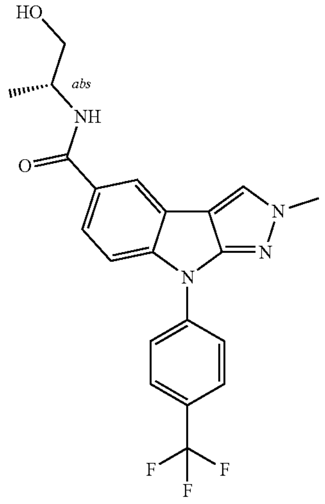 [SMILES: C[C@H](CO)NC(=O)c1ccc2c(c1)c1cn(C)nc1n2-c1ccc(C(F)(F)F)cc1] Absolute configuration known/assigned N-[(2R)-1-hydroxypropan-2-yl]-2-methyl-8-[4-(trifluoromethyl)phenyl]-2H,8H-pyrazolo[3,4-b]indole-5-carboxamide |
| 381 | 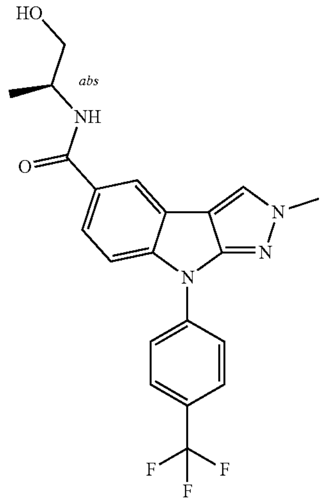 [SMILES: C[C@@H](CO)NC(=O)c1ccc2c(c1)c1cn(C)nc1n2-c1ccc(C(F)(F)F)cc1] Absolute configuration known/assigned N-[(2S)-1-hydroxypropan-2-yl]-2-methyl-8-[4-(trifluoromethyl)phenyl]-2H,8H-pyrazolo[3,4-b]indole-5-carboxamide |

-continued

| Compound No. | Structure and Name |
|---|---|
| 382 | 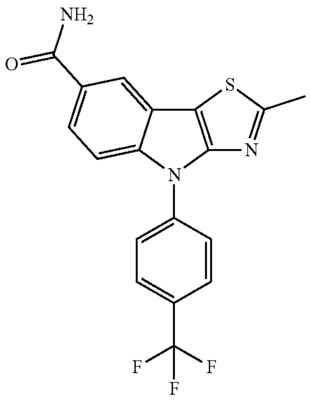<br>2-methyl-4-[4-(trifluoromethyl)phenyl]-4H-[1,3]thiazolo[4,5-b]indole-7-carboxamide |
| 383 | 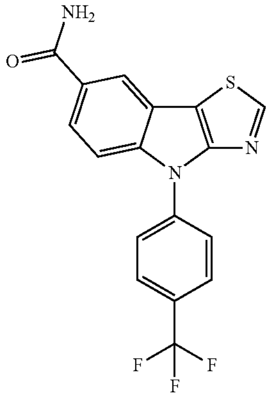 [SMILES: NC(=O)c1ccc2c(c1)c1scnc1n2-c1ccc(C(F)(F)F)cc1]<br>4-[4-(trifluoromethyl)phenyl]-4H-[1,3]thiazolo[4,5-b]indole-7-carboxamide |
| 384 | 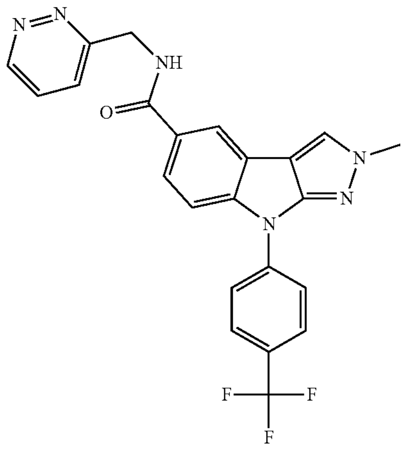 [SMILES: Cn1cc2c3cc(C(=O)NCc4cccnn4)ccc3n(-c3ccc(C(F)(F)F)cc3)c2n1]<br>2-methyl-N-[(pyridazin-3-yl)methyl]-8-[4-(trifluoromethyl)phenyl]-2H,8H-pyrazolo[3,4-b]indole-5-carboxamide |
| 385 | 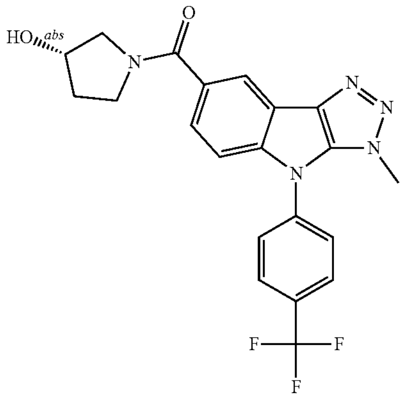 [SMILES: Cn1nnc2c3cc(C(=O)N4CC[C@H](O)C4)ccc3n(-c3ccc(C(F)(F)F)cc3)c21]<br>Absolute configuration known/assigned<br>(3S)-1-{3-methyl-4-[4-(trifluoromethyl)phenyl]-3H,4H-[1,2,3]triazolo[4,5-b]indole-7-carbonyl}pyrrolidin-3-ol |
| 386 | 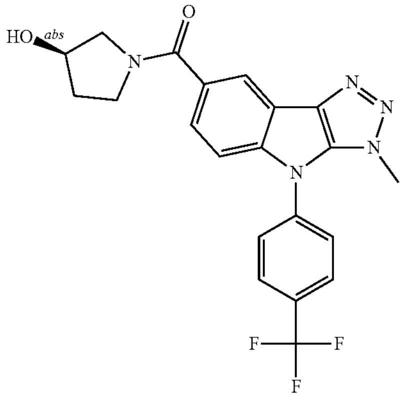 [SMILES: Cn1nnc2c3cc(C(=O)N4CC[C@@H](O)C4)ccc3n(-c3ccc(C(F)(F)F)cc3)c21]<br>Absolute configuration known/assigned<br>(3R)-1-{3-methyl-4-[4-(trifluoromethyl)phenyl]-3H,4H-[1,2,3]triazolo[4,5-b]indole-7-carbonyl}pyrrolidin-3-ol |
| 387 | 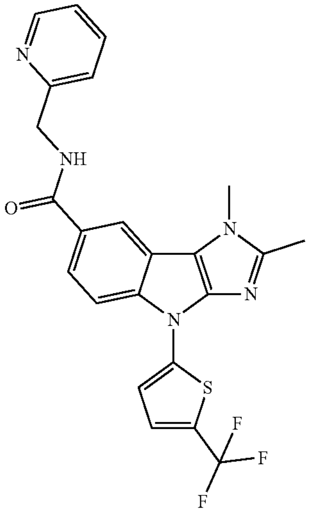 [SMILES: Cc1nc2c(c3cc(C(=O)NCc4ccccn4)ccc3n2-c2ccc(C(F)(F)F)s2)n1C]<br>1,2-dimethyl-N-[(pyridin-2-yl)methyl]-4-[5-(trifluoromethyl)thiophen-2-yl]-1H,4H-imidazo[4,5-b]indole-7-carboxamide |

-continued

| Compound No. | Structure and Name |
|---|---|
| 388 | 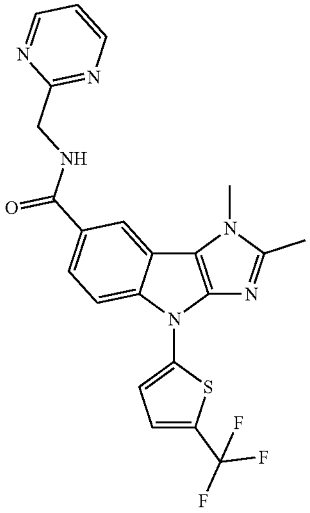 [SMILES: Cc1nc2c(c3cc(C(=O)NCc4ncccn4)ccc3n2-c2ccc(C(F)(F)F)s2)n1C]<br>1,2-dimethyl-N-[(pyrimidin-2-yl)methyl]-4-[5-(trifluoromethyl)thiophen-2-yl]-1H,4H-imidazo[4,5-b]indole-7-carboxamide |
| 389 | 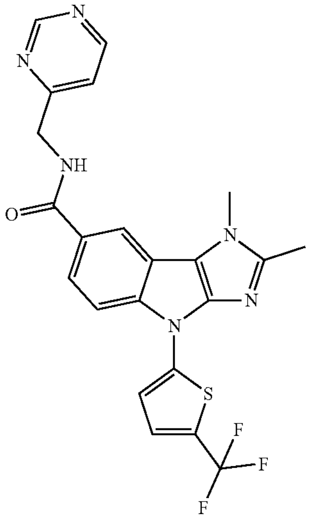 [SMILES: Cc1nc2c(c3cc(C(=O)NCc4ccncn4)ccc3n2-c2ccc(C(F)(F)F)s2)n1C]<br>1,2-dimethyl-N-[(pyrimidin-4-yl)methyl]-4-[5-(trifluoromethyl)thiophen-2-yl]-1H,4H-imidazo[4,5-b]indole-7-carboxamide |

-continued

| Compound No. | Structure and Name |
|---|---|
| 390 | 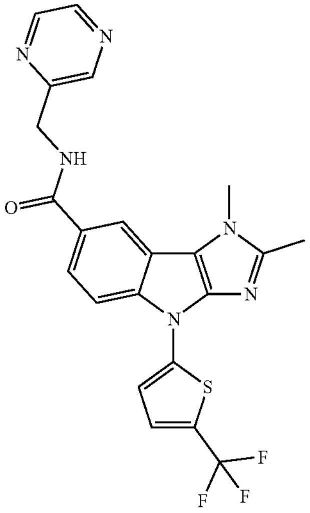 [SMILES: Cc1nc2c(c3cc(C(=O)NCc4cnccn4)ccc3n2-c2ccc(C(F)(F)F)s2)n1C]<br>1,2-dimethyl-N-[(pyrazin-2-yl)methyl]-4-[5-(trifluoromethyl)thiophen-2-yl]-1H,4H-imidazo[4,5-b]indole-7-carboxamide |
| 391 | 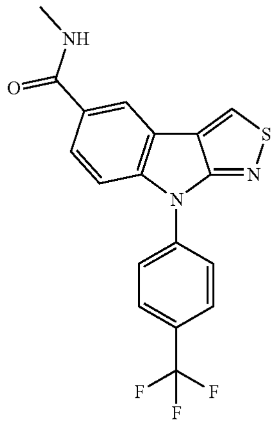 [SMILES: CNC(=O)c1ccc2c(c1)c1csnc1n2-c1ccc(C(F)(F)F)cc1]<br>N-methyl-8-[4-(trifluoromethyl)phenyl]-8H-[1,2]thiazolo[3,4-b]indole-5-carboxamide |
| 392 | 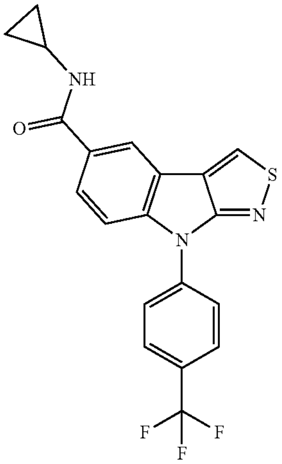 [SMILES: O=C(NC1CC1)c1ccc2c(c1)c1csnc1n2-c1ccc(C(F)(F)F)cc1] |

| Compound No. | Structure and Name |
| --- | --- |
| | N-cyclopropyl-8-[4-(trifluoromethyl)phenyl]-8H-[1,2]thiazolo[3,4-b]indole-5-carboxamide |
| 393 | 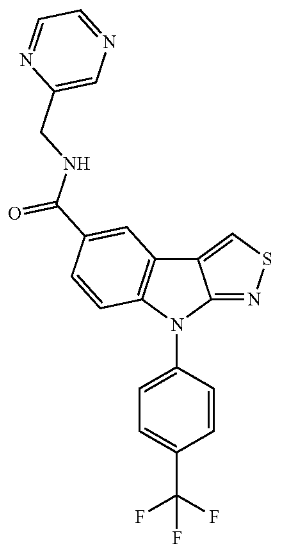 [SMILES: O=C(NCc1cnccn1)c1ccc2c(c1)c1csnc1n2-c1ccc(C(F)(F)F)cc1] N-[(pyrazin-2-yl)methyl]-8-[4-(trifluoromethyl)phenyl]-8H-[1,2]thiazolo[3,4-b]indole-5-carboxamide |
| 394 | 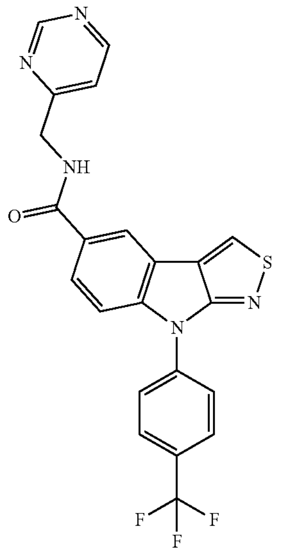 [SMILES: O=C(NCc1ccncn1)c1ccc2c(c1)c1csnc1n2-c1ccc(C(F)(F)F)cc1] N-[(pyrimidin-4-yl)methyl]-8-[4-(trifluoromethyl)phenyl]-8H-[1,2]thiazolo[3,4-b]indole-5-carboxamide |

| Compound No. | Structure and Name |
| --- | --- |
| 395 | 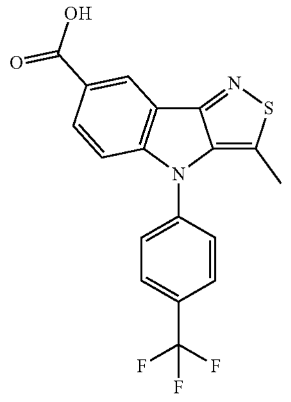 [SMILES: Cc1snc2c3cc(C(=O)O)ccc3n(-c3ccc(C(F)(F)F)cc3)c12] 3-methyl-4-[4-(trifluoromethyl)phenyl]-4H-[1,2]thiazolo[4,3-b]indole-7-carboxylic acid |
| 396 | 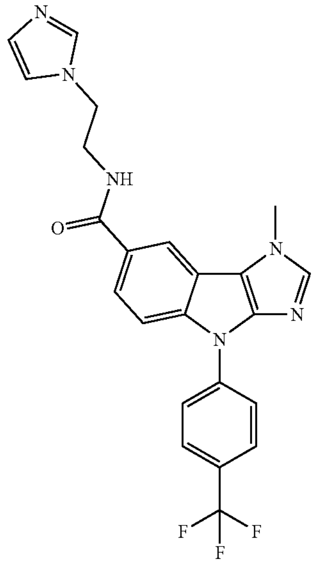 [SMILES: Cn1cnc2c1c1cc(C(=O)NCCn3ccnc3)ccc1n2-c1ccc(C(F)(F)F)cc1] N-[2-(1H-imidazol-1-yl)ethyl]-1-methyl-4-[4-(trifluoromethyl)phenyl]-1H,4H-imidazo[4,5-b]indole-7-carboxamide |

| Compound No. | Structure and Name |
|---|---|
| 397 | 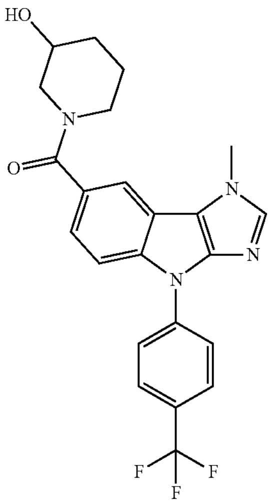 [SMILES: Cn1cnc2c1c1cc(C(=O)N3CCCC(O)C3)ccc1n2-c1ccc(C(F)(F)F)cc1] 1-{1-methyl-4-[4-(trifluoromethyl)phenyl]-1H,4H-imidazo[4,5-b]indole-7-carbonyl}piperidin-3-ol |
| 398 | 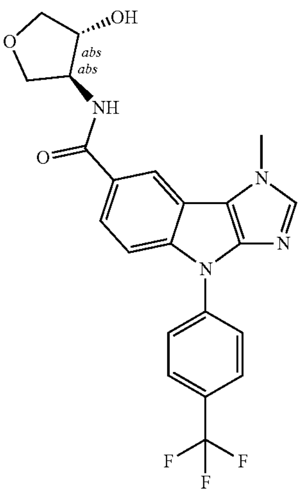 [SMILES: Cn1cnc2c1c1cc(C(=O)N[C@H]3COC[C@@H]3O)ccc1n2-c1ccc(C(F)(F)F)cc1] Absolute configuration known/assigned N-[(3S,4R)-4-hydroxyoxolan-3-yl]-1-methyl-4-[4-(trifluoromethyl)phenyl]-1H,4H-imidazo[4,5-b]indole-7-carboxamide |

| Compound No. | Structure and Name |
|---|---|
| 399 | 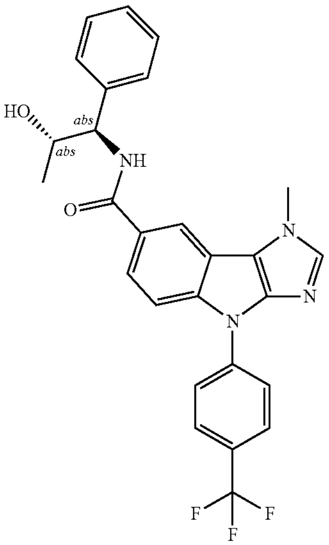 [SMILES: C[C@H](O)[C@H](NC(=O)c1ccc2c(c1)c1c(ncn1C)n2-c1ccc(C(F)(F)F)cc1)c1ccccc1] Absolute configuration known/assigned N-[(1R,2S)-2-hydroxy-1-phenylpropyl]-1-methyl-4-[4-(trifluoromethyl)phenyl]-1H,4H-imidazo[4,5-b]indole-7-carboxamide |
| 400 | 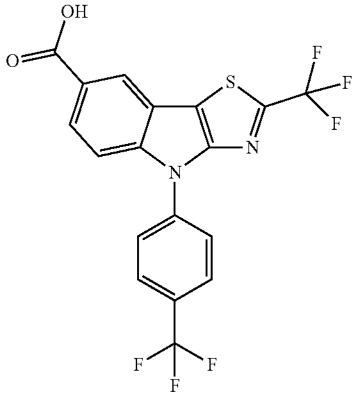 [SMILES: O=C(O)c1ccc2c(c1)c1sc(C(F)(F)F)nc1n2-c1ccc(C(F)(F)F)cc1] 2-(trifluoromethyl)-4-[4-(trifluoromethyl)phenyl]-4H-[1,3]thiazolo[4,5-b]indole-7-carboxylic acid |
| 401 | 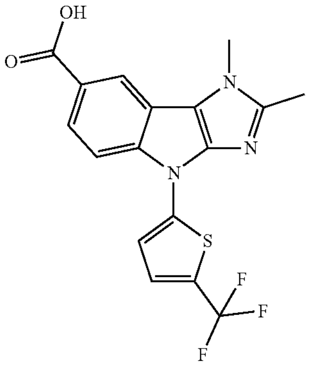 [SMILES: Cc1nc2c(c3cc(C(=O)O)ccc3n2-c2ccc(C(F)(F)F)s2)n1C] 1,2-dimethyl-4-[5-(trifluoromethyl)thiophen-2-yl]-1H,4H-imidazo[4,5-b]indole-7-carboxylic acid |

-continued

| Compound No. | Structure and Name |
|---|---|
| 402 | 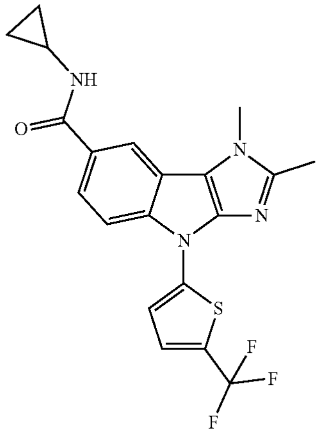 [SMILES: Cc1nc2c(c3cc(C(=O)NC4CC4)ccc3n2-c2ccc(C(F)(F)F)s2)n1C]<br>N-cyclopropyl-1,2-dimethyl-4-[5-(trifluoromethyl)thiophen-2-yl]-1H,4H-imidazo[4,5-b]indole-7-carboxamide |
| 403 | 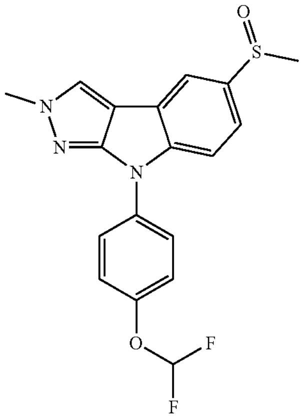<br>8-[4-(difluoromethoxy)phenyl]-5-methanesulfinyl-2-methyl-2H,8H-pyrazolo[3,4-b]indole |
| 404 | 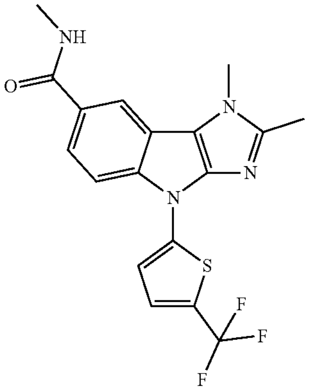 [SMILES: CNC(=O)c1ccc2c(c1)c1c(nc(C)n1C)n2-c1ccc(C(F)(F)F)s1]<br>N,1,2-trimethyl-4-[5-(trifluoromethyl)thiophen-2-yl]-1H,4H-imidazo[4,5-b]indole-7-carboxamide |

-continued

| Compound No. | Structure and Name |
|---|---|
| 405 | 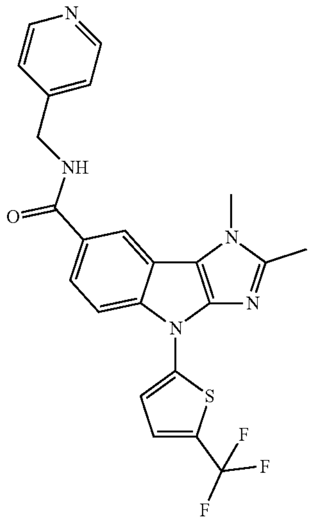 [SMILES: Cc1nc2c(c3cc(C(=O)NCc4ccncc4)ccc3n2-c2ccc(C(F)(F)F)s2)n1C]<br>1,2-dimethyl-N-[(pyridin-4-yl)methyl]-4-[5-(trifluoromethyl)thiophen-2-yl]-1H,4H-imidazo[4,5-b]indole-7-carboxamide |
| 406 | 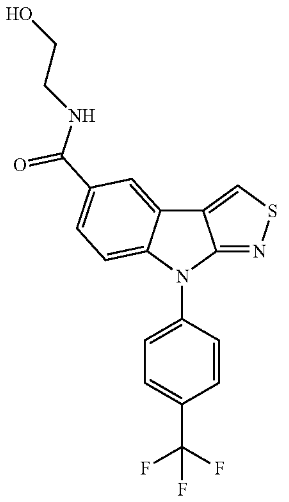 [SMILES: O=C(NCCO)c1ccc2c(c1)c1csnc1n2-c1ccc(C(F)(F)F)cc1]<br>N-(2-hydroxyethyl)-8-[4-(trifluoromethyl)phenyl]-8H-[1,2]thiazolo[3,4-b]indole-5-carboxamide |

| Compound No. | Structure and Name |
|---|---|
| 407 | 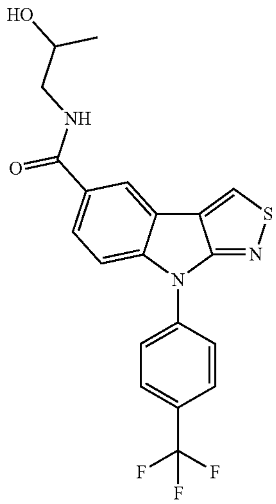 [SMILES: CC(O)CNC(=O)c1ccc2c(c1)c1csnc1n2-c1ccc(C(F)(F)F)cc1] N-(2-hydroxypropyl)-8-[4-(trifluoromethyl)phenyl]-8H-[1,2]thiazolo[3,4-b]indole-5-carboxamide |
| 408 | 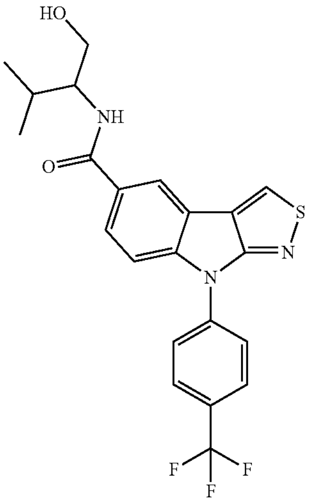 [SMILES: CC(C)C(CO)NC(=O)c1ccc2c(c1)c1csnc1n2-c1ccc(C(F)(F)F)cc1] N-(1-hydroxy-3-methylbutan-2-yl)-8-[4-(trifluoromethyl)phenyl]-8H-[1,2]thiazolo[3,4-b]indole-5-carboxamide |

| Compound No. | Structure and Name |
|---|---|
| 409 | 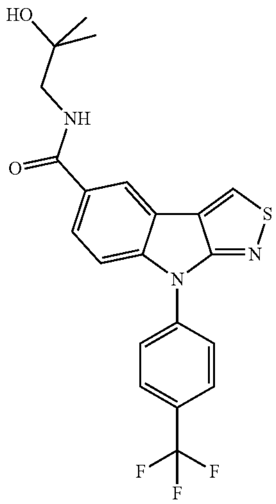 [SMILES: CC(C)(O)CNC(=O)c1ccc2c(c1)c1csnc1n2-c1ccc(C(F)(F)F)cc1] N-(2-hydroxy-2-methylpropyl)-8-[4-(trifluoromethyl)phenyl]-8H-[1,2]thiazolo[3,4-b]indole-5-carboxamide |
| 410 | 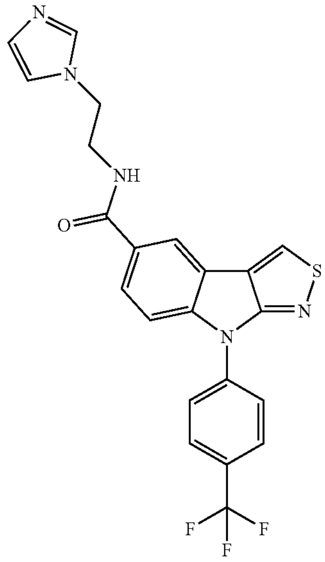 [SMILES: O=C(NCCn1ccnc1)c1ccc2c(c1)c1csnc1n2-c1ccc(C(F)(F)F)cc1] N-[2-(1H-imidazol-1-yl)ethyl]-8-[4-(trifluoromethyl)phenyl]-8H-[1,2]thiazolo[3,4-b]indole-5-carboxamide |

-continued

| Compound No. | Structure and Name |
|---|---|
| 411 | 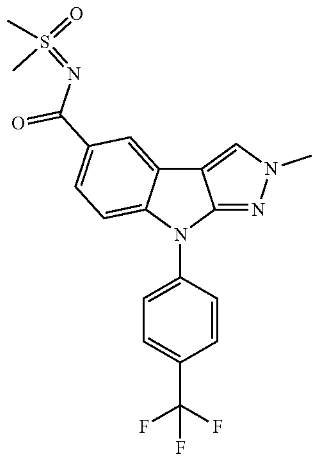 N-[dimethyl(oxo)-$\lambda^6$-sulfanylidene]-2-methyl-8-[4-(trifluoromethyl)phenyl]-2H,8H-pyrazolo[3,4-b]indole-5-carboxamide |
| 412 | 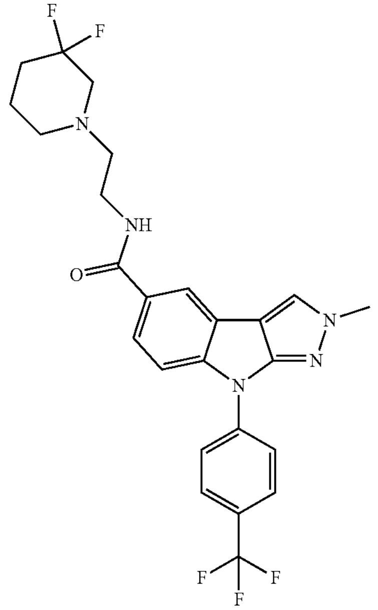 [SMILES: Cn1cc2c3cc(C(=O)NCCN4CCCC(F)(F)C4)ccc3n(-c3ccc(C(F)(F)F)cc3)c2n1] N-[2-(3,3-difluoropiperidin-1-yl)ethyl]-2-methyl-8-[4-(trifluoromethyl)phenyl]-2H,8H-pyrazolo[3,4-b]indole-5-carboxamide |

-continued

| Compound No. | Structure and Name |
|---|---|
| 413 | 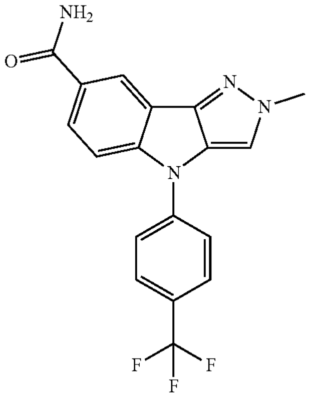 [SMILES: Cn1cc2c(n1)c1cc(C(N)=O)ccc1n2-c1ccc(C(F)(F)F)cc1] 2-methyl-4-[4-(trifluoromethyl)phenyl]-2H,4H-pyrazolo[4,3-b]indole-7-carboxamide |
| 414 | 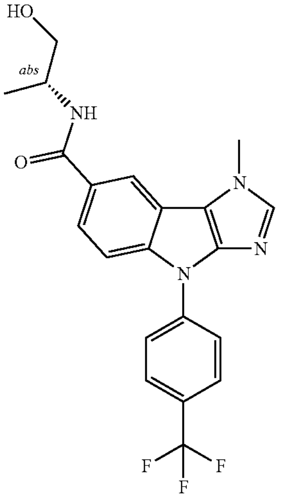 [SMILES: C[C@H](CO)NC(=O)c1ccc2c(c1)c1c(ncn1C)n2-c1ccc(C(F)(F)F)cc1] Absolute configuration assigned/known N-[(2R)-1-hydroxypropan-2-yl]-1-methyl-4-[4-(trifluoromethyl)phenyl]-1H,4H-imidazo[4,5-b]indole-7-carboxamide |
| 415 | 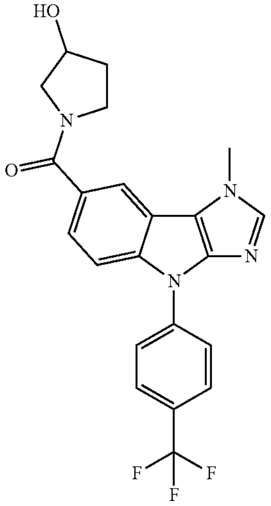 [SMILES: Cn1cnc2c1c1cc(C(=O)N3CCC(O)C3)ccc1n2-c1ccc(C(F)(F)F)cc1] |

-continued

| Compound No. | Structure and Name |
|---|---|
| | 1-{1-methyl-4-[4-(trifluoromethyl)phenyl]-1H,4H-imidazo[4,5-b]indole-7-carbonyl}pyrrolidin-3-ol |
| 416 | 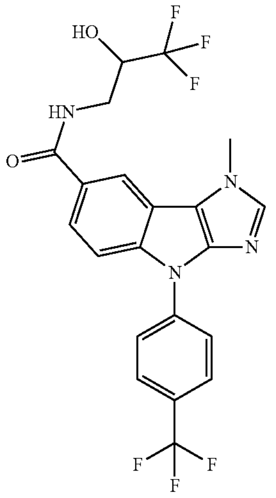 [SMILES: Cn1cnc2c1c1cc(C(=O)NCC(O)C(F)(F)F)ccc1n2-c1ccc(C(F)(F)F)cc1] 1-methyl-N-(3,3,3-trifluoro-2-hydroxypropyl)-4-[4-(trifluoromethyl)phenyl]-1H,4H-imidazo[4,5-b]indole-7-carboxamide |
| 417 | 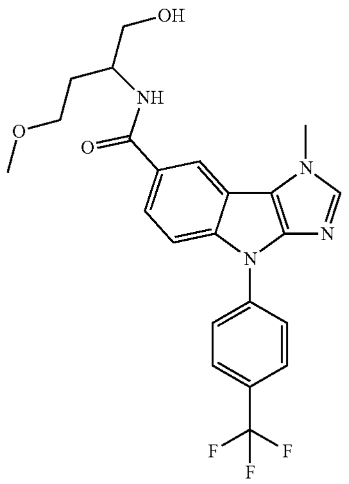 [SMILES: COCCC(CO)NC(=O)c1ccc2c(c1)c1c(ncn1C)n2-c1ccc(C(F)(F)F)cc1] N-(1-hydroxy-4-methoxybutan-2-yl)-1-methyl-4-[4-(trifluoromethyl)phenyl]-1H,4H-imidazo[4,5-b]indole-7-carboxamide |

-continued

| Compound No. | Structure and Name |
|---|---|
| 418 | 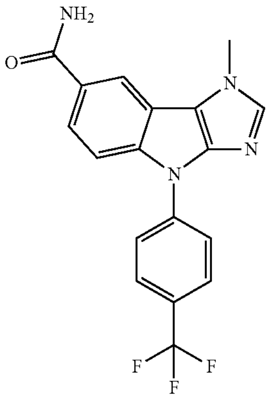 [SMILES: Cn1cnc2c1c1cc(C(N)=O)ccc1n2-c1ccc(C(F)(F)F)cc1] 1-methyl-4-[4-(trifluoromethyl)phenyl]-1H,4H-imidazo[4,5-b]indole-7-carboxamide |
| 419 | 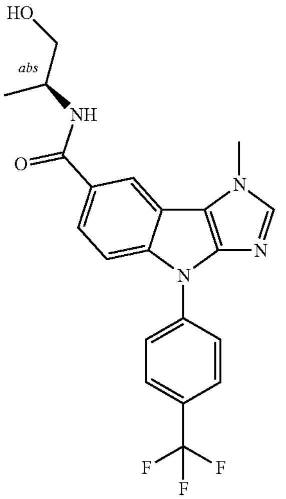 [SMILES: C[C@@H](CO)NC(=O)c1ccc2c(c1)c1c(ncn1C)n2-c1ccc(C(F)(F)F)cc1] Absolute configuration known/assigned N-[(2S)-1-hydroxypropan-2-yl]-1-methyl-4-[4-(trifluoromethyl)phenyl]-1H,4H-imidazo[4,5-b]indole-7-carboxamide |
| 420 | 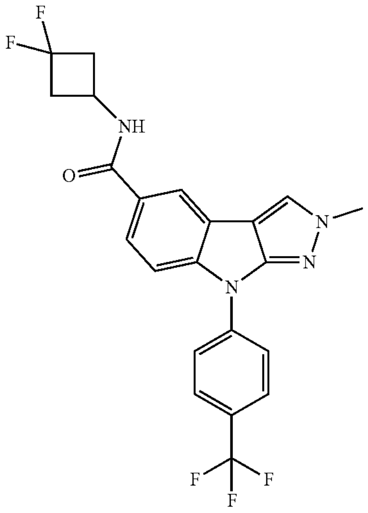 [SMILES: Cn1cc2c3cc(C(=O)NC4CC(F)(F)C4)ccc3n(-c3ccc(C(F)(F)F)cc3)c2n1] |

| Compound No. | Structure and Name |
|---|---|
| | N-(3,3-difluorocyclobutyl)-2-methyl-8-[4-(trifluoromethyl)phenyl]-2H,8H-pyrazolo[3,4-b]indole-5-carboxamide |
| 421 | 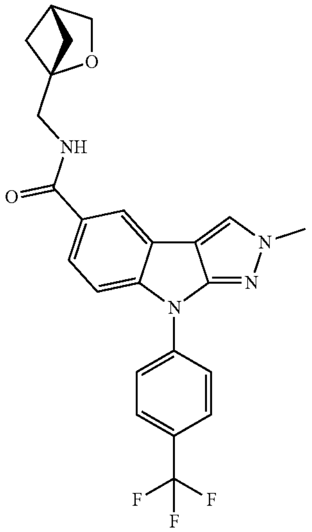 [SMILES: Cn1cc2c3cc(C(=O)NC[C@]45C[C@H](CO4)C5)ccc3n(-c3ccc(C(F)(F)F)cc3)c2n1] 2-methyl-N-({2-oxabicyclo[2.1.1]hexan-1-yl}methyl)-8-[4-(trifluoromethyl)phenyl]-2H,8H-pyrazolo[3,4-b]indole-5-carboxamide |
| 422 | 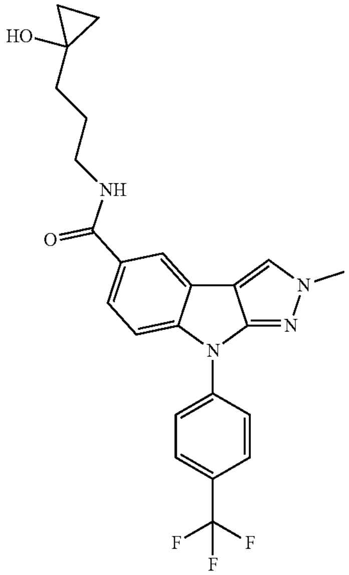 [SMILES: Cn1cc2c3cc(C(=O)NCCCC4(O)CC4)ccc3n(-c3ccc(C(F)(F)F)cc3)c2n1] N-[3-(1-hydroxycyclopropyl)propyl]-2-methyl-8-[4-(trifluoromethyl)phenyl]-2H,8H-pyrazolo[3,4-b]indole-5-carboxamide |

| Compound No. | Structure and Name |
|---|---|
| 423 | 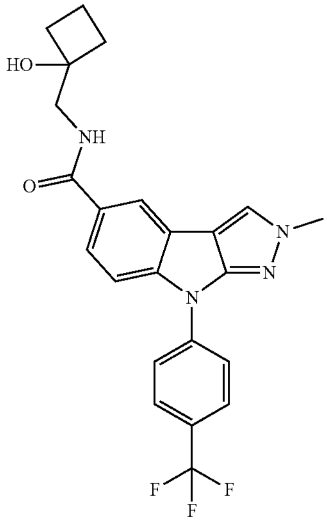 [SMILES: Cn1cc2c3cc(C(=O)NCC4(O)CCC4)ccc3n(-c3ccc(C(F)(F)F)cc3)c2n1] N-[(1-hydroxycyclobutyl)methyl]-2-methyl-8-[4-(trifluoromethyl)phenyl]-2H,8H-pyrazolo[3,4-b]indole-5-carboxamide |
| 424 | 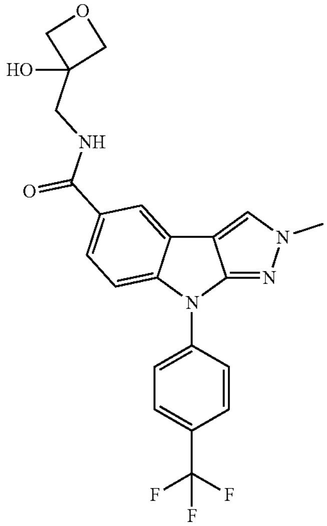 [SMILES: Cn1cc2c3cc(C(=O)NCC4(O)COC4)ccc3n(-c3ccc(C(F)(F)F)cc3)c2n1] N-[(3-hydroxyoxetan-3-yl)methyl]-2-methyl-8-[4-(trifluoromethyl)phenyl]-2H,8H-pyrazolo[3,4-b]indole-5-carboxamide |

| Compound No. | Structure and Name |
|---|---|
| 425 | 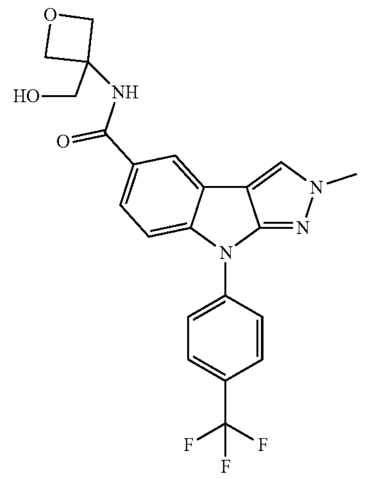 [SMILES: Cn1cc2c3cc(C(=O)NC4(CO)COC4)ccc3n(-c3ccc(C(F)(F)F)cc3)c2n1] N-[3-(hydroxymethyl)oxetan-3-yl]-2-methyl-8-[4-(trifluoromethyl)phenyl]-2H,8H-pyrazolo[3,4-b]indole-5-carboxamide |
| 426 | 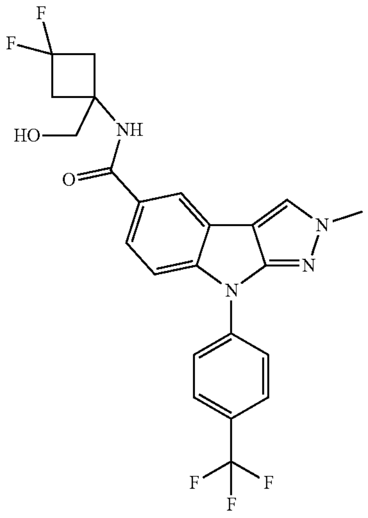 [SMILES: Cn1cc2c3cc(C(=O)NC4(CO)CC(F)(F)C4)ccc3n(-c3ccc(C(F)(F)F)cc3)c2n1] N-[3,3-difluoro-1-(hydroxymethyl)cyclobutyl]-2-methyl-8-[4-(trifluoromethyl)phenyl]-2H,8H-pyrazolo[3,4-b]indole-5-carboxamide |
| 427 | 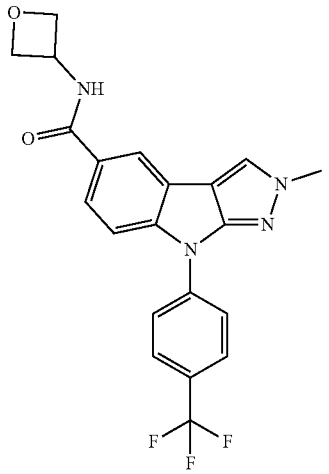 [SMILES: Cn1cc2c3cc(C(=O)NC4COC4)ccc3n(-c3ccc(C(F)(F)F)cc3)c2n1] 2-methyl-N-(oxetan-3-yl)-8-[4-(trifluoromethyl)phenyl]-2H,8H-pyrazolo[3,4-b]indole-5-carboxamide |
| 428 | 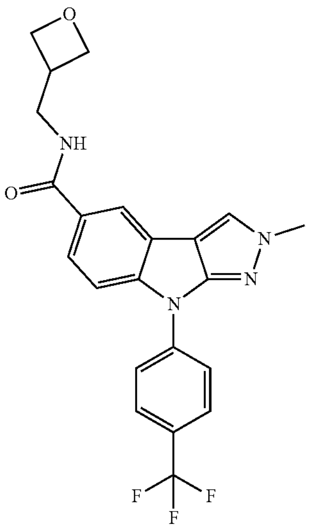 [SMILES: Cn1cc2c3cc(C(=O)NCC4COC4)ccc3n(-c3ccc(C(F)(F)F)cc3)c2n1] 2-methyl-N-[(oxetan-3-yl)methyl]-8-[4-(trifluoromethyl)phenyl]-2H,8H-pyrazolo[3,4-b]indole-5-carboxamide |
| 429 | 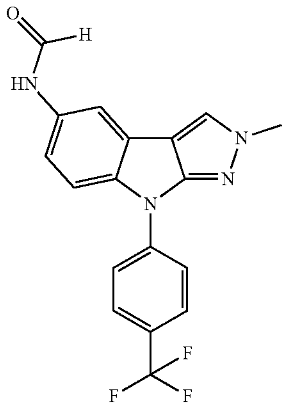 [SMILES: Cn1cc2c3cc(NC=O)ccc3n(-c3ccc(C(F)(F)F)cc3)c2n1] |

-continued

| Compound No. | Structure and Name |
|---|---|
| | N-{2-methyl-8-[4-(trifluoromethyl)phenyl]-2H,8H-pyrazolo[3,4-b]indol-5-yl}formamide |
| 430 | 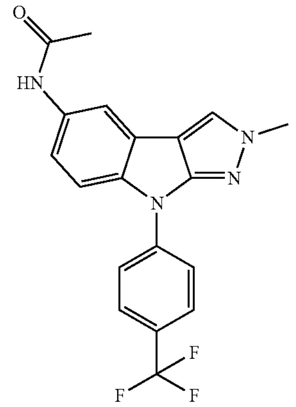 [SMILES: CC(=O)Nc1ccc2c(c1)c1cn(C)nc1n2-c1ccc(C(F)(F)F)cc1] N-{2-methyl-8-[4-(trifluoromethyl)phenyl]-2H,8H-pyrazolo[3,4-b]indol-5-yl}acetamide |
| 431 | 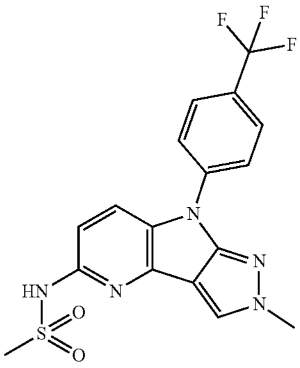 N-{4-methyl-7-[4-(trifluoromethyl)phenyl]-4,5,7,12-tetraazatricyclo[6.4.0.0$^{2,6}$]dodeca-1(8),2,5,9,11-pentaen-11-yl}methanesulfonamide |
| 432 | 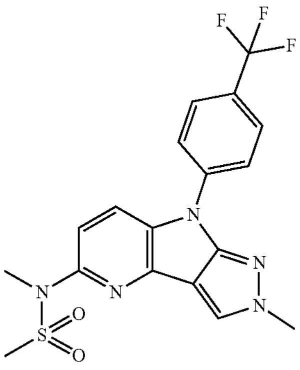 N-methyl-N-{4-methyl-7-[4-(trifluoromethyl)phenyl]-4,5,7,12-tetraazatricyclo[6.4.0.0$^{2,6}$]dodeca-1(8),2,5,9,11-pentaen-11-yl}methanesulfonamide |

-continued

| Compound No. | Structure and Name |
|---|---|
| 433 | 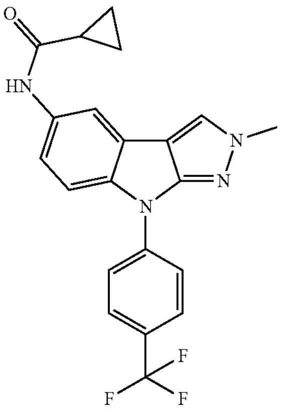 [SMILES: Cn1cc2c3cc(NC(=O)C4CC4)ccc3n(-c3ccc(C(F)(F)F)cc3)c2n1] N-{2-methyl-8-[4-(trifluoromethyl)phenyl]-2H,8H-pyrazolo[3,4-b]indol-5-yl}cyclopropanecarboxamide |
| 434 | 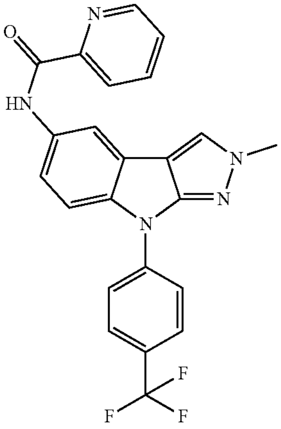 [SMILES: Cn1cc2c3cc(NC(=O)c4ccccn4)ccc3n(-c3ccc(C(F)(F)F)cc3)c2n1] N-{2-methyl-8-[4-(trifluoromethyl)phenyl]-2H,8H-pyrazolo[3,4-b]indol-5-yl}pyridine-2-carboxamide |
| 435 | 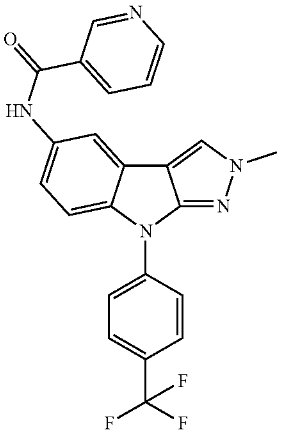 [SMILES: Cn1cc2c3cc(NC(=O)c4cccnc4)ccc3n(-c3ccc(C(F)(F)F)cc3)c2n1] N-{2-methyl-8-[4-(trifluoromethyl)phenyl]-2H,8H-pyrazolo[3,4-b]indol-5-yl}pyridine-3-carboxamide |

-continued

| Compound No. | Structure and Name |
|---|---|
| 436 | 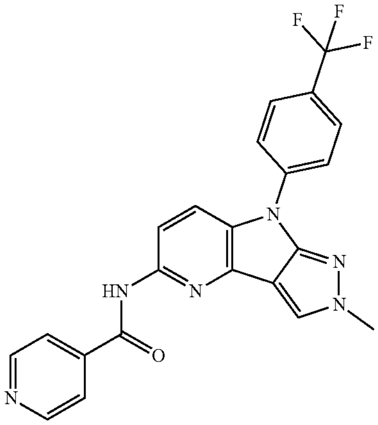 [SMILES: Cn1cc2c3nc(NC(=O)c4ccncc4)ccc3n(-c3ccc(C(F)(F)F)cc3)c2n1] N-{4-methyl-7-[4-(trifluoromethyl)phenyl]-4,5,7,12-tetraazatricyclo[6.4.0.0$^{2,6}$]dodeca-1(8),2,5,9,11-pentaen-11-yl}pyridine-4-carboxamide |
| 437 | 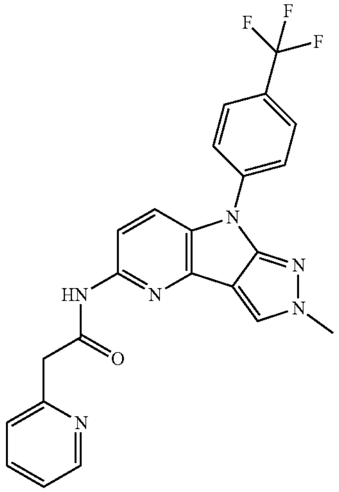 [SMILES: Cn1cc2c3nc(NC(=O)Cc4ccccn4)ccc3n(-c3ccc(C(F)(F)F)cc3)c2n1] N-{4-methyl-7-[4-(trifluoromethyl)phenyl]-4,5,7,12-tetraazatricyclo[6.4.0.0$^{2,6}$]dodeca-1(8),2,5,9,11-pentaen-11-yl}-2-(pyridin-2-yl)acetamide |
| 438 | 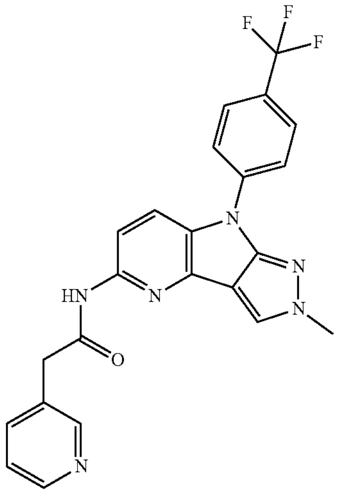 [SMILES: Cn1cc2c3nc(NC(=O)Cc4cccnc4)ccc3n(-c3ccc(C(F)(F)F)cc3)c2n1] N-{4-methyl-7-[4-(trifluoromethyl)phenyl]-4,5,7,12-tetraazatricyclo[6.4.0.0$^{2,6}$]dodeca-1(8),2,5,9,11-pentaen-11-yl}-2-(pyridin-3-yl)acetamide |
| 439 | 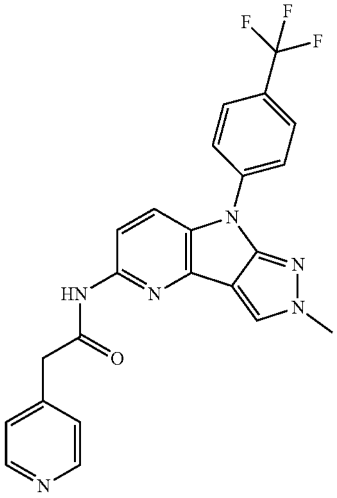 [SMILES: Cn1cc2c3nc(NC(=O)Cc4ccncc4)ccc3n(-c3ccc(C(F)(F)F)cc3)c2n1] N-{4-methyl-7-[4-(trifluoromethyl)phenyl]-4,5,7,12-tetraazatricyclo[6.4.0.0$^{2,6}$]dodeca-1(8),2,5,9,11-pentaen-11-yl}-2-(pyridin-4-yl)acetamide |
| 440 | 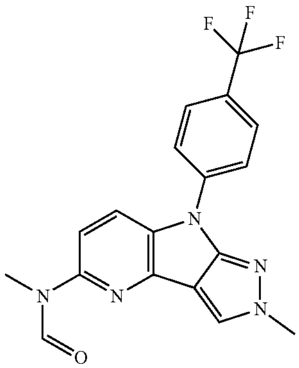 N-methyl-N-{4-methyl-7-[4-(trifluoromethyl)phenyl]-4,5,7,12-tetraazatricyclo[6.4.0.0$^{2,6}$]dodeca-1(8),2,5,9,11-pentaen-11-yl}formamide |
| 441 | 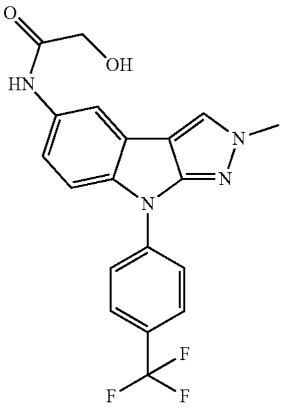 [SMILES: Cn1cc2c3cc(NC(=O)CO)ccc3n(-c3ccc(C(F)(F)F)cc3)c2n1] |

-continued

| Compound No. | Structure and Name |
|---|---|
| | 2-hydroxy-N-{2-methyl-8-[4-(trifluoromethyl)phenyl]-2H,8H-pyrazolo[3,4-b]indol-5-yl}acetamide |
| 442 | 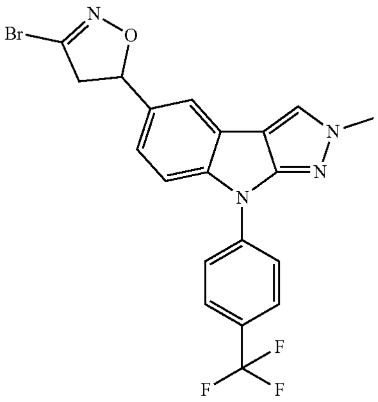 [SMILES: Cn1cc2c3cc(C4CC(Cl)=NO4)ccc3n(-c3ccc(C(F)(F)F)cc3)c2n1] 3-bromo-5-{2-methyl-8-[4-(trifluoromethyl)phenyl]-2H,8H-pyrazolo[3,4-b]indol-5-yl}-4,5-dihydro-1,2-oxazole |
| 443 | 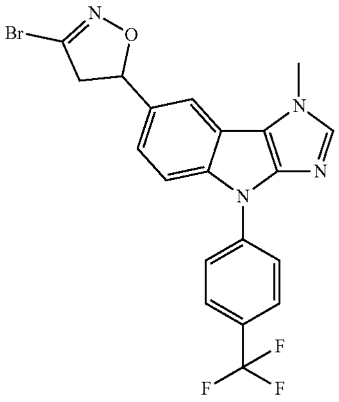 [SMILES: Cn1cnc2c1c1cc(C3CC(Cl)=NO3)ccc1n2-c1ccc(C(F)(F)F)cc1] 3-bromo-5-{1-methyl-4-[4-(trifluoromethyl)phenyl]-1H,4H-imidazo[4,5-b]indol-7-yl}-4,5-dihydro-1,2-oxazole |
| 444 | 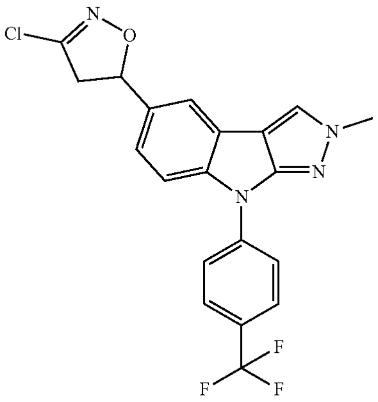 3-chloro-5-{2-methyl-8-[4-(trifluoromethyl)phenyl]-2H,8H-pyrazolo[3,4-b]indol-5-yl}-4,5-dihydro-1,2-oxazole |

-continued

| Compound No. | Structure and Name |
|---|---|
| 445 | 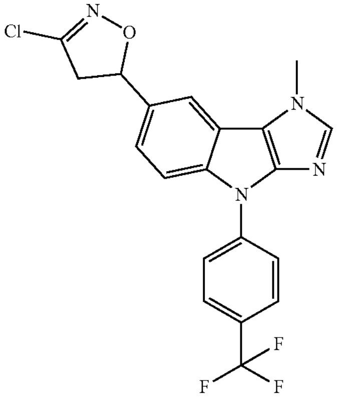 3-chloro-5-{1-methyl-4-[4-(trifluoromethyl)phenyl]-1H,4H-imidazo[4,5-b]indol-7-yl}-4,5-dihydro-1,2-oxazole |
| 446 | 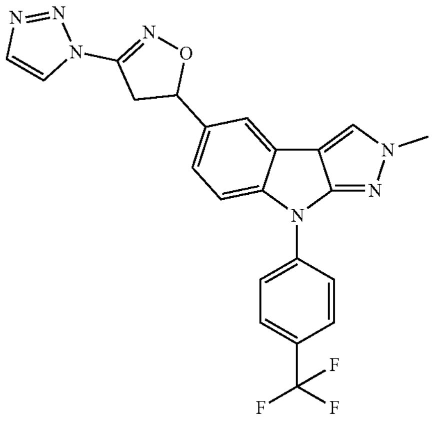 [SMILES: Cn1cc2c3cc(C4CC(n5ccnn5)=NO4)ccc3n(-c3ccc(C(F)(F)F)cc3)c2n1] 1-(5-{2-methyl-8-[4-(trifluoromethyl)phenyl]-2H,8H-pyrazolo[3,4-b]indol-5-yl}-4,5-dihydro-1,2-oxazol-3-yl)-1H-1,2,3-triazole |
| 447 | 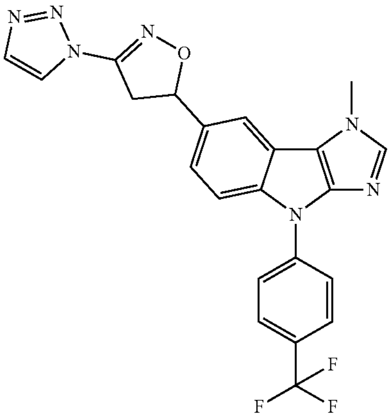 [SMILES: Cn1cnc2c1c1cc(C3CC(n4ccnn4)=NO3)ccc1n2-c1ccc(C(F)(F)F)cc1] 1-(5-{1-methyl-4-[4-(trifluoromethyl)phenyl]-1H,4H-imidazo[4,5-b]indol-7-yl}-4,5-dihydro-1,2-oxazol-3-yl)-1H-1,2,3-triazole |

-continued

| Compound No. | Structure and Name |
|---|---|
| 448 | 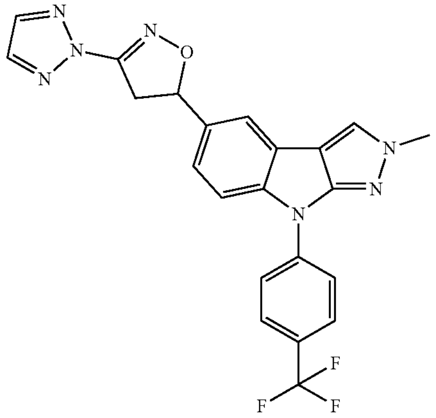 [SMILES: Cn1cc2c3cc(C4CC(n5nccn5)=NO4)ccc3n(-c3ccc(C(F)(F)F)cc3)c2n1] 2-(5-{2-methyl-8-[4-(trifluoromethyl)phenyl]-2H,8H-pyrazolo[3,4-b]indol-5-yl}-4,5-dihydro-1,2-oxazol-3-yl)-2H-1,2,3-triazole |
| 449 | 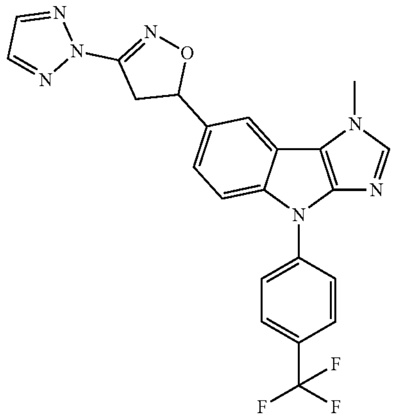 [SMILES: Cn1cnc2c1c1cc(C3CC(n4nccn4)=NO3)ccc1n2-c1ccc(C(F)(F)F)cc1] 2-(5-{1-methyl-4-[4-(trifluoromethyl)phenyl]-1H,4H-imidazo[4,5-b]indol-7-yl}-4,5-dihydro-1,2-oxazol-3-yl)-2H-1,2,3-triazole |
| 450 | 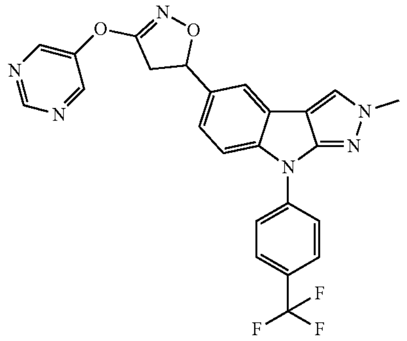 [SMILES: Cn1cc2c3cc(C4CC(Oc5cncnc5)=NO4)ccc3n(-c3ccc(C(F)(F)F)cc3)c2n1] 5-[(5-{2-methyl-8-[4-(trifluoromethyl)phenyl]-2H,8H-pyrazolo[3,4-b]indol-5-yl}-4,5-dihydro-1,2-oxazol-3-yl)oxy]pyrimidine |

-continued

| Compound No. | Structure and Name |
|---|---|
| 451 | 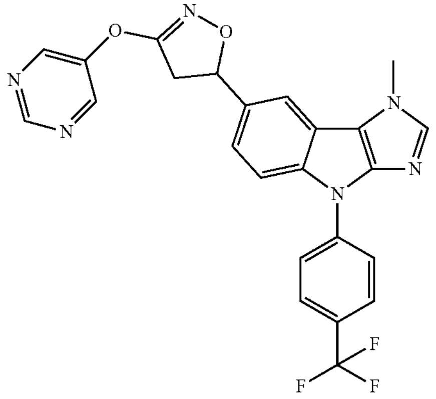 [SMILES: Cn1cnc2c1c1cc(C3CC(Oc4cncnc4)=NO3)ccc1n2-c1ccc(C(F)(F)F)cc1] 5-[(5-{1-methyl-4-[4-(trifluoromethyl)phenyl]-1H,4H-imidazo[4,5-b]indol-7-yl}-4,5-dihydro-1,2-oxazol-3-yl)oxy]pyrimidine |
| 452 | 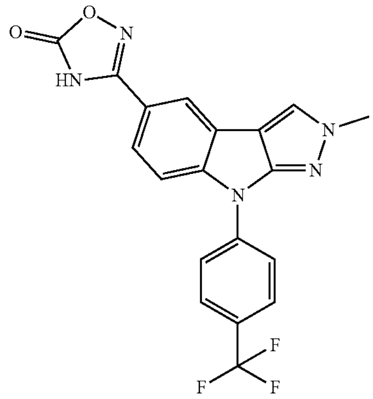 [SMILES: Cn1cc2c3cc(-c4noc(=O)[nH]4)ccc3n(-c3ccc(C(F)(F)F)cc3)c2n1] 3-{2-methyl-8-[4-(trifluoromethyl)phenyl]-2H,8H-pyrazolo[3,4-b]indol-5-yl}-4,5-dihydro-1,2,4-oxadiazol-5-one |
| 453 | 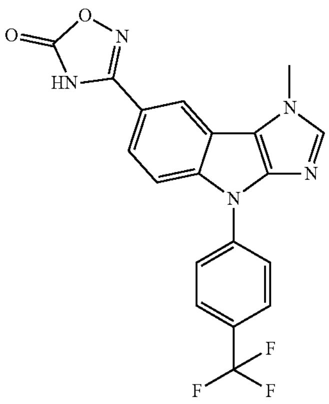 [SMILES: Cn1cnc2c1c1cc(-c3noc(=O)[nH]3)ccc1n2-c1ccc(C(F)(F)F)cc1] 3-{1-methyl-4-[4-(trifluoromethyl)phenyl]-1H,4H-imidazo[4,5-b]indol-7-yl}-4,5-dihydro-1,2,4-oxadiazol-5-one |

-continued

| Compound No. | Structure and Name |
|---|---|
| 454 | 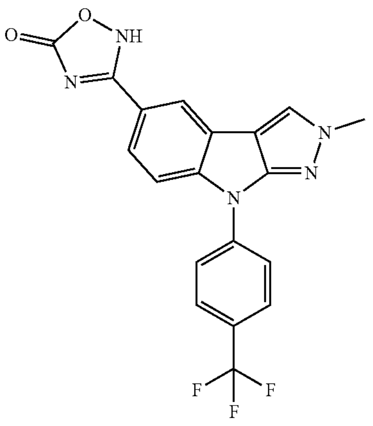 [SMILES: Cn1cc2c3cc(-c4nc(=O)o[nH]4)ccc3n(-c3ccc(C(F)(F)F)cc3)c2n1] 3-{2-methyl-8-[4-(trifluoromethyl)phenyl]-2H,8H-pyrazolo[3,4-b]indol-5-yl}-2,5-dihydro-1,2,4-oxadiazol-5-one |
| 455 | 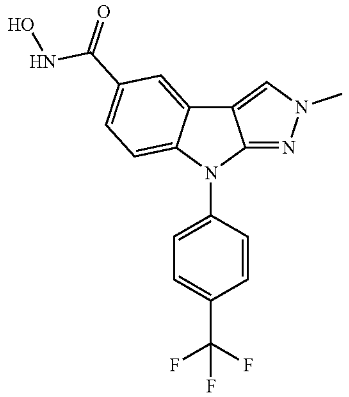 [SMILES: Cn1cc2c3cc(C(=O)NO)ccc3n(-c3ccc(C(F)(F)F)cc3)c2n1] N-hydroxy-2-methyl-8-[4-(trifluoromethyl)phenyl]-2H,8H-pyrazolo[3,4-b]indole-5-carboxamide |
| 456 | 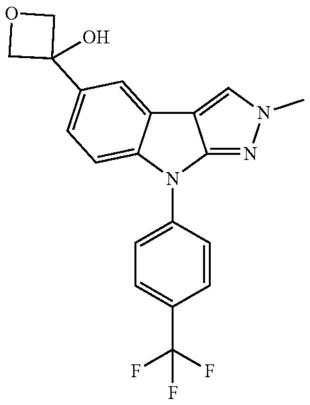 [SMILES: Cn1cc2c3cc(C4(O)COC4)ccc3n(-c3ccc(C(F)(F)F)cc3)c2n1] 3-{2-methyl-8-[4-(trifluoromethyl)phenyl]-2H,8H-pyrazolo[3,4-b]indol-5-yl}oxetan-3-ol |

-continued

| Compound No. | Structure and Name |
|---|---|
| 457 | 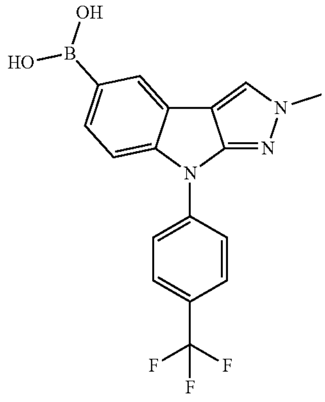 [SMILES: Cn1cc2c3cc(B(O)O)ccc3n(-c3ccc(C(F)(F)F)cc3)c2n1] {2-methyl-8-[4-(trifluoromethyl)phenyl]-2H,8H-pyrazolo[3,4-b]indol-5-yl}boronic acid |
| 458 | 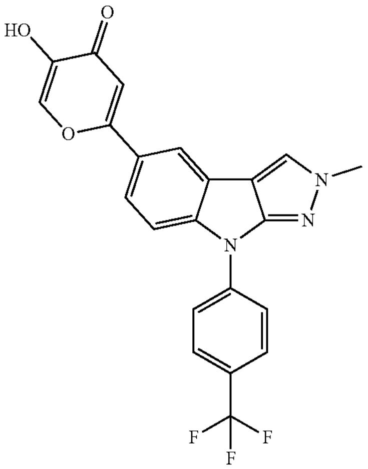 [SMILES: Cn1cc2c3cc(-c4cc(=O)c(O)co4)ccc3n(-c3ccc(C(F)(F)F)cc3)c2n1] 5-hydroxy-2-{2-methyl-8-[4-(trifluoromethyl)phenyl]-2H,8H-pyrazolo[3,4-b]indol-5-yl}-4H-pyran-4-one |
| 459 | 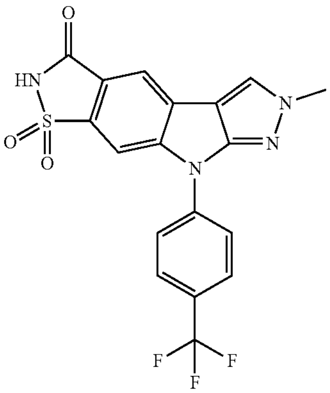 [SMILES: Cn1cc2c3cc4c(cc3n(-c3ccc(C(F)(F)F)cc3)c2n1)S(=O)(=O)NC4=O] 12-methyl-15-[4-(trifluoromethyl)phenyl]-4-$\lambda^6$-thia-5,12,13,15-tetraazatetracyclo[7.6.0.0$^{3,7}$.0$^{10,14}$]pentadeca-1,3(7),8,10,13-pentaene-4,4,6-trione |

-continued

| Compound No. | Structure and Name |
|---|---|
| 460 | 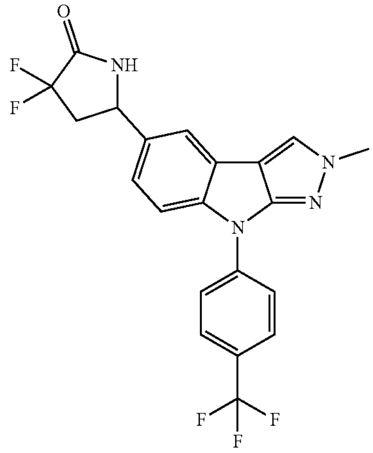 [SMILES: Cn1cc2c3cc(C4CC(F)(F)C(=O)N4)ccc3n(-c3ccc(C(F)(F)F)cc3)c2n1]<br>3,3-difluoro-5-{2-methyl-8-[4-(trifluoromethyl)phenyl]-2H,8H-pyrazolo[3,4-b]indol-5-yl}pyrrolidin-2-one |
| 461 | 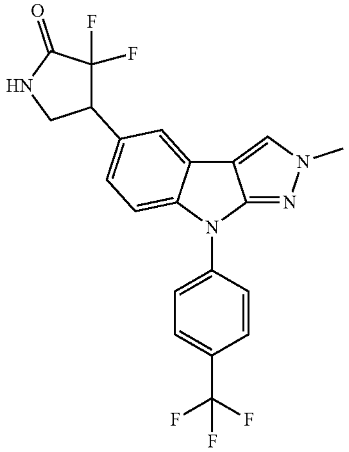 [SMILES: Cn1cc2c3cc(C4CNC(=O)C4(F)F)ccc3n(-c3ccc(C(F)(F)F)cc3)c2n1]<br>3,3-difluoro-4-{2-methyl-8-[4-(trifluoromethyl)phenyl]-2H,8H-pyrazolo[3,4-b]indol-5-yl}pyrrolidin-2-one |
| 462 | 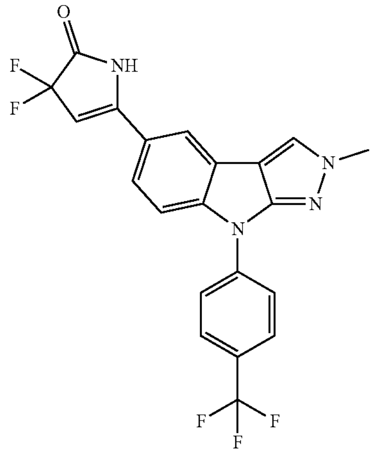 [SMILES: Cn1cc2c3cc(C4=CC(F)(F)C(=O)N4)ccc3n(-c3ccc(C(F)(F)F)cc3)c2n1]<br>3,3-difluoro-5-{2-methyl-8-[4-(trifluoromethyl)phenyl]-2H,8H-pyrazolo[3,4-b]indol-5-yl}-2,3-dihydro-1H-pyrrol-2-one |

-continued

| Compound No. | Structure and Name |
|---|---|
| 463 | 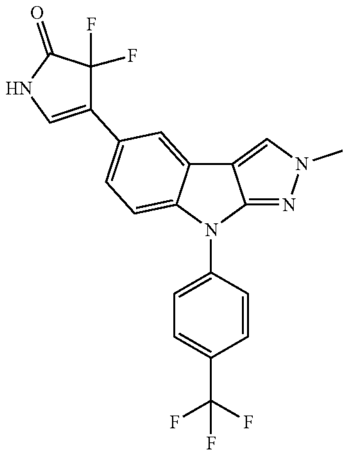 [SMILES: Cn1cc2c3cc(C4=CNC(=O)C4(F)F)ccc3n(-c3ccc(C(F)(F)F)cc3)c2n1]<br>3,3-difluoro-4-{2-methyl-8-[4-(trifluoromethyl)phenyl]-2H,8H-pyrazolo[3,4-b]indol-5-yl}-2,3-dihydro-1H-pyrrol-2-one |
| 465 | 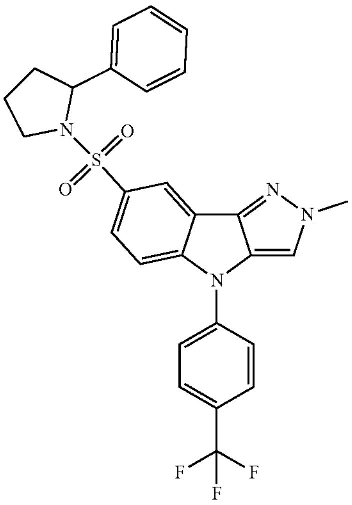 [SMILES: Cn1cc2c(n1)c1cc(S(=O)(=O)N3CCCC3c3ccccc3)ccc1n2-c1ccc(C(F)(F)F)cc1]<br>1-({2-methyl-4-[4-(trifluoromethyl)phenyl]-2H,4H-pyrazolo[4,3-b]indol-7-yl}sulfonyl)-2-phenylpyrrolidine |

-continued

| Compound No. | Structure and Name |
|---|---|
| 466 | 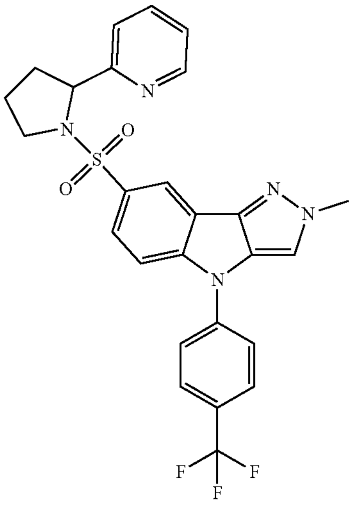 [SMILES: Cn1cc2c(n1)c1cc(S(=O)(=O)N3CCCC3c3ccccn3)ccc1n2-c1ccc(C(F)(F)F)cc1]<br>2-[1-({2-methyl-4-[4-(trifluoromethyl)phenyl]-2H,4H-pyrazolo[4,3-b]indol-7-yl}sulfonyl)pyrrolidin-2-yl]pyridine |
| 467 | 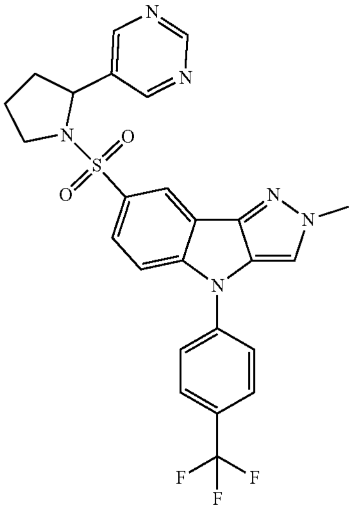 [SMILES: Cn1cc2c(n1)c1cc(S(=O)(=O)N3CCCC3c3cncnc3)ccc1n2-c1ccc(C(F)(F)F)cc1]<br>5-[1-({2-methyl-4-[4-(trifluoromethyl)phenyl]-2H,4H-pyrazolo[4,3-b]indol-7-yl}sulfonyl)pyrrolidin-2-yl]pyrimidine |

-continued

| Compound No. | Structure and Name |
|---|---|
| 468 | 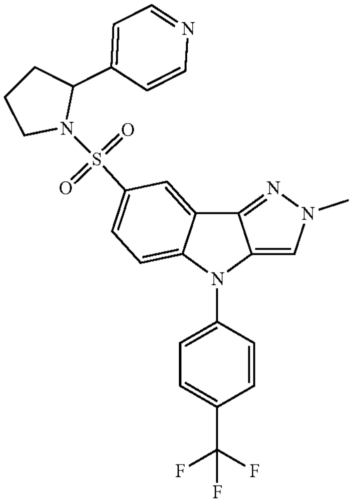 [SMILES: Cn1cc2c(n1)c1cc(S(=O)(=O)N3CCCC3c3ccncc3)ccc1n2-c1ccc(C(F)(F)F)cc1]<br>4-[1-({2-methyl-4-[4-(trifluoromethyl)phenyl]-2H,4H-pyrazolo[4,3-b]indol-7-yl}sulfonyl)pyrrolidin-2-yl]pyridine |
| 469 | 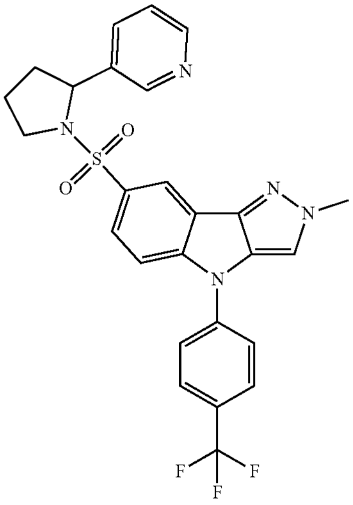 [SMILES: Cn1cc2c(n1)c1cc(S(=O)(=O)N3CCCC3c3cccnc3)ccc1n2-c1ccc(C(F)(F)F)cc1]<br>3-[1-({2-methyl-4-[4-(trifluoromethyl)phenyl]-2H,4H-pyrazolo[4,3-b]indol-7-yl}sulfonyl)pyrrolidin-2-yl]pyridine |

-continued

| Compound No. | Structure and Name |
|---|---|
| 470 | 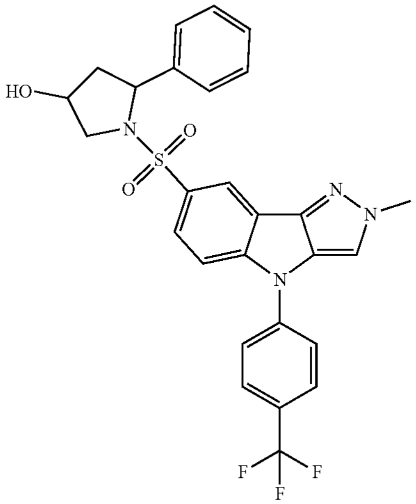 [SMILES: Cn1cc2c(n1)c1cc(S(=O)(=O)N3CC(O)CC3c3ccccc3)ccc1n2-c1ccc(C(F)(F)F)cc1]<br>1-({2-methyl-4-[4-(trifluoromethyl)phenyl]-2H,4H-pyrazolo[4,3-b]indol-7-yl}sulfonyl)-5-phenylpyrrolidin-3-ol |
| 472 | 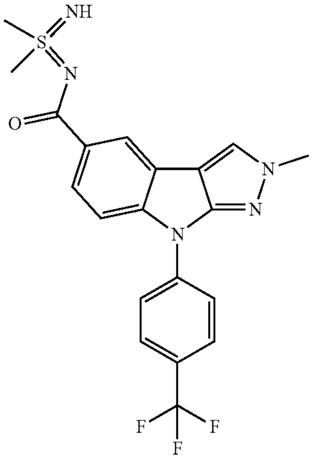<br>N-(iminodimethyl-λ$^6$-sulfanylidene)-2-methyl-8-[4-(trifluoromethyl)phenyl]-2H,8H-pyrazolo[3,4-b]indole-5-carboxamide |
| 473 | 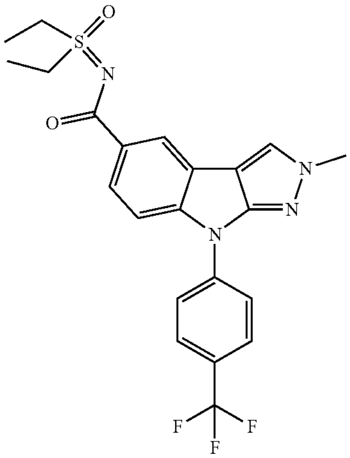 [SMILES: CCS(=O)(CC)=NC(=O)c1ccc2c(c1)c1cn(C)nc1n2-c1ccc(C(F)(F)F)cc1] |

-continued

| Compound No. | Structure and Name |
|---|---|
| | N-[diethyl(oxo)-λ$^6$-sulfanylidene]-2-methyl-8-[4-(trifluoromethyl)phenyl]-2H,8H-pyrazolo[3,4-b]indole-5-carboxamide |
| 474 | 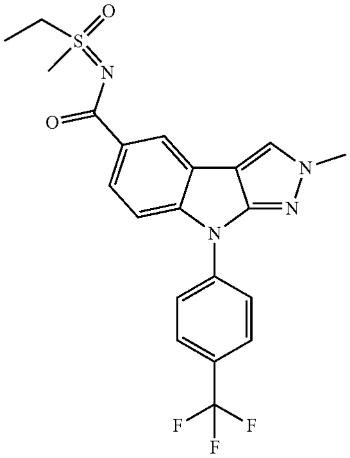<br>Racemate<br>N-[ethyl(methyl)oxo-λ$^6$-sulfanylidene]-2-methyl-8-[4-(trifluoromethyl)phenyl]-2H,8H-pyrazolo[3,4-b]indole-5-carboxamide |
| 475 | 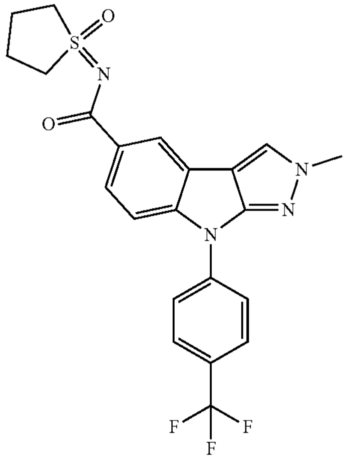 [SMILES: Cn1cc2c3cc(C(=O)N=S4(=O)CCCC4)ccc3n(-c3ccc(C(F)(F)F)cc3)c2n1]<br>2-methyl-N-(1-oxo-1 λ$^6$-thiolan-1-ylidene)-8-[4-(trifluoromethyl)phenyl]-2H,8H-pyrazolo[3,4-b]indole-5-carboxamide |

-continued

| Compound No. | Structure and Name |
|---|---|
| 476 | 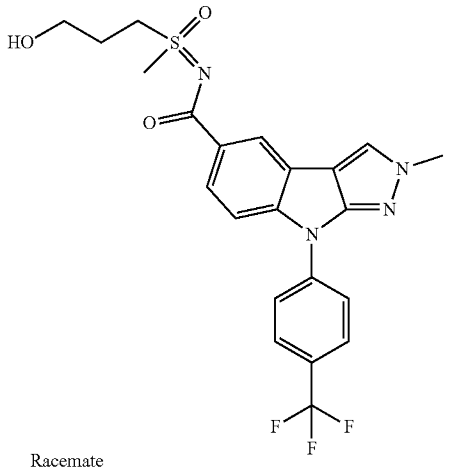 [SMILES: Cn1cc2c3cc(C(=O)N=S(C)(=O)CCCO)ccc3n(-c3ccc(C(F)(F)F)cc3)c2n1]<br>Racemate<br>N-[(3-hydroxypropyl)(methyl)oxo-λ$^6$-sulfanylidene]-2-methyl-8-[4-(trifluoromethyl)phenyl]-2H,8H-pyrazolo[3,4-b]indole-5-carboxamide |
| 477 | 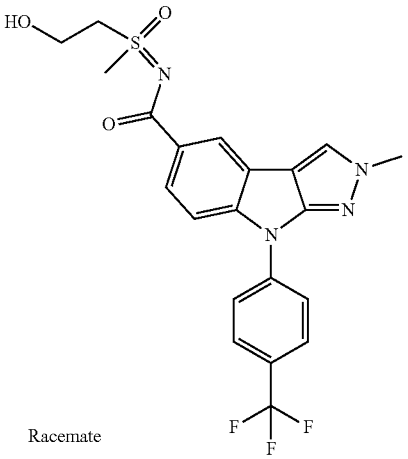 [SMILES: Cn1cc2c3cc(C(=O)N=S(C)(=O)CCO)ccc3n(-c3ccc(C(F)(F)F)cc3)c2n1]<br>Racemate<br>N-[(2-hydroxyethyl)(methyl)oxo-λ$^6$-sulfanylidene]-2-methyl-8-[4-(trifluoromethyl)phenyl]-2H,8H-pyrazolo[3,4-b]indole-5-carboxamide |
| 478 | 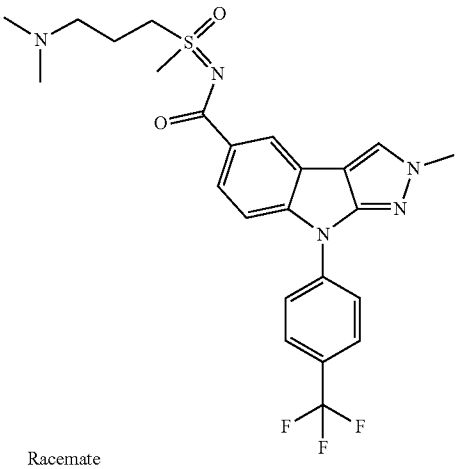<br>Racemate<br>N-{[3-(dimethylamino)propyl](methyl)oxo-λ$^6$-sulfanylidene}-2-methyl-8-[4-(trifluoromethyl)phenyl]-2H,8H-pyrazolo[3,4-b]indole-5-carboxamide |
| 479 | 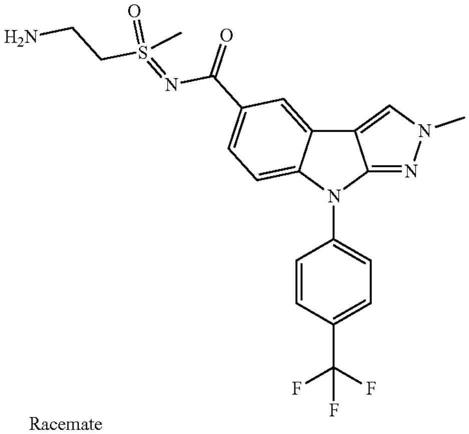 [SMILES: Cn1cc2c3cc(C(=O)N=S(C)(=O)CCN)ccc3n(-c3ccc(C(F)(F)F)cc3)c2n1]<br>Racemate<br>N-[(2-aminoethyl)(methyl)oxo-λ$^6$-sulfanylidene]-2-methyl-8-[4-(trifluoromethyl)phenyl]-2H,8H-pyrazolo[3,4-b]indole-5-carboxamide |
| 480 | 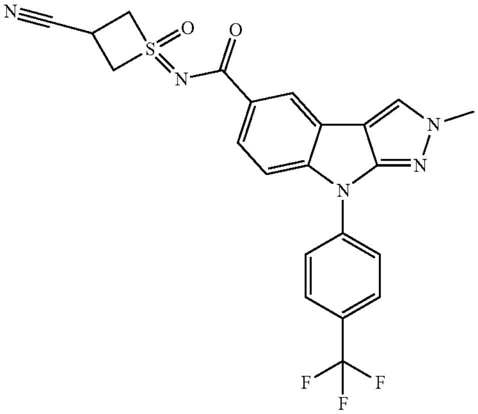 [SMILES: Cn1cc2c3cc(C(=O)N=S4(=O)CC(C#N)C4)ccc3n(-c3ccc(C(F)(F)F)cc3)c2n1]<br>N-(3-cyano-1-oxo-1-λ$^6$-thietan-1-ylidene)-2-methyl-8-[4-(trifluoromethyl)phenyl]-2H,8H-pyrazolo[3,4-b]indole-5-carboxamide |
| 481 | 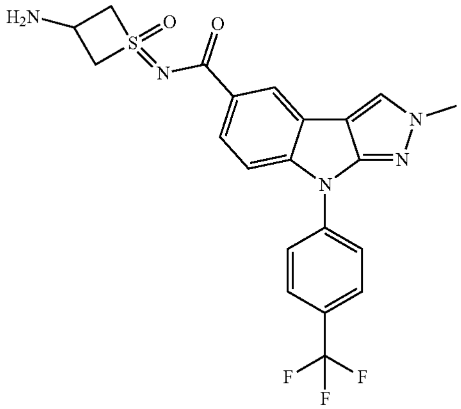 [SMILES: Cn1cc2c3cc(C(=O)N=S4(=O)CC(N)C4)ccc3n(-c3ccc(C(F)(F)F)cc3)c2n1] |

-continued

| Compound No. | Structure and Name |
| --- | --- |
| | N-(3-amino-1-oxo-1 $\lambda^6$-thietan-1-ylidene)-2-methyl-8-[4-(trifluoromethyl)phenyl]-2H,8H-pyrazolo[3,4-b]indole-5-carboxamide |
| 482 | 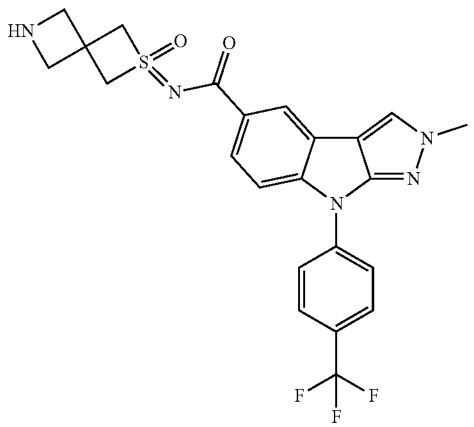 [SMILES: Cn1cc2c3cc(C(=O)N=S4(=O)CC5(CNC5)C4)ccc3n(-c3ccc(C(F)(F)F)cc3)c2n1] |
| | 2-methyl-N-{2-oxo-2 $\lambda^6$-thia-6-azaspiro[3.3]heptan-2-ylidene}-8-[4-(trifluoromethyl)phenyl]-2H,8H-pyrazolo[3,4-b]indole-5-carboxamide |
| 483 | 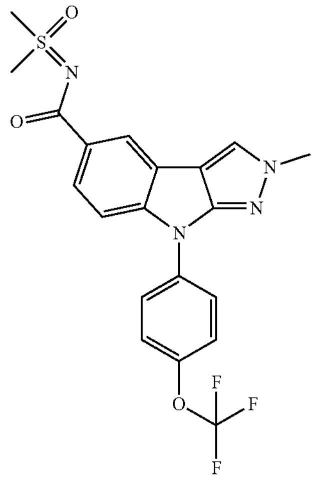 |
| | N-[dimethyl(oxo)-$\lambda^6$-sulfanylidene]-2-methyl-8-[4-(trifluoromethoxy)phenyl]-2H,8H-pyrazolo[3,4-b]indole-5-carboxamide |
| 484 | 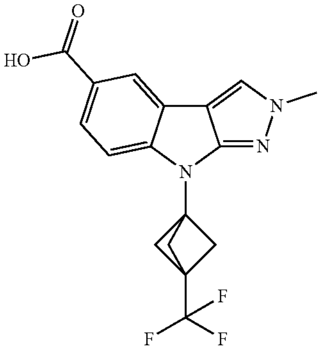 [SMILES: Cn1cc2c3cc(C(=O)O)ccc3n(C34CC(C(F)(F)F)(C3)C4)c2n1] |
| | 2-methyl-8-[3-(trifluoromethyl)bicyclo[1.1.1]pentan-1-yl]-2H,8H-pyrazolo[3,4-b]indole-5-carboxylic acid |
| 485 | 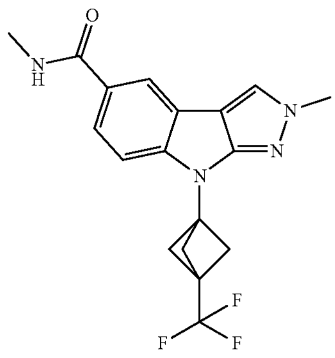 |
| | N,2-dimethyl-8-[3-(trifluoromethyl)bicyclo[1.1.1]pentan-1-yl]-2H,8H-pyrazolo[3,4-b]indole-5-carboxamide |
| 486 | 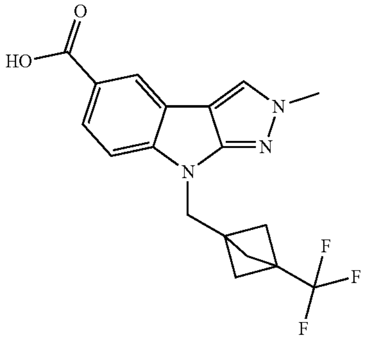 [SMILES: Cn1cc2c3cc(C(=O)O)ccc3n(CC34CC(C(F)(F)F)(C3)C4)c2n1] |
| | 2-methyl-8-{[3-(trifluoromethyl)bicyclo[1.1.1]pentan-1-yl]methyl}-2H,8H-pyrazolo[3,4-b]indole-5-carboxylic acid |
| 487 | 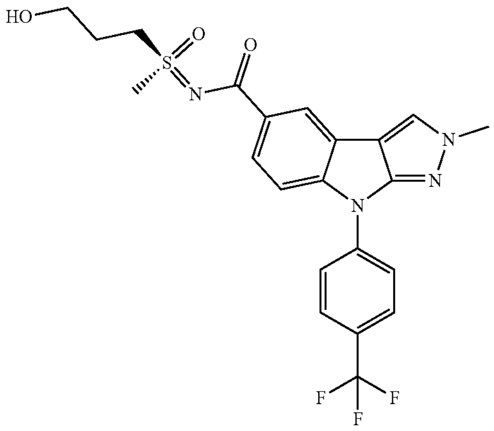 [SMILES: Cn1cc2c3cc(C(=O)N=[S@](C)(=O)CCCO)ccc3n(-c3ccc(C(F)(F)F)cc3)c2n1] |
| | Absolute configuration assigned arbitrarily |

-continued

| Compound No. | Structure and Name |
|---|---|
| 488 | 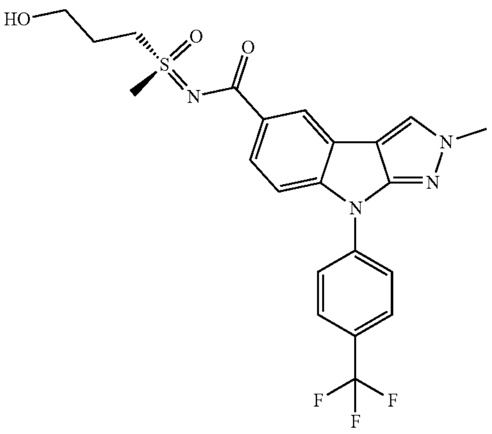 [SMILES: Cn1cc2c3cc(C(=O)N=[S@@](C)(=O)CCCO)ccc3n(-c3ccc(C(F)(F)F)cc3)c2n1] Absolute configuration assigned arbitrarily |
| 489 | 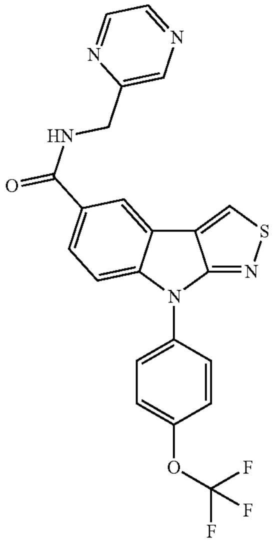 [SMILES: O=C(NCc1cnccn1)c1ccc2c(c1)c1csnc1n2-c1ccc(OC(F)(F)F)cc1] N-[(pyrazin-2-yl)methyl]-8-[4-(trifluoromethoxy)phenyl]-8H-[1,2]thiazolo[3,4-b]indole-5-carboxamide |

-continued

| Compound No. | Structure and Name |
|---|---|
| 490 | 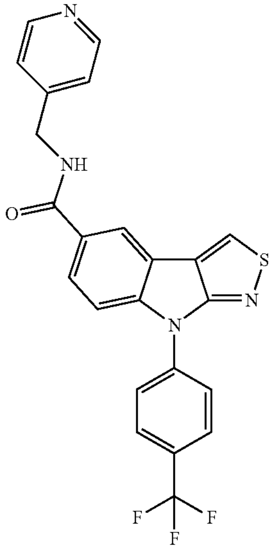 [SMILES: O=C(NCc1ccncc1)c1ccc2c(c1)c1csnc1n2-c1ccc(C(F)(F)F)cc1] N-[(pyridin-4-yl)methyl]-8-[4-(trifluoromethyl)phenyl]-8H-[1,2]thiazolo[3,4-b]indole-5-carboxamide |
| 491 | Absolute 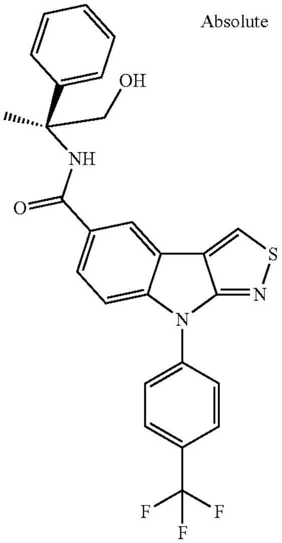 [SMILES: C[C@](CO)(NC(=O)c1ccc2c(c1)c1csnc1n2-c1ccc(C(F)(F)F)cc1)c1ccccc1] N-[(2S)-1-hydroxy-2-phenylpropan-2-yl]-8-[4-(trifluoromethyl)phenyl]-8H-[1,2]thiazolo[3,4-b]indole-5-carboxamide |

| Compound No. | Structure and Name |
|---|---|
| 492 | 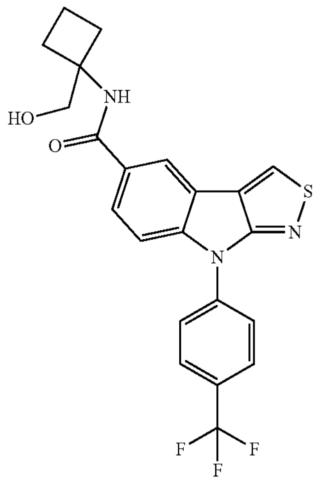 [SMILES: O=C(NC1(CO)CCC1)c1ccc2c(c1)c1csnc1n2-c1ccc(C(F)(F)F)cc1] N-[1-(hydroxymethyl)cyclobutyl]-8-[4-(trifluoromethyl)phenyl]-8H-[1,2]thiazolo[3,4-b]indole-5-carboxamide |
| 493 | 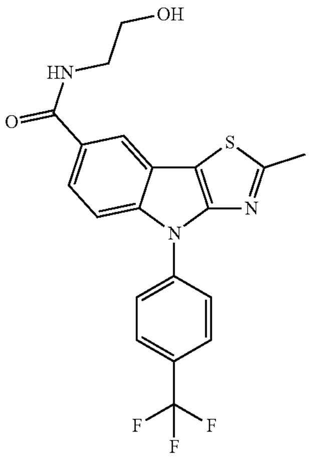 [SMILES: Cc1nc2c(s1)c1cc(C(=O)NCCO)ccc1n2-c1ccc(C(F)(F)F)cc1] N-(2-hydroxyethyl)-2-methyl-4-[4-(trifluoromethyl)phenyl]-4H-[1,3]thiazolo[4,5-b]indole-7-carboxamide |

| Compound No. | Structure and Name |
|---|---|
| 494 | 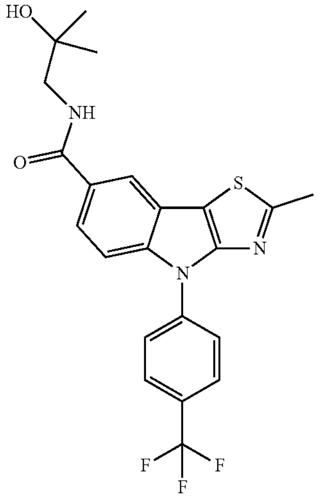 [SMILES: Cc1nc2c(s1)c1cc(C(=O)NCC(C)(C)O)ccc1n2-c1ccc(C(F)(F)F)cc1] N-(2-hydroxy-2-methylpropyl)-2-methyl-4-[4-(trifluoromethyl)phenyl]-4H-[1,3]thiazolo[4,5-b]indole-7-carboxamide |
| 495 | 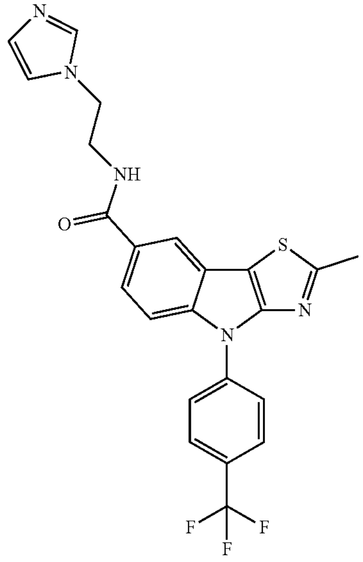 [SMILES: Cc1nc2c(s1)c1cc(C(=O)NCCn3ccnc3)ccc1n2-c1ccc(C(F)(F)F)cc1] N-[2-(1H-imidazol-1-yl)ethyl]-2-methyl-4-[4-(trifluoromethyl)phenyl]-4H-[1,3]thiazolo[4,5-b]indole-7-carboxamide |

-continued

| Compound No. | Structure and Name |
|---|---|
| 496 | 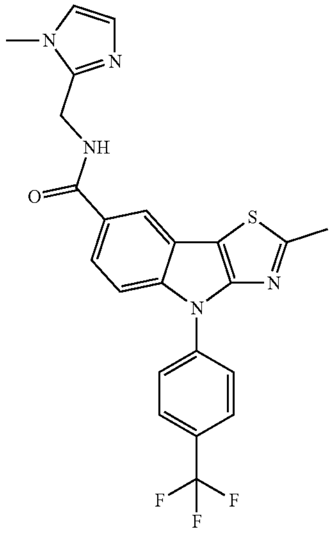 2-methyl-N-[(1-methyl-1H-imidazol-2-yl)methyl]-4-[4-(trifluoromethyl)phenyl]-4H-[1,3]thiazolo[4,5-b]indole-7-carboxamide |
| 497 | 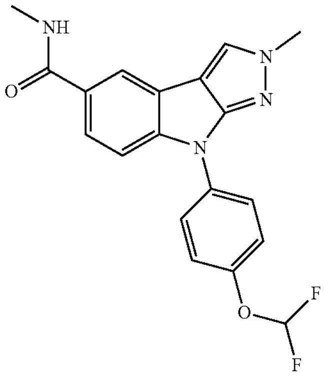 [SMILES: CNC(=O)c1ccc2c(c1)c1cn(C)nc1n2-c1ccc(OC(F)F)cc1] 8-[4-(difluoromethoxy)phenyl]-N,2-dimethyl-2H,8H-pyrazolo[3,4-b]indole-5-carboxamide |
| 498 | 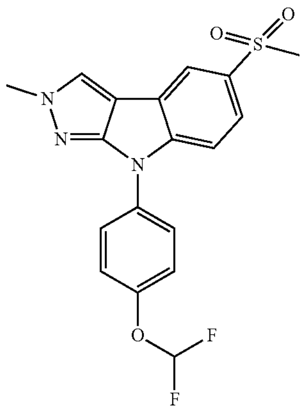 8-[4-(difluoromethoxy)phenyl]-5-methanesulfonyl-2-methyl-2H,8H-pyrazolo[3,4-b]indole |
| 499 | 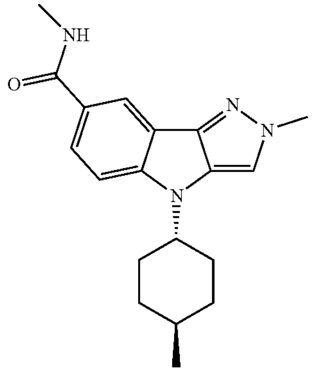 [SMILES: CNC(=O)c1ccc2c(c1)c1nn(C)cc1n2[C@H]1CC[C@H](C)CC1] Absolute configuration assigned arbitrarily N,2-dimethyl-4-[(1r,4r)-4-methylcyclohexyl]-2H,4H-pyrazolo[4,3-b]indole-7-carboxamide |
| 500 | 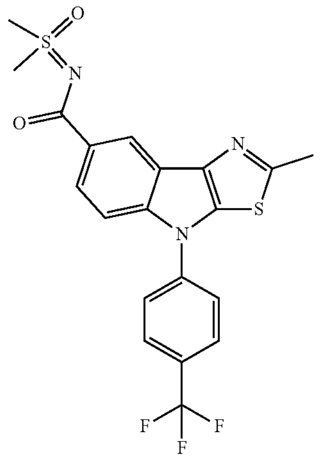 N-[dimethyl(oxo)-$\lambda^6$-sulfanylidene]-2-methyl-4-[4-(trifluoromethyl)phenyl]-4H-[1,3]thiazolo[5,4-b]indole-7-carboxamide |
| 501 | 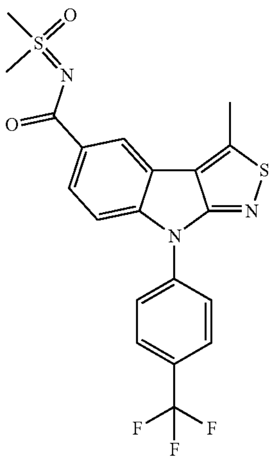 [SMILES: Cc1snc2c1c1cc(C(=O)N=S(C)(C)=O)ccc1n2-c1ccc(C(F)(F)F)cc1] N-[dimethyl(oxo)-$\lambda^6$-sulfanylidene]-3-methyl-8-[4-(trifluoromethyl)phenyl]-8H-[1,2]thiazolo[3,4-b]indole-5-carboxamide |

-continued

| Compound No. | Structure and Name |
|---|---|
| 502 | Absolute 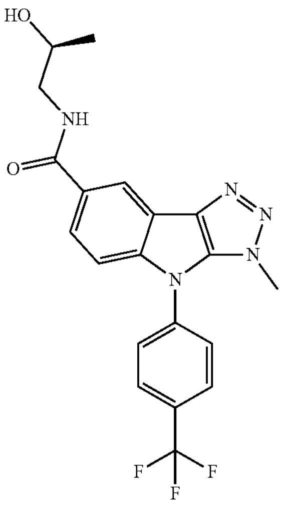 Absolute configuration assigned arbitrarily N-[(2S)-2-hydroxypropyl]-3-methyl-4-[4-(trifluoromethyl)phenyl]-3H,4H-[1,2,3]triazolo[4,5-b]indole-7-carboxamide |
| 503 | Absolute 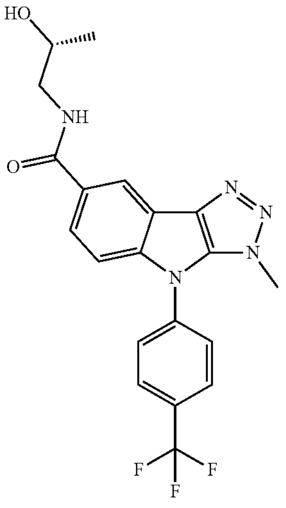 Absolute configuration assigned arbitrarily N-[(2R)-2-hydroxypropyl]-3-methyl-4-[4-(trifluoromethyl)phenyl]-3H,4H-[1,2,3]triazolo[4,5-b]indole-7-carboxamide |

-continued

| Compound No. | Structure and Name |
|---|---|
| 504 | Absolute 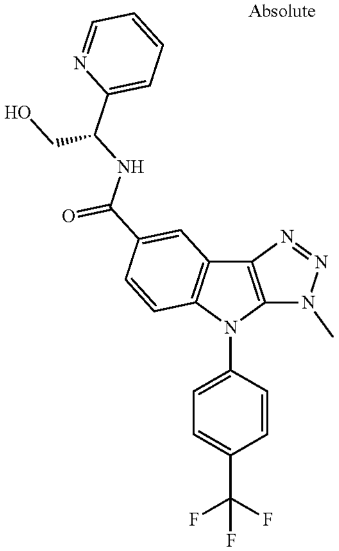 [SMILES: Cn1nnc2c3cc(C(=O)N[C@H](CO)c4ccccn4)ccc3n(-c3ccc(C(F)(F)F)cc3)c21] Absolute configuration assigned arbitrarily N-[(1S)-2-hydroxy-1-(pyridin-2-yl)ethyl]-3-methyl-4-[4-(trifluoromethyl)phenyl]-3H,4H-[1,2,3]triazolo[4,5-b]indole-7-carboxamide |
| 505 | Absolute 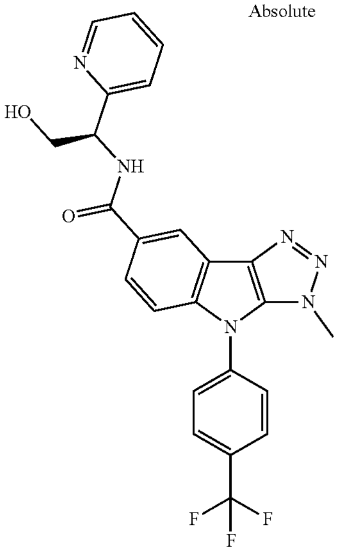 [SMILES: Cn1nnc2c3cc(C(=O)N[C@@H](CO)c4ccccn4)ccc3n(-c3ccc(C(F)(F)F)cc3)c21] Absolute configuration assigned arbitrarily N-[(1R)-2-hydroxy-1-(pyridin-2-yl)ethyl]-3-methyl-4-[4-(trifluoromethyl)phenyl]-3H,4H-[1,2,3]triazolo[4,5-b]indole-7-carboxamide |

| Compound No. | Structure and Name |
|---|---|
| 506 | 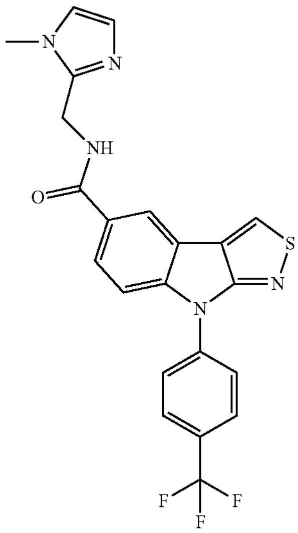 [SMILES: Cn1ccnc1CNC(=O)c1ccc2c(c1)c1csnc1n2-c1ccc(C(F)(F)F)cc1] N-[(1-methyl-1H-imidazol-2-yl)methyl]-8-[4-(trifluoromethyl)phenyl]-8H-[1,2]thiazolo[3,4-b]indole-5-carboxamide |
| 507 | 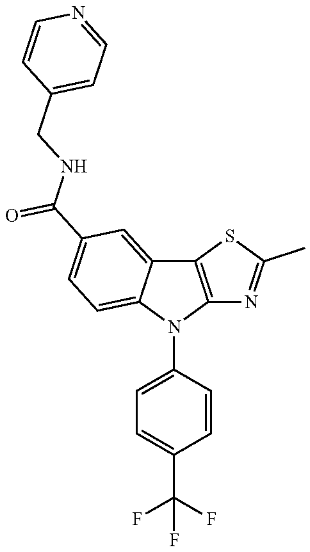 [SMILES: Cc1nc2c(s1)c1cc(C(=O)NCc3ccncc3)ccc1n2-c1ccc(C(F)(F)F)cc1] 2-methyl-N-[(pyridin-4-yl)methyl]-4-[4-(trifluoromethyl)phenyl]-4H-[1,3]thiazolo[4,5-b]indole-7-carboxamide |

| Compound No. | Structure and Name |
|---|---|
| 508 | 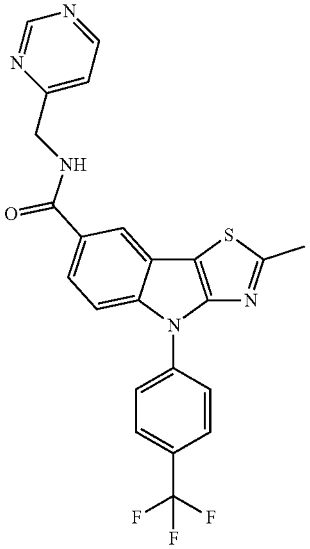 [SMILES: Cc1nc2c(s1)c1cc(C(=O)NCc3ccncn3)ccc1n2-c1ccc(C(F)(F)F)cc1] 2-methyl-N-[(pyrimidin-4-yl)methyl]-4-[4-(trifluoromethyl)phenyl]-4H-[1,3]thiazolo[4,5-b]indole-7-carboxamide |
| 509 | 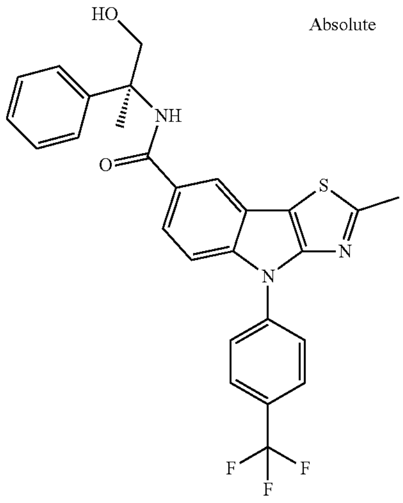 [SMILES: Cc1nc2c(s1)c1cc(C(=O)N[C@](C)(CO)c3ccccc3)ccc1n2-c1ccc(C(F)(F)F)cc1] N-[(2S)-1-hydroxy-2-phenylpropan-2-yl]-2-methyl-4-[4-(trifluoromethyl)phenyl]-4H-[1,3]thiazolo[4,5-b]indole-7-carboxamide |

| Compound No. | Structure and Name |
|---|---|
| 510 | 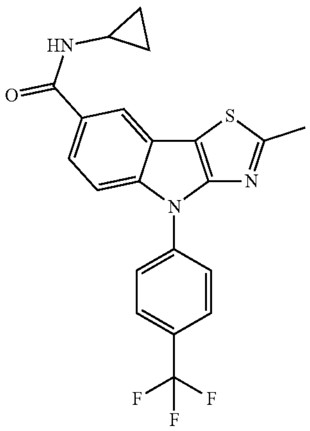 [SMILES: Cc1nc2c(s1)c1cc(C(=O)NC3CC3)ccc1n2-c1ccc(C(F)(F)F)cc1] N-cyclopropyl-2-methyl-4-[4-(trifluoromethyl)phenyl]-[1,3]thiazolo[4,5-b]indole-7-carboxamide |
| 511 | Absolute 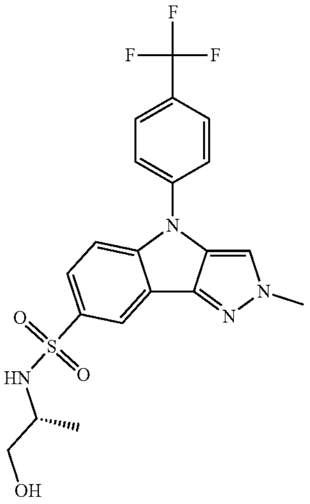 N-[(2R)-1-hydroxypropan-2-yl]-2-methyl-4-[4-(trifluoromethyl)phenyl]-2H,4H-pyrazolo[4,3-b]indole-7-sulfonamide |

| Compound No. | Structure and Name |
|---|---|
| 512 | 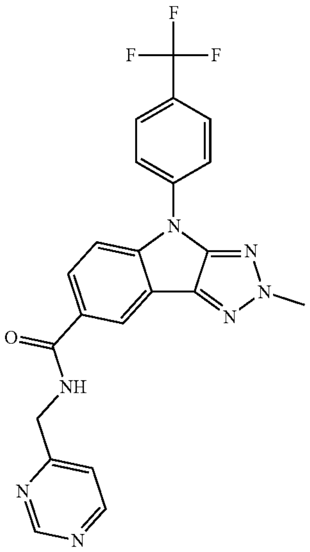 [SMILES: Cn1nc2c3cc(C(=O)NCc4ccncn4)ccc3n(-c3ccc(C(F)(F)F)cc3)c2n1] 2-methyl-N-[(pyrimidin-4-yl)methyl]-4-[4-(trifluoromethyl)phenyl]-2H,4H-[1,2,3]triazolo[4,5-b]indole-7-carboxamide |
| 513 | 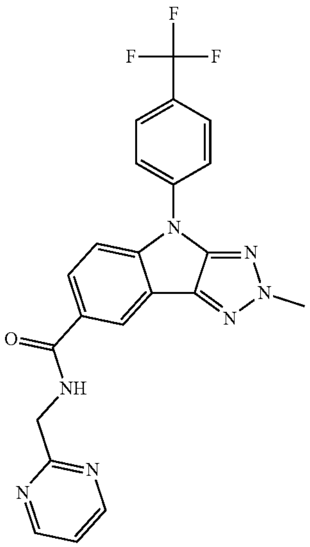 2-methyl-N-[(pyrimidin-2-yl)methyl]-4-[4-(trifluoromethyl)phenyl]-2H,4H-[1,2,3]triazolo[4,5-b]indole-7-carboxamide |

| Compound No. | Structure and Name |
| --- | --- |
| 514 | Absolute 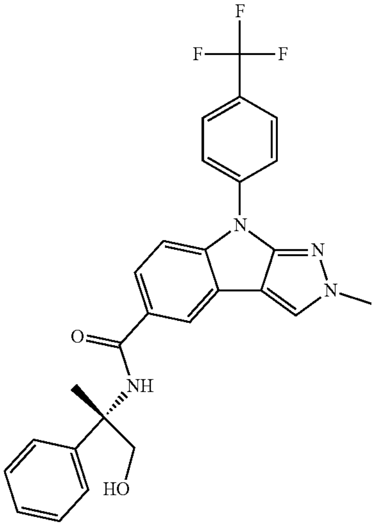 N-[(2S)-1-hydroxy-2-phenylpropan-2-yl]-2-methyl-8-[4-(trifluoromethyl)phenyl]-2H,8H-pyrazolo[3,4-b]indole-5-carboxamide |
| 515 | 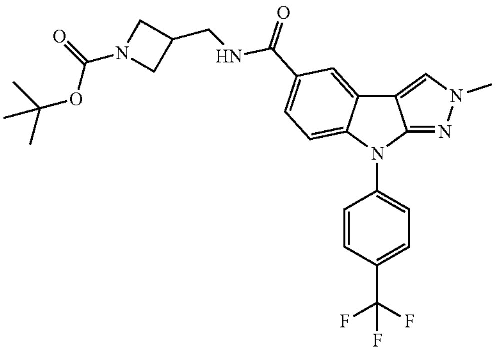 [SMILES: Cn1cc2c3cc(C(=O)NCC4CN(C(=O)OC(C)(C)C)C4)ccc3n(-c3ccc(C(F)(F)F)cc3)c2n1] tert-butyl 3-[({2-methyl-8-[4-(trifluoromethyl)phenyl]-2H,8H-pyrazolo[3,4-b]indol-5-yl}formamido)methyl]azetidine-1-carboxylate |

| Compound No. | Structure and Name |
| --- | --- |
| 516 | 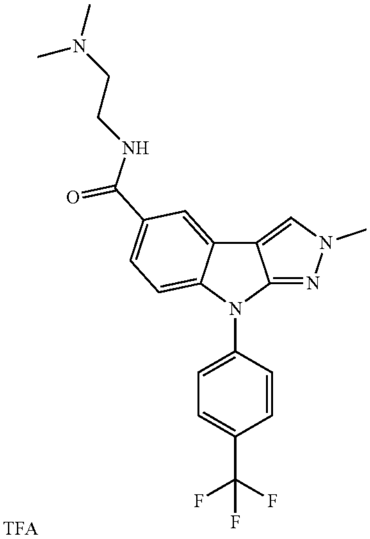 TFA N-[2-(dimethylamino)ethyl]-2-methyl-8-[4-(trifluoromethyl)phenyl]-2H,8H-pyrazolo[3,4-b]indole-5-carboxamide trifluoroacetate |
| 517 | 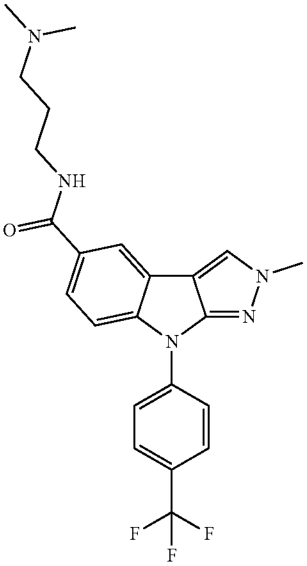 TFA N-[3-(dimethylamino)propyl]-2-methyl-8-[4-(trifluoromethyl)phenyl]-2H,8H-pyrazolo[3,4-b]indole-5-carboxamide trifluoracetate |

| Compound No. | Structure and Name |
|---|---|
| 518 | 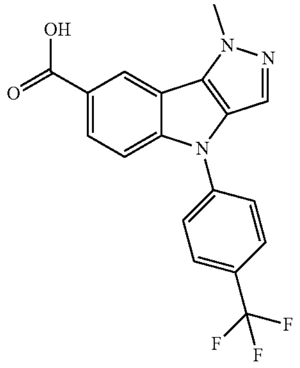 [SMILES: Cn1ncc2c1c1cc(C(=O)O)ccc1n2-c1ccc(C(F)(F)F)cc1] 1-methyl-4-[4-(trifluoromethyl)phenyl]-1H,4H-pyrazolo[4,3-b]indole-7-carboxylic acid |
| 519 | Absolute 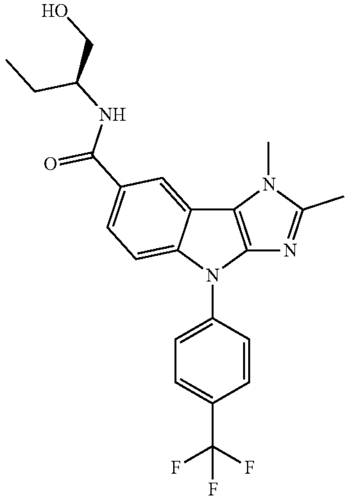 Absolute configuration assigned arbitrarily N-[(2S)-1-hydroxybutan-2-yl]-1,2-dimethyl-4-[4-(trifluoromethyl)phenyl]-1H,4H-imidazo[4,5-b]indole-7-carboxamide |

| Compound No. | Structure and Name |
|---|---|
| 520 | Absolute 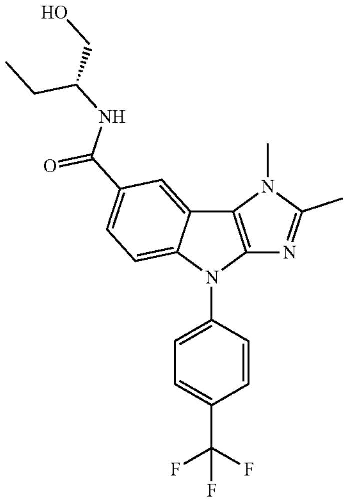 Absolute configuration assigned arbitrarily N-[(2R)-1-hydroxybutan-2-yl]-1,2-dimethyl-4-[4-(trifluoromethyl)phenyl]-1H,4H-imidazo[4,5-b]indole-7-carboxamide |
| 521 | 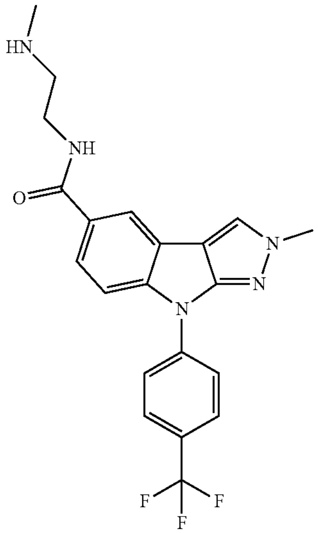 [SMILES: CNCCNC(=O)c1ccc2c(c1)c1cn(C)nc1n2-c1ccc(C(F)(F)F)cc1] 2-methyl-N-[2-(methylamino)ethyl]-8-[4-(trifluoromethyl)phenyl]-2H,8H-pyrazolo[3,4-b]indole-5-carboxamide |

| Compound No. | Structure and Name |
| --- | --- |
| 522 | 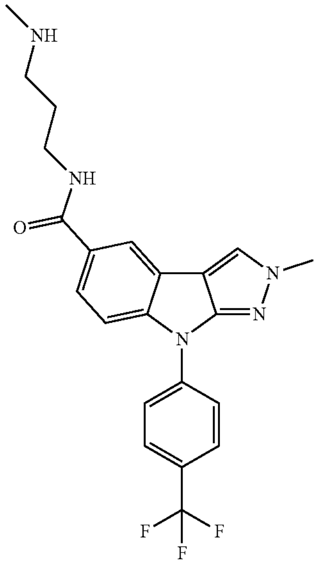 2-methyl-N-[3-(methylamino)propyl]-8-[4-(trifluoromethyl)phenyl]-2H,8H-pyrazolo[3,4-b]indole-5-carboxamide |
| 523 | Absolute 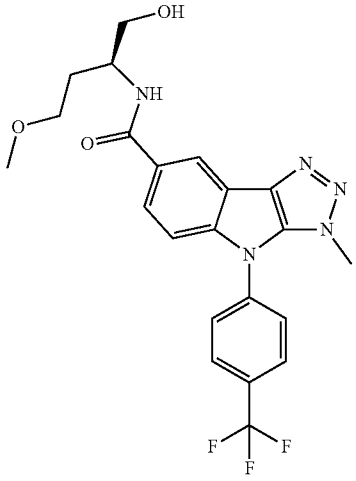 Absolute configuration assigned arbitrarily N-[(2S)-1-hydroxy-4-methoxybutan-2-yl]-3-methyl-4-[4-(trifluoromethyl)phenyl]-3H,4H-[1,2,3]triazolo[4,5-b]indole-7-carboxamide |

| Compound No. | Structure and Name |
| --- | --- |
| 524 | Absolute 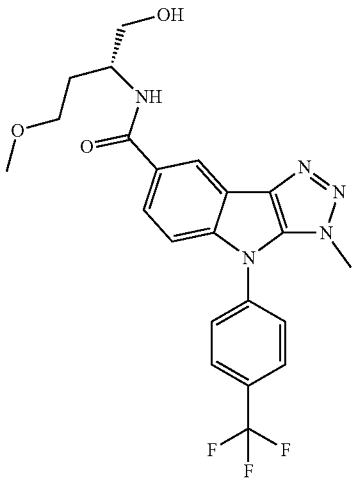 Absolute configuration assigned arbitrarily N-[(2R)-1-hydroxy-4-methoxybutan-2-yl]-3-methyl-4-[4-(trifluoromethyl)phenyl]-3H,4H-[1,2,3]triazolo[4,5-b]indole-7-carboxamide |
| 525 | 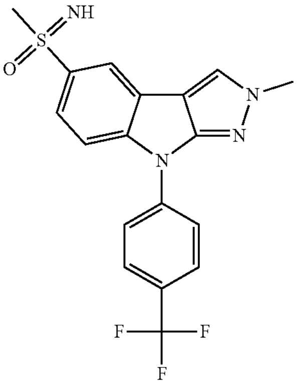 HCl imino(methyl){2-methyl-8-[4-(trifluoromethyl)phenyl]-2H,8H-pyrazolo[3,4-b]indol-5-yl}-$\lambda^6$-sulfanone |

-continued

| Compound No. | Structure and Name |
| --- | --- |
| 526 | 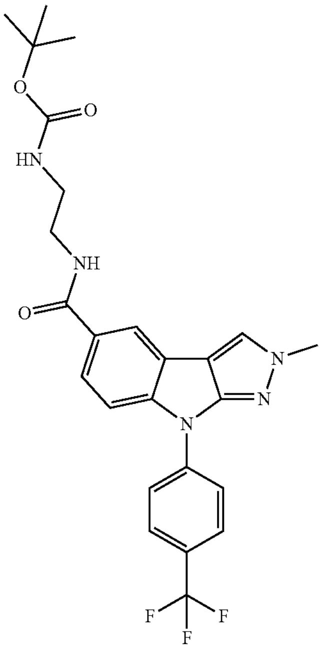 [SMILES: Cn1cc2c3cc(C(=O)NCCNC(=O)OC(C)(C)C)ccc3n(-c3ccc(C(F)(F)F)cc3)c2n1] tert-butyl N-[2-({2-methyl-8-[4-(trifluoromethyl)phenyl]-2H,8H-pyrazolo[3,4-b]indol-5-yl}formamido)ethyl]carbamate |
| 527 | Absolute 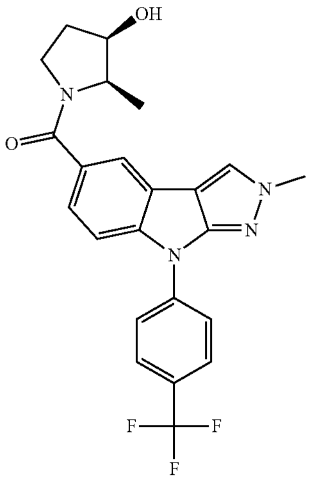 Absolute configuration assigned arbitrarily (2R,3R)-2-methyl-1-{2-methyl-8-[4-(trifluoromethyl)phenyl]-2H,8H-pyrazolo[3,4-b]indole-5-carbonyl}pyrrolidin-3-ol |
| 528 | Absolute 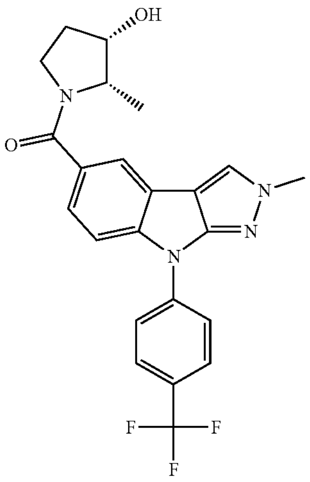 Absolute configuration assigned arbitrarily (2S,3S)-2-methyl-1-{2-methyl-8-[4-(trifluoromethyl)phenyl]-2H,8H-pyrazolo[3,4-b]indole-5-carbonyl}pyrrolidin-3-ol |
| 529 | Absolute 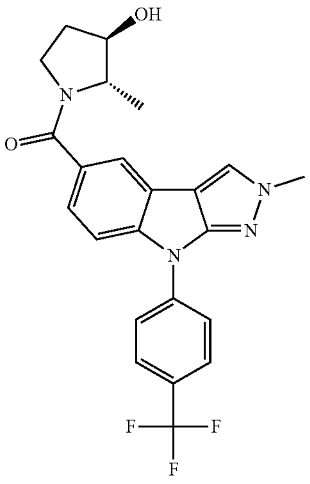 Absolute configuration assigned arbitrarily (2S,3R)-2-methyl-1-{2-methyl-8-[4-(trifluoromethyl)phenyl]-2H,8H-pyrazolo[3,4-b]indole-5-carbonyl}pyrrolidin-3-ol |

| Compound No. | Structure and Name |
| --- | --- |
| 530 | Absolute 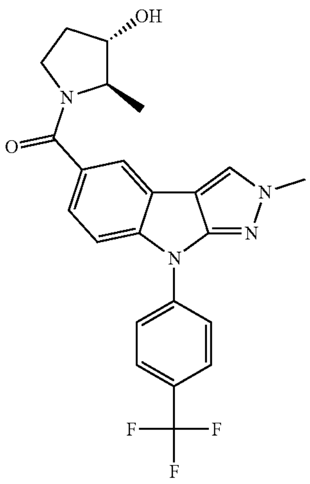 Absolute configuration assigned arbitrarily (2R,3S)-2-methyl-1-{2-methyl-8-[4-(trifluoromethyl)phenyl]-2H,8H-pyrazolo[3,4-b]indole-5-carbonyl}pyrrolidin-3-ol |
| 531 | 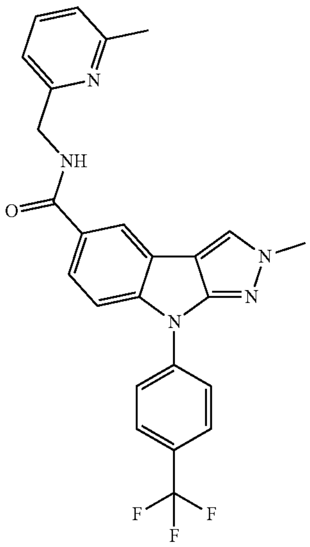 [SMILES: Cc1cccc(CNC(=O)c2ccc3c(c2)c2cn(C)nc2n3-c2ccc(C(F)(F)F)cc2)n1] 2-methyl-N-[(6-methylpyridin-2-yl)methyl]-8-[4-(trifluoromethyl)phenyl]-2H,8H-pyrazolo[3,4-b]indole-5-carboxamide |
| 532 | Absolute 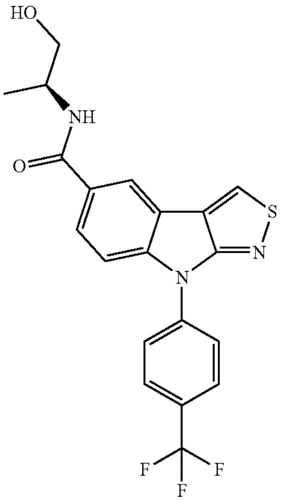 N-[(2S)-1-hydroxypropan-2-yl]-8-[4-(trifluoromethyl)phenyl]-8H-[1,2]thiazolo[3,4-b]indole-5-carboxamide |
| 533 | 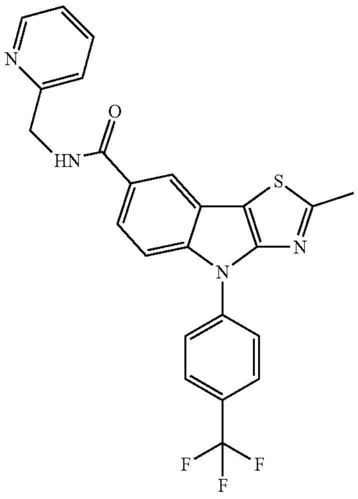 [SMILES: Cc1nc2c(s1)c1cc(C(=O)NCc3ccccn3)ccc1n2-c1ccc(C(F)(F)F)cc1] 2-methyl-N-[(pyridin-2-yl)methyl]-4-[4-(trifluoromethyl)phenyl]-4H-[1,3]thiazolo[4,5-b]indole-7-carboxamide |

| Compound No. | Structure and Name |
|---|---|
| 534 | 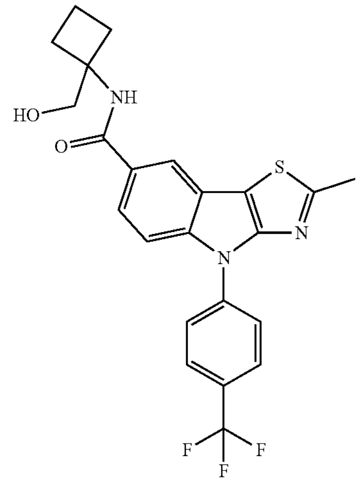 [SMILES: Cc1nc2c(s1)c1cc(C(=O)NC3(CO)CCC3)ccc1n2-c1ccc(C(F)(F)F)cc1] N-[1-(hydroxymethyl)cyclobutyl]-2-methyl-4-[4-(trifluoromethyl)phenyl]-4H-[1,3]thiazolo[4,5-b]indole-7-carboxamide |
| 535 | Absolute 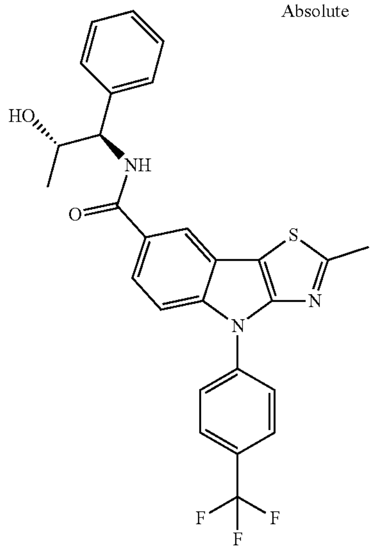 [SMILES: Cc1nc2c(s1)c1cc(C(=O)N[C@H](c3ccccc3)[C@H](C)O)ccc1n2-c1ccc(C(F)(F)F)cc1] N-[(1R,2S)-2-hydroxy-1-phenylpropyl]-2-methyl-4-[4-(trifluoromethyl)phenyl]-4H-[1,3]thiazolo[4,5-b]indole-7-carboxamide |

| Compound No. | Structure and Name |
|---|---|
| 536 | 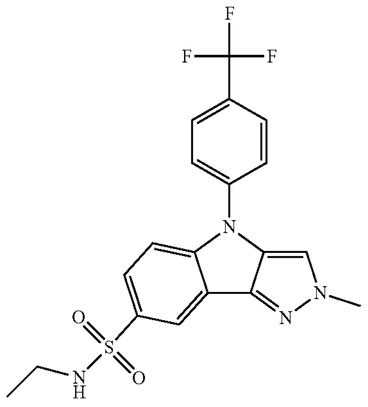 [SMILES: CCNS(=O)(=O)c1ccc2c(c1)c1nn(C)cc1n2-c1ccc(C(F)(F)F)cc1] N-ethyl-2-methyl-4-[4-(trifluoromethyl)phenyl]-2H,4H-pyrazolo[4,3-b]indole-7-sulfonamide |
| 537 | 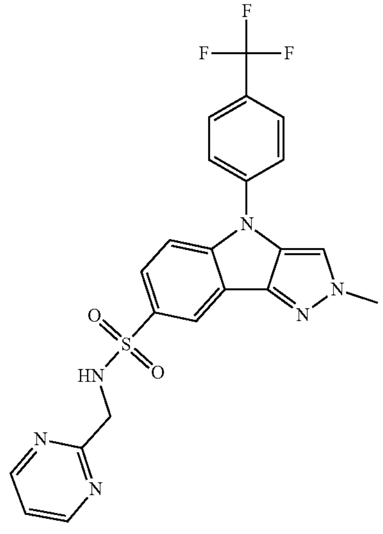 [SMILES: Cn1cc2c(n1)c1cc(S(=O)(=O)NCc3ncccn3)ccc1n2-c1ccc(C(F)(F)F)cc1] 2-methyl-N-[(pyrimidin-2-yl)methyl]-4-[4-(trifluoromethyl)phenyl]-2H,4H-pyrazolo[4,3-b]indole-7-sulfonamide |

-continued

| Compound No. | Structure and Name |
| --- | --- |
| 538 | Absolute 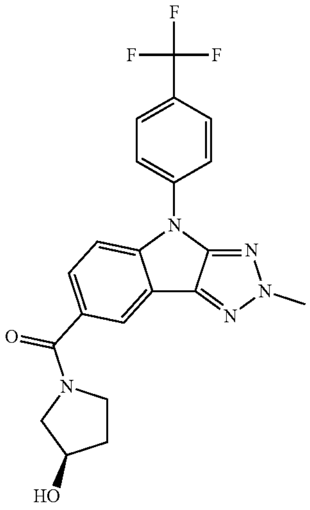 (3R)-1-{2-methyl-4-[4-(trifluoromethyl)phenyl]-2H,4H-[1,2,3]triazolo[4,5-b]indole-7-carbonyl}pyrrolidin-3-ol |
| 539 | 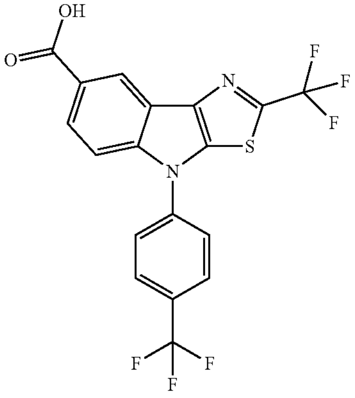 [SMILES: O=C(O)c1ccc2c(c1)c1nc(C(F)(F)F)sc1n2-c1ccc(C(F)(F)F)cc1] 2-(trifluoromethyl)-4-[4-(trifluoromethyl)phenyl]-4H-[1,3]thiazolo[5,4-b]indole-7-carboxylic acid |

-continued

| Compound No. | Structure and Name |
| --- | --- |
| 540 | Absolute 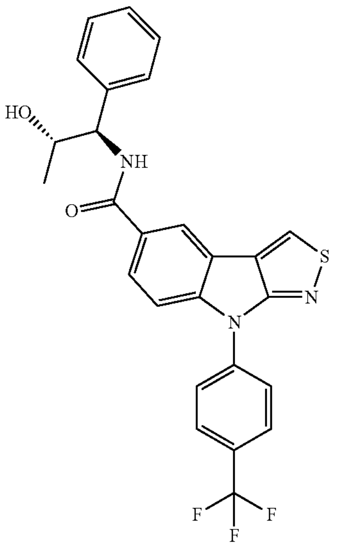 N-[(1R,2S)-2-hydroxy-1-phenylpropyl]-8-[4-(trifluoromethyl)phenyl]-8H-[1,2]thiazolo[3,4-b]indole-5-carboxamide |
| 541 | Absolute 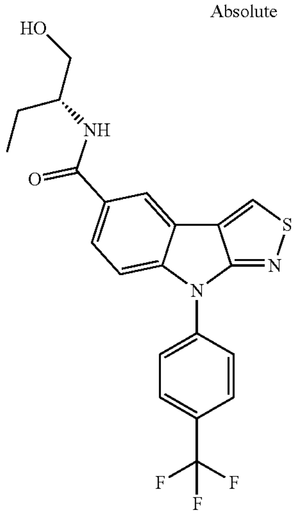 [SMILES: CC[C@H](CO)NC(=O)c1ccc2c(c1)c1csnc1n2-c1ccc(C(F)(F)F)cc1] N-[(2R)-1-hydroxybutan-2-yl]-8-[4-(trifluoromethyl)phenyl]-8H-[1,2]thiazolo[3,4-b]indole-5-carboxamide |

-continued

| Compound No. | Structure and Name |
| --- | --- |
| 542 | Absolute 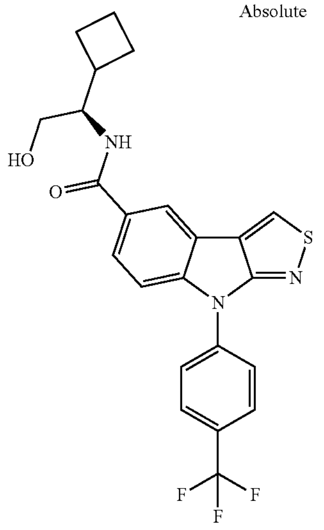 [SMILES: O=C(N[C@@H](CO)C1CCC1)c1ccc2c(c1)c1csnc1n2-c1ccc(C(F)(F)F)cc1] N-[(1R)-1-cyclobutyl-2-hydroxyethyl]-8-[4-(trifluoromethyl)phenyl]-8H-[1,2]thiazolo[3,4-b]indole-5-carboxamide |
| 543 | Absolute 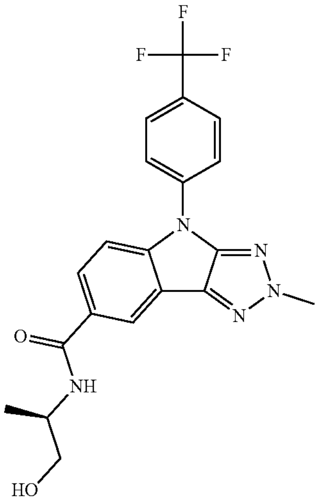 N-[(2R)-1-hydroxypropan-2-yl]-2-methyl-4-[4-(trifluoromethyl)phenyl]-2H,4H-[1,2,3]triazolo[4,5-b]indole-7-carboxamide |

-continued

| Compound No. | Structure and Name |
| --- | --- |
| 544 | 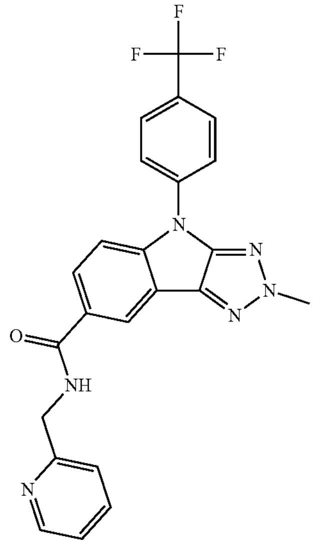 [SMILES: Cn1nc2c3cc(C(=O)NCc4ccccn4)ccc3n(-c3ccc(C(F)(F)F)cc3)c2n1] 2-methyl-N-[(pyridin-2-yl)methyl]-4-[4-(trifluoromethyl)phenyl]-2H,4H-[1,2,3]triazolo[4,5-b]indole-7-carboxamide |
| 545 | Absolute 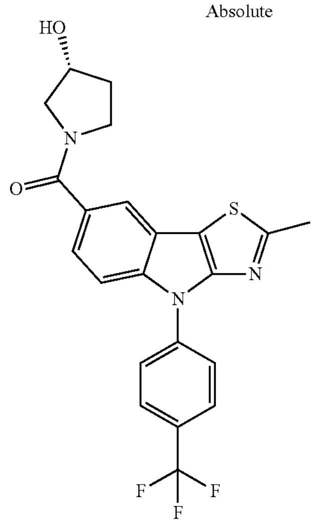 [SMILES: Cc1nc2c(s1)c1cc(C(=O)N3CC[C@@H](O)C3)ccc1n2-c1ccc(C(F)(F)F)cc1] (3R)-1-{2-methyl-4-[4-(trifluoromethyl)phenyl]-4H-[1,3]thiazolo[4,5-b]indole-7-carbonyl}pyrrolidin-3-ol |

-continued

| Compound No. | Structure and Name |
|---|---|
| 546 | Absolute<br>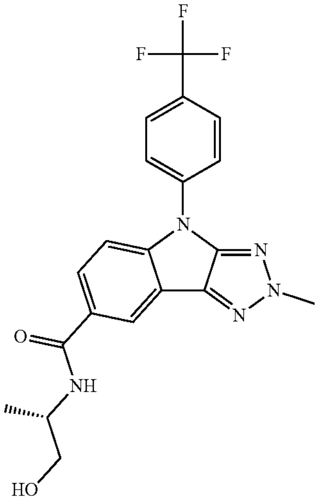<br>N-[(2S)-1-hydroxypropan-2-yl]-2-methyl-4-[4-(trifluoromethyl)phenyl]-2H,4H-[1,2,3]triazolo[4,5-b]indole-7-carboxamide |
| 547 | Absolute<br>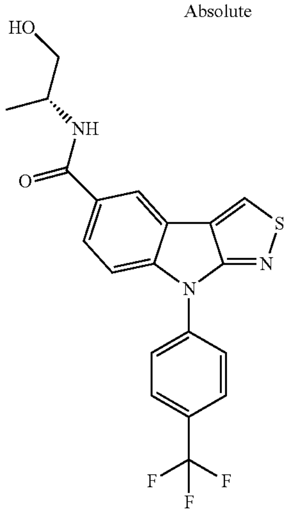 [SMILES: C[C@H](CO)NC(=O)c1ccc2c(c1)c1csnc1n2-c1ccc(C(F)(F)F)cc1]<br>N-[(2R)-1-hydroxypropan-2-yl]-8-[4-(trifluoromethyl)phenyl]-8H-[1,2]thiazolo[3,4-b]indole-5-carboxamide |

-continued

| Compound No. | Structure and Name |
|---|---|
| 548 | Absolute<br>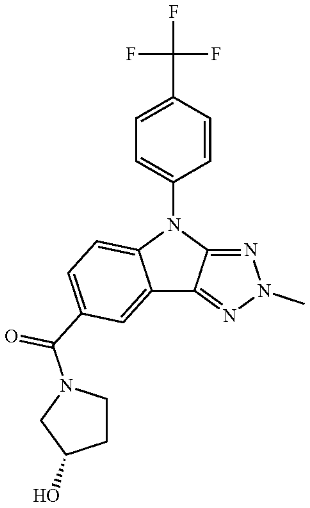<br>(3S)-1-{2-methyl-4-[4-(trifluoromethyl)phenyl]-2H,4H-[1,2,3]triazolo[4,5-b]indole-7-carbonyl}pyrrolidin-3-ol |
| 549 | Absolute<br>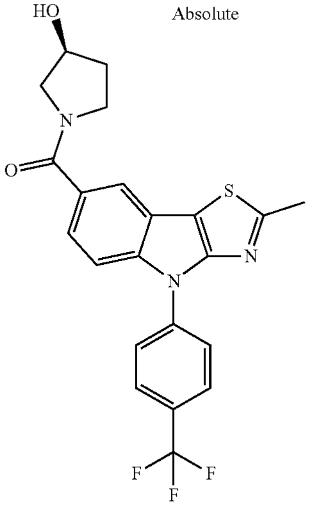 [SMILES: Cc1nc2c(s1)c1cc(C(=O)N3CC[C@H](O)C3)ccc1n2-c1ccc(C(F)(F)F)cc1]<br>(3S)-1-{2-methyl-4-[4-(trifluoromethyl)phenyl]-4H-[1,3]thiazolo[4,5-b]indole-7-carbonyl}pyrrolidin-3-ol |
| 550 | 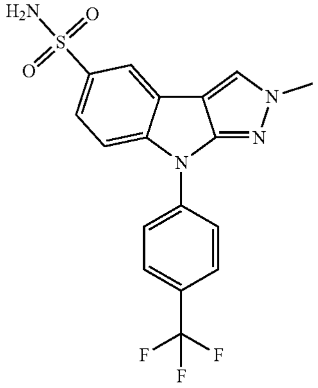 [SMILES: Cn1cc2c3cc(S(N)(=O)=O)ccc3n(-c3ccc(C(F)(F)F)cc3)c2n1] |

-continued

| Compound No. | Structure and Name |
|---|---|
| | 2-methyl-8-[4-(trifluoromethyl)phenyl]-2H,8H-pyrazolo[3,4-b]indole-5-sulfonamide |
| 551 | 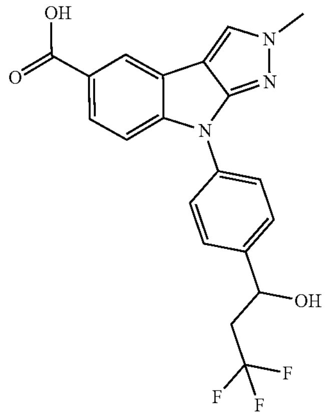 [SMILES: Cn1cc2c3cc(C(=O)O)ccc3n(-c3ccc(C(O)CC(F)(F)F)cc3)c2n1] 2-methyl-8-[4-(3,3,3-trifluoro-1-hydroxypropyl)phenyl]-2H,8H-pyrazolo[3,4-b]indole-5-carboxylic acid |
| 552 | 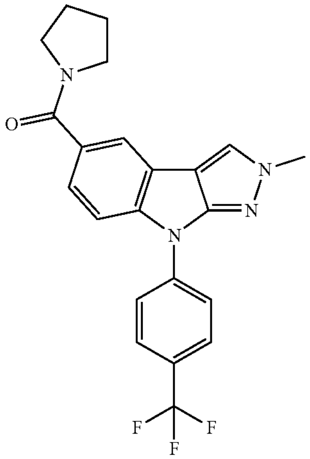 [SMILES: Cn1cc2c3cc(C(=O)N4CCCC4)ccc3n(-c3ccc(C(F)(F)F)cc3)c2n1] 1-{2-methyl-8-[4-(trifluoromethyl)phenyl]-2H,8H-pyrazolo[3,4-b]indole-5-carbonyl}pyrrolidine |
| 553 | 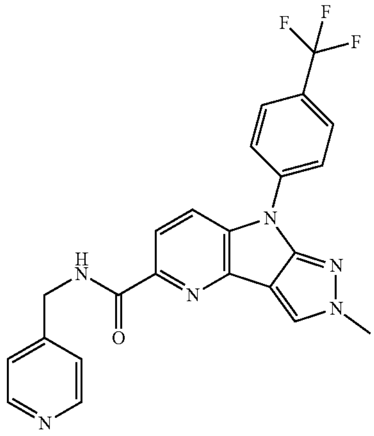 [SMILES: Cn1cc2c3nc(C(=O)NCc4ccncc4)ccc3n(-c3ccc(C(F)(F)F)cc3)c2n1] |

-continued

| Compound No. | Structure and Name |
|---|---|
| | 4-methyl-N-[(pyridin-4-yl)methyl]-7-[4-(trifluoromethyl)phenyl]-4,5,7,12-tetraazatricyclo[6.4.0.0$^{2,6}$]dodeca-1(8),2,5,9,11-pentaene-11-carboxamide |
| 554 | 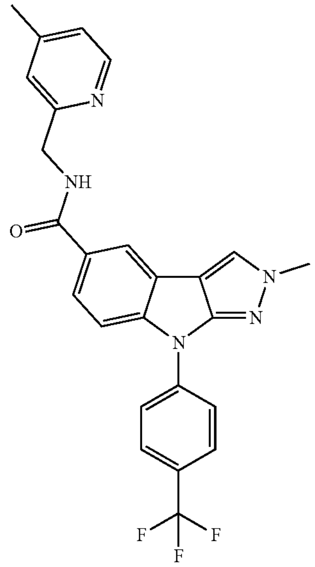 2-methyl-N-[(4-methylpyridin-2-yl)methyl]-8-[4-(trifluoromethyl)phenyl]-2H,8H-pyrazolo[3,4-b]indole-5-carboxamide |
| 555 | 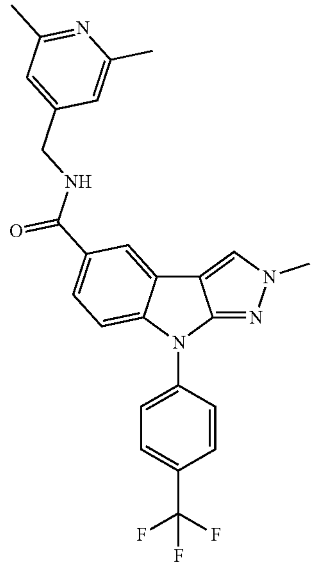 N-[(2,6-dimethylpyridin-4-yl)methyl]-2-methyl-8-[4-(trifluoromethyl)phenyl]-2H,8H-pyrazolo[3,4-b]indole-5-carboxamide |

-continued

| Compound No. | Structure and Name |
| --- | --- |
| 556 | Absolute 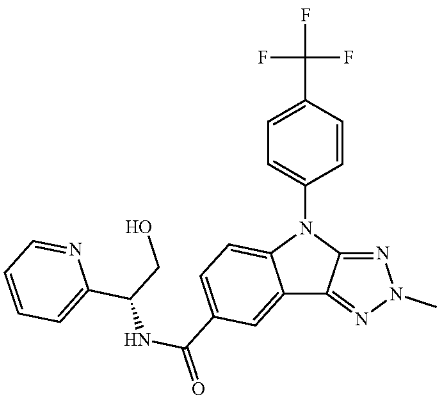 N-[(1R)-2-hydroxy-1-(pyridin-2-yl)ethyl]-2-methyl-4-[4-(trifluoromethyl)phenyl]-2H,4H-[1,2,3]triazolo[4,5-b]indole-7-carboxamide |
| 557 | Absolute 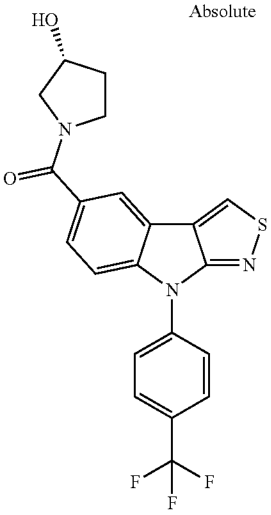 [SMILES: O=C(c1ccc2c(c1)c1csnc1n2-c1ccc(C(F)(F)F)cc1)N1CC[C@@H](O)C1] (3R)-1-{8-[4-(trifluoromethyl)phenyl]-8H-[1,2]thiazolo[3,4-b]indole-5-carbonyl}pyrrolidin-3-ol |

-continued

| Compound No. | Structure and Name |
| --- | --- |
| 558 | Absolute 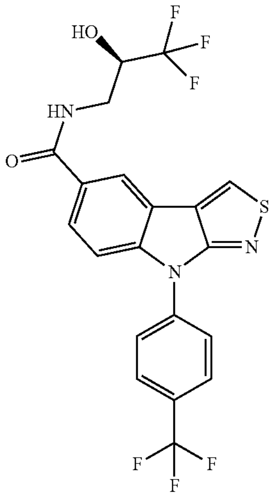 N-[(2R)-3,3,3-trifluoro-2-hydroxypropyl]-8-[4-(trifluoromethyl)phenyl]-8H-[1,2]thiazolo[3,4-b]indole-5-carboxamide |
| 559 | 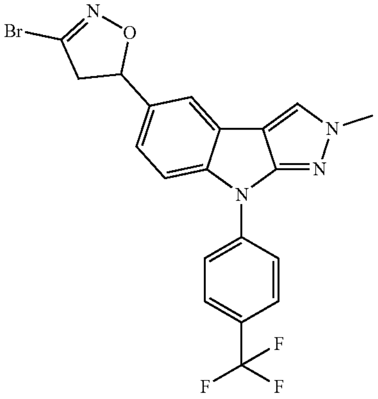 3-bromo-5-{2-methyl-8-[4-(trifluoromethyl)phenyl]-2H,8H-pyrazolo[3,4-b]indol-5-yl}-4,5-dihydro-1,2-oxazole |
| 560 | 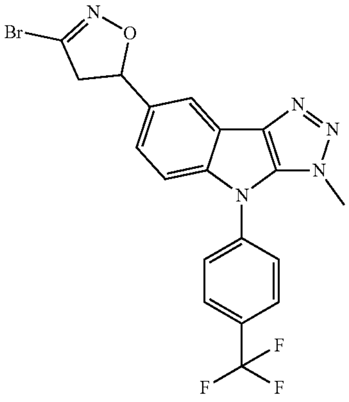 [SMILES: Cn1nnc2c3cc(C4CC(Br)=NO4)ccc3n(-c3ccc(C(F)(F)F)cc3)c21] 3-bromo-5-{3-methyl-4-[4-(trifluoromethyl)phenyl]-3H,4H-[1,2,3]triazolo[4,5-b]indol-7-yl}-4,5-dihydro-1,2-oxazole |

-continued

| Compound No. | Structure and Name |
| --- | --- |
| 561 | Absolute 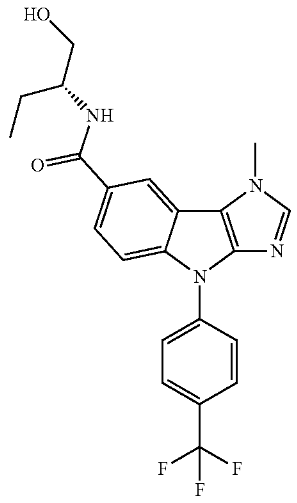 N-[(2R)-1-hydroxybutan-2-yl]-1-methyl-4-[4-(trifluoromethyl)phenyl]-1H,4H-imidazo[4,5-b]indole-7-carboxamide |
| 562 | 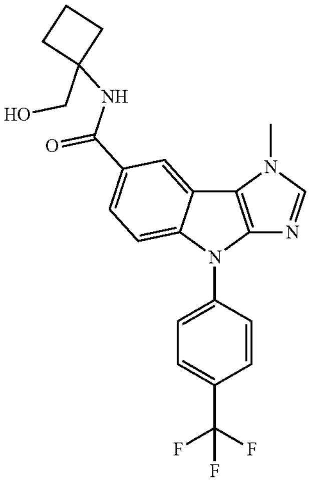 [SMILES: Cn1cnc2c1c1cc(C(=O)NC3(CO)CCC3)ccc1n2-c1ccc(C(F)(F)F)cc1] N-[1-(hydroxymethyl)cyclobutyl]-1-methyl-4-[4-(trifluoromethyl)phenyl]-1H,4H-imidazo[4,5-b]indole-7-carboxamide |
| 563 | Absolute 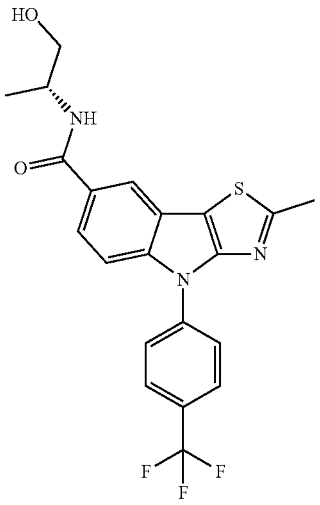 N-[(2R)-1-hydroxypropan-2-yl]-2-methyl-4-[4-(trifluoromethyl)phenyl]-4H-[1,3]thiazolo[4,5-b]indole-7-carboxamide |
| 564 | 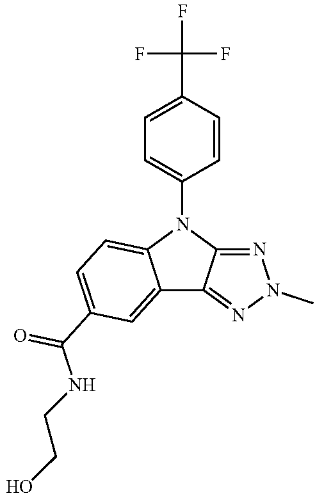 [SMILES: Cn1nc2c3cc(C(=O)NCCO)ccc3n(-c3ccc(C(F)(F)F)cc3)c2n1] N-(2-hydroxyethyl)-2-methyl-4-[4-(trifluoromethyl)phenyl]-2H,4H-[1,2,3]triazolo[4,5-b]indole-7-carboxamide |

-continued

| Compound No. | Structure and Name |
|---|---|
| 565 | 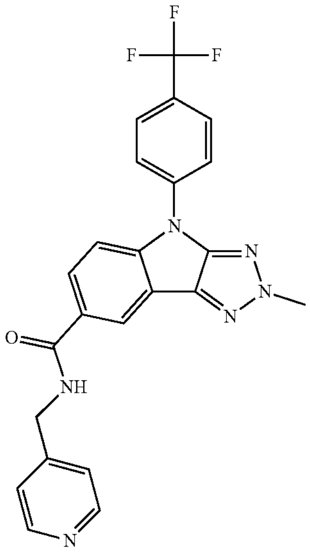 [SMILES: Cn1nc2c3cc(C(=O)NCc4ccncc4)ccc3n(-c3ccc(C(F)(F)F)cc3)c2n1] 2-methyl-N-[(pyridin-4-yl)methyl]-4-[4-(trifluoromethyl)phenyl]-2H,4H-[1,2,3]triazolo[4,5-b]indole-7-carboxamide |
| 566 | Absolute 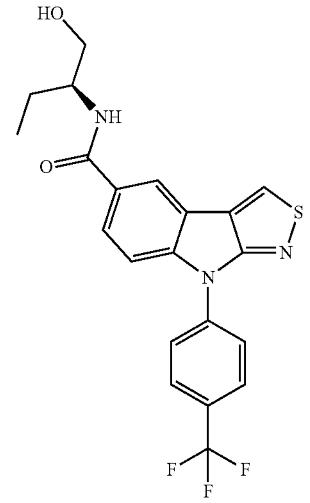 N-[(2S)-1-hydroxybutan-2-yl]-8-[4-(trifluoromethyl)phenyl]-8H-[1,2]thiazolo[3,4-b]indole-5-carboxamide |

-continued

| Compound No. | Structure and Name |
|---|---|
| 567 | Absolute 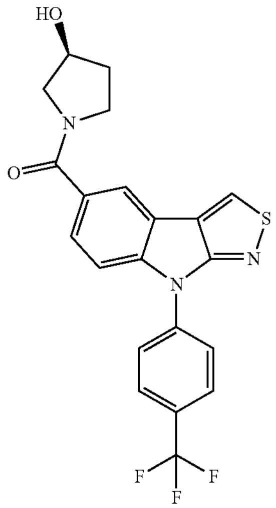 (3S)-1-{8-[4-(trifluoromethyl)phenyl]-8H-[1,2]thiazolo[3,4-b]indole-5-carbonyl}pyrrolidin-3-ol |
| 568 | Absolute 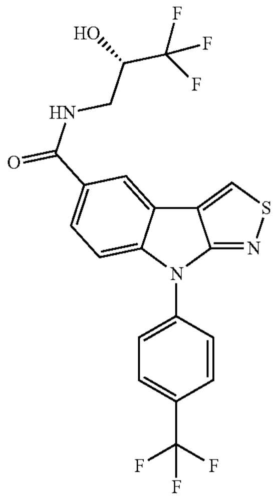 N-[(2S)-3,3,3-trifluoro-2-hydroxypropyl]-8-[4-(trifluoromethyl)phenyl]-8H-[1,2]thiazolo[3,4-b]indole-5-carboxamide |

-continued

| Compound No. | Structure and Name |
|---|---|
| 569 | Absolute 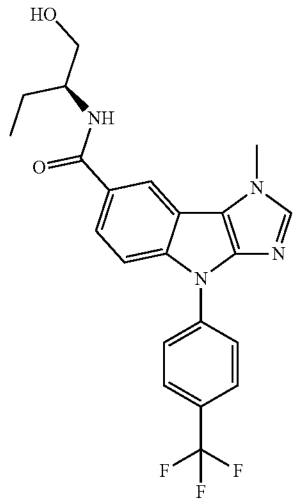 N-[(2S)-1-hydroxybutan-2-yl]-1-methyl-4-[4-(trifluoromethyl)phenyl]-1H,4H-imidazo[4,5-b]indole-7-carboxamide |
| 570 | Absolute 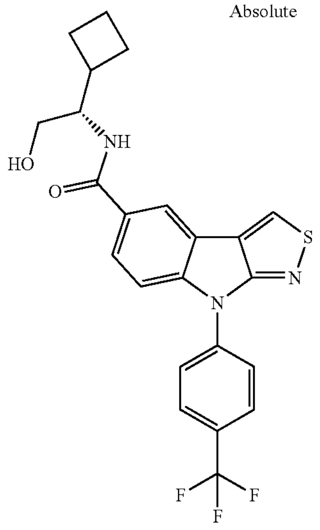 [SMILES: O=C(N[C@H](CO)C1CCC1)c1ccc2c(c1)c1csnc1n2-c1ccc(C(F)(F)F)cc1] N-[(1S)-1-cyclobutyl-2-hydroxyethyl]-8-[4-(trifluoromethyl)phenyl]-8H-[1,2]thiazolo[3,4-b]indole-5-carboxamide |

-continued

| Compound No. | Structure and Name |
|---|---|
| 571 | Absolute 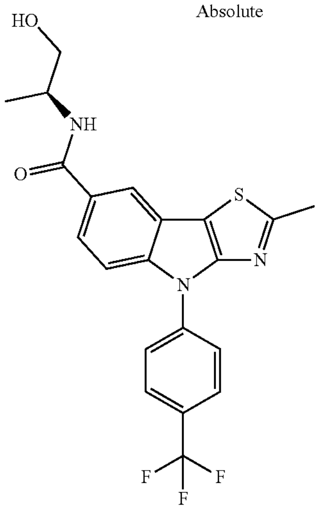 [SMILES: Cc1nc2c(s1)c1cc(C(=O)N[C@@H](C)CO)ccc1n2-c1ccc(C(F)(F)F)cc1] N-[(2S)-1-hydroxypropan-2-yl]-2-methyl-4-[4-(trifluoromethyl)phenyl]-4H-[1,3]thiazolo[4,5-b]indole-7-carboxamide |
| 572 | Absolute 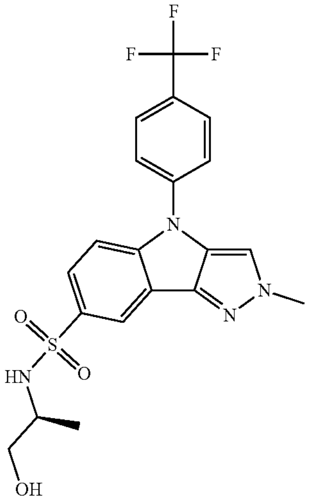 N-[(2S)-1-hydroxypropan-2-yl]-2-methyl-4-[4-(trifluoromethyl)phenyl]-2H,4H-pyrazolo[4,3-b]indole-7-sulfonamide |

-continued

| Compound No. | Structure and Name |
|---|---|
| 573 | 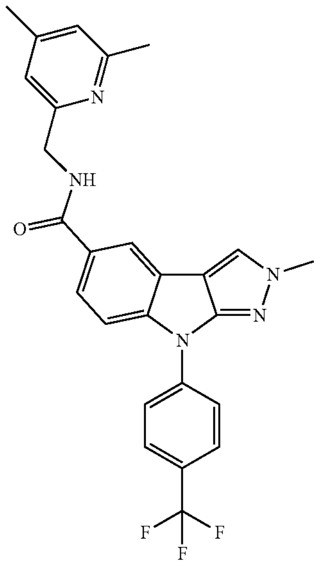 N-[(4,6-dimethylpyridin-2-yl)methyl]-2-methyl-8-[4-(trifluoromethyl)phenyl]-2H,8H-pyrazolo[3,4-b]indole-5-carboxamide |
| 574 | 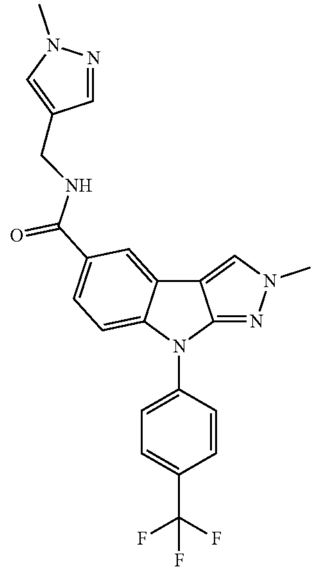 [SMILES: Cn1cc(CNC(=O)c2ccc3c(c2)c2cn(C)nc2n3-c2ccc(C(F)(F)F)cc2)cn1] 2-methyl-N-[(1-methyl-1H-pyrazol-4-yl)methyl]-8-[4-(trifluoromethyl)phenyl]-2H,8H-pyrazolo[3,4-b]indole-5-carboxamide |
| 575 | Absolute 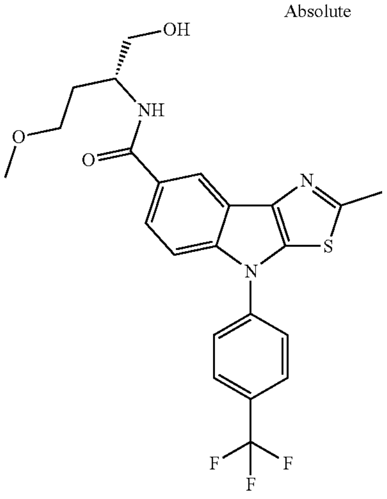 Absolute configuration assigned arbitrarily N-[(2R)-1-hydroxy-4-methoxybutan-2-yl]-2-methyl-4-[4-(trifluoromethyl)phenyl]-4H-[1,3]thiazolo[5,4-b]indole-7-carboxamide |
| 576 | Absolute 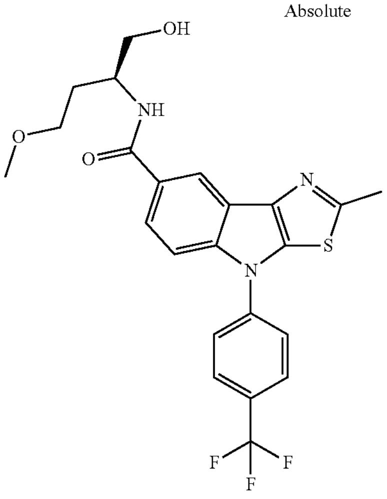 Absolute configuratin assigned arbitrarily N-[(2S)-1-hydroxy-4-methoxybutan-2-yl]-2-methyl-4-[4-(trifluoromethyl)phenyl]-4H-[1,3]thiazolo[5,4-b]indole-7-carboxamide |

-continued

| Compound No. | Structure and Name |
|---|---|
| 577 | Absolute<br>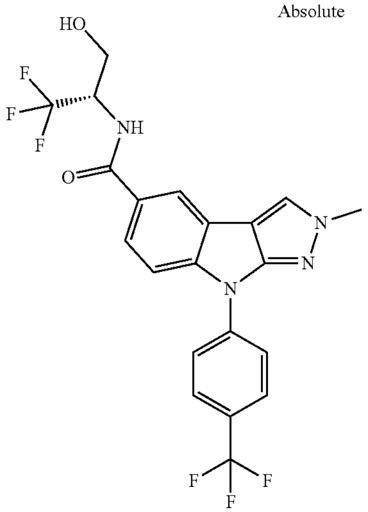 [SMILES: Cn1cc2c3cc(C(=O)N[C@@H](CO)C(F)(F)F)ccc3n(-c3ccc(C(F)(F)F)cc3)c2n1]<br>2-methyl-N-[(2S)-1,1,1-trifluoro-3-hydroxypropan-2-yl]-8-[4-(trifluoromethyl)phenyl]-2H,8H-pyrazolo[3,4-b]indole-5-carboxamide |
| 578 | 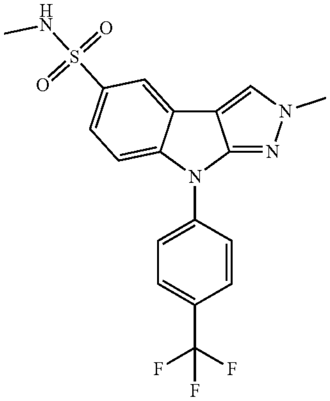<br>N,2-dimethyl-8-[4-(trifluoromethyl)phenyl]-2H,8H-pyrazolo[3,4-b]indole-5-sulfonamide |
| 579 | 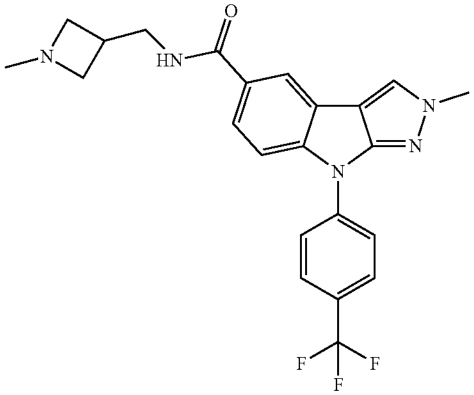<br>2-methyl-N-[(1-methylazetidin-3-yl)methyl]-8-[4-(trifluoromethyl)phenyl]-2H,8H-pyrazolo[3,4-b]indole-5-carboxamide |

-continued

| Compound No. | Structure and Name |
|---|---|
| 580 | 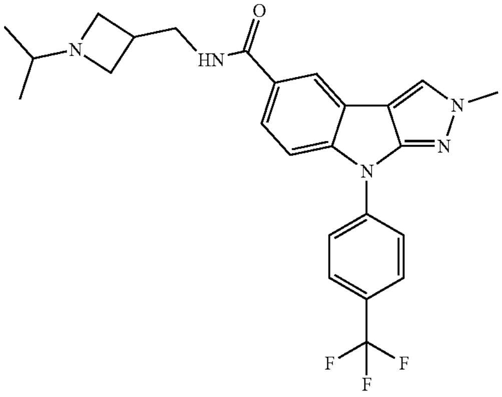 [SMILES: CC(C)N1CC(CNC(=O)c2ccc3c(c2)c2cn(C)nc2n3-c2ccc(C(F)(F)F)cc2)C1]<br>2-methyl-N-{[1-(propan-2-yl)azetidin-3-yl]methyl}-8-[4-(trifluoromethyl)phenyl]-2H,8H-pyrazolo[3,4-b]indole-5-carboxamide |
| 581 | 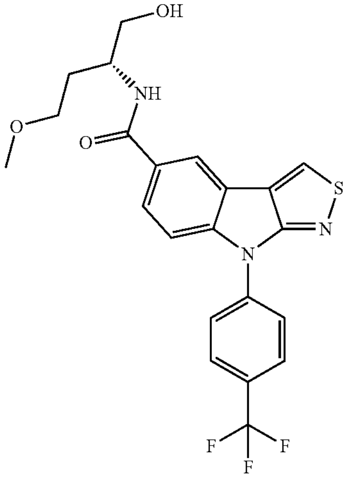 [SMILES: COCC[C@H](CO)NC(=O)c1ccc2c(c1)c1csnc1n2-c1ccc(C(F)(F)F)cc1]<br>Absolute configuration assigned arbitrarily<br>N-[(2R)-1-hydroxy-4-methoxybutan-2-yl]-8-[4-(trifluorosmethyl)phenyl]-8H-[1,2]thiazolo[3,4-b]indole-5-carboxamide |

-continued

| Compound No. | Structure and Name |
| --- | --- |
| 582 | Absolute<br>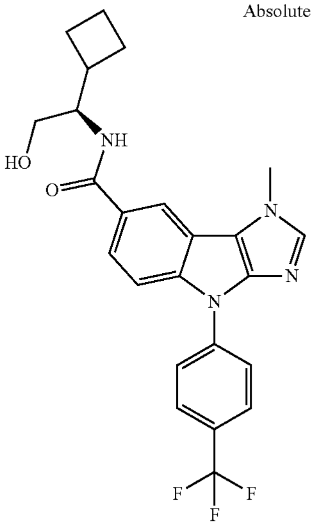 [SMILES: Cn1cnc2c1c1cc(C(=O)N[C@@H](CO)C3CCC3)ccc1n2-c1ccc(C(F)(F)F)cc1]<br>N-[(1R)-1-cyclobutyl-2-hydroxyethyl]-1-methyl-4-[4-(trifluoromethyl)phenyl]-1H,4H-imidazo[4,5-b]indole-7-carboxamide |
| 583 | 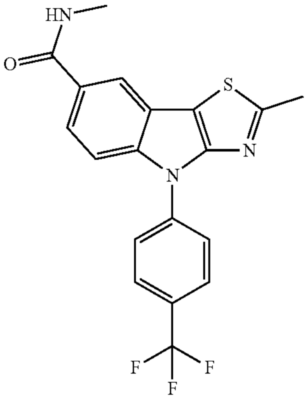 [SMILES: CNC(=O)c1ccc2c(c1)c1sc(C)nc1n2-c1ccc(C(F)(F)F)cc1]<br>N,2-dimethyl-4-[4-(trifluoromethyl)phenyl]-4H-[1,3]thiazolo[4,5-b]indole-7-carboxamide |
| 584 | Absolute<br>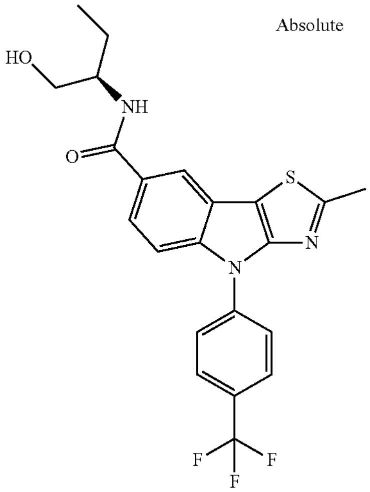 [SMILES: CC[C@H](CO)NC(=O)c1ccc2c(c1)c1sc(C)nc1n2-c1ccc(C(F)(F)F)cc1]<br>N-[(2R)-1-hydroxybutan-2-yl]-2-methyl-4-[4-(trifluoromethyl)phenyl]-4H-[1,3]thiazolo[4,5-b]indole-7-carboxamide |
| 585 | Absolute<br>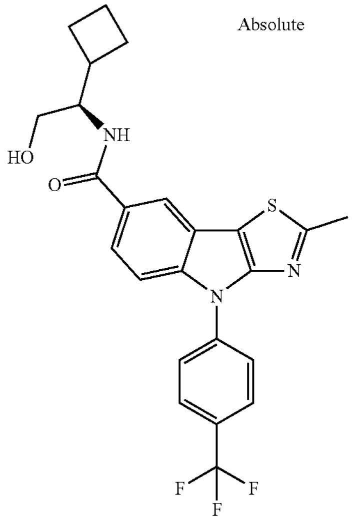 [SMILES: Cc1nc2c(s1)c1cc(C(=O)N[C@@H](CO)C3CCC3)ccc1n2-c1ccc(C(F)(F)F)cc1]<br>N-[(1R)-1-cyclobutyl-2-hydroxyethyl]-2-methyl-4-[4-(trifluoromethyl)phenyl]-4H-[1,3]thiazolo[4,5-b]indole-7-carboxamide |
| 586 | 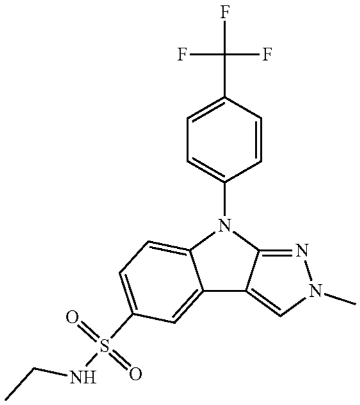 [SMILES: CCNS(=O)(=O)c1ccc2c(c1)c1cn(C)nc1n2-c1ccc(C(F)(F)F)cc1]<br>N-ethyl-2-methyl-8-[4-(trifluoromethyl)phenyl]-2H,8H-pyrazolo[3,4-b]indole-5-sulfonamide |

-continued

| Compound No. | Structure and Name |
|---|---|
| 587 | 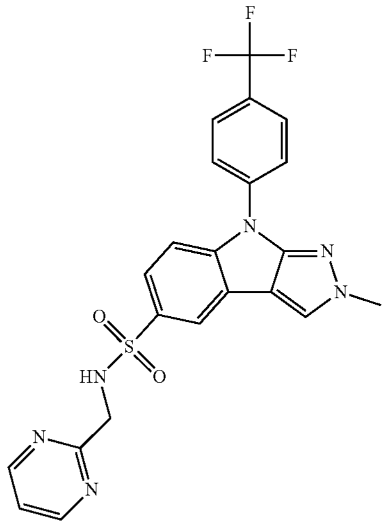 [SMILES: Cn1cc2c3cc(S(=O)(=O)NCc4ncccn4)ccc3n(-c3ccc(C(F)(F)F)cc3)c2n1] 2-methyl-N-[(pyrimidin-2-yl)methyl]-8-[4-(trifluoromethyl)phenyl]-2H,8H-pyrazolo[3,4-b]indole-5-sulfonamide |
| 588 | 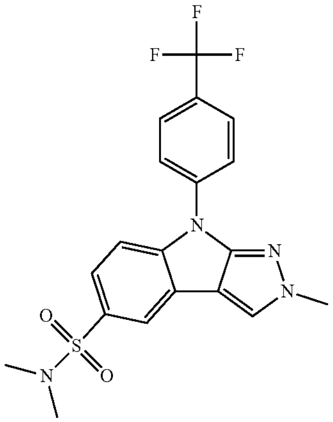 N,N,2-trimethyl-8-[4-(trifluoromethyl)phenyl]-2H,8H-pyrazolo[3,4-b]indole-5-sulfonamide |

-continued

| Compound No. | Structure and Name |
|---|---|
| 589 | Absolute 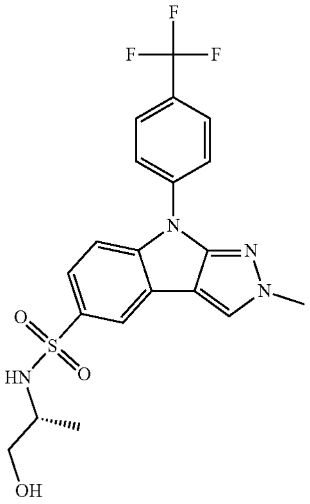 N-[(2R)-1-hydroxypropan-2-yl]-2-methyl-8-[4-(trifluoromethyl)phenyl]-2H,8H-pyrazolo[3,4-b]indole-5-sulfonamide |
| 590 | Absolute 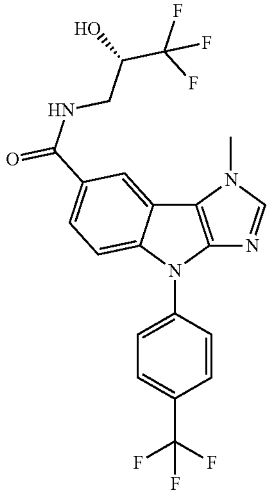 1-methyl-N-[(2S)-3,3,3-trifluoro-2-hydroxypropyl]-4-[4-(trifluoromethyl)phenyl]-1H,4H-imidazo[4,5-b]indole-7-carboxamide |

-continued

| Compound No. | Structure and Name |
| --- | --- |
| 591 | 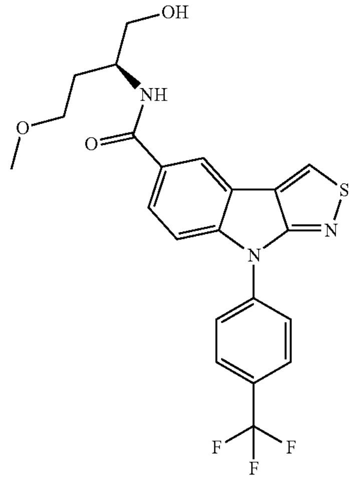 [SMILES: COCC[C@@H](CO)NC(=O)c1ccc2c(c1)c1csnc1n2-c1ccc(C(F)(F)F)cc1] Absolute configuration assigned arbitrarily N-[(2S)-1-hydroxy-4-methoxybutan-2-yl]-8-[4-(trifluoromethyl)phenyl]-8H-[1,2]thiazolo[3,4-b]indole-5-carboxamide |
| 592 | Absolute 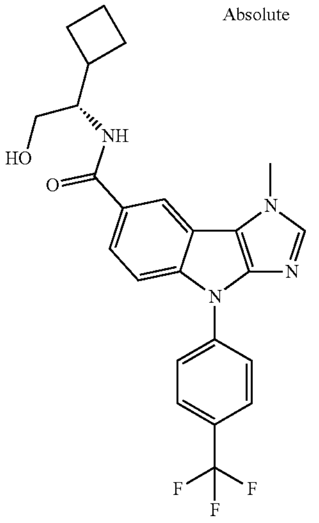 [SMILES: Cn1cnc2c1c1cc(C(=O)N[C@H](CO)C3CCC3)ccc1n2-c1ccc(C(F)(F)F)cc1] N-[(1S)-1-cyclobutyl-2-hydroxyethyl]-1-methyl-4-[4-(trifluoromethyl)phenyl]-1H,4H-imidazo[4,5-b]indole-7-carboxamide |

-continued

| Compound No. | Structure and Name |
| --- | --- |
| 593 | Absolute 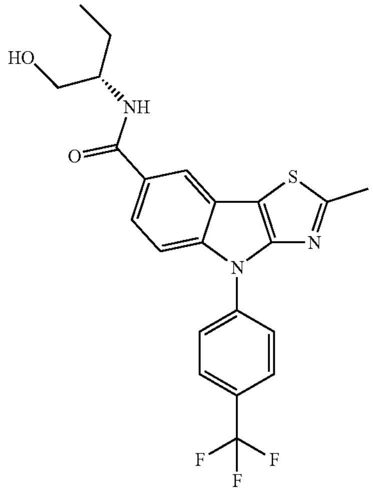 N-[(2S)-1-hydroxybutan-2-yl]-2-methyl-4-[4-(trifluoromethyl)phenyl]-4H-[1,3]thiazolo[4,5-b]indole-7-carboxamide |
| 594 | Absolute 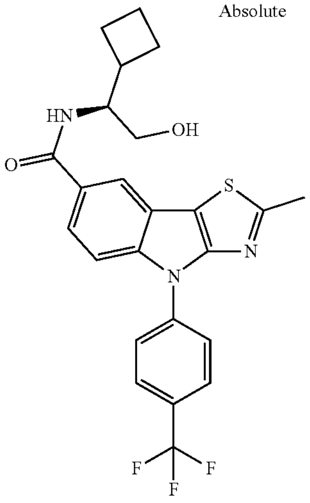 [SMILES: Cc1nc2c(s1)c1cc(C(=O)N[C@H](CO)C3CCC3)ccc1n2-c1ccc(C(F)(F)F)cc1] N-[(1S)-1-cyclobutyl-2-hydroxyethyl]-2-methyl-4-[4-(trifluoromethyl)phenyl]-4H-[1,3]thiazolo[4,5-b]indole-7-carboxamide |

| Compound No. | Structure and Name |
|---|---|
| 595 | Absolute<br>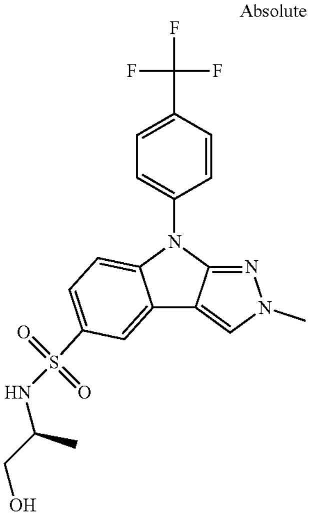 [SMILES: C[C@@H](CO)NS(=O)(=O)c1ccc2c(c1)c1cn(C)nc1n2-c1ccc(C(F)(F)F)cc1]<br>N-[(2S)-1-hydroxypropan-2-yl]-2-methyl-8-[4-(trifluoromethyl)phenyl]-2H,8H-pyrazolo[3,4-b]indole-5-sulfonamide |
| 596 | Absolute<br>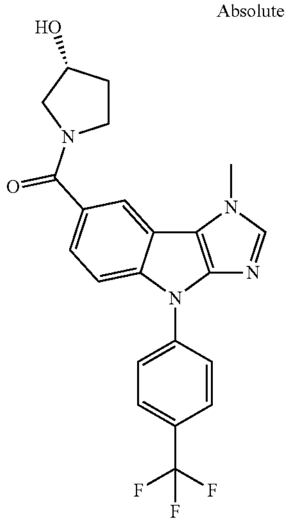 [SMILES: Cn1cnc2c1c1cc(C(=O)N3CC[C@@H](O)C3)ccc1n2-c1ccc(C(F)(F)F)cc1]<br>(3R)-1-{1-methyl-4-[4-(trifluoromethyl)phenyl]-1H,4H-imidazo[4,5-b]indole-7-carbonyl}pyrrolidin-3-ol |

| Compound No. | Structure and Name |
|---|---|
| 597 | Absolute<br>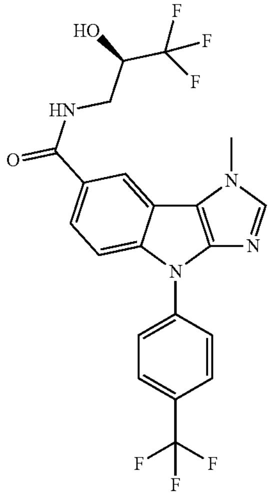<br>1-methyl-N-[(2R)-3,3,3-trifluoro-2-hydroxypropyl]-4-[4-(trifluoromethyl)phenyl]-1H,4H-imidazo[4,5-b]indole-7-carboxamide |
| 598 | Absolute<br>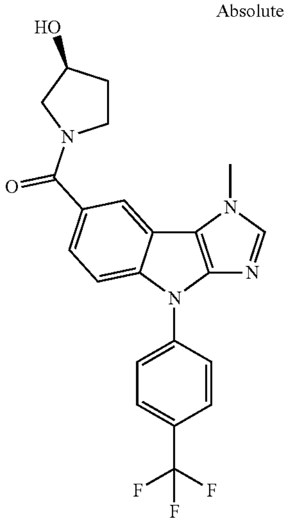 [SMILES: Cn1cnc2c1c1cc(C(=O)N3CC[C@H](O)C3)ccc1n2-c1ccc(C(F)(F)F)cc1]<br>(3S)-1-{1-methyl-4-[4-(trifluoromethyl)phenyl]-1H,4H-imidazo[4,5-b]indole-7-carbonyl}pyrrolidin-3-ol |

-continued

| Compound No. | Structure and Name |
|---|---|
| 599 | Absolute 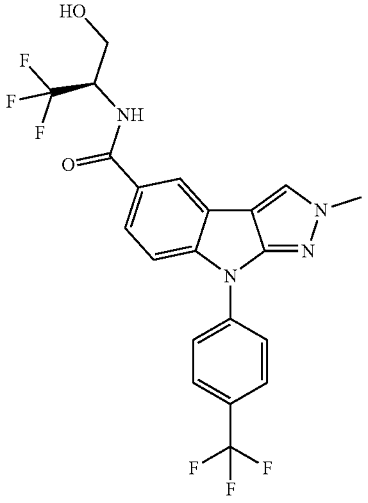 2-methyl-N-[(2R)-1,1,1-trifluoro-3-hydroxypropan-2-yl]-8-[4-(trifluoromethyl)phenyl]-2H,8H-pyrazolo[3,4-b]indole-5-carboxamide |
| 600 | 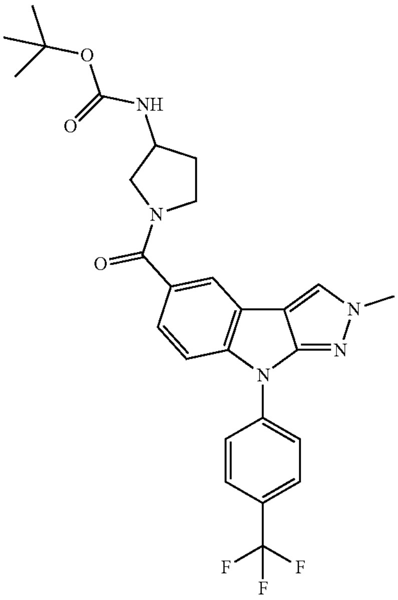 [SMILES: Cn1cc2c3cc(C(=O)N4CCC(NC(=O)OC(C)(C)C)C4)ccc3n(-c3ccc(C(F)(F)F)cc3)c2n1] tert-butyl N-(1-{2-methyl-8-[4-(trifluoromethyl)phenyl]-2H,8H-pyrazolo[3,4-b]indole-5-carbonyl}pyrrolidin-3-yl)carbamate |

-continued

| Compound No. | Structure and Name |
|---|---|
| 601 | 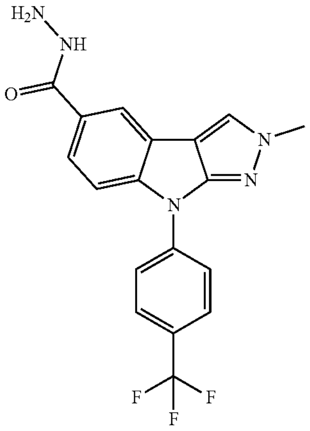 [SMILES: Cn1cc2c3cc(C(=O)NN)ccc3n(-c3ccc(C(F)(F)F)cc3)c2n1] 2-methyl-8-[4-(trifluoromethyl)phenyl]-2H,8H-pyrazolo[3,4-b]indole-5-carbohydrazide |
| 602 | 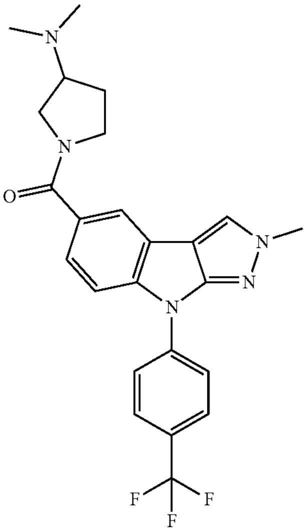 [SMILES: CN(C)C1CCN(C(=O)c2ccc3c(c2)c2cn(C)nc2n3-c2ccc(C(F)(F)F)cc2)C1] N,N-dimethyl-1-{2-methyl-8-[4-(trifluoromethyl)phenyl]-2H,8H-pyrazolo[3,4-b]indole-5-carbonyl}pyrrolidin-3-amine |

-continued

| Compound No. | Structure and Name |
|---|---|
| 603 | Absolute 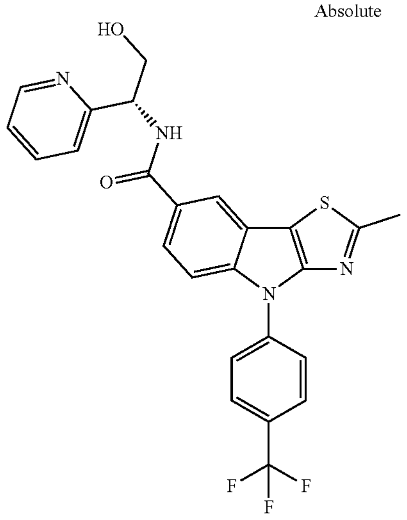 [SMILES: Cc1nc2c(s1)c1cc(C(=O)N[C@@H](CO)c3ccccn3)ccc1n2-c1ccc(C(F)(F)F)cc1] N-[(1R)-2-hydroxy-1-(pyridin-2-yl)ethyl]-2-methyl-4-[4-(trifluoromethyl)phenyl]-4H-[1,3]thiazolo[4,5-b]indole-7-carboxamide |
| 604 | Absolute 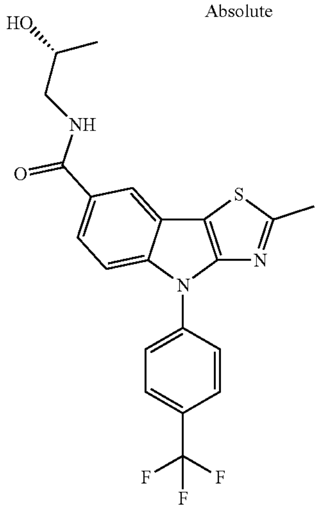 [SMILES: Cc1nc2c(s1)c1cc(C(=O)NC[C@@H](C)O)ccc1n2-c1ccc(C(F)(F)F)cc1] N-[(2R)-2-hydroxypropyl]-2-methyl-4-[4-(trifluoromethyl)phenyl]-4H-[1,3]thiazolo[4,5-b]indole-7-carboxamide |
| 605 | Absolute 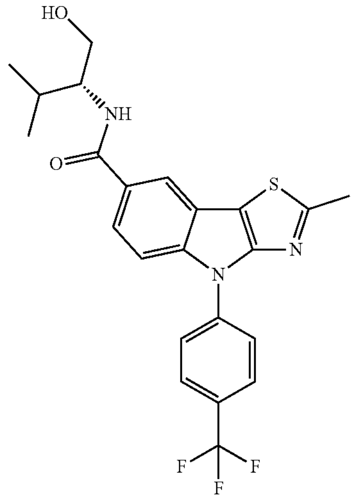 N-[(2R)-1-hydroxy-3-methylbutan-2-yl]-2-methyl-4-[4-(trifluoromethyl)phenyl]-4H-[1,3]thiazolo[4,5-b]indole-7-carboxamide |
| 606 | Absolute 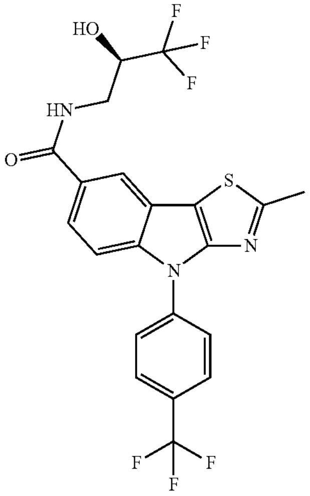 2-methyl-N-[(2R)-3,3,3-trifluoro-2-hydroxypropyl]-4-[4-(trifluoromethyl)phenyl]-4H-[1,3]thiazolo[4,5-b]indole-7-carboxamide |

-continued

| Compound No. | Structure and Name |
|---|---|
| 607 | 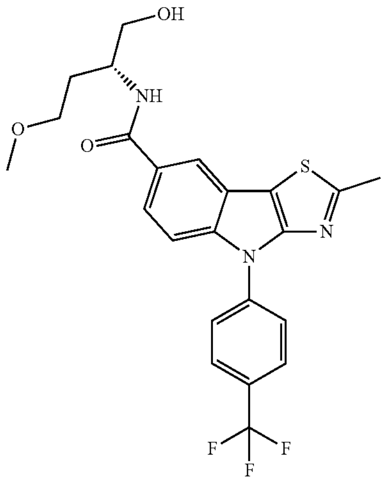<br>Absolute configuration assigned arbitrarily<br>N-[(2R)-1-hydroxy-4-methoxybutan-2-yl]-2-methyl-4-[4-(trifluoromethyl)phenyl]-4H-[1,3]thiazolo[4,5-b]indole-7-carboxamide |
| 608 | 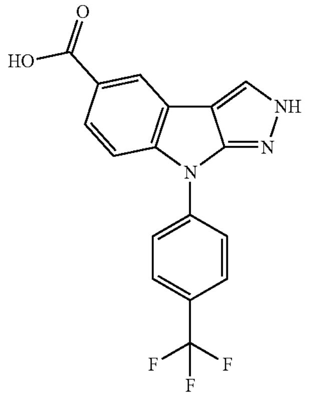 [SMILES: O=C(O)c1ccc2c(c1)c1c[nH]nc1n2-c1ccc(C(F)(F)F)cc1]<br>8-[4-(trifluoromethyl)phenyl]-2H,8H-pyrazolo[3,4-b]indole-5-carboxylic acid |
| 609 | Absolute<br>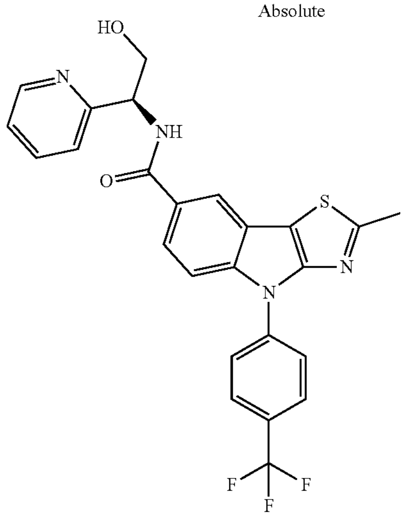 [SMILES: Cc1nc2c(s1)c1cc(C(=O)N[C@H](CO)c3ccccn3)ccc1n2-c1ccc(C(F)(F)F)cc1] |

-continued

| Compound No. | Structure and Name |
|---|---|
| | N-[(1S)-2-hydroxy-1-(pyridin-2-yl)ethyl]-2-methyl-4-[4-(trifluoromethyl)phenyl]-4H-[1,3]thiazolo[4,5-b]indole-7-carboxamide |
| 610 | Absolute<br>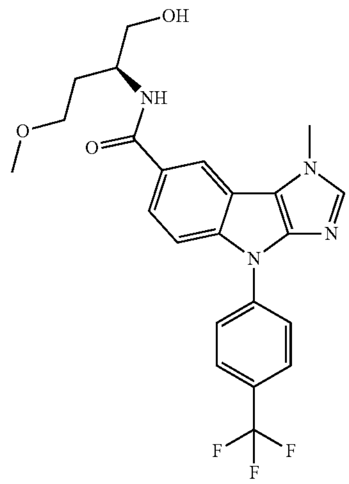<br>N-[(2S)-1-hydroxy-4-methoxybutan-2-yl]-1-methyl-4-[4-(trifluoromethyl)phenyl]-1H,4H-imidazo[4,5-b]indole-7-carboxamide |
| 611 | Absolute<br>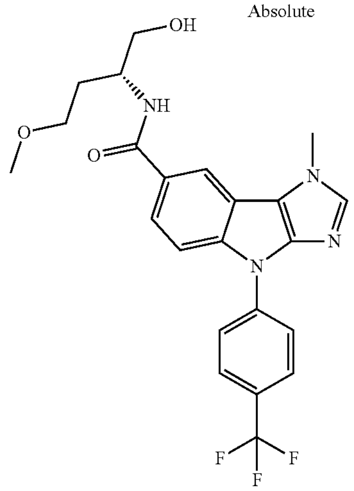 [SMILES: COCC[C@H](CO)NC(=O)c1ccc2c(c1)c1c(ncn1C)n2-c1ccc(C(F)(F)F)cc1]<br>N-[(2R)-1-hydroxy-4-methoxybutan-2-yl]-1-methyl-4-[4-(trifluoromethyl)phenyl]-1H,4H-imidazo[4,5-b]indole-7-carboxamide |

-continued

| Compound No. | Structure and Name |
| --- | --- |
| 612 | Absolute 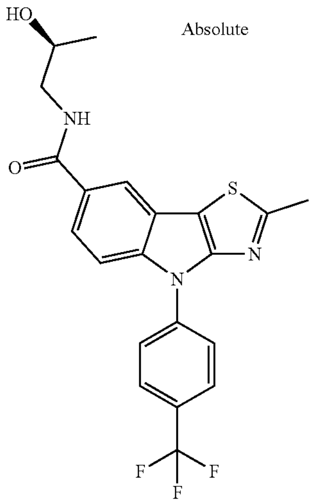 [SMILES: Cc1nc2c(s1)c1cc(C(=O)NC[C@H](C)O)ccc1n2-c1ccc(C(F)(F)F)cc1] N-[(2S)-2-hydroxypropyl]-2-methyl-4-[4-(trifluoromethyl)phenyl]-4H-[1,3]thiazolo[4,5-b]indole-7-carboxamide |
| 613 | Absolute 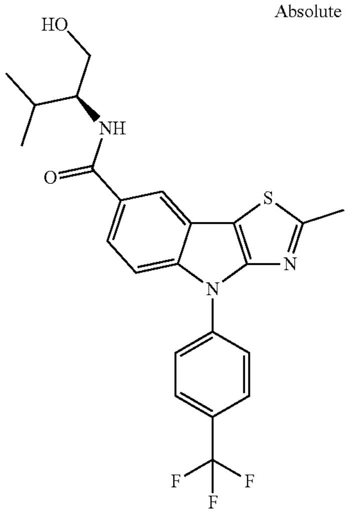 [SMILES: Cc1nc2c(s1)c1cc(C(=O)N[C@H](CO)C(C)C)ccc1n2-c1ccc(C(F)(F)F)cc1] N-[(2S)-1-hydroxy-3-methylbutan-2-yl]-2-methyl-4-[4-(trifluoromethyl)phenyl]-4H-[1,3]thiazolo[4,5-b]indole-7-carboxamide |
| 614 | Absolute 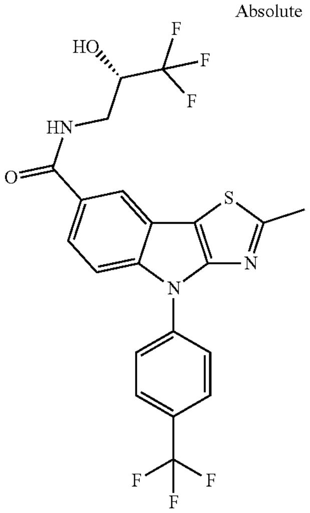 [SMILES: Cc1nc2c(s1)c1cc(C(=O)NC[C@H](O)C(F)(F)F)ccc1n2-c1ccc(C(F)(F)F)cc1] 2-methyl-N-[(2S)-3,3,3-trifluoro-2-hydroxypropyl]-4-[4-(trifluoromethyl)phenyl]-4H-[1,3]thiazolo[4,5-b]indole-7-carboxamide |
| 615 | 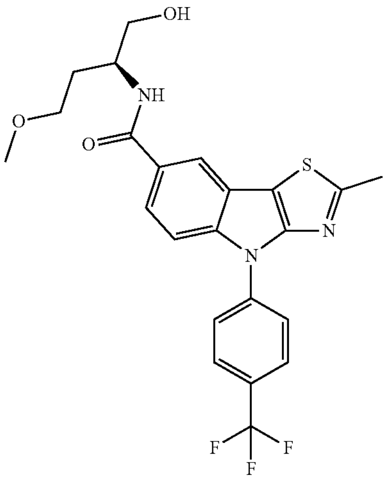 Absolute configuration assigned arbitrarily N-[(2S)-1-hydroxy-4-methoxybutan-2-yl]-2-methyl-4-[4-(trifluoromethyl)phenyl]-4H-[1,3]thiazolo[4,5-b]indole-7-carboxamide |
| 616 | 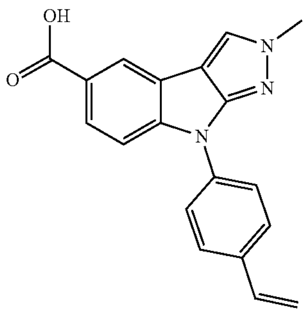 [SMILES: C=Cc1ccc(-n2c3ccc(C(=O)O)cc3c3cn(C)nc32)cc1] 8-(4-ethenylphenyl)-2-methyl-2H,8H-pyrazolo[3,4-b]indole-5-carboxylic acid |

| Compound No. | Structure and Name |
| --- | --- |
| 617 | 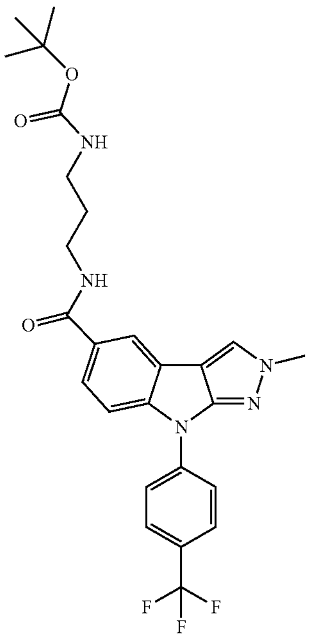 [SMILES: Cn1cc2c3cc(C(=O)NCCCNC(=O)OC(C)(C)C)ccc3n(-c3ccc(C(F)(F)F)cc3)c2n1] tert-butyl N-[3-({2-methyl-8-[4-(trifluoromethyl)phenyl]-2H,8H-pyrazolo[3,4-b]indol-5-yl}formamido)propyl]carbamate |
| 618 | 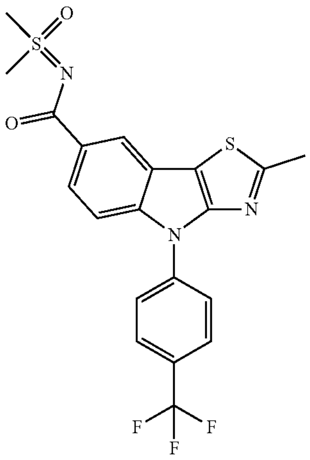 N-[dimethyl(oxo)-λ$^6$-sulfanylidene]-2-methyl-4-[4-(trifluoromethyl)phenyl]-4H-[1,3]thiazolo[4,5-b]indole-7-carboxamide |

| Compound No. | Structure and Name |
| --- | --- |
| 619 | 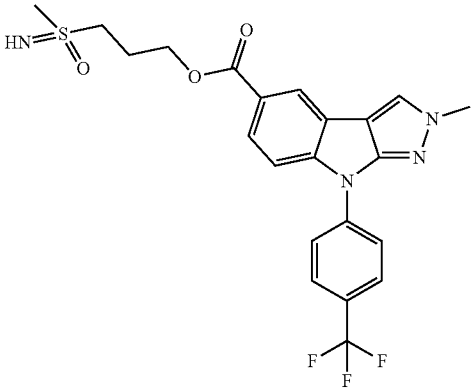 [SMILES: Cn1cc2c3cc(C(=O)OCCCS(C)(=N)=O)ccc3n(-c3ccc(C(F)(F)F)cc3)c2n1] 3-[imino(methyl)oxo-λ$^6$-sulfanyl]propyl 2-methyl-8-[4-(trifluoromethyl)phenyl]-2H,8H-pyrazolo[3,4-b]indole-5-carboxylate |
| 620 | 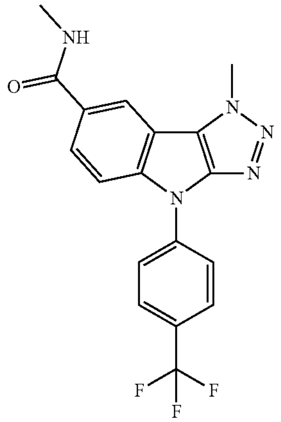 [SMILES: CNC(=O)c1ccc2c(c1)c1c(nnn1C)n2-c1ccc(C(F)(F)F)cc1] N,1-dimethyl-4-[4-(trifluoromethyl)phenyl]-1H,4H-[1,2,3]triazolo[4,5-b]indole-7-carboxamide |
| 621 | 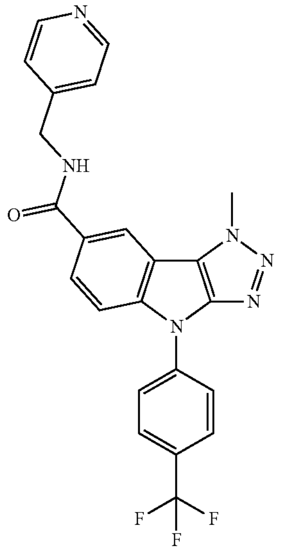 [SMILES: Cn1nnc2c1c1cc(C(=O)NCc3ccncc3)ccc1n2-c1ccc(C(F)(F)F)cc1] |

-continued

| Compound No. | Structure and Name |
|---|---|
| | 1-methyl-N-[(pyridin-4-yl)methyl]-4-[4-(trifluoromethyl)phenyl]-1H,4H-[1,2,3]triazolo[4,5-b]indole-7-carboxamide |
| 622 | Absolute 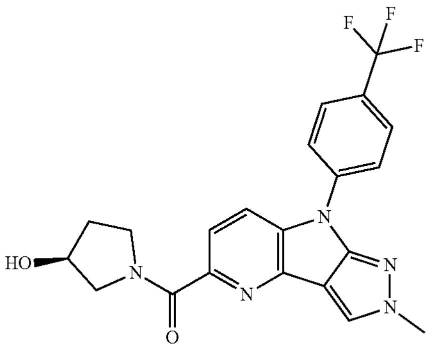 (3S)-1-{4-methyl-7-[4-(trifluoromethyl)phenyl]-4,5,7,12-tetraazatricyclo[6.4.0.0Â$^{2}$,?]dodeca-1(8),2,5,9,11-pentaene-11-carbonyl}pyrrolidin-3-ol |
| 623 | Absolute 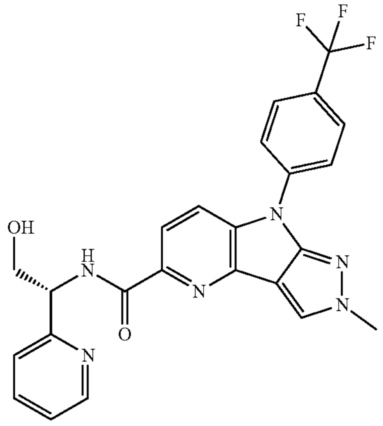 N-[(1R)-2-hydroxy-1-(pyridin-2-yl)ethyl]-4-methyl-7-[4-(trifluoromethyl)phenyl]-4,5,7,12-tetraazatricyclo[6.4.0.0$^{2,6}$]dodeca-1(8),2,5,9,11-pentaene-11-carboxamide |
| 624 | Absolute 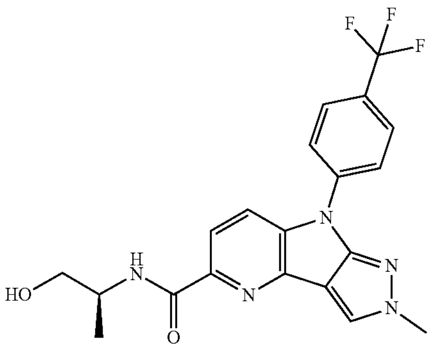 |

-continued

| Compound No. | Structure and Name |
|---|---|
| | N-[(2S)-1-hydroxypropan-2-yl]-4-methyl-7-[4-(trifluoromethyl)phenyl]-4,5,7,12-tetraazatricyclo[6.4.0.0Â$^{2}$,?]dodeca-1(8),2,5,9,11-pentaene-11-carboxamide |
| 625 | Absolute 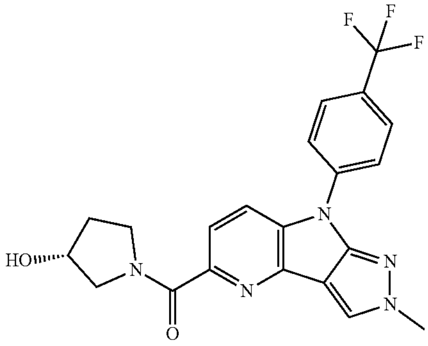 (3R)-1-{4-methyl-7-[4-(trifluoromethyl)phenyl]-4,5,7,12-tetraazatricyclo[6.4.0.0$^{2,6}$]dodeca-1(8),2,5,9,11-pentaene-11-carbonyl}pyrrolidin-3-ol |
| 626 | Absolute 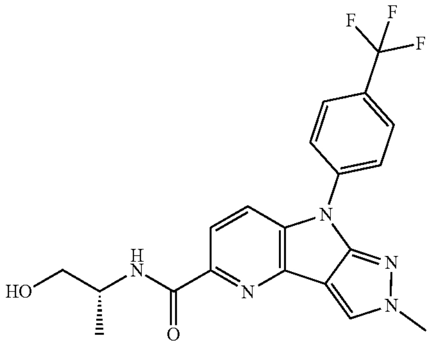 N-[(2R)-1-hydroxypropan-2-yl]-4-methyl-7-[4-(trifluoromethyl)phenyl]-4,5,7,12-tetraazatricyclo[6.4.0.0$^{2,6}$]dodeca-1(8),2,5,9,11-pentaene-11-carboxamide |

| Compound No. | Structure and Name |
|---|---|
| 627 | 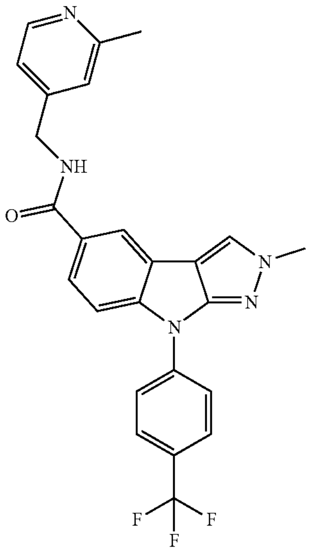 [SMILES: Cc1cc(CNC(=O)c2ccc3c(c2)c2cn(C)nc2n3-c2ccc(C(F)(F)F)cc2)ccn1] 2-methyl-N-[(2-methylpyridin-4-yl)methyl]-8-[4-(trifluoromethyl)phenyl]-2H,8H-pyrazolo[3,4-b]indole-5-carboxamide |
| 628 | 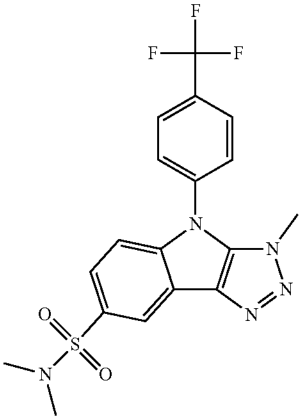 N,N,3-trimethyl-4-[4-(trifluoromethyl)phenyl]-3H,4H-[1,2,3]triazolo[4,5-b]indole-7-sulfonamide |
| 629 | Absolute 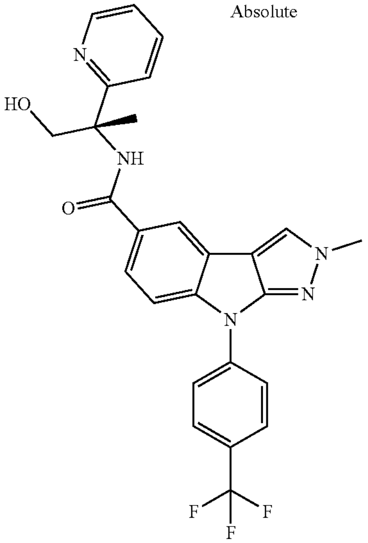 [SMILES: Cn1cc2c3cc(C(=O)N[C@](C)(CO)c4ccccn4)ccc3n(-c3ccc(C(F)(F)F)cc3)c2n1] Absolute configuration assigned arbitrarily N-[(2S)-1-hydroxy-2-(pyridin-2-yl)propan-2-yl]-2-methyl-8-[4-(trifluoromethyl)phenyl]-2H,8H-pyrazolo[3,4-b]indole-5-carboxamide |
| 630 | 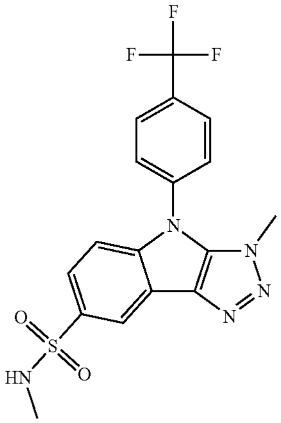 [SMILES: CNS(=O)(=O)c1ccc2c(c1)c1nnn(C)c1n2-c1ccc(C(F)(F)F)cc1] N,3-dimethyl-4-[4-(trifluoromethyl)phenyl]-3H,4H-[1,2,3]triazolo[4,5-b]indole-7-sulfonamide |

-continued

| Compound No. | Structure and Name |
| --- | --- |
| 631 | 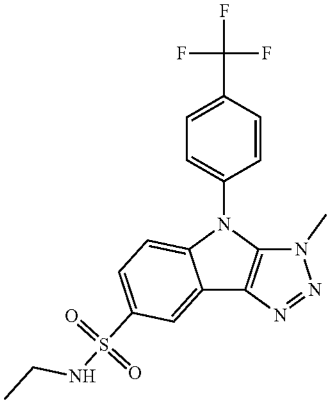 [SMILES: CCNS(=O)(=O)c1ccc2c(c1)c1nnn(C)c1n2-c1ccc(C(F)(F)F)cc1] N-ethyl-3-methyl-4-[4-(trifluoromethyl)phenyl]-3H,4H-[1,2,3]triazolo[4,5-b]indole-7-sulfonamide |
| 632 | 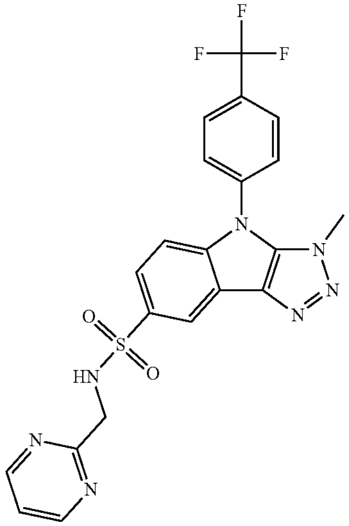 [SMILES: Cn1nnc2c3cc(S(=O)(=O)NCc4ncccn4)ccc3n(-c3ccc(C(F)(F)F)cc3)c21] 3-methyl-N-[(pyrimidin-2-yl)methyl]-4-[4-(trifluoromethyl)phenyl]-3H,4H-[1,2,3]triazolo[4,5-b]indole-7-sulfonamide |

-continued

| Compound No. | Structure and Name |
| --- | --- |
| 633 | Absolute 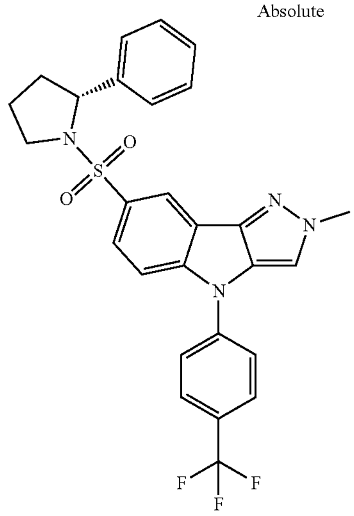 [SMILES: Cn1cc2c(n1)c1cc(S(=O)(=O)N3CCC[C@@H]3c3ccccc3)ccc1n2-c1ccc(C(F)(F)F)cc1] (2R)-1-({2-methyl-4-[4-(trifluoromethyl)phenyl]-2H,4H-pyrazolo[4,3-b]indol-7-yl}sulfonyl)-2-phenylpyrrolidine |
| 634 | Absolute 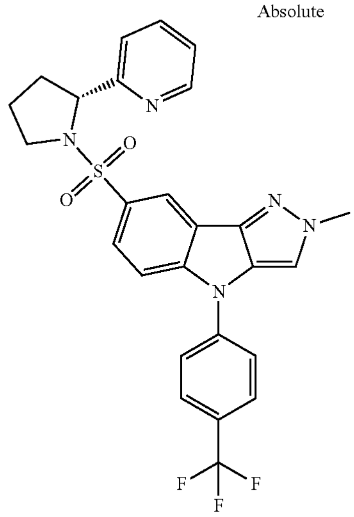 [SMILES: Cn1cc2c(n1)c1cc(S(=O)(=O)N3CCC[C@@H]3c3ccccn3)ccc1n2-c1ccc(C(F)(F)F)cc1] 2-[(2R)-1-({2-methyl-4-[4-(trifluoromethyl)phenyl]-2H,4H-pyrazolo[4,3-b]indol-7-yl}sulfonyl)pyrrolidin-2-yl]pyridine |

| Compound No. | Structure and Name |
|---|---|
| 635 | Absolute 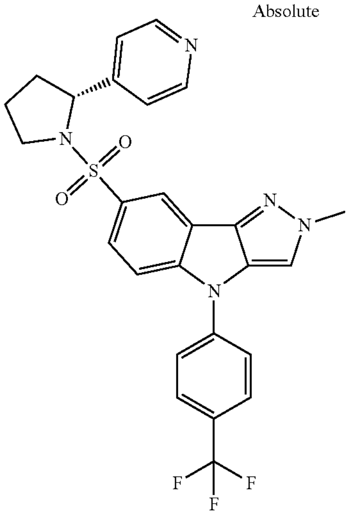 [SMILES: Cn1cc2c(n1)c1cc(S(=O)(=O)N3CCC[C@@H]3c3ccncc3)ccc1n2-c1ccc(C(F)(F)F)cc1] 4-[(2R)-1-({2-methyl-4-[4-(trifluoromethyl)phenyl]-2H,4H-pyrazolo[4,3-b]indol-7-yl}sulfonyl)pyrrolidin-2-yl]pyridine |
| 636 | Absolute 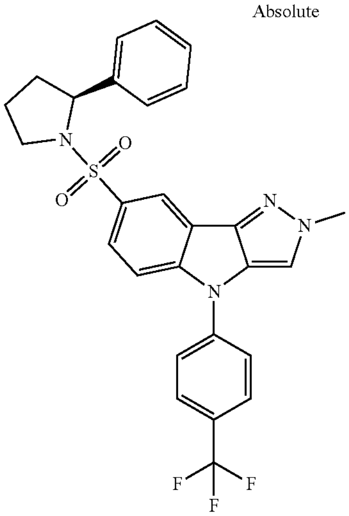 [SMILES: Cn1cc2c(n1)c1cc(S(=O)(=O)N3CCC[C@H]3c3ccccc3)ccc1n2-c1ccc(C(F)(F)F)cc1] (2S)-1-({2-methyl-4-[4-(trifluoromethyl)phenyl]-2H,4H-pyrazolo[4,3-b]indol-7-yl}sulfonyl)-2-phenylpyrrolidine |

| Compound No. | Structure and Name |
|---|---|
| 637 | Absolute 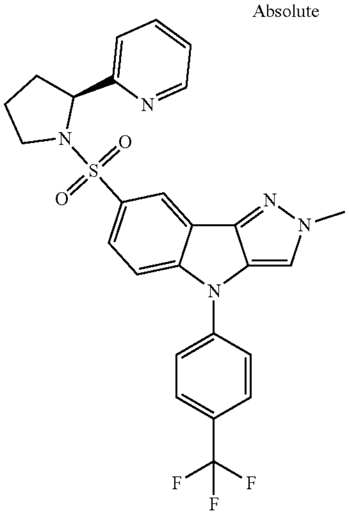 [SMILES: Cn1cc2c(n1)c1cc(S(=O)(=O)N3CCC[C@H]3c3ccccn3)ccc1n2-c1ccc(C(F)(F)F)cc1] 2-[(2S)-1-({2-methyl-4-[4-(trifluoromethyl)phenyl]-2H,4H-pyrazolo[4,3-b]indol-7-yl}sulfonyl)pyrrolidin-2-yl]pyridine |
| 638 | Absolute 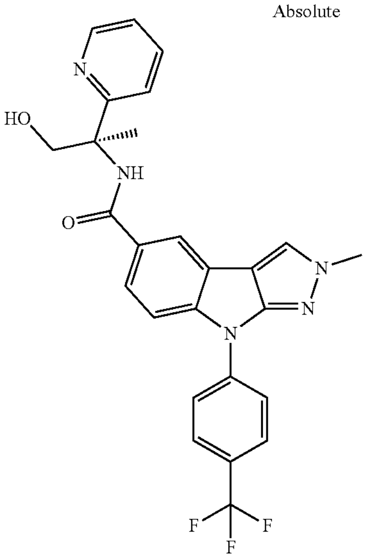 [SMILES: Cn1cc2c3cc(C(=O)N[C@@](C)(CO)c4ccccn4)ccc3n(-c3ccc(C(F)(F)F)cc3)c2n1] N-[(2R)-1-hydroxy-2-(pyridin-2-yl)propan-2-yl]-2-methyl-8-[4-(trifluoromethyl)phenyl]-2H,8H-pyrazolo[3,4-b]indole-5-carboxamide |

| Compound No. | Structure and Name |
|---|---|
| 639 | Absolute<br>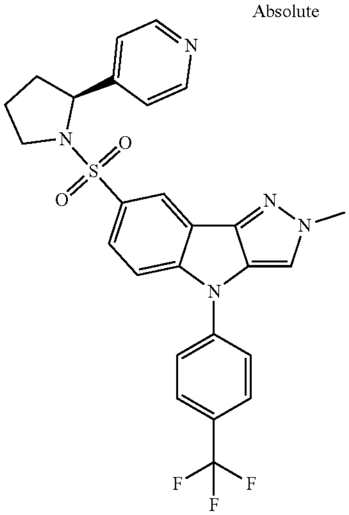 [SMILES: Cn1cc2c(n1)c1cc(S(=O)(=O)N3CCC[C@H]3c3ccncc3)ccc1n2-c1ccc(C(F)(F)F)cc1]<br>4-[(2S)-1-({2-methyl-4-[4-(trifluoromethyl)phenyl]-2H,4H-pyrazolo[4,3-b]indol-7-yl}sulfonyl)pyrrolidin-2-yl]pyridine |

| Compound No. | Structure and Name |
|---|---|
| 640 | 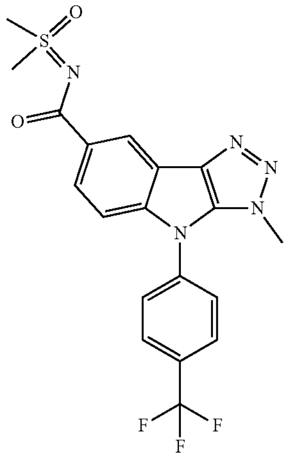<br>N-[dimethyl(oxo)-λ6-sulfanylidene]-3-methyl-4-[4-(trifluoromethyl)phenyl]-3H,4H-[1,2,3]triazolo[4,5-b]indole-7-carboxamide. |

15. A compound, or any N-oxide, tautomer or stereoisomer thereof and/or any pharmaceutically acceptable salt of each of the foregoing, including mixtures thereof in all ratios, selected from the table below:

| Compound No. | Structure and Name |
|---|---|
| B1 | 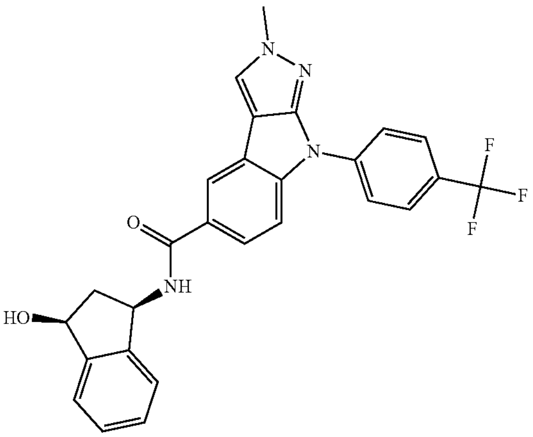 [SMILES: Cn1cc2c3cc(C(=O)N[C@@H]4C[C@H](O)c5ccccc54)ccc3n(-c3ccc(C(F)(F)F)cc3)c2n1]<br>racemic diastereomer with known relative stereochemistry, cis<br>N-[(1R,3S)-3-hydroxy-2,3-dihydro-1H-inden-1-yl]-2-methyl-8-[4-(trifluoromethyl)phenyl]-2H,8H-pyrazolo[3,4-b]indole-5-carboxamide |

-continued

| Compound No. | Structure and Name |
|---|---|
| B2 | 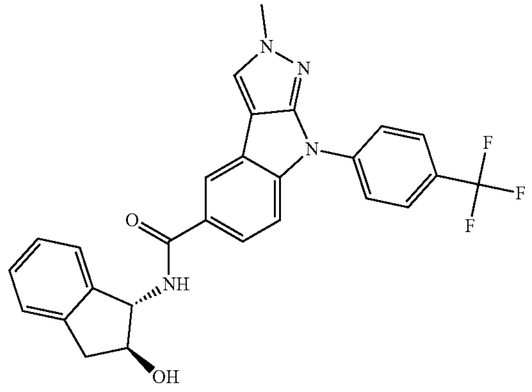 [SMILES: Cn1cc2c3cc(C(=O)N[C@H]4c5ccccc5C[C@@H]4O)ccc3n(-c3ccc(C(F)(F)F)cc3)c2n1] stereochemistry assigned/known; single diastereomer N-[(1S,2S)-2-hydroxy-2,3-dihydro-1H-inden-1-yl]-2-methyl-8-[4-(trifluoromethyl)phenyl]-2H,8H-pyrazolo[3,4-b]indole-5-carboxamide |
| B3 | 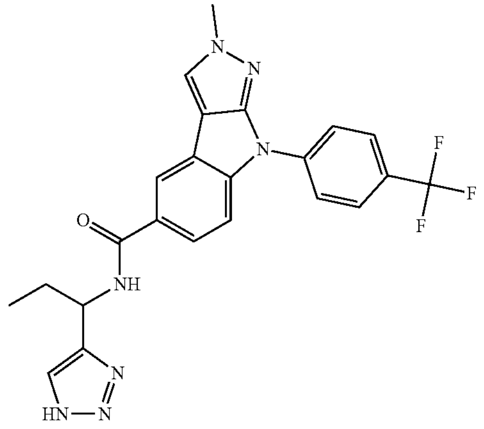 [SMILES: CCC(NC(=O)c1ccc2c(c1)c1cn(C)nc1n2-c1ccc(C(F)(F)F)cc1)c1c[nH]nn1] 2-methyl-N-[1-(1H-1,2,3-triazol-4-yl)propyl]-8-[4-(trifluoromethyl)phenyl]-2H,8H-pyrazolo[3,4-b]indole-5-carboxamide |
| B4 | 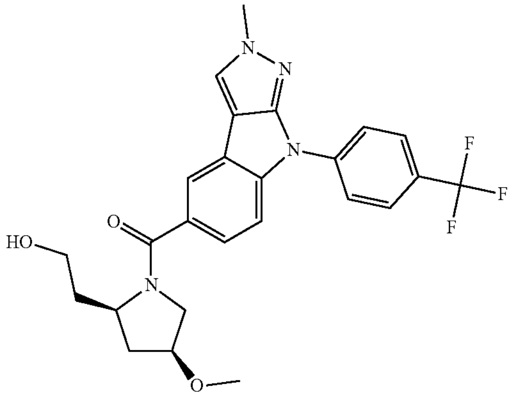 [SMILES: CO[C@H]1C[C@@H](CCO)N(C(=O)c2ccc3c(c2)c2cn(C)nc2n3-c2ccc(C(F)(F)F)cc2)C1] stereochemistry assigned/known; single diastereomer 2-[(2R,4S)-4-methoxy-1-{2-methyl-8-[4-(trifluoromethyl)phenyl]-2H,8H-pyrazolo[3,4-b]indole-5-carbonyl}pyrrolidin-2-yl]ethan-1-ol |

-continued
| Compound No. | Structure and Name |
|---|---|
| B5 | 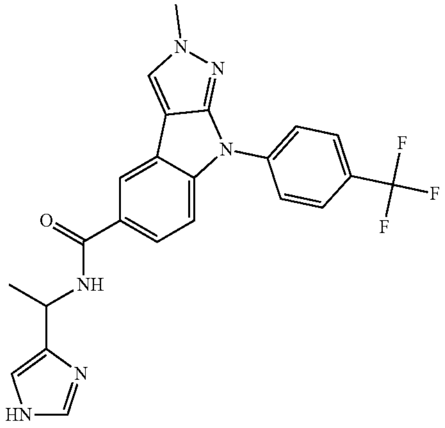 [SMILES: CC(NC(=O)c1ccc2c(c1)c1cn(C)nc1n2-c1ccc(C(F)(F)F)cc1)c1c[nH]cn1]<br>N-[1-(1H-imidazol-4-yl)ethyl]-2-methyl-8-[4-(trifluoromethyl)phenyl]-2H,8H-pyrazolo[3,4-b]indole-5-carboxamide |
| B6 | 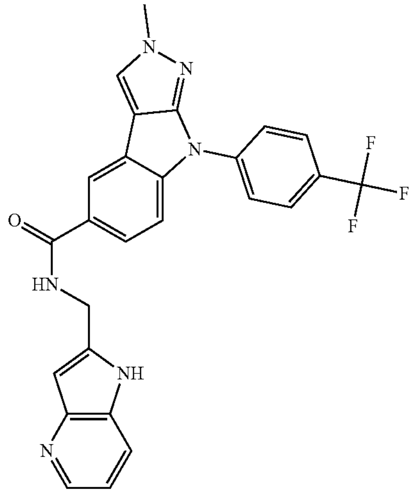 [SMILES: Cn1cc2c3cc(C(=O)NCc4cc5ncccc5[nH]4)ccc3n(-c3ccc(C(F)(F)F)cc3)c2n1]<br>2-methyl-N-({1H-pyrrolo[3,2-b]pyridin-2-yl}methyl)-8-[4-(trifluoromethyl)phenyl]-2H,8H-pyrazolo[3,4-b]indole-5-carboxamide |
| B7 | 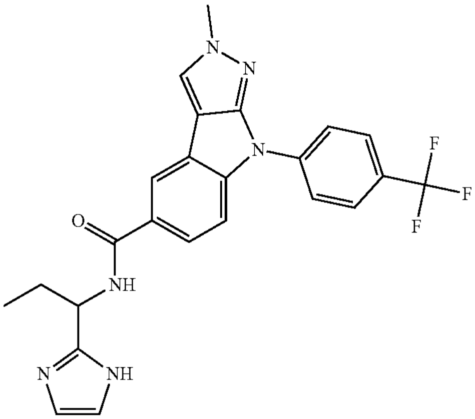 [SMILES: CCC(NC(=O)c1ccc2c(c1)c1cn(C)nc1n2-c1ccc(C(F)(F)F)cc1)c1ncc[nH]1]<br>N-[1-(1H-imidazol-2-yl)propyl]-2-methyl-8-[4-(trifluoromethyl)phenyl]-2H,8H-pyrazolo[3,4-b]indole-5-carboxamide |

-continued
| Compound No. | Structure and Name |
|---|---|
| B8 | 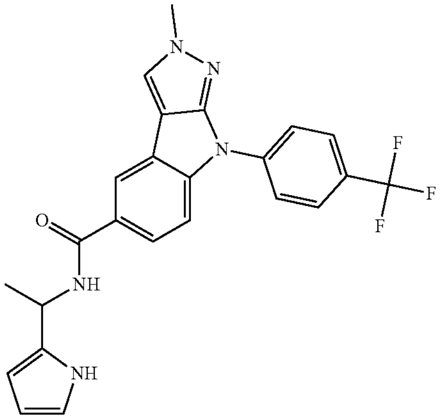 [SMILES: CC(NC(=O)c1ccc2c(c1)c1cn(C)nc1n2-c1ccc(C(F)(F)F)cc1)c1ccc[nH]1]<br>2-methyl-N-[1-(1H-pyrrol-2-yl)ethyl]-8-[4-(trifluoromethyl)phenyl]-2H,8H-pyrazolo[3,4-b]indole-5-carboxamide |
| B9 | 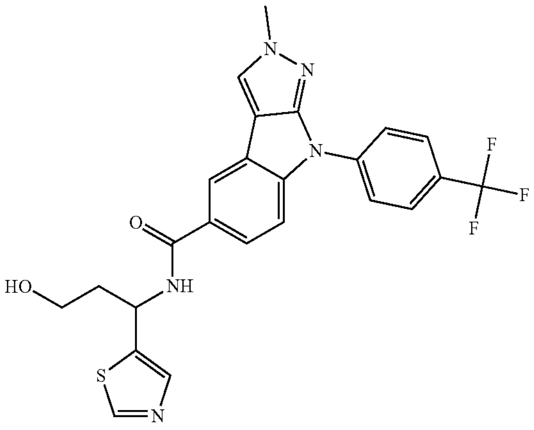 [SMILES: Cn1cc2c3cc(C(=O)NC(CCO)c4cncs4)ccc3n(-c3ccc(C(F)(F)F)cc3)c2n1]<br>N-[3-hydroxy-1-(1,3-thiazol-5-yl)propyl]-2-methyl-8-[4-(trifluoromethyl)phenyl]-2H,8H-pyrazolo[3,4-b]indole-5-carboxamide |
| B10 | 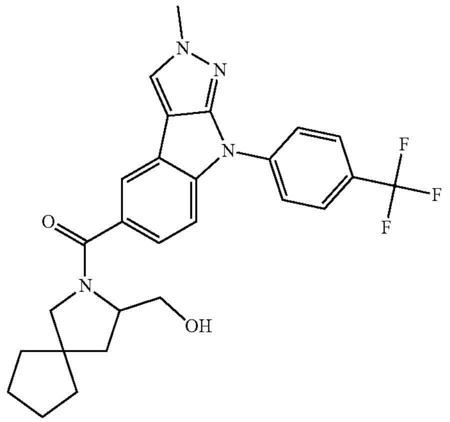 [SMILES: Cn1cc2c3cc(C(=O)N4CC5(CCCC5)CC4CO)ccc3n(-c3ccc(C(F)(F)F)cc3)c2n1]<br>(2-{2-methyl-8-[4-(trifluoromethyl)phenyl]-2H,8H-pyrazolo[3,4-b]indole-5-carbonyl}-2-azaspiro[4.4]nonan-3-yl)methanol |

-continued
| Compound No. | Structure and Name |
| --- | --- |
| B11 | 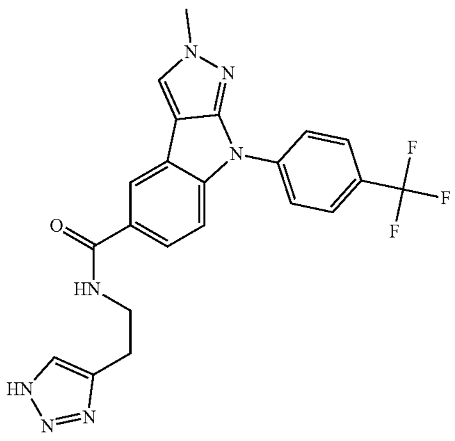 [SMILES: Cn1cc2c3cc(C(=O)NCCc4c[nH]nn4)ccc3n(-c3ccc(C(F)(F)F)cc3)c2n1]<br>2-methyl-N-[2-(1H-1,2,3-triazol-4-yl)ethyl]-8-[4-(trifluoromethyl)phenyl]-2H,8H-pyrazolo[3,4-b]indole-5-carboxamide |
| B12 | 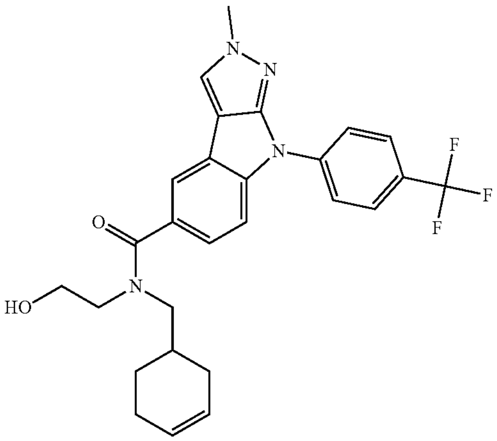 [SMILES: Cn1cc2c3cc(C(=O)N(CCO)CC4CC=CCC4)ccc3n(-c3ccc(C(F)(F)F)cc3)c2n1]<br>N-[(cyclohex-3-en-1-yl)methyl]-N-(2-hydroxyethyl)-2-methyl-8-[4-(trifluoromethyl)phenyl]-2H,8H-pyrazolo[3,4-b]indole-5-carboxamide |
| B13 | 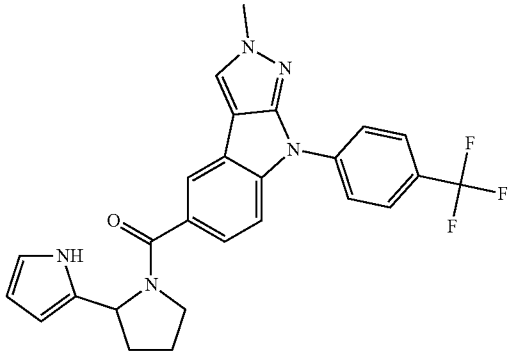 [SMILES: Cn1cc2c3cc(C(=O)N4CCCC4c4ccc[nH]4)ccc3n(-c3ccc(C(F)(F)F)cc3)c2n1]<br>2-(1-{2-methyl-8-[4-(trifluoromethyl)phenyl]-2H,8H-pyrazolo[3,4-b]indole-5-carbonyl}pyrrolidin-2-yl)-1H-pyrrole |

-continued
| Compound No. | Structure and Name |
|---|---|
| B14 | 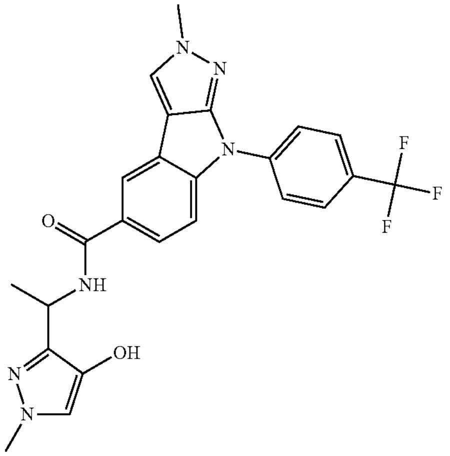 [SMILES: CC(NC(=O)c1ccc2c(c1)c1cn(C)nc1n2-c1ccc(C(F)(F)F)cc1)c1nn(C)cc1O]<br>N-[1-(4-hydroxy-1-methyl-1H-pyrazol-3-yl)ethyl]-2-methyl-8-[4-(trifluoromethyl)phenyl]-2H,8H-pyrazolo[3,4-b]indole-5-carboxamide |
| B15 | 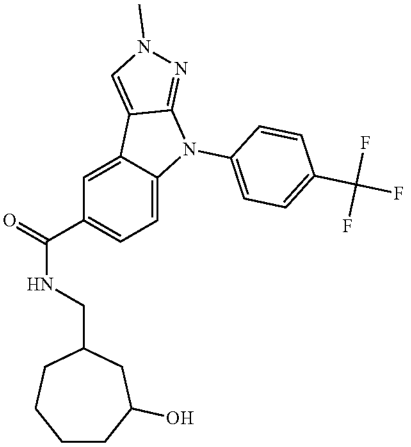 [SMILES: Cn1cc2c3cc(C(=O)NCC4CCCCC(O)C4)ccc3n(-c3ccc(C(F)(F)F)cc3)c2n1]<br>diastereomeric mixture<br>N-[(3-hydroxycycloheptyl)methyl]-2-methyl-8-[4-(trifluoromethyl)phenyl]-2H,8H-pyrazolo[3,4-b]indole-5-carboxamide |
| B16 | 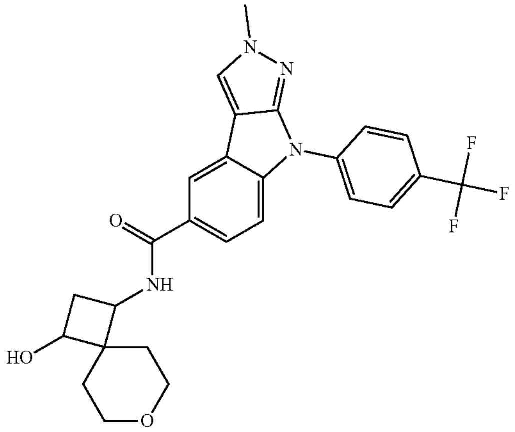 [SMILES: Cn1cc2c3cc(C(=O)NC4CC(O)C45CCOCC5)ccc3n(-c3ccc(C(F)(F)F)cc3)c2n1] |

-continued

| Compound No. | Structure and Name |
|---|---|
| | diastereomeric mixture N-{3-hydroxy-7-oxaspiro[3.5]nonan-1-yl}-2-methyl-8-[4-(trifluoromethyl)phenyl]-2H,8H-pyrazolo[3,4-b]indole-5-carboxamide |
| B17 | 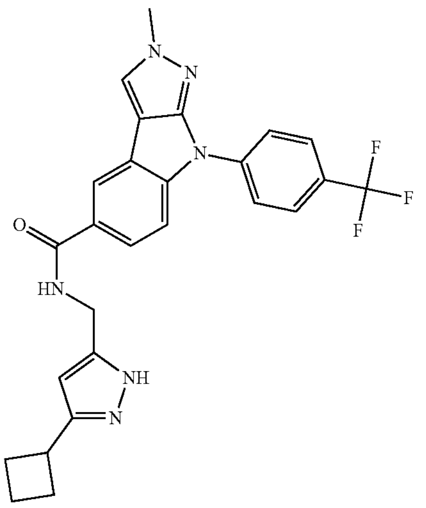 [SMILES: Cn1cc2c3cc(C(=O)NCc4cc(C5CCC5)n[nH]4)ccc3n(-c3ccc(C(F)(F)F)cc3)c2n1] N-[(3-cyclobutyl-1H-pyrazol-5-yl)methyl]-2-methyl-8-[4-(trifluoromethyl)phenyl]-2H,8H-pyrazolo[3,4-b]indole-5-carboxamide |
| B18 stereochemistry assinged; single enantiomer | 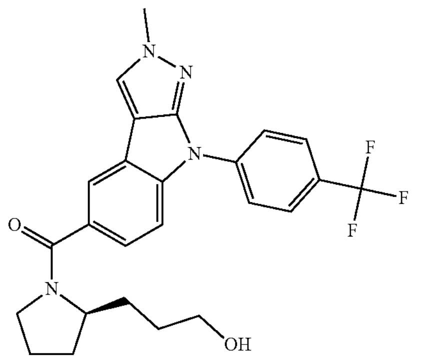 [SMILES: Cn1cc2c3cc(C(=O)N4CCC[C@@H]4CCCO)ccc3n(-c3ccc(C(F)(F)F)cc3)c2n1] stereochemistry assigned/known; single enantiomer 3-[(2R)-1-{2-methyl-8-[4-(trifluoromethyl)phenyl]-2H,8H-pyrazolo[3,4-b]indole-5-carbonyl}pyrrolidin-2-yl]propan-1-ol |

-continued
| Compound No. | Structure and Name |
|---|---|
| B19 | 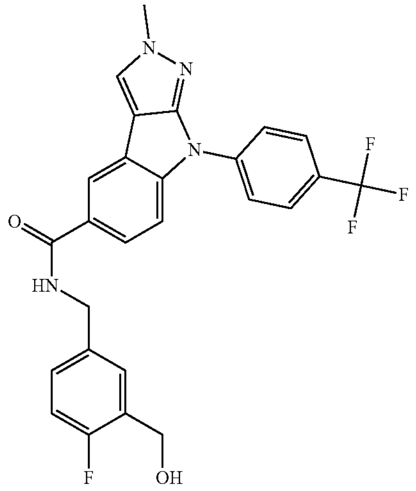 [SMILES: Cn1cc2c3cc(C(=O)NCc4ccc(F)c(CO)c4)ccc3n(-c3ccc(C(F)(F)F)cc3)c2n1]<br>N-{[4-fluoro-3-(hydroxymethyl)phenyl]methyl}-2-methyl-8-[4-(trifluoromethyl)phenyl]-2H,8H-pyrazolo[3,4-b]indole-5-carboxamide |
| B20 | 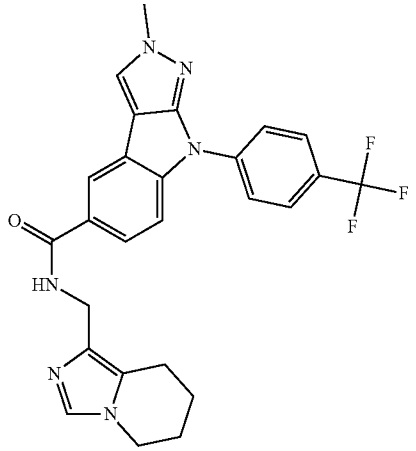 [SMILES: Cn1cc2c3cc(C(=O)NCc4ncn5c4CCCC5)ccc3n(-c3ccc(C(F)(F)F)cc3)c2n1]<br>N-({5H,6H,7H,8H-imidazo[1,5-a]pyridin-1-yl}methyl)-2-methyl-8-[4-(trifluoromethyl)phenyl]-2H,8H-pyrazolo[3,4-b]indole-5-carboxamide |
| B21 | 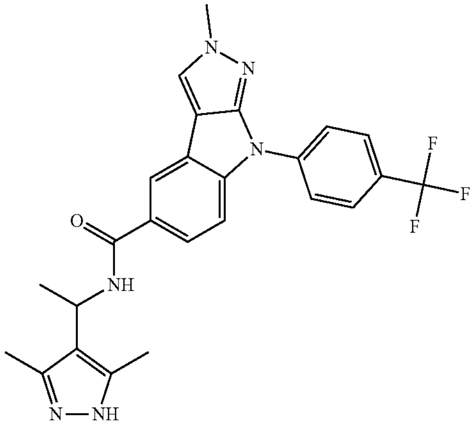 [SMILES: Cc1n[nH]c(C)c1C(C)NC(=O)c1ccc2c(c1)c1cn(C)nc1n2-c1ccc(C(F)(F)F)cc1]<br>N-[1-(3,5-dimethyl-1H-pyrazol-4-yl)ethyl]-2-methyl-8-[4-(trifluoromethyl)phenyl]-2H,8H-pyrazolo[3,4-b]indole-5-carboxamide |

-continued

| Compound No. | Structure and Name |
|---|---|
| B22 | 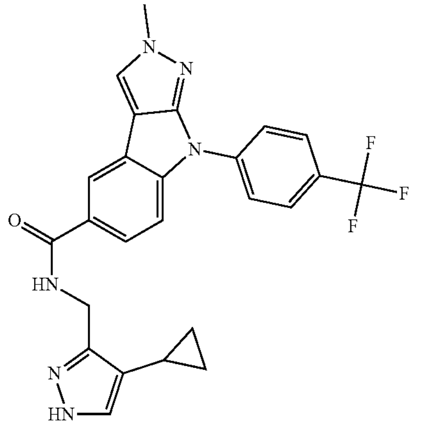 [SMILES: Cn1cc2c3cc(C(=O)NCc4n[nH]cc4C4CC4)ccc3n(-c3ccc(C(F)(F)F)cc3)c2n1] N-[(4-cyclopropyl-1H-pyrazol-3-yl)methyl]-2-methyl-8-[4-(trifluoromethyl)phenyl]-2H,8H-pyrazolo[3,4-b]indole-5-carboxamide |
| B23 | 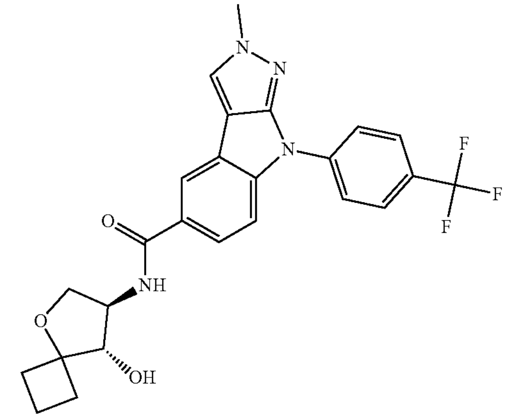 [SMILES: Cn1cc2c3cc(C(=O)N[C@@H]4COC5(CCC5)[C@H]4O)ccc3n(-c3ccc(C(F)(F)F)cc3)c2n1] racemic diastereomer with known relative stereochemistry, trans N-[(7R,8S)-8-hydroxy-5-oxaspiro[3.4]octan-7-yl]-2-methyl-8-[4-(trifluoromethyl)phenyl]-2H,8H-pyrazolo[3,4-b]indole-5-carboxamide |
| B24 | 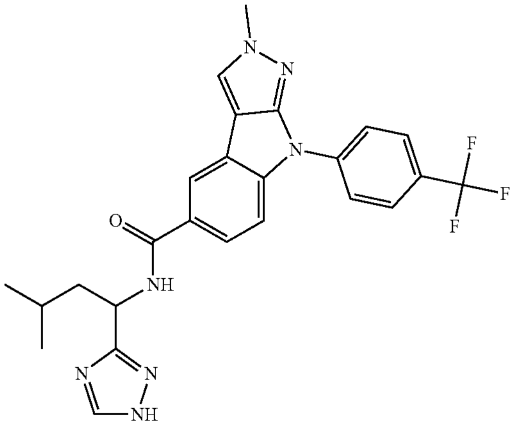 [SMILES: CC(C)CC(NC(=O)c1ccc2c(c1)c1cn(C)nc1n2-c1ccc(C(F)(F)F)cc1)c1nc[nH]n1] 2-methyl-N-[3-methyl-1-(1H-1,2,4-triazol-3-yl)butyl]-8-[4-(trifluoromethyl)phenyl]-2H,8H-pyrazolo[3,4-b]indole-5-carboxamide |

-continued

| Compound No. | Structure and Name |
|---|---|
| B25 | 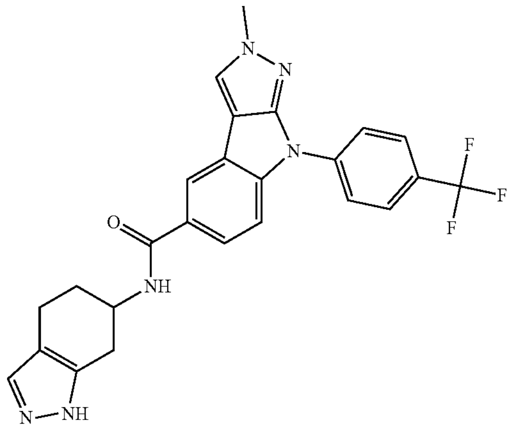 [SMILES: Cn1cc2c3cc(C(=O)NC4CCc5cn[nH]c5C4)ccc3n(-c3ccc(C(F)(F)F)cc3)c2n1]<br>2-methyl-N-(4,5,6,7-tetrahydro-1H-indazol-6-yl)-8-[4-(trifluoromethyl)phenyl]-2H,8H-pyrazolo[3,4-b]indole-5-carboxamide |
| B26 | 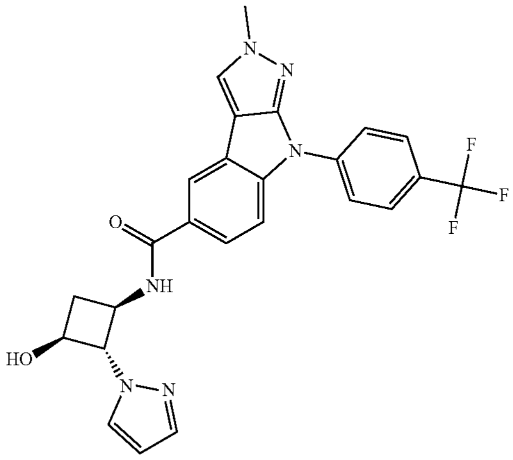 [SMILES: Cn1cc2c3cc(C(=O)N[C@@H]4C[C@H](O)[C@H]4n4cccn4)ccc3n(-c3ccc(C(F)(F)F)cc3)c2n1]<br>racemic diastereomer with known relative stereochemistry<br>N-[(1R,2S,3S)-3-hydroxy-2-(1H-pyrazol-1-yl)cyclobutyl]-2-methyl-8-[4-(trifluoromethyl)phenyl]-2H,8H-pyrazolo[3,4-b]indole-5-carboxamide |
| B27 | 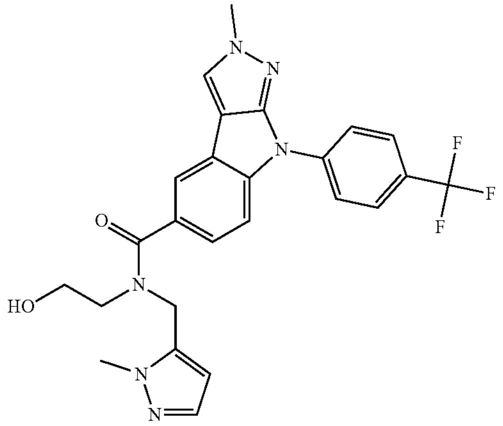 [SMILES: Cn1cc2c3cc(C(=O)N(CCO)Cc4ccnn4C)ccc3n(-c3ccc(C(F)(F)F)cc3)c2n1]<br>N-(2-hydroxyethyl)-2-methyl-N-[(1-methyl-1H-pyrazol-5-yl)methyl]-8-[4-(trifluoromethyl)phenyl]-2H,8H-pyrazolo[3,4-b]indole-5-carboxamide |

-continued
| Compound No. | Structure and Name |
|---|---|
| B28 | 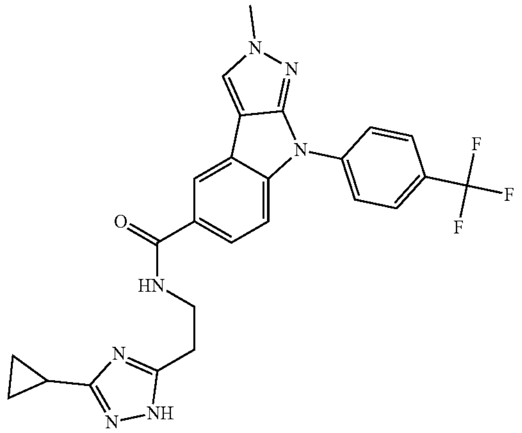 [SMILES: Cn1cc2c3cc(C(=O)NCCc4nc(C5CC5)n[nH]4)ccc3n(-c3ccc(C(F)(F)F)cc3)c2n1] N-[2-(3-cyclopropyl-1H-1,2,4-triazol-5-yl)ethyl]-2-methyl-8-[4-(trifluoromethyl)phenyl]-2H,8H-pyrazolo[3,4-b]indole-5-carboxamide |
| B29 | 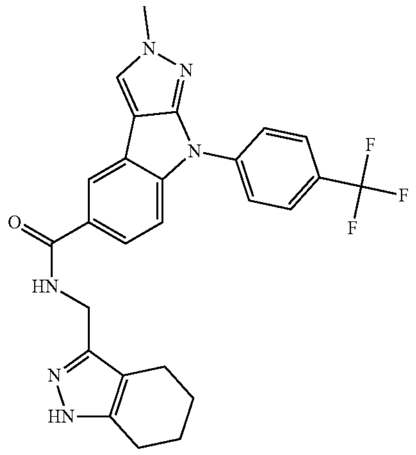 [SMILES: Cn1cc2c3cc(C(=O)NCc4n[nH]c5c4CCCC5)ccc3n(-c3ccc(C(F)(F)F)cc3)c2n1] 2-methyl-N-[(4,5,6,7-tetrahydro-1H-indazol-3-yl)methyl]-8-[4-(trifluoromethyl)phenyl]-2H,8H-pyrazolo[3,4-b]indole-5-carboxamide |
| B30 | 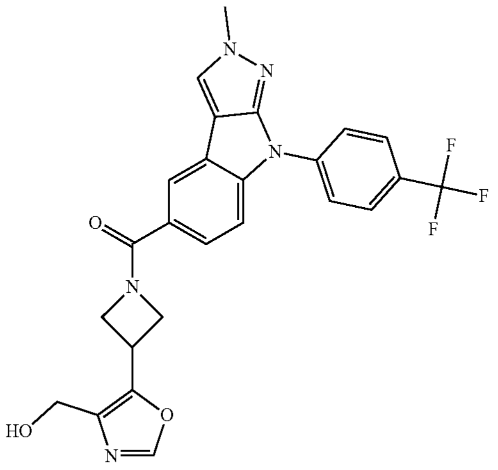 [SMILES: Cn1cc2c3cc(C(=O)N4CC(c5ocnc5CO)C4)ccc3n(-c3ccc(C(F)(F)F)cc3)c2n1] |

-continued

| Compound No. | Structure and Name |
|---|---|
| | [5-(1-{2-methyl-8-[4-(trifluoromethyl)phenyl]-2H,8H-pyrazolo[3,4-b]indole-5-carbonyl}azetidin-3-yl)-1,3-oxazol-4-yl] methanol |
| B31 | 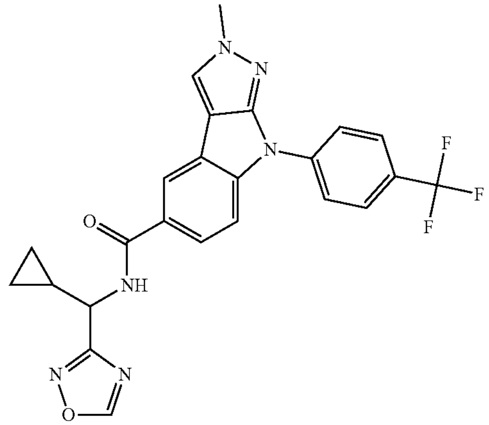 [SMILES: Cn1cc2c3cc(C(=O)NC(c4ncon4)C4CC4)ccc3n(-c3ccc(C(F)(F)F)cc3)c2n1] N-[cyclopropyl(1,2,4-oxadiazol-3-yl)methyl]-2-methyl-8-[4-(trifluoromethyl)phenyl]-2H,8H-pyrazolo[3,4-b]indole-5-carboxamide |
| B32 | 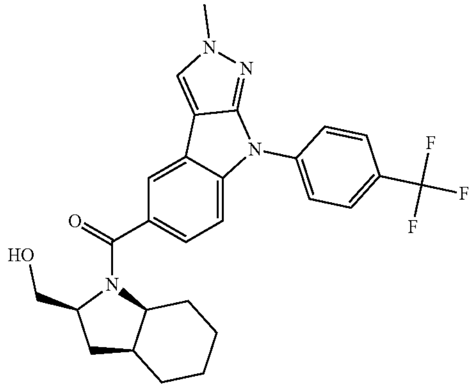 [SMILES: Cn1cc2c3cc(C(=O)N4[C@H](CO)C[C@@H]5CCCC[C@@H]54)ccc3n(-c3ccc(C(F)(F)F)cc3)c2n1] stereochemistry assigned/known; single enantiomer [(2S,3aS,7aS)-1-{2-methyl-8-[4-(trifluoromethyl)phenyl]-2H,8H-pyrazolo[3,4-b]indole-5-carbonyl}-octahydro-1H-indol-2-yl]methanol |
| B33 | 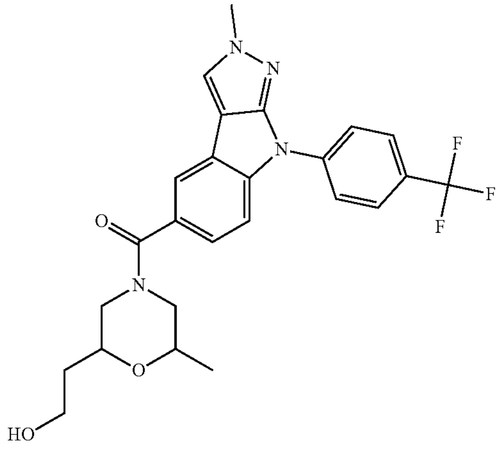 [SMILES: CC1CN(C(=O)c2ccc3c(c2)c2cn(C)nc2n3-c2ccc(C(F)(F)F)cc2)CC(CCO)O1] |

-continued

| Compound No. | Structure and Name |
| --- | --- |
| | diastereomeric mixture 2-(6-methyl-4-{2-methyl-8-[4-(trifluoromethyl)phenyl]-2H,8H-pyrazolo[3,4-b]indole-5-carbonyl}morpholin-2-yl)ethan-1-ol |
| B34 | 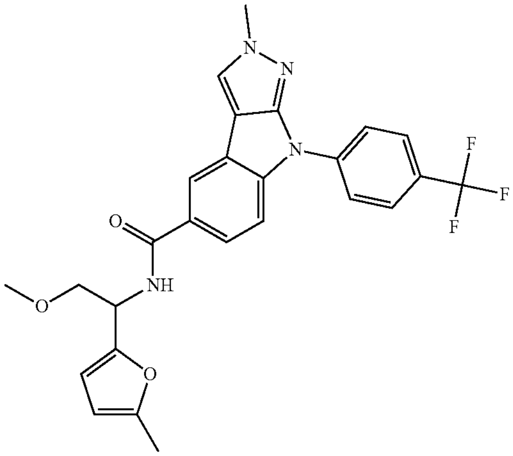 [SMILES: COCC(NC(=O)c1ccc2c(c1)c1cn(C)nc1n2-c1ccc(C(F)(F)F)cc1)c1ccc(C)o1] N-[2-methoxy-1-(5-methylfuran-2-yl)ethyl]-2-methyl-8-[4-(trifluoromethyl)phenyl]-2H,8H-pyrazolo[3,4-b]indole-5-carboxamide |
| B35 | 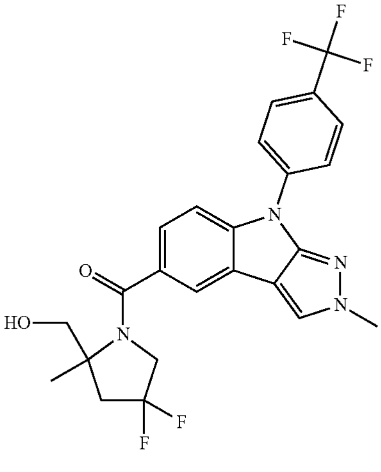 [SMILES: Cn1cc2c3cc(C(=O)N4CC(F)(F)CC4(C)CO)ccc3n(-c3ccc(C(F)(F)F)cc3)c2n1] (4,4-difluoro-2-methyl-1-{2-methyl-8-[4-(trifluoromethyl)phenyl]-2H,8H-pyrazolo[3,4-b]indole-5-carbonyl}pyrrolidin-2-yl)methanol |

-continued
| Compound No. | Structure and Name |
|---|---|
| B36 | 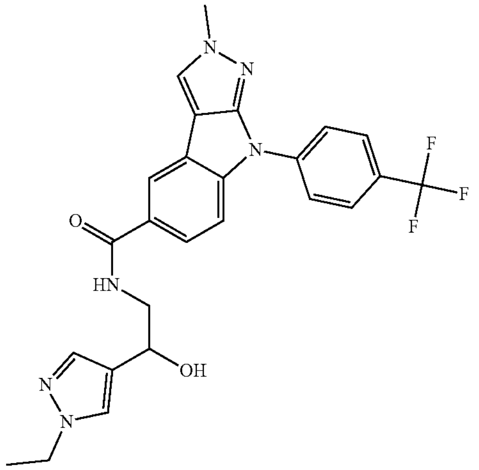 [SMILES: CCn1cc(C(O)CNC(=O)c2ccc3c(c2)c2cn(C)nc2n3-c2ccc(C(F)(F)F)cc2)cn1]<br>N-[2-(1-ethyl-1H-pyrazol-4-yl)-2-hydroxyethyl]-2-methyl-8-[4-(trifluoromethyl)phenyl]-2H,8H-pyrazolo[3,4-b]indole-5-carboxamide |
| B37 | 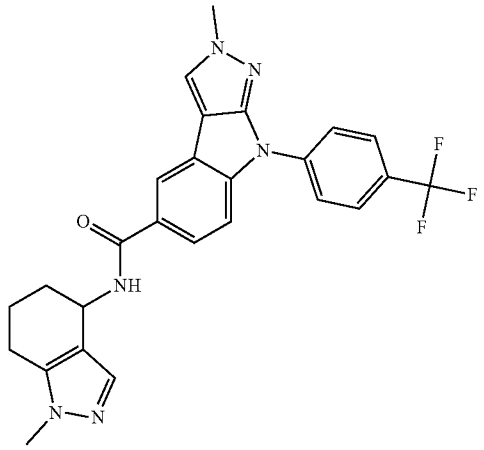 [SMILES: Cn1cc2c3cc(C(=O)NC4CCCc5c4cnn5C)ccc3n(-c3ccc(C(F)(F)F)cc3)c2n1]<br>2-methyl-N-(1-methyl-4,5,6,7-tetrahydro-1H-indazol-4-yl)-8-[4-(trifluoromethyl)phenyl]-2H,8H-pyrazolo[3,4-b]indole-5-carboxamide |
| B38 | 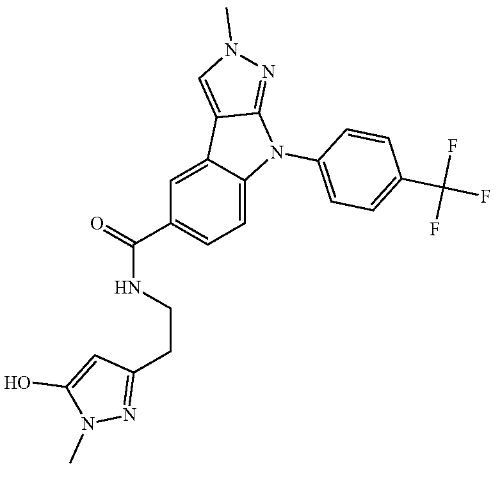 [SMILES: Cn1cc2c3cc(C(=O)NCCc4cc(O)n(C)n4)ccc3n(-c3ccc(C(F)(F)F)cc3)c2n1] |

-continued

| Compound No. | Structure and Name |
| --- | --- |
| | N-[2-(5-hydroxy-1-methyl-1H-pyrazol-3-yl)ethyl]-2-methyl-8-[4-(trifluoromethyl)phenyl]-2H,8H-pyrazolo[3,4-b]indole-5-carboxamide |
| B39 | 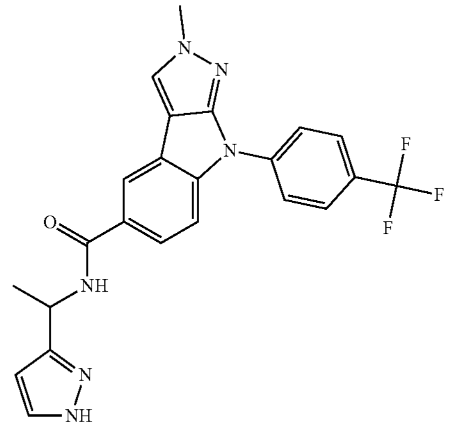 [SMILES: CC(NC(=O)c1ccc2c(c1)c1cn(C)nc1n2-c1ccc(C(F)(F)F)cc1)c1cc[nH]n1]<br>2-methyl-N-[1-(1H-pyrazol-5-yl)ethyl]-8-[4-(trifluoromethyl)phenyl]-2H,8H-pyrazolo[3,4-b]indole-5-carboxamide |
| B40 | 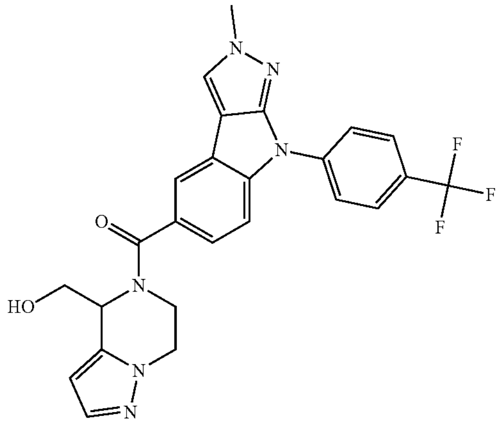 [SMILES: Cn1cc2c3cc(C(=O)N4CCn5nccc5C4CO)ccc3n(-c3ccc(C(F)(F)F)cc3)c2n1]<br>(5-{2-methyl-8-[4-(trifluoromethyl)phenyl]-2H,8H-pyrazolo[3,4-b]indole-5-carbonyl}-4H,5H,6H,7H-pyrazolo[1,5-a]pyrazin-4-yl)methanol |
| B41 | 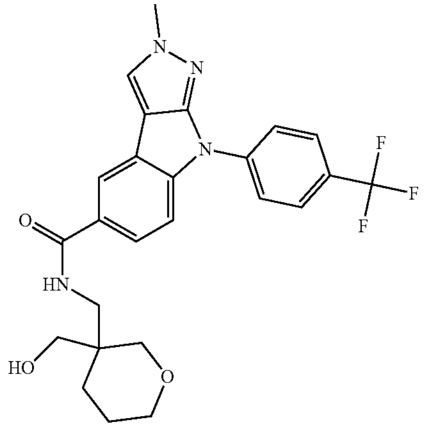 [SMILES: Cn1cc2c3cc(C(=O)NCC4(CO)CCCOC4)ccc3n(-c3ccc(C(F)(F)F)cc3)c2n1]<br>N-{[3-(hydroxymethyl)oxan-3-yl]methyl}-2-methyl-8-[4-(trifluoromethyl)phenyl]-2H,8H-pyrazolo[3,4-b]indole-5-carboxamide |

-continued

| Compound No. | Structure and Name |
| --- | --- |
| B42 | 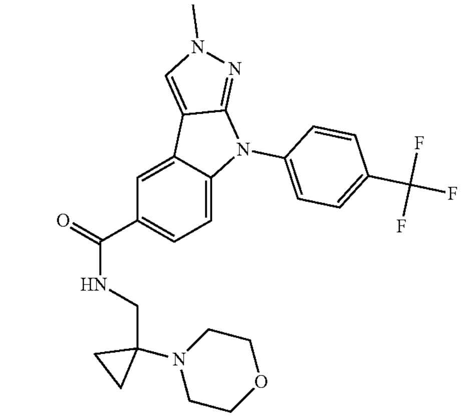 [SMILES: Cn1cc2c3cc(C(=O)NCC4(N5CCOCC5)CC4)ccc3n(-c3ccc(C(F)(F)F)cc3)c2n1] 2-methyl-N-{[1-(morpholin-4-yl)cyclopropyl]methyl}-8-[4-(trifluoromethyl)phenyl]-2H,8H-pyrazolo[3,4-b]indole-5-carboxamide |
| B43 | 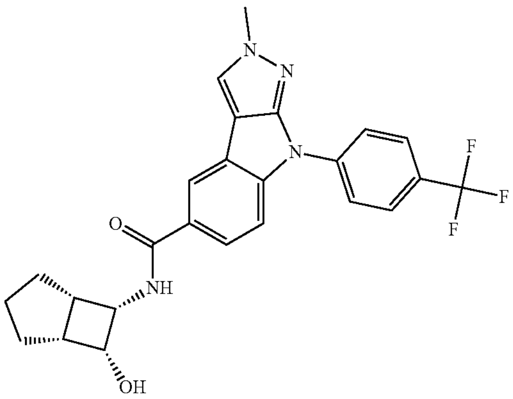 [SMILES: Cn1cc2c3cc(C(=O)N[C@@H]4[C@H](O)[C@@H]5CCC[C@@H]54)ccc3n(-c3ccc(C(F)(F)F)cc3)c2n1] racemic diastereomer with known relative stereochemistry N-[(1R,5S,6S,7R)-7-hydroxybicyclo[3.2.0]heptan-6-yl]-2-methyl-8-[4-(trifluoromethyl)phenyl]-2H,8H-pyrazolo[3,4-b]indole-5-carboxamide |
| B44 | 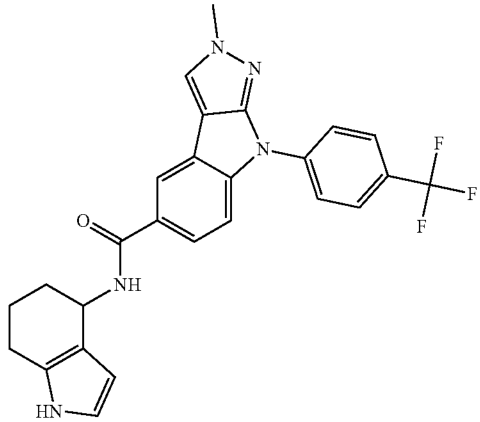 [SMILES: Cn1cc2c3cc(C(=O)NC4CCCc5[nH]ccc54)ccc3n(-c3ccc(C(F)(F)F)cc3)c2n1] 2-methyl-N-(4,5,6,7-tetrahydro-1H-indol-4-yl)-8-[4-(trifluoromethyl)phenyl]-2H,8H-pyrazolo[3,4-b]indole-5-carboxamide |

-continued
| Compound No. | Structure and Name |
| --- | --- |
| B45 | 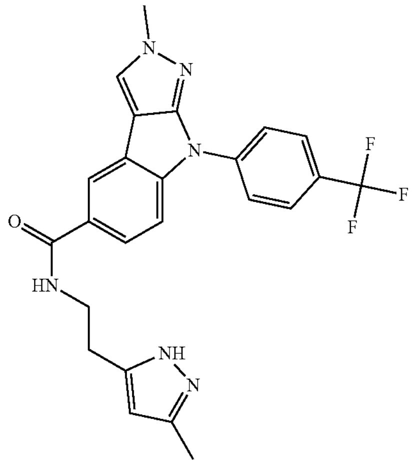 [SMILES: Cc1cc(CCNC(=O)c2ccc3c(c2)c2cn(C)nc2n3-c2ccc(C(F)(F)F)cc2)[nH]n1] 2-methyl-N-[2-(3-methyl-1H-pyrazol-5-yl)ethyl]-8-[4-(trifluoromethyl)phenyl]-2H,8H-pyrazolo[3,4-b]indole-5-carboxamide |
| B46 | 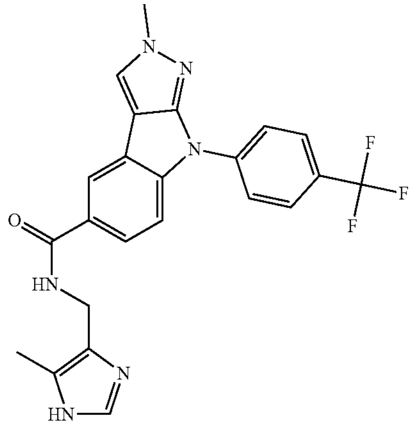 [SMILES: Cc1[nH]cnc1CNC(=O)c1ccc2c(c1)c1cn(C)nc1n2-c1ccc(C(F)(F)F)cc1] 2-methyl-N-[(5-methyl-1H-imidazol-4-yl)methyl]-8-[4-(trifluoromethyl)phenyl]-2H,8H-pyrazolo[3,4-b]indole-5-carboxamide |
| B47 | 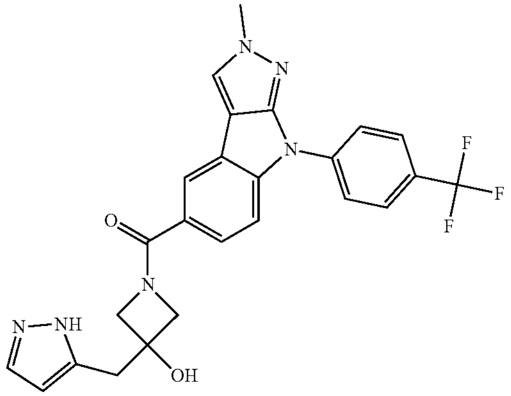 [SMILES: Cn1cc2c3cc(C(=O)N4CC(O)(Cc5ccn[nH]5)C4)ccc3n(-c3ccc(C(F)(F)F)cc3)c2n1] 1-{2-methyl-8-[4-(trifluoromethyl)phenyl]-2H,8H-pyrazolo[3,4-b]indole-5-carbonyl}-3-[(1H-pyrazol-5-yl)methyl]azetidin-3-ol |

-continued

| Compound No. | Structure and Name |
|---|---|
| B48 | 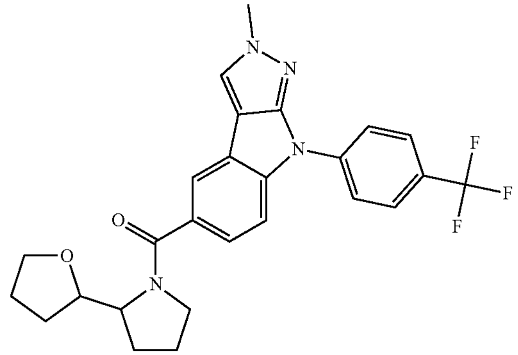 [SMILES: Cn1cc2c3cc(C(=O)N4CCCC4C4CCCO4)ccc3n(-c3ccc(C(F)(F)F)cc3)c2n1]<br>diastereomeric mixture<br>1-{2-methyl-8-[4-(trifluoromethyl)phenyl]-2H,8H-pyrazolo[3,4-b]indole-5-carbonyl}-2-(oxolan-2-yl)pyrrolidine |
| B49 | 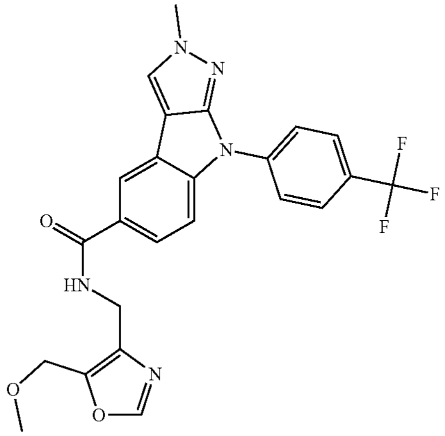 [SMILES: COCc1ocnc1CNC(=O)c1ccc2c(c1)c1cn(C)nc1n2-c1ccc(C(F)(F)F)cc1]<br>N-{[5-(methoxymethyl)-1,3-oxazol-4-yl]methyl}-2-methyl-8-[4-(trifluoromethyl)phenyl]-2H,8H-pyrazolo[3,4-b]indole-5-carboxamide |
| B50 | 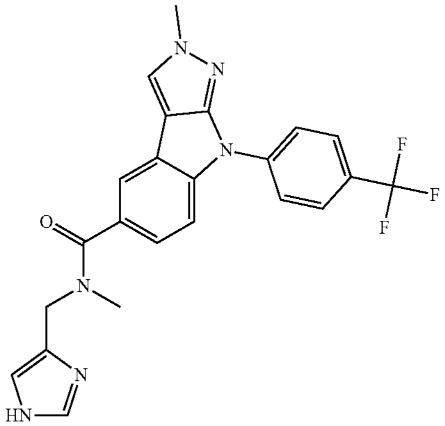 [SMILES: CN(Cc1c[nH]cn1)C(=O)c1ccc2c(c1)c1cn(C)nc1n2-c1ccc(C(F)(F)F)cc1]<br>N-[(1H-imidazol-4-yl)methyl]-N,2-dimethyl-8-[4-(trifluoromethyl)phenyl]-2H,8H-pyrazolo[3,4-b]indole-5-carboxamide |

-continued
| Compound No. | Structure and Name |
|---|---|
| B51 | 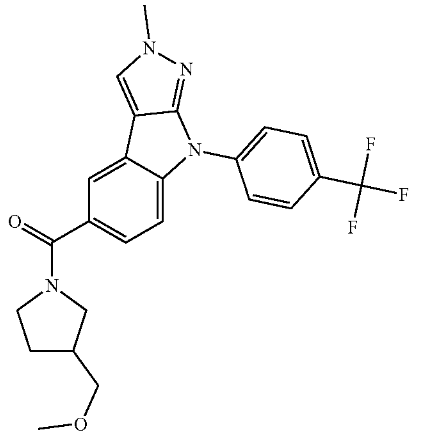 [SMILES: COCC1CCN(C(=O)c2ccc3c(c2)c2cn(C)nc2n3-c2ccc(C(F)(F)F)cc2)C1] 3-(methoxymethyl)-1-{2-methyl-8-[4-(trifluoromethyl)phenyl]-2H,8H-pyrazolo[3,4-b]indole-5-carbonyl}pyrrolidine |
| B52 | 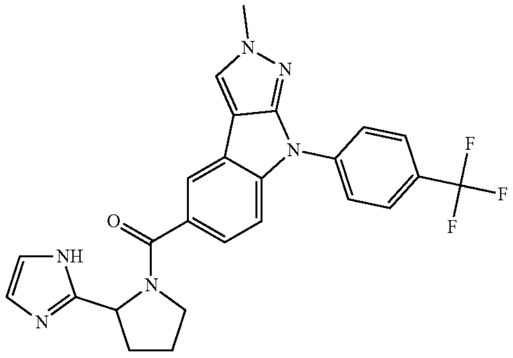 [SMILES: Cn1cc2c3cc(C(=O)N4CCCC4c4ncc[nH]4)ccc3n(-c3ccc(C(F)(F)F)cc3)c2n1] 2-(1-{2-methyl-8-[4-(trifluoromethyl)phenyl]-2H,8H-pyrazolo[3,4-b]indole-5-carbonyl}pyrrolidin-2-yl)-1H-imidazole |
| B53 | 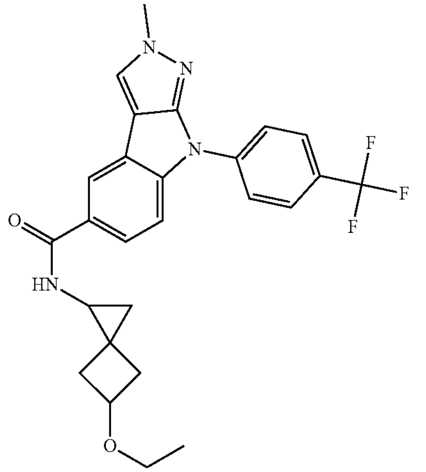 [SMILES: CCOC1CC2(C1)CC2NC(=O)c1ccc2c(c1)c1cn(C)nc1n2-c1ccc(C(F)(F)F)cc1] diastereomeric mixture N-{5-ethoxyspiro[2.3]hexan-1-yl}-2-methyl-8-[4-(trifluoromethyl)phenyl]-2H,8H-pyrazolo[3,4-b]indole-5-carboxamide |

-continued
| Compound No. | Structure and Name |
|---|---|
| B54 | 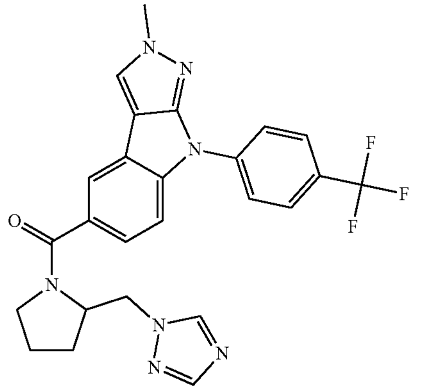 [SMILES: Cn1cc2c3cc(C(=O)N4CCCC4Cn4cncn4)ccc3n(-c3ccc(C(F)(F)F)cc3)c2n1]<br>1-[(1-{2-methyl-8-[4-(trifluoromethyl)phenyl]-2H,8H-pyrazolo[3,4-b]indole-5-carbonyl}pyrrolidin-2-yl)methyl]-1H-1,2,4-triazole |
| B55 | 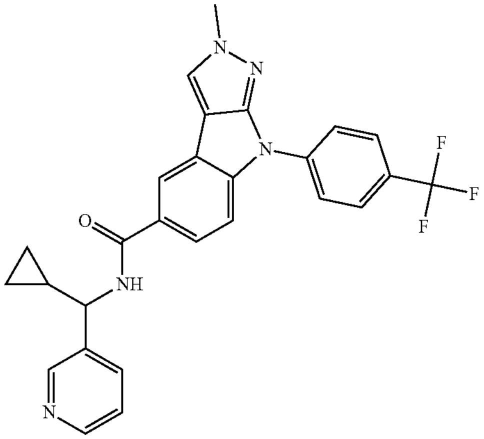 [SMILES: Cn1cc2c3cc(C(=O)NC(c4cccnc4)C4CC4)ccc3n(-c3ccc(C(F)(F)F)cc3)c2n1]<br>N-[cyclopropyl(pyridin-3-yl)methyl]-2-methyl-8-[4-(trifluoromethyl)phenyl]-2H,8H-pyrazolo[3,4-b]indole-5-carboxamide |
| B56 | 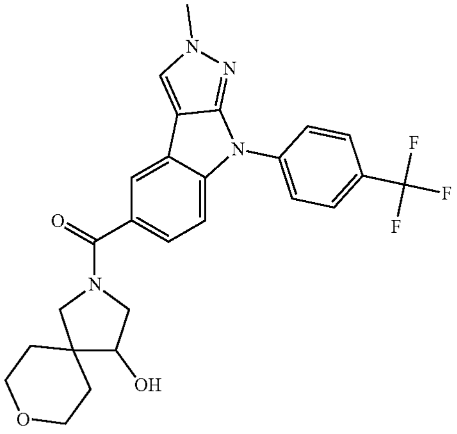 [SMILES: Cn1cc2c3cc(C(=O)N4CC(O)C5(CCOCC5)C4)ccc3n(-c3ccc(C(F)(F)F)cc3)c2n1]<br>2-{2-methyl-8-[4-(trifluoromethyl)phenyl]-2H,8H-pyrazolo[3,4-b]indole-5-carbonyl}-8-oxa-2-azaspiro[4.5]decan-4-ol |

-continued
| Compound No. | Structure and Name |
|---|---|
| B57 | 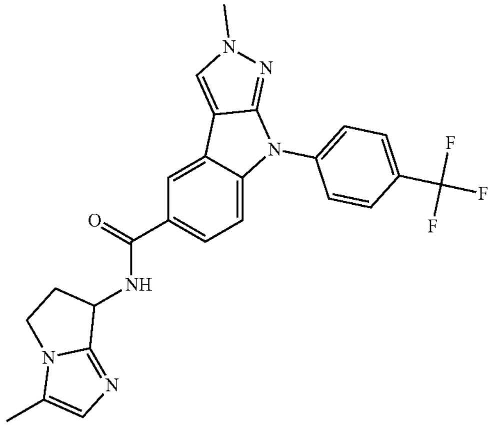 [SMILES: Cc1cnc2n1CCC2NC(=O)c1ccc2c(c1)c1cn(C)nc1n2-c1ccc(C(F)(F)F)cc1] 2-methyl-N-{3-methyl-5H,6H,7H-pyrrolo[1,2-a]imidazol-7-yl}-8-[4-(trifluoromethyl)phenyl]-2H,8H-pyrazolo[3,4-b]indole-5-carboxamide |
| B58 | 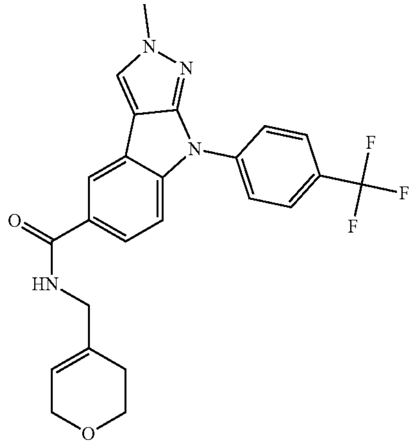 [SMILES: Cn1cc2c3cc(C(=O)NCC4=CCOCC4)ccc3n(-c3ccc(C(F)(F)F)cc3)c2n1] N-[(3,6-dihydro-2H-pyran-4-yl)methyl]-2-methyl-8-[4-(trifluoromethyl)phenyl]-2H,8H-pyrazolo[3,4-b]indole-5-carboxamide |
| B59 | 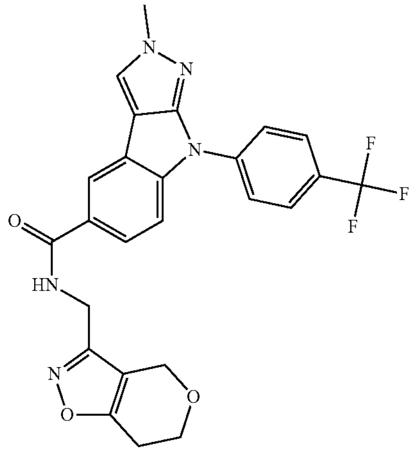 [SMILES: Cn1cc2c3cc(C(=O)NCc4noc5c4COCC5)ccc3n(-c3ccc(C(F)(F)F)cc3)c2n1] 2-methyl-N-({4H,6H,7H-pyrano[3,4-d][1,2]oxazol-3-yl}methyl)-8-[4-(trifluoromethyl)phenyl]-2H,8H-pyrazolo[3,4-b]indole-5-carboxamide |

-continued
| Compound No. | Structure and Name |
|---|---|
| B60 | 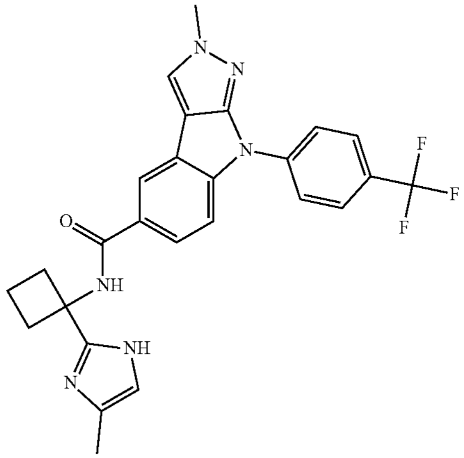 [SMILES: Cc1c[nH]c(C2(NC(=O)c3ccc4c(c3)c3cn(C)nc3n4-c3ccc(C(F)(F)F)cc3)CCC2)n1]<br>2-methyl-N-[1-(4-methyl-1H-imidazol-2-yl)cyclobutyl]-8-[4-(trifluoromethyl)phenyl]-2H,8H-pyrazolo[3,4-b]indole-5-carboxamide |
| B61 | 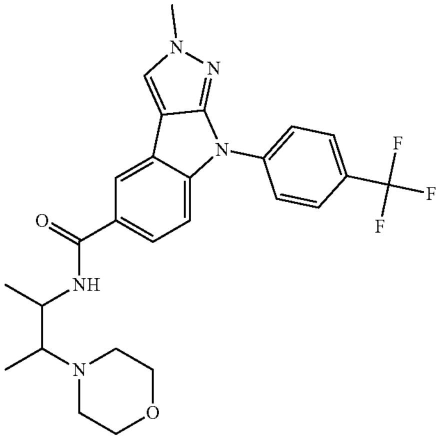 [SMILES: CC(NC(=O)c1ccc2c(c1)c1cn(C)nc1n2-c1ccc(C(F)(F)F)cc1)C(C)N1CCOCC1]<br>diastereomeric mixture<br>2-methyl-N-[3-(morpholin-4-yl)butan-2-yl]-8-[4-(trifluoromethyl)phenyl]-2H,8H-pyrazolo[3,4-b]indole-5-carboxamide |
| B62 | 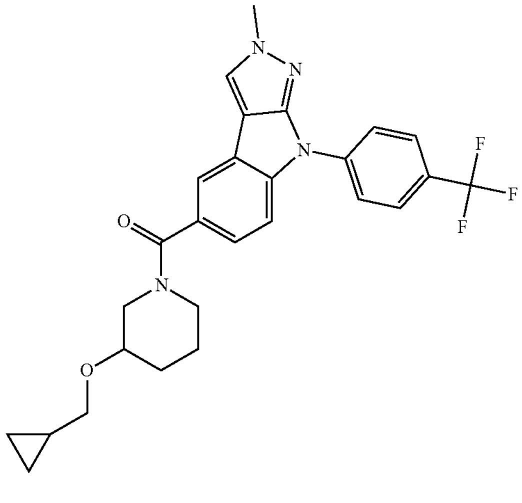 [SMILES: Cn1cc2c3cc(C(=O)N4CCCC(OCC5CC5)C4)ccc3n(-c3ccc(C(F)(F)F)cc3)c2n1] |

-continued
| Compound No. | Structure and Name |
|---|---|
| | 3-(cyclopropylmethoxy)-1-{2-methyl-8-[4-(trifluoromethyl)phenyl]-2H,8H-pyrazolo[3,4-b]indole-5-carbonyl}piperidine |
| B63 | 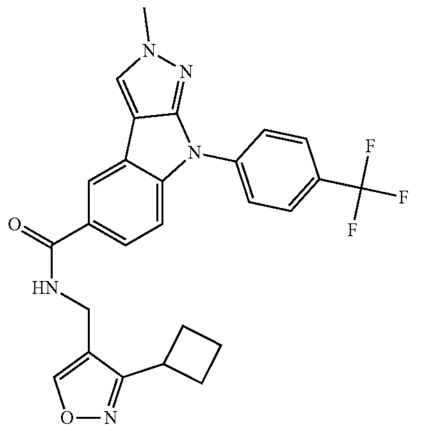 [SMILES: Cn1cc2c3cc(C(=O)NCc4conc4C4CCC4)ccc3n(-c3ccc(C(F)(F)F)cc3)c2n1] N-[(3-cyclobutyl-1,2-oxazol-4-yl)methyl]-2-methyl-8-[4-(trifluoromethyl)phenyl]-2H,8H-pyrazolo[3,4-b]indole-5-carboxamide |
| B64 | 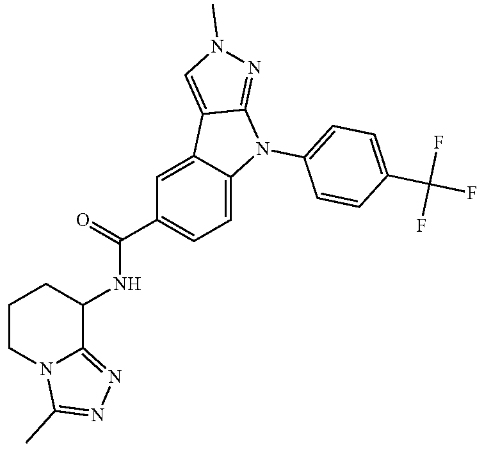 [SMILES: Cc1nnc2n1CCCC2NC(=O)c1ccc2c(c1)c1cn(C)nc1n2-c1ccc(C(F)(F)F)cc1] 2-methyl-N-{3-methyl-5H,6H,7H,8H-[1,2,4]triazolo[4,3-a]pyridin-8-yl}-8-[4-(trifluoromethyl)phenyl]-2H,8H-pyrazolo[3,4-b]indole-5-carboxamide |
| B65 | 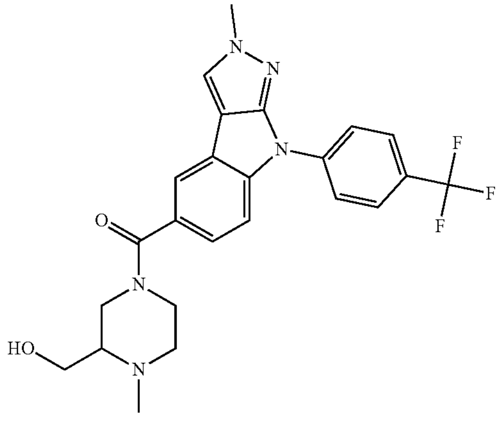 [SMILES: CN1CCN(C(=O)c2ccc3c(c2)c2cn(C)nc2n3-c2ccc(C(F)(F)F)cc2)CC1CO] |

-continued
| Compound No. | Structure and Name |
|---|---|
| | (1-methyl-4-{2-methyl-8-[4-(trifluoromethyl)phenyl]-2H,8H-pyrazolo[3,4-b]indole-5-carbonyl}piperazin-2-yl)methanol |
| B66 | 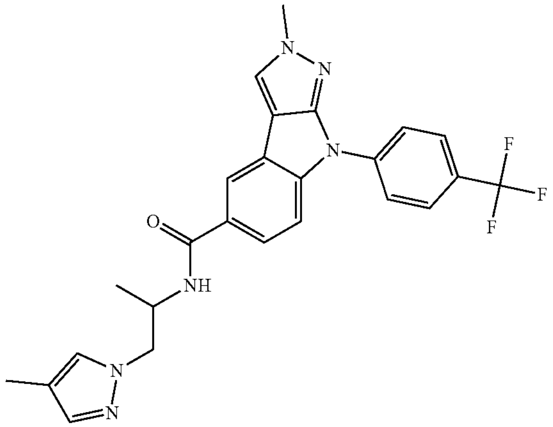 [SMILES: Cc1cnn(CC(C)NC(=O)c2ccc3c(c2)c2cn(C)nc2n3-c2ccc(C(F)(F)F)cc2)c1] 2-methyl-N-[1-(4-methyl-1H-pyrazol-1-yl)propan-2-yl]-8-[4-(trifluoromethyl)phenyl]-2H,8H-pyrazolo[3,4-b]indole-5-carboxamide |
| B67 | 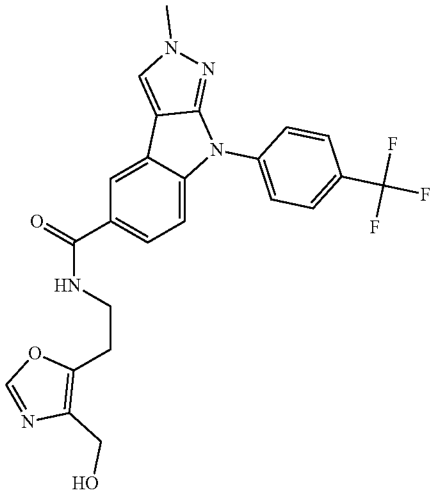 [SMILES: Cn1cc2c3cc(C(=O)NCCc4ocnc4CO)ccc3n(-c3ccc(C(F)(F)F)cc3)c2n1] N-{2-[4-(hydroxymethyl)-1,3-oxazol-5-yl]ethyl}-2-methyl-8-[4-(trifluoromethyl)phenyl]-2H,8H-pyrazolo[3,4-b]indole-5-carboxamide |

-continued
| Compound No. | Structure and Name |
| --- | --- |
| B68 | 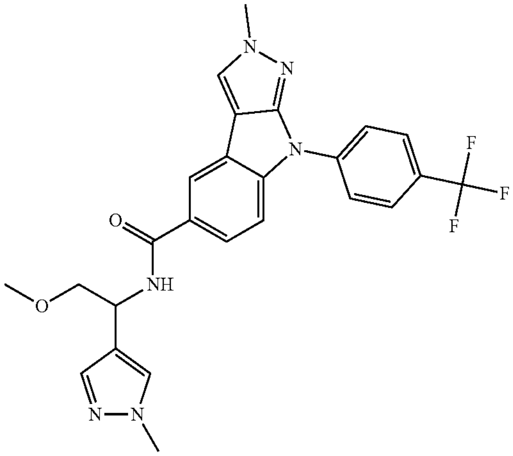 [SMILES: COCC(NC(=O)c1ccc2c(c1)c1cn(C)nc1n2-c1ccc(C(F)(F)F)cc1)c1cnn(C)c1]<br>N-[2-methoxy-1-(1-methyl-1H-pyrazol-4-yl)ethyl]-2-methyl-8-[4-(trifluoromethyl)phenyl]-2H,8H-pyrazolo[3,4-b]indole-5-carboxamide |
| B69 | 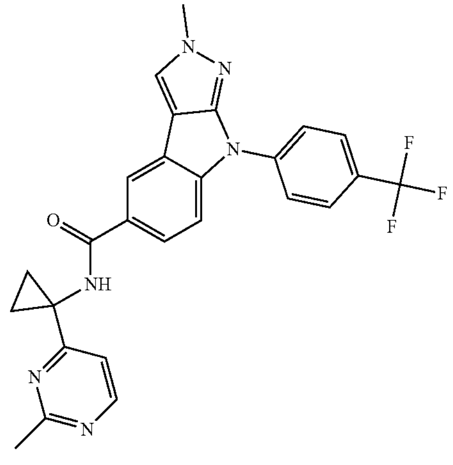 [SMILES: Cc1nccc(C2(NC(=O)c3ccc4c(c3)c3cn(C)nc3n4-c3ccc(C(F)(F)F)cc3)CC2)n1]<br>2-methyl-N-[1-(2-methylpyrimidin-4-yl)cyclopropyl]-8-[4-(trifluoromethyl)phenyl]-2H,8H-pyrazolo[3,4-b]indole-5-carboxamide |
| B70 | 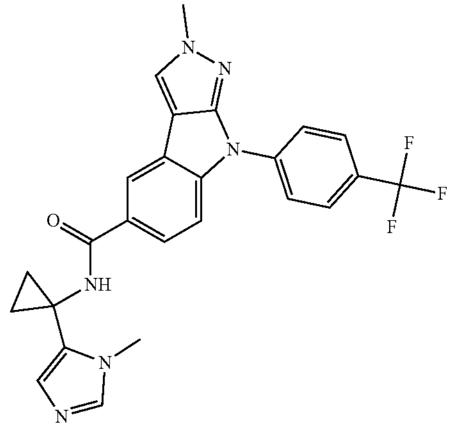 [SMILES: Cn1cc2c3cc(C(=O)NC4(c5cncn5C)CC4)ccc3n(-c3ccc(C(F)(F)F)cc3)c2n1]<br>2-methyl-N-[1-(1-methyl-1H-imidazol-5-yl)cyclopropyl]-8-[4-(trifluoromethyl)phenyl]-2H,8H-pyrazolo[3,4-b]indole-5-carboxamide |

-continued

| Compound No. | Structure and Name |
| --- | --- |
| B71 | 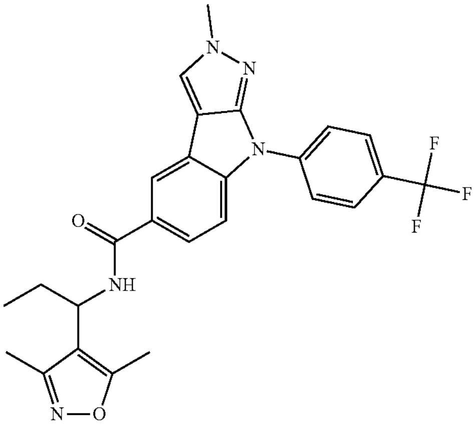 [SMILES: CCC(NC(=O)c1ccc2c(c1)c1cn(C)nc1n2-c1ccc(C(F)(F)F)cc1)c1c(C)noc1C]<br>N-[1-(3,5-dimethyl-1,2-oxazol-4-yl)propyl]-2-methyl-8-[4-(trifluoromethyl)phenyl]-2H,8H-pyrazolo[3,4-b]indole-5-carboxamide |
| B72 | 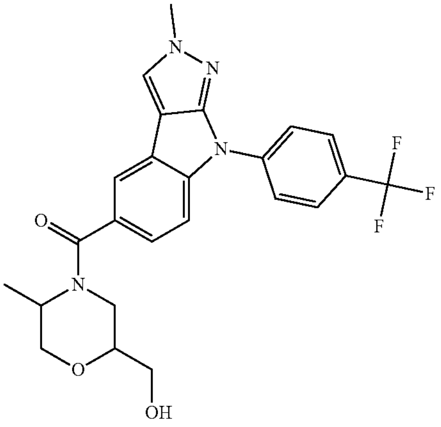 [SMILES: CC1COC(CO)CN1C(=O)c1ccc2c(c1)c1cn(C)nc1n2-c1ccc(C(F)(F)F)cc1]<br>diastereomeric mixture (5-methyl-4-{2-methyl-8-[4-(trifluoromethyl)phenyl]-2H,8H-pyrazolo[3,4-b]indole-5-carbonyl}morpholin-2-yl)methanol |
| B73 | 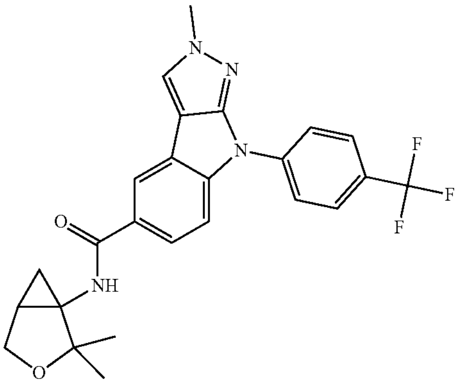 [SMILES: Cn1cc2c3cc(C(=O)NC45CC4COC5(C)C)ccc3n(-c3ccc(C(F)(F)F)cc3)c2n1]<br>diastereomeric mixture N-{2,2-dimethyl-3-oxabicyclo[3.1.0]hexan-1-yl}-2-methyl-8-[4-(trifluoromethyl)phenyl]-2H,8H-pyrazolo[3,4-b]indole-5-carboxamide |

-continued
| Compound No. | Structure and Name |
| --- | --- |
| B74 | 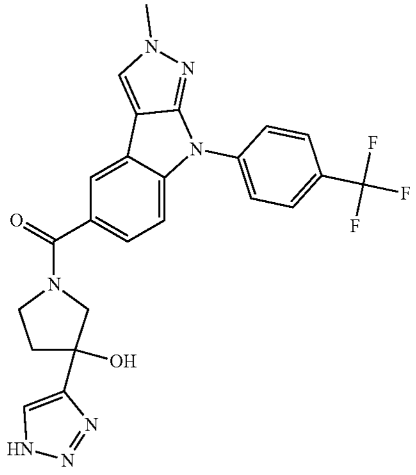 [SMILES: Cn1cc2c3cc(C(=O)N4CCC(O)(c5c[nH]nn5)C4)ccc3n(-c3ccc(C(F)(F)F)cc3)c2n1] 1-{2-methyl-8-[4-(trifluoromethyl)phenyl]-2H,8H-pyrazolo[3,4-b]indole-5-carbonyl}-3-(1H-1,2,3-triazol-4-yl)pyrrolidin-3-ol |
| B75 | 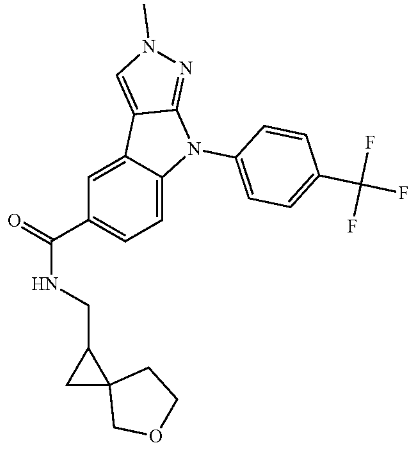 [SMILES: Cn1cc2c3cc(C(=O)NCC4CC45CCOC5)ccc3n(-c3ccc(C(F)(F)F)cc3)c2n1] diastereomeric mixture 2-methyl-N-({5-oxaspiro[2.4]heptan-1-yl}methyl)-8-[4-(trifluoromethyl)phenyl]-2H,8H-pyrazolo[3,4-b]indole-5-carboxamide |
| B76 | 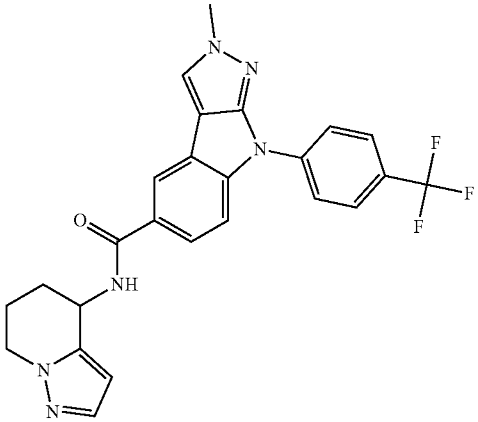 [SMILES: Cn1cc2c3cc(C(=O)NC4CCCn5nccc54)ccc3n(-c3ccc(C(F)(F)F)cc3)c2n1] 2-methyl-N-{4H,5H,6H,7H-pyrazolo[1,5-a]pyridin-4-yl}-8-[4-(trifluoromethyl)phenyl]-2H,8H-pyrazolo[3,4-b]indole-5-carboxamide |

-continued
| Compound No. | Structure and Name |
|---|---|
| B77 | 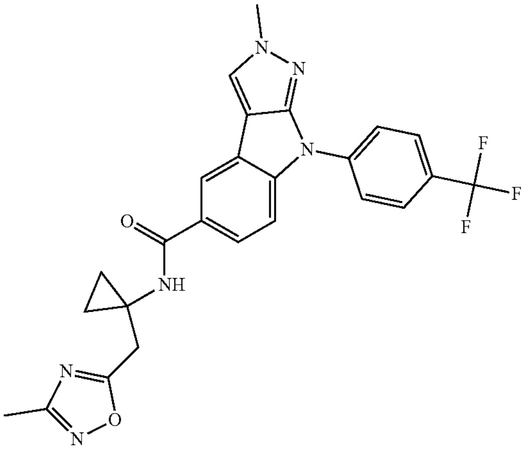 [SMILES: Cc1noc(CC2(NC(=O)c3ccc4c(c3)c3cn(C)nc3n4-c3ccc(C(F)(F)F)cc3)CC2)n1] 2-methyl-N-{1-[(3-methyl-1,2,4-oxadiazol-5-yl)methyl]cyclopropyl}-8-[4-(trifluoromethyl)phenyl]-2H,8H-pyrazolo[3,4-b]indole-5-carboxamide |
| B78 | 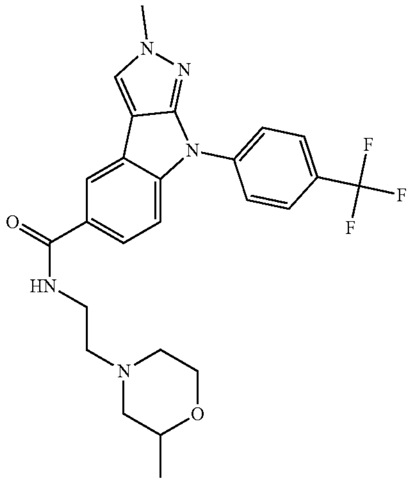 [SMILES: CC1CN(CCNC(=O)c2ccc3c(c2)c2cn(C)nc2n3-c2ccc(C(F)(F)F)cc2)CCO1] 2-methyl-N-[2-(2-methylmorpholin-4-yl)ethyl]-8-[4-(trifluoromethyl)phenyl]-2H,8H-pyrazolo[3,4-b]indole-5-carboxamide |

-continued
| Compound No. | Structure and Name |
| --- | --- |
| B79 | 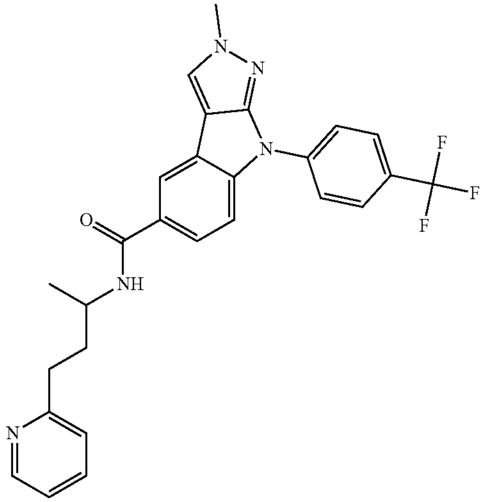 [SMILES: CC(CCc1ccccn1)NC(=O)c1ccc2c(c1)c1cn(C)nc1n2-c1ccc(C(F)(F)F)cc1]<br>2-methyl-N-[4-(pyridin-2-yl)butan-2-yl]-8-[4-(trifluoromethyl)phenyl]-2H,8H-pyrazolo[3,4-b]indole-5-carboxamide |
| B80 | 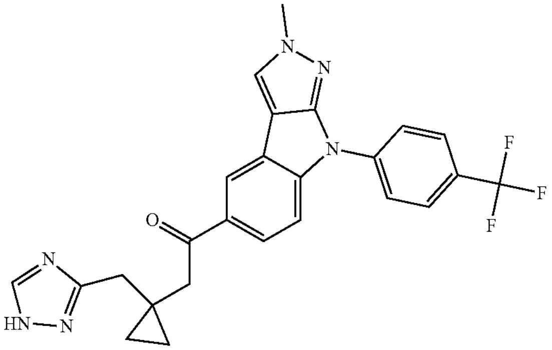 [SMILES: Cn1cc2c3cc(C(=O)CC4(Cc5nc[nH]n5)CC4)ccc3n(-c3ccc(C(F)(F)F)cc3)c2n1]<br>2-methyl-N-{1-[(1H-1,2,4-triazol-3-yl)methyl]cyclopropyl}-8-[4-(trifluoromethyl)phenyl]-2H,8H-pyrazolo[3,4-b]indole-5-carboxamide |
| B81 | 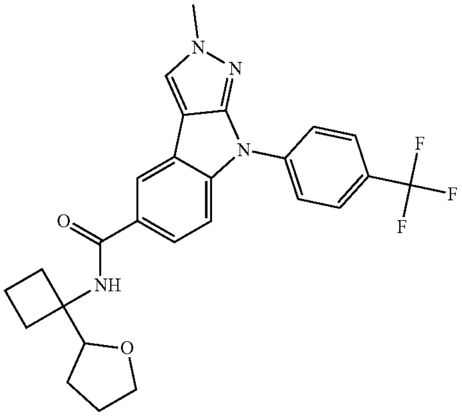 [SMILES: Cn1cc2c3cc(C(=O)NC4(C5CCCO5)CCC4)ccc3n(-c3ccc(C(F)(F)F)cc3)c2n1]<br>2-methyl-N-[1-(oxolan-2-yl)cyclobutyl]-8-[4-(trifluoromethyl)phenyl]-2H,8H-pyrazolo[3,4-b]indole-5-carboxamide |

-continued
| Compound No. | Structure and Name |
|---|---|
| B82 | 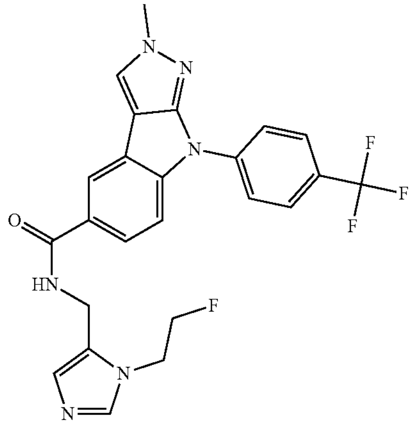 [SMILES: Cn1cc2c3cc(C(=O)NCc4cncn4CCF)ccc3n(-c3ccc(C(F)(F)F)cc3)c2n1] N-{[1-(2-fluoroethyl)-1H-imidazol-5-yl]methyl}-2-methyl-8-[4-(trifluoromethyl)phenyl]-2H,8H-pyrazolo[3,4-b]indole-5-carboxamide |
| B83 | 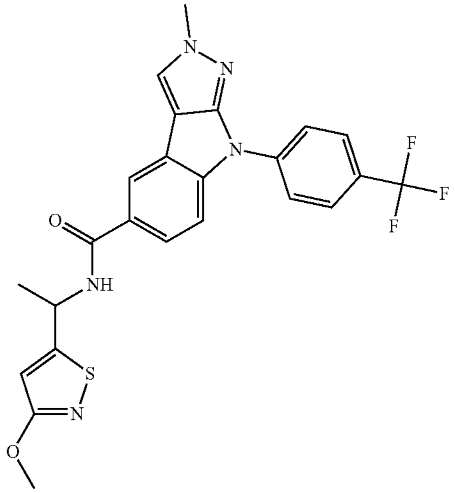 [SMILES: COc1cc(C(C)NC(=O)c2ccc3c(c2)c2cn(C)nc2n3-c2ccc(C(F)(F)F)cc2)sn1] N-[1-(3-methoxy-1,2-thiazol-5-yl)ethyl]-2-methyl-8-[4-(trifluoromethyl)phenyl]-2H,8H-pyrazolo[3,4-b]indole-5-carboxamide |
| B84 | 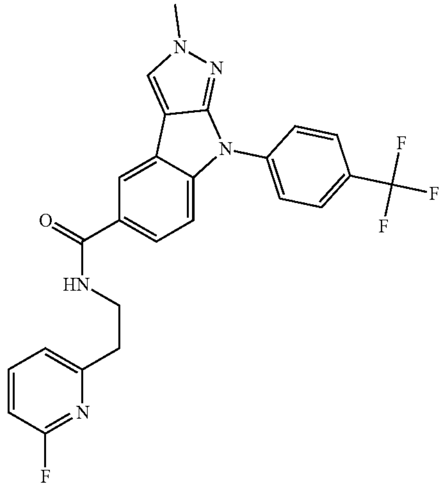 [SMILES: Cn1cc2c3cc(C(=O)NCCc4cccc(F)n4)ccc3n(-c3ccc(C(F)(F)F)cc3)c2n1] |

-continued
| Compound No. | Structure and Name |
|---|---|
| | N-[2-(6-fluoropyridin-2-yl)ethyl]-2-methyl-8-[4-(trifluoromethyl)phenyl]-2H,8H-pyrazolo[3,4-b]indole-5-carboxamide |
| B85 | 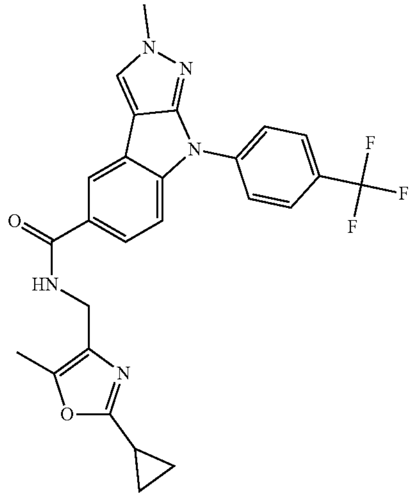 [SMILES: Cc1oc(C2CC2)nc1CNC(=O)c1ccc2c(c1)c1cn(C)nc1n2-c1ccc(C(F)(F)F)cc1] N-[(2-cyclopropyl-5-methyl-1,3-oxazol-4-yl)methyl]-2-methyl-8-[4-(trifluoromethyl)phenyl]-2H,8H-pyrazolo[3,4-b]indole-5-carboxamide |
| B86 | 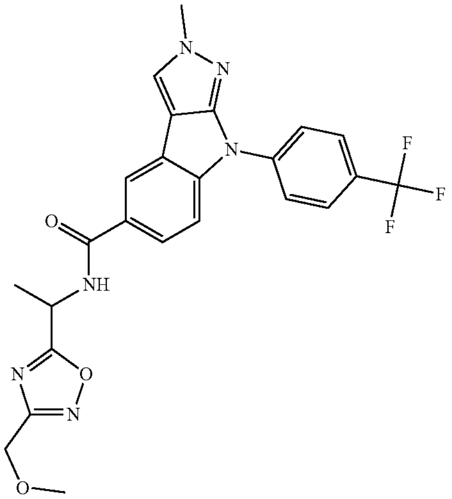 [SMILES: COCc1noc(C(C)NC(=O)c2ccc3c(c2)c2cn(C)nc2n3-c2ccc(C(F)(F)F)cc2)n1] N-{1-[3-(methoxymethyl)-1,2,4-oxadiazol-5-yl]ethyl}-2-methyl-8-[4-(trifluoromethyl)phenyl]-2H,8H-pyrazolo[3,4-b]indole-5-carboxamide |

-continued

| Compound No. | Structure and Name |
| --- | --- |
| B87 | 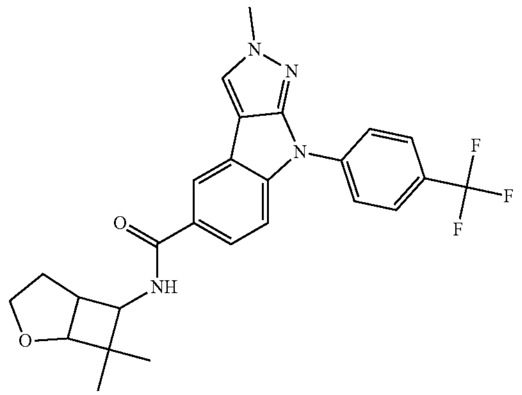 [SMILES: Cn1cc2c3cc(C(=O)NC4C5CCOC5C4(C)C)ccc3n(-c3ccc(C(F)(F)F)cc3)c2n1]<br>diastereomeric mixture<br>N-{7,7-dimethyl-2-oxabicyclo[3.2.0]heptan-6-yl}-2-methyl-8-[4-(trifluoromethyl)phenyl]-2H,8H-pyrazolo[3,4-b]indole-5-carboxamide |
| B88 | 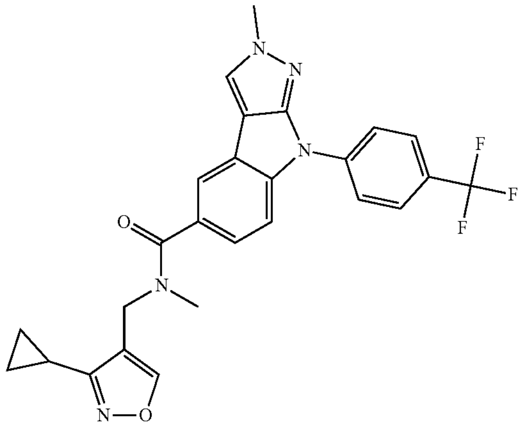 [SMILES: CN(Cc1conc1C1CC1)C(=O)c1ccc2c(c1)c1cn(C)nc1n2-c1ccc(C(F)(F)F)cc1]<br>N-[(3-cyclopropyl-1,2-oxazol-4-yl)methyl]-N,2-dimethyl-8-[4-(trifluoromethyl)phenyl]-2H,8H-pyrazolo[3,4-b]indole-5-carboxamide |
| B89 | 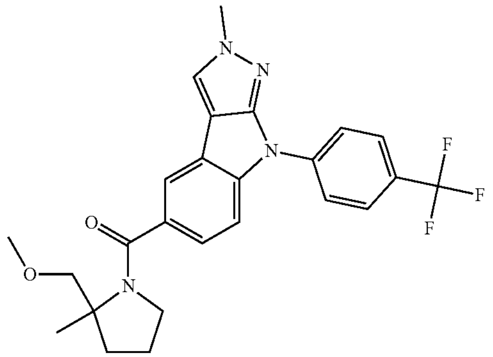 [SMILES: COCC1(C)CCCN1C(=O)c1ccc2c(c1)c1cn(C)nc1n2-c1ccc(C(F)(F)F)cc1]<br>2-(methoxymethyl)-2-methyl-1-{2-methyl-8-[4-(trifluoromethyl)phenyl]-2H,8H-pyrazolo[3,4-b]indole-5-carbonyl}pyrrolidine |

-continued
| Compound No. | Structure and Name |
| --- | --- |
| B90 | 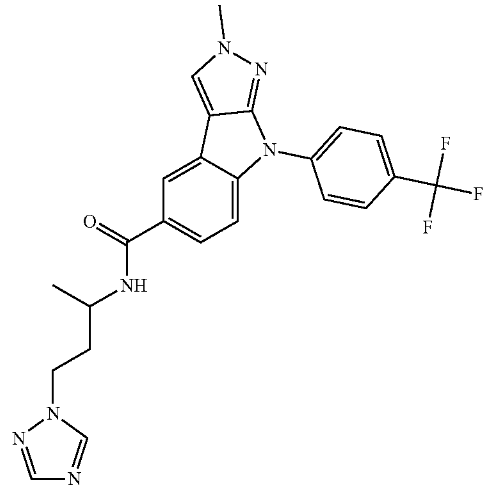 [SMILES: CC(CCn1cncn1)NC(=O)c1ccc2c(c1)c1cn(C)nc1n2-c1ccc(C(F)(F)F)cc1] 2-methyl-N-[4-(1H-1,2,4-triazol-1-yl)butan-2-yl]-8-[4-(trifluoromethyl)phenyl]-2H,8H-pyrazolo[3,4-b]indole-5-carboxamide |
| B91 | 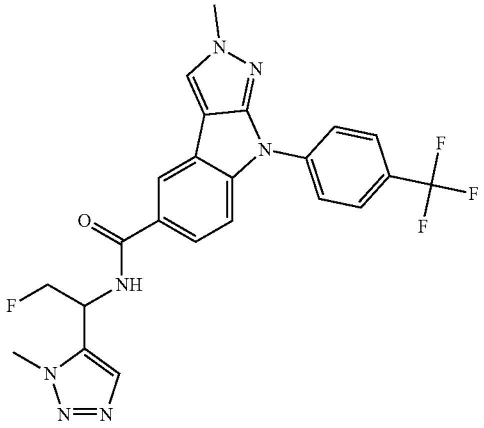 [SMILES: Cn1cc2c3cc(C(=O)NC(CF)c4cnnn4C)ccc3n(-c3ccc(C(F)(F)F)cc3)c2n1] N-[2-fluoro-1-(1-methyl-1H-1,2,3-triazol-5-yl)ethyl]-2-methyl-8-[4-(trifluoromethyl)phenyl]-2H,8H-pyrazolo[3,4-b]indole-5-carboxamide |
| B92 | 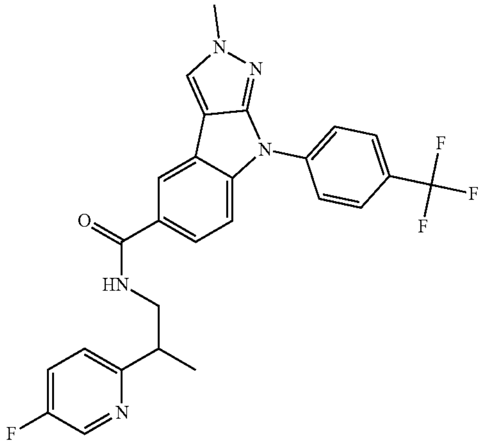 [SMILES: CC(CNC(=O)c1ccc2c(c1)c1cn(C)nc1n2-c1ccc(C(F)(F)F)cc1)c1ccc(F)cn1] N-[2-(5-fluoropyridin-2-yl)propyl]-2-methyl-8-[4-(trifluoromethyl)phenyl]-2H,8H-pyrazolo[3,4-b]indole-5-carboxamide |

-continued

| Compound No. | Structure and Name |
|---|---|
| B93 | 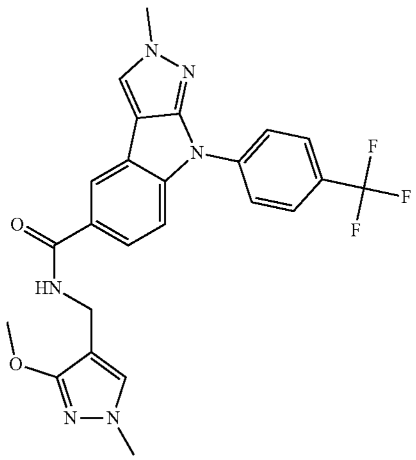 [SMILES: COc1nn(C)cc1CNC(=O)c1ccc2c(c1)c1cn(C)nc1n2-c1ccc(C(F)(F)F)cc1]<br>N-[(3-methoxy-1-methyl-1H-pyrazol-4-yl)methyl]-2-methyl-8-[4-(trifluoromethyl)phenyl]-2H,8H-pyrazolo[3,4-b]indole-5-carboxamide |
| B94 | 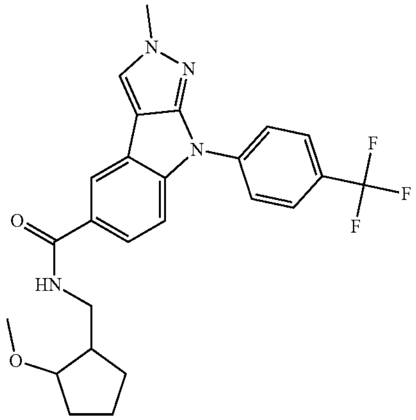 [SMILES: COC1CCCC1CNC(=O)c1ccc2c(c1)c1cn(C)nc1n2-c1ccc(C(F)(F)F)cc1]<br>diastereomeric mixture<br>N-[(2-methoxycyclopentyl)methyl]-2-methyl-8-[4-(trifluoromethyl)phenyl]-2H,8H-pyrazolo[3,4-b]indole-5-carboxamide |
| B95 | 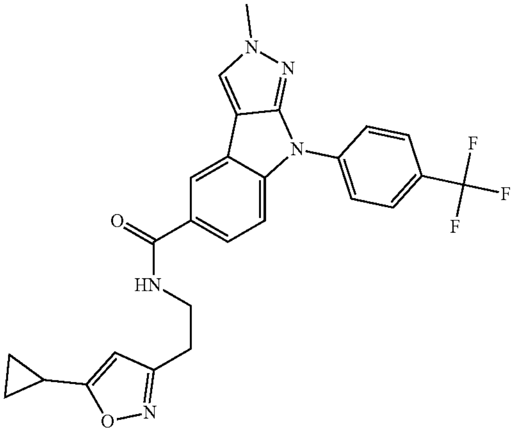 [SMILES: Cn1cc2c3cc(C(=O)NCCc4cc(C5CC5)on4)ccc3n(-c3ccc(C(F)(F)F)cc3)c2n1]<br>N-[2-(5-cyclopropyl-1,2-oxazol-3-yl)ethyl]-2-methyl-8-[4-(trifluoromethyl)phenyl]-2H,8H-pyrazolo[3,4-b]indole-5-carboxamide |

-continued
| Compound No. | Structure and Name |
|---|---|
| B96 | 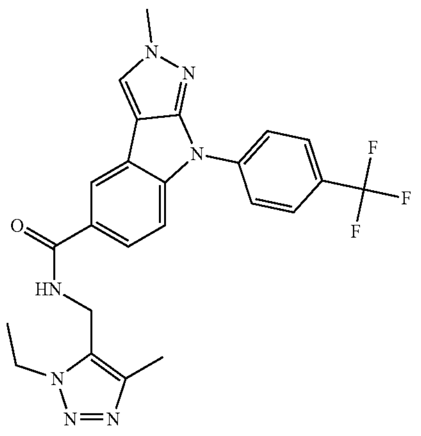 [SMILES: CCn1nnc(C)c1CNC(=O)c1ccc2c(c1)c1cn(C)nc1n2-c1ccc(C(F)(F)F)cc1] N-[(1-ethyl-4-methyl-1H-1,2,3-triazol-5-yl)methyl]-2-methyl-8-[4-(trifluoromethyl)phenyl]-2H,8H-pyrazolo[3,4-b]indole-5-carboxamide |
| B97 | 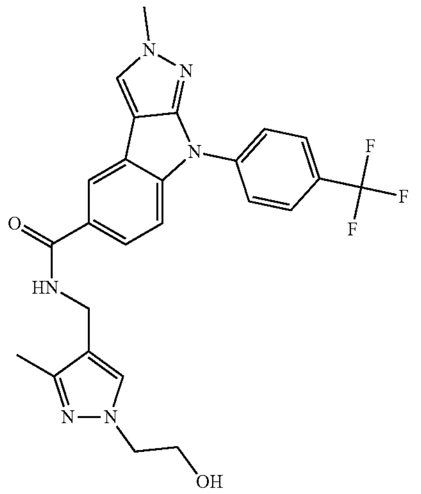 [SMILES: Cc1nn(CCO)cc1CNC(=O)c1ccc2c(c1)c1cn(C)nc1n2-c1ccc(C(F)(F)F)cc1] N-{[1-(2-hydroxyethyl)-3-methyl-1H-pyrazol-4-yl]methyl}-2-methyl-8-[4-(trifluoromethyl)phenyl]-2H,8H-pyrazolo[3,4-b]indole-5-carboxamide |
| B98 | 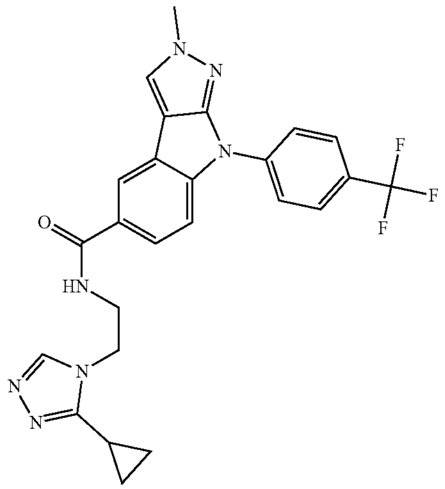 [SMILES: Cn1cc2c3cc(C(=O)NCCn4cnnc4C4CC4)ccc3n(-c3ccc(C(F)(F)F)cc3)c2n1] |

-continued

| Compound No. | Structure and Name |
|---|---|
| | N-[2-(3-cyclopropyl-4H-1,2,4-triazol-4-yl)ethyl]-2-methyl-8-[4-(trifluoromethyl)phenyl]-2H,8H-pyrazolo[3,4-b]indole-5-carboxamide |
| B99 | 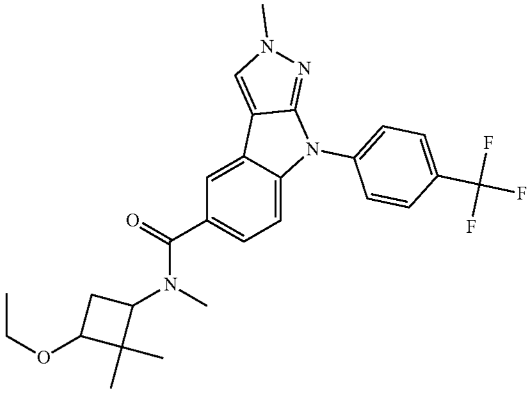 [SMILES: CCOC1CC(N(C)C(=O)c2ccc3c(c2)c2cn(C)nc2n3-c2ccc(C(F)(F)F)cc2)C1(C)C]<br>diastereomeric mixture<br>N-(3-ethoxy-2,2-dimethylcyclobutyl)-N,2-dimethyl-8-[4-(trifluoromethyl)phenyl]-2H,8H-pyrazolo[3,4-b]indole-5-carboxamide |
| B100 | 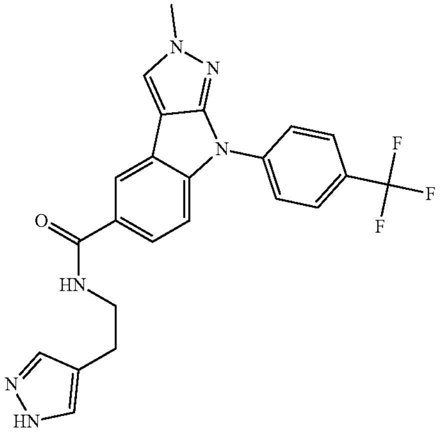 [SMILES: Cn1cc2c3cc(C(=O)NCCc4cn[nH]c4)ccc3n(-c3ccc(C(F)(F)F)cc3)c2n1]<br>2-methyl-N-[2-(1H-pyrazol-4-yl)ethyl]-8-[4-(trifluoromethyl)phenyl]-2H,8H-pyrazolo[3,4-b]indole-5-carboxamide |
| B101 | 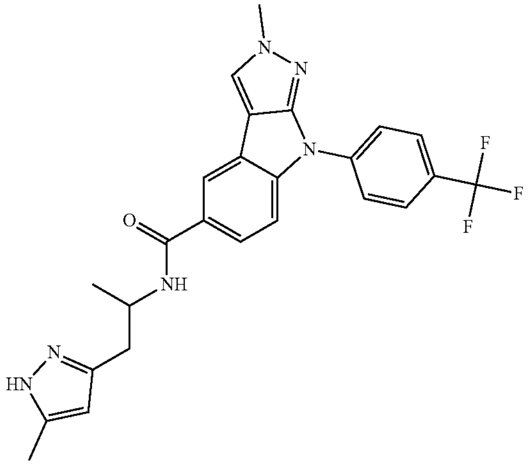 [SMILES: Cc1cc(CC(C)NC(=O)c2ccc3c(c2)c2cn(C)nc2n3-c2ccc(C(F)(F)F)cc2)n[nH]1] |

-continued

| Compound No. | Structure and Name |
| --- | --- |
| | 2-methyl-N-[1-(5-methyl-1H-pyrazol-3-yl)propan-2-yl]-8-[4-(trifluoromethyl)phenyl]-2H,8H-pyrazolo[3,4-b]indole-5-carboxamide |
| B102 | 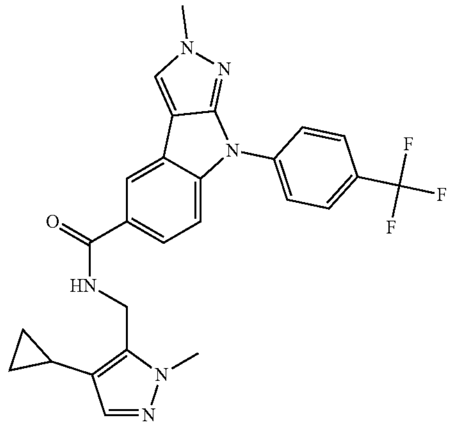 [SMILES: Cn1cc2c3cc(C(=O)NCc4c(C5CC5)cnn4C)ccc3n(-c3ccc(C(F)(F)F)cc3)c2n1] N-[(4-cyclopropyl-1-methyl-1H-pyrazol-5-yl)methyl]-2-methyl-8-[4-(trifluoromethyl)phenyl]-2H,8H-pyrazolo[3,4-b]indole-5-carboxamide |
| B103 | 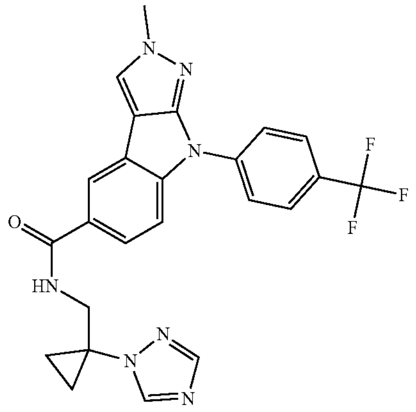 [SMILES: Cn1cc2c3cc(C(=O)NCC4(n5cncn5)CC4)ccc3n(-c3ccc(C(F)(F)F)cc3)c2n1] 2-methyl-N-{[1-(1H-1,2,4-triazol-1-yl)cyclopropyl]methyl}-8-[4-(trifluoromethyl)phenyl]-2H,8H-pyrazolo[3,4-b]indole-5-carboxamide |
| B104 | 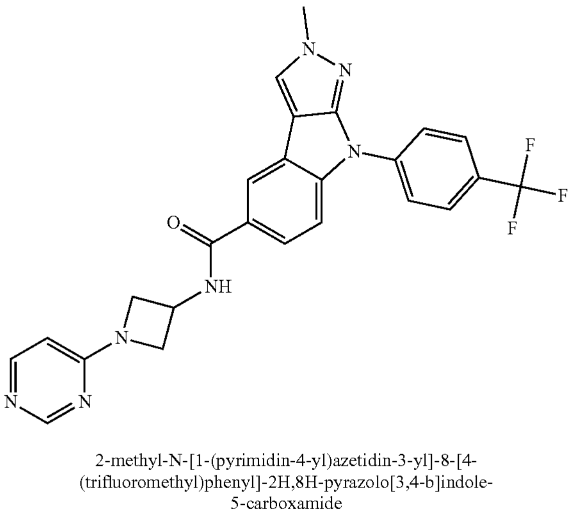 2-methyl-N-[1-(pyrimidin-4-yl)azetidin-3-yl]-8-[4-(trifluoromethyl)phenyl]-2H,8H-pyrazolo[3,4-b]indole-5-carboxamide |

-continued
| Compound No. | Structure and Name |
|---|---|
| B105 | 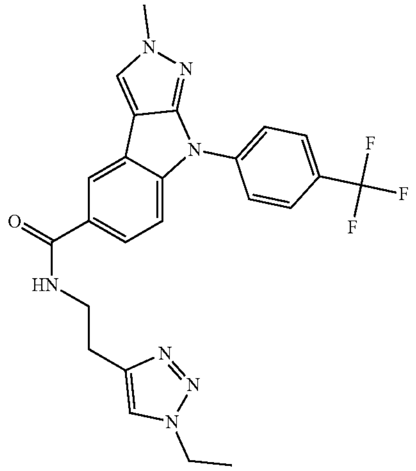 [SMILES: CCn1cc(CCNC(=O)c2ccc3c(c2)c2cn(C)nc2n3-c2ccc(C(F)(F)F)cc2)nn1]<br>N-[2-(1-ethyl-1H-1,2,3-triazol-4-yl)ethyl]-2-methyl-8-[4-(trifluoromethyl)phenyl]-2H,8H-pyrazolo[3,4-b]indole-5-carboxamide |
| B106 | 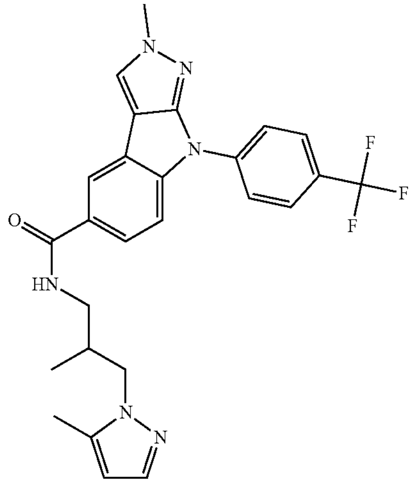 [SMILES: Cc1ccnn1CC(C)CNC(=O)c1ccc2c(c1)c1cn(C)nc1n2-c1ccc(C(F)(F)F)cc1]<br>2-methyl-N-{2-[(5-methyl-1H-pyrazol-1-yl)methyl]propyl}-8-[4-(trifluoromethyl)phenyl]-2H,8H-pyrazolo[3,4-b]indole-5-carboxamide |

-continued
| Compound No. | Structure and Name |
|---|---|
| B107 | 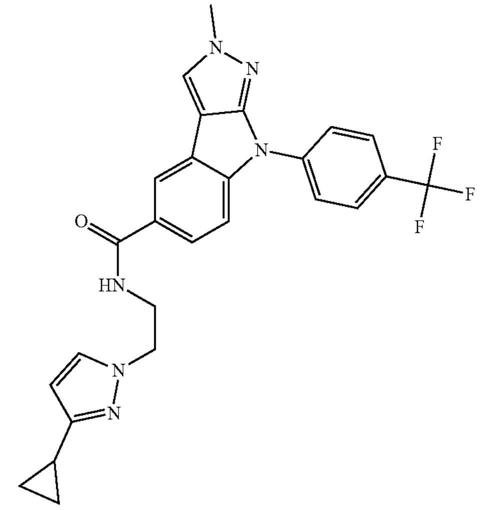 [SMILES: Cn1cc2c3cc(C(=O)NCCn4ccc(C5CC5)n4)ccc3n(-c3ccc(C(F)(F)F)cc3)c2n1]<br>N-[2-(3-cyclopropyl-1H-pyrazol-1-yl)ethyl]-2-methyl-8-[4-(trifluoromethyl)phenyl]-2H,8H-pyrazolo[3,4-b]indole-5-carboxamide |
| B108 | 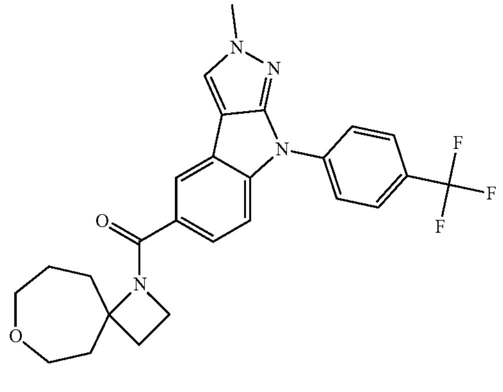 [SMILES: Cn1cc2c3cc(C(=O)N4CCC45CCCOCC5)ccc3n(-c3ccc(C(F)(F)F)cc3)c2n1]<br>1-{2-methyl-8-[4-(trifluoromethyl)phenyl]-2H,8H-pyrazolo[3,4-b]indole-5-carbonyl}-7-oxa-1-azaspiro[3.6]decane |
| B109 | 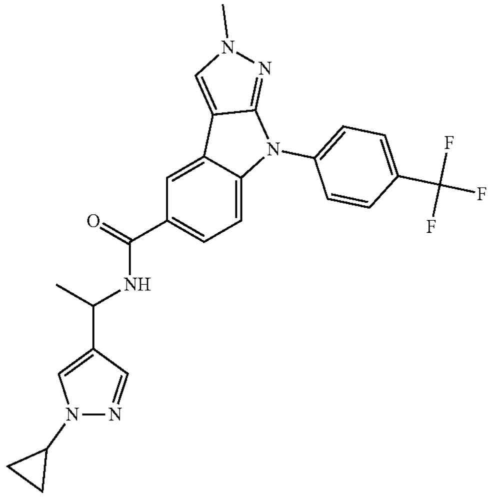 [SMILES: CC(NC(=O)c1ccc2c(c1)c1cn(C)nc1n2-c1ccc(C(F)(F)F)cc1)c1cnn(C2CC2)c1] |

-continued
| Compound No. | Structure and Name |
| --- | --- |
| | Racemate<br>N-[1-(1-cyclopropyl-1H-pyrazol-4-yl)ethyl]-2-methyl-8-[4-(trifluoromethyl)phenyl]-2H,8H-pyrazolo[3,4-b]indole-5-carboxamide |
| B110 | 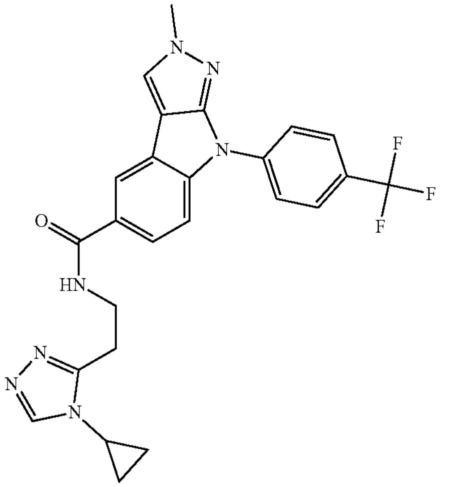 [SMILES: Cn1cc2c3cc(C(=O)NCCc4nncn4C4CC4)ccc3n(-c3ccc(C(F)(F)F)cc3)c2n1]<br>N-[2-(4-cyclopropyl-4H-1,2,4-triazol-3-yl)ethyl]-2-methyl-8-[4-(trifluoromethyl)phenyl]-2H,8H-pyrazolo[3,4-b]indole-5-carboxamide |
| B111 | 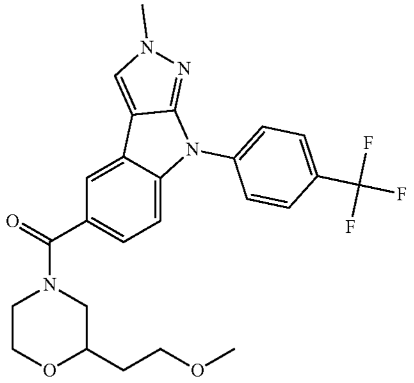 [SMILES: COCCC1CN(C(=O)c2ccc3c(c2)c2cn(C)nc2n3-c2ccc(C(F)(F)F)cc2)CCO1]<br>2-(2-methoxyethyl)-4-{2-methyl-8-[4-(trifluoromethyl)phenyl]-2H,8H-pyrazolo[3,4-b]indole-5-carbonyl}morpholine |
| B112 | 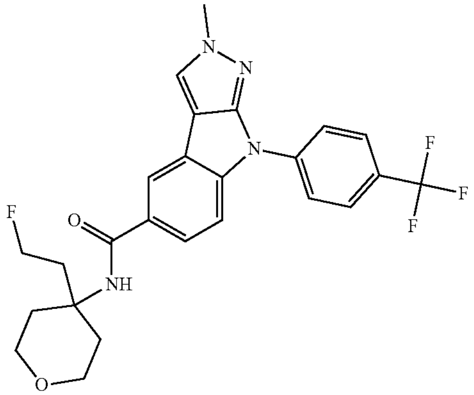 [SMILES: Cn1cc2c3cc(C(=O)NC4(CCF)CCOCC4)ccc3n(-c3ccc(C(F)(F)F)cc3)c2n1] |

-continued

| Compound No. | Structure and Name |
|---|---|
| | N-[4-(2-fluoroethyl)oxan-4-yl]-2-methyl-8-[4-(trifluoromethyl)phenyl]-2H,8H-pyrazolo[3,4-b]indole-5-carboxamide |
| B113 | 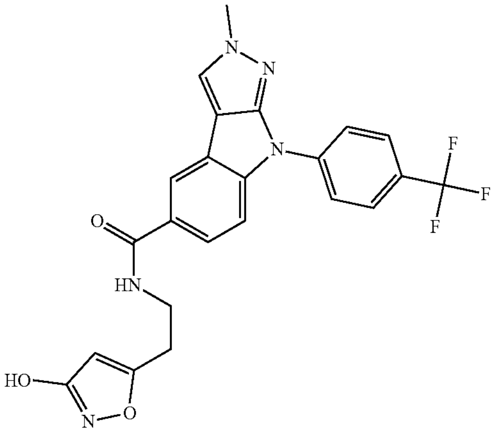 [SMILES: Cn1cc2c3cc(C(=O)NCCc4cc(O)no4)ccc3n(-c3ccc(C(F)(F)F)cc3)c2n1] N-[2-(3-hydroxy-1,2-oxazol-5-yl)ethyl]-2-methyl-8-[4-(trifluoromethyl)phenyl]-2H,8H-pyrazolo[3,4-b]indole-5-carboxamide |
| B114 | 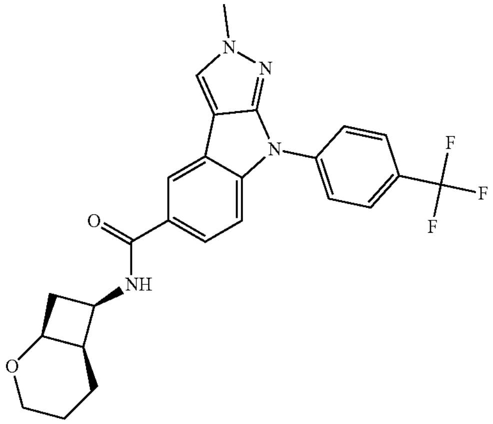 [SMILES: Cn1cc2c3cc(C(=O)N[C@@H]4C[C@@H]5OCCC[C@@H]54)ccc3n(-c3ccc(C(F)(F)F)cc3)c2n1] racemic diastereomer with known relative stereochemistry 2-methyl-N-[(1S,6R,7R)-2-oxabicyclo[4.2.0]octan-7-yl]-8-[4-(trifluoromethyl)phenyl]-2H,8H-pyrazolo[3,4-b]indole-5-carboxamide |
| B115 | 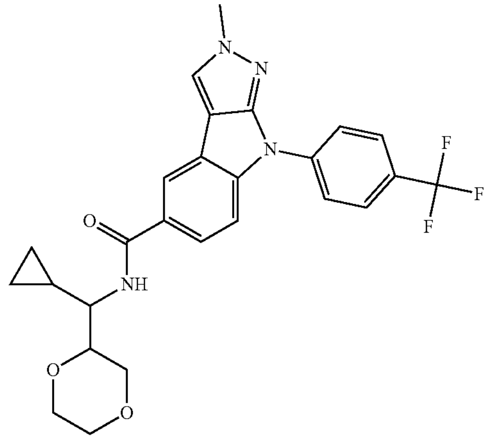 [SMILES: Cn1cc2c3cc(C(=O)NC(C4CC4)C4COCCO4)ccc3n(-c3ccc(C(F)(F)F)cc3)c2n1] |

-continued

| Compound No. | Structure and Name |
|---|---|
| | diastereomeric mixture N-[cyclopropyl(1,4-dioxan-2-yl)methyl]-2-methyl-8-[4-(trifluoromethyl)phenyl]-2H,8H-pyrazolo[3,4-b]indole-5-carboxamide |
| B116 | 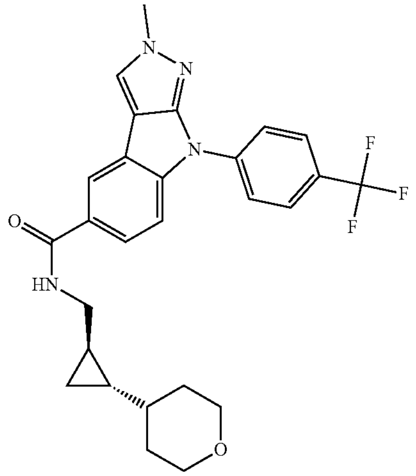 [SMILES: Cn1cc2c3cc(C(=O)NC[C@@H]4C[C@H]4C4CCOCC4)ccc3n(-c3ccc(C(F)(F)F)cc3)c2n1] racemic diastereomer with known relative stereochemistry, trans 2-methyl-N-{[(1R,2S)-2-(oxan-4-yl)cyclopropyl]methyl}-8-[4-(trifluoromethyl)phenyl]-2H,8H-pyrazolo[3,4-b]indole-5-carboxamide |
| B117 | 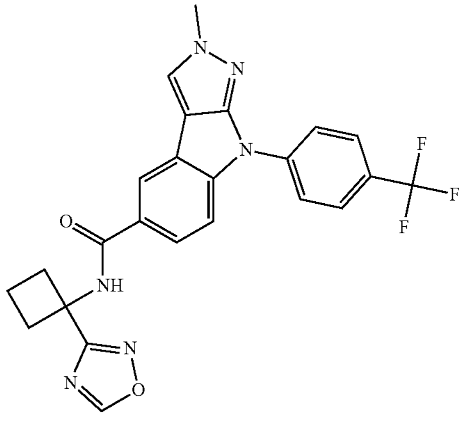 [SMILES: Cn1cc2c3cc(C(=O)NC4(c5ncon5)CCC4)ccc3n(-c3ccc(C(F)(F)F)cc3)c2n1] 2-methyl-N-[1-(1,2,4-oxadiazol-3-yl)cyclobutyl]-8-[4-(trifluoromethyl)phenyl]-2H,8H-pyrazolo[3,4-b]indole-5-carboxamide |

-continued

| Compound No. | Structure and Name |
| --- | --- |
| B118 | 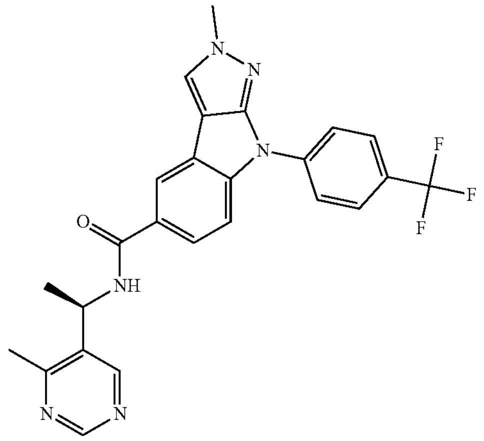 [SMILES: Cc1ncncc1[C@@H](C)NC(=O)c1ccc2c(c1)c1cn(C)nc1n2-c1ccc(C(F)(F)F)cc1] stereochemistry assigned/known; single enantiomer 2-methyl-N-[(1R)-1-(4-methylpyrimidin-5-yl)ethyl]-8-[4-(trifluoromethyl)phenyl]-2H,8H-pyrazolo[3,4-b]indole-5-carboxamide |
| B119 | 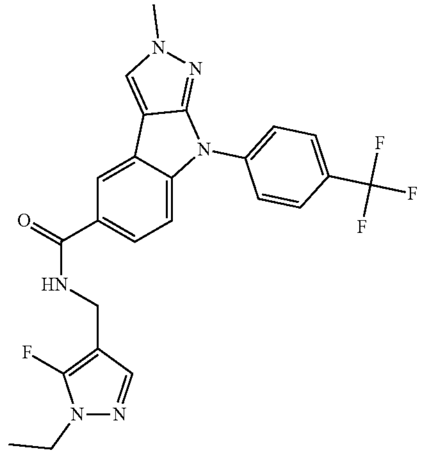 [SMILES: CCn1ncc(CNC(=O)c2ccc3c(c2)c2cn(C)nc2n3-c2ccc(C(F)(F)F)cc2)c1F] N-[(1-ethyl-5-fluoro-1H-pyrazol-4-yl)methyl]-2-methyl-8-[4-(trifluoromethyl)phenyl]-2H,8H-pyrazolo[3,4-b]indole-5-carboxamide |
| B120 | 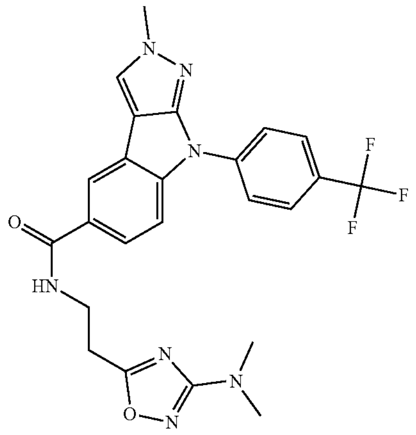 [SMILES: CN(C)c1noc(CCNC(=O)c2ccc3c(c2)c2cn(C)nc2n3-c2ccc(C(F)(F)F)cc2)n1] N-{2-[3-(dimethylamino)-1,2,4-oxadiazol-5-yl]ethyl}-2-methyl-8-[4-(trifluoromethyl)phenyl]-2H,8H-pyrazolo[3,4-b]indole-5-carboxamide |

-continued
| Compound No. | Structure and Name |
| --- | --- |
| B121 | 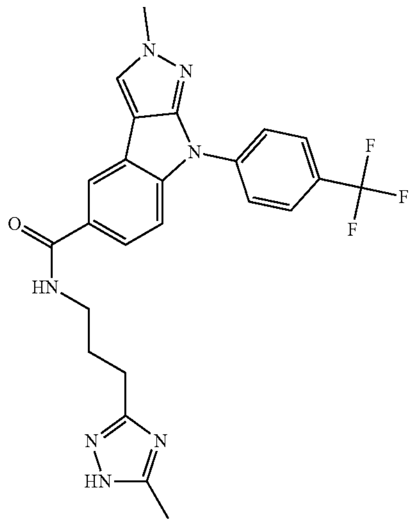 [SMILES: Cc1nc(CCCNC(=O)c2ccc3c(c2)c2cn(C)nc2n3-c2ccc(C(F)(F)F)cc2)n[nH]1] 2-methyl-N-[3-(5-methyl-1H-1,2,4-triazol-3-yl)propyl]-8-[4-(trifluoromethyl)phenyl]-2H,8H-pyrazolo[3,4-b]indole-5-carboxamide |
| B122 | 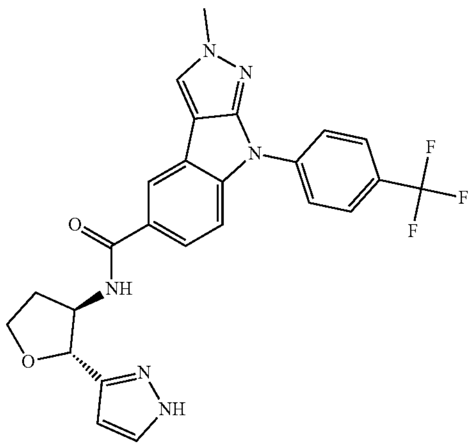 [SMILES: Cn1cc2c3cc(C(=O)N[C@@H]4CCO[C@H]4c4cc[nH]n4)ccc3n(-c3ccc(C(F)(F)F)cc3)c2n1] racemic diastereomer with known relative stereochemistry, trans 2-methyl-N-[(2R,3R)-2-(1H-pyrazol-3-yl)oxolan-3-yl]-8-[4-(trifluoromethyl)phenyl]-2H,8H-pyrazolo[3,4-b]indole-5-carboxamide |

-continued
| Compound No. | Structure and Name |
| --- | --- |
| B123 | 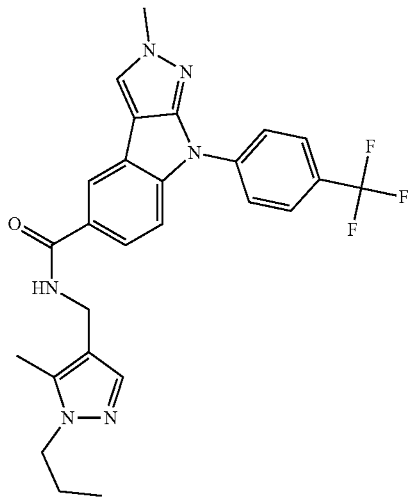 [SMILES: CCCn1ncc(CNC(=O)c2ccc3c(c2)c2cn(C)nc2n3-c2ccc(C(F)(F)F)cc2)c1C]<br>2-methyl-N-[(5-methyl-1-propyl-1H-pyrazol-4-yl)methyl]-8-[4-(trifluoromethyl)phenyl]-2H,8H-pyrazolo[3,4-b]indole-5-carboxamide |
| B124 | 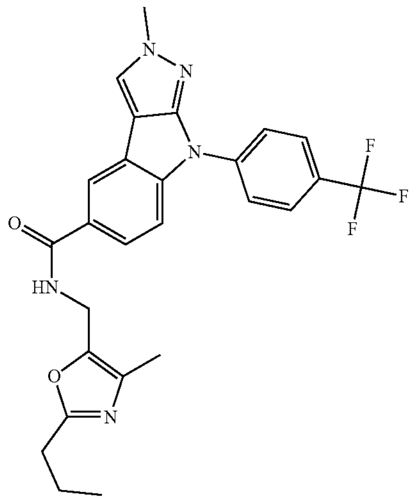 [SMILES: CCCc1nc(C)c(CNC(=O)c2ccc3c(c2)c2cn(C)nc2n3-c2ccc(C(F)(F)F)cc2)o1]<br>2-methyl-N-[(4-methyl-2-propyl-1,3-oxazol-5-yl)methyl]-8-[4-(trifluoromethyl)phenyl]-2H,8H-pyrazolo[3,4-b]indole-5-carboxamide |

-continued
| Compound No. | Structure and Name |
|---|---|
| B125 | 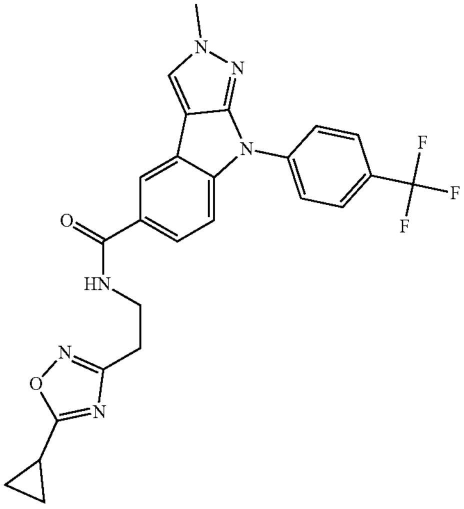 [SMILES: Cn1cc2c3cc(C(=O)NCCc4noc(C5CC5)n4)ccc3n(-c3ccc(C(F)(F)F)cc3)c2n1]<br>N-[2-(5-cyclopropyl-1,2,4-oxadiazol-3-yl)ethyl]-2-methyl-8-[4-(trifluoromethyl)phenyl]-2H,8H-pyrazolo[3,4-b]indole-5-carboxamide |
| B126 | 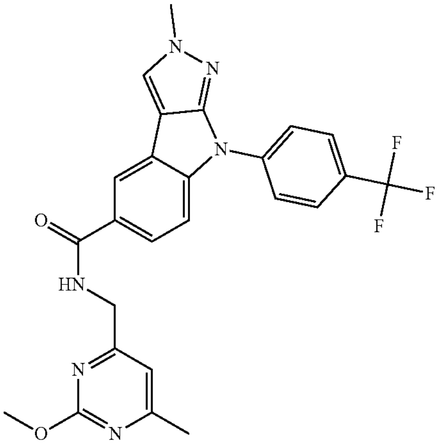 [SMILES: COc1nc(C)cc(CNC(=O)c2ccc3c(c2)c2cn(C)nc2n3-c2ccc(C(F)(F)F)cc2)n1]<br>N-[(2-methoxy-6-methylpyrimidin-4-yl)methyl]-2-methyl-8-[4-(trifluoromethyl)phenyl]-2H,8H-pyrazolo[3,4-b]indole-5-carboxamide |
| B127 | 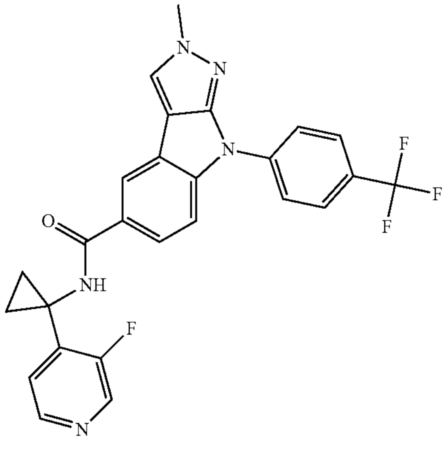 [SMILES: Cn1cc2c3cc(C(=O)NC4(c5ccncc5F)CC4)ccc3n(-c3ccc(C(F)(F)F)cc3)c2n1] |

-continued

| Compound No. | Structure and Name |
|---|---|
| | N-[1-(3-fluoropyridin-4-yl)cyclopropyl]-2-methyl-8-[4-(trifluoromethyl)phenyl]-2H,8H-pyrazolo[3,4-b]indole-5-carboxamide |
| B128 | 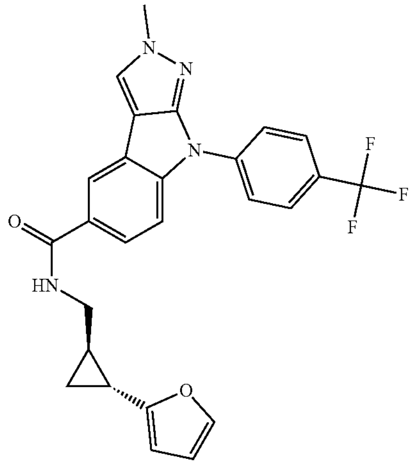 [SMILES: Cn1cc2c3cc(C(=O)NC[C@@H]4C[C@H]4c4ccco4)ccc3n(-c3ccc(C(F)(F)F)cc3)c2n1]<br>racemic diastereomer with known relative stereochemistry, trans N-{[(1R,2R)-2-(furan-2-yl)cyclopropyl]methyl}-2-methyl-8-[4-(trifluoromethyl)phenyl]-2H,8H-pyrazolo[3,4-bindole-5-carboxamide |
| B129 | 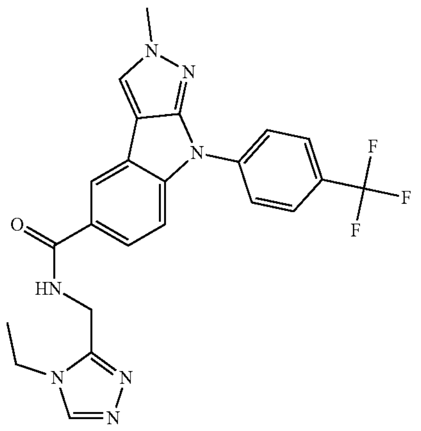 [SMILES: CCn1cnnc1CNC(=O)c1ccc2c(c1)c1cn(C)nc1n2-c1ccc(C(F)(F)F)cc1]<br>N-[(4-ethyl-4H-1,2,4-triazol-3-yl)methyl]-2-methyl-8-[4-(trifluoromethyl)phenyl]-2H,8H-pyrazolo[3,4-b]indole-5-carboxamide |

-continued
| Compound No. | Structure and Name |
| --- | --- |
| B130 | 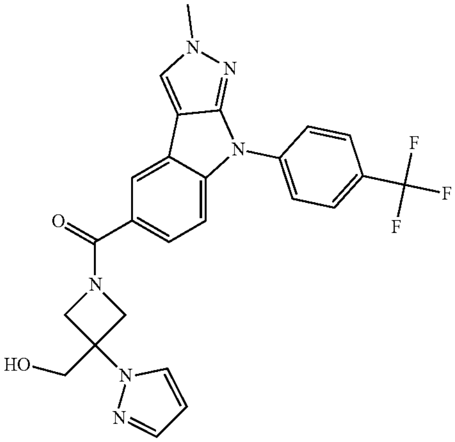 [SMILES: Cn1cc2c3cc(C(=O)N4CC(CO)(n5cccn5)C4)ccc3n(-c3ccc(C(F)(F)F)cc3)c2n1]<br>(1-{2-methyl-8-[4-(trifluoromethyl)phenyl]-2H,8H-pyrazolo[3,4-b]indole-5-carbonyl}-3-(1H-pyrazol-1-yl)azetidin-3-yl)methanol |
| B131 | 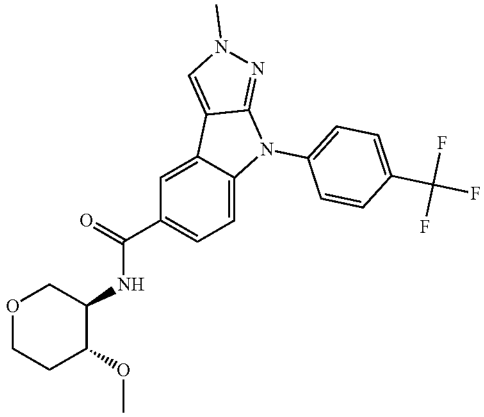 [SMILES: CO[C@@H]1CCOC[C@H]1NC(=O)c1ccc2c(c1)c1cn(C)nc1n2-c1ccc(C(F)(F)F)cc1]<br>racemic diastereomer with known relative stereochemistry, trans N-[(3R,4R)-4-methoxyoxan-3-yl]-2-methyl-8-[4-(trifluoromethyl)phenyl]-2H,8H-pyrazolo[3,4-b]indole-5-carboxamide |
| B132 | 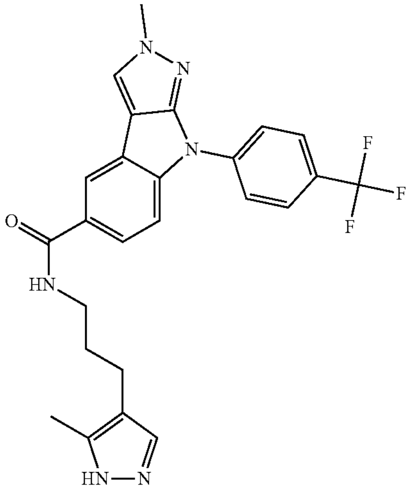 [SMILES: Cc1[nH]ncc1CCCNC(=O)c1ccc2c(c1)c1cn(C)nc1n2-c1ccc(C(F)(F)F)cc1] |

-continued
| Compound No. | Structure and Name |
| --- | --- |
| | 2-methyl-N-[3-(5-methyl-1H-pyrazol-4-yl)propyl]-8-[4-(trifluoromethyl)phenyl]-2H,8H-pyrazolo[3,4-b]indole-5-carboxamide |
| B133 | 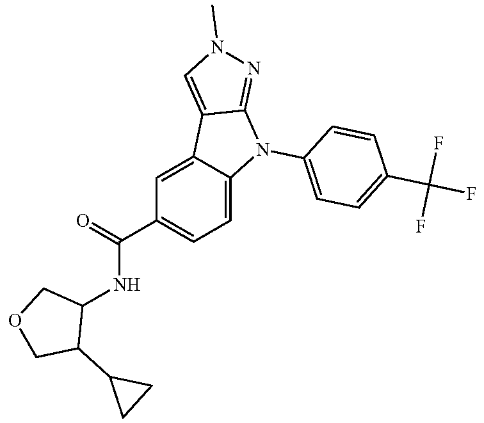 [SMILES: Cn1cc2c3cc(C(=O)NC4COCC4C4CC4)ccc3n(-c3ccc(C(F)(F)F)cc3)c2n1]<br>diastereomeric mixture<br>N-(4-cyclopropyloxolan-3-yl)-2-methyl-8-[4-(trifluoromethyl)phenyl]-2H,8H-pyrazolo[3,4-b]indole-5-carboxamide |
| B134 | 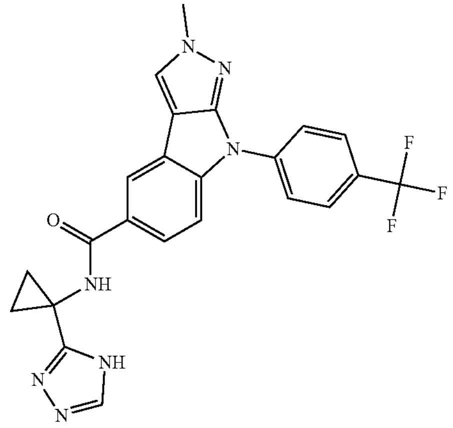 [SMILES: Cn1cc2c3cc(C(=O)NC4(c5nnc[nH]5)CC4)ccc3n(-c3ccc(C(F)(F)F)cc3)c2n1]<br>2-methyl-N-[1-(4H-1,2,4-triazol-3-yl)cyclopropyl]-8-[4-(trifluoromethyl)phenyl]-2H,8H-pyrazolo[3,4-b]indole-5-carboxamide |
| B135 | 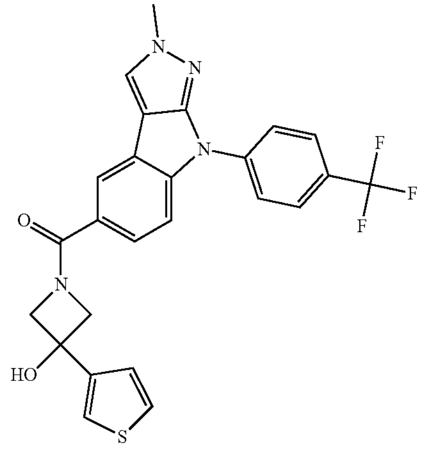 [SMILES: Cn1cc2c3cc(C(=O)N4CC(O)(c5ccsc5)C4)ccc3n(-c3ccc(C(F)(F)F)cc3)c2n1] |

-continued
| Compound No. | Structure and Name |
| --- | --- |
| | 1-{2-methyl-8-[4-(trifluoromethyl)phenyl]-2H,8H-pyrazolo[3,4-b]indole-5-carbonyl}-3-(thiophen-3-yl)azetidin-3-ol |
| B136 | 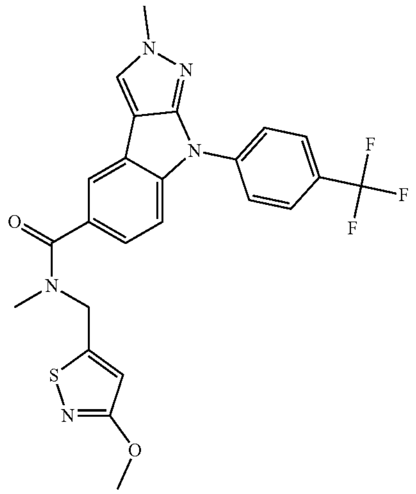 [SMILES: COc1cc(CN(C)C(=O)c2ccc3c(c2)c2cn(C)nc2n3-c2ccc(C(F)(F)F)cc2)sn1]<br>N-[(3-methoxy-1,2-thiazol-5-yl)methyl]-N,2-dimethyl-8-[4-(trifluoromethyl)phenyl]-2H,8H-pyrazolo[3,4-b]indole-5-carboxamide |
| B137 | 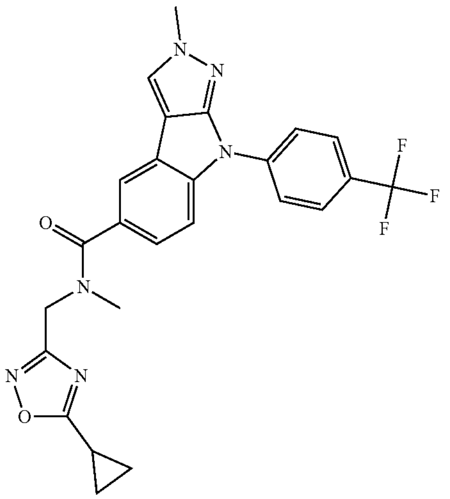 [SMILES: CN(Cc1noc(C2CC2)n1)C(=O)c1ccc2c(c1)c1cn(C)nc1n2-c1ccc(C(F)(F)F)cc1]<br>N-[(5-cyclopropyl-1,2,4-oxadiazol-3-yl)methyl]-N,2-dimethyl-8-[4-(trifluoromethyl)phenyl]-2H,8H-pyrazolo[3,4-b]indole-5-carboxamide |

-continued
| Compound No. | Structure and Name |
| --- | --- |
| B138 | 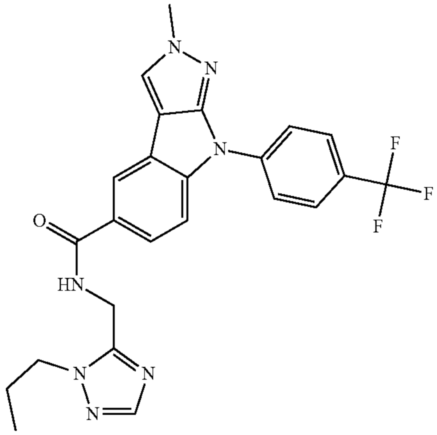 [SMILES: CCCn1ncnc1CNC(=O)c1ccc2c(c1)c1cn(C)nc1n2-c1ccc(C(F)(F)F)cc1]<br>2-methyl-N-[(1-propyl-1H-1,2,4-triazol-5-yl)methyl]-8-[4-(trifluoromethyl)phenyl]-2H,8H-pyrazolo[3,4-b]indole-5-carboxamide |
| B139 | 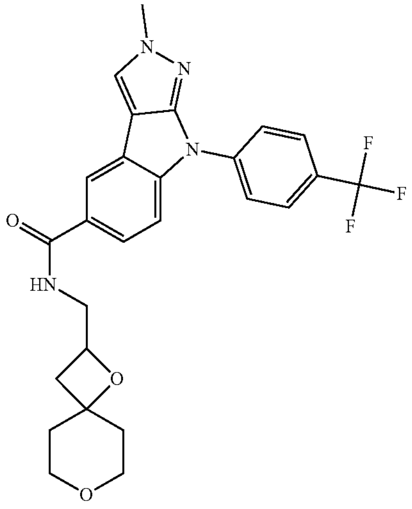 [SMILES: Cn1cc2c3cc(C(=O)NCC4CC5(CCOCC5)O4)ccc3n(-c3ccc(C(F)(F)F)cc3)c2n1]<br>N-({1,7-dioxaspiro[3.5]nonan-2-yl}methyl)-2-methyl-8-[4-(trifluoromethyl)phenyl]-2H,8H-pyrazolo[3,4-b]indole-5-carboxamide |

-continued
| Compound No. | Structure and Name |
| --- | --- |
| B140 | 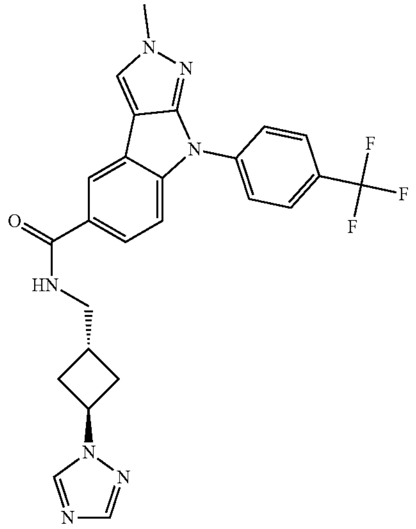 [SMILES: Cn1cc2c3cc(C(=O)NC[C@H]4C[C@H](n5cncn5)C4)ccc3n(-c3ccc(C(F)(F)F)cc3)c2n1]<br>Relative configuration known, trans<br>2-methyl-N-{[(1r,3r)-3-(1H-1,2,4-triazol-1-yl)cyclobutyl]methyl}-8-[4-(trifluoromethyl)phenyl]-2H,8H-pyrazolo[3,4-b]indole-5-carboxamide |
| B141 | 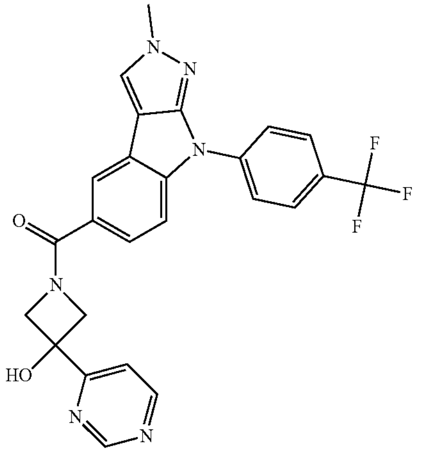 [SMILES: Cn1cc2c3cc(C(=O)N4CC(O)(c5ccncn5)C4)ccc3n(-c3ccc(C(F)(F)F)cc3)c2n1]<br>1-{2-methyl-8-[4-(trifluoromethyl)phenyl]-2H,8H-pyrazolo[3,4-b]indole-5-carbonyl}-3-(pyrimidin-4-yl)azetidin-3-ol |

-continued
| Compound No. | Structure and Name |
| --- | --- |
| B142 | 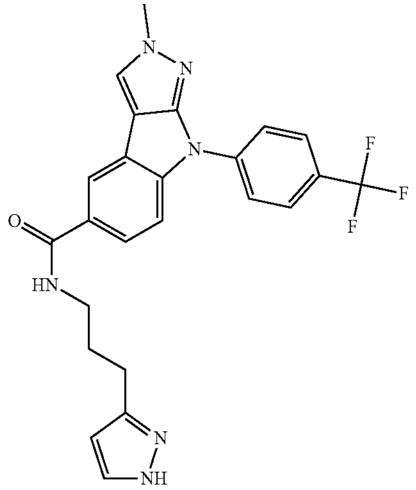 [SMILES: Cn1cc2c3cc(C(=O)NCCCc4cc[nH]n4)ccc3n(-c3ccc(C(F)(F)F)cc3)c2n1]<br>2-methyl-N-[3-(1H-pyrazol-3-yl)propyl]-8-[4-(trifluoromethyl)phenyl]-2H,8H-pyrazolo[3,4-b]indole-5-carboxamide |
| B143 | 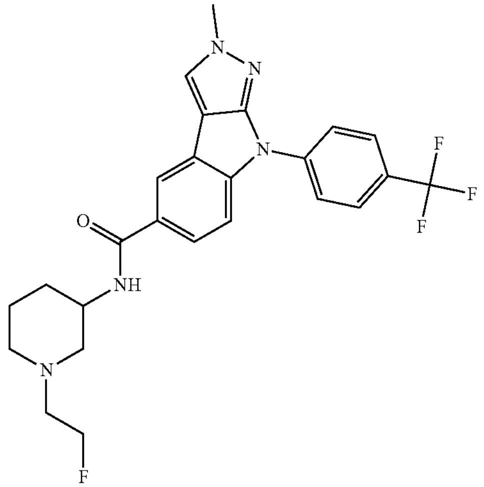 [SMILES: Cn1cc2c3cc(C(=O)NC4CCCN(CCF)C4)ccc3n(-c3ccc(C(F)(F)F)cc3)c2n1]<br>N-[1-(2-fluoroethyl)piperidin-3-yl]-2-methyl-8-[4-(trifluoromethyl)phenyl]-2H,8H-pyrazolo[3,4-b]indole-5-carboxamide |
| B144 | 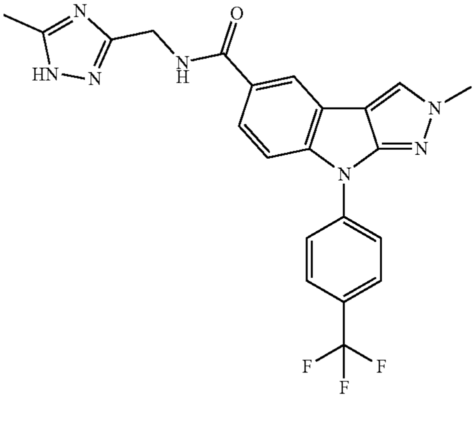 |

-continued

| Compound No. | Structure and Name |
| --- | --- |
| | 2-methyl-N-[(5-methyl-1H-1,2,4-triazol-3-yl)methyl]-8-[4-(trifluoromethyl)phenyl]-2H,8H-pyrazolo[3,4-b]indole-5-carboxamide |
| B145 | 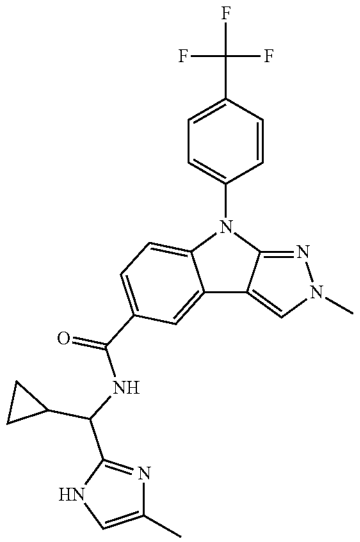 [SMILES: Cc1c[nH]c(C(NC(=O)c2ccc3c(c2)c2cn(C)nc2n3-c2ccc(C(F)(F)F)cc2)C2CC2)n1] N-[cyclopropyl(4-methyl-1H-imidazol-2-yl)methyl]-2-methyl-8-[4-(trifluoromethyl)phenyl]-2H,8H-pyrazolo[3,4-b]indole-5-carboxamide |

16. A medicament, comprising:

a compound of formula I-A

I-A

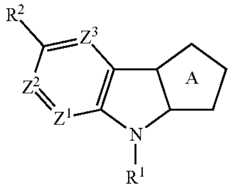

wherein

Ring A represents a five-membered heteroaromatic ring moiety selected from the group consisting of:

A-1

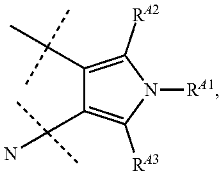

A-2

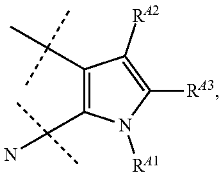

-continued

A-3

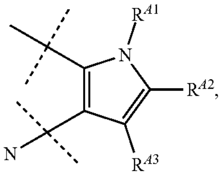

A-4

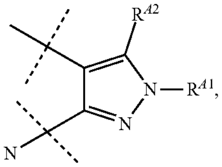

A-5

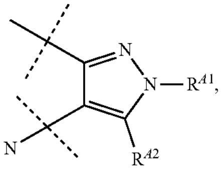

A-6

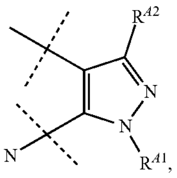

-continued
A-7
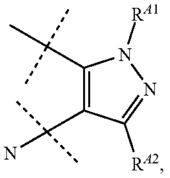
A-8
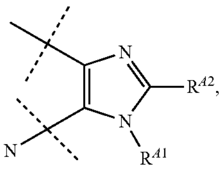
A-9
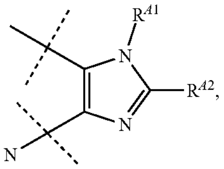
A-10
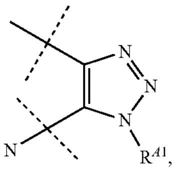
A-11
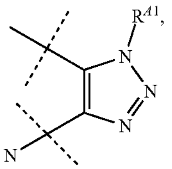
A-12
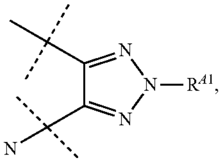
A-13
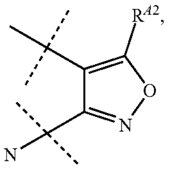
A-14
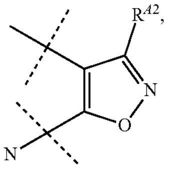
A-15
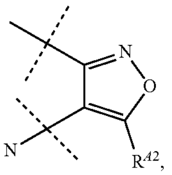
-continued
A-16
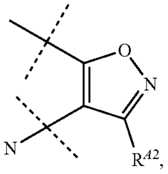
A-17
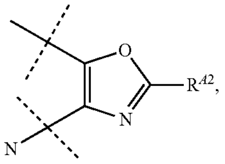
A-18
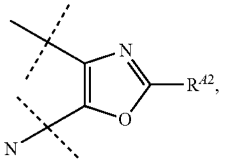
A-19
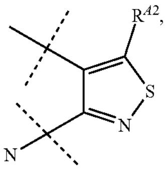
A-20
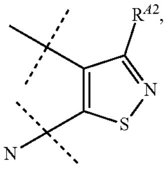
A-21
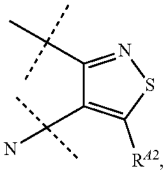
A-22
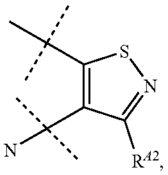
A-23
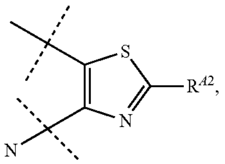
A-24
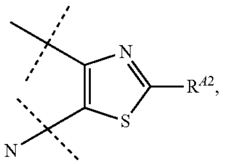

-continued

A-25

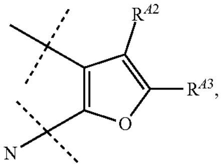

A-26

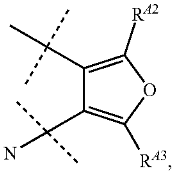

A-27

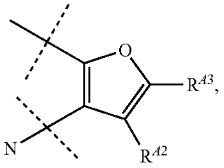

A-28

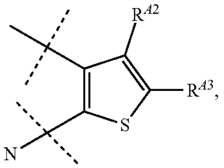

A-29

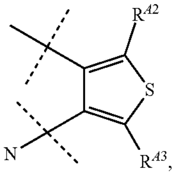

A-30

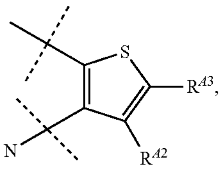

A-31

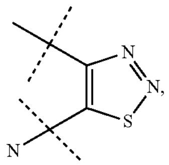

A-32

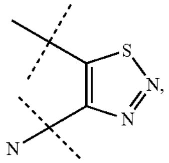 and

A-33

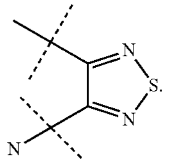

wherein $R^{A1}$ represents H, D, $C_{1-6}$-aliphatic, —$CH_2$—$Ar^{A1}$, or —$CH_2$—$CH_2$—$Ar^{A1}$;

$R^{A2}$ represents H, D, halogen, $C_{1-6}$-aliphatic, —$CH_2$—$Ar^{A2}$, or —$CH_2$—$CH_2$—$Ar^{A2}$;

$R^{A3}$ represents H, D, $C_{1-6}$-aliphatic, —$CH_2$—$Ar^{A3}$, or —$CH_2$—$CH_2$—$Ar^{A3}$;

$Z^1$ is $CR^{Z1}$ or N;

$Z^2$ is $CR^{Z2}$ or N;

$Z^3$ is $CR^{Z3}$ or N;

wherein at least two of $Z^1$, $Z^2$ and $Z^3$, are not N;

$R^1$ is selected from the group consisting of:

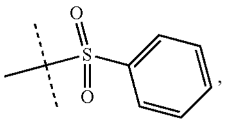 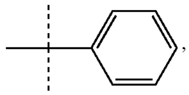

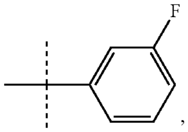 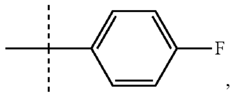

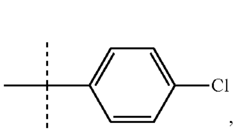 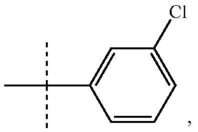

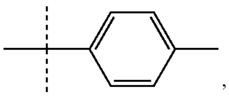 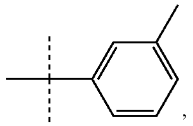

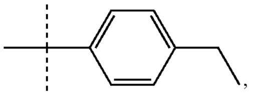 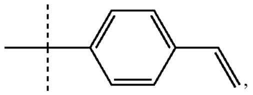

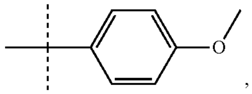 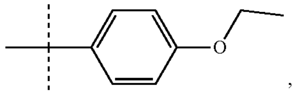

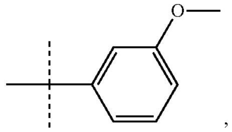 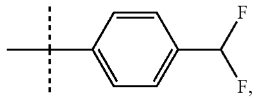

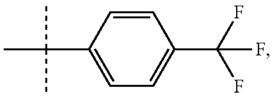 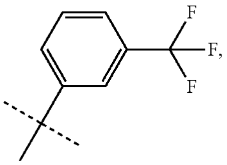

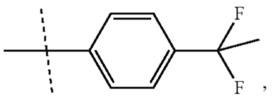 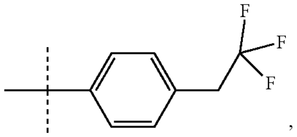

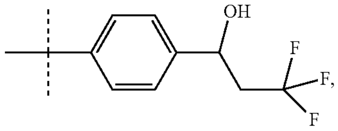

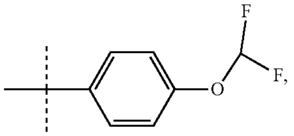

-continued
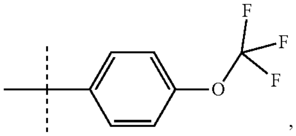
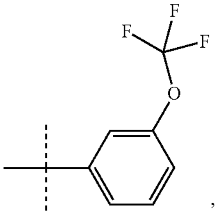
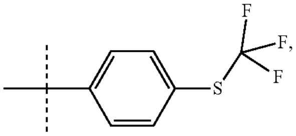
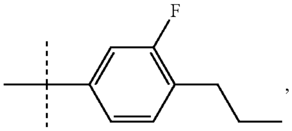
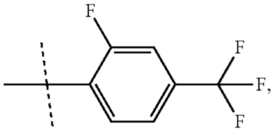
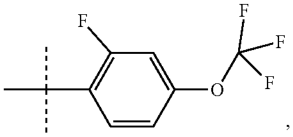
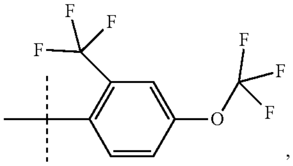
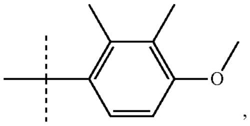
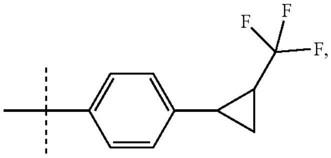
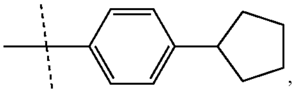
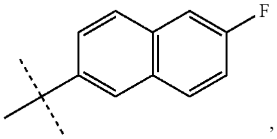
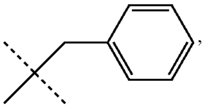
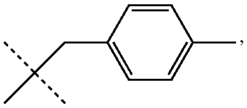
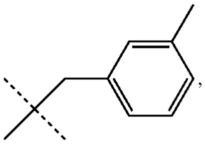
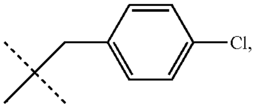
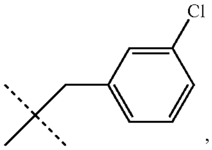
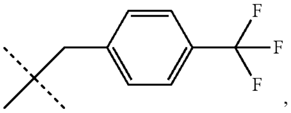
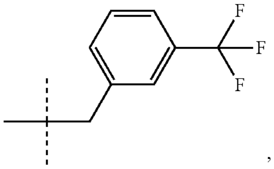
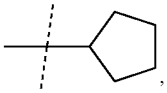
-continued
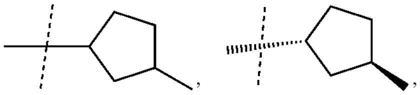
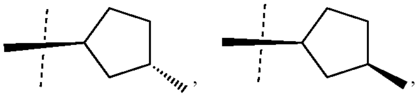
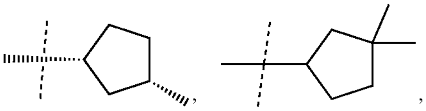
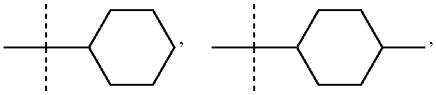
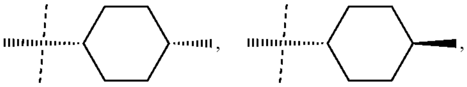
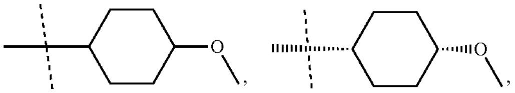
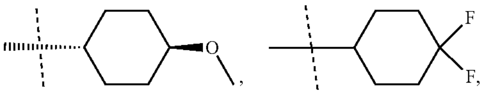
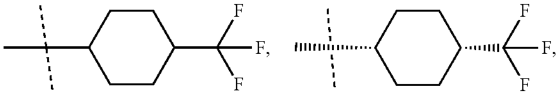
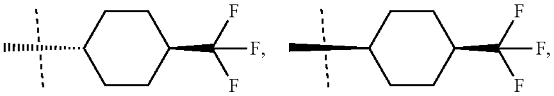
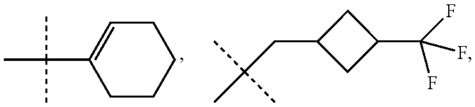
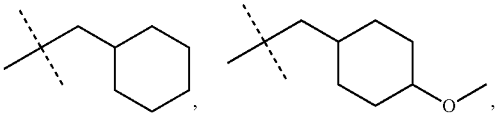
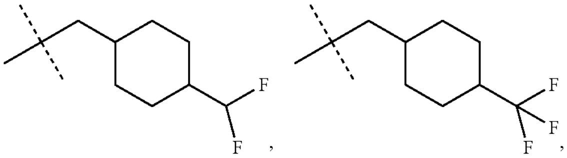
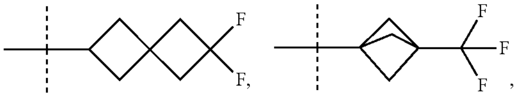
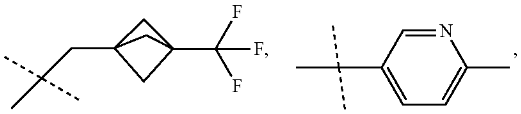
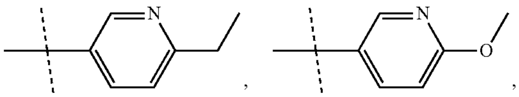
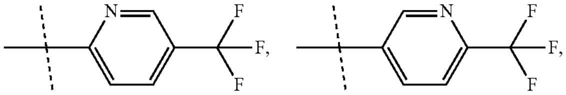

-continued

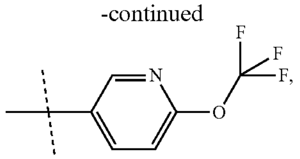

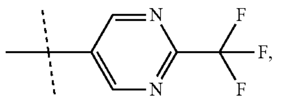

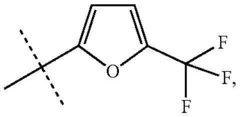

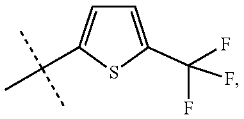

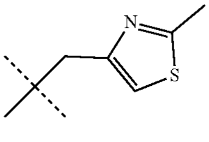

,

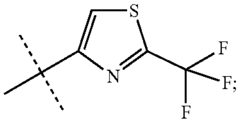

R$^2$ represents —C(=O)—OR$^{2a}$—C(=O)—NR$^{2b}$R$^{2c}$—(CH$_2$)$_w$—C(=O)—NR$^{2b}$R$^{2c}$—(CH$_2$)$_x$—NR$^{2d}$—C(=O)—R$^{2e}$, —S—R$^{2f}$—S(=O)—R$^{2f}$—S(=O)$_2$—R$^{2g}$, S(=O)$_2$—NR$^{2h}$R$^{2i}$—S(=O)$_2$—OH, —S(=O)(=NR$^{2j}$)—OH, —S(=O)(=NR$^{2j}$)—R$^{2g}$—S(=O)(=NR$^{2k}$)—NR$^{2l}$R$^{2m}$, (CH$_2$)$_y$—CN, —P(=O)(OR$^{2o}$)(OR$^{2p}$), —(CH$_2$)$_z$—NR$^{2d}$—S(=O)$_2$—R$^{2g}$—C(=O)—N=S(=O)—R$^{2s}$R$^{2t}$—C(=O)—N=S(=N—R$^{2u}$)—R$^{2s}$R$^{2t}$, —B(OH)$_2$, or Hetcyc$^X$;

Ar$^{A1}$, Ar$^{A2}$, Ar$^{A3}$ represent independently from each other phenyl which may be unsubstituted or mono- or di-substituted with independently from each other R$^{A11}$ and/or R$^{A12}$;

R$^{Z1}$ represents H or halogen;

R$^{Z2}$ represents H; or forms together with R$^2$ a divalent radical —S(=O)$_2$—N(H)—C(=O)—;

R$^{Z3}$ represents H or halogen;

R$^{2a}$ represents H, un-substituted or substituted C$_{1-8}$-aliphatic, aryl, heteroaryl, saturated or partially unsaturated heterocyclyl, or carbohydrate derived radical, or Cat;

Cat represents a monovalent cation;

R$^{2b}$, R$^{2c}$, R$^{2q}$, R$^{2r}$ represent independently from each other H, un-substituted or substituted C$_{1-8}$-aliphatic including C$_{3-7}$-cycloaliphatic; or form together with the nitrogen atom to which they are attached to an unsubstituted or substituted saturated, partially unsaturated or aromatic heterocycle with 3, 4, 5, 6, 7 ring atoms wherein 1 of said ring atoms is said nitrogen atom and no or one further ring atom is a hetero atom selected from N, O, or S and the remaining are carbon atoms; wherein said heterocycle may optionally be fused with Hetar$^Z$; or one of R$^{2b}$ and R$^{2c}$ represents —CN, —NH$_2$, —OH, —O—C$_{1-6}$-alkyl, —S(=O)$_2$—R$^{2g}$, Ar$^2$, Hetar$^2$, Cyc$^2$, or Hetcyc$^2$, while an other of R$^{2b}$ and R$^{2c}$ represents H or un-substituted or substituted C$_{1-8}$-aliphatic:

R$^{2d}$, R$^{2j}$, R$^{2k}$, R$^{2o}$, R$^{2p}$ represent independently from each other H, un-substituted or substituted C$_{1-8}$-aliphatic:

R$^{2e}$ represents H, halogen, un-substituted or substituted C$_{1-8}$-aliphatic, heteroaryl;

R$^{2f}$, R$^{2g}$ represent independently from each other un-substituted or substituted C$_{1-8}$-aliphatic;

R$^{2h}$, R$^{2i}$ represent independently from each other H, un-substituted or substituted C$_{1-8}$-aliphatic, aryl, heterocyclyl, heteroaryl; or form together with the nitrogen atom to which they are attached to an unsubstituted or substituted saturated, partially unsaturated or aromatic heterocycle with 3, 4, 5, 6, 7 ring atoms wherein 1 of said ring atoms is said nitrogen atom and no or one further ring atom is a hetero atom selected from N, O, or S and the remaining are carbon atoms;

R$^{2l}$, R$^{2m}$ represent independently from each other H, un-substituted or substituted C$_{1-8}$-aliphatic; or form together with the nitrogen atom to which they are attached to an unsubstituted or substituted saturated, partially unsaturated or aromatic heterocycle with 3, 4, 5, 6, 7 ring atoms wherein 1 of said ring atoms is said nitrogen atom and no or one further ring atom is a hetero atom selected from N, O, or S and the remaining are carbon atoms;

R$^{2s}$, R$^{2t}$ represent independently from each other unsubstituted or substituted C$_{1-8}$-aliphatic; or form together an unsubstituted or substituted divalent C$_{3-6}$-alkylene radical;

R$^{2u}$ represents hydrogen or unsubstituted or substituted C$_{1-6}$-aliphatic;

R$^{A11}$, R$^{A12}$ represent independently from each other halogen or un-substituted or substituted, straight-chain or branched C$_{1-6}$-aliphatic;

Ar$^2$ is a mono- or bicyclic aryl with 5, 6, 7, 8, 9, 10 ring carbon atoms, wherein that aryl may be unsubstituted or substituted with substituents R$^{D1}$, R$^{D2}$, R$^{D3}$, R$^{D4}$, and/or R$^{D5}$ which may be the same or different;

Hetar$^2$ is a mono- or bicyclic heteroaryl with 5, 6, 7, 8, 9, 10 ring atoms wherein 1, 2, 3, 4, 5 of said ring atoms is/are a hetero atom(s) selected from N, O, and/or S and the remaining are carbon atoms, wherein that heteroaryl may be unsubstituted or substituted with substituents R$^{D1}$, R$^{D2}$, R$^{D3}$, R$^{D4}$, and/or R$^{D5}$ which may be the same or different;

Cyc$^2$ is a saturated or partially unsaturated monocyclic carbocycle with 3, 4, 5, 6, or 7 ring carbon atoms, wherein that carbocycle may be unsubstituted or substituted with R$^{D6}$, R$^{D7}$, R$^{D8}$, R$^{D9}$, and/or R$^{D10}$ which may be the same or different; wherein that carbocycle may optionally be fused to Ar$^Z$ or Hetar$^Z$ via 2 adjacent ring atoms of said Ar$^Z$ or Hetar$^Z$ and wherein that fused carbocycle may further be unsubstituted or substituted with R$^{C1}$, R$^{C2}$, R$^{C3}$, R$^{C4}$, R$^{C5}$, R$^{C6}$ which may be the same or different;

Hetcyc$^2$ is a saturated or partially unsaturated, monocyclic heterocycle with 3, 4, 5, 6, 7 ring atoms wherein 1 or 2 of said ring atoms is/are a hetero atom(s) selected from N, O, and/or S and the remaining are carbon atoms, wherein that heterocycle may be unsubstituted or substituted with R$^{D6}$, R$^{D7}$, R$^{D8}$, R$^{D9}$, and/or R$^{D10}$ which may be the same or different; wherein that heterocycle may optionally be fused to Ar$^Z$ or Hetar$^Z$ via 2 adjacent ring atoms of said Ar$^Z$ or Hetar$^Z$ and wherein that fused heterocycle may further be unsubstituted or substituted with R$^{C1}$, R$^{C2}$, R$^{C3}$, R$^{C4}$, R$^{C5}$, R$^{C6}$ which may be the same or different;

Ar$^X$, Ar$^Z$ are independently from each other an un-substituted or substituted benzo ring;

Ar$^Y$ is an un-substituted or mono- or di-substituted phenyl;

Hetar$^{Y1}$ is a 5 or 6 membered monocyclic heteroaryl wherein 1, 2, 3, 4 ring atoms are hetero atoms selected from N, O, and/or S and the remaining are carbon atoms, wherein that heteroaryl may be unsubstituted or substituted with halogen, $C_{1-4}$-alkyl which may optionally be substituted with OH;

$Hetar^{Z}$ is an unsubstituted or substituted 5 or 6 membered heteroaryl ring selected from the group consisting of pyrrole, furan, thiophene, pyrazole, imidazole, oxazole, isoxazole, thiazole, oxadiazole, triazole, tetrazole, pyridine, pyrimidine, pyrazine, pyrane;

$Cyc^{Y1}$ is a saturated monocyclic carbocycle with 3, 4, 5, 6, or 7 ring carbon atoms, wherein that carbocycle may be unsubstituted or substituted with halogen, OH, $C_{1-4}$-alkyl;

$Hetcyc^{X}$ is a saturated, partially unsaturated or aromatic, monocyclic heterocycle with 3, 4, 5, 6, 7 ring atoms wherein 1, 2, 3, 4 of said ring atoms is/are a hetero atom(s) selected from N, O, and/or S and the remaining are carbon atoms, wherein said heterocycle may be unsubstituted or substituted with $R^{X1}$, $R^{X2}$, $R^{X3}$, $R^{X4}$, $R^{X5}$, $R^{X6}$, $R^{X7}$, and/or $R^{X8}$ which may be the same or different, and wherein that heterocycle is optionally a carboxylic acid bioisostere;

$Hetcyc^{Y}$ is a saturated, partially unsaturated or aromatic, monocyclic heterocycle with 3, 4, 5, 6, 7 ring atoms wherein 1, 2, 3, 4 of said ring atoms is/are a hetero atom(s) selected from N, O, and/or S and the remaining are carbon atoms;

$Hetcyc^{Y1}$ is a saturated or partially unsaturated monocyclic heterocycle with 5 or 6 ring atoms wherein 1 or 2 of said ring atoms are heteroatoms selected from N, O, and/or S and the remaining are carbon atoms;

$R^{C1}$, $R^{C2}$, $R^{C3}$, $R^{C4}$, $R^{C5}$, $R^{C6}$ represent independently from each other un-substituted or substituted $C_{1-6}$-aliphatic;

$R^{D1}$, $R^{D2}$, $R^{D3}$, $R^{D4}$, $R^{D5}$ represent independently from each other un-substituted or substituted $C_{1-6}$-aliphatic:

$R^{D6}$, $R^{D7}$, $R^{D8}$, $R^{D9}$, $R^{D10}$ represent independently from each other un-substituted or substituted $C_{1-6}$-aliphatic, unsubstituted or substituted $C_{1-6}$-aliphatoxy, halogen, hydroxy; $Hetar^{Y1}$, $CH_2$-$Hetar^{Y1}$, $Cyc^{Y1}$, $Hetcyc^{Y1}$, —$CH_2$-$Hetcyc^{Y1}$; and/or two of $R^{D6}$, $R^{D7}$, $R^{D8}$, $R^{D9}$, $R^{D10}$ which are attached to the same ring atom of said carbocycle or heterocycle may form a divalent $C_{2-6}$-alkylene radical, wherein one or two non-adjacent carbon units of said alkylene radical may optionally be replaced by independently from each other O, N—H, or N—$C_{1-4}$-alkyl, and wherein that alkylene radical may optionally be substituted with OH, $C_{1-4}$-alkyl, or —O—$C_{1-4}$-alkyl; and/or two of $R^{D6}$, $R^{D7}$, $R^{D8}$, $R^{D9}$, $R^{D10}$ which are attached to different ring atoms of said carbocycle or heterocycle may form a divalent $C_{1-6}$-alkylene radical, wherein one or two non-adjacent carbon units of said alkylene radical may optionally be replaced by independently from each other O, N—H, or N—$C_{1-4}$-alkyl;

$R^{X1}$, $R^{X2}$, $R^{X3}$, $R^{X4}$, $R^{X5}$, $R^{X6}$, $R^{X7}$, $R^{X8}$ represent independently from each other un-substituted or substituted $C_{1-6}$-aliphatic, $C_{1-6}$-aliphatoxy, halogen, —OH, —$NR^{2d}$—$S(=O)_2$—$R^{2g}$, $Hetcyc^{Y}$, O-$Hetcyc^{Y}$; and/or two of $R^{X1}$, $R^{X2}$, $R^{X3}$, $R^{X4}$, $R^{X5}$, $R^{X6}$, $R^{X7}$, $R^{X8}$ which are attached to the same carbon atom of said heterocycle form a divalent oxo (=O) group; and/or two of $R^{X1}$, $R^{X2}$, $R^{X3}$, $R^{X4}$, $R^{X5}$, $R^{X6}$, $R^{X7}$, $R^{X8}$ or four of $R^{X1}$, $R^{X2}$, $R^{X3}$, $R^{X4}$, $R^{X5}$, $R^{X6}$, $R^{X7}$, $R^{X8}$ which are attached to the same sulfur atom of said heterocycle form a divalent oxo (=O) group thereby forming either an —S(=O)— or an —$S(=O)_2$-moiety;

halogen is F, Cl, Br, I;

v is 1 or 2;

w is 1 or 2;

x is 0, 1 or 2;

y is 0, 1 or 2;

z is 0, 1 or 2;

or any N-oxide, tautomer or stereoisomer thereof and/or any pharmaceutically acceptable salt of each of the foregoing, including mixtures thereof in all ratios.

17. A method, comprising:

treating a medical condition or disease by inhibiting YAP-TEAD and/or TAZ-TEAD interaction by administering to a subject in need of said treatment, the compound according to claim 1, or any N-oxide, tautomer or stereoisomer thereof and/or the pharmaceutically acceptable salts of each of the foregoing, including mixtures thereof in all ratios.

18. A method, comprising:

treating a medical condition or disease by administering to a subject in need of said treatment, the compound according to claim 1, or any N-oxide, tautomer or stereoisomer thereof and/or the pharmaceutically acceptable salts of each of the foregoing, including mixtures thereof in all ratios, wherein the medical condition or disease selected from the group consisting of: cancer, solid tumors, breast cancer, lung cancer, liver cancer, ovarian cancer, squamous cancer, renal cancer, gastric cancer, medulloblastoma, colon cancer, pancreatic cancer; cardiovascular diseases, and fibrosis.

19. A pharmaceutical composition comprising at least one compound according to claim 1, or any N-oxide, tautomer or stereoisomer thereof and/or the pharmaceutically acceptable salts of each of the foregoing, including mixtures thereof in all ratios, as active ingredient, together with a pharmaceutically acceptable carrier.

20. The pharmaceutical composition according to claim 19, further comprising a second active ingredient or any N-oxide, tautomer or stereoisomer thereof and/or the pharmaceutically acceptable salts of each of the foregoing, including mixtures thereof in all ratios, wherein that second active ingredient is other than a compound according to claim 1.

21. A kit, comprising:

separate packs of a) an effective amount of the compound of formula I-A according to claim 1, or any N-oxide, tautomer or stereoisomer thereof and/or the pharmaceutically acceptable salts of each of the foregoing, including mixtures thereof in all ratios; and b) an effective amount of a further active ingredient that further active ingredient not being the compound of formula I-A according to claim 1.

22. A method of manufacturing the compound according to claim 1, or any N-oxide, tautomer or stereoisomer thereof and/or the pharmaceutically acceptable salts of each of the foregoing, including mixtures thereof in all ratios, the method comprising:

(a)(1) reacting a compound of formula II-a or II-A-a

II-a

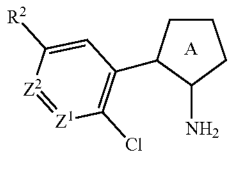

-continued

II-A-a

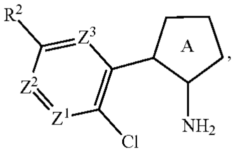

wherein $Z^1$, $Z^2$, $Z^3$, ring A and $R^2$ are as defined for the compound of formula I-A in claim 1, wherein $R^2$ is not —C(═O)—OH or —C(═O)—OCat;

with a compound of formula III $R^1$-Hal III, wherein $R^1$ is as defined for the compound of formula I-A in claim 1 and Hal represents Cl, Br, or I, in a C—N cross coupling reaction under suitable reaction conditions;

or (a)(2) first converting the compound of formula II-a or II-A-a into the tricyclic compound of formula IV or IV-A

IV

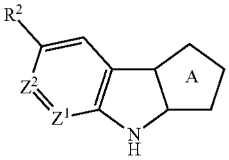

IV-A

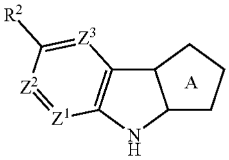

in a C—N cross coupling reaction under suitable reaction conditions; and then reacting with a compound of formula III $R^1$-Hal III, in another C—N cross coupling reaction under suitable reaction conditions;

to provide (a)(3) a compound of formula I or I-A as defined in claim 1; and optionally (a)(4) if in the compound of formula I or I-A $R^2$ is —C(═O)—$OR^{2a}$ with $R^{2a}$ being unsubstituted or substituted $C_{1-8}$-aliphatic, then this compound of formula I or I-A is subjected to a saponification reaction under suitable conditions to provide the respective compound of formula I or I-A with $R^2$ being —C(═O)—OH or —C(═O)—OCat;

or reacting (b) a compound of formula II-b or II-A-b

II-b

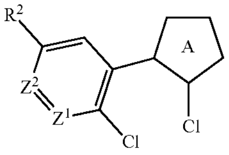

II-A-b

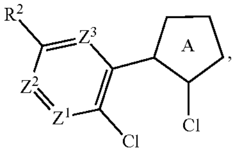

wherein $Z^1$, $Z^2$, $Z^3$, ring A and $R^2$ are as defined for the compound of formula I or I-A in claim 1, wherein $R^2$ is not —C(═O)—OH or —C(═O)—OCat;

(b)(1) with a compound of formula V $R^1$—$NH_2$ V, wherein $R^1$ is as defined for the compound of formula I or I-A in claim 1, in a C—N cross coupling reaction under suitable reaction conditions to provide a compound of formula I or I-A as defined in claim 1; and optionally (b)(2) if in the compound of formula I or I-A $R^2$ is —C(═O)—$OR^{2a}$ with $R^{2a}$ being unsubstituted or substituted $C_{1-8}$-aliphatic, then this compound of formula I or I-A is subjected to a saponification reaction under suitable conditions to provide the respective compound of formula I or I-A with $R^2$ being —C(═O)—OH or —C(═O)—OCat.

* * * * *